(12) United States Patent
Braun et al.

(10) Patent No.: US 12,344,603 B2
(45) Date of Patent: Jul. 1, 2025

(54) PYRIDO-PYRIMIDINONE AND PTERIDINONE COMPOUNDS AND METHODS OF USE

(71) Applicant: Genentech, Inc., South San Francisco, CA (US)

(72) Inventors: Marie-Gabrielle Braun, San Francisco, CA (US); Georgette Castanedo, Redwood City, CA (US); Paul Gibbons, San Francisco, CA (US); Joachim Rudolph, Burlingame, CA (US); William Vernier, San Bruno, CA (US); Ramsay Beveridge, Montreal (CA); Yao Wu, Beijing (CN); Guosheng Wu, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 913 days.

(21) Appl. No.: 17/366,923

(22) Filed: Jul. 2, 2021

(65) Prior Publication Data

US 2023/0047209 A1    Feb. 16, 2023

Related U.S. Application Data

(63) Continuation of application No. PCT/US2020/012058, filed on Jan. 2, 2020.

(51) Int. Cl.
*C07D 471/04* (2006.01)
*C07D 475/00* (2006.01)

(52) U.S. Cl.
CPC ......... *C07D 471/04* (2013.01); *C07D 475/00* (2013.01)

(58) Field of Classification Search
CPC .............................. C07D 471/04; C07D 475/00
See application file for complete search history.

(56) References Cited

U.S. PATENT DOCUMENTS

| | | | |
|---|---|---|---|
| 3,773,919 A | 11/1973 | Boswell et al. | |
| 7,868,177 B2 | 1/2011 | Cee et al. | |
| 7,880,000 B2 | 2/2011 | Geuns-Meyer et al. | |
| 8,476,434 B2 | 7/2013 | Geuns-Meyer et al. | |
| 8,815,885 B2 | 8/2014 | Walter et al. | |
| 9,382,230 B2 | 7/2016 | Walter et al. | |
| 2010/0048597 A1 | 2/2010 | Beckwith et al. | |
| 2016/0024094 A1 | 1/2016 | Backes et al. | |
| 2018/0346447 A1 | 12/2018 | Vacca et al. | |

FOREIGN PATENT DOCUMENTS

| | | | |
|---|---|---|---|
| JP | A 2007/536280 | 12/2007 | |
| JP | A 2010/514689 | 5/2010 | |
| JP | 6925435 B2 | 8/2021 | |
| JP | A 2021/536496 | 12/2021 | |
| WO | WO 96/15111 | 5/1996 | |
| WO | WO 01/19825 | 3/2001 | |
| WO | WO-2002018380 A1 * | 2/2002 | |
| WO | WO 02/18380 | 3/2002 | |
| WO | WO-0218380 A1 * | 3/2002 | ........... C07D 471/04 |
| WO | WO 2004/063195 | 7/2004 | |
| WO | WO 2005/034869 | 4/2005 | |
| WO | WO 2005/113494 A2 | 12/2005 | |
| WO | WO 2006/002367 | 1/2006 | |
| WO | WO 2006/002367 A1 | 1/2006 | |
| WO | WO 2006/039718 A2 | 4/2006 | |
| WO | WO 2006/056863 A1 | 6/2006 | |
| WO | WO-2006082492 A1 * | 8/2006 | ................ A61P 1/00 |
| WO | WO 2007/100646 A1 | 9/2007 | |
| WO | WO 2007/136465 A2 | 11/2007 | |
| WO | WO 2008/033999 A1 | 3/2008 | |
| WO | WO 2008/055842 A1 | 5/2008 | |
| WO | WO 2010/031056 A2 | 3/2010 | |
| WO | WO-2011097526 A1 * | 8/2011 | ........... A61K 31/444 |
| WO | WO 2013/067423 A1 | 5/2013 | |
| WO | WO 2013/090840 A1 | 6/2013 | |
| WO | WO 2014/052669 A1 | 4/2014 | |
| WO | WO 2014/179496 A1 | 11/2014 | |
| WO | WO 2014/182829 | 11/2014 | |
| WO | WO-2014179498 A1 * | 11/2014 | ........... A61K 31/519 |
| WO | WO 2018/102751 A1 | 6/2018 | |
| WO | WO 2018/222917 A1 | 12/2018 | |
| WO | WO 2018/222918 | 12/2018 | |
| WO | WO 2020/117635 A1 | 6/2020 | |
| WO | WO 2020/142612 A1 | 7/2020 | |
| WO | WO 2020/227020 A1 | 11/2020 | |

(Continued)

OTHER PUBLICATIONS

Kar et al., Current Developments in Excipient Science: Implication of Quantitative Selection of Each Excipient in Product Development, Press,2019, pp. 29-83, ISBN 9780128179093 (Year: 2019).*
Ren L, Ahrendt KA, Grina J, Laird ER, Buckmelter AJ, Hansen JD, Newhouse B, Moreno D, Wenglowsky S, Dinkel V, Gloor SL, Hastings G, Rana S, Rasor K, Risom T, Sturgis HL, Voegtli WC, Mathieu S. Bioorg Med Chem Lett. May 15, 2012;22(10):3387-91 (Year: 2012).*
Beveridge RE, Wallweber HA, Ashkenazi A, Beresini M, Clark KR, Gibbons P, Ghiro E, Kaufman S, Larivée A, Leblanc M, Leclerc JP, Lemire A, Ly C, Rudolph J, Schwarz JB, Srivastava S, Wang W, Zhao L, Braun MG, ACS Med Chem Lett. Oct. 16, 2020; 11(12): 2389-2396 (Year: 2020).*
Adachi, Y. et al., "ATF6 Is a Transcription Factor Specializing in the Regulation of Quality Control Proteins in the Endoplasmic Reticulum," Cell Struct. and Func., 33:75-89, (2008).

(Continued)

*Primary Examiner* — Clinton A Brooks
*Assistant Examiner* — Izabela Schmidt
(74) *Attorney, Agent, or Firm* — Alston & Bird LLP

(57) ABSTRACT

Described herein are pyrido-pyrimidinone and pteridinone compounds or stereoisomers, tautomers, or pharmaceutically acceptable salts thereof, and with the substituents and structural features described herein. Also described are pharmaceutical compositions and medicaments that include the compounds described herein, as well as methods treating cancer, alone and in combination with other therapeutic agents.

26 Claims, No Drawings

Specification includes a Sequence Listing.

(56) References Cited

FOREIGN PATENT DOCUMENTS

WO    WO 2021/145521 A1    7/2021

OTHER PUBLICATIONS

Arai, M. et al., "Transformation-associated gene regulation by ATF6α during hepatocarcinogenesis," FEBS Letts., 580:184-190, (2006).
Baek, H.A. et al., "Involvement of Endoplasmic Reticulum Stress in Myofibroblastic Differentiation of Lung Fibroblasts," Am. J. Resp. Cell Mol. Bio., 46:731-739, (2012).
Binet, F. et al., "Neuronal ER Stress Impedes Myeloid-Cell-Induced Vascular Regeneration through IRE1α Degradation of Netrin-1," Cell Metabol., 17:353-371, (2013).
Bogaert, S. et al., "Involvement of Endoplasmic Reticulum Stress in Inflammatory Bowel Disease: A Different Implication for Colonic and Ileal Disease?," PloS One, 6(10):e25589, (2011).
Bowen, T. et al., "MicroRNAs, transforming growth factor beta-1, and tissue fibrosis," J. Pathol., 229:274-285, (2013).
Cao, S.S. et al., "The Unfolded Protein Response and Chemical Chaperones Reduce Protein Misfolding and Colitis in Mice," Gastroent., 144(5):989-1000, (2013).
Chen, Y. et al., "IRE1: ER stress sensor and cell fate executor," Trends Cell Biol., 23:547-555, (2013).
Chiang et al., "Endoplasmic reticulum stress implicated in the development of renal fibrosis," Mol. Med., 17:1295-1305, (2011).
Cross, B.C.S et al., "The molecular basis for selective inhibition of unconventional mRNA splicing by an IRE1-Binding small molecule," PNAS, 109:E869-878, (2012).
Davis, M., "Comprehensive analysis of kinase inhibitor selectivity," Nature Biotechnology, 29(11):1046-1051, (Nov. 1, 2011).
Galligan, J. et al., "Oxidative Stress and the ER Stress Response in a Murine Model for Early-Stage Alcoholic Liver Disease," J. Toxicol. 2012(207594), 12 pgs., (2012).
Ghosh, R. et al., "Allosteric Inhibition of the IRE1α RNase Preserves Cell Viability and Function during Endoplasmic Reticulum Stress," Cell, 158:534-548 (2014).
Harrington, P.E. et al., "Unfolded Protein Response in Cancer: IRE1α Inhibition by Selective Kinase Ligands Does Not Impair Tumor Cell Viability," ACS Medical Chemistry Letters, 6:68072, (2015).
Heindryckx, F. et al., "Endoplasmic reticulum stress enhances fibrosis through IRE1α-mediated degradation of miR-150 and XBP-1 splicing," EMBO Molecular Medicine, 8(7):729-744, 2016.
Hollien, J. et al., "Decay of Endoplasmic Reticulum-Localized mRNAs During the Unfolded Protein Response," Science, 313:104-107, (2006).
Ji, et al., "New Insights into the Pathogenesis of Alcohol-Induced ER Stress and Liver Diseases," Int. J. Hepatol., 2014(513787), 11 pgs., (2014).
Lu, M. et al., "Opposing unfolded-protein-response signals converge on death receptor 5 to control apoptosis," Science, 345:98-101, (2014).
Ranatunga, S. et al., "Synthesis of Novel Tricyclic Chromenone-Based Inhibitors of IRE-1 RNase Activity," J. Med. Chem., 57:4289-4301, (2014).
Schröder, et al., "ER stress and the unfolded protein response," Mutat Res., 569(1-2):29-63, (2005).
Shin, et al., "SIRT7 Represses Myc Activity to Suppress ER Stress and Prevent Fatty Liver Disease," Cell Reports, 5:654-665, (2013).
Sovolyova, N. et al., "Stressed to death—mechanisms of ER stress-induced cell death," Biol. Chem., 395:1-13, (2014).
Spitler, K. et al., "Endoplasmic Reticulum Stress Contributes to Aortic Stiffening via Proapoptotic and Fibrotic Signaling Mechanisms, " Hypertension, 63:e40-e45, (2014).
Sriburi, R. et al., "XBP1: a link between the unfolded protein response, lipid biosynthesis, and biogenesis of the endoplasmic reticulum," J. Cell. Bio., 167:35-41, (2004).
Tanjore, H. et al., "Endoplasmic Reticulum Stress as a Pro-Fibrotic Stimulus," Biochim. Biophys. Acta., 1832(7):940-947, (2013).
Tirasophon, W. et al., "The endoribonuclease activity of mammalian IRE1 autoregulates its mRNA and is required for the unfolded protein response," Genes & Develop., 14:2725-2736, (2000).
Upton, J.-P. et al., "IRE1αcleaves select microRNAs during ER stress to derepress translation of proapoptotic Caspase-2," Science, 338:818-822, (2012).
Volkmann, K. et al., "Potent and Selective Inhibitors of the Inositol-requiring Enzyme 1 Endoribonuclease," J. Biol. Chem., 286:12743-12755, (2011).
Walter, P. et al., "The Unfolded Protein Response: From Stress Pathway to Homeostatic Regulation," Science, 334:1081-1086, (2011).
Wang, L. et al., "Divergent allosteric control of the IRE1α endoribonuclease using kinase inhibitors," Nat. Chem. Biol. 8:982-989 (2012).
Wang, M. et al., "Protein misfolding in the endoplasmic reticulum as a conduit to human disease," Nature, 529:326-335 (2016).
Yamamoto, K. et al., "Differential Contributions of ATF6 and XBP1 to the Activation of Endoplasmic Reticulum Stress-Responsive cis-Acting Elements ERSE, UPRE and ERSE-II," J. Biomchem., 136:343-350, (2004).
EP Application No. 20711446.3, Office Action mailed May 19, 2023.
WIPO Application No. PCT/US2020/037233, PCT International Preliminary Report on Patentability mailed Dec. 23, 2021.
Cee, Victor J. et al., "Pyridyl-pyrimidine benzimidazole derivatives as potent, selective, and orally bioavailable inhibitors of Tie-2 kinase," Bioorganic & Medicinal Chemistry Letters, 19:424-427, (2009).
Cheng, A. C. et al., "Analysis of Kinase Inhibitor Selectivity using a Thermodynamics-Based Partition Index," J. Med. Chem. 53(11):4502-4510, (2010).
Okamoto, J. Chromatogr., 513:375-378, (1990).
Ren, L. et al., "The discovery of potent and selective pyridopyrimidin-7-one based inhibitors of B-RafV600E kinase," Bioorganic & Medicinal Chemistry Letters, 22:3387-3391, (2012).
EP Application No. 20 702 937.2, Communication pursuant to Article 94(3) EPC mailed Nov. 18, 2022.
GC Application No. 2019-38265, Examination Report dated Jul. 28, 2021.
JP Application No. 2021-513790, Office Action and Search Report issued Mar. 15, 2022.
Taiwanese Application No. 108132813, Office Action dated Oct. 29, 2020.
WIPO Application No. PCT/US2019/050698, PCT International Preliminary Report on Patentability mailed Mar. 25, 2021.
WIPO Application No. PCT/US2019/050698, PCT International Search Report and Written Opinion of the International Searching Authority mailed Nov. 18, 2019.
WIPO Application No. PCT/US2019/050749, PCT International Preliminary Report on Patentability mailed Mar. 25, 2021.
WIPO Application No. PCT/US2019/050749, PCT International Search Report and Written Opinion of the International Searching Authority mailed Nov. 21, 2019.
WIPO Application No. PCT/US2020/018499, PCT International Search Report and Written Opinion of the International Searching Authority mailed Jun. 17, 2020.
Beveridge et al., "Identification of BRaf-Sparing Amino-Thienopyrimidines with Potent IRE1α Inhibitory Activity," ACS Medicinal Chemistry Letters, 11(12):2389-2396, (Oct. 16, 2020).
Registry(STN) [online], Dec. 7, 2011, [search date: Jan. 5, 2024] CAS No. 1348150-26-4.
Registry(STN) [online], Dec. 7, 2011, [search date: Jan. 5, 2024] CAS No. 1350015-88-1.
EP Application No. 20702937.2, Office Action mailed Oct. 30, 2023.
JP Application No. 2021-539020, Reason for Refusal mailed Feb. 6, 2024.

(56) References Cited

OTHER PUBLICATIONS

JP Application No. 2021-548153, Reason for Refusal mailed Jan. 16, 2024.

* cited by examiner

PYRIDO-PYRIMIDINONE AND PTERIDINONE COMPOUNDS AND METHODS OF USE

CROSS-REFERENCE TO RELATED APPLICATIONS

This application is a Continuation of International Application No. PCT/US2020/012058, filed Jan. 2, 2020, which claims the benefit of and priority to International Patent Application No. PCT/CN2019/070275, filed Jan. 3, 2019, and to International Patent Application No. PCT/CN2019/081673, filed Apr. 8, 2019, each of which is incorporated herein by reference in its entirety and for all purposes.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 560905_SEQUENCE.TXT, created on Jul. 2, 2021, and having a size of 531 bytes and is filed concurrently with the specification. The sequence listing contained in this ASCII formatted document is part of the specification and is herein incorporated by reference in its entirety.

BACKGROUND OF THE INVENTION

The kinase/endoribonuclease inositol requiring enzyme 1 (IRE1α), one of the key sensors of misfolded protein accumulation in the endoplasmic reticulum that triggers the unfolded protein response (UPR), is a potential therapeutic target for diverse diseases including cancer for inhibitors that bind to the ATP-binding site on the kinase moiety of IRE1α and block its endoribonuclease activity. IRE1α is a transmembrane, bifunctional protein with a luminal domain that binds to misfolded proteins, a transmembrane segment, and a cytoplasmic portion consisting of a kinase moiety and a tandem endoribonuclease domain. Structure-activity relationship (SAR) studies led to compounds selective in recombinant IRE1α kinase screens and potent against endoribonuclease activity of recombinant IRE1α as well as cellular IRE1α. IRE1α activity mediates certain cytoprotective and pro-survival functions of the UPR, increases viability and growth in certain tumor cell lines, and can be an effective therapeutic target for specific small molecule inhibitors that block malignant tumor growth, contrary to an earlier report (Harrington, P. E. et al (2015) ACS Med. Chem. Lett. 6:68-72). In addition, inhibitors of IRE1α can be therapeutically useful for other types of diseases besides cancer including certain autoimmune, neurodegenerative, fibrotic and metabolic disorders (Wang M. and Kaufman, R. J. (2016) Nature 529:326-335).

Homeostatic regulation of protein folding in the endoplasmic reticulum (ER) is under the control of three key intracellular signaling pathways: IRE1α, PERK, and ATF6, which together orchestrate the unfolded protein response (UPR) (Schroder, et al (2005) Mutat Res-Fund Mol Mech Metagenesis 569:29-63). An increase in demand for protein folding in the ER or certain types of cellular injury or stress lead to the accumulation of unfolded proteins in the ER—a condition called ER stress. Cells respond to ER stress by activating the UPR to help adjust or maintain their high-fidelity protein synthetic capacity (Walter, P. and Ron, D. (2011) Science, 334:1081-1086). IRE1α is the most evolutionarily conserved of the three branches of the UPR. Importantly, the UPR makes life/death decisions for the cell, depending on the severity and duration of ER stress, and the final outcome is either cell survival and recovery or programmed cell death (apoptosis) (Sovolyova et al, (2014) Biol Chem 395: 1-13). All three pathways of the UPR form a coordinated reaction to the accumulation of unfolded proteins; and several studies have demonstrated that there is cross talk between the different pathways (Yamamoto et al, J. Biochem. (2004) 136:343-350); Arai et al, FEBS Letts. (2006) 580:184-190; Adachi et al, Cell Struct. Func. (2008) 33:75-89). ER stress and activation of the UPR can be caused by mechanical injury, inflammation, genetic mutations, infections, oxidative stress, metabolic stress, and other types of cellular stress associated with malignancy. ER stress has also been implicated in diseases that result in fibrotic remodeling of internal organs, such as chronic liver diseases (Galligan et al, J. Toxicol. (2012) Vol. 2012, Article ID 207594, 12 pgs.; Shin et al, Cell Reports (2013) 5:654-665; Ji, Int. J. Hepatol. (2014) Vol. 2014, Article ID 513787, 11 pages), pulmonary fibrosis (Baek et al, Am. J. Resp. Cell Mol. Bio. (2012) 46:731-739); Tanjore et al, Biochim Biophys Acta (2012, online), (2013) 1832:940-947), kidney fibrosis (Chiang et al, Mol. Med. (2011) 17:1295-1305), cardiovascular disease (Spitler & Webb, Hypertension (2014) 63:e40-e45), and inflammatory bowel disease (Bogaert et al, PLoS One (2011) 6(10) e25589; Cao et al, Gastroent (2013) 144:989-1000).

IRE1α is a transmembrane, bifunctional protein with cytoplasmic kinase and endoribonuclease activity. The N-terminal domain of IRE1α is proposed to sense the presence of unfolded proteins in the ER lumen, triggering activation of the cytoplasmic kinase domain, which, in turn, activates the C-terminal endoribonuclease. IRE1α transmits information across the ER lipid bilayer (Tirasophon et al, Genes & Develop. (2000) 14:2725-2736). Increased ER protein load and presence of unfolded proteins leads to the dissociation of the ER chaperone GRP78/BiP from IRE1α molecules, which bind to misfolded proteins and then undergo dimerization and trans-autophosphorylation in the cytoplasmic kinase domain. This leads to activation of the IRE1α endoribonuclease moiety in the cytosol. The IRE1α endoribonuclease has the ability to cleave the mRNA that encodes unspliced X box protein 1 (XBP1u); this excises a 26-nucleotide intron and leads to formation of spliced XBP1 (XBP1s) mRNA, which encodes a potent transcription factor. After transport into the nucleus, the XBP1s protein binds to UPR promoter elements to initiate transcription of genes that enhance the ability of the ER to cope with unfolded proteins, for example, through enhanced ER-associated degradation of misfolded proteins, and through elevated levels of chaperones and disulfide isomerases that support protein folding in the ER. IRE1α activation is also associated with enlargement of the ER volume, which has been interpreted as an adaptive mechanism to increase protein folding capacity (Sriburi et al, J. Cell. Bio. (2004) 167:35-41); (Chen, Y. (2013) Trends Cell Biol., 23,547-555). In addition, the IRE1α endoribonuclease cleaves various mRNAs in a process called regulated IRE1α-dependent decay of mRNA (RIDD), which reduces both protein translation and import of proteins into the ER to help reestablish homeostasis (Hollien & Weissman, Science (2006) 313:104-107). In cancer cells, IRE1α suppresses ER-stress-induced apoptosis by reducing the mRNA levels of death receptor 5 (DR5) through RIDD (Lu et al., Science (2014) 345:98-101).

Besides degrading mRNA (Binet et al, Cell Metabol. (2013) 17:353-371), it was recently shown that IRE1α also has the ability to degrade microRNAs (miRs) (Upton et al, Science (2012) 338:818-822). miRs are short noncoding RNA oligonucleotides consisting of 17-nucleotides that generally act to inhibit gene expression by binding to complementary sequences in the 30-untranslated region of target mRNAs, either to repress mRNA translation or to induce mRNA cleavage. A number of cellular functions such as proliferation, differentiation, and apoptosis are regulated by miRs, and aberrant miR expression is observed in a variety of human diseases including fibrosis (Bowen et al, J. Pathol (2013) 229:274-285). Inhibitors that specifically target individual components of the UPR have recently been described. The inhibitor 4μ8C that stably binds to lysine 907 in the IRE1α endoribonuclease domain has been shown to inhibit both RIDD activity and XBP-1 splicing (Cross et al, Proc Natl. Acad. Sci. (2012) 109:E869-E878). High levels of 4μ8C cause no measurable toxicity in cells and concentrations ranging from 80 to 128 1M of 4μ8C completely block XBP1 splicing without affecting IRE1α (alpha) kinase activity (Cross et al, 2012). The inhibitor 4μ8C thus represents an important tool to delineate the functions of IRE1α in vivo as IRE1α-knockout mice die during embryonic development. Inhibition of IRE1α prevents activation of myofibroblasts and reduces fibrosis in animal models of liver and skin fibrosis. Pharmacological inhibition of IRE1α could revert the profibrotic phenotype of activated myofibroblasts isolated from patients with scleroderma and indicates that ER stress inhibitors should be taken into consideration when developing new strategies for the treatment of fibrotic diseases (Heindryckx, F. et al (2016) EMBO Molecular Medicine Vol 8(7):729-744).

Activation of the UPR has been shown to be an important survival pathway for tumors of secretory cell origin like multiple myeloma that have a very high protein synthesis burden. Therefore, efforts to disrupt the UPR by blocking the IRE1α endoribonuclease cleavage and activation of XBP1 have been an active area of cancer research. As a specific IRE1α RNase product, XBP1s is a direct indicator of functional IRE1 inhibition. A potent and selective IRE1α inhibitor would serve as an important tool to test the hypothesis that, without full UPR activation, tumor cells would be driven to apoptosis. IRE1α inhibitors and activating compounds have been reported (Harrington, P. E. et al (2015) ACS Med. Chem. Lett. 6:68-72; Volkmann, K., et al (2011) J. Biol. Chem., 286:12743-12755; Cross, B. C. S., et al (2012) Proc. Natl. Acad. Sci. U.S.A., 109:E869-E878; Wang, L., et al (2012) Nat. Chem. Biol., 8:982-989; Ghosh, R., et al (2014) Cell, 158:534-548; Ranatunga, S., et al (2014) J. Med. Chem., 57, 4289-4301; U.S. Pat. Nos. 9,382,230; 8,815,885).

There remains a need for potent and selective inhibitors having suitable pharmacological properties for the treatment of IRE1-related diseases or disorders in patients.

BRIEF SUMMARY OF THE INVENTION

Disclosed are pyrido-pyrimidinone and pteridinone compounds that target IRE1α, compositions containing these compounds, and methods for the treatment of IRE1-related diseases or disorders.

In one aspect, provided is a compound as described herein or a stereoisomer, tautomer, or pharmaceutically acceptable salt thereof as detailed herein. Also provided is a pharmaceutical composition comprising a compound as described herein or a stereoisomer, tautomer, or pharmaceutically acceptable salt thereof, and one or more pharmaceutically acceptable excipients.

In another aspect, provided is a method for treating an IRE1-related disease or disorder in a subject in need thereof comprising administering to the subject an effective amount of a compound as described herein or a stereoisomer, tautomer, or pharmaceutically acceptable salt thereof. In some embodiments, the subject is a human. In some embodiments, the IRE1-related disease or disorder is a cancer. In some embodiments, the method further comprises administering an anti-cancer agent to the subject.

Also provided is a compound as described herein or a stereoisomer, tautomer, or pharmaceutically acceptable salt thereof for use in a method of treating an IRE1-related disease or disorder.

Still further provided herein is a compound as described herein or a stereoisomer, tautomer, or pharmaceutically acceptable salt thereof for use in a method of treating cancer.

Also provided is use of a compound as described herein or a stereoisomer, tautomer, or pharmaceutically acceptable salt thereof, in a method detailed herein (e.g., treatment of an IRE1-related disease or disorder).

Also provided is use of a compound as described herein or a stereoisomer, tautomer, or pharmaceutically acceptable salt thereof, for the manufacture of a medicament for use in a method detailed herein (e.g., treatment of an IRE1-related disease or disorder).

Also provided is a kit for treating an IRE1-related disease or disorder, the kit comprising a pharmaceutical composition comprising a compound as described herein or a stereoisomer, tautomer, or pharmaceutically acceptable salt thereof; and instructions for use.

In still another aspect provided herein is a method of inhibiting or killing a cancer cell expressing IRE1, where the method comprises contacting the cancer cell expressing IRE1 with a compound or pharmaceutically acceptable salt thereof described herein.

In yet another aspect provided herein is a method of modulating IRE1 activity, where the method comprises contacting IRE1 with a compound or pharmaceutically acceptable salt thereof described herein.

Also provided is a kit for treating cancer, where the kit comprises a pharmaceutical composition comprising a the compound described herein, or a pharmaceutically acceptable salt thereof; and instructions for use.

In another aspect provided herein is a method of making a compound as described herein or a stereoisomer, tautomer, or pharmaceutically acceptable salt thereof. Also provided are compound intermediates useful in synthesis of a compound as described herein or a stereoisomer, tautomer, or pharmaceutically acceptable salt thereof described herein.

DETAILED DESCRIPTION OF THE INVENTION

Disclosed herein, are pyrido-pyrimidinone and pteridinone compounds as described herein or a stereoisomer, tautomer, or pharmaceutically acceptable salt thereof and pharmaceutical compositions thereof that, in certain embodiments, are inhibitors or modulators of IRE1α. As such, the compounds and compositions are useful in treating diseases and disorders mediated by IRE1α.

While the disclosure herein provides enumerated embodiments, it will be understood that they are not intended to limit the invention to those embodiments. On the contrary, the disclosure is intended to cover all alternatives, modifications, and equivalents which can be included within the scope of the present invention as defined by the claims. One skilled in the art will recognize many methods and materials similar or equivalent to those described herein. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the methods and materials are described below. All publications, patent applications, patents, and other references mentioned herein are incorporated by reference in their entirety. The nomenclature used in this application is based on IUPAC systematic nomenclature, unless indicated otherwise.

Definitions

"Alkyl" as used herein refers to a saturated linear (i.e. unbranched) or branched univalent hydrocarbon chain or combination thereof, having the number of carbon atoms designated (i.e., $C_{1-10}$ means one to ten carbon atoms). Particular alkyl groups are those having 1 to 20 carbon atoms (a "$C_{1-20}$ alkyl"), having a 1 to 8 carbon atoms (a "$C_{1-8}$ alkyl"), having 1 to 6 carbon atoms (a "$C_{1-6}$ alkyl"), having 2 to 6 carbon atoms (a "$C_{2-6}$ alkyl"), or having 1 to 4 carbon atoms (a "$C_{1-4}$ alkyl"). Examples of alkyl group include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_{2-10}$ means two to ten carbon atoms). The alkenyl group can be in "cis" or "trans" configurations, or alternatively in "E" or "Z" configurations. Particular alkenyl groups are those having 2 to 20 carbon atoms (a "$C_{2-20}$ alkenyl"), having a 2 to 8 carbon atoms (a "$C_{2-8}$ alkenyl"), having 2 to 6 carbon atoms (a "$C_{2-6}$ alkenyl"), or having 2 to 4 carbon atoms (a "$C_{2-4}$ alkenyl"). Example of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear (i.e. unbranched) or branched univalent hydrocarbon chain or combination thereof, having at least one site of acetylenic unsaturation (i.e., having at least one moiety of the formula C≡C) having the number of carbon atoms designated (i.e., $C_{2-10}$ means two to ten carbon atoms). Particular alkynyl groups are those having 2 to 20 carbon atoms (a "$C_{2-20}$ alkynyl"), having a 2 to 8 carbon atoms (a "$C_{2-8}$ alkynyl"), having 2 to 6 carbon atoms (a "$C_{2-6}$ alkynyl"), having 2 to 4 carbon atoms (a "$C_{2-4}$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkylene" as used herein refers to the same residues as alkyl, but having bivalency. Particular alkylene groups are those having 1 to 6 carbon atoms (a "$C_{1-6}$ alkylene"), 1 to 5 carbon atoms (a "$C_{1-5}$ alkylene"), having 1 to 4 carbon atoms (a "$C_{1-4}$ alkylene"), or 1 to 3 carbon atoms (a "$C_{1-3}$ alkylene"). Examples of alkylene include, but are not limited to, groups such as methylene (—$CH_2$—), ethylene (—$CH_2$—$CH_2$—), propylene (—$CH_2$—$CH_2$—$CH_2$—), butylene (—$CH_2$—$CH_2$—$CH_2$—$CH_2$—), and the like.

"Cycloalkyl" as used herein refers to non-aromatic, saturated or unsaturated cyclic univalent hydrocarbon structures having the number of carbon atoms designated (i.e., ($C_{3-10}$ means three to ten carbon atoms). Cycloalkyl can consist of one ring, such as cyclohexyl, or multiple rings, such as adamantly, but excludes aryl groups. A cycloalkyl comprising more than one ring can be fused, spiro, or bridged, or combinations thereof. Particular cycloalkyl groups are those having from 3 to 12 annular carbon atoms. A preferred cycloalkyl is a cyclic hydrocarbon having from 3 to 8 annular carbon atoms (a "Cwt cycloalkyl"), or having 3 to 6 carbon atoms (a "$C_{3-6}$ cycloalkyl"). Examples of cycloalkyl include, but are not limited to, cyclopropyl, cyclobutyl, cyclopentyl, cyclohyxyl, 1-cyclohexenyl, 3-cyclohexenyl, cycloheptyl, norbornyl, and the like.

"Aryl" as used herein refers to an unsaturated aromatic carbocyclic group having a single ring (e.g., phenyl) or multiple condensed rings (e.g., naphthyl or anthryl) which condensed rings can or can not be aromatic. Particular aryl groups are those having from 6 to 14 annular (i.e., ring) carbon atoms (a "$C_{6-14}$ aryl"). An aryl group having more than one ring where at least one ring is non-aromatic can be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, phosphorus, oxygen and sulfur. A heteroaryl group can have a single ring (e.g., pyridyl, furyl) or multiple condensed rings (e.g., indolizinyl, benzothienyl) which condensed rings can or can not be aromatic. Particular heteroaryl groups are 5- to 14-membered rings having 1 to 12 annular (i.e., ring) carbon atoms and 1 to 6 annular (i.e., ring) heteroatoms independently selected from nitrogen, phosphorus, oxygen and sulfur; 5- to 10-membered rings having 1 to 8 annular carbon atoms and 1 to 4 annular heteroatoms independently selected from nitrogen, phosphorus, oxygen and sulfur; and 5-, 6- or 7-membered rings having 1 to 5 annular carbon atoms and 1 to 4 annular heteroatoms independently selected from nitrogen, oxygen and sulfur In one variation, heteroaryl include monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, phosphorus, oxygen and sulfur. A heteroaryl group having more than one ring where at least one ring is non-aromatic can be connected to the parent structure at either an aromatic ring position or at a non-aromatic ring position. In one variation, a heteroaryl group having more than one ring where at least one ring is non-aromatic is connected to the parent structure at an aromatic ring position.

"Heterocycle", "heterocyclic", or "heterocyclyl" as used herein refers to a saturated or an unsaturated non-aromatic cyclic group having a single ring or multiple condensed rings, and having from 1 to 14 annular (i.e., ring) carbon atoms and from 1 to 6 annular (i.e., ring) heteroatoms, such as nitrogen, phosphorus, sulfur or oxygen, and the like. A heterocycle comprising more than one ring can be fused, spiro or bridged, or any combination thereof. In fused ring systems, one or more can be fused rings can be cycloalkyl. Particular heterocyclyl groups are 3- to 14-membered rings having 1 to 13 annular carbon atoms and 1 to 6 annular heteroatoms independently selected from nitrogen, phosphorus, oxygen and sulfur; 3- to 12-membered rings having 1 to 11 annular carbon atoms and 1 to 6 annular heteroatoms independently selected from nitrogen, phosphorus, oxygen and sulfur; 3- to 10-membered rings having 1 to 9 annular carbon atoms and 1 to 4 annular heteroatoms independently selected from nitrogen, phosphorus, oxygen and sulfur; 3- to 8-membered rings having 1 to 7 annular carbon atoms and 1 to 4 annular heteroatoms independently selected from nitrogen, phosphorus, oxygen and sulfur; and 3- to 6-membered rings having 1 to S annular carbon atoms and 1 to 4 annular heteroatoms independently selected from nitrogen, phosphorus, oxygen and sulfur. In one variation, heterocyclyl include monocyclic 3-, 4-, 5-, 6- or 7-membered rings having from 1 to 2, 1 to 3, 1 to 4, 1 to 5 or 1 to 6 annular carbon atoms and 1 to 2, 1 to 3 or 1 to 4 annular heteroatoms independently selected from from nitrogen, phosphorus, oxygen and sulfur. In another variation, heterocyclyl includes polycyclic non-aromatic rings having from 1 to 12 annular carbon atoms and 1 to 6 annular heteroatoms independently selected from nitrogen, phosphorus, oxygen and sulfur.

"Halo" or Halogen" refers to fluoro, chloro, bromo and/or iodo. Where a residue is substituted with more than one halogen, it can be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which can be but are not necessarily the same halo; thus 4-chloro-3-fluorophenyl is within the scope of dihaloaryl. An alkyl group in which one or more hydrogen is replaced with a halo group is referred to as a "haloalkyl", for example, "$C_{1-6}$ haloalkyl." An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Oxo" refers to the moiety =O.

The terms "treat" and "treatment" refer to therapeutic treatment that when administered as described herein slows down (lessens) or stops (e.g. inhibits) an undesired physiological change or disorder, such as the development, progression, or spreading of a disease described herein (e.g. arthritis or cancer). "Treatment" also refers to any clinical intervention designed to alter the natural course of the patient or cell being treated during the course of clinical pathology. For example, a patient is successfully "treated" if one or more symptoms associated with the disease described herein are mitigated or eliminated. Beneficial or desired clinical results include, but are not limited to, alleviation of or decreasing symptoms of a disease described herein, diminishment of extent of disease described herein, reducing the proliferation of (or destroying) cancerous cells, stabilized (i.e., not worsening) state of disease described herein, delaying or slowing of disease progression, amelioration or palliation of the disease state, increasing the quality of life of those suffering from the disease, decreasing the dose of other medications required to treat the disease, and/or remission (whether partial or total), whether detectable or undetectable. "Treatment" can also mean prolonging survival as compared to expected survival if not receiving treatment. Those in need of treatment include those with the condition or disorder. In certain embodiments, treatment can refer to a measured clinical outcome (e.g. increased OS, ORR, TTP, DOR, PFS, CBR, PR, CR, or SD).

The term "delaying progression" of a disease refers to deferring, hindering, slowing, retarding, stabilizing, and/or postponing development of a disease described herein. This delay can be of varying lengths of time, depending on the history of the cancer and/or patient being treated. As is evident to one skilled in the art, a sufficient or significant delay can, in effect, encompass prevention, in that the patient does not develop cancer.

An "IRE1-related disease" and the like refer to a disease described herein (e.g. a cancer described herein) having symptoms or requiring treatment as set forth herein that is/are wholly or partly associated with, a result of, a function of, or otherwise correlated to IRE1 activity as described herein.

The phrase "effective amount" means an amount of a compound or pharmaceutically acceptable salt thereof that (i) treats the particular disease, condition, or disorder, (ii) attenuates, ameliorates, or eliminates one or more symptoms of the particular disease, condition, or disorder, (iii) lessens the severity of the disease, (iv) increases the quality of life of those suffering from the disease, (v) decreases the dose of other medications required to treat the disease, (vi) enhances the effect of another medication such as via targeting, delaying the progression of the disease, (vii) prevents or delays the onset of one or more symptoms of the particular disease, condition, or disorder described herein (including biochemical, histological and/or behavioral symptoms of the disease, its complications and intermediate pathological phenotypes presenting during development of the disease), or (viii) favorably alters the clinical response of a patient to the treatment, where the inhibition and favorability is relative to a control (e.g. non-treatment or prior treatment with an anti-cancer agent such as that described herein). In the case of cancer, the effective amount of the drug can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. For cancer therapy, efficacy can be measured, for example, by assessing the time to disease progression (TTP) and/or determining the response rate (RR). An effective amount can be administered in one or more administrations. An effective amount of drug, compound, pharmaceutical composition, or combination therapy described herein can be an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition, or combination therapy. An "effective amount" may be considered in the context of administering one or more therapeutic agents, and a single agent may be considered to be given in an effective amount if, in conjunction with one or more other agents, a desirable result may be or is achieved.

An "administration period" or "cycle" refers to a period of time comprising administration of a compound or pharmaceutically acceptable salt thereof described herein and an optional period of time comprising no administration of the compound or pharmaceutically acceptable salt thereof described herein. For example, a cycle can be 28 days in total length and include administration for 21 days and a rest period of 7 days. A "rest period" refers to a period of time where the compound or pharmaceutically acceptable salt thereof described herein is not administered. A rest period as provided herein can in some instances include administration of another agent that is not compound or pharmaceutically acceptable salt thereof described herein (e.g. an anticancer agent described herein). In such instances, administration of another agent during a rest period should not interfere or detriment administration of a compound or pharmaceutically acceptable salt thereof described herein.

A "dosing regimen" refers to a period of administration of a compound or pharmaceutically acceptable salt thereof described herein comprising one or more cycles, where each cycle can include administration of the compound or pharmaceutically acceptable salt thereof described herein at different times or in different amounts.

The term "clinical response" refers to inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. In general, clinical response refers to primary or secondary measures of efficacy known and understood in the art. Treatment and clinical response as described herein can be assessed using international standards for a given condition.

The term "Time To Progression" or "TTP" as used herein refers to the time from treatment onset until tumor progression.

The term "Progression Free Survival" or "PFS" refers to the time from treatment onset until tumor progression or death. In one embodiment, PFS rates can be computed using the Kaplan-Meier estimates.

The clinical response of a patient described herein can be characterized as a complete or partial response. "Complete response" (CR) refers to an absence of clinically detectable cancer with normalization of any previously abnormal radiographic studies, bone marrow, and cerebrospinal fluid (CSF) or abnormal monoclonal protein measurements. "Partial response" (PR) refers to at least about a 10%, 20%, 30%, 40%, 50%, 60%, 70%, 80%, or 90% decrease in all measurable cancer burden (i.e., the number of malignant cells present in the subject, or the measured bulk of tumor masses or the quantity of abnormal monoclonal protein). The term "treatment" includes both a complete and a partial response.

The terms "patient" and "subject" are used interchangeably herein and refer to an animal, including, but not limited to, an animal such as a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having cancer, in particular, a cancer described herein. In one embodiment, a patient is a human having histologically or cytologically-confirmed cancer, including subjects who have progressed on (or not been able to tolerate) standard anticancer therapy or for whom no standard anticancer therapy exists.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms (i.e. cancer), and they are generally treated by specialists in hematology and/or oncology. Hematological malignancies can derive from either of the two major blood cell lineages: myeloid and lymphoid cell lines. Lymphomas, lymphocytic leukemias, and myeloma are from the lymphoid line, while acute and chronic myelogenous leukemia, myelodysplastic syndromes and myeloproliferative diseases are myeloid in origin. Exemplary leukemias include acute lymphoblastic leukemia (ALL), acute myelogenous leukemia (AML), chronic lymphocytic leukemia (CLL), chronic myelogenous leukemia (CML), acute monocytic leukemia (AMOL) and small lymphocytic lymphoma (SLL). Exemplary lymphomas include Hodgkin's lymphomas (all four subtypes) and Non-Hodgkin's lymphomas (NHL, all subtypes).

A "1 L therapy" refers to the first line therapy administered to a treatment naïve cancer patient. Likewise, a 2 L, 3 L, and the like refer to subsequent therapies administered to a patient.

A "anti-cancer agent" is a chemical compound useful in the treatment of cancer, regardless of mechanism of action. Classes of anti-cancer agents include, but are not limited to: alkylating agents, antimetabolites, anti-hormone therapies, endocrine therapies, immunomodulatory agents, spindle poison plant alkaloids, cytotoxic/antitumor antibiotics, topoisomerase inhibitors, antibodies, photosensitizers, and kinase inhibitors. Anti-cancer agents include compounds used in targeted therapy and conventional chemotherapy.

Examplary anti-cancer agents include proteasome inhibitors such as bortezomib (VELCADE), carfilzomib (KYPROLIS) and ixazomib (NINLARO). Other examples include immunomodulatory agents such as lenalidomide (REVLIMID) and pomalidomide (POMALYST).

Other exemplary anti-cancer agents include inhibitors of B-cell receptor targets such as BTK, Bcl-2 and JAK inhibitors and include, for example, venetoclax (VENCLEXTA) and ibrutinib (IMBRUVICA).

Additional anti-cancer agents include, for example, Abemaciclib (VERZENIO); abiraterone (ZYTIGA, YONSA); aclarubicin; acivicin; acodazole; acronine; actinomycin; acylfulvene; adecypenol; adozelesin; adriamycin; aldesleukin; altretamine; ambamustine; ambomycin; ametantrone; amidox; amifostine; aminoglutethimide; aminolevulinic acid; amrubicin; amsacrine; anagrelide; anastrozole; andrographolide; antarelix; anthramycin; aphidicolin glycinate; apurinic acid; ARRY-300; arabinoside; asperlin; asulacrine; atamestane; atrimustine; azasetron; azatoxin; azatyrosine; azacitidine; AZD6244; AZD8330; azetepa; azotomycin; balanol; batimastat; bendamustine; benzochlorins; benzodopa; benzoylstaurosporine; beta-alethine; beta-clamycin B; betulinic acid; bicalutamide; binimetinib; bisantrene; bisaziridinylspermine; bisnafide; bistratene; bleomycin; busulfan; bizelesin; breflate; bortezomib; brequinar; bropirimine; budotitane; buthionine; bryostatin; cactinomycin; calusterone; calcipotriol; calphostin C; camptothecin; capecitabine (XELODA); caracemide; carbetimer; carboplatin; carboquone; carmustine; carubicin; carzelesin; castanospermine; celecoxib; cetrorelix; cetuximab (ERBITUX); chloroquinoxaline; cicaprost; chlorambucil; chlorofusin; cisplatin; cladribine; clomifene; clotrimazole; crisnatol; crisnatol; cypemycin; cyclophosphamide; cytarabine; cytostatin; dacarbazine; dactinomycin; daratumamab; daunorubicin; decarbazine; dacliximab; dasatinib; decitabine; deslorelin; dexamethasone; dexifosfamide; dexrazoxane; dexverapamil; dexormaplatin; dezaguanine; diaziquone; dihydrotaxol; docosanol; dolasetron; docetaxel; doxorubicin; doxifluridine; droloxifene; dromostanolone; dronabinol; duazomycin; ebselen; ecomustine; edelfosine; edrecolomab; edatrexate; eflornithine; elemene; emitefur; elsamitrucin; enloplatin; enpromate; epipropidine; epirubicin; episteride; erbulozole; erlotinib (TARCEVA); esorubicin; estramustine; etanidazole; etoposide; etoprine; exemestane; fadrozole; fazarabine; fenretinide; filgrastim; finasteride; flavopiridol; flezelastine; fluasterone; floxuridine; fludarabine; fludarabine; fluorodaunorubicin; forfenimex; formestane; fluorouracil; floxouridine; flurocitabine; fosquidone; fostriecin; fotemustine; fulvestrant (FASLODEX); gadolinium; gallium; galocitabine; ganirelix; gemcitabine; geldanamycin; gefitinib; gossyphol; hydroxyurea; hepsulfam; heregulin; ibandronate; ibrutinib; idarubicin; idelalisib (ZYDELIG), ifosfamide; canfosfamide; ilmofosine; iproplatin; idoxifene; idramantone; ilmofosine; ilomastat; imatinib mesylate (GLEEVEC); imiquimod; iobenguane; iododoxorubicin; ipomeanol; irinotecan; itasetron; ilmofosine; lanreotide; lapatinib (TYKERB); leinamycin; lenograstim; lentinan; leptolstatin; letrozole; leuprorelin; levamisole; liarozole; lobaplatin; lombricine; lometrexol; lonidamine; lonafarnib (SARASAR); losoxantrone; lovastatin; loxoribine; lurtotecan; lapatinib; leucovorin; lometrexol; lomustine; maitansine; marimastat; masoprocol; maspin; menogaril; merbarone; meterelin; methioninase; metoclopramide; mifepristone; miltefosine; mirimostim; mitoguazone; mitolactol; mitonafide; mitoxantrone; mofarotene; molgramostim; mopidamol; maytansine; megestrol acetate; melengestrol acetate; melphalan; mercaptopurine; methotrexate; methotrexate sodium; metoprine; meturedepa; mitinmitomycin; mitosper; mitotane; mitoxantrone; mycophenolic acid; nafarelin; nagrestip; napavin; nedaplatin; nemorubicin; neridronic acid; nilutamide; nisamycin; oblimersen (GENASENSE); octreotide; okicenone; onapristone; ondansetron; ormaplatin; oxisuran; oxaloplatin; osaterone; oxaliplatin; oxaunomycin; palauamine; palbociclib (IBRANCE); panitumumab (VECTIBIX); panomifene; pegaspargase; picibanil; pirarubicin; piritrexim; prednisone; prednisolone, paclitaxel; nab-paclitaxel (ABRAXANE); prednimustine; procarbazine; puromycin; raltitrexed; ramosetron; rapamycin (RAPAMUNE); rhizoxin; ribociclib (KISQALI), rituximab; rogletimide; rohitukine; romurtide; roquinimex; romidepsin; safingol; saintopin; sargramostim; semustine; sizofiran; sobuzoxane; sorafenib (NEXAVAR); sunitinib; spiromustine; squalamine; suradista; suramin; swainsonine; spiroplatin; streptonigrin; streptozocin; sulofenur; tallimustine; tamoxifen; tauromustine; tazarotene; tellurapyrylium; temoporfin; temozolomide; tenipo-side; tetrachlorodecaoxide; tetrazomine; thrombopoietin; thymalfasin; thymotrinan; tirapazamine; toremifene; tretinoin; trimetrexate; triptorelin; tropisetron; talisomycin; taxotere; teroxirone; testolactone; thiamiprine; thiotepa; tirapazamine; toremifene; trastuzumab; trastuzumab emtansine; trestolone acetate; triciribine phosphate; trimetrexate; uracil mustard; vandetanib (CAPRELSA); variolin B; velaresol; veramine; verteporfin; vemurafenib; vinorelbine; vinxaltine; vitaxin; vinblastine; vincristine; vindesine; vinepidine; vinglycinate; vinleurosine; vinorelbine; vinrosidine; vinzolidine; vorozole; wortmannin; zanoterone; zeniplatin; zilascorb; zinostatin stimalamer; zinostatin; and zorubicin.

In some embodiments, an anti-cancer agent includes, for example, idelalisib (ZYDELIG), docetaxel, fluorouracil, gemcitabine (GEMZAR), cisplatin, cis-diamine, carboplatin, paclitaxel, nab-paclitaxel, trastuzumab (HERCEPTIN), temozolomide, tamoxifen, 4-hydroxytamoxifen, and doxorubicin.

Also included in the definition of anti-cancer agent are: (i) anti-estrogens and selective estrogen receptor modulators (SERMs), including, for example, tamoxifen, raloxifene, droloxifene, 4-hydroxytamoxifen, trioxifene, ketoxifene, LY117018, onapristone, and toremifine citrate; (ii) selective estrogen receptor modulators (SERDs) such as brilanestrant, GDC-0927, GDC-9545, AZ9496, AZ9833, GNE-274, and fulvestrant (FASLODEX); (iii) aromatase inhibitors such as, for example, 4(5)-imidazoles, aminoglutethimide, megestrol acetate, exemestane, formestanie, fadrozole, vorozole, letrozole, and anastrozole; (iv) anti-androgens such as apalutamide, abiraterone, enzalutamide, flutamide, nilutamide, bicalutamide, leuprolide, and goserelin.

Further included in the definition of anti-cancer agents are: (iv) MEK inhibitors such as cobimetinib; (v) lipid kinase inhibitors, such as taselisib; (vi) antisense oligonucleotides such as oblimersen; (vii) ribozymes such as VEGF expression inhibitors such as angiozyme; (viii) vaccines such as gene therapy vaccines, for example, ALLOVECTIN, LEUVECTIN, and VAXID; (ix) topoisomerase 1 inhibitors such as LURTOTECAN®; ABARELIX® rmRH; and (x) anti-angiogenic agents such as bevacizumab.

In some embodiments herein, the anti-cancer agents is a therapeutic antibody such as atezolizumab, nivolumab, daratumumab, pembrolizumab, alemtuzumab, bevacizumab; cetuximab; panitumumab, rituximab, pertuzumab, trastuzumab, trastuzumab emtansine, or tositumomab.

A "metabolite" is a product produced through metabolism in the body of a specified compound or salt thereof. Metabolites of a compound can be identified using routine techniques and their activities determined using tests such as those described herein. Such products can result for example from the oxidation, reduction, hydrolysis, amidation, deamidation, esterification, deesterification, enzymatic cleavage, and the like, of the administered compound. Accordingly, provided herein are metabolites of compounds or pharmaceutically acceptable salts thereof described herein, including compounds produced by a process comprising contacting a compound or a pharmaceutically acceptable salt thereof with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds or pharmaceutically acceptable salts thereof described herein can contain asymmetric or chiral centers, and therefore exist in different stereoisomeric forms. It is intended that all stereoisomeric forms of the compounds or pharmaceutically acceptable salts thereof described herein, including but not limited to, diastereomers, enantiomers and atropisomers, as well as mixtures thereof such as racemic mixtures, form part of this disclosure. Many organic compounds exist in optically active forms, i.e., they have the ability to rotate the plane of plane-polarized light. In describing an optically active compound, the prefixes D and L, or R and S, are used to denote the absolute configuration of the molecule about its chiral centers). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity. Enantiomers can be separated from a racemic mixture by a chiral separation method, such as supercritical fluid chromatography (SFC). Assignment of configuration at chiral centers in separated stereoisomers can be tentative, and depicted in Table 1 or Table 2 structures for illustrative purposes, before stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

A "solvate" refers to an association or complex of one or more solvent molecules and a compound described herein. Examples of solvents that form solvates include, but are not limited to, water (i.e., "hydrate"), isopropanol, ethanol, methanol, DMSO, ethylacetate (EtOAc), acetic acid (AcOH), and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., can be calculated.

Any formula or structure given herein, including compounds described herein, is also intended to represent hydrates, solvates, and polymorphs of such compounds, and mixtures thereof.

Any formula or structure given herein, including compounds described herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds or pharmaceutically acceptable salts thereof described herein described herein include isotopes of hydrogen, carbon, nitrogen, oxygen, phosphorous, fluorine, and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds or pharmaceutically acceptable salts thereof described herein, for example those into which radioactive isotopes such as $^{3}H$ and $^{14}C$ are incorporated. Such isotopically labeled compounds can be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds or pharmaceutically acceptable salts thereof described herein can have improved DMPK (drug metabolism and pharmacokinetics) properties, relating to distribution, metabolism, and excretion (ADME). Substitution with heavier isotopes such as deuterium can afford certain therapeutic advantages resulting from greater metabolic stability, for example increased in vivo half-life or reduced dosage requirements. An 18F labeled compound can be useful for PET or SPECT studies. Isotopically labeled compounds or pharmaceutically acceptable salts thereof described herein thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^{2}H$ or D) can afford certain therapeutic advantages resulting from greater metabolic stability, for example increased in vivo half-life or reduced dosage requirements or an improvement in therapeutic index. It is understood that deuterium in this context is regarded as a substituent in a compound described herein. The concentration of such a heavier isotope, specifically deuterium, can be defined by an isotopic enrichment factor. In the compounds or pharmaceutically acceptable salts thereof described herein described herein, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or pharmaceutically acceptable salts thereof described herein any atom specifically designated as a deuterium (D) is meant to represent deuterium.

Compounds

The compounds disclosed herein or a stereoisomer, tautomer, or pharmaceutically acceptable salt thereof, solvates (e.g., hydrates), prodrugs, metabolites, or derivatives thereof, and pharmaceutical compositions thereof, are useful in the treatment of diseases, conditions and/or disorders, including those modulated by inositol requiring enzyme 1 (IRE1). In one aspect provided herein are compounds as described herein or a stereoisomer, tautomer, or pharmaceutically acceptable salt thereof, and pharmaceutical compositions comprising such compounds.

In one aspect provided herein is a compound of Formula (I):

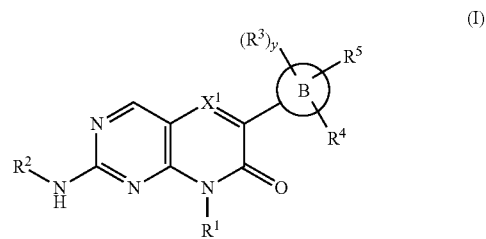

or a stereoisomer, tautomer, or pharmaceutically acceptable salt thereof, wherein $X^1$ is —$CR^x$ or —N, wherein $R^x$ is hydrogen, $C_1$-$C_4$ alkyl, cyclopropyl, or halogen;

Ring B is 5- to 7-membered aryl or 5- to 7-membered heteroaryl comprising at least one nitrogen atom;

y is 1, 2, 3, or 4;

$R^1$ is $C_1$-$C_4$ alkyl, $C_3$-$C_6$ cycloalkyl, or 3- to 14-membered heterocyclyl, each of which is unsubstituted or substituted with one or more substituents selected from the group consisting of —$CH_2F$, —$CHF_2$, —$CF_3$, halogen, $C_3$-$C_6$ cycloalkyl, hydroxyl, and —O—($C_1$-$C_4$)alkyl, such as methoxyl;

$R^2$ is $C_1$-$C_4$ alkyl, $C_3$-$C_6$ cycloalkyl, or 4- to 10-membered-heterocyclyl, each of which is unsubstituted or substituted with one or more $R^{2A}$;

$R^{2A}$ is selected from the group consisting of hydrogen, $R^{2C}$-substituted or -unsubstituted $C_1$-$C_4$ alkyl, $C_1$-$C_4$ fluoroalkyl, halogen, —OH, —$(CH_2)_q$—$N(R^{2B})_2$, wherein q is 1 or zero, —$CH_2F$, —$CHF_2$, and —$CF_3$;

or wherein two $R^{2A}$ together with the carbon to which each is attached form a substituted or unsubstituted aziridinyl, azetidinyl, pyrrolidinyl, imidazolyl, piperidinyl, piperazinyl, morpholino;

$R^{2B}$ is hydrogen, $R^{2C}$-substituted or -unsubstituted $C_1$-$C_3$ alkyl, unsubstituted $C_3$-$C_6$ cycloalkyl; or unsubstituted $C_3$-$C_6$ heterocyclyl;

or wherein two $R^{2B}$ together form a substituted or unsubstituted heterocyclyl, wherein the heterocyclyl can be spiro, an unsubstituted aziridinyl, azetidinyl, pyrrolidinyl, imidazolyl, piperidinyl, piperazinyl, morpholino;

$R^{2C}$ is halogen, —OH, —$OCH_3$, or $C_3$-$C_5$ heterocyclyl;

each $R^3$ is independently hydrogen, halogen, —CN, $C_1$-$C_6$ alkyl, $C_1$-$C_6$ haloalkyl, $C_3$-$C_6$ cycloalkyl, $O(C_{1-6}$ alkyl), or —$O(C_1$-$C_6$ haloalkyl);

each $R^4$ and $R^5$ are independently hydrogen, halogen, —CN, —$NO_2$, $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, —OR⁶, —NR⁸ᴬR⁹, —NR⁸C(O)R⁹, —NR⁸C(O)OR⁶, —NR⁸C(O)NR⁸ᴬR⁸ᴮ, —NR⁸SO₂R⁹, —NR⁸SO₂NR⁸ᴬR⁸ᴮ, —NR⁸S(O)(=NR⁸ᶜ)R⁹, —C(O)N(R⁸)SO₂R⁹, —C(O)NR⁸R⁹, —C(O)R⁷, —C(O)OR⁶, —SO₂R⁹, —NR⁸S(O)(=NR⁸ᶜ)R⁹, or —SO₂NR⁸R⁹; wherein the C₁-C₆ alkyl, C₃-C₁₂ cycloalkyl, C₆-C₂₀ aryl, 3- to 14-membered heterocyclyl, and 5- to 14-membered heteroaryl of R⁴ and R⁵ are optionally substituted with 1, 2, 3, 4 or 5 substituents independently selected from R¹⁰, wherein at least one of R⁴ and R⁵ is —NR⁸ᴬR⁹, —C(O)NR⁸R⁹, —NR⁸C(O)R⁹, —SO₂NR⁸R⁹, or —NR⁸SO₂R⁹;

each R⁶ and R⁷ is independently hydrogen, C₁-C₆ alkyl, C₂-C₆ alkenyl, C₃-C₈ cycloalkyl, C₆-C₁₀ aryl, 5- to 14-membered heteroaryl, or 3- to 12-membered heterocyclyl, each of which is unsubstituted or substituted with one or more R¹⁰;

each R⁸, R⁸ᴬ, and R⁸⁰ are independently hydrogen or C₁-C₆ alkyl;

each R⁸ᴮ is independently hydrogen, C₁-C₆ alkyl, C₂-C₆ alkenyl, C₃-C₈ cycloalkyl, C₆-C₁₀ aryl, or 3- to 12-membered heterocyclyl, each of which is unsubstituted or substituted with one or more R¹⁰;

each R⁹ is independently C₁-C₆ alkyl, C₂-C₆ alkenyl, C₃-C₈ cycloalkyl, C₆-C₁₀ aryl, 5- to 14-membered heteroaryl, or 3- to 12-membered heterocyclyl, each of which is unsubstituted or substituted with one or more R¹⁰;

or R⁸ and R⁹ together with the atom to which each is attached form a substituted or unsubstituted 5- or 6-member lactam ring, such as:

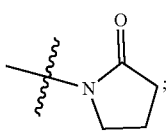 [SMILES: *N1CCCC1=O]

each R¹⁰ is independently oxo, C₁-C₆ alkyl, C₂-C₆ alkenyl, C₃-C₈ cycloalkyl, C₆-C₁₀ aryl, 4- to 10-membered heteroaryl, 3- to 12-membered heterocyclyl, halogen, cyano, —C(O)H, —C(O)CH₃, —C(O)OH, —C(O)OCH₃, —C(O)NH₂, —OH, —O—CF₃, —CF₃, —CH₂F, CHF₂, —OCH₃, —OC(O)H, —OC(O)CH₃, —OC(O)NH₂, —SH, —S(O)H, —S(O)₂H, —S(O)(=NH)H, —S(O)₂NH₂, —NH₂, —NHC(O)H, —NHC(O)OH, —N(H)C(O)NH₂, —NHS(O)₂H, —NHS(O)₂NH₂, or —P(O)(CH₃)₂, wherein each C₁-C₆ alkyl, C₂-C₆ alkenyl, C₂-C₆ alkynyl, C₃-C₈ cycloalkyl, C₆-C₁₀ aryl, 4- to 10-membered heteroaryl, 3- to 12-membered heterocyclyl is unsubstituted or substituted with one or more R¹¹;

or two R¹⁰ together with the carbon to which each is attached forms a C₃-C₈ cycloalkyl; and each R¹¹ is independently C₁₋₆ alkyl, C₃-C₆ cycloalkyl, 4- to 6-membered-heteroaryl, phenyl, halogen, cyano, —SO₂CH₃, —O(C₁₋₃ alkyl), —CH₂F, —CHF₂, or —(CH₂)_f—CF₃, wherein f is zero or 1.

In one aspect provided herein is a compound of Formula (Ia):

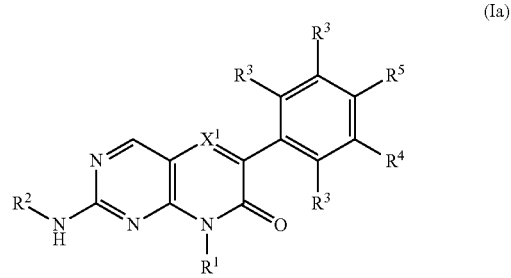

or a stereoisomer, tautomer, or pharmaceutically acceptable salt thereof,
where:
X¹ is —CRˣ or —N, wherein Rˣ is hydrogen, C₁-C₄ alkyl, cyclopropyl, or halogen;

R¹ is C₁-C₄ alkyl, C₃-C₆ cycloalkyl, or 3- to 14-membered heterocyclyl, each of which is unsubstituted or substituted with one or more substituents selected from the group consisting of —CH₂F, —CHF₂, —CF₃, halogen, C₃-C₆ cycloalkyl, and hydroxyl;

R² is C₁-C₄ alkyl, C₃-C₆ cycloalkyl, or 4- to 10-membered-heterocyclyl, each of which is unsubstituted or substituted with one or more R²ᴬ;

R²ᴬ is selected from the group consisting of hydrogen, R²ᶜ-substituted or -unsubstituted C₁-C₄ alkyl, C₁-C₄ fluoroalkyl, halogen, —OH, —(CH₂)_q—N(R²ᴮ)₂, wherein q is 1 or zero, —CH₂F, —CHF₂, and —CF₃;

or wherein two R²ᴬ together with the carbon to which each is attached form a substituted or unsubstituted aziridinyl, azetidinyl, pyrrolidinyl, imidazolyl, piperidinyl, piperazinyl, morpholino;

R²ᴮ is hydrogen, R²ᶜ-substituted or -unsubstituted C₁-C₃ alkyl, unsubstituted C₃-C₆ cycloalkyl; or unsubstituted C₃-C₆ heterocyclyl;

or wherein two R²ᴮ together form a substituted or unsubstituted heterocyclyl, wherein the heterocyclyl can be spiro, an unsubstituted aziridinyl, azetidinyl, pyrrolidinyl, imidazolyl, piperidinyl, piperazinyl, morpholino;

R²ᶜ is halogen, —OH, —OCH₃, or C₃-C₅ heterocyclyl;

each R³ is independently hydrogen, halogen, —CN, C₁-C₆ alkyl, C₁-C₆ haloalkyl, C₃-C₆ cycloalkyl, O(C₁₋₆ alkyl), or —O(C₁-C₆ haloalkyl);

R⁴ is hydrogen, halogen, —CN, —NO₂, C₁-C₆ alkyl, C₂-C₆ alkenyl, C₂-C₆ alkynyl, C₃-C₁₂ cycloalkyl, C₆-C₂₀ aryl, 3- to 14-membered heterocyclyl, 5- to 14-membered heteroaryl, —OR⁶, —NR⁸ᴬR⁸ᴮ, —NR⁸C(O)R⁷, —NR⁸C(O)OR⁶, —NR⁸C(O)NR⁸ᴬR⁸ᴮ, —NR⁸SO₂R⁹, —NR⁸SO₂NR⁸ᴬR⁸ᴮ, —NR⁸S(O)(=NR⁸ᶜ)R⁹, —C(O)N(R⁸)SO₂R⁹, —C(O)NR⁷R⁸, —C(O)R⁷, —C(O)OR⁶, —SO₂R⁹, —NR⁸S(O)(=NR⁸ᶜ)R⁹, or —SO₂NR⁸R⁹; wherein the C₁-C₆ alkyl, C₃-C₁₂ cycloalkyl, C₆-C₂₀ aryl, 3- to 14-membered heterocyclyl, and 5- to 14-membered heteroaryl of R⁴ and R⁵ are optionally substituted with 1, 2, 3, 4 or 5 substituents independently selected from R¹⁰;

R⁵ is —NR⁸ᴬR⁹, —C(O)NR⁸R⁹, —NR⁸C(O)R⁹, —SO₂NR⁸R⁹, or —NR⁸SO₂R⁹;

each R⁶ and R⁷ is independently hydrogen, C₁-C₆ alkyl, C₂-C₆ alkenyl, C₃-C₈ cycloalkyl, C₆-C₁₀ aryl, 5- to 14-membered heteroaryl, or 3- to 12-membered heterocyclyl, each of which is unsubstituted or substituted with one or more R¹⁰;

each R⁸, R⁸ᴬ, and R⁸ᶜ are independently hydrogen or C₁-C₆ alkyl;

each $R^{8B}$ is independently hydrogen, $C_1$-$C_6$ alkyl, $C_2$-$C_6$ alkenyl, $C_3$-$C_8$ cycloalkyl, $C_6$-$C_{10}$ aryl, or 3- to 12-membered heterocyclyl, each of which is unsubstituted or substituted with one or more $R^{10}$;

each $R^9$ is independently $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$;

each $R^{10}$ is independently oxo, $C_1$-$C_6$ alkyl, $C_2$-$C_6$ alkenyl, $C_3$-$C_8$ cycloalkyl, $C_6$-$C_{10}$ aryl, 4- to 10-membered heteroaryl, 3- to 12-membered heterocyclyl, halogen, cyano, —C(O)H, —C(O)CH$_3$, —C(O)OH, —C(O)OCH$_3$, —C(O)NH$_2$, —OH, —OCH$_3$, —OC(O)H, —OC(O)CH$_3$, —OC(O)NH$_2$, —SH, —S(O)H, —S(O)$_2$H, —S(O)(=NH)H, —S(O)$_2$NH$_2$, —NH$_2$, —NHC(O)H, —NHC(O)OH, —N(H)C(O)NH$_2$, —NHS(O)$_2$H, —NHS(O)$_2$NH$_2$, or —P(O)(CH$_3$)$_2$, wherein each $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 10-membered heteroaryl, 3- to 12-membered heterocyclyl is unsubstituted or substituted with one or more $R^{11}$;

or two $R^{10}$ together with the carbon to which each is attached forms a $C_3$-$C_8$ cycloalkyl; and each $R^{11}$ is independently $C_{1-6}$ alkyl, $C_3$-$C_6$ cycloalkyl, 4- to 6-membered-heteroaryl, phenyl, halogen, cyano, —SO$_2$CH$_3$, —O(C$_{1-3}$ alkyl), —CH$_2$F, —CHF$_2$, or —(CH$_2$)$_f$—CF$_3$, wherein f is zero or 1.

In another aspect provided herein is a compound of formula (Ib):

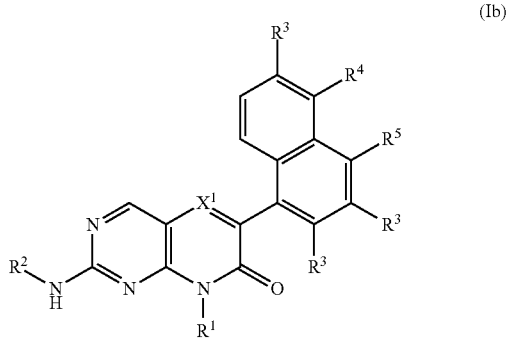

(Ib)

or a stereoisomer, tautomer, or pharmaceutically acceptable salt thereof, where $X^1$, $R^1$, $R^2$, and $R^3$ are as described herein; and each $R^4$ and $R^5$ are independently hydrogen, halogen, —CN, —NO$_2$, $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, —OR$^6$, —NR$^{8A}$R$^9$, —NR$^8$C(O)R$^9$, —NR$^8$C(O)R$^6$, —NR$^8$C(O)NR$^{8A}$R$^{8B}$, —NR$^8$SO$_2$R$^9$, —NR$^8$SO$_2$NR$^{8A}$R$^{8B}$, —NR$^8$S(O)(=NR$^{8C}$)R$^9$, —C(O)N(R$^8$)SO$_2$R$^9$, —C(O)NR$^8$R$^9$, —C(O)R$^7$, —C(O)OR$^6$, —SO$_2$R$^9$, —NR$^8$S(O)(=NR$^{8C}$)R$^9$, or —SO$_2$NR$^8$R$^9$; wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl of R$^4$ and R$^5$ are optionally substituted with 1, 2, 3, 4 or 5 substituents independently selected from $R^{10}$; and wherein at least one of R$^4$ and R$^5$ is —NR$^{8A}$R$^9$, —C(O)NR$^8$R$^9$, —NR$^8$C(O)R$^9$, —SO$_2$NR$^8$R$^9$, or —NR$^8$SO$_2$R$^9$ In some embodiments of the compounds described herein or a stereoisomer, tautomer, or pharmaceutically acceptable salt thereof, $X^1$ is —CR$^x$, wherein R$^x$ is hydrogen, $C_1$-$C_4$ alkyl, cyclopropyl, or halogen. In another embodiment of the compounds or a pharmaceutically acceptable salt thereof described herein, $X^1$ is —N—. In one embodiment, $X^1$ is CH. In another embodiment, $X^1$ is —CR$^x$, wherein R$^x$ is $C_1$-$C_4$ alkyl. In still another embodiment, $X^1$ is —CR$^x$, wherein R$^x$ is cyclopropyl. In yet another embodiment, $X^1$ is —CR$^x$, wherein R$^x$ is halogen (e.g. F or Cl).

In some embodiments of the compounds described herein or a stereoisomer, tautomer, or pharmaceutically acceptable salt thereof, R$^1$ is $C_1$-$C_4$ alkyl unsubstituted or substituted with one or more substituents selected from the group consisting of —CH$_2$F, —CHF$_2$, —CF$_3$, halogen, $C_3$-$C_6$ cycloalkyl, and hydroxyl. In one embodiment, R$^1$ is methyl, ethyl, propyl, or isopropyl. In still another embodiment, R$^1$ is ethyl or isopropyl. In another embodiment of the compounds or a pharmaceutically acceptable salt thereof described herein, R$^1$ is $C_3$-$C_6$ cycloalkyl, or 3- to 14-membered heterocyclyl, each of which is unsubstituted or substituted with one or more substituents selected from the group consisting of —CH$_2$F, —CHF$_2$, —CF$_3$, halogen, $C_3$-$C_6$ cycloalkyl, and hydroxyl.

In one embodiment, R$^2$ is $C_1$-$C_4$ alkyl, $C_3$-$C_6$ cycloalkyl, or 4- to 6-membered-heterocyclyl, each of which is unsubstituted or substituted with one or more R$^{2A}$; R$^M$ is selected from the group consisting of hydrogen, $C_1$-$C_4$ alkyl, $C_1$-$C_4$ fluoroalkyl, halogen, —OH, —N(R$^{2B}$)$_2$, —CH$_2$F, —CHF$_2$, and —CF$_3$; and R$^{2B}$ is hydrogen or $C_1$-$C_3$ alkyl.

In some embodiments of the compounds described herein or a stereoisomer, tautomer, or pharmaceutically acceptable salt thereof, R$^2$ is $C_1$-$C_4$ alkyl unsubstituted or substituted with one or more R$^M$ as described herein. In a preferred embodiment of the compounds or a pharmaceutically acceptable salt thereof described herein, R$^2$ is $C_3$-$C_6$ cycloalkyl, or 4- to 10-membered-heterocyclyl, each of which is unsubstituted or substituted with one or more R$^M$. In one such embodiment, R$^2$ is cyclohexyl or piperidinyl. In one embodiment of the compounds or a pharmaceutically acceptable salt thereof described herein, R$^{2A}$ is selected from the group consisting of hydrogen, halogen, —OH, —N(R$^{2B}$)$_2$—CH$_2$F, —CHF$_2$, and —CF$_3$. In one embodiment of the compounds or a pharmaceutically acceptable salt thereof described herein R$^{2A}$ is R$^{2C}$-substituted or -unsubstituted $C_1$-$C_4$ alkyl or $C_1$-$C_4$ fluoroalkyl as described herein. In one such embodiment, R$^{2C}$ is halogen or —OCH$_3$. In one embodiment of the compounds or a pharmaceutically acceptable salt thereof described herein R$^{2B}$ is hydrogen. In another embodiment of the compounds or a pharmaceutically acceptable salt thereof described herein R$^{2B}$ is $C_{1-3}$ alkyl.

In some embodiments of the compounds described herein or a stereoisomer, tautomer, or pharmaceutically acceptable salt thereof, R$^2$ is $C_1$-$C_4$ alkyl, $C_3$-$C_8$ cycloalkyl, or 4- to 8-membered-heterocyclyl, each of which is unsubstituted or substituted with one or more R$^{2A}$; R$^{2A}$ is selected from the group consisting of hydrogen, $C_1$-$C_4$ alkyl, $C_1$-$C_4$ fluoroalkyl, halogen, —OR$^{3b}$, —OH, —N(R$^{2B}$)$_2$—CH$_2$F, —CHF$_2$, and —CF$_3$; and R$^{2B}$ is hydrogen, $C_1$-$C_3$ alkyl, or $C_1$-$C_6$ haloalkyl.

In one embodiment, R$^2$ is 4- to 10-membered-heterocyclyl unsubstituted or substituted with one or more R$^{2A}$, where such heterocyclyl is a spirocycle moiety. In one such embodiment, R$^2$ is a 4,4; 4,5; or 4,6 spirocyclic moiety comprising one nitrogen atom. In one embodiment, R$^2$ is 2-azaspiro[3.5]nonanyl.

In some embodiments of the compounds described herein or a stereoisomer, tautomer, or pharmaceutically acceptable salt thereof, each R$^3$ is independently hydrogen, halogen, or —CN. In another embodiment of the compounds or a pharmaceutically acceptable salt thereof described herein, each $R^3$ is independently hydrogen, $C_1$-$C_6$ alkyl, $C_1$-$C_6$ haloalkyl, $C_3$-$C_6$ cycloalkyl, $O(C_1$-$C_6$ alkyl), or —$O(C_1$-$C_6$ haloalkyl). In another embodiment of the compounds or a pharmaceutically acceptable salt thereof described herein, each $R^3$ is independently hydrogen or halogen (e.g. F). In another embodiment of the compounds or a pharmaceutically acceptable salt thereof described herein, at least one $R^3$ is F.

In some embodiments of the compounds described herein or a stereoisomer, tautomer, or pharmaceutically acceptable salt thereof, each $R^3$ is independently hydrogen, halogen, —CN, —$SO_2R^6$, $C_1$-$C_6$ alkyl, $C_1$-$C_6$ haloalkyl, $C_3$-$C_6$ cycloalkyl, $O(C_1$-$C_6$ alkyl), or —$O(C_1$-$C_6$ haloalkyl).

In some embodiments of the compounds of formula (I) and (Ib) described herein or a stereoisomer, tautomer, or pharmaceutically acceptable salt thereof, each $R^4$ and $R^5$ is independently hydrogen, halogen, —CN, —$NO_2$, —$OR^6$, —$NR^{8A}R^9$, —$NR^8C(O)R^9$, —$NR^8C(O)OR^6$, —$NR^8C(O)NR^{8A}R^{8B}$, —$NR^8SO_2R^9$, —$NR^8SO_2NR^{8A}R^{8B}$, —$NR^8S(O)(=NR^8R^{8C})R^9$, —$C(O)N(R^8)SO_2R^9$, —$C(O)NR^8R^9$, —$C(O)R^7$, —$C(O)OR^6$, —$SO_2R^9$, —$NR^8S(O)(=NR^{8C})R^9$, or —$SO_2NR^8R^9$. In another embodiment of the compounds of formula (I) and (Ib) or a pharmaceutically acceptable salt thereof described herein, each $R^4$ and $R^5$ is independently $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$ as described herein. In one embodiment of the compounds of formula (I) or formula (Ib), one of $R^4$ and $R^5$ is —$NR^{8A}R^9$, —$NR^8C(O)R^9$, or —$NR^8SO_2R^9$. In another embodiment of the compounds of formula (I) or formula (Ib), $R^5$ is —$NR^{8A}R^9$, —$NR^8C(O)R^9$, or —$NR^8SO_2R^9$. In a preferred embodiment of the compounds of formula (I), $R^4$ is not —$NR^{8A}R^9$, —$NR^8C(O)R^9$, or —$NR^8SO_2R^9$.

In some embodiments of the compounds of formula (Ia) described herein or a stereoisomer, tautomer, or pharmaceutically acceptable salt thereof, $R^4$ is hydrogen, halogen, —CN, —$NO_2$, —$OR^6$, —$NR^{8A}R^{8B}$, —$NR^8C(O)OR^6$, —$NR^8C(O)NR^{8A}R^{8B}$, —$NR^8SO_2NR^{8A}R^{8B}$, —$NR^8S(O)(=NR^8R^{8C})R^9$, —$C(O)N(R^8)SO_2R^9$, —$C(O)NR^7R^8$, —$C(O)R^7$, —$C(O)OR^6$, —$SO_2R^9$, —$NR^8S(O)(=NR^{8C})R^9$, or —$SO_2NR^8R^9$. In another embodiment of the compounds of formula (Ia) or a pharmaceutically acceptable salt thereof described herein, $R^4$ is $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl is optionally substituted with 1, 2, 3, 4 or 5 substituents independently selected from $R^{10}$ as described herein. In one embodiment of the compounds of formula (Ia), $R^4$ is hydrogen, halogen, —CN, or $C_1$-$C_4$ alkyl, where the $C_1$-$C_4$ alkyl is optionally substituted with one or more $R^{10}$ as described herein. In one embodiment, of the compounds of formula (Ia) $R^4$ is halogen (e.g. F). In one embodiment, of the compounds of formula (Ia) $R^4$ is hydrogen.

In one preferred embodiment of the compounds of formula (Ia), $R^5$ is —$NR^{8A}R^9$, —$NR^8C(O)R^9$, —$C(O)NR^8R^9$, —$SO_2NR^8R^9$, or —$NR^8SO_2R^9$. In a preferred embodiment of the compounds of formula (Ia), $R^5$ is —$NR^{8A}R^9$, —$NR^8C(O)R^9$, or —$NR^8SO_2R^9$. In one embodiment of the compounds of formula (Ia), $R^5$ is —$NR^{8A}R^9$. In one embodiment of the compounds of formula (Ia), $R^5$ is —$NR^8C(O)R^9$. In one preferred embodiment of the compounds of formula (Ia), $R^5$ is —$NR^8SO_2R^9$.

In some embodiments of the compounds described herein or a stereoisomer, tautomer, or pharmaceutically acceptable salt thereof, each $R^6$ and $R^7$ is independently hydrogen, $C_1$-$C_6$ alkyl, or $C_2$-$C_6$ alkenyl, each of which is unsubstituted or substituted with one or more $R^{10}$. In another embodiment of the compounds or a pharmaceutically acceptable salt thereof described herein, each $R^6$ and $R^7$ is independently hydrogen, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$.

In some embodiments of the compounds described herein or a stereoisomer, tautomer, or pharmaceutically acceptable salt thereof, each $R^8$, $R^{8A}$, and $R^{8C}$ are independently hydrogen or $C_1$-$C_6$ alkyl. In one embodiment of the compounds or a pharmaceutically acceptable salt thereof described herein, each $R^8$, $R^{8A}$, and $R^{8C}$ are independently hydrogen or $C_1$-$C_3$ alkyl. In one embodiment of the compounds or a pharmaceutically acceptable salt thereof described herein, each $R^8$, $R^{8A}$, and $R^{8C}$ are independently hydrogen, methyl, ethyl, propyl, or isopropyl. In one embodiment of the compounds or a pharmaceutically acceptable salt thereof described herein, each $R^{8B}$ is independently hydrogen, $C_1$-$C_6$ alkyl, or $C_2$-$C_6$ alkenyl each of which is unsubstituted or substituted with one or more $R^{10}$. In one embodiment of the compounds or a pharmaceutically acceptable salt thereof described herein, each $R^{8B}$ is independently hydrogen, $C_3$-$C_8$ cycloalkyl, $C_6$-$C_{10}$ aryl, or 3- to 12-membered heterocyclyl, each of which is unsubstituted or substituted with one or more $R^{10}$.

In some embodiments of the compounds described herein or a stereoisomer, tautomer, or pharmaceutically acceptable salt thereof, each $R^9$ is independently $C_1$-$C_6$ alkyl or $C_2$-$C_6$ alkenyl, each of which is unsubstituted or substituted with one or more $R^{10}$. In one embodiment of the compounds or a pharmaceutically acceptable salt thereof described herein, each $R^9$ is independently $C_3$-$C_8$ cycloalkyl, $C_6$-$C_{10}$ aryl, 5- to 14-membered heteroaryl or 3- to 12-membered heterocyclyl, each of which is unsubstituted or substituted with one or more $R^{10}$.

In one embodiment, $R^9$ is $R^{10}$-substituted or unsubstituted $C_1$-$C_6$ alkyl. In one embodiment, $R^9$ is $R^{10}$-substituted or unsubstituted $C_3$-$C_7$ cycloalkyl or $R^{10}$-substituted or unsubstituted 3 to 7 membered heterocycloalkyl. In one embodiment, $R^9$ is $R^{10}$-substituted or unsubstituted 3 to 7 membered heterocycloalkyl. In one embodiment, $R^9$ is $R^{10}$-substituted or unsubstituted pyrrolidinyl, pyrazolinyl, tetrahydrofuranyl, piperidinyl, piperazinyl, tetrahydropyranyl, or morpholino. In a particular embodiment, $R^9$ is $R^{10}$-substituted or unsubstituted 4 to 6 membered heterocycloalkyl comprising at least one nitrogen heteroatom.

In one embodiment, $R^9$ is $R^{10}$-substituted or unsubstituted $C_5$-$C_7$ aryl or $R^{10}$-substituted or unsubstituted 5 to 7 membered heteroaryl.

In another embodiment, $R^9$ is $R^{10}$-substituted or unsubstituted benzyl, $R^{10}$-substituted or unsubstituted pyrrolidinyl, or $R^{10}$-substituted or unsubstituted piperidinyl. $R^{10}$ can be halogen, —CN, $R^{11}$-substituted or unsubstituted $C_1$-$C_6$ alkoxy, or $R^{11}$-substituted or unsubstituted $C_1$-$C_6$ alkyl.

In one embodiment, $R^9$ is $R^{10}$-substituted or unsubstituted benzyl. In a particular embodiment, $R^9$ is unsubstituted benzyl. In some embodiments, $R^9$ is $R^{10}$-substituted benzyl, where $R^{10}$ is hydrogen, halogen, —OH, —CN, —$CF_3$, —$CHF_2$, —$CH_2F$, —$C(CH_3)_2F$, —$C(CH_3)F_2$, methyl, propyl, or ethyl. In another embodiment, $R^9$ is $R^{10}$-substituted benzyl, where $R^{10}$ is hydrogen, halogen, —OH, or —CN.

In another embodiment, $R^9$ is $R^{10}$-substituted or unsubstituted piperidinyl. In some embodiments, $R^9$ is $R^{10}$-substituted piperidinyl where $R^{10}$ is hydrogen, halogen, —OH, —CN, —CF$_3$, —CHF$_2$, —CH$_2$F, —C(CH$_3$)$_2$F, —C(CH$_3$)F$_2$, methyl, propyl, or ethyl.

In another embodiment, $R^9$ is $R^{10}$-substituted or -unsubstituted $C_5$-$C_{10}$ aryl comprising two fused rings. In one such embodiment, $R^9$ is $R^{10}$-substituted or -unsubstituted indanyl or tetrahydronaphthalenyl.

In still another embodiment, $R^9$ is $R^{10}$-substituted or -unsubstituted $C_5$-$C_8$ cycloalkyl comprising two fused rings. In one such embodiment, $R^9$ is $R^{10}$-substituted or -unsubstituted 3,5; 3,6; 4,5; or 5,5 fused cycloalkyl. In still another embodiment, $R^9$ is $R^{10}$-substituted or -unsubstituted $C_5$-$C_8$ spiro-cycloalkyl. In one such embodiment, $R^9$ is $R^{10}$-substituted or -unsubstituted spiro[2.2]pentanyl, spiro[2.3]hexanyl, spiro[3.3]heptanyl.

In still another embodiment, $R^9$ is $R^{10}$-substituted or unsubstituted $C_1$-$C_6$ alkyl or $R^{10}$-substituted or unsubstituted 3 to 6 membered cycloalkyl. In some embodiments, $R^9$ is $R^{10}$-substituted or unsubstituted $C_1$-$C_6$ alkyl or $R^{10}$-substituted or unsubstituted 3 to 6 membered cycloalkyl where $R^{10}$ is halogen, —CN, or $R^{11}$-substituted or unsubstituted $C_1$-$C_6$ alkyl. In another embodiment, $R^9$ is $R^{10}$-substituted or unsubstituted $C_1$-$C_6$ alkyl or $R^{10}$-substituted or unsubstituted 3 to 6 membered cycloalkyl where $R^{10}$ is hydrogen, halogen, —OH, —CN, —CF$_3$, —CHF$_2$, —CH$_2$F, —C(CH$_3$)$_2$F, —C(CH$_3$)F$_2$, methyl, propyl, or ethyl. In one preferred embodiment, $R^9$ is $R^{10}$-substituted $C_1$-$C_6$ alkyl where $R^{10}$ is hydrogen, halogen, —CF$_3$, —CHF$_2$, —CH$_2$F, —C(CH$_3$)$_2$F, or —C(CH$_3$)F$_2$. In a particular embodiment, $R^9$ is $R^{10}$-substituted $C_1$-$C_6$ alkyl where $R^{10}$ is hydrogen, halogen, —OH, —CN, —CF$_3$, —CHF$_2$, —CH$_2$F, —C(CH$_3$)$_2$F, —C(CH$_3$)F$_2$, methyl, propyl, or ethyl.

In still another embodiment, $R^9$ is $R^{10}$-substituted or unsubstituted $C_1$-$C_6$ haloalkyl. In some embodiments, $R^9$ is $R^{10}$-substituted or unsubstituted $C_1$-$C_6$ haloalkyl where $R^{10}$ is halogen, —CN, or $R^{11}$-substituted or unsubstituted $C_1$-$C_6$ alkyl. In another embodiment, $R^9$ is $R^{10}$-substituted or unsubstituted $C_1$-$C_6$ haloalkyl where $R^{10}$ is hydrogen, halogen, —OH, —CN, —CF$_3$, —CHF$_2$, —CH$_2$F, —C(CH$_3$)$_2$F, —C(CH$_3$)F$_2$, methyl, propyl, or ethyl. In one embodiment, $R^9$ is trifluoropropanyl. In another embodiment, $R^9$ is difluorobutanyl or difluoropropanyl.

In some embodiments of the compounds described herein or a stereoisomer, tautomer, or pharmaceutically acceptable salt thereof, each $R^{10}$ is independently oxo, halogen, cyano, —C(O)H, —C(O)CH$_3$, —C(O)OH, —C(O)OCH$_3$, —C(O)NH$_2$, —OH, —OCH$_3$, —OC(O)H, —OC(O)CH$_3$, —OC(O)NH$_2$, —CF$_3$, —CHF$_2$, —CH$_2$F, —C(CH$_3$)$_2$F, or —C(CH$_3$)F$_2$, —SH, —S(O)H, —S(O)$_2$H, —S(O)(=NH)H, —S(O)$_2$NH$_2$, —NH$_2$, —NHC(O)H, —NHC(O)OH, —N(H)C(O)NH$_2$, —NHS(O)$_2$H, —NHS(O)$_2$NH$_2$, or —P(O)(CH$_3$)$_2$. In one embodiment of the compounds or a pharmaceutically acceptable salt thereof described herein, each $R^{10}$ is independently $C_1$-$C_6$ alkyl, $C_1$-$C_6$ haloalkyl, $C_2$-$C_6$ alkenyl, $C_3$-$C_8$ cycloalkyl, $C_6$-$C_{10}$ aryl, 4- to 10-membered heteroaryl, or 3- to 12-membered heterocyclyl, wherein each $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $C_6$-$C_{10}$ aryl, 4- to 10-membered heteroaryl, or 3- to 12-membered heterocyclyl is unsubstituted or substituted with one or more $R^{11}$.

In some embodiments of the compounds described herein or a stereoisomer, tautomer, or pharmaceutically acceptable salt thereof, each $R^{11}$ is independently $C_1$-$C_6$ alkyl, halogen, cyano, —O($C_1$-$C_3$ alkyl), —CH$_2$F, —CHF$_2$, or —CF$_3$. In one embodiment of the compounds or a pharmaceutically acceptable salt thereof described herein, each $R^{11}$ is independently $C_3$-$C_6$ cycloalkyl, 4- to 6-membered-heteroaryl, or phenyl.

In some embodiments of the compounds described herein or a stereoisomer, tautomer, or pharmaceutically acceptable salt thereof, each $R^{11}$ is independently $C_1$-$C_6$ alkyl, $C_{1-6}$ haloalkyl, $C_3$-$C_6$ cycloalkyl, 4- to 6-membered-heteroaryl, phenyl, halogen, cyano, —O($C_1$-$C_3$ alkyl), —CH$_2$F, —CHF$_2$, or —CF$_3$.

In some embodiments of the compounds described herein or a stereoisomer, tautomer, or pharmaceutically acceptable salt thereof, $X^1$ is —CH or —N. In one embodiment of the compounds described herein or a stereoisomer, tautomer, or pharmaceutically acceptable salt thereof, $X^1$ is —CH. In one embodiment of the compounds described herein or a stereoisomer, tautomer, or pharmaceutically acceptable salt thereof, $X^1$ is —N.

In some embodiments of the compounds described herein or a stereoisomer, tautomer, or pharmaceutically acceptable salt thereof, $R^1$ is $C_1$-$C_4$ alkyl, $C_3$-$C_6$ cycloalkyl, or $C_3$-$C_6$ heterocyclyl, each of which is unsubstituted or substituted with one or more substituents selected from the group consisting of halogen, $C_3$-$C_6$ cycloalkyl, and hydroxyl.

In some embodiments of the compounds described herein or a stereoisomer, tautomer, or pharmaceutically acceptable salt thereof, $R^1$ is $C_1$-$C_4$ alkyl, which is unsubstituted or substituted with one or more of fluoro, $C_3$-$C_6$ cycloalkyl, or hydroxyl.

In some embodiments of the compounds described herein or a stereoisomer, tautomer, or pharmaceutically acceptable salt thereof, $R^1$ is $C_3$-$C_6$ cycloalkyl.

In some embodiments of the compounds described herein or a stereoisomer, tautomer, or pharmaceutically acceptable salt thereof, $R^1$ is selected from the group consisting of methyl, ethyl, isopropyl, cyclopropyl, cyclobutyl, cyclopentyl, —CH$_2$CHF$_2$, —CHCH$_3$CHF$_2$, —CH$_2$CF$_3$, —CHCH$_3$CF$_3$, —CH$_2$CHOHCH$_2$CH$_3$, and —CH$_2$-cyclopropyl. In a preferred embodiment, $R^1$ is methyl, ethyl, or isopropyl. In another embodiment, $R^1$ is ethyl, or isopropyl. In one embodiment, $R^1$ is cyclopropyl or cyclobutyl. In still another embodiment, $R^1$ is cyclopropyl.

In some embodiments of the compounds described herein or a stereoisomer, tautomer, or pharmaceutically acceptable salt thereof, $R^1$ is oxetanyl or tetrahydrafuranyl.

In some embodiments of the compounds described herein or a stereoisomer, tautomer, or pharmaceutically acceptable salt thereof, $R^2$ is selected from the group consisting of isopropyl, cyclohexyl, or piperidinyl, each of which is unsubstituted or substituted with one or more methyl, fluoro, hydroxyl, —NH$_2$, —NHCH$_3$, or —N(CH$_3$)$_2$. In a preferred embodiment, $R^2$ is cyclohexyl or piperidinyl. In one embodiment, $R^2$ is cyclohexyl substituted with one or more methyl, fluoro, or —N(R$^{2B}$)$_2$, where R$^{2B}$ is as defined herein. In one embodiment, each R$^{2B}$ is methyl. In another embodiment, R$^{2B}$ is independently hydrogen and methyl. In one embodiment, $R^2$ is cyclohexyl substituted with —N(R$^{2B}$)$_2$, where R$^{2B}$ is as defined herein. In still another embodiment, R$^{2B}$ is independently methyl and R$^{2C}$-substituted $C_1$-$C_3$ alkyl. In still another embodiment, R$^{2B}$ is independently methyl and unsubstituted $C_3$-$C_6$ cycloalkyl. In still another embodiment, R$^{2B}$ is independently methyl and unsubstituted $C_3$-$C_6$ heterocyclyl. In another embodiment, $R^2$ is piperidinyl substituted with one or more R$^{2A}$, where R$^{2A}$ is $C_1$-$C_3$ alkyl, $C_1$-$C_3$ fluoroalkyl, or halogen.

In one embodiment, $R^2$ is cyclohexyl substituted with one or more methyl, $C_{1-6}$ haloalkyl, $R^6$-optionally substituted cyclopropyl, fluoro, or $-N(R^{2B})_2$, where $R^{2B}$ is as defined herein. In one embodiment, each $R^{2B}$ is methyl. In another embodiment, each $R^{2B}$ is independently hydrogen and methyl. In one embodiment, $R^2$ is cyclohexyl substituted with $-N(R^{2B})_2$, where $R^{2B}$ is as defined herein. In still another embodiment, $R^{2B}$ is independently methyl and $R^{2C}$-substituted $C_1$-$C_3$ alkyl. In still another embodiment, $R^{2B}$ is independently methyl and unsubstituted $C_3$-$C_6$ cycloalkyl. In still another embodiment, $R^{2B}$ is independently methyl and unsubstituted $C_3$-$C_6$ heterocyclyl.

In one embodiment, $R^2$ is:

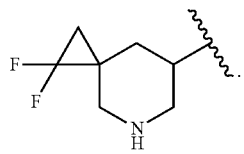 [SMILES: *C1CNCC2(C1)CC2(F)F]

In one embodiment, $R^2$ is:

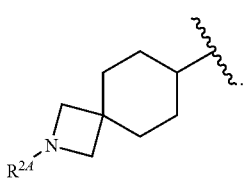

In some embodiments of the compounds described herein or a stereoisomer, tautomer, or pharmaceutically acceptable salt thereof, $R^2$ is selected from the group consisting of isopropyl, cyclohexyl substituted with hydroxyl, cyclohexyl substituted with $-N(CH_3)_2$, piperidinyl, piperidinyl substituted with fluoro, piperidinyl substituted with methyl, and piperidinyl substituted with methyl and fluoro.

In some embodiments of the compounds described herein or a stereoisomer, tautomer, or pharmaceutically acceptable salt thereof, $R^2$ is selected from the group consisting of isopropyl, cyclohexyl substituted with hydroxyl, cyclohexyl substituted with $-N(CH_3)_2$, piperidinyl, piperidinyl substituted with fluoro, piperidinyl substituted with methyl, piperidinyl substituted with $C_{1-6}$ fluoroalkyl, piperidinyl substituted with $C_{1-6}$ fluoroalkyl and methyl, piperidinyl substituted with $C_{1-6}$ fluoroakyl and fluoro, and piperidinyl substituted with methyl and fluoro.

In another embodiment of the compounds described herein or a stereoisomer, tautomer, or pharmaceutically acceptable salt thereof, $R^2$ is cyclohexyl or piperidinyl substituted with halogen and one or more groups consisting of $R^{2C}$-substituted or -unsubstituted $C_1$-$C_4$ alkyl or $-N(R^{2B})_2$. In one such embodiment, two $R^{2B}$ together form a substituted or unsubstituted heterocyclyl, wherein the heterocyclyl can be spiro, an unsubstituted aziridinyl, azetidinyl, pyrrolidinyl, imidazolyl, piperidinyl, piperazinyl, morpholino. In another such embodiment, one $R^{2B}$ is methyl and one $R^{2B}$ is $R^{2C}$-substituted or unsubstituted $C_1$-$C_3$ alkyl, unsubstituted $C_3$-$C_6$ cycloalkyl; or unsubstituted $C_3$-$C_6$ heterocyclyl. In such embodiments, $R^{2B}$ is cyclopropyl, cyclobutyl, cyclopentyl, azetidinyl, or pyrrolidinyl.

In one embodiment, Ring B of formula (I) is phenyl or a 6-membered heteroaryl comprising at least one nitrogen atom. In a preferred embodiment, Ring B is phenyl. In one embodiment, Ring B of formula (I) is 6-membered heteroaryl comprising at least one nitrogen atom. In another embodiment, Ring B of formula (I) is pyridinyl, pyrazinyl, or pyridazinyl. In one embodiment, Ring B corresponds to:

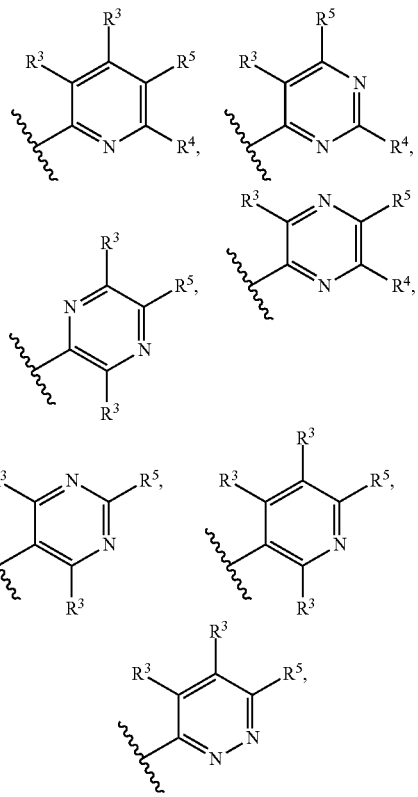

where $R^3$, $R^4$, and $R^5$ are as defined herein.

In one preferred embodiment, Ring B corresponds to:

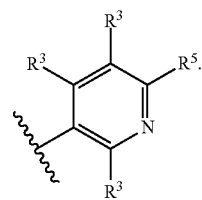

Provided herein in one embodiment are compounds or a pharmaceutically acceptable salt thereof having formula (Ia1);

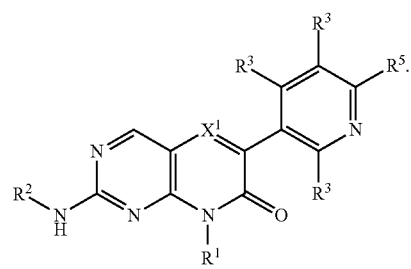

where $X^1$, $R^1$, $R^2$, $R^3$, and $R^5$ are as described herein, for example in the compounds of formula (Ia).

In another embodiment, are compounds or a pharmaceutically acceptable salt thereof having formula (Ia2), (Ia3), (Ia4), (Ia5), (Ia6), or (Ia7):

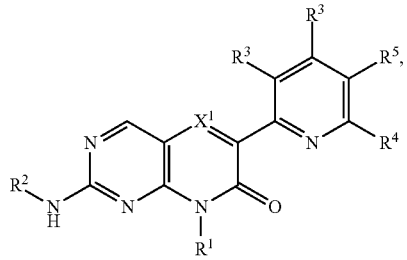
(Ia2)

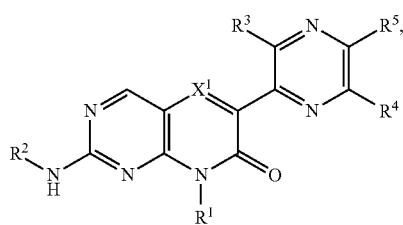
(Ia3)

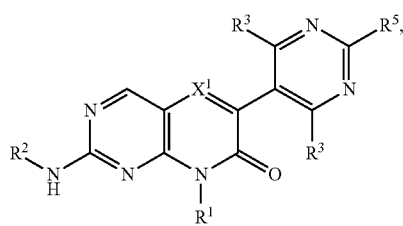
(Ia4)

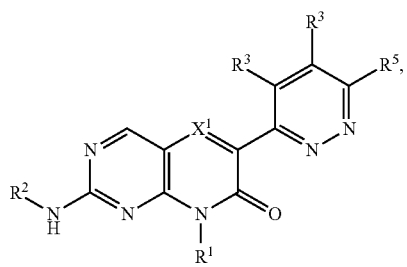
(Ia5)

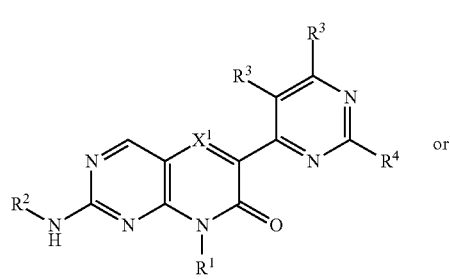
(Ia6)

or

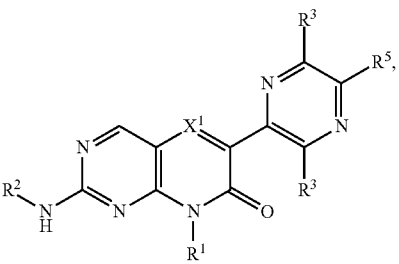
(Ia7)

where $X^1$, $R^1$, $R^2$, $R^3$, $R^4$, and $R^5$ are as described herein, for example in the compounds of formula (Ia).

In some embodiments of the compounds described herein or a stereoisomer, tautomer, or pharmaceutically acceptable salt thereof, the compound has formula (Ic):

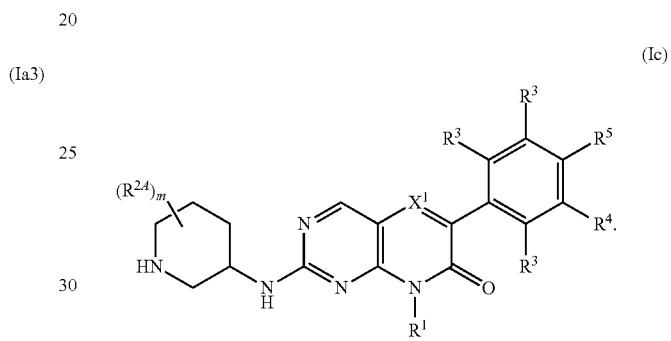
(Ic)

where $X^1$, $R^1$, $R^{2A}$, $R^3$, $R^4$ and $R^5$ are as described herein and m is 1, 2, 3, or 4.

In one embodiment of the compounds or a pharmaceutically acceptable salt thereof described herein, is a compound having formula (Ic1):

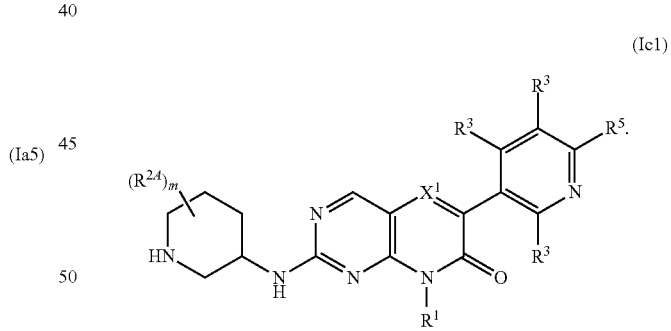
(Ic1)

where $X^1$, $R^1$, $R^{2A}$, $R^3$, and $R^5$ are as described herein and m is 1, 2, 3, or 4.

In some embodiments of the compounds of Formula (Ic) or (Ic1) or a stereoisomer, tautomer, or pharmaceutically acceptable salt thereof, $R^{2A}$ is —$CH_3$ and m is 1.

In some embodiments of the compounds of Formula (Ic) or (Ic1) or a stereoisomer, tautomer, or pharmaceutically acceptable salt thereof, $R^{2A}$ is —F and m is 1.

In some embodiments of the compounds of Formula (Ic) or (Ic1) or a stereoisomer, tautomer, or pharmaceutically acceptable salt thereof, $R^{2A}$ is —$CH_2F$ and m is 1.

In some embodiments of the compounds of Formula (Ic) or (Ic1) or a stereoisomer, tautomer, or pharmaceutically acceptable salt thereof, $R^{2A}$ is —F and m is 2.

In some embodiments of the compounds of Formula (Ic) or (Ic1) or a stereoisomer, tautomer, or pharmaceutically acceptable salt thereof, $R^{2A}$ is —F and —$CH_3$ and m is 2.

In some embodiments of the compounds of Formula (Ic) or (Ic1) or a stereoisomer, tautomer, or pharmaceutically acceptable salt thereof, $R^{2A}$ is —$CH_2F$ and —$CH_3$ and m is 2.

In some embodiments of the compounds of Formula (Ic) or (Ic1) or a stereoisomer, tautomer, or pharmaceutically acceptable salt thereof, $R^{2A}$ is —$CH_2F$ and F and m is 2.

In some embodiments of the compounds of Formula (Ic) or (Ic1) or a stereoisomer, tautomer, or pharmaceutically acceptable salt thereof, $R^{2A}$ is —$CF_2H$ and —$CH_3$ and m is 2.

In some embodiments of the compounds of Formula (Ic) or (Ic1) or a stereoisomer, tautomer, or pharmaceutically acceptable salt thereof, $R^{2A}$ is —$CF_2H$ and F and m is 2.

In some embodiments of the compounds described herein or a stereoisomer, tautomer, or pharmaceutically acceptable salt thereof, the compound has formula (Id):

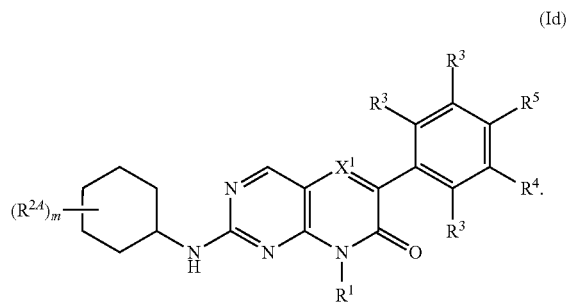

where $X^1$, $R^1$, $R^{2A}$, $R^3$, $R^4$ and $R^5$ are as described herein and m is 1, 2, 3, or 4.

In one embodiment of the compounds or a pharmaceutically acceptable salt thereof described herein, is a compound having formula (Id1):

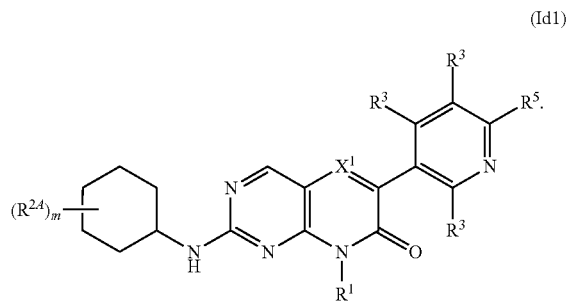

where $X^1$, $R^1$, $R^{2A}$, $R^3$, and $R^5$ are as described herein and m is 1, 2, 3, or 4.

In one embodiment of the compounds of Formula (Id) or (Id1) or a stereoisomer, tautomer, or pharmaceutically acceptable salt thereof, $R^{2A}$ is as defined above for Formula (Ic).

In some embodiments of the compounds of Formula (Id) or (Id1) or a stereoisomer, tautomer, or pharmaceutically acceptable salt thereof, $R^{2A}$ is —$CH_2F$ and m is 1.

In some embodiments of the compounds of Formula (Id) or (Id1) or a stereoisomer, tautomer, or pharmaceutically acceptable salt thereof, $R^{2A}$ is —$NHCH_3$ and m is 1.

In some embodiments of the compounds of Formula (Id) or (Id1) or a stereoisomer, tautomer, or pharmaceutically acceptable salt thereof, $R^{2A}$ is —$NH_2$ and m is 1.

In some embodiments of the compounds of Formula (Id) or (Id1) or a stereoisomer, tautomer, or pharmaceutically acceptable salt thereof, $R^{2A}$ is —$N(CH_3)_2$ and m is 1.

In some embodiments of the compounds of Formula (Id) or (Id1) or a stereoisomer, tautomer, or pharmaceutically acceptable salt thereof, $R^{2A}$ is —$N(CH_3)_2$ and —F and m is 2.

In some embodiments of the compounds of Formula (Id) or (Id1) or a stereoisomer, tautomer, or pharmaceutically acceptable salt thereof, $R^{2A}$ is —$N(CH_3)_2$ and —OH and m is 2.

In some embodiments of the compounds of Formula (Id) or (Id1) or a stereoisomer, tautomer, or pharmaceutically acceptable salt thereof, $R^{2A}$ is —$N(R^{2B})_2$, where $R^{2B}$ is independently —$CH_3$ and —$CH_2CH_2OCH_3$ and m is 1.

In some embodiments of the compounds of Formula (Id) or (Id1) or a stereoisomer, tautomer, or pharmaceutically acceptable salt thereof, $R^{2A}$ is F and —$N(R^{2B})_2$, where $R^{2B}$ is independently —$CH_3$ and —$CH_2CH_2OCH_3$ and m is 2.

In some embodiments of the compounds of Formula (Id) or (Id1) or a stereoisomer, tautomer, or pharmaceutically acceptable salt thereof, $R^{2A}$ is —$N(CH_2CH_2OCH_3)_2$ and m is 1.

In some embodiments of the compounds of Formula (Id) or (Id1) or a stereoisomer, tautomer, or pharmaceutically acceptable salt thereof, $R^{2A}$ is F and —$N(CH_2CH_2OCH_3)_2$ and m is 2.

In some embodiments of the compounds of Formula (Id) or (Id1) or a stereoisomer, tautomer, or pharmaceutically acceptable salt thereof, $R^{2A}$ is —$N(R^{2B})_2$, where $R^{2B}$ is independently —$CH_3$ and —$CH_2CH_2F$ and m is 1.

In some embodiments of the compounds of Formula (Id) or (Id1) or a stereoisomer, tautomer, or pharmaceutically acceptable salt thereof, $R^{2A}$ is F and —$N(R^{2B})_2$, where $R^{2B}$ is independently —$CH_3$ and —$CH_2CH_2F$ and m is 2.

In some embodiments of the compounds of Formula (Id) or (Id1) or a stereoisomer, tautomer, or pharmaceutically acceptable salt thereof, $R^{2A}$ is unsubstituted morpholino or 2-oxa-6-azaspiro[3.3]heptanyl and m is 1.

In some embodiments of the compounds of Formula (Id) or (Id1) or a stereoisomer, tautomer, or pharmaceutically acceptable salt thereof, $R^{2A}$ is F and unsubstituted morpholino or 2-oxa-6-azaspiro[3.3]heptanyl and m is 2.

In some embodiments of the compounds of Formula (Id) or (Id1) or a stereoisomer, tautomer, or pharmaceutically acceptable salt thereof, $R^{2A}$ is —$CH_2N(CH_3)_2$ and m is 1.

In some embodiments of the compounds of Formula (Id) or (Id1) or a stereoisomer, tautomer, or pharmaceutically acceptable salt thereof, $R^{2A}$ is F and —$CH_2N(CH_3)_2$ and m is 2.

In some embodiments of the compounds described herein or a stereoisomer, tautomer, or pharmaceutically acceptable salt thereof, each $R^3$ is independently hydrogen or halogen.

In some embodiments of the compounds described herein or a stereoisomer, tautomer, or pharmaceutically acceptable salt thereof, at least one $R^3$ is halogen.

In some embodiments of the compounds described herein or a stereoisomer, tautomer, or pharmaceutically acceptable salt thereof, at least one $R^3$ is fluoro.

In some embodiments of the compounds described herein or a stereoisomer, tautomer, or pharmaceutically acceptable salt thereof, at least one $R^3$ is chloro.

In some embodiments of the compounds described herein or a stereoisomer, tautomer, or pharmaceutically acceptable salt thereof, each $R^3$ and $R^4$ are independently hydrogen or fluoro, and $R^5$ is —$NR^{8A}R^9$, —$NR^8C(O)R^9$, or —$NR^8SO_2R^9$. In some embodiments of the compounds described herein or a stereoisomer, tautomer, or pharmaceutically acceptable salt thereof, at least one of $R^3$ or $R^4$ is fluoro.

In one embodiment of the compounds of Formula (Ia), $R^5$ is —$NR^{8A}R^9$, —$NR^8C(O)R^9$, or —$NR^8SO_2R^9$. In a preferred embodiment of the compounds of Formula (Ia), $R^5$ is —$NR^8C(O)R^9$ or —$NR^8SO_2R^9$. In one embodiment, where $R^5$ of the compounds of Formula (Ia) is —$NR^8C(O)R^9$ or —$NR^8SO_2R^9$, $R^4$ is not is —$NR^{8A}R^9$, —$NR^8C(O)R^7$, or —$NR^8C(O)R^9$.

In one embodiment of the compounds of Formula (Ia), $R^4$ is —$NR^{8A}R^9$, —$NR^8C(O)R^7$, or —$NR^8SO_2R^9$. In one embodiment of the compounds of Formula (Ia), $R^4$ is —$NR^8C(O)R^7$ or —$NR^8SO_2R^9$. In another embodiment of the compounds of Formula (Ia), $R^4$ is —$NR^8C(O)R^7$. In another embodiment of the compounds of Formula (Ia), $R^4$ is or —$NR^8SO_2R^9$. In one embodiment, where $R^4$ of the compounds of Formula (Ia) is —$NR^8C(O)R^7$, or —$NR^8SO_2R^9$, $R^5$ is not is —$NR^{8A}R^9$, —$NR^8C(O)R^9$, or —$NR^8SO_2R^9$.

In one embodiment of the compounds or a pharmaceutically acceptable salt thereof of Formula (Ia1), $R^4$ and $R^5$ are as described herein for compounds of Formula (Ia).

In one embodiment of the compounds of Formula (Ib), $R^4$ is —$NR^{8A}R^9$, —$NR^8C(O)R^9$, or —$NR^8SO_2R^9$. In one embodiment of the compounds of Formula (Ib), $R^4$ is —$NR^8C(O)R^9$ or —$NR^8SO_2R^9$. In another embodiment of the compounds of Formula (Ib), $R^4$ is —$NR^8C(O)R^9$. In a embodiment of the compounds of Formula (Ib), $R^4$ is —$NR^8SO_2R^9$. In one embodiment where $R^4$ of the compounds of Formula (Ib) is —$NR^8C(O)R^9$ or —$NR^8SO_2R^9$. $R^5$ is not is —$NR^{8A}R^9$, —$NR^8C(O)R^9$, —$NR^8SO_2R^9$.

In one embodiment of the compounds of Formula (Ib), $R^5$ is —$NR^{8A}R^9$, —$NR^8C(O)R^9$, or —$NR^8SO_2R^9$. In one embodiment of the compounds of Formula (Ib), $R^5$ is —$NR^8C(O)R^9$ or —$NR^8SO_2R^9$. In another embodiment of the compounds of Formula (Ib), $R^5$ is —$NR^8C(O)R^9$. In one embodiment of the compounds of Formula (Ib), $R^5$ is or —$NR^8SO_2R^9$. In one embodiment where $R^5$ of the compounds of Formula (Ib) is —$NR^8C(O)R^9$ or —$NR^8SO_2R^9$. $R^4$ is not is —$NR^{8A}R^9$, —$NR^8C(O)R^9$, or —$NR^8SO_2R^9$.

In some embodiments of the compounds of formula (I) or (Ib) described herein or a stereoisomer, tautomer, or pharmaceutically acceptable salt thereof, each $R^3$ is independently hydrogen or fluoro, and $R^4$ is —$NR^{8A}R^9$, —$NR^8C(O)R^9$, or —$NR^8SO_2R^9$. In some embodiments of the compounds described herein or a stereoisomer, tautomer, or pharmaceutically acceptable salt thereof, at least one $R^3$ is fluoro. In some embodiments of the compounds of formula (I) or (Ib) described herein or a stereoisomer, tautomer, or pharmaceutically acceptable salt thereof, $R^5$ is hydrogen or fluoro.

In some embodiments of the compounds described herein or a stereoisomer, tautomer, or pharmaceutically acceptable salt thereof, each $R^3$ is independently hydrogen or fluoro, and $R^5$ is —$NR^{8A}R^9$, —$NR^8C(O)R^9$, or —$NR^8SO_2R^9$. In some embodiments of the compounds described herein or a stereoisomer, tautomer, or pharmaceutically acceptable salt thereof, at least one $R^3$ is fluoro. In some embodiments of the compounds described herein or a stereoisomer, tautomer, or pharmaceutically acceptable salt thereof, $R^4$ is hydrogen or fluoro.

In some embodiments of the compounds described herein or a stereoisomer, tautomer, or pharmaceutically acceptable salt thereof, the compound has formula (Ie):

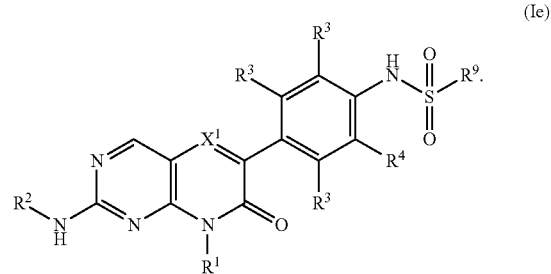

(Ie)

where $X^1$, $R^1$, $R^2$, $R^3$, $R^4$, and $R^9$ are as described herein.

In some embodiments of the compounds described herein or a stereoisomer, tautomer, or pharmaceutically acceptable salt thereof, the compound has formula (Ie1):

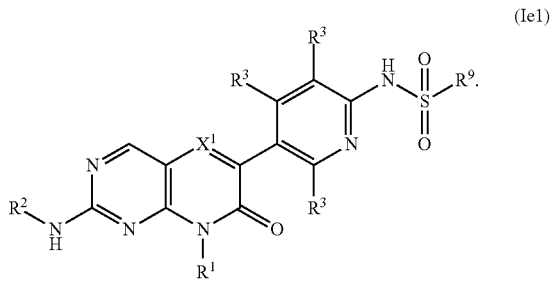

(Ie1)

where $X^1$, $R^1$, $R^2$, $R^3$, and $R^9$ are as described herein.

In some embodiments of the compounds of Formula (Ie) or (Ie1) or a stereoisomer, tautomer, or pharmaceutically acceptable salt thereof, at least one of $R^3$ or $R^4$ is fluoro.

In one embodiment of the compounds or a pharmaceutically acceptable salt thereof described herein, $R^9$ is $C_1$-$C_6$ alkyl or $C_2$-$C_6$ alkenyl, each of which is unsubstituted or substituted with one or more $R^{10}$. In another embodiment of the compounds or a pharmaceutically acceptable salt thereof described herein, $R^9$ is $C_3$-$C_8$ cycloalkyl, $C_6$-$C_{10}$ aryl, 5- to 14-membered heteroaryl or 3- to 12-membered heterocyclyl, each of which is unsubstituted or substituted with one or more $R^{10}$.

In some embodiments of the compounds of Formula (Ie) or (Ie1) or a stereoisomer, tautomer, or pharmaceutically acceptable salt thereof, $R^9$ is benzyl, phenyl, pyrazolyl, pyridinyl, or $C_1$-$C_6$ alkyl optionally substituted with halogen, phenyl, cyclopropyl, or cyclobutyl.

In some embodiments of the compounds of Formula (Ie) or (Ie1) or a stereoisomer, tautomer, or pharmaceutically acceptable salt thereof, $R^9$ is $C_2$-$C_4$ alkyl optionally substituted with halogen or $C_3$-$C_6$ cycloalkyl. In one preferred embodiment of the compounds of Formula (Ie) or (Ie1) or a stereoisomer, tautomer, or pharmaceutically acceptable salt thereof, $R^9$ is $C_2$-$C_4$ alkyl optionally substituted with halogen. In one embodiment, of the compounds of Formula (Ie) or (Ie1) or a stereoisomer, tautomer, or pharmaceutically acceptable salt thereof, $R^9$ is ethyl, propyl, isopropyl, difluoropropyl, trifluoropropyl, or difluorobutyl. In one embodiment, of the compounds of Formula (Ie) or (Ie1) or a stereoisomer, tautomer, or pharmaceutically acceptable salt thereof, $R^9$ is $C_2$-$C_4$ alkyl substituted with cyclopropyl or cyclobutyl, where the cyclopropyl or cyclobutyl is optionally substituted with F or Cl.

In one preferred embodiment of the compounds of Formula (Ie) or (Ie1) or a stereoisomer, tautomer, or pharmaceutically acceptable salt thereof, $R^9$ is benzyl optionally substituted with one or more —CN, halogen (e.g. F or Cl), methoxy, or —$CF_3$. In one embodiment, of a compound of Formula (Ie) or (Ie1) or a stereoisomer, tautomer, or pharmaceutically acceptable salt thereof, $R^9$ is unsubstituted benzyl. In one embodiment of Formula (Ie) or (Ie1) or a stereoisomer, tautomer, or pharmaceutically acceptable salt thereof, at least one $R^3$ is fluoro.

In some embodiments of the compounds described herein or a stereoisomer, tautomer, or pharmaceutically acceptable salt thereof, the compound has formula (If):

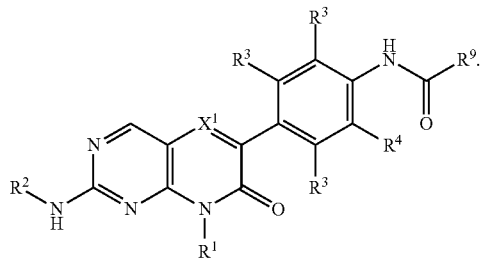

(If)

where $X^1$, $R^1$, $R^2$, $R^3$, $R^4$, and $R^9$ are as described herein.

In some embodiments of the compounds described herein or a stereoisomer, tautomer, or pharmaceutically acceptable salt thereof, the compound has formula (If1):

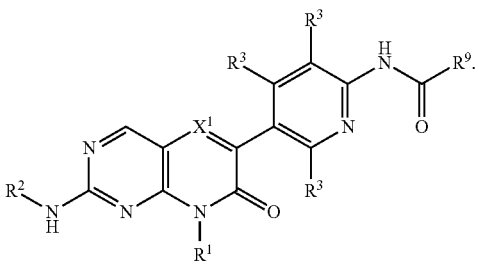

(If1)

where $X^1$, $R^1$, $R^2$, $R^3$, and $R^9$ are as described herein.

In some embodiments of the compounds of Formula (If) or (If1) or a stereoisomer, tautomer, or pharmaceutically acceptable salt thereof, at least one of $R^3$ or $R^4$ is fluoro. In one embodiment of Formula (If) or (If1) or a stereoisomer, tautomer, or pharmaceutically acceptable salt thereof, at least one $R^3$ is fluoro.

In some embodiments of the compounds described herein or a stereoisomer, tautomer, or pharmaceutically acceptable salt thereof, the compound has formula (Ig) or (Ig1):

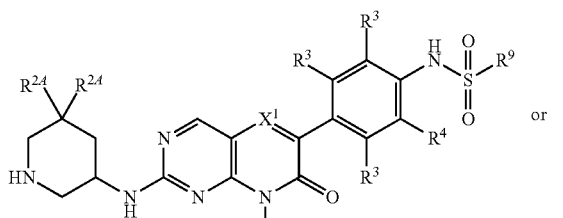

(Ig)

(Ig1)

where $X^1$, $R^1$, $R^{2A}$, $R^3$, $R^4$, and $R^9$ are as described herein and m is 1, 2, 3, 4, or 5.

In one embodiment, m is 1.

In another embodiment of the compounds described herein or a stereoisomer, tautomer, or pharmaceutically acceptable salt thereof, the compound has formula (Ig2) or (Ig3):

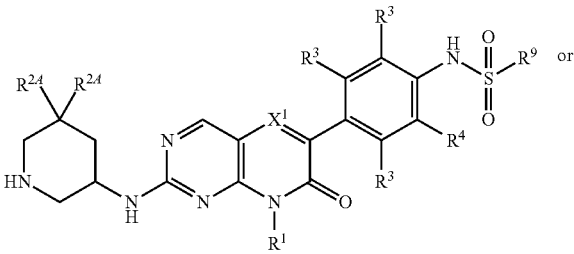

(Ig2)

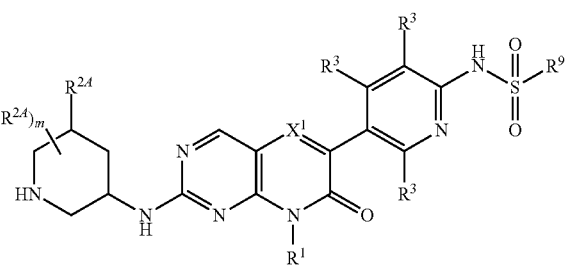

(Iq3)

where $X^1$, $R^1$, $R^{2A}$, $R^3$, and $R^9$ are as described herein and m is 1, 2, 3, 4, or 5.

In one embodiment, $R^9$ of the compounds of Formula (Ig), (Ig1), (Ig2), or (Ig3) or a stereoisomer, tautomer, or pharmaceutically acceptable salt thereof, is the same as $R^9$ as described herein for compounds of Formula (Ie).

In some embodiments of the compounds of Formula (Ig), (Ig1), (Ig2), or (Ig3) or a stereoisomer, tautomer, or pharmaceutically acceptable salt thereof, each $R^{2A}$ is independently hydrogen, methyl, fluoro, or —$CH_2F$.

In some embodiments of the compounds of Formula (Ig), (Ig1), (Ig2), or (Ig3) or a stereoisomer, tautomer, or pharmaceutically acceptable salt thereof, each $R^{2A}$ is independently hydrogen, methyl, fluoro, —$CHF_2$, or —$CH_2F$.

In some embodiments of the compounds of Formula (Ig) or (Ig1) or a stereoisomer, tautomer, or pharmaceutically acceptable salt thereof, at least one of $R^3$ or $R^4$ is fluoro. In one embodiment of Formula (Ig), (Ig1), (Ig2), or (Ig3) or a stereoisomer, tautomer, or pharmaceutically acceptable salt thereof, at least one $R^3$ is fluoro.

In some embodiments of the compounds of Formula (Ig), (Ig1), (Ig2), or (Ig3) or a stereoisomer, tautomer, or pharmaceutically acceptable salt thereof, $X^1$ is N.

In some embodiments of the compounds of Formula (Ig), (Ig1), (Ig2), or (Ig3) or a stereoisomer, tautomer, or pharmaceutically acceptable salt thereof, $X^1$ is CH.

In some embodiments of the compounds described herein or a stereoisomer, tautomer, or pharmaceutically acceptable salt thereof, the compound has formula (Ih) or (Ih1):

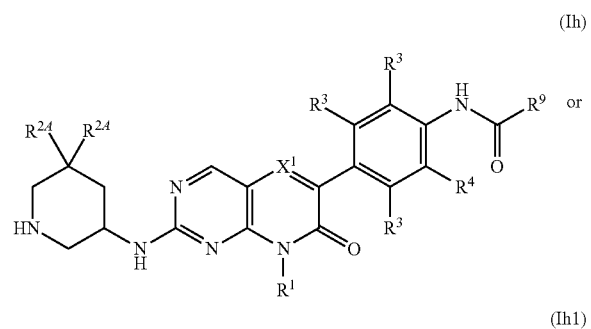

(Ih)

(Ih1)

where $X^1$, $R^1$, $R^{2A}$, $R^3$, $R^4$, and $R^9$ are as described herein and m is 1, 2, 3, 4, or 5.

In some embodiments of the compounds described herein or a stereoisomer, tautomer, or pharmaceutically acceptable salt thereof, the compound has formula (Ih2) or (Ih3):

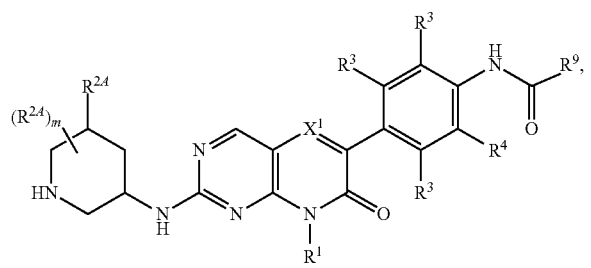

(Ih2)

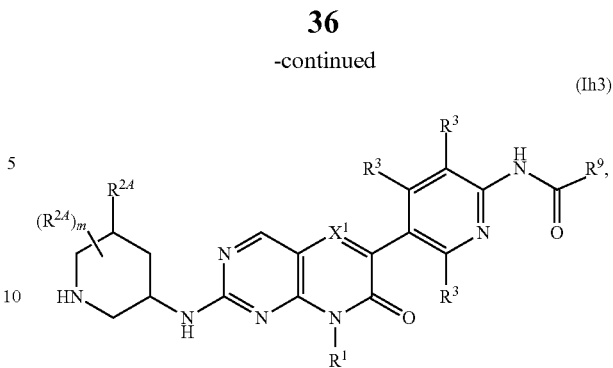

(Ih3)

where $X^1$, $R^1$, $R^{2A}$, $R^3$, and $R^9$ are as described herein and m is 1, 2, 3, 4, or 5.

In one embodiment, m is 1.

In some embodiments of the compounds of Formula (Ih), (Ih1), (Ih2), or (Ih3) or a stereoisomer, tautomer, or pharmaceutically acceptable salt thereof, each $R^{2A}$ is independently hydrogen, methyl, fluoro, or —$CH_2F$.

In some embodiments of the compounds of Formula (Ih) or (Ih1) or a stereoisomer, tautomer, or pharmaceutically acceptable salt thereof, at least one of $R^3$ and $R^4$ is fluoro. In one embodiment of Formula (Ih), (Ih1), (Ih2), or (Ih3) or a stereoisomer, tautomer, or pharmaceutically acceptable salt thereof, at least one $R^3$ is fluoro.

In some embodiments of the compounds of Formula (Ih), (Ih1), (Ih2), or (Ih3) or a stereoisomer, tautomer, or pharmaceutically acceptable salt thereof, $X^1$ is N.

In some embodiments of the compounds of Formula (Ih), (Ih1), (Ih2), or (Ih3) or a stereoisomer, tautomer, or pharmaceutically acceptable salt thereof, $X^1$ is CH.

In some embodiments of the compounds described herein or a stereoisomer, tautomer, or pharmaceutically acceptable salt thereof, the compound has formula (Ii) or (Ij):

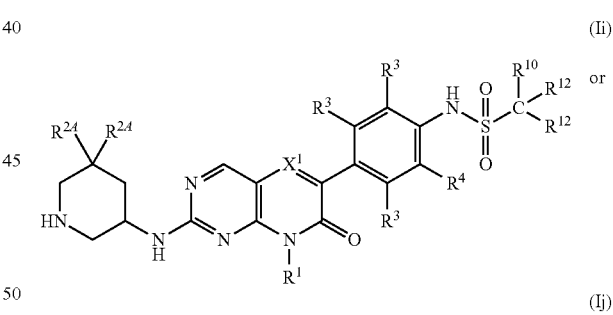

(Ii)

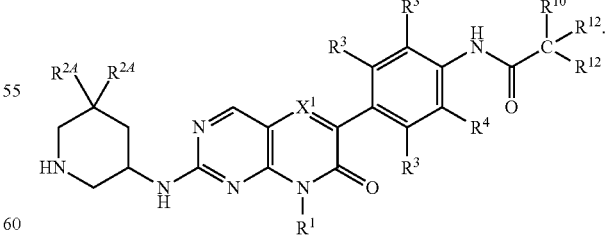

(Ij)

where $X^1$, $R^1$, $R^{2A}$, $R^3$, $R^4$, $R^{10}$, and $R^{12}$ are as described herein.

In some embodiments of the compounds described herein or a stereoisomer, tautomer, or pharmaceutically acceptable salt thereof, the compound has formula (Ii1) or (Ij1):

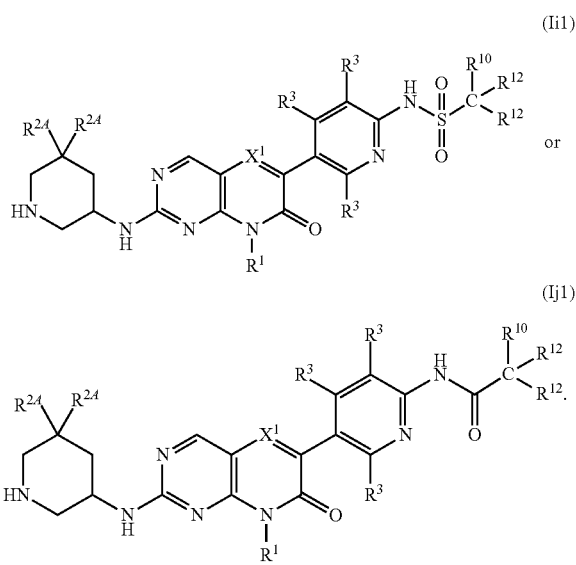

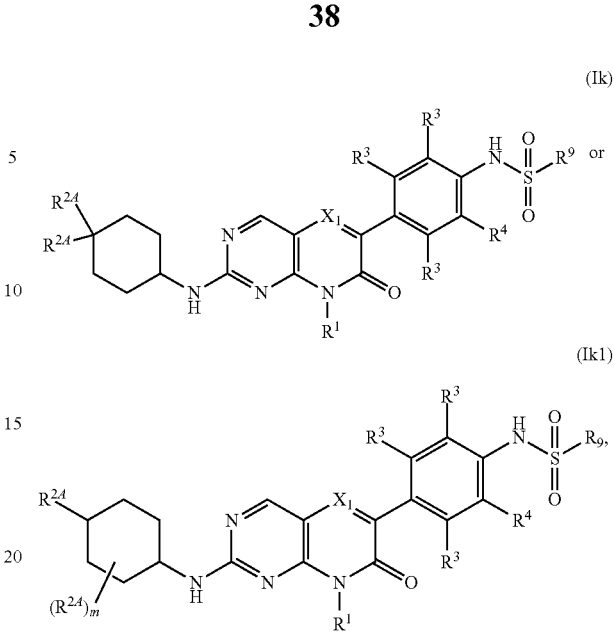

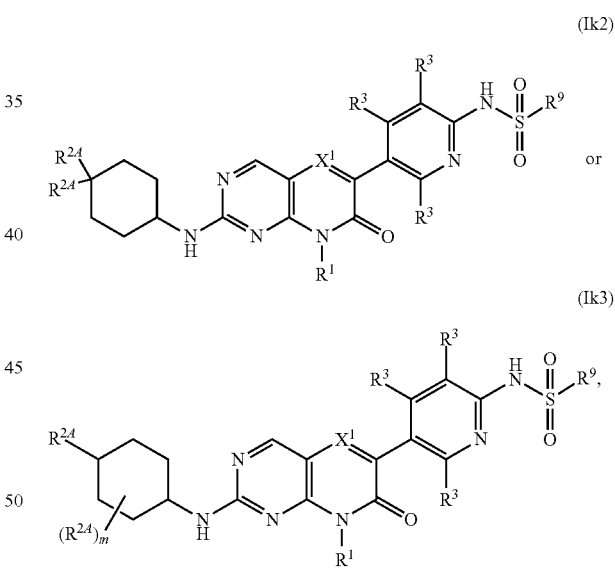

where $X^1$, $R^1$, $R^{2A}$, $R^3$, $R^{10}$, and $R^{12}$ are as described herein.

In some embodiments of the compounds of Formula (Ii), (Ij), (Ii1), or (Ij1) or a stereoisomer, tautomer, or pharmaceutically acceptable salt thereof, each $R^{2A}$ is independently hydrogen, methyl, fluoro, or —CH$_2$F; $R^{10}$ is substituted phenyl or substituted $C_{1-3}$ alkyl; and $R^{12}$ is hydrogen, halogen, or $C_{1-3}$ alkyl or wherein both $R^{12}$ together form a cyclopropanyl, which may be unsubstituted or substituted with methyl or fluoro.

In one embodiment of the compounds of Formula (Ii), (Ij), (Ii1), or (Ij1) or a stereoisomer, tautomer, or pharmaceutically acceptable salt thereof, $R^{10}$ is phenyl optionally substituted as described herein with, for example, —CN, halogen (e.g. F or Cl), methoxy, or —CF$_3$.

In one embodiment of the compounds of Formula (Ii), (Ij), (Ii1), or (Ij1) or a stereoisomer, tautomer, or pharmaceutically acceptable salt thereof, $R^{10}$ is optionally substituted $C_1$-$C_4$ alkyl, wherein the alkyl is optionally substituted with halogen (e.g. F or Cl), $C_3$-$C_6$ cycloalkyl (e.g. cyclopropyl or cyclobutyl), pyrazolyl, or pyridinyl.

In one embodiment of the compounds of Formula (Ij) or (Ij1) or a stereoisomer, tautomer, or pharmaceutically acceptable salt thereof, $R^{10}$ is cyclopropyl or cyclobutyl.

In some embodiments of the compounds of Formula (Ii) or (Ij) or a stereoisomer, tautomer, or pharmaceutically acceptable salt thereof, at least one of $R^3$ and $R^4$ is fluoro. In one embodiment of Formula (Ii), (Ij), (Ii1), or (Ij1) or a stereoisomer, tautomer, or pharmaceutically acceptable salt thereof, at least one $R^3$ is fluoro.

In some embodiments of the compounds of Formula (Ii), (Ij), (Ii1), or (Ij1) or a stereoisomer, tautomer, or pharmaceutically acceptable salt thereof, $X^1$ is N.

In some embodiments of the compounds of Formula (Ii), (Ij), (Ii1), or (Ij1) or a stereoisomer, tautomer, or pharmaceutically acceptable salt thereof, $X^1$ is CH.

In some embodiments of the compounds described herein or a stereoisomer, tautomer, or pharmaceutically acceptable salt thereof, the compound has formula (Ik) or (Ik1):

where $X^1$, $R^1$, $R^{2A}$, $R^3$, $R^4$, and $R^9$ are as described herein and m is 1, 2, 3, 4, or 5.

In some embodiments of the compounds described herein or a stereoisomer, tautomer, or pharmaceutically acceptable salt thereof, the compound has formula (Ik2) or (Ik3):

where $X^1$, $R^1$, $R^{2A}$, $R^3$, and $R^9$ are as described herein and m is 1, 2, 3, 4, or 5.

In one embodiment, m is 1.

In some embodiments of the compounds of Formula (Ik), (Ik1), (Ik2), or (Ik3), or a stereoisomer, tautomer, or pharmaceutically acceptable salt thereof, each $R^{2A}$ is independently hydrogen, hydroxyl, or —N(CH$_3$)$_2$. In some embodiments of the compounds of Formula (Ik), (Ik1), (Ik2), or (Ik3), or a stereoisomer, tautomer, or pharmaceutically acceptable salt thereof, $R^9$ can be as defined herein, for example, as set forth in Formula (Ie).

In some embodiments of the compounds of Formula (Ik) or (Ik1) or a stereoisomer, tautomer, or pharmaceutically acceptable salt thereof, at least one of $R^3$ and $R^4$ is fluoro. In one embodiment of Formula (Ik), (Ik1), (Ik2), or (Ik3) or a stereoisomer, tautomer, or pharmaceutically acceptable salt thereof, at least one $R^3$ is fluoro.

In some embodiments of the compounds of Formula (Ik), (Ik1), (Ik2), or (Ik3), or a stereoisomer, tautomer, or pharmaceutically acceptable salt thereof, $X^1$ is N.

In some embodiments of the compounds of Formula (Ik), (Ik1), (Ik2), or (Ik3), or a stereoisomer, tautomer, or pharmaceutically acceptable salt thereof, $X^1$ is CH.

In some embodiments of the compounds described herein or a stereoisomer, tautomer, or pharmaceutically acceptable salt thereof, the compound has formula (II):

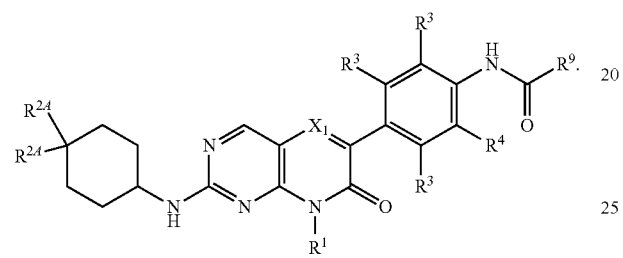

(II)

where $X^1$, $R^1$, $R^{2A}$, $R^3$, $R^4$, and $R^9$ are as described herein.

In some embodiments of the compounds described herein or a stereoisomer, tautomer, or pharmaceutically acceptable salt thereof, the compound has formula (Il1):

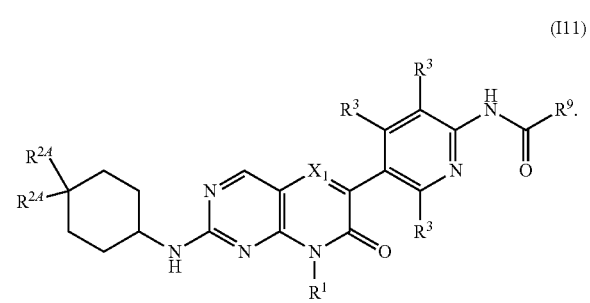

(Il1)

where $X^1$, $R^1$, $R^{2A}$, $R^3$, and $R^9$ are as described herein.

In some embodiments of the compounds of Formula (II) or (Il1) or a stereoisomer, tautomer, or pharmaceutically acceptable salt thereof, each $R^{2A}$ is independently hydrogen, hydroxyl, or —N(CH$_3$)$_2$.

In some embodiments of the compounds of Formula (II) or a stereoisomer, tautomer, or pharmaceutically acceptable salt thereof, at least one of $R^3$ and $R^4$ is fluoro. In one embodiment of Formula (Il) or (Il1) or a stereoisomer, tautomer, or pharmaceutically acceptable salt thereof, at least one $R^3$ is fluoro.

In some embodiments of the compounds of Formula (Il1) or (Il1) or a stereoisomer, tautomer, or pharmaceutically acceptable salt thereof, $X^1$ is N.

In some embodiments of the compounds of Formula (Il1) or (Il1) or a stereoisomer, tautomer, or pharmaceutically acceptable salt thereof, $X^1$ is CH.

In some embodiments of the compounds described herein or a stereoisomer, tautomer, or pharmaceutically acceptable salt thereof, the compound has formula (Im):

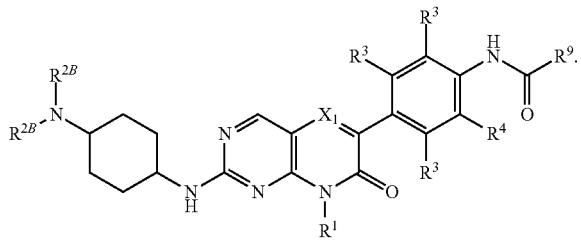

(Im)

where $X^1$, $R^1$, $R^{2B}$, $R^3$, $R^4$, and $R^9$ are as described herein.

In some embodiments of the compounds described herein or a stereoisomer, tautomer, or pharmaceutically acceptable salt thereof, the compound has formula (Im1):

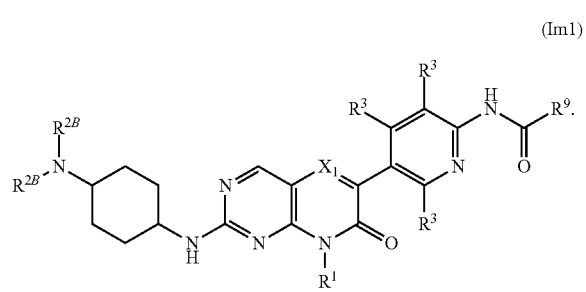

(Im1)

where $X^1$, $R^1$, $R^{2B}$, $R^3$, and $R^7$ are as described herein.

In some embodiments of the compounds of Formula (Im) or a stereoisomer, tautomer, or pharmaceutically acceptable salt thereof, at least one of $R^3$ and $R^4$ is fluoro. In one embodiment of Formula (Im) or (Im1) or a stereoisomer, tautomer, or pharmaceutically acceptable salt thereof, at least one $R^3$ is fluoro.

In one embodiment, the cyclohexyl ring is further substituted with one $R^{2A}$ as defined herein.

In some embodiments of the compounds of Formula (Im) or (Im1) or a stereoisomer, tautomer, or pharmaceutically acceptable salt thereof, $X^1$ is N.

In some embodiments of the compounds of Formula (Im) or (Im1) or a stereoisomer, tautomer, or pharmaceutically acceptable salt thereof, $X^1$ is CH.

In some embodiments of the compounds of Formula (Im) or (Im1) or a stereoisomer, tautomer, or pharmaceutically acceptable salt thereof, each $R^{2B}$ is CH$_3$.

In some embodiments of the compounds described herein or a stereoisomer, tautomer, or pharmaceutically acceptable salt thereof, the compound has formula (In) or (Io):

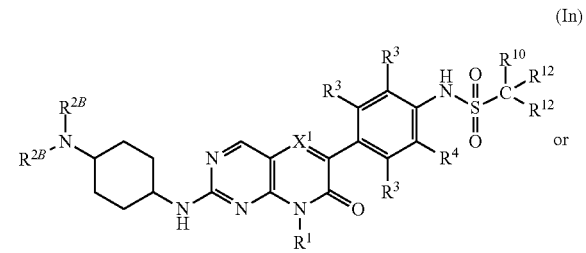

(In)

or

-continued (Io)

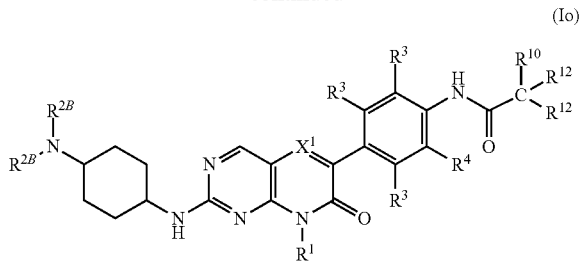

where $X^1$, $R^1$, $R^{2B}$, $R^3$, $R^4$, $R^{10}$, and $R^{12}$ are as described herein.

In some embodiments of the compounds described herein or a stereoisomer, tautomer, or pharmaceutically acceptable salt thereof, the compound has formula (In1) or (Io1):

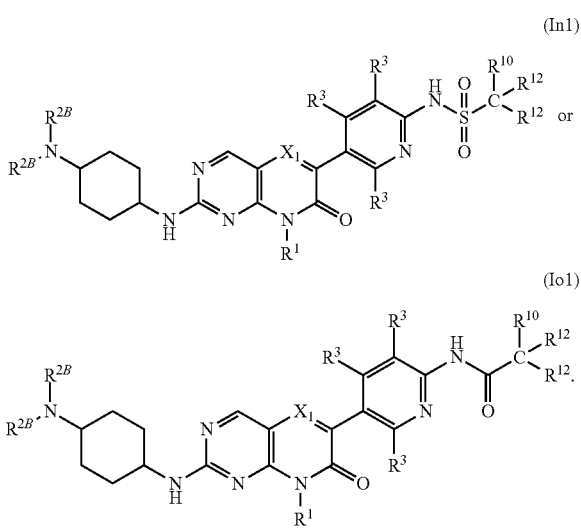

where $X^1$, $R^1$, $R^{2B}$, $R^3$, $R^{10}$, and $R^{12}$ are as described herein.

In some embodiments of the compounds of Formula (In), (Io), (In1), or (Io1), or a stereoisomer, tautomer, or pharmaceutically acceptable salt thereof, $R^{10}$ is substituted phenyl or substituted $C_1$-$C_3$ alkyl; and $R^{12}$ is hydrogen, halogen, or $C_1$-$C_3$ alkyl or wherein both $R^{12}$ together form a cyclopropanyl, which may be unsubstituted or substituted with methyl or fluoro.

In some embodiments of the compounds of Formula (In), (Io), (In1), or (Io1), or a stereoisomer, tautomer, or pharmaceutically acceptable salt thereof, $R^{10}$ and $R^{12}$ can be as defined herein, for example, as set forth in Formula (Ii) and (Ij), respectively.

In some embodiments of the compounds of Formula (In) or (Io) or a stereoisomer, tautomer, or pharmaceutically acceptable salt thereof, at least one of $R^3$ and $R^4$ is fluoro. In one embodiment of Formula (In), (Io), (In1), or (Io1) or a stereoisomer, tautomer, or pharmaceutically acceptable salt thereof, at least one $R^3$ is fluoro.

In some embodiments of the compounds of Formula (In), (Io), (In1), or (Io1), or a stereoisomer, tautomer, or pharmaceutically acceptable salt thereof, $X^1$ is N.

In some embodiments of the compounds of Formula (In), (Io), (In1), or (Io1), or a stereoisomer, tautomer, or pharmaceutically acceptable salt thereof, $X^1$ is CH.

In some embodiments of the compounds of Formula (In), (Io), (In1), or (Io1), or a stereoisomer, tautomer, or pharmaceutically acceptable salt thereof, each $R^{2B}$ is $CH_3$.

In some embodiments of the compounds described herein or a stereoisomer, tautomer, or pharmaceutically acceptable salt thereof, the compound has formula (Ip):

(Ip)

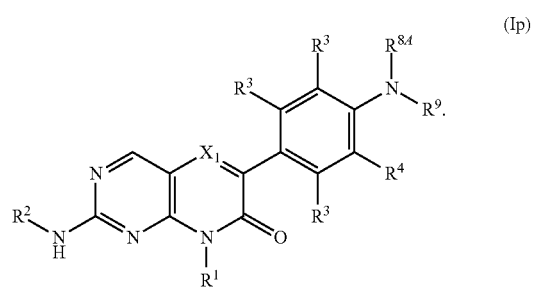

wherein $X^1$, $R^1$, $R^2$, $R^3$, $R^4$, $R^{8A}$, and $R^9$ are as defined herein.

In some embodiments of the compounds described herein or a stereoisomer, tautomer, or pharmaceutically acceptable salt thereof, the compound has formula (Iq) or (Iq1):

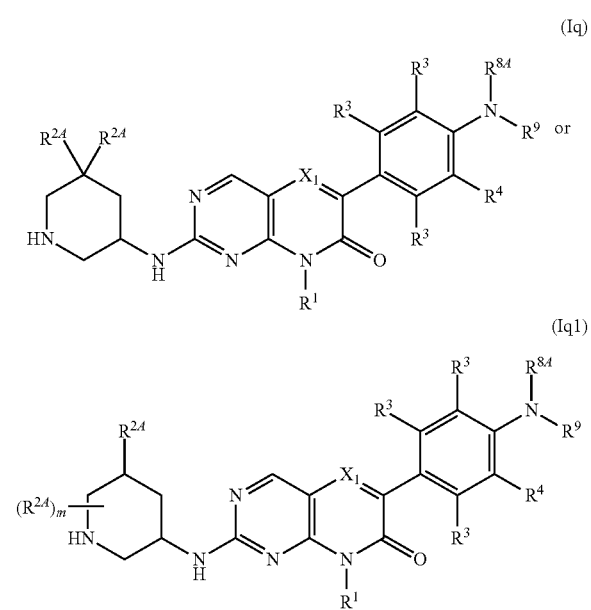

wherein $X^1$, $R^1$, $R^{2A}$, $R^3$, $R^4$, $R^{8A}$, and $R^9$ are as defined herein and m is 1, 2, 3, or 4.

In some embodiments of the compounds described herein or a stereoisomer, tautomer, or pharmaceutically acceptable salt thereof, the compound has formula (Iq2) or (Iq3):

(Iq2)

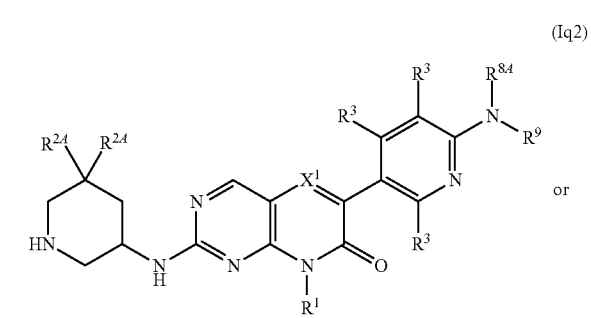

or

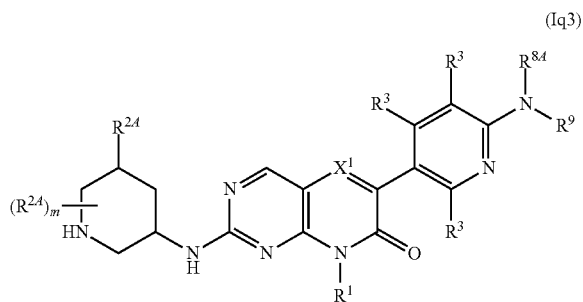

(Iq3)

wherein $X^1$, $R^1$, $R^{2A}$, $R^3$, $R^4$, $R^{8A}$, and $R^9$ are as defined herein and m is 1, 2, 3, or 4.

In some embodiments of the compounds described herein or a stereoisomer, tautomer, or pharmaceutically acceptable salt thereof, the compound has formula (Ir) or (Ir1):

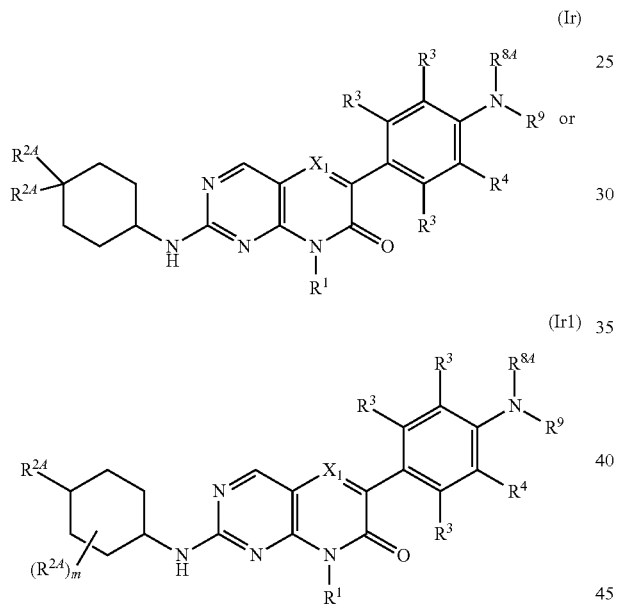

where $X^1$, $R^1$, $R^{2A}$, $R^3$, $R^4$, $R^{8A}$, and $R^9$ are as defined herein and m is 1, 2, 3, or 4.

In some embodiments of the compounds described herein or a stereoisomer, tautomer, or pharmaceutically acceptable salt thereof, the compound has formula (Ir2) or (Ir3):

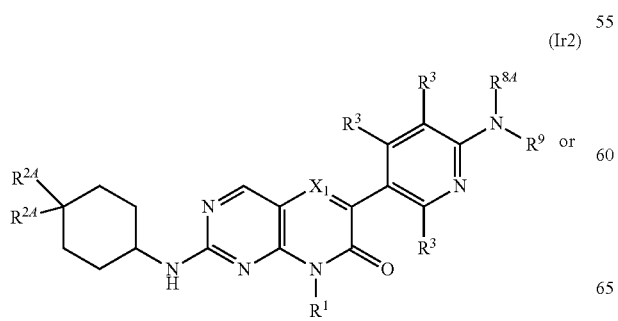

(Ir2)

wherein $X^1$, $R^1$, $R^{2A}$, $R^3$, $R^4$, $R^{8A}$, and $R^9$ are as defined herein and m is 1, 2, 3, or 4.

In one embodiment provided herein are compounds or a stereoisomer, tautomer, or pharmaceutically acceptable salt thereof having Formula (Ib1) or (Ib2):

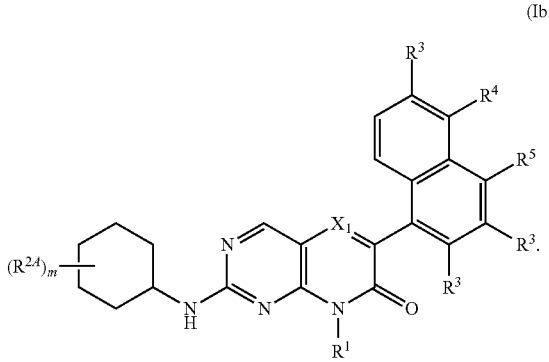

wherein $X^1$, $R^1$, $R^{2A}$, $R^3$, $R^4$, $R^5$, are as defined herein and m is 0, 1, 2, 3, or 4.

In one embodiment provided herein are compounds or a stereoisomer, tautomer, or pharmaceutically acceptable salt thereof having Formula (Ib1a) or (Ib1b):

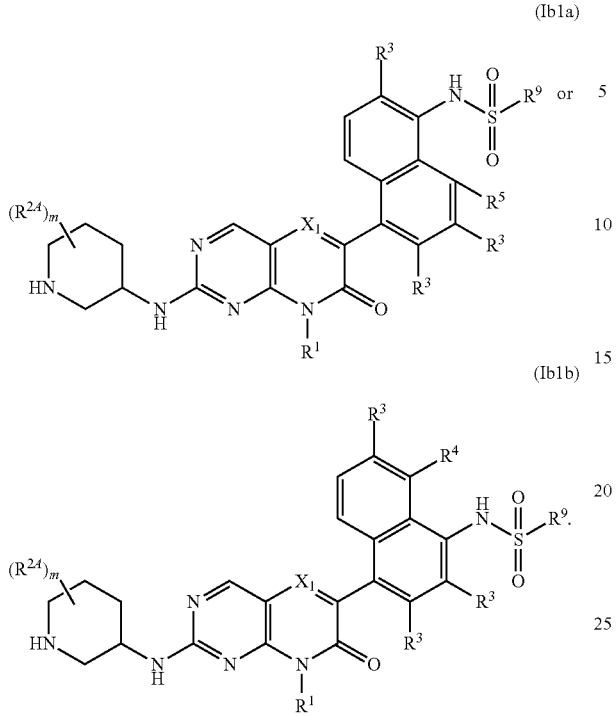

(Ib1a)

(Ib1b)

wherein $X^1$, $R^1$, $R^{2A}$, $R^3$, $R^4$, $R^5$, $R^9$, are as defined herein and m is 0, 1, 2, 3, or 4.

In one embodiment provided herein are compounds or a stereoisomer, tautomer, or pharmaceutically acceptable salt thereof having Formula (Ib1c) or (Ib1d):

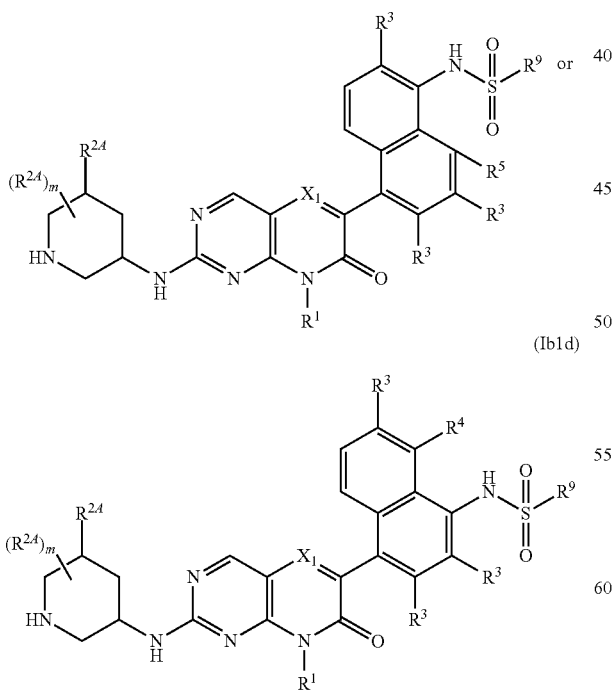

(Ib1c)

(Ib1d)

wherein $X^1$, $R^1$, $R^{2A}$, $R^3$, $R^4$, $R^5$, $R^9$, are as defined herein and m is 0, 1, 2, 3, or 4.

In one embodiment provided herein are compounds or a stereoisomer, tautomer, or pharmaceutically acceptable salt thereof having Formula (Ib1e) or (Ib1f):

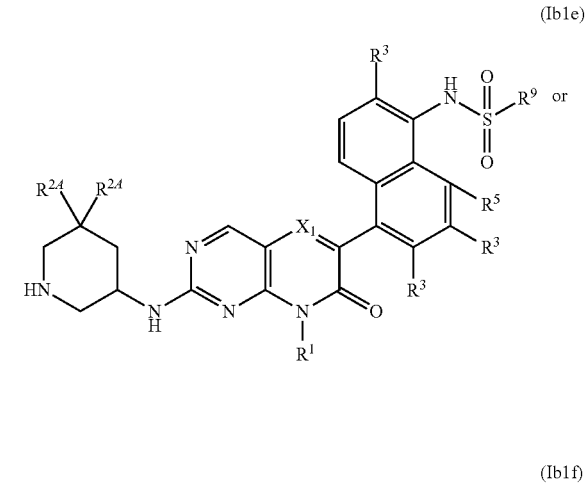

(Ib1e)

(Ib1f)

wherein $X^1$, $R^1$, $R^{2A}$, $R^3$, $R^4$, $R^5$, and $R^9$ are as defined herein.

In one embodiment provided herein are compounds or a stereoisomer, tautomer, or pharmaceutically acceptable salt thereof having Formula (Ib1g) or (Ib1h):

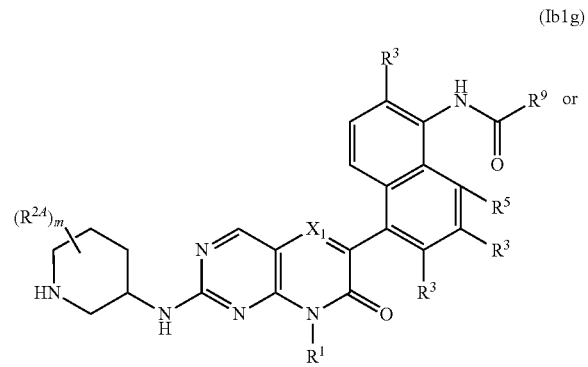

(Ib1g)

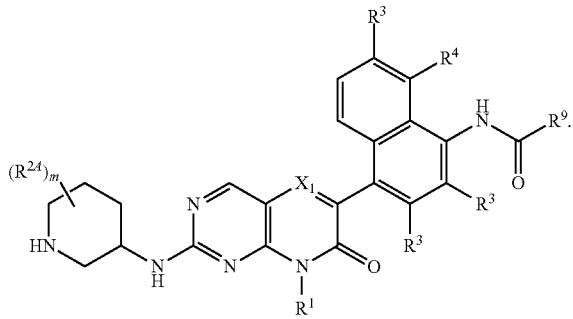

(Ib1h)

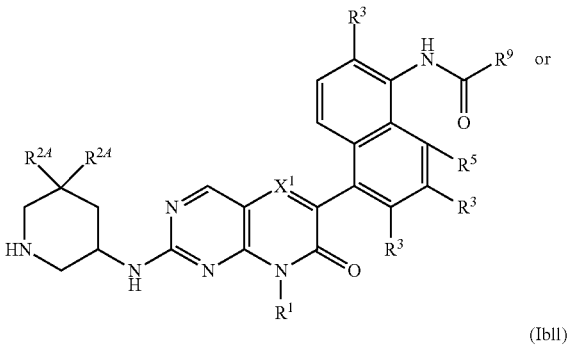

(Ib1k)

wherein $X^1$, $R^1$, $R^{2A}$, $R^3$, $R^4$, $R^5$, $R^9$, are as defined herein and m is 0, 1, 2, 3, or 4.

In one embodiment provided herein are compounds or a stereoisomer, tautomer, or pharmaceutically acceptable salt thereof having Formula (Ib1i) or (Ib1j):

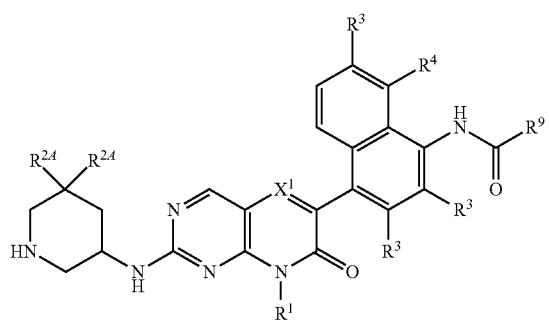

(Ib1l)

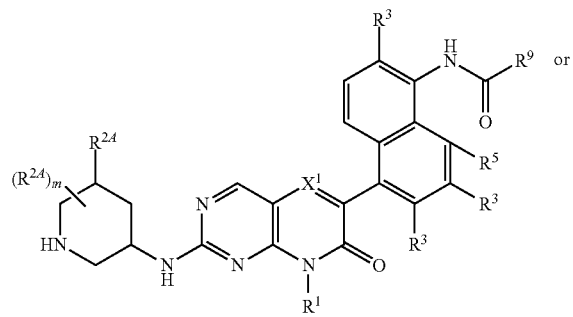

(Ib1i)

wherein $X^1$, $R^1$, $R^{2A}$, $R^3$, $R^4$, $R^5$, and $R^9$ are as defined herein.

In one embodiment provided herein are compounds or a stereoisomer, tautomer, or pharmaceutically acceptable salt thereof having Formula (Ib2A) or (Ib2B):

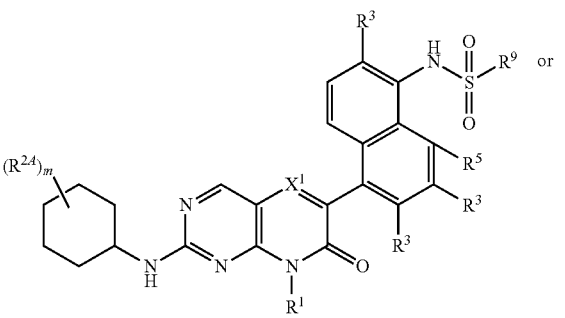

(Ib2A)

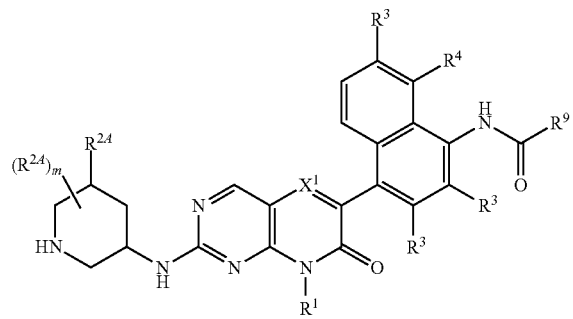

(Ib1j)

wherein $X^1$, $R^1$, $R^{2A}$, $R^3$, $R^4$, $R^5$, $R^9$, are as defined herein and m is 0, 1, 2, 3, or 4.

In one embodiment provided herein are compounds or a stereoisomer, tautomer, or pharmaceutically acceptable salt thereof having Formula (Ib1k) or (Ib1l):

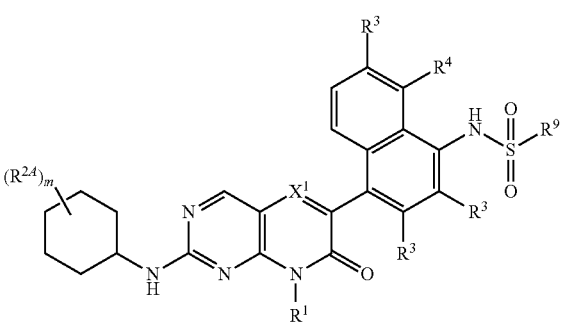

(Ib2B)

wherein $X^1$, $R^1$, $R^{2A}$, $R^3$, $R^4$, $R^5$, $R^9$, are as defined herein and m is 0, 1, 2, 3, or 4.

In one embodiment provided herein are compounds or a stereoisomer, tautomer, or pharmaceutically acceptable salt thereof having Formula (Ib2c) or (Ib2d):

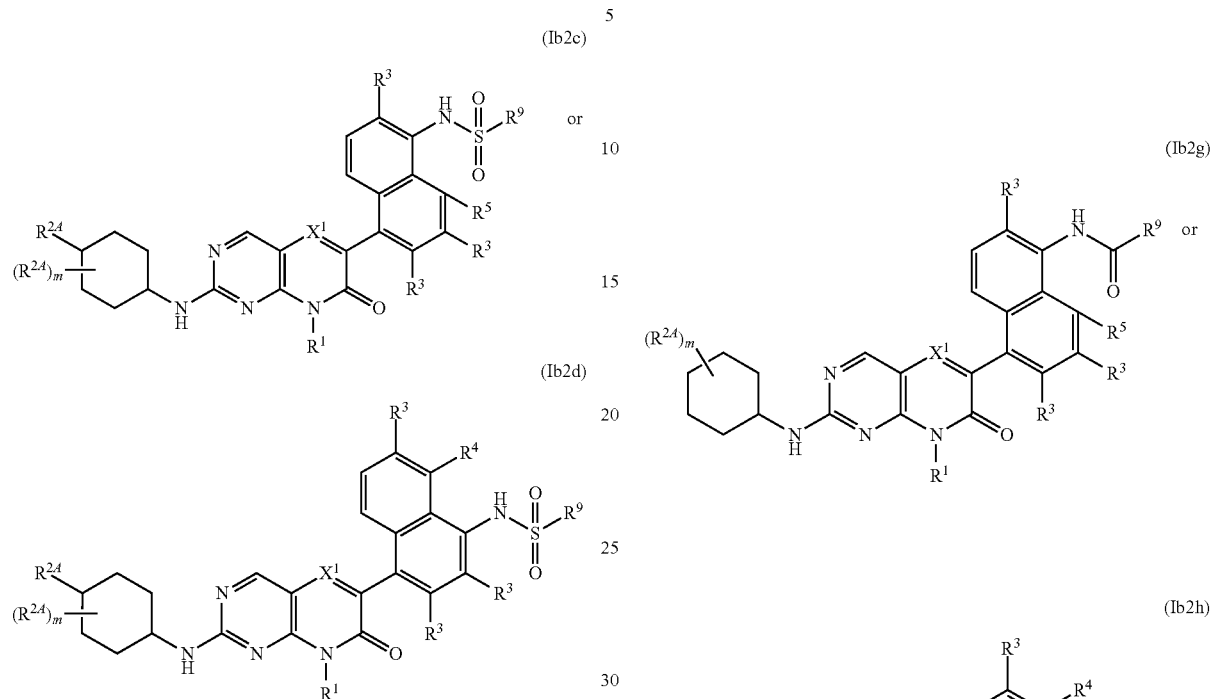

wherein $X^1$, $R^1$, $R^{2A}$, $R^3$, $R^4$, $R^5$, $R^9$, are as defined herein and m is 0, 1, 2, 3, or 4.

In one embodiment provided herein are compounds or a stereoisomer, tautomer, or pharmaceutically acceptable salt thereof having Formula (Ib2e) or (Ib2f):

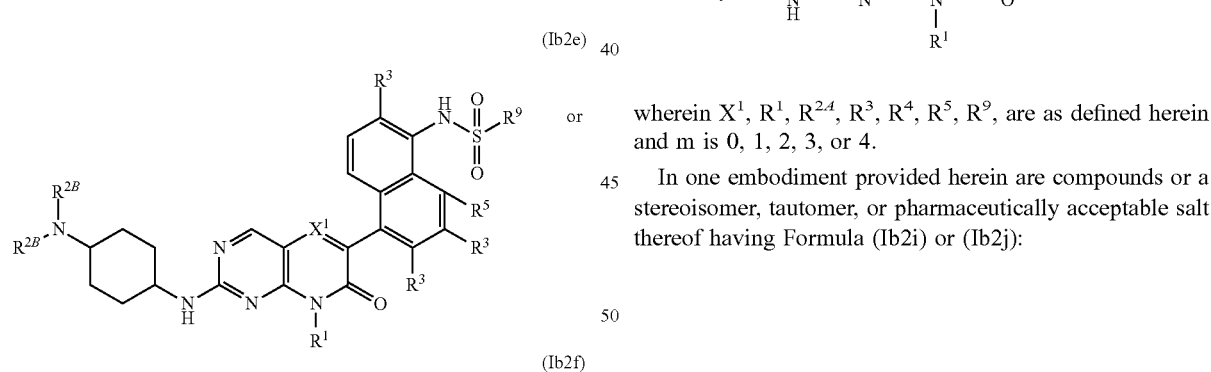

wherein $X^1$, $R^1$, $R^{2B}$, $R^3$, $R^4$, $R^5$, and $R^9$ are as defined herein.

In one embodiment provided herein are compounds or a stereoisomer, tautomer, or pharmaceutically acceptable salt thereof having Formula (Ib2g) or (Ib2h):

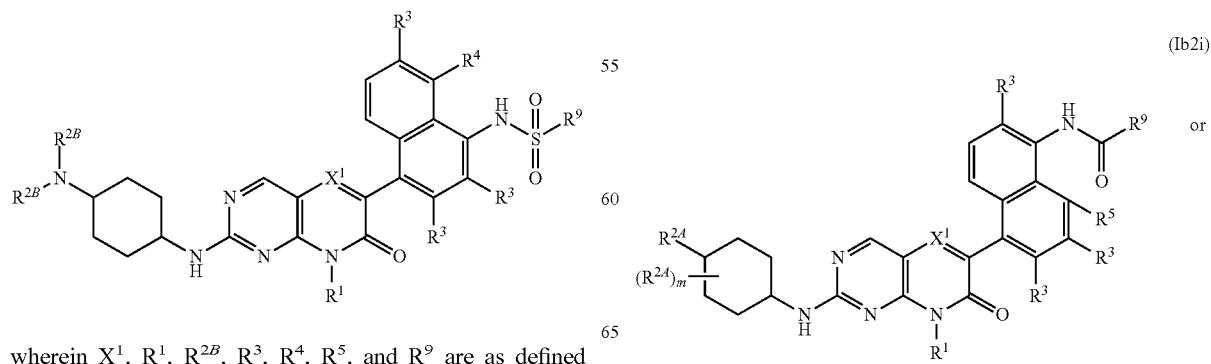

wherein $X^1$, $R^1$, $R^{2A}$, $R^3$, $R^4$, $R^5$, $R^9$, are as defined herein and m is 0, 1, 2, 3, or 4.

In one embodiment provided herein are compounds or a stereoisomer, tautomer, or pharmaceutically acceptable salt thereof having Formula (Ib2i) or (Ib2j):

-continued (Ib2j)

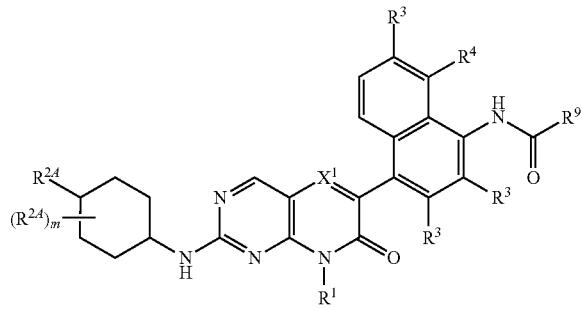

wherein X¹, R¹, R²ᴬ, R³, R⁴, R⁵, R⁹, are as defined herein and m is 0, 1, 2, 3, or 4.

In one embodiment provided herein are compounds or a stereoisomer, tautomer, or pharmaceutically acceptable salt thereof having Formula (Ib2k) or (Ib2l):

(Ib2k)

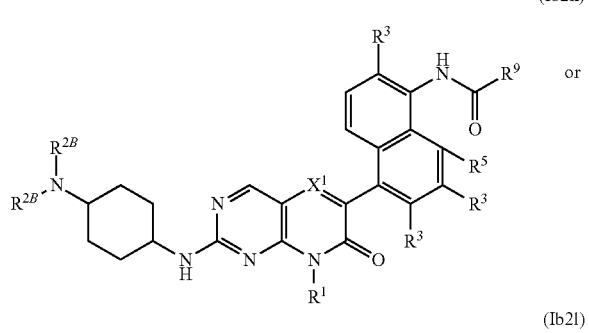

(Ib2l)

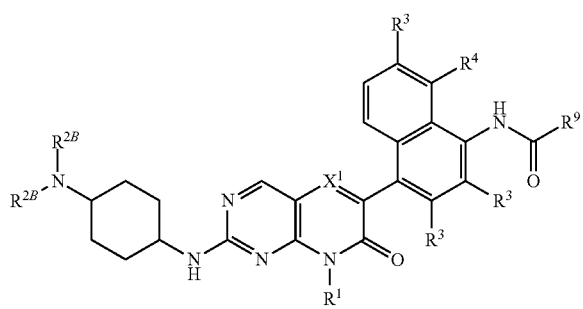

wherein X¹, R¹, R²ᴮ, R³, R⁴, R⁵, R⁹, are as defined herein and m is 0, 1, 2, 3, or 4.

In another aspect provided herein are compounds having Formula (II):

(II)

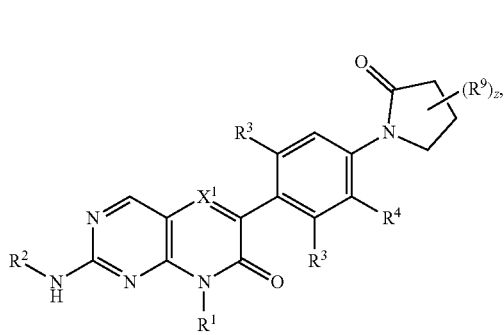

wherein, X¹, R¹, R², R³, R⁴, and R⁹ are as defined herein and z is 1, 2, or 3. In a preferred embodiment, z is 1.

In one aspect provided herein are compounds having formula (V):

(V)

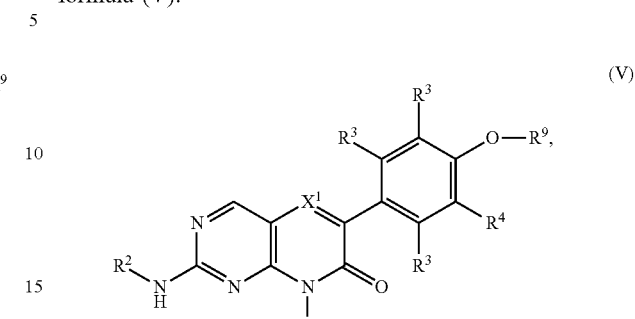

where R¹, R², R³, R⁴, and R⁹ are as defined herein for compounds of formula (Ia).

In one embodiment of the compounds of formula (V), R⁹ is $C_1$-$C_6$ alkyl, optionally substituted with one or more $R^{10}$ as described herein. In another embodiment of the compounds of formula (V), R⁹ is $C_1$-$C_6$ unsubstituted alkyl. In still another embodiment of the compounds of formula (V), R⁹ is methyl, ethyl, propyl, or isopropyl.

In some embodiments of compounds described herein or a stereoisomer, tautomer, or pharmaceutically acceptable salt thereof, the compound is selected from the group consisting of: Compound 25, Compound 33, Compound 102, Compound 102A, Compound 102B, Compound 110, Compound 110A, Compound 110B, Compound 118, compound 118A, Compound 118B, Compound 126, Compound 138, Compound 154, Compound 157, Compound 165, Compound 179B, Compound 154, Compound 157, Compound 203, Compound 203A, Compound 203B, Compound 206, Compound 213, Compound 221, Compound 231, Compound 105, Compound 106, Compound 146, Compound 67, Compound 107, Compound 112, Compound 122, Compound 123, Compound 129, Compound 141, Compound 170, and Compound 175.

In some embodiments of compounds described herein or a stereoisomer, tautomer, or pharmaceutically acceptable salt thereof, the compound is selected from the group consisting of Compound 25, Compound 33, Compound 102, Compound 102A, Compound 102B, Compound 110A, Compound 118A, Compound 118B, Compound 126, Compound 138, Compound 154, Compound 157, Compound 165, Compound 179, Compound 179A, Compound 179B, Compound 154, Compound 157, Compound 203, Compound 203A, Compound 203B, Compound 206, Compound 213, Compound 221, and Compound 231.

In some embodiments of compounds described herein or a stereoisomer, tautomer, or pharmaceutically acceptable salt thereof, the compound is selected from the group consisting of Compound 105, Compound 106, and Compound 146.

In some embodiments of compounds described herein or a stereoisomer, tautomer, or pharmaceutically acceptable salt thereof, the compound is selected from the group consisting of Compound 67, Compound 107, Compound 110, Compound 110A, Compound 110B, Compound 112, Compound 122, Compound 123, Compound 129, Compound 141, Compound 170, and Compound 175.

In some embodiments of compounds described herein or a stereoisomer, tautomer, or pharmaceutically acceptable salt thereof, the compound is selected from the group consisting of Compound 176, Compound 167, Compound 68, Compound 166, Compound 170, Compound 171, Compound 175, Compound 176, Compound 181, Compound 181A, Compound 181B, Compound 183, Compound 185, Compound 190, Compound 192, Compound 192A, Compound 192B, Compound 67, Compound 168, Compound 168A, Compound 168B, Compound 179, Compound 179A, and Compound 179B.

In some embodiments of compounds described herein or a stereoisomer, tautomer, or pharmaceutically acceptable salt thereof, the compound is selected from the group consisting of Compound 176, and Compound 167.

In some embodiments of compounds described herein or a stereoisomer, tautomer, or pharmaceutically acceptable salt thereof, the compound is selected from the group consisting of Compound 68, Compound 166, Compound 170, Compound 171, Compound 175, Compound 176, Compound 181, Compound 181A, Compound 181B, Compound 183, Compound 185, Compound 190, Compound 192, Compound 192A, and Compound 192B.

In some embodiments of compounds described herein or a stereoisomer, tautomer, or pharmaceutically acceptable salt thereof, the compound is selected from the group consisting of Compound 67, Compound 168A, Compound 168B, and Compound 179B.

Representative compounds are listed in Tables 1 and 2. It is understood that individual enatiomers and diastereomers are included in the Tables below by Compound No. and Compound Name, and their corresponding structures can be readily determined therefrom. Assignment of configuration at chiral centers in separated stereoisomers may be tentative, and depicted in Tables 1 and 2 structures for illustrative purposes, before stereochemistry is definitively established, such as from x-ray crystallographic data. In some cases, stereoisomers are separated and tested for biological activity before the stereochemistry of the separated stereoisomers is determined. In some cases, the compounds are tested as racemic or diastereomeric mixtures. Where more than one potency value is entered on a row, separated stereoisomers represented by the structure and name on that row were tested. In some instances, the enantiomers or diastereomers are identified by their respective perperties, for example, retention times on a chiral HPLC or its biological activities, and the absolute stereo configurations of the chiral centers are arbitrarily assigned.

Where more than one name is associated with a compound or intermediate in Tables 1 and 2, or in the Example provided herein, the chemical structure shall define the compound.

TABLE 1

Representative compounds:

| | Structure | Name | IRE1α HTRF (IC$_{50}$) (μM) | Mass Spec. M + H$^+$ |
|---|---|---|---|---|
| 1 | 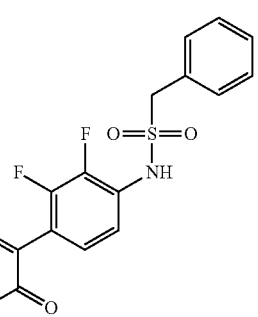 | (S)-N-(2,3-difluoro-4-(8-methyl-7-oxo-2-(piperidin-3-ylamino)-7,8-dihydropyrido[2,3-d]pyrimidin-6-yl)phenyl)-1-phenylmethane sulfonamide | 0.0028 | 541.2 |
| 2 | 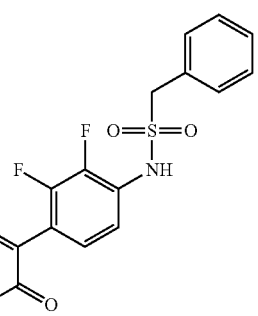 | N-(2,3-difluoro-4-(2-(((3S,5S)-5-fluoro-piperidin-3-yl)amino)-8-methyl-7-oxo-7,8-dihydropyrido[2,3-d]-pyrimidin-6-yl)phenyl)-1-phenylmethane sulfonamide | 0.0021 | 559.2 |

TABLE 1-continued

Representative compounds:

| | | | | |
|---|---|---|---|---|
| 3 |  | (S)-N-(4-(8-ethyl-7-oxo-2-(piperidin-3-yl-amino)-7,8-dihydro-pyrido[2,3-d]pyrimidin-6-yl)-2,3-difluorophen-yl)-1-phenylmethane sulfonamide | 0.00068 | 555.2 |
| 4 | 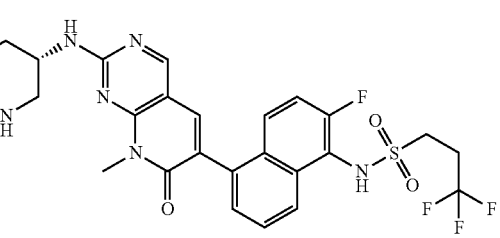 | (S)-3,3,3-trifluoro-N-(2-fluoro-5-(8-methyl-7-oxo-2-(piperidin-3-ylamino)-7,8-dihydro-pyrido[2,3-d]pyrimidin-6-yl)naphthalen-1-yl)-propane-1-sulfonamide | 0.005 | 579.2 |
| 5 | 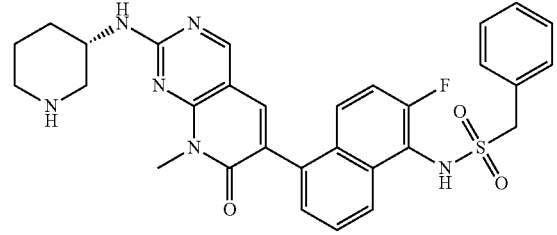 [SMILES: Cn1c(=O)c(-c2cccc3c(NS(=O)(=O)Cc4ccccc4)c(F)ccc23)cc2cnc(N[C@H]3CCCNC3)nc21] | (S)-N-(2-fluoro-5-(8-methyl-7-oxo-2-(piperidin-3-ylamino)-7,8-dihydropyrido[2,3-d]-pyrimidin-6-yl)naphthalen-1-yl)-1-phenyl-methane sulfonamide | 0.00028 | 573.2 |
| 6 | 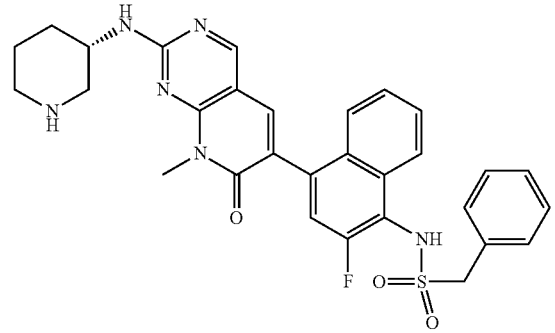 [SMILES: Cn1c(=O)c(-c2cc(F)c(NS(=O)(=O)Cc3ccccc3)c3ccccc23)cc2cnc(N[C@H]3CCCNC3)nc21] | (S)-N-(2-fluoro-4-(8-methyl-7-oxo-2-(piperidin-3-ylamino)-7,8-dihydropyrido[2,3-d]pyrimidin-6-yl)naphthalen-1-yl)-1-phenyl-methane sulfonamide | 0.00089 | 573.2 |
| 7 | 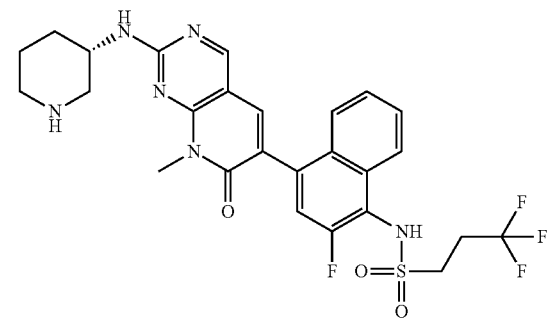 [SMILES: Cn1c(=O)c(-c2cc(F)c(NS(=O)(=O)CCC(F)(F)F)c3ccccc23)cc2cnc(N[C@H]3CCCNC3)nc21] | (S)-3,3,3-trifluoro-N-(2-fluoro-4-(8-methyl-7-oxo-2-(piperidin-3-ylamino)-7,8-dihydro-pyrido[2,3-d]pyrimidin-6-yl)naphthalen-1-yl)propane-1-sulfonamide | 0.0059 | 579.2 |

TABLE 1-continued

Representative compounds:

| # | Structure | Name | | |
|---|---|---|---|---|
| 8 | | (S)-N-(2-Fluoro-5-(8-methyl-7-oxo-2-(piperidin-3-yl)amino)-7,8-dihydropyrido[2,3-d]pyrimidin-6-yl)naphthalen-1-yl)propane-1-sulfonamide | 0.036 | 525.3 |
| 9 | | N-(2,3-difluoro-4-(2-(((3S,5S)-5-fluoropiperidin-3-yl)amino)-8-isopropyl-7-oxo-7,8-dihydropyrido[2,3-d]-pyrimidin-6-yl)phenyl)-1-phenylmethane sulfonamide | 0.00028 | 587.2 |
| 10 | | N-(4-(8-cyclopropyl-2-(((3S,5S)-5-fluoropiperidin-3-yl)amino)-7-oxo-7,8-dihydropyrido[2,3-d]pyrimidin-6-yl)-2,3-difluorophenyl)-1-phenylmethane sulfonamide | 0.0011 | 585.2 |
| 11 | | N-(4-(8-(2,2-difluoroethyl)-2-(((3S,5S)-5-fluoropiperidin-3-yl)-amino)-7-oxo-7,8-dihydropyrido[2,3-d]-pyrimidin-6-yl)-2,3-difluorophenyl)-1-phenylmethane sulfonamide | 0.0011 | 609.2 |

TABLE 1-continued

Representative compounds:

| | | | | |
|---|---|---|---|---|
| 12 | | N-(4-(8-ethyl-2-(((3S,5S)-5-fluoropiperidin-3-yl)amino)-7-oxo-7,8-dihydropyrido[2,3-d]pyrimidin-6-yl)-2,3-difluorophenyl)-1-phenylmethane sulfonamide | 0.00057 | 573.1 |
| 13 | | N-(4-(8-ethyl-2-(((3S,5S)-5-fluoro-piperidin-3-yl)amino)-7-oxo-7,8-dihydro-pyrido[2,3-d]pyrimidin-6-yl)-2,3-difluorophen-yl)propane-1-sulfonamide | 0.0083 | 525.2 |
| 14 | | N-(4-(8-ethyl-2-(((3S,5S)-5-fluoro-piperidin-3-yl)amino)-7-oxo-7,8-dihydro-pyrido[2,3-d]pyrimidin-6-yl)-2,3-difluorophen-yl)-3,3,3-trifluoropro-pane-1-sulfonamide | 0.0050 | 579.2 |
| 15 | | N-(4-(8-ethyl-2-(((3S,5S)-5-fluoro-piperidin-3-yl)amino)-7-oxo-7,8-dihydropyr-ido[2,3-d]pyrimidin-6-yl)-2,3,6-trifluoro-phenyl)-1-phenyl-methane sulfonamide | 0.00021 | 591.2 |

TABLE 1-continued

Representative compounds:

| | | | | |
|---|---|---|---|---|
| 16 | 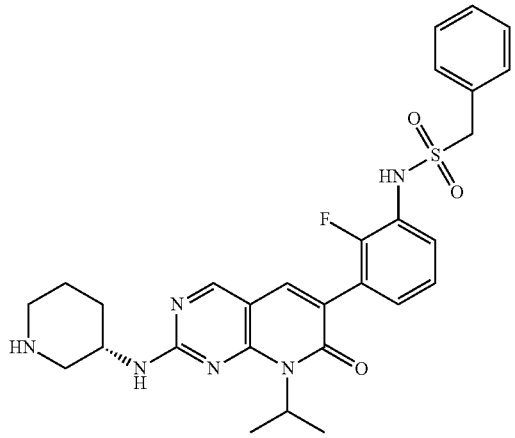 [SMILES: CC(C)n1c(=O)c(-c2cccc(NS(=O)(=O)Cc3ccccc3)c2F)cc2cnc(N[C@H]3CCCNC3)nc21] | (S)-N-(2-fluoro-3-(8-isopropyl-7-oxo-2-(piperidin-3-ylamino)-7,8-dihydropyrido[2,3-d]pyrimidin-6-yl)phenyl)-1-phenylmethane sulfonamide | 0.00580 | 551.2 |
| 17 | 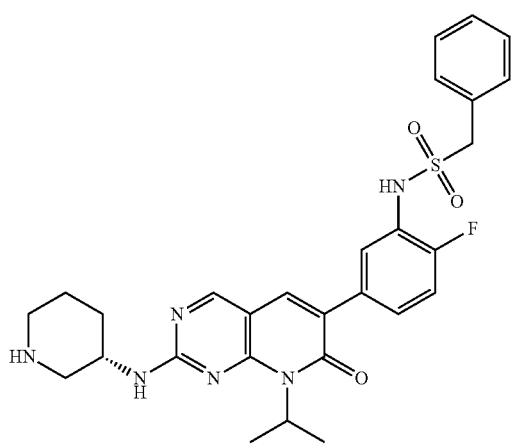 [SMILES: CC(C)n1c(=O)c(-c2ccc(F)c(NS(=O)(=O)Cc3ccccc3)c2)cc2cnc(N[C@H]3CCCNC3)nc21] | (S)-N-(2-fluoro-5-(8-isopropyl-7-oxo-2-(piperidin-3-ylamino)-7,8-dihydropyrido[2,3-d]pyrimidin-6-yl)phenyl)-1-phenylmethane sulfonamide hydrochloride | 0.01100 | 551.2 |
| 18 | 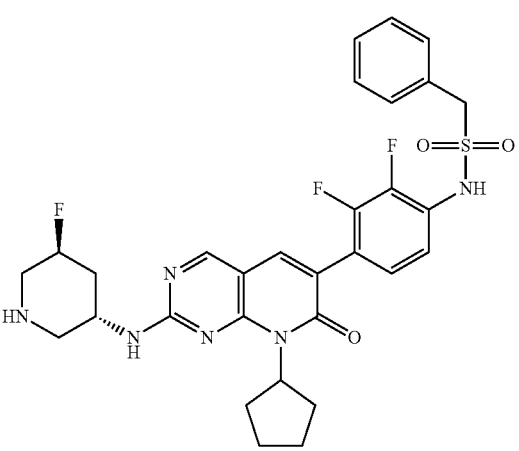 [SMILES: O=c1c(-c2ccc(NS(=O)(=O)Cc3ccccc3)c(F)c2F)cc2cnc(N[C@@H]3CNC[C@@H](F)C3)nc2n1C1CCCC1] | N-(4-(8-cyclopentyl-2-(((3S,5S)-5-fluoro-piperidin-3-yl)amino)-7-oxo-7,8-dihydro-pyrido[2,3-d]pyrimidin-6-yl)-2,3-difluorophenyl)-1-phenylmethane sulfonamide | 0.00041 | 613.2 |

TABLE 1-continued

Representative compounds:

| | | | | |
|---|---|---|---|---|
| 19 | 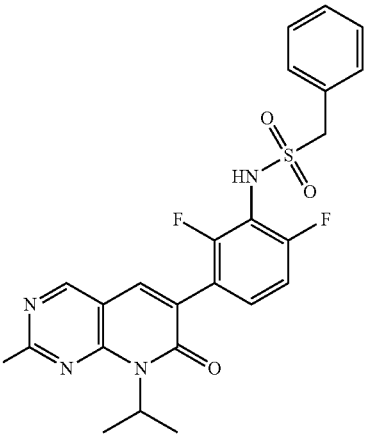 | (S)-N-(2,6-difluoro-3-(8-isopropyl-7-oxo-2-(piperidin-3-ylamino)-7,8-dihydropyrido[2,3-d]pyrimidin-6-yl)phenyl)-1-phenylmethane sulfonamide | 0.00220 | 569.2 |
| 20 | 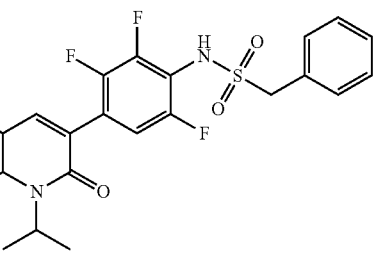 | 1-phenyl-N-(2,3,6-trifluoro-4-(8-isopropyl-2-(isopropylamino)-7-oxo-7,8-dihydropyrido-[2,3-d]pyrimidin-6-yl)-phenyl)methane sulfonamide | 0.00120 | 546.2 |
| 21 | 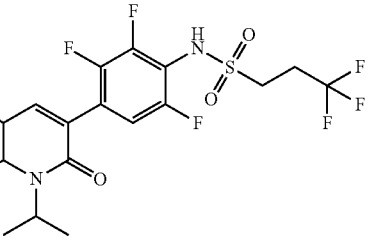 | 3,3,3-trifluoro-N-(2,3,6-trifluoro-4-(8-isopropyl-2-(isopropylamino)-7-oxo-7,8-dihydropyrido-[2,3-d]pyrimidin-6-yl)-phenyl)propane-1-sulfonamide | 0.01600 | 552.1 |
| 22 | 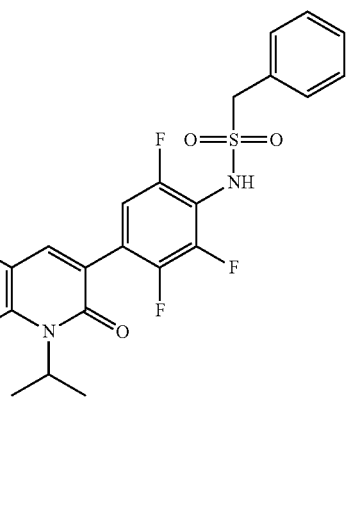 | 1-phenyl-N-(2,3,6-trifluoro-4-(2-(((1r,4r)-4-hydroxycyclohexyl)-amino)-8-isopropyl-7-oxo-7,8-dihydropyrido-[2,3-d]pyrimidin-6-yl)-phenyl)methane sulfonamide | 0.00024 | 602.1 |

TABLE 1-continued

Representative compounds:

| 23 | [structure] | N-(4-(8-(1,1-difluoro-propan-2-yl)-2-(((3S,5S)-5-fluoro-piperidin-3-yl)amino)-7-oxo-7,8-dihydro-pyrido[2,3-d]pyrimidin-6-yl)-2,3-difluorophen-yl)-1-phenylmethane sulfonamide | 0.00064, 0.00043 | 623.1 |
|---|---|---|---|---|
| 24 | [structure] | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2,3,6-trifluorophenyl)-1-phenylmethane sulfon-amide | 0.00270 | 629.2 |
| 25 | [structure] | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2,3,6-trifluorophenyl)-3,3,3-trifluoropropane-1-sulfonamide | 0.00033 | 635.2 |
| 26 | [structure] | 1-phenyl-N-(2,3,6-trifluoro-4-(2-(((3S,5S)-5-fluoropiperidin-3-yl)-amino)-8-isopropyl-7-oxo-7,8-dihydropyrido-[2,3-d]pyrimidin-6-yl)-phenyl)methane sulfon-amide | 0.00019 | 605.2 |

TABLE 1-continued

Representative compounds:

| # | Structure | Name | | |
|---|---|---|---|---|
| 27 | | 1-phenyl-N-(2,3,6-trifluoro-4-(2-(((3S,5S)-5-fluoro-5-methylpiperidin-3-yl)amino)-8-isopropyl-7-oxo-7,8-dihydropyrido[2,3-d]pyrimidin-6-yl)phenyl)-methane sulfonamide | 0.00022 | 619.2 |
| 28 | | N-(4-(8-cyclobutyl-2-(((3S,5S)-5-fluoropiperidin-3-yl)amino)-7-oxo-7,8-dihydropyrido[2,3-d]pyrimidin-6-yl)-2,3,6-trifluorophenyl)-1-phenyl-methane sulfonamide | 0.00019 | 617.2 |
| 29 | | 1-(4-cyanophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)-methane sulfonamide | 0.00021 | 630.2 |
| 30 | | 1-(3-cyanophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)-methane sulfonamide | 0.00021 | 630.2 |
| 31 | | 1-(3-methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)-methane sulfonamide hydrochloride | 0.00011 | 635.3 |

TABLE 1-continued

Representative compounds:

| 32 | | 1-(2-cyanophenyl)-N-(2,3,6-trifluoro-4-(2-(((3S,5S)-5-fluoro-piperidin-3-yl)amino)-8-isopropyl-7-oxo-7,8-dihydropyrido[2,3-d]-pyrimidin-6-yl)phenyl)-methane sulfonamide | 0.00034 | 630.1 |
|---|---|---|---|---|
| 33 | | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2,3,6-trifluorophenyl)-3,3-difluorobutane-1-sulfon-amide | 0.00098 | 631.1 |
| 34 | | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2,3,6-trifluorophenyl)pro-pane-1-sulfonamide | 0.00028 | 581.2 |
| 35 | | 1-phenyl-N-(2,3,6-trifluoro-4-(2-(((3S,5S)-5-fluoropiperidin-3-yl)-amino)-7-oxo-8-(tetra-hydrofuran-3-yl)-7,8-dihydropyrido[2,3-d]-pyrimidin-6-yl)phenyl)-methane sulfonamide | 0.00024, 0.00038 | 633.2 |
| 36 | | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2,3,6-trifluorophenyl)-2,2-difluorobutane-1-sulfonamide | 0.00018 | 631.2 |

TABLE 1-continued

Representative compounds:

| | | | | |
|---|---|---|---|---|
| 37 | 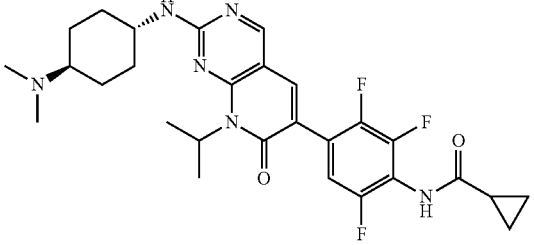 | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2,3,6-trifluorophenyl)cyclo-propanecarboxamide | 0.00140 | 543.3 |
| 38 | 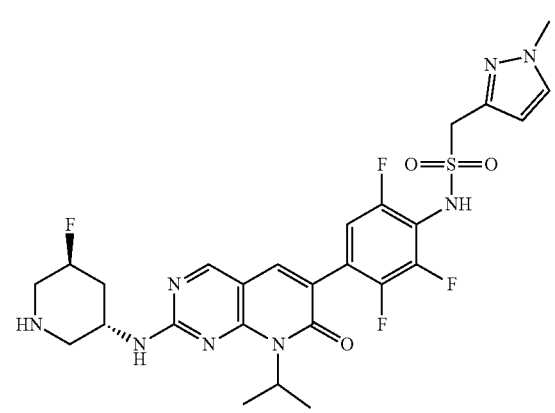 [SMILES: CC(C)n1c(=O)c(-c2cc(F)c(NS(=O)(=O)Cc3ccn(C)n3)c(F)c2F)cc2cnc(N[C@@H]3CNC[C@@H](F)C3)nc21] | 1-(1-methyl-1H-pyrazol-3-yl)-N-(2,3,6-trifluoro-4-(2-(((3S,5S)-5-fluoro-piperidin-3-yl)amino)-8-isopropyl-7-oxo-7,8-dihydropyrido[2,3-d]-pyrimidin-6-yl)phenyl)-methane sulfonamide | 0.00039 | 609.2 |
| 39 | 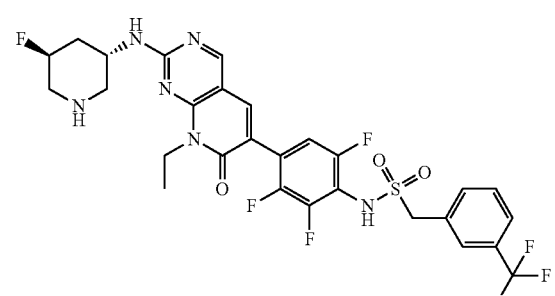 | N-(4-(8-ethyl-2-(((3S,5S)-5-fluoropiper-idin-3-yl)amino)-7-oxo-7,8-dihydropyrido[2,3-d]pyrimidin-6-yl)-2,3,6-trifluorophenyl)-1-(3-(trifluoromethyl)phen-yl)methanesulfonamide | 0.0004 | 659.2 |
| 40 | 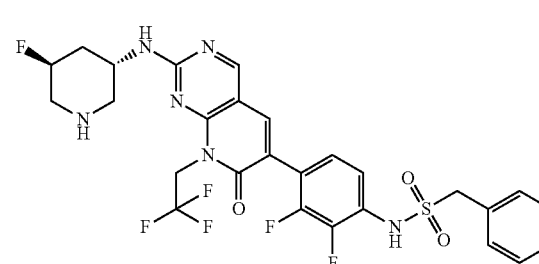 | N-(2,3-difluoro-4-(2-(((3S,5S)-5-fluoro-piperidin-3-yl)amino)-7-oxo-8-(2,2,2-trifluoro-ethyl)-7,8-dihydro-pyrido[2,3-d]pyrimidin-6-yl)phenyl)-1-phenyl-methane sulfonamide | 0.0017 | 627.2 |
| 41 | 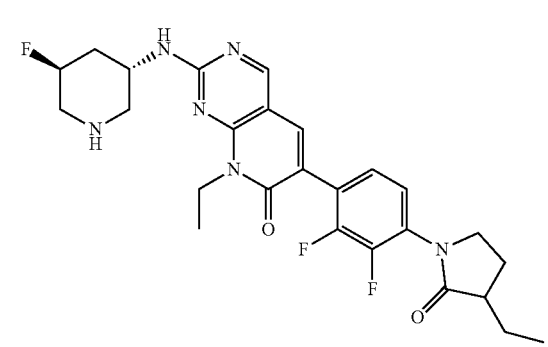 [SMILES: CCC1CCN(c2ccc(-c3cc4cnc(N[C@@H]5CNC[C@@H](F)C5)nc4n(CC)c3=O)c(F)c2F)C1=O] | 8-ethyl-6-(4-(3-ethyl-2-oxopyrrolidin-1-yl)-2,3-difluorophenyl)-2-(((3S,5S)-5-fluoropiper-idin-3-yl)amino)pyrido-[2,3-d]pyrimidin-7(8H)-one | 0.087 | 515.3 |

TABLE 1-continued

Representative compounds:

| # | Structure | Name | | |
|---|---|---|---|---|
| 42 | | N-(2,3-difluoro-4-(2-(((3S,5S)-5-fluoro-piperidin-3-yl)amino)-7-oxo-8-(1,1,1-trifluoropropan-2-yl)-7,8-dihydropyrido[2,3-d]-pyrimidin-6-yl)phenyl)-1-phenylmethane sulfonamide trifluoroacetate salt | 0.0036 | 641.2 |
| 43 | | (S)-N-(6-fluoro-2,3-dimethyl-4-((3-(2-(piperidin-3-ylamino)-pyrimidin-4-yl)pyridin-2-yl)oxy)phenyl)-1-phenyl methanesulfonamide | 0.00071 | 588.2 |
| 44 | | N-(2-fluoro-4-(2-(((3S,5S)-5-fluoro-piperidin-3-yl)amino)-8-isopropyl-7-oxo-7,8-dihydropteridin-6-yl)-phenyl)-1-phenyl methanesulfonamide | 0.00028 | 570.2 |
| 45 | | N-(2,6-difluoro-4-(2-(((3S,5S)-5-fluoro-piperidin-3-yl)amino)-8-isopropyl-7-oxo-7,8-dihydropteridin-6-yl)-phenyl)-1-phenyl methanesulfonamide | 0.00022 | 588.2 |
| 46 | | N-(2,6-difluoro-4-(2-(((3S,5S)-5-fluoro-piperidin-3-yl)amino)-8-isopropyl-7-oxo-7,8-dihydropteridin-6-yl)-phenyl)-3,3,3-trifluoropropane-1-sulfonamide | 0.00047 | 594.2 |

TABLE 1-continued

Representative compounds:

| 47 | 1-(4-cyanophenyl)-N-(4-(8-ethyl-2-(((3S,5S)-5-fluoropiperidin-3-yl)-amino)-7-oxo-7,8-dihydropyrido[2,3-d]-pyrimidin-6-yl)-2,3,6-trifluorophenyl)methanesulfonamide | 0.00037 | 616.2 |
| --- | --- | --- | --- |
| 48 | N-(4-(8-ethyl-2-(((3S,5S)-5-fluoro-piperidin-3-yl)amino)-7-oxo-7,8-dihydro-pyrido[2,3-d]pyrimidin-6-yl)-2,3,6-trifluoro-phenyl)-1-(1-fluoro-cyclopropyl)methane-sulfonamide | 0.028 | 573.4 |
| 49 | N-(4-(8-ethyl-2-(((3S,5S)-5-fluoro-piperidin-3-yl)amino)-7-oxo-7,8-dihydro-pyrido[2,3-d]pyrimidin-6-yl)-2,3,6-trifluoro-phenyl)-1-(pyridin-2-yl)methanesulfonamide | 0.005 | 592.2 |
| 50 | N-(4-(8-ethyl-2-(((3S,5S)-5-fluoro-piperidin-3-yl)amino)-7-oxo-7,8-dihydro-pyrido[2,3-d]pyrimidin-6-yl)-2,3,6-trifluoro-phenyl)-1-(4-(trifluoro-methyl)phenyl)methane-sulfonamide hydro-chloride | 0.00022 | 659.2 |
| 51 | 1-(2,6-difluorophenyl)-N-(4-(8-ethyl-2-((3S,5S)-5-fluoro-piperidin-3-yl)amino)-7-oxo-7,8-dihydro-pyrido[2,3-d]pyrimidin-6-yl)-2,3,6-trifluoro-phenyl)methanesulfon-amide | 0.0007 | 627.2 |

TABLE 1-continued

Representative compounds:

| | | | | |
|---|---|---|---|---|
| 52 | | N-(4-(8-(cyclopropyl-methyl)-2-(((3S,5S)-5-fluoropiperidin-3-yl)-amino)-7-oxo-7,8-dihydropyrido[2,3-d]-pyrimidin-6-yl)-2,3-difluorophenyl)-1-phenylmethane sulfon-amide trifluoroacetate salt | 0.0008 | 599.2 |
| 53 | | N-(2,3-difluoro-4-(8-(2-fluoroethyl)-2-(((3S,5S)-5-fluoropiperidin-3-yl)-amino)-7-oxo-7,8-dihydropyrido[2,3-d]-pyrimidin-6-yl)phenyl)-1-phenyl methanesul-fonamide | 0.00071 | 591.2 |
| 54 | | N-(2,3,6-trifluoro-4-(2-(((3S,5S)-5-fluoro-piperidin-3-yl)amino)-8-isopropyl-7-oxo-7,8-dihydropyrido[2,3-d]-pyrimidin-6-yl)phenyl)-benzenesulfonamide | 0.00034 | 591.1 |
| 55 | | N-(4-(8-(3,3-difluoro-cyclobutyl)-2-(((3S,5S)-5-fluoropiperidin-3-yl)-amino)-7-oxo-7,8-dihydropyrido[2,3-d]-pyrimidin-6-yl)-2,3,6-trifluorophenyl)-1-phenylmethane sulfon-amide hydrochloride | 0.00042 | 653.3 |

TABLE 1-continued

Representative compounds:

| | | | | |
|---|---|---|---|---|
| 56 | | N-(4-(2-(((1r,4r)-4-aminocyclohexyl)-amino)-8-isopropyl-7-oxo-7,8-dihydropyrido-[2,3-d]pyrimidin-6-yl)-2,3,6-trifluoro-phenyl)-1-phenyl-methane sulfonamide | 0.00017 | 601.3 |
| 57 | | 1-(4-methoxyphenyl)-N-(2,3,6-trifluoro-4-(2-(((3S,5S)-5-fluoro-piperidin-3-yl)amino)-8-isopropyl-7-oxo-7,8-dihydropyrido[2,3-d]-pyrimidin-6-yl)phenyl)-methane sulfonamide | 0.00014 | 635.1 |
| 58<br>58A<br>58B<br>58C<br>58D | | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2,3,6-trifluorophenyl)-2-methylcyclopropane-1-carboxamide | 0.0057 | 557.5 |

TABLE 1-continued

Representative compounds:

| | | | | |
|---|---|---|---|---|
| | 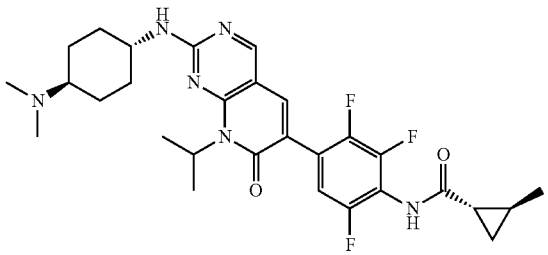 | | | |
| | 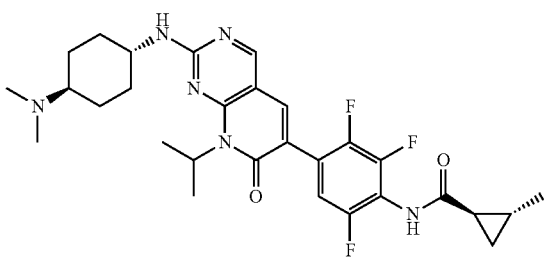 | | | |
| 59 | | N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-3-methylbutanamide | 0.0032 | 559.5 |
| 60 | | N-(4-(2-((4-(dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide | 0.0002 | 653.3 |
| 61 | | 2-chloro-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)benzenesulfonamide hydrochloride | 0.00031 | 625.3 |

TABLE 1-continued

Representative compounds:

| 62 | | 2-cyclobutyl-N-(4-(2-(((1r,4r)-4-(dimethyl-amino)cyclohexyl)-amino)-8-isopropyl-7-oxo-7,8-dihydropyrido-[2,3-d]pyrimidin-6-yl)-2,3,6-trifluorophenyl)-acetamide | 0.0022 | 571.3 |
|---|---|---|---|---|
| 63 | | (1R,2R)-N-(4-(2-(((1r,4r)-4-(dimethyl-amino)cyclohexyl)-amino)-8-isopropyl-7-oxo-7,8-dihydropyrido-[2,3-d]pyrimidin-6-yl)-2,3,6-trifluorophenyl)-2-fluorocyclopropane-1-carboxamide hydrochloride | 0.0041 | 561.5 |
| 64 | | N-(2-fluoro-4-(2-(((3S,5S)-5-fluoro-5-methylpiperidin-3-yl)-amino)-8-isopropyl-7-oxo-7,8-dihydropter-idin-6-yl)phenyl)-1-phenyl methanesulfon-amide | 0.00021 | 584.2 |
| 65 | | N-(2-fluoro-4-(2-(((3S,5R)-5-(fluoro-methyl)piperidin-3-yl)-amino)-8-isopropyl-7-oxo-7,8-dihydropter-idin-6-yl)phenyl)-1-phenyl methanesulfon-amide | 0.00024 | 584.2 |
| 66 | | N-(4-(2-(((1r,4r)-4-(dimethylamino)cyclo-hexyl)amino)-8-iso-propyl-7-oxo-7,8-dihydropteridin-6-yl)-2-fluorophenyl)-3,3-difluorobutane-1-sulfonamide | 0.00029 | 596.3 |

TABLE 1-continued

Representative compounds:

| 67 | N-(4-(2-(((1r,4r)-4-(dimethylamino)cyclohexyl)amino)-8-isopropyl-7-oxo-7,8-dihydropteridin-6-yl)-2-fluorophenyl)-3,3,3-trifluoropropane-1-sulfonamide | 0.00018 | 600.2 |
| --- | --- | --- | --- |
| 68 | N-(4-(2-(((1r,4r)-4-(dimethylamino)cyclohexyl)amino)-8-isopropyl-7-oxo-7,8-dihydropteridin-6-yl)-2-fluorophenyl)-1-phenyl-methane sulfonamide | 0.00013 | 594.3 |
| 69 | N-(5-(8-ethyl-2-((3S,5S)-5-fluoropiperidin-3-yl)amino)-7-oxo-7,8-dihydropyrido[2,3-d]pyrimidin-6-yl)-1-methyl-1H-pyrazol-3-yl)-1-phenylmethane sulfonamide | 0.098 | 541.2 |
| 70 | N-(4-(2-(((1,4-trans)-4-(dimethylamino)cyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide | 0.00026 | 617.0 |
| 71 | N-(4-(2-(((1,4-trans)-4-(dimethylamino)cyclohexyl)amino)-8-isopropyl-7-oxo-7,8-dihydropyrido[2,3-d]pyrimidin-6-yl)-2,5-difluorophenyl)-3,3,3-trifluoropropane-1-sulfonamide formate | 0.00025 | 617.0 |
| 72 | N-[2-fluoro-4-[2-[[(3S,5S)-5-fluoro-3-piperidyl]amino]-8-isopropyl-7-oxo-pteridin-6-yl]-6-methylphenyl]-1-phenyl-methanesulfonamide | 0.0005 | 584.3 |

TABLE 1-continued

Representative compounds:

| | | | | |
|---|---|---|---|---|
| 73 | 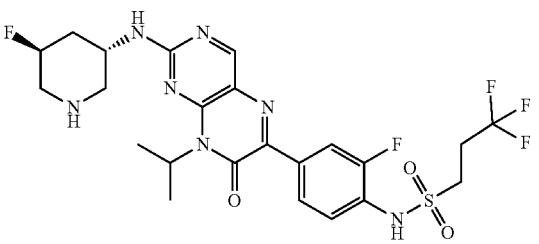 | 3,3,3-trifluoro-N-(2-fluoro-4-[2-[[(3S,5S)-5-fluoro-3-piperidyl]-amino]-8-isopropyl-7-oxo-pteridin-6-yl]-phenyl]propane-1-sulfonamide | 0.0005 | 576.2 |
| 74 | 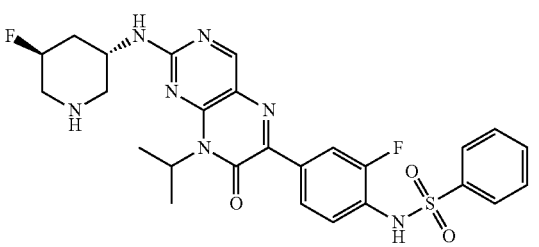 [SMILES: CC(C)n1c(=O)c(-c2ccc(NS(=O)(=O)c3ccccc3)c(F)c2)nc2cnc(N[C@@H]3CNC[C@@H](F)C3)nc21] | N-[2-fluoro-4-[2-[[(3S,5S)-5-fluoro-3-piperidyl]amino]-8-isopropyl-7-oxo-pteridin-6-yl]phenyl]benzenesulfonamide | 0.0006 | 556.2 |
| 75 | 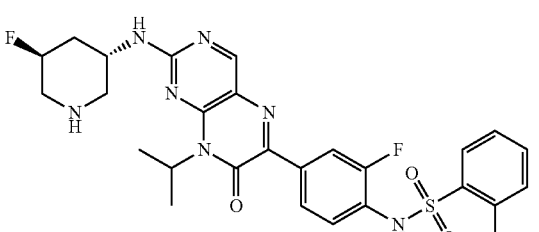 | 2-chloro-N-[2-fluoro-4-[2-[[(3S,5S)-5-fluoro-3-piperidyl]amino]-8-isopropyl-7-oxo-pteridin-6-yl]phenyl]-benzenesulfonamide | 0.0003 | 590.2 |
| 76 | 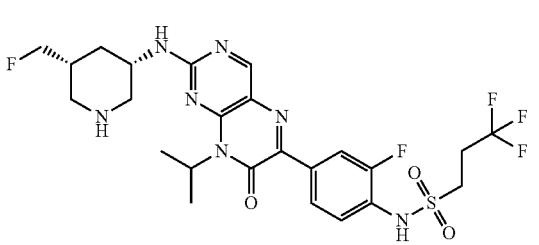 [SMILES: CC(C)n1c(=O)c(-c2ccc(NS(=O)(=O)CCC(F)(F)F)c(F)c2)nc2cnc(N[C@@H]3CNC[C@H](CF)C3)nc21] | 3,3,3-trifluoro-N-[2-fluoro-4-[2-[[(3S,5R)-5-(fluoromethyl)-3-piperidyl]amino]-8-isopropyl-7-oxo-pteridin-6-yl]phenyl]propane-1-sulfonamide | 0.0009 | 590.2 |
| 77 | 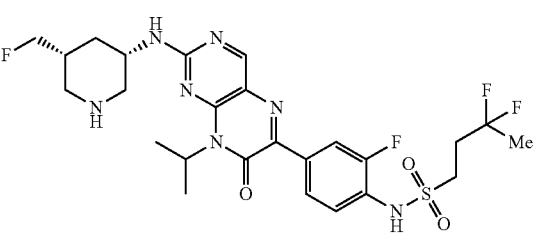 [SMILES: CC(C)n1c(=O)c(-c2ccc(NS(=O)(=O)CCC(C)(F)F)c(F)c2)nc2cnc(N[C@@H]3CNC[C@H](CF)C3)nc21] | 3,3-difluoro-N-[2-fluoro-4-[2-[[(3S,5R)-5-(fluoromethyl)-3-piperidyl]amino]-8-isopropyl-7-oxo-pteridin-6-yl]phenyl]butane-1-sulfonamide | 0.0008 | 586.3 |
| 78 | 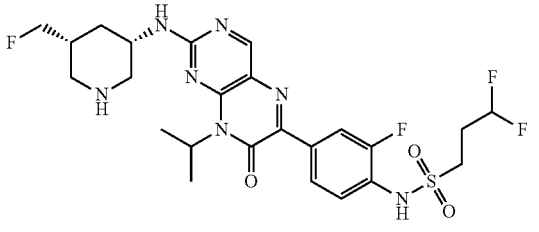 [SMILES: CC(C)n1c(=O)c(-c2ccc(NS(=O)(=O)CCC(F)F)c(F)c2)nc2cnc(N[C@@H]3CNC[C@H](CF)C3)nc21] | 3,3-difluoro-N-[2-fluoro-4-(2-[[(3S,5R)-5-(fluoromethyl)-3-piperidyl]amino]-8-isopropyl-7-oxo-pteridin-6-yl]phenyl]propane-1-sulfonamide | 0.001 | 572.3 |

TABLE 1-continued

Representative compounds:

| 79 | | N-[2-fluoro-4-[2-[[(3S,5R)-5-(fluoromethyl)-3-piperidyl]amino]-8-isopropyl-7-oxo-pteridin-6-yl)phenyl]propane-1-sulfonamide | 0.0015 | 536.3 |
|---|---|---|---|---|
| 80 | | 1-(2-cyanophenyl)-N-[2-fluoro-4-[2-[[(3S,5S)-5-fluoro-3-piperidyl]amino]-8-isopropyl-7-oxo-pteridin-6-yl]phenyl]methanesulfonamide | 0.0002 | 595.2 |
| 81 | | 1-(4-cyanophenyl)-N-[2-fluoro-4-[2-[[(3S,5S)-5-fluoro-3-piperidyl]amino]-8-isopropyl-7-oxo-pteridin-6-yl]phenyl]methanesulfonamide | 0.0001 | 595.2 |
| 82 | | N-[2-fluoro-4-[2-[[(3S,5S)-5-fluoro-3-piperidyl)amino]-8-isopropyl-7-oxo-pteridin-6-yl]phenyl]propane-1-sulfonamide | 0.0008 | 522.2 |
| 83 | | 2,2-difluoro-N-[2-fluoro-4-(2-[[(3S,5S)-5-fluoro-3-piperidyl]amino]-8-isopropyl-7-oxo-pteridin-6-yl]phenyl]butane-1-sulfonamide | 0.0004 | 572.3 |
| 84 | | 3,3-difluoro-N-[2-fluoro-4-(2-[[(3S,5S)-5-fluoro-3-piperidyl]amino]-8-isopropyl-7-oxo-pteridin-6-yl]phenyl]butane-1-sulfonamide | 0.0004 | 572.2 |

TABLE 1-continued

Representative compounds:

| | | | | |
|---|---|---|---|---|
| 85 | | 3,3,3-trifluoro-N-(5-(2-(((3S,5S)-5-fluoro-piperidin-3-yl)amino)-8-isopropyl-7-oxo-7,8-dihydropyrido[2,3-d]-pyrimidin-6-yl)-1-methyl-1H-pyrazol-3-yl)propane-1-sulfon-amide | 0.016 | 561.2 |
| 86 | | 1-(2-fluorophenyl)-N-(2,3,6-trifluoro-4-(2-(((3S,5S)-5-fluoro-piperidin-3-yl)amino)-8-isopropyl-7-oxo-7,8-dihydropyrido[2,3-d]-pyrimidin-6-yl)phenyl)-methanesulfonamide | 0.00016 | 623.2 |
| 87 87A | | 1-(2-fluorophenyl)-N-(2,3,6-trifluoro-4-(2-((5-hydroxypiperidin-3-yl)amino)-8-iso-propyl-7-oxo-7,8-dihydropyrido[2,3-d]-pyrimidin-6-yl)phenyl)-methanesulfonamide | 0.00063 | 621.2 |
| 88 | | 1-(2-fluorophenyl)-N-(2,3,6-trifluoro-4-(2-(((3R,5S)-5-hydroxy-piperidin-3-yl)amino)-8-isopropyl-7-oxo-7,8-dihydropyrido[2,3-d]-pyrimidin-6-yl)phenyl)-methanesulfonamide | 0.0085 | 621.2 |
| 89 | | 1-(2-fluorophenyl)-N-(2,3,6-trifluoro-4-(2-(((3S,5R)-5-hydroxy-piperidin-3-yl)amino)-8-isopropyl-7-oxo-7,8-dihydropyrido[2,3-d]-pyrimidin-6-yl)phenyl)-methanesulfonamide | 0.00034 | 621.2 |

TABLE 1-continued

Representative compounds:

| 90 | 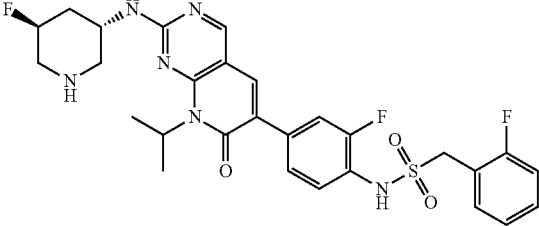 | N-(2-fluoro-4-(2-(((3S,5S)-5-fluoro-piperidin-3-yl)amino)-8-isopropyl-7-oxo-7,8-dihydropyrido[2,3-d]-pyrimidin-6-yl)phenyl)-1-(2-fluorophenyl)-methanesulfonamide | 0.00021 | 587.2 |
| --- | --- | --- | --- | --- |
| 91 | 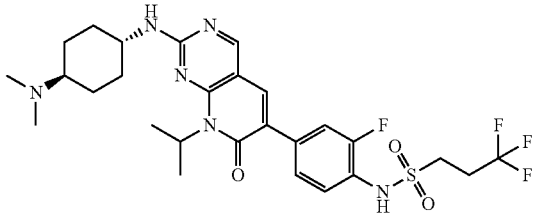 [SMILES: CC(C)n1c(=O)c(-c2ccc(NS(=O)(=O)CCC(F)(F)F)c(F)c2)cc2cnc(N[C@H]3CC[C@H](N(C)C)CC3)nc21] | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2-fluorophenyl)-3,3,3-trifluoropropane-1-sulfonamide | 0.00013 | 599.3 |
| 92 | 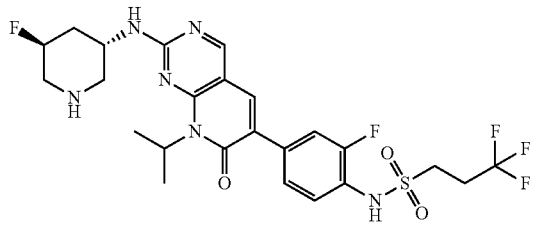 [SMILES: CC(C)n1c(=O)c(-c2ccc(NS(=O)(=O)CCC(F)(F)F)c(F)c2)cc2cnc(N[C@@H]3CNC[C@@H](F)C3)nc21] | 3,3,3-trifluoro-N-(2-fluoro-4-(2-(((3S,5S)-5-fluoropiperidin-3-yl)-amino)-8-isopropyl-7-oxo-7,8-dihydropyrido-[2,3-d]pyrimidin-6-yl)-phenyl)propane-1-sulfonamide | 0.0003 | 575.2 |
| 93 | 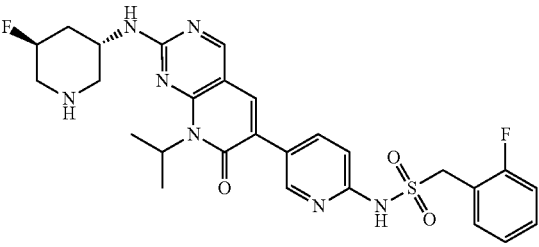 [SMILES: CC(C)n1c(=O)c(-c2ccc(NS(=O)(=O)Cc3ccccc3F)nc2)cc2cnc(N[C@@H]3CNC[C@@H](F)C3)nc21] | 1-(2-fluorophenyl)-N-(5-(2-(((3S,5S)-5-fluoro-piperidin-3-yl)amino)-8-isopropyl-7-oxo-7,8-dihydropyrido[2,3-d]-pyrimidin-6-yl)pyridin-2-yl)methanesulfon-amide | 0.00024 | 570.2 |
| 94 | 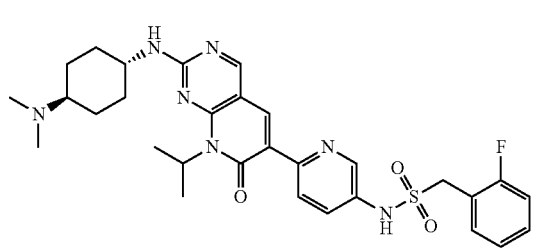 [SMILES: CC(C)n1c(=O)c(-c2ccc(NS(=O)(=O)Cc3ccccc3F)cn2)cc2cnc(N[C@H]3CC[C@H](N(C)C)CC3)nc21] | N-(6-(2-(((1r,4r)-4-(dimethylamino)cyclo-hexyl)amino)-8-iso-propyl-7-oxo-7,8-dihydropyrido[2,3-d]-pyrimidin-6-yl)pyridin-3-yl)-1-(2-fluorophenyl)-methanesulfonamide | 0.00027 | 594.3 |
| 95 | 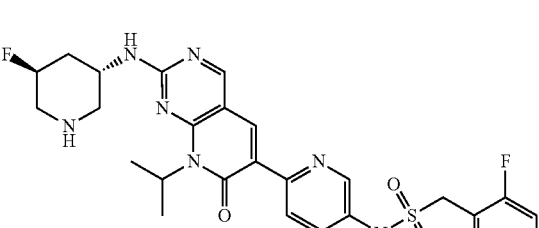 | 1-(2-fluorophenyl)-N-(6-(2-(((3S,5S)-5-fluoro-piperidin-3-yl)amino)-8-isopropyl-7-oxo-7,8-dihydropyrido[2,3-d]-pyrimidin-6-yl)pyridin-3-yl)methanesulfon-amide | 0.00046 | 570.3 |

TABLE 1-continued

Representative compounds:

| EX No | Structure | Name | IRE1α(alpha) HTRF (IC$_{50}$) (μM) | Mass Spec. M + H/1 |
|---|---|---|---|---|
| 96 | 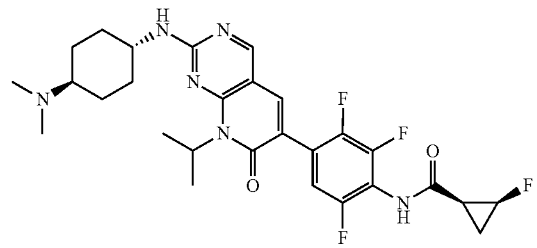 [SMILES: CC(C)n1c(=O)c(-c2cc(F)c(NC(=O)[C@@H]3C[C@@H]3F)c(F)c2F)cc2cnc(N[C@H]3CC[C@H](N(C)C)CC3)nc21] | (1S,2S)-N-(4-(2-(((1r,4r)-4-(dimethyl-amino)cyclohexyl)-amino)-8-isopropyl-7-oxo-7,8-dihydropyrido-[2,3-d]pyrimidin-6-yl)-2,3,6-trifluorophenyl)-2-fluorocyclopropane-1-carboxamide | 0.0016 | 561.5 |
| 97 | 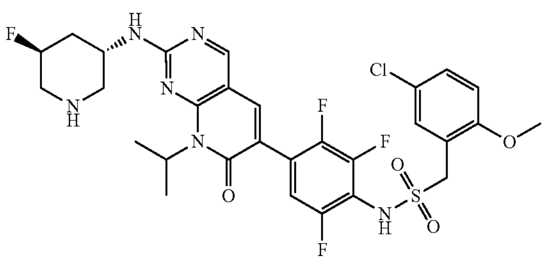 [SMILES: COc1ccc(Cl)cc1CS(=O)(=O)Nc1c(F)cc(-c2cc3cnc(N[C@@H]4CNC[C@@H](F)C4)nc3n(C(C)C)c2=O)c(F)c1F] | 1-(5-chloro-2-methoxy-phenyl)-N-(2,3,6-trifluoro-4-(2-(((3S,5S)-5-fluoropiperidin-3-yl)-amino)-8-isopropyl-7-oxo-7,8-dihydropyrido-[2,3-d]pyrimidin-6-yl)-phenyl)methanesulfon-amide hydrochloride | 0.00027 | 669.2 |
| 98 98A 98B | | N-(4-(2-(((1r,4r)-4-(dimethylamino)cyclo-hexyl)amino)-8-iso-propyl-7-oxo-7,8-dihydropyrido[2,3-d]-pyrimidin-6-yl)-2,3,6-trifluorophenyl)-2-fluorocyclopropane-1-carboxamide | 0.0028 0.0022 | 561.4 |

TABLE 1-continued

Representative compounds:

| # | Structure | Name | IC50 (µM) | MS |
|---|---|---|---|---|
| 99<br>99A | 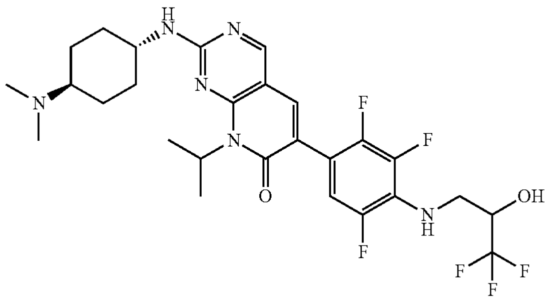 [SMILES: CC(C)n1c(=O)c(-c2cc(F)c(NCC(O)C(F)(F)F)c(F)c2F)cc2cnc(N[C@H]3CC[C@H](N(C)C)CC3)nc21] | 2-(((1r,4r)-4-(dimethyl-amino)cyclohexyl)-amino)-8-isopropyl-6-(2,3,5-trifluoro-4-((3,3,3-trifluoro-2-hydroxypropyl)amino)-phenyl)pyrido[2,3-d]-pyrimidin-7(8H)-one | 0.046<br>0.068 | 587.3 |
| 100 | 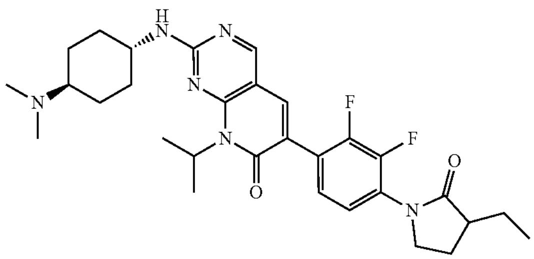 [SMILES: CCC1CCN(c2ccc(-c3cc4cnc(N[C@H]5CC[C@H](N(C)C)CC5)nc4n(C(C)C)c3=O)c(F)c2F)C1=O] | 2-(((1r,4r)-4-(dimethyl-amino)cyclohexyl)-amino)-6-(4-(3-ethyl-2-oxopyrrolidin-1-yl)-2,3-difluorophenyl)-8-iso-propylpyrido[2,3-d]-pyrimidin-7(8H)-one | 0.00078<br>0.0088 | 553.6 |
| 101<br>101A<br>101B | | N-(2,3,6-trifluoro-4-(8-isopropyl-2-((4-((2-methoxyethyl)(methyl)-amino)cyclohexyl)-amino)-7-oxo-7,8-dihydropyrido[2,3-d]-pyrimidin-6-yl)phenyl)-propane-1-sulfonamide | 0.00035<br>0.12 | 625.3 |

TABLE 1-continued

Representative compounds:

| | | | | |
|---|---|---|---|---|
| 102 102A 102B | | 1-phenyl-N-(2,3,6-trifluoro-4-(8-isopropyl-2-((4-((2-methoxyethyl)-(methyl)amino)cyclohexyl)amino)-7-oxo-7,8-dihydropyrido[2,3-d]pyrimidin-6-yl)phenyl)methanesulfonamide | 0.00016 0.066 | 673.3 |
| 103 | | N-(4-(2-(((1S,3S)-3-aminocyclohexyl)-amino)-8-isopropyl-7-oxo-7,8-dihydropyrido-[2,3-d]pyrimidin-6-yl)-2-fluorophenyl)-3,3,3-trifluoropropane-1-sulfonamide | 0.026 | 571.2 |
| 104 | | N-(4-(2-(((1S,3S)-3-aminocyclohexyl)-amino)-8-isopropyl-7-oxo-7,8-dihydropyrido-[2,3-d]pyrimidin-6-yl)-2-fluorophenyl)-3,3,3-trifluoropropane-1-sulfonamide hydrochloride | 0.072 | 599.3 |
| 105 | | 2-chloro-N-(5-(2-(((1r,4r)-4-(dimethylamino)cyclohexyl)-amino)-8-isopropyl-7-oxo-7,8-dihydropyrido-[2,3-d]pyrimidin-6-yl)-pyridin-2-yl)benzenesulfonamide | 0.00016 | 596.1 |

TABLE 1-continued

Representative compounds:

| | | | | |
|---|---|---|---|---|
| 106 | | N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)benzenesulfonamide | 0.00015 | 562.5 |
| 107 | | 1-(2-cyano-4-methylphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide | 0.00013 | 644.3 |
| 108 | | N-(4-(2-(((1S,3R)-3-aminocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide hydrochloride | 0.023 | 571.2 |
| 109 | | 1-cyclopentyl-N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)methanesulfonamide | 0.00013 | 585.4 |
| 110<br>110A<br>110B | | N-(4-(2-((4-(dimethylamino)-3-fluorocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide | 0.00018<br>0.0007 | 617.2 |

TABLE 1-continued

Representative compounds:

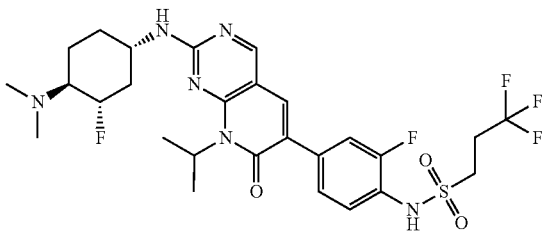 [SMILES: CC(C)n1c(=O)c(-c2ccc(NS(=O)(=O)CCC(F)(F)F)c(F)c2)cc2cnc(N[C@H]3CC[C@H](N(C)C)[C@@H](F)C3)nc21]

| 111 | 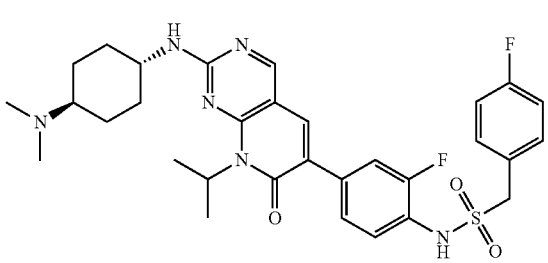 [SMILES: CC(C)n1c(=O)c(-c2ccc(NS(=O)(=O)Cc3ccc(F)cc3)c(F)c2)cc2cnc(N[C@H]3CC[C@H](N(C)C)CC3)nc21] | N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)-1-(4-fluorophenyl)methanesulfonamide | 0.00013 | 611.4 |
| 112 | 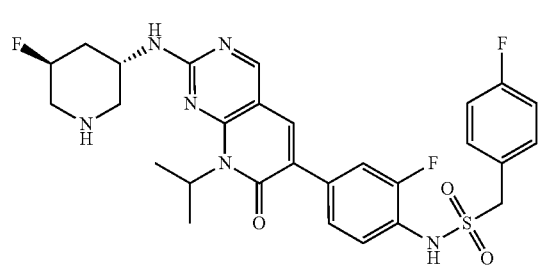 [SMILES: CC(C)n1c(=O)c(-c2ccc(NS(=O)(=O)Cc3ccc(F)cc3)c(F)c2)cc2cnc(N[C@@H]3CNC[C@@H](F)C3)nc21] | N-(2-fluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(4-fluorophenyl)-methanesulfonamide hydrochloride | 0.00013 | 587.2 |
| 113 | | 1-(2-cyano-4-methylphenyl)-N-(4-(2-(((1r,4r)-4-(dimethylamino)cyclohexyl)-amino)-8-isopropyl-7-oxo-7,8-dihydropyrido-[2,3-d]pyrimidin-6-yl)-2,3,6-trifluorophenyl)-methanesulfonamide | 0.00022 | 668.3 |
| 114 | 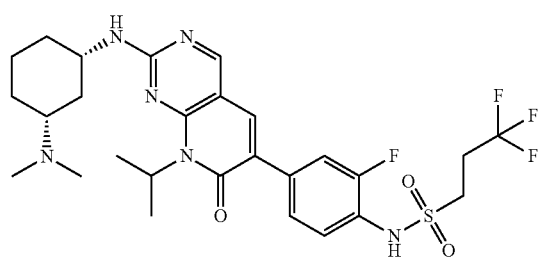 [SMILES: CC(C)n1c(=O)c(-c2ccc(NS(=O)(=O)CCC(F)(F)F)c(F)c2)cc2cnc(N[C@H]3CCC[C@@H](N(C)C)C3)nc21] | N-(4-(2-(((1S,3R)-3-dimethylamino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide | 0.18 | 599.3 |

TABLE 1-continued

Representative compounds:

| # | Structure | Name | | |
|---|---|---|---|---|
| 115 | | 1-cyclohexyl-N-(4-(2-(((1r,4r)-4-(dimethyl-amino)cyclohexyl)-amino)-8-isopropyl-7-oxo-7,8-dihydropyrido-[2,3-d]pyrimidin-6-yl)-2-fluorophenyl)-methanesulfonamide | 0.00015 | 599.3 |
| 116 | | 1-(4-chlorophenyl)-N-(4-(2-(((1r,4r)-4-(dimethylamino)cyclo-hexyl)amino)-8-isopropyl-7-oxo-7,8-dihydropyrido[2,3-d]-pyrimidin-6-yl)-2,6-difluorophenyl)-methanesulfonamide | 0.00025 | 645.2 |
| 117 | | N-(4-(2-(((1r,4r)-4-(dimethylamino)cyclo-hexyl)amino)-8-isopropyl-7-oxo-7,8-dihydropyrido[2,3-d]-pyrimidin-6-yl)-2,6-difluorophenyl)-1-phenylmethanesulfon-amide | 0.00018 | 611.4 |
| 118<br>118A<br>118B | | N-(4-(2-((4-(dimethyl-amino)-3-fluorocyclo-hexyl)amino)-8-isopropyl-7-oxo-7,8-dihydropyrido[2,3-d]-pyrimidin-6-yl)-2,6-difluorophenyl)-3,3,3-trifluoropropane-1-sulfonamide | 0.00073<br>0.00032 | 635.3 |

TABLE 1-continued

Representative compounds:

| | | | | |
|---|---|---|---|---|
| 119 | | N-(4-(2-(((1r,4r)-4-(dimethylamino)cyclo-hexyl)amino)-8-isopropyl-7-oxo-7,8-dihydropyrido[2,3-d]pyrimidin-6-yl)-2-fluorophenyl)cyclo-hexanesulfonamide | 0.00016 | 585.3 |
| 120 | | N-(4-(2-(((1r,4r)-4-(dimethylamino)cyclo-hexyl)amino)-8-isopropyl-7-oxo-7,8-dihydropyrido[2,3-d]pyrimidin-6-yl)-2,6-difluorophenyl)-1-(p-tolyl)methanesulfon-amide | 0.0017 | 625.3 |
| 121 | | N-(5-(2-(((1r,4r)-4-(dimethylamino)cyclo-hexyl)amino)-8-isopropyl-7-oxo-7,8-dihydropyrido[2,3-d]pyrimidin-6-yl)pyridin-2-yl)-1-(4-fluorophen-yl)methanesulfonamide | 0.00012 | 694.5 |
| 122 | | N-(2,6-difluoro-4-(8-isopropyl-2-(((1r,4r)-4-((2-methoxyethyl)-(methyl)amino)cyclo-hexyl)amino)-7-oxo-7,8-dihydropyrido[2,3-d]pyrimidin-6-yl)-phenyl)-1-(4-fluoro-phenyl)methanesulfon-amide | 0.00012 | 673.3 |
| 123 | | N-(2-fluoro-4-(8-iso-propyl-2-(((1r,4r)-4-((2-methoxyethyl)-(methyl)amino)cyclo-hexyl)amino)-7-oxo-7,8-dihydropyrido[2,3-d]pyrimidin-6-yl)-phenyl)-1-(4-fluoro-phenyl)methanesulfon-amide | 0.00005 | 655.3 |
| 124 | | N-(2-fluoro-4-(8-iso-propyl-2-(((1r,4r)-4-((2-methoxyethyl)-(methyl)amjno)cyclo-hexyl)amino)-7-oxo-7,8-dihydropyrido[2,3-d]pyrimidin-6-yl)-phenyl)-1-phenyl-methanesulfonamide hydrochloride | 0.00012 | 637.3 |

TABLE 1-continued

Representative compounds:

| | | | | | |
|---|---|---|---|---|---|
| 125 | | | 1-(4-(difluoromethyl)-phenyl)-N-(4-(2-(((1r,4r)-4-(dimethyl-amino)cyclohexyl)-amino)-8-isopropyl-7-oxo-7,8-dihydropyrido-[2,3-d]pyrimidin-6-yl)-2,6-difluorophenyl)-methanesulfonamide | 0.00019 | 661.4 |
| 126 | | | 3,3,3-trifluoro-N-(5-(8-isopropyl-2-(((1r,4r)-4-((2-methoxyethyl)-(methyl)amino)cyclo-hexyl)amino)-7-oxo-7,8-dihydropyrido[2,3-d]-pyrimidin-6-yl)pyridin-2-yl)propane-1-sulfon-amide | 0.00024 | 626.3 |
| 127 | | | N-(4-(2-(((1r,4r)-4-(dimethylamino)cyclo-hexyl)amino)-8-isopropyl-7-oxo-7,8-dihydropyrido[2,3-d]-pyrimidin-6-yl)-2,5-difluorophenyl)-1-(4-fluorophenyl)methane-sulfonamide | 0.00011 | 629.2 |
| 128 | | | N-(4-(2-(((1r,4r)-4-(dimethylamino)cyclo-hexyl)amino)-8-isopropyl-7-oxo-7,8-dihydropyrido[2,3-d]-pyrimidin-6-yl)-2,3,5-trifluorophenyl)-1-(4-fluorophenyl)methane-sulfonamide | 0.00015 | 647.3 |
| 129 | | | N-(4-(2-(((1r,4r)-4-(dimethylamino)cyclo-hexyl)amino)-8-isopropyl-7-oxo-7,8-dihydropyrido[2,3-d]-pyrimidin-6-yl)-3,5-difluorophenyl)-1-(4-fluorophenyl)methane-sulfonamide hydro-chloride | 0.00008 | 629.3 |

TABLE 1-continued

Representative compounds:

| | | | | |
|---|---|---|---|---|
| 130 | 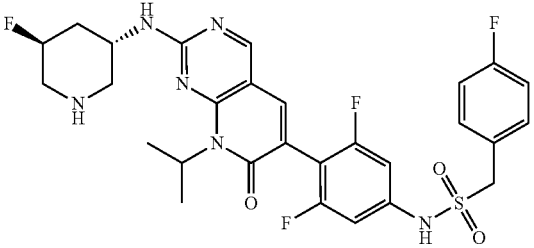 [SMILES: CC(C)n1c(=O)c(-c2c(F)cc(NS(=O)(=O)Cc3ccc(F)cc3)cc2F)cc2cnc(N[C@@H]3CNC[C@@H](F)C3)nc21] | N-(3,5-difluoro-4-(2-(((3S,5S)-5-fluoro-piperidin-3-yl)amino)-8-isopropyl-7-oxo-7,8-dihydropyrido[2,3-d]pyrimidin-6-yl)phenyl)-1-(4-fluorophenyl)-methanesulfonamide hydrochloride | 0.00038 | 605.2 |
| 131 | 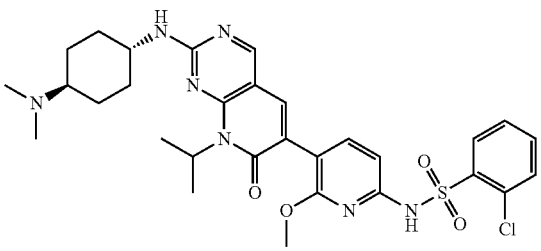 [SMILES: COc1nc(NS(=O)(=O)c2ccccc2Cl)ccc1-c1cc2cnc(N[C@H]3CC[C@H](N(C)C)CC3)nc2n(C(C)C)c1=O] | 2-chloro-N-(5-(2-(((1r,4r)-4-(dimethyl-amino)cyclohexyl)-amino)-8-isopropyl-7-oxo-7,8-dihydropyrido-[2,3-d]pyrimidin-6-yl)-6-methoxypyridin-2-yl)benzenesulfonamide | 0.00021 | 626.3 |
| 132 | 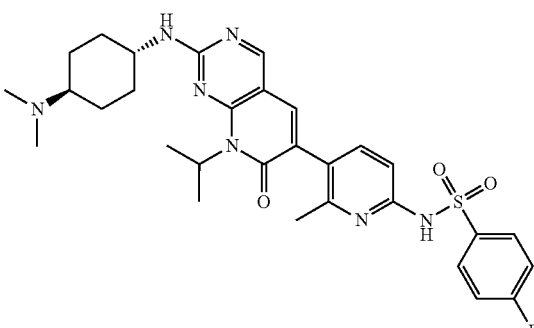 | N-(5-(2-(((1r,4r)-4-(dimethylamino)cyclo-hexyl)amino)-8-isopropyl-7-oxo-7,8-dihydropyrido[2,3-d]-pyrimidin-6-yl)-6-1methylpyridin-2-yl)-4-fluorobenzenesulfon-amide | 0.00052 | 594.3 |
| 133 | 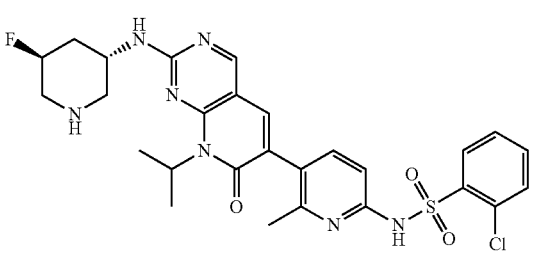 [SMILES: Cc1nc(NS(=O)(=O)c2ccccc2Cl)ccc1-c1cc2cnc(N[C@@H]3CNC[C@@H](F)C3)nc2n(C(C)C)c1=O] | 2-chloro-N-(5-(2-(((3S,5S)-5-fluoro-piperidin-3-yl)amino)-8-isopropyl-7-oxo-7,8-dihydropyrido[2,3-d]-pyrimidin-6-yl)-6-methylpyridin-2-yl)-benzenesulfonamide | 0.00062 | 586.2 |
| 134 | 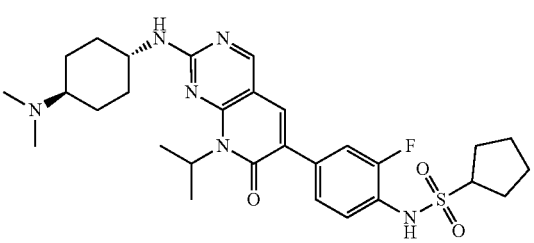 [SMILES: CC(C)n1c(=O)c(-c2ccc(NS(=O)(=O)C3CCCC3)c(F)c2)cc2cnc(N[C@H]3CC[C@H](N(C)C)CC3)nc21] | N-(4-(2-(((1r,4r)-4-(dimethylamino)cyclo-hexyl)amino)-8-isopropyl-7-oxo-7,8-dihydropyrido[2,3-d]-pyrimidin-6-yl)-2-fluorophenyl)cyclo-pentanesulfonamide hydrochloride | 0.00019 | 571.3 |
| 135 | 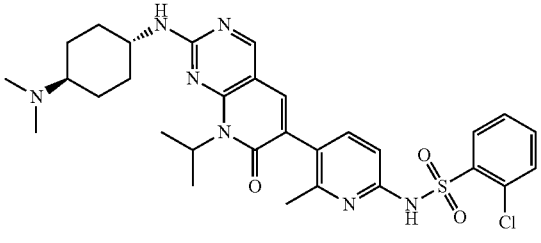 | 2-chloro-N-(5-(2-(((1r,4r)-4-(dimethyl-amino)cyclohexyl)-amino)-8-isopropyl-7-oxo-7,8-dihydropyrido-[2,3-d]pyrimidin-6-yl)-6-methylpyridin-2-yl)benzenesulfonamide | 0.00043 | 610.3 |

TABLE 1-continued

Representative compounds:

| | | | | |
|---|---|---|---|---|
| 136 | | 2-cyano-N-(5-(2-(((1r,4r)-4-(dimethyl-amino)cyclohexyl)-amino)-8-isopropyl-7-oxo-7,8-dihydropyrido-[2,3-d]pyrimidin-6-yl)-6-methylpyridin-2-yl)-benzenesulfonamide | 0.00029 | 601.3 |
| 137 | | N-(5-(2-(((1r,4r)-4-(dimethylamino)cyclo-hexyl)amino)-8-isopropyl-7-oxo-7,8-dihydropyrido[2,3-d]-pyrimidin-6-yl)-6-methylpyridin-2-yl)-2-fluoro-3-methyl-benzenesulfonamide | 0.00048 | 608.4 |
| 138 | | 3,3,3-trifluoro-N-(2-fluoro-4-(8-isopropyl-2-(((1r,4r)-4-((2-methoxyethyl)(methyl)-amino)cyclohexyl)-amino)-7-oxo-7,8-dihydropyrido[2,3-d]-pyrimidin-6-yl)phenyl)-propane-1-sulfonamide | 0.00019 | 643.3 |
| 139 | | N-(2,3,6-trifluoro-4-(2-(((3S,5S)-5-fluoro-piperidin-3-yl)amino)-8-isopropyl-7-oxo-7,8-dihydropyrido[2,3-d]-pyrimidin-6-yl)phenyl)-1-(2-(trifluoromethyl)-pyridin-3-yl)methane-sulfonamide | 0.00027 | 674.2 |

TABLE 1-continued

Representative compounds:

| 140 | 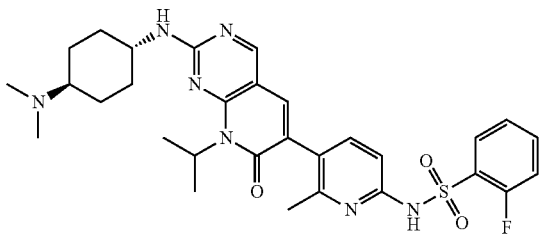 [SMILES: Cc1nc(NS(=O)(=O)c2ccccc2Cl)ccc1-c1cc2cnc(N[C@H]3CC[C@H](N(C)C)CC3)nc2n(C(C)C)c1=O] | N-(5-(2-(((1r,4r)-4-(dimethylamino)cyclohexyl)amino)-8-isopropyl-7-oxo-7,8-dihydropyrido[2,3-d]pyrimidin-6-yl)-6-methylpyridin-2-yl)-2-fluorobenzenesulfonamide | 0.0003 | 594.4 |
|---|---|---|---|---|
| 141 | 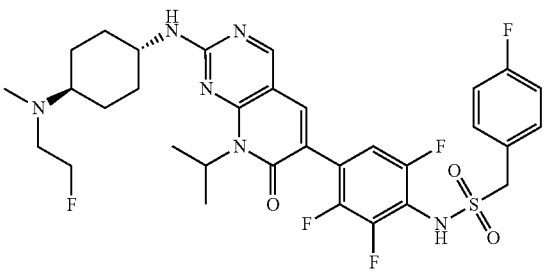 [SMILES: CC(C)n1c(=O)c(-c2cc(F)c(NS(=O)(=O)Cc3ccc(F)cc3)c(F)c2F)cc2cnc(N[C@H]3CC[C@H](N(C)CCF)CC3)nc21] | 1-(4-fluorophenyl)-N-(2,3,6-trifluoro-4-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)phenyl)-methanesulfonamide | 0.00018 | 679.3 |
| 142 | 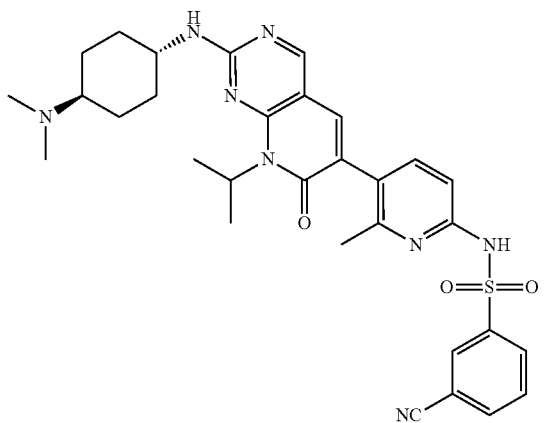 [SMILES: Cc1nc(NS(=O)(=O)c2cccc(C#N)c2)ccc1-c1cc2cnc(N[C@H]3CC[C@H](N(C)C)CC3)nc2n(C(C)C)c1=O] | 3-cyano-N-(5-(2-(((1r,4r}-4-(dimethylamino)cyclohexyl)-amino)-8-isopropyl-7-oxo-7,8-dihydropyrido-[2,3-d]pyrimidin-6-yl)-6-methylpyridin-2-yl)-benzenesulfonamide | 0.00069 | 601.4 |
| 143 | 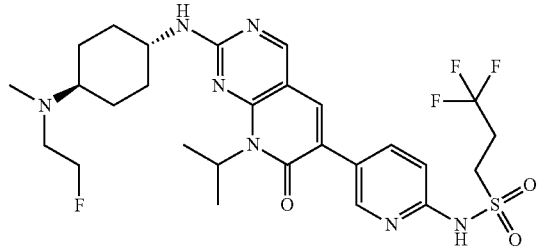 [SMILES: CC(C)n1c(=O)c(-c2ccc(NS(=O)(=O)CCC(F)(F)F)nc2)cc2cnc(N[C@H]3CC[C@H](N(C)CCF)CC3)nc21] | 3,3,3-trifluoro-N-(5-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)pyridin-2-yl)propane-1-sulfonamide | 0.0003 | 614.3 |
| 144 | 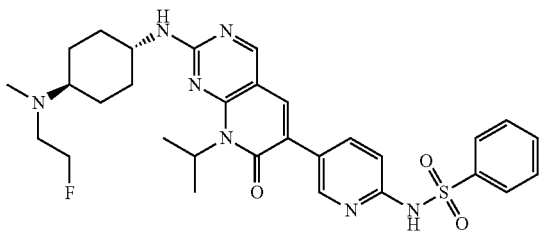 [SMILES: CC(C)n1c(=O)c(-c2ccc(NS(=O)(=O)c3ccccc3)nc2)cc2cnc(N[C@H]3CC[C@H](N(C)CCF)CC3)nc21] | N-(5-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)pyridin-2-yl)benzenesulfonamide | 0.00018 | 594.3 |

TABLE 1-continued

Representative compounds:

| # | Structure | Name | | |
|---|---|---|---|---|
| 145 | | 2-chloro-N-(5-(2-(((1r,4r)-4-((2-fluoro-ethyl)(methyl)amino)-cyclohexyl)amino)-8-isopropyl-7-oxo-7,8-dihydropyrido[2,3-d]-pyrimidin-6-yl)-6-methylpyridin-2-yl)-benzenesulfonamide | 0.00027 | 642.2 |
| 146 | | 2-chloro-N-(5-(2-(((1r,4r)-4-((2-fluoro-ethyl)(methyl)amino)-cyclohexyl)amino)-8-isopropyl-7-oxo-7,8-dihydropyrido[2,3-d]-pyrimidin-6-yl)pyridin-2-yl]benzenesulfon-amide hydrochloride | 0.00016 | 628.3 |
| 147 | | 2-chloro-N-(5-(2-(((3S,5S)-5-fluoro-piperidin-3-yl)amino)-8-isopropyl-7-oxo-7,8-dihydropyrido[2,3-d]-pyrimidin-6-yl)pyridin-2-yl)benzenesulfon-amide | 0.00027 | 572.2 |
| 148 | | 2-cyano-N-(5-(2-(((1r,4r)-4-((2-fluoro-ethyl)(methyl)amino)-cyclohexyl)amino)-8-isopropyl-7-oxo-7,8-dihydropyrido[2,3-d]-pyrimidin-6-yl)pyridin-2-yl)benzenesulfon-amide | 0.00023 | 619.3 |
| 149 | | N-(5-(2-(((1r,4r)-4-(dimethylamino)cyclo-hexyl)amino)-8-isopropyl-7-oxo-7,8-dihydropyrido[2,3-d]-pyrimidin-6-yl)pyridin-2-yl)-2-(trifluoromethyl)benzenesulfonamide | 0.00021 | 630.2 |

TABLE 1-continued

Representative compounds:

| | | | | |
|---|---|---|---|---|
| 150 | | N-(5-(2-(((1r,4r)-4-(dimethylamino)cyclo-hexyl)amino)-8-isopropyl-7-oxo-7,8-dihydropyrido[2,3-d]-pyrimidin-6-yl)pyridin-2-yl)-2-(trifluorometh-oxy)benzenesulfon-amide | 0.00026 | 646.3 |
| 151 | | 1-(3,3-difluorocyclo-butyl)-N-(4-(2-(((1r,4r)-4-(dimethylamino)-cyclohexyl)amino)-8-isopropyl-7-oxo-7,8-dihydropyrido[2,3-d]-pyrimidin-6-yl)-2-fluorophenyl)methane-sulfonamide | 0.00019 | 607.3 |
| 152 | | 1-cyclohexyl-N-(5-(2-(((1r,4r)-4-(dimethyl-amino)cyclohexyl)-amino)-8-isopropyl-7-oxo-7,8-dihydropyrido-[2,3-d]pyrimidin-6-yl)-pyridin-2-yl)methane-sulfonamide | 0.00018 | 582.3 |
| 153<br>153A<br>153B | | 1-(2,2-difluorocyclo-butyl)-N-(4-(2-(((1r,4r)-4-(dimethylamino)-cyclohexyl)amino)-8-isopropyl-7-oxo-7,8-dihydropyrido[2,3-d]-pyrimidin-6-yl)-2-fluorophenyl)methane-sulfonamide | 0.00021<br>0.00016 | 607.3 |

TABLE 1-continued

Representative compounds:

| 154 | | (N-(4-(2-((4-(dimethyl-amino)-3-fluorocyclo-hexyl)amino)-8-isopropyl-7-oxo-7,8-dihydropyrido[2,3-d]-pyrimidin-6-yl)-2-fluorophenyl)-3,3,3-trifluoropropane-1-sulfonamide hydro-chloride | 0.00013 | 617.3 |
|---|---|---|---|---|
| 155 | | N-(2-fluoro-4-(2-(((1r,4r)-4-((2-fluoro-ethyl)(methyl)amino)-cyclohexyl)amino)-8-isopropyl-7-oxo-7,8-dihydropyrido[2,3-d]-pyrimidin-6-yl)phenyl)-1-(4-fluorophenyl)-methanesulfonamide | 0.00023 | 643.3 |
| 156 | | 1-(3,3-difluorocyclo-butyl)-N-(2-fluoro-4-(2-(((1r,4r)-4-((2-fluoroethyl)(methyl)-amino)cyclohexyl)-amino)-8-isopropyl-7-oxo-7,8-dihydropyrido-[2,3-d]pyrimidin-6-yl)phenyl)methanesul-fonamide | 0.00018 | 639.4 |
| 157 | | 3,3,3-trifluoro-N-(2-fluoro-4-(2-(((1r,4r)-4-((2-fluoroethyl)(meth-yl)amino)cyclohexyl)-amino)-8-isopropyl-7-oxo-7,8-dihydropyrido-[2,3-d]pyrimidin-6-yl)-phenyl)propane-1-sul-fonamide | 0.00014 | 631.3 |
| 158 | | N-(2,3,6-trifluoro-4-(2-(((3S,5S)-5-fluoro-piperidin-3-yl)amino)-8-isopropyl-7-oxo-7,8-dihydropyrido[2,3-d]-pyrimidin-6-yl)phenyl)-1-(1-(2,2,2-trifluoro-ethyl)-1H-pyrazol-3-yl)methanesulfonamide | 0.00057 | 677.3 |
| 159 | | 2-chloro-N-(5-(2-((4-(dimethylamino)-3-fluorocyclohexyl)-amino)-8-isopropyl-7-oxo-7,8-dihydropyrido-[2,3-d]pyrimidin-6-yl)-pyridin-2-yl)benzene-sulfonamide hydro-chloride | | 614.3 |

TABLE 1-continued

Representative compounds:

| # | Structure | Name | | |
|---|---|---|---|---|
| 160 | | 2-chloro-N-(5-(2-((4-(dimethylamino)-3-fluorocyclohexyl)-amino)-8-isopropyl-7-oxo-7,8-dihydropteridin-6-yl)-6-methylpyridin-2-yl)benzenesulfonamide hydrochloride | | 6629.3 |
| 161 | | N-(4-(2-(((1r,4r)-4-(dimethylamino)cyclohexyl)amino)-8-isopropyl-7-oxo-7,8-dihydropteridin-6-yl)-3-fluorophenyl)propane-1-sulfonamide | 0.00018 | 546.3 |
| 162 | | N-(2-fluoro-4-(2-(((3S,5S)-5-fluoropiperidin-3-yl)amino)-8-isopropyl-7-oxo-7,8-dihydropteridin-6-yl)phenyl)piperidine-1-sulfonamide | 0.0013 | 563.3 |
| 163 | | N-(2-fluoro-4-(2-(((3S,5S)-5-fluoropiperidin-3-yl)amino)-8-isopropyl-7-oxo-7,8-dihydropteridin-6-yl)phenyl)pyrrolidine-1-sulfonamide | 0.00097 | 549.2 |
| 164 | | 6-(4-(dimethylsulfamoylamino)-3-fluorophenyl)-2-(((3S,5S)-5-fluoro-3-piperidyl)-amino)-8-isopropyl-7-oxo-pteridine | 0.00043 | 523.2 |
| 165 | | N-4-(2-(((1r,4r)-4-(dimethylamino)cyclohexyl)amino)-8-isopropyl-7-oxo-7,8-dihydropteridin-6-yl)-2-fluorophenyl)-2,2-difluorobutane-1-sulfonamide hydrochloride | 0.0001 | 596.4 |

TABLE 1-continued

Representative compounds:

| 166 | 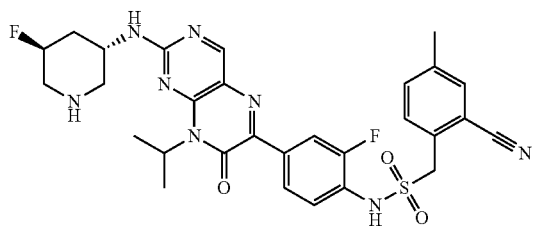 [SMILES: Cc1ccc(CS(=O)(=O)Nc2ccc(-c3nc4cnc(N[C@@H]5CNC[C@@H](F)C5)nc4n(C(C)C)c3=O)cc2F)c(C#N)c1] | 1-(2-cyano-4-methyl-phenyl)-N-(2-fluoro-4-(2-(((3S,5S)-5-fluoro-piperidin-3-yl)amino)-8-isopropyl-7-oxo-7,8-dihydropteridin-6-yl)-phenyl)methanesulfon-amide | 0.00009 | 609.3 |
|---|---|---|---|---|
| 167 | 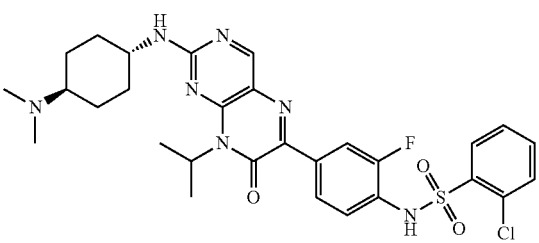 [SMILES: CC(C)n1c(=O)c(-c2ccc(NS(=O)(=O)c3ccccc3Cl)c(F)c2)nc2cnc(N[C@H]3CC[C@H](N(C)C)CC3)nc21] | 2-chloro-N-(4-(2-(((1r,4r)-4-(dimethyl-amino)cyclohexyl)-amino)-8-isopropyl-7-oxo-7,8-dihydropter-idin-6-yl)-2-fluoro-phenyl)benzenesulfon-amide | 0.00018 | 614.2 |
| 168 168A 168B | 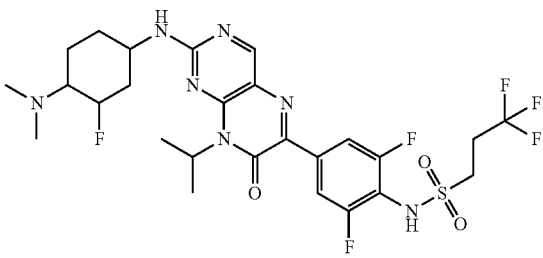 [SMILES: CC(C)n1c(=O)c(-c2cc(F)c(NS(=O)(=O)CCC(F)(F)F)c(F)c2)nc2cnc(NC3CCC(N(C)C)C(F)C3)nc21] 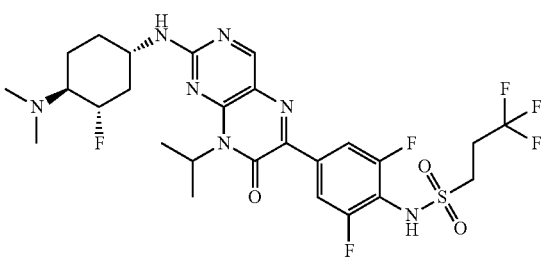 [SMILES: CC(C)n1c(=O)c(-c2cc(F)c(NS(=O)(=O)CCC(F)(F)F)c(F)c2)nc2cnc(N[C@H]3CC[C@H](N(C)C)[C@@H](F)C3)nc21] 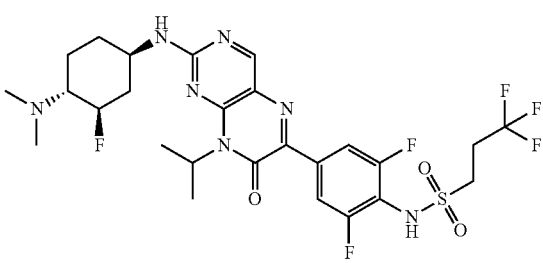 [SMILES: CC(C)n1c(=O)c(-c2cc(F)c(NS(=O)(=O)CCC(F)(F)F)c(F)c2)nc2cnc(N[C@@H]3CC[C@@H](N(C)C)[C@H](F)C3)nc21] | N-(4-(2-((4-(dimethyl-amino)-3-fluorocyclo-hexyl)amino)-8-isopropyl-7-oxo-7,8-dihydropteridin-6-yl)-2,6-difluorophenyl)-3,3,3-trifluoropropane-1-sulfonamide | 0.00024 0.00023 | 636.3 |
| 169 | 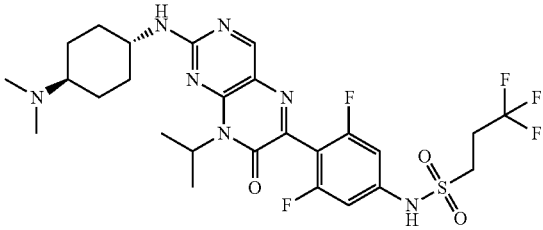 [SMILES: CC(C)n1c(=O)c(-c2c(F)cc(NS(=O)(=O)CCC(F)(F)F)cc2F)nc2cnc(N[C@H]3CC[C@H](N(C)C)CC3)nc21] | N-(4-(2-(((1r,4r)-4-(dimethylamino)cyclo-hexyl)amino)-8-isopropyl-7-oxo-7,8-dihydropteridin-6-yl)-3,5-difluorophenyl)-3,3,3-trifluoropropane-1-sulfonamide | 0.00069 | 618.2 |

TABLE 1-continued

Representative compounds:

| | | | | |
|---|---|---|---|---|
| 170 | 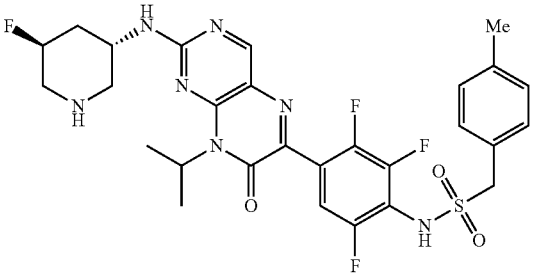 [SMILES: Cc1ccc(CS(=O)(=O)Nc2c(F)cc(-c3nc4cnc(N[C@@H]5CNC[C@@H](F)C5)nc4n(C(C)C)c3=O)c(F)c2F)cc1] | 1-p-tolyl-N-(2,3,6-trifluoro-4-(2-(((3S,5S)-5-fluoropiperidin-3-yl)amino)-8-isopropyl-7-oxo-7,8-dihydropteridin-6-yl)phenyl)-methanesulfonamide hydrochloride | 0.00013 | 620.3 |
| 171 | 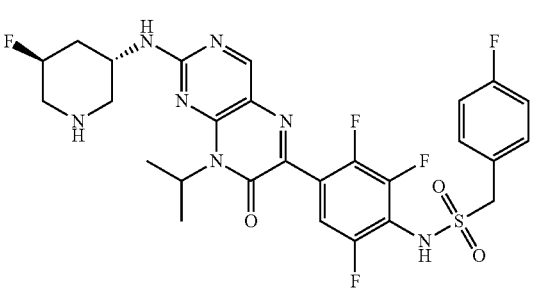 [SMILES: CC(C)n1c(=O)c(-c2cc(F)c(NS(=O)(=O)Cc3ccc(F)cc3)c(F)c2F)nc2cnc(N[C@@H]3CNC[C@@H](F)C3)nc21] | 1-(4-fluorophenyl)-N-(2,3,6-trifluoro-4-(2-(((3S,5S)-5-fluoropiperidin-3-yl)amino)-8-isopropyl-7-oxo-7,8-dihydropteridin-6-yl)phenyl)methanesulfonamide hydrochloride | 0.00012 | 624.2 |
| 172 | 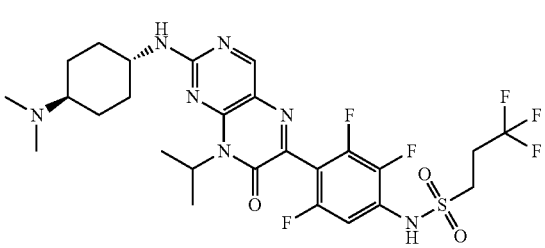 [SMILES: CC(C)n1c(=O)c(-c2c(F)cc(NS(=O)(=O)CCC(F)(F)F)c(F)c2F)nc2cnc(N[C@H]3CC[C@H](N(C)C)CC3)nc21] | N-(4-(2-(((1r,4r)-4-(dimethylamino)cyclohexyl)amino)-8-isopropyl-7-oxo-7,8-dihydropteridin-6-yl)-2,3,5-trifluorophenyl)-3,3,3-trifluoropropane-1-sulfonamide | 0.00035 | 636.3 |
| 173 | 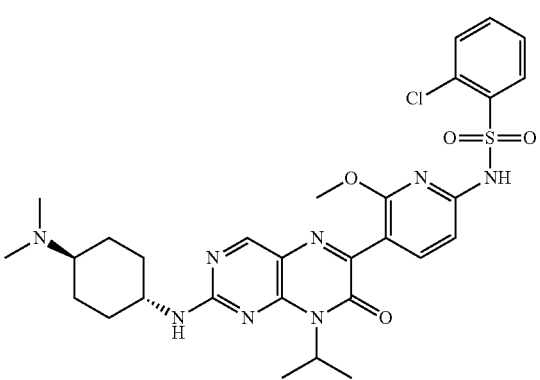 [SMILES: COc1nc(NS(=O)(=O)c2ccccc2Cl)ccc1-c1nc2cnc(N[C@H]3CC[C@H](N(C)C)CC3)nc2n(C(C)C)c1=O] | 2-chloro-N-(5-(2-(((1r,4r)-4-(dimethylamino)cyclohexyl)amino)-8-isopropyl-7-oxo-7,8-dihydropteridin-6-yl)-6-methoxypyridin-2-yl)benzenesulfonamide | 0.00027 | 627.3 |
| 174 | 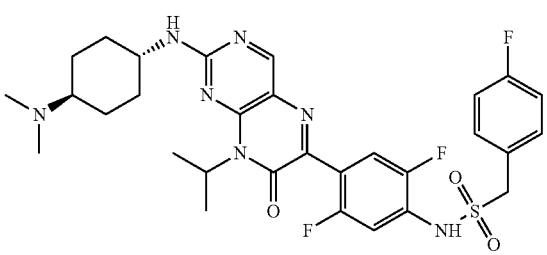 [SMILES: CC(C)n1c(=O)c(-c2cc(F)c(NS(=O)(=O)Cc3ccc(F)cc3)cc2F)nc2cnc(N[C@H]3CC[C@H](N(C)C)CC3)nc21] | N-(4-(2-(((1r,4r)-4-(dimethylamino)cyclohexyl)amino)-8-isopropyl-7-oxo-7,8-dihydropteridin-6-yl)-2,5-difluorophenyl)-1-(4-fluorophenyl)-methanesulfonamide hydrochloride | 0.00026 | 630.3 |

TABLE 1-continued

Representative compounds:

| 175 | 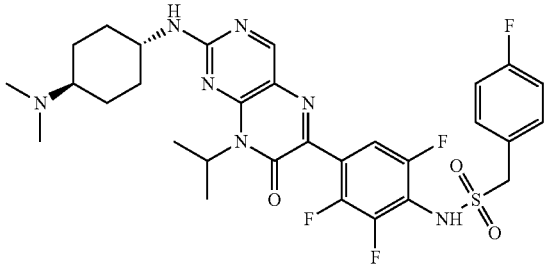 [SMILES: CC(C)n1c(=O)c(-c2cc(F)c(NS(=O)(=O)Cc3ccc(F)cc3)c(F)c2F)nc2cnc(N[C@H]3CC[C@H](N(C)C)CC3)nc21] | N-(4-(2-(((1r,4r)-4-(dimethylamino)cyclohexyl)amino)-8-isopropyl-7-oxo-7,8-dihydropteridin-6-yl)-2,3,6-trifluorophenyl)-1-(4-fluorophenyl)-methanesulfonamide hydrochloride | 0.00014 | 648.4 |
| --- | --- | --- | --- | --- |
| 176 | 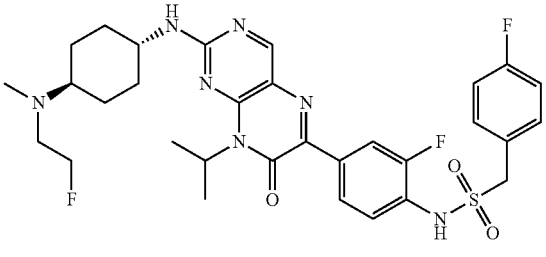 [SMILES: CC(C)n1c(=O)c(-c2ccc(NS(=O)(=O)Cc3ccc(F)cc3)c(F)c2)nc2cnc(N[C@H]3CC[C@H](N(C)CCF)CC3)nc21] | N-(2-(fluoro-4-(2-(((1r,4r)-4-((2-fluoroethyl)(methyl)amino)-cyclohexyl)amino)-8-isopropyl-7-oxo-7,8-dihydropteridin-6-yl)-phenyl)-1-(4-fluorophenyl)methanesulfonamide | 0.00014 | 644.3 |
| 177 | 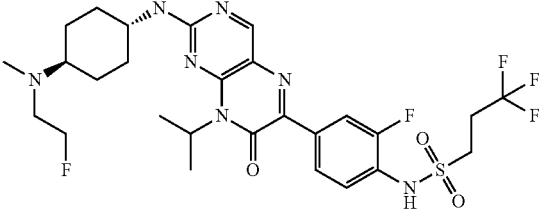 | 3,3,3-trifluoro-N-(2-fluoro-4-(2-(((1r,4r)-4-((2-fluoroethyl)(methyl)amino)cyclohexyl)-amino)-8-isopropyl-7-oxo-7,8-dihydropteridin-6-yl)phenyl)-propane-1-sulfonamide | 0.00024 | 632.3 |
| 178 | 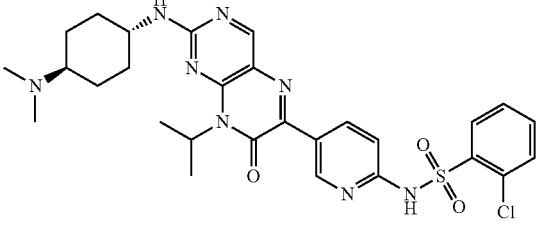 | 2-chloro-N-(5-(2-(((1r,4r)-4-(dimethylamino)cyclohexyl)-amino)-8-isopropyl-7-oxo-7,8-dihydropteridin-6-yl)pyridin-2-yl)-benzenesulfonamide | 0.00026 | 597.3 |
| 179<br>179A<br>179B | 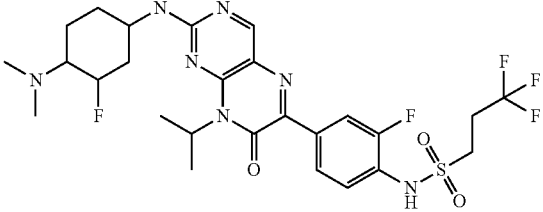<br>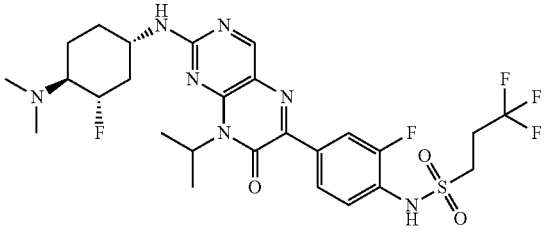 [SMILES: CC(C)n1c(=O)c(-c2ccc(NS(=O)(=O)CCC(F)(F)F)c(F)c2)nc2cnc(N[C@H]3CC[C@H](N(C)C)[C@@H](F)C3)nc21] | N-(4-(2-((4-(dimethylamino)-3-fluorocyclohexyl)amino)-8-isopropyl-7-oxo-7,8-dihydropteridin-6-yl)-2-fluorophenyl)-3,3,3-trifluoropropane-1-sulfonamide hydrochloride | 0.00022<br>0.00015 | 618.3 |

TABLE 1-continued
Representative compounds:
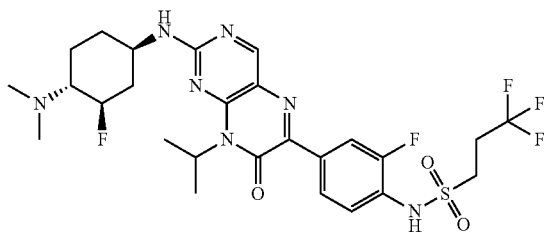 [SMILES: CC(C)n1c(=O)c(-c2ccc(NS(=O)(=O)CCC(F)(F)F)c(F)c2)nc2cnc(N[C@@H]3CC[C@@H](N(C)C)[C@H](F)C3)nc21]
| 180 | 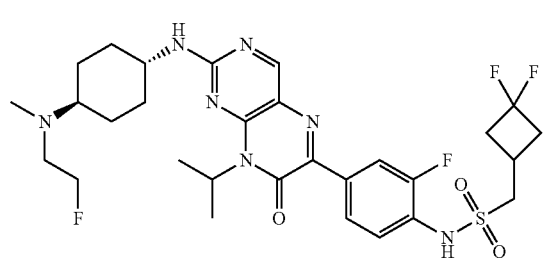 [SMILES: CC(C)n1c(=O)c(-c2ccc(NS(=O)(=O)CC3CC(F)(F)C3)c(F)c2)nc2cnc(N[C@H]3CC[C@H](N(C)CCF)CC3)nc21] | 1-(3,3-difluorocyclo-butyl)-N-(2-fluoro-4-(2-(((1r,4r)-4-((2-fluoroethyl)(methyl)-amino)cyclohexyl)-amino)-8-isopropyl-7-oxo-7,8-dihydropter-idin-6-yl)phenyl)-methanesulfonamide | 0.00029 | 640.3 |
|---|---|---|---|---|
| 181<br>181A<br>181B | 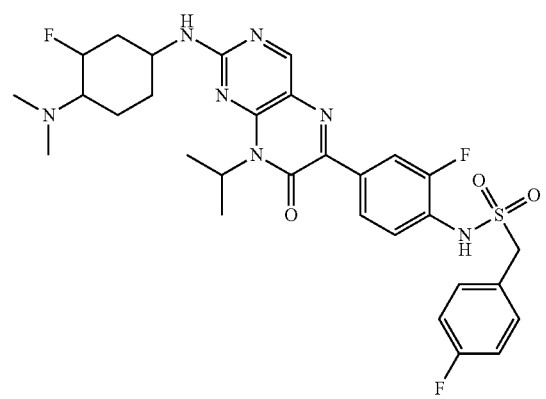 [SMILES: CC(C)n1c(=O)c(-c2ccc(NS(=O)(=O)Cc3ccc(F)cc3)c(F)c2)nc2cnc(NC3CCC(N(C)C)C(F)C3)nc21]<br><br>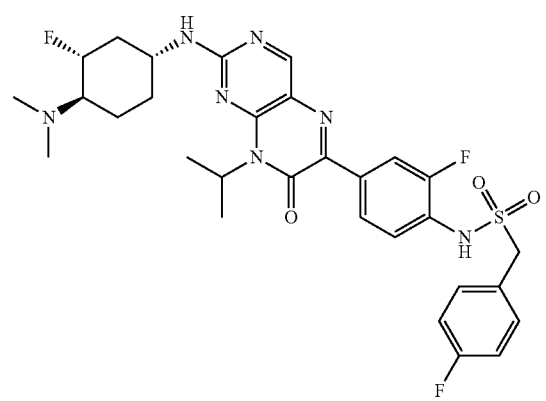 [SMILES: CC(C)n1c(=O)c(-c2ccc(NS(=O)(=O)Cc3ccc(F)cc3)c(F)c2)nc2cnc(N[C@@H]3CC[C@@H](N(C)C)[C@H](F)C3)nc21] | N-(4-(2-((4-(dimethyl-amino)-3-fluorocyclo-hexyl)amino)-8-isopropyl-7-oxo-7,8-dihydropteridin-6-yl)-2-fluorophenyl)-1-(4-fluorophenyl)methane-sulfonamide | 0.00016<br>0.00015 | 630.3 |

TABLE 1-continued

Representative compounds:

| | | | |
|---|---|---|---|
| 182 | 2-(3,3-difluoroazetidin-1-yl)-N-(4-(2-(((1r,4r)-4-(dimethylamino)cyclohexyl)amino)-8-isopropyl-7-oxo-7,8-dihydropteridin-6-yl)-2-fluorophenyl)ethane-1-sulfonamide | 0.00087 | 623.6 |
| 183 | N-(2-fluoro-4-(2-(((1r,4r)-4-((2-fluoroethyl)(methyl)amino)cyclohexyl)amino-8-isopropyl-7-oxo-7,8-dihydropteridin-6-yl)phenyl)-1-phenyl-methanesulfonamide | 0.00012 | 626.4 |
| 184 | N-(4-(2-(((1r,4r)-4-(dimethylamino)cyclohexyl)amino)-8-isopropyl-7-oxo-7,8-dihydropteridin-6-yl)-2-fluorophenyl)-1-(4-fluorophenyl)methanesulfonamide | 0.00025 | 612.4 |
| 185 | 1-phenyl-N-(2,3,6-trifluoro-4-(2-(((3S,5S)-5-fluoropiperidin-3-yl)amino)-8-isopropyl-7-oxo-7,8-dihydropteridin-6-yl)phenyl)methanesulfonamide | 0.00017 | 606.2 |

TABLE 1-continued

Representative compounds:

| | | | | |
|---|---|---|---|---|
| 186 | 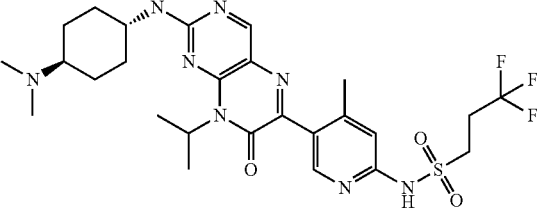 | N-(5-(2-(((1r,4r)-4-(dimethylamino)cyclo-hexyl)amino)-8-isopropyl-7-oxo-7,8-dihydropteridin-6-yl)-4-methylpyridin-2-yl)-3,3,3-trifluoropropane-1-sulfonamide | 0.00095 | 597.3 |
| 187 | 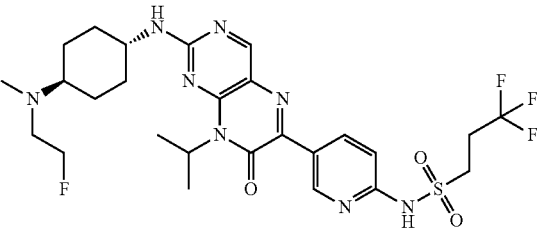 [SMILES: CC(C)n1c(=O)c(-c2ccc(NS(=O)(=O)CCC(F)(F)F)nc2)nc2cnc(N[C@H]3CC[C@H](N(C)CCF)CC3)nc21] | 3,3,3-trifluoro-N-(5-(2-(((1r,4r)-4-((2-fluoro-ethyl)(methyl)amino)-cyclohexyl)amino)-8-isopropyl-7-oxo-7,8-dihydropteridin-6-yl)-pyridin-2-yl)propane-1-sulfonamide | 0.00031 | 615.4 |
| 188 | 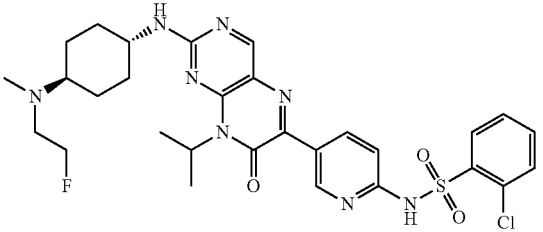 [SMILES: CC(C)n1c(=O)c(-c2ccc(NS(=O)(=O)c3ccccc3Cl)nc2)nc2cnc(N[C@H]3CC[C@H](N(C)CCF)CC3)nc21] | 2-chloro-N-(5-(2-(((1r,4r)-4-((2-fluoro-ethyl)(methyl)amino)-cyclohexyl)amino)-8-isopropyl-7-oxo-7,8-dihydropteridin-6-yl)-pyridin-2-yl)benzene-sulfonamide hydro-chloride | 0.00027 | 629.3 |
| 189 | 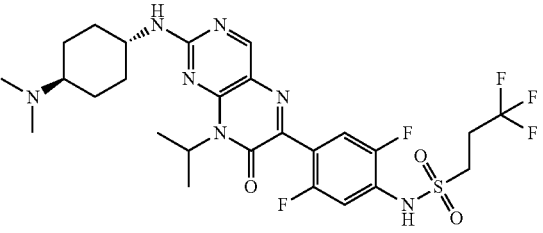 [SMILES: CC(C)n1c(=O)c(-c2cc(F)c(NS(=O)(=O)CCC(F)(F)F)cc2F)nc2cnc(N[C@H]3CC[C@H](N(C)C)CC3)nc21] | N-(4-(2-(((1r,4r)-4-(dimethylamino)cyclo-hexyl)amino)-8-isopropyl-7-oxo-7,8-dihydropteridin-6-yl)-2,5-difluorophenyl]-3,3,3-trifluoropropane-1-sulfonamide | 0.00049 | 618.3 |
| 190 | 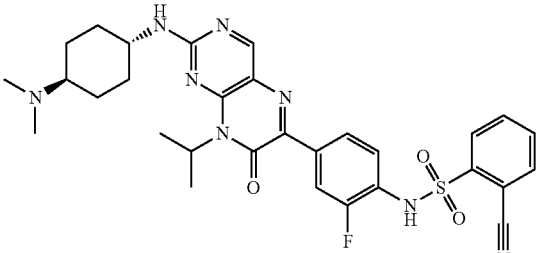 | 2-cyano-N-(4-(2-(((1r,4r)-4-(dimethyl-amino)cyclohexyl)-amino)-8-isopropyl-7-oxo-7,8-dihydropter-idin-6-yl)-2-fluoro-phenyl)benzenesulfon-amide | 0.00018 | 605.4 |
| 191 | 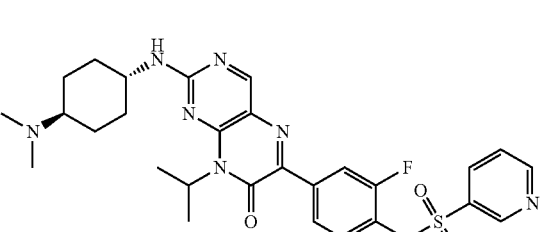 | N-(4-(2-(((1r,4r)-4-(dimethylamino)cyclo-hexyl)amino)-8-isopropyl-7-oxo-7,8-dihydropteridin-6-yl)-2-fluorophenyl)pyridine-3-sulfonamide hydro-chloride | 0.00025 | 581.4 |

TABLE 1-continued
Representative compounds:
| 192 192A 192B | 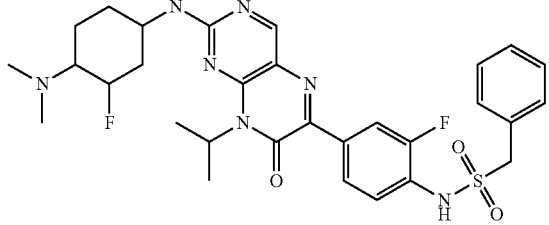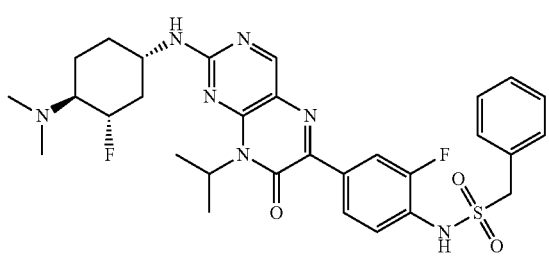 [SMILES: CC(C)n1c(=O)c(-c2ccc(NS(=O)(=O)Cc3ccccc3)c(F)c2)nc2cnc(N[C@H]3CC[C@H](N(C)C)[C@@H](F)C3)nc21]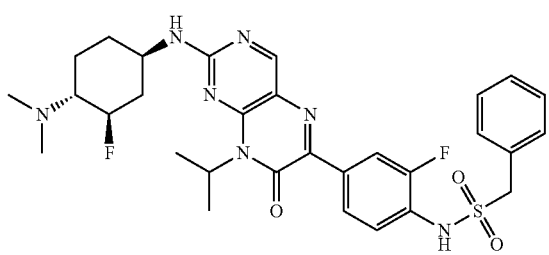 [SMILES: CC(C)n1c(=O)c(-c2ccc(NS(=O)(=O)Cc3ccccc3)c(F)c2)nc2cnc(N[C@@H]3CC[C@@H](N(C)C)[C@H](F)C3)nc21] | N-(4-(2-((4-(dimethyl-amino)-3-fluorocyclo-hexyl)amino)-8-isopropyl-7-oxo-7,8-dihydropteridin-6-yl)-2-fluorophenyl)-1-phenylmethanesulfon-amide | 0.00011 0.00009 | 612.3 |
|---|---|---|---|---|
| 193 193A 193B | 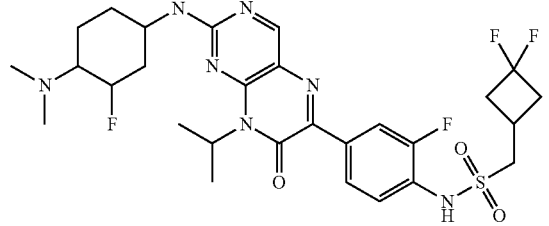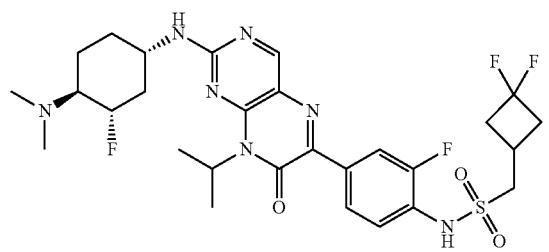 [SMILES: CC(C)n1c(=O)c(-c2ccc(NS(=O)(=O)CC3CC(F)(F)C3)c(F)c2)nc2cnc(N[C@H]3CC[C@H](N(C)C)[C@@H](F)C3)nc21]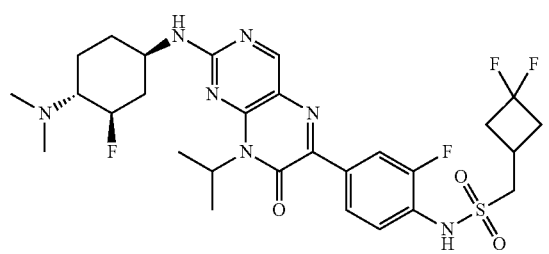 [SMILES: CC(C)n1c(=O)c(-c2ccc(NS(=O)(=O)CC3CC(F)(F)C3)c(F)c2)nc2cnc(N[C@@H]3CC[C@@H](N(C)C)[C@H](F)C3)nc21] | 1-(3,3-difluorocyclo-butyl)-N-(4-(2-((4-(dimethylamino)-3-fluorocyclohexyl)-amino)-8-isopropyl-7-oxo-7,8-dihydropter-idin-6-yl)-2-fluoro-phenyl)methanesulfon-amide | 0.0002 0.00017 | 626.3 |

TABLE 1-continued

Representative compounds:

| | | | | |
|---|---|---|---|---|
| 194 | 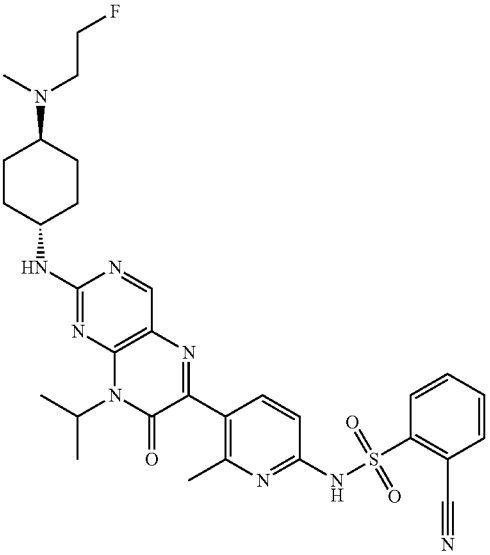 [SMILES: Cc1nc(NS(=O)(=O)c2ccccc2C#N)ccc1-c1nc2cnc(N[C@H]3CC[C@H](N(C)CCF)CC3)nc2n(C(C)C)c1=O] | 2-cyano-N-(5-(2-(((1r,4r)-4-((2-fluoro-ethyl)(methyl)amino)-cyclohexyl)amino)-8-isopropyl-7-oxo-7,8-dihydropteridin-6-yl)-6-methylpyridin-2-yl)-benzenesulfonamide | 0.00031 | 634.3 |
| 195 | 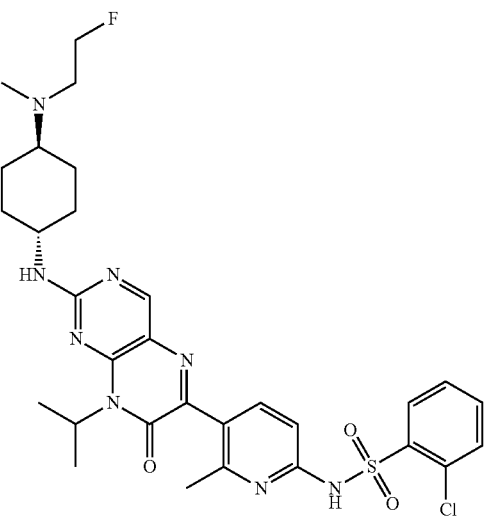 [SMILES: Cc1nc(NS(=O)(=O)c2ccccc2Cl)ccc1-c1nc2cnc(N[C@H]3CC[C@H](N(C)CCF)CC3)nc2n(C(C)C)c1=O] | 2-chloro-N-(5-(2-(((1r,4r)-4-((2-fluoro-ethyl)(methyl)amino)-cyclohexyl)amino)-8-isopropyl-7-oxo-7,8-dihydropteridin-6-yl)-6-methylpyridin-2-yl)-benzenesulfonamide | 0.00029 | 643.3 |
| 196 | 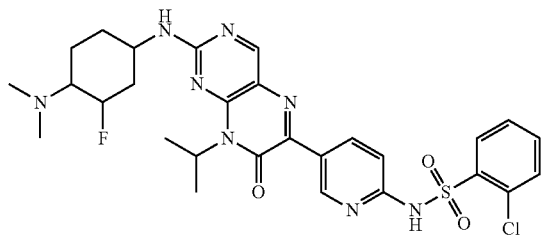 [SMILES: CC(C)n1c(=O)c(-c2ccc(NS(=O)(=O)c3ccccc3Cl)nc2)nc2cnc(NC3CCC(N(C)C)C(F)C3)nc21] | 2-chloro-N-(5-(2-((4-(dimethylamino)-3-fluorocyclohexyl)-amino)-8-isopropyl-7-oxo-7,8-dihydropter-idin-6-yl)pyridin-2-yl)-benzenesulfonamide hydrochoride | | 615.3 |
| 197 | 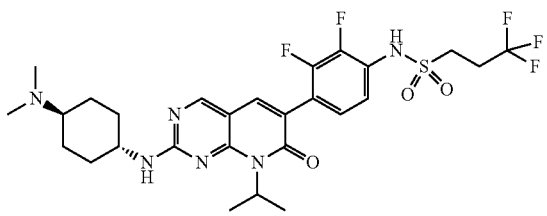 [SMILES: CC(C)n1c(=O)c(-c2ccc(NS(=O)(=O)CCC(F)(F)F)c(F)c2F)cc2cnc(N[C@H]3CC[C@H](N(C)C)CC3)nc21] | N-(4-(2-(((1,4-trans)-4-(Dimethylamino)cyclo-hexyl)amino)-8-isopropyl-7-oxo-7,8-dihydropyrido[2,3-d]-pyrimidin-6-yl)-2,3-difluorophenyl)-3,3,3-trifluoropropane-1-sulfonamide | 0.00026 | 617.2 |

TABLE 1-continued

Representative compounds:

| | | | |
|---|---|---|---|
| 198 | N-(4-(2-(((1,4-trans)-4-(azetidin-1-yl)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide formulate | 0.00041 | 611.2 |
| 199 | 3,3,3-trifluoro-N-(2-fluoro-4-(8-isopropyl-7-oxo-2-(((1,4-trans))-4-(pyrrolidin-1-yl)cyclohexyl)amino)-7,8-dihydropyrido[2,3-d]pyrimidin-6-yl)phenyl)propane-1-sulfonamide | 0.00025 | 625.1 |
| 200 | 3.3.3-trifluoro-N-(2-fluoro-4-(8-isopropyl-2-((1-methylpiperidin-4-yl)amino)-7-oxo-7,8-dihydropyrido[2,3-d]pyrimidin-6-yl)phenyl)propane-1-sulfonamide formate | 0.02 | 571.1 |
| 201 | 3,3,3-trifluoro-N-(2-fluoro-4-(8-isopropyl-7-oxo-2-(piperidin-4-ylamino)-7,8-dihydropyrido[2,3-d]pyrimidin-6-yl)phenyl)propane-1-sulfonamide | 0.0087 | 557.1 |
| 202<br>202A<br>202B | N-(4-(8-(sec-butyl)-2-(((3S,5S)-5-fluoropiperidin-3-yl)amino)-7-oxo-7,8-dihydropyrido[2,3-d]pyrimidin-6-yl)-2-fluorophenyl)-1-(2-fluorophenyl)methanesulfonamide hydrochloride | 0.00026<br>0.00026 | 601.0 |

TABLE 1-continued

Representative compounds:

| | | | | |
|---|---|---|---|---|
| 203 | 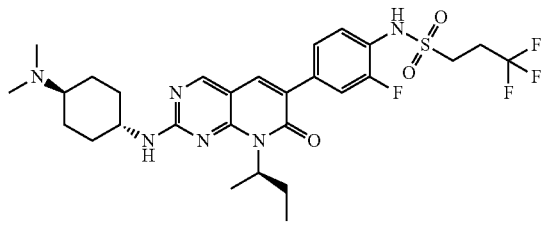 [SMILES: CC[C@@H](C)n1c(=O)c(-c2ccc(NS(=O)(=O)CCC(F)(F)F)c(F)c2)cc2cnc(N[C@H]3CC[C@H](N(C)C)CC3)nc21] | N-(4-(8-((R)-sec-butyl)-2-(((1r,4R)-4-(dimethyl-amino)cyclohexyl)-amino)-7-oxo-7,8-dihydropyrido[2,3-d]-pyrimidin-6-yl)-2-fluorophenyl)-3,3,3-trifluoropropane-1-sulfonamide | 0.00021<br>0.0001 | 613.0<br>613.0 |
| 203A | 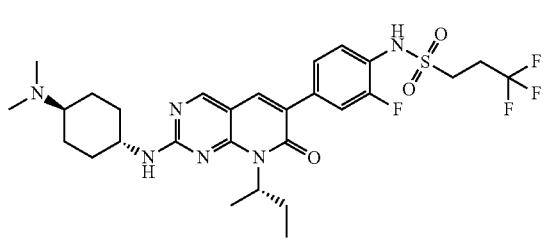 [SMILES: CC[C@H](C)n1c(=O)c(-c2ccc(NS(=O)(=O)CCC(F)(F)F)c(F)c2)cc2cnc(N[C@H]3CC[C@H](N(C)C)CC3)nc21] | N-(4-(8-((S)-sec-butyl)-2-(((1r,4R)-4-(dimethyl-amino)cyclohexyl)-amino)-7-oxo-7,8-dihydropyrido[2,3-d]-pyrimidin-6-yl)-2-fluorophenyl)-3,3,3-trifluoropropane-1-sulfonamide | | |
| 204 | 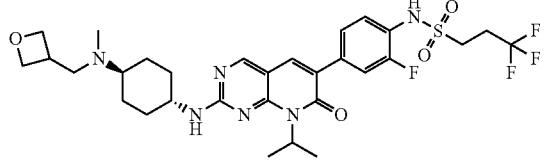 | 3,3,3-trifluoro-N-(2-fluoro-4-(8-isopropyl-2-(((1,4-trans)-4-(methyl(oxetan-3-yl-methyl)amino)cyclohex-yl)amino)-7-oxo-7,8-dihydropyrido[2,3-d]-pyrimidin-6-yl)phenyl)-propane-1-sulfonamide | 0.001 | 655.1 |
| 205 | 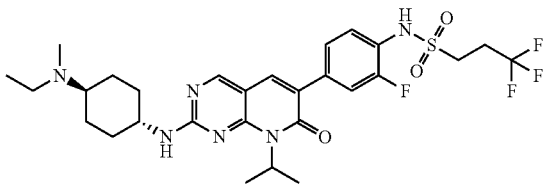 [SMILES: CCN(C)[C@H]1CC[C@H](Nc2ncc3cc(-c4ccc(NS(=O)(=O)CCC(F)(F)F)c(F)c4)c(=O)n(C(C)C)c3n2)CC1] | N-(4-(2-(((1,4-trans)-4-(ethyl(methyl)amino)-cyclohexyl)amino)-8-isopropyl-7-oxo-7,8-dihydropyrido[2,3-d]-pyrimidin-6-yl)-2-fluorophenyl)-3,3,3-trifluoropropane-1-sulfonamide | 0.00014 | 613.0 |
| 206 | 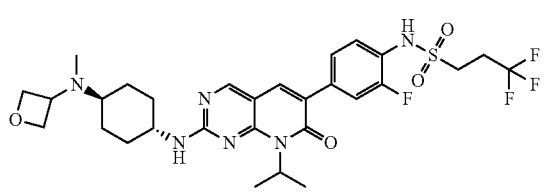 [SMILES: CC(C)n1c(=O)c(-c2ccc(NS(=O)(=O)CCC(F)(F)F)c(F)c2)cc2cnc(N[C@H]3CC[C@H](N(C)C4COC4)CC3)nc21] | 3,3,3-trifluoro-N-(2-fluoro-4-(8-isopropyl-2-(((1,4-trans)-4-(methyl-(oxetan-3-yl)amino)-cyclohexyl)amino)-7-oxo-7,8-dihydropyrido-[2,3-d]pyrimidin-6-yl)-phenyl)propane-1-sulfonamide | 0.00017 | 641.1 |
| 207 | 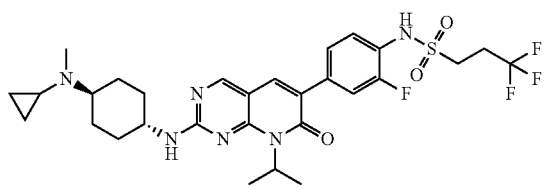 [SMILES: CC(C)n1c(=O)c(-c2ccc(NS(=O)(=O)CCC(F)(F)F)c(F)c2)cc2cnc(N[C@H]3CC[C@H](N(C)C4CC4)CC3)nc21] | N-(4-(2-(((1,4-trans)-4-(cyclopropyl(methyl)-amino)cyclohexyl)-amino)-8-isopropyl-7-oxo-7,8-dihydropyrido-[2,3-d]pyrimidin-6-yl)-2-fluorophenyl)-3,3,3-trifluoropropane-1-sul-fonamide | 0.00021 | 625.3 |

TABLE 1-continued

Representative compounds:

| 208 | 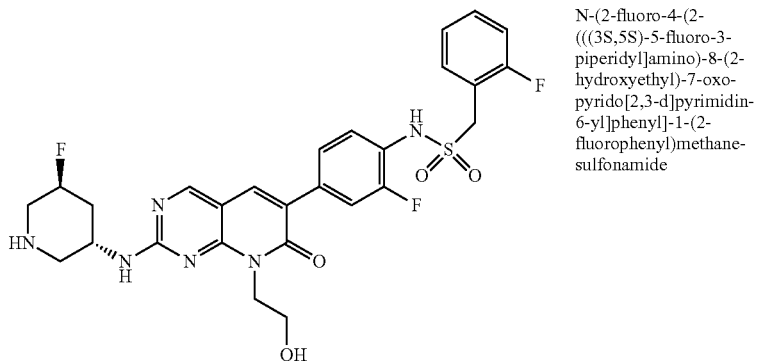 | N-(2-fluoro-4-(2-(((3S,5S)-5-fluoro-3-piperidyl]amino)-8-(2-hydroxyethyl)-7-oxo-pyrido[2,3-d]pyrimidin-6-yl]phenyl]-1-(2-fluorophenyl)methane-sulfonamide | 0.0012 | 589.2 |
|---|---|---|---|---|
| 209 | 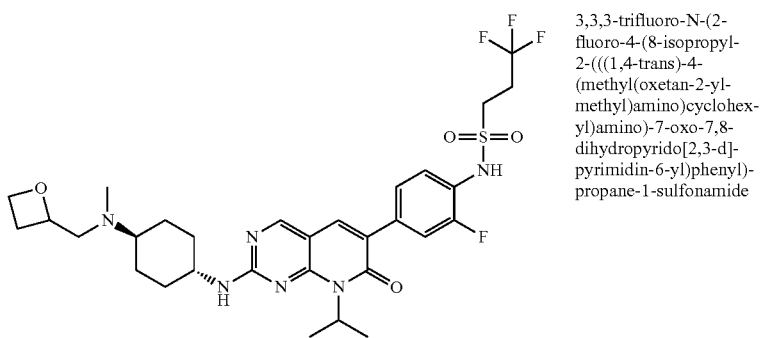 | 3,3,3-trifluoro-N-(2-fluoro-4-(8-isopropyl-2-(((1,4-trans)-4-(methyl(oxetan-2-yl-methyl)amino)cyclohex-yl)amino)-7-oxo-7,8-dihydropyrido[2,3-d]-pyrimidin-6-yl)phenyl)-propane-1-sulfonamide | 0.00019 | 655.4 |
| 210 | 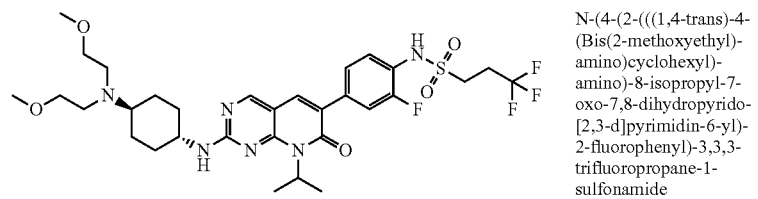 | N-(4-(2-(((1,4-trans)-4-(Bis(2-methoxyethyl)-amino)cyclohexyl)-amino)-8-isopropyl-7-oxo-7,8-dihydropyrido-[2,3-d]pyrimidin-6-yl)-2-fluorophenyl)-3,3,3-trifluoropropane-1-sulfonamide | 0.00025 | 687.4 |
| 211 | 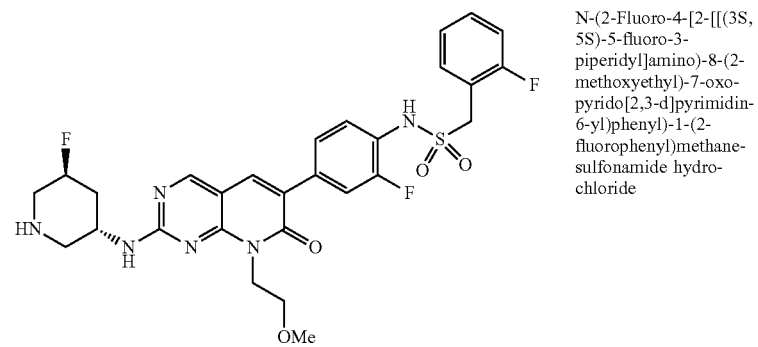 | N-(2-Fluoro-4-[2-[[(3S,5S)-5-fluoro-3-piperidyl]amino)-8-(2-methoxyethyl)-7-oxo-pyrido[2,3-d]pyrimidin-6-yl)phenyl]-1-(2-fluorophenyl)methane-sulfonamide hydro-chloride | 0.00088 | 565.1 |
| 212 | 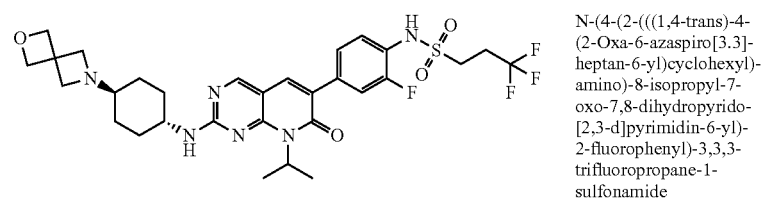 | N-(4-(2-(((1,4-trans)-4-(2-Oxa-6-azaspiro[3.3]-heptan-6-yl)cyclohexyl)-amino)-8-isopropyl-7-oxo-7,8-dihydropyrido-[2,3-d]pyrimidin-6-yl)-2-fluorophenyl)-3,3,3-trifluoropropane-1-sulfonamide | 0.00024 | 653.2 |

TABLE 1-continued

Representative compounds:

| 213 | | 3,3,3-Trifluoro-N-(2-fluoro-4-(8-isopropyl-2-(((1,4-trans)-4-morpholinocyclohexyl)amino)-7-oxo-7,8-dihydropyrido[2,3-d]pyrimidin-6-yl)phenyl)propane-1-sulfonamide | 0.00014 | 641.2 |
|---|---|---|---|---|
| 214<br>214A<br>214B<br>214C<br>214D | | N-(4-(2-((4-(dimethylamino)-4-methylcyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide cis and trans mixture | 0.017<br>0.054<br>0.0074 | 649.3 |

TABLE 1-continued

Representative compounds:

| # | Structure | Name | | |
|---|---|---|---|---|
| 215 | | N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)-3,3,3-trifluoropropane-1-sulfonamide | 0.0003 | 582.3 |
| 216 | | 3,3,3-trifluoro-N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)propane-1-sulfonamide | 0.0017 | 558.2 |
| 217<br>217A<br>217B<br>217C<br>217D | | N-(4-(2-((4-((dimethylamino)methyl)cyclohexyl)amino)-8-isopropyl-7-oxo-7,8-dihydropyrido-[2,3-d]pyrimidin-6-yl)-2-fluorophenyl)-3,3,3-trifluoropropane-1-sulfonamide cis or trans | 0.0009<br>0.0003 | 613.3 |

TABLE 1-continued

Representative compounds:

| 218 | N-(6-(2-(((1r,4r)-4-(dimethylamino)cyclohexyl)amino)-8-isopropyl-7-oxo-7,8-dihydropyrido[2,3-d]pyrimidin-6-yl)pyridin-3-yl)-3,3,3-trifluoropropane-1-sulfonamide | 0.0002 | 582.3 |
|---|---|---|---|
| 219 | 3,3,3-trifluoro-N-(6-(2-(((3S,5S)-5-fluoropiperidin-3-yl)amino)-8-isopropyl-7-oxo-7,8-dihydropyrido[2,3-d]pyrimidin-6-yl)pyridin-3-yl)propane-1-sulfonamide | 0.0034 | 558.2 |
| 220 | N-(4-(2-((2-azaspiro-[3.5]nonan-7-yl)amino)-8-isopropyl-7-oxo-7,8-dihydropyrido[2,3-d]pyrimidin-6-yl)-2-fluorophenyl)-3,3,3-trifluoropropane-1-sulfonamide | 0.005 | 597.3 |
| 221 | 3,3,3-trifluoro-N-(2-fluoro-4-(8-isopropyl-2-((2-methyl-2-azaspiro-[3.5]nonan-7-yl)amino)-7-oxo-7,8-dihydropyrido[2,3-d]pyrimidin-6-yl)phenyl)propane-1-sulfonamide | 0.0002 | 611.3 |
| 222 | N-(5-(2-(((1r,4r)-4-(dimethylamino)cyclohexyl)amino)-8-isopropyl-7-oxo-7,8-dihydropyrido[2,3-d]pyrimidin-6-yl)-3-fluoropyridin-2-yl)-3,3,3-trifluoropropane-1-sulfonamide | 0.0003 | 600.3 |
| 223 | N-(6-(2-(((1S,3R,4S)-4-(dimethylamino)-3-fluorocyclohexyl)amino)-8-isopropyl-7-oxo-7,8-dihydropyrido[2,3-d]pyrimidin-6-yl)pyridin-3-yl)-3,3,3-trifluoropropane-1-sulfonamide | 0.0005 | 600.3 |
| 224 | N-(6-(2-(((1S,3R,4S)-(dimethylamino)-3-fluorocyclohexyl)amino)-8-isopropyl-7-oxo-7,8-dihydropyrido[2,3-d]pyrimidin-6-yl)pyridin-3-yl)-3,3,3-trifluoropropane-1-sulfonamide | 0.0002 | 600.3 |

TABLE 1-continued

Representative compounds:

| | | | | |
|---|---|---|---|---|
| 225 | 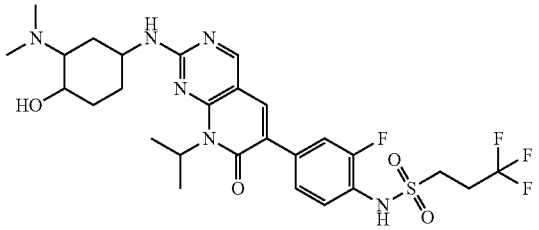 [SMILES: CC(C)n1c(=O)c(-c2ccc(NS(=O)(=O)CCC(F)(F)F)c(F)c2)cc2cnc(NC3CCC(O)C(N(C)C)C3)nc21] | N-(4-(2-((3-(dimethyl-amino)-4-hydroxycyclo-hexyl)amino)-8-isopropyl-7-oxo-7,8-dihydropyrido[2,3-d]-pyrimidin-6-yl)-2-fluorophenyl)-3,3,3-trifluoropropane-1-sulfonamide | 0.0054 | 615.3 |
| 226 | 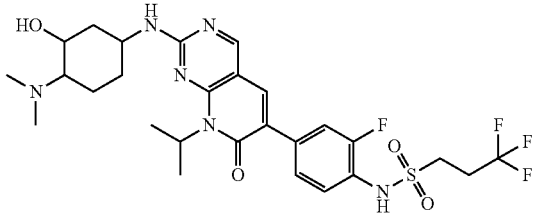 [SMILES: CC(C)n1c(=O)c(-c2ccc(NS(=O)(=O)CCC(F)(F)F)c(F)c2)cc2cnc(NC3CCC(N(C)C)C(O)C3)nc21] | N-(4-(2-((4-(dimethyl-amino)-3-hydroxycyclo-hexyl)amino)-8-isopropyl-7-oxo-7,8-dihydropyrido[2,3-d]-pyrimidin-6-yl)-2-fluorophenyl)-3,3,3-trifluoropropane-1-sulfonamide | 0.0003 | 615.3 |
| 227 | 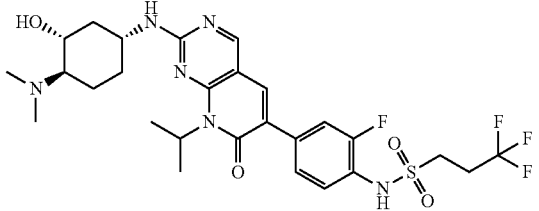 [SMILES: CC(C)n1c(=O)c(-c2ccc(NS(=O)(=O)CCC(F)(F)F)c(F)c2)cc2cnc(N[C@@H]3CC[C@@H](N(C)C)[C@H](O)C3)nc21] | N-(4-(2-(((1R,3R,4R)-4-(dimethylamino)-3-hydroxycyclohexyl)-amino)-8-isopropyl-7-oxo-7,8-dihydropyrido-[2,3-d]pyrimidin-6-yl)-2-fluorophenyl)-3,3,3-trifluoropropane-1-sulfonamide | 0.0003 | 615.3 |
| 228 | 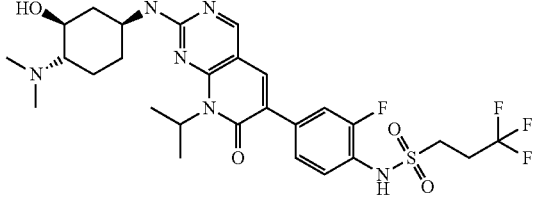 | N-(4-(2-(((1S,3S,4S)-4-(dimethylamino)-3-hydroxycyclohexyl)-amino)-8-isopropyl-7-oxo-7,8-dihydropyrido-[2,3-d]pyrimidin-6-yl)-2-fluorophenyl)-3,3,3-trifluoropropane-1-sulfonamide | 0.0002 | 615.3 |
| 229 | 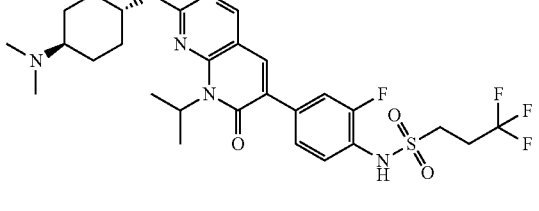 | N-(4-(2-(((1r,4r)-4-(dimethylamino)cyclo-hexyl)amino)-8-isopropyl-7-oxo-7,8-dihydropyrido[2,3-d]-pyrimidin-6-yl)-2-fluorophenyl)-3,3-difluorobutane-1-sulfonamide | 0.0003 | 595.4 |
| 230 | 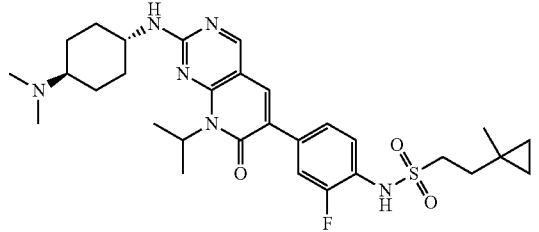 [SMILES: CC(C)n1c(=O)c(-c2ccc(NS(=O)(=O)CCC3(C)CC3)c(F)c2)cc2cnc(N[C@H]3CC[C@H](N(C)C)CC3)nc21] | N-(4-(2-(((1r,4r)-4-(dimethylamino)cyclo-hexyl)amino)-8-isopropyl-7-oxo-7,8-dihydropyrido[2,3-d]-pyrimidin-6-yl)-2-fluorophenyl)-2-(1-methylcyclopropyl)-ethane-1-sulfonamide | 0.0002 | 585.5 |

TABLE 1-continued

Representative compounds:

| # | Structure | Name | | |
|---|---|---|---|---|
| 231 | | 2-cyclobutyl-N-(4-(2-(((1r,4r)-4-(dimethyl-amino)cyclohexyl)-amino)-8-isopropyl-7-oxo-7,8-dihydropyrido-[2,3-d]pyrimidin-6-yl)-2-fluorophenyl)ethane-1-sulfonamide | 0.0001 | 585.5 |
| 232 | | 3-cyclopropyl-N-(4-(2-(((1r,4r)-4-(dimethyl-amino)cyclohexyl)-amino)-8-isopropyl-7-oxo-7,8-dihydropyrido-[2,3-d]pyrimidin-6-yl)-2-fluorophenyl)propane-1-sulfonamide | 0.0002 | 585.5 |
| 233 | | N-(5-(2-(((1r,4r)-4-(dimethylamino)cyclo-hexyl)amino)-8-isopropyl-7-oxo-7,8-dihydropyrido[2,3-d]-pyrimidin-6-yl)pyrim-idin-2-yl)-3,3,3-trifluoropropane-1-sulfonamide | 0.0013 | 583.3 |
| 234 | | 3,3,3-trifluoro-N-(2-fluoro-4-(8-isopropyl-2-((2-(2-methoxyethyl)-2-azaspiro[3.5]nonan-7-yl)amino)-7-oxo-7,8-dihydropyrido[2,3-d]-pyrimidin-6-yl)phenyl)-propane-1-sulfonamide | 0.0002 | 655.3 |
| 235 | | 3,3,3-trifluoro-N-(2-fluoro-4-(2-((2-(2-fluoroethyl)-2-azaspiro-[3.5]nonan-7-yl)amino)-8-isopropyl-7-oxo-7,8-dihydropyrido[2,3-d]-pyrimidin-6-yl)phenyl)-propane-1-sulfonamide | 0.0003 | 643.4 |
| 236 | | N-[5[2-[[((3S,5S)-5-fluoro-3-piperidyl]-amino]-8-isopropyl-7-oxo-pteridin-6-yl]-2-pyridyl]-1-phenyl-methanesulfonamide | 0.0005 | 553.3 |

TABLE 1-continued

Representative compounds:

| | | | | |
|---|---|---|---|---|
| 237 | 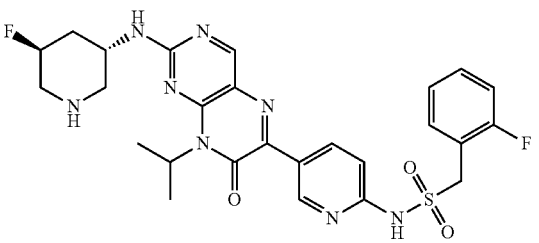 [SMILES: CC(C)n1c(=O)c(-c2ccc(NS(=O)(=O)Cc3ccccc3F)nc2)nc2cnc(N[C@@H]3CNC[C@@H](F)C3)nc21] | 1-(2-fluorophenyl)-N-[5-[2-[[(3S,5S)-5-fluoro-3-piperidyl]-amino]-8-isopropyl-7-oxo-pteridin-6-yl]-2-pyridyl]methanesulfon-amide | 0.0003 | 571.3 |
| 238 | 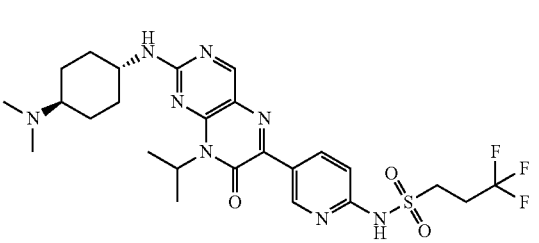 [SMILES: CC(C)n1c(=O)c(-c2ccc(NS(=O)(=O)CCC(F)(F)F)nc2)nc2cnc(N[C@H]3CC[C@H](N(C)C)CC3)nc21] | N-[5-[2-[[4-(dimethyl-amino)cyclohexyl]-amino]-8-isopropyl-7-oxo-pteridin-6-yl]-2-pyridyl]-3,3-difluoro-butane-1-sulfonamide | 0.0004 | 579.3 |
| 239 | 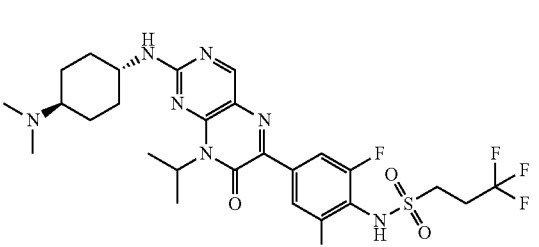 | N-[4-[2-[[4-(dimethyl-amino)cyclohexyl]-amino]-8-isopropyl-7-oxo-pteridin-6-yl]-2,6-difluoro-phenyl]-3,3,3-trifluoro-propane-1-sulfonamide | 0.0002 | 618.3 |
| 240 | 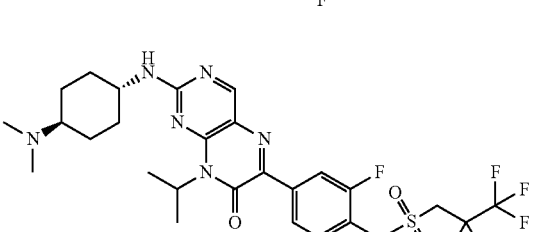 | N-[4-[2-[[4-(dimethyl-amino)cyclohexyl]-amino]-8-isopropyl-7-oxo-pteridin-6-yl]-2,6-difluoro-phenyl]-1-[1-(trifluoromethyl)cyclo-propyl)methanesulfon-amide | 0.0001 | 644.3 |
| 241 | 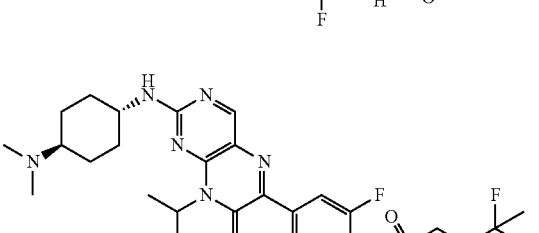 | N-[4-[2-[[4-(dimethyl-amino)cyclohexyl]-amino]-8-isopropyl-7-oxo-pteridin-6-yl]-2,6-difluoro-phenyl]-3,3-difluoro-butane-1-sulfonamide | 0.0002 | 614.3 |
| 242 | 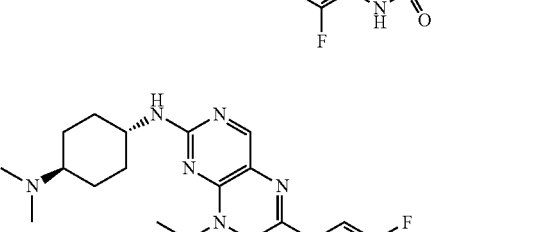 | N-[4-[2-[[4-(dimethyl-amino)cyclohexyl]-amino]-8-isopropyl-7-oxo-pteridin-6-yl]-2,6-difluoro-phenyl]pro-pane-1-sulfonamide | 0.0001 | 564.3 |

TABLE 1-continued

Representative compounds:

| 243 | 1-(4-chlorophenyl)-N-[4-[2-((4-(dimethyl-amino)cyclohexyl]-amino]-8-isopropyl-7-oxo-pteridin-6-yl]-2,6-difluoro-phenyl]-methanesulfonamide | 0.0008 | 646.3 |
|---|---|---|---|
| 244 | 1-[4-(difluoromethyl)-phenyl)-N-[4-[2-[[4-(dimethylamino)cyclo-hexyl]amino]-8-isopropyl-7-oxo-pteridin-6-yl]-2,6-difluoro-phenyl]-methanesulfonamide | 0.0002 | 662.3 |
| 245 | N-[4-[2-[[4-(dimethyl-amino)cyclohexyl]-amino]-8-isopropyl-7-oxo-pteridin-6-yl]-2,6-difluoro-phenyl]-1-(4-fluorophenyl)methane-sulfonamide | 0.0001 | 630.3 |
| 246 | N[4-[2-[[4-(dimethyl-amino)cyclohexyl]-amino]-8-isopropyl-7-oxo-pteridin-6-yl]-2,6-difluoro-phenyl]-1-(p-tolyl)methanesulfon-amide | 0.0002 | 626.3 |
| 247 | N-[4-[2-[[4-(dimethyl-amino)cyclohexyl]-amino]-8-isopropyl-7-oxo-pteridin-6-yl]-2,6-difluoro-phenyl]-1-phenyl-methanesulfon-amide | 0.0001 | 612.3 |
| 248 | 3-cyclopropyl-N-[4-[2-[[4-(dimethylamino)-cyclohexyl]amino]-8-isopropyl-7-oxo-pter-idin-6-yl]-2,6-difluoro-phenyl]-2,2-difluoro-propane-1-sulfonamide | 0.0002 | 640.3 |

TABLE 1-continued

Representative compounds:

| | | | | |
|---|---|---|---|---|
| 249 | | 1-(3,3-difluorocyclobutyl)-N-[4-[2-[[4-(dimethylamino)cyclohexyl]amino]-8-isopropyl-7-oxo-pteridin-6-yl]-2,6-difluorophenyl]methanesulfonamide | 0.0002 | 626.3 |
| 250 | | 1-(2,2-difluorocyclobutyl)-N-[4-[2-[[4-(dimethylamino)cyclohexyl]amino]-8-isopropyl-7-oxo-pteridin-6-yl]-2,6-difluorophenyl]methanesulfonamide | 0.0002 | 626.3 |
| 251 | | N-[5-[2-[[4-(dimethylamino)cyclohexyl]amino]-8-isopropyl-7-oxo-pteridin-6-yl]-6-methyl-2-pyridyl]-3,3,3-trifluoropropane-1-sulfonamide | 0.007 | 597.3 |
| 252 | | N-[5-[2-[[4-(dimethylamino)cyclohexyl]amino]-8-isopropyl-7-oxo-pteridin-6-yl]-6-methyl-2-pyridyl]-1-(4-fluorophenyl)methanesulfonamide | 0.001 | 609.3 |
| 253 | | N-[5-[2-[[4-(dimethylamino)cyclohexyl]amino]-8-isopropyl-7-oxo-pteridin-6-yl]-6-methyl-2-pyridyl]-2-fluoro-benzenesulfonamide | 0.0003 | 595.3 |
| 254 | | N-[5-[2-[[4-(dimethylamino)cyclohexyl]amino]-8-isopropyl-7-oxo-pteridin-6-yl]-6-methyl-2-pyridyl]-2-chloro-benzenesulfonamide | 0.0003 | 611.3 |

TABLE 1-continued

Representative compounds:

| | | | | |
|---|---|---|---|---|
| 255 | | N-[5-[2-[[4-(dimethyl-amino)cyclohexyl]-amino]-8-isopropyl-7-oxo-pteridin-6-yl]-6-methyl-2-pyridyl]-2-cyano-benzenesulfon-amide | 0.0002 | 602.3 |
| 256 | | N-[4-[2-[[4-(dimethyl-amino)cyclohexyl]-amino]-8-isopropyl-7-oxo-pteridin-6-yl]-2-fluoro-phenyl]-1-spiro-[2.2]pentan-2-yl-methanesulfonamide | 0.0003 | 584.3 |
| 257 | | 1-(2,2-difluorospiro-[2.3]hexan-1-yl)-N-[4-[2-[[4-(dimethylamino)-cyclohexyl]amino]-8-isopropyl-7-oxo-pter-idin-6-yl]-2-fluoro-phenyl]methanesulfon-amide | 0.0002 | 634.3 |
| 258 | | 1-[1-(1,1-difluoroethyl)-cyclopropyl]-N-[4-[2-[[4-(dimethylamino)-cyclohexyl]amino]-8-isopropyl-7-oxo-pter-idin-6-yl]-2-fluoro-phenyl]methanesulfon-amide | 0.0002 | 622.3 |
| 259 | | 2-(2,2-difluorocyclo-propyl)-N-[4-[2-[[4-(dimethylamino)cyclo-hexyl]amino]-8-isopropyl-7-oxo-pter-idin-6-yl]-2-fluoro-phenyl]ethanesulfon-amide | 0.0002 | 608.3 |
| 260 | | N-[4-[2-[[4-(dimethyl-amino)cyclohexyl]-amino]-8-isopropyl-7-oxo-pteridin-6-yl]-2-fluoro-phenyl]-1-spiro-[3.3]heptan-2-yl-methanesulfonamide | 0.0002 | 612.3 |

TABLE 1-continued

Representative compounds:

| | | | | |
|---|---|---|---|---|
| 261 | 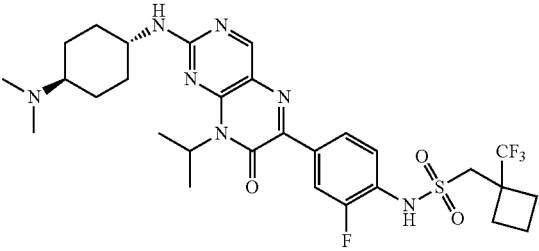 [SMILES: CC(C)n1c(=O)c(-c2ccc(NS(=O)(=O)CC3(C(F)(F)F)CCC3)c(F)c2)nc2cnc(N[C@H]3CC[C@H](N(C)C)CC3)nc21] | N-[4-[2-[[4-(dimethyl-amino)cyclohexyl]-amino]-8-isopropyl-7-oxo-pteridin-6-yl]-2-fluoro-phenyl]-1-[1-(trifluoromethyl)cyclo-butyl]methanesulfon-amide | 0.0002 | 640.3 |
| 262 | 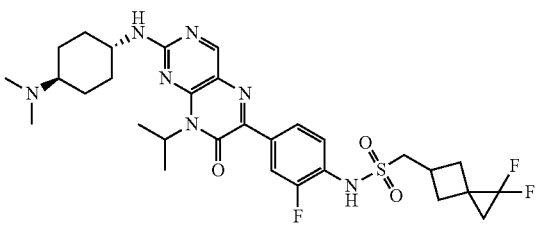 [SMILES: CC(C)n1c(=O)c(-c2ccc(NS(=O)(=O)CC3CC4(C3)CC4(F)F)c(F)c2)nc2cnc(N[C@H]3CC[C@H](N(C)C)CC3)nc21] | 1-(2,2-difluorospiro-[2.3]hexan-5-yl)-N-[4-[2-((4-(dimethylamino)-cyclohexyl]amino]-8-isopropyl-7-oxo-pter-idin-6-yl]-2-fluoro-phenyl]methanesulfon-amide | 0.0003 | 634.3 |
| 263 | 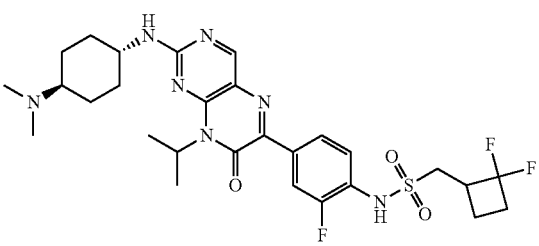 [SMILES: CC(C)n1c(=O)c(-c2ccc(NS(=O)(=O)CC3CCC3(F)F)c(F)c2)nc2cnc(N[C@H]3CC[C@H](N(C)C)CC3)nc21] | 1-(2,2-difluorocyclo-butyl)-N-[4-[2-[[4-(dimethylamino)cyclo-hexyl]amino]-8-isopropyl-7-oxo-pter-idin-6-yl]-2-fluoro-phenyl]methanesulfon-amide | 0.0001 | 608.3 |
| 264 | 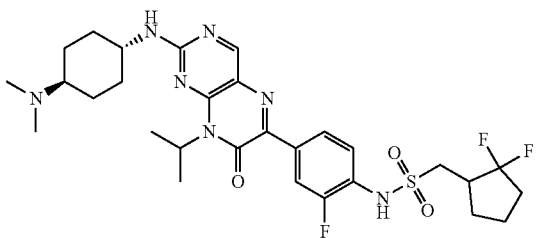 [SMILES: CC(C)n1c(=O)c(-c2ccc(NS(=O)(=O)CC3CCCC3(F)F)c(F)c2)nc2cnc(N[C@H]3CC[C@H](N(C)C)CC3)nc21] | 1-(2,2-difluorocyclo-pentyl)-N-[4-[2-[[4-(dimethylamino)cyclo-hexyl]amino]-8-isopropyl-7-oxo-pter-idin-6-yl]-2-fluoro-phenyl)methanesulfon-amide | 0.0001 | 622.3 |
| 265 | 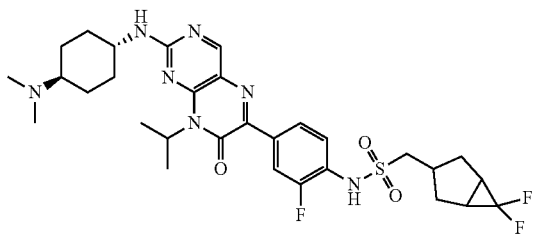 [SMILES: CC(C)n1c(=O)c(-c2ccc(NS(=O)(=O)CC3CC4C(C3)C4(F)F)c(F)c2)nc2cnc(N[C@H]3CC[C@H](N(C)C)CC3)nc21] | 1-(6,6-difluoro-3-bicyclo[3.1.0]hexanyl)-N-4-[2-[[4-(dimethyl-amino)cyclohexyl]-amino]-8-isopropyl-7-oxo-pteridin-6-yl]-2-fluorophenyl]methane-sulfonamide | 0.0002 | 634.3 |
| 266 | 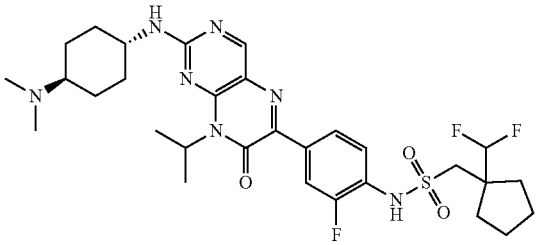 [SMILES: CC(C)n1c(=O)c(-c2ccc(NS(=O)(=O)CC3(C(F)F)CCCC3)c(F)c2)nc2cnc(N[C@H]3CC[C@H](N(C)C)CC3)nc21] | 1-[1-(difluoromethyl)-cyclopentyl]-N[4-[2-[[4-(dimethylamino)-cyclohexyl]amino]-8-isopropyl-7-oxo-pter-idin-6-yl]-2-fluoro-phenyl]methanesulfon-amide | 0.0002 | 636.3 |

TABLE 1-continued

Representative compounds:

| | | | | |
|---|---|---|---|---|
| 267 | | 1-cyclopentyl-N-[4-[2-[[4-(dimethylamino)-cyclohexyl]amino]-8-isopropyl-7-oxo-pteridin-6-yl]-2-fluoro-phenyl]methanesulfon-amide | 0.0001 | 586.3 |
| 268 | | N-(4-[2-[[4-(dimethyl-amino)cyclohexyl]-amino]-8-isopropyl-7-oxo-pteridin-6-yl]-2-fluoro-phenyl]-1-indan-2-yl-methanesulfon-amide | 0.0001 | 634.3 |
| 269 | | 1-cyclohexyl-N-[4-[2-[[4-(dimethylamino)-cyclohexyl]amino]-8-isopropyl-7-oxo-pter-idin-6-yl]-2-fluoro-phenyl]methanesulfon-amide | 0.0002 | 600.3 |
| 270 | | N-[4-[2-[[4-(dimethyl-amino]cyclohexyl]-amino]-8-isopropyl-7-oxo-pteridin-6-yl]-2-fluoro-phenyl]-1-norbornan-1-yl-methanesulfonamide | 0.0003 | 612.4 |
| 271 | | 1-(4,4-difluorocyclo-hexyl)-N-(4-[2-[[4-(dimethylamino)cyclo-hexyl]amino]-8-isopropyl-7-oxo-pter-idin-6-yl]-2-fluoro-phenyl]methanesulfon-amide | 0.0002 | 636.3 |
| 272 | | 1-(2,2-difluorocyclo-hexyl)-N-[4-[2-[[4-(dimethylamino)cyclo-hexyl]amino]-8-isopropyl-7-oxo-pter-idin-6-yl]-2-fluoro-phenyl]methanesulfon-amide | 0.0002 | 636.3 |

TABLE 1-continued

Representative compounds:

| | | | | |
|---|---|---|---|---|
| 273 | | 1-(7,7-difluoronorcaran-3-yl)-N-[4-[2-[[4-(dimethylamino)cyclohexyl]amino]-8-isopropyl-7-oxo-pteridin-6-yl]-2-fluoro-phenyl]methanesulfonamide | 0.0002 | 648.3 |
| 274 | | (1R,2S)-N-(4-(2-(((1r,4r)-4-(dimethyl-amino)cyclohexyl)-amino)-8-isopropyl-7-oxo-7,8-dihydropter-idin-6-yl)-2-fluoro-phenyl)-2-phenylcyclo-propane-1-sulfonamide | 0.0002 | 620.3 |
| 275 | | N-[4-[2-[[4-(dimethyl-amino)cyclohexyl]-amino]-8-isopropyl-7-oxo-pteridin-6-yl]-2-fluoro-phenyl]nor-carane-7-sulfonamide | 0.0004 | 598.3 |
| 276 | | N-[4-[2-[[4-(dimethyl-amino)cyclohexyl]-amino]-8-isopropyl-7-oxo-pteridin-6-yl]-2-fluoro-phenyl]cyclo-butanesulfonamide | 0.0009 | 558.3 |
| 277 | | N-[4-[2-[[4-(dimethyl-amino)cyclohexyl]-amino]-8-isopropyl-7-oxo-pteridin-6-yl]-2-fluoro-phenyl]spiro-[3.3]heptane-2-sulfon-amide | 0.0002 | 598.3 |
| 278 | | 1-cyclobutyl-N-[4-[2-[[4-(dimethylamino)-cyclohexyl]amino]-8-isopropyl-7-oxo-pter-idin-6-yl]-2-fluoro-phenyl]methanesulfon-amide | 0.0002 | 572.3 |

TABLE 1-continued

Representative compounds:

| | | | | |
|---|---|---|---|---|
| 279 | 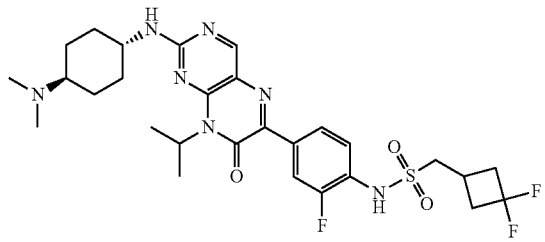 [SMILES: CC(C)n1c(=O)c(-c2ccc(NS(=O)(=O)CC3CC(F)(F)C3)c(F)c2)nc2cnc(N[C@H]3CC[C@H](N(C)C)CC3)nc21] | 1-(3,3-difluorocyclo-butyl)-N-[4-[2-[[4-(dimethylamino)cyclo-hexyl]amino]-8-isopropyl-7-oxo-pter-idin-6-yl]-2-fluoro-phenyl]methanesulfon-amide | 0.0003 | 608.3 |
| 280 | 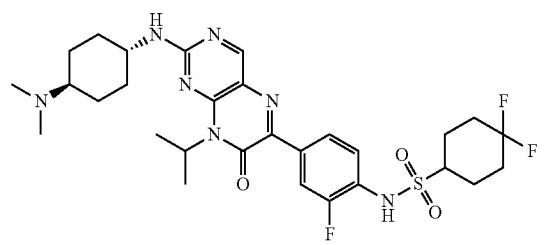 [SMILES: CC(C)n1c(=O)c(-c2ccc(NS(=O)(=O)C3CCC(F)(F)CC3)c(F)c2)nc2cnc(N[C@H]3CC[C@H](N(C)C)CC3)nc21] | N-[4-[2-[[4-(dimethyl-amino)cyclohexyl]-amino]-8-isopropyl-7-oxo-pteridin-6-yl]-2-fluoro-phenyl]-4,4-difluorocyclohexane-sulfonamide | 0.0002 | 622.3 |
| 281 | 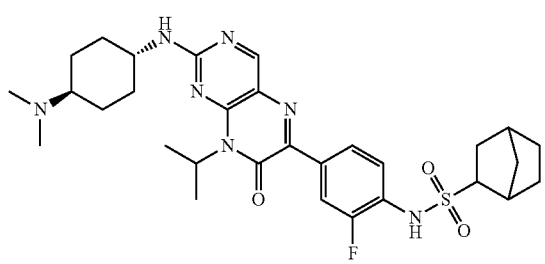 [SMILES: CC(C)n1c(=O)c(-c2ccc(NS(=O)(=O)C3CC4CCC3C4)c(F)c2)nc2cnc(N[C@H]3CC[C@H](N(C)C)CC3)nc21] | N-(4-(2-(((1r,4r)-4-(dimethylamino)cyclo-hexyl)amino)-8-iso-propyl-7-oxo-7,8-dihydropteridin-6-yl)-2-fluorophenyl)bicyclo-[2.2.1]heptane-2-sulfon-amide | 0.0005 | 598.3 |
| 282 | 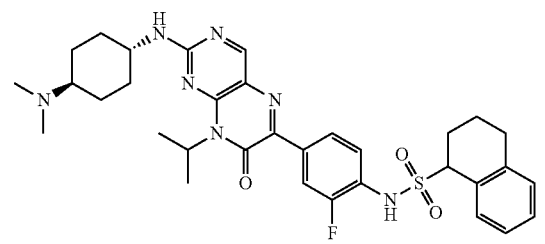 [SMILES: CC(C)n1c(=O)c(-c2ccc(NS(=O)(=O)C3CCCc4ccccc43)c(F)c2)nc2cnc(N[C@H]3CC[C@H](N(C)C)CC3)nc21] | N-[4-[2-[[4-(dimethyl-amino)cyclohexyl]-amino]-8-isopropyl-7-oxo-pteridin-6-yl]-2-fluoro-phenyl]tetralin-2-sulfonamide | 0.0005 | 634.3 |

TABLE 2

Representative Compounds

| | Structure | Name | Mw (m/z) |
|---|---|---|---|
| 501 | 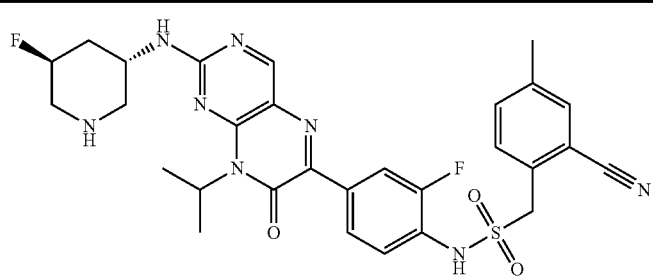 | 1-(2-cyano-4-methylphenyl)-N-(2-fluoro-4-(2-(((3S,5S)-5-fluoropiperidin-3-yl)amino)-8-isopropyl-7-oxo-7,8-dihydropteridin-6-yl)phenyl)methanesulfonamide | 608.21 |

TABLE 2-continued

Representative Compounds

| | Structure | Name | Mw (m/z) |
|---|---|---|---|
| 502 | 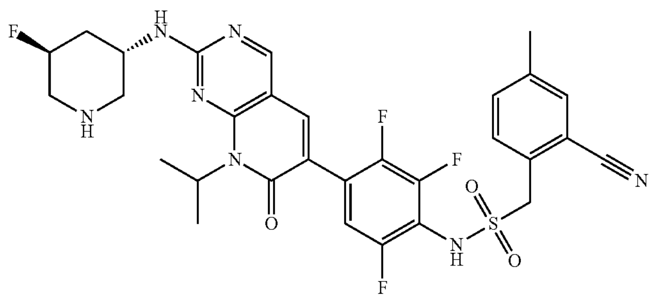 [SMILES: Cc1ccc(CS(=O)(=O)Nc2c(F)cc(-c3cc4cnc(N[C@@H]5CNC[C@@H](F)C5)nc4n(C(C)C)c3=O)c(F)c2F)c(C#N)c1] | 1-(2-cyano-4-methylphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide | 643.20 |
| 503 | 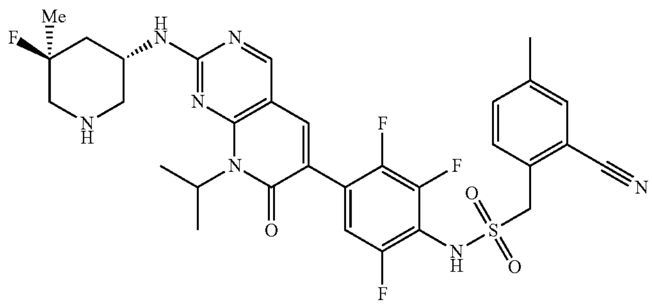 [SMILES: Cc1ccc(CS(=O)(=O)Nc2c(F)cc(-c3cc4cnc(N[C@@H]5CNC[C@@](C)(F)C5)nc4n(C(C)C)c3=O)c(F)c2F)c(C#N)c1] | 1-(2-cyano-4-methylphenyl)-N-(2,3,6-trifluoro-4-(2-(((3S,5S)-5-fluoro-5-methylpiperidin-3-yl)amino)-8-isopropyl-7-oxo-7,8-dihydropyrido[2,3-d]pyrimidin-6-yl)phenyl)methanesulfonamide | 657.21 |
| 504 | 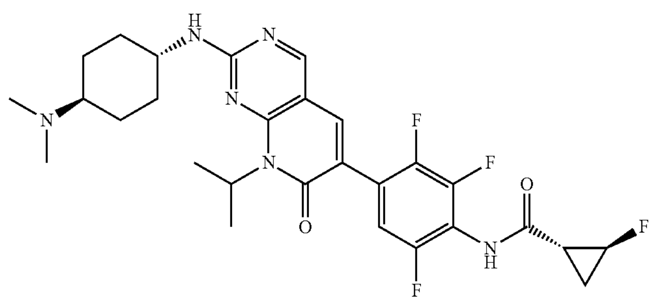 [SMILES: CC(C)n1c(=O)c(-c2cc(F)c(NC(=O)[C@H]3C[C@@H]3F)c(F)c2F)cc2cnc(N[C@H]3CC[C@H](N(C)C)CC3)nc21] | (1R,2S)-N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide | 560.25 |
| 505 | 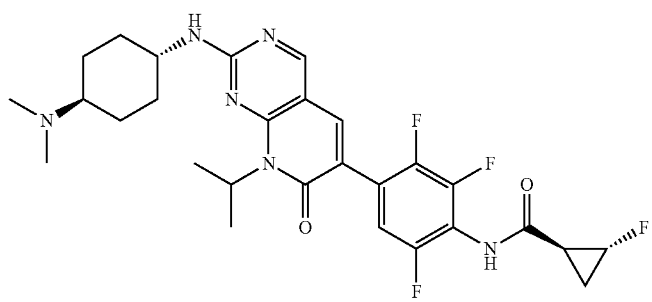 [SMILES: CC(C)n1c(=O)c(-c2cc(F)c(NC(=O)[C@@H]3C[C@H]3F)c(F)c2F)cc2cnc(N[C@H]3CC[C@H](N(C)C)CC3)nc21] | (1S,2R)-N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide | 560.25 |
| 506 | 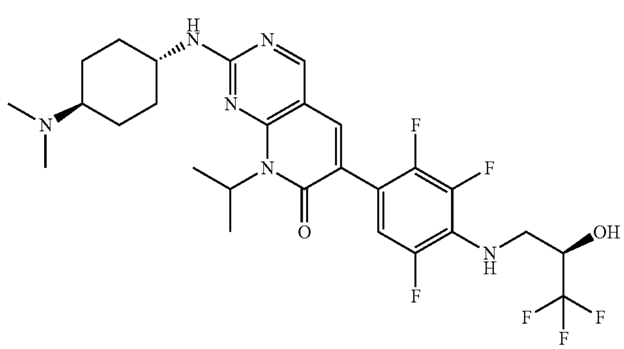 [SMILES: CC(C)n1c(=O)c(-c2cc(F)c(NC[C@@H](O)C(F)(F)F)c(F)c2F)cc2cnc(N[C@H]3CC[C@H](N(C)C)CC3)nc21] | 2-(((1r,4r)-4-(dimethylamino)cyclohexyl)amino)-8-isopropyl-6-(2,3,5-trifluoro-4-(((R)-3,3,3-trifluoro-2-hydroxypropyl)amino)phenyl)pyrido[2,3-d]pyrimidin-7(8H)-one | 586.25 |

TABLE 2-continued

Representative Compounds

| | Structure | Name | Mw (m/z) |
|---|---|---|---|
| 507 | 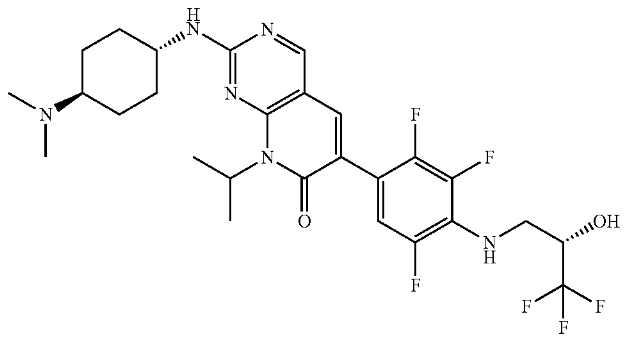 [SMILES: CC(C)n1c(=O)c(-c2cc(F)c(NC[C@H](O)C(F)(F)F)c(F)c2F)cc2cnc(N[C@H]3CC[C@H](N(C)C)CC3)nc21] | 2-(((1r,4r)-4-(dimethylamino)cyclohexyl)amino)-8-isopropyl-6-(2,3,5-trifluoro-4-(((S)-3,3,3-trifluoro-2-hydroxypropyl)amino)phenyl)pyrido[2,3-d]pyrimidin-7(8H)-one | 586.25 |
| 508 | 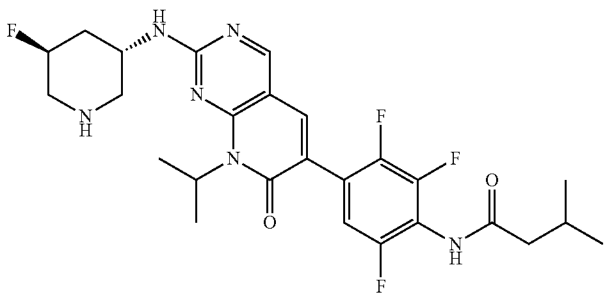 [SMILES: CC(C)CC(=O)Nc1c(F)cc(-c2cc3cnc(N[C@@H]4CNC[C@@H](F)C4)nc3n(C(C)C)c2=O)c(F)c1F] | 3-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)butanamide | 534.24 |
| 509 | 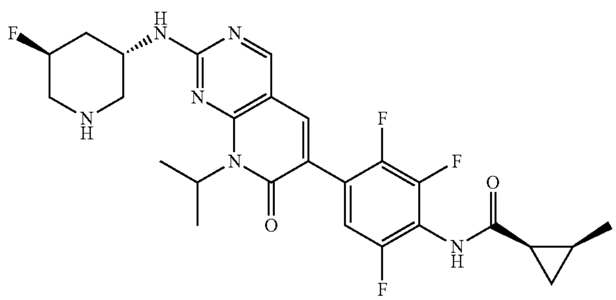 [SMILES: CC(C)n1c(=O)c(-c2cc(F)c(NC(=O)[C@@H]3C[C@@H]3C)c(F)c2F)cc2cnc(N[C@@H]3CNC[C@@H](F)C3)nc21] | (1R,2S)-2-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)cyclopropane-1-carboxamide | 532.22 |
| 510 | 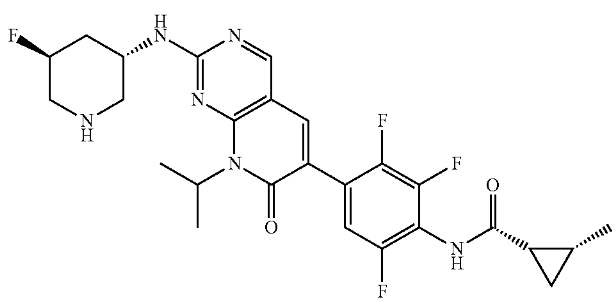 | (1S,2R)-2-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)cyclopropane-1-carboxamide | 532.22 |
| 511 | 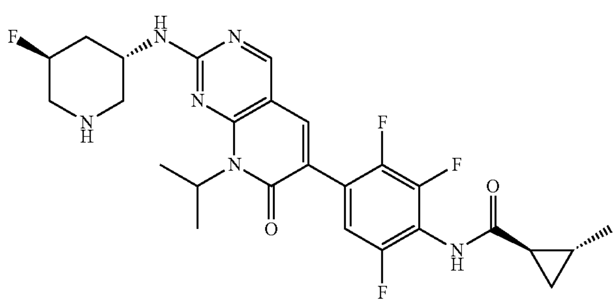 [SMILES: CC(C)n1c(=O)c(-c2cc(F)c(NC(=O)[C@@H]3C[C@H]3C)c(F)c2F)cc2cnc(N[C@@H]3CNC[C@@H](F)C3)nc21] | (1R,2R)-2-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)cyclopropane-1-carboxamide | 532.22 |

TABLE 2-continued

Representative Compounds

| | Structure | Name | Mw (m/z) |
|---|---|---|---|
| 512 | 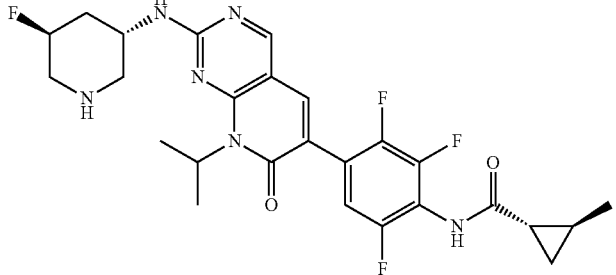 | (1S,2S)-2-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)cyclopropane-1-carboxamide | 532.22 |
| 513 | 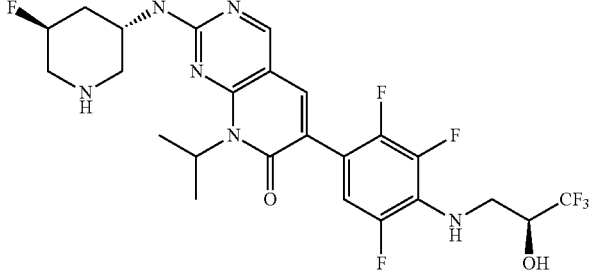 | 2-(((3S,5S)-5-fluoropiperidin-3-yl)amino)-8-isopropyl-6-(2,3,5-trifluoro-4-(((S)-3,3,3-trifluoro-2-hydroxypropyl)amino)phenyl)pyrido[2,3-d]pyrimidin-7(8H)-one | 562.19 |
| 514 | 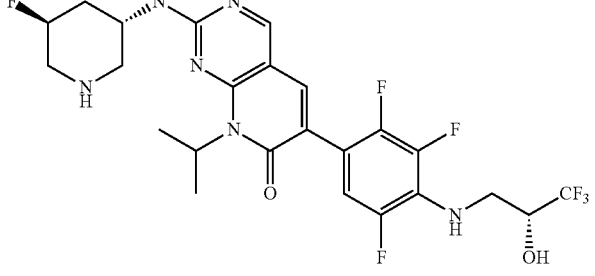 | 2-(((3S,5S)-5-fluoropiperidin-3-yl)amino)-8-isopropyl-6-(2,3,5-trifluoro-4-(((R)-3,3,3-trifluoro-2-hydroxypropyl)amino)phenyl)pyrido[2,3-d]pyrimidin-7(8H)-one | 562.19 |
| 515 | 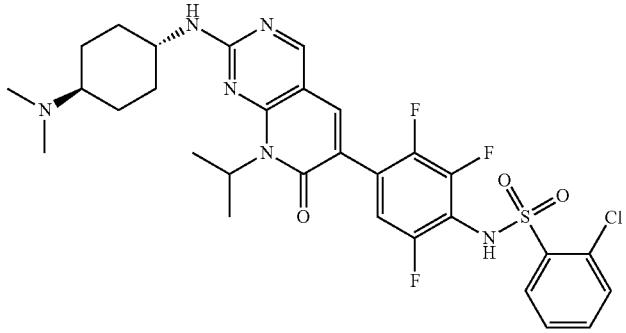 [SMILES: CC(C)n1c(=O)c(-c2cc(F)c(NS(=O)(=O)c3ccccc3Cl)c(F)c2F)cc2cnc(N[C@H]3CC[C@H](N(C)C)CC3)nc21] | 2-chloro-N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)benzenesulfonamide | 648.19 |
| 516 | 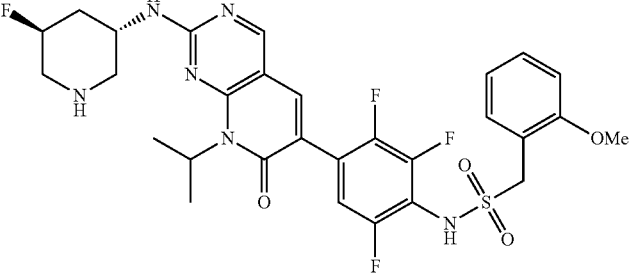 | 1-(2-methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide | 634.20 |

TABLE 2-continued

Representative Compounds

| | Structure | Name | Mw (m/z) |
|---|---|---|---|
| 517 | 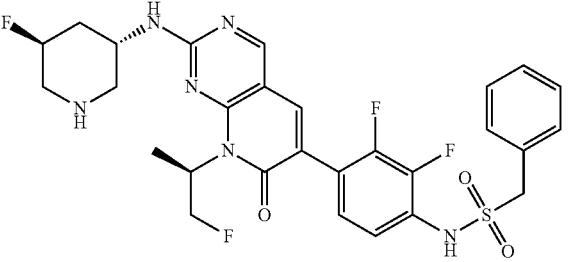 [SMILES: C[C@H](CF)n1c(=O)c(-c2ccc(NS(=O)(=O)Cc3ccccc3)c(F)c2F)cc2cnc(N[C@@H]3CNC[C@@H](F)C3)nc21] | N-(2,3-difluoro-4-(2-(((3S,5S)-5-fluoropiperidin-3-yl)amino)-8-((R)-1-fluoropropan-2-yl)-7-oxo-7,8-dihydropyrido[2,3-d]pyrimidin-6-yl)phenyl)-1-phenylmethanesulfonamide | 604.19 |
| 518 | 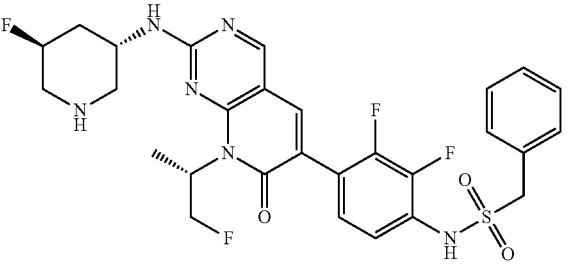 [SMILES: C[C@@H](CF)n1c(=O)c(-c2ccc(NS(=O)(=O)Cc3ccccc3)c(F)c2F)cc2cnc(N[C@@H]3CNC[C@@H](F)C3)nc21] | N-(2,3-difluoro-4-(2-(((3S,5S)-5-fluoropiperidin-3-yl)amino)-8-((S)-1-fluoropropan-2-yl)-7-oxo-7,8-dihydropyrido[2,3-d]pyrimidin-6-yl)phenyl)-1-phenylmethanesulfonamide | 604.19 |
| 519 | 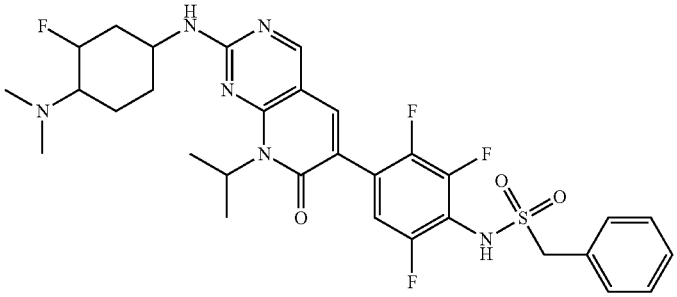 [SMILES: CC(C)n1c(=O)c(-c2cc(F)c(NS(=O)(=O)Cc3ccccc3)c(F)c2F)cc2cnc(NC3CCC(N(C)C)C(F)C3)nc21] | N-(4-(2-((4-(dimethylamino)-3-fluorocyclohexyl)amino)-8-isopropyl-7-oxo-7,8-dihydropyrido[2,3-d]pyrimidin-6-yl)-2,3,6-trifluorophenyl)-1-phenylmethanesulfonamide | 646.23 |
| 520 | 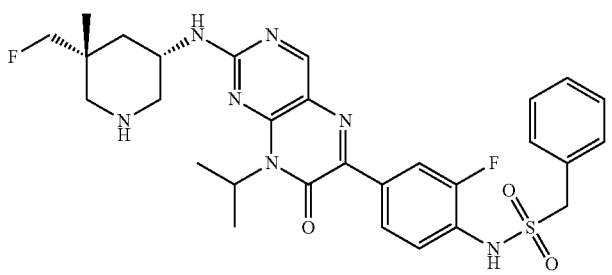 [SMILES: CC(C)n1c(=O)c(-c2ccc(NS(=O)(=O)Cc3ccccc3)c(F)c2)nc2cnc(N[C@@H]3CNC[C@](C)(CF)C3)nc21] | N-(2-fluoro-4-(2-(((3S,5R)-5-(fluoromethyl)-5-methylpiperidin-3-yl)amino)-8-isopropyl-7-oxo-7,8-dihydropteridin-6-yl)phenyl)-1-phenylmethanesulfonamide | 597.23 |
| 521 | 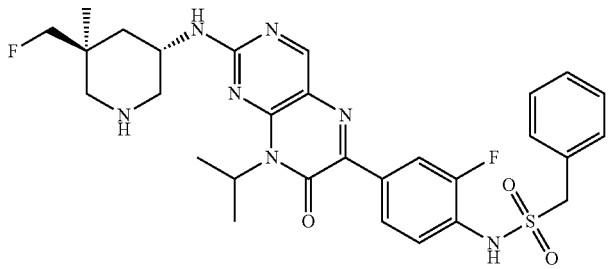 [SMILES: CC(C)n1c(=O)c(-c2ccc(NS(=O)(=O)Cc3ccccc3)c(F)c2)nc2cnc(N[C@@H]3CNC[C@@](C)(CF)C3)nc21] | N-(2-fluoro-4-(2-(((3S,5S)-5-(fluoromethyl)-5-methylpiperidin-3-yl)amino)-8-isopropyl-7-oxo-7,8-dihydropteridin-6-yl)phenyl)-1-phenylmethanesulfonamide | 597.23 |

TABLE 2-continued

Representative Compounds

| | Structure | Name | Mw (m/z) |
|---|---|---|---|
| 522 | 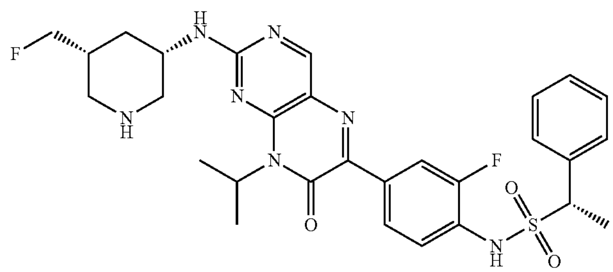 [SMILES: CC(C)n1c(=O)c(-c2ccc(NS(=O)(=O)[C@@H](C)c3ccccc3)c(F)c2)nc2cnc(N[C@@H]3CNC[C@H](CF)C3)nc21] | (S)-N-(2-fluoro-4-(2-(((3S,5R)-5-(fluoromethyl)piperidin-3-yl)amino)-8-isopropyl-7-oxo-7,8-dihydropteridin-6-yl)phenyl)-1-phenylethane-1-sulfonamide | 597.23 |
| 523 | 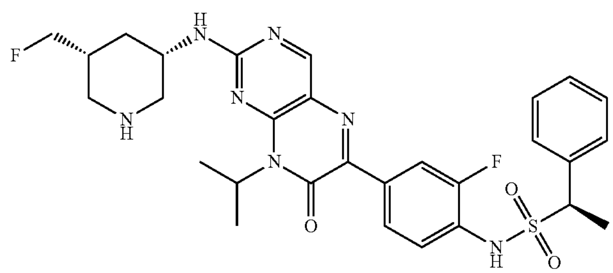 [SMILES: CC(C)n1c(=O)c(-c2ccc(NS(=O)(=O)[C@H](C)c3ccccc3)c(F)c2)nc2cnc(N[C@@H]3CNC[C@H](CF)C3)nc21] | (R)-N-(2-fluoro-4-(2-(((3S,5R)-5-(fluoromethyl)piperidin-3-yl)amino)-8-isopropyl-7-oxo-7,8-dihydropteridin-6-yl)phenyl)-1-phenylethane-1-sulfonamide | 597.23 |
| 524 | 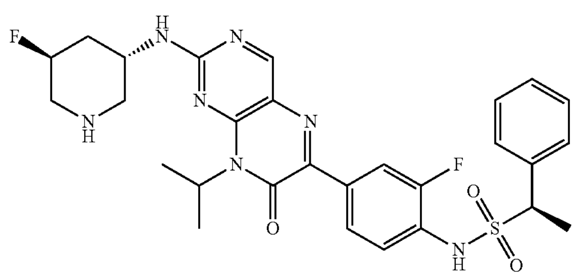 [SMILES: CC(C)n1c(=O)c(-c2ccc(NS(=O)(=O)[C@H](C)c3ccccc3)c(F)c2)nc2cnc(N[C@@H]3CNC[C@@H](F)C3)nc21] | (R)-N-(2-fluoro-4-(2-(((3S,5S)-5-fluoropiperidin-3-yl)amino)-8-isopropyl-7-oxo-7,8-dihydropteridin-6-yl)phenyl)-1-phenylethane-1-sulfonamide | 583.22 |
| 525 | 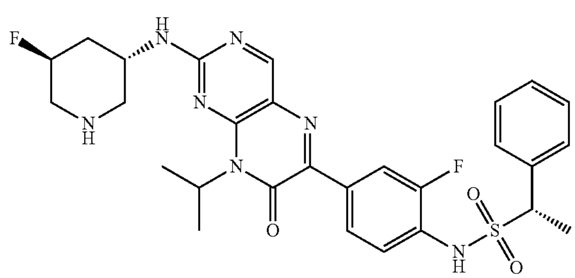 [SMILES: CC(C)n1c(=O)c(-c2ccc(NS(=O)(=O)[C@@H](C)c3ccccc3)c(F)c2)nc2cnc(N[C@@H]3CNC[C@@H](F)C3)nc21] | (S)-N-(2-fluoro-4-(2-(((3S,5S)-5-fluoropiperidin-3-yl)amino)-8-isopropyl-7-oxo-7,8-dihydropteridin-6-yl)phenyl)-1-phenylethane-1-sulfonamide | 583.22 |
| 526 | 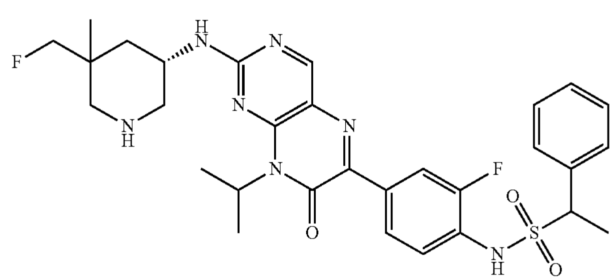 [SMILES: CC(C)n1c(=O)c(-c2ccc(NS(=O)(=O)C(C)c3ccccc3)c(F)c2)nc2cnc(N[C@@H]3CNCC(C)(CF)C3)nc21] | N-(2-fluoro-4-(2-(((3S)-5-(fluoromethyl)-5-methylpiperidin-3-yl)amino)-8-isopropyl-7-oxo-7,8-dihydropteridin-6-yl)phenyl)-1-phenylethane-1-sulfonamide | 611.25 |

TABLE 2-continued

Representative Compounds

| | Structure | Name | Mw (m/z) |
|---|---|---|---|
| 527 | 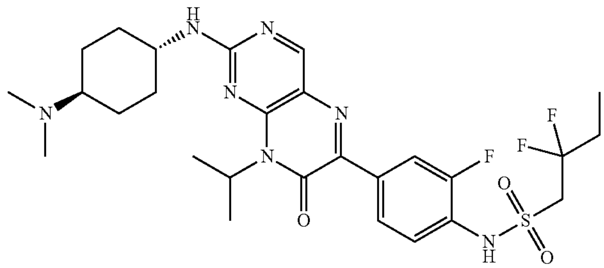 [SMILES: CCC(F)(F)CS(=O)(=O)Nc1ccc(-c2nc3cnc(N[C@H]4CC[C@H](N(C)C)CC4)nc3n(C(C)C)c2=O)cc1F] | N-(4-(2-(((1r,4r)-4-(dimethylamino)cyclohexyl) amino)-8-isopropyl-7-oxo-7,8-dihydropteridin-6-yl)-2-fluorophenyl)-2,2-difluorobutane-1-sulfonamide | 595.26 |
| 528 | 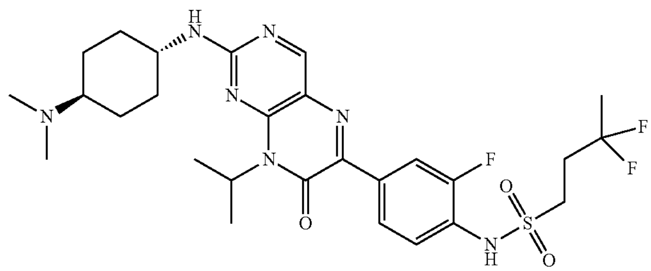 [SMILES: CC(C)n1c(=O)c(-c2ccc(NS(=O)(=O)CCC(C)(F)F)c(F)c2)nc2cnc(N[C@H]3CC[C@H](N(C)C)CC3)nc21] | N-(4-(2-(((1r,4r)-4-(dimethylamino)cyclohexyl) amino)-8-isopropyl-7-oxo-7,8-dihydropteridin-6-yl)-2-fluorophenyl)-3,3-difluorobutane-1-sulfonamide | 595.26 |
| 529 | 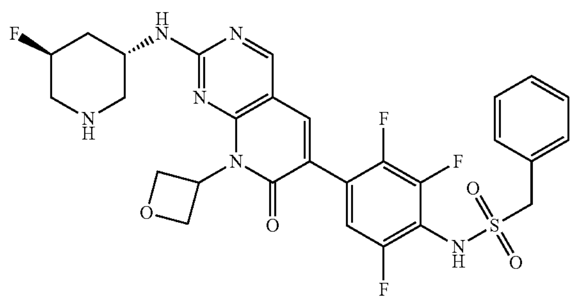 [SMILES: O=c1c(-c2cc(F)c(NS(=O)(=O)Cc3ccccc3)c(F)c2F)cc2cnc(N[C@@H]3CNC[C@@H](F)C3)nc2n1C1COC1] | 1-phenyl-N-(2,3,6-trifluoro-4-(2-(((3S,5S)-5-fluoropiperidin-3-yl)amino)-8-(oxetan-3-yl)-7-oxo-7,8-dihydropyrido[2,3-d]pyrimidin-6-yl)phenyl)methanesulfonamide | 618.17 |
| 530 | 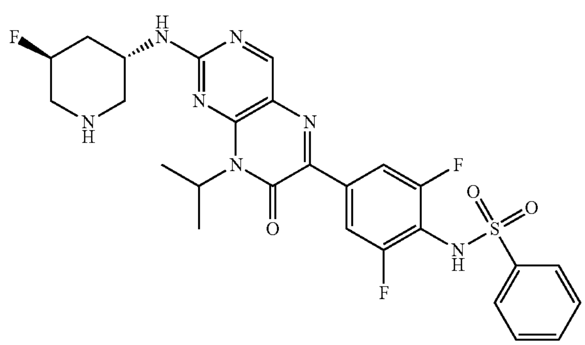 [SMILES: CC(C)n1c(=O)c(-c2cc(F)c(NS(=O)(=O)c3ccccc3)c(F)c2)nc2cnc(N[C@@H]3CNC[C@@H](F)C3)nc21] | N-(2,6-difluoro-4-(2-(((3S,5S)-5-fluoropiperidin-3-yl)amino)-8-isopropyl-7-oxo-7,8-dihydropteridin-6-yl)phenyl)benzenesulfonamide | 573.18 |
| 531 | 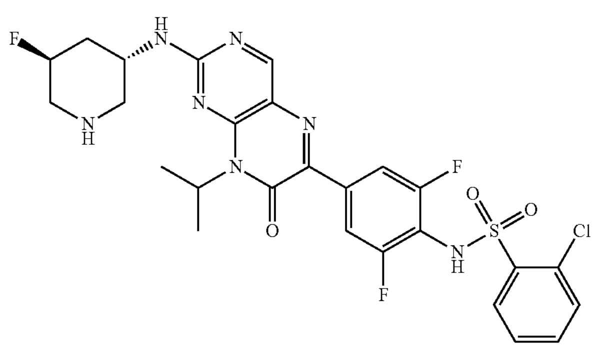 [SMILES: CC(C)n1c(=O)c(-c2cc(F)c(NS(=O)(=O)c3ccccc3Cl)c(F)c2)nc2cnc(N[C@@H]3CNC[C@@H](F)C3)nc21] | 2-chloro-N-(2,6-difluoro-4-(2-(((3S,5S)-5-fluoropiperidin-3-yl)amino)-8-isopropyl-7-oxo-7,8-dihydropteridin-6-yl)phenyl)benzenesulfonamide | 607.14 |

TABLE 2-continued

Representative Compounds

| | Structure | Name | Mw (m/z) |
|---|---|---|---|
| 532 | 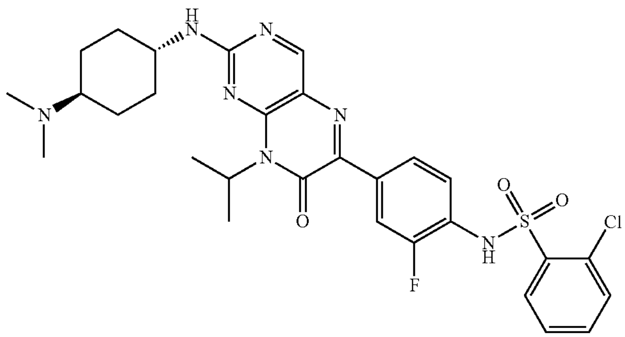 [SMILES: CC(C)n1c(=O)c(-c2ccc(NS(=O)(=O)c3ccccc3Cl)c(F)c2)nc2cnc(N[C@H]3CC[C@H](N(C)C)CC3)nc21] | 2-chloro-N-(4-(2-(((1r,4r)-4-(dimethylamino)cyclohexyl)amino)-8-isopropyl-7-oxo-7,8-dihydropteridin-6-yl)-2-fluorophenyl)benzenesulfonamide | 613.20 |
| 533 | 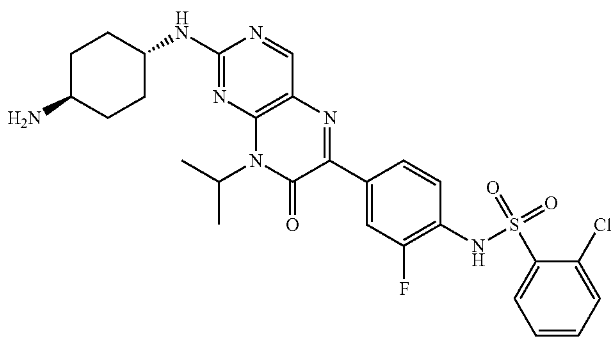 [SMILES: CC(C)n1c(=O)c(-c2ccc(NS(=O)(=O)c3ccccc3Cl)c(F)c2)nc2cnc(N[C@H]3CC[C@H](N)CC3)nc21] | N-(4-(2-(((1r,4r)-4-aminocyclohexyl)amino)-8-isopropyl-7-oxo-7,8-dihydropteridin-6-yl)-2-fluorophenyl)-2-chlorobenzenesulfonamide | 585.17 |
| 534 | 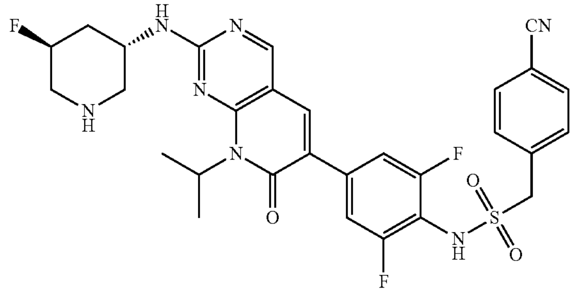 [SMILES: CC(C)n1c(=O)c(-c2cc(F)c(NS(=O)(=O)Cc3ccc(C#N)cc3)c(F)c2)cc2cnc(N[C@@H]3CNC[C@@H](F)C3)nc21] | 1-(4-cyanophenyl)-N-(2,6-difluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide | 611.19 |
| 535 | 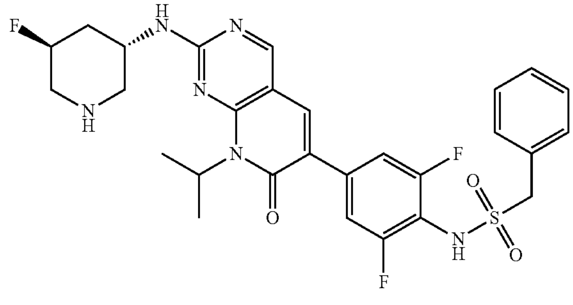 [SMILES: CC(C)n1c(=O)c(-c2cc(F)c(NS(=O)(=O)Cc3ccccc3)c(F)c2)cc2cnc(N[C@@H]3CNC[C@@H](F)C3)nc21] | N-(2,6-difluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-phenylmethanesulfonamide | 586.20 |

TABLE 2-continued

Representative Compounds

| | Structure | Name | Mw (m/z) |
|---|---|---|---|
| 536 | 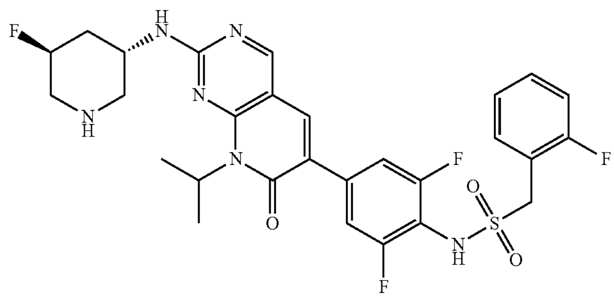 [SMILES: CC(C)n1c(=O)c(-c2cc(F)c(NS(=O)(=O)Cc3ccccc3F)c(F)c2)cc2cnc(N[C@@H]3CNC[C@@H](F)C3)nc21] | N-(2,6-difluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(2-fluorophenyl)methanesulfonamide | 604.19 |
| 537 | 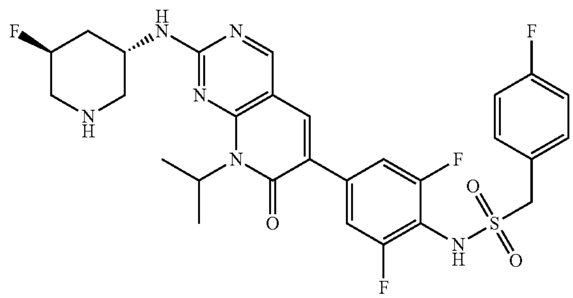 [SMILES: CC(C)n1c(=O)c(-c2cc(F)c(NS(=O)(=O)Cc3ccc(F)cc3)c(F)c2)cc2cnc(N[C@@H]3CNC[C@@H](F)C3)nc21] | N-(2,6-difluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(4-fluorophenyl)methanesulfonamide | 604.19 |
| 538 | 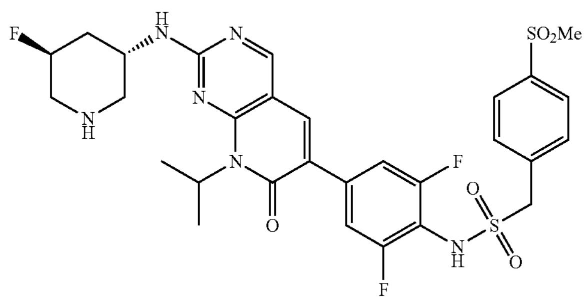 [SMILES: CC(C)n1c(=O)c(-c2cc(F)c(NS(=O)(=O)Cc3ccc(S(C)(=O)=O)cc3)c(F)c2)cc2cnc(N[C@@H]3CNC[C@@H](F)C3)nc21] | N-(2,6-difluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(4-(methylsulfonyl)phenyl)methanesulfonamide | 664.17 |
| 539 | 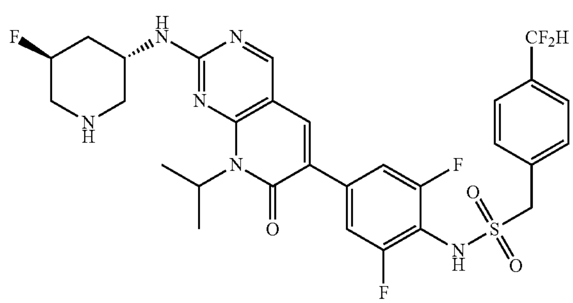 | N-(2,6-difluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(4-(difluoromethyl)phenyl)methanesulfonamide | 636.19 |
| 540 | 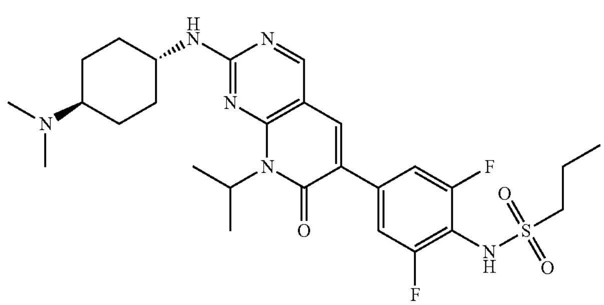 [SMILES: CCCS(=O)(=O)Nc1c(F)cc(-c2cc3cnc(N[C@H]4CC[C@H](N(C)C)CC4)nc3n(C(C)C)c2=O)cc1F] | N-(4-(2-(((1r,4r)-4-(dimethylamino)cyclohexyl)amino)-8-isopropyl-7-oxo-7,8-dihydropyrido[2,3-d]pyrimidin-6-yl)2,6-difluorophenyl)propane-1-sulfonamide | 562.25 |

TABLE 2-continued

Representative Compounds

| | Structure | Name | Mw (m/z) |
|---|---|---|---|
| 541 | 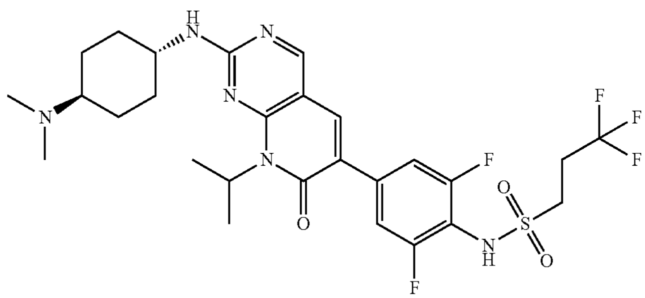 [SMILES: CC(C)n1c(=O)c(-c2cc(F)c(NS(=O)(=O)CCC(F)(F)F)c(F)c2)cc2cnc(N[C@H]3CC[C@H](N(C)C)CC3)nc21] | N-(4-(2-(((1r,4r)-4-(dimethylamino)cyclohexyl)amino)-8-isopropyl-7-oxo-7,8-dihydropyrido[2,3-d]pyrimidin-6-yl)2,6-difluorophenyl)-3,3,3-trifluoropropane-1-sulfonamide | 616.23 |
| 542 | 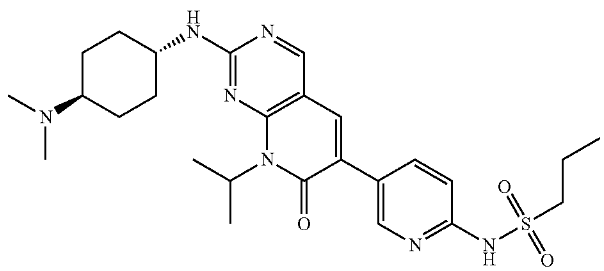 | N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)propane-1-sulfonamide | 527.27 |
| 543 | 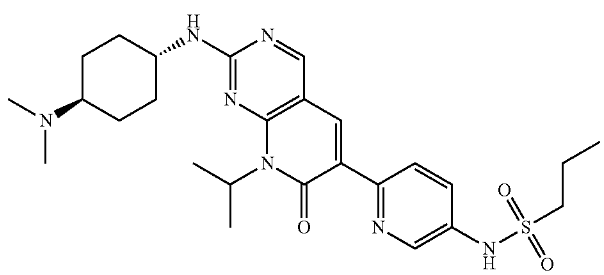 [SMILES: CCCS(=O)(=O)Nc1ccc(-c2cc3cnc(N[C@H]4CC[C@H](N(C)C)CC4)nc3n(C(C)C)c2=O)nc1] | N-(6-(2-(((1r,4r)-4-(dimethylamino)cyclohexyl)amino)-8-isopropyl-7-oxo-7,8-dihydropyrido[2,3-d]pyrimidin-6-yl)pyridin-3-yl)propane-1-sulfonamide | 527.27 |
| 544 | 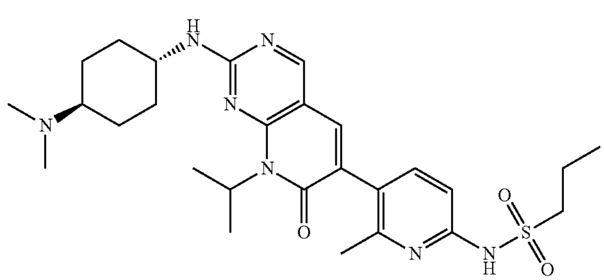 [SMILES: CCCS(=O)(=O)Nc1ccc(-c2cc3cnc(N[C@H]4CC[C@H](N(C)C)CC4)nc3n(C(C)C)c2=O)c(C)n1] | N-(5-(2-(((1r,4r)-4-(dimethylamino)cyclohexyl)amino)-8-isopropyl-7-oxo-7,8-dihydropyrido[2,3-d]pyrimidin-6-yl)-6-methylpyridin-2-yl)propane-1-sulfonamide | 541.28 |
| 545 | 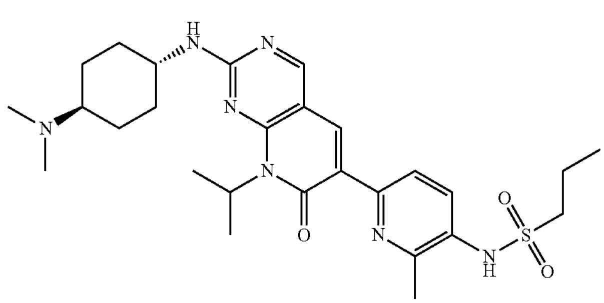 [SMILES: CCCS(=O)(=O)Nc1ccc(-c2cc3cnc(N[C@H]4CC[C@H](N(C)C)CC4)nc3n(C(C)C)c2=O)nc1C] | N-(6-(2-(((1r,4r)-4-(dimethylamino)cyclohexyl)amino)-8-isopropyl-7-oxo-7,8-dihydropyrido[2,3-d]pyrimidin-6-yl)-2-methylpyridin-3-yl)propane-1-sulfonamide | 541.28 |

TABLE 2-continued

Representative Compounds

| | Structure | Name | Mw (m/z) |
|---|---|---|---|
| 546 | 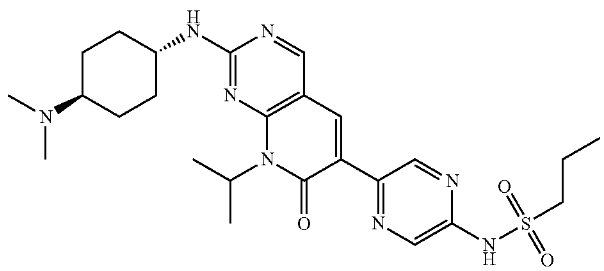 | N-(5-(2-(((1r,4r)-4-(dimethylamino)cyclohexyl)amino)-8-isopropyl-7-oxo-7,8-dihydropyrido[2,3-d]pyrimidin-6-yl)pyrazin-2-yl)propane-1-sulfonamide | 528.26 |
| 547 | 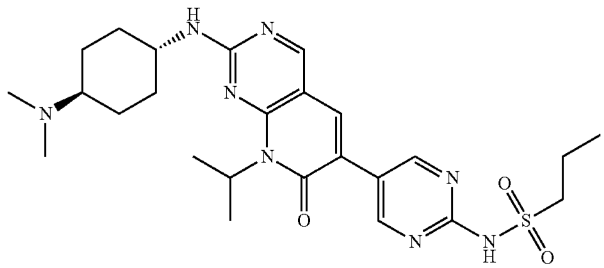 | N-(5-(2-(((1r,4r)-4-(dimethylamino)cyclohexyl)amino)-8-isopropyl-7-oxo-7,8-dihydropyrido[2,3-d]pyrimidin-6-yl)pyrimidin-2-yl)propane-1-sulfonamide | 528.26 |
| 548 | 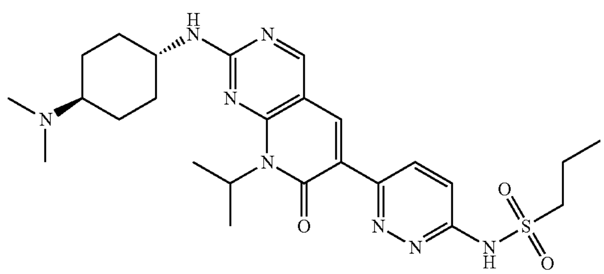 [SMILES: CCCS(=O)(=O)Nc1ccc(-c2cc3cnc(N[C@H]4CC[C@H](N(C)C)CC4)nc3n(C(C)C)c2=O)nn1] | N-(6-(2-(((1r,4r)-4-(dimethylamino)cyclohexyl)amino)-8-isopropyl-7-oxo-7,8-dihydropyrido[2,3-d]pyrimidin-6-yl)pyridazin-3-yl)propane-1-sulfonamide | 528.26 |
| 549 | 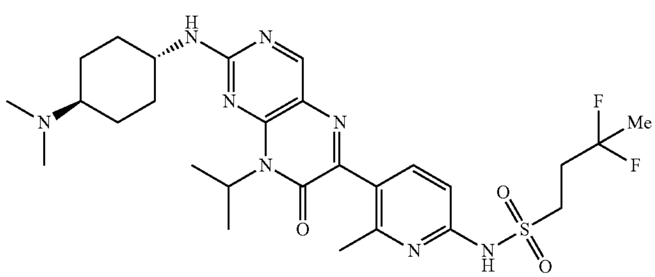 [SMILES: Cc1nc(NS(=O)(=O)CCC(C)(F)F)ccc1-c1nc2cnc(N[C@H]3CC[C@H](N(C)C)CC3)nc2n(C(C)C)c1=O] | N-(5-(2-(((1r,4r)-4-(dimethylamino)cyclohexyl)amino)-8-isopropyl-7-oxo-7,8-dihydropteridin-6-yl)-6-methylpyridin-2-yl)-3,3-difluorobutane-1-sulfonamide | 592.28 |
| 550 | 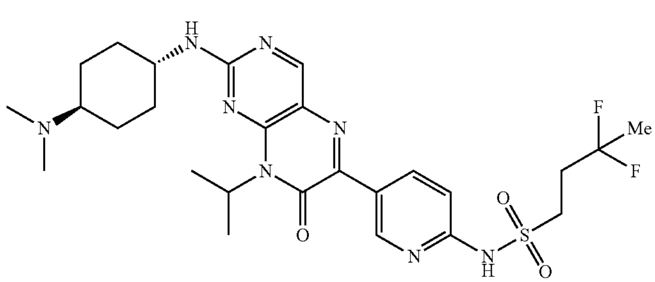 [SMILES: CC(C)n1c(=O)c(-c2ccc(NS(=O)(=O)CCC(C)(F)F)nc2)nc2cnc(N[C@H]3CC[C@H](N(C)C)CC3)nc21] | N-(5-(2-(((1r,4r)-4-(dimethylamino)cyclohexyl)amino)-8-isopropyl-7-oxo-7,8-dihydropteridin-6-yl)pyridin-2-yl)-3,3-difluorobutane-1-sulfonamide | 578.26 |

TABLE 2-continued

Representative Compounds

| | Structure | Name | Mw (m/z) |
|---|---|---|---|
| 551 | 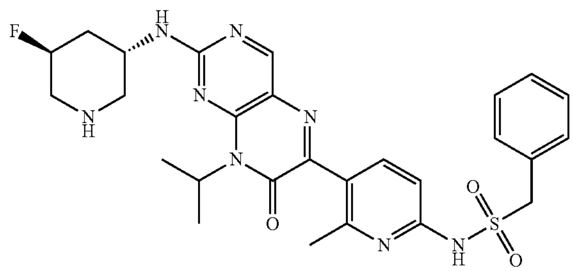 [SMILES: Cc1nc(NS(=O)(=O)Cc2ccccc2)ccc1-c1nc2cnc(N[C@@H]3CNC[C@@H](F)C3)nc2n(C(C)C)c1=O] | N-(5-(2-(((3S,5S)-5-fluoropiperidin-3-yl)amino)-8-isopropyl-7-oxo-7,8-dihydropteridin-6-yl)-6-methylpyridin-2-yl)-1-phenylmethanesulfonamide | 566.22 |
| 552 | 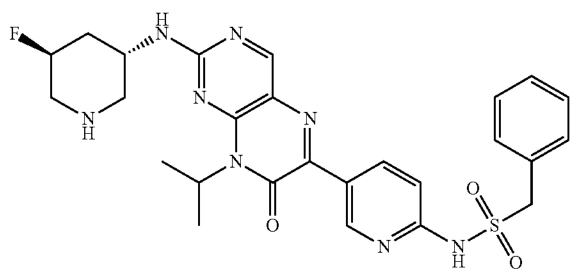 [SMILES: CC(C)n1c(=O)c(-c2ccc(NS(=O)(=O)Cc3ccccc3)nc2)nc2cnc(N[C@@H]3CNC[C@@H](F)C3)nc21] | N-(5-(2-(((3S,5S)-5-fluoropiperidin-3-yl)amino)-8-isopropyl-7-oxo-7,8-dihydropteridin-6-yl)pyridin-2-yl)-1-phenylmethanesulfonamide | 552.21 |
| 553 | 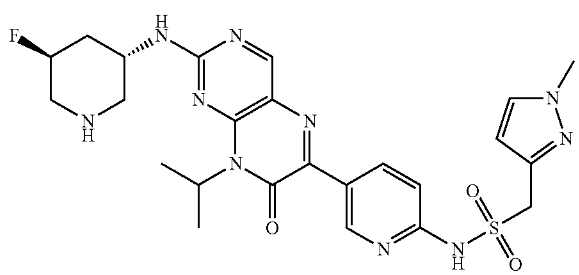 [SMILES: CC(C)n1c(=O)c(-c2ccc(NS(=O)(=O)Cc3ccn(C)n3)nc2)nc2cnc(N[C@@H]3CNC[C@@H](F)C3)nc21] | N-(5-(2-(((3S,5S)-5-fluoropiperidin-3-yl)amino)-8-isopropyl-7-oxo-7,8-dihydropteridin-6-yl)pyridin-2-yl)-1-(1-methyl-1H-pyrazol-3-yl)methanesulfonamide | 556.21 |
| 554 | 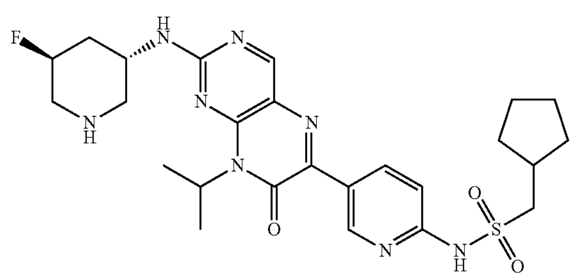 [SMILES: CC(C)n1c(=O)c(-c2ccc(NS(=O)(=O)CC3CCCC3)nc2)nc2cnc(N[C@@H]3CNC[C@@H](F)C3)nc21] | 1-cyclopentyl-N-(5-(2-(((3S,5S)-5-fluoropiperidin-3-yl)amino)-8-isopropyl-7-oxo-7,8-dihydropteridin-6-yl)pyridin-2-yl)methanesulfonamide | 544.24 |
| 555 | 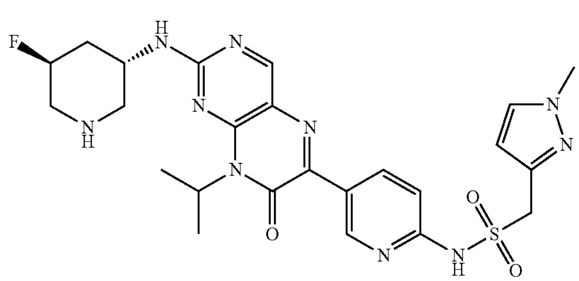 | N-(5-(2-(((3S,5S)-5-fluoropiperidin-3-yl)amino)-8-isopropyl-7-oxo-7,8-dihydropteridin-6-yl)pyridin-2-yl)-1-(1-methyl-1H-pyrazol-3-yl)methanesulfonamide | 556.21 |

TABLE 2-continued

Representative Compounds

| | Structure | Name | Mw (m/z) |
|---|---|---|---|
| 556 | 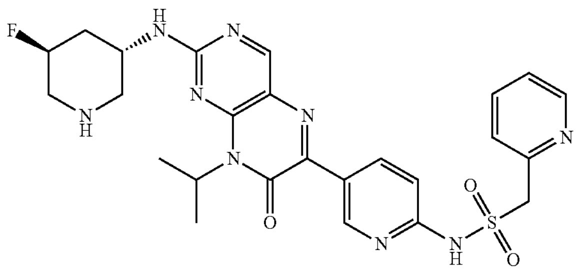 [SMILES: CC(C)n1c(=O)c(-c2ccc(NS(=O)(=O)Cc3ccccn3)nc2)nc2cnc(N[C@@H]3CNC[C@@H](F)C3)nc21] | N-(5-(2-(((3S,5S)-5-fluoropiperidin-3-yl)amino)-8-isopropyl-7-oxo-7,8-dihydropteridin-6-yl)pyridin-2-yl)-1-(pyridin-2-yl)methanesulfonamide | 553.20 |
| 557 | 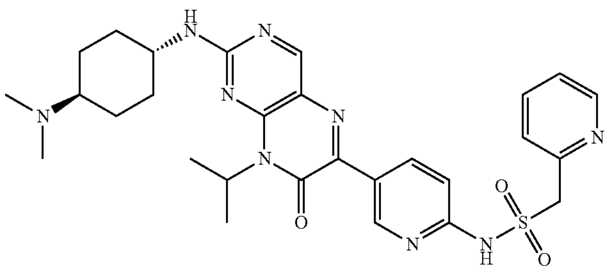 [SMILES: CC(C)n1c(=O)c(-c2ccc(NS(=O)(=O)Cc3ccccn3)nc2)nc2cnc(N[C@H]3CC[C@H](N(C)C)CC3)nc21] | N-(5-(2-(((1r,4r)-4-(dimethylamino)cyclohexyl)amino)-8-isopropyl-7-oxo-7,8-dihydropteridin-6-yl)pyridin-2-yl)-1-(pyridin-2-yl)methanesulfonamide | 577.26 |
| 558 | 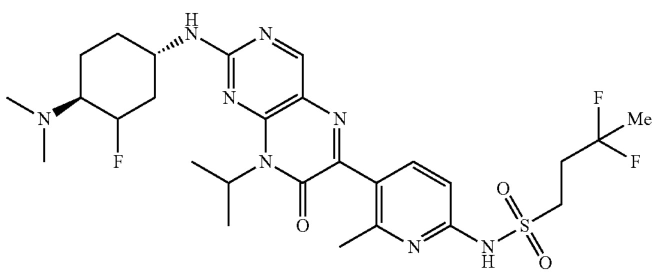 [SMILES: Cc1nc(NS(=O)(=O)CCC(C)(F)F)ccc1-c1nc2cnc(N[C@H]3CC[C@H](N(C)C)C(F)C3)nc2n(C(C)C)c1=O] | N-(5-(2-(((1S,4S)-4-(dimethylamino)-3-fluorocyclohexyl)amino)-8-isopropyl-7-oxo-7,8-dihydropteridin-6-yl)-6-methylpyridin-2-yl)-3,3-difluorobutane-1-sulfonamide | 610.27 |
| 559 | 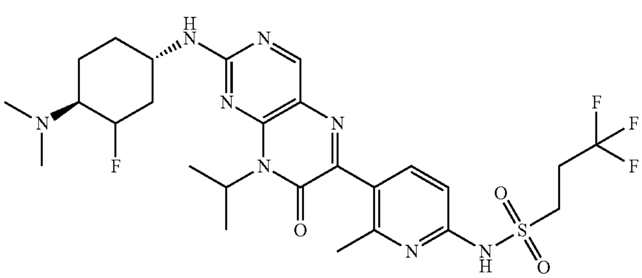 [SMILES: Cc1nc(NS(=O)(=O)CCC(F)(F)F)ccc1-c1nc2cnc(N[C@H]3CC[C@H](N(C)C)C(F)C3)nc2n(C(C)C)c1=O] | N-(5-(2-(((1S,4S)-4-(dimethylamino)-3-fluorocyclohexyl)amino)-8-isopropyl-7-oxo-7,8-dihydropteridin-6-yl)-6-methylpyridin-2-yl)3,3,3-trifluoropropane-1-sulfonamide | 614.24 |
| 560 | 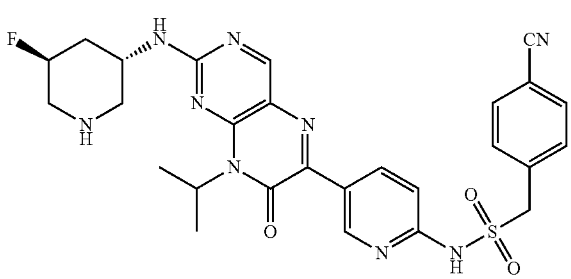 [SMILES: CC(C)n1c(=O)c(-c2ccc(NS(=O)(=O)Cc3ccc(C#N)cc3)nc2)nc2cnc(N[C@@H]3CNC[C@@H](F)C3)nc21] | 1-(4-cyanophenyl)-N-(5-(2-(((3S,5S)-5-fluoropiperidin-3-yl)amino)-8-isopropyl-7-oxo-7,8-dihydropteridin-6-yl)pyridin-2-yl)methanesulfonamide | 577.20 |

TABLE 2-continued

Representative Compounds

| | Structure | Name | Mw (m/z) |
|---|---|---|---|
| 561 | 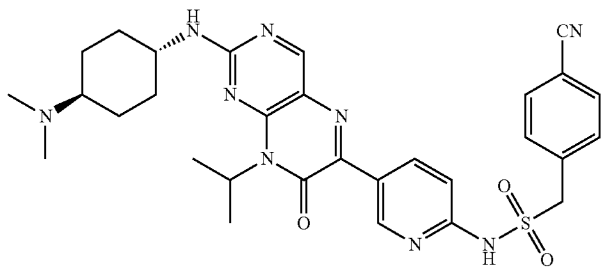 [SMILES: CC(C)n1c(=O)c(-c2ccc(NS(=O)(=O)Cc3ccc(C#N)cc3)nc2)nc2cnc(N[C@H]3CC[C@H](N(C)C)CC3)nc21] | 1-(4-cyanophenyl)-N-(5-(2-(((1r,4r)-4-(dimethylamino)cyclohexyl)amino)-8-isopropyl-7-oxo-7,8-dihydropteridin-6-yl)pyridin-2-yl)methanesulfonamide | 601.26 |
| 562 | 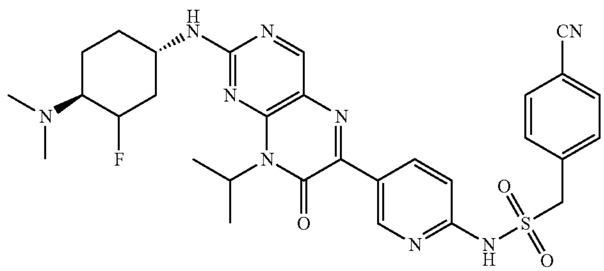 [SMILES: CC(C)n1c(=O)c(-c2ccc(NS(=O)(=O)Cc3ccc(C#N)cc3)nc2)nc2cnc(N[C@H]3CC[C@H](N(C)C)C(F)C3)nc21] | 1-(4-cyanophenyl)-N-(5-(2-(((1S,4S)-4-(dimethylamino)-3-fluorocyclohexyl)amino)-8-isopropyl-7-oxo-7,8-dihydropteridin-6-yl)pyridin-2-yl)methanesulfonamide | 619.25 |
| 563 | 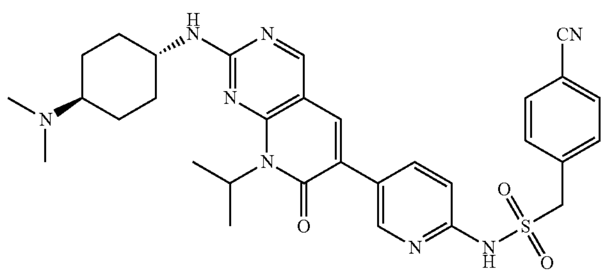 | 1-(4-cyanophenyl)-N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)methanesulfonamide | 600.26 |
| 564 | 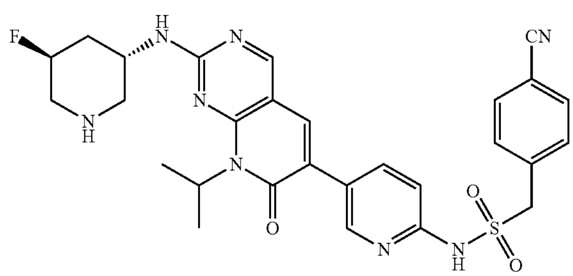 [SMILES: CC(C)n1c(=O)c(-c2ccc(NS(=O)(=O)Cc3ccc(C#N)cc3)nc2)cc2cnc(N[C@@H]3CNC[C@@H](F)C3)nc21] | 1-(4-cyanophenyl)-N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)methanesulfonamide | 576.21 |
| 565 | 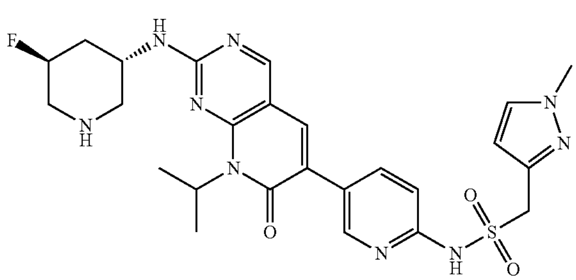 | N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)-1-(1-methyl-1H-pyrazol-3-yl)methanesulfonamide | 555.22 |

TABLE 2-continued

Representative Compounds

| | Structure | Name | Mw (m/z) |
|---|---|---|---|
| 566 | 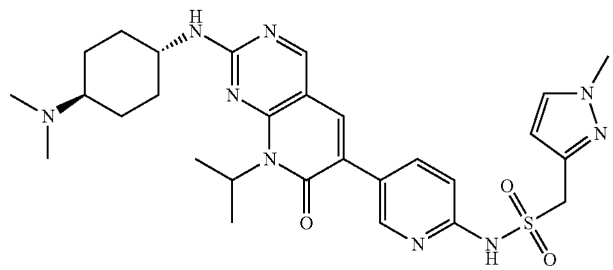 | N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)-1-(1-methyl-1H-pyrazol-3-yl)methanesulfonamide | 579.27 |
| 567 | 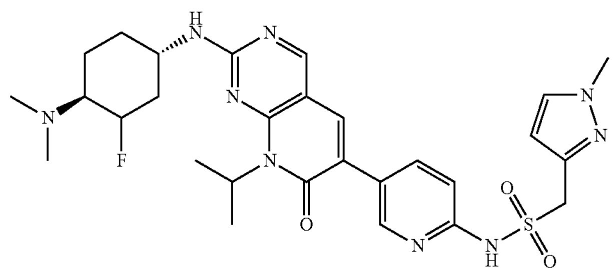 | N-(5-(2-(((1S,4S)-4-(dimethylamino)-3-fluorocyclohexyl)amino)-8-isopropyl-7-oxo-7,8-dihydropyrido[2,3-d]pyrimidin-6-yl)pyridin-2-yl)-1-(1-methyl-1H-pyrazol-3-yl)methanesulfonamide | 597.26 |
| 568 | 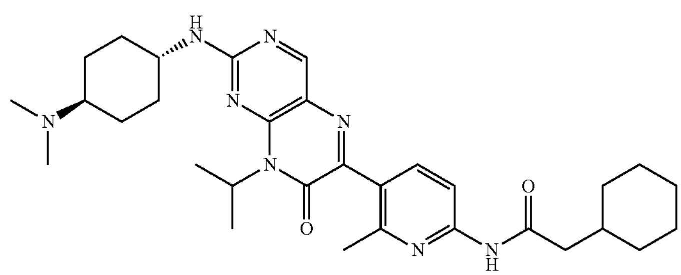 [SMILES: Cc1nc(NC(=O)CC2CCCCC2)ccc1-c1nc2cnc(N[C@H]3CC[C@H](N(C)C)CC3)nc2n(C(C)C)c1=O] | 2-cyclohexyl-N-(5-(2-(((1r,4r)-4-(dimethylamino)cyclohexyl)amino)-8-isopropyl-7-oxo-7,8-dihydropteridin-6-yl)-6-methylpyridin-2-yl)acetamide | 560.36 |
| 569 | 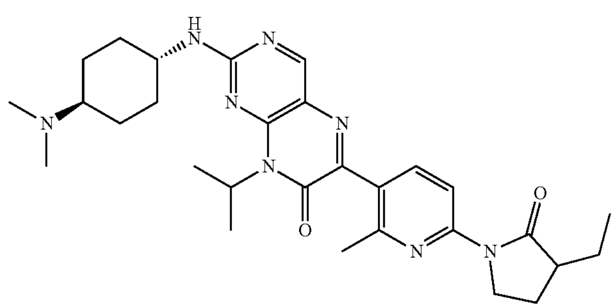 [SMILES: CCC1CCN(c2ccc(-c3nc4cnc(N[C@H]5CC[C@H](N(C)C)CC5)nc4n(C(C)C)c3=O)c(C)n2)C1=O] | 2-(((1r,4r)-4-(dimethylamino)cyclohexyl)amino)-6-(6-(3-ethyl-2-oxopyrrolidin-1-yl)-2-methylpyridin-3-yl)-8-isopropylpteridin-7(8H)-one | 532.33 |
| 570 | 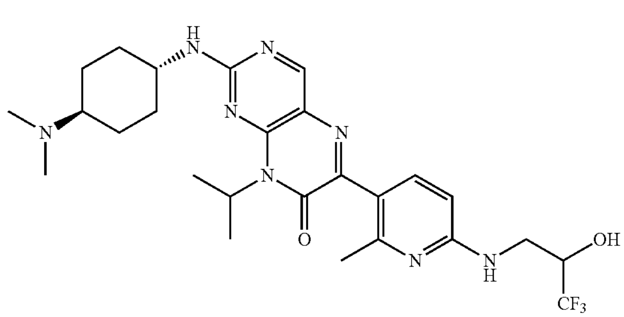 [SMILES: Cc1nc(NCC(O)C(F)(F)F)ccc1-c1nc2cnc(N[C@H]3CC[C@H](N(C)C)CC3)nc2n(C(C)C)c1=O] | 2-(((1r,4r)-4-(dimethylamino)cyclohexyl)amino)-8-isopropyl-6-(2-methyl-6-((3,3,3-trifluoro-2-hydroxypropyl)amino)pyridin-3-yl)pteridin-7(8H)-one | 548.28 |

TABLE 2-continued

Representative Compounds

| | Structure | Name | Mw (m/z) |
|---|---|---|---|
| 571 | 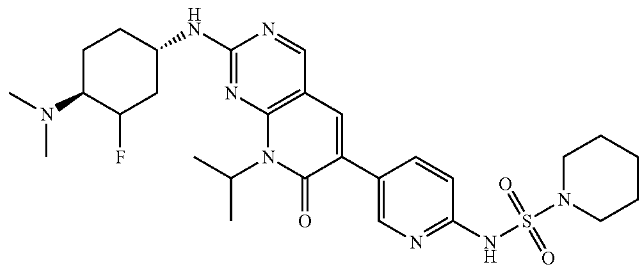 [SMILES: CC(C)n1c(=O)c(-c2ccc(NS(=O)(=O)N3CCCCC3)nc2)cc2cnc(N[C@H]3CC[C@H](N(C)C)C(F)C3)nc21] | N-(5-(2-(((1S,4S)-4-(dimethylamino)-3-fluorocyclohexyl)amino)-8-isopropyl-7-oxo-7,8-dihydropyrido[2,3-d]pyrimidin-6-yl)pyridin-2-yl)piperidine-1-sulfonamide | 586.28 |
| 572 | 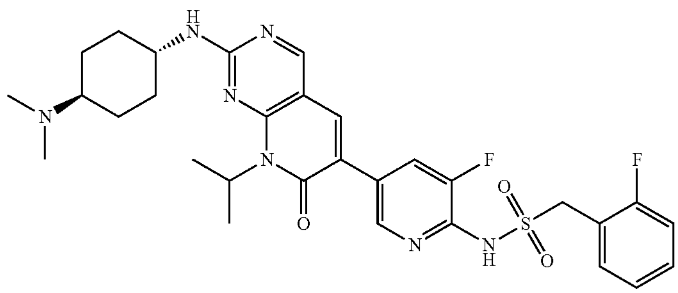 [SMILES: CC(C)n1c(=O)c(-c2cnc(NS(=O)(=O)Cc3ccccc3F)c(F)c2)cc2cnc(N[C@H]3CC[C@H](N(C)C)CC3)nc21] | N-(5-(2-(((1r,4r)-4-(dimethylamino)cyclohexyl)amino)-8-isopropyl-7-oxo-7,8-dihydropyrido[2,3-d]pyrimidin-6-yl)-3-fluoropyridin-2-yl)-1-(2-fluorophenyl)methanesulfonamide | 611.25 |
| 573 | 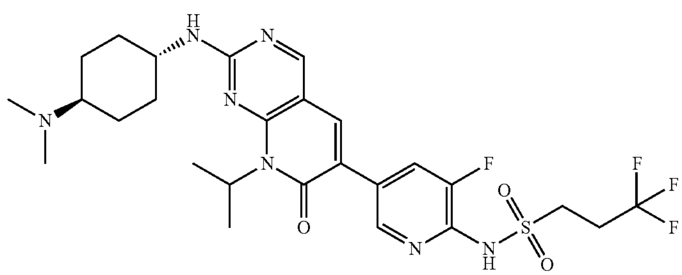 [SMILES: CC(C)n1c(=O)c(-c2cnc(NS(=O)(=O)CCC(F)(F)F)c(F)c2)cc2cnc(N[C@H]3CC[C@H](N(C)C)CC3)nc21] | N-(5-(2-(((1r,4r)-4-(dimethylamino)cyclohexyl)amino)-8-isopropyl-7-oxo-7,8-dihydropyrido[2,3-d]pyrimidin-6-yl)-3-fluoropyridin-2-yl)-3,3,3-trifluoropropane-1-sulfonamide | 599.23 |
| 574 | 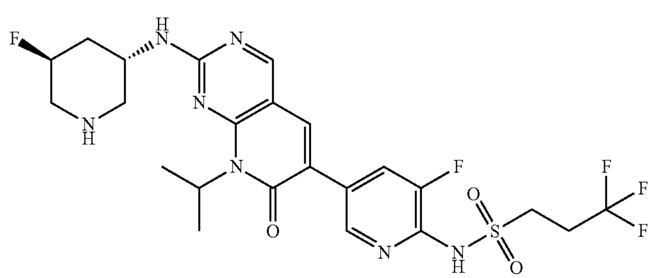 [SMILES: CC(C)n1c(=O)c(-c2cnc(NS(=O)(=O)CCC(F)(F)F)c(F)c2)cc2cnc(N[C@@H]3CNC[C@@H](F)C3)nc21] | 3,3,3-trifluoro-N-(3-fluoro-5-(2-(((3S,5S)-5-fluoropiperidin-3-yl)amino)-8-isopropyl-7-oxo-7,8-dihydropyrido[2,3-d]pyrimidin-6-yl)pyridin-2-yl)propane-1-sulfonamide | 575.17 |
| 575 | 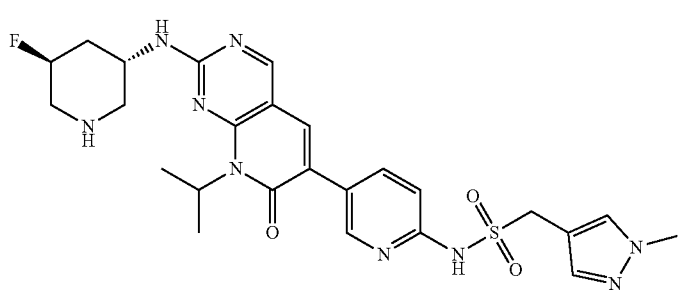 [SMILES: CC(C)n1c(=O)c(-c2ccc(NS(=O)(=O)Cc3cnn(C)c3)nc2)cc2cnc(N[C@@H]3CNC[C@@H](F)C3)nc21] | N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)-1-(1-methyl-1H-pyrazol-4-yl)methanesulfonamide | 555.22 |

TABLE 2-continued

Representative Compounds

| | Structure | Name | Mw (m/z) |
|---|---|---|---|
| 576 | 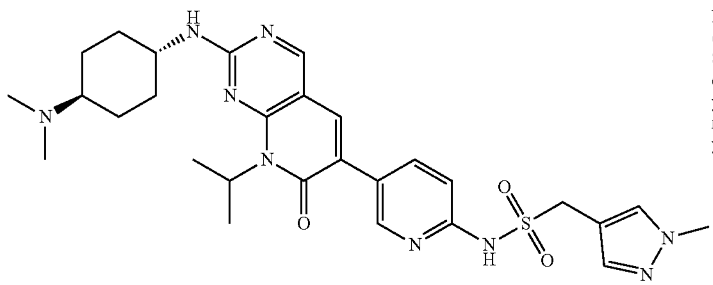 | N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)-1-(1-methyl-1H-pyrazol-4-yl)methanesulfonamide | 579.27 |
| 577 | 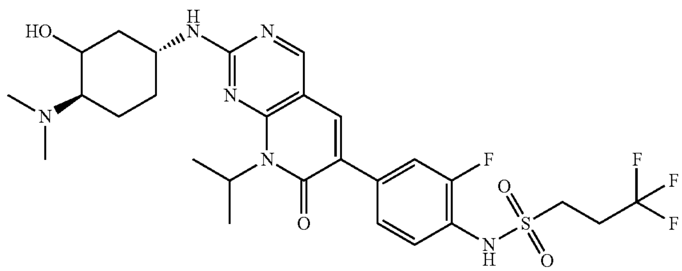 [SMILES: CC(C)n1c(=O)c(-c2ccc(NS(=O)(=O)CCC(F)(F)F)c(F)c2)cc2cnc(N[C@@H]3CC[C@@H](N(C)C)C(O)C3)nc21] | N-(4-(2-(((1R,4R)-4-(dimethylamino)-3-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide | 614.23 |
| 578 | 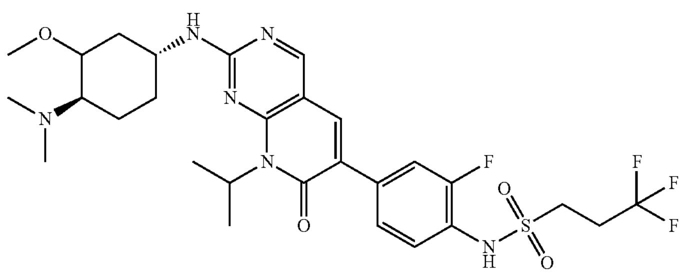 [SMILES: COC1C[C@H](Nc2ncc3cc(-c4ccc(NS(=O)(=O)CCC(F)(F)F)c(F)c4)c(=O)n(C(C)C)c3n2)CC[C@H]1N(C)C] | N-(4-(2-(((1R,4R)-4-(dimethylamino)-3-methoxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide | 628.25 |
| 579 | 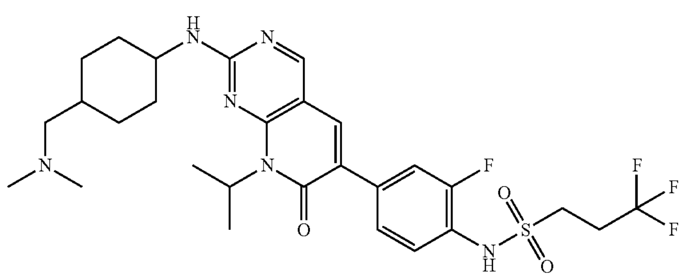 [SMILES: CC(C)n1c(=O)c(-c2ccc(NS(=O)(=O)CCC(F)(F)F)c(F)c2)cc2cnc(NC3CCC(CN(C)C)CC3)nc21] | N-(4-(2-((4-((dimethylamino)methyl)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide | 612.25 |
| 580 | 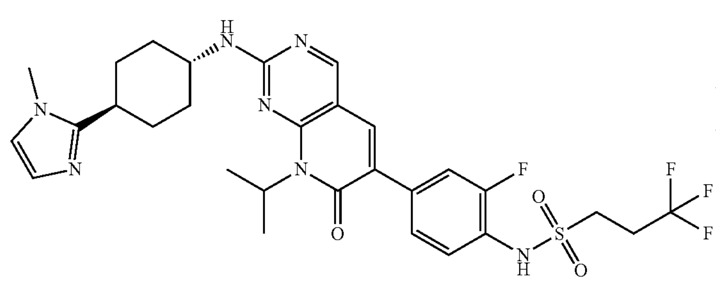 | 3,3,3-trifluoro-N-(2-fluoro-4-(8-isopropyl-2-(((1r,4r)-4-(1-methyl-1H-imidazol-2-yl)cyclohexyl)amino)-7-oxo-7,8-dihydropyrido[2,3-d]pyrimidin-6-yl)phenyl)propane-1-sulfonamide | 635.23 |

TABLE 2-continued

Representative Compounds

| | Structure | Name | Mw (m/z) |
|---|---|---|---|
| 581 | 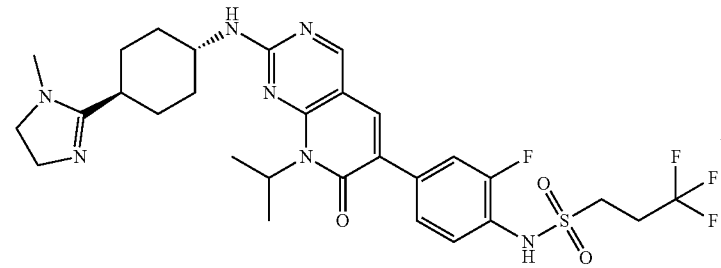 | 3,3,3-trifluoro-N-(2-fluoro-4-(8-isopropyl-2-(((1r,4r)-4-(1-methyl-4,5-dihydro-1H-imidazol-2-yl)cyclohexyl)amino)-7-oxo-7,8-dihydropyrido[2,3-d]pyrimidin-6-yl)phenyl)propane-1-sulfonamide | 637.25 |
| 582 | 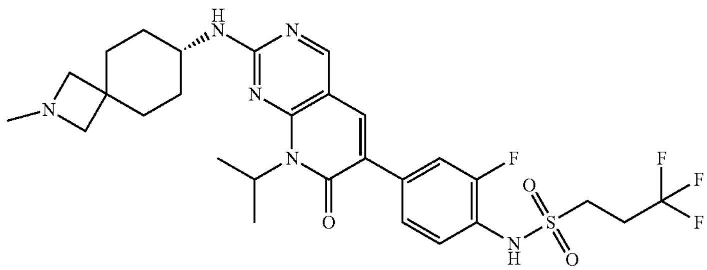 | 3,3,3-trifluoro-N-(2-fluoro-4-(8-isopropyl-2-((2-methyl-2-azaspiro[3.5]nonan-7-yl)amino)-7-oxo-7,8-dihydropyrido[2,3-d]pyrimidin-6-yl)phenyl)propane-1-sulfonamide | 610.23 |
| 583 | 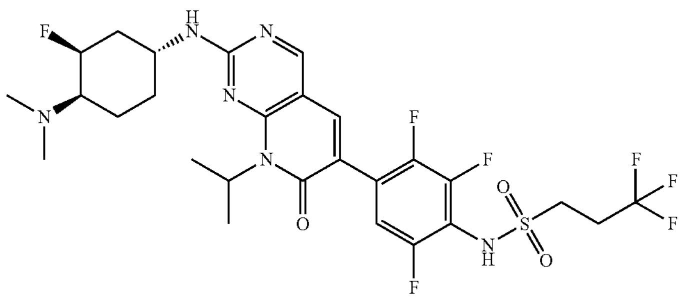 [SMILES: CC(C)n1c(=O)c(-c2cc(F)c(NS(=O)(=O)CCC(F)(F)F)c(F)c2F)cc2cnc(N[C@@H]3CC[C@@H](N(C)C)[C@@H](F)C3)nc21] | N-(4-(2-(((1R,3S,4R)-4-(dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide | 652.21 |
| 584 | 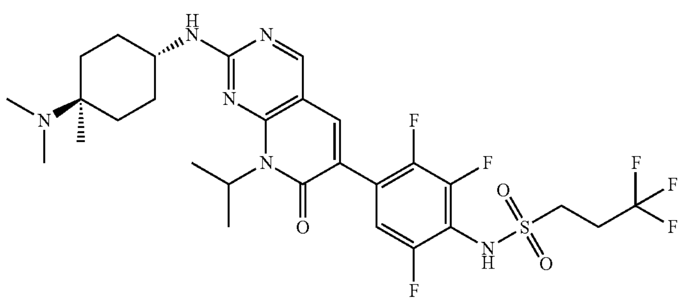 [SMILES: CC(C)n1c(=O)c(-c2cc(F)c(NS(=O)(=O)CCC(F)(F)F)c(F)c2F)cc2cnc(N[C@H]3CC[C@](C)(N(C)C)CC3)nc21] | N-(4-(2-(((1r,4r)-4-(dimethylamino)-4-methylcyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide | 648.23 |
| 585 | 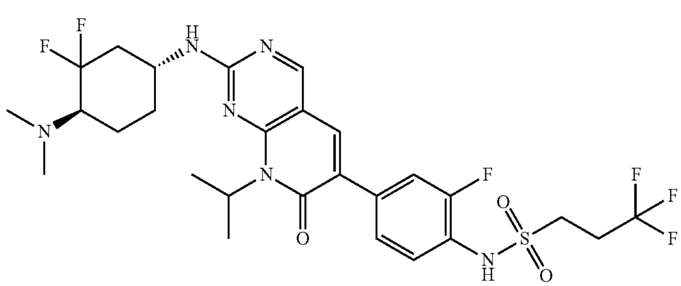 [SMILES: CC(C)n1c(=O)c(-c2ccc(NS(=O)(=O)CCC(F)(F)F)c(F)c2)cc2cnc(N[C@@H]3CC[C@@H](N(C)C)C(F)(F)C3)nc21] | N-(4-(2-(((1R,4R)-4-(dimethylamino)-3,3-difluorocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide | 634.22 |

TABLE 2-continued

Representative Compounds

| | Structure | Name | Mw (m/z) |
|---|---|---|---|
| 586 | 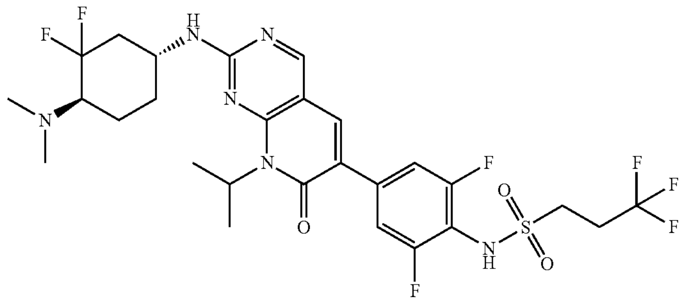 [SMILES: CC(C)n1c(=O)c(-c2cc(F)c(NS(=O)(=O)CCC(F)(F)F)c(F)c2)cc2cnc(N[C@@H]3CC[C@@H](N(C)C)C(F)(F)C3)nc21] | N-(4-(2-(((1R,4R)-4-(dimethylamino)-3,3-difluorocyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide | 652.21 |
| 587 | 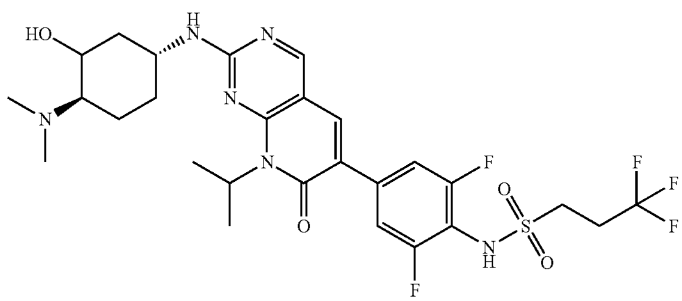 [SMILES: CC(C)n1c(=O)c(-c2cc(F)c(NS(=O)(=O)CCC(F)(F)F)c(F)c2)cc2cnc(N[C@@H]3CC[C@@H](N(C)C)C(O)C3)nc21] | N-(4-(2-(((1R,4R)-4-(dimethylamino)-3-hydroxycyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide | 632.22 |
| 588 | 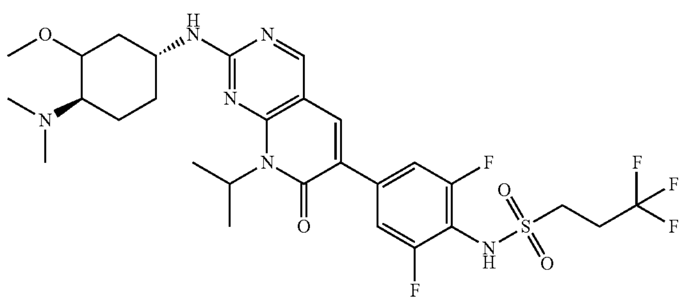 [SMILES: COC1C[C@H](Nc2ncc3cc(-c4cc(F)c(NS(=O)(=O)CCC(F)(F)F)c(F)c4)c(=O)n(C(C)C)c3n2)CC[C@H]1N(C)C] | N-(4-(2-(((1R,4R)-4-(dimethylamino)-3-methoxycyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide | 646.24 |
| 589 | 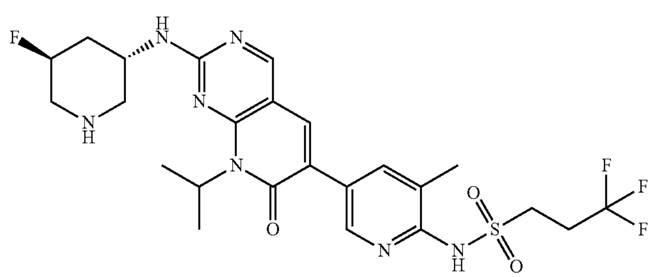 [SMILES: Cc1cc(-c2cc3cnc(N[C@@H]4CNC[C@@H](F)C4)nc3n(C(C)C)c2=O)cnc1NS(=O)(=O)CCC(F)(F)F] | 3,3,3-trifluoro-N-(5-(2-(((3S,5S)-5-fluoropiperidin-3-yl)amino)-8-isopropyl-7-oxo-7,8-dihydropyrido[2,3-d]pyrimidin-6-yl)-3-methylpyridin-2-yl)propane-1-sulfonamide | 571.20 |
| 590 | 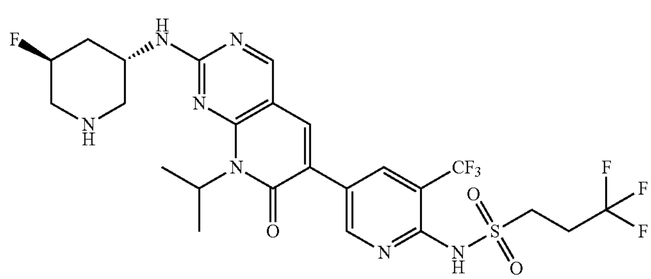 [SMILES: CC(C)n1c(=O)c(-c2cnc(NS(=O)(=O)CCC(F)(F)F)c(C(F)(F)F)c2)cc2cnc(N[C@@H]3CNC[C@@H](F)C3)nc21] | 3,3,3-trifluoro-N-(5-(2-(((3S,5S)-5-fluoropiperidin-3-yl)amino)-8-isopropyl-7-oxo-7,8-dihydropyrido[2,3-d]pyrimidin-6-yl)-3-(trifluoromethyl)pyridin-2-yl)propane-1-sulfonamide | 625.17 |

TABLE 2-continued

Representative Compounds

| | Structure | Name | Mw (m/z) |
|---|---|---|---|
| 591 | 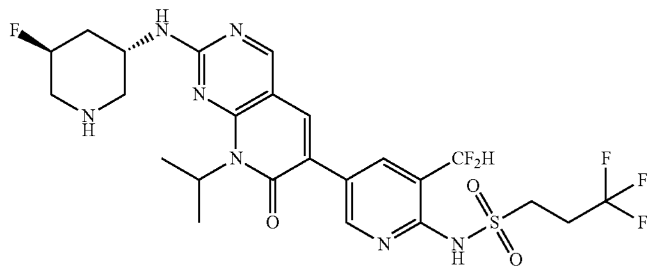 [SMILES: CC(C)n1c(=O)c(-c2cnc(NS(=O)(=O)CCC(F)(F)F)c(C(F)F)c2)cc2cnc(N[C@@H]3CNC[C@@H](F)C3)nc21] | N-(3-(difluoromethyl)-5-(2-(((3S,5S)-5-fluoropiperidin-3-yl)amino)-8-isopropyl-7-oxo-7,8-dihydropyrido[2,3-d]pyrimidin-6-yl)pyridin-2-yl)-3,3,3-trifluoropropane-1-sulfonamide | 607.18 |
| 592 | 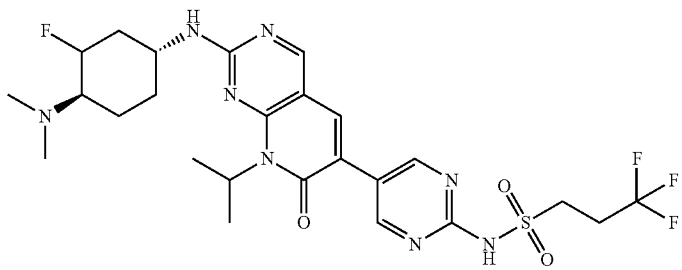 [SMILES: CC(C)n1c(=O)c(-c2cnc(NS(=O)(=O)CCC(F)(F)F)nc2)cc2cnc(N[C@@H]3CC[C@@H](N(C)C)C(F)C3)nc21] | N-(5-(2-(((1R,4R)-4-(dimethylamino)-3-fluorocyclohexyl)amino)-8-isopropyl-7-oxo-7,8-dihydropyrido[2,3-d]pyrimidin-6-yl)pyrimidin-2-yl)-3,3,3-trifluoropropane-1-sulfonamide | 600.23 |
| 593 | 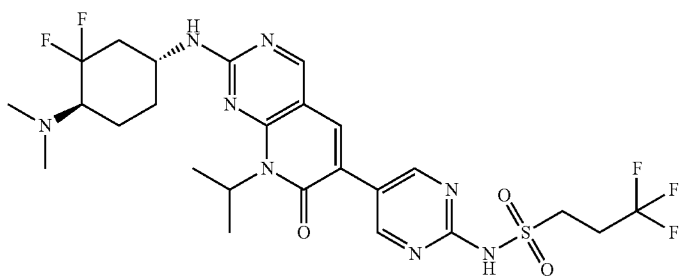 [SMILES: CC(C)n1c(=O)c(-c2cnc(NS(=O)(=O)CCC(F)(F)F)nc2)cc2cnc(N[C@@H]3CC[C@@H](N(C)C)C(F)(F)C3)nc21] | N-(5-(2-(((1R,4R)-4-(dimethylamino)-3,3-difluorocyclohexyl)amino)-8-isopropyl-7-oxo-7,8-dihydropyrido[2,3-d]pyrimidin-6-yl)pyrimidin-2-yl)-3,3,3-trifluoropropane-1-sulfonamide | 618.22 |
| 594 | 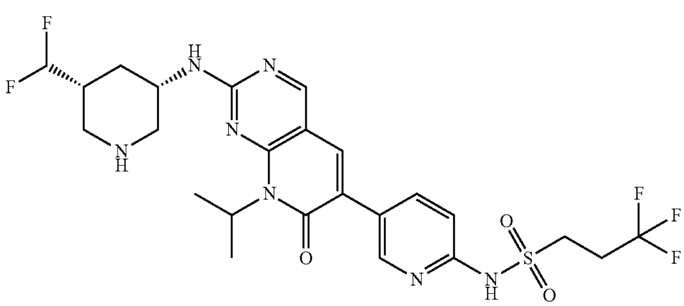 [SMILES: CC(C)n1c(=O)c(-c2ccc(NS(=O)(=O)CCC(F)(F)F)nc2)cc2cnc(N[C@@H]3CNC[C@H](C(F)F)C3)nc21] | N-(5-(2-(((3S,5R)-5-(difluoromethyl)piperidin-3-yl)amino)-8-isopropyl-7-oxo-7,8-dihydropyrido[2,3-d]pyrimidin-6-yl)pyridin-2-yl) 3,3,3-trifluoropropane-1-sulfonamide | 589.19 |
| 595 | 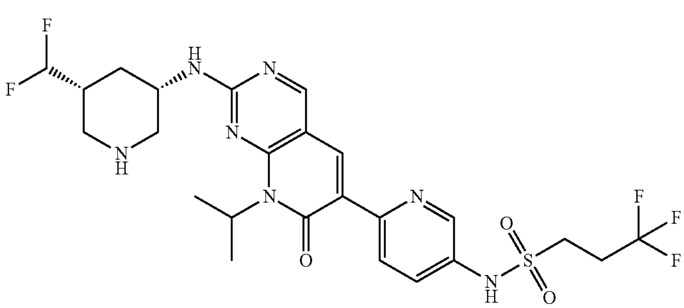 [SMILES: CC(C)n1c(=O)c(-c2ccc(NS(=O)(=O)CCC(F)(F)F)cn2)cc2cnc(N[C@@H]3CNC[C@H](C(F)F)C3)nc21] | N-(6-(2-(((3S,5R)-5-(difluoromethyl)piperidin-3-yl)amino)-8-isopropyl-7-oxo-7,8-dihydropyrido[2,3-d]pyrimidin-6-yl)pyridin-3-yl) 3,3,3-trifluoropropane-1-sulfonamide | 589.19 |

TABLE 2-continued

Representative Compounds

| | Structure | Name | Mw (m/z) |
|---|---|---|---|
| 596 | 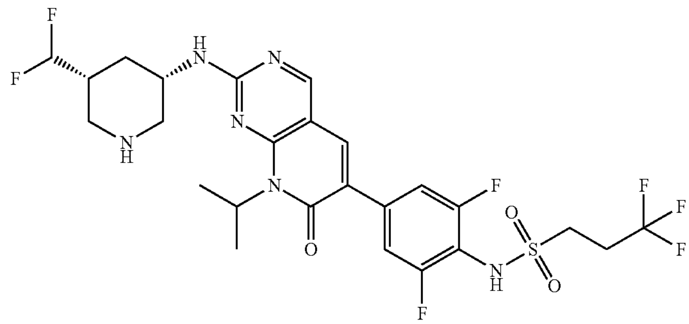 [SMILES: CC(C)n1c(=O)c(-c2cc(F)c(NS(=O)(=O)CCC(F)(F)F)c(F)c2)cc2cnc(N[C@@H]3CNC[C@H](C(F)F)C3)nc21] | N-(4-(2-(((3S,5R)-5-(difluoromethyl)piperidin-3-yl)amino)-8-isopropyl-7-oxo-7,8-dihydropyrido[2,3-d]pyrimidin-6-yl)-2,6-difluorophenyl)-3,3,3-trifluoropropane-1-sulfonamide | 624.18 |

In some embodiments provided herein is a compound as shown in Table 1 or a stereoisomer, tautomer, or pharmaceutically acceptable salt thereof. In one embodiment, the compound is a compound selected from Compound 1-95 or a stereoisomer, tautomer, or pharmaceutically acceptable salt thereof. In another embodiment, the compound is a compound selected from Compound 1-95 or a pharmaceutically acceptable salt thereof. In another embodiment, the compound is a compound selected from Compound 96-282 or a stereoisomer, tautomer, or pharmaceutically acceptable salt thereof. In another embodiment, the compound is a compound selected from Compound 96-282 or a pharmaceutically acceptable salt thereof. In another embodiment provided herein is a compound as shown in Table 2, or a stereoisomer, tautomer, or pharmaceutically acceptable salt thereof.

Preparation of Compounds

Compounds described herein can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9): 1910-16, (1985); Helvetica Chimica Acta, 41:1052-60, (1958); Arzneimittel-Forschung, 40(12): 1328-31, (1990), each of which are expressly incorporated by reference. Starting materials are generally available from commercial sources such as Aldrich Chemicals (Milwaukee, WI) or are readily prepared using methods (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database). Compounds described herein can also be made following the procedures found in U.S. Pat. Nos. 8,476,434, 7,880,000, WO 2005/113494, U.S. Pat. No. 7,868,177, and WO 2007/100646.

Synthetic chemistry transformations and protecting group methodologies (protection and deprotection) useful in synthesizing compounds described herein and necessary reagents and intermediates include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); and L. Paquette, ed., Encyclopedia of Reagents for Organic Synthesis, John Wiley and Sons (1995) and subsequent editions thereof.

Compounds described herein can be prepared singly or as compound libraries comprising at least 2, for example 5 to 1,000 compounds, or 10 to 100 compounds. Libraries of compounds of the formulae described herein can be prepared by a combinatorial split and mix approach or by multiple parallel syntheses using, for example, either solution phase or solid phase chemistry. Thus according to a further aspect provided herein is a compound library comprising at least 2 compounds, or pharmaceutically acceptable salts thereof as described herein.

The Examples provide exemplary methods for preparing compounds described herein. Those skilled in the art will appreciate that other synthetic routes can be used to synthesize the compounds described herein. Although specific starting materials and reagents are depicted and discussed in the Examples, other starting materials and reagents can be easily substituted to provide a variety of derivatives and/or reaction conditions. In addition, many of the exemplary compounds prepared by the described methods can be further modified in light of this disclosure using conventional chemistry.

In preparing compounds as described herein protection of remote functionality (e.g., primary or secondary amine) of intermediates can be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection can be readily determined. For a general description of protecting groups and their use, see T. W. Greene, Protective Groups in Organic Synthesis, John Wiley & Sons, New York, 1991.

In the methods of preparing compounds described herein, it can be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds or pharmaceutically acceptable salts thereof described herein can be atropisomers (e.g., substituted biaryls). Enantiomers can also be separated by use of a chiral HPLC column.

A single stereoisomer, e.g., an enantiomer, substantially free of its stereoisomer can be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds or pharmaceutically acceptable salts thereof described herein can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts can be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob I I I. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Administration of Compounds

Compounds described herein can be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound is administered orally, it can be formulated as a pill, capsule, tablet, etc. with a pharmaceutically acceptable carrier or excipient. Where the compound is administered parenterally, it can be formulated with a pharmaceutically acceptable parenteral vehicle and in a unit dosage injectable form, as detailed below.

Thus, in one aspect provided herein is a pharmaceutical composition comprising a compound or pharmaceutically acceptable salt thereof as described herein and one or more pharmaceutically acceptable excipients. In one embodiment, compounds described herein are administered as pharmaceutical compositions capable of being administered to a subject orally or parenterally. The compounds described herein can be formulated for topical or parenteral use where the compound is dissolved or otherwise suspended in a solution suitable for injections, suspensions, syrups, creams, ointments, gels, sprays, solutions and emulsions.

Oral administration can promote patient compliance in taking the compound (e.g. formulated as a pharmaceutical composition), thereby increasing compliance and efficacy. Oral pharmaceutical compositions comprising a compound described herein include, but are not limited to, tablets (e.g. coated, non-coated and chewable) and capsules (e.g. hard gelatin capsules, soft gelatin capsules, enteric coated capsules, and sustained release capsules). Tablets can be prepared by direct compression, by wet granulation, or by dry granulation. Oral pharmaceutical compositions comprising a compound described herein can be formulated for delayed or prolonged release.

A dose to treat human patients can range from about 10 mg to about 1000 mg of a compound described herein. A typical dose can be about 100 mg to about 300 mg of the compound. A dose can be administered once a day (QID), twice per day (BID), or more frequently, depending on the pharmacokinetic and pharmacodynamic properties, including absorption, distribution, metabolism, and excretion of the particular compound. Administration as used herein refers to the frequency of dosing and not, for example, the number of individual units a patient described herein must take for a dose. Thus, in some embodiments, a patient may take two or more dosage units (e.g. two or more pills/tablets/capsules) QD. In addition, toxicity factors can influence the dosage and administration regimen. When administered orally, the pill, capsule, or tablet can be ingested daily or less frequently for a specified period of time. The regimen can be repeated for a number of cycles of therapy.

Methods of Treatment

In one aspect provided herein, compounds or pharmaceutically acceptable salts thereof are useful for treating a patient having a disease or disorder arising from: abnormal cell growth, function, or behavior associated with the UPR pathway such as cancer; an immune disorder; cardiovascular disease; viral infection; inflammation; a metabolism/endocrine disorder; or a neurological disorder by administering an effective amount of a compound or pharmaceutically acceptable salt thereof described herein. In one embodiment of the methods provided herein, compounds or pharmaceutically acceptable salts thereof are useful for treating a patient having an IRE1-related disease or disorder arising from: abnormal cell growth, function, or behavior associated with the UPR pathway such as cancer; an immune disorder; cardiovascular disease; viral infection; inflammation; a metabolism/endocrine disorder; or a neurological disorder by administering an effective amount of a compound or pharmaceutically acceptable salt thereof described herein.

Provided herein are methods of treating an IRE1-related disease or disorder by administering to a patient having an IRE1-related disease or disorder as described herein, an effective amount of a compound or a pharmaceutically acceptable salt thereof described herein. In another embodiment is a method of treating cancer by administering to a patient having cancer an effective amount of a compound or pharmaceutically acceptable salt thereof described herein. In one embodiment, the cancer is an IRE1-related disease or disorder.

The methods provided herein include treatment of solid tumors/cancers. For example, administration of a compound or pharmaceutically acceptable salt thereof described herein can be performed for patients having breast cancer, ovary cancer, cervix cancer, prostate cancer, testis cancer, genitourinary tract cancer, esophagus cancer, larynx cancer, glioblastoma, neuroblastoma, stomach cancer, skin cancer, keratoacanthoma, lung cancer, epidermoid carcinoma, large cell cancer, non-small cell lung cancer (NSCLC), small cell carcinoma, lung adenocarcinoma, bone cancer, colon cancer, adenoma, pancreatic cancer, adenocarcinoma, thyroid cancer, follicular carcinoma, undifferentiated carcinoma, papillary carcinoma, seminoma, melanoma, sarcoma, bladder carcinoma, liver carcinoma and biliary passages, kidney carcinoma, buccal cavity cancer, naso-pharyngeal cancer, pharynx cancer, lip cancer, tongue cancer, mouth cancer, small intestine cancer, colon-rectum cancer, large intestine cancer, rectum cancer, bronchial cancer, hepatocellular cancer, gastric cancer, endometrial cancer, melanoma, renal cancer, urinary bladder cancer, uterine corpus cancer, and uterine cervix cancer.

In another embodiment, the methods provided herein include treatment of cancer by administering to a patient having cancer an effective amount of a compound or pharmaceutically acceptable salt thereof where the cancer comprises squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

In certain embodiments, the cancer is breast cancer. The breast cancer can be Stage I, II, III, or IV as understood in the art. In one embodiment, the breast cancer is triple negative breast cancer (TNBC). In another embodiment, the breast cancer is Her2 negative breast cancer.

In another aspect provided herein are methods of treating hematological cancers such as, for example, lymphoma, lymphocytic leukemia (acute (ALL) and chronic (CLL)), multiple myeloma (MM), acute myelogenous leukemia (AML), chronic myelogenous leukemia (CML), myelodysplastic syndrome (MDS), myeloproliferative disease (MPD), or non-Hodgkin lymphoma. In one embodiment, the methods herein include treatment of lymphoma, lymphocytic leukemia, multiple myeloma (MM), acute myelogenous leukemia (AML), chronic myelogenous leukemia (CML), myelodysplastic syndrome (MDS), or myeloproliferative disease (MPD) by administering an effective amount of a compound described herein.

In one embodiment, is a method of treating MM by administering to a patient having MM an effective amount of compound described herein. The MM can be stage I, II, III, or IV as understood in the art. In another embodiment is a method of treating AML by administering to a patient having AML an effective amount of a compound or pharmaceutically acceptable salt thereof described herein. The AML can be stage I, II, III, or IV as understood in the art. In another embodiment is a method of treating CML by administering to a patient having CML an effective amount of a compound or pharmaceutically acceptable salt thereof described herein. The CML can be stage I, II, III, or IV as understood in the art. In another embodiment is a method of treating MDS by administering to a patient having MDS an effective amount of a compound or pharmaceutically acceptable salt thereof described herein. It is further understood that such cancers can be relapsed or refractory as provided herein.

In one aspect, provided is a method of treating an IRE1-related disease or disorder in a patient comprising administering an effective amount of a compound as described herein or pharmaceutically acceptable salt thereof, to a patient with an IRE1-related disease or condition. In another aspect, the method comprises administering to a patient with an IRE1-related disease or condition an effective amount of a pharmaceutical composition comprising a compound as described herein or a pharmaceutically acceptable salt thereof, and one or more pharmaceutically acceptable carrier excipients. In some embodiments, the compound is selected from Table 1 or Table 2, or a pharmaceutically acceptable salt thereof. In some embodiments, the patient is a human patient.

In one embodiment, the cancer is an IRE1-mediated cancer (i.e. a cancer having abnormal expression or activity of IRE1 relative to a control). In one embodiment, the IRE1-mediated cancer has increased expression of IRE1. In another embodiment, the IRE1-mediated cancer has increased activity of IRE1. Such increases can be measured against a control (e.g. against a patient having predetermined IRE1 function, expression, activity; or for example measure in a single patient before, during, or after treatment with a compound or pharmaceutically acceptable salt thereof described herein). Cancers as provided above include IRE1-mediated cancers.

In another aspect provided herein is a compound as described herein or pharmaceutically acceptable salt thereof, for use in a method for treating an IRE1-related disease or disorder. In one aspect, provided is a use of a compound as described herein or pharmaceutically acceptable salt thereof, in the manufacture of a medicament for the treatment of an IRE1-related disease or disorder.

In some embodiments of the method of treating an IRE1-related disease or disorder in a patient comprising administering an effective amount of a compound as described herein or pharmaceutically acceptable salt thereof, to a patient with an IRE1-related disease or condition, the method further comprising administering one or more additional therapeutic agent(s) selected from the group consisting of an anti-inflammatory agent, a corticosteroid, an immunomodulatory agent, anti-cancer agent as described herein, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, an agent for treating immunodeficiency disorders, and combinations thereof. In some embodiments, the additional therapeutic agent is a corticosteroid, a proteasome inhibitor, an IMiD, an antibody, or a combination thereof. In some embodiments, the additional therapeutic agent is a proteasome inhibitor (e.g. carfilzomib, bortezomib, or ixazomib). In some embodiments, the additional therapeutic agent is an IMiD (e.g. lenalidomide or pomalidomide). In some embodiments, the additional therapeutic agent is an antibody (e.g., an anti-CD38 antibody, an anti-VEGF-A antibody, an anti-PD-1 antibody, an anti-PD-L1 antibody or an anti-interleukin-6 antibody). In some embodiments, the additional therapeutic agent is a corticosteroid (e.g., dexamethasone). In some embodiments, the method further comprises radiotherapy.

The methods and uses described herein also include embodiments where a compound or pharmaceutically acceptable salt thereof is administered in combination with one or more additional therapeutic agent(s) selected from the group consisting of an anti-inflammatory agent, a corticosteroid, an immunomodulatory agent, anti-cancer agent as described herein, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, an agent for treating immunodeficiency disorders, and combinations thereof.

In one embodiment of the methods provided herein a compound or pharmaceutically acceptable salt thereof is administered in combination with one or more additional therapeutic agents comprising a corticosteroid, a proteasome inhibitor, an immunomodulatory agent, an anti-CD38 antibody, an anti-VEGF-A antibody, an anti-PD-1 antibody, an anti-PD-L1 antibody, or an anti-interleukin-6 antibody, or a combination thereof.

In another embodiment of the methods provided herein a compound or pharmaceutically acceptable salt thereof is administered in combination as described herein where the additional therapeutic agent is a corticosteroid, a proteasome inhibitor, an IMiD, an antibody, or a combination thereof.

In one embodiment, a compound or pharmaceutically acceptable salt thereof is administered in combination with a proteasome inhibitor. In one embodiment, the proteasome inhibitor comprises carfilzomib, bortezomib, or ixazomib. In one embodiment, a compound or pharmaceutically acceptable salt thereof is administered in combination with a IMiD, where the IMiD is lenalidomide or pomalidomide. In one embodiment of the methods provided herein a compound or pharmaceutically acceptable salt thereof is administered in combination with a corticosteroid where the corticosteroid comprises dexamethasone.

In another embodiment, a compound or pharmaceutically acceptable salt thereof is administered in combination with an anti-PD-L1 antibody. The anti-PD-L1 antibody can be avelumab, durvalumab, or atezolizumab. In still another embodiment, a compound or pharmaceutically acceptable salt thereof is administered in combination with an anti-PD-1 antibody. The anti-PD-1 antibody can be pembrolizumab or nivolumab.

The methods provided herein can also further comprise administration of radiotherapy. In certain embodiments, the radiotherapy can be administered before administration of a compound or pharmaceutically acceptable salt thereof described herein.

Further provided herein is a compound or pharmaceutically acceptable salt thereof described herein, for use in a method for treating an IRE1-related disease or disorder, where the IRE1-related disease or disorder is as set forth herein. In one embodiment the compound or pharmaceutically acceptable salt thereof as described herein is for use in a method of treating a cancer as set forth above. In a preferred embodiment, the cancer is MM, AML, CML, or MDS.

Further provided herein is a use of a compound or pharmaceutically acceptable salt thereof described herein in the manufacture of a medicament for the treatment of an IRE1-related disease or disorder, where the IRE1-related disease or disorder is as set forth herein. In one embodiment the IRE1-related disease or disorder is a cancer as set forth above. In a preferred embodiment, the cancer is MM, AML, CML, or MDS. It is to be understood that embodiments herein referring to a method (e.g. a method of treating) can further refer to a use or or a compound for use as set forth herein.

The methods and uses described herein are also applicable to patients that have been previously treated with one or more therapies prior to receiving administration of a compound or pharmaceutically acceptable salt thereof described herein. It is well known in the art that patients may be treated with one or more treatment regimens—especially for hematological cancers such as those described herein. Cancers can be relapse or refractory (r/r) (e.g. a patient having rrMM, rrAML, rrCML, or rrMDS). A "refractory" cancer refers to cancer that progresses despite active treatment. A "relapse" cancer generally refers to cancer that occurs in the absence of therapy following successful treatment with one or more anticancer agents. Accordingly, in one embodiment provided herein are methods of treating r/r cancer (e.g. rrMM, rrAML, rrCML, or rrMDS) in a patient having such a cancer by administering a compound or pharmaceutically acceptable salt thereof described herein. Such methods can include co-administration with one or more anticancer agents described herein as set forth above.

Accordingly, in one embodiment, a patient may have been treated with one or more anticancer agents. In one particular embodiment, a patient has been treated with 2 or more anticancer agents as provided herein for the treatment of a hematological disease, such as for example MM or AML. In one embodiment, a patient treated according to the methods provided herein has been previously administered one or more proteasome inhibitors such as bortezomib, carfllzomib, or ixazomib. In one embodiment, a patient treated according to the methods provided herein has been previously administered one or more IMiDs such as thalidomide, lenalidomide, or pomalidomide. In another embodiment, a patient treated according to the methods provided herein has been previously administered chemotherapy (e.g. cytarbine, cladribine, fludarabine, mitoxantrone, etoposide, 6-TG, hydroxyurea, methotrexate, decitabine, or an anthracyclin). In another embodiment, a patient treated according to the methods provided herein has been previously administered one or more corticosteroids such as dexamethasone. Such corticosteroids are often administered with other anticancer agents as understood in the art. In still another embodiment, a patient treated according to the methods provided herein has been previously administered one or more antibodies such as, for example, daratumumab, gemtuzumab ozogamicin, atezolizumab, alemtuzumab, rituximab, obinutuzumab, or ofatumumab. In still another embodiment, a patient treated according to the methods provided herein has been previously administered one or more FLT3 inhibitor (e.g. midostaurin or gilteritinib). In yet another embodiment, a patient treated according to the methods provided herein has been previously administered one or more Bcl-2 inhibitors such as venetoclax or navitoclax. In yet another embodiment, a patient treated according to the methods provided herein has been previously administered one or more of ibrutinib, idelalisib, or duvelisib. In another embodiment, a patient treated according to the methods provided herein has been previously administered an IMiD as described herein in combination with a proteasome inhibitor and optionally a corticosteroid.

A compound or pharmaceutically acceptable salt thereof described herein can be administered as a first line (1 L) therapy (e.g. administration prior to administration of another anticancer agent, including chemotherapy). Thus, in certain instances a patient may be chemotherapy naïve.

It is understood that the methods described herein include administration of a pharmaceutical composition comprising a compound or pharmaceutically acceptable salt thereof as provided herein. Such pharmaceutical compositions also comprise one or more pharmaceutically acceptable carrier excipients. In some embodiments, the compound is selected from Table 1 or Table 2, or a pharmaceutically acceptable salt thereof. In one embodiment, the compound or pharmaceutically acceptable salt thereof is one set forth in Table 1. In one embodiment, the compound or pharmaceutically acceptable salt thereof is one set forth in Table 2.

Also provided herein is a method of treating a disease caused by abnormal levels of IRE1 activity in a human or animal patient in need of such treatment with a compound or a pharmaceutically acceptable salt thereof described herein. The disease can be caused by an amount of IRE1 activity that is too low or too high. For example, the disease can be caused by a deficiency in IRE1 activity or by abnormally high IRE1 activity (e.g., hyperactivity of IRE1). The method includes administering to the patient a effective amount of a compound or a pharmaceutically acceptable salt thereof described herein that modulates IRE1 activity (an IRE1 modulator compound).

Also provided herein is a method of treating a disease caused by abnormal levels of IRE1 activity in a human or animal patient in need of such treatment with a compound or a pharmaceutically acceptable salt thereof described herein. The disease can be caused by an amount of IRE1 activity that is too low or too high. For example, the disease can be caused by a deficiency in IRE1 activity or by abnormally high IRE1 activity (e.g., hyperactivity of IRE1). The method includes administering to the patient a effective amount of an IRE1 modulator compound or a pharmaceutically acceptable salt thereof described herein.

IRE1 deficiency is a decreased amount of IRE1 activity compared to normal levels of IRE1 activity in a particular subject or a population of healthy subjects. The decreased amount of IRE1 activity results in excessive amounts of misfolded protein accumulation thereby causing the disease state.

IRE1 hyperactivity is an increased amount of IRE1 activity compared to normal levels of IRE1 activity in a particular subject or a population of healthy subjects. The increased amount of IRE1 activity can result in, for example, excessive amounts of cell proliferation thereby causing the disease state.

In some embodiments, the disease is associated with IRE1 deficiency. Such diseases include, but are not limited to, cystic fibrosis, retinitis pigmentosa, diabetes, or a neurodegenerative disease. The neurodegenerative disease can include Alexander's disease, Alper's disease, Alzheimer's disease, Amyotrophic lateral sclerosis, Ataxia telangiectasia, Batten disease (also known as Spielmeyer-Vogt-Sjogren-Batten disease). Bovine spongiform encephalopathy (BSF), Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

In other embodiments, the disease is associated with abnormally high IRE1. Such diseases include, but are not limited, to cancers, inflammatory diseases, and autoimmune diseases. Exemplary cancers include, but am not limited to, breast cancer and multiple myeloma. In one embodiment, the disease is multiple myeloma. In one embodiment, the disease is a triple-negative breast cancer. Exemplary inflammatory diseases include, but are not limited to, asthma, chronic inflammation, chronic prostatitis, glomerulonephritis, hypersensitivities, inflammatory bowel diseases, pelvic inflammatory disease; reperfusion injury, rheumatoid arthritis, transplant rejection, and vasculitis. Exemplary autoimmune diseases include, but are not limited to, XBP1-linked Crohn's disease, Coeliac disease, diabetes mellitus type 1 (IDDM), systemic lupus erythematosus (SLE), Sjogren's syndrome, Churg-Strauss Syndrome, Hashimoto's thyroiditis, Graves' disease, idiopathic thrombocytopenic purpura, and rheumatoid arthritis. In one embodiment, the disease is XBP1-linked. Crohn's disease.

In one aspect provided herein is a method of treating atherosclerosis or the progression of atherosclerosis by administering an effective amount of a compound or pharmaceutically acceptable salt thereof described herein. In one embodiment, administration of a compound or pharmaceutically acceptable salt thereof described herein reduces the number of macrophages in an atherosclerotic lesion. Such reduction can be imparted, in some embodiments, without altering apoptosis state. In another embodiment, administration of a compound or pharmaceutically acceptable salt thereof as described herein inhibits or reduces the production of IL-1β, CCL2, and chemokine receptor 2.

Pharmaceutical Formulations

Compounds or pharmaceutically acceptable salts thereof as described herein can be formulated in accordance with standard pharmaceutical practice as a pharmaceutical composition. Thus, further provided herein is a pharmaceutical composition comprising a compound or pharmaceutically acceptable salt thereof and one or more pharmaceutically acceptable excipients.

A typical formulation is prepared by mixing a compound or pharmaceutically acceptable salt thereof as described herein and an excipient. Suitable carriers, diluents and excipients include, but are not limited to, materials such as carbohydrates, waxes, water soluble and/or swellable polymers, hydrophilic or hydrophobic materials, gelatin, oils, solvents, water and the like. The particular excipient used will depend upon the means and purpose for which the compound or pharmaceutically acceptable salt thereof as described herein is being applied. Solvents are generally selected based on solvents recognized as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound described herein or pharmaceutical composition thereof) or aid in the manufacturing of the pharmaceutical product (i.e., medicament).

The formulations can be prepared using conventional dissolution and mixing procedures. For example, the bulk drug substance (i.e., compound or pharmaceutically acceptable salt thereof as described herein or stabilized form thereof (e.g., complex with a cyclodextrin derivative or other known complexation agent) is dissolved in a suitable solvent in the presence of one or more of the excipients described above. The compound or pharmaceutically acceptable salt thereof as described herein is typically formulated into pharmaceutical dosage forms to provide an easily controllable dosage of the drug and to enable patient compliance with the prescribed regimen.

The pharmaceutical composition (or formulation) for application can be packaged in a variety of ways depending upon the method used for administering the drug. Generally, an article for distribution includes a container having deposited therein the pharmaceutical formulation in an appropriate form. Suitable containers include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical formulations of the compounds or pharmaceutically acceptable salts thereof as described herein can be prepared for various routes and types of administration. For example, a compound or pharmaceutically acceptable salt thereof as described herein having the desired degree of purity can optionally be mixed with one or more pharmaceutically acceptable excipients (Remington's Pharmaceutical Sciences (1980) 16th edition, Osol, A. Ed.), in the form of a lyophilized formulation, milled powder, or an aqueous solution. Formulation can be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8. For example, formulation in an acetate buffer at pH S can be a suitable embodiment.

The pharmaceutical composition ordinarily can be stored as a solid composition, a lyophilized formulation or as an aqueous solution.

The pharmaceutical compositions described herein can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to IS mg/kg/day. In another embodiment, a pharmaceutical composition described herein comprises an effective amount of a compound or pharmaceutically acceptable salt thereof in an amount of about: 1 mg-10 mg; 10 mg-25 mg; 20 mg-50 mg; 50 mg-75 mg; 70 mg-100 mg; 100 mg-150 mg; 100 mg-200 mg; 100 mg-500 mg; 200 mg-500 mg; 250 mg-500 mg; 500 mg-1000 mg; or 750 mg-1000 mg.

Acceptable pharmaceutically acceptable excipients are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds or pharmaceutically acceptable salts thereof as described herein may be prepared. Suitable examples of sustained-release preparations include semipermeable matrices of solid hydrophobic polymers containing a compound or pharmaceutically acceptable salt thereof as described herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(–)-3-hydroxybutyric acid.

The formulations include those suitable for the administration routes detailed herein. The formulations can conveniently be presented in unit dosage form and can be prepared by any methods. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound or pharmaceutically acceptable salt thereof as described herein suitable for oral administration can be prepared as discrete units such as pills, capsules, cachets or tablets each containing a predetermined amount of such compound or pharmaceutically acceptable salt thereof. Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs can be prepared for oral use. Formulations of compounds or pharmaceutically acceptable salts thereof as described herein intended for oral use can be prepared according to any method for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

For treatment of the eye or other external tissues, e.g., mouth and skin, the formulations are preferably applied as a topical ointment or cream containing the active ingredient (s) in an amount of, for example, 0.075 to 20% w/w. When formulated in an ointment, the active ingredients can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs. The oily phase of the emulsions of compositions provided herein can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizers) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of described herein include Tween® 60, Span® 80, cetostearyl alcohol, benzyl alcohol, myristyl alcohol, glyceryl mono-stearate and sodium lauryl sulfate.

Aqueous suspensions comprising compounds or pharmaceutically acceptable salts thereof as described herein can contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds or pharmaceutically acceptable salts thereof as described herein can be in the form of a sterile injectable preparation, such as a sterile injectable aqueous or oleaginous suspension. This suspension can be formulated using suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis disorders as described below.

Formulations suitable for vaginal administration can be presented as pessaries, tampons, creams, gels, pastes, foams or spray formulations containing in addition to the active ingredient such carriers considered to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The compounds or pharmaceutically acceptable salts thereof as described herein can be used in veterinary compositions comprising at least one active ingredient as above defined together with a veterinary carrier. Veterinary carriers are materials useful for the purpose of administering the composition and can be solid, liquid or gaseous materials which are otherwise inert or acceptable in the veterinary field and are compatible with the active ingredient. These veterinary compositions can be administered parenterally, orally or by any other desired route.

Combination Therapy

The compounds and pharmaceutically acceptable salts thereof described herein can be employed alone or in combination with additional therapeutic agents for the treatment of a disease or disorder described herein, such as inflammation or a hyperproliferative disorder (e.g., cancer). In certain embodiments, a compound described herein or a pharmaceutically acceptable salt thereof as described herein is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic can be a Bcl-2 inhibitor, a JAK inhibitor, a PI3K inhibitor, an mTOR inhibitor, an anti-inflammatory agent, an immunomodulatory agent, anti-cancer agent as described herein, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent can be an NSAID anti-inflammatory agent. The second therapeutic agent can be an anti-cancer agent as described herein. The second compound of the pharmaceutical combination formulation or dosing regimen preferably has complementary activities to compound described herein such that they do not adversely affect each other. Such compounds are suitably present in combination in amounts that are effective for the purpose intended. In one embodiment, a composition provided herein comprises a compound as described herein or a stereoisomer, tautomer, solvate, metabolite, or pharmaceutically acceptable salt thereof, in combination with a therapeutic agent such as an NSAID.

The combination therapy can be administered as a simultaneous or sequential regimen. When administered sequentially, the combination can be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and can be lowered due to the combined action (synergy) of the newly identified agent and other therapeutic agents or treatments.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound described herein or a or pharmaceutically acceptable salt thereof, can be combined with other therapeutic, hormonal or antibody agents such as those described herein, as well as combined with surgical therapy and radiotherapy. Combination therapies provided herein thus comprise the administration of at least one the compounds described herein or pharmaceutically acceptable salt thereof, and the use of at least one other cancer treatment method. The amounts of the compound(s) described herein or pharmaceutically acceptable salts thereof described herein, and the other pharmaceutically active therapeutic agent(s) and the relative timings of administration will be selected in order to achieve the desired combined therapeutic effect.

In some embodiments, a compound as described herein or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, a SERM, a SERD, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a pharmaceutical composition comprising a compound as described herein or a pharmaceutically acceptable salt thereof, is administered in combination with a therapeutic agent selected from paclitaxel, anastrozole, exemestane, cyclophosphamide, epirubicin, fulvestrant, letrozole, palbociclib, gemcitabine, trastuzumab (HERCEPTIN®, Genentech), trastuzumab emtansine (KADCYLA®, Genentech), pegfilgrastim, filgrastim, tamoxifen, docetaxel, toremifene, vinorelbine, capecitabine, and ixabepilone.

In some embodiments, a compound as described herein or a pharmaceutically acceptable salt thereof, is used in combination with hormone blocking therapy, chemotherapy, radiation therapy, monoclonal antibodies, or combinations thereof.

Also provided herein are methods of inhibiting or killing a cancer cell expressing Ire1 by contacting the cancer cell expressing Ire1 with a compound or pharmaceutically acceptable salt thereof described herein. In one embodiment of the methods, the contacting is performed in vivo (e.g. the contacting is a result of administration of a compound or pharmaceutically acceptable salt thereof described herein). Thus, in another embodiment of the methods the inhibition or killing of the cancer cell occurs in vivo. In still another embodiment, the cancer cell expressing IRE1 is in a human patient described herein.

Metabolites

Also provided herein are in vivo metabolic products of compounds or pharmaceutically acceptable salts thereof as described herein. Such products can result for example from the oxidation, reduction, hydrolysis, amidation, deamidation, esterification, deesterification, enzymatic cleavage, and the like, of the administered compound. Accordingly, provided herein are compounds produced by a process comprising contacting a compound or pharmaceutically acceptable salt thereof described herein with a mammal for a period of time sufficient to yield a metabolic product thereof.

Metabolite products typically are identified by preparing a radiolabelled (e.g., 14C or 3H) isotope of a compound or pharmaceutically acceptable salt thereof as described herein, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies. The metabolite products, so long as they are not otherwise found in vivo, are useful in diagnostic assays for therapeutic dosing of the compounds or pharmaceutically acceptable salts thereof described herein.

Articles of Manufacture

In another aspect provided herein is an article of manufacture, or kit, containing materials useful for the treatment of the diseases and disorders described above is provided. In one embodiment, the kit comprises a container comprising a compound described herein or pharmaceutically acceptable salt thereof. The kit can further comprise a label or package insert on or associated with the container. Suitable containers include, for example, bottles, vials, syringes, blister pack, etc. The container can be formed from a variety of materials such as glass or plastic. The container can hold a compound described herein or a formulation thereof which is effective for treating the condition and can have a sterile access port (for example, the container can be an intravenous solution bag or a vial having a stopper pierceable by a hypodermic injection needle). At least one active agent in the composition is a compound described herein or a pharmaceutically acceptable salt thereof. The label or package insert indicates that the composition is used for treating the condition of choice, such as cancer. In addition, the label or package insert can indicate that the patient to be treated is one having a disorder such as a hyperproliferative disorder, atherosclerosis, neurodegeneration, cardiac hypertrophy, pain, migraine or a neurotraumatic disease or event. In one embodiment, the label or package inserts indicates that the composition comprising a compound described herein or a pharmaceutically acceptable salt thereof can be used to treat a disorder resulting from abnormal cell growth. In one embodiment, the label or package inserts indicates that the composition comprising a compound described herein or a pharmaceutically acceptable salt thereof can be used to treat a disorder resulting from atherosclerosis. The label or package insert can also indicate that the composition can be used to treat other disorders. Alternatively, or additionally, the article of manufacture can further comprise a second container comprising a pharmaceutically acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

The kit can further comprise directions for the administration of the compounds described herein or a pharmaceutically acceptable salt thereof and, if present, the second pharmaceutical formulation. For example, if the kit comprises a first composition comprising a compound described herein or a pharmaceutically acceptable salt thereof and a second pharmaceutical formulation, the kit can further comprise directions for the simultaneous, sequential or separate administration of the first and second pharmaceutical compositions to a patient in need thereof.

In another embodiment, the kits are suitable for the delivery of solid oral forms of a compound described herein or a pharmaceutically acceptable salt thereof, such as tablets or capsules. Such a kit preferably includes a number of unit dosages. Such kits can include a card having the dosages oriented in the order of their intended use. An example of such a kit is a blister pack. Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit can comprise (a) a first container with a compound described herein or a pharmaceutically acceptable salt thereof contained therein; and optionally (b) a second container with a second pharmaceutical formulation contained therein, wherein the second pharmaceutical formulation comprises a second compound with anti-hyperproliferative activity. Alternatively, or additionally, the kit can further comprise a third container comprising a pharmaceutically-acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

In certain other embodiments wherein the kit comprises a composition of a compound described herein or a pharmaceutically acceptable salt thereof and a second therapeutic agent, the kit can comprise a container for containing the separate compositions such as a divided bottle or a divided foil packet, however, the separate compositions can also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EMBODIMENTS

Provided below are non-limiting, exemplary embodiments of the invention described herein.

Embodiment 1. A compound having a formula (I):

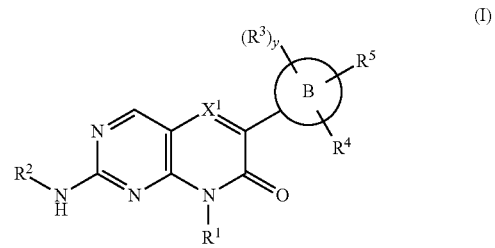

or a stereoisomer, tautomer, or pharmaceutically acceptable salt thereof,
wherein
$X^1$ is —$CR^x$ or —N, wherein $R^x$ is hydrogen, $C_1$-$C_4$ alkyl, cyclopropyl, or halogen;
Ring B is 5- to 7-membered aryl or 5- to 7-membered heteroaryl comprising at least one nitrogen atom;
y is 1, 2, 3, or 4;
$R^1$ is $C_1$-$C_4$ alkyl, $C_3$-$C_6$ cycloalkyl, or 3- to 14-membered heterocyclyl, each of which is unsubstituted or substituted with one or more substituents selected from the group consisting of —$CH_2F$, —$CHF_2$, —$CF_3$, halogen, $C_3$-$C_6$ cycloalkyl, hydroxyl, and —O—($C_1$-$C_4$)alkyl, such as methoxyl;
$R^2$ is $C_1$-$C_4$ alkyl, $C_3$-$C_6$ cycloalkyl, or 4- to 10-membered-heterocyclyl, each of which is unsubstituted or substituted with one or more $R^{2A}$;
$R^{2A}$ is selected from the group consisting of hydrogen, $R^{2C}$-substituted or -unsubstituted $C_1$-$C_4$ alkyl, $C_1$-$C_4$ fluoroalkyl, halogen, —OH, —$(CH_2)_q$—$N(R^{2B})_2$, wherein q is 1 or zero, —$CH_2F$, —$CHF_2$, and —$CF_3$;
or wherein two $R^{2A}$ together with the carbon to which each is attached form a substituted or unsubstituted aziridinyl, azetidinyl, pyrrolidinyl, imidazolyl, piperidinyl, piperazinyl, morpholino;
$R^{2B}$ is hydrogen, $R^{2C}$-substituted or -unsubstituted $C_1$-$C_3$ alkyl, unsubstituted $C_3$-$C_6$ cycloalkyl; or unsubstituted $C_3$-$C_6$ heterocyclyl;
or wherein two $R^{2B}$ together form a substituted or unsubstituted heterocyclyl, wherein the heterocyclyl can be spiro, an unsubstituted aziridinyl, azetidinyl, pyrrolidinyl, imidazolyl, piperidinyl, piperazinyl, morpholino;
$R^{2C}$ is halogen, —OH, —$OCH_3$, or $C_3$-$C_5$ heterocyclyl;
each $R^3$ is independently hydrogen, halogen, —CN, $C_1$-$C_6$ alkyl, $C_1$-$C_6$ haloalkyl, $C_3$-$C_6$ cycloalkyl, $O(C_{1-6}$ alkyl), or —$O(C_1$-$C_6$ haloalkyl);
each $R^4$ and $R^5$ are independently hydrogen, halogen, —CN, —$NO_2$, $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, —$OR^6$, —$NR^{8A}R^9$, —$NR^8C(O)R^9$, —$NR*C(O)OR^6$, —$NR^8C(O)NR^{8A}R^{8B}$, —$NR^8SO_2R^9$, —$NR^8SO_2NR^{8A}R^{8B}$, —$NR^8S(O)(=NR^{8C})$ $R^9$, —$C(O)N(R^8)SO_2R^9$, —$C(O)NR^8R^9$, —$C(O)R^7$, —$C(O)OR^6$, —$SO_2R^9$, —$NR^8S(O)(=NR^{8C})R^9$, or —$SO_2NR^8R^9$; wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$,
wherein at least one of $R^4$ and $R^5$ is —$NR^{8A}R^9$, —$C(O)NR^8R^9$, —$NR^8C(O)R^9$, —$SO_2NR^8R^9$, or —$NR^8SO_2R^9$;
each $R^6$ and $R^7$ is independently hydrogen, $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$;

each $R^8$, $R^{8A}$, and $R^{8C}$ are independently hydrogen or $C_1$-$C_6$ alkyl;

each $R^{8B}$ is independently hydrogen, $C_1$-$C_6$ alkyl, $C_2$-$C_6$ alkenyl, $C_3$-$C_8$ cycloalkyl, $C_6$-$C_{10}$ aryl, or 3- to 12-membered heterocyclyl, each of which is unsubstituted or substituted with one or more $R^{10}$;

each $R^9$ is independently $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$;

or $R^8$ and $R^9$ together with the atom to which each is attached form a substituted or unsubstituted 5- or 6-member lactam ring, such as:

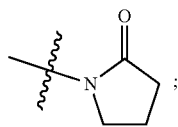 [SMILES: *N1CCCC1=O]

each $R^{10}$ is independently oxo, $C_1$-$C_6$ alkyl, $C_2$-$C_6$ alkenyl, $C_3$-$C_8$ cycloalkyl, $C_6$-$C_{10}$ aryl, 4- to 10-membered heteroaryl, 3- to 12-membered heterocyclyl, halogen, cyano, —C(O)H, —C(O)CH$_3$, —C(O)OH, —C(O)OCH$_3$, —C(O)NH$_2$, —OH, —O—CF$_3$, —CF$_3$, —CHF$_2$, —OCH$_3$, —OC(O)H, —OC(O)CH$_3$, —OC(O)NH$_2$, —SH, —S(O)H, —S(O)$_2$H, —S(O)(=NH)H, —S(O)$_2$NH$_2$, —NH$_2$, —NHC(O)H, —NHC(O)OH, —N(H)C(O)NH$_2$, —NHS(O)H, —NHS(O)$_2$NH$_2$, or —P(O)(CH$_3$)$_2$, wherein each $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 10-membered heteroaryl, 3- to 12-membered heterocyclyl is unsubstituted or substituted with one or more $R^{11}$;

or two $R^{10}$ together with the carbon to which each is attached forms a $C_3$-$C_8$ cycloalkyl; and each $R^{11}$ is independently $C_{1-6}$ alkyl, $C_3$-$C_6$ cycloalkyl, 4- to 6-membered-heteroaryl, phenyl, halogen, cyano, —SO$_2$CH$_3$, —O($C_{1-3}$ alkyl), —CH$_2$F, —CHF$_2$, or —(CH$_2$)$_f$—CF$_3$, wherein f is zero or 1.

Embodiment 1a. A compound having a formula (I):

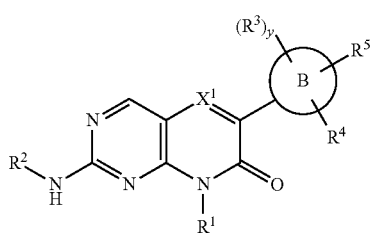

or a stereoisomer, tautomer, or pharmaceutically acceptable salt thereof, wherein $X^1$ is —$CR^x$ or —N, wherein $R^x$ is hydrogen, $C_1$-$C_4$ alkyl, cyclopropyl, or halogen;

Ring B is 5- to 7-membered aryl or 5- to 7-membered heteroaryl comprising at least one nitrogen atom;

y is 1, 2, 3, or 4;

$R^1$ is $C_1$-$C_4$ alkyl, $C_3$-$C_6$ cycloalkyl, or 3- to 14-membered heterocyclyl, each of which is unsubstituted or substituted with one or more substituents selected from the group consisting of —CH$_2$F, —CHF$_2$, —CF$_3$, halogen, $C_3$-$C_6$ cycloalkyl, and hydroxyl;

$R^2$ is $C_1$-$C_4$ alkyl, $C_3$-$C_6$ cycloalkyl, or 4- to 6-membered-heterocyclyl, each of which is unsubstituted or substituted with one or more $R^{2A}$;

$R^{2A}$ is selected from the group consisting of hydrogen, $C_1$-$C_4$ alkyl, $C_1$-$C_4$ fluoroalkyl, halogen, —OH, —N($R^{2B}$)$_2$—CH$_2$F, —CHF$_2$, and —CF$_3$;

$R^{2B}$ is hydrogen or $C_{1-3}$ alkyl;

each $R^3$ is independently hydrogen, halogen, —CN, $C_1$-$C_6$ alkyl, $C_1$-$C_6$ haloalkyl, $C_3$-$C_6$ cycloalkyl, O($C_{1-6}$ alkyl), or —O($C_1$-$C_6$ haloalkyl);

each $R^4$ and $R^5$ are independently hydrogen, halogen, —CN, —NO$_2$, $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, —OR$^6$, —NR$^{8A}$R$^9$, —NR$^8$C(O)R$^9$, —NR$^8$C(O)OR$^6$, —NR$^8$C(O)NR$^{8A}$R$^{8B}$, —NR$^8$SO$_2$R$^9$, —NR$^8$SO$_2$NR$^{8A}$R$^9$, —NR$^8$S(O)(=NR$^{8C}$)R$^9$, —C(O)N(R$^8$)SO$_2$R$^9$, —C(O)NR$^8$R$^9$, —C(O)R$^7$, —C(O)OR$^6$, —SO$_2$R$^9$, —NR$^8$S(O)(=NR$^{8C}$)R$^9$, or —SO$_2$NR$^8$R$^9$; wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$;

wherein at least one of $R^4$ and $R^5$ is —NR$^{8A}$R$^{8B}$, —NR$^8$C(O)R$^7$, —NR$^8$SO$_2$R$^9$—, —C(O)NR$^7$R$^8$, or —SO$_2$NR$^8$R$^9$;

each $R^6$ and $R^7$ is independently hydrogen, $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$;

each $R^8$, $R^{8A}$, and $R^{8C}$ are independently hydrogen or $C_1$-$C_6$ alkyl;

each $R^{8B}$ is independently hydrogen, $C_1$-$C_6$ alkyl, $C_2$-$C_6$ alkenyl, $C_3$-$C_8$ cycloalkyl, $C_6$-$C_{10}$ aryl, or 3- to 12-membered heterocyclyl, each of which is unsubstituted or substituted with one or more $R^{10}$;

each $R^9$ is independently $C_1$-$C_6$ alkyl, $C_2$-$C_6$ alkenyl, $C_3$-$C_8$ cycloalkyl, $C_6$-$C_{10}$ aryl, 5- to 14-membered heteroaryl and 3- to 12-membered heterocyclyl, each of which is unsubstituted or substituted with one or more $R^{10}$;

each $R^{10}$ is independently oxo, $C_1$-$C_6$ alkyl, $C_1$-$C_6$ haloalkyl, $C_2$-$C_6$ alkenyl, $C_3$-$C_8$ cycloalkyl, $C_6$-$C_{10}$ aryl, 4- to 10-membered heteroaryl, 3- to 12-membered heterocyclyl, halogen, cyano, —C(O)H, —C(O)CH$_3$, —C(O)OH, —C(O)OCH$_3$, —C(O)NH$_2$, —OH, —OCH$_3$, —OC(O)H, —OC(O)CH$_3$, —OC(O)NH$_2$, —CF$_3$, —CHF$_2$, —CH$_2$F, —C(CH$_3$)$_2$F, —C(CH$_3$)F$_2$, —SH, —S(O)H, —S(O)$_2$H, —S(O)(=NH)H, —S(O)$_2$NH$_2$, —NH$_2$, —NHC(O)H, —NHC(O)OH, —N(H)C(O)NH$_2$, —NHS(O)$_2$H, —NHS(O)$_2$NH$_2$, or —P(O)(CH$_3$)$_2$, wherein each $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $C_6$-$C_{10}$ aryl, 4- to 10-membered heteroaryl, 3- to 12-membered heterocyclyl is unsubstituted or substituted with one or more $R^{11}$; and each $R^{11}$ is independently $C_{1-6}$ alkyl, $C_3$-$C_6$ cycloalkyl, 4- to 6-membered-heteroaryl, phenyl, halogen, cyano, —O($C_{1-3}$ alkyl), —CH$_2$F, —CHF$_2$, or —CF$_3$.

Embodiment 2: A compound having a formula:

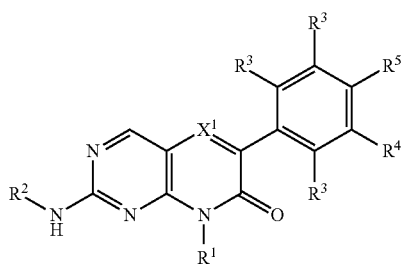

(Ia)

or a stereoisomer, tautomer, or pharmaceutically acceptable salt thereof, wherein:

$X^1$ is —$CR^x$ or —N, wherein $R^x$ is hydrogen, $C_1$-$C_4$ alkyl, cyclopropyl, or halogen;

$R^1$ is $C_1$-$C_4$ alkyl, $C_3$-$C_6$ cycloalkyl, or 3- to 14-membered heterocyclyl, each of which is unsubstituted or substituted with one or more substituents selected from the group consisting of —$CH_2F$, —$CHF_2$, —$CF_3$, halogen, $C_3$-$C_6$ cycloalkyl, and hydroxyl;

$R^2$ is $C_1$-$C_4$ alkyl, $C_3$-$C_6$ cycloalkyl, or 4- to 6-membered-heterocyclyl, each of which is unsubstituted or substituted with one or more $R^{2A}$;

$R^{2A}$ is selected from the group consisting of hydrogen, $C_1$-$C_4$ alkyl, $C_1$-$C_4$ fluoroalkyl, halogen, —OH, —$N(R^{2B})_2$—$CH_2F$, —$CHF_2$, and —$CF_3$;

$R^{2B}$ is hydrogen or $C_{1-3}$ alkyl;

each $R^3$ is independently hydrogen, halogen, —CN, $C_1$-$C_6$ alkyl, $C_1$-$C_6$ haloalkyl, $C_3$-$C_6$ cycloalkyl, $O(C_{1-6}$ alkyl), or —$O(C_1$-$C_6$ haloalkyl);

$R^4$ is hydrogen, halogen, —CN, —$NO_2$, $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, —$OR^6$, —$NR^{8A}R^{8B}$, —$NR^8C(O)R^7$, —$NR^8C(O)OR^6$, —$NR^8C(O)NR^{8A}R^{8B}$, —$NR^8SO_2R^9$, —$NR^8SO_2NR^{8A}R^{8B}$, —$NR^8S(O)(=NR^{8C})R^9$, —$C(O)N(R^8)SO_2R^9$, —$C(O)NR^{8A}R^{8B}$, —$C(O)R^7$, —$C(O)OR^6$, —$SO_2R^9$, —$NR^8S(O)(=NR^{8C})R^9$, or —$SO_2NR^{8A}R^{8B}$; wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$;

$R^5$ is —$NR^{8A}R^9$, —$NR^8C(O)R^9$, —$NR^8SO_2R^9$—, —$C(O)NR^8R^9$, or —$SO_2NR^8R^9$;

each $R^6$ and $R^7$ is independently hydrogen, $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$;

each $R^8$, $R^{8A}$, and $R^{8C}$ are independently hydrogen or $C_1$-$C_6$ alkyl;

each $R^{8B}$ is independently hydrogen, $C_1$-$C_6$ alkyl, $C_2$-$C_6$ alkenyl, $C_3$-$C_8$ cycloalkyl, $C_6$-$C_{10}$ aryl, or 3- to 12-membered heterocyclyl, each of which is unsubstituted or substituted with one or more $R^{10}$;

each $R^9$ is independently $C_1$-$C_6$ alkyl, $C_2$-$C_6$ alkenyl, $C_3$-$C_8$ cycloalkyl, $C_6$-$C_{10}$ aryl,5- to 14-membered heteroaryl and 3- to 12-membered heterocyclyl, each of which is unsubstituted or substituted with one or more $R^{10}$;

each $R^{10}$ is independently oxo, $C_1$-$C_6$ alkyl, $C_2$-$C_6$ alkenyl, $C_3$-$C_8$ cycloalkyl, $C_6$-$C_{10}$ aryl, 4- to 10-membered heteroaryl, 3- to 12-membered heterocyclyl, halogen, cyano, —C(O)H, —$C(O)CH_3$, —C(O)OH, —$C(O)OCH_3$, —$C(O)NH_2$, —OH, —$OCH_3$, —OC(O)H, —$OC(O)CH_3$, —OC(O)$NH_2$, —SH, —S(O)H, —$S(O)_2H$, —S(O)(=NH)H, —$S(O)_2NH_2$, —$NH_2$, —NHC(O)H, —NHC(O)OH, —N(H)C(O)$NH_2$, —$NHS(O)_2H$, —$NHS(O)_2NH_2$, or —$P(O)(CH_3)_2$, wherein each $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 10-membered heteroaryl, 3- to 12-membered heterocyclyl is unsubstituted or substituted with one or more $R^{11}$; and each $R^{11}$ is independently $C_{1-6}$ alkyl, $C_3$-$C_6$ cycloalkyl, 4- to 6-membered-heteroaryl, phenyl, halogen, cyano, —$O(C_{1-3}$ alkyl), —$CH_2F$, —$CHF_2$, or —$CF_3$.

Embodiment 3: A compound having a formula:

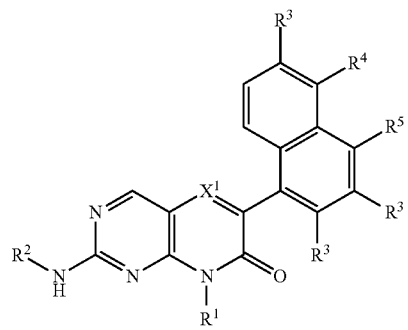

(Ib)

or a stereoisomer, tautomer, or pharmaceutically acceptable salt thereof, wherein:

$X^1$ is —$CR^x$ or —N, wherein $R^x$ is hydrogen, $C_1$-$C_4$ alkyl, cyclopropyl, or halogen;

$R^1$ is $C_1$-$C_4$ alkyl, $C_3$-$C_6$ cycloalkyl, or 3- to 14-membered heterocyclyl, each of which is unsubstituted or substituted with one or more substituents selected from the group consisting of —$CH_2F$, —$CHF_2$, —$CF_3$, halogen, $C_3$-$C_6$ cycloalkyl, and hydroxyl;

$R^2$ is $C_1$-$C_4$ alkyl, $C_3$-$C_6$ cycloalkyl, or 4- to 6-membered-heterocyclyl, each of which is unsubstituted or substituted with one or more $R^{2A}$;

$R^{2A}$ is selected from the group consisting of hydrogen, $C_1$-$C_4$ alkyl, $C_1$-$C_4$ fluoroalkyl, halogen, —OH, —$N(R^{2B})_2$—$CH_2F$, —$CHF_2$, and —$CF_3$;

$R^{2B}$ is hydrogen or $C_{1-3}$ alkyl;

each $R^3$ is independently hydrogen, halogen, —CN, $C_1$-$C_6$ alkyl, $C_1$-$C_6$ haloalkyl, $C_3$-$C_6$ cycloalkyl, $O(C_{1-6}$ alkyl), or —$O(C_1$-$C_6$ haloalkyl);

each $R^4$ and $R^5$ are independently hydrogen, halogen, —CN, —$NO_2$, $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, —$OR^6$, —$NR^{8A}R^9$, —$NR^8C(O)R^9$, —$NR^8C(O)OR^6$, —$NR^8C(O)NR^{8A}R^{8B}$, —$NR^8SO_2R^9$, —$NR^8SO_2NR^{8A}R^{8B}$, —$NR^8S(O)(=NR^{8C})R^9$, —$C(O)N(R^8)SO_2R^9$, —$C(O)NR^8R^9$, —$C(O)R^7$, —$C(O)OR^6$, —$SO_2R^9$, —$NR^8S(O)(=NR^{8C})R^9$, or —$SO_2NR^8R^9$; wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$;

wherein at least one of $R^4$ and $R^5$ is —$NR^{8A}R^9$, —$NR^8C(O)R^9$, —$NR^8SO_2R^9$—, —$C(O)NR^8R^9$, or —$SO_2NR^8R^9$;

each $R^6$ and $R^7$ is independently hydrogen, $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$;

each $R^8$, $R^{8A}$, and $R^{8C}$ are independently hydrogen or $C_1$-$C_6$ alkyl;

each $R^{8B}$ is independently hydrogen, $C_1$-$C_6$ alkyl, $C_2$-$C_6$ alkenyl, $C_3$-$C_8$ cycloalkyl, $C_6$-$C_{10}$ aryl, or 3- to 12-membered heterocyclyl, each of which is unsubstituted or substituted with one or more $R^{10}$;

each $R^9$ is independently $C_1$-$C_6$ alkyl, $C_2$-$C_6$ alkenyl, $C_3$-$C_8$ cycloalkyl, $C_6$-$C_{10}$ aryl, 5- to 14-membered heteroaryl and 3- to 12-membered heterocyclyl, each of which is unsubstituted or substituted with one or more $R^{10}$;

each $R^{10}$ is independently oxo, $C_1$-$C_6$ alkyl, $C_2$-$C_6$ alkenyl, $C_3$-$C_8$ cycloalkyl, $C_6$-$C_{10}$ aryl, 4- to 10-membered heteroaryl, 3- to 12-membered heterocyclyl, halogen, cyano, —C(O)H, —C(O)CH₃, —C(O)OH, —C(O)OCH₃, —C(O)NH₂, —OH, —OCH₃, —OC(O)H, —OC(O)CH₃, —OC(O)NH₂, —SH, —S(O)H, —S(O)₂H, —S(O)(=NH)H, —S(O)₂NH₂, —NH₂, —NHC(O)H, —NHC(O)OH, —N(H)C(O)NH₂, —NHS(O)₂H, —NHS(O)₂NH₂, or —P(O)(CH₃)₂, wherein each $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 10-membered heteroaryl, 3- to 12-membered heterocyclyl is unsubstituted or substituted with one or more $R^{11}$; and each $R^{11}$ is independently $C_{1-6}$ alkyl, $C_3$-$C_6$ cycloalkyl, 4- to 6-membered-heteroaryl, phenyl, halogen, cyano, —O($C_{1-3}$ alkyl), —CH₂F, —CHF₂, or —CF₃.

Embodiment 4: The compound of any one of embodiments 1-3 or a stereoisomer, tautomer, or pharmaceutically acceptable salt thereof, wherein $X^1$ is —CH or —N.

Embodiment 5: The compound of any one of embodiments 1-4 or a stereoisomer, tautomer, or pharmaceutically acceptable salt thereof, wherein $R^1$ is $C_1$-$C_4$ alkyl, $C_3$-$C_6$ cycloalkyl, or $C_3$-$C_6$ heterocyclyl, each of which is unsubstituted or substituted with one or more substituents selected from the group consisting of halogen, $C_3$-$C_6$ cycloalkyl, and hydroxyl.

Embodiment 6: The compound of any one of embodiments 1-5 or a stereoisomer, tautomer, or pharmaceutically acceptable salt thereof, wherein $R^1$ is $C_1$-$C_4$ alkyl, which is unsubstituted or substituted with one or more of fluoro, $C_3$-$C_6$ cycloalkyl, or hydroxyl.

Embodiment 7: The compound of any one of embodiments 1-6 or a stereoisomer, tautomer, or pharmaceutically acceptable salt thereof, wherein $R^1$ is $C_3$-$C_6$ cycloalkyl.

Embodiment 8: The compound of any one of embodiments 1-5 or a stereoisomer, tautomer, or pharmaceutically acceptable salt thereof, wherein $R^1$ is $C_3$-$C_6$ heterocyclyl.

Embodiment 9: The compound of any one of embodiments 1-8 or a stereoisomer, tautomer, or pharmaceutically acceptable salt thereof, wherein $R^1$ is selected from the group consisting of methyl, ethyl, isopropyl, cyclopropyl, cyclobutyl, cyclopentyl, —CH₂CHF₂, —CHCH₃CHF₂, —CH₂CF₃, —CHCH₃CF₃, —CH₂CHOHCH₂CH₃, and —CH₂-cyclopropyl.

Embodiment 10: The compound of any one of embodiments 1-8 or a stereoisomer, tautomer, or pharmaceutically acceptable salt thereof, wherein $R^1$ is oxetanyl or tetrahydrafuranyl.

Embodiment 11: The compound of any one of embodiments 1-10 or a stereoisomer, tautomer, or pharmaceutically acceptable salt thereof, wherein $R^2$ is selected from the group consisting of isopropyl, cyclohexyl, or piperidinyl, each of which is unsubstituted or substituted with one or more methyl, fluoro, hydroxyl, —NH₂, —NHCH₃, and —N(CH₃)₂.

Embodiment 12: The compound of any one of embodiments 1-11 or a stereoisomer, tautomer, or pharmaceutically acceptable salt thereof, wherein $R^2$ is selected from the group consisting of isopropyl, cyclohexyl substituted with hydroxyl, cyclohexyl substituted with —N(CH₂)₂, piperidinyl, piperidinyl substituted with fluoro, piperidinyl substituted with methyl, and piperidinyl substituted with methyl and fluoro.

Embodiment 13: The compound of any one of embodiments 1, 2 or 4-12 or a stereoisomer, tautomer, or pharmaceutically acceptable salt thereof, wherein the compound has formula (Ic):

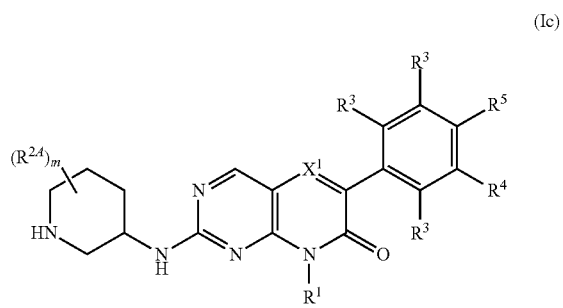

wherein:
m is 1, 2, 3, or 4.

Embodiment 14: The compound of any one of embodiments 1, 2 or 4-13 or a stereoisomer, tautomer, or pharmaceutically acceptable salt thereof, wherein $R^{2A}$ is —F and m is 1.

Embodiment 15: The compound of any one of embodiments 1, 2 or 4-13 or a stereoisomer, tautomer, or pharmaceutically acceptable salt thereof, wherein $R^{2A}$ is —CH₂F and m is 1.

Embodiment 16: The compound of any one of embodiments 1, 2 or 4-13 or a stereoisomer, tautomer, or pharmaceutically acceptable salt thereof, wherein $R^{2A}$ is —F and —CH₃ and m is 2.

Embodiment 17: The compound of any one of embodiments 1, 2 or 4-13 or a stereoisomer, tautomer, or pharmaceutically acceptable salt thereof, wherein $R^{2A}$ is —CH₂F and —CH₃ and m is 2.

Embodiment 18: The compound of any one of embodiments 1, 2 or 4-12 or a stereoisomer, tautomer, or pharmaceutically acceptable salt thereof, wherein the compound has formula (Id):

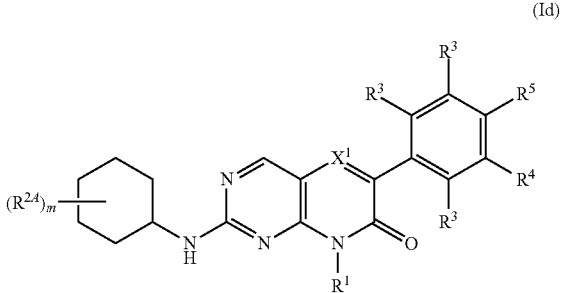

wherein:
m is 1, 2, 3, or 4.

Embodiment 19: The compound of any one of embodiments 1, 2 or 4-12 or 18, or a stereoisomer, tautomer, or pharmaceutically acceptable salt thereof, wherein $R^{2A}$ is —N(CH₃)₂ and m is 1.

Embodiment 20: The compound of any one of embodiments 1, 2 or 4-12 or 18-19, or a stereoisomer, tautomer, or pharmaceutically acceptable salt thereof, wherein $R^{2A}$ is —N(CH$_3$)$_2$ and —F and m is 2.

Embodiment 21: The compound of any one of embodiments 1-20, or a stereoisomer, tautomer, or pharmaceutically acceptable salt thereof, wherein each $R^3$ is independently hydrogen or halogen.

Embodiment 22: The compound of any one of embodiments 1-21, or a stereoisomer, tautomer, or pharmaceutically acceptable salt thereof, wherein at least one $R^3$ is halogen.

Embodiment 23: The compound of any one of embodiments 1-22 or a stereoisomer, tautomer, or pharmaceutically acceptable salt thereof, wherein at least one $R^3$ is fluoro.

Embodiment 24: The compound of any one of embodiments 1, 2 or 4-23 or a stereoisomer, tautomer, or pharmaceutically acceptable salt thereof, wherein each $R^3$ and $R^4$ are independently hydrogen or fluoro, and $R^5$ is —NR$^{8A}$R$^9$, —NR$^8$C(O)R$^9$, —NR$^8$SO$_2$R$^9$.

Embodiment 25: The compound of any one of embodiments 1-24 or a stereoisomer, tautomer, or pharmaceutically acceptable salt thereof, wherein at least one of $R^3$ or $R^4$ is fluoro.

Embodiment 26: The compound of embodiment 3 or a stereoisomer, tautomer, or pharmaceutically acceptable salt thereof, wherein each $R^3$ and $R^4$ is independently hydrogen or fluoro, and $R^4$ is —NR$^{8A}$R$^9$, —NR$^8$C(O)R$^9$, or —NR$^8$SO$_2$R$^9$.

Embodiment 27: The compound of any one of embodiments 3 or 26 or a stereoisomer, tautomer, or pharmaceutically acceptable salt thereof, wherein at least one $R^3$ is fluoro.

Embodiment 28: The compound of any one of embodiments 3 or 26-27 or a stereoisomer, tautomer, or pharmaceutically acceptable salt thereof, wherein $R^5$ is hydrogen or fluoro.

Embodiment 29: The compound of any one of embodiments 1, 2 or 4-25 or a stereoisomer, tautomer, or pharmaceutically acceptable salt thereof, wherein the compound has formula (Ie):

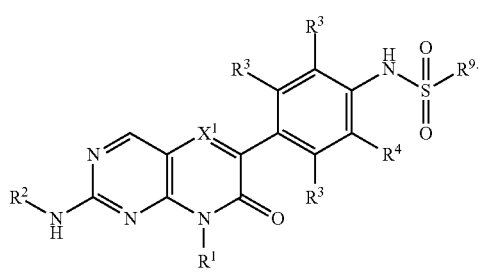

(Ie)

Embodiment 30: The compound of embodiment 29 or a stereoisomer, tautomer, or pharmaceutically acceptable salt thereof, wherein at least one of $R^3$ and $R^4$ is fluoro.

Embodiment 31: The compound of any one of embodiments 1, 2 or 4-25 or a stereoisomer, tautomer, or pharmaceutically acceptable salt thereof, wherein the compound has formula (If):

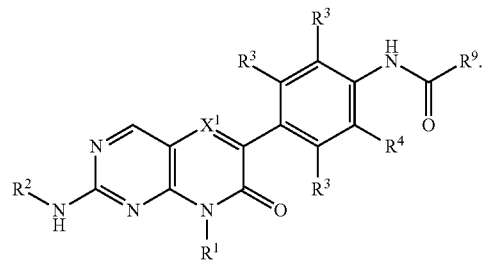

(If)

Embodiment 32: The compound of embodiment 31 or a stereoisomer, tautomer, or pharmaceutically acceptable salt thereof, wherein at least one of $R^3$ and $R^4$ is fluoro.

Embodiment 33: The compound of any one of embodiments 1, 2 or 4-25 or a stereoisomer, tautomer, or pharmaceutically acceptable salt thereof, wherein the compound has formula (Ig):

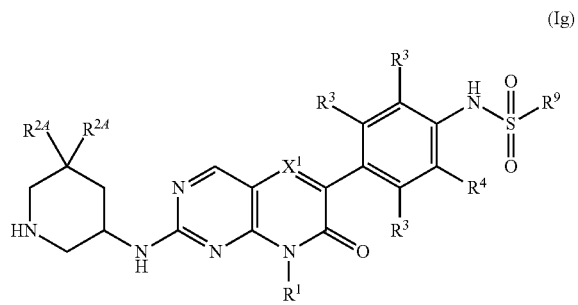

(Ig)

wherein:
each $R^{2A}$ is independently hydrogen, methyl, fluoro, or —CH$_2$F.

Embodiment 34: The compound of embodiment 33 or a stereoisomer, tautomer, or pharmaceutically acceptable salt thereof, wherein at least one of $R^3$ and $R^4$ is fluoro.

Embodiment 35: The compound of any one of embodiments 33-34 or a stereoisomer, tautomer, or pharmaceutically acceptable salt thereof, wherein $X^1$ is N.

Embodiment 36: The compound of any one of embodiments 33-34 or a stereoisomer, tautomer, or pharmaceutically acceptable salt thereof, wherein $X^1$ is CH.

Embodiment 37: The compound of any one of embodiments 1, 2 or 4-25 or a stereoisomer, tautomer, or pharmaceutically acceptable salt thereof, wherein the compound has formula (Ih):

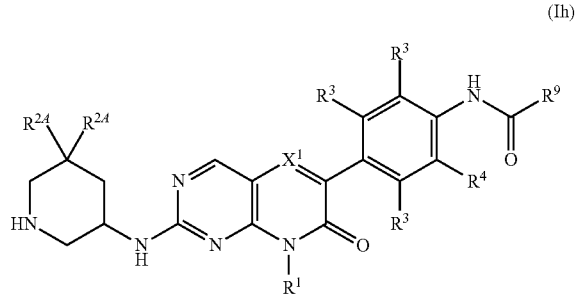

(Ih)

wherein:

each $R^{24}$ is independently hydrogen, methyl, fluoro, or —CH$_2$F.

Embodiment 38: The compound of embodiment 37 or a stereoisomer, tautomer, or pharmaceutically acceptable salt thereof, wherein at least one of $R^3$ and $R^4$ is fluoro.

Embodiment 39: The compound of any one of embodiments 37-38 or a stereoisomer, tautomer, or pharmaceutically acceptable salt thereof, wherein $X^1$ is N.

Embodiment 40: The compound of any one of embodiments 37-38 or a stereoisomer, tautomer, or pharmaceutically acceptable salt thereof, wherein $X^1$ is CH.

Embodiment 41: The compound of any one of embodiments 1, 2 or 4-25 or a stereoisomer, tautomer, or pharmaceutically acceptable salt thereof, wherein the compound has the formula (Ii) or (Ij):

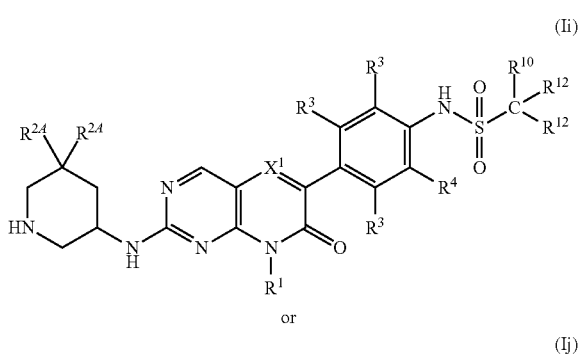

wherein:

each $R^{24}$ is independently hydrogen, methyl, fluoro, or —CH$_2$F;

$R^{10}$ is substituted phenyl or substituted C$_{1-3}$ alkyl; and $R^{12}$ is hydrogen, halogen, or C$_{1-3}$ alkyl or wherein both $R^{12}$ together form a cyclopropanyl, which may be unsubstituted or substituted with methyl or fluoro.

Embodiment 42: The compound of embodiment 41 or a stereoisomer, tautomer, or pharmaceutically acceptable salt thereof, wherein at least one of $R^3$ and $R^4$ is fluoro.

Embodiment 43: The compound of any one of embodiments 41-42 or a stereoisomer, tautomer, or pharmaceutically acceptable salt thereof, wherein $X^1$ is N.

Embodiment 44: The compound of any one of embodiments 41-42 or a stereoisomer, tautomer, or pharmaceutically acceptable salt thereof, wherein $X^1$ is CH.

Embodiment 45: The compound of any one of embodiments 1, 2 or 4-25 or a stereoisomer, tautomer, or pharmaceutically acceptable salt thereof, wherein the compound has formula (Ik):

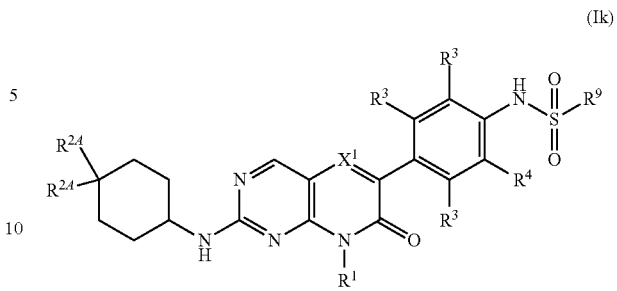

wherein:

each $R^{24}$ is independently hydrogen, hydroxyl, or —N(CH$_3$)$_2$.

Embodiment 46: The compound of embodiment 45 or a stereoisomer, tautomer, or pharmaceutically acceptable salt thereof, wherein at least one of $R^3$ and $R^4$ is fluoro.

Embodiment 47: The compound of any one of embodiments 45-46 or a stereoisomer, tautomer, or pharmaceutically acceptable salt thereof, wherein $X^1$ is N.

Embodiment 48: The compound of any one of embodiments 45-46 or a stereoisomer, tautomer, or pharmaceutically acceptable salt thereof, wherein $X^1$ is CH.

Embodiment 49: The compound of any one of embodiments 1, 2 or 4-25 or a stereoisomer, tautomer, or pharmaceutically acceptable salt thereof, wherein the compound has formula (Il):

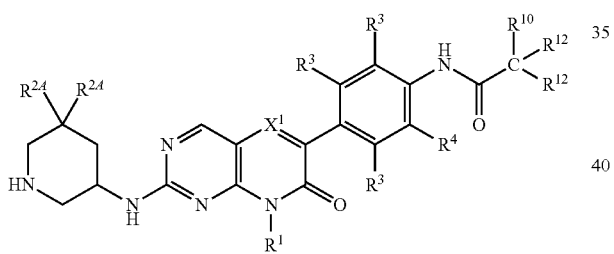

wherein:

each $R^{24}$ is independently hydrogen, hydroxyl, or —N(CH$_3$)$_2$.

Embodiment 50: The compound of embodiment 49 or a stereoisomer, tautomer, or pharmaceutically acceptable salt thereof, wherein at least one of $R^3$ and $R^4$ is fluoro.

Embodiment 51: The compound of any one of embodiments 49-50 or a stereoisomer, tautomer, or pharmaceutically acceptable salt thereof, wherein $X^1$ is N.

Embodiment 52: The compound of any one of embodiments 49-50 or a stereoisomer, tautomer, or pharmaceutically acceptable salt thereof, wherein $X^1$ is CH.

Embodiment 53: The compound of any one of embodiments 1, 2 or 4-25 or a stereoisomer, tautomer, or pharmaceutically acceptable salt thereof, wherein the compound has formula (Im):

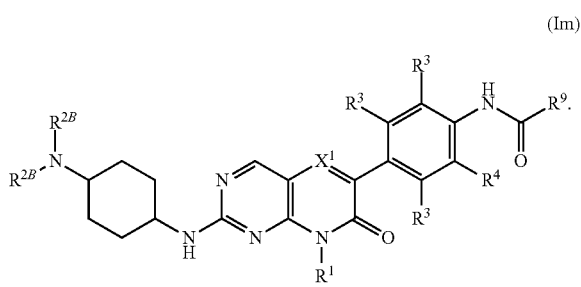

(Im)

Embodiment 54: The compound of embodiment 53 or a stereoisomer, tautomer, or pharmaceutically acceptable salt thereof, wherein at least one of $R^3$ and $R^4$ is fluoro.

Embodiment 55: The compound of any one of embodiments 53-54 or a stereoisomer, tautomer, or pharmaceutically acceptable salt thereof, wherein $X^1$ is N.

Embodiment 56: The compound of any one of embodiments 53-54 or a stereoisomer, tautomer, or pharmaceutically acceptable salt thereof, wherein $X^1$ is CH.

Embodiment 57: The compound of any one of embodiments 53-56 or a stereoisomer, tautomer, or pharmaceutically acceptable salt thereof, wherein each $R^{2B}$ is $CH_3$.

Embodiment 58: The compound of any one of embodiments 1, 2 or 4-25 or a stereoisomer, tautomer, or pharmaceutically acceptable salt thereof, wherein the compound has the formula (In) or (Io)):

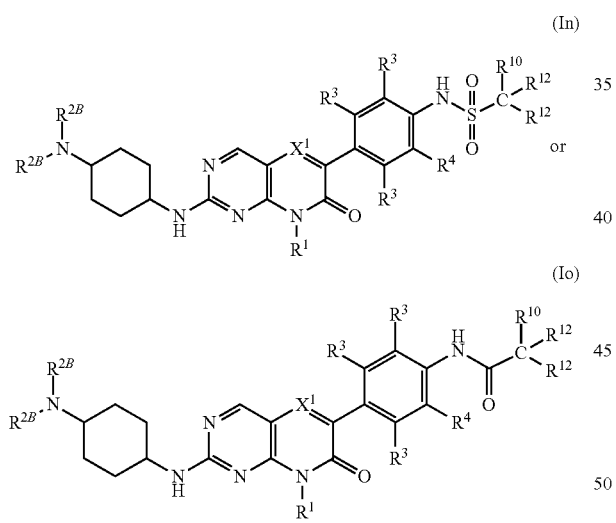

wherein:
$R^{10}$ is substituted phenyl or substituted $C_{1-3}$ alkyl; and
$R^{12}$ is hydrogen, halogen, or $C_{1-3}$ alkyl or wherein both $R^{12}$ together form a cyclopropanyl, which may be unsubstituted or substituted with methyl or fluoro.

Embodiment 59: The compound of embodiment 58 or a stereoisomer, tautomer, or pharmaceutically acceptable salt thereof, wherein at least one of $R^3$ and $R^4$ is fluoro.

Embodiment 60: The compound of any one of embodiments 58-59 or a stereoisomer, tautomer, or pharmaceutically acceptable salt thereof, wherein $X^1$ is N.

Embodiment 61: The compound of any one of embodiments 58-59 or a stereoisomer, tautomer, or pharmaceutically acceptable salt thereof, wherein $X^1$ is CH.

Embodiment 62: The compound of any one of embodiments 58-61 or a stereoisomer, tautomer, or pharmaceutically acceptable salt thereof, wherein each $R^{2B}$ is $CH_3$.

Embodiment 63: The compound of embodiment 1, wherein Ring B is phenyl or a 6-membered heteroaryl comprising at least one nitrogen atom.

Embodiment 64: The compound of embodiment 1 or 63, wherein Ring B is phenyl.

Embodiment 65: The compound of embodiment 1 or 63, wherein Ring B is a 6-membered heteroaryl comprising at least one nitrogen atom.

Embodiment 66: The compound of embodiment 65, wherein Ring B is pyridinyl, pyrazinyl, or pyradazinyl.

Embodiment 67: The compound of embodiment 1 or 63, wherein Ring B is:

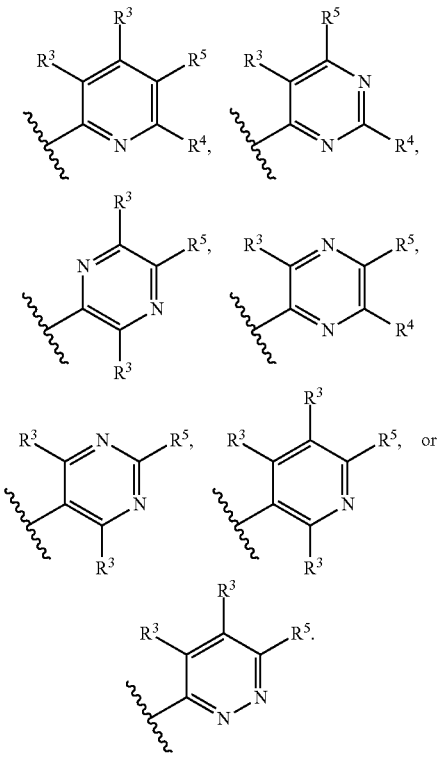

Embodiment 68: The compound of any one of embodiments 65-67, wherein $R^1$, $R^2$, $R^3$, $R^4$, and $R^5$ are as provided in embodiments 1, 2 or 4-25.

Embodiment 69: A compound or a stereoisomer, tautomer, or pharmaceutically acceptable salt thereof, selected from the compounds of Table 1 and Table 2.

Embodiment 69a: A compound or a stereoisomer, tautomer, or pharmaceutically acceptable salt thereof, selected from the group consisting of:
(S)—N-(2,3-difluoro-4-(8-methyl-7-oxo-2-(piperidin-3-ylamino)-7,8-dihydropyrido[2,3-d]pyrimidin-6-yl)phenyl)-1-phenylmethanesulfonamide;
N-(2,3-difluoro-4-(2-(((3S,5S)-5-fluoropiperidin-3-yl)amino)-8-methyl-7-oxo-7,8-dihydropyrido[2,3-d]pyrimidin-6-yl)phenyl)-1-phenylmethanesulfonamide;
(S)—N-(4-(8-ethyl-7-oxo-2-(piperidin-3-ylamino)-7,8-dihydropyrido[2,3-d]pyrimidin-6-yl)-2,3-difluorophenyl)-1-phenylmethanesulfonamide;
(S)-3,3,3-trifluoro-N-(2-fluoro-5-(8-methyl-7-oxo-2-(piperidin-3-ylamino)-7,8-dihydropyrido[2,3-d]pyrimidin-6-yl)naphthalen-1-yl)propane-1-sulfonamide;

(S)—N-(2-fluoro-5-(8-methyl-7-oxo-2-(piperidin-3-ylamino)-7,8-dihydropyrido[2,3-d]pyrimidin-6-yl)naphthalen-1-yl)-1-phenylmethanesulfonamide;

(S)—N-(2-fluoro-4-(8-methyl-7-oxo-2-(piperidin-3-ylamino)-7,8-dihydropyrido[2,3-d]pyrimidin-6-yl)naphthalen-1-yl)-1-phenylmethanesulfonamide;

(S)-3,3,3-trifluoro-N-(2-fluoro-4-(8-methyl-7-oxo-2-(piperidin-3-ylamino)-7,8-dihydropyrido[2,3-d]pyrimidin-6-yl)naphthalen-1-yl)propane-1-sulfonamide;

(S)—N-(2-Fluoro-5-(8-methyl-7-oxo-2-(piperidin-3-ylamino)-7,8-dihydropyrido[2,3-d]pyrimidin-6-yl)naphthalen-1-yl)propane-1-sulfonamide;

N-(2,3-difluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-phenylmethanesulfonamide;

N-(4-(8-cyclopropyl-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide;

N-(4-(8-(2,2-difluoroethyl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide;

N-(4-(8-ethyl-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide;

N-(4-(8-ethyl-2-(((3S,5S)-5-fluoropiperidin-3-yl)amino)-7-oxo-7,8-dihydropyrido[2,3-d]pyrimidin-6-yl)-2,3-difluorophenyl)propane-1-sulfonamide;

N-(4-(8-ethyl-2-(((3S,5S)-5-fluoropiperidin-3-yl)amino)-7-oxo-7,8-dihydropyrido[2,3-d]pyrimidin-6-yl)-2,3-difluorophenyl)-3,3,3-trifluoropropane-1-sulfonamide;

N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-phenylmethanesulfonamide;

(S)—N-(2-fluoro-3-(8-isopropyl-7-oxo-2-(piperidin-3-ylamino)-7,8-dihydropyrido[2,3-d]pyrimidin-6-yl)phenyl)-1-phenylmethanesulfonamide;

(S)—N-(2-fluoro-5-(8-isopropyl-7-oxo-2-(piperidin-3-ylamino)-7,8-dihydropyrido[2,3-d]pyrimidin-6-yl)phenyl)-1-phenylmethanesulfonamide hydrochloride;

N-(4-(8-cyclopentyl-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide;

(S)—N-(2,6-difluoro-3-(8-isopropyl-7-oxo-2-(piperidin-3-ylamino)-7,8-dihydropyrido[2,3-d]pyrimidin-6-yl)phenyl)-1-phenylmethanesulfonamide;

1-phenyl-N-(2,3,6-trifluoro-4-(8-isopropyl-2-(isopropylamino)-7-oxo-7,8-dihydropyrido[2,3-d]pyrimidin-6-yl)phenyl)methanesulfonamide;

3,3,3-trifluoro-N-(2,3,6-trifluoro-4-(8-isopropyl-2-(isopropylamino)-7-oxo-7,8-dihydropyrido[2,3-d]pyrimidin-6-yl)phenyl)propane-1-sulfonamide;

1-phenyl-N-(2,3,6-trifluoro-4-(2-(((1r,4r)-4-hydroxycyclohexyl)amino)-8-isopropyl-7-oxo-7,8-dihydropyrido[2,3-d]pyrimidin-6-yl)phenyl)methanesulfonamide;

N-(4-(8-(1,1-difluoropropan-2-yl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide;

N-(4-(8-(1,1-difluoropropan-2-yl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-1-phenylmethanesulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide;

1-phenyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

1-phenyl-N-(2,3,6-trifluoro-4-(2-(((3S,5S)-5-fluoro-5-methylpiperidin-3-yl)amino)-8-isopropyl-7-oxo-7,8-dihydropyrido[2,3-d]pyrimidin-6-yl)phenyl)methanesulfonamide;

N-(4-(8-cyclobutyl-2-(((3S,5S)-5-fluoropiperidin-3-yl)amino)-7-oxo-7,8-dihydropyrido[2,3-d]pyrimidin-6-yl)-2,3,6-trifluorophenyl)-1-phenylmethanesulfonamide;

1-(4-cyanophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

1-(3-cyanophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

1-(3-methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide hydrochloride;

1-(2-cyanophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-3,3-difluorobutane-1-sulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)propane-1-sulfonamide;

1-phenyl-N-(2,3,6-trifluoro-4-(2-(((3S,5S)-5-fluoropiperidin-3-yl)amino)-7-oxo-8-(tetrahydrofuran-3-yl)-7,8-dihydropyrido[2,3-d]pyrimidin-6-yl)phenyl)methanesulfonamide;

1-phenyl-N-(2,3,6-trifluoro-4-(2-(((3S,5S)-5-fluoropiperidin-3-yl)amino)-7-oxo-8-(tetrahydrofuran-3-yl)-7,8-dihydropyrido[2,3-d]pyrimidin-6-yl)phenyl)methanesulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2,2-difluorobutane-1-sulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)cyclopropanecarboxamide;

1-(1-methyl-1H-pyrazol-3-yl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(3-(trifluoromethyl)phenyl)methanesulfonamide;

N-(2,3-difluoro-4-(2-(((3S,5S)-5-fluoropiperidin-3-yl)amino)-7-oxo-8-(2,2,2-trifluoroethyl)-7,8-dihydropyrido[2,3-d]pyrimidin-6-yl)phenyl)-1-phenylmethanesulfonamide;

8-ethyl-6-(4-(3-ethyl-2-oxopyrrolidin-1-yl)-2,3-difluorophenyl)-2-(((3S,5S)-5-fluoropiperidin-3-yl)amino)pyrido[2,3-d]pyrimidin-7(8H)-one;

N-(2,3-difluoro-4-(2-(((3S,5S)-5-fluoropiperidin-3-yl)amino)-7-oxo-8-(1,1,1-trifluoropropan-2-yl)-7,8-dihydropyrido[2,3-d]pyrimidin-6-yl)phenyl)-1-phenylmethanesulfonamide trifluoroacetate salt;

(S)—N-(6-fluoro-2,3-dimethyl-4-((3-(2-(piperidin-3-ylamino)pyrimidin-4-yl)pyridin-2-yl)oxy)phenyl)-1-phenylmethanesulfonamide;

N-(2-fluoro-4-(2-(((3S,5S)-5-fluoropiperidin-3-yl)amino)-8-isopropyl-7-oxo-7,8-dihydropteridin-6-yl)phenyl)-1-phenylmethanesulfonamide;

N-(2,6-difluoro-4-(2-(((3S,5S)-5-fluoropiperidin-3-yl)amino)-8-isopropyl-7-oxo-7,8-dihydropteridin-6-yl)phenyl)-1-phenylmethanesulfonamide;

N-(2,6-difluoro-4-(2-(((3S,5S)-5-fluoropiperidin-3-yl)amino)-8-isopropyl-7-oxo-7,8-dihydropteridin-6-yl)phenyl)-3,3,3-trifluoropropane-1-sulfonamide;

1-(4-cyanophenyl)-N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)methanesulfonamide;

N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(1-fluorocyclopropyl)methanesulfonamide;

N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(pyridin-2-yl)methanesulfonamide;

N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(4-(trifluoromethyl)phenyl)methanesulfonamide hydrochloride;

1-(2,6-difluorophenyl)-N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)methanesulfonamide;

N-(4-(8-(cyclopropylmethyl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide trifluoroacetate salt;

N-(2,3-difluoro-4-(8-(2-fluoroethyl)-2-(((3S,5S)-5-fluoropiperidin-3-yl)amino)-7-oxo-7,8-dihydropyrido[2,3-d]pyrimidin-6-yl)phenyl)-1-phenylmethanesulfonamide;

N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)benzenesulfonamide;

N-(4-(8-(3,3-difluorocyclobutyl)-2-(((3S,5S)-5-fluoropiperidin-3-yl)amino)-7-oxo-7,8-dihydropyrido[2,3-d]pyrimidin-6-yl)-2,3,6-trifluorophenyl)-1-phenylmethanesulfonamide hydrochloride;

N-(4-(2-(((1r,4r)-4-aminocyclohexyl)amino)-8-isopropyl-7-oxo-7,8-dihydropyrido[2,3-d]pyrimidin-6-yl)-2,3,6-trifluorophenyl)-1-phenylmethanesulfonamide;

1-(4-methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-3-methylbutanamide;

N-(4-(2-((4-(dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide;

N-(4-(2-((4-(dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide;

2-chloro-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)benzenesulfonamide hydrochloride;

2-cyclobutyl-N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)acetamide;

(1R,2R)—N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide hydrochloride;

N-(2-fluoro-4-(2-(((3S,5S)-5-fluoro-5-methylpiperidin-3-yl)amino)-8-isopropyl-7-oxo-7,8-dihydropteridin-6-yl)phenyl)-1-phenylmethanesulfonamide;

N-(2-fluoro-4-(2-(((3S,5R)-5-(fluoromethyl)piperidin-3-yl)amino)-8-isopropyl-7-oxo-7,8-dihydropteridin-6-yl)phenyl)-1-phenylmethanesulfonamide;

N-(4-(2-(((1r,4r)-4-(dimethylamino)cyclohexyl)amino)-8-isopropyl-7-oxo-7,8-dihydropteridin-6-yl)-2-fluorophenyl)-3,3-difluorobutane-1-sulfonamide;

N-(4-(2-(((1r,4r)-4-(dimethylamino)cyclohexyl)amino)-8-isopropyl-7-oxo-7,8-dihydropteridin-6-yl)-2-fluorophenyl)-3,3,3-trifluoropropane-1-sulfonamide;

N-(4-(2-(((1r,4r)-4-(dimethylamino)cyclohexyl)amino)-8-isopropyl-7-oxo-7,8-dihydropteridin-6-yl)-2-fluorophenyl)-1-phenylmethanesulfonamide;

N-(5-(8-ethyl-2-(((3S,5S)-5-fluoropiperidin-3-yl)amino)-7-oxo-7,8-dihydropyrido[2,3-d]pyrimidin-6-yl)-1-methyl-1H-pyrazol-3-yl)-1-phenylmethanesulfonamide;

1-(5-(8-ethyl-2-(((3S,5S)-5-fluoropiperidin-3-yl)amino)-7-oxo-7,8-dihydropyrido[2,3-d]pyrimidin-6-yl)-1-methyl-1H-pyrazol-3-yl)-3-(3-(trifluoromethyl)phenyl)urea;

N-(4-(2-(((1,4-trans)-4-(dimethylamino)cyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide;

N-(4-(2-(((1,4-trans)-4-(dimethylamino)cyclohexyl)amino)-8-isopropyl-7-oxo-7,8-dihydropyrido[2,3-d]pyrimidin-6-yl)-2,5-difluorophenyl)-3,3,3-trifluoropropane-1-sulfonamide formate;

N-[2-fluoro-4-[2-[[(3S,5S)-5-fluoro-3-piperidyl]amino]-8-isopropyl-7-oxo-pteridin-6-yl]-6-methyl-phenyl]-1-phenyl-methanesulfonamide;

3,3,3-trifluoro-N-[2-fluoro-4-[2-[[(3S,5S)-5-fluoro-3-piperidyl]amino]-8-isopropyl-7-oxo-pteridin-6-yl]phenyl]propane-1-sulfonamide;

N-[2-fluoro-4-[2-[[(3S,5S)-5-fluoro-3-piperidyl]amino]-8-isopropyl-7-oxo-pteridin-6-yl]phenyl]benzenesulfonamide;

2-chloro-N-[2-fluoro-4-[2-[[(3S,5S)-5-fluoro-3-piperidyl]amino]-8-isopropyl-7-oxo-pteridin-6-yl]phenyl]benzenesulfonamide;

3,3,3-trifluoro-N-[2-fluoro-4-[2-[[(3S,5R)-5-(fluoromethyl)-3-piperidyl]amino]-8-isopropyl-7-oxo-pteridin-6-yl]phenyl]propane-1-sulfonamide;

3,3-difluoro-N-[2-fluoro-4-[2-[[(3S,5R)-5-(fluoromethyl)-3-piperidyl]amino]-8-isopropyl-7-oxo-pteridin-6-yl]phenyl]butane-1-sulfonamide;

3,3-difluoro-N-[2-fluoro-4-[2-[[(3S,5R)-5-(fluoromethyl)-3-piperidyl]amino]-8-isopropyl-7-oxo-pteridin-6-yl]phenyl]propane-1-sulfonamide;

N-[2-fluoro-4-[2-[[(3S,5R)-5-(fluoromethyl)-3-piperidyl]amino]-8-isopropyl-7-oxo-pteridin-6-yl]phenyl]propane-1-sulfonamide;

1-(2-cyanophenyl)-N-[2-fluoro-4-[2-[[(3S,5S)-5-fluoro-3-piperidyl]amino]-8-isopropyl-7-oxo-pteridin-6-yl]phenyl]methanesulfonamide;

1-(4-cyanophenyl)-N-[2-fluoro-4-[2-[[(3S,5S)-5-fluoro-3-piperidyl]amino]-8-isopropyl-7-oxo-pteridin-6-yl]phenyl]methanesulfonamide;

N-[2-fluoro-4-[2-[[(3S,5S)-5-fluoro-3-piperidyl]amino]-8-isopropyl-7-oxo-pteridin-6-yl]phenyl]propane-1-sulfonamide;

2,2-difluoro-N-[2-fluoro-4-[2-[[(3S,5S)-5-fluoro-3-piperidyl]amino]-8-isopropyl-7-oxo-pteridin-6-yl]phenyl]butane-1-sulfonamide;

3,3-difluoro-N-[2-fluoro-4-[2-[[(3S,5S)-5-fluoro-3-piperidyl]amino]-8-isopropyl-7-oxo-pteridin-6-yl]phenyl]butane-1-sulfonamide;

3,3,3-trifluoro-N-(5-(2-(((3S,5S)-5-fluoropiperidin-3-yl)amino)-8-isopropyl-7-oxo-7,8-dihydropyrido[2,3-d]pyrimidin-6-yl)-1-methyl-1H-pyrazol-3-yl)propane-1-sulfonamide;

1-(2-fluorophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

1-(2-fluorophenyl)-N-(2,3,6-trifluoro-4-(2-((5-hydroxypiperidin-3-yl)amino)-8-isopropyl-7-oxo-7,8-dihydropyrido[2,3-d]pyrimidin-6-yl)phenyl)methanesulfonamide cis racemic mixture;

1-(2-fluorophenyl)-N-(2,3,6-trifluoro-4-(2-((5-hydroxypiperidin-3-yl)amino)-8-isopropyl-7-oxo-7,8-dihydropyrido[2,3-d]pyrimidin-6-yl)phenyl)methanesulfonamide trans racemic mixture;

1-(2-fluorophenyl)-N-(2,3,6-trifluoro-4-(2-(((3R,5S)-5-hydroxypiperidin-3-yl)amino)-8-isopropyl-7-oxo-7,8-dihydropyrido[2,3-d]pyrimidin-6-yl)phenyl)methanesulfonamide;

1-(2-fluorophenyl)-N-(2,3,6-trifluoro-4-(2-(((3S,5R)-5-hydroxypiperidin-3-yl)amino)-8-isopropyl-7-oxo-7,8-dihydropyrido[2,3-d]pyrimidin-6-yl)phenyl)methanesulfonamide;

N-(2-fluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(2-fluorophenyl)methanesulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide;

3,3,3-trifluoro-N-(2-fluoro-4-(2-(((3S,5S)-5-fluoropiperidin-3-yl)amino)-8-isopropyl-7-oxo-7,8-dihydropyrido[2,3-d]pyrimidin-6-yl)phenyl)propane-1-sulfonamide;

1-(2-fluorophenyl)-N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)methanesulfonamide;

N-(6-(2-(((1r,4r)-4-(dimethylamino)cyclohexyl)amino)-8-isopropyl-7-oxo-7,8-dihydropyrido[2,3-d]pyrimidin-6-yl)pyridin-3-yl)-1-(2-fluorophenyl)methanesulfonamide; and 1-(2-fluorophenyl)-N-(6-(2-(((3S,5S)-5-fluoropiperidin-3-yl)amino)-8-isopropyl-7-oxo-7,8-dihydropyrido[2,3-d]pyrimidin-6-yl)pyridin-3-yl)methanesulfonamide.

Embodiment 70: A compound or a stereoisomer, tautomer, or pharmaceutically acceptable salt thereof, selected from the group consisting of:

1-(2-cyano-4-methylphenyl)-N-(2-fluoro-4-(2-(((3S,5S)-5-fluoropiperidin-3-yl)amino)-8-isopropyl-7-oxo-7,8-dihydropteridin-6-yl)phenyl)methanesulfonamide;

1-(2-cyano-4-methylphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

1-(2-cyano-4-methylphenyl)-N-(2,3,6-trifluoro-4-(2-(((3S,5S)-5-fluoro-5-methylpiperidin-3-yl)amino)-8-isopropyl-7-oxo-7,8-dihydropyrido[2,3-d]pyrimidin-6-yl)phenyl)methanesulfonamide;

(1R,2S)—N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide;

(1S,2R)—N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide;

2-(((1r,4r)-4-(dimethylamino)cyclohexyl)amino)-8-isopropyl-6-(2,3,5-trifluoro-4-(((R)-3,3,3-trifluoro-2-hydroxypropyl)amino)phenyl)pyrido[2,3-d]pyrimidin-7(8H)-one;

2-(((1r,4r)-4-(dimethylamino)cyclohexyl)amino)-8-isopropyl-6-(2,3,5-trifluoro-4-(((S)-3,3,3-trifluoro-2-hydroxypropyl)amino)phenyl)pyrido[2,3-d]pyrimidin-7(8H)-one;

3-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)butanamide;

(1R,2S)-2-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)cyclopropane-1-carboxamide;

(1S,2R)-2-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)cyclopropane-1-carboxamide;

(1R,2R)-2-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)cyclopropane-1-carboxamide;

(1S,2S)-2-methyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)cyclopropane-1-carboxamide;

2-(((3S,5S)-5-fluoropiperidin-3-yl)amino)-8-isopropyl-6-(2,3,5-trifluoro-4-(((S)-3,3,3-trifluoro-2-hydroxypropyl)amino)phenyl)pyrido[2,3-d]pyrimidin-7(8H)-one;

2-(((3S,5S)-5-fluoropiperidin-3-yl)amino)-8-isopropyl-6-(2,3,5-trifluoro-4-(((R)-3,3,3-trifluoro-2-hydroxypropyl)amino)phenyl)pyrido[2,3-d]pyrimidin-7(8H)-one;

2-chloro-N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)benzenesulfonamide;

1-(2-methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

N-(2,3-difluoro-4-(2-(((3S,5S)-5-fluoropiperidin-3-yl) amino)-8-((R)-1-fluoropropan-2-yl)-7-oxo-7,8-dihydropyrido[2,3-d]pyrimidin-6-yl)phenyl)-1-phenylmethanesulfonamide;

N-(2,3-difluoro-4-(2-(((3S,5S)-5-fluoropiperidin-3-yl) amino)-8-((S)-1-fluoropropan-2-yl)-7-oxo-7,8-dihydropyrido[2,3-d]pyrimidin-6-yl)phenyl)-1-phenylmethanesulfonamide N-(4-(2-((4-(dimethylamino)-3-fluorocyclohexyl)amino)-8-isopropyl-7-oxo-7,8-dihydropyrido[2,3-d]pyrimidin-6-yl)-2,3,6-trifluorophenyl)-1-phenylmethanesulfonamide;

N-(2-fluoro-4-(2-(((3S,5R)-5-(fluoromethyl)-5-methylpiperidin-3-yl)amino)-8-isopropyl-7-oxo-7,8-dihydropteridin-6-yl)phenyl)-1-phenylmethanesulfonamide;

N-(2-fluoro-4-(2-(((3S,5S)-5-(fluoromethyl)-5-methylpiperidin-3-yl)amino)-8-isopropyl-7-oxo-7,8-dihydropteridin-6-yl)phenyl)-1-phenylmethanesulfonamide;

(S)—N-(2-fluoro-4-(2-(((3S,5R)-5-(fluoromethyl)piperidin-3-yl)amino)-8-isopropyl-7-oxo-7,8-dihydropteridin-6-yl)phenyl)-1-phenylethane-1-sulfonamide;

(R)—N-(2-fluoro-4-(2-(((3S,5R)-5-(fluoromethyl)piperidin-3-yl)amino)-8-isopropyl-7-oxo-7,8-dihydropteridin-6-yl)phenyl)-1-phenylethane-1-sulfonamide;

(R)—N-(2-fluoro-4-(2-(((3S,5S)-5-fluoropiperidin-3-yl)amino)-8-isopropyl-7-oxo-7,8-dihydropteridin-6-yl)phenyl)-1-phenylethane-1-sulfonamide;

(S)—N-(2-fluoro-4-(2-(((3S,5S)-5-fluoropiperidin-3-yl)amino)-8-isopropyl-7-oxo-7,8-dihydropteridin-6-yl)phenyl)-1-phenylethane-1-sulfonamide;

N-(2-fluoro-4-(2-(((3S)-5-(fluoromethyl)-5-methylpiperidin-3-yl)amino)-8-isopropyl-7-oxo-7,8-dihydropteridin-6-yl)phenyl)-1-phenylethane-1-sulfonamide;

N-(4-(2-(((1r,4r)-4-(dimethylamino)cyclohexyl)amino)-8-isopropyl-7-oxo-7,8-dihydropteridin-6-yl)-2-fluorophenyl)-2,2-difluorobutane-1-sulfonamide;

N-(4-(2-(((1r,4r)-4-(dimethylamino)cyclohexyl)amino)-8-isopropyl-7-oxo-7,8-dihydropteridin-6-yl)-2-fluorophenyl)-3,3-difluorobutane-1-sulfonamide;

1-phenyl-N-(2,3,6-trifluoro-4-(2-(((3S,5S)-5-fluoropiperidin-3-yl)amino)-8-(oxetan-3-yl)-7-oxo-7,8-dihydropyrido[2,3-d]pyrimidin-6-yl)phenyl)methanesulfonamide;

N-(2,6-difluoro-4-(2-(((3S,5S)-5-fluoropiperidin-3-yl) amino)-8-isopropyl-7-oxo-7,8-dihydropteridin-6-yl)phenyl)benzenesulfonamide;

2-chloro-N-(2,6-difluoro-4-(2-(((3S,5S)-5-fluoropiperidin-3-yl)amino)-8-isopropyl-7-oxo-7,8-dihydropteridin-6-yl)phenyl)benzenesulfonamide;

2-chloro-N-(4-(2-(((1r,4r)-4-(dimethylamino)cyclohexyl) amino)-8-isopropyl-7-oxo-7,8-dihydropteridin-6-yl)-2-fluorophenyl)benzenesulfonamide;

N-(4-(2-(((1r,4r)-4-aminocyclohexyl)amino)-8-isopropyl-7-oxo-7,8-dihydropteridin-6-yl)-2-fluorophenyl)-2-chlorobenzenesulfonamide;

1-(4-cyanophenyl)-N-(2,6-difluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide;

N-(2,6-difluoro-4-(2-(((3S,5S)-5-fluoropiperidin-3-yl) amino)-8-isopropyl-7-oxo-7,8-dihydropyrido[2,3-d]pyrimidin-6-yl)phenyl)-1-phenylmethanesulfonamide;

N-(2,6-difluoro-4-(2-(((3S,5S)-5-fluoropiperidin-3-yl) amino)-8-isopropyl-7-oxo-7,8-dihydropyrido[2,3-d]pyrimidin-6-yl)phenyl)-1-(2-fluorophenyl)methanesulfonamide;

N-(2,6-difluoro-4-(2-(((3S,5S)-5-fluoropiperidin-3-yl) amino)-8-isopropyl-7-oxo-7,8-dihydropyrido[2,3-d]pyrimidin-6-yl)phenyl)-1-(4-fluorophenyl)methanesulfonamide;

N-(2,6-difluoro-4-(2-(((3S,5S)-5-fluoropiperidin-3-yl) amino)-8-isopropyl-7-oxo-7,8-dihydropyrido[2,3-d]pyrimidin-6-yl)phenyl)-1-(4-(methylsulfonyl)phenyl)methanesulfonamide;

N-(2,6-difluoro-4-(2-(((3S,5S)-5-fluoropiperidin-3-yl) amino)-8-isopropyl-7-oxo-7,8-dihydropyrido[2,3-d]pyrimidin-6-yl)phenyl)-1-(4-(difluoromethyl)phenyl)methanesulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,6-difluorophenyl)propane-1-sulfonamide;

N-(4-(2-(((1r,4r)-4-(dimethylamino)cyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide;

N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)propane-1-sulfonamide;

N-(6-(2-(((1r,4r)-4-(dimethylamino)cyclohexyl)amino)-8-isopropyl-7-oxo-7,8-dihydropyrido[2,3-d]pyrimidin-6-yl)pyridin-3-yl)propane-1-sulfonamide;

N-(5-(2-(((1r,4r)-4-(dimethylamino)cyclohexyl)amino)-8-isopropyl-7-oxo-7,8-dihydropyrido[2,3-d]pyrimidin-6-yl)-6-methylpyridin-2-yl)propane-1-sulfonamide;

N-(6-(2-(((1r,4r)-4-(dimethylamino)cyclohexyl)amino)-8-isopropyl-7-oxo-7,8-dihydropyrido[2,3-d]pyrimidin-6-yl)-2-methylpyridin-3-yl)propane-1-sulfonamide;

N-(5-(2-(((1r,4r)-4-(dimethylamino)cyclohexyl)amino)-8-isopropyl-7-oxo-7,8-dihydropyrido[2,3-d]pyrimidin-6-yl)pyrazin-2-yl)propane-1-sulfonamide;

N-(5-(2-(((1r,4r)-4-(dimethylamino)cyclohexyl)amino)-8-isopropyl-7-oxo-7,8-dihydropyrido[2,3-d]pyrimidin-6-yl)pyrimidin-2-yl)propane-1-sulfonamide;

N-(6-(2-(((1r,4r)-4-(dimethylamino)cyclohexyl)amino)-8-isopropyl-7-oxo-7,8-dihydropyrido[2,3-d]pyrimidin-6-yl)pyridazin-3-yl)propane-1-sulfonamide;

N-(5-(2-(((1r,4r)-4-(dimethylamino)cyclohexyl)amino)-8-isopropyl-7-oxo-7,8-dihydropteridin-6-yl)-6-methylpyridin-2-yl)-3,3-difluorobutane-1-sulfonamide;

N-(5-(2-(((1r,4r)-4-(dimethylamino)cyclohexyl)amino)-8-isopropyl-7-oxo-7,8-dihydropteridin-6-yl)pyridin-2-yl)-3,3-difluorobutane-1-sulfonamide;

N-(5-(2-(((3S,5S)-5-fluoropiperidin-3-yl)amino)-8-isopropyl-7-oxo-7,8-dihydropteridin-6-yl)-6-methylpyridin-2-yl)-1-phenylmethanesulfonamide;

N-(5-(2-(((3S,5S)-5-fluoropiperidin-3-yl)amino)-8-isopropyl-7-oxo-7,8-dihydropteridin-6-yl)pyridin-2-yl)-1-phenylmethanesulfonamide;

N-(5-(2-(((3S,5S)-5-fluoropiperidin-3-yl)amino)-8-isopropyl-7-oxo-7,8-dihydropteridin-6-yl)pyridin-2-yl)-1-(1-methyl-1H-pyrazol-3-yl)methanesulfonamide;

1-cyclopentyl-N-(5-(2-(((3S,5S)-5-fluoropiperidin-3-yl) amino)-8-isopropyl-7-oxo-7,8-dihydropteridin-6-yl)pyridin-2-yl)methanesulfonamide;

N-(5-(2-(((3S,5S)-5-fluoropiperidin-3-yl)amino)-8-isopropyl-7-oxo-7,8-dihydropteridin-6-yl)pyridin-2-yl)-1-(1-methyl-1H-pyrazol-3-yl)methanesulfonamide;

N-(5-(2-(((3S,5S)-5-fluoropiperidin-3-yl)amino)-8-isopropyl-7-oxo-7,8-dihydropteridin-6-yl)pyridin-2-yl)-1-(pyridin-2-yl)methanesulfonamide;

N-(5-(2-(((1r,4r)-4-(dimethylamino)cyclohexyl)amino)-8-isopropyl-7-oxo-7,8-dihydropteridin-6-yl)pyridin-2-yl)-1-(pyridin-2-yl)methanesulfonamide;

N-(5-(2-(((1S,4S)-4-(dimethylamino)-3-fluorocyclohexyl)amino)-8-isopropyl-7-oxo-7,8-dihydropteridin-6-yl)-6-methylpyridin-2-yl)-3,3-difluorobutane-1-sulfonamide;

N-(5-(2-(((1S,4S)-4-(dimethylamino)-3-fluorocyclohexyl)amino)-8-isopropyl-7-oxo-7,8-dihydropteridin-6-yl)-6-methylpyridin-2-yl)-3,3,3-trifluoropropane-1-sulfonamide;

1-(4-cyanophenyl)-N-(5-(2-(((3S,5S)-5-fluoropiperidin-3-yl)amino)-8-isopropyl-7-oxo-7,8-dihydropteridin-6-yl)pyridin-2-yl)methanesulfonamide;

1-(4-cyanophenyl)-N-(5-(2-(((1r,4r)-4-(dimethylamino)cyclohexyl)amino)-8-isopropyl-7-oxo-7,8-dihydropteridin-6-yl)pyridin-2-yl)methanesulfonamide;

1-(4-cyanophenyl)-N-(5-(2-(((1S,4S)-4-(dimethylamino)-3-fluorocyclohexyl)amino)-8-isopropyl-7-oxo-7,8-dihydropteridin-6-yl)pyridin-2-yl)methanesulfonamide;

1-(4-cyanophenyl)-N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)methanesulfonamide;

1-(4-cyanophenyl)-N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)methanesulfonamide;

N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)-1-(1-methyl-1H-pyrazol-3-yl)methanesulfonamide;

N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)-1-(1-methyl-1H-pyrazol-3-yl)methanesulfonamide;

N-(5-(2-(((1S,4S)-4-(dimethylamino)-3-fluorocyclohexyl)amino)-8-isopropyl-7-oxo-7,8-dihydropyrido[2,3-d]pyrimidin-6-yl)pyridin-2-yl)-1-(1-methyl-1H-pyrazol-3-yl)methanesulfonamide;

2-cyclohexyl-N-(5-(2-(((1r,4r)-4-(dimethylamino)cyclohexyl)amino)-8-isopropyl-7-oxo-7,8-dihydropteridin-6-yl)-6-methylpyridin-2-yl)acetamide;

2-(((1r,4r)-4-(dimethylamino)cyclohexyl)amino)-6-(6-(3-ethyl-2-oxopyrrolidin-1-yl)-2-methylpyridin-3-yl)-8-isopropylpteridin-7(8H)-one;

2-(((1r,4r)-4-(dimethylamino)cyclohexyl)amino)-8-isopropyl-6-(2-methyl-6-((3,3,3-trifluoro-2-hydroxypropyl)amino)pyridin-3-yl)pteridin-7(8H)-one;

N-(5-(2-(((1S,4S)-4-(dimethylamino)-3-fluorocyclohexyl)amino)-8-isopropyl-7-oxo-7,8-dihydropyrido[2,3-d]pyrimidin-6-yl)pyridin-2-yl)piperidine-1-sulfonamide;

N-(5-(2-(((1r,4r)-4-(dimethylamino)cyclohexyl)amino)-8-isopropyl-7-oxo-7,8-dihydropyrido[2,3-d]pyrimidin-6-yl)-3-fluoropyridin-2-yl)-1-(2-fluorophenyl)methanesulfonamide;

N-(5-(2-(((1r,4r)-4-(dimethylamino)cyclohexyl)amino)-8-isopropyl-7-oxo-7,8-dihydropyrido[2,3-d]pyrimidin-6-yl)-3-fluoropyridin-2-yl)-3,3,3-trifluoropropane-1-sulfonamide;

3,3,3-trifluoro-N-(3-fluoro-5-(2-(((3S,5S)-5-fluoropiperidin-3-yl)amino)-8-isopropyl-7-oxo-7,8-dihydropyrido[2,3-d]pyrimidin-6-yl)pyridin-2-yl)propane-1-sulfonamide;

N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)-1-(1-methyl-1H-pyrazol-4-yl)methanesulfonamide;

N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)-1-(1-methyl-1H-pyrazol-4-yl)methanesulfonamide;

N-(4-(2-(((1R,4R)-4-(dimethylamino)-3-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide;

N-(4-(2-(((1R,4R)-4-(dimethylamino)-3-methoxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide;

N-(4-(2-((4-((dimethylamino)methyl)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide;

3,3,3-trifluoro-N-(2-fluoro-4-(8-isopropyl-2-(((1r,4r)-4-(1-methyl-1H-imidazol-2-yl)cyclohexyl)amino)-7-oxo-7,8-dihydropyrido[2,3-d]pyrimidin-6-yl)phenyl)propane-1-sulfonamide 3,3,3-trifluoro-N-(2-fluoro-4-(8-isopropyl-2-(((1r,4r)-4-(1-methyl-4,5-dihydro-1H-imidazol-2-yl)cyclohexyl)amino)-7-oxo-7,8-dihydropyrido[2,3-d]pyrimidin-6-yl)phenyl)propane-1-sulfonamide;

3,3,3-trifluoro-N-(2-fluoro-4-(8-isopropyl-2-((2-methyl-2-azaspiro[3.5]nonan-7-yl)amino)-7-oxo-7,8-dihydropyrido[2,3-d]pyrimidin-6-yl)phenyl)propane-1-sulfonamide;

N-(4-(2-(((1R,3S,4R)-4-(dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide;

N-(4-(2-(((1r,4r)-4-(dimethylamino)-4-methylcyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide;

N-(4-(2-(((1R,4R)-4-(dimethylamino)-3,3-difluorocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide;

N-(4-(2-(((1R,4R)-4-(dimethylamino)-3,3-difluorocyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide;

N-(4-(2-(((1R,4R)-4-(dimethylamino)-3-hydroxycyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide;

N-(4-(2-(((1R,4R)-4-(dimethylamino)-3-methoxycyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide;

3,3,3-trifluoro-N-(5-(2-(((3S,5S)-5-fluoropiperidin-3-yl)amino)-8-isopropyl-7-oxo-7,8-dihydropyrido[2,3-d]pyrimidin-6-yl)-3-methylpyridin-2-yl)propane-1-sulfonamide;

3,3,3-trifluoro-N-(5-(2-(((3S,5S)-5-fluoropiperidin-3-yl)amino)-8-isopropyl-7-oxo-7,8-dihydropyrido[2,3-d]pyrimidin-6-yl)-3-(trifluoromethyl)pyridin-2-yl)propane-1-sulfonamide;

N-(3-(difluoromethyl)-5-(2-(((3S,5S)-5-fluoropiperidin-3-yl)amino)-8-isopropyl-7-oxo-7,8-dihydropyrido[2,3-d]pyrimidin-6-yl)pyridin-2-yl)-3,3,3-trifluoropropane-1-sulfonamide;

N-(5-(2-(((1R,4R)-4-(dimethylamino)-3-fluorocyclohexyl)amino)-8-isopropyl-7-oxo-7,8-dihydropyrido[2,3-d]pyrimidin-6-yl)pyrimidin-2-yl)-3,3,3-trifluoropropane-1-sulfonamide;

N-(5-(2-(((1R,4R)-4-(dimethylamino)-3,3-difluorocyclohexyl)amino)-8-isopropyl-7-oxo-7,8-dihydropyrido[2,3-d]pyrimidin-6-yl)pyrimidin-2-yl)-3,3,3-trifluoropropane-1-sulfonamide;

N-(5-(2-(((3S,5R)-5-(difluoromethyl)piperidin-3-yl)amino)-8-isopropyl-7-oxo-7,8-dihydropyrido[2,3-d]pyrimidin-6-yl)pyridin-2-yl)-3,3,3-trifluoropropane-1-sulfonamide;

N-(6-(2-(((3S,5R)-5-(difluoromethyl)piperidin-3-yl)amino)-8-isopropyl-7-oxo-7,8-dihydropyrido[2,3-d]pyrimidin-6-yl)pyridin-3-yl)-3,3,3-trifluoropropane-1-sulfonamide; and N-(4-(2-(((3S,5R)-5-(difluoromethyl)piperidin-3-yl)amino)-8-isopropyl-7-oxo-7,8-dihydropyrido[2,3-d]pyrimidin-6-yl)-2,6-difluorophenyl)-3,3,3-trifluoropropane-1-sulfonamide.

Embodiment 71: A pharmaceutical composition comprising a compound of any of embodiments 1 to 70, or a pharmaceutically acceptable salt thereof, and one or more pharmaceutically acceptable excipients.

Embodiment 72: A method of treating an IRE1-related disease or disorder, the method comprising administering to the subject having an IRE1-related disease or disorder an effective amount of the compound of any of embodiments 1 to 70 or a pharmaceutically acceptable salt thereof, or the pharmaceutical composition of embodiment 71.

Embodiment 73: The method of embodiment 72, wherein the IRE1-related disease or disorder is cancer.

Embodiment 74: The method of embodiment 72 or 73, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

Embodiment 75: The method of any one of embodiments 72-74, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

Embodiment 76: The method of any one of embodiments 72-75, wherein the IRE1-related disease or disorder is multiple myeloma.

Embodiment 77: The method of any one of embodiments 72-75, wherein the IRE1-related disease or disorder is a triple-negative breast cancer (TNBC).

Embodiment 78: The method of any one of embodiments 72-77, further comprising administering one or more additional therapeutic agent(s) selected from the group consisting of an anti-inflammatory agent, a corticosteroid, an immunomodulatory agent, anti-cancer agent, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, and an agent for treating immunodeficiency disorders.

Embodiment 79: The method of embodiment 78, wherein the additional therapeutic agent is a corticosteroid, a proteasome inhibitor, an immunomodulatory agent, an anti-CD38 antibody, an anti-VEGF-A antibody, an anti-PD-1 antibody, an anti-PD-L1 antibody, or an anti-interleukin-6 antibody, or a combination thereof.

Embodiment 80: The method of embodiment 78 or 79, wherein the corticosteroid comprises dexamethasone.

Embodiment 81: The method of embodiment 78 or 79, wherein proteasome inhibitor comprises carfilzomib, ixazomib or bortezomib.

Embodiment 82: The method of embodiment 78 or 79, wherein immunomodulatory agent comprises lenalidomide or pomalidomide.

Embodiment 83: The method of embodiment 78 or 79, wherein the anti-PD-L1 antibody comprises, avelumab, durvalumab, or atezolizumab.

Embodiment 84: The method of embodiment 78 or 79, wherein the anti-PD-1 antibody comprises pembrolizumab or nivolumab.

Embodiment 85: The method of any one of embodiments 72 to 84, further comprising administering radiotherapy.

Embodiment 86: Use of a compound or a pharmaceutically acceptable salt thereof according to any of embodiments 1 to 70, or the pharmaceutical composition of embodiment 71, in the manufacture of a medicament for the treatment of an IRE1-related disease or disorder.

Embodiment 87: The use of embodiment 86, wherein the IRE1-related disease or disorder is cancer.

Embodiment 88: The use of embodiment 86 or 87, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

Embodiment 89: The use of any one of embodiments 86-88, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

Embodiment 90: The use of any one of embodiments 86-88, wherein the IRE1-related disease or disorder is multiple myeloma.

Embodiment 91: The use of any one of embodiments 86-88, wherein the IRE1-related disease or disorder is a triple-negative breast cancer (TNBC).

Embodiment 92: A compound or a pharmaceutically acceptable salt thereof according to any of embodiments 1 to 70, or the pharmaceutical composition of embodiment 71, for use in a method for treating an IRE1-related disease or disorder.

Embodiment 93: The compound or a pharmaceutically acceptable salt thereof of embodiment 92, wherein the IRE1-related disease or disorder is cancer.

Embodiment 94: The compound or a pharmaceutically acceptable salt thereof of embodiment 92 or 93, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

Embodiment 95: The compound or a pharmaceutically acceptable salt thereof of any one of embodiments 92-94, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

Embodiment 96: The compound or a pharmaceutically acceptable salt thereof of any one of embodiments 92-95, wherein the IRE1-related disease or disorder is multiple myeloma.

Embodiment 97: The compound or a pharmaceutically acceptable salt thereof of any one of embodiments 92-95, wherein the IRE1-related disease or disorder is a triple-negative breast cancer (TNBC).

Embodiment 98: A method of inhibiting or killing a cancer cell expressing IRE1, the method comprising contacting the cancer cell expressing IRE1 with a compound or pharmaceutically acceptable salt thereof, of any one of embodiments 1 to 70 or the pharmaceutical composition of embodiment 71.

Embodiment 99: The method of embodiment 98, wherein the inhibiting or killing is performed in vivo Embodiment 100: The method of embodiment 98, wherein the cancer cell expressing IRE1 is in a human Embodiment 101: A method of modulating IRE1 activity, the method comprising contacting IRE1 with a compound or pharmaceutically acceptable salt thereof of any one of embodiments 1 to 70 or the pharmaceutical composition of embodiment 71.

Embodiment 102: A kit for treating a condition mediated by IRE1, comprising:
a) a pharmaceutical composition of embodiment 71; and
b) instructions for use.

The following examples are offered by way of illustration and not by way of limitation.

EXAMPLES

Synthetic Examples

Exemplary compounds described herein, including those for example found in Table 1 were made, characterized, and tested for binding to IRE1α (alpha). Where more than one name is associated with a compound or intermediate, the chemical structure shall define the compound. Unless otherwise noted, NMR was run at room temperature.

Abbreviations

ACN: acetonitrile
DCM: dichloromethane
DMF: N,N-dimethylformamide
DMSO: dimethyl sulfoxide
EtOAc: ethyl acetate
EtOH: ethanol
h: hour
HCl: hydrochloric acid
HPLC: High-performance liquid chromatography
IPA: isopropyl acetate
LCMS: Liquid chromatography-mass spectrometry
$Na_2SO_4$: sodium sulfate
THF: tetrahydrofuran Example 1: (S)—N-(2,3-Difluoro-4-(8-methyl-7-oxo-2-(piperidin-3-ylamino)-7,8-dihydropyrido[2,3-d]pyrimidin-6-yl)phenyl)-1-phenylmethanesulfonamide Compound 1

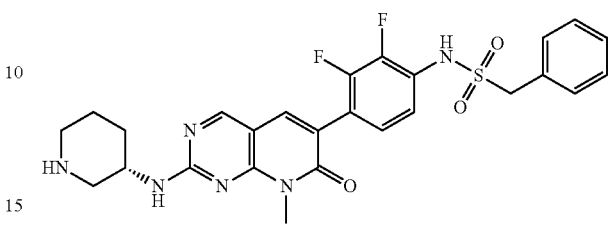

Step 1: 6-Bromo-8-methyl-2-methylsulfonyl-pyrido[2,3-d]pyrimidin-7-one

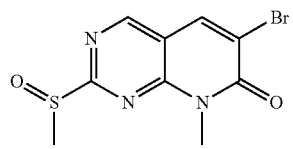 [SMILES: Cn1c(=O)c(Br)cc2cnc(S(C)=O)nc21]

A solution of 6-bromo-8-methyl-2-methylsulfanyl-pyrido[2,3-d]pyrimidin-7-one (200 mg, 0.70 mmol) in dichloromethane (20 mL) was added 3-chloroperoxybenzoic acid (312 mg, 1.54 mmol) and stirred for 2 h at rt. The reaction was quenched with sat. sodium bisulfite and extracted with dichloromethane. The organic layer was washed with brine. The solvent was removed to afford the title compound (210 mg, 94.4% yield) as a white solid. LCMS (ESI): $[M+H]^+$=302.2

Step 2: tert-Butyl (S)-3-((6-bromo-8-methyl-7-oxo-7,8-dihydropyrido[2,3-d]pyrimidin-2-yl)amino)piperidine-1-carboxylate

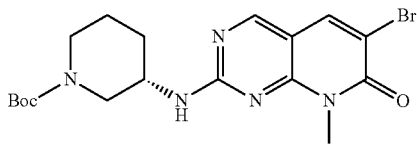 [SMILES: Cn1c(=O)c(Br)cc2cnc(N[C@H]3CCCN(C(=O)OC(C)(C)C)C3)nc21]

Under nitrogen, a solution of 6-bromo-8-methyl-2-methylsulfonyl-pyrido[2,3-d]pyrimidin-7-one (210 mg, 0.66 mmol), tert-butyl (3S)-3-amino-1-piperidinecarboxylate (158 mg, 0.79 mmol), caesium fluoride (200 mg, 1.32 mmol), N,N-Diisopropylethylamine (0.35 mL, 2.12 mmol) in dimethyl sulfoxide (5 mL) was stirred for 2 h at 80° C. The reaction was quenched with brine and extracted with ethyl acetate. The organic layers were washed with brine. The solvent was removed and the residue was purified by silica flash chromatography eluting with ethyl acetate/petroleum ether (1/1) to afford the title compound (220 mg, 76% yield) as a white solid. LCMS (ESI, m/z): $[M+H]^+$=438.2.

Step 3: tert-Butyl (S)-3-((6-(4-amino-2,3-difluorophenyl)-8-methyl-7-oxo-7,8-dihydropyrido[2,3-d]pyrimidin-2-yl)amino)piperidine-1-carboxylate

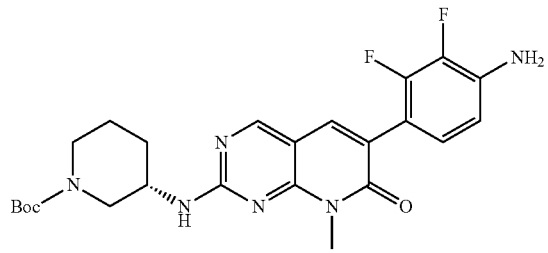 [SMILES: Cn1c(=O)c(-c2ccc(N)c(F)c2F)cc2cnc(N[C@H]3CCCN(C(=O)OC(C)(C)C)C3)nc21]

Under nitrogen, a solution of tert-butyl (3S)-3-((6-bromo-8-methyl-7-oxo-pyrido[2,3-d]pyrimidin-2-yl)amino)piperidine-1-carboxylate (210 mg, 0.48 mmol), 2,3-difluoro-4-(4,4,5,5-tetramethyl-1,3,2-dioxaborolan-2-yl)aniline (148 mg, 0.58 mmol), [1,1'-bis(diphenylphosphino)ferrocene]dichloropalladium(II) (40 mg, 0.05 mmol), sodium carbonate (150 mg, 1.42 mmol) in 1,4-dioxane (10 mL) and water (2 mL) was stirred for 2 h at 90° C. The solvent was removed under vacuum. The residue was purified by silica flash chromatography eluting with ethyl acetate/petroleum ether (3/1) to afford the title compound (170 mg, 72.9% yield) as a yellow solid. LCMS (ESI): [M+H]$^+$=487.2.

Step 4: (S)—N-(2,3-Difluoro-4-(8-methyl-7-oxo-2-(piperidin-3-ylamino)-7,8-dihydropyrido[2,3-d]pyrimidin-6-yl)phenyl)-1-phenylmethanesulfonamide

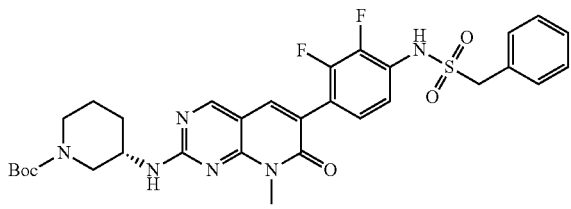 [SMILES: Cn1c(=O)c(-c2ccc(NS(=O)(=O)Cc3ccccc3)c(F)c2F)cc2cnc(N[C@H]3CCCN(C(=O)OC(C)(C)C)C3)nc21]

Under nitrogen, a solution of tert-butyl (S)-3-((6-(4-amino-2,3-difluorophenyl)-8-methyl-7-oxo-7,8-dihydropyrido[2,3-d]pyrimidin-2-yl)amino)piperidine-1-carboxylate (170 mg, 0.35 mmol) in pyridine (158 mg, 2 mmol) was added alpha-toluenesulfonylchloride (80 mg, 0.42 mmol) and stirred for 4 h at rt. The reaction was quenched with brine and extracted with ethyl acetate. The solvent was removed and the residue was purified by silica flash chromatography eluting with ethyl acetate/petroleum ether (2/1) to afford the title compound (90 mg, 40.2% yield) as a yellow solid. LCMS (ESI): [M+H]$^+$=641.2.

A solution of tert-butyl (S)-3-((6-(2,3-difluoro-4-((phenylmethyl)sulfonamido)phenyl)-8-methyl-7-oxo-7,8-dihydropyrido[2,3-d]pyrimidin-2-yl)amino)piperidine-1-carboxylate (90 mg, 0.14 mmol) in dichloromethane (5 mL) was added 4 M HCl in dioxane (1 mL) and stirred for 2 h at rt. The solvent was removed under vacuum. The residue was purified by Prep-HPLC to afford the title compound (32.6 mg, 42.9% yield) as a yellow solid.

Example 2: N-(2,3-Difluoro-4-(2-(((3S,5S)-5-fluoropiperidin-3-yl)amino)-8-methyl-7-oxo-7,8-dihydropyrido[2,3-d]pyrimidin-6-yl)phenyl)-1-phenylmethanesulfonamide Compound 2

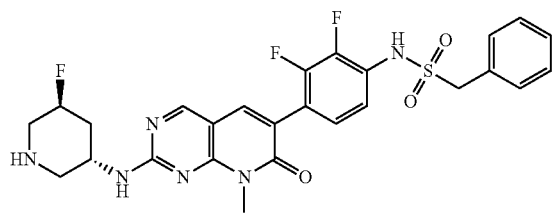 [SMILES: Cn1c(=O)c(-c2ccc(NS(=O)(=O)Cc3ccccc3)c(F)c2F)cc2cnc(N[C@@H]3CNC[C@@H](F)C3)nc21]

Step 1: 6-(4-Amino-2,3-difluorophenyl)-8-methyl-2-(methylthio)pyrido[2,3-d]pyrimidin-7(8H)-one

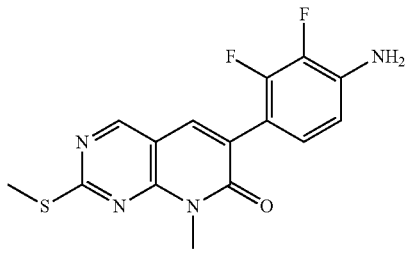 [SMILES: CSc1ncc2cc(-c3ccc(N)c(F)c3F)c(=O)n(C)c2n1]

Under nitrogen, a solution of 6-bromo-8-methyl-2-methylsulfanyl-pyrido[2,3-d]pyrimidin-7-one (150 mg, 0.52 mmol), 2,3-difluoro-4-(4,4,5,5-tetramethyl-1,3,2-dioxaborolan-2-yl)aniline (147 mg, 0.58 mmol), [1,1'-bis(diphenylphosphino)ferrocene]dichloropalladium(II) (38 mg, 0.05 mmol), sodium carbonate (120 mg, 1.13 mmol) in 1,4-dioxane (10 mL) and water (2 mL) was stirred at 90° C. for 2 h. The solvent was removed under vacuum. The residue was purified by silica flash chromatography eluting with ethyl acetate/petroleum ether (1/1) to afford the title compound (150 mg, 85.6% yield) as a yellow solid. LCMS (ESI): [M+H]$^+$=335.2.

Step 2: N-(2,3-Difluoro-4-(8-methyl-2-(methylthio)-7-oxo-7,8-dihydropyrido[2,3-d]pyrimidin-6-yl)phenyl)-1-phenylmethanesulfonamide

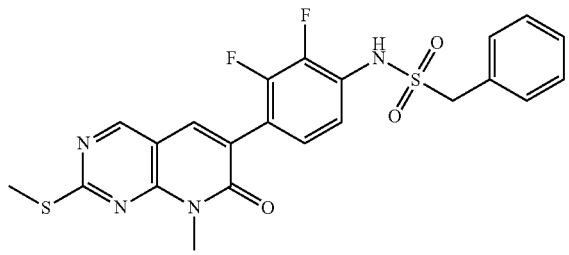 [SMILES: CSc1ncc2cc(-c3ccc(NS(=O)(=O)Cc4ccccc4)c(F)c3F)c(=O)n(C)c2n1]

A solution of 6-(4-amino-2,3-difluoro-phenyl)-8-methyl-2-methylsulfanyl-pyrido[2,3-d]pyrimidin-7-one (150 mg, 0.45 mmol) and alpha-toluenesulfonylchloride (128 mg, 0.67 mmol) in pyridine (5 mL) was stirred for 2 h at 25° C.

The reaction was quenched with brine and extracted with dichloromethane. The solvent was removed under vacuum. The residue was purified by silica flash chromatography eluting with ethyl acetate/petroleum ether (1/1) to afford the title compound (200 mg, 91.3% yield) as a yellow solid. LCMS (ESI): [M+H]⁺=489.2.

Step 3: N-(2,3-Difluoro-4-(8-methyl-2-(methylsulfonyl)-7-oxo-7,8-dihydropyrido[2,3-d]pyrimidin-6-yl)phenyl)-1-phenylmethanesulfonamide

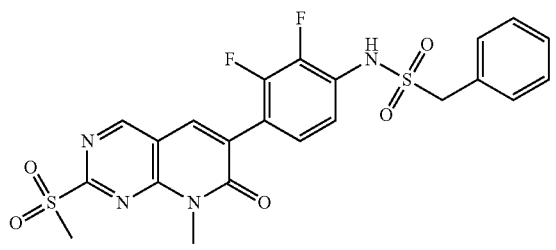 [SMILES: Cn1c(=O)c(-c2ccc(NS(=O)(=O)Cc3ccccc3)c(F)c2F)cc2cnc(S(C)(=O)=O)nc21]

A solution of N-(2,3-difluoro-4-(8-methyl-2-(methylthio)-7-oxo-7,8-dihydropyrido[2,3-d]pyrimidin-6-yl)phenyl)-1-phenylmethanesulfonamide (200 mg, 0.41 mmol) in dichloromethane (20 mL) was added 3-chloroperoxybenzoic acid (200 mg, 0.98 mmol) and stirred for 2 h at 25° C. The reaction was quenched with sat. sodium bisulfite and extracted with dichloromethane. The organic layer was washed with sat. sodium carbonate. The solvent was removed under vacuum to afford the title compound (200 mg, 93.9% yield) as a yellow solid. LCMS (ESI): [M+H]=520.2.

Step 4: Benzyl (3S,5S)-3-((6-(2,3-difluoro-4-((phenylmethyl)sulfonamido)phenyl)-8-methyl-7-oxo-7,8-dihydropyrido[2,3-d]pyrimidin-2-yl)amino)-5-fluoropiperidine-1-carboxylate

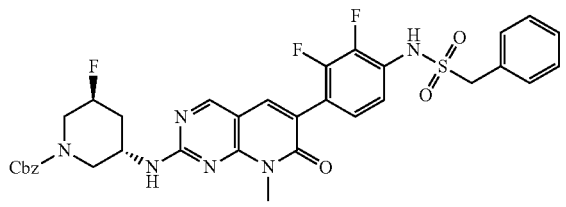 [SMILES: Cn1c(=O)c(-c2ccc(NS(=O)(=O)Cc3ccccc3)c(F)c2F)cc2cnc(N[C@H]3C[C@H](F)CN(C(=O)OCc4ccccc4)C3)nc21]

Under nitrogen, a solution of benzyl (3S,5S)-3-amino-5-fluoro-piperidine-1-carboxylate hydrochloride (55 mg, 0.19 mmol), N-(2,3-difluoro-4-(8-methyl-2-(methylsulfonyl)-7-oxo-7,8-dihydropyrido[2,3-d]pyrimidin-6-yl)phenyl)-1-phenylmethanesulfonamide (125 mg, 0.24 mmol), caesium fluoride (55 mg, 0.36 mmol), N,N-diisopropylethylamine (0.15 mL, 0.91 mmol) in dimethyl sulfoxide (5 mL) was stirred at 80° C. for 2 h. The reaction was quenched with brine and extracted with ethyl acetate. The organic layer was washed with brine. The solvent was removed under vacuum. The residue was purified by silica flash chromatography eluting with ethyl acetate/petroleum ether (1/1) to afford the title compound (70 mg, 42.1% yield) as a yellow solid. LCMS (ESI): [M+H]⁺=693.2.

Step 5: N-(2,3-Difluoro-4-(2-(((3S,5S)-5-fluoropiperidin-3-yl)amino)-8-methyl-7-oxo-7,8-dihydropyrido[2,3-d]pyrimidin-6-yl)phenyl)-1-phenylmethanesulfonamide

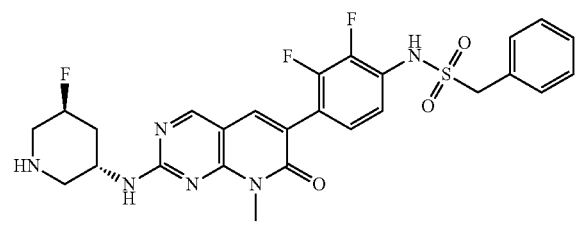 [SMILES: Cn1c(=O)c(-c2ccc(NS(=O)(=O)Cc3ccccc3)c(F)c2F)cc2cnc(N[C@@H]3CNC[C@@H](F)C3)nc21]

A solution of benzyl (3S,5S)-3-((6-(2,3-difluoro-4-((phenylmethyl)sulfonamido)phenyl)-8-methyl-7-oxo-7,8-dihydropyrido[2,3-d]pyrimidin-2-yl)amino)-5-fluoropiperidine-1-carboxylate (70 mg, 0.10 mmol) in dichloromethane (4 mL) was added 33% HBr in acetic acid (1 mL) and stirred for 2 h at rt. The solvent was removed under vacuum. The residue was purified by Prep-HPLC to afford the title compound (22.0 mg, 39% yield) as a white solid.

Example 3: (S)—N-(4-(8-Ethyl-7-oxo-2-(piperidin-3-ylamino)-7,8-dihydropyrido[2,3-d]pyrimidin-6-yl)-2,3-difluorophenyl)-1-phenylmethanesulfonamide Compound 3


Step 1: 6-Bromo-8-ethyl-2-(methylthio)pyrido[2,3-d]pyrimidin-7(8H)-one

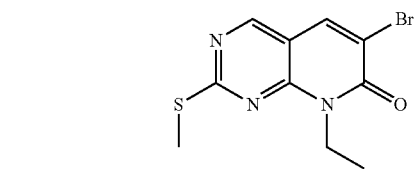 [SMILES: CCn1c(=O)c(Br)cc2cnc(SC)nc21]

A mixture of 6-bromo-2-methylsulfanyl-8H-pyrido[2,3-d]pyrimidin-7-one (130 mg, 0.48 mmol) and cesium carbonate (520 mg, 1.6 mmol) in N,N-dimethylformamide (5 mL) was added bromoethane (78 mg, 0.72 mmol) and stirred for 3 h at 25° C. The reaction was quenched with brine and extracted with ethyl acetate. The solvent was removed under vacuum. The residue was purified by silica flash chromatography eluting with ethyl acetate/petroleum ether (1/3) to afford the title compound (70 mg, 48.8% yield) as a white solid. LCMS (ESI): [M+H]⁺=300.2.

Step 2: 6-Bromo-8-ethyl-2-(methylsulfonyl)pyrido[2,3-d]pyrimidin-7(8H)-one

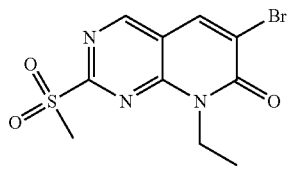 [SMILES: CCn1c(=O)c(Br)cc2cnc(S(C)(=O)=O)nc21]

A solution of 6-bromo-8-ethyl-2-methylsulfanyl-pyrido[2,3-d]pyrimidin-7-one (70 mg, 0.23 mmol) in dichloromethane (10 mL) was added 3-chloroperoxybenzoic acid (120 mg, 0.59 mmol) at 25° C. and stirred for 2 h at 25° C. The reaction was quenched with sat. sodium bisulfite and extracted with dichloromethane. The organic layer was washed with brine. The solvent was removed to afford the title compound (77 mg, 99.4% yield) as a white solid. LCMS (ESI): [M+H]$^+$=332.2.

Step 3: tert-Butyl (S)-3-((6-bromo-8-ethyl-7-oxo-7,8-dihydropyrido[2,3-d]pyrimidin-2-yl)amino)piperidine-1-carboxylate

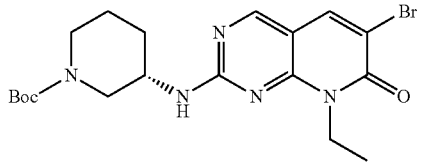 [SMILES: CCn1c(=O)c(Br)cc2cnc(N[C@H]3CCCN(C(=O)OC(C)(C)C)C3)nc21]

Under nitrogen, a solution of 6-bromo-8-ethyl-2-methylsulfonyl-pyrido[2,3-d]pyrimidin-7-one (77 mg, 0.23 mmol), tert-butyl (3S)-3-amino-1-piperidinecarboxylate (60 mg, 0.30 mmol), caesium fluoride (70 mg, 0.46 mmol), N,N-diisopropylethylamine (0.15 mL, 0.91 mmol) in dimethyl sulfoxide (3 mL) was stirred at 80° C. for 2 h. The reaction was quenched with brine and extracted with ethyl acetate. The organic layer was washed with brine. The solvent was removed and the residue was purified by silica flash chromatography eluting with ethyl acetate/petroleum ether (1/1) to afford the title compound (60 mg, 57.2% yield) as a white solid. LCMS (ESI): [M+H]$^+$=452.2.

Step 4: tert-Butyl (S)-3-((6-(4-amino-2,3-difluorophenyl)-8-ethyl-7-oxo-7,8-dihydropyrido[2,3-d]pyrimidin-2-yl)amino)piperidine-1-carboxylate

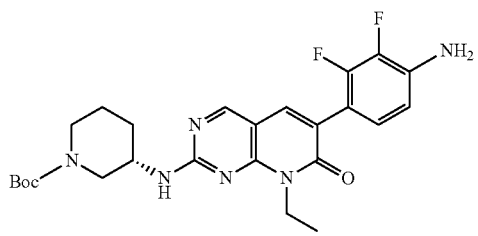 [SMILES: CCn1c(=O)c(-c2ccc(N)c(F)c2F)cc2cnc(N[C@H]3CCCN(C(=O)OC(C)(C)C)C3)nc21]

Under nitrogen, a solution of tert-butyl (S)-3-((6-bromo-8-ethyl-7-oxo-7,8-dihydropyrido[2,3-d]pyrimidin-2-yl)amino)piperidine-1-carboxylate (60 mg, 0.13 mmol), 2,3-difluoro-4-(4,4,5,5-tetramethyl-1,3,2-dioxaborolan-2-yl)aniline (42 mg, 0.16 mmol), [1,1'-bis(diphenylphosphino)ferrocene]dichloropalladium(II) (15 mg, 0.02 mmol), sodium carbonate (42 mg, 0.40 mmol) in 1,4-dioxane (3 mL) and water (0.5 mL) was stirred for 2 h at 90° C. The solvent was removed under vacuum. The residue was purified by silica flash chromatography eluting with ethyl acetate/petroleum ether (3/1) to afford the title compound (58 mg, 87.4% yield) as a yellow solid. LCMS (ESI): [M+H]$^+$=501.2.

Step 5: tert-Butyl (S)-3-((6-(2,3-difluoro-4-((phenylmethyl)sulfonamido)phenyl)-8-ethyl-7-oxo-7,8-dihydropyrido[2,3-d]pyrimidin-2-yl)amino)piperidine-1-carboxylate

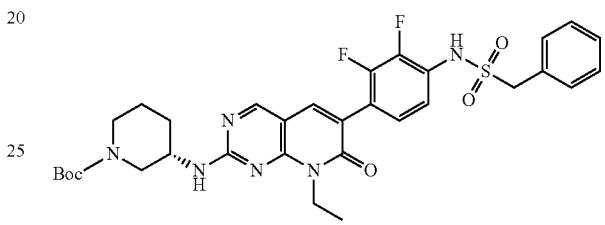

Under nitrogen, a solution of tert-butyl (S)-3-((6-(4-amino-2,3-difluorophenyl)-8-ethyl-7-oxo-7,8-dihydropyrido[2,3-d]pyrimidin-2-yl)amino)piperidine-1-carboxylate (58 mg, 0.12 mmol) in pyridine (1 ml) was added alpha-toluenesulfonylchloride (34 mg, 0.18 mmol) at 25° C. and stirred for 2 h. The reaction was quenched with brine and extracted with dichloromethane. The solvent was removed and the residue was purified by silica flash chromatography eluting with ethyl acetate/petroleum ether (2/1) to afford the title compound (68 mg, 89.6% yield) as a yellow solid LCMS (ESI): [M+H]$^+$=655.2.

Step 6: (S)—N-(4-(8-Ethyl-7-oxo-2-(piperidin-3-ylamino)-7,8-dihydropyrido[2,3-d]pyrimidin-6-yl)-2,3-difluorophenyl)-1-phenylmethanesulfonamide

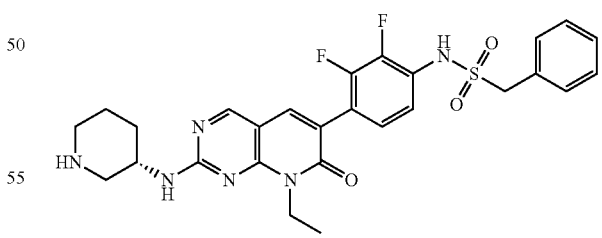 [SMILES: CCn1c(=O)c(-c2ccc(NS(=O)(=O)Cc3ccccc3)c(F)c2F)cc2cnc(N[C@H]3CCCN(C(=O)OC(C)(C)C)C3)nc21]

A solution of tert-butyl (S)-3-((6-(2,3-difluoro-4-((phenylmethyl)sulfonamido) phenyl)-8-ethyl-7-oxo-7,8-dihydropyrido[2,3-d]pyrimidin-2-yl)amino)piperidine-1-carboxylate (68 mg, 0.10 mmol) in 5% TFA in hexafluoroisopropanol (5 mL) was stirred for 1 h at rt. The solvent was removed under vacuum. The residue was purified by Prep-HPLC to afford the title compound (25.4 mg, 44.1% yield) as a white solid.

Example 4: (S)-3,3,3-Trifluoro-N-(2-fluoro-5-(8-methyl-7-oxo-2-(piperidin-3-ylamino)-7,8-dihydropyrido[2,3-d]pyrimidin-6-yl)naphthalen-1-yl)propane-1-sulfonamide Compound 4

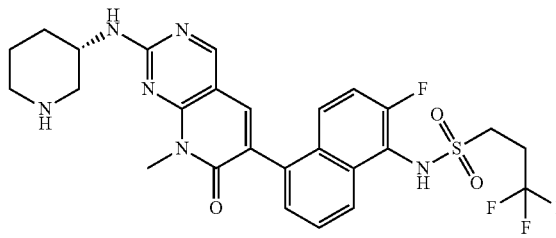

Step 1: 2-Fluoro-5-(4,4,5,5-tetramethyl-1,3,2-dioxaborolan-2-yl)naphthalen-1-amine

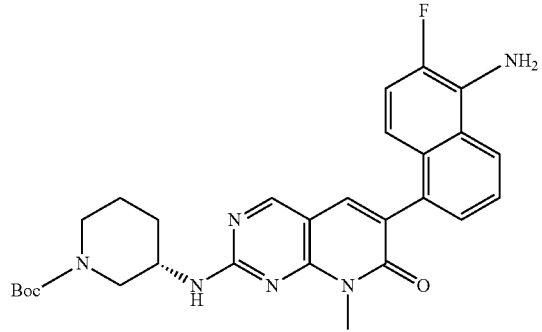 [SMILES: Cn1c(=O)c(-c2cccc3c(N)c(F)ccc23)cc2cnc(N[C@H]3CCCN(C(=O)OC(C)(C)C)C3)nc21]

Under nitrogen, a solution of 5-bromo-2-fluoro-naphthalen-1-amine (200 mg, 0.83 mmol), bis(pinacolato)diboron (0.60 g, 2.36 mmol), potassium acetate (240 mg, 2.45 mmol) and [1,1'-bis(diphenylphosphino)ferrocene]dichloropalladium(II) (60 mg, 0.08 mmol) in 1,4-dioxane (4 mL) was stirred for 2 h at 90° C. The solvent was removed under vacuum. The residue was purified by silica flash chromatography eluting with petroleum ether/ethyl acetate (10/1) to afford the title compound (200 mg, 79.4% yield) as a red solid. LCMS (ESI): [M+H]$^+$=288.1.

Step 2: tert-Butyl (S)-3-((6-(5-amino-6-fluoronaphthalen-1-yl)-8-methyl-7-oxo-7,8-dihydropyrido[2,3-d]pyrimidin-2-yl)amino)piperidine-1-carboxylate

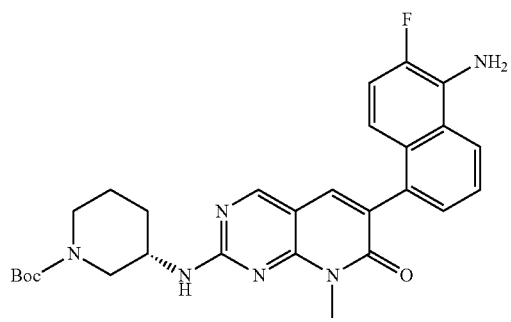 [SMILES: Cn1c(=O)c(-c2cccc3c(N)c(F)ccc23)cc2cnc(N[C@H]3CCCN(C(=O)OC(C)(C)C)C3)nc21]

Under nitrogen, a solution of tert-butyl (3S)-3-((6-bromo-8-methyl-7-oxo-pyrido[2,3-d]pyrimidin-2-yl)amino)piperidine-1-carboxylate (450 mg, 1.03 mmol), 2-fluoro-5-(4,4,5,5-tetramethyl-1,3,2-dioxaborolan-2-yl)naphthalen-1-amine (380 mg, 1.32 mmol), sodium carbonate (280 mg, 2.64 mmol) and [1,1'-bis(diphenylphosphino)ferrocene]dichloropalladium(II) (90 mg, 0.12 mmol) in 1,4-dioxane (9 mL) was stirred for 2 h at 75° C. The solvent was removed under vacuum. The residue was purified by silica flash chromatography eluting with petroleum ether/ethyl acetate (3:7) to afford the title compound (440 mg, 78.5% yield) as a red solid. LCMS (ESI): [M+H]$^+$=519.2.

Step 3: tert-Butyl (S)-3-((6-(6-fluoro-5-((3,3,3-trifluoropropyl)sulfonamido) naphthalen-1-yl)-8-methyl-7-oxo-7,8-dihydropyrido[2,3-d]pyrimidin-2-yl)amino)piperidine-1-carboxylate

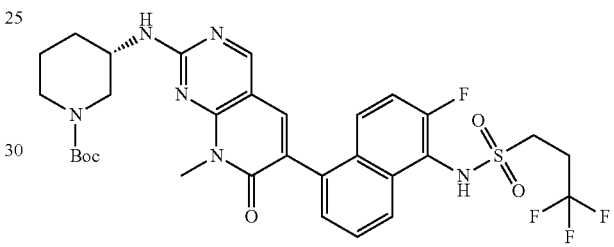

Under nitrogen, to a solution of tert-butyl (S)-3-((6-(5-amino-6-fluoronaphthalen-1-yl)-8-methyl-7-oxo-7,8-dihydropyrido[2,3-d]pyrimidin-2-yl)amino)piperidine-1-carboxylate (100 mg, 0.19 mmol) in pyridine (0.5 mL) was added 3,3,3-trifluoropropane-1-sulfonylchloride (120 mg, 0.61 mmol) and stirred for 2 h at rt. The reaction mixture was diluted with water, extracted with ethyl acetate, washed with brine, dried over anhydrous sodium sulfate and concentrated under vacuum. The residue was purified by silica flash chromatography eluting with petroleum ether/ethyl acetate (1:1) to afford the title compound (110 mg, 79.8% yield) as a brown solid. LCMS (ESI): [M+H]$^+$=679.2.

Step 4: (S)-3,3,3-Trifluoro-N-(2-fluoro-5-(8-methyl-7-oxo-2-(piperidin-3-ylamino)-7,8-dihydropyrido[2,3-d]pyrimidin-6-yl)naphthalen-1-yl)propane-1-sulfonamide

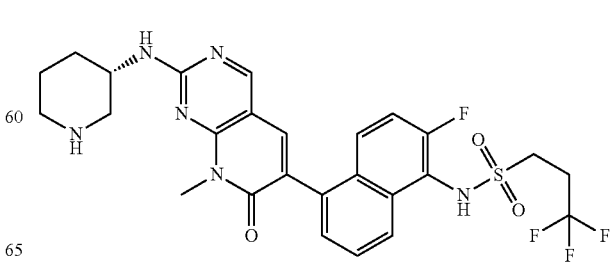

To a solution of tert-butyl (S)-3-((6-(6-fluoro-5-((3,3,3-trifluoropropyl)sulfonamido)naphthalen-1-yl)-8-methyl-7-oxo-7,8-dihydropyrido[2,3-d]pyrimidin-2-yl)amino)piperidine-1-carboxylate (100 mg, 0.15 mmol) in dichloromethane (2 mL) was added 4 M HCl in 1,4-dioxane (3 mL) and stirred for 1 h at rt. The organic layer was concentrated under vacuum. The residue was purified by Prep-HPLC to afford the title compound (37.6 mg, 42.5% yield) as an off-white solid.

Example 5: (S)—N-(2-Fluoro-5-(8-methyl-7-oxo-2-(piperidin-3-ylamino)-7,8-dihydropyrido[2,3-d]pyrimidin-6-yl)naphthalen-1-yl)-1-phenylmethanesulfonamide Compound 5

The title compound was prepared according to example 4. This provides the title compound (55.8 mg, 59% yield) as an off-white solid.

Example 6: (S)—N-(2-Fluoro-4-(8-methyl-7-oxo-2-(piperidin-3-ylamino)-7,8-dihydropyrido[2,3-d]pyrimidin-6-yl)naphthalen-1-yl)-1-phenylmethanesulfonamide Compound 6

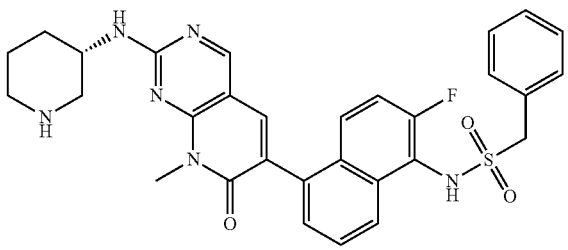 [SMILES: Cn1c(=O)c(-c2cccc3c(NS(=O)(=O)Cc4ccccc4)c(F)ccc23)cc2cnc(N[C@H]3CCCNC3)nc21]

The title compound was prepared according to example 4. This provides the title compound (20.6 mg, 28.8% yield) as a yellow solid.

Example 7: (S)-3,3,3-Trifluoro-N-(2-fluoro-4-(8-methyl-7-oxo-2-(piperidin-3-ylamino)-7,8-dihydropyrido[2,3-d]pyrimidin-6-yl)naphthalen-1-yl)propane-1-sulfonamide Compound 7

The title compound was prepared according to example 4. This provides the title compound (41 mg, 47.2% yield) as a yellow solid.

Example 8: (S)—N-(2-Fluoro-5-(8-methyl-7-oxo-2-(piperidin-3-ylamino)-7,8-dihydropyrido[2,3-d]pyrimidin-6-yl)naphthalen-1-yl)propane-1-sulfonamide Compound 8

The title compound was prepared according to example 4. This provides the title compound (41.0 mg, 47.2% yield) as a yellow solid. (25.2 mg, 29.7% yield) as an off-white solid.

Example 9: N-(2,3-Difluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-phenylmethanesulfonamide Compound

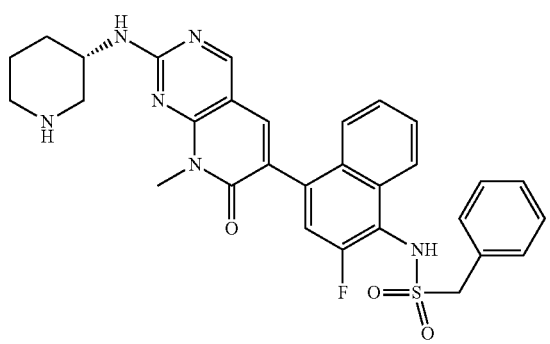 [SMILES: Cn1c(=O)c(-c2cc(F)c(NS(=O)(=O)Cc3ccccc3)c3ccccc23)cc2cnc(N[C@H]3CCCNC3)nc21]

The title compound was prepared according to example 2. This provides the title compound (41.3 mg, 39.2% yield) as a yellow solid.

Example 10: N-(4-(8-cyclopropyl-2-(((3S,5S)-5-fluoropiperidin-3-yl)amino)-7-oxo-7,8-dihydro-pyrido[2,3-d]pyrimidin-6-yl)-2,3-difluorophenyl)-1-phenylmethanesulfonamide Compound 10

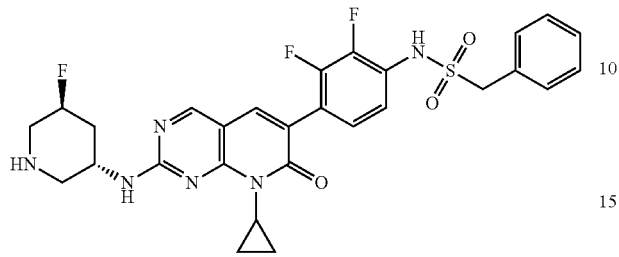

Step 1: 6-Bromo-8-cyclopropyl-2-methylsulfanyl-pyrido[2,3-d]pyrimidin-7-one

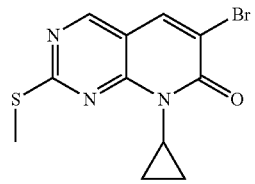 [SMILES: CSc1ncc2cc(Br)c(=O)n(C3CC3)c2n1]

A mixture of 6-bromo-2-methylsulfanyl-8H-pyrido[2,3-d]pyrimidin-7-one (200 mg, 0.73 mmol), cyclopropyl bromide (150 mg, 1.24 mmol), copper(I) iodide (30 mg, 0.16 mmol), L-proline (40 mg, 0.35 mmol) and potassium carbonate (200 mg, 1.45 mmol) in dimethyl sulfoxide (10 mL) was stirred at 90° C. for 4 h under nitrogen. The resulting solution was diluted with water, extracted with ethyl acetate, washed with brine, dried over Sodium sulfate and concentrated. The residue was purified by silica flash chromatography eluting with ethyl acetate/petroleum ether (1/4) to afford the title compound (136 mg, 59.3% yield) as a white solid. LCMS (ESI): [M+H]$^+$=312.0.

Step 2: 6-Bromo-8-cyclopropyl-2-methylsulfonyl-pyrido[2,3-d]pyrimidin-7-one

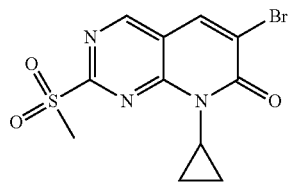 [SMILES: CS(=O)(=O)c1ncc2cc(Br)c(=O)n(C3CC3)c2n1]

To a mixture of 6-bromo-8-cyclopropyl-2-methylsulfanyl-pyrido[2,3-d]pyrimidin-7-one (136 mg, 0.44 mmol) in dichloromethane (4 mL) was added 3-chloroperoxybenzoicacid (300 mg, 1.39 mmol), the mixture was stirred for 2 h at room temperature. The reaction was quenched with saturated sodium sulfite and extracted with ethyl acetate, concentrated in vacuum. The crude would be directly used in the next step without purification. LCMS (ESI): [M+H]$^+$=344.0.

Step 3: Benzyl (3S,5S)-3-((6-bromo-8-cyclopropyl-7-oxo-pyrido[2,3-d]pyrimidin-2-yl)amino)-5-fluoro-piperidine-1-carboxylate

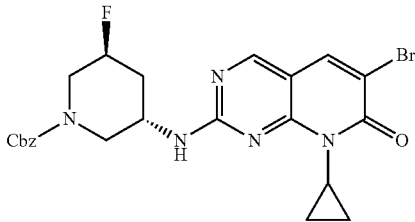 [SMILES: O=C(OCc1ccccc1)N1C[C@@H](F)C[C@H](Nc2ncc3cc(Br)c(=O)n(C4CC4)c3n2)C1]

A mixture of benzyl (3S,5S)-3-amino-5-fluoro-piperidine-1-carboxylate (0.12 g, 0.49 mmol), 6-bromo-8-cyclopropyl-2-methylsulfonyl-pyrido[2,3-d]pyrimidin-7-one (0.14 g, 0.41 mmol), N,N-diisopropylethylamine (0.2 mL, 1.15 mmol) and cesium fluoride (0.18 g, 1.22 mmol) in dimethyl sulfoxide (3 mL) was stirred at 90° C. for 2 h under nitrogen. The resulting solution was diluted with water, extracted with ethyl acetate, washed with brine, dried over sodium sulfate and concentrated. The residue was purified by silica flash chromatography eluting with ethyl acetate/petroleum ether (7/3) to afford the title compound (110 mg, 52.4% yield) as a yellow solid. LCMS (ESI): [M+H]$^+$=516.1.

Step 4: Benzyl (3S,5S)-3-((6-(4-amino-2,3-difluoro-phenyl)-8-cyclopropyl-7-oxo-7,8-dihydropyrido[2,3-d]pyrimidin-2-yl)amino)-5-fluoropiperidine-1-carboxylate

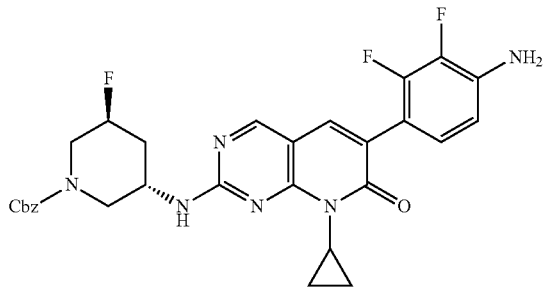 [SMILES: Nc1ccc(-c2cc3cnc(N[C@H]4C[C@H](F)CN(C(=O)OCc5ccccc5)C4)nc3n(C3CC3)c2=O)c(F)c1F]

Under nitrogen, a mixture of benzyl (3S,5S)-3-((6-bromo-8-cyclopropyl-7-oxo-pyrido[2,3-d]pyrimidin-2-yl)amino)-5-fluoro-piperidine-1-carboxylate (190 mg, 0.37 mmol), sodium carbonate (120 mg, 1.11 mmol), 2,3-difluoro-4-(4,4,5,5-tetramethyl-1,3,2-dioxaborolan-2-yl)aniline (120 mg, 0.47 mmol) and [1,1'-bis(diphenylphosphino)ferrocene]dichloropalladium(II) (30 mg, 0.04 mmol) in 1,4-dioxane (4 mL) and water (0.40 mL) was stirred for 2 h at 80° C. The resulting solution was diluted with water, extracted with ethyl acetate and concentrated in vacuum. The residue was purified by silica flash chromatography eluting with ethyl acetate/petroleum ether (4/1) to afford the title compound (150 mg, 72.2% yield) as a brown solid. LCMS (ESI): [M+H]$^+$=565.2.

Step 5: Benzyl (3S,5S)-3-((8-cyclopropyl-6-(2,3-difluoro-4-((phenylmethyl)sulfonamido)phenyl)-7-oxo-7,8-dihydropyrido[2,3-d]pyrimidin-2-yl)amino)-5-fluoropiperidine-1-carboxylate

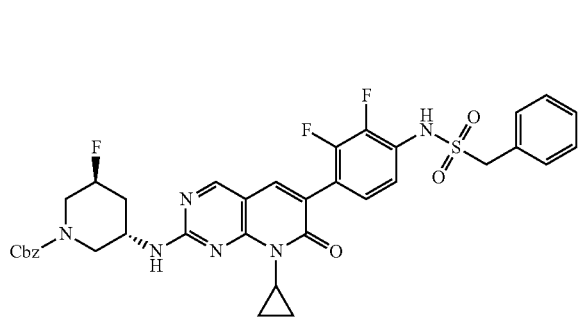 [SMILES: O=C(OCc1ccccc1)N1C[C@@H](F)C[C@H](Nc2ncc3cc(-c4ccc(NS(=O)(=O)Cc5ccccc5)c(F)c4F)c(=O)n(C4CC4)c3n2)C1]

To a mixture of benzyl (3S,5S)-3-((6-(4-amino-2,3-difluorophenyl)-8-cyclopropyl-7-oxo-7,8-dihydropyrido[2,3-d]pyrimidin-2-yl)amino)-5-fluoropiperidine-1-carboxylate (200 mg, 0.35 mmol) in pyridine (1 mL) was added alpha-toluenesulfonylchloride (350 mg, 1.84 mmol), the mixture was stirred for 1 h at room temperature. The resulting solution was diluted with water, extracted with ethyl acetate and concentrated in vacuum. The residue was purified by silica flash chromatography eluting with ethyl acetate/petroleum ether (95/5) to afford the title compound (190 mg, 74.6% yield) as a yellow solid. LCMS (ESI): $[M+H]^+=719.2$.

Step 6: N-(4-(8-Cyclopropyl-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide

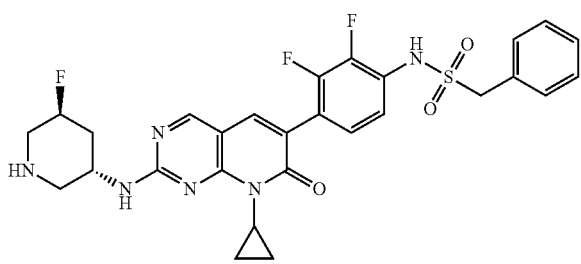 [SMILES: O=c1c(-c2ccc(NS(=O)(=O)Cc3ccccc3)c(F)c2F)cc2cnc(N[C@@H]3CNC[C@@H](F)C3)nc2n1C1CC1]

To a mixture of benzyl (3S,5S)-3-((8-cyclopropyl-6-(2,3-difluoro-4-((phenylmethyl)sulfonamido)phenyl)-7-oxo-7,8-dihydropyrido[2,3-d]pyrimidin-2-yl)amino)-5-fluoropiperidine-1-carboxylat (180 mg, 0.25 mmol) in acetonitrile (1 mL) and dichloromethane (1 mL) was added dimethyl sulfide (0.5 mL) and boron trifluoride diethyl etherate (0.5 mL), the mixture was stirred for 1 h at room temperature. The reaction was quenched with saturated sodium bicarbonate, extracted with ethyl acetate and concentrated in vacuum. The residue was purified by Prep-HPLC to afford the title compound (10.9 mg, 7.4% yield) as a white solid.

Example 11: N-(4-(8-(2,2-Difluoroethyl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide Compound 11

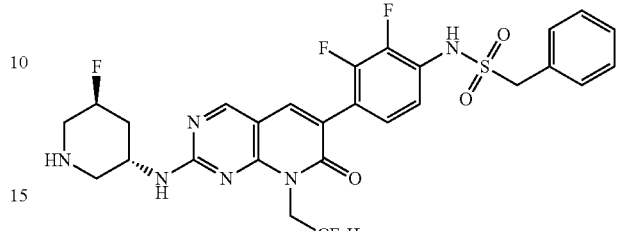

The title compound was prepared according to example 2. This provides the title compound (33.8 mg, 26.9% yield) as a white solid.

Example 12: N-(4-(8-Ethyl-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide Compound 12


The title compound was prepared according to example 2. This provides the title compound (4.4 mg, 6.8% yield) as yellow solid.

Example 13: N-(4-(8-Ethyl-2-(((3S,5S)-5-fluoropiperidin-3-yl)amino)-7-oxo-7,8-dihydropyrido[2,3-d]pyrimidin-6-yl)-2,3-difluorophenyl)propane-1-sulfonamide Compound 13

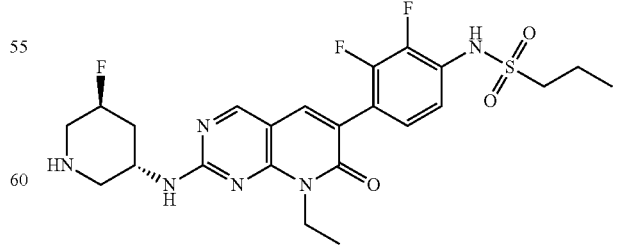

The title compound was prepared according to example 2. This provides the title compound (14.0 mg, 71.3% yield) as a yellow solid.

Example 14: N-(4-(8-Ethyl-2-(((3S,5S)-5-fluoropiperidin-3-yl)amino)-7-oxo-7,8-dihydropyrido[2,3-d]pyrimidin-6-yl)-2,3-difluorophenyl)-3,3,3-trifluoropropane-1-sulfonamide Compound 14

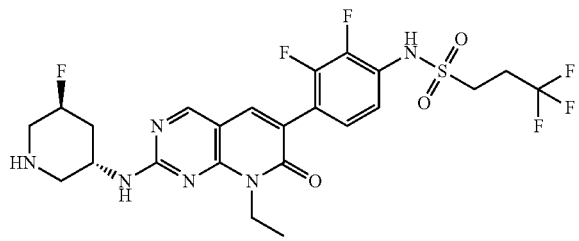 [SMILES: CCn1c(=O)c(-c2ccc(NS(=O)(=O)CCC(F)(F)F)c(F)c2F)cc2cnc(N[C@@H]3CNC[C@@H](F)C3)nc21]

The title compound was prepared according to example 2. This provides the title compound (21.0 mg, 32.6% yield) as a yellow solid.

Example 15: N-(4-(8-Ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-phenylmethanesulfonamide Compound 15

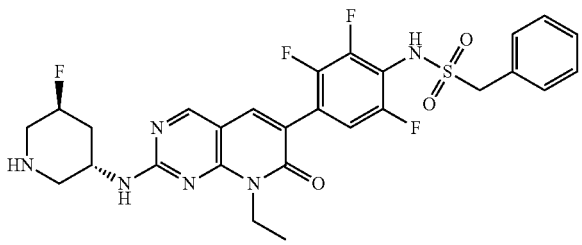 [SMILES: CCn1c(=O)c(-c2cc(F)c(NS(=O)(=O)Cc3ccccc3)c(F)c2F)cc2cnc(N[C@@H]3CNC[C@@H](F)C3)nc21]

The title compound was prepared according to example 2. This provides the title compound (7.0 mg, 21.5% yield) as a yellow solid.

Example 16: (S)—N-(2-Fluoro-3-(8-isopropyl-7-oxo-2-(piperidin-3-ylamino)-7,8-dihydropyrido[2,3-d]pyrimidin-6-yl)phenyl)-1-phenylmethanesulfonamide Compound 16

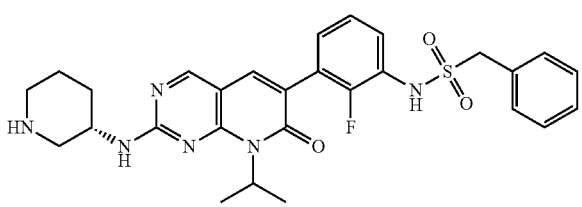 [SMILES: CC(C)n1c(=O)c(-c2cccc(NS(=O)(=O)Cc3ccccc3)c2F)cc2cnc(N[C@H]3CCCNC3)nc21]

The title compound was prepared according to example 1. This provides the title compound (48.5 mg, 57.3% yield) as a yellow solid.

Example 17: (S)—N-(2-Fluoro-5-(8-isopropyl-7-oxo-2-(piperidin-3-ylamino)-7,8-dihydropyrido[2,3-d]pyrimidin-6-yl)phenyl)-1-phenylmethanesulfonamide hydrochloride Compound 17

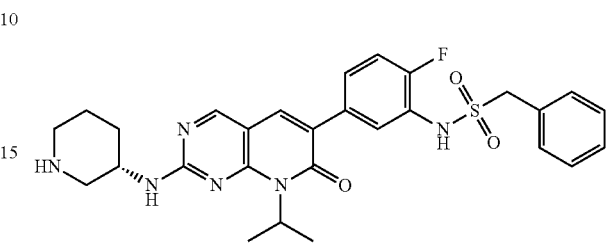

The title compound was prepared according to example 1. This provides the title compound (20.0 mg, 26.1% yield) as a yellow solid and as HCl salt.

Example 18: N-(4-(8-Cyclopentyl-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide Compound 18

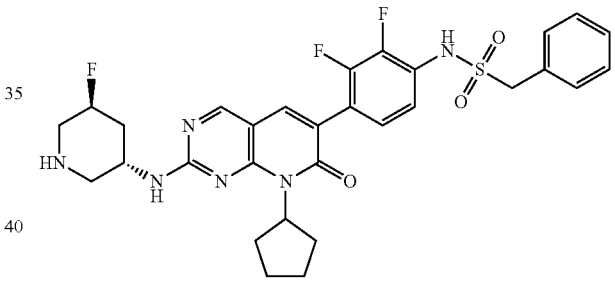

The title compound was prepared according to example 2. This provides the title compound (6.0 mg, 5.8% yield) as a yellow solid.

Example 19: (S)—N-(2,6-Difluoro-3-(8-isopropyl-7-oxo-2-(piperidin-3-ylamino)-7,8-dihydropyrido[2,3-d]pyrimidin-6-yl)phenyl)-1-phenylmethanesulfonamide Compound 19

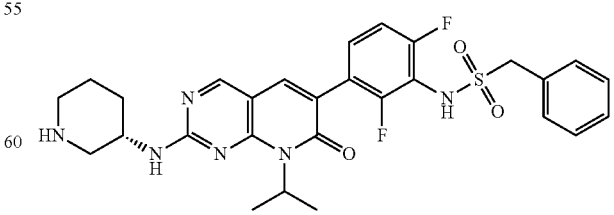

The title compound was prepared according to example 1. This provides the title compound (12.0 mg, 16.6% yield) as a yellow solid.

Example 20: 1-Phenyl-N-(2,3,6-trifluoro-4-(8-iso-propyl-2-(isopropylamino)-7-oxo-7,8-dihydropyrido[2,3-d]pyrimidin-6-yl)phenyl)methanesulfonamide Compound 20

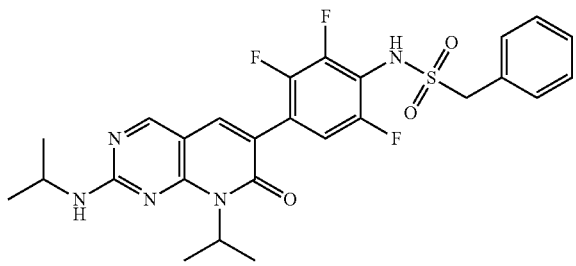 [SMILES: CC(C)Nc1ncc2cc(-c3cc(F)c(NS(=O)(=O)Cc4ccccc4)c(F)c3F)c(=O)n(C(C)C)c2n1]

Step 1: 1-Phenyl-N-(2,3,6-trifluoro-4-(8-isopropyl-2-(methylsulfonyl)-7-oxo-7,8-dihydropyrido[2,3-d]pyrimidin-6-yl)phenyl)methanesulfonamide

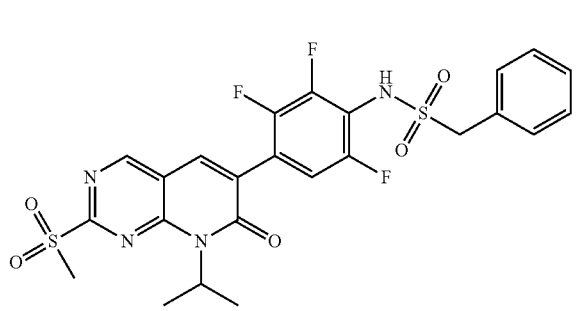 [SMILES: CC(C)n1c(=O)c(-c2cc(F)c(NS(=O)(=O)Cc3ccccc3)c(F)c2F)cc2cnc(S(C)(=O)=O)nc21]

The title compound was prepared according to step 3 of example 2. This provides the title compound (60 mg, 95% yield) as a yellow solid. LCMS (ESI):[M+1]=567.5.

Step 2: 1-Phenyl-N-(2,3,6-trifluoro-4-(8-isopropyl-2-(isopropylamino)-7-oxo-7,8-dihydropyrido[2,3-d]pyrimidin-6-yl)phenyl)methanesulfonamide

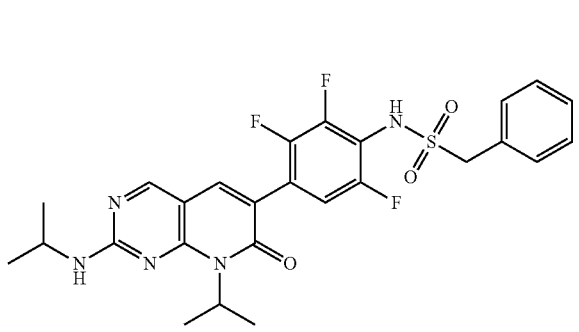 [SMILES: CC(C)Nc1ncc2cc(-c3cc(F)c(NS(=O)(=O)Cc4ccccc4)c(F)c3F)c(=O)n(C(C)C)c2n1]

Under nitrogen, a solution of 1-phenyl-N-(2,3,6-trifluoro-4-(8-isopropyl-2-(methylsulfonyl)-7-oxo-7,8-dihydropyrido[2,3-d]pyrimidin-6-yl)phenyl)methanesulfonamide (60 mg, 0.11 mmol) and propan-2-amine (40 mg, 0.58 mmol) in dimethyl sulfoxide (1 mL) was added caesium fluoride (50 mg, 0.33 mmol) and N,N-diisopropylethylamine (65 mg, 0.5 mmol) at rt. The resulting solution was stirred for 2 h at 85° C. The reaction mixture was diluted with water. The resulting solution was extracted with ethyl acetate and the organic layers were combined. The organic layer was dried over anhydrous sodium sulfate and concentrated under vacuum. The crude product was purified by Prep-HPLC to afford the title compound (9.6 mg, 16.6% yield) as a white solid.

Example 21: 3,3,3-Trifluoro-N-(2,3,6-trifluoro-4-(8-isopropyl-2-(isopropylamino)-7-oxo-7,8-dihydro-pyrido[2,3-d]pyrimidin-6-yl)phenyl)propane-1-sulfonamide Compound 21

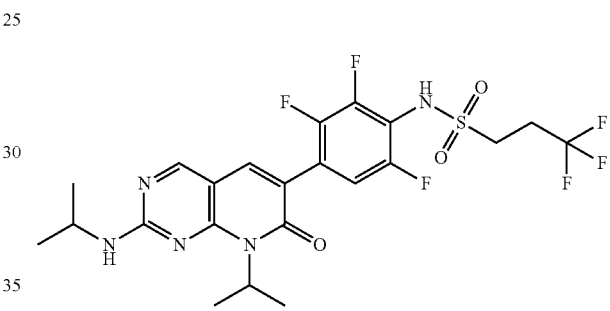

The title compound was prepared according to example 20. This provides the title compound (22.2 mg, 38% yield) as a white solid.

Example 22: 1-Phenyl-N-(2,3,6-trifluoro-4-(2-(((1r,4r)-4-hydroxycyclohexyl)amino)-8-isopropyl-7-oxo-7,8-dihydropyrido[2,3-d]pyrimidin-6-yl)phenyl)methanesulfonamide Compound

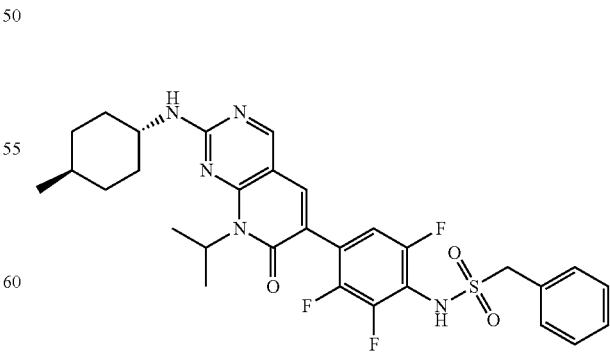

The title compound was prepared according to example 20. This provides the title compound (10.7 mg, 16.8% yield) as a white solid.

Example 23: N-(4-(8-(1,1-Difluoropropan-2-yl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide & N-(4-(8-(1,1-difluoropropan-2-yl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide Compound 23

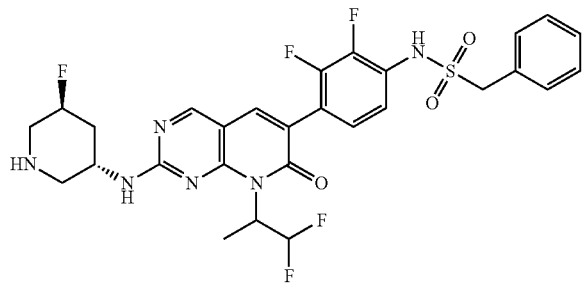

Step 1: Mixture of 6-bromo-8-(1,1-difluoropropan-2-yl)-2-(methylthio)pyrido[2,3-d]pyrimidin-7(8H)-one & 6-bromo-7-((1,1-difluoropropan-2-yl)oxy)-2-(methylthio)pyrido[2,3-d]pyrimidine

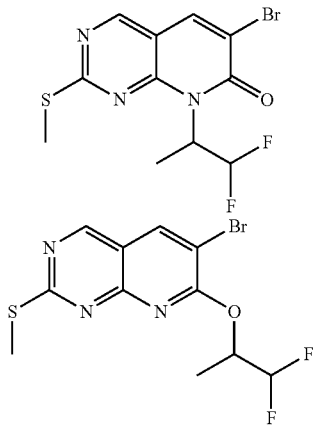

A solution of 6-bromo-2-methylsulfanyl-8H-pyrido[2,3-d]pyrimidin-7-one (200 mg, 0.73 mmol) and 1,1-difluoropropan-2-ol (320 mg, 3.33 mmol) in tetrahydrofuran (20 mL) was added triphenylphosphine (600 mg, 2.28 mmol) and diethyl azodicarboxylate (0.5 mL, 3.18 mmol) at 25° C. The resulting solution was stirred for 16 h at rt. The reaction was quenched with brine and extracted with ethyl acetate. The solvent was removed under vacuum. The residue was purified by silica flash chromatography eluting with ethyl acetate/petroleum ether (1/5) to afford the title compound (150 mg, 58.3% yield) as a yellow solid. LCMS (ESI): [M+1]+=350.2

Step 2: 6-(4-Amino-2,3-difluorophenyl)-8-(1,1-difluoropropan-2-yl)-2-(methylthio)pyrido[2,3-d]pyrimidin-7(8H)-one & 4-(7-((1,1-difluoropropan-2-yl)oxy)-2-(methylthio)pyrido[2,3-d]pyrimidin-6-yl)-2,3-difluoroaniline

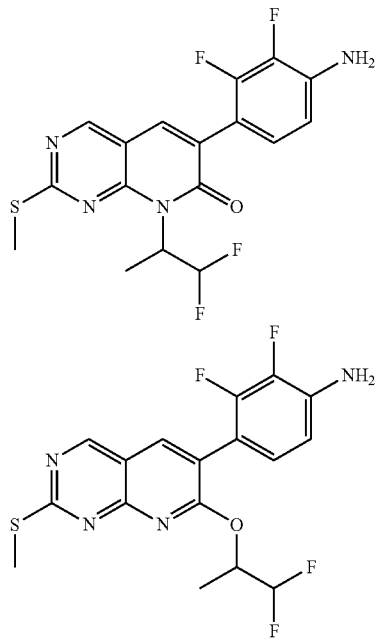

Under nitrogen, a mixture of 6-bromo-8-(1,1-difluoropropan-2-yl)-2-(methylthio)pyrido[2,3-d]pyrimidin-7(8H)-one & 6-bromo-7-((1,1-difluoropropan-2-yl)oxy)-2-(methylthio)pyrido[2,3-d]pyrimidine (150 mg, 0.43 mmol), [1,1'-bis(diphenylphosphino)ferrocene]dichloropalladium(II) (35 mg, 0.05 mmol), sodium carbonate (140 mg, 1.32 mmol) in water (0.8 mL) and 1,4-dioxane (5 mL) was stirred for 2 h at 90° C. The solvent was removed under vacuum. The residue was purified by silica flash chromatography eluting with ethyl acetate/petroleum ether (1/1) to afford the title compound (160 mg, 93.8% yield) as a yellow solid. LCMS (ESI, m/z): [M+H]+=399.1.

Step 3: N-(4-(8-(1,1-Difluoropropan-2-yl)-2-(methylthio)-7-oxo-7,8-dihydropyrido[2,3-d]pyrimidin-6-yl)-2,3-difluorophenyl)-1-phenylmethanesulfonamide & N-(4-(7-((1,1-difluoropropan-2-yl)oxy)-2-(methylthio)pyrido[2,3-d]pyrimidin-6-yl)-2,3-difluorophenyl)-1-phenylmethanesulfonamide

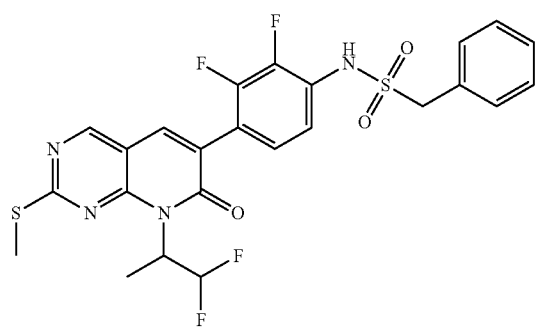

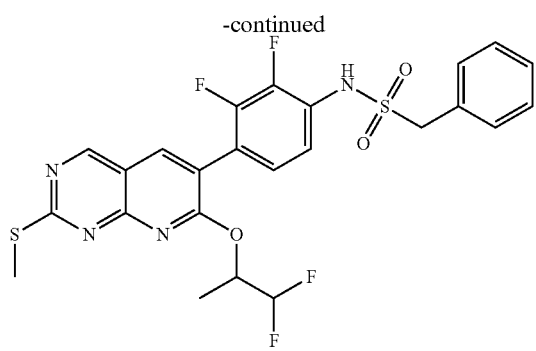

A solution of 6-(4-amino-2,3-difluorophenyl)-8-(1,1-difluoropropan-2-yl)-2-(methylthio)pyrido[2,3-d]pyrimidin-7(8H)-one & 4-(7-((1,1-difluoropropan-2-yl)oxy)-2-(methylthio)pyrido[2,3-d]pyrimidin-6-yl)-2,3-difluoroaniline (160 mg, 0.40 mmol), alpha-toluenesulfonylchloride (150 mg, 0.79 mmol) in dichloromethane (5 mL) was added triethylamine (0.2 mL, 1.44 mmol) at rt and stirred for 2 h at rt. The reaction was quenched with brine and extracted with ethyl acetate. The solvent was removed. The residue was purified by silica flash chromatography eluting with ethyl acetate/petroleum ether (3/1) to afford the title compound (180 mg, 81.1% yield) as a yellow solid. LCMS (ESI, m/z): [M+H]+=553.2.

Step 4: N-(4-(8-(1,1-Difluoropropan-2-yl)-2-(methylsulfonyl)-7-oxo-7,8-dihydropyrido[2,3-d]pyrimidin-6-yl)-2,3-difluorophenyl)-1-phenylmethanesulfonamide & N-(4-(7-((1,1-difluoropropan-2-yl)oxy)-2-(methylsulfonyl)pyrido[2,3-d]pyrimidin-6-yl)-2,3-difluorophenyl)-1-phenylmethanesulfonamide

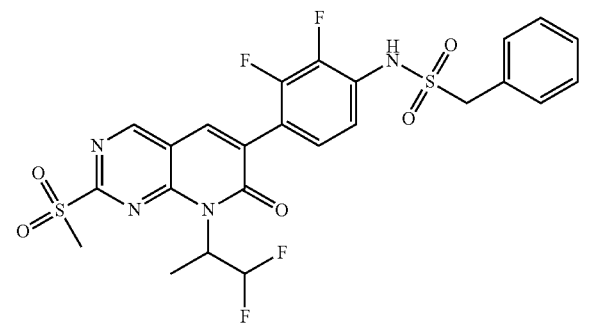

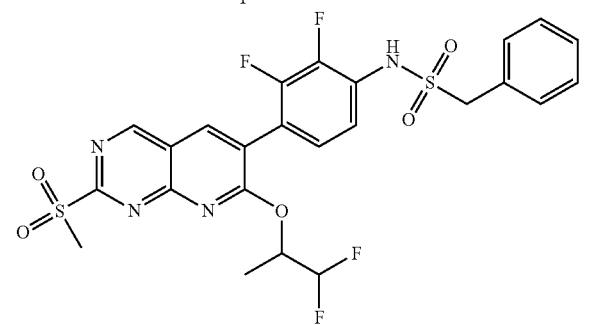

A solution of N-(4-(8-(1,1-difluoropropan-2-yl)-2-(methylthio)-7-oxo-7,8-dihydropyrido[2,3-d]pyrimidin-6-yl)-2,3-difluorophenyl)-1-phenylmethanesulfonamide & N-(4-(7-((1,1-difluoropropan-2-yl)oxy)-2-(methylthio)pyrido[2,3-d]pyrimidin-6-yl)-2,3-difluorophenyl)-1-phenylmethanesulfonamide (180 mg, 0.33 mmol) in dichloromethane (10 mL) was added 3-chloroperoxybenzoic acid (198 mg, 0.98 mmol) at 25° C. and stirred for 2 h at rt. The reaction was quenched with sat. sodium bisulfite and extracted with ethyl acetate. The organic layers were combined and washed with saturated sodium carbonate. The solvent was removed under vacuum to afford the title compound (180 mg, 94.5% yield). LCMS (ESI, m/z): [M+H]+=585.2.

Step 5: Benzyl (3S,5S)-3-((6-(2,3-difluoro-4-((phenylmethyl)sulfonamido)phenyl)-8-(1,1-difluoropropan-2-yl)-7-oxo-7,8-dihydropyrido[2,3-d]pyrimidin-2-yl)amino)-5-fluoropiperidine-1-carboxylate & benzyl (3S,5S)-3-((6-(2,3-difluoro-4-((phenylmethyl)sulfonamido)phenyl)-7-((1,1-difluoropropan-2-yl)oxy)pyrido[2,3-d]pyrimidin-2-yl)amino)-5-fluoropiperidine-1-carboxylate

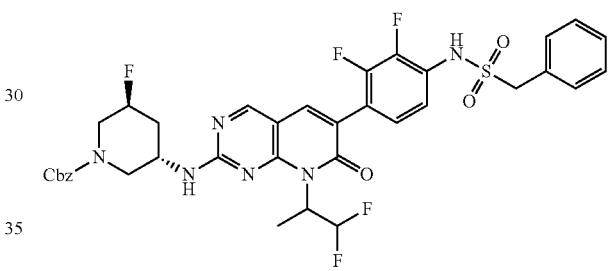

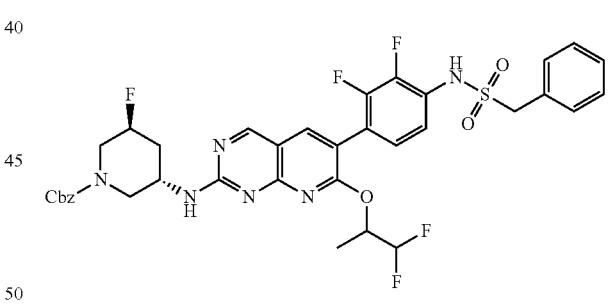

Under nitrogen, a solution of N-(4-(8-(1,1-difluoropropan-2-yl)-2-(methylsulfonyl)-7-oxo-7,8-dihydropyrido[2,3-d]pyrimidin-6-yl)-2,3-difluorophenyl)-1-phenylmethanesulfonamide & N-(4-(7-((1,1-difluoropropan-2-yl)oxy)-2-(methylsulfonyl)pyrido[2,3-d]pyrimidin-6-yl)-2,3-difluorophenyl)-1-phenylmethanesulfonamide (180 mg, 0.31 mmol), benzyl (3S,5S)-3-amino-5-fluoro-piperidine-1-carboxylate hydrochloride (90 mg, 0.31 mmol), caesium fluoride (140 mg, 0.92 mmol), N,N-diisopropylethylamine (0.3 mL, 1.82 mmol) in dimethyl sulfoxide (3 mL) was stirred for 2 h at 80° C. The reaction was quenched with brine and extracted with ethyl acetate. The solvent was removed under vacuum. The residue was purified by silica flash chromatography eluting with ethyl acetate/petroleum ether (5/1) to afford the title compound (160 mg, 68.7% yield) as a yellow solid. LCMS (ESI, m/z): [M+H]+=757.2.

Step 6: N-(4-(8-(1,1-Difluoropropan-2-yl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide N-(4-(8-(1,1-Difluoropropan-2-yl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide

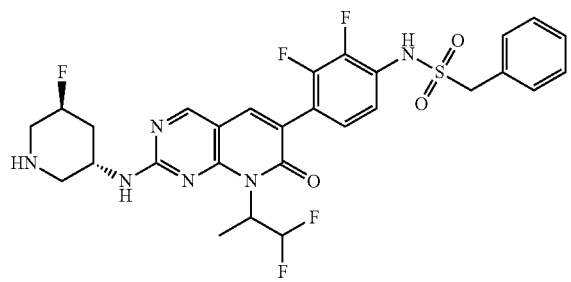

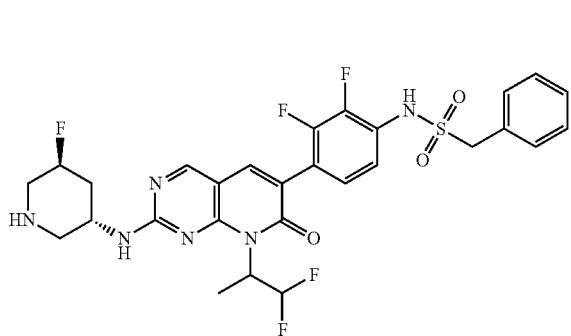 [SMILES: CC(C(F)F)n1c(=O)c(-c2ccc(NS(=O)(=O)Cc3ccccc3)c(F)c2F)cc2cnc(N[C@@H]3CNC[C@@H](F)C3)nc21]

A solution of benzyl (3S,5S)-3-((6-(2,3-difluoro-4-((phenylmethyl)sulfonamido) phenyl)-8-(1,1-difluoropropan-2-yl)-7-oxo-7,8-dihydropyrido[2,3-d]pyrimidin-2-yl)amino)-5-fluoropiperidine-1-carboxylate & benzyl (3S,5S)-3-((6-(2,3-difluoro-4-((phenylmethyl) sulfonamido)phenyl)-7-((1,1-difluoropropan-2-yl)oxy)pyrido[2,3-d]pyrimidin-2-yl)amino)-5-fluoropiperidine-1-carboxylate (160 mg, 0.21 mmol) in trifluoroacetic acid (10 mL) was stirred for 16 h at 50° C. The solvent was removed under vacuum. The residue was purified by Prep-HPLC and Chiral HPLC to afford the title compound.

N-(4-(8-(1,1-Difluoropropan-2-yl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide (8.2 mg, 6.2% yield as white solid. (rt=1.542 min, CHIRALPAK IC-3, 0.46×5 cm; 3 μm, MtBE (0.1% DEA): EtOH=80:20, 1.0 mL/min).

N-(4-(8-(1,1-Difluoropropan-2-yl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide (6.9 mg, 5.2% yield as white solid. (rt=2.529 min, CHIRALPAK IC-3, 0.46×5 cm; 3 μm, MtBE (0.1% DEA): EtOH=80:20, 1.0 mL/min).

Example 24: N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-1-phenylmethanesulfonamide Compound 24

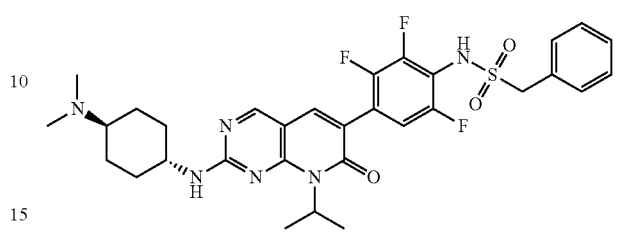

The title compound was prepared according to example 20. This provides the title compound (4.2 mg, 6.3% yield) as a white solid.

Example 25: N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide Compound 25

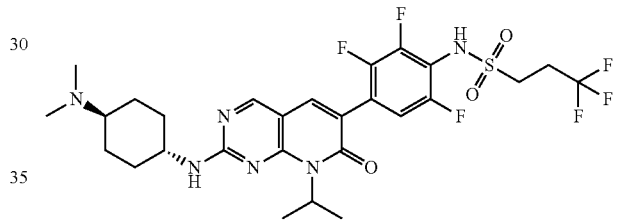

The title compound was prepared according to example 20. This provides the title compound (10.5 mg, 15.8% yield) as a white solid.

Example 26: 1-Phenyl-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide Compound 26

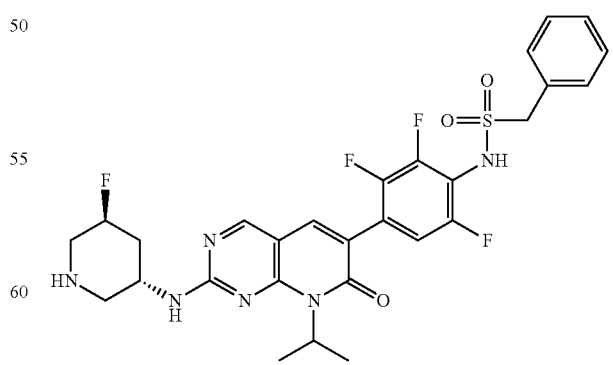

The title compound was prepared according to example 2. This provides the title compound (12.0 mg, 41.9% yield) as a white solid.

Example 27: 1-Phenyl-N-(2,3,6-trifluoro-4-(2-(((3S,5S)-5-fluoro-5-methylpiperidin-3-yl)amino)-8-isopropyl-7-oxo-7,8-dihydropyrido[2,3-d]pyrimidin-6-yl)phenyl)methanesulfonamide Compound 27

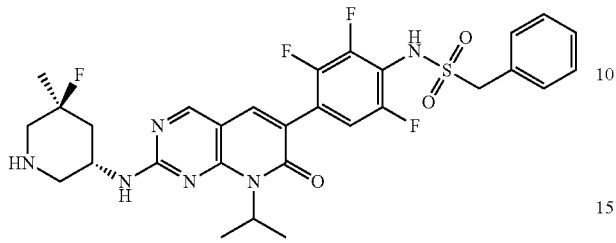

The title compound was prepared according to example 2. This provides the title compound (5.4 mg, 23.5% yield) as a white solid.

Example 28: N-(4-(8-Cyclobutyl-2-(((3S,5S)-5-fluoropiperidin-3-yl)amino)-7-oxo-7,8-dihydropyrido[2,3-d]pyrimidin-6-yl)-2,3,6-trifluorophenyl)-1-phenylmethanesulfonamide Compound 28

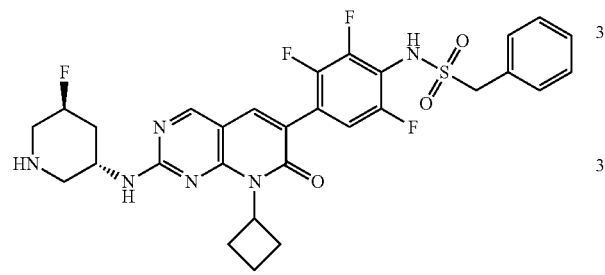

The title compound was prepared according to example 2. This provides the title compound (9.3 mg, 56.6% yield) as a white solid.

Example 29: 1-(4-Cyanophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide Compound 29

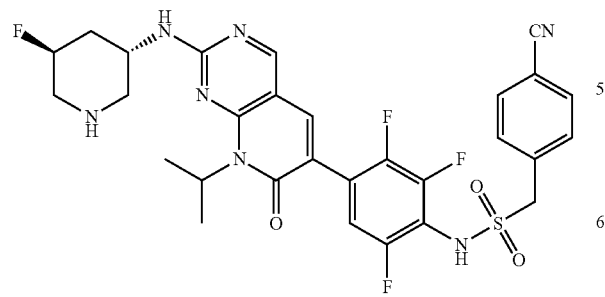

The title compound was prepared according to example 2. This provides the title compound (6.7 mg, 27.1% yield) as a white solid.

Example 30: 1-(3-Cyanophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide Compound 30

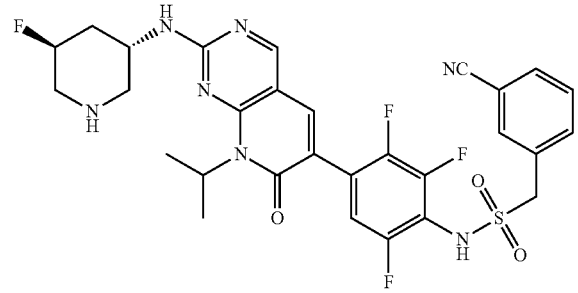 [SMILES: CC(C)n1c(=O)c(-c2cc(F)c(NS(=O)(=O)Cc3cccc(C#N)c3)c(F)c2F)cc2cnc(N[C@@H]3CNC[C@@H](F)C3)nc21]

The title compound was prepared according to example 2. This provides the title compound (23.6 mg, 35.8% yield) as a white solid.

Example 31: 1-(3-Methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide hydrochloride Compound 31

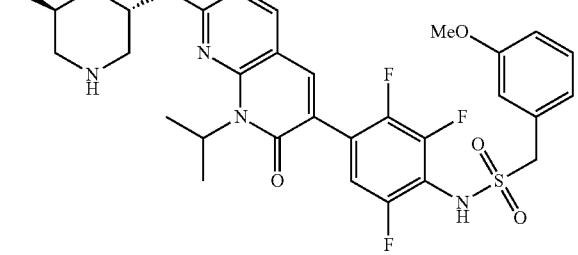

The title compound was prepared according to example 2. This provides the title compound (17.9 mg, 34.2% yield) as a white solid and HCl salt.

Example 32: 1-(2-Cyanophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide Compound 32

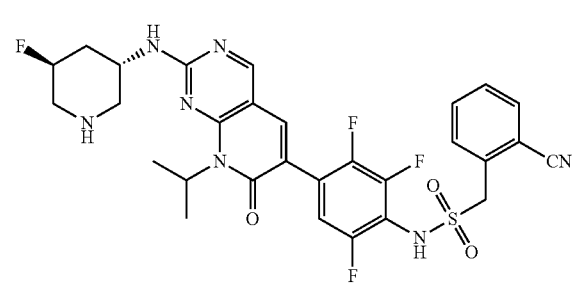 [SMILES: CC(C)n1c(=O)c(-c2cc(F)c(NS(=O)(=O)Cc3ccccc3C#N)c(F)c2F)cc2cnc(N[C@@H]3CNC[C@@H](F)C3)nc21]

The title compound was prepared according to example 2. This provides the title compound (14.0 mg, 26.1% yield) as a white solid.

Example 33: N-(4-(2-(((1r,4r)-4-(Dimethylamino) cyclohexyl)amino)-8-isopropyl-7-oxo-7,8-dihydro-pyrido[2,3-d]pyrimidin-6-yl)-2,3,6-trifluorophenyl)-3,3-difluorobutane-1-sulfonamide Compound 33

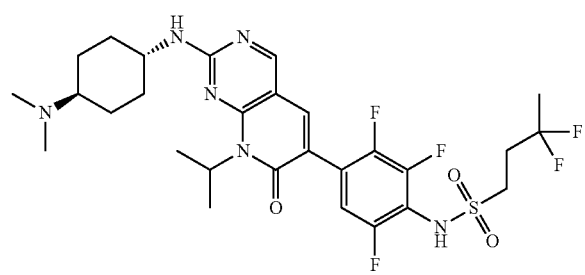 [SMILES: CC(C)n1c(=O)c(-c2cc(F)c(NS(=O)(=O)CCC(C)(F)F)c(F)c2F)cc2cnc(N[C@H]3CC[C@H](N(C)C)CC3)nc21]

The title compound was prepared according to example 20. This provides the title compound (10.7 mg, 13.4% yield) as a white solid.

Example 34: N-(4-(2-(((1r,4r)-4-(Dimethylamino) cyclohexyl)amino)-8-isopropyl-7-oxo-7,8-dihydro-pyrido[2,3-d]pyrimidin-6-yl)-2,3,6-trifluorophenyl) propane-1-sulfonamide Compound 34

The title compound was prepared according to example 20. This provides the title compound (13.7 mg, 25.5% yield) as a white solid.

Example 35: 1-Phenyl-N-(2,3,6-trifluoro-4-(2-(((3S, 5S)-5-fluoropiperidin-3-yl)amino)-7-oxo-8-(tetrahydrofuran-3-yl)-7,8-dihydropyrido[2,3-d]pyrimidin-6-yl)phenyl)methanesulfonamide & 1-phenyl-N-(2,3,6-trifluoro-4-(2-(((3S,5S)-5-fluoropiperidin-3-yl) amino)-7-oxo-8-(tetrahydrofuran-3-yl)-7,8-dihydropyrido[2,3-d]pyrimidin-6-yl)phenyl) methanesulfonamide Compound 35

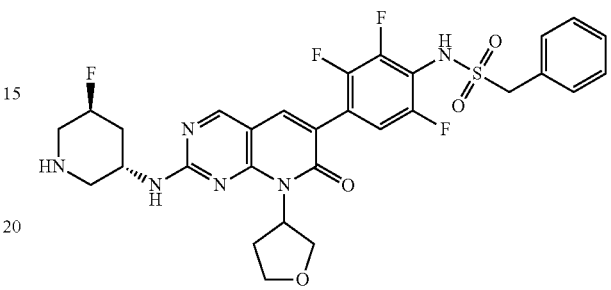

The title compound was prepared according to Example 23. This provides the title compound.

1-Phenyl-N-(2,3,6-trifluoro-4-(2-(((3S,5S)-5-fluoropiperidin-3-yl)amino)-7-oxo-8-(tetrahydrofuran-3-yl)-7,8-dihydropyrido[2,3-d]pyrimidin-6-yl)phenyl)methanesulfonamide (4.1 mg, 4.1% yield) as white solid. (rt=1.654 min, ANAL_SFC Lux 3 um Cellulose-4, 4.6*100 mm; 3 um, MeOH:ACN=1:1 (0.1% DEA) with 50% Co-Solvent, 4.0 mL/min).

1-Phenyl-N-(2,3,6-trifluoro-4-(2-(((3S,5S)-5-fluoropiperidin-3-yl)amino)-7-oxo-8-(tetrahydrofuran-3-yl)-7,8-dihydropyrido[2,3-d]pyrimidin-6-yl)phenyl)methanesulfonamide (6.3 mg, 6.3% yield) as white solid. (rt=2.909 min, ANAL_SFC Lux 3 um Cellulose-4, 4.6*100 mm; 3 um, MeOH:ACN=1:1 (0.1% DEA) with 50% Co-Solvent, 4.0 mL/min).

Example 36: N-(4-(2-(((1r,4r)-4-(Dimethylamino) cyclohexyl)amino)-8-isopropyl-7-oxo-7,8-dihydro-pyrido[2,3-d]pyrimidin-6-yl)-2,3,6-trifluorophenyl)-2,2-difluorobutane-1-sulfonamide Compound 36

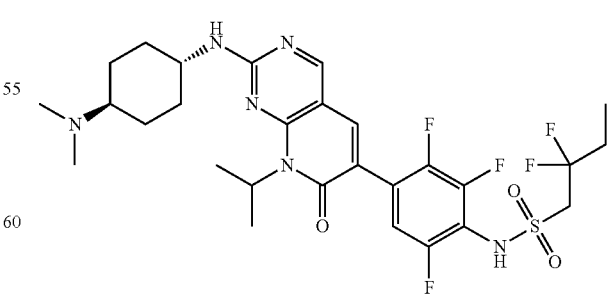

The title compound was prepared according to example 20. This provides the title compound (24.2 mg, 27.2% yield) as a white solid.

Example 37: N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)cyclopropanecarboxamide Compound 37

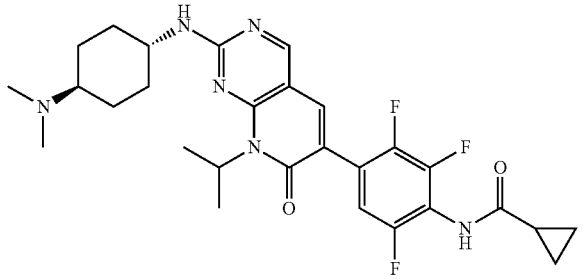 [SMILES: CC(C)n1c(=O)c(-c2cc(F)c(NC(=O)C3CC3)c(F)c2F)cc2cnc(N[C@H]3CC[C@H](N(C)C)CC3)nc21]

The title compound was prepared according to example 20. This provides the title compound (13.3 mg, 14.7% yield) as a white solid.

Example 38: 1-(1-Methyl-1H-pyrazol-3-yl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide Compound 38

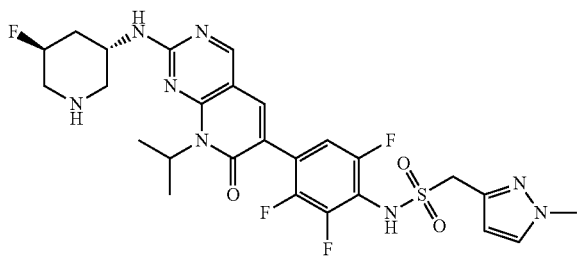 [SMILES: CC(C)n1c(=O)c(-c2cc(F)c(NS(=O)(=O)Cc3ccn(C)n3)c(F)c2F)cc2cnc(N[C@@H]3CNC[C@@H](F)C3)nc21]

The title compound was prepared according to Example 10. This provides the title compound (33.4 mg, 44.1% yield) as a white solid.

Example 39: N-(4-(8-Ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(3-(trifluoromethyl)phenyl)methanesulfonamide Compound 39

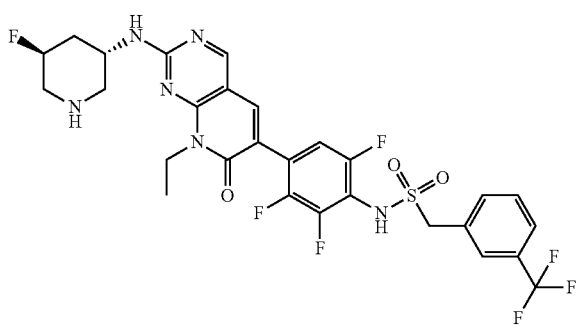 [SMILES: CCn1c(=O)c(-c2cc(F)c(NS(=O)(=O)Cc3cccc(C(F)(F)F)c3)c(F)c2F)cc2cnc(N[C@@H]3CNC[C@@H](F)C3)nc21]

Step 1: 6-Bromo-2-(methylthio)pyrido[2,3-d]pyrimidin-7(8H)-one

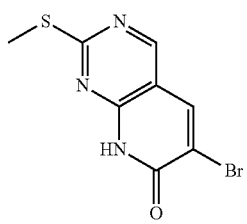

To a cooled to 0° C. solution of 2-methylsulfanyl-8H-pyrido[2,3-d]pyrimidin-7-one (5.0 g, 25.9 mmol) in N,N-dimethylformamide (129 mL) was added N-bromosuccinimide (5.53 g, 31.1 mmol). The reaction mixture was stirred at 0° C. to room temperature for 18 h. The reaction was quenched with 1N aq. $Na_2S_2O_5$ (2.6 mL) and brine (260 mL). The mixture was stirred at 25° C. for 18 h. The solid was collected by filtration, washed with water ($2X^10$ mL) and dried under high vacuum to afford the title compound (5.69 g, 81% yield) as a white solid. LCMS (ESI): $[M+H]^+$ =272.1; $^1$H NMR (400 MHz, DMSO-$d_6$) δ 12.90 (s, 1H), 8.85 (s, 1H), 8.48 (s, 1H), 2.57 (s, 3H).

Step 2: 6-Bromo-8-ethyl-2-(methylthio)pyrido[2,3-d]pyrimidin-7(8H)-one

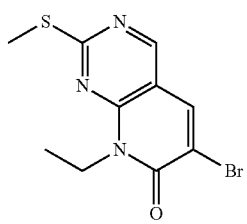 [SMILES: CCn1c(=O)c(Br)cc2cnc(SC)nc21]

To a solution of 6-bromo-2-(methylthio)pyrido[2,3-d]pyrimidin-7(8H)-one (1.0 g, 3.67 mmol) and potassium carbonate (1.02 g, 7.34 mmol) in N,N-dimethylformamide (12.2 mL) was slowly added iodoethane (0.38 mL, 4.77 mL). The reaction mixture was then stirred at 25° C. for 18 h. The reaction was quenched with 1N aq. $NH_4Cl$ (2.9 mL) and water (20 mL) and stirred at 25° C. for 24 h. The solid was collected by filtration, washed with water (2×5 mL) and dried under high vacuum to afford the title compound (0.916 g, 83% yield) as a white solid. LCMS (ESI): $[M+H]^+$=300.1; $^1$H NMR (400 MHz, DMSO-$d_6$) δ 8.88 (s, 1H), 8.52 (s, 1H), 4.39 (q, J=7.0 Hz, 2H), 2.60 (s, 3H), 1.24 (t, J=7.1 Hz, 3H).

Step 3: 6-Bromo-8-ethyl-2-(methylsulfonyl)pyrido[2,3-d]pyrimidin-7(8H)-one

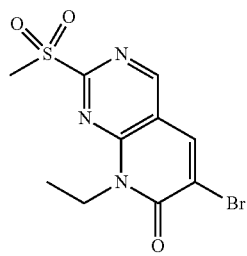 [SMILES: CCn1c(=O)c(Br)cc2cnc(S(C)(=O)=O)nc21]

To a solution of 6-bromo-8-ethyl-2-(methylthio)pyrido[2,3-d]pyrimidin-7(8H)-one (1285 mg, 4.28 mmol) in 1,4-dioxane (29 mL) was added potassium peroxymonosulfate (5530 mg, 8.99 mmol) in water (7.25 mL). The reaction mixture was stirred at 25° C. for 18 h. The reaction mixture was diluted with dichloromethane (60 mL) and aq. 1N NaHCO₃ (10 mL). The aqueous layer was extracted with dichloromethane (10 mL). The combined organic layer was dried (Na₂SO₄) and concentrated under reduced pressure to afford the title compound (1367 mg, 96% yield) as a beige solid. LCMS (ESI): [M+H]$^+$=332.1.

Step 4: Benzyl (3S,5S)-3-((6-bromo-8-ethyl-7-oxo-7,8-dihydropyrido[2,3-d]pyrimidin-2-yl)amino)-5-fluoropiperidine-1-carboxylate

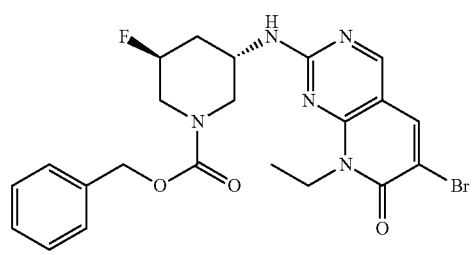 [SMILES: CCn1c(=O)c(Br)cc2cnc(N[C@H]3C[C@H](F)CN(C(=O)OCc4ccccc4)C3)nc21]

A solution of 6-bromo-8-ethyl-2-(methylsulfonyl)pyrido[2,3-d]pyrimidin-7(8H)-one mg, 3.35 mmol), cesium fluoride (1524 mg, 10.1 mmol), N,N-diisopropylethylamine (1.75 mL, 10.1 mmol) and benzyl (3S,5S)-3-amino-5-fluoro-piperidine-1-carboxylate hydrochloride (1062 mg, 3.68 mmol) in DMSO (16.7 mL) was stirred at 60° C. for 18 h. The reaction mixture was diluted with aq. 1N NH₄Cl (10 mL), water (100 mL) and dichloromethane (50 mL). The organic layer was washed with water (50 mL) and concentrated under reduced pressure. The residue was purified by column chromatography (silica gel, 10% methanol in isopropyl acetate/heptane) to afford the title compound (902 mg, 54% yield) as an off-white solid. LCMS (ESI): [M+H]$^+$=504.2; $^1$H NMR (400 MHz, DMSO-d₆) δ 12.38 (s, 1H), 8.50 (s, 1H), 8.18 (s, 1H), 4.19 (q, J=7.0 Hz, 2H), 1.15 (t, J=7.0 Hz, 3H).

Step 5: 4-Bromo-2,3,6-trifluoroaniline

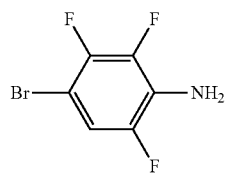

To a cooled to 0° C. solution of 2,3,6-trifluoroaniline (3.0 g, 20.4 mmol) in N,N-dimethylformamide (15 mL) was added N-bromosuccinimide (3.99 g, 22.4 mmol). The reaction mixture was stirred at 0° C. to room temperature for 2 h. The reaction mixture was diluted with water (60 mL) and dichloromethane (10 mL). The aqueous layer was extracted with dichloromethane (10 mL). The combined organic layer was dried (Na₂SO₄) and concentrated under reduced pressure to afford the title compound (7.14 g, 100% yield) as a brown oil. LCMS (ESI): [M+H]$^+$=225.9; $^1$H NMR (400 MHz, DMSO-d₆) δ 7.33 (ddd, J=10.6, 6.0, 2.5 Hz, 1H), 6.00-5.55 (m, 2H).

Step 6: 2,3,6-Trifluoro-4-(4,4,5,5-tetramethyl-1,3,2-dioxaborolan-2-yl)aniline

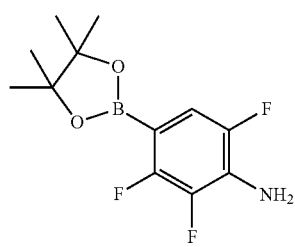 [SMILES: CC1(C)OB(c2cc(F)c(N)c(F)c2F)OC1(C)C]

A solution of 4-bromo-2,3,6-trifluoro-aniline (1.0 g, 4.43 mmol), [1,1'-Bis(diphenylphosphino)ferrocene]dichloropalladium(II) (183 mg, 0.221 mmol), Bis(pinacolato)diboron (1385 mg, 5.31 mmol) and potassium acetate (1303 mg, 13.3 mmol) in 1,4-dioxane (14.8 mL) was stirred at 80° C. for 6 h and 90° C. for 6 h. The reaction mixture was diluted with aq. sat. NH₄Cl (20 mL), water (20 mL) and dichloromethane (20 mL). The aqueous layer was extracted with dichloromethane (2×5 mL). The combined organic layer was dried over anhydrous Na₂SO₄ and concentrated under reduced pressure to afford the title compound (1.45 g, 100% yield) as a black semi-solid. LCMS (ESI): [M+H]$^+$=274.2; $^1$H NMR (400 MHz, DMSO-d₆) δ 7.00-6.89 (m, 1H), 6.08 (s, 2H), 1.17 (s, 12H).

Step 7: Benzyl (3S,5S)-3-((6-(4-amino-2,3,5-trifluorophenyl)-8-ethyl-7-oxo-7,8-dihydropyrido[2,3-d]pyrimidin-2-yl)amino)-5-fluoropiperidine-1-carboxylate

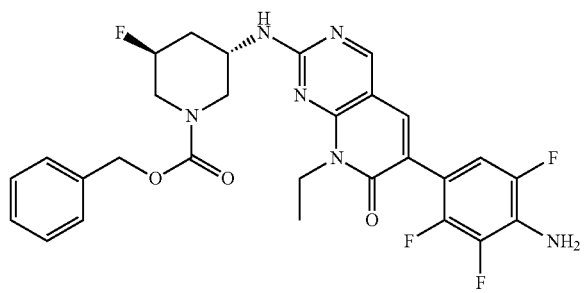 [SMILES: CCn1c(=O)c(-c2cc(F)c(N)c(F)c2F)cc2cnc(N[C@H]3C[C@H](F)CN(C(=O)OCc4ccccc4)C3)nc21]

A solution of benzyl (3S,5S)-3-((6-bromo-8-ethyl-7-oxo-7,8-dihydropyrido[2,3-d]pyrimidin-2-yl)amino)-5-fluoropiperidine-1-carboxylate (400 mg, 0.79 mmol), cesium fluoride (361 mg, 2.38 mmol), Bis(di-tert-butyl(4-dimethylaminophenyl)phosphine)dichloropalladium(II) (56 mg, 0.079 mmol) and 2,3,6-trifluoro-4-(4,4,5,5-tetramethyl-1,3,2-dioxaborolan-2-yl)aniline (541 mg, 1.98 mmol) in 1,4-dioxane (4.0 mL) was stirred at 80° C. for 18 h. The reaction mixture was diluted with water (10 mL) and 10% methanol in dichloromethane (5 mL). The aqueous layer was extracted with 10% methanol in dichloromethane (2×5 mL). The combined organic layer was dried (Na₂SO₄) and concentrated under reduced pressure to afford the title compound (940 mg, 100% yield) as a black semi-solid. LCMS (ESI): [M+H]⁺=571.3.

Step 8: Benzyl (3S,5S)-3-((8-ethyl-7-oxo-6-(2,3,5-trifluoro-4-(((3-(trifluoromethyl)phenyl)methyl)sulfonamido)phenyl)-7,8-dihydropyrido[2,3-d]pyrimidin-2-yl)amino)-5-fluoropiperidine-1-carboxylate

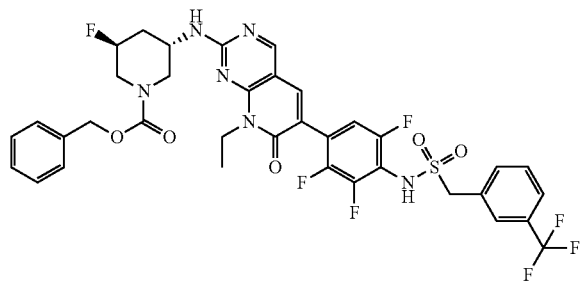 [SMILES: CCn1c(=O)c(-c2cc(F)c(NS(=O)(=O)Cc3cccc(C(F)(F)F)c3)c(F)c2F)cc2cnc(N[C@H]3C[C@H](F)CN(C(=O)OCc4ccccc4)C3)nc21]

A cooled to 0° C. solution of benzyl (3S,5S)-3-((6-(4-amino-2,3,5-trifluorophenyl)-8-ethyl-7-oxo-7,8-dihydropyrido[2,3-d]pyrimidin-2-yl)amino)-5-fluoropiperidine-1-carboxylate (60 mg, 0.105 mmol), [3-(trifluoromethyl)phenyl]methanesulfonyl chloride (82 mg, 0.316 mmol) and 4-methylmorpholine (0.035 mL, 0.316 mmol) in dichloromethane (0.526 mL) was stirred at 0° C. to room temperature for 1 h. MeOH (0.5 mL), water (0.5 mL) and potassium carbonate (69 mg, 0.5 mmol) were added and the reaction mixture was stirred at room temperature for 4 h. The reaction mixture was diluted with aq. 1N NH₄Cl (1 mL), water (4 mL) and 10% methanol in dichloromethane (5 mL). The aqueous layer was extracted with 10% methanol in dichloromethane (2×5 mL). The combined organic layer was concentrated under reduced pressure. The residue was purified by column chromatography (silica gel, 10% methanol in isopropyl acetate/heptane) to afford the title compound (15 mg, 18% yield) as a beige solid. LCMS (ESI): [M+H]⁺=793.3.

Step 9: N-(4-(8-Ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(3-(trifluoromethyl)phenyl)methanesulfonamide

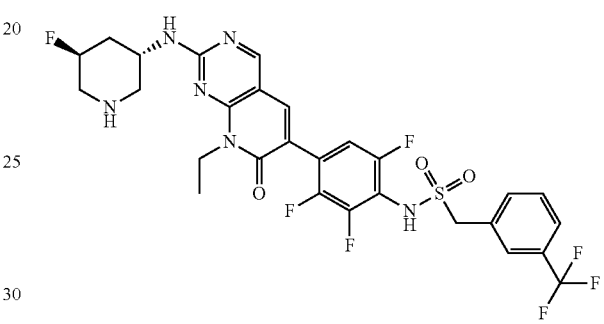

Benzyl (3S,5S)-3-((8-ethyl-7-oxo-6-(2,3,5-trifluoro-4-(((3-(trifluoromethyl)phenyl) methyl)sulfonamido)phenyl)-7,8-dihydropyrido[2,3-d]pyrimidin-2-yl)amino)-5-fluoropiperidine-1-carboxylate (15 mg, 0.019 mmol) in trifluoroacetic acid (0.19 mL) was stirred at 50° C. for 4 h. The reaction mixture was neutralized with aq. 1N NaHCO₃ and aq. sat. NH₄Cl and diluted with dichloromethane (5 mL). The aqueous layer was extracted with 10% methanol in dichloromethane (2×5 mL). The combined organic layer was concentrated under reduced pressure to afford the title compound (12.7 mg, 100% yield) as a beige solid.

Example 40: N-(2,3-Difluoro-4-(2-(((3S,5S)-5-fluoropiperidin-3-yl)amino)-7-oxo-8-(2,2,2-trifluoroethyl)-7,8-dihydropyrido[2,3-d]pyrimidin-6-yl)phenyl)-1-phenylmethanesulfonamide Compound 40

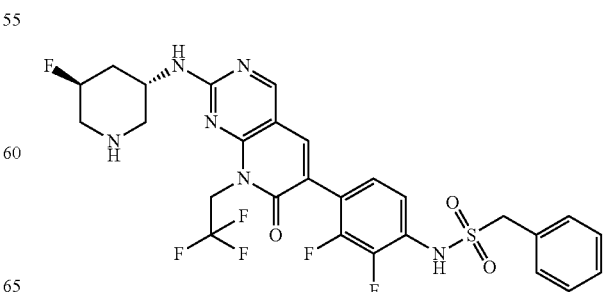

Step 1: 6-Bromo-2-(methylthio)-8-(2,2,2-trifluoroethyl)pyrido[2,3-d]pyrimidin-7(8H)-one

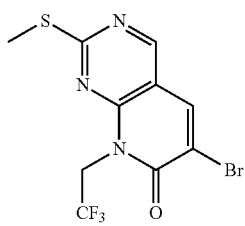 [SMILES: CSc1ncc2cc(Br)c(=O)n(CC(F)(F)F)c2n1]

To a solution of 6-bromo-2-(methylthio)pyrimidin-7(8H)-one (140 mg, 0.514 mmol) in N,N-dimethylformamide (2.57 mL) was added 2,2,2-trifluoroethyl iodide (389 mg, 1.85 mmol) and cesium carbonate (502 mg, 1.85 mmol). The reaction mixture was then stirred at 60° C. for 24 h. Additional 2,2,2-trifluoroethyl iodide (389 mg, 1.85 mmol) and cesium carbonate (502 mg, 1.85 mmol) was added and the reaction mixture was then stirred at 60° C. for 18 h and 70° C. for 24 h. The reaction mixture was diluted with water (20 mL), and dichloromethane (10 mL). The aqueous layer was extracted with dichloromethane (2×5 mL). The combined organic layer was washed with water (10 mL) and concentrated under reduced pressure to afford the title compound (138 mg, 76% yield) as a brown semi-solid. LCMS (ESI): [M+H]=354.1.

Step 2: 6-Bromo-2-(methylsulfonyl)-8-(2,2,2-trifluoroethyl)pyrido[2,3-d]pyrimidin-7(8H)-one

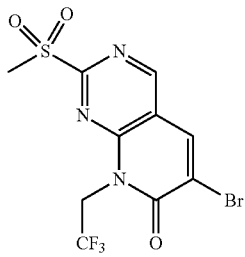 [SMILES: CS(=O)(=O)c1ncc2cc(Br)c(=O)n(CC(F)(F)F)c2n1]

To a solution of 6-bromo-2-(methylthio)-8-(2,2,2-trifluoroethyl)pyrido[2,3-d]pyrimidin-7(8H)-one (138 mg, 0.390 mmol) in dichloromethane (3.9 mL) was added meta-Chloroperoxybenzoic acid (197 mg, 0.857 mmol). The reaction mixture was stirred at 25° C. for 24 h. Additional meta-chloroperoxybenzoic acid (100 mg, 0.429 mmol) was added and the reaction mixture was stirred at 25° C. 4 h. The reaction mixture was diluted with aq. sat. NaHCO$_3$ (5 mL) and 1N aq. Na$_2$S$_2$O$_5$ (0.4 mL). The aqueous layer was extracted with dichloromethane (2×5 mL). The combined combined organic layer was washed with aq. sat. NaHCO$_3$ (5 mL), dried and concentrated under reduced pressure to afford the title compound (106 mg, 70% yield) as a brown solid. LCMS (ESI): [M+H]$^+$=386.1.

Step 3: Benzyl (3S,5S)-3-((6-bromo-7-oxo-8-(2,2,2-trifluoroethyl)-7,8-dihydropyrido[2,3-d]pyrimidin-2-yl)amino)-5-fluoropiperidine-1-carboxylate

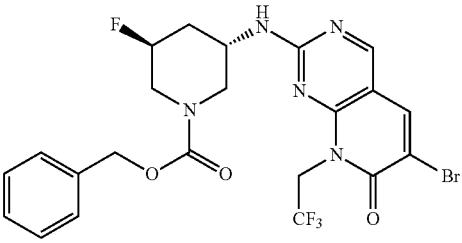 [SMILES: O=C(OCc1ccccc1)N1C[C@@H](F)C[C@H](Nc2ncc3cc(Br)c(=O)n(CC(F)(F)F)c3n2)C1]

A solution of 6-bromo-2-(methylsulfonyl)-8-(2,2,2-trifluoroethyl)pyrido[2,3-d]pyrimidin-7(8H)-one (106 mg, 0.275 mmol), cesium fluoride (125 mg, 0.824 mmol), N,N-diisopropylethylamine (0.14 mL, 0.824 mmol) and benzyl (3S,5S)-3-amino-5-fluoro-piperidine-1-carboxylate hydrochloride (87 mg, 0.302 mmol) in DMSO (1.37 mL) was stirred at 60° C. for 18 h. The reaction mixture was diluted with water (20 mL) and dichloromethane (5 mL). The aqueous layer was extracted with dichloromethane (2×5 mL). The combined organic layer was washed with water (10 mL) and concentrated under reduced pressure. The residue was purified by column chromatography (silica gel, 10% methanol in isopropyl acetate/heptane) to afford the title compound (30 mg, 20% yield) as a beige solid. LCMS (ESI): [M+H]$^+$=558.2; $^1$H NMR (400 MHz, DMSO-d$_6$) δ 8.67 (s, 1H), 8.40 (s, 1H), 8.32 (d, J=7.1 Hz, 1H), 7.40-7.20 (m, 5H), 5.20-4.85 (m, 6H), 4.30-3.95 (m, 3H), 2.35-2.15 (m, 2H), 2.00-1.70 (m, 2H).

Step 4: N-(4-Bromo-2,3-difluorophenyl)-1-phenylmethanesulfonamide

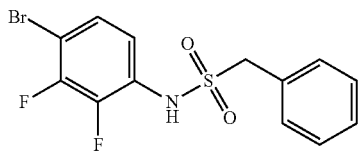 [SMILES: O=S(=O)(Cc1ccccc1)Nc1ccc(Br)c(F)c1F]

A solution of 1,4-dibromo-2,3-difluoro-benzene (1000 mg, 3.678 mmol), phenylmethanesulfonamide (756 mg, 4.41 mmol), copper iodide (140 mg, 0.736 mmol), N,N'-dimethylethylenediamine (65 mg, 0.736 mmol), and cesium carbonate (1798 mg, 5.52 mmol) in 1,4-dioxane (18 mL) was stirred at 100° C. for 48 h. The reaction mixture was diluted with aq. sat. NH$_4$Cl (25 mL) and 10% methanol in dichloromethane (25 mL). The aqueous layer was extracted with 10% methanol in dichloromethane (2×25 mL). The combined organic layer was concentrated. The residue was purified by column chromatography (silica gel, 10% methanol in isopropyl acetate/heptane) to afford the title compound (700 mg, 53% yield) as a white solid. LCMS (ESI): [M–H]$^-$=360.0; $^1$H NMR (400 MHz, DMSO-d$_6$) δ 10.09 (s, 1H), 7.44 (ddd, J=9.3, 7.1, 2.2 Hz, 1H), 7.37-7.33 (m, 5H), 7.12 (ddd, J=9.3, 7.6, 2.1 Hz, 1H), 4.55 (s, 2H).

Step 5: N-(2,3-Difluoro-4-(4,4,5,5-tetramethyl-1,3, 2-dioxaborolan-2-yl)phenyl)-1-phenylmethanesulfonamide

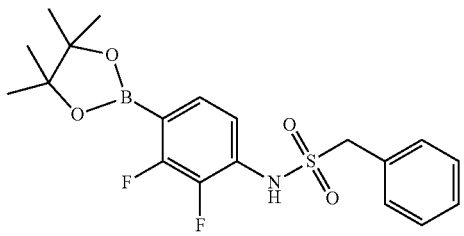 [SMILES: CC1(C)OB(c2ccc(NS(=O)(=O)Cc3ccccc3)c(F)c2F)OC1(C)C]

A solution of N-(4-bromo-2,3-difluorophenyl)-1-phenylmethanesulfonamide (0.4 g, 1.10 mmol), [1,1'-Bis(diphenylphosphino)ferrocene]dichloropalladium(II) (46 mg, 0.055 mmol), bis(pinacolato)diboron (337 mg, 1.33 mmol) and potassium acetate (326 mg, 3.31 mmol) in 1,4-dioxane (3.7 mL) was stirred at 80° C. for 18 h and 90° C. for 48 h. Additional bis(pinacolato)diboron (40 mg, 0.157 mmol) and [1,1'-bis(diphenylphosphino)ferrocene]dichloropalladium (II) (5 mg, 0.006 mmol) was added and the reaction mixture was stirred at 90° C. for 18 h. The reaction mixture was diluted with aq. sat. NH$_4$Cl (5 mL), water (5 mL) and dichloromethane (10 mL). The aqueous layer was extracted with dichloromethane (2×5 mL). The combined organic layer was dried (Na$_2$SO$_4$) and concentrated under reduced pressure to afford the title compound (738 mg, 100% yield) as a black oil. LCMS (ESI): [M+H]$^+$=410.3; $^1$H NMR (400 MHz, DMSO-d$_6$) δ 10.17 (s, 1H), 7.39-7.24 (m, 6H), 7.20-7.12 (m, 1H), 4.52 (s, 2H), 1.29 (s, 12H).

Step 6: Benzyl (3S,5S)-3-((6-(2,3-difluoro-4-((phenylmethyl)sulfonamido)phenyl)-7-oxo-8-(2,2,2-trifluoroethyl)-7,8-dihydropyrido[2,3-d]pyrimidin-2-yl) amino)-5-fluoropiperidine-1-carboxylate

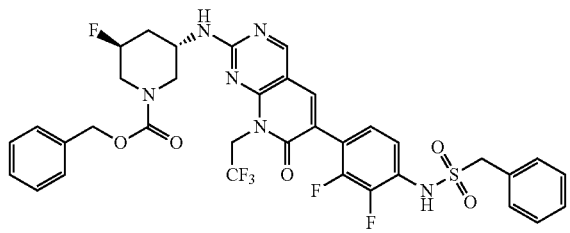

A solution of benzyl (3S,5S)-3-((6-bromo-7-oxo-8-(2,2, 2-trifluoroethyl)-7,8-dihydropyrido[2,3-d]pyrimidin-2-yl) amino)-5-fluoropiperidine-1-carboxylate (31 mg, 0.056 mmol), cesium fluoride (25 mg, 0.167 mmol), bis(di-tert-butyl(4-dimethylaminophenyl)phosphine)dichloropalladium(II) (4 mg, 0.006 mmol) and N-(2,3-difluoro-4-(4,4,5, 5-tetramethyl-1,3,2-dioxaborolan-2-yl)phenyl)-1-phenylmethanesulfonamide (59 mg, 0.139 mmol) in 1,4-dioxane (0.28 mL) was stirred at 80° C. for 6 h and 90° C. for 6 h. Additional Bis(di-tert-butyl(4-dimethylaminophenyl)phosphine)dichloropalladium(II) (4 mg, 0.006 mmol) and N-(2,3-difluoro-4-(4,4,5,5-tetramethyl-1,3,2-dioxaborolan-2-yl)phenyl)-1-phenylmethanesulfonamide (30 mg, 0.070 mmol) was added and the reaction mixture was stirred at 90° C. for 18 h. The reaction mixture was diluted with aq. sat. NH$_4$Cl (1 mL) and 10% methanol in dichloromethane (5 mL). The aqueous layer was extracted with 10% methanol in dichloromethane (2×5 mL). The combined organic layer was dried (Na$_2$SO$_4$) and concentrated under reduced pressure. The residue was purified by column chromatography (silica gel, 10% methanol in isopropyl acetate/heptane) to afford the title compound (27 mg, 64% yield) as a black semi-solid. LCMS (ESI): [M+H]$^+$=761.5.

Step 7: N-(2,3-Difluoro-4-(2-(((3S,5S)-5-fluoropiperidin-3-yl)amino)-7-oxo-8-(2,2,2-trifluoroethyl)-7, 8-dihydropyrido[2,3-d]pyrimidin-6-yl)phenyl)-1-phenylmethanesulfonamide

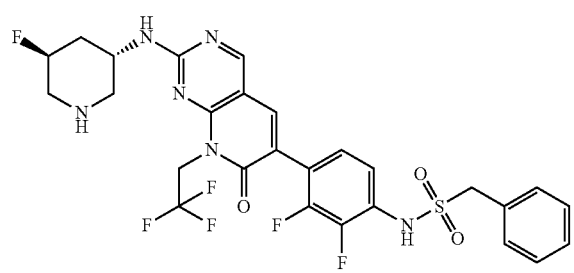 [SMILES: O=c1c(-c2ccc(NS(=O)(=O)Cc3ccccc3)c(F)c2F)cc2cnc(N[C@@H]3CNC[C@@H](F)C3)nc2n1CC(F)(F)F]

Benzyl (3S,5S)-3-((6-(2,3-difluoro-4-((phenylmethyl) sulfonamido)phenyl)-7-oxo-8-(2,2,2-trifluoroethyl)-7,8-dihydropyrido[2,3-d]pyrimidin-2-yl)amino)-5-fluoropiperidine-1-carboxylate (27 mg, 0.0369 mmol) in trifluoroacetic acid (0.36 mL) was stirred at 50° C. for 4 h. The reaction mixture was neutralized with aq. 1N NaHCO$_3$ and aq. sat. NH$_4$Cl and diluted with dichloromethane (5 mL). The aqueous layer was extracted with 10% methanol in dichloromethane (2×5 mL). The combined organic layer was concentrated under reduced pressure. The residue was purified by prep-HPLC and lyophilized to afford the title compound (21.7 mg, 94% yield) as a beige solid.

Example 41: 8-Ethyl-6-(4-(3-ethyl-2-oxopyrrolidin-1-yl)-2,3-difluorophenyl)-2-(((3S,5S)-5-fluoropiperidin-3-yl)amino)pyrido[2,3-d]pyrimidin-7(8H)-one Compound 41

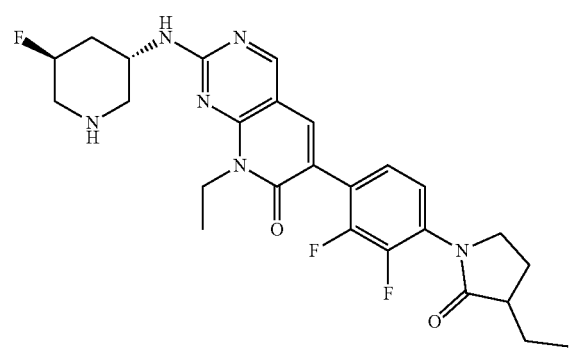 [SMILES: CCC1CCN(c2ccc(-c3cc4cnc(N[C@@H]5CNC[C@@H](F)C5)nc4n(CC)c3=O)c(F)c2F)C1=O]

Step 1: 1-(4-Bromo-2,3-difluorophenyl)-3-ethylpyrrolidin-2-one

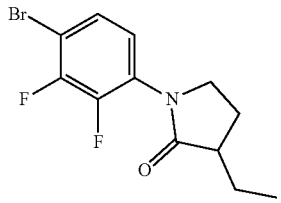 [SMILES: CCC1CCN(c2ccc(Br)c(F)c2F)C1=O]

A solution of 1,4-dibromo-2,3-difluoro-benzene (250 mg, 0.920 mmol), 3-ethylpyrrolidin-2-one (115 mg, 1.01 mmol), copper iodide (35 mg, 0.184 mmol), N,N'-dimethylethylenediamine (16 mg, 0.184 mmol), and cesium carbonate (449 mg, 1.34 mmol) in 1,4-dioxane (4.6 mL) was stirred at 100° C. for 18 h. The reaction mixture was diluted with aq. sat. ammonium chloride (5 mL) and 10% methanol in dichloromethane (5 mL). The aqueous layer was extracted with 10% methanol in dichloromethane (2×5 mL). The combined organic layer was concentrated. The residue was purified by column chromatography (silica gel, 10% methanol in isopropyl acetate/heptane) to afford the title compound (106 mg, 38% yield) as an off-white solid. LCMS (ESI): $[M+H]^+$=304.1; $^1$H NMR (400 MHz, DMSO-$d_6$) δ 7.59 (ddd, J=9.2, 7.0, 2.2 Hz, 1H), 7.32 (ddd, J=9.2, 7.1, 2.1 Hz, 1H), 3.83-3.64 (m, 2H), 2.49-2.42 (m, 1H), 2.36-2.24 (m, 1H), 1.89-1.68 (m, 2H), 1.45 (ddd, J=15.5, 14.2, 7.6 Hz, 1H), 0.95 (t, J=7.5 Hz, 3H).

Step 2: Benzyl (3S,5S)-3-((8-ethyl-6-(4-(3-ethyl-2-oxopyrrolidin-1-yl)-2,3-difluorophenyl)-7-oxo-7,8-dihydropyrido[2,3-d]pyrimidin-2-yl)amino)-5-fluoropiperidine-1-carboxylate

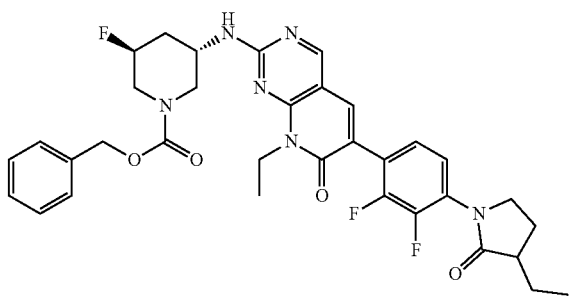 [SMILES: CCC1CCN(c2ccc(-c3cc4cnc(N[C@H]5C[C@H](F)CN(C(=O)OCc6ccccc6)C5)nc4n(CC)c3=O)c(F)c2F)C1=O]

A solution of 1-(4-bromo-2,3-difluorophenyl)-3-ethylpyrrolidin-2-one (102 mg, 0.335 mmol), [1,1'-Bis(diphenylphosphino)ferrocene]dichloropalladium(II) (14 mg, 0.017 mmol), Bis(pinacolato)diboron (102 mg, 0.403 mmol) and potassium acetate (99 mg, 1.01 mmol) in 1,4-dioxane (1.1 mL) was stirred at 80° C. for 18 h and 100° C. for 4 d. Added benzyl (3S,5S)-3-((6-bromo-8-ethyl-7-oxo-7,8-dihydropyrido[2,3-d]pyrimidin-2-yl)amino)-5-fluoropiperidine-1-carboxylate (60 mg, 0.12 mmol), bis(di-tert-butyl(4-dimethylaminophenyl)phosphine)dichloropalladium(II) (9 mg, 0.012 mmol) and cesium fluoride (54 mg, 0.36 mmol) to the reaction mixture and stirred at 80° C. for 18 h. The reaction mixture was diluted with aq. sat. NH$_4$Cl (5 mL) and 10% methanol in dichloromethane (5 mL). The aqueous layer was extracted with 10% methanol in dichloromethane (2×5 mL). The combined organic layer was concentrated under reduced pressure. The residue was purified by prep-HPLC to afford the title compound (25 mg, 12% yield) as a white solid. LCMS (ESI): $[M+H]^+$=649.4.

Step 3: 8-Ethyl-6-(4-(3-ethyl-2-oxopyrrolidin-1-yl)-2,3-difluorophenyl)-2-(((3S,5S)-5-fluoropiperidin-3-yl)amino)pyrido[2,3-d]pyrimidin-7(8H)-one

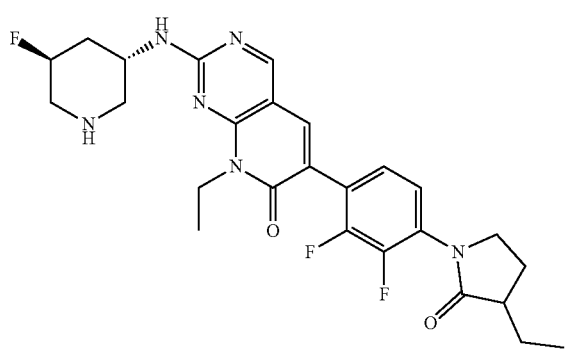

Benzyl (3S,5S)-3-((8-ethyl-6-(4-(3-ethyl-2-oxopyrrolidin-1-yl)-2,3-difluorophenyl)-7-oxo-7,8-dihydropyrido[2,3-d]pyrimidin-2-yl)amino)-5-fluoropiperidine-1-carboxylate (25 mg, 0.039 mmol) in trifluoroacetic acid (0.39 mL) was stirred at 35° C. for 18 h. The reaction mixture was neutralized with aq. sat. NaHCO$_3$ and diluted with dichloromethane (5 mL). The aqueous layer was extracted with 10% methanol in dichloromethane (2×5 mL). The combined organic layer was concentrated under reduced pressure. The residue was dissolved in ethyl acetate (0.2 mL) at 75° C. Heptane (0.2 mL) was slowly added and the mixture stirred at 75 to 25° C. for 48 h. The solid was collected, washed with heptane and dried under high vacuum to afford the title compound (20 mg, 100% yield) as a beige solid and as a mixture of diastereoisomers.

Example 42: N-(2,3-difluoro-4-(2-(((3S,5S)-5-fluoropiperidin-3-yl)amino)-7-oxo-8-(1,1,1-trifluoropropan-2-yl)-7,8-dihydropyrido[2,3-d]pyrimidin-6-yl)phenyl)-1-phenylmethanesulfonamide trifluoroacetate salt Compound 42

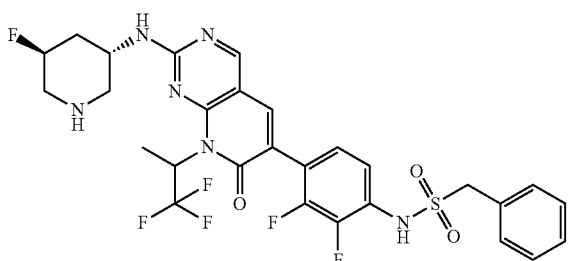

Step 1: 6-Bromo-2-(methylthio)-8-(1,1,1-trifluoropropan-2-yl)pyrido[2,3-d]pyrimidin-7(8H)-one

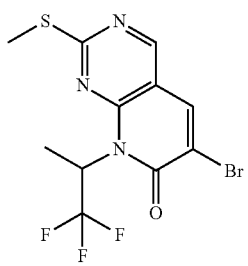 [SMILES: CSc1ncc2cc(Br)c(=O)n(C(C)C(F)(F)F)c2n1]

To a solution of 6-bromo-4-methyl-2-(methylthio)pyrido[2,3-d]pyrimidin-7(8H)-one (500 mg, 1.84 mmol) and 1,1,1-trifluoropropan-2-ol (419 mg, 3.68 mmol) in 1,4-dioxane (18.4 mL) was added triphenylphosphine (964 mg, 3.68 mmol) and DIAD (1.09 mL, 5.52 mmol). The reaction mixture was stirred at 25° C. for 18 h. Additional 1,1,1-trifluoropropan-2-ol (419 mg, 3.68 mmol), triphenylphosphine (964 mg, 3.68 mmol) and DIAD (1.09 mL, 5.52 mmol) was added and the reaction mixture stirred at 25° C. for 18 h. The reaction mixture was diluted with water (100 mL). The aqueous layer was saturated with sodium chloride and extracted with ethyl acetate (100 and 25 mL). The combined organic layer was dried (Na$_2$SO$_4$) and concentrated under reduced pressure. The residue was purified by column chromatography (silica gel, 10% methanol in isopropyl acetate/heptane) to afford the title compound (391 mg, 58% yield) as a beige solid. LCMS (ESI): [M+H]$^+$=368.1; $^1$H NMR (400 MHz, DMSO-d$_6$) δ 9.28 (s, 1H), 8.90 (s, 1H), 6.20-6.09 (m, 1H), 2.63 (s, 3H), 1.58 (d, J=6.6 Hz, 3H).

Step 2: N-(2,3-Difluoro-4-(2-(methylthio)-7-oxo-8-(1,1,1-trifluoropropan-2-yl)-7,8-dihydropyrido[2,3-d]pyrimidin-6-yl)phenyl)-1-phenylmethanesulfonamide

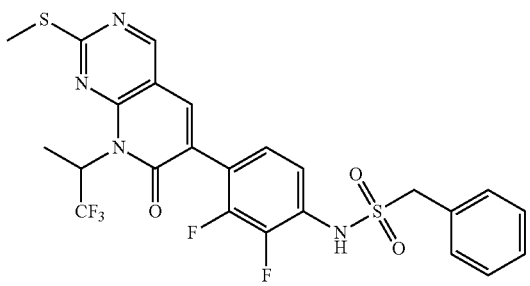 [SMILES: CSc1ncc2cc(-c3ccc(NS(=O)(=O)Cc4ccccc4)c(F)c3F)c(=O)n(C(C)C(F)(F)F)c2n1]

A solution of 6-bromo-2-(methylthio)-8-(1,1,1-trifluoropropan-2-yl)pyrido[2,3-d]pyrimidin-7(8H)-one (75 mg, 0.204 mmol), cesium fluoride (93 mg, 0.611 mmol), Bis(di-tert-butyl(4-dimethylaminophenyl)phosphine)dichloropalladium(II) (14 mg, 0.020 mmol) and N-(2,3-difluoro-4-(4,4,5,5-tetramethyl-1,3,2-dioxaborolan-2-yl)phenyl)-1-phenylmethanesulfonamide (208 mg, 0.509 mmol) in 1,4-dioxane (1.0 mL) was stirred at 80° C. for 18 h. The reaction mixture was diluted with aq. 1N NH$_4$Cl (1 mL) and 10% methanol in dichloromethane (5 mL). The aqueous layer was extracted with 10% methanol in dichloromethane (2×5 mL). The combined organic layer was concentrated under reduced pressure to afford the title compound (309 mg, 100% yield) as a black semi-solid. LCMS (ESI): [M+H]$^+$=571.2.

Step 3: N-(2,3-Difluoro-4-(2-(methylsulfonyl)-7-oxo-8-(1,1,1-trifluoropropan-2-yl)-7,8-dihydropyrido[2,3-d]pyrimidin-6-yl)phenyl)-1-phenylmethanesulfonamide

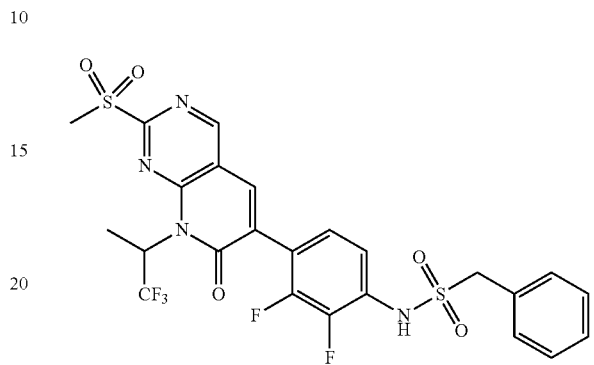

To a solution of N-(2,3-difluoro-4-(2-(methylthio)-7-oxo-8-(1,1,1-trifluoropropan-2-yl)-7,8-dihydropyrido[2,3-d]pyrimidin-6-yl)phenyl)-1-phenylmethanesulfonamide (309 mg, 0.204 mmol) in 1,4-dioxane (1.4 mL) was added potassium peroxymonosulfate (263 mg, 0.428 mmol) in water (0.4 mL). The reaction mixture was stirred at 25° C. for 18 h. The reaction mixture was diluted with dichloromethane (5 mL) and aq. 1N NaHCO$_3$ (1 mL). The aqueous layer was extracted with dichloromethane (2×5 mL). The combined organic layer was dried (Na$_2$SO$_4$) and concentrated under reduced pressure to afford the title compound (273 mg, 100% yield) as a black semi-solid. LCMS (ESI): [M+H]$^+$=603.2.

Step 4: Benzyl (3S,5S)-3-((6-(2,3-difluoro-4-((phenylmethyl)sulfonamido)phenyl)-7-oxo-8-(1,1,1-trifluoropropan-2-yl)-7,8-dihydropyrido[2,3-d]pyrimidin-2-yl)amino)-5-fluoropiperidine-1-carboxylate

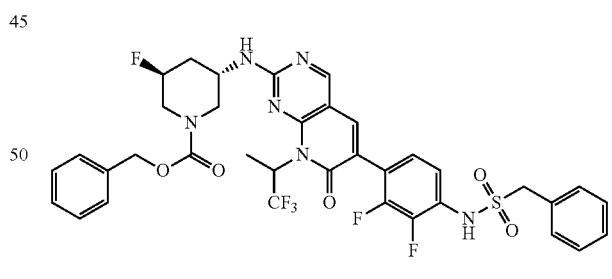

A solution of N-(2,3-difluoro-4-(2-(methylsulfonyl)-7-oxo-8-(1,1,1-trifluoropropan-2-yl)-7,8-dihydropyrido[2,3-d]pyrimidin-6-yl)phenyl)-1-phenylmethanesulfonamide (273 mg, 0.204 mmol), cesium fluoride (93 mg, 0.611 mmol), N,N-diisopropylethylamine (0.11 mL, 0.611 mmol) and benzyl (3S,5S)-3-amino-5-fluoro-piperidine-1-carboxylate hydrochloride (65 mg, 0.224 mmol) in DMSO (1.02 mL) was stirred at 60° C. for 18 h. The reaction mixture was diluted with aq. sat. NH$_4$Cl (10 mL) and dichloromethane (10 mL). The aqueous layer was extracted with dichloromethane (5 mL). The combined organic layer was concentrated under reduced pressure. The residue was purified Step 5: N-(2,3-Difluoro-4-(2-(((3S,5S)-5-fluoropiperidin-3-yl)amino)-7-oxo-8-(1,1,1-trifluoropropan-2-yl)-7,8-dihydropyrido[2,3-d]pyrimidin-6-yl)phenyl)-1-phenylmethanesulfonamide trifluoroacetate salt

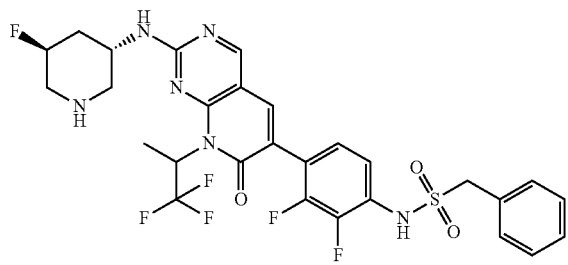 [SMILES: CC(n1c(=O)c(-c2ccc(NS(=O)(=O)Cc3ccccc3)c(F)c2F)cc2cnc(N[C@@H]3CNC[C@@H](F)C3)nc21)C(F)(F)F]

Benzyl (3S,5S)-3-((6-(2,3-difluoro-4-((phenylmethyl)sulfonamido)phenyl)-7-oxo-8-(1,1,1-trifluoropropan-2-yl)-7,8-dihydropyrido[2,3-d]pyrimidin-2-yl)amino)-5-fluoropiperidine-1-carboxylate (24 mg, 0.031 mmol) in trifluoroacetic acid (0.31 mL) was stirred at 50° C. for 5 h. The reaction mixture was concentrated and purified by prep-HPLC to afford the title compound (8 mg, 38% yield) as a beige solid and a mixture of diastereoisomers.

Example 43: (S)—N-(6-Fluoro-2,3-dimethyl-4-((3-(2-(piperidin-3-ylamino) pyrimidin-4-yl)pyridin-2-yl)oxy)phenyl)-1-phenylmethanesulfonamide Compound 43

Step 1:
2-Chloro-N-isopropyl-5-nitropyrimidin-4-amine

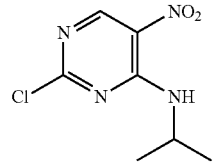

To a solution of 2,4-dichloro-5-nitropyrimidine (5.13 g, 26.4 mmol) in THF (106 mL) was added isopropylamine (2.4 mL, 27.8 mmol) at −40° C. and the reaction mixture was stirred at −40° C. for 4 h. The reaction mixture was diluted with H$_2$O (200 mL) and extracted with EtOAc (50 mL×3). The combined organic layers were washed with water and brine, dried over Mg$_2$SO$_4$, filtered and concentrated to afford 5.55 g (97% yield) of the title compound. The crude intermediate was taken onto the next step without further purification. [M+H]$^+$=217.

Step 2: Benzyl (3S,5S)-3-fluoro-5-((4-(isopropylamino)-5-nitropyrimidin-2-yl)amino)piperidine-1-carboxylate

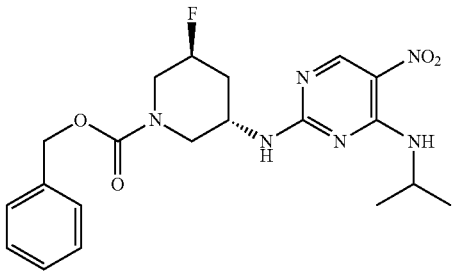 [SMILES: CC(C)Nc1nc(N[C@H]2C[C@H](F)CN(C(=O)OCc3ccccc3)C2)ncc1[N+](=O)[O-]]

Into a 20 mL sealed tube was placed 2-chloro-N-isopropyl-5-nitro-pyrimidin-4-amine (1.0 g, 4.61 mmol), DMSO (16 mL), benzyl (3S,5S)-3-amino-5-fluoro-piperidine-1-carboxylate (1.2 g, 4.85 mmol), N,N-diisopropylethylamine (2.4 mL, 13.85 mmol), and cesium fluoride (0.7 g, 4.61 mmol). The resulting solution was stirred for 3 h at 80° C. in a sand bath. The reaction mixture was cooled and diluted with 100 mL of H$_2$O. The resulting solid was filtered and dried under vacuum to afford 2 g (quantitative yield) of the title compound. The intermediate was used in the following step without further purification. [M+H]$^+$=433.

Step 3: Benzyl (3S,5S)-3-((5-amino-4-(isopropylamino)pyrimidin-2-yl)amino)-5-fluoropiperidine-1-carboxylate

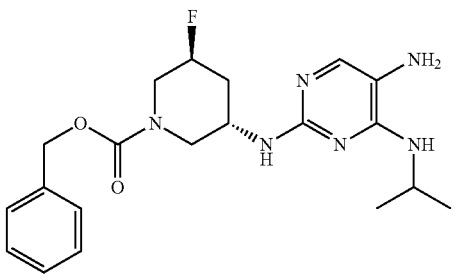 [SMILES: CC(C)Nc1nc(N[C@H]2C[C@H](F)CN(C(=O)OCc3ccccc3)C2)ncc1N]

A mixture of benzyl (3S,5S)-3-fluoro-5-[[4-(isopropylamino)-5-nitro-pyrimidin-2-yl]amino]piperidine-1-carboxylate (2.0 g, 4.62 mmol) and Pd/C (0.2 g, 1.85 mmol) in EtOH (20 mL) was stirred under H$_2$ atmosphere for 3 h. The reaction mixture was filtered over celite and evaporated to afford the title compound (1.86 g, quantitative yield) as a reddish oil which was used in the next step without further purification. LCMS (ESI): [M+H]$^+$=403.

Step 4: Benzyl (3S,5S)-3-fluoro-5-((8-isopropyl-7-oxo-7,8-dihydropteridin-2-yl)amino)piperidine-1-carboxylate

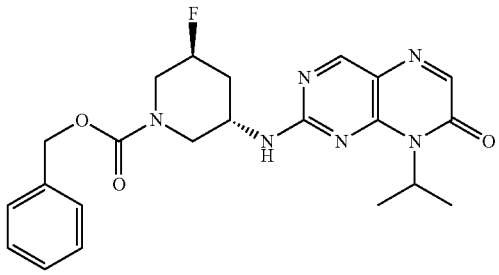 [SMILES: CC(C)n1c(=O)cnc2cnc(N[C@H]3C[C@H](F)CN(C(=O)OCc4ccccc4)C3)nc21]

A mixture of benzyl (3S,5S)-3-[[5-amino-4-(isopropylamino)pyrimidin-2-yl]amino]-5-fluoro-piperidine-1-carboxylate (1.86 g, 4.62 mmol), ethyl glyoxylate (1.0 mL, 4.86 mmol) and acetic acid (0.53 mL, 9.23 mmol) in EtOH (18.5 mL) was stirred at 100° C. for 24 h. The reaction mixture was cooled, concentrated to dryness and purified by silica column chromatography (heptanes/IprOAc gradient) to afford the title compound as a yellow solid (0.41 g, 20% yield). LCMS (ESI): [M+H]$^+$=441.

Step 5: Benzyl (3S,5S)-3-((6-bromo-8-isopropyl-7-oxo-7,8-dihydropteridin-2-yl)amino)-5-fluoropiperidine-1-carboxylate

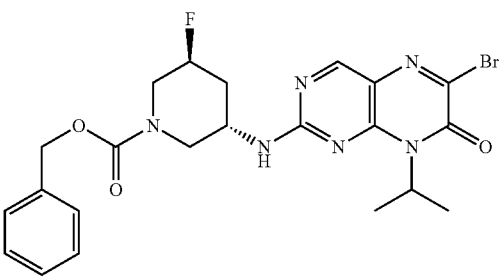 [SMILES: CC(C)n1c(=O)c(Br)nc2cnc(N[C@H]3C[C@H](F)CN(C(=O)OCc4ccccc4)C3)nc21]

To a solution of benzyl (3S,5S)-3-fluoro-5-[(8-isopropyl-7-oxo-pteridin-2-yl)amino]piperidine-1-carboxylate (0.41 g, 0.93 mmol) in DMF (18 mL) was added NBS (205 mg, 1.12 mmol) and the reaction mixture was stirred at rt overnight. Water (100 mL) was added to the reaction mixture and the resultant solid that crashed out was filtered and dried under vacuum to afford the title compound (240 mg, 50% yield). This intermediate was used in subsequent reactions without further purification. LCMS (ESI): [M+H]$^+$=520.

Step 6: Benzyl (3S,5S)-3-((6-(2,3-difluoro-4-((phenylmethyl)sulfonamido) phenyl)-8-isopropyl-7-oxo-7,8-dihydropteridin-2-yl)amino)-5-fluoropiperidine-1-carboxylate

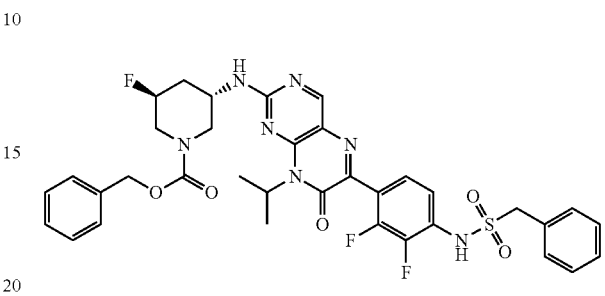

A solution of benzyl (3S,5S)-3-[(6-bromo-8-isopropyl-7-oxo-pteridin-2-yl)amino]-5-fluoro-piperidine-1-carboxylate (50 mg, 0.09 mmol), cesium fluoride (3 equiv., 0.29 mmol), AmPhos (22 mg, 0.009 mmol) and N-[2,3-difluoro-4-(4,4,5,5-tetramethyl-1,3,2-dioxaborolan-2-yl)phenyl]-1-phenyl-methanesulfonamide (98.5 mg, 0.24 mmol) in 1,4-dioxane (0.5 mL, 0.096 mmol) was stirred at 80° C. for 18 h. The reaction was diluted with DCM (25 mL) and extracted with H$_2$O (25 ml). The aqueous layer was back extracted 5× with DCM and the combined organics were dried with Mg$_2$SO$_4$, filtered, concentrated and purified by silica column chromatography (3:1 IprOAc-MeOH/heptanes gradient) to afford 40 mg (58% yield) of the title compound as a yellow solid. LCMS (ESI): [M+H]$^+$=722.

Step 7: N-(2,3-Difluoro-4-(2-(((3S,5S)-5-fluoropiperidin-3-yl)amino)-8-isopropyl-7-oxo-7,8-dihydropteridin-6-yl)phenyl)-1-phenylmethanesulfonamide

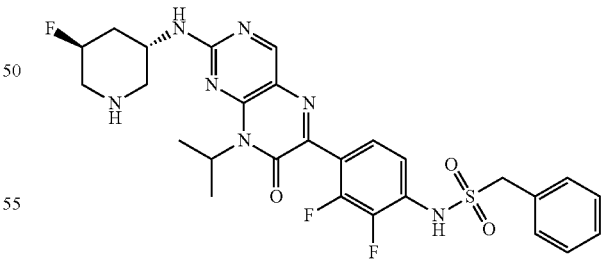

To a solution of benzyl (3S,5S)-3-[[6-[4-(benzylsulfonylamino)-2,3-difluoro-phenyl]-8-isopropyl-7-oxo-pteridin-2-yl]amino]-5-fluoro-piperidine-1-carboxylate in DCM (2 mL) was added hydrobromic acid (5 mol/L in acetic acid; 0.1 mL, 0.48 mmol). The reaction mixture was stirred for 3 h and quenched with MeOH (5 ml) and H$_2$O (0.1 mL), concentrated to dryness and purified via reverse phase HPLC to afford the title compound (16 mg, 49% yield).

Example 44: N-(2-Fluoro-4-(2-(((3S,5S)-5-fluoropiperidin-3-yl)amino)-8-isopropyl-7-oxo-7,8-dihydropteridin-6-yl)phenyl)-1-phenylmethanesulfonamide Compound 44

Step 1: Benzyl (3S,5S)-3-((6-(4-amino-3-fluorophenyl)-8-isopropyl-7-oxo-7,8-dihydropteridin-2-yl)amino)-5-fluoropiperidine-1-carboxylate

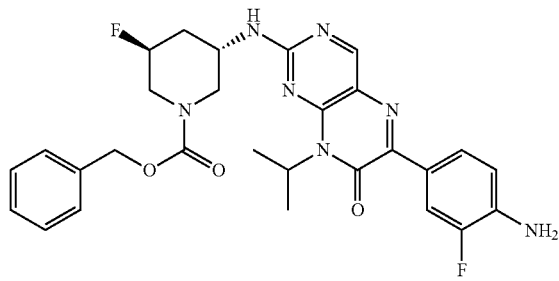 [SMILES: CC(C)n1c(=O)c(-c2ccc(N)c(F)c2)nc2cnc(N[C@H]3C[C@H](F)CN(C(=O)OCc4ccccc4)C3)nc21]

A solution of benzyl (3S,5S)-3-[(6-bromo-8-isopropyl-7-oxo-pteridin-2-yl)amino]-5-fluoro-piperidine-1-carboxylate (50 mg, 0.09 mmol), PdCl$_2$(PPh$_3$)$_2$ (6.8 mg, 0.009 mmol), Na$_2$CO$_3$ (21 mg, 0.19 mmol) and 4-amino-3-fluorophenylboronic acid pinacol ester (29 mg, 0.12 mmol) in 1,4-dioxane (0.5 mL) and H$_2$O (0.5 mL) was stirred at 75° C. for 18 h. The reaction was diluted with H$_2$O (5 mL) whereby the resultant solid that crashed out was filtered and re-suspended in DCM (50 mL). The organic layer was extracted with water, dried with Mg$_2$SO$_4$, filtered and concentrated to afford the title compound (53 mg, quantitative yield) which was used in the next step without further purification. LCMS (ESI): [M+H]$^+$=550.

Step 2: benzyl (3S,5S)-3-fluoro-5-((6-(3-fluoro-4-((phenylmethyl)sulfonamido)phenyl)-8-isopropyl-7-oxo-7,8-dihydropteridin-2-yl)amino)piperidine-1-carboxylate

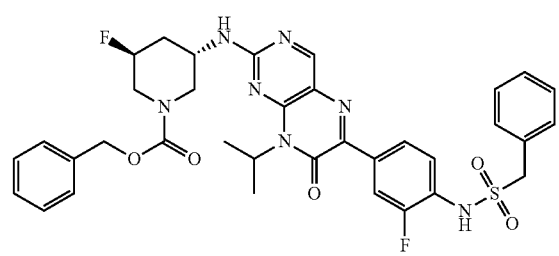 [SMILES: CC(C)n1c(=O)c(-c2ccc(NS(=O)(=O)Cc3ccccc3)c(F)c2)nc2cnc(N[C@H]3C[C@H](F)CN(C(=O)OCc4ccccc4)C3)nc21]

To a vial containing benzyl (3S,5S)-3-[[6-(4-amino-3-fluoro-phenyl)-8-isopropyl-7-oxo-pteridin-2-yl]amino]-5-fluoro-piperidine-1-carboxylate (53 mg, 0.09 mmol) in DCM (1 mL) was added pyridine (0.04 mL, 0.48 mmol) and alpha-toluenesulfonyl chloride (37 mg, 0.19 mmol). The reaction was stirred for 18 h, quenched with 2 mL of saturated bicarbonate solution and 400 mg of Fast-WoRX-S sorbent powder was added. The excess organics were rotovapped off and the powder was filtered thru a frit. The powder was then rinsed with DCM (2×5 mL) and the organics were concentrated to dryness to afford the title compound (68 mg, quantitative yield). The crude intermediate was taken directly into the next step. LCMS (ESI): [M+H]$^+$=704.

Step 3: N-(2-Fluoro-4-(2-(((3S,5S)-5-fluoropiperidin-3-yl)amino)-8-isopropyl-7-oxo-7,8-dihydropteridin-6-yl)phenyl)-1-phenylmethanesulfonamide

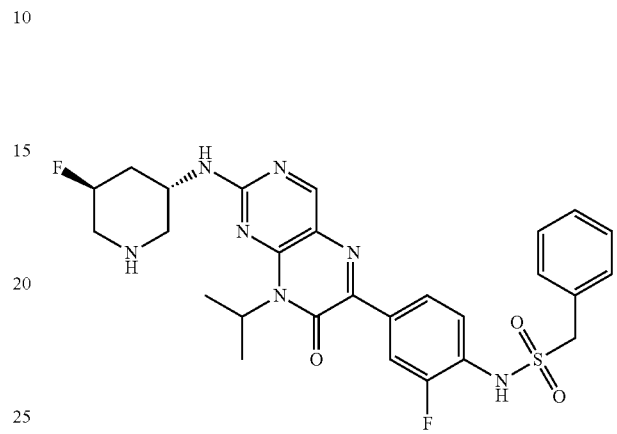

To a solution of benzyl (3S,5S)-3-[[6-[4-(benzylsulfonylamino)-3-fluoro-phenyl]-8-isopropyl-7-oxo-pteridin-2-yl]amino]-5-fluoro-piperidine-1-carboxylate (68 mg, 0.09 mmol) in DCM (3 mL) was added hydrobromic acid (5 mol/L in acetic acid; 0.1 mL, 0.48 mmol). The reaction mixture was stirred for 3 h and quenched with MeOH (5 ml) and H$_2$O (0.1 mL), concentrated to dryness and purified via reverse phase HPLC to afford the title compound (29.7 mg, 53% yield).

Example 45: N-(2,6-Difluoro-4-(2-(((3S,5S)-5-fluoropiperidin-3-yl)amino)-8-isopropyl-7-oxo-7,8-dihydropteridin-6-yl)phenyl)-1-phenylmethanesulfonamide Compound 45

Step 1: 2,6-Difluoro-4-(4,4,5,5-tetramethyl-1,3,2-dioxaborolan-2-yl)aniline

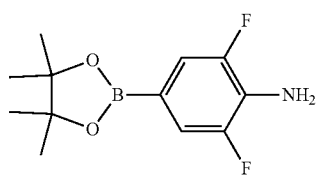 [SMILES: CC1(C)OB(c2cc(F)c(N)c(F)c2)OC1(C)C]

A solution of 4-bromo-2,6-difluoro-aniline (2.0 g, 9.62 mmol), bis(pinacolato)diboron (2.69 g, 10.6 mmol), potassium acetate (2.83 g, 28.9 mmol) and [1,1'-bis(diphenylphosphino)ferrocene]dichloropalladium(II) (0.37 g, 0.48 mmol) in 1,4-dioxane (32 mL) was stirred at 90° C. overnight. The reaction mixture was diluted with sat. NH$_4$Cl (40 mL) and DCM (40 mL) and the aqueous layer was back extracted with DCM (20 mL). The combined organic layer was dried with Mg$_2$SO$_4$ and concentrated to afford the title compound as a brown semi-solid (3.17 g, 129% yield).

Step 2: Benzyl (3S,5S)-3-((6-(4-amino-3,5-difluoro-phenyl)-8-isopropyl-7-oxo-7,8-dihydropteridin-2-yl)amino)-5-fluoropiperidine-1-carboxylate

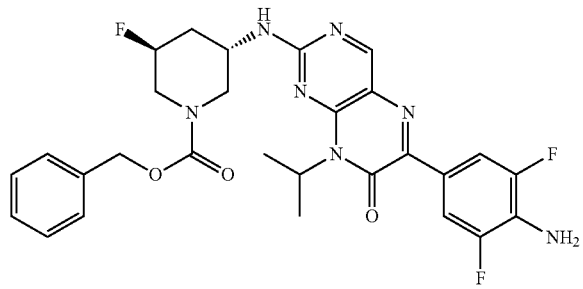 [SMILES: CC(C)n1c(=O)c(-c2cc(F)c(N)c(F)c2)nc2cnc(N[C@H]3C[C@H](F)CN(C(=O)OCc4ccccc4)C3)nc21]

A solution of benzyl (3S,5S)-3-[(6-bromo-8-isopropyl-7-oxo-pteridin-2-yl)amino]-5-fluoro-piperidine-1-carboxylate (140 mg, 0.27 mmol), PdCl$_2$(PPh$_3$)$_2$ (19 mg, 0.027 mmol), Na$_2$CO$_3$ (57 mg, 0.54 mmol) and 2,6-difluoro-4-(4,4,5,5-tetramethyl-1,3,2-dioxaborolan-2-yl)aniline (145 mg, 0.54 mmol) in 1,4-dioxane (0.5 mL) and H$_2$O (0.5 mL) was stirred at 75° C. for 18 h. The reaction was diluted with H$_2$O (5 mL) whereby the resultant solid that crashed out was filtered and re-suspended in DCM (50 mL). The organic layer was extracted with water, dried with Mg$_2$SO$_4$, filtered, concentrated and purified by silica column chromatography (3:1 IprOAc-MeOH/Heptanes gradient) to afford the title compound (130 mg, 85% yield) as a yellow solid. LCMS (ESI): [M+H]$^+$=568.

Step 3: Benzyl (3S,5S)-3-((6-(3,5-difluoro-4-((phenylmethyl)sulfonamido)phenyl)-8-isopropyl-7-oxo-7,8-dihydropteridin-2-yl)amino)-5-fluoropiperidine-1-carboxylate

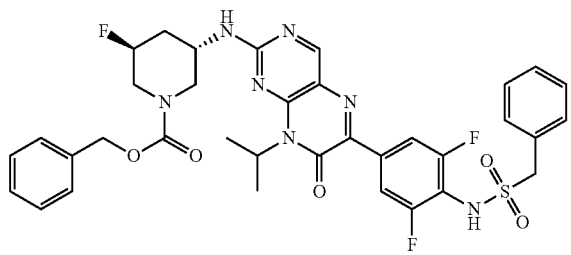 [SMILES: CC(C)n1c(=O)c(-c2cc(F)c(NS(=O)(=O)Cc3ccccc3)c(F)c2)nc2cnc(N[C@H]3C[C@H](F)CN(C(=O)OCc4ccccc4)C3)nc21]

To a vial containing benzyl (3S,5S)-3-((6-(4-amino-3,5-difluorophenyl)-8-isopropyl-7-oxo-7,8-dihydropteridin-2-yl)amino)-5-fluoropiperidine-1-carboxylate (60 mg, 0.11 mmol) in DCM (1 mL) was added 1,8-diazabicyclo[5.4.0]undec-7-ene (0.06 mL, 0.42 mmol) and alpha-toluenesulfonyl chloride (80 mg, 0.42 mmol). The reaction was stirred for 2 h then MeOH (0.5 mL), water (0.5 mL) and K$_2$CO$_3$ (0.53 mmol, 73 mg) were added and the reaction was stirred at room temperature for 18 h. The reaction mixture was diluted with 1N NH$_4$Cl (1 mL), H$_2$O (4 mL) and 10% MeOH in DCM (5 mL). The aqueous layer was extracted with 10% MeOH in DCM (5×10 mL). The combined organic layer was concentrated under reduced pressure to afford the title compound (76 mg, quantitative yield). LCMS (ESI): [M+H]$^+$=722.

Step 4: N-(2,6-difluoro-4-(2-(((3S,5S)-5-fluoropiperidin-3-yl)amino)-8-isopropyl-7-oxo-7,8-dihydropteridin-6-yl)phenyl)-1-phenylmethanesulfonamide

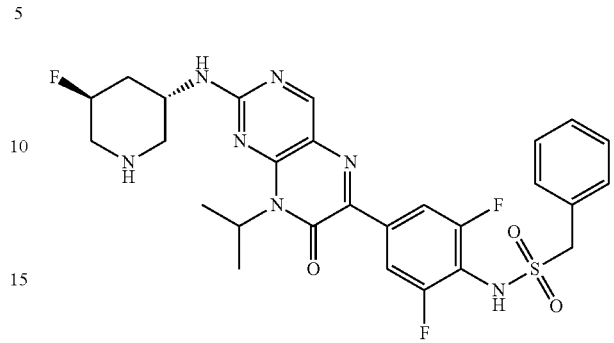

To a solution of benzyl (3S,5S)-3-((6-(3,5-difluoro-4-((phenylmethyl)sulfonamido)phenyl)-8-isopropyl-7-oxo-7,8-dihydropteridin-2-yl)amino)-5-fluoropiperidine-1-carboxylate (76 mg, 0.11 mmol) in DCM (3 mL) was added hydrobromic acid (5 mol/L in acetic acid; 0.1 mL, 0.53 mmol). The reaction mixture was stirred for 3 h and quenched with MeOH (5 ml) and H$_2$O (0.1 mL), concentrated to dryness and purified via reverse phase HPLC to afford the title compound (15.8 mg, 25% yield).

Example 46: N-(2,6-Difluoro-4-(2-(((3S,5S)-5-fluoropiperidin-3-yl)amino)-8-isopropyl-7-oxo-7,8-dihydropteridin-6-yl)phenyl)-3,3,3-trifluoropropane-1-sulfonamide Compound 46

Step 1: Benzyl (3S,5S)-3-((6-(3,5-difluoro-4-((3,3,3-trifluoropropyl)sulfonamido)phenyl)-8-isopropyl-7-oxo-7,8-dihydropteridin-2-yl)amino)-5-fluoropiperidine-1-carboxylate

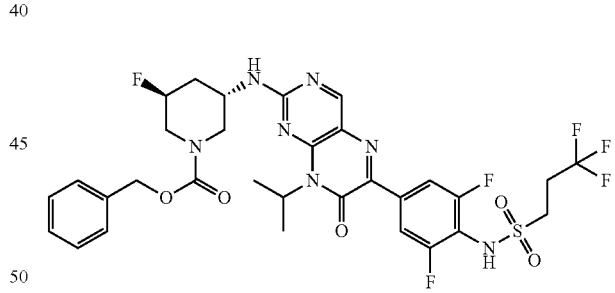

To a vial containing benzyl (3S,5S)-3-((6-(4-amino-3,5-difluorophenyl)-8-isopropyl-7-oxo-7,8-dihydropteridin-2-yl)amino)-5-fluoropiperidine-1-carboxylate (60 mg, 0.11 mmol) in DCM (1 mL) was added 1,8-diazabicyclo[5.4.0]undec-7-ene (0.06 mL, 0.42 mmol) and 3,3,3-trifluoropropane-1-sulfonyl chloride (84 mg, 0.44 mmol). The reaction was stirred for 2 h then MeOH (0.5 mL), H$_2$O (0.5 mL) and K$_2$CO$_3$ (0.53 mmol, 73 mg) were added and the reaction was stirred at room temperature for 18 h. The reaction mixture was diluted with 1N NH$_4$Cl (1 mL), H$_2$O (4 mL) and 10% MeOH in DCM (5 mL). The aqueous layer was extracted with 10% MeOH in DCM (5×10 mL). The combined organic layer was concentrated under reduced pressure to afford the title compound (77 mg, quantitative yield). LCMS (ESI): [M+H]$^+$=728.

Step 2: N-(2,6-Difluoro-4-(2-(((3S,5S)-5-fluoropiperidin-3-yl)amino)-8-isopropyl-7-oxo-7,8-dihydropteridin-6-yl)phenyl)-3,3,3-trifluoropropane-1-sulfonamide

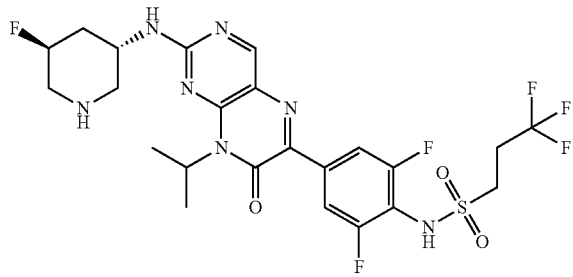 [SMILES: CC(C)n1c(=O)c(-c2cc(F)c(NS(=O)(=O)CCC(F)(F)F)c(F)c2)nc2cnc(N[C@@H]3CNC[C@@H](F)C3)nc21]

To a solution of benzyl (3S,5S)-3-((6-(3,5-difluoro-4-((3,3,3-trifluoropropyl)sulfonamido)phenyl)-8-isopropyl-7-oxo-7,8-dihydropteridin-2-yl)amino)-5-fluoropiperidine-1-carboxylate (77 mg, 0.11 mmol) in DCM (3 mL) was added hydrobromic acid (5 mol/L in acetic acid; 0.1 mL, 0.53 mmol). The reaction mixture was stirred for 3 h and quenched with MeOH (5 ml) and water (0.1 mL), concentrated to dryness and purified via reverse phase HPLC to afford the title compound (18 mg, 28% yield).

Example 47: 1-(4-cyanophenyl)-N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)methanesulfonamide (Compound 47)

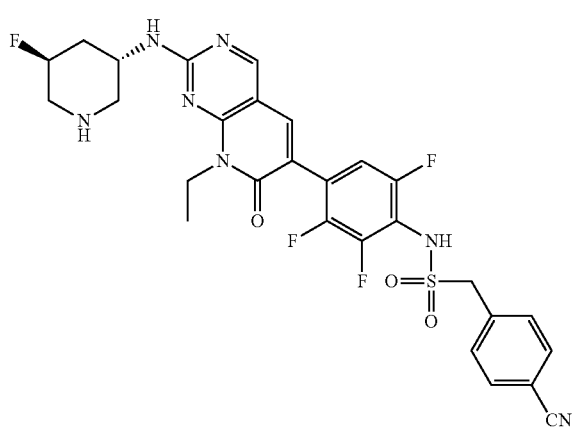 [SMILES: CCn1c(=O)c(-c2cc(F)c(NS(=O)(=O)Cc3ccc(C#N)cc3)c(F)c2F)cc2cnc(N[C@@H]3CNC[C@@H](F)C3)nc21]

The title compound was prepared according to Example 39.

Example 48: N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(1-fluorocyclopropyl)methanesulfonamide (Compound 48)

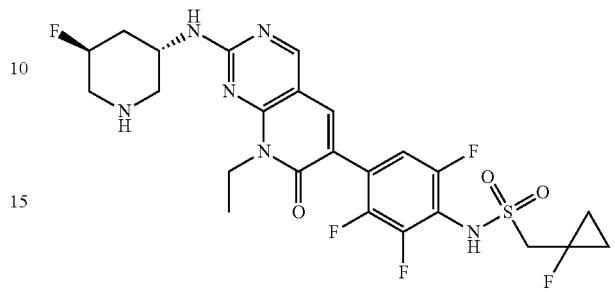

The title compound was prepared according to Example 39.

Example 49: N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(pyridin-2-yl)methanesulfonamide (Compound 49)

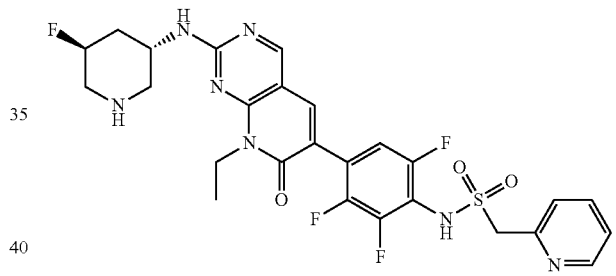

The title compound was prepared according to Example 39.

Example 50: N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)-1-(4-(trifluoromethyl)phenyl)methanesulfonamide hydrochloride (Compound 50)

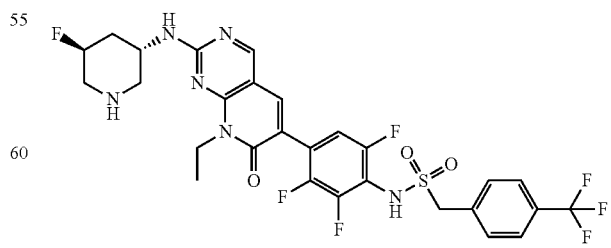

The title compound was prepared according to Example 39.

Example 51: 1-(2,6-difluorophenyl)-N-(4-(8-ethyl-2-(((3S,5S)-5-fluoropiperidin-3-yl)amino)-7-oxo-7,8-dihydropyrido[2,3-d]pyrimidin-6-yl)-2,3,6-trifluorophenyl)methanesulfonamide (Compound 51)

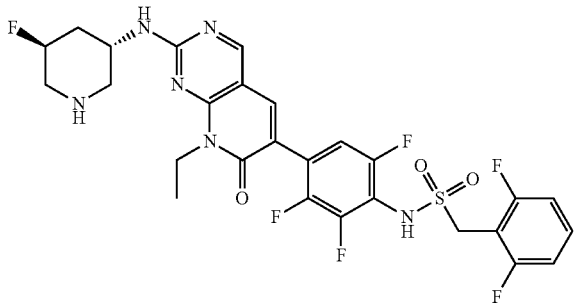 [SMILES: CCn1c(=O)c(-c2cc(F)c(NS(=O)(=O)Cc3c(F)cccc3F)c(F)c2F)cc2cnc(N[C@@H]3CNC[C@@H](F)C3)nc21]

The title compound was prepared according to Example 39.

Example 52: N-(4-(8-(cyclopropylmethyl)-2-(((3S,5S)-5-fluoropiperidin-3-yl)amino)-7-oxo-7,8-dihydropyrido[2,3-d]pyrimidin-6-yl)-2,3-difluorophenyl)-1-phenylmethanesulfonamide trifluoroacetate salt (Compound 52)

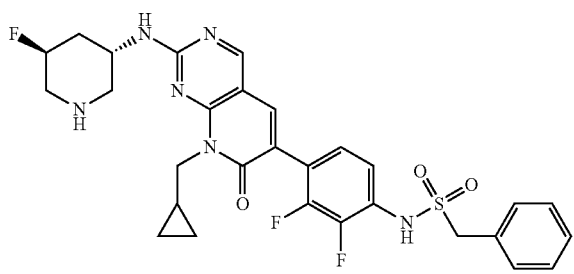 [SMILES: O=c1c(-c2ccc(NS(=O)(=O)Cc3ccccc3)c(F)c2F)cc2cnc(N[C@@H]3CNC[C@@H](F)C3)nc2n1CC1CC1]

The title compound was prepared according to Example 39.

Example 53: N-(2,3-Difluoro-4-(8-(2-fluoroethyl)-2-(((3S,5S)-5-fluoropiperidin-3-yl)amino)-7-oxo-7,8-dihydropyrido[2,3-d]pyrimidin-6-yl)phenyl)-1-phenylmethanesulfonamide (Compound 53)

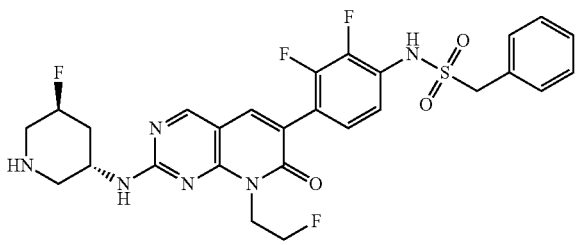 [SMILES: O=c1c(-c2ccc(NS(=O)(=O)Cc3ccccc3)c(F)c2F)cc2cnc(N[C@@H]3CNC[C@@H](F)C3)nc2n1CCF]

The title compound was prepared according to Example 23. This provides the title compound (49.7 mg, 44.0% yield) as a yellow solid.

Example 54: N-(2,3,6-Trifluoro-4-(2-(((3S,5S)-5-fluoropiperidin-3-yl)amino)-8-isopropyl-7-oxo-7,8-dihydropyrido[2,3-d]pyrimidin-6-yl)phenyl)benzenesulfonamide (Compound 54)

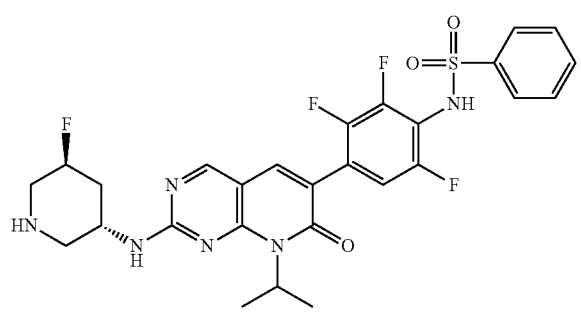 [SMILES: CC(C)n1c(=O)c(-c2cc(F)c(NS(=O)(=O)c3ccccc3)c(F)c2F)cc2cnc(N[C@@H]3CNC[C@@H](F)C3)nc21]

The title compound was prepared according to Example 2. This provides the title compound (37.7 mg, 42.1% yield) as a yellow solid.

Example 55: N-(4-(8-(3,3-Difluorocyclobutyl)-2-(((3S,5S)-5-fluoropiperidin-3-yl)amino)-7-oxo-7,8-dihydropyrido[2,3-d]pyrimidin-6-yl)-2,3,6-trifluorophenyl)-1-phenylmethanesulfonamide hydrochloride (Compound 55)

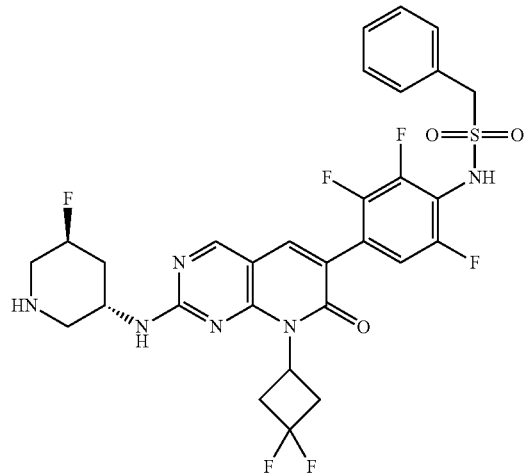 [SMILES: O=c1c(-c2cc(F)c(NS(=O)(=O)Cc3ccccc3)c(F)c2F)cc2cnc(N[C@@H]3CNC[C@@H](F)C3)nc2n1C1CC(F)(F)C1]

The title compound was prepared according to Example 2. This provides the title compound (27.1 mg, 27.9% yield) as off-white solid and as HCl salt.

Example 56: N-(4-(2-(((1r,4r)-4-Aminocyclohexyl)amino)-8-isopropyl-7-oxo-7,8-dihydropyrido[2,3-d]pyrimidin-6-yl)-2,3,6-trifluorophenyl)-1-phenyl-methanesulfonamide (Compound 56)

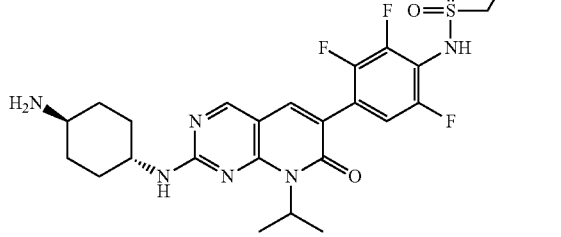

The title compound was prepared according to example Example 20. This provides the title compound (26.6 mg, 41.9% yield) as a white solid.

Example 57: 1-(4-Methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide (Compound 57)

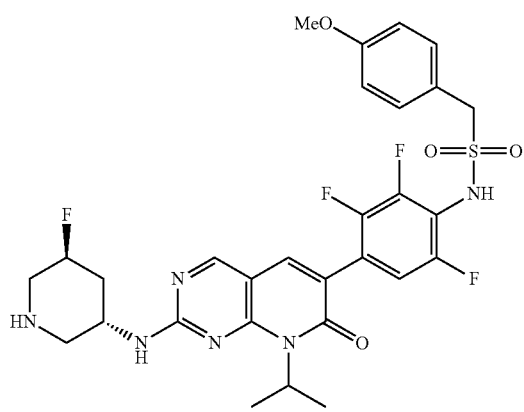 [SMILES: COc1ccc(CS(=O)(=O)Nc2c(F)cc(-c3cc4cnc(N[C@@H]5CNC[C@@H](F)C5)nc4n(C(C)C)c3=O)c(F)c2F)cc1]

The title compound was prepared according to Example 2. This provides the title compound (46.9 mg, 54.3% yield) as white solid.

Example 58: (1S,2R)—N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide (Compound 58)

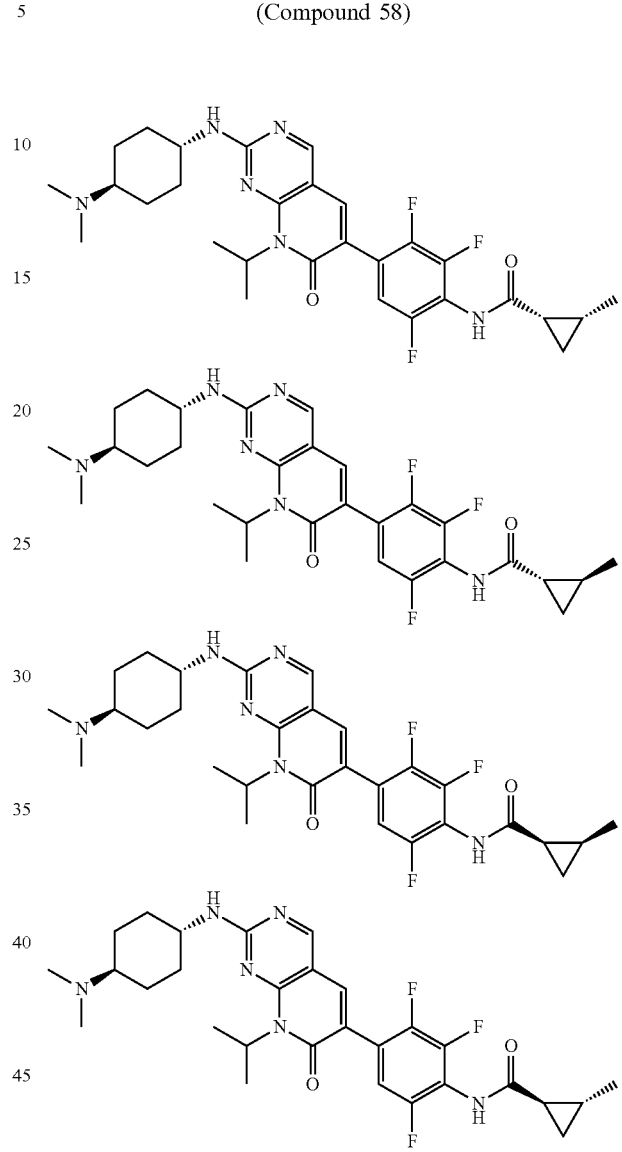

To a mixture of 2-methylcyclopropanecarboxylic acid (0.19 g, 1.9 mmol) and N,N-dimethylformamide (0.01 g, 0.1300 mmol) in dichloromethane (0.5 mL) was dropwised oxalyl chloride (0.24 g, 1.9 mmol) at 0° C., the mixture was stirred for 0.5 h at 0° C. The above solution was added to a mixture of 6-(4-amino-2,3,5-trifluorophenyl)-2-(((1r,4r)-4-(dimethylamino)cyclohexyl)amino)-8-isopropylpyrido[2,3-d]pyrimidin-7(8H)-one (0.32 g, 0.63 mmol) in pyridine (0.50 mL) at 0° C., the solution was stirred for 0.5 h at 0° C. The reaction mixture was diluted with water and extracted with dichloromethane. The organic layers were combined. The organic layer was dried over anhydrous sodium sulfate and concentrated under vacuum. The residue was purified by Prep-HPLC and chiral HPLC to afford the title compound.

N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide (4.7 mg, 1.3% yield) as white solid. (rt=2.539 min, CHIRAL Cellulose-SB, 0.46*10 cm, 3.5 μm; MtBE (0.1% DEA):MeOH=95:5; 1 mL/min).

N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide (25.5 mg, 7.2% yield) as white solid. (tR=3.510 min, CHIRAL Cellulose-SB, 0.46*10 cm, 3.5 μm, MtBE (0.1% DEA):MeOH=95:5; 1 mL/min).

N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide (4.2 mg, 1.2% yield) as white solid. (rt=4.331 min, CHIRAL Cellulose-SB, 0.46*10 cm, 3.5 μm; MtBE (0.1% DEA):MeOH=95:5; 1 mL/min).

N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-2-methylcyclopropane-1-carboxamide (22.8 mg, 6.5% yield) as white solid. (rt=4.581 min, CHIRAL Cellulose-SB, 0.46*10 cm, 3.5 μm; MtBE (0.1% DEA):MeOH=95:5; 1 mL/min).

Example 59: N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-3-methylbutanamide (Compound 59)

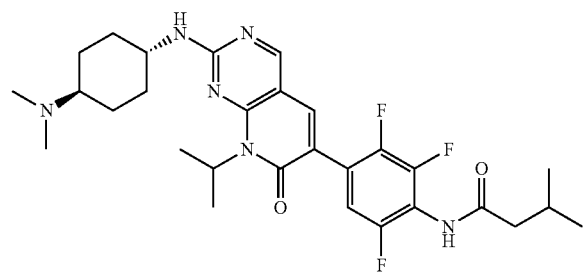 [SMILES: CC(C)CC(=O)Nc1c(F)cc(-c2cc3cnc(N[C@H]4CC[C@H](N(C)C)CC4)nc3n(C(C)C)c2=O)c(F)c1F]

A mixture of 6-(4-amino-2,3,5-trifluorophenyl)-2-(((1r,4r)-4-(dimethylamino)cyclohexyl)amino)-8-isopropylpyrido[2,3-d]pyrimidin-7(8H)-one (100 mg, 0.21 mmol) and isovalericanhydride (0.12 g, 0.63 mmol) in pyridine (0.5 mL) was stirred for 2 h at rt. The reaction was quenched with water and extracted with dichloromethane. The organic layer was washed with brine and dried over sodium sulfate. The solvent was removed. The residue was purified by Prep-HPLC to afford the title compound (21.5 mg, 18.3% yield) as a white solid.

Example 60: N-(4-(2-((4-(dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide (Compound 60)

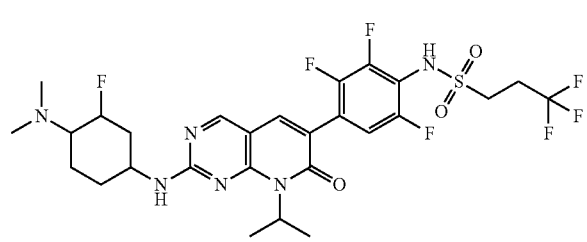 [SMILES: CC(C)n1c(=O)c(-c2cc(F)c(NS(=O)(=O)CCC(F)(F)F)c(F)c2F)cc2cnc(NC3CCC(N(C)C)C(F)C3)nc21]

Step 1: Ethyl 3-fluoro-4-oxocyclohexane-1-carboxylate

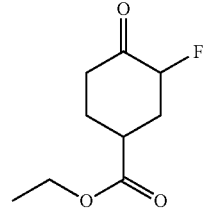

Under nitrogen, a solution of ethyl 4-oxocyclohexanecarboxylate (10 mL, 62.8 mmol) in methyl alcohol (200 mL) was added 1-chloromethyl-4-fluoro-1,4-diazoniabicyclo[2.2.2]octane bis(tetrafluoroborate) (30 g, 94 mmol) and con. sulfuric acid (0.1 mL). The resulting solution was stirred for 16 h at 60° C. The reaction was quenched with brine and extracted with ethyl acetate. The solvent was removed under vacuum. The crude product was dissolved in dichloromethane (50 mL). And 2,2,2-trifluoroacetic acid (20 mL) was added. The resulting solution was stirred for 2 h at rt. The solvent was removed. The residue was dissolved in ethyl acetate and washed with sat. sodium bicarbonate. The solvent was removed. The residue was purified by silica flash chromatography eluting with ethyl acetate/petroleum ether (1/10) to afford the title compound (11.2 g, 94.8% yield) as a yellow solid. $^1$H NMR (400 MHz, DMSO-$d_6$) δ 5.38-5.08 (m, 1H), 4.19-4.08 (m, 2H), 3.11-2.95 (m, 1H), 2.63-2.52 (m, 2H), 2.52-2.13 (m, 2H), 2.12-1.89 (m, 1H), 1.92-1.59 (m, 1H), 1.22 (dt, J=13.5, 7.1 Hz, 3H).

Step 2: Ethyl 4-(dimethylamino)-3-fluorocyclohexane-1-carboxylate

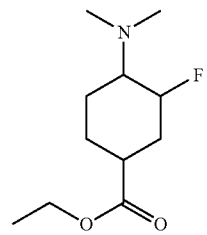

A solution of ethyl 3-fluoro-4-oxo-cyclohexanecarboxylate (10.0 g, 53.1 mmol) in 1,2-dichloroethane (150 mL) was added N,N-dimethylamine (35 mL, 70 mmol) and sodium triacetoxyborohydride (17 g, 80.2 mmol). Then acetic acid (3 mL) was added. The resulting solution was stirred for 12 h at rt. The reaction was quenched with sat. sodium carbonate and extracted with ethyl acetate. The solvent was removed under vacuum. The residue was purified by silica flash chromatography eluting with dichloromethane/methanol (5:1) to afford the title compound (9.5 g, 82.3% yield) as yellow oil. LCMS (ESI): [M+H]$^+$=218.

Step 3: 4-(Dimethylamino)-3-fluorocyclohexane-1-carboxylic acid hydrochloride

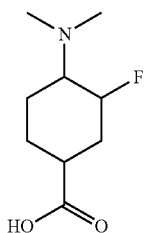

A solution of ethyl 4-(dimethylamino)-3-fluorocyclohexane-1-carboxylate (9.5 g, 46.7 mmol) in 1,4-dioxane (50 mL) was added 6 M HCl in dioxane (50 mL) and stirred for 24 h at 100° C. The solvent was removed under vacuum to afford the title compound (10 g, 94.8% yield) as a yellow solid. LCMS (ESI): [M+H]$^+$=190.

Step 4: Benzyl (4-(dimethylamino)-3-fluorocyclohexyl)carbamate

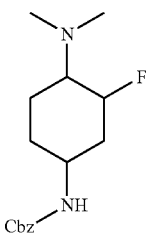

Under nitrogen, a solution of 4-(dimethylamino)-3-fluoro-cyclohexanecarboxylic acid hydrochloride (10.0 g, 44.3 mmol) in toluene (200 mL) was added diphenylphosphoryl azide (11 mL, 51.1 mmol) and N,N-diisopropylethylamine (40 mL, 241.9 mmol) at rt and then stirred for 4 h at 100° C. Then the solution was cooled to 50° C. Benzyl alcohol (20 mL, 193.3 mmol) was added and stirred for 2 h at 100° C. The reaction was quenched with brine and extracted with ethyl acetate. The residue was purified by silica flash chromatography eluting with dichloromethane/methanol (10/1) and reverse phase (ACN/10 mM NH$_4$HCO$_3$) to afford the title compound (4.6 g, 35.3% yield) as a yellow oil. LCMS (ESI): [M+H]$^+$=295.

Step 5: 2-Fluoro-N$^1$, N$^1$-dimethylcyclohexane-1,4-diamine hydrochloride

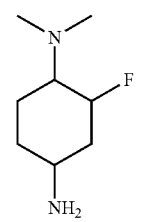

Under hydrogen, a mixture of benzyl (4-(dimethylamino)-3-fluorocyclohexyl)carbamate (2.0 g, 6.79 mmol) and 10% Pd/C (0.2 g) in methyl alcohol (30 mL) was added con. HCl (0.1 mL) and stirred for 2 h at rt. The solids were filtered out. The filtrate was concentrated under vacuum to afford the title compound (1.2 g, 89.8% yield) as a white solid. LCMS (ESI): [M+H]$^+$=161.

Step 6: N-(4-(2-((4-(Dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide & N-(4-(2-((4-(dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide (Compound 60)

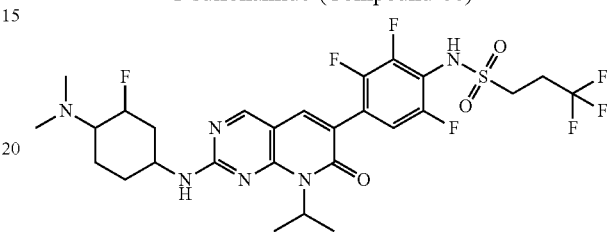

A solution of 3,3,3-trifluoro-N-(2,3,6-trifluoro-4-(8-isopropyl-2-(methylsulfonyl)-7-oxo-7,8-dihydropyrido[2,3-d]pyrimidin-6-yl)phenyl)propane-1-sulfonamide (1.0 g, 1.75 mmol), 2-fluoro-N$^1$, N$^1$-dimethylcyclohexane-1,4-diamine hydrochloride (350 mg, 2.18 mmol), caesium fluoride (850 mg, 5.59 mmol) and N,N-diisopropylethylamine (850 mg, 6.59 mmol) in dimethyl sulfoxide (20 mL) was stirred for 2 h at 80° C. under nitrogen. The resulting solution was diluted with water and extracted with ethyl acetate. The organic layers was washed with brine, dried over anhydrous sodium sulfate and concentrated. The residue was purified by silica flash chromatography eluting with dichloromethane/methanol (5/1). The crude product was further purified by Prep-HPLC and Chiral SFC.

N-(4-(2-((4-(Dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide (44.9 mg, 3.9% yield) as light yellow solid.

N-(4-(2-((4-(Dimethylamino)-3-fluorocyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide (184.2 mg, 16.2% yield) as light yellow solid.

Example 61: 2-Chloro-N-(2,3,6-trifluoro-4-(2-(((3S, 5S)-5-fluoropiperidin-3-yl)amino)-8-isopropyl-7-oxo-7,8-dihydropyrido[2,3-d]pyrimidin-6-yl)phenyl)benzenesulfonamide hydrochloride (Compound 61)

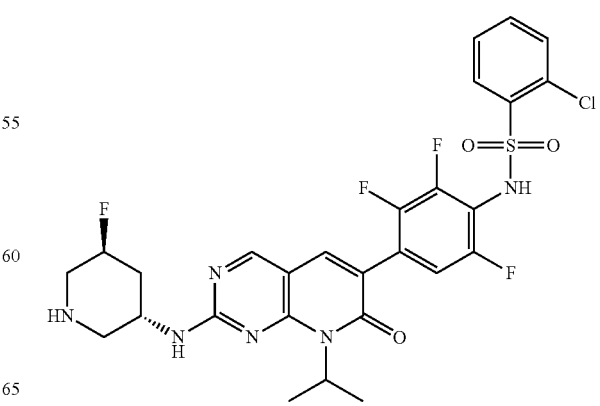

The title compound was prepared according to example Example 2. This provides the title compound (9.4 mg, 10.1% yield) as a yellow solid and as HCl salt.

Example 62: 2-Cyclobutyl-N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)acetamide (Compound 62)

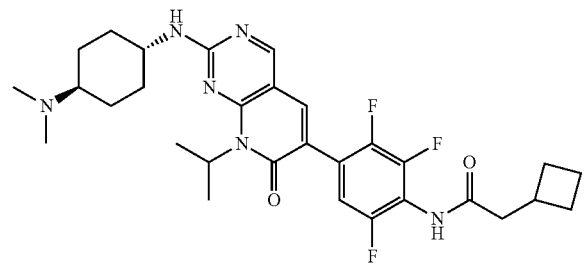 [SMILES: CC(C)n1c(=O)c(-c2cc(F)c(NC(=O)CC3CCC3)c(F)c2F)cc2cnc(N[C@H]3CC[C@H](N(C)C)CC3)nc21]

The title compound was prepared according to Example 58. This provides the title compound (25.6 mg, 21.3% yield) as a white solid.

Example 63: (1R,2R)—N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide hydrochloride (Compound 63)

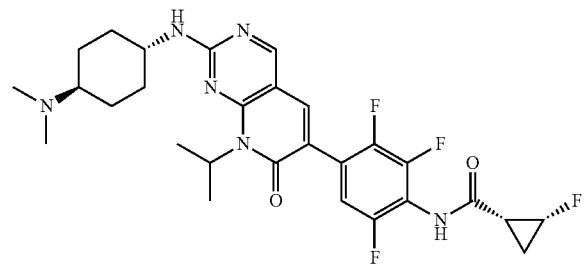 [SMILES: CC(C)n1c(=O)c(-c2cc(F)c(NC(=O)[C@H]3C[C@H]3F)c(F)c2F)cc2cnc(N[C@H]3CC[C@H](N(C)C)CC3)nc21]

The title compound was prepared according to Example 58. This provides the title compound (27.0 mg, 21.3% yield) as a yellow solid and as HCl salt.

Example 64: N-(2-Fluoro-4-(2-(((3S,5S)-5-fluoro-5-methylpiperidin-3-yl)amino)-8-isopropyl-7-oxo-7,8-dihydropteridin-6-yl)phenyl)-1-phenylmethanesulfonamide (Compound 64)

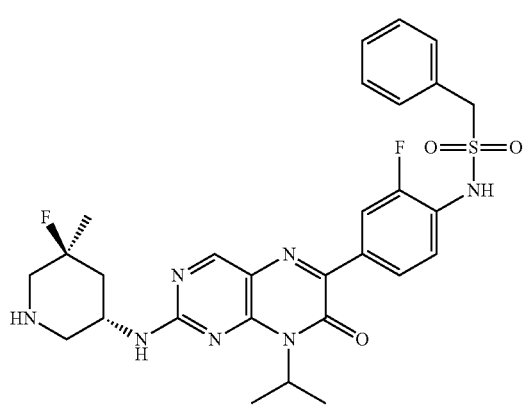 [SMILES: CC(C)n1c(=O)c(-c2ccc(NS(=O)(=O)Cc3ccccc3)c(F)c2)nc2cnc(N[C@@H]3CNC[C@@](C)(F)C3)nc21]

Step 1: 2-Chloro-N-isopropyl-5-nitropyrimidin-4-amine

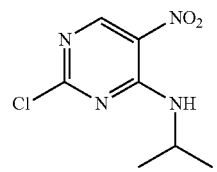

A solution of 2, 4-dichloro-5-nitropyrimidine (11.8 g, 60.6 mmol) in tetrahydrofuran (200 mL) was added N,N-diisopropylethylamine (40 g, 310 mmol) and isopropylamine (6 mL, 60 mmol) at 25° C. and stirred for 1 h. The reaction mixture was diluted with water and extracted with dichloromethane. The organic layers were combined. The organic layer was dried over anhydrous sodium sulfate and concentrated under vacuum. The residue was purified by silica flash chromatography eluting with ethyl acetate/petroleum ether (1:2) to afford the title compound (6.7 g, 51.1% yield) as a yellow solid. LCMS (ESI): [M+1]+=217.0.

Step 2: N-Isopropyl-2-(methylthio)-5-nitropyrimidin-4-amine

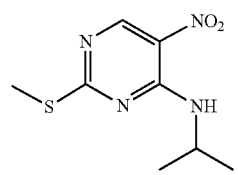

A solution of 2-chloro-N-isopropyl-5-nitro-pyrimidin-4-amine (8.0 g, 36.9 mmol) in tetrahydrofuran (40 mL) was added sodium thiomethoxide (5.0 g, 70.4 mmol) and stirred for 1 h at 25° C. The reaction mixture was diluted with water and extracted with dichloromethane. The organic layers were combined. The organic layer was dried over anhydrous sodium sulfate and concentrated under vacuum. The residue was purified by silica flash chromatography eluting with ethyl acetate/petroleum ether (1:2) to afford the title compound (8 g, 94.9% yield) as a yellow solid. LCMS (ESI): [M+1]=229.1.

Step 3: $N^4$—Isopropyl-2-(methylthio)pyrimidine-4,5-diamine

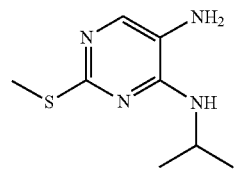

A solution of N-isopropyl-2-methylsulfanyl-5-nitro-pyrimidin-4-amine (2.38 g, 10.4 mmol) in methyl alcohol (30 mL) was added 10% Pd/C (1.0 g) and stirred for 2 h at 25° C. under hydrogen. The solids were filtered out. The solvent was concentrated under vacuum. The residue was purified by silica flash chromatography eluting with dichloromethane/methanol (10:1) to afford the title compound (1.65 g, 79.8% yield) as a purple solid. LCMS (ESI): [M+1]+=199.0.

Step 4: 8-Isopropyl-2-(methylthio)pteridin-7(8H)-one

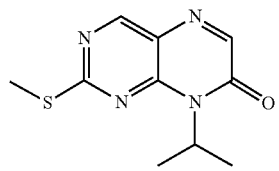

A solution of N⁴-isopropyl-2-(methylthio)pyrimidine-4,5-diamine (1.9 g, 9.58 mmol) in ethanol (500 mL) was added ethyl 2-oxoacetate (2.5 mL, 12.61 mmol) and acetic acid glacial (3 mL, 9.58 mmol) and stirred for overnight at 85° C. The reaction was quenched with water and extracted with ethyl acetate. The organic layer was dried over anhydrous sodium sulfate and concentrated under vacuum. The residue was purified by silica flash chromatography eluting with ethyl acetate/petroleum ether (1/5) to afford the title compound (1.09 g, 48.1% yield) as a yellow solid. LCMS (ESI): [M+1]=237.1.

Step 5: 6-(4-Bromo-3-fluorophenyl)-8-isopropyl-2-(methylthio)pteridin-7(8H)-one

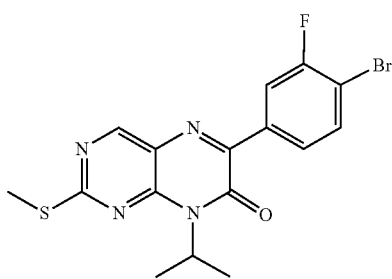 [SMILES: CSc1ncc2nc(-c3ccc(Br)c(F)c3)c(=O)n(C(C)C)c2n1]

Under nitrogen, a solution of 4-bromo-3-fluoro-aniline (1.6 g, 8.42 mmol) in acetonitrile (50 mL) was added nitrous acid tert-butyl ester (1.3 g, 12.6 mmol) at 0° C. The resulting solution was stirred for 30 min at the same temperature. Then the mixture was added to a solution of 8-isopropyl-2-(methylthio)pteridin-7(8H)-one (500 mg, 2.1 mmol) in acetonitrile (5 mL) at 0° C. and stirred for overnight at rt. The reaction mixture was diluted with water and extracted with dichloromethane. The organic layers were combined. The organic layer was dried over anhydrous sodium sulfate and concentrated under vacuum. The residue was purified by silica flash chromatography eluting with ethyl acetate/petroleum ether (1/9) to afford the title compound (320 mg, 36.9% yield) as a yellow solid. LCMS (ESI): [M+1]=409.3.

Step 6: N-(2-Fluoro-4-(8-isopropyl-2-(methylthio)-7-oxo-7,8-dihydropteridin-6-yl)phenyl)-1-phenyl-methanesulfonamide

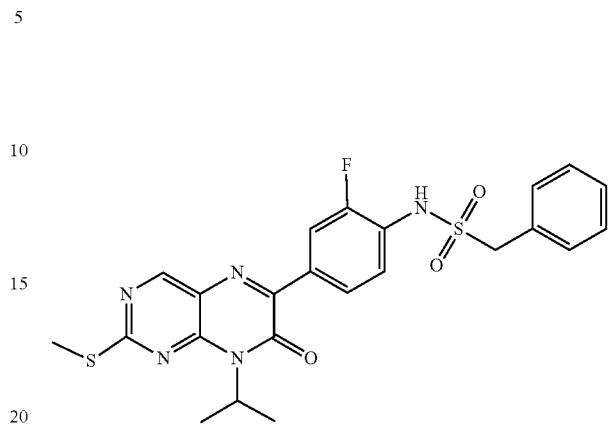

Under nitrogen, a solution of 6-(4-bromo-3-fluoro-phenyl)-8-isopropyl-2-methylsulfanyl-pteridin-7-one (500 mg, 1.22 mmol) in 1,4-dioxane (12 mL) was added potassium carbonate (860 mg, 6.23 mmol), [(2-Di-tert-butylphosphino-3,6-dimethoxy-2',4',6'-triisopropyl-1,1'-biphenyl)-2-(2'-amino-1,1'-biphenyl)]palladium(II) methanesulfonate (320 mg, 0.37 mmol) and benzyl sulfonamide (275 mg, 1.61 mmol) and stirred for 1 h at 80° C. for 1 h. The reaction mixture was diluted with water and extracted with dichloromethane. The organic layers were combined. The organic layer was dried over anhydrous sodium sulfate and concentrated under vacuum. The residue was purified by silica flash chromatography eluting with ethyl acetate/petroleum ether (1:2) to afford the title compound (195 mg, 32% yield) as a yellow solid. LCMS (ESI): [M+1]+=500.1.

Step 7: N-(2-Fluoro-4-(8-isopropyl-2-(methylsulfonyl)-7-oxo-7,8-dihydropteridin-6-yl)phenyl)-1-phenylmethanesulfonamide

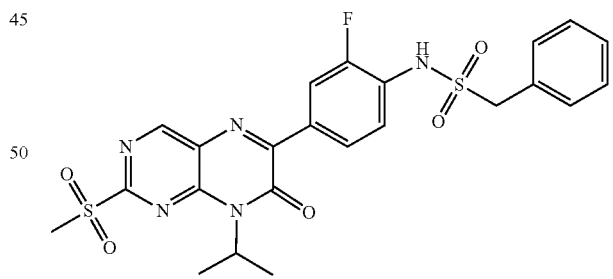

A solution of N-(2-fluoro-4-(8-isopropyl-2-(methylthio)-7-oxo-7,8-dihydropteridin-6-yl)phenyl)-1-phenylmethanesulfonamide (90 mg, 0.18 mmol) in dichloromethane (5 mL) was added 3-chloroperoxybenzoic acid (96 mg, 0.56 mmol) and stirred for 1 h at 25° C. The reaction was quenched with sat. sodium sulfite solution. The resulting solution was extracted with dichloromethane and washed with sat. sodium carbonate. The organic layer was dried over anhydrous sodium sulfate and concentrated under vacuum to afford the title compound (80 mg, 83.5% yield) as a yellow solid. LCMS (ESI): [M+1]⁺=532.1.

Step 8: Benzyl (3S,5S)-3-fluoro-5-((6-(3-fluoro-4-((phenylmethyl)sulfonamido)phenyl)-8-isopropyl-7-oxo-7,8-dihydropteridin-2-yl)amino)-3-methylpiperidine-1-carboxylate

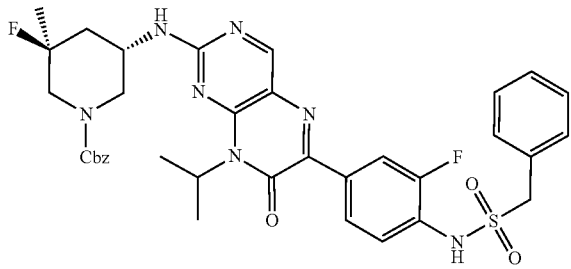 [SMILES: CC(C)n1c(=O)c(-c2ccc(NS(=O)(=O)Cc3ccccc3)c(F)c2)nc2cnc(N[C@@H]3CN(C(=O)OCc4ccccc4)C[C@@](C)(F)C3)nc21]

Under nitrogen, a solution of N-(2-fluoro-4-(8-isopropyl-2-(methylsulfonyl)-7-oxo-7,8-dihydropteridin-6-yl)phenyl)-1-phenylmethanesulfonamide (120 mg, 0.23 mmol) and benzyl (3S,5S)-5-amino-3-fluoro-3-methyl-piperidine-1-carboxylate (62 mg, 0.23 mmol) in dimethyl sulfoxide (5 mL) was added N,N-diisopropylethylamine (152 mg, 1.18 mmol) and caesium fluoride (72 mg, 0.47 mmol) and stirred for 2 h at 80° C. The reaction mixture was diluted with water and extracted with ethyl acetate. The organic layers were combined. The organic layer was washed with brine. The residue was purified by silica flash chromatography eluting with ethyl acetate/petroleum ether (1:1) to afford the title compound (60 mg, 37% yield) as a yellow solid. LCMS (ESI): [M+1]=718.3.

Step 9: N-(2-Fluoro-4-(2-(((3S,5S)-5-fluoro-5-methylpiperidin-3-yl)amino)-8-isopropyl-7-oxo-7,8-dihydropteridin-6-yl)phenyl)-1-phenylmethanesulfonamide (Compound 64)

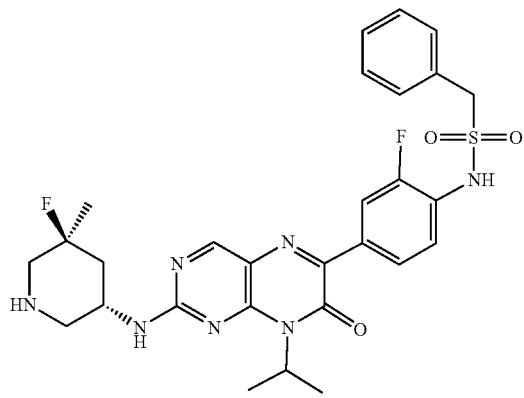 [SMILES: CC(C)n1c(=O)c(-c2ccc(NS(=O)(=O)Cc3ccccc3)c(F)c2)nc2cnc(N[C@@H]3CNC[C@@](C)(F)C3)nc21]

A solution of benzyl (3S,5S)-3-fluoro-5-((6-(3-fluoro-4-((phenylmethyl)sulfonamido)phenyl)-8-isopropyl-7-oxo-7,8-dihydropteridin-2-yl)amino)-3-methylpiperidine-1-carboxylate (100 mg, 0.14 mmol) in dichloromethane (3 mL) was added 33% HBr in acetic acid (1 mL) and stirred for 1 h at 25° C. The solvent was concentrated under vacuum. The residue was purified by Prep-HPLC to afford the title compound (33.9 mg, 41.7% yield) as a yellow solid.

Example 65: N-(2-Fluoro-4-(2-(((3S,5R)-5-(fluoromethyl)piperidin-3-yl)amino)-8-isopropyl-7-oxo-7,8-dihydropteridin-6-yl)phenyl)-1-phenylmethanesulfonamide (Compound 65)

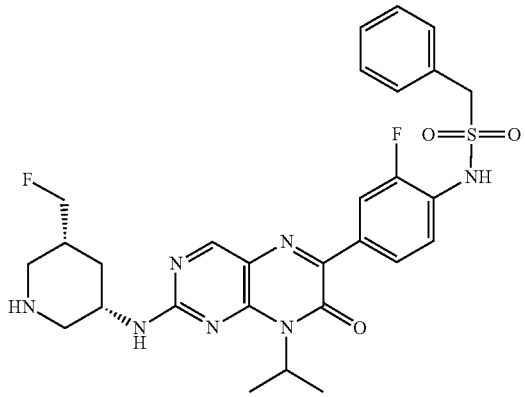 [SMILES: CC(C)n1c(=O)c(-c2ccc(NS(=O)(=O)Cc3ccccc3)c(F)c2)nc2cnc(N[C@@H]3CNC[C@H](CF)C3)nc21]

The title compound was prepared according to Example 64. This provides the title compound (40.1 mg, 44.3% yield) as a white solid.

Example 66: N-(4-(2-(((1r,4r)-4-(Dimethylamino)cyclohexyl)amino)-8-isopropyl-7-oxo-7,8-dihydropteridin-6-yl)-2-fluorophenyl)-3,3-difluorobutane-1-sulfonamide (Compound 66)

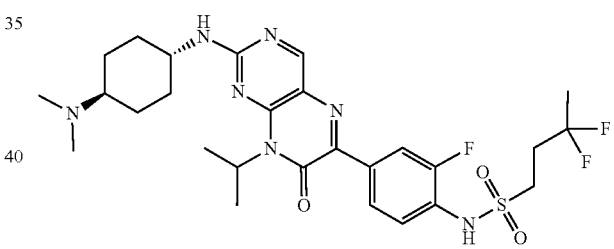

Step 1: 6-(4-((Diphenylmethylene)amino)-3-fluorophenyl)-8-isopropyl-2-(methylthio)pteridin-7(8H)-one

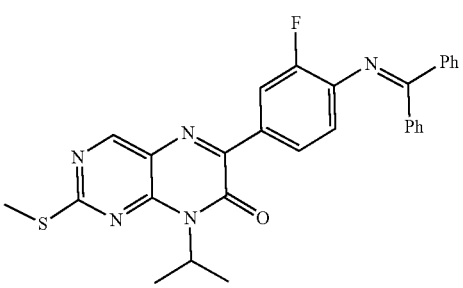 [SMILES: CSc1ncc2nc(-c3ccc(N=C(c4ccccc4)c4ccccc4)c(F)c3)c(=O)n(C(C)C)c2n1]

A mixture of 6-(4-bromo-3-fluoro-phenyl)-8-isopropyl-2-methylsulfanyl-pteridin-7-one (600 mg, 1.47 mmol), benzophenone imine (420 mg, 2.32 mmol), tris(dibenzylideneacetone)dipalladium(0) (180 mg, 0.20 mmol), 4,5-bis (diphenylphosphino)-9,9-dimethylxanthene (180 mg, 0.31 mmol) and cesium carbonate (960 mg, 2.93 mmol) in 1,4-dioxane (10 mL) was stirred for 1 h at 100° C. under nitrogen. The resulting solution was diluted with water, extracted with ethyl acetate, washed with brine, dried over sodium sulfate and concentrated. The residue was purified by silica flash chromatography eluting with ethyl acetate/petroleum ether (15:85) to afford the title compound (570 mg, 76.3% yield) as a yellow solid. LCMS (ESI): [M+H]$^+$=510.0.

Step 2: 6-(4-Amino-3-fluoro-phenyl)-8-isopropyl-2-methylsulfanyl-pteridin-7-one

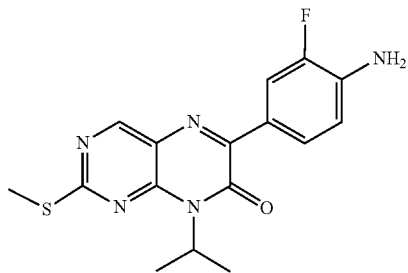 [SMILES: CSc1ncc2nc(-c3ccc(N)c(F)c3)c(=O)n(C(C)C)c2n1]

A mixture of 6-(4-((diphenylmethylene)amino)-3-fluoro-phenyl)-8-isopropyl-2-(methylthio)pteridin-7(8H)-one (570 mg, 1.12 mmol) and acetic Acid (10 mL) in water (2 mL) and tetrahydrofuran (10 mL) was stirred for 4 h at 50° C. The resulting solution was concentrated in vacuum. The residue was purified by silica flash chromatography eluting with ethyl acetate/petroleum ether (70:30) to afford the title compound (270 mg, 69.9% yield) as a yellow solid. LCMS (ESI): [M+H]$^+$=346.1.

Step 3: 3,3-Difluoro-N-(2-fluoro-4-(8-isopropyl-2-(methylthio)-7-oxo-7,8-dihydropteridin-6-yl)phenyl)butane-1-sulfonamide

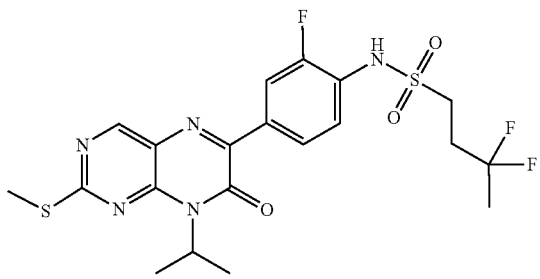 [SMILES: CSc1ncc2nc(-c3ccc(NS(=O)(=O)CCC(C)(F)F)c(F)c3)c(=O)n(C(C)C)c2n1]

To a mixture of 6-(4-amino-3-fluoro-phenyl)-8-isopropyl-2-methylsulfanyl-pteridin-7-one (110 mg, 0.32 mmol) in pyridine (1 mL) was added 3,3-difluorobutane-1-sulfonyl chloride (90 mg, 0.47 mmol), the mixture was stirred for 1 h at rt. The reaction was quenched with water and extracted with dichloromethane. The organic layer was concentrated in vacuum. Then the resulting mixture was dissolved in tetrahydrofuran (3 mL). After saturate lithium hydroxide solution (3 mL) was added, the resulting solution was stirred for 0.5 h at rt. The resulting solution was diluted with water, extracted with dichloromethane and concentrated. The residue was purified by silica flash chromatography eluting with ethyl acetate/petroleum ether (1:1) to afford the title compound (110 mg, 68.9% yield) as a yellow solid. LCMS (ESI): [M+H]$^+$=502.1.

Step 4: 3,3-Difluoro-N-(2-fluoro-4-(8-isopropyl-2-(methylsulfonyl)-7-oxo-7,8-dihydropteridin-6-yl)phenyl)butane-1-sulfonamide

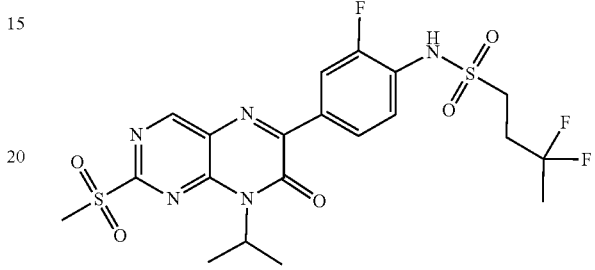

To a mixture of 3,3-difluoro-N-(2-fluoro-4-(8-isopropyl-2-(methylthio)-7-oxo-7,8-dihydropteridin-6-yl)phenyl)butane-1-sulfonamide (120 mg, 0.24 mmol) in dichloromethane (3 mL) was added 3-chloroperoxybenzoicacid (120 mg, 0.59 mmol), the mixture was stirred for 2 h at rt. The reaction was quenched with sat. sodium sulfite and extracted with ethyl acetate, washed with brine, dried over Sodium sulfate and concentrated. The crude would be directly used in the next step without purification. LCMS (ESI): [M+H]$^+$=534.1.

Step 5: N-(4-(2-(((1r,4r)-4-(Dimethylamino)cyclohexyl)amino)-8-isopropyl-7-oxo-7,8-dihydropteridin-6-yl)-2-fluorophenyl)-3,3-difluorobutane-1-sulfonamide (Compound 66)

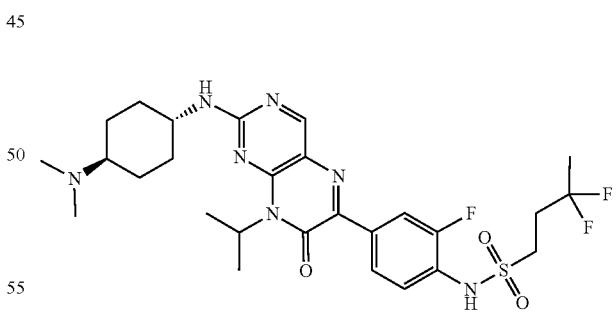

A mixture of 3,3-difluoro-N-(2-fluoro-4-(8-isopropyl-2-(methylsulfonyl)-7-oxo-7,8-dihydropteridin-6-yl)phenyl)butane-1-sulfonamide (100 mg, 0.19 mmol), (1r,4r)-N$^1$,N$^1$-dimethylcyclohexane-1,4-diamine hydrochloride (40 mg, 0.22 mmol), Caesium fluoride (100 mg, 0.66 mmol) and N,N-diisopropylethylamine (150 mg, 1.16 mmol) in dimethyl sulfoxide (2 mL) was stirred for 2 h at 90° C. under nitrogen. The resulting residue was purified by Prep-HPLC to afford the title compound (31.7 mg, 28.2% yield) as a yellow solid.

Example 67: N-(4-(2-(((1r,4r)-4-(Dimethylamino)cyclohexyl)amino)-8-isopropyl-7-oxo-7,8-dihydropteridin-6-yl)-2-fluorophenyl)-3,3,3-trifluoropropane-1-sulfonamide (Compound 67)

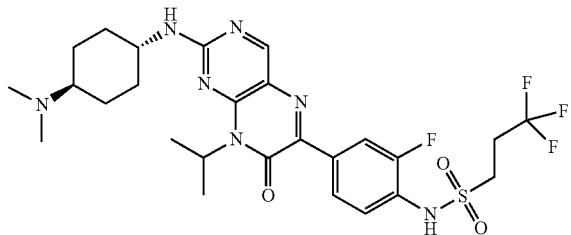 [SMILES: CC(C)n1c(=O)c(-c2ccc(NS(=O)(=O)CCC(F)(F)F)c(F)c2)nc2cnc(N[C@H]3CC[C@H](N(C)C)CC3)nc21]

The title compound was prepared according to Example 66. This provides the title compound (32.7 mg, 26.5% yield) as a yellow solid.

Example 68: N-(4-(2-(((1r,4r)-4-(Dimethylamino)cyclohexyl)amino)-8-isopropyl-7-oxo-7,8-dihydropteridin-6-yl)-2-fluorophenyl)-1-phenylmethanesulfonamide (Compound 68)

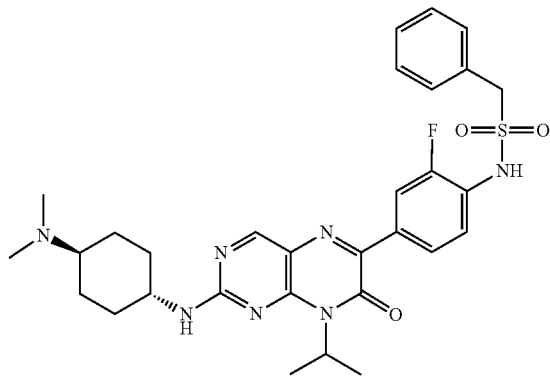 [SMILES: CC(C)n1c(=O)c(-c2ccc(NS(=O)(=O)Cc3ccccc3)c(F)c2)nc2cnc(N[C@H]3CC[C@H](N(C)C)CC3)nc21]

The title compound was prepared according to Example 64. This provided the title compound (34.6 mg, 27.5% yield) as a yellow solid.

Example 69: N-(5-(8-ethyl-2-(((3S,5S)-5-fluoropiperidin-3-yl)amino)-7-oxo-7,8-dihydropyrido[2,3-d]pyrimidin-6-yl)-1-methyl-1H-pyrazol-3-yl)-1-phenylmethanesulfonamide (Compound 69)

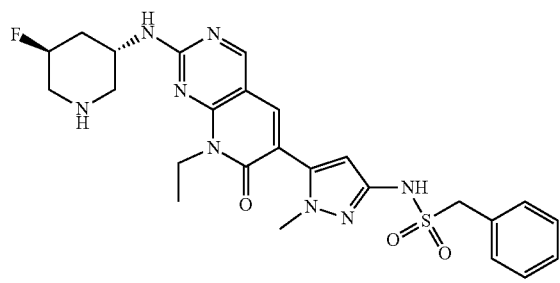 [SMILES: CCn1c(=O)c(-c2cc(NS(=O)(=O)Cc3ccccc3)nn2C)cc2cnc(N[C@@H]3CNC[C@@H](F)C3)nc21]

Step 1: benzyl (3S,5S)-3-((6-(3-amino-1-methyl-1H-pyrazol-5-yl)-8-ethyl-7-oxo-7,8-dihydropyrido[2,3-d]pyrimidin-2-yl)amino)-5-fluoropiperidine-1-carboxylate

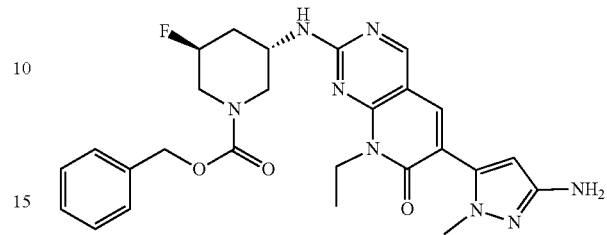

A solution of 5-bromo-1-methyl-1H-pyrazol-3-amine (88 mg, 0.50 mmol), [1,1'-Bis(diphenylphosphino)ferrocene]dichloropalladium(II) (21 mg, 0.025 mmol), Bis(pinacolato)diboron (153 mg, 0.60 mmol) and potassium acetate (148 mg, 1.50 mmol) in 1,4-dioxane (1.7 mL) was stirred at 80° C. for 8 h and 90° C. for 18 h. Added benzyl (3S,5S)-3-((6-bromo-8-ethyl-7-oxo-7,8-dihydropyrido[2,3-d]pyrimidin-2-yl)amino)-5-fluoropiperidine-1-carboxylate (121 mg, 0.40 mmol), Bis(di-tert-butyl(4-dimethylaminophenyl)phosphine)dichloropalladium(II) (11 mg, 0.02 mmol) and cesium fluoride (137 mg, 0.12 mmol) to the reaction mixture and stirred at 70° C. for 18 h. The reaction mixture was diluted with aq. sat. NH$_4$Cl (5 mL) and 10% methanol in dicholoromethane (5 mL). The aqueous layer was extracted with 10% methanol in dicholoromethane (2×5 mL). The combined organic layer was concentrated under reduced pressure. The residue was purified by column chromatography (silica gel, 10% methanol in isopropyl acetate/heptane) to afford the title compound (38 mg, 15% yield) as a brown solid. LCMS (ESI): [M+H]$^+$=521.4; $^1$H NMR (400 MHz, DMSO-d$_6$) δ 8.68 (s, 1H), 8.07 (d, J=6.9 Hz, 1H), 7.81 (s, 1H), 7.40-7.20 (m, 5H), 5.52 (s, 1H), 5.20-4.90 (m, 3H), 4.53 (s, 2H), 4.40-4.00 (m, 5H), 3.45 (s, 3H), 2.28-2.24 (m, 1H), 1.30-1.00 (m, 5H).

Step 2: benzyl (3S,5S)-3-((8-ethyl-6-(1-methyl-3-((phenylmethyl)sulfonamido)-1H-pyrazol-5-yl)-7-oxo-7,8-dihydropyrido[2,3-d]pyrimidin-2-yl)amino)-5-fluoropiperidine-1-carboxylate

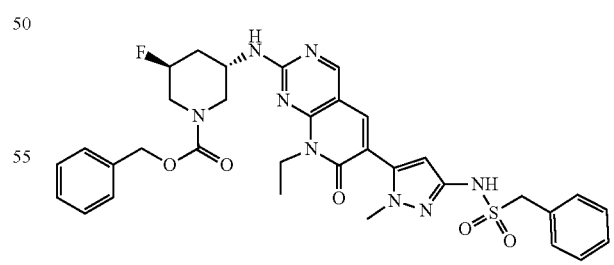

A cooled to 0° C. solution of benzyl (3S,5S)-3-((6-(3-amino-1-methyl-1H-pyrazol-5-yl)-8-ethyl-7-oxo-7,8-dihydropyrido[2,3-d]pyrimidin-2-yl)amino)-5-fluoropiperidine-1-carboxylate (21 mg, 0.040 mmol), phenylmethanesulfonyl chloride (9.3 mg, 0.048 mmol) and N,N-diisopropylethylamine (0.011 mL, 0.061 mmol) in dichloromethane (0.202 mL) was stirred at 0° C. to room temperature for 18 h.

MeOH (0.5 mL), water (0.5 mL) and potassium carbonate (69 mg, 0.5 mmol) were added and the reaction mixture was stirred at room temperature for 4 h. The reaction mixture was diluted with aq. 1N NH₄Cl (1 mL), water (4 mL) and 10% methanol in dicholoromethane (5 mL). The aqueous layer was extracted with 10% methanol in dicholoromethane (2×5 mL). The combined organic layer was concentrated under reduced pressure to afford the title compound (74 mg, 100% yield) as a beige solid. LCMS (ESI): [M+H]+=675.4.

Step 3: N-(5-(8-ethyl-2-(((3S,5S)-5-fluoropiperidin-3-yl)amino)-7-oxo-7,8-dihydropyrido[2,3-d]pyrimidin-6-yl)-1-methyl-1H-pyrazol-3-yl)-1-phenylmethanesulfonamide

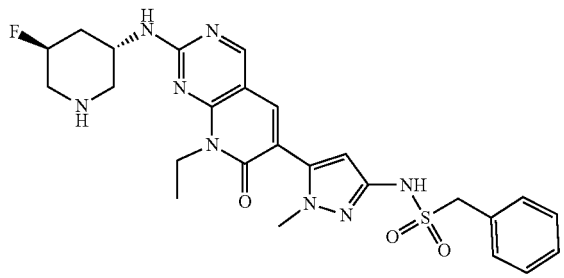 [SMILES: CCn1c(=O)c(-c2cc(NS(=O)(=O)Cc3ccccc3)nn2C)cc2cnc(N[C@@H]3CNC[C@@H](F)C3)nc21]

Benzyl (3S,5S)-3-((8-ethyl-6-(1-methyl-3-((phenylmethyl)sulfonamido)-1H-pyrazol-5-yl)-7-oxo-7,8-dihydropyrido[2,3-d]pyrimidin-2-yl)amino)-5-fluoropiperidine-1-carboxylate (27 mg, 0.040 mmol) in trifluoroacetic acid (0.4 mL) was stirred at 50° C. for 18 h. The reaction mixture was neutralized with aq. sat. NaHCO₃ and diluted with dicholoromethane (5 mL). The aqueous layer was extracted with dicholoromethane (2×5 mL). The combined organic layer was concentrated under reduced pressure and purified by prep-HPLC to afford the title compound (2.2 mg, 10% yield) as a white solid.

Example 70: N-(4-(2-(((1,4-trans)-4-(Dimethylamino)cyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide (Compound 70)

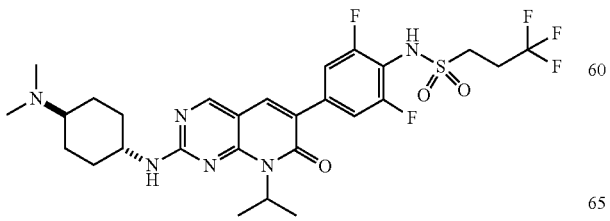

Step 1: 6-Bromo-8-isopropyl-2-(methylthio)pyrido[2,3-d]pyrimidin-7(8H)-one

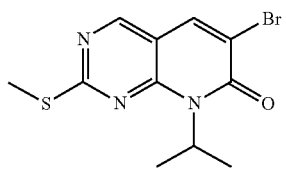 [SMILES: CSc1ncc2cc(Br)c(=O)n(C(C)C)c2n1]

To a solution of 6-bromo-2-(methylthio)pyrido[2,3-d]pyrimidin-7(8H)-one (1.00 g, 3.67 mmol) in DMF (20 mL) was added potassium carbonate (1.52 g, 11.0 mmol) and 2-iodopropane (0.48 mL, 4.78 mmol) and the mixture stirred at rt. After 90 min, a further portion of 2-iodopropane (0.10 mL, 0.99 mmol) was added and continued stirring at rt. After 16 h, a further portion of 2-iodopropane (0.10 mL, 0.99 mmol) was added and continued stirring at rt. After 20 h, a further portion of 2-iodopropane (0.10 mL, 0.99 mmol) was added and continued stirring at rt. After 20 h, the mixture was diluted with water and stirred for 10 min. The resulting solids were filtered off and rinsed with water. The solid thus obtained was dissolved in DCM and passed through a phase cartridge separator to remove residual water and the filtrate was concentrated under reduced pressure to provide the title compound (1.15 g, 99% yield). LCMS (ESI) [M+H]=315.8.

Step 2: 6-Bromo-8-isopropyl-2-(methylsulfonyl)pyrido[2,3-d]pyrimidin-7(8H)-one

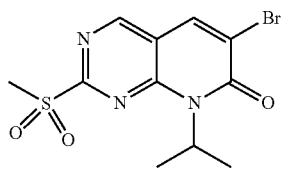 [SMILES: CC(C)n1c(=O)c(Br)cc2cnc(S(C)(=O)=O)nc21]

To a solution of 6-bromo-8-isopropyl-2-(methylthio)pyrido[2,3-d]pyrimidin-7(8H)-one (1.15 g, 3.66 mmol) in DCM (20 mL) was added 3-chloroperbenzoic acid (1.89 g, 11.0 mmol) and the mixture stirred at rt. After 1 h, the mixture was washed with saturated aqueous sodium bicarbonate (4×30 mL), dried (Na₂SO₄), filtered and concentrated under reduced pressure. The crude material was purified by flash chromatography through silica gel (0-40% EtOAc/DCM) to provide the title compound (950 mg, 75% yield). LCMS (ESI) [M+H]⁺=345.9.

Step 3: 6-Bromo-2-(((1,4-trans)-4-(dimethylamino)cyclohexyl)amino)-8-isopropylpyrido[2,3-d]pyrimidin-7(8H)-one

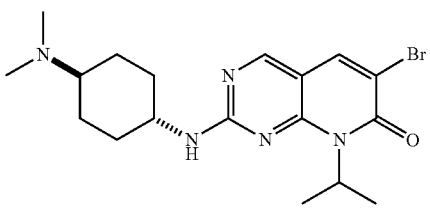 [SMILES: CC(C)n1c(=O)c(Br)cc2cnc(N[C@H]3CC[C@H](N(C)C)CC3)nc21]

To a solution of 6-bromo-8-isopropyl-2-(methylsulfonyl)pyrido[2,3-d]pyrimidin-7(8H)-one (552 mg, 1.59 mmol) in isopropanol (8.3 mL) was added (1,4-trans)-N,N'-dimethylcyclohexane-1,4-diamine (249 mg, 1.75 mmol) and N,N-diisopropylethylamine (0.83 mL, 4.78 mmol) and the mixture placed in a 50° C. oil bath. After 22 h, the mixture was cooled to rt and volatiles removed under reduced pressure. The crude mixture was directly purified by C18 reverse phase flash chromatography (10-50% Acetonitrile/10 mM aqueous ammonium formate, pH=3.8) to provide the title compound (161 mg, 25% yield). LCMS (ESI) [M+H]$^+$=408.1, 410.1.

Step 4: 6-(4-Amino-3,5-difluorophenyl)-2-(((1,4-trans)-4-(dimethylamino)cyclohexyl)amino)-8-isopropylpyrido[2,3-d]pyrimidin-7(8H)-one

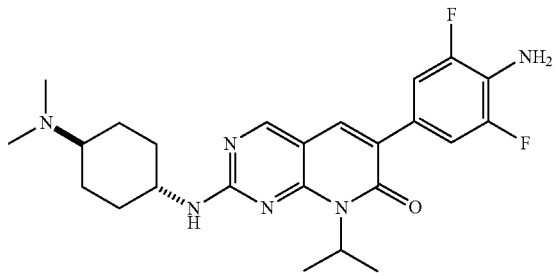 [SMILES: CC(C)n1c(=O)c(-c2cc(F)c(N)c(F)c2)cc2cnc(N[C@H]3CC[C@H](N(C)C)CC3)nc21]

A flask was charged with 6-bromo-2-(((1,4-trans)-4-(dimethylamino)cyclohexyl)amino)-8-isopropylpyrido[2,3-d]pyrimidin-7(8H)-one (45 mg, 0.11 mmol), 2,6-difluoro-4-(4,4,5,5-tetramethyl-1,3,2-dioxaborolan-2-yl)aniline (34 mg, 0.13 mmol), and sodium carbonate (35 mg, 0.33 mmol) in that order. To this mixture was then added N$_2$ sparged 1,4-dioxane (2.3 mL) and N$_2$ sparged water (0.48 mL) and 1,1-bis(diphenylphosphino)ferrocene-palladium dichloride (8.2 mg, 0.01 mmol). The flask was capped and N$_2$ purged for 5 min then placed in a 90° C. oil bath. After 3 h, the mixture was cooled to rt and diluted with EtOAc and water. The phases were separated and the organic extract was washed with saturated aqueous sodium chloride, dried over anhydrous Na$_2$SO$_4$, filtered and concentrated under reduced pressure. The crude material was purified by C18 reverse phase flash chromatography (10-80% acetonitrile/10 mM aqueous ammonium formate, pH=3.8). Appropriate fractions were combined and lyophilized. The material thus obtained was dissolved in DCM and washed with saturated aqueous sodium bicarbonate, dried over anhydrous Na$_2$SO$_4$, filtered and concentrated under reduced pressure to provide the title product (20 mg, 40% yield). LCMS (ESI) [M+H]$^+$=457.1.

Step 5: N-(4-(2-(((1,4-trans)-4-(Dimethylamino)cyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide

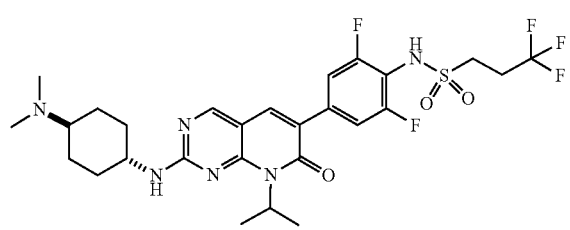 [SMILES: CC(C)n1c(=O)c(-c2cc(F)c(NS(=O)(=O)CCC(F)(F)F)c(F)c2)cc2cnc(N[C@H]3CC[C@H](N(C)C)CC3)nc21]

To a solution of 6-(4-amino-3,5-difluorophenyl)-2-(((1,4-trans)-4-(dimethylamino)cyclohexyl)amino)-8-isopropylpyrido[2,3-d]pyrimidin-7(8H)-one (20 mg, 0.04 mmol) in a mixture of DCM (0.22 mL) and pyridine (0.07 mL, 0.88 mmol) was added 3,3,3-trifluoropropane-1-sulfonyl chloride (12 mg, 0.06 mmol) and the mixture stirred at rt. After 2 h, a further portion of 3,3,3-trifluoropropane-1-sulfonyl chloride (6 mg, 0.03 mmol) was added and continued stirring at rt. After 16 h, the mixture was diluted with DCM and washed with saturated aqueous sodium bicarbonate, dried (Na$_2$SO$_4$), filtered and concentrated under reduced pressure to provide mostly the undesired bis-sulfonamide N-(4-(2-(((1,4-trans)-4-(dimethylamino)cyclohexyl)amino)-8-isopropyl-7-oxo-7,8-dihydropyrido[2,3-d]pyrimidin-6-yl)-2,6-difluorophenyl)-3,3,3-trifluoro-N-((3,3,3-trifluoropropyl)sulfonyl)propane-1-sulfonamide. This material was dissolved in THF (0.22 mL) and treated with 1M tetrabutylammonium fluoride in THF (0.043 mL, 0.04 mmol) and the mixture stirred at rt. After 16 h, near complete conversion to the desired mono sulfonamide title product was observed. Volatiles were removed under reduced pressure and the crude residue was purified by C18 reverse phase flash chromatography (20-80% Acetonitrile/10 mM aqueous ammonium bicarbonate, pH=10) to provide the title product (11.5 mg, 43% yield).

Example 71: N-(4-(2-(((1,4-trans)-4-(Dimethylamino)cyclohexyl)amino)-8-isopropyl-7-oxo-7,8-dihydropyrido[2,3-d]pyrimidin-6-yl)-2,5-difluorophenyl)-3,3,3-trifluoropropane-1-sulfonamide formate (Compound 71)

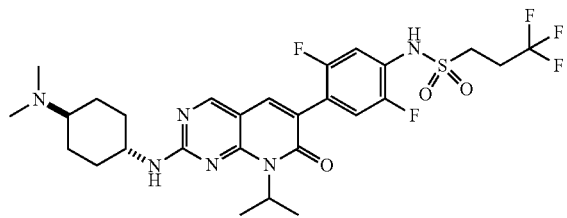 [SMILES: CC(C)n1c(=O)c(-c2cc(F)c(NS(=O)(=O)CCC(F)(F)F)cc2F)cc2cnc(N[C@H]3CC[C@H](N(C)C)CC3)nc21]

Step 1: 6-(4-Amino-2,5-difluorophenyl)-2-(((1r,4r)-4-(dimethylamino)cyclohexyl)amino)-8-isopropylpyrido[2,3-d]pyrimidin-7(8H)-one

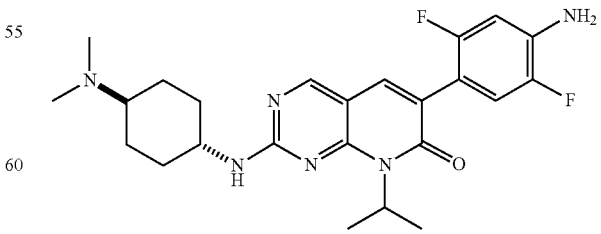

Prepared according to step 4 in Example 70 to provide the title compound (21 mg, 34% yield). LCMS (ESI) [M+H]$^+$=457.0.

Step 2: N-(4-(2-(((1,4-trans)-4-(Dimethylamino)cyclohexyl)amino)-8-isopropyl-7-oxo-7,8-dihydropyrido[2,3-d]pyrimidin-6-yl)-2,5-difluorophenyl)-3,3,3-trifluoropropane-1-sulfonamide formate

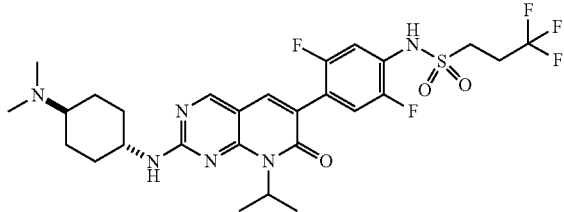 [SMILES: CC(C)n1c(=O)c(-c2cc(F)c(NS(=O)(=O)CCC(F)(F)F)cc2F)cc2cnc(N[C@H]3CC[C@H](N(C)C)CC3)nc21]

To a solution of 6-(4-amino-2,5-difluorophenyl)-2-(((1r,4r)-4-(dimethylamino)cyclohexyl)amino)-8-isopropylpyrido[2,3-d]pyrimidin-7(8H)-one (21 mg, 0.05 mmol) in a mixture of DCM (0.5 mL) and pyridine (0.09 mL, 1.14 mmol) was added 3,3,3-trifluoropropane-1-sulfonyl chloride (12 mg, 0.06 mmol) and the mixture stirred at rt. After 2 h, the mixture was diluted with DCM and washed with saturated aqueous sodium bicarbonate, dried over anhydrous MgSO$_4$, filtered and concentrated under reduced pressure. The crude residue was purified by C18 reverse phase flash chromatography (0-50% acetonitrile/10 mM aqueous ammonium formate, pH=3.8) to provide the title product (10 mg, 32% yield).

Example 72: N-[2-Fluoro-4-[2-[[(3S,5S)-5-fluoro-3-piperidyl]amino]-8-isopropyl-7-oxo-pteridin-6-yl]-6-methyl-phenyl]-1-phenyl-methanesulfonamide (Compound 72)

Step 1: 2-Fluoro-6-methyl-4-(4,4,5,5-tetramethyl-1,3,2-dioxaborolan-2-yl)aniline

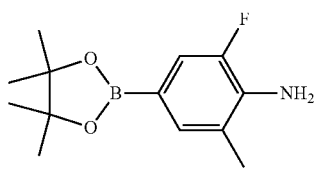 [SMILES: Cc1cc(B2OC(C)(C)C(C)(C)O2)cc(F)c1N]

A solution of 4-bromo-2-fluoro-6-methylaniline (1.0 g, 4.66 mmol), bis(pinacolato)diboron (1.30 g, 5.12 mmol), potassium acetate (1.37 g, 14.0 mmol) and [1,1'-bis(diphenylphosphino)ferrocene]dichloropalladium(II) (0.18 g, 0.23 mmol) in 1,4-dioxane (15.5 mL) was stirred at 90° C. overnight. The reaction mixture was diluted with sat. NH$_4$Cl (40 mL) and DCM (40 mL) and the aqueous layer was back extracted with DCM (20 mL). The combined organic layer was dried with Mg$_2$SO$_4$ and concentrated to afford the title compound as a brown semi-solid (1.45 g, 120% yield).

Step 2: tert-Butyl (3S,5S)-3-[(6-bromo-8-isopropyl-7-oxo-pteridin-2-yl)amino]-5-fluoro-piperidine-1-carboxylate

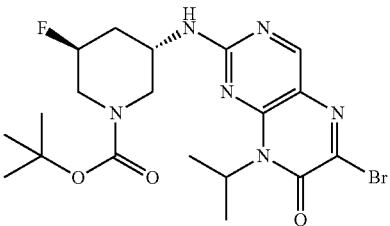 [SMILES: CC(C)n1c(=O)c(Br)nc2cnc(N[C@H]3C[C@H](F)CN(C(=O)OC(C)(C)C)C3)nc21]

The compound above was made in an analogous fashion to Example 43, following steps 2-5 and using tert-butyl (3S,5S)-3-amino-5-fluoropiperidine-1-carboxylate. LCMS (ESI): [M]$^+$=485.

Step 3: tert-Butyl (3S,5S)-3-[[6-(4-amino-3-fluoro-5-methyl-phenyl)-8-isopropyl-7-oxo-pteridin-2-yl]amino]-5-fluoro-piperidine-1-carboxylate

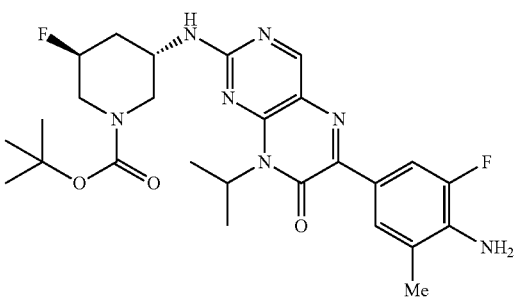 [SMILES: Cc1cc(-c2nc3cnc(N[C@H]4C[C@H](F)CN(C(=O)OC(C)(C)C)C4)nc3n(C(C)C)c2=O)cc(F)c1N]

A solution of tert-butyl (3S,5S)-3-[(6-bromo-8-isopropyl-7-oxo-pteridin-2-yl)amino]-5-fluoro-piperidine-1-carboxylate (100 mg, 0.18 mmol), PdCl$_2$(PPh$_3$)$_2$ (13 mg, 0.02 mmol), Na$_2$CO$_3$ (38 mg, 0.36 mmol) and 2-fluoro-6-methyl-4-(4,4,5,5-tetramethyl-1,3,2-dioxaborolan-2-yl)aniline (90 mg, 0.36 mmol) in 1,4-dioxane (0.9 mL) and H$_2$O (0.9 mL) was stirred at 75° C. for 18 h. The reaction was diluted with H$_2$O (5 mL) whereby the resultant gooey solid that crashed out was filtered and re-suspended in DCM (50 mL). The organic layer was extracted with water, dried with Mg$_2$SO$_4$, filtered, concentrated and purified by reverse phase HPLC (5-85% over 10 mins) to afford the title compound (80 mg, 84% yield) as a yellow solid. LCMS (ESI): [M+H]530.

Step 4: tert-Butyl (3S,5S)-3-[[6-[4-(benzylsulfonylamino)-3-fluoro-5-methyl-phenyl]-8-isopropyl-7-oxo-pteridin-2-yl]amino]-5-fluoro-piperidine-1-carboxylate

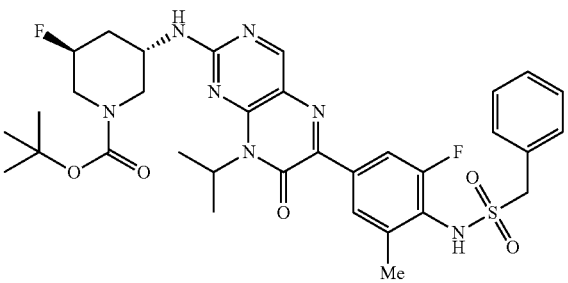 [SMILES: Cc1cc(-c2nc3cnc(N[C@H]4C[C@H](F)CN(C(=O)OC(C)(C)C)C4)nc3n(C(C)C)c2=O)cc(F)c1NS(=O)(=O)Cc1ccccc1]

To a solution of tert-butyl (3S,5S)-3-[[6-(4-amino-3-fluoro-5-methyl-phenyl)-8-isopropyl-7-oxo-pteridin-2-yl]amino]-5-fluoro-piperidine-1-carboxylate (80 mg, 0.15 mmol) in DCM (1 mL) was added 1,8-diazabicyclo[5.4.0]undec-7-ene (112 µL, 0.75 mmol) and alpha-toluenesulfonyl chloride (35 mg, 0.18 mmol). The reaction was stirred at room temperature overnight then quenched with saturated sodium bicarbonate solution and extracted with 5 mL DCM. The organic layer was dried with magnesium sulfate and filtered to collect title compound (103 mg, quantitative yield) as a crude intermediate which was taken into the next step without purification. LCMS (ESI): [M+H]$^+$=684.

Step 5: N-[2-Fluoro-4-[2-[[(3S,5S)-5-fluoro-3-piperidyl]amino]-8-isopropyl-7-oxo-pteridin-6-yl]-6-methyl-phenyl]-1-phenyl-methanesulfonamide

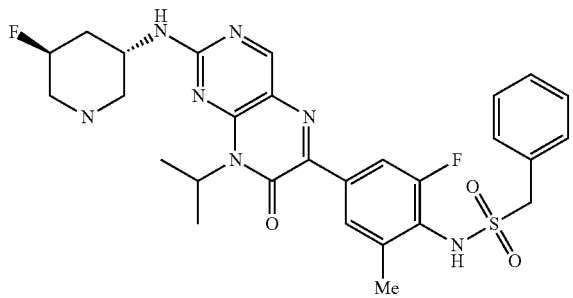 [SMILES: Cc1cc(-c2nc3cnc(N[C@@H]4CNC[C@@H](F)C4)nc3n(C(C)C)c2=O)cc(F)c1NS(=O)(=O)Cc1ccccc1]

To a solution of tert-butyl (3S,5S)-3-[[6-[4-(benzylsulfonylamino)-3-fluoro-5-methyl-phenyl]-8-isopropyl-7-oxo-pteridin-2-yl]amino]-5-fluoro-piperidine-1-carboxylate (103 mg, 0.15 mmol) was added 4N HCl in dioxane (0.19 mL, 0.75 mmol). The reaction was stirred at room temperature overnight then concentrated to dryness and purified via reverse phase HPLC to afford the title compound (10.5 mg, 110% yield).

Example 73: 3,3,3-Trifluoro-N-[2-fluoro-4-[2-[[(3S,5S)-5-fluoro-3-piperidyl]amino]-8-isopropyl-7-oxo-pteridin-6-yl]phenyl]propane-1-sulfonamide (Compound 73)

Step 1: tert-Butyl (3S,5S)-3-[[6-(4-amino-3-fluoro-phenyl)-8-isopropyl-7-oxo-pteridin-2-yl]amino]-5-fluoro-piperidine-1-carboxylate

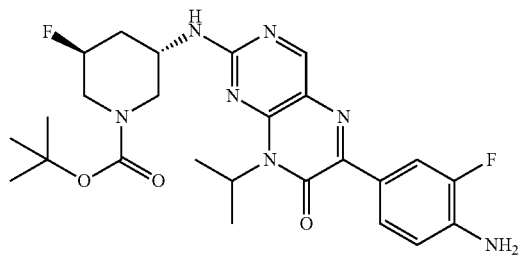 [SMILES: CC(C)n1c(=O)c(-c2ccc(N)c(F)c2)nc2cnc(N[C@H]3C[C@H](F)CN(C(=O)OC(C)(C)C)C3)nc21]

A solution tert-butyl (3S,5S)-3-[(6-bromo-8-isopropyl-7-oxo-pteridin-2-yl)amino]-5-fluoro-piperidine-1-carboxylate (160 mg, 0.29 mmol), PdCl$_2$(PPh$_3$)$_2$ (20 mg, 0.03 mmol), Na$_2$CO$_3$ (60 mg, 0.58 mmol) and 4-amino-3-fluorophenyl-boronic acid pinacol ester (83 mg, 0.34 mmol) in 1,4-dioxane (1.4 mL) and water (1.4 mL) was stirred at 75° C. for 18 h. The reaction was diluted with water (5 mL) whereby the resultant gooey solid that crashed out was filtered and re-suspended in DCM (50 mL). The organic layer was extracted with water, dried over anydrous Mg$_2$SO$_4$, filtered, concentrated and purified by reverse phase HPLC (5-85% over 10 mins) to afford the title compound (80 mg, 54% yield) as a yellow solid. LCMS (ESI): [M+H]$^+$=516.

Step 2: tert-Butyl (3S,5S)-3-fluoro-5-[[6-[3-fluoro-4-(3,3,3-trifluoropropylsulfonylamino)phenyl]-8-isopropyl-7-oxo-pteridin-2-yl]amino]piperidine-1-carboxylate

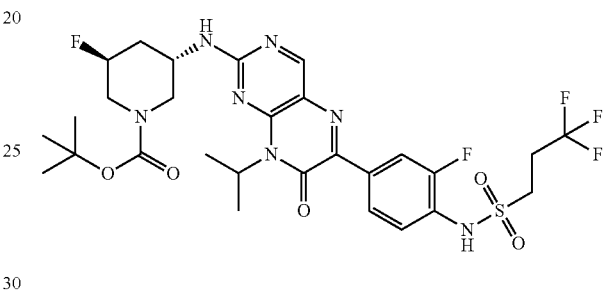

To a solution of tert-butyl (3S,5S)-3-[[6-(4-amino-3-fluoro-phenyl)-8-isopropyl-7-oxo-pteridin-2-yl]amino]-5-fluoro-piperidine-1-carboxylate (80 mg, 0.16 mmol) in pyridine (1 mL) was added 3,3,3-trifluoropropane-1-sulfonyl chloride (31 µL, 0.23 mmol). The reaction was stirred overnight at room temperature, concentrated to dryness and purified by reverse phase HPLC (15-85% over 10 mins) to afford the title compound (40 mg, 38% yield) as a yellow solid. LCMS (ESI): [M+H]$^+$=676.

Step 3: 3,3,3-Trifluoro-N-[2-fluoro-4-[2-[[(3S,5S)-5-fluoro-3-piperidyl]amino]-8-isopropyl-7-oxo-pteridin-6-yl]phenyl]propane-1-sulfonamide

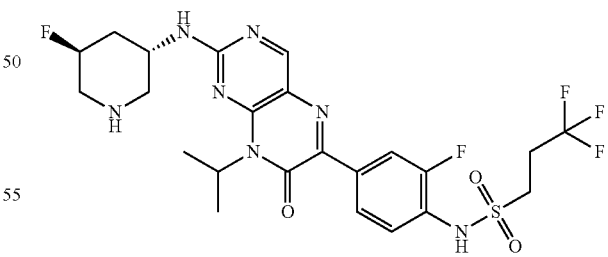

To a solution of tert-butyl (3S,5S)-3-fluoro-5-[[6-[3-fluoro-4-(3,3,3-trifluoropropylsulfonylamino)phenyl]-8-isopropyl-7-oxo-pteridin-2-yl]amino]piperidine-1-carboxylate (40 mg, 0.06 mmol) was added 4N HCl in dioxane (75 µL, 0.30 mmol). The reaction was stirred at room temperature overnight then concentrated to dryness and purified via reverse phase HPLC to afford the title compound (28.8 mg, 84% yield).

Example 74: N-[2-Fluoro-4-[2-[[(3S,5S)-5-fluoro-3-piperidyl]amino]-8-isopropyl-7-oxo-pteridin-6-yl]phenyl]benzenesulfonamide (Compound 74)

Step 1: tert-Butyl (3S,5S)-3-[[6-[4-(benzenesulfonamido)-3-fluoro-phenyl]-8-isopropyl-7-oxo-pteridin-2-yl]amino]-5-fluoro-piperidine-1-carboxylate

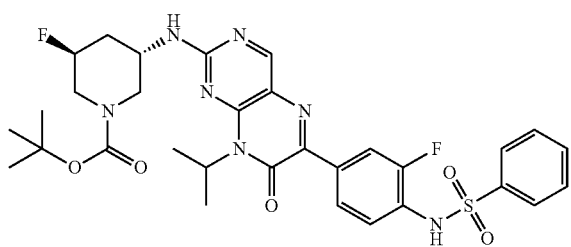 [SMILES: CC(C)n1c(=O)c(-c2ccc(NS(=O)(=O)c3ccccc3)c(F)c2)nc2cnc(N[C@H]3C[C@H](F)CN(C(=O)OC(C)(C)C)C3)nc21]

To a solution of tert-butyl (3S,5S)-3-[[6-(4-amino-3-fluoro-phenyl)-8-isopropyl-7-oxo-pteridin-2-yl]amino]-5-fluoro-piperidine-1-carboxylate (35 mg, 0.07 mmol) in pyridine (0.8 mL) was added benzenesulfonyl chloride (11 µL, 0.08 mmol). The reaction was stirred overnight at room temperature, concentrated to dryness to afford the title compound (~quantitative yield) which was taken directly into the next step. LCMS (ESI): [M+H]$^+$=656.

Step 2: N-[2-Fluoro-4-[2-[[(3S,5S)-5-fluoro-3-piperidyl]amino]-8-isopropyl-7-oxo-pteridin-6-yl]phenyl]benzenesulfonamide

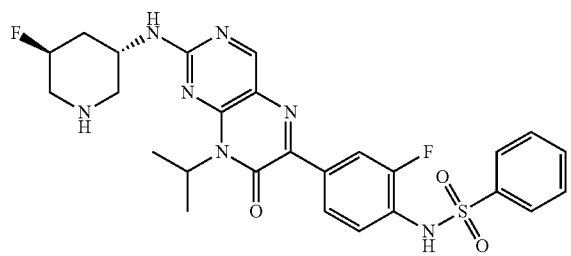 [SMILES: CC(C)n1c(=O)c(-c2ccc(NS(=O)(=O)c3ccccc3)c(F)c2)nc2cnc(N[C@@H]3CNC[C@@H](F)C3)nc21]

To a solution of tert-butyl (3S,5S)-3-[[6-[4-(benzenesulfonamido)-3-fluoro-phenyl]-8-isopropyl-7-oxo-pteridin-2-yl]amino]-5-fluoro-piperidine-1-carboxylate (44 mg, 0.07 mmol) was added 4N HCl in dioxane (85 µL, 0.34 mmol). The reaction was stirred at room temperature overnight then concentrated to dryness and purified via reverse phase HPLC to afford the title compound (20.7 mg, 55% yield).

Example 75: 2-Chloro-N-[2-fluoro-4-[2-[[(3S,5S)-5-fluoro-3-piperidyl]amino]-8-isopropyl-7-oxo-pteridin-6-yl]phenyl]benzenesulfonamide (Compound 75)

Step 1: tert-Butyl (3S,5S)-3-[[6-[4-[(2-chlorophenyl)sulfonylamino]-3-fluoro-phenyl]-8-isopropyl-7-oxo-pteridin-2-yl]amino]-5-fluoro-piperidine-1-carboxylate

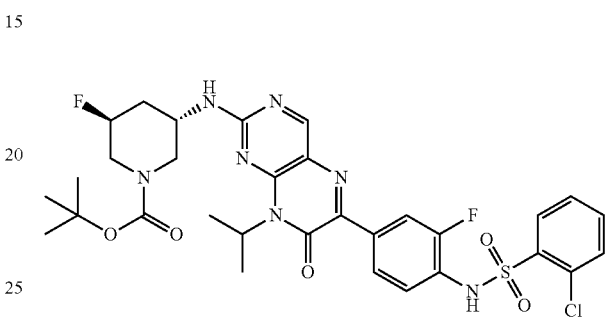

To a solution of tert-butyl (3S,5S)-3-[[6-(4-amino-3-fluoro-phenyl)-8-isopropyl-7-oxo-pteridin-2-yl]amino]-5-fluoro-piperidine-1-carboxylate (35 mg, 0.07 mmol) in pyridine (0.8 mL) was added 2-chlorobenzenesulfonyl chloride (12 µL, 0.08 mmol). The reaction was stirred overnight at room temperature, concentrated to dryness to afford the title compound (~quantitative yield) which was taken directly into the next step. LCMS (ESI): [M+H]$^+$=690.

Step 2: 2-Chloro-N-[2-fluoro-4-[2-[[(3S,5S)-5-fluoro-3-piperidyl]amino]-8-isopropyl-7-oxo-pteridin-6-yl]phenyl]benzenesulfonamide

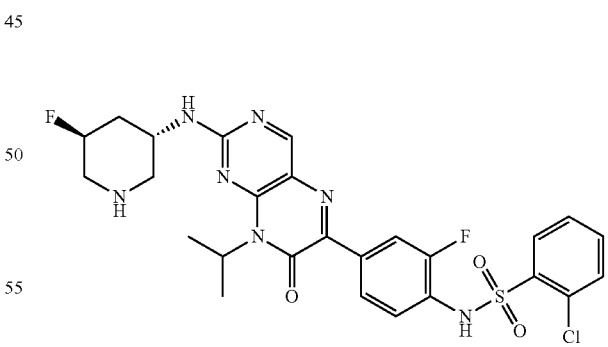

To a solution of tert-butyl (3S,5S)-3-fluoro-5-[[6-[3-fluoro-4-(3,3,3-trifluoropropylsulfonylamino)phenyl]-8-isopropyl-7-oxo-pteridin-2-yl]amino]piperidine-1-carboxylate (47 mg, 0.07 mmol) was added 4N HCl in dioxane (75 µL, 0.30 mmol). The reaction was stirred at room temperature overnight then concentrated to dryness and purified via reverse phase HPLC to afford the title compound (22 mg, 50% yield).

Example 76: 3,3,3-Trifluoro-N-[2-fluoro-4-[2-[[(3S, 5R)-5-(fluoromethyl)-3-piperidyl]amino]-8-isopropyl-7-oxo-pteridin-6-yl]phenyl]propane-1-sulfonamide (Compound 76)

Step 1: 2-Chloro-N⁴-isopropylpyrimidine-4,5-diamine

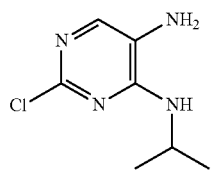

2-Chloro-N-isopropyl-5-nitropyrimidin-4-amine (202.0 g, 932.5 mmol), MeOH (2000 mL), NH₄Cl (423.98 g, 7.93 mol), and H₂O (500 mL) were added into the 5 L three-neck flask at 15° C.

The reaction mixture was heated to 50° C. Fe (182.3 g, 3.26 mol) was added into the above mixture at −70° C. in portions. The mixture was stirred at 50° C. for 1 hr. The reaction mixture was cooled and celite (800 g) was added to the reaction mixture and stirred for 20 min. This reaction was performed five times in total on the same scale and all reactions were combined and filtered through Celite. The organic filtrates were reduced under vacuum and the resultant aqueous layer was extracted with ethyl acetate (3 L). The Celite cake was washed with ethyl acetate (3 L, 2 L, 1 L) and combine with the extract phase (3 L). The combined organic phases were concentrated under vacuum to give the crude product which was purified by column chromatography (SiO₂, Petroleum ether/Ethyl acetate=10/1 to 0:1) to afford the title compound (440.0 g, 51% yield) as yellow solid.

¹H NMR (400 MHz, DMSO-d₆) δ: 7.61 (s., 1H), 4.86 (s, 1H), 4.34 (m, 1H), 2.91 (s, 2H), 1.27 (d, J=6.8 Hz, 6H).

Step 2: 2-Chloro-8-isopropylpteridin-7(8H)-one

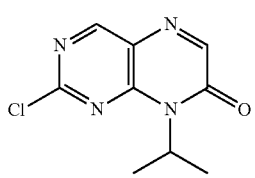

Six of the following reactions were carried out on parallel. 2-chloro-N⁴-isopropylpyrimidine-4,5-diamine (50.0 g, 267.9 mmol), ethyl 2-oxoacetate (152.6 g, 747.4 mmol, 50% purity) and HOAc (1.53 mL, 26.79 mmol,) were added into MeOH (500 mL) at 15° C. The reactions were stirred at 100° C. for 120 hrs. The reaction mixtures were combined at this stage and concentrated in vacuum to give a residue which was purified by silica gel chromatography (100-200 mesh silica gel) eluted with petroleum ether/ethyl acetate (20/1~3/1) to afford the title compound (47 g, 206.7 mmol, 12.9% yield, 98.8% purity) as yellow solid. LCMS (ESI): [M+H]+=225

¹H NMR (400 MHz, DMSO-d₆) δ: 9.9 (s, 1H), 8.28 (s, 1H), 5.43 (m, 1H), 1.52 (d, J=6.8 Hz, 6H).

Step 3: tert-Butyl (3R,5S)-3-(fluoromethyl)-5-[(8-isopropyl-7-oxo-pteridin-2-yl)amino]piperidine-1-carboxylate

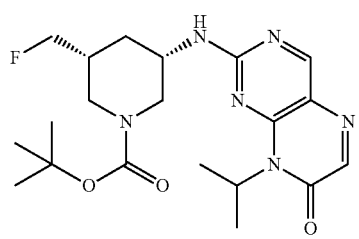 [SMILES: CC(C)n1c(=O)cnc2cnc(N[C@H]3C[C@@H](CF)CN(C(=O)OC(C)(C)C)C3)nc21]

To a solution of 2-chloro-8-isopropylpteridin-7(8H)-one (0.5 g, 2.2 mmol) and tert-butyl (3S,5R)-3-amino-5-(fluoromethyl)piperidine-1-carboxylate (0.52 g, 2.2 mmol) in DMSO (7.4 ml) was added DIPEA (1.2 mL, 6.7 mmol) and cesium fluoride (0.41 g, 2.7 mmol). The reaction was stirred at 90° C. for 18 h. Water (20 mL) was added to triturate product from the reaction mixture which was collected by filtration to afford a gummy solid. The solid was re-dissolved in DCM (100 mL) and extracted with saturated ammonium chloride. The organic layer was dried with magnesium sulfate, filtered and dried under vacuum to afford the title compound as a crude reddish brown oil (0.83 g, 89% crude yield). LCMS (ESI): [M+H]⁺=421.

Step 4: tert-Butyl (3S,5R)-3-[(6-bromo-8-isopropyl-7-oxo-pteridin-2-yl)amino]-5-(fluoromethyl)piperidine-1-carboxylate

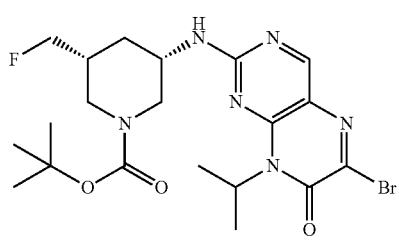 [SMILES: CC(C)n1c(=O)c(Br)nc2cnc(N[C@H]3C[C@@H](CF)CN(C(=O)OC(C)(C)C)C3)nc21]

To a solution of tert-butyl (3R,5S)-3-(fluoromethyl)-5-[(8-isopropyl-7-oxo-pteridin-2-yl)amino]piperidine-1-carboxylate (0.89 g, 1.78 mmol) in DMF (8 mL) was added NBS (543 mg, 2.96 mmol). The reaction mixture was stirred at room temperature for 48 h whereupon the product was triturated via the addition of water (20 mL) and filtered to afford the title compound (0.89 g, 94% crude yield). LCMS (ESI): [M]=499.

Step 5: tert-Butyl (3S,5R)-3-[[6-(4-amino-3-fluoro-phenyl)-8-isopropyl-7-oxo-pteridin-2-yl]amino]-5-(fluoromethyl)piperidine-1-carboxylate

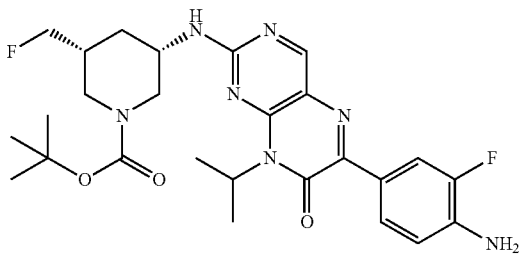 [SMILES: CC(C)n1c(=O)c(-c2ccc(N)c(F)c2)nc2cnc(N[C@H]3C[C@@H](CF)CN(C(=O)OC(C)(C)C)C3)nc21]

tert-Butyl (3S,5R)-3-[(6-bromo-8-isopropyl-7-oxo-pteridin-2-yl)amino]-5-(fluoromethyl)piperidine-1-carboxylate (0.89 g, 1.78 mmol) was reacted as in Example 73 (step 1) and purified by normal phase chromatography (0-80% Heptanes to 3:1 Ipr/MeOH gradient over 20 mins) to afford the title compound (0.82 g, 87%) as a reddish brown solid. LCMS (ESI): $[M+H]^+=530$.

Step 6: tert-Butyl (3R,5S)-3-(fluoromethyl)-5-[[6-[3-fluoro-4-(3,3,3-trifluoropropylsulfonylamino)phenyl]-8-isopropyl-7-oxo-pteridin-2-yl]amino]piperidine-1-carboxylate

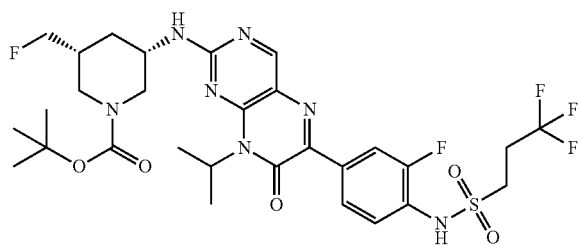 [SMILES: CC(C)n1c(=O)c(-c2ccc(NS(=O)(=O)CCC(F)(F)F)c(F)c2)nc2cnc(N[C@H]3C[C@@H](CF)CN(C(=O)OC(C)(C)C)C3)nc21]

tert-Butyl (3S,5R)-3-[[6-(4-amino-3-fluoro-phenyl)-8-isopropyl-7-oxo-pteridin-2-yl]amino]-5-(fluoromethyl)piperidine-1-carboxylate (170 mg, 0.32 mmol) was reacted as in Example 73 (step 2) and purified via normal phase chromatography (0-100% Heptanes to IprOAc) to afford the title compound (40 mg, 18% yield). LCMS (ESI): $[M+H]^+=690$.

Step 7: 3,3,3-Trifluoro-N-[2-fluoro-4-[2-[[(3S,5R)-5-(fluoromethyl)-3-piperidyl]amino]-8-isopropyl-7-oxo-pteridin-6-yl]phenyl]propane-1-sulfonamide

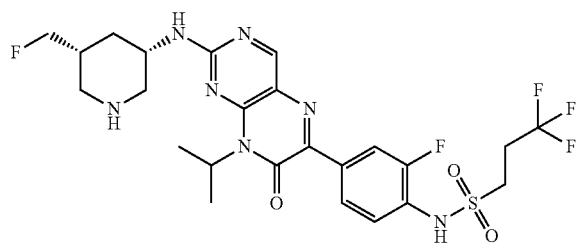 [SMILES: CC(C)n1c(=O)c(-c2ccc(NS(=O)(=O)CCC(F)(F)F)c(F)c2)nc2cnc(N[C@@H]3CNC[C@H](CF)C3)nc21]

tert-Butyl (3R,5S)-3-(fluoromethyl)-5-[[6-[3-fluoro-4-(3,3,3-trifluoropropylsulfonylamino)phenyl]-8-isopropyl-7-oxo-pteridin-2-yl]amino]piperidine-1-carboxylate (40 mg, 0.06 mmol) was reacted as in example Example 73_(step 3) and purified by reverse phase chromatography to afford the title compound (13 mg, 38% yield).

Example 77: 3,3-Difluoro-N-[2-fluoro-4-[2-[[(3S,5R)-5-(fluoromethyl)-3-piperidyl]amino]-8-isopropyl-7-oxo-pteridin-6-yl]phenyl]butane-1-sulfonamide (Compound 77)

Step 1: tert-Butyl (3S,5R)-3-[[6-[4-(3,3-difluorobutylsulfonylamino)-3-fluoro-phenyl]-8-isopropyl-7-oxo-pteridin-2-yl]amino]-5-(fluoromethyl)piperidine-1-carboxylate

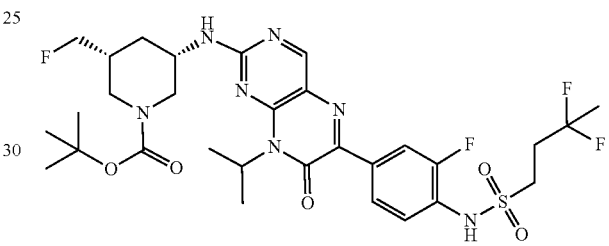

tert-Butyl (3S,5R)-3-[[6-(4-amino-3-fluoro-phenyl)-8-isopropyl-7-oxo-pteridin-2-yl]amino]-5-(fluoromethyl)piperidine-1-carboxylate (0.17 g, 0.32 mmol) was reacted with 3,3-difluorobutane-1-sulfonyl chloride (104 mg, 0.51 mmol) as in Example 73 (step 2) and purified via normal phase chromatography (0-100% Heptanes to IprOAc over 25 mins) to afford the title compound (50 mg, 23% yield). LCMS (ESI): $[M+H]^+=686$.

Step 2: 3,3-Difluoro-N-[2-fluoro-4-[2-[[(3S,5R)-5-(fluoromethyl)-3-piperidyl]amino]-8-isopropyl-7-oxo-pteridin-6-yl]phenyl]butane-1-sulfonamide

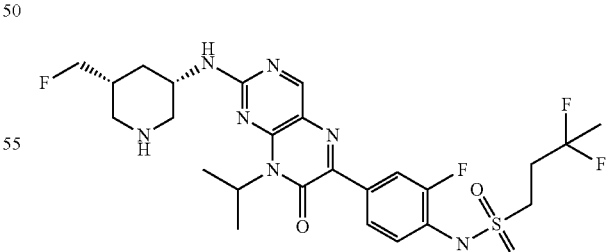

tert-Butyl (3S,5R)-3-[[6-[4-(3,3-difluorobutylsulfonylamino)-3-fluoro-phenyl]-8-isopropyl-7-oxo-pteridin-2-yl]amino]-5-(fluoromethyl)piperidine-1-carboxylate (50 mg, 0.07 mmol) was reacted as in Example 73 (step 3) and purified by reverse phase chromatography to afford the title compound (15.2 mg, 36% yield).

Example 78: 3,3-Difluoro-N-[2-fluoro-4-[2-[[(3S,5R)-5-(fluoromethyl)-3-piperidyl]amino]-8-isopropyl-7-oxo-pteridin-6-yl]phenyl]propane-1-sulfonamide (Compound 78)

Step 1: tert-Butyl (3S,5R)-3-[[6-[4-(3,3-difluoropropylsulfonylamino)-3-fluoro-phenyl]-8-isopropyl-7-oxo-pteridin-2-yl]amino]-5-(fluoromethyl)piperidine-1-carboxylate

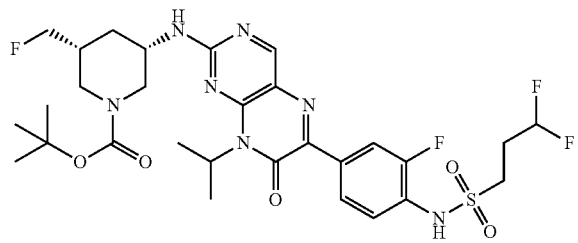 [SMILES: CC(C)n1c(=O)c(-c2ccc(NS(=O)(=O)CCC(F)F)c(F)c2)nc2cnc(N[C@H]3C[C@@H](CF)CN(C(=O)OC(C)(C)C)C3)nc21]

tert-Butyl (3S,5R)-3-[[6-(4-amino-3-fluoro-phenyl)-8-isopropyl-7-oxo-pteridin-2-yl]amino]-5-(fluoromethyl)piperidine-1-carboxylate (0.17 g, 0.32 mmol) was reacted with 3,3-difluoro-1-propanesulfonyl chloride (97 mg, 0.51 mmol) as in Example 73 (step 2) and purified via normal phase chromatography (0-100% heptanes to IprOAc) to afford the title compound (50 mg, 23% yield). LCMS (ESI): [M+H]$^+$=672.

Step 2: 3,3-Difluoro-N-[2-fluoro-4-[2-[[(3S,5R)-5-(fluoromethyl)-3-piperidyl]amino]-8-isopropyl-7-oxo-pteridin-6-yl]phenyl]propane-1-sulfonamide

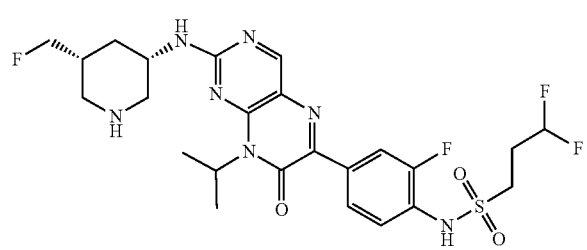 [SMILES: CC(C)n1c(=O)c(-c2ccc(NS(=O)(=O)CCC(F)F)c(F)c2)nc2cnc(N[C@@H]3CNC[C@H](CF)C3)nc21]

tert-Butyl (3S,5R)-3-[[6-[4-(3,3-difluoropropylsulfonylamino)-3-fluoro-phenyl]-8-isopropyl-7-oxo-pteridin-2-yl]amino]-5-(fluoromethyl)piperidine-1-carboxylate (50 mg, 0.07 mmol) was reacted as in Example 73 (step 3) and purified by reverse phase chromatography to afford the title compound (11 mg, 26% yield).

Example 79: N-[2-Fluoro-4-[2-[[(3S,5R)-5-(fluoromethyl)-3-piperidyl]amino]-8-isopropyl-7-oxo-pteridin-6-yl]phenyl]propane-1-sulfonamide (Compound 79)

Step 1: tert-Butyl (3R,5S)-3-(fluoromethyl)-5-[[6-[3-fluoro-4-(propylsulfonylamino)phenyl]-8-isopropyl-7-oxo-pteridin-2-yl]amino]piperidine-1-carboxylate

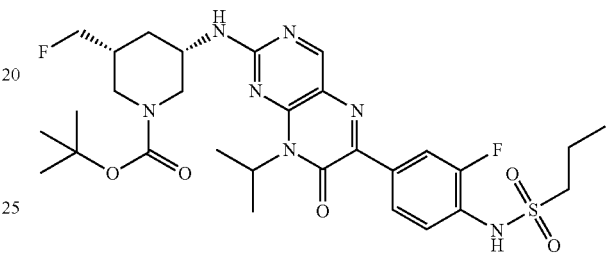

tert-Butyl (3S,5R)-3-[[6-(4-amino-3-fluoro-phenyl)-8-isopropyl-7-oxo-pteridin-2-yl]amino]-5-(fluoromethyl)piperidine-1-carboxylate (0.17 g, 0.32 mmol) was reacted with 1-propanesulfonyl chloride (58 μL, 0.51 mmol) as in Example 73 (step 2) and purified via normal phase chromatography (0-100% Heptanes to IprOAc) to afford the title compound (50 mg, 25% yield). LCMS (ESI): [M+H]$^+$=636.

Step 2: N-[2-Fluoro-4-[2-[[(3S,5R)-5-(fluoromethyl)-3-piperidyl]amino]-8-isopropyl-7-oxo-pteridin-6-yl]phenyl]propane-1-sulfonamide

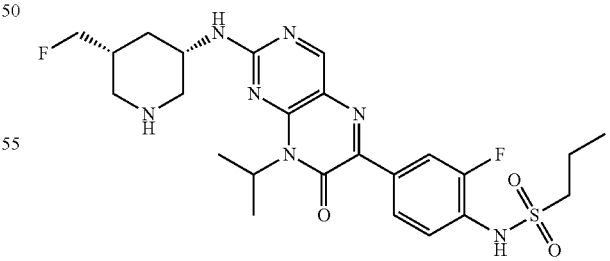

tert-Butyl (3R,5S)-3-(fluoromethyl)-5-[[6-[3-fluoro-4-(propylsulfonylamino)phenyl]-8-isopropyl-7-oxo-pteridin-2-yl]amino]piperidine-1-carboxylate (50 mg, 0.08 mmol) was reacted as in Example 73 (step 3) and purified by reverse phase chromatography to afford the title compound (11.6 mg, 28% yield).

Example 80: 1-(2-Cyanophenyl)-N-[2-fluoro-4-[2-[[(3S,5S)-5-fluoro-3-piperidyl]amino]-8-isopropyl-7-oxo-pteridin-6-yl]phenyl]methanesulfonamide (Compound 80)

Step 1: tert-Butyl (3S,5S)-3-[[6-[4-[(2-cyanophenyl)methylsulfonylamino]-3-fluoro-phenyl]-8-isopropyl-7-oxo-pteridin-2-yl]amino]-5-fluoro-piperidine-1-carboxylate

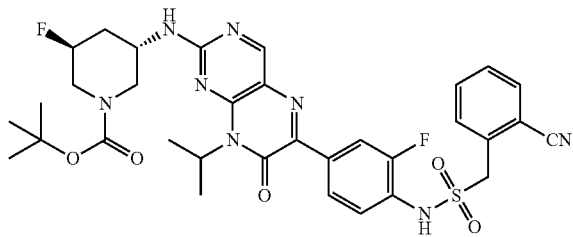 [SMILES: CC(C)n1c(=O)c(-c2ccc(NS(=O)(=O)Cc3ccccc3C#N)c(F)c2)nc2cnc(N[C@H]3C[C@H](F)CN(C(=O)OC(C)(C)C)C3)nc21]

To a solution of tert-butyl (3S,5S)-3-[[6-(4-amino-3-fluoro-phenyl)-8-isopropyl-7-oxo-pteridin-2-yl]amino]-5-fluoro-piperidine-1-carboxylate (100 mg, 0.19 mmol) in pyridine (0.8 mL) was added (2-cyanophenyl)methanesulfonyl chloride (66 mg, 0.29 mmol). The reaction was stirred overnight at room temperature, concentrated to dryness and purified by normal phase chromatography (0-80% heptanes to 3:1 Ipr/MeOH gradient over 20 mins) to afford the title compound (45 mg, 33% yield) as a yellow solid. LCMS (ESI): [M+H]$^+$=695.

Step 2: 1-(2-Cyanophenyl)-N-[2-fluoro-4-[2-[[(3S,5S)-5-fluoro-3-piperidyl]amino]-8-isopropyl-7-oxo-pteridin-6-yl]phenyl]methanesulfonamide

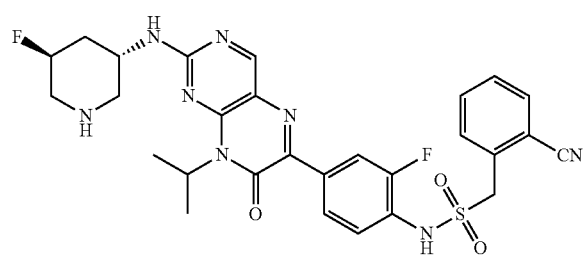 [SMILES: CC(C)n1c(=O)c(-c2ccc(NS(=O)(=O)Cc3ccccc3C#N)c(F)c2)nc2cnc(N[C@@H]3CNC[C@@H](F)C3)nc21]

To a solution of tert-butyl (3S,5S)-3-[[6-[4-[(2-cyanophenyl)methylsulfonylamino]-3-fluoro-phenyl]-8-isopropyl-7-oxo-pteridin-2-yl]amino]-5-fluoro-piperidine-1-carboxylate (45 mg, 0.06 mmol) was added 4N HCl in dioxane (81 µL, 0.32 mmol). The reaction was stirred at room temperature overnight then concentrated to dryness and purified via reverse phase HPLC to afford the title compound (31.5 mg, 82% yield).

Example 81: 1-(4-Cyanophenyl)-N-[2-fluoro-4-[2-[[(3S,5S)-5-fluoro-3-piperidyl]amino]-8-isopropyl-7-oxo-pteridin-6-yl]phenyl]methanesulfonamide (Compound 81)

Step 1: tert-Butyl (3S,5S)-3-[[6-[4-[(4-cyanophenyl)methylsulfonylamino]-3-fluoro-phenyl]-8-isopropyl-7-oxo-pteridin-2-yl]amino]-5-fluoro-piperidine-1-carboxylate

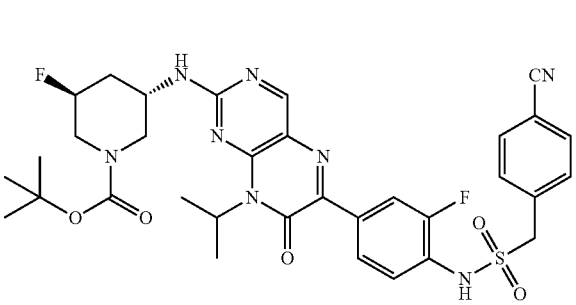 [SMILES: CC(C)n1c(=O)c(-c2ccc(NS(=O)(=O)Cc3ccc(C#N)cc3)c(F)c2)nc2cnc(N[C@H]3C[C@H](F)CN(C(=O)OC(C)(C)C)C3)nc21]

To a solution of tert-butyl (3S,5S)-3-[[6-(4-amino-3-fluoro-phenyl)-8-isopropyl-7-oxo-pteridin-2-yl]amino]-5-fluoro-piperidine-1-carboxylate (100 mg, 0.19 mmol) in pyridine (0.8 mL) was added (4-cyanophenyl)methanesulfonyl chloride (66 mg, 0.29 mmol). The reaction was stirred overnight at room temperature, concentrated to dryness and purified by normal phase chromatography (0-80% Heptanes to 3:1 Ipr/MeOH gradient over 20 mins) to afford the title compound (45 mg, 33% yield) as a yellow solid. LCMS (ESI): [M+H]$^+$=695.

Step 2: 1-(4-Cyanophenyl)-N-[2-fluoro-4-[2-[[(3S,5S)-5-fluoro-3-piperidyl]amino]-8-isopropyl-7-oxo-pteridin-6-yl]phenyl]methanesulfonamide

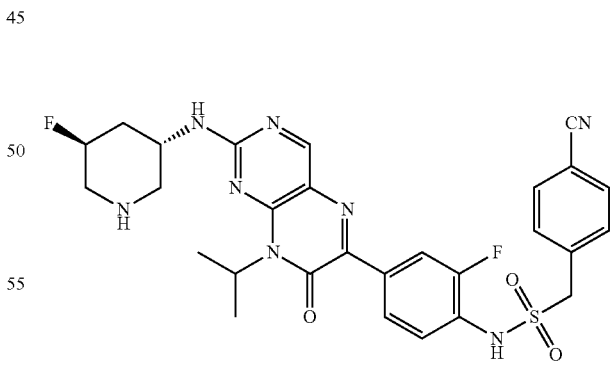

To a solution tert-butyl (3S,5S)-3-[[6-[4-[(4-cyanophenyl)methylsulfonylamino]-3-fluoro-phenyl]-8-isopropyl-7-oxo-pteridin-2-yl]amino]-5-fluoro-piperidine-1-carboxylate (45 mg, 0.06 mmol) was added 4N HCl in dioxane (81 µL, 0.32 mmol). The reaction was stirred at room temperature overnight then concentrated to dryness and purified via reverse phase HPLC to afford the title compound (21.4 mg, 56% yield).

Example 82: N-[2-Fluoro-4-[2-[[(3S,5S)-5-fluoro-3-piperidyl]amino]-8-isopropyl-7-oxo-pteridin-6-yl]phenyl]propane-1-sulfonamide (Compound 82)

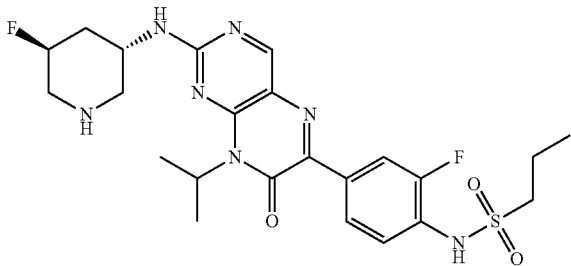 [SMILES: CCCS(=O)(=O)Nc1ccc(-c2nc3cnc(N[C@@H]4CNC[C@@H](F)C4)nc3n(C(C)C)c2=O)cc1F]

The title compound was prepared according to Example 80. This provides the title compound (25.3 mg, 50% yield) as a yellow solid.

Example 83: 2,2-Difluoro-N-[2-fluoro-4-[2-[[(3S,5S)-5-fluoro-3-piperidyl]amino]-8-isopropyl-7-oxo-pteridin-6-yl]phenyl]butane-1-sulfonamide (Compound 83)

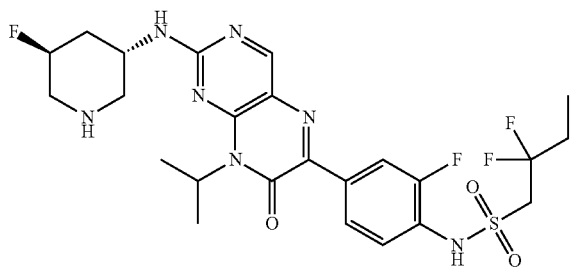 [SMILES: CCC(F)(F)CS(=O)(=O)Nc1ccc(-c2nc3cnc(N[C@@H]4CNC[C@@H](F)C4)nc3n(C(C)C)c2=O)cc1F]

The title compound was prepared according to Example 80. This provides the title compound (8.6 mg, 20% yield) as a yellow solid.

Example 84: 3,3-Difluoro-N-[2-fluoro-4-[2-[[(3S,5S)-5-fluoro-3-piperidyl]amino]-8-isopropyl-7-oxo-pteridin-6-yl]phenyl]butane-1-sulfonamide (Compound 84)

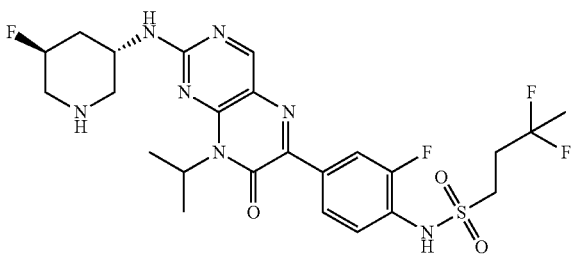 [SMILES: CC(C)n1c(=O)c(-c2ccc(NS(=O)(=O)CCC(C)(F)F)c(F)c2)nc2cnc(N[C@@H]3CNC[C@@H](F)C3)nc21]

The title compound was prepared according to Example 80. This provides the title compound (28.9 mg, 76% yield) as a yellow solid.

Example 85: 3,3-Difluoro-N-[2-fluoro-4-[2-[[(3S,5S)-5-fluoro-3-piperidyl]amino]-8-isopropyl-7-oxo-pteridin-6-yl]phenyl]butane-1-sulfonamide (Compound 85)

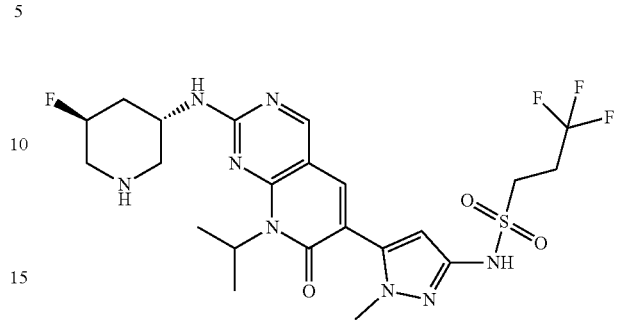

The title compound was prepared according to Example 86.

Example 86: 1-(2-Fluorophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide (Compound 86)

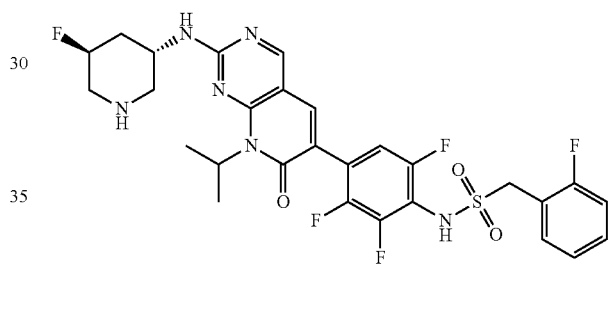

Step 1: 6-Bromo-8-isopropyl-2-(methylthio)pyrido[2,3-d]pyrimidin-7(8H)-one

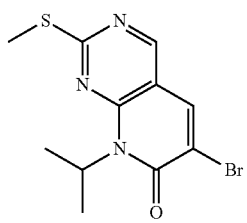 [SMILES: CSc1ncc2cc(Br)c(=O)n(C(C)C)c2n1]

To a solution of 6-bromo-4-methyl-2-(methylthio)pyrido[2,3-d]pyrimidin-7(8H)-one (2.00 g, 7.36 mmol) and potassium carbonate (2.04 g, 14.72 mmol) in DMF (24.5 mL) was slowly added isopropyl iodide (1.29 mL, 12.88 mmol). The reaction mixture was then stirred at 25° C. for 18 h. The reaction was quenched with 1N aq. NH$_4$Cl (15 mL) and stirred at 25° C. for 18 h. The solid was collected by filtration, washed with water (2×5 mL) and 5% ethyl acetate in heptane (10 mL) and dried under high vacuum to afford the title compound (1.91 g, 83% yield) as a white solid. LCMS (ESI): [M+H]$^+$=314.0; H NMR (400 MHz, DMSO-d$_6$) δ 8.86 (s, 1H), 8.49 (s, 1H), 5.83-5.67 (m, 1H), 2.61 (s, 3H), 1.55 (d, J=7.0 Hz, 6H).

Step 2: 6-(4-Amino-2,3,5-trifluorophenyl)-8-isopropyl-2-(methylthio)pyrido[2,3-d]pyrimidin-7(8H)-one

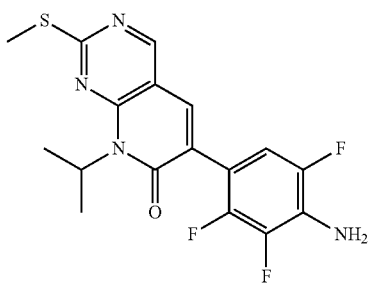 [SMILES: CSc1ncc2cc(-c3cc(F)c(N)c(F)c3F)c(=O)n(C(C)C)c2n1]

A solution of 6-bromo-8-isopropyl-2-(methylthio)pyrido[2,3-d]pyrimidin-7(8H)-one (A, 250 mg, 0.80 mmol), cesium fluoride (365 mg, 2.40 mmol), bis(di-tert-butyl(4-dimethylaminophenyl)phosphine)dichloropalladium(II) (57 mg, 0.08 mmol) and 2,3,6-trifluoro-4-(4,4,5,5-tetramethyl-1,3,2-dioxaborolan-2-yl)aniline (481 mg, 1.76 mmol) in 1,4-dioxane (4 mL) was stirred at 80° C. for 18 h. The reaction mixture was diluted with water (10 mL) and 10% methanol in dichloromethane (5 mL). The aqueous layer was extracted with 10% methanol in dichloromethane (2×5 mL). The combined organic layer was concentrated under reduced pressure. The residue was purified by prep-HPLC to afford the title compound (115 mg, 38% yield) as a black semi-solid. LCMS (ESI): [M+H]$^+$=381.2; $^1$H NMR (400 MHz, DMSO-$d_6$) δ 8.89 (s, 1H), 7.99 (s, 1H), 7.09 (dd, J=11.8, 6.1 Hz, 1H), 5.82 (s, 2H), 5.79-5.71 (m, 1H), 2.62 (s, 3H), 1.57 (d, J=6.8 Hz, 6H).

Step 3: 1-(2-Fluorophenyl)-N-(2,3,6-trifluoro-4-(8-isopropyl-2-(methylthio)-7-oxo-7,8-dihydropyrido[2,3-d]pyrimidin-6-yl)phenyl)methanesulfonamide

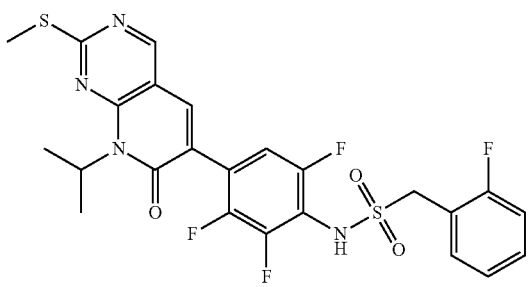 [SMILES: CSc1ncc2cc(-c3cc(F)c(NS(=O)(=O)Cc4ccccc4F)c(F)c3F)c(=O)n(C(C)C)c2n1]

A cooled to 0° C. solution of 6-(4-amino-2,3,5-trifluorophenyl)-8-isopropyl-2-(methylthio)pyrido[2,3-d]pyrimidin-7(8H)-one (113 mg, 0.297 mmol), (2-fluorophenyl)methanesulfonyl chloride (93 mg, 0.446 mmol) and pyridine (0.12 mL, 1.485 mmol) in dichloromethane (1.49 mL) was stirred at 0° C. to room temperature for 18 h. 2-fluorophenyl)methanesulfonyl chloride (50 mg, 0.240 mmol) was added and the mixture stirred at 0° C. to room temperature for 4 h. Water (0.5 mL), MeOH (0.5 mL) and potassium carbonate (166 mg, 1.20 mmol) were added and the mixture stirred at 25° C. for 18 h. The crude mixture was purified by prep-HPLC to afford the title compound (118 mg, 72% yield) as a beige solid. LCMS (ESI): [M+H]$^+$=553.2; $^1$H NMR (400 MHz, DMSO-$d_6$) δ 10.15 (s, 1H), 8.93 (s, 1H), 8.17 (s, 1H), 7.53 (t, J=7.6 Hz, 1H), 7.49-7.37 (m, 2H), 7.32-7.21 (m, 2H), 5.81-5.73 (m, 1H), 4.61 (s, 2H), 2.64 (s, 3H), 1.59 (d, J=6.8 Hz, 6H).

Step 4: 1-(2-Fluorophenyl)-N-(2,3,6-trifluoro-4-(8-isopropyl-2-(methylsulfonyl)-7-oxo-7,8-dihydropyrido[2,3-d]pyrimidin-6-yl)phenyl)methanesulfonamide

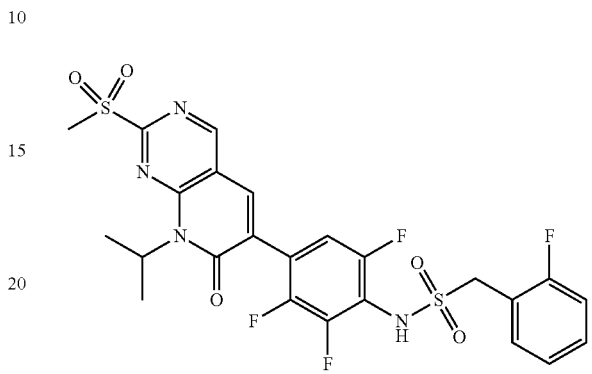

To a solution of 1-(2-fluorophenyl)-N-(2,3,6-trifluoro-4-(8-isopropyl-2-(methylthio)-7-oxo-7,8-dihydropyrido[2,3-d]pyrimidin-6-yl)phenyl)methanesulfonamide (114 mg, 0.206 mmol) in 1,4-dioxane (1.40 mL) was added oxone (279 mg, 0.454 mmol) and water (0.35 mL). The reaction mixture was stirred at 25° C. for 18 h. The reaction mixture was diluted with dichloromethane (5 mL), brine (2 mL) and 1N aq. $Na_2S_2O_3$ (0.4 mL). The aqueous layer was extracted with dichloromethane (2×5 mL). The combined organic layer was dried ($Na_2SO_4$) and concentrated under reduced pressure to afford the title compound (136 mg, 113% yield) as a black solid. LCMS (ESI): [M+H]$^+$=585.3.

Step 5: tert-Butyl (3S,5S)-3-fluoro-5-((8-isopropyl-7-oxo-6-(2,3,5-trifluoro-4-(((2-fluorophenyl)methyl)sulfonamido)phenyl)-7,8-dihydropyrido[2,3-d]pyrimidin-2-yl)amino)piperidine-1-carboxylate

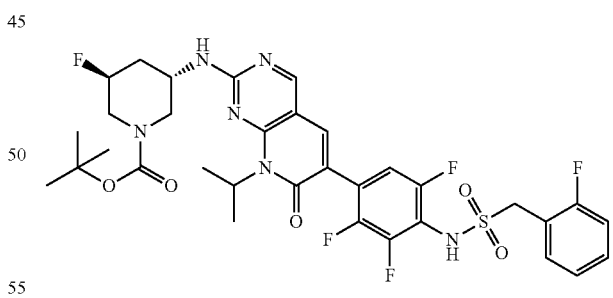

A solution of 1-(2-fluorophenyl)-N-(2,3,6-trifluoro-4-(8-isopropyl-2-(methylsulfonyl)-7-oxo-7,8-dihydropyrido[2,3-d]pyrimidin-6-yl)phenyl)methanesulfonamide (45 mg, 0.077 mmol), cesium fluoride (35 mg, 0.231 mmol), DIEA (0.040 mL, 0.231 mmol) and tert-butyl (3S,5S)-3-amino-5-fluoro-piperidine-1-carboxylate (19 mg, 0.085 mmol) in DMSO (0.385 mL) was stirred at 60° C. for 18 h. The reaction mixture was diluted with dichloromethane (3 mL), 1N aq. $NH_4Cl$ (10 mL) and water (10 mL). The aqueous layer was extracted with dichloromethane (3 mL). The combined organic layer was concentrated under reduced pressure to afford the title compound (80 mg, 144% yield) as a beige solid. LCMS (ESI): [M+H]⁺=723.4.

Step 6: 1-(2-Fluorophenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide

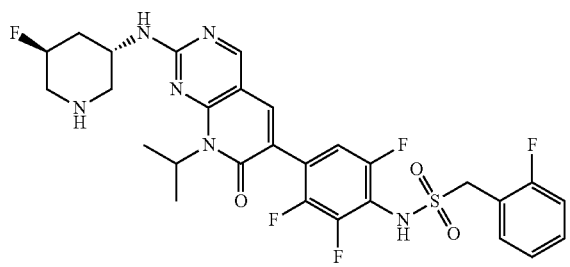 [SMILES: CC(C)n1c(=O)c(-c2cc(F)c(NS(=O)(=O)Cc3ccccc3F)c(F)c2F)cc2cnc(N[C@@H]3CNC[C@@H](F)C3)nc21]

To tert-butyl (3S,5S)-3-fluoro-5-((8-isopropyl-7-oxo-6-(2,3,5-trifluoro-4-(((2-fluorophenyl)methyl)sulfonamido)phenyl)-7,8-dihydropyrido[2,3-d]pyrimidin-2-yl)amino)piperidine-1-carboxylate (80 mg, 0.077 mmol) in dichloromethane (0.38 mL) was slowly added TFA (0.059 mL, 0.770 mmol). The reaction mixture was stirred at 25° C. for 18 h. The reaction mixture was diluted with dichloromethane (5 mL), 1N aq. NaHCO₃ (1 mL) and 1N aq. NH₄Cl (0.5 mL). The aqueous layer was extracted with 10% methanol in dichloromethane (2×3 mL). The combined organic layer was concentrated under reduced pressure. The residue was purified by prep-HPLC to afford the title compound (29 mg, 610% yield) as a beige solid. LCMS (ESI): [M+H]⁺=623.2; ¹H NMR (400 MHz, DMSO-d₆) δ 8.68 (s, 1H), 8.01 (d, J=7.9 Hz, 1H), 7.93 (s, 1H), 7.53 (t, J=7.6 Hz, 1H), 7.47-7.37 (m, 1H), 7.34-7.19 (m, 3H), 5.85-5.68 (m, 1H), 5.07-4.85 (m, 1H), 4.52 (s, 2H), 4.39-4.18 (m, 1H), 3.18-3.12 (m, 2H), 2.98-2.81 (m, 1H), 2.66-2.55 (m, 1H), 2.31-2.20 (m, 1H), 1.93-1.72 (m, 1H), 1.55 (dd, J=14.5, 6.8 Hz, 6H).

Example 87: 1-(2-Fluorophenyl)-N-(2,3,6-trifluoro-4-(2-((5-hydroxypiperidin-3-yl)amino)-8-isopropyl-7-oxo-7,8-dihydropyrido[2,3-d]pyrimidin-6-yl)phenyl)methanesulfonamide (trans racemic mixture) (Compound 87)

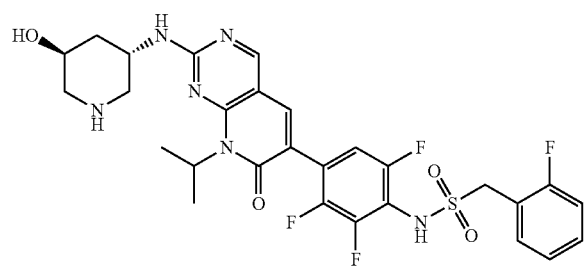 [SMILES: CC(C)n1c(=O)c(-c2cc(F)c(NS(=O)(=O)Cc3ccccc3F)c(F)c2F)cc2cnc(N[C@@H]3CNC[C@@H](O)C3)nc21]

The title compound was prepared according to Example 86.

Example 88 and Example 89: 1-(2-Fluorophenyl)-N-(2,3,6-trifluoro-4-(2-(((3R,5S)-5-hydroxypiperidin-3-yl)amino)-8-isopropyl-7-oxo-7,8-dihydropyrido[2,3-d]pyrimidin-6-yl)phenyl) methanesulfonamide and 1-(2-fluorophenyl)-N-(2,3,6-trifluoro-4-(2-(((3S,5R)-5-hydroxypiperidin-3-yl)amino)-8-isopropyl-7-oxo-7,8-dihydropyrido[2,3-d]pyrimidin-6-yl)phenyl)methanesulfonamide (Compound 88) and (Compound 89)

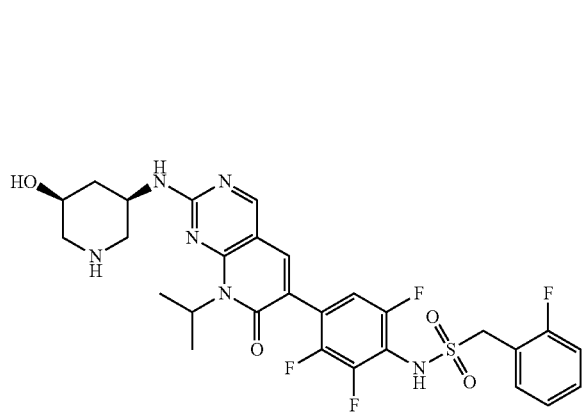

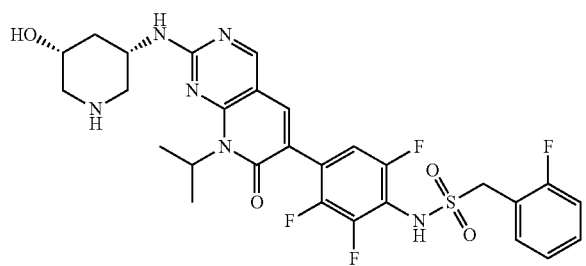

The title compounds were obtained after chiral SFC separation of 1-(2-fluorophenyl)-N-(2,3,6-trifluoro-4-(2-((5-hydroxypiperidin-3-yl)amino)-8-isopropyl-7-oxo-7,8-dihydropyrido[2,3-d]pyrimidin-6-yl)phenyl)methanesulfonamide cis racemic mixture. The absolute stereochemistry was assigned based on cellular potency.

Peak 1: LCMS (ESI): [M+H]⁺=621.2; ¹H NMR (400 MHz, DMSO-d₆) δ 8.66 (s, 1H), 7.88 (s, 1H), 7.81-7.73 (m, 1H), 7.53 (td, J=7.6, 1.8 Hz, 1H), 7.41-7.31 (m, 1H), 7.23-7.08 (m, 3H), 5.82-5.65 (m, 1H), 5.22-5.12 (m, 1H), 4.35 (s, 2H), 4.20-3.97 (m, 1H), 3.74-3.62 (m, 1H), 3.12-2.90 (m, 2H), 2.47-2.35 (m, 2H), 2.25-2.10 (m, 1H), 1.62-1.42 (m, 7H); tR=1.25 min, Chiralpak IE, CO₂:EtOH (0.1% NH₄OH)=55:45.

Peak 2: LCMS (ESI): [M+H]⁺=621.2; ¹H NMR (400 MHz, DMSO-d₆) δ 8.70 (s, 1H), 7.94 (s, 1H), 7.91-7.83 (m, 1H), 7.53 (td, J=7.6, 1.8 Hz, 1H), 7.47-7.37 (m, 1H), 7.32-7.18 (m, 3H), 5.82-5.68 (m, 1H), 5.50-5.35 (m, 1H), 4.51 (s, 2H), 4.30-4.10 (m, 1H), 3.90-3.70 (m, 1H), 3.25-3.15 (m, 2H), 2.77-2.55 (m, 2H), 2.27-2.12 (m, 1H), 1.65-1.45 (m, 7H). tR=1.81 min, Chiralpak IE, CO₂:EtOH (0.1% NH₄OH)=55:45.

Example 90: N-(2-Fluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(2-fluorophenyl)methanesulfonamide (Compound 90)

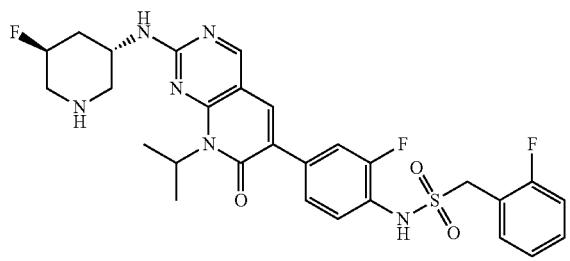 [SMILES: CC(C)n1c(=O)c(-c2ccc(NS(=O)(=O)Cc3ccccc3F)c(F)c2)cc2cnc(N[C@@H]3CNC[C@@H](F)C3)nc21]

Step 1: N-(4-Bromo-2-fluorophenyl)-1-(2-fluorophenyl)methanesulfonamide

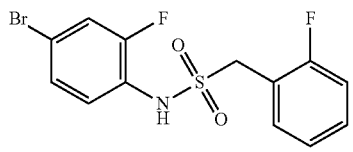 [SMILES: O=S(=O)(Cc1ccccc1F)Nc1ccc(Br)cc1F]

A cooled to 0° C. solution of 4-bromo-2-fluoro-aniline (190 mg, 1.00 mmol), (2-fluorophenyl)methanesulfonyl chloride (313 mg, 1.50 mmol) and pyridine (0.40 mL, 5.00 mmol) in dichloromethane (5.0 mL) was stirred at 0° C. to room temperature for 3 h. The crude mixture was purified by prep-HPLC to afford the title compound (283 mg, 78% yield) as a beige solid. LCMS (ESI): [M+H]$^+$=362.0; $^1$H NMR (400 MHz, DMSO-d$_6$) δ 9.98 (s, 1H), 7.61 (dd, J=10.0, 2.2 Hz, 1H), 7.47-7.38 (m, 2H), 7.37-7.26 (m, 2H), 7.25-7.17 (m, 2H), 4.56 (s, 2H).

Step 2: N-(2-Fluoro-4-(8-isopropyl-2-(methylthio)-7-oxo-7,8-dihydropyrido[2,3-d]pyrimidin-6-yl)phenyl)-1-(2-fluorophenyl)methanesulfonamide

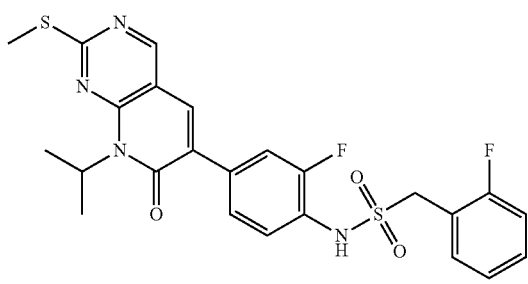 [SMILES: CSc1ncc2cc(-c3ccc(NS(=O)(=O)Cc4ccccc4F)c(F)c3)c(=O)n(C(C)C)c2n1]

A solution of N-(4-bromo-2-fluorophenyl)-1-(2-fluorophenyl)methanesulfonamide (145 mg, 0.40 mmol), bis(diphenylphosphino)ferrocene]dichloropalladium(II) (16.5 mg, 0.02 mmol), bis(pinacolato)diboron (132 mg, 0.520 mmol) and potassium acetate (118 mg, 1.20 mmol) in 1,4-dioxane (1.33 mL) was stirred at 80° C. for 4 h. Potassium phosphate (170 mg, 0.80 mmol), SPhos Pd G3 (16 mg, 0.02 mmol), 6-bromo-8-isopropyl-2-(methylthio)pyrido[2,3-d]pyrimidin-7(8H)-one (126 mg, 0.40 mmol) and water (0.13 mL) were added and the mixture was stirred at 80° C. for 18 h. The crude mixture was purified by prep-HPLC to afford the title compound (124 mg, 60% yield) as a beige solid. LCMS (ESI): [M+H]$^+$=517.2; $^1$H NMR (400 MHz, DMSO-d$_6$) δ 10.00 (s, 1H), 8.91 (s, 1H), 8.15 (s, 1H), 7.65 (dd, J=12.3, 2.0 Hz, 1H), 7.54-7.36 (m, 4H), 7.28-7.19 (m, 2H), 5.83-5.73 (m, 1H), 4.58 (s, 2H), 2.63 (s, 3H), 1.60 (d, J=6.9 Hz, 6H).

Step 3-5: N-(2-Fluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(2-fluorophenyl)methanesulfonamide

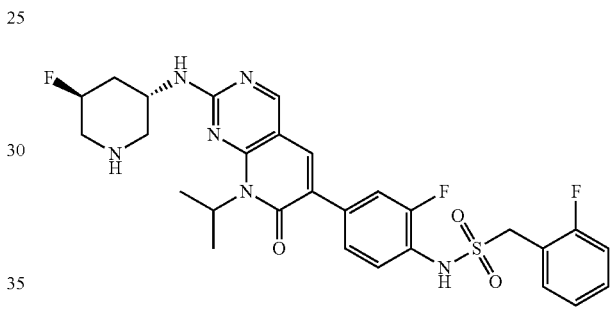

Starting with N-(2-fluoro-4-(8-isopropyl-2-(methylthio)-7-oxo-7,8-dihydropyrido[2,3-d]pyrimidin-6-yl)phenyl)-1-(2-fluorophenyl)methanesulfonamide and following step 4-6 of Example 86, the title compound was obtained as a beige solid. LCMS (ESI): [M+H]$^+$=587.2; $^1$H NMR (400 MHz, DMSO-d$_6$) δ 8.72-8.59 (m, 1H), 7.96 (s, 1H), 7.81 (d, J=8.0 Hz, 1H), 7.60 (dd, J=12.5, 2.0 Hz, 1H), 7.51-7.32 (m, 4H), 7.28-7.18 (m, 2H), 5.85-5.69 (m, 1H), 4.92-4.75 (m, 1H), 4.53 (s, 2H), 4.27-4.10 (m, 1H), 3.10-2.90 (m, 2H), 2.81-2.65 (m, 1H), 2.57-2.52 (m, 1H), 2.28-2.10 (m, 1H), 1.93-1.70 (m, 1H), 1.61-1.51 (m, 6H).

Example 91: N-(4-(2-(((1r,4r)-4-(Dimethylamino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide (Compound 91)

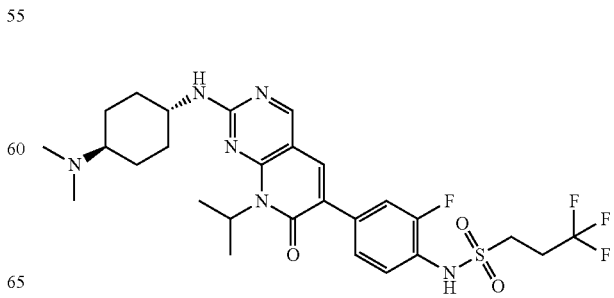

Step 1: N-(4-Bromo-2-fluorophenyl)-3,3,3-trifluoropropane-1-sulfonamide

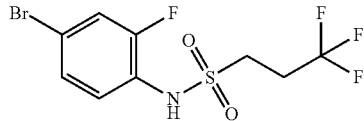 [SMILES: O=S(=O)(CCC(F)(F)F)Nc1ccc(Br)cc1F]

A cooled to 0° C. solution of 4-bromo-2-fluoro-aniline (950 mg, 5.00 mmol), 3,3,3-trifluoropropane-1-sulfonyl chloride (1470 mg, 7.50 mmol) and pyridine (2.02 mL, 25.00 mmol) in dichloromethane (25.0 mL) was stirred at 0° C. to room temperature for 18 h. The reaction mixture was diluted with water (10 mL), 2N aq. HCl (13 mL) and dichloromethane (25 mL). The aqueous layer was extracted with dichloromethane (5 mL). The combined organic layer was concentrated under reduced pressure. The residue was purified by column chromatography (silica gel, 10% methanol in isopropyl acetate/heptane) to afford the title compound (1522 mg, 87% yield) as a white solid. LCMS (ESI): $[M-H]^-=347.9$; $^1$H NMR (400 MHz, DMSO-$d_6$) δ 10.06 (s, 1H), 7.67 (dd, J=10.0, 2.1 Hz, 1H), 7.43 (dd, J=8.6, 2.1 Hz, 1H), 7.37 (t, J=8.5 Hz, 1H), 3.44-3.35 (m, 2H), 2.86-2.69 (m, 2H).

Step 2: 3,3,3-Trifluoro-N-(2-fluoro-4-(8-isopropyl-2-(methylthio)-7-oxo-7,8-dihydropyrido[2,3-d]pyrimidin-6-yl)phenyl)propane-1-sulfonamide

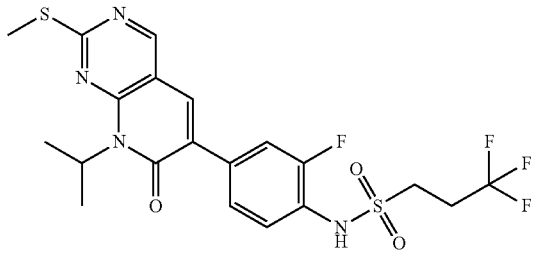 [SMILES: CSc1ncc2cc(-c3ccc(NS(=O)(=O)CCC(F)(F)F)c(F)c3)c(=O)n(C(C)C)c2n1]

A solution of 6-bromo-8-isopropyl-2-(methylthio)pyrido[2,3-d]pyrimidin-7(8H)-one (471 mg, 1.50 mmol), cataCxium Pd G4 (56 mg, 0.075 mmol), bis(pinacolato)diboron (495 mg, 1.95 mmol) and potassium acetate (442 mg, 4.50 mmol) in 1,4-dioxane (5.0 mL) was stirred at 60° C. for 18 h. 2.0 mL of the reaction mixture was added to a solution of N-(4-bromo-2-fluorophenyl)-3,3,3-trifluoropropane-1-sulfonamide (210 mg, 0.600 mmol), potassium phosphate (255 mg, 1.20 mmol) and SPhos Pd G3 (23.4 mg, 0.075 mmol) in dioxane (1.0 mL) and water (0.30 mL). The reaction mixture was stirred at 60° C. for 18 h. The reaction mixture was diluted with 1N aq. NH$_4$Cl (5 mL) and 10% methanol in dichloromethane (5 mL). The aqueous layer was extracted with 10% methanol in dichloromethane (2×5 mL). The combined organic layer was concentrated under reduced pressure. The residue was purified by column chromatography (silica gel, 10% methanol in isopropyl acetate/heptane) to afford the title compound (306 mg, 100% yield) as a beige oil. LCMS (ESI): $[M+H]^+=505.2$.

Step 3: 3,3,3-Trifluoro-N-(2-fluoro-4-(8-isopropyl-2-(methylsulfonyl)-7-oxo-7,8-dihydropyrido[2,3-d]pyrimidin-6-yl)phenyl)propane-1-sulfonamide

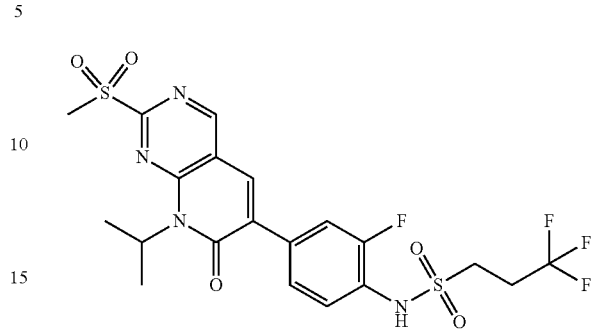

To a solution of 3,3,3-trifluoro-N-(2-fluoro-4-(8-isopropyl-2-(methylthio)-7-oxo-7,8-dihydropyrido[2,3-d]pyrimidin-6-yl)phenyl)propane-1-sulfonamide (306 mg, 0.60 mmol) in 1,4-dioxane (4.0 mL) was added oxone (811 mg, 1.32 mmol) and water (1.0 mL). The reaction mixture was stirred at 25° C. for 18 h. The reaction mixture was diluted with dichloromethane (5 mL), brine (4 mL) and 1N aq. Na$_2$S$_2$O$_3$ (1.4 mL). The aqueous layer was extracted with dichloromethane (2×5 mL). The combined organic layer was dried (Na$_2$SO$_4$) and concentrated under reduced pressure to afford the title compound (305 mg, 95% yield) as a brown semi-solid. LCMS (ESI): $[M+H]^+=537.2$.

Step 4: N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide

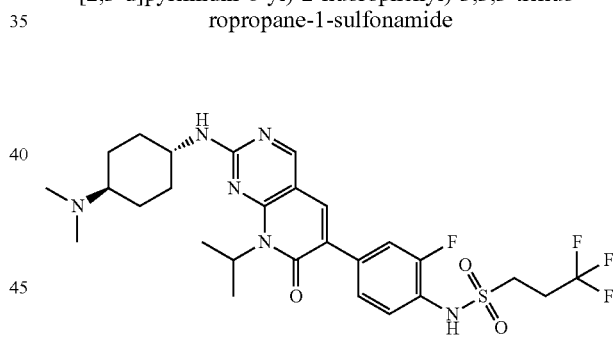

A solution of 3,3,3-trifluoro-N-(2-fluoro-4-(8-isopropyl-2-(methylsulfonyl)-7-oxo-7,8-dihydropyrido[2,3-d]pyrimidin-6-yl)phenyl)propane-1-sulfonamide (152 mg, 0.30 mmol), cesium fluoride (137 mg, 0.90 mmol), diisopropylethylamine (0.157 mL, 0.90 mmol) and (1r,4r)-N$^1$,N$^1$-dimethylcyclohexane-1,4-diamine (47 mg, 0.33 mmol) in DMSO (1.5 mL) was stirred at 60° C. for 18 h. The reaction mixture was diluted with dichloromethane (5 mL), 1N aq. NH$_4$Cl (3 mL) and water (15 mL). The aqueous layer was extracted with dichloromethane (5 mL). The combined organic layer was concentrated under reduced pressure. The residue was purified by prep-HPLC to afford the title compound (52 mg, 29% yield) as a beige solid. LCMS (ESI): $[M+H]^+=599.3$; $^1$H NMR (400 MHz, DMSO-$d_6$) δ 8.64 (s, 1H), 7.96 (s, 1H), 7.89 (d, J=7.7 Hz, 1H), 7.62 (dd, J=12.3, 1.9 Hz, 1H), 7.48 (dd, J=8.5, 2.0 Hz, 1H), 7.42 (t, J=8.4 Hz, 1H), 5.84-5.66 (m, 1H), 3.90-3.68 (m, 1H), 3.22-3.01 (m, 2H), 2.88-2.71 (m, 3H), 2.58 (s, 6H), 2.13-1.93 (m, 4H), 1.62-1.51 (m, 6H), 1.50-1.31 (m, 4H).

Example 92: 3,3,3-Trifluoro-N-(2-fluoro-4-(2-(((3S, 5S)-5-fluoropiperidin-3-yl)amino)-8-isopropyl-7-oxo-7,8-dihydropyrido[2,3-d]pyrimidin-6-yl)phenyl)propane-1-sulfonamide (Compound 92)

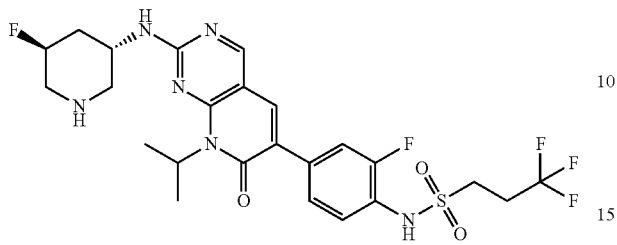

Starting with 3,3,3-trifluoro-N-(2-fluoro-4-(8-isopropyl-2-(methylsulfonyl)-7-oxo-7,8-dihydropyrido[2,3-d]pyrimidin-6-yl)phenyl)propane-1-sulfonamide and following step 5-6 of Example 86, the title compound was obtained as a beige solid. LCMS (ESI): [M+H]$^+$=575.2; $^1$H NMR (400 MHz, DMSO-d$_6$) δ 8.71 (br s, 1H), 8.08 (d, J=7.6 Hz, 1H), 8.02 (s, 1H), 7.64 (dd, J=12.1, 1.9 Hz, 1H), 7.51 (dd, J=8.4, 1.9 Hz, 1H), 7.45 (t, J=8.3 Hz, 1H), 5.86-5.76 (m, 1H), 5.30-5.10 (m, 1H), 4.58-4.34 (m, 1H), 3.56-3.37 (m, 4H), 3.21-3.11 (m, 1H), 2.90-2.73 (m, 3H), 2.40-2.25 (m, 1H), 2.00-1.77 (m, 1H), 1.61-1.51 (m, 6H).

Example 93: 1-(2-Fluorophenyl)-N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)methanesulfonamide (Compound 93)

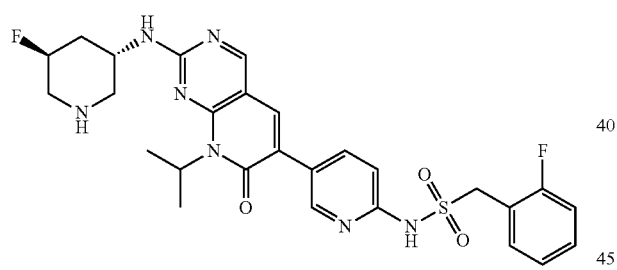

The title compound was prepared according to Example 90.

Example 94: N-(6-(2-(((1r,4r)-4-(Dimethylamino)cyclohexyl)amino)-8-isopropyl-7-oxo-7,8-dihydropyrido[2,3-d]pyrimidin-6-yl)pyridin-3-yl)-1-(2-fluorophenyl)methanesulfonamide (Compound 94)

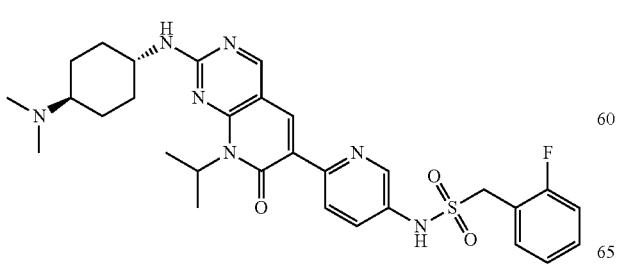

Step 1-3: 1-(2-Fluorophenyl)-N-(6-(8-isopropyl-2-(methylsulfonyl)-7-oxo-7,8-dihydropyrido[2,3-d]pyrimidin-6-yl)pyridin-3-yl)methanesulfonamide

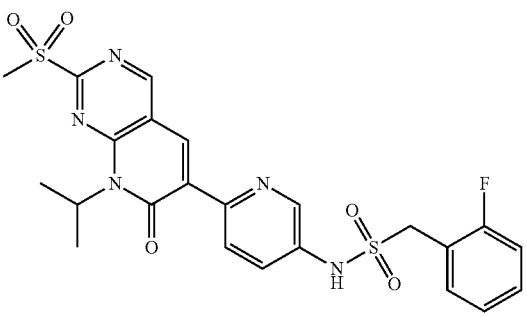 [SMILES: CC(C)n1c(=O)c(-c2ccc(NS(=O)(=O)Cc3ccccc3F)cn2)cc2cnc(S(C)(=O)=O)nc21]

Starting with 6-bromopyridin-3-amine and following step 1-3 of Example 90, the title compound was obtained as a brown solid. LCMS (ESI): [M+H]$^+$=532.2.

Step 4: N-(6-(2-(((1r,4r)-4-(Dimethylamino)cyclohexyl)amino)-8-isopropyl-7-oxo-7,8-dihydropyrido[2,3-d]pyrimidin-6-yl)pyridin-3-yl)-1-(2-fluorophenyl)methanesulfonamide

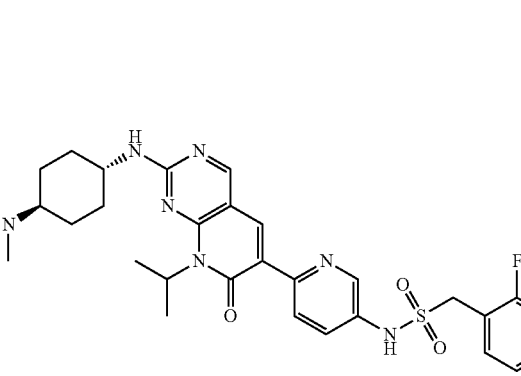

Starting with 1-(2-fluorophenyl)-N-(6-(8-isopropyl-2-(methylsulfonyl)-7-oxo-7,8-dihydropyrido[2,3-d]pyrimidin-6-yl)pyridin-3-yl)methanesulfonamide and following step 4 of Example 91, the title compound was obtained as a beige solid. LCMS (ESI): [M+H]$^+$=594.3; $^1$H NMR (400 MHz, CD$_3$OD-d$_4$) δ 8.60 (s, 1H), 8.34 (d, J=2.6 Hz, 1H), 8.16 (s, 1H), 7.99 (d, J=8.8 Hz, 1H), 7.60 (dd, J=8.7, 2.7 Hz, 1H), 7.45 (t, J=7.6 Hz, 1H), 7.34 (q, J=7.1, 6.5 Hz, 1H), 7.16 (t, J=7.6 Hz, 1H), 7.06 (t, J=9.1 Hz, 1H), 5.98-5.82 (m, 1H), 4.53 (s, 2H), 3.93-3.80 (m, 1H), 2.54-2.45 (m, 1H), 2.42 (s, 6H), 2.27-2.13 (m, 2H), 2.10-2.00 (m, 2H), 1.68-1.64 (m, 4H), 1.29 (s, 6H).

Example 95: 1-(2-Fluorophenyl)-N-(6-(2-(((3S,5S)-5-fluoropiperidin-3-yl)amino)-8-isopropyl-7-oxo-7,8-dihydropyrido[2,3-d]pyrimidin-6-yl)pyridin-3-yl)methanesulfonamide (Compound 95)

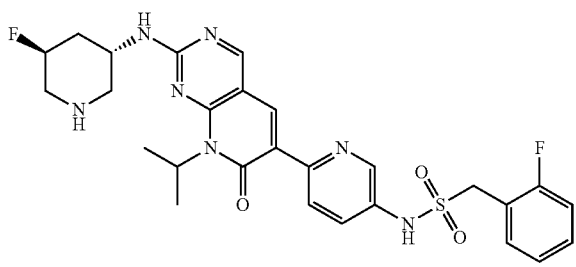 [SMILES: CC(C)n1c(=O)c(-c2ccc(NS(=O)(=O)Cc3ccccc3F)cn2)cc2cnc(N[C@@H]3CNC[C@@H](F)C3)nc21]

The title compound was prepared according to Example 90.

Example 96: (1S,2S)—N-(4-(2-(((r,4r)-4-(dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide Compound 96

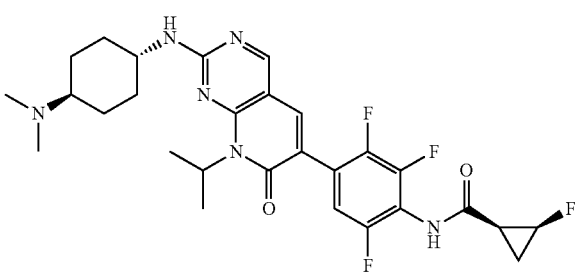 [SMILES: CC(C)n1c(=O)c(-c2cc(F)c(NC(=O)[C@@H]3C[C@@H]3F)c(F)c2F)cc2cnc(N[C@H]3CC[C@H](N(C)C)CC3)nc21]

The title compound was prepared according to example 58 to provide the title compound (41.3 mg, 31.4% yield) as a white solid.

Example 97; 1-(5-Chloro-2-methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide hydrochloride Compound 97

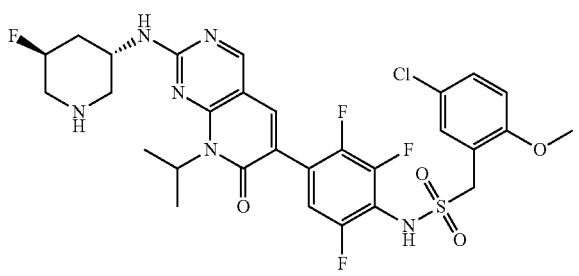 [SMILES: COc1ccc(Cl)cc1CS(=O)(=O)Nc1c(F)cc(-c2cc3cnc(N[C@@H]4CNC[C@@H](F)C4)nc3n(C(C)C)c2=O)c(F)c1F]

Step 1: 2-Methoxybenzyl carbamimidothioate

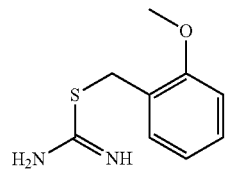

To a solution of 2-methoxybenzyl alcohol (3.0 g, 22 mmol) in dichloromethane (90 mL) was added methanesulfonyl chloride (2.6 mL, 34 mmol) and N,N-diisopropylethylamine (10 mL, 66 mmol) and stirred at rt for 2 h. The solution was diluted with dichloromethane and washed with brine. The organic layer was dried over anhydrous sodium sulfate and concentrated under vacuum. The residue was diluted with acetone (100 mL). Then thiourea (1.0 g, 13 mmol) was added. The solution was stirred for 16 h at 60° C. The solid was collected by filtration to afford the title compound (2.3 g, 97.5% yield) as a white solid. LCMS (ESI): [M+H]$^+$=197.0

Step 2: (5-Chloro-2-methoxy-phenyl)methanesulfonyl chloride

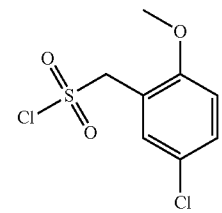

To a mixture of 2-methoxybenzyl carbamimidothioate (120 mg, 0.61 mmol) in acetonitrile (10 mL) was added hydrochloric acid (0.3 mL, 0.6 mmol, 2 M). The mixture was stirred at rt for 5 min. tert-butyl chlorite (0.28 mL, 2.2 mmol) in acetonitrile (1 mL) was added dropwise at 0° C. The solution was stirred at 0° C. for 20 min. The solution was diluted with water and extracted with ethyl acetate. The solution was dried over anhydrous sodium sulfate and concentrated under vacuum to afford the title compound (120 mg, 76.9% yield) as colorless oil.

Step 3: tert-Butyl (3S,5S)-3-((6-(4-(((5-chloro-2-methoxyphenyl)methyl)sulfonamido)-2,3,5-trifluorophenyl)-8-isopropyl-7-oxo-7,8-dihydropyrido[2,3-d]pyrimidin-2-yl)amino)-5-fluoropiperidine-1-carboxylate

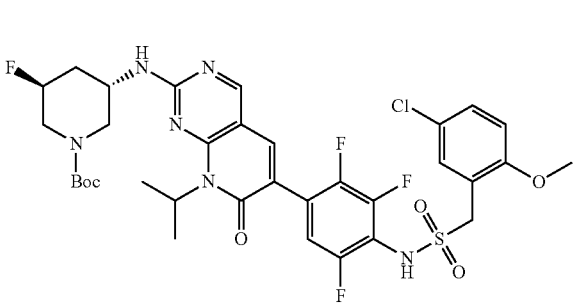 [SMILES: COc1ccc(Cl)cc1CS(=O)(=O)Nc1c(F)cc(-c2cc3cnc(N[C@H]4C[C@H](F)CN(C(=O)OC(C)(C)C)C4)nc3n(C(C)C)c2=O)c(F)c1F]

To a solution of tert-butyl (3S,5S)-3-((6-(4-amino-2,3,5-trifluoro-phenyl)-8-isopropyl-7-oxo-pyrido[2,3-d]pyrimidin-2-yl)amino)-5-fluoro-piperidine-1-carboxylate (100 mg, 0.18 mmol) in pyridine (1 mL) was added (5-chloro-2-methoxy-phenyl)methanesulfonyl chloride (240 mg, 0.94 mmol). The solution was stirred at rt for 1 h. The reaction was diluted with dichloromethane and washed with brine. The solution was dried over anhydrous sodium sulfate and concentrated under vacuum. The residue was purified by silica flash chromatography eluting with ethyl acetate/petroleum ether (40%-80%) to afford the title compound (110 mg, 78.7% yield) as a light yellow solid. LCMS (ESI): [M+H]$^+$=769.2.

Step 4: 1-(5-Chloro-2-methoxyphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide hydrochloride Compound 97

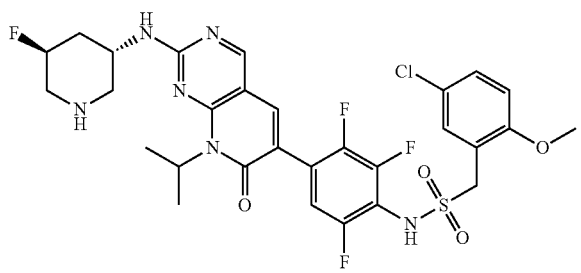 [SMILES: COc1ccc(Cl)cc1CS(=O)(=O)Nc1c(F)cc(-c2cc3cnc(N[C@@H]4CNC[C@@H](F)C4)nc3n(C(C)C)c2=O)c(F)c1F]

To a solution of tert-butyl (3S,5S)-3-((6-(4-(((5-chloro-2-methoxyphenyl)methyl)sulfonamido)-2,3,5-trifluorophenyl)-8-isopropyl-7-oxo-7,8-dihydropyrido[2,3-d]pyrimidin-2-yl)amino)-5-fluoropiperidine-1-carboxylate (100 mg, 0.13 mmol) in dichloromethane (3 mL) was added 4 M HCl in 1,4-dioxane (3 mL, 12 mmol). The solution was stirred at rt for 30 min. The solution was concentrated under vacuum. The residue was purified by Prep-HPLC to afford the title compound (25.8 mg, 28.1% yield) as a white solid and as HCl salt.

Example 98: N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide Compound 98

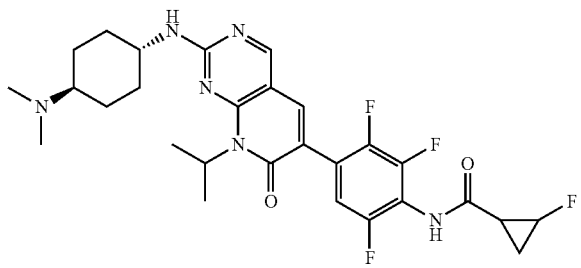 [SMILES: CC(C)n1c(=O)c(-c2cc(F)c(NC(=O)C3CC3F)c(F)c2F)cc2cnc(N[C@H]3CC[C@H](N(C)C)CC3)nc21]

The title compound was prepared according to example 58. The residue was purified by Prep-HPLC and Chiral HPLC to afford the title compound. After Chiral HPLC, two peaks were isolated out. The fast peak was assigned isomer 1. The slow peak was assigned isomer 2.

N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide (isomer 1) (24.3 mg, 10.3% yield) as a white solid. (rt=1.913 min, chiral Cellulose-SB4.6*100 mm 3 μm, Hex (0.10% DEA):EtOH=50:50; 1 mL/min).

N-(4-(2-(((1r,4r)-4-(Dimethylamino)cyclohexyl)amino)-8-isopropyl-7-oxo-7,8-dihydropyrido[2,3-d]pyrimidin-6-yl)-2,3,6-trifluorophenyl)-2-fluorocyclopropane-1-carboxamide (isomer 2) (31.1 mg, 13.2% yield) as white solid. (rt=1.913 min, chiral Cellulose-SB4.6*100 mm 3 μm, Hex (0.1% DEA):EtOH=50:50; 1 mL/min).

Example 99: 2-(((1r,4r)-4-(Dimethylamino)cyclohexyl)amino)-8-isopropyl-6-(2,3,5-trifluoro-4-((3,3,3-trifluoro-2-hydroxypropyl)amino)phenyl)pyrido[2,3-d]pyrimidin-7(8H)-one Compound 99

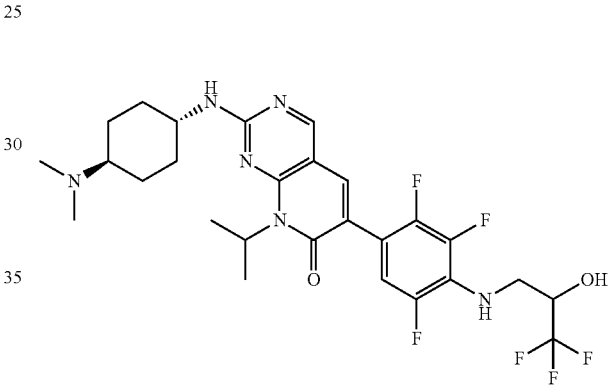

A mixture of 6-(4-amino-2,3,5-trifluoro-phenyl)-2-((4-(dimethylamino)cyclohexyl)amino)-8-isopropyl-pyrido[2,3-d]pyrimidin-7-one (200 mg, 0.42 mmol) and calcium trifluoromethanesulfonate (430 mg, 1.3 mmol) in methyl alcohol (5 mL) was added 1,1,1-trifluoro-2,3-epoxypropane (120 mg, 1.07 mmol) and stirred at 50° C. for 72 h. The solids were filtered out and the filtrate was concentrated under vacuum. The crude product was purified by Prep-HPLC and Chiral HPLC to afford the title compound. After Chiral HPLC, two peaks were isolated out.

2-(((1r,4r)-4-(Dimethylamino)cyclohexyl)amino)-8-isopropyl-6-(2,3,5-trifluoro-4-((3,3,3-trifluoro-2-hydroxypropyl)amino)phenyl)pyrido[2,3-d]pyrimidin-7(8H)-one (isomer 1) (24.1 mg, 9.7% yield) as a light yellow solid. (rt=3.015 min, chiralpak IG-3, 4.6*100 mm 3 μm, (Hex: DCM=3:1)(0.1% DEA&0.1% FA):EtOH=80:20; 1 mL/min).

2-(((1r,4r)-4-(Dimethylamino)cyclohexyl)amino)-8-isopropyl-6-(2,3,5-trifluoro-4-((3,3,3-trifluoro-2-hydroxypropyl)amino)phenyl)pyrido[2,3-d]pyrimidin-7(8H)-one (isomer 2) (22.6 mg, 9.1% yield) as a light yellow solid. (rt=4.141 min, chiralpak IG-3, 4.6*100 mm 3 μm, (Hex: DCM=3:1)(0.1% DEA&0.1% FA): EtOH=80:20; 1 mL/min).

Example 100: 2-(((1r,4r)-4-(Dimethylamino)cyclohexyl)amino)-6-(4-(3-ethyl-2-oxopyrrolidin-1-yl)-2,3-difluorophenyl)-8-isopropylpyrido[2,3-d]pyrimidin-7(8H)-one Compound 100

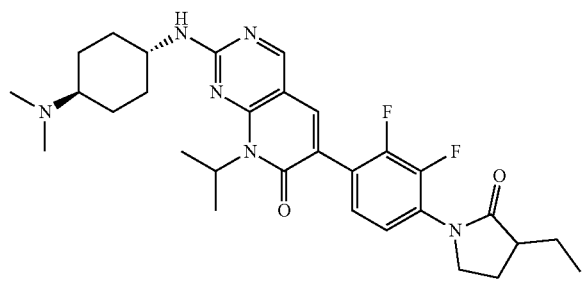 [SMILES: CCC1CCN(c2ccc(-c3cc4cnc(N[C@H]5CC[C@H](N(C)C)CC5)nc4n(C(C)C)c3=O)c(F)c2F)C1=O]

Step 1: 2,3-Difluoro-4-(4,4,5,5-tetramethyl-1,3,2-dioxaborolan-2-yl)phenol

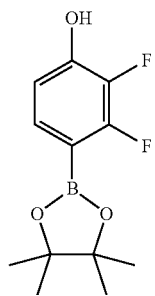 [SMILES: CC1(C)OB(c2ccc(O)c(F)c2F)OC1(C)C]

Under nitrogen, a solution of 4-bromo-2,3-difluorophenol (1.0 g, 4.78 mmol), bis(pinacolato)diboron (1.34 g, 5.28 mmol), potassium acetate (1.41 g, 14.39 mmol), [1,1'-bis(diphenylphosphino)ferrocene]dichloropalladium(II) (350 mg, 0.48 mmol) in 1,4-dioxane (20 mL) was stirred for 4 h at 85° C. The reaction was quenched with brine and extracted with ethyl acetate. The solvent was removed under vacuum. The residue was purified by silica flash chromatography eluting with ethyl acetate/petroleum ether (1/5) to afford the title compound (430 mg, 35.1% yield) as a white solid. LCMS (ESI): [M−H]$^-$=255.1.

Step 2: 6-(2,3-Difluoro-4-hydroxyphenyl)-8-isopropyl-2-(methylthio)pyrido[2,3-d]pyrimidin-7(8H)-one

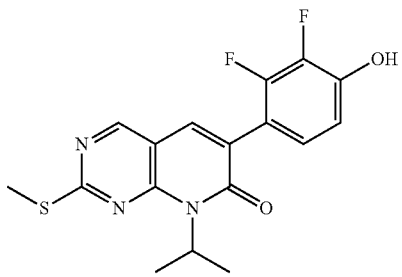 [SMILES: CSc1ncc2cc(-c3ccc(O)c(F)c3F)c(=O)n(C(C)C)c2n1]

Under nitrogen, a solution of 6-bromo-8-isopropyl-2-methylsulfanyl-pyrido[2,3-d]pyrimidin-7-one (500 mg, 1.59 mmol), 2,3-difluoro-4-(4,4,5,5-tetramethyl-1,3,2-dioxaborolan-2-yl)phenol (430 mg, 1.68 mmol), [1,1'-bis(diphenylphosphino)ferrocene]dichloropalladium(II) (125 mg, 0.17 mmol), sodium carbonate (500 mg, 4.72 mmol) in 1,4-dioxane (25 mL) and water (5 mL) was stirred for 4 h at 85° C. The solvent was removed. The residue was purified by silica flash chromatography eluting with ethyl acetate/petroleum ether (1/1) to afford the title compound (410 mg, 70.9% yield) as a yellow solid. LCMS (ESI): [M+H]$^+$=364.2.

Step 3: 2,3-Difluoro-4-(8-isopropyl-2-(methylthio)-7-oxo-7,8-dihydropyrido[2,3-d]pyrimidin-6-yl)phenyl trifluoromethanesulfonate

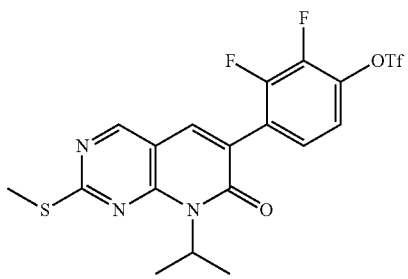 [SMILES: CSc1ncc2cc(-c3ccc(OS(=O)(=O)C(F)(F)F)c(F)c3F)c(=O)n(C(C)C)c2n1]

To a solution of 6-(2,3-difluoro-4-hydroxy-phenyl)-8-isopropyl-2-methylsulfanyl-pyrido[2,3-d]pyrimidin-7-one (410 mg, 1.13 mmol) and N-phenylbis(trifluoromethanesulfonimide) (600 mg, 1.68 mmol) in dichloromethane (20 mL) was added triethylamine (0.3 mL, 2.16 mmol) at rt and stirred for 4 h at the same temperature. The reaction was quenched with brine and extracted with dichloromethane. The solvent was removed under vacuum. The residue was purified by silica flash chromatography eluting with ethyl acetate/petroleum ether (1/5) to afford the title compound (400 mg, 71.6% yield) as a white solid. LCMS (ESI): [M+H]$^+$=496.1.

Step 4: 6-(4-(3-Ethyl-2-oxopyrrolidin-1-yl)-2,3-difluorophenyl)-8-isopropyl-2-(methylthio)pyrido[2,3-d]pyrimidin-7(8H)-one

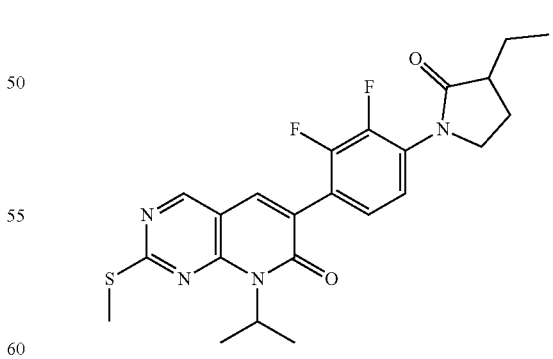

Under nitrogen, a solution of 2,3-difluoro-4-(8-isopropyl-2-(methylthio)-7-oxo-7,8-dihydropyrido[2,3-d]pyrimidin-6-yl)phenyl trifluoromethanesulfonate (400 mg, 0.81 mmol), 3-ethylpyrrolidin-2-one (120 mg, 1.06 mmol), tris(dibenzylideneacetone)dipalladium(0) (70 mg, 0.08 mmol), Xantphos (90 mg, 0.16 mmol), cesium carbonate (800 mg, 2.45 mmol) in toluene (20 mL) was stirred for 4 h at 110° C. The solids were filtered out. The filtrate was concentrated. The residue was purified by silica flash chromatography eluting with ethyl acetate/petroleum ether (1/1) to afford the title compound (289 mg, 78.1% yield) as a yellow solid. LCMS (ESI): [M+H]$^+$=459.1.

Step 5: 6-(4-(3-Ethyl-2-oxopyrrolidin-1-yl)-2,3-difluorophenyl)-8-isopropyl-2-(methylsulfonyl)pyrido[2,3-d]pyrimidin-7(8H)-one

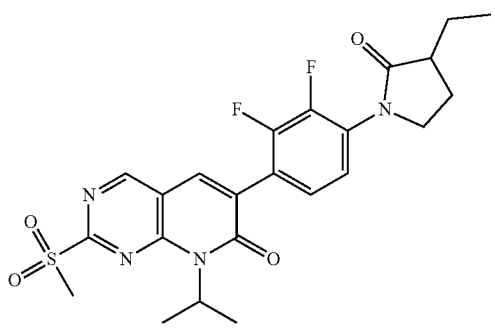 [SMILES: CCC1CCN(c2ccc(-c3cc4cnc(S(C)(=O)=O)nc4n(C(C)C)c3=O)c(F)c2F)C1=O]

A solution of 6-(4-(3-ethyl-2-oxopyrrolidin-1-yl)-2,3-difluorophenyl)-8-isopropyl-2-(methylthio)pyrido[2,3-d]pyrimidin-7(8H)-one (289 mg, 0.63 mmol) in dichloromethane (20 mL) was added 3-chloroperoxybenzoic acid (320 mg, 1.57 mmol) at 0° C. and stirred for 2 h at rt. The reaction was quenched with sodium bisulfite and extracted with dichloromethane. The organic layer was washed with sat. sodium carbonate and dried over anhydrous sodium sulfate. The solvent was removed under vacuum to afford the title compound (300 mg, 97% yield) as a yellow solid. LCMS (ESI, m/z): [M+H]$^+$=491.3.

Step 6: 2-(((1r,4r)-4-(Dimethylamino)cyclohexyl)amino)-6-(4-(3-ethyl-2-oxopyrrolidin-1-yl)-2,3-difluorophenyl)-8-isopropylpyrido[2,3-d]pyrimidin-7(8H)-one Compound 100

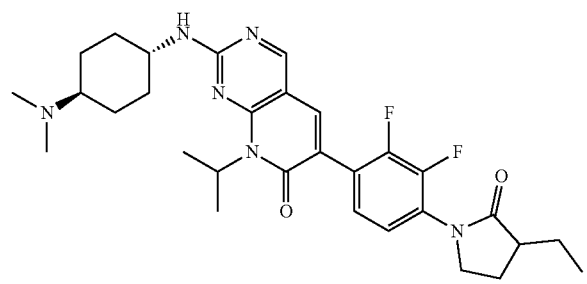 [SMILES: CCC1CCN(c2ccc(-c3cc4cnc(N[C@H]5CC[C@H](N(C)C)CC5)nc4n(C(C)C)c3=O)c(F)c2F)C1=O]

Under nitrogen, a solution of 6-(4-(3-ethyl-2-oxopyrrolidin-1-yl)-2,3-difluorophenyl)-8-isopropyl-2-(methylsulfonyl)pyrido[2,3-d]pyrimidin-7(8H)-one (300 mg, 0.61 mmol), N$^4$,N$^4$-dimethylcyclohexane-1,4-diamine hydrochloride (130 mg, 0.73 mmol), caesium fluoride (275 mg, 1.81 mmol), N,N-diisopropylethylamine (0.3 mL, 1.81 mmol) in dimethyl sulfoxide (3 mL) was stirred for 2 h at 80° C. The reaction was quenched with brine and extracted with ethyl acetate. The solvent was removed. The residue was purified by Prep-HPLC and chiral HPLC to afford the title compound. After Chiral HPLC, two peaks were isolated out.

2-(((1r,4r)-4-(Dimethylamino)cyclohexyl)amino)-6-(4-(3-ethyl-2-oxopyrrolidin-1-yl)-2,3-difluorophenyl)-8-isopropylpyrido[2,3-d]pyrimidin-7(8H)-one (isomer 1) (34.3 mg, 10.1% yield) as white solid. (rt=1.423 min, CHIRALPAK IC-3, 0.46*5 cm; 3 μm, MeOH (0.1% IPA):DCM=50:50, 1.0 mL/min).

2-(((1r,4r)-4-(Dimethylamino)cyclohexyl)amino)-6-(4-(3-ethyl-2-oxopyrrolidin-1-yl)-2,3-difluorophenyl)-8-isopropylpyrido[2,3-d]pyrimidin-7(8H)-one (isomer 2) (34.5 mg, 10.2% yield) as white solid. (rt=1.789 min, CHIRALPAK IC-3, 0.46*5 cm; 3 μm, MeOH (0.1% IPA):DCM=50:50, 1.0 mL/min).

Example 101; N-(2,3,6-Trifluoro-4-(8-isopropyl-2-((4-((2-methoxyethyl)(methyl)amino)cyclohexyl)amino)-7-oxo-7,8-dihydropyrido[2,3-d]pyrimidin-6-yl)phenyl)propane-1-sulfonamide Compound 101

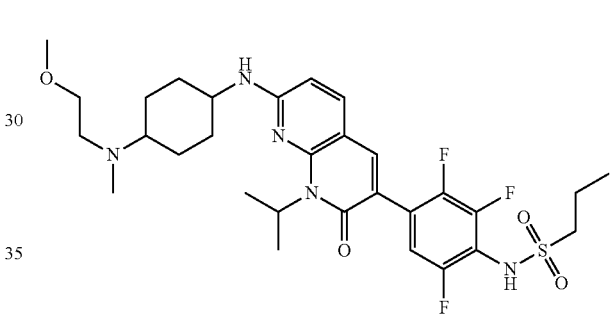

Step 1: Benzyl (4-((2-methoxyethyl)(methyl)amino)cyclohexyl)carbamate

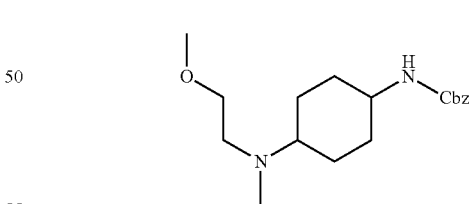

To a mixture of N-(2-methoxyethyl)-N-methylamine (1.04 mL, 9.65 mmol) and (4-oxocyclohexyl)carbamic acid benzyl ester (2.0 g, 8.1 mmol) in methyl alcohol (30 mL) was added sodiumcyanoborohydride (3.0 g, 48 mmol), the mixture was stirred for overnight at rt. The resulting solution was diluted with water and extracted with ethyl acetate. The organic layer was concentrated under vacuum. The residue was purified by silica flash chromatography eluting with dichloromethane/methanol (95:5) to afford the title compound (2.2 g, 84.9% yield) as colorless oil. LCMS (ESI): [M+H]$^+$=321.2.

Step 2: N¹-(2-methoxyethyl)-N¹-methylcyclohexane-1,4-diamine

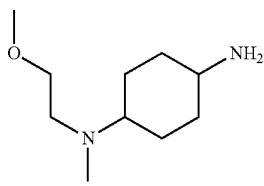

Under hydrogen, a mixture of benzyl N-(4-(2-methoxyethyl(methyl)amino)cyclohexyl)carbamate (2.1 g, 6.6 mmol) and Pd/C (2.0 g, 1.9 mmol) in methyl alcohol (40 mL) was stirred at rt for 3 h. After filtration, the filtrate was concentrated under reduced pressure to afford the title compound (1.2 g, 98.3% yield) as a colorless oil. LCMS (ESI): [M+H]⁺=187.2.

Step 3: N-(2,3,6-trifluoro-4-(8-isopropyl-2-((4-((2-methoxyethyl)(methyl)amino)cyclohexyl)amino)-7-oxo-7,8-dihydropyrido[2,3-d]pyrimidin-6-yl)phenyl)propane-1-sulfonamide Compound 101

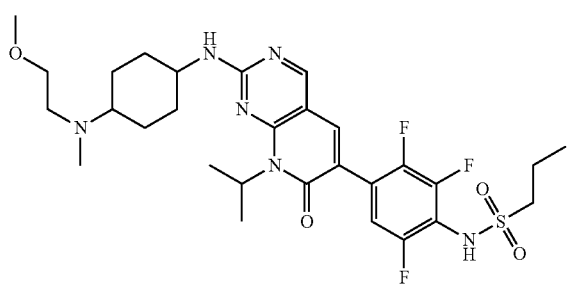 [SMILES: CCCS(=O)(=O)Nc1c(F)cc(-c2cc3cnc(NC4CCC(N(C)CCOC)CC4)nc3n(C(C)C)c2=O)c(F)c1F]

The title compound was prepared according to example 2. The residue was purified by Prep-HPLC to afford the title compound. Two peaks were isolated out.

N-(2,3,6-trifluoro-4-(8-isopropyl-2-((4-((2-methoxyethyl)(methyl)amino)cyclohexyl)amino)-7-oxo-7,8-dihydropyrido[2,3-d]pyrimidin-6-yl)phenyl)propane-1-sulfonamide (isomer 1) (74.9 mg, 15.8% yield) as a yellow solid.

N-(2,3,6-trifluoro-4-(8-isopropyl-2-((4-((2-methoxyethyl)(methyl)amino)cyclohexyl)amino)-7-oxo-7,8-dihydropyrido[2,3-d]pyrimidin-6-yl)phenyl)propane-1-sulfonamide (isomer 2) (52.2 mg, 11.0% yield) as a yellow solid.

Example 102: 1-Phenyl-N-(2,3,6-trifluoro-4-(8-isopropyl-2-((4-((2-methoxyethyl)(methyl)amino)cyclohexyl)amino)-7-oxo-7,8-dihydropyrido[2,3-d]pyrimidin-6-yl)phenyl)methanesulfonamide Compound 102

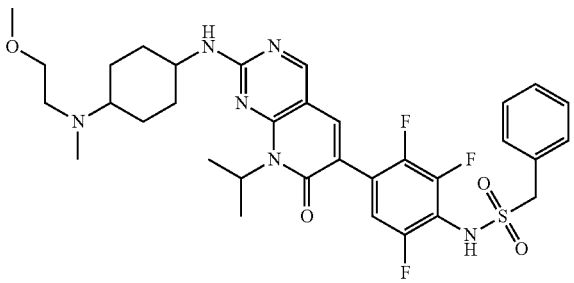 [SMILES: COCCN(C)C1CCC(Nc2ncc3cc(-c4cc(F)c(NS(=O)(=O)Cc5ccccc5)c(F)c4F)c(=O)n(C(C)C)c3n2)CC1]

The title compound was prepared according to example 101. The residue was purified by Prep-HPLC to afford the title compound. Two peaks were isolated out.

1-Phenyl-N-(2,3,6-trifluoro-4-(8-isopropyl-2-((4-((2-methoxyethyl)(methyl)amino)cyclohexyl)amino)-7-oxo-7,8-dihydropyrido[2,3-d]pyrimidin-6-yl)phenyl)methanesulfonamide (isomer 1) (55.3 mg, 15.7% yield) as a white solid.

1-Phenyl-N-(2,3,6-trifluoro-4-(8-isopropyl-2-((4-((2-methoxyethyl)(methyl)amino)cyclohexyl)amino)-7-oxo-7,8-dihydropyrido[2,3-d]pyrimidin-6-yl)phenyl)methanesulfonamide (isomer 2) (30.7 mg, 8.7% yield) as a light yellow solid.

Example 103: N-(4-(2-(((1S,3S)-3-Aminocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 103

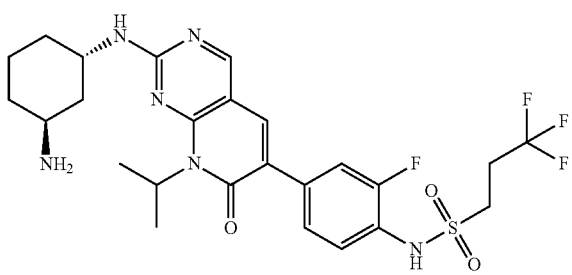 [SMILES: CC(C)n1c(=O)c(-c2ccc(NS(=O)(=O)CCC(F)(F)F)c(F)c2)cc2cnc(N[C@H]3CCC[C@H](N)C3)nc21]

The title compound was prepared according to example 2. This provides the title compound (47.3 mg, 55.6% yield) as a white solid.

Example 104: N-(4-(2-(((1S,3S)-3-Aminocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide hydrochloride Compound 104

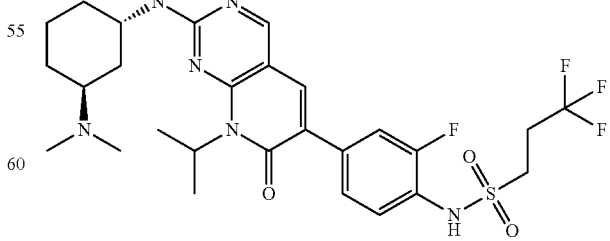

The title compound was prepared according to example 2. This provides the title compound (60.5 mg, 41.3% yield) as a yellow solid and as a HCl salt.

Example 105: 2-Chloro-N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)benzenesulfonamide Compound 105

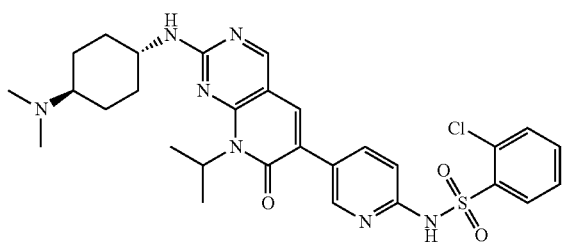 [SMILES: CC(C)n1c(=O)c(-c2ccc(NS(=O)(=O)c3ccccc3Cl)nc2)cc2cnc(N[C@H]3CC[C@H](N(C)C)CC3)nc21]

Step 1: 6-Bromo-2-(((1r,4r)-4-(dimethylamino)cyclohexyl)amino)-8-isopropylpyrido[2,3-d]pyrimidin-7(8H)-one

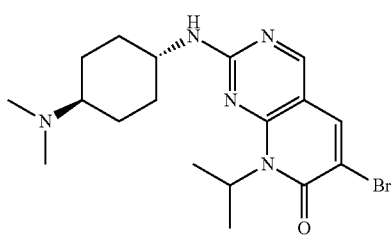 [SMILES: CC(C)n1c(=O)c(Br)cc2cnc(N[C@H]3CC[C@H](N(C)C)CC3)nc21]

Under nitrogen, to a solution of 6-bromo-8-isopropyl-2-methylsulfonyl-pyrido[2,3-d]pyrimidin-7-one (6.07 g, 17 mmol) in dimethyl sulfoxide (60 mL) was added N,N-diisopropylethylamine (11.3 g, 87 mmol) and caesium fluoride (5.37 g, 35 mmol), the reaction mixture stirred for 1 h at 85° C. The residue was purified by reverse phase chromatography eluting with 0.1% ammonium bicarbonate in water/methanol (4:1) to afford the title compound (4.86 g, 67.9% yield) as a yellow solid. LCMS (ESI): [M+1]=408.3.

Step 2: 6-(6-Aminopyridin-3-yl)-2-(((1r,4r)-4-(dimethylamino)cyclohexyl)amino)-8-isopropylpyrido[2,3-d]pyrimidin-7(8H)-one

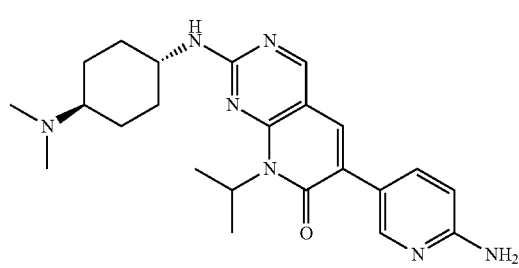 [SMILES: CC(C)n1c(=O)c(-c2ccc(N)nc2)cc2cnc(N[C@H]3CC[C@H](N(C)C)CC3)nc21]

Under nitrogen, a solution of 6-bromo-2-(((1r,4r)-4-(dimethylamino)cyclohexyl)amino)-8-isopropylpyrido[2,3-d]pyrimidin-7(8H)-one (1.0 g, 2.5 mmol) in N,N-dimethylformamide (8 mL) and water (1.6 mL) was added [1,1'-bis(diphenylphosphino)ferrocene]dichloropalladium(II) (180 mg, 0.25 mmol), sodium carbonate (780 mg, 7.4 mmol) and 5-(4,4,5,5-tetramethyl-1,3,2-dioxaborolan-2-yl)-2-pyridinylamine (704 mg, 3.2 mmol) at rt and stirred at 80° C. for 1 h. The residue was purified by reverse phase chromatography eluting with 0.1% ammonium bicarbonate in water/methanol (9:1) to afford the title compound (750 mg, 72.7% yield) as a yellow solid. LCMS (ESI): [M+1]=422.3.

Step 3: 2-Chloro-N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)benzenesulfonamide Compound 105

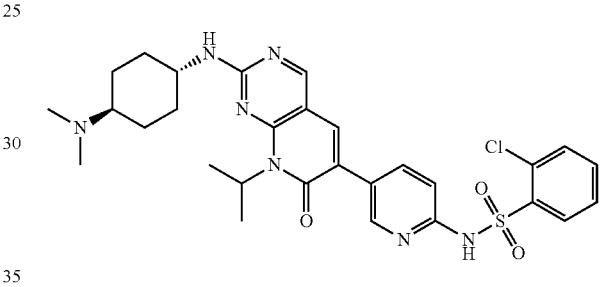

Under nitrogen, a solution of 6-(6-aminopyridin-3-yl)-2-(((1r,4r)-4-(dimethylamino)cyclohexyl)amino)-8-isopropylpyrido[2,3-d]pyrimidin-7(8H)-on (100 mg, 0.24 mmol) in pyridine (1 mL) was added 2-chlorobenzenesulfonylchloride (150 mg, 0.71 mmol) at rt and stirred for 1 h at 60° C. The residue was directly purified by reverse phase chromatography and Prep-HPLC to afford the title compound (27.0 mg, 19.2% yield) as a yellow solid.

Example 106: N-(5-(2-(((1r,4r)-4-(Dimethylamino)cyclohexyl)amino)-8-isopropyl-7-oxo-7,8-dihydropyrido[2,3-d]pyrimidin-6-yl)pyridin-2-yl)benzenesulfonamide Compound 106

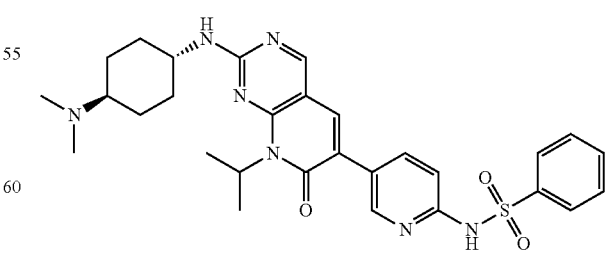

The title compound was prepared according to Example 105. This provides the title compound (25 mg, 19% yield) as a yellow solid.

Example 107: 1-(2-Cyano-4-methylphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide Compound 107

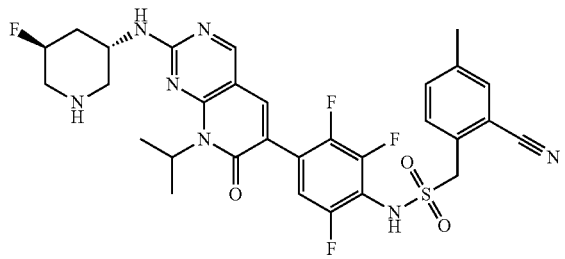 [SMILES: Cc1ccc(CS(=O)(=O)Nc2c(F)cc(-c3cc4cnc(N[C@@H]5CNC[C@@H](F)C5)nc4n(C(C)C)c3=O)c(F)c2F)c(C#N)c1]

Step 1: (2-Bromo-4-methylphenyl)methanol

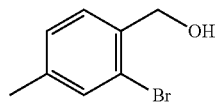

Under nitrogen, a mixture of 2-bromo-4-methylbenzoic acid (2.0 g, 9.3 mmol) in 1 M borane in tetrahydrofuran (30 mL) was stirred for 2 h at rt. The reaction was quenched with methanol. The reaction mixture was adjusted to pH=3 with 1M HCl and stirred for 0.5 h. The reaction mixture was adjusted to pH=7 with sat. sodium bicarbonate solution. The resulting solution was extracted with ethyl acetate, dried over anhydrous sodium sulfate and concentrated under vacuum. The residue was purified by silica flash chromatography eluting with ethyl acetate/petroleum ether (1:20) to afford the title compound (1.58 g, 84.5% yield) as a white solid. $^1$H NMR (300 MHz, DMSO-$d_6$) δ 7.49-7.33 (m, 2H), 7.27-7.12 (m, 1H), 5.35 (t, J=5.6 Hz, 1H), 4.47 (d, J=5.6 Hz, 2H), 2.29 (s, 3H).

Step 2: 2-Bromo-1-(chloromethyl)-4-methylbenzene

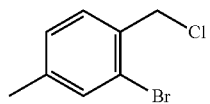

To a solution of (2-bromo-4-methyl-phenyl) methanol (1.54 g, 7.66 mmol) in dichloromethane (10 mL) was added thionyl chloride (9.10 g, 76.49 mmol) at 0° C. The resulting solution was stirred for 1 h at room temperature. The reaction was concentrated under vacuum. The residue was dissolved in ethyl acetate and washed with brine and sat. sodium bicarbonate solution. The organic layer was dried over anhydrous sodium sulfate and concentrated under vacuum to afford the title compound (1.38 g, 82.1% yield) as colorless oil. $^1$H NMR (300 MHz, DMSO-$d_6$) δ 7.55-7.45 (m, 2H), 7.26-7.18 (m, 1H), 4.78 (s, 2H), 2.31 (s, 3H).

Step 3: S-(2-Bromo-4-methylbenzyl) ethanethioate

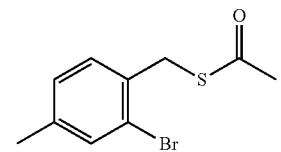

To a mixture of 2-bromo-1-(chloromethyl)-4-methyl-benzene (1.20 g, 5.47 mmol) and cesium carbonate (2.67 g, 8.20 mmol) in N,N-dimethylformamide (10 mL) was added potassium thioacetate (0.93 g, 8.20 mmol) at 0° C. The resulting solution was stirred for 2 h at rt. The reaction was quenched with water, extracted with ethyl acetate, washed with brine, dried over anhydrous sodium sulfate and concentrated under vacuum to afford the title compound (1.20 g, 84.7% yield) as yellow oil. $^1$H NMR (300 MHz, DMSO-$d_6$) δ 7.45 (t, J=1.2 Hz, 1H), 7.33 (d, J=7.8 Hz, 1H), 7.18-7.10 (m, 1H), 4.14 (s, 2H), 2.34 (s, 3H), 2.27 (s, 3H).

Step 4: (2-bromo-4-methylphenyl)methanesulfonyl chloride

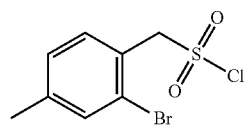

Under nitrogen, a solution of 2M hydrochloric acid (0.5 mL, 1 mmol) in acetonitrile (2.5 mL) was added N-chlorosuccinimide (438 mg, 3.28 mmol) and stirred for 5 min at 0° C. Then a solution of S-(2-bromo-4-methylbenzyl) ethanethioate (500 mg, 1.93 mmol) in acetonitrile (2.5 mL) was added dropwise and stirred at 0° C. for 20 min. The reaction mixture was poured in ethyl acetate and then washed with brine. The organic phase was dried over anhydrous sodium sulfate and concentrated under vacuum. The residue was purified by silica flash chromatography eluting with ethyl acetate/petroleum ether (10%) to afford the title compound (453 mg, 82.8% yield) as a yellow oil. $^1$H NMR (300 MHz, CDCl$_3$) δ 7.54 (d, J=1.4 Hz, 1H), 7.51 (d, J=7.9 Hz, 1H), 7.26-7.21 (m, 1H), 5.13 (s, 2H), 2.40 (s, 3H).

Step 5: 1-(2-Bromo-4-methylphenyl)-N-(2,3,6-trifluoro-4-(8-isopropyl-2-(methylthio)-7-oxo-7,8-dihydropyrido[2,3-d]pyrimidin-6-yl)phenyl)methanesulfonamidee

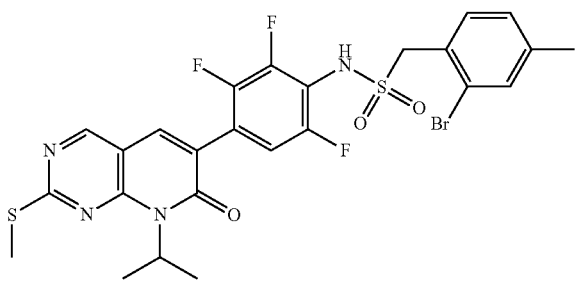 [SMILES: CSc1ncc2cc(-c3cc(F)c(NS(=O)(=O)Cc4ccc(C)cc4Br)c(F)c3F)c(=O)n(C(C)C)c2n1]

To a mixture of 6-(4-amino-2,3,5-trifluoro-phenyl)-8-isopropyl-2-methylsulfanyl-pyrido[2,3-d]pyrimidin-7-one (100 mg, 0.26 mmol) in pyridine (0.20 mL) was added (2-bromo-4-methyl-phenyl)methanesulfonyl chloride (253 mg, 0.89 mmol), the mixture was stirred for 1 h at rt. The reaction was quenched with water, extracted with ethyl acetate, washed with brine, dried over anhydrous sodium sulfate and concentrated under vacuum. The residue was purified by silica flash chromatography eluting with ethyl acetate/petroleum ether (1:20) to afford the title compound (107 mg, 64.9% yield) as a white solid. LCMS (ESI): [M+H]$^+$=627.0.

Step 6: 1-(2-Bromo-4-methylphenyl)-N-(2,3,6-trifluoro-4-(8-isopropyl-2-(methylsulfonyl)-7-oxo-7,8-dihydropyrido[2,3-d]pyrimidin-6-yl)phenyl)methanesulfonamide

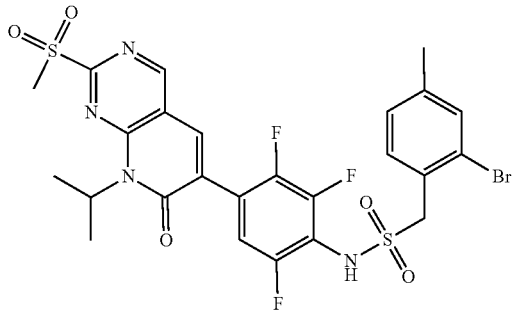 [SMILES: Cc1ccc(CS(=O)(=O)Nc2c(F)cc(-c3cc4cnc(S(C)(=O)=O)nc4n(C(C)C)c3=O)c(F)c2F)c(Br)c1]

To a mixture of 1-(2-bromo-4-methyl-phenyl)-N-(2,3,6-trifluoro-4-(8-isopropyl-2-methylsulfanyl-7-oxo-pyrido[2,3-d]pyrimidin-6-yl)phenyl)methanesulfonamide (200 mg, 0.32 mmol) in dichloromethane (2 mL) was added 3-chloroperoxybenzoicacid (160 mg, 0.93 mmol), the mixture was stirred for 3 h at rt. The reaction was quenched with water, extracted with ethyl acetate, washed with brine, dried over anhydrous sodium sulfate and concentrated under vacuum. The residue was purified by silica flash chromatography eluting with ethyl acetate/petroleum ether (70%) to afford the title compound (200 mg, 95.1% yield) as a yellow solid. LCMS (ESI): [M+H]$^+$=659.0.

Step 7: tert-Butyl (3S,5S)-3-((6-(4-(((2-bromo-4-methylphenyl)methyl)sulfonamido)-2,3,5-trifluorophenyl)-8-isopropyl-7-oxo-7,8-dihydropyrido[2,3-d]pyrimidin-2-yl)amino)-5-fluoropiperidine-1-carboxylate

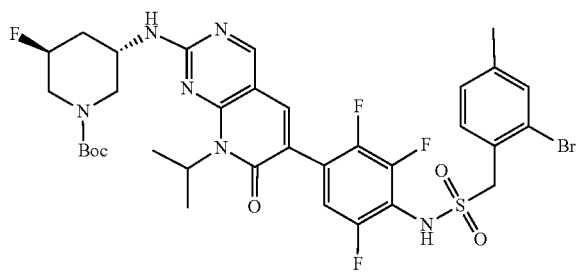 [SMILES: Cc1ccc(CS(=O)(=O)Nc2c(F)cc(-c3cc4cnc(N[C@H]5C[C@H](F)CN(C(=O)OC(C)(C)C)C5)nc4n(C(C)C)c3=O)c(F)c2F)c(Br)c1]

A mixture of 1-(2-bromo-4-methylphenyl)-N-(2,3,6-trifluoro-4-(8-isopropyl-2-(methylsulfonyl)-7-oxo-7,8-dihydropyrido[2,3-d]pyrimidin-6-yl)phenyl)methanesulfonamide (200 mg, 0.30 mmol), tert-butyl (3S,5S)-3-amino-5-fluoro-piperidine-1-carboxylate (60 mg, 0.27 mmol), caesium fluoride (436 mg, 2.9 mmol) and N,N-diisopropylethylamine (124 mg, 0.96 mmol) in dimethyl sulfoxide (2 mL) was stirred for 4 h at 80° C. under nitrogen. The reaction was quenched with water, extracted with ethyl acetate, washed with brine, dried over anhydrous sodium sulfate and concentrated under vacuum. The residue was purified by silica flash chromatography eluting with ethyl acetate/petroleum ether (70%) to afford the title compound (167 mg, 69% yield) as a brown solid. LCMS (ESI): [M+H]$^+$=797.2

Step 8: tert-Butyl (3S,5S)-3-((6-(4-(((2-cyano-4-methylphenyl)methyl)sulfonamido)-2,3,5-trifluorophenyl)-8-isopropyl-7-oxo-7,8-dihydropyrido[2,3-d]pyrimidin-2-yl)amino)-5-fluoropiperidine-1-carboxylate

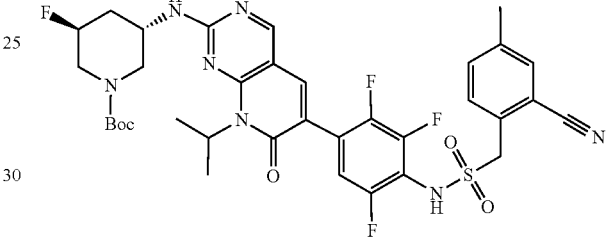

A mixture of tert-butyl (3S,5S)-3-((6-(4-(((2-bromo-4-methylphenyl)methyl)sulfonamido)-2,3,5-trifluorophenyl)-8-isopropyl-7-oxo-7,8-dihydropyrido[2,3-d]pyrimidin-2-yl)amino)-5-fluoropiperidine-1-carboxylate (250 mg, 0.32 mmol), tetrakis(triphenylphosphine)palladium (240 mg, 0.21 mmol) and zinc cyanide (250 mg, 2.13 mmol) in N,N-dimethylformamide (3 mL) was stirred for 4 h at 120° C. under nitrogen. The reaction was quenched with water, extracted with ethyl acetate, washed with brine, dried over anhydrous sodium sulfate and concentrated under vacuum. The residue was purified by silica flash chromatography eluting with methyl alcohol/dichloromethane (10%) to afford the title compound (130 mg, 54.5% yield) as a yellow solid. LCMS (ESI): [M+H]+=744.3.

Step 9: 1-(2-Cyano-4-methylphenyl)-N-(2,3,6-trifluoro-4-(2-(((3S,5S)-5-fluoropiperidin-3-yl)amino)-8-isopropyl-7-oxo-7,8-dihydropyrido[2,3-d]pyrimidin-6-yl)phenyl)methanesulfonamide Compound 107

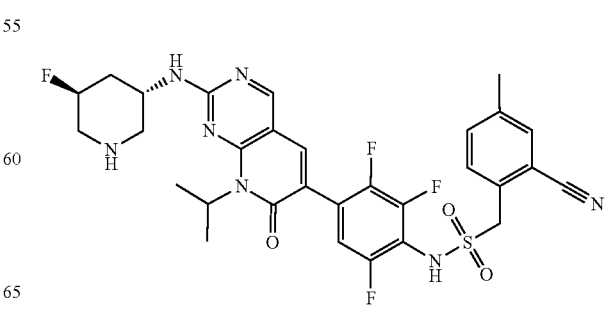

To a mixture of tert-butyl (3S,5S)-3-((6-(4-(((2-cyano-4-methylphenyl)methyl)sulfonamido)-2,3,5-trifluorophenyl)-8-isopropyl-7-oxo-7,8-dihydropyrido[2,3-d]pyrimidin-2-yl)amino)-5-fluoropiperidine-1-carboxylate (128 mg, 0.17 mmol) in dichloromethane (4 mL) was added 4 M HCl in dioxane (4 mL), the mixture was stirred for 2 h at rt. The reaction was concentrated under vacuum and the residue was purified by Prep-HPLC to afford the title compound (30 mg, 27.1% yield) as a light yellow solid.

Example 108; N-(4-(2-(((1S,3R)-3-Aminocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide hydrochloride Compound 108

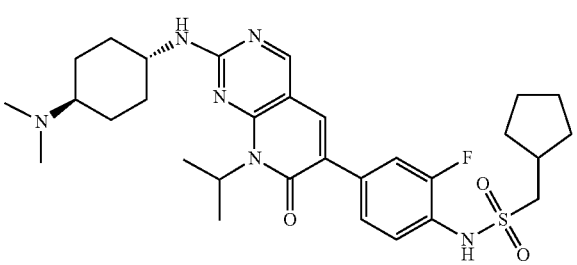

The title compound was prepared according to example 2. This provides the title compound (48.8 mg, 53.9% yield) as a yellow solid and as HCl salt.

Example 109: 1-Cyclopentyl-N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)methanesulfonamide Compound 109

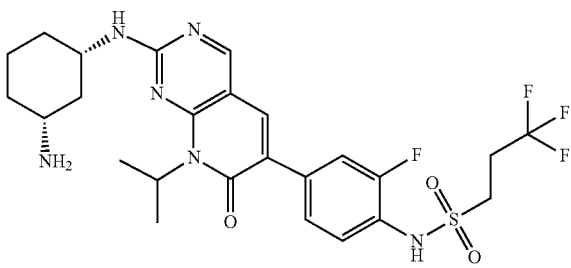 [SMILES: CC(C)n1c(=O)c(-c2ccc(NS(=O)(=O)CCC(F)(F)F)c(F)c2)cc2cnc(N[C@H]3CCC[C@@H](N)C3)nc21]

The title compound was prepared according to example 10. This provides the title compound (26.7 mg, 22.6% yield) as a yellow solid.

Example 110: N-(4-(2-((4-(Dimethylamino)-3-fluorocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 110 Compound 110A Compound 110B

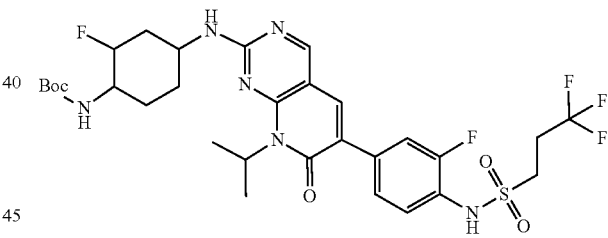

Step 1: tert-Butyl (2-fluoro-4-((6-(3-fluoro-4-((3,3,3-trifluoropropyl)sulfonamido)phenyl)-8-isopropyl-7-oxo-7,8-dihydropyrido[2,3-d]pyrimidin-2-yl)amino)cyclohexyl)carbamate (Cyclohexane is racemate of (1S,2S,4S) or (1R,2R,4R))

Under nitrogen, a solution of 3,3,3-trifluoro-N-(2-fluoro-4-(8-isopropyl-2-methylsulfonyl-7-oxo-pyrido[2,3-d]pyrimidin-6-yl)phenyl)propane-1-sulfonamide (300 mg, 0.56 mmol), tert-butyl (4-amino-2-fluorocyclohexyl)carbamate (cyclohexane is racemate of (1S,2S,4S) or (1R,2R,4R)) (120 mg, 0.52 mmol), caesium fluoride (255 mg, 1.68 mmol), N,N-diisopropylethylamine (0.28 mL, 1.68 mmol) in dimethyl sulfoxide (3 mL) was stirred for 2 h at 80° C. The reaction was quenched with water and extracted with ethyl acetate. The solvent was removed. The residue was purified by silica flash chromatography eluting with ethyl acetate/petroleum ether (1:1) to afford the title compound (225 mg, 58.4% yield) as a yellow solid. LCMS (ESI): [M+H]$^+$=689.2.

Step 2: N-(4-(2-((4-Amino-3-fluorocyclohexyl)amino)-8-isopropyl-7-oxo-7,8-dihydropteridin-6-yl)-2-fluorophenyl)-3,3,3-trifluoropropane-1-sulfonamide hydrochloride

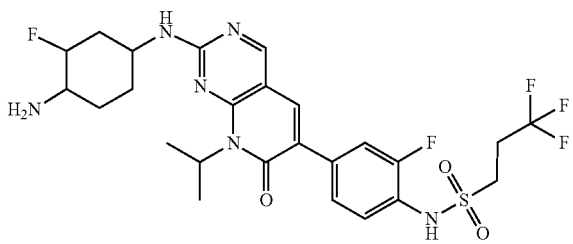 [SMILES: CC(C)n1c(=O)c(-c2ccc(NS(=O)(=O)CCC(F)(F)F)c(F)c2)cc2cnc(NC3CCC(N)C(F)C3)nc21]

A solution of tert-butyl (2-fluoro-4-((6-(3-fluoro-4-((3,3,3-trifluoropropyl)sulfonamido)phenyl)-8-isopropyl-7-oxo-7,8-dihydropyrido[2,3-d]pyrimidin-2-yl)amino)cyclohexyl)carbamate (220 mg, 0.32 mmol) in dichloromethane (2 mL) was added 4 M HCl in dioxane (5 mL, 20 mmol) and stirred for 2 h at rt. The solvent was removed to afford the title compound (200 mg, 99.7% yield) as a HCl salt. LCMS (ESI): [M+H]=589.3.

Step 3: N-(4-(2-((4-(Dimethylamino)-3-fluorocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 110 Compound 110A Compound 110B

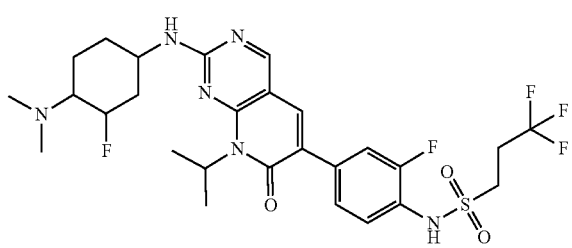 [SMILES: CC(C)n1c(=O)c(-c2ccc(NS(=O)(=O)CCC(F)(F)F)c(F)c2)cc2cnc(NC3CCC(N(C)C)C(F)C3)nc21]

To a mixture of N-(4-(2-((4-amino-3-fluorocyclohexyl)amino)-8-isopropyl-7-oxo-7,8-dihydropteridin-6-yl)-2-fluorophenyl)-3,3,3-trifluoropropane-1-sulfonamide hydrochloride (Cyclohexane is (1S,3S,4S) or (1R,3R,4R)) (200 mg, 0.32 mmol) and 37% formaldehyde solution (2 mL, 73 mmol) in methyl alcohol (25 mL) was added sodiumcyanoborohydride (60 mg, 0.96 mmol) and acetic acid (2 mL, 35 mmol), the mixture was stirred for 1 h at rt. The crude product was purified by reverse phase, Prep-HPLC and SFC to afford the title compound. After SFC, two peaks were isolated out.

N-(4-(2-((4-(Dimethylamino)-3-fluorocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide (isomer 1, cyclohexane is (1S,3S,4S) or (1R,3R,4R)) (18.2 mg, 6.1% yield) as a yellow solid. (rt=3.632 min, enantiocel C4-3, 4.6*100 mm, 3 μm, Co-Solvent: MeOH (0.1% DEA); 1 mL/min).

N-(4-(2-((4-(Dimethylamino)-3-fluorocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide (isomer 2, cyclohexane is (1S,3S,4S) or (1R,3R,4R)) (15.2 mg, 5.1% yield) as yellow solid. (rt=3.955 min, enantiocel C4-3, 4.6*100 mm, 3 μm, Co-Solvent: MeOH (0.1% DEA); 1 mL/min).

Example 111: N-(4-(2-(((1r,4r)-4-(Dimethylamino)cyclohexyl)amino)-8-isopropyl-7-oxo-7,8-dihydropyrido[2,3-d]pyrimidin-6-yl)-2-fluorophenyl)-1-(4-fluorophenyl)methanesulfonamide Compound 111

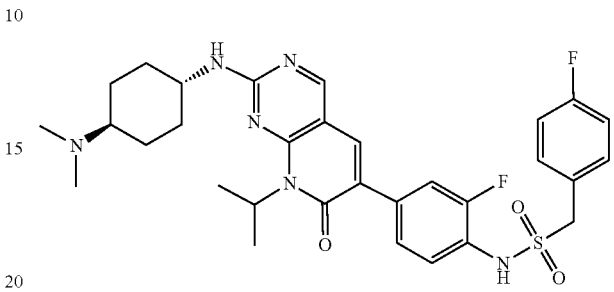

The title compound was prepared according to example 2 to provide the title compound (17.3 mg, 15.5% yield) as a yellow solid.

Example 112: N-(2-Fluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(4-fluorophenyl)methanesulfonamide hydrochloride Compound 112

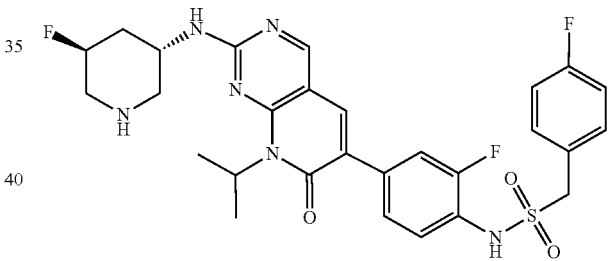

The title compound was prepared according to example 2 to provide the title compound (52.8 mg, 44.8% yield) as a yellow solid and as a HCl salt.

Example 113: 1-(2-Cyano-4-methylphenyl)-N-(4-(2-(((1r,4r)-4-(dimethylamino)cyclohexyl)amino)-8-isopropyl-7-oxo-7,8-dihydropyrido[2,3-d]pyrimidin-6-yl)-2,3,6-trifluorophenyl)methanesulfonamide Compound 113

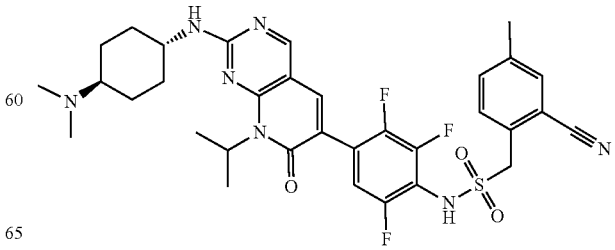

The title compound was prepared according to Example 107 to provide the title compound (17.3 mg, 15.5% yield) as a yellow solid.

Example 114: N-(4-(2-(((1S,3R)-3-(Dimethylamino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 114

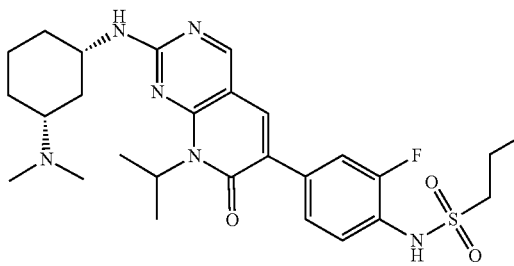

The title compound was prepared according to example 2 to provide the title compound (56.1 mg, 28.4% yield) as a yellow solid.

Example 115; 1-Cyclohexyl-N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)methanesulfonamide Compound 115

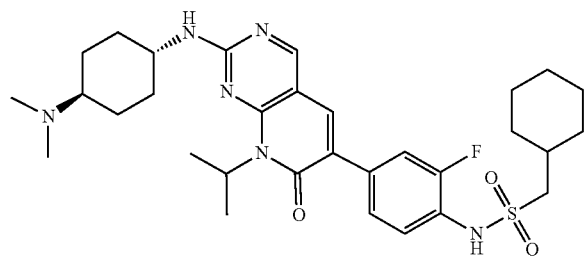 [SMILES: CC(C)n1c(=O)c(-c2ccc(NS(=O)(=O)CC3CCCCC3)c(F)c2)cc2cnc(N[C@H]3CC[C@H](N(C)C)CC3)nc21]

The title compound was prepared according to example 10 to provide the title compound (22.7 mg, 18.8% yield) as a yellow solid.

Example 116: 1-(4-Chlorophenyl)-N-(4-(2-(((1r,4r)-4-(dimethylamino)cyclohexyl)amino)-8-isopropyl-7-oxo-7,8-dihydropyrido[2,3-d]pyrimidin-6-yl)-2,6-difluorophenyl)methanesulfonamide Compound 116

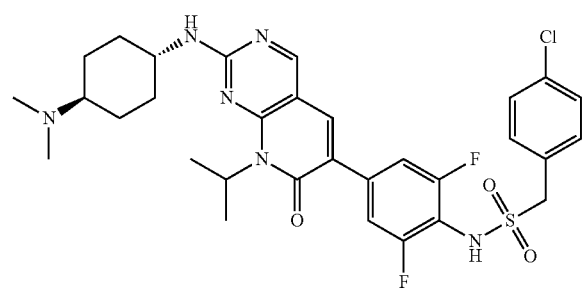

The title compound was prepared according to example 10 to provide the title compound (49.9 mg, 27.2% yield) as a yellow solid.

Example 117: N-(4-(2-(((1r,4r)-4-(Dimethylamino)cyclohexyl)amino)-8-isopropyl-7-oxo-7,8-dihydropyrido[2,3-d]pyrimidin-6-yl)-2,6-difluorophenyl)-1-phenylmethanesulfonamide Compound 117

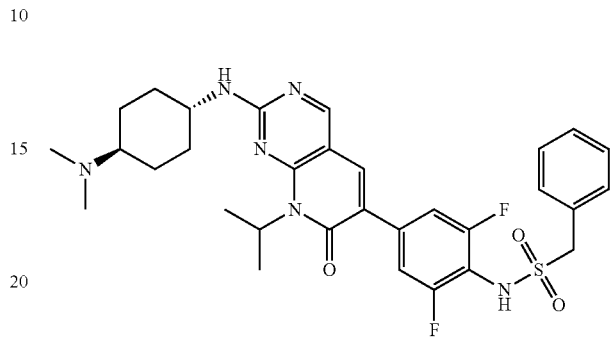

The title compound was prepared according to example 10 to provide the title compound (30.6 mg, 24.6% yield) as a yellow solid.

Example 118; N-(4-(2-((4-(Dimethylamino)-3-fluorocyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide Compound 118 (Compound 118A Compound 118B)

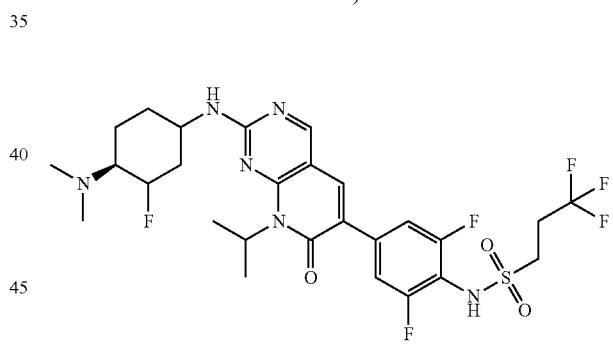

The title compound was prepared according to Example 110. The residue was purified by Prep-HPLC and Chiral HPLC to afford the title compound. After Chiral HPLC, two peaks were isolated out.

N-(4-(2-((4-(Dimethylamino)-3-fluorocyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide (isomer 1, cyclohexane is (1S,3S,4S) or (1R,3R,4R)) (24.6 mg, 8.3% yield) as a white solid. (rt=1.366 min, CHIRALPAK IC-3, 0.46*5 cm, 3 μm; (Hex:DCM=3:1)(0.1% DEA):EtOH=50:50, 1 mL/min).

N-(4-(2-((4-(Dimethylamino)-3-fluorocyclohexyl)amino)-8-isopropyl-7-oxo-7,8-dihydropyrido[2,3-d]pyrimidin-6-yl)-2,6-difluorophenyl)-3,3,3-trifluoropropane-1-sulfonamide (isomer 2, cyclohexane is (1S,3S,4S) or (1R,3R,4R)) (28.8 mg, 9.7% yield) as yellow solid. (rt=2.208 min, CHIRALPAK IC-3, 0.46*5 cm, 3 um; (Hex:DCM=3:1)(0.1% DEA):EtOH=50:50, 1 mL/min).

Example 119; N-(4-(2-(((1r,4r)-4-(Dimethylamino)cyclohexyl)amino)-8-isopropyl-7-oxo-7,8-dihydropyrido[2,3-d]pyrimidin-6-yl)-2-fluorophenyl)cyclohexanesulfonamide Compound 119

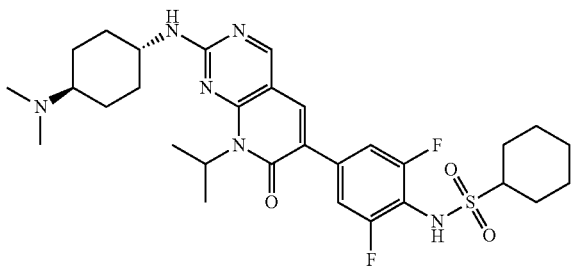 [SMILES: CC(C)n1c(=O)c(-c2cc(F)c(NS(=O)(=O)C3CCCCC3)c(F)c2)cc2cnc(N[C@H]3CC[C@H](N(C)C)CC3)nc21]

To a mixture of 6-(4-amino-3-fluoro-phenyl)-2-((4-(dimethylamino)cyclohexyl)amino)-8-isopropyl-pyrido[2,3-d]pyrimidin-7-one (200 mg, 0.46 mmol) in pyridine (1 mL) was added cyclohexanesulfonylchloride (340 mg, 1.86 mmol), the mixture was stirred for 4 h at 80° C. The reaction was quenched with water, extracted with ethyl acetate, washed with brine, dried over anhydrous sodium sulfate and concentrated under vacuum. The residue was purified by Prep-HPLC to afford the title compound (26 mg, 9.7% yield) as a light yellow solid.

Example 120; N-(4-(2-(((1r,4r)-4-(Dimethylamino)cyclohexyl)amino)-8-isopropyl-7-oxo-7,8-dihydropyrido[2,3-d]pyrimidin-6-yl)-2,6-difluorophenyl)-1-(p-tolyl)methanesulfonamide Compound 120

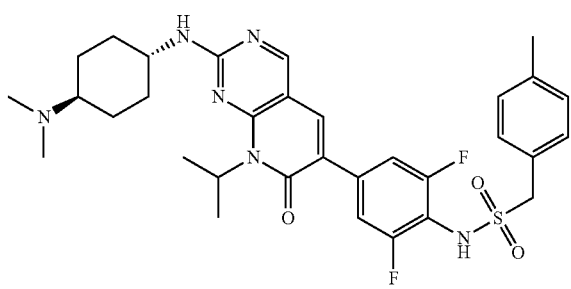

The title compound was prepared according to example 10 to provide the title compound (44.2 mg, 24.8% yield) as a yellow solid.

Example 121: N-(5-(2-(((1r,4r)-4-(Dimethylamino)cyclohexyl)amino)-8-isopropyl-7-oxo-7,8-dihydropyrido[2,3-d]pyrimidin-6-yl)pyridin-2-yl)-1-(4-fluorophenyl)methanesulfonamide Compound 121

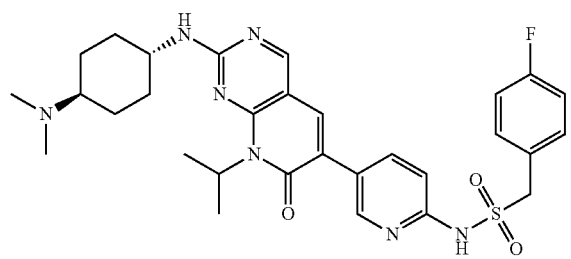 [SMILES: CC(C)n1c(=O)c(-c2ccc(NS(=O)(=O)Cc3ccc(F)cc3)nc2)cc2cnc(N[C@H]3CC[C@H](N(C)C)CC3)nc21]

The title compound was prepared according to Example 105 to provide the title compound (21.0 mg, 15.1% yield) as a yellow solid.

Example 122; N-(2,6-Difluoro-4-(8-isopropyl-2-(((1r,4r)-4-((2-methoxyethyl)(methyl)amino)cyclohexyl)amino)-7-oxo-7,8-dihydropyrido[2,3-d]pyrimidin-6-yl)phenyl)-1-(4-fluorophenyl)methanesulfonamide Compound 122

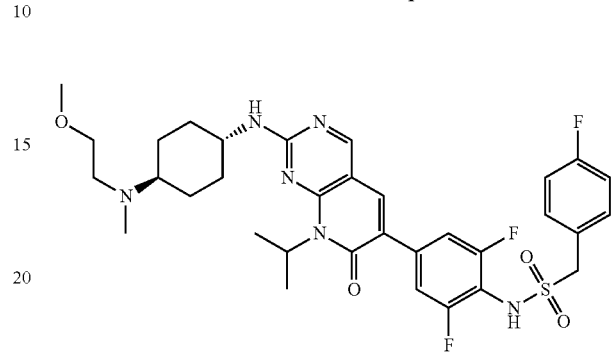

Step 1: Benzyl ((1r,4r)-4-((2-methoxyethyl)amino)cyclohexyl)carbamate

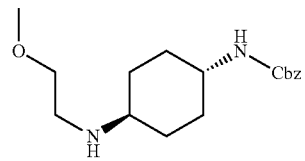 [SMILES: COCCN[C@H]1CC[C@H](NC(=O)OCc2ccccc2)CC1]

A mixture of benzyl N-(4-aminocyclohexyl)carbamate (3.0 g, 12 mmol), 2-bromoethyl methyl ether (2.04 g, 15 mmol) and potassium carbonate (3.36 g, 24 mmol) in N,N-dimethylformamide (70 mL) was stirred for 2 h at 85° C. The resulting solution was diluted with water, extracted with ethyl acetate, washed with brine, dried over anhydrous sodium sulfate and concentrated. The resulting residue was purified by reverse phase chromatography (methanol/0.1% HCl in water) to afford the title compound (2.4 g, 64.8% yield) as a white solid. LCMS (ESI): [M+H]$^+$=307.2.

Step 2: Benzyl ((1r,4r)-4-((2-methoxyethyl)(methyl)amino)cyclohexyl)carbamate

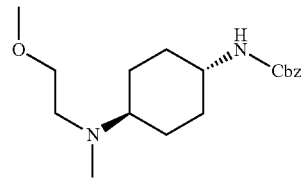 [SMILES: COCCN(C)[C@H]1CC[C@H](NC(=O)OCc2ccccc2)CC1]

A solution of benzyl N-(4-(2-methoxyethylamino)cyclohexyl)carbamate (2.4 g, 7.8 mmol) and 37% formaldehyde solution (6.5 g, 80.09 mmol) in methyl alcohol (40 mL) was added sodium cyanoborohydride (1.0 g, 16 mmol) and acetic acid (0.5 g, 7.83 mmol), the mixture was stirred for 1 h at rt. The resulting solution was diluted with water, extracted with ethyl acetate and concentrated under vacuum. The residue was purified by silica flash chromatography eluting with dichloromethane/methanol (90:10) to afford the title compound (2.3 g, 91.6% yield) as a colorless oil. LCMS (ESI): [M+H]$^+$=321.2.

Step 3: (1r,4r)-N$^1$-(2-Methoxyethyl)-N$^1$-methylcyclohexane-1,4-diamine hydrochloride

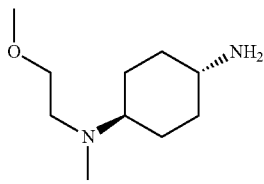

To a mixture of benzyl ((1r,4r)-4-((2-methoxyethyl)(methyl)amino)cyclohexyl)carbamate (2.20 g, 6.9 mmol) in methyl alcohol (100 mL) was added 5% Pd/C (880 mg) and hydrochloric acid (0.1 mL), the mixture was stirred for 8 h under hydrogen at room temperature. The solids were filtered out. The filtrate was concentrated under reduced pressure to provide the tittle compound (1.5 g, 99% yield) as a crude and as a HCl salt. LCMS (ESI): [M+H]$^+$=187.2.

Step 4: 6-Bromo-8-isopropyl-2-(((1r,4r)-4-((2-methoxyethyl)(methyl)amino)cyclohexyl)amino)pyrido[2,3-d]pyrimidin-7(8H)-one

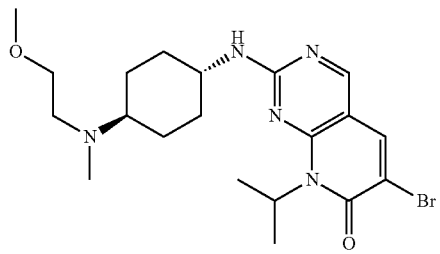 [SMILES: COCCN(C)[C@H]1CC[C@H](Nc2ncc3cc(Br)c(=O)n(C(C)C)c3n2)CC1]

A mixture of 6-bromo-8-isopropyl-2-methylsulfonyl-pyrido[2,3-d]pyrimidin-7-one (1.1 g, 3.18 mmol), (1r,4r)-N$^1$-(2-methoxyethyl)-N$^1$-methylcyclohexane-1,4-diamine hydrochloride (1.0 g, 4.49 mmol), caesium fluoride (1.5 g, 9.87 mmol) and N,N-diisopropylethylamine (3 mL, 18.19 mmol) in dimethyl sulfoxide (15 mL) was stirred for 2 h at 80° C. under nitrogen. The resulting solution was diluted with water, extracted with ethyl acetate, washed with brine, dried over anydroud sodium sulfate and concentrated. The resulting residue was purified by reverse phase chromatography (acetonitrile/0.1% NH$_4$HCO$_3$ in water) to afford the title compound (875 mg, 60.9% yield) as a brown solid. LCMS (ESI): [M+H]$^+$=452.2.

Step 5: 6-(4-Amino-3,5-difluorophenyl)-8-isopropyl-2-(((1r,4r)-4-((2-methoxyethyl)(methyl)amino)cyclohexyl)amino)pyrido[2,3-d]pyrimidin-7(8H)-one

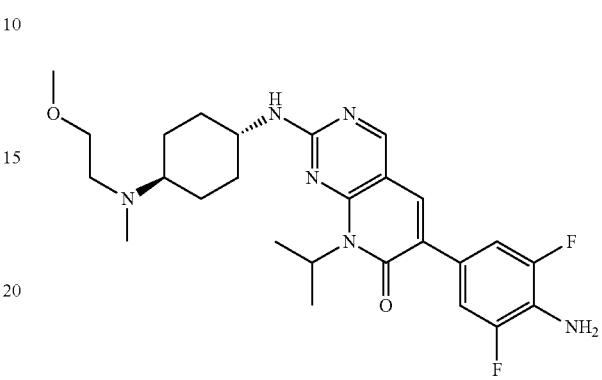

To a mixture of 6-bromo-8-isopropyl-2-(((1r,4r)-4-((2-methoxyethyl)(methyl)amino)cyclohexyl)amino)pyrido[2,3-d]pyrimidin-7(8H)-one (200 mg, 0.44 mmol), 1,1'-bis(diphenylphosphino)ferrocene-palladium(II)dichloride dichloromethane complex (20 mg, 0.02 mmol), sodium carbonate (160 mg, 1.5 mmol) in N,N-dimethylformamide (3 mL) and water (0.60 mL) was added 2,6-difluoro-4-(4,4,5,5-tetramethyl-1,3,2-dioxaborolan-2-yl)aniline (120 mg, 0.47 mmol) at rt under nitrogen, the mixture was stirred for 4 h at 80° C. The resulting residue was purified by reverse phase chromatography eluting with acetonitrile/0.1% HCl in water (0-50%) to afford the title compound (200 mg, 90.4% yield) as a yellow solid. LCMS (ESI): [M+H]$^+$=501.3.

Step 4: N-(2,6-Difluoro-4-(8-isopropyl-2-(((1r,4r)-4-((2-methoxyethyl)(methyl)amino)cyclohexyl)amino)-7-oxo-7,8-dihydropyrido[2,3-d]pyrimidin-6-yl)phenyl)-1-(4-fluorophenyl)methanesulfonamide Compound 122

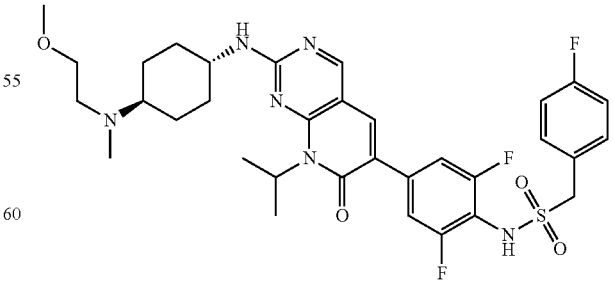

The title compound was prepared according to example 10 to provide the title compound (40.0 mg, 39.7% yield) as a white solid.

Example 123: N-(2-Fluoro-4-(8-isopropyl-2-(((1r,4r)-4-((2-methoxyethyl)(methyl)amino)cyclohexyl)amino)-7-oxo-7,8-dihydropyrido[2,3-d]pyrimidin-6-yl)phenyl)-1-(4-fluorophenyl)methanesulfonamide Compound 123

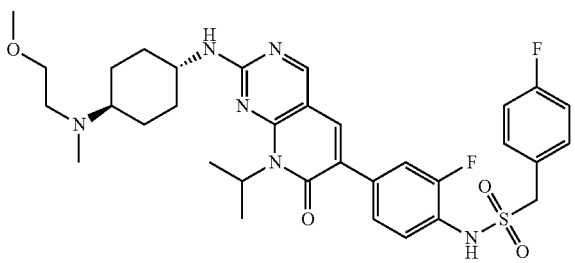 [SMILES: COCCN(C)[C@H]1CC[C@H](Nc2ncc3cc(-c4ccc(NS(=O)(=O)Cc5ccc(F)cc5)c(F)c4)c(=O)n(C(C)C)c3n2)CC1]

The title compound was prepared according to Example 122. This provides the title compound (36.9 mg, 19.5% yield) as a yellow solid.

Example 124: N-(2-Fluoro-4-(8-isopropyl-2-(((1r,4r)-4-((2-methoxyethyl)(methyl)amino)cyclohexyl)amino)-7-oxo-7,8-dihydropyrido[2,3-d]pyrimidin-6-yl)phenyl)-1-phenylmethanesulfonamide hydrochloride Compound 124

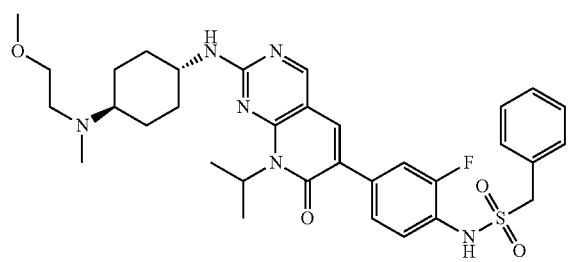

The title compound was prepared according to Example 122 to provide the title compound (61.5 mg, 31.6% yield) as a yellow solid and as a HCl salt.

Example 125: 1-(4-(Difluoromethyl)phenyl)-N-(4-(2-(((1r,4r)-4-(dimethylamino)cyclohexyl)amino)-8-isopropyl-7-oxo-7,8-dihydropyrido[2,3-d]pyrimidin-6-yl)-2,6-difluorophenyl)methanesulfonamide Compound 125

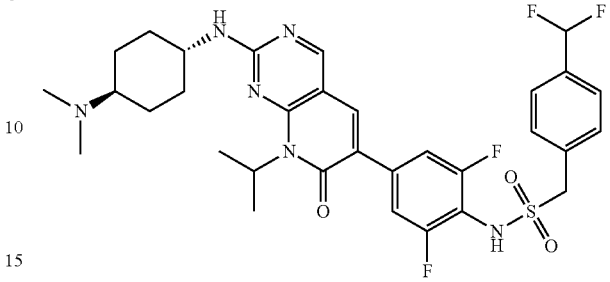

The title compound was prepared according to example 10 to provide the title compound (55.4 mg, 31.9% yield) as a yellow solid.

Example 126: 3,3,3-Trifluoro-N-(5-(8-isopropyl-2-(((1r,4r)-4-((2-methoxyethyl)(methyl)amino)cyclohexyl)amino)-7-oxo-7,8-dihydropyrido[2,3-d]pyrimidin-6-yl)pyridin-2-yl)propane-1-sulfonamide Compound 126

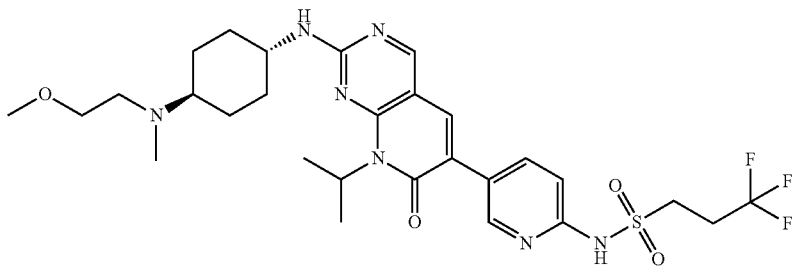 [SMILES: COCCN(C)[C@H]1CC[C@H](Nc2ncc3cc(-c4ccc(NS(=O)(=O)CCC(F)(F)F)nc4)c(=O)n(C(C)C)c3n2)CC1]

The title compound was prepared according to Example 105. This provides the title compound (32 mg, 27% yield) as a yellow solid.

Example 127: N-(4-(2-(((1r,4r)-4-(Dimethylamino)cyclohexyl)amino)-8-isopropyl-7-oxo-7,8-dihydropyrido[2,3-d]pyrimidin-6-yl)-2,5-difluorophenyl)-1-(4-fluorophenyl)methanesulfonamide Compound 127

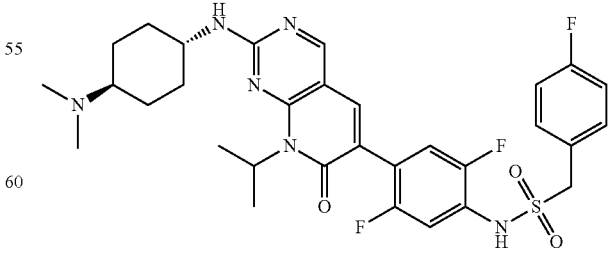

The title compound was prepared according to example 10. This provides the title compound (32.0 mg, 27% yield) as a yellow solid.

Example 128: N-(4-(2-(((1r,4r)-4-(Dimethylamino)cyclohexyl)amino)-8-isopropyl-7-oxo-7,8-dihydropyrido[2,3-d]pyrimidin-6-yl)-2,3,5-trifluorophenyl)-1-(4-fluorophenyl)methanesulfonamide Compound 128

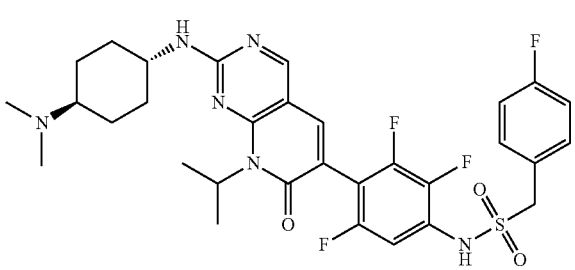 [SMILES: CC(C)n1c(=O)c(-c2c(F)cc(NS(=O)(=O)Cc3ccc(F)cc3)c(F)c2F)cc2cnc(N[C@H]3CC[C@H](N(C)C)CC3)nc21]

The title compound was prepared according to example 10. This provides the title compound (37.2 mg, 21% yield) as a yellow solid.

Example 129: N-(4-(2-(((1r,4r)-4-(Dimethylamino)cyclohexyl)amino)-8-isopropyl-7-oxo-7,8-dihydropyrido[2,3-d]pyrimidin-6-yl)-3,5-difluorophenyl)-1-(4-fluorophenyl)methanesulfonamide hydrochloride Compound 129

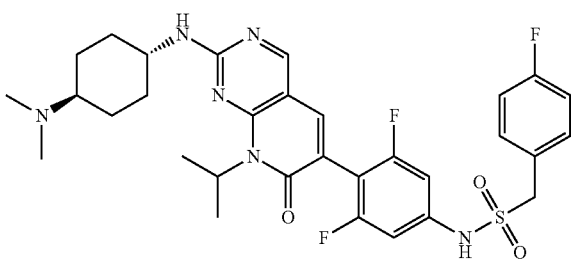 [SMILES: CC(C)n1c(=O)c(-c2c(F)cc(NS(=O)(=O)Cc3ccc(F)cc3)cc2F)cc2cnc(N[C@H]3CC[C@H](N(C)C)CC3)nc21]

The title compound was prepared according to example 10. This provides the title compound (40.9 mg, 29% yield) as a yellow solid and as a HCl salt.

Example 130: N-(3,5-Difluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(4-fluorophenyl)methanesulfonamide hydrochloride Compound 130

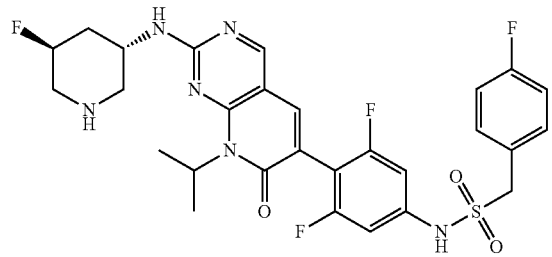 [SMILES: CC(C)n1c(=O)c(-c2c(F)cc(NS(=O)(=O)Cc3ccc(F)cc3)cc2F)cc2cnc(N[C@@H]3CNC[C@@H](F)C3)nc21]

The title compound was prepared according to example 2. This provides the title compound (51.3 mg, 56.4% yield) as a white solid and as a HCl salt.

Example 131: 2-Chloro-N-(5-(2-(((1r,4r)-4-(dimethylamino)cyclohexyl)amino)-8-isopropyl-7-oxo-7,8-dihydropyrido[2,3-d]pyrimidin-6-yl)-6-methoxypyridin-2-yl)benzenesulfonamide Compound 131

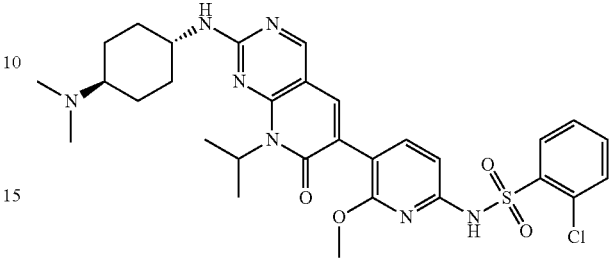

The title compound was prepared according to Example 105. This provides the title compound (45.8 mg, 23.6% yield) as a yellow solid.

Example 132: N-(5-(2-(((1r,4r)-4-(Dimethylamino)cyclohexyl)amino)-8-isopropyl-7-oxo-7,8-dihydropyrido[2,3-d]pyrimidin-6-yl)-6-methylpyridin-2-yl)-4-fluorobenzenesulfonamide Compound 132

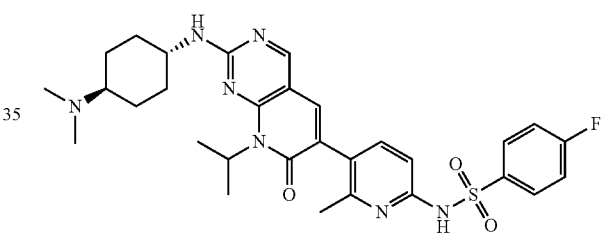

The title compound was prepared according to Example 105. This provides the title compound (24.5 mg, 12.0% yield) as a white solid.

Example 133: 2-Chloro-N-(5-(2-(((3S,5S)-5-fluoropiperidin-3-yl)amino)-8-isopropyl-7-oxo-7,8-dihydropyrido[2,3-d]pyrimidin-6-yl)-6-methylpyridin-2-yl)benzenesulfonamide Compound 133

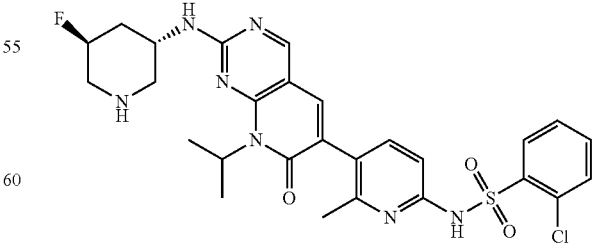

The title compound was prepared according to Example 105. This provides the title compound (37.4 mg, 30.8% yield) as a white solid.

Example 134; N-(4-(2-(((1r,4r)-4-(Dimethylamino)cyclohexyl)amino)-8-isopropyl-7-oxo-7,8-dihydropyrido[2,3-d]pyrimidin-6-yl)-2-fluorophenyl)cyclopentanesulfonamide hydrochloride Compound 134

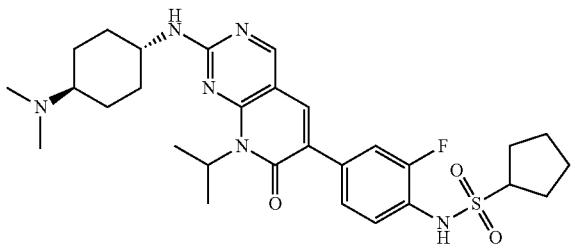 [SMILES: CC(C)n1c(=O)c(-c2ccc(NS(=O)(=O)C3CCCC3)c(F)c2)cc2cnc(N[C@H]3CC[C@H](N(C)C)CC3)nc21]

To a solution of 6-(4-amino-3-fluoro-phenyl)-2-((4-(dimethylamino)cyclohexyl)amino)-8-isopropyl-pyrido[2,3-d]pyrimidin-7-one (120 mg, 0.26 mmol) in 1,8-diazabicyclo[5.4.0]undec-7-ene (0.5 mL) was added cyclopentanesulfonylchloride (180 mg, 1.1 mmol) and stirred at 25° C. for 4 days. The reaction mixture was diluted with water and extracted with ethyl acetate. The organic layers were combined. The organic layer was washed with brine. The residue was purified by Prep-HPLC to afford the title compound (17.2 mg, 10.8% yield) as a yellow solid and as HCl salt.

Example 135: 2-Chloro-N-(5-(2-(((1r,4r)-4-(dimethylamino)cyclohexyl)amino)-8-isopropyl-7-oxo-7,8-dihydropyrido[2,3-d]pyrimidin-6-yl)-6-methylpyridin-2-yl)benzenesulfonamide Compound 135

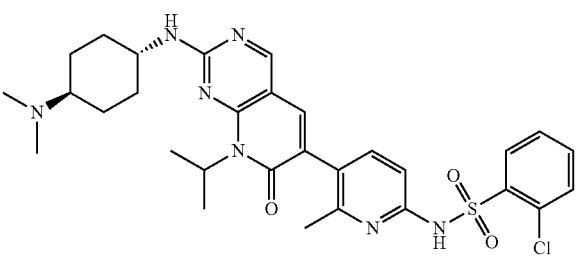 [SMILES: Cc1nc(NS(=O)(=O)c2ccccc2Cl)ccc1-c1cc2cnc(N[C@H]3CC[C@H](N(C)C)CC3)nc2n(C(C)C)c1=O]

The title compound was prepared according to Example 105. This provides the title compound (23.4 mg, 10.5% yield) as a white solid. LCMS (ESI): [M+1]=610.3.

Example 136: 2-Cyano-N-(5-(2-(((1r,4r)-4-(dimethylamino)cyclohexyl)amino)-8-isopropyl-7-oxo-7,8-dihydropyrido[2,3-d]pyrimidin-6-yl)-6-methylpyridin-2-yl)benzenesulfonamide Compound 136

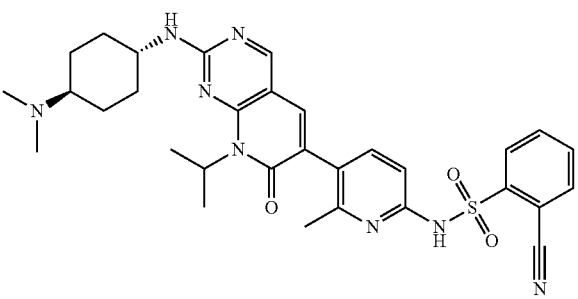 [SMILES: Cc1nc(NS(=O)(=O)c2ccccc2C#N)ccc1-c1cc2cnc(N[C@H]3CC[C@H](N(C)C)CC3)nc2n(C(C)C)c1=O]

The title compound was prepared according to Example 105. This provides the title compound (46.7 mg, 33.9% yield) as a light yellow solid.

Example 137: N-(5-(2-(((1r,4r)-4-(Dimethylamino)cyclohexyl)amino)-8-isopropyl-7-oxo-7,8-dihydropyrido[2,3-d]pyrimidin-6-yl)-6-methylpyridin-2-yl)-2-fluoro-3-methylbenzenesulfonamide Compound 137

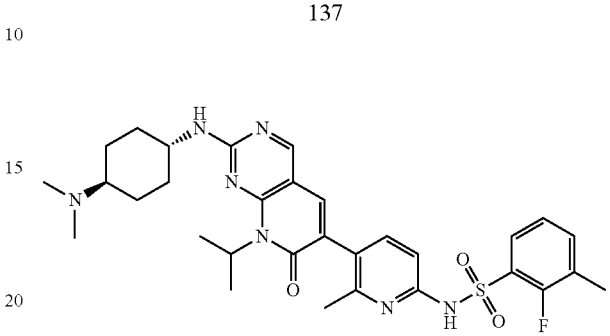

The title compound was prepared according to Example 105. This provides the title compound (57.1 mg, 27.3% yield) as a white solid.

Example 138; 3,3,3-Trifluoro-N-(2-fluoro-4-(8-isopropyl-2-(((1r,4r)-4-((2-methoxyethyl)(methyl)amino)cyclohexyl)amino)-7-oxo-7,8-dihydropyrido[2,3-d]pyrimidin-6-yl)phenyl)propane-1-sulfonamide Compound 138

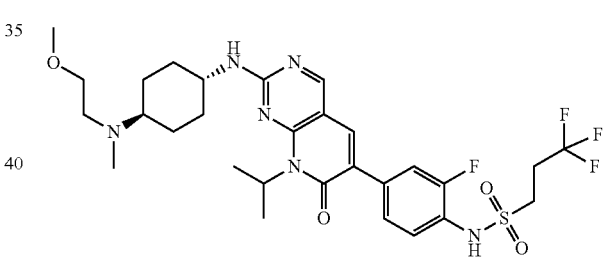

The title compound was prepared according to Example 122. This provides the title compound (58.4 mg, 29.2% yield) as a yellow solid.

Example 139; N-(2,3,6-Trifluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(2-(trifluoromethyl)pyridin-3-yl)methanesulfonamide Compound 139

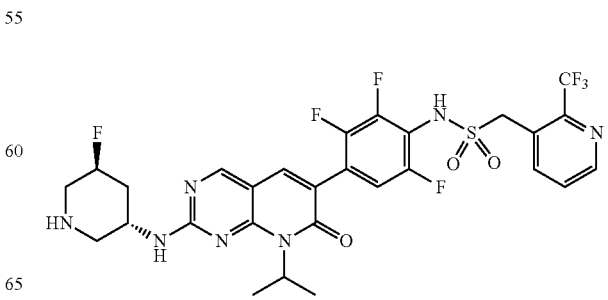

The title compound was prepared according to example 2. This provides the title compound (30.4 mg, 31.7% yield) as off-white solid.

Example 140: N-(5-(2-(((1r,4r)-4-(Dimethylamino)cyclohexyl)amino)-8-isopropyl-7-oxo-7,8-dihydropyrido[2,3-d]pyrimidin-6-yl)-6-methylpyridin-2-yl)-2-fluorobenzenesulfonamide Compound 140

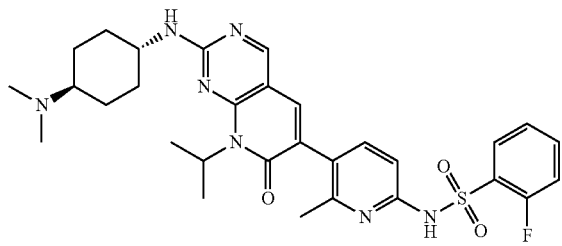 [SMILES: Cc1nc(NS(=O)(=O)c2ccccc2F)ccc1-c1cc2cnc(N[C@H]3CC[C@H](N(C)C)CC3)nc2n(C(C)C)c1=O]

The title compound was prepared according to Example 105. This provides the title compound (46.3 mg, 24.5% yield) as a yellow solid.

Example 141: 1-(4-Fluorophenyl)-N-(2,3,6-trifluoro-4-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)phenyl)methanesulfonamide Compound 141

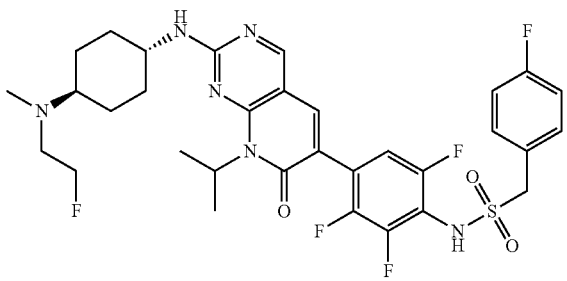 [SMILES: CC(C)n1c(=O)c(-c2cc(F)c(NS(=O)(=O)Cc3ccc(F)cc3)c(F)c2F)cc2cnc(N[C@H]3CC[C@H](N(C)CCF)CC3)nc21]

Step 1: Benzyl ((1r,4r)-4-((2-fluoroethyl)amino)cyclohexyl)carbamate

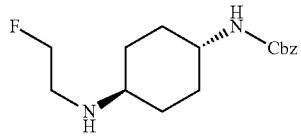 [SMILES: O=C(N[C@H]1CC[C@H](NCCF)CC1)OCc1ccccc1]

A mixture of benzyl N-(4-aminocyclohexyl)carbamate (10 g, 40 mmol), 1-bromo-2-fluoroethane (6.2 g, 49 mmol) and potassium carbonate (11.2 g, 81 mmol) in N,N-dimethylformamide (80 mL) was stirred at 85° C. for 16 h. The resulting solution was diluted with water and extracted with ethyl acetate. The organic layers were washed with brine, dried over anhydrous sodium sulfate and concentrated. The residue was purified by reverse phase chromatography eluting with methanol/0.1% HCl in water (10%-60%) to afford the title compound (5 g, 41.8% yield) as a white solid. LCMS (ESI): [M+H]$^+$=295.2.

Step 2: Benzyl ((1r,4r)-4-((2-fluoroethyl)(methyl)amino)cyclohexyl)carbamate

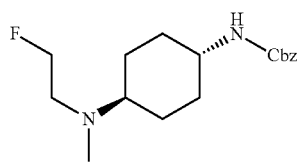 [SMILES: CN(CCF)[C@H]1CC[C@H](NC(=O)OCc2ccccc2)CC1]

To a solution of benzyl ((1r,4r)-4-((2-fluoroethyl)amino)cyclohexyl)carbamate (5.0 g, 17 mmol), acetic acid (1.02 g, 17 mmol) and 37% formaldehyde solution (20 mL) in methyl alcohol (80 mL) was added sodium cyanoborohydride (1.1 g, 17.5 mmol) at 0° C. The resulting solution stirred at 25° C. for 1 h. The reaction was quenched with water. The solvent was concentrated under vacuum. The residue was purified by reverse phase chromatography eluting with acetonitrile/10 mM ammonium bicarbonate in water (10%-60%) to afford the title compound (4.4 g, 79.8% yield) as a white solid. LCMS (ESI): [M+H]$^+$=309.2.

Step 3: (1r,4r)-N$^1$-(2-Fluoroethyl)-N$^1$-methylcyclohexane-1,4-diamine

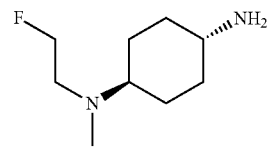

Under hydrogen, a mixture of benzyl ((1r,4r)-4-((2-fluoroethyl)(methyl)amino)cyclohexyl)carbamate (4.0 g, 12.99 mmol), 15% Pd/C (900 mg) in methyl alcohol (40 mL) was stirred at 25° C. for 3 h. After filtration, the filtrate was concentrated under vacuum to afford the title compound (2.3 g, 96.5% yield) as a white solid. LCMS (ESI): [M+H]$^+$=175.2.

Step 4: 1-(4-Fluorophenyl)-N-(2,3,6-trifluoro-4-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)phenyl)methanesulfonamide Compound 141

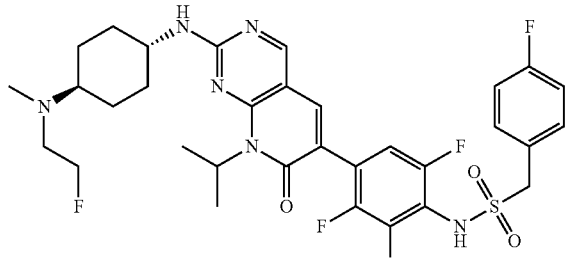

The title compound was prepared according to Example 122. This provides the title compound (26.5 mg, 19.6% yield) as a yellow solid.

Example 142: 3-Cyano-N-(5-(2-(((1r,4r)-4-(dimethylamino)cyclohexyl)amino)-8-isopropyl-7-oxo-7,8-dihydropyrido[2,3-d]pyrimidin-6-yl)-6-methylpyridin-2-yl)benzenesulfonamide Compound 142

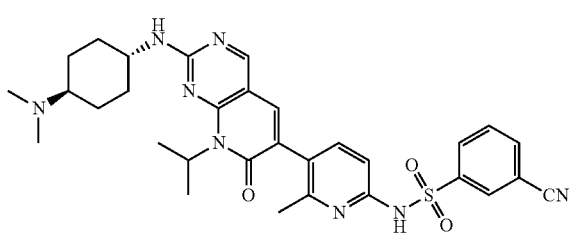 [SMILES: Cc1nc(NS(=O)(=O)c2cccc(C#N)c2)ccc1-c1cc2cnc(N[C@H]3CC[C@H](N(C)C)CC3)nc2n(C(C)C)c1=O]

The title compound was prepared according to Example 105. This provides the title compound (41.6 mg, 20.1% yield) as a yellow solid.

Example 143: 3,3,3-Trifluoro-N-(5-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)pyridin-2-yl)propane-1-sulfonamide Compound 143

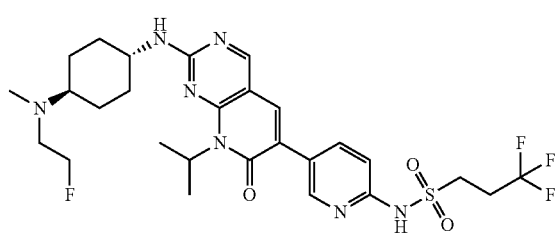 [SMILES: CC(C)n1c(=O)c(-c2ccc(NS(=O)(=O)CCC(F)(F)F)nc2)cc2cnc(N[C@H]3CC[C@H](N(C)CCF)CC3)nc21]

The title compound was prepared according to Example 105. This provides the title compound (39.6 mg, 36.2% yield) as a white solid.

Example 144: N-(5-(2-(((1r,4r)-4-((2-Fluoroethyl)(methyl)amino)cyclohexyl)amino)-8-isopropyl-7-oxo-7,8-dihydropyrido[2,3-d]pyrimidin-6-yl)pyridin-2-yl)benzenesulfonamide Compound 144

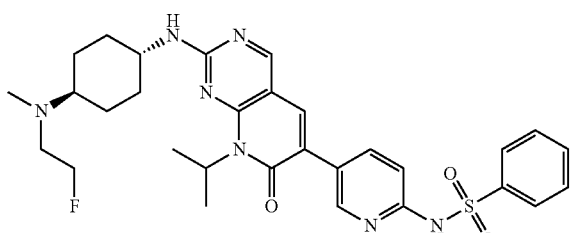

The title compound was prepared according to Example 105. This provides the title compound (30.6 mg, 28.9% yield) as a white solid.

Example 145: 2-Chloro-N-(5-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)-6-methylpyridin-2-yl)benzenesulfonamide Compound 145

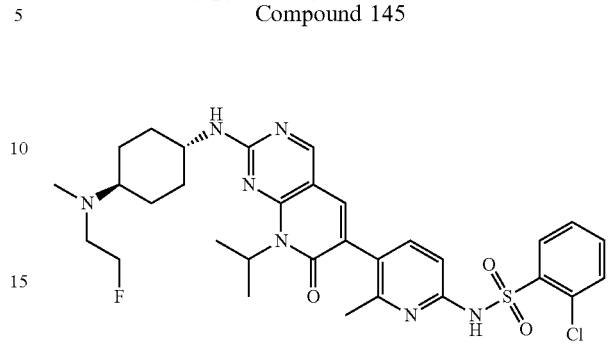

The title compound was prepared according to Example 105. This provides the title compound (22.6 mg, 13.5% yield) as a light yellow solid.

Example 146: 2-Chloro-N-(5-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)pyridin-2-yl)benzenesulfonamide hydrochloride Compound 146

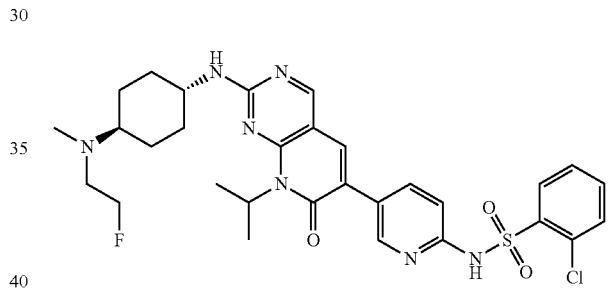

The title compound was prepared according to Example 105. This provides the title compound (24.6 mg, 20.8% yield) as a light yellow solid and as HCl salt.

Example 147: 2-Chloro-N-(5-(2-(((3S,5S)-5-fluoropiperidin-3-yl)amino)-8-isopropyl-7-oxo-7,8-dihydropyrido[2,3-d]pyrimidin-6-yl)pyridin-2-yl)benzenesulfonamide Compound 147

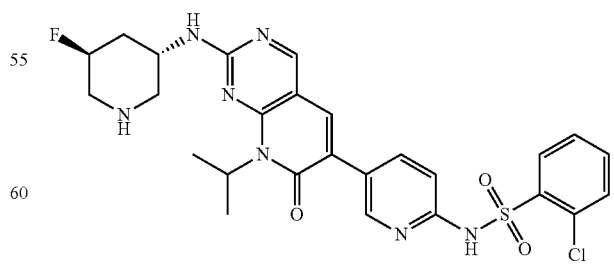

The title compound was prepared according to Example 105. This provides the title compound (31.4 mg, 46.1% yield) as a brown solid.

Example 148: 2-Cyano-N-(5-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)pyridin-2-yl)benzenesulfonamide Compound 148

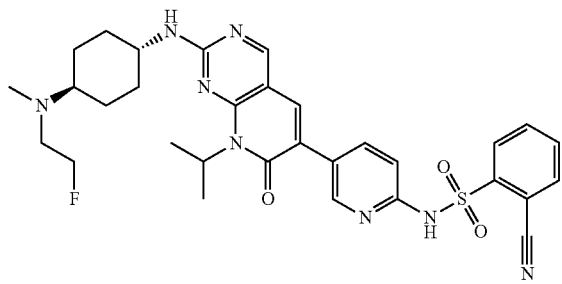 [SMILES: CC(C)n1c(=O)c(-c2ccc(NS(=O)(=O)c3ccccc3C#N)nc2)cc2cnc(N[C@H]3CC[C@H](N(C)CCF)CC3)nc21]

The title compound was prepared according to Example 105. This provides the title compound (20.5 mg, 11.7% yield) as an off-white solid.

Example 149: N-(5-(2-(((1r,4r)-4-(Dimethylamino)cyclohexyl)amino)-8-isopropyl-7-oxo-7,8-dihydropyrido[2,3-d]pyrimidin-6-yl)pyridin-2-yl)-2-(trifluoromethyl)benzenesulfonamide Compound 149

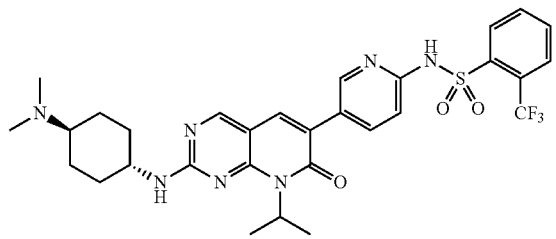 [SMILES: CC(C)n1c(=O)c(-c2ccc(NS(=O)(=O)c3ccccc3C(F)(F)F)nc2)cc2cnc(N[C@H]3CC[C@H](N(C)C)CC3)nc21]

The title compound was prepared according to Example 105. This provides the title compound (37.7 mg, 25.2% yield) as a white solid.

Example 150: N-(5-(2-(((1r,4r)-4-(Dimethylamino)cyclohexyl)amino)-8-isopropyl-7-oxo-7,8-dihydropyrido[2,3-d]pyrimidin-6-yl)pyridin-2-yl)-2-(trifluoromethoxy)benzenesulfonamide Compound 150

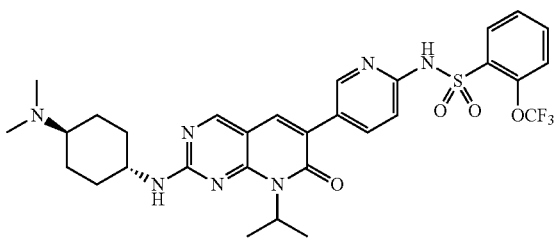 [SMILES: CC(C)n1c(=O)c(-c2ccc(NS(=O)(=O)c3ccccc3OC(F)(F)F)nc2)cc2cnc(N[C@H]3CC[C@H](N(C)C)CC3)nc21]

The title compound was prepared according to Example 105. This provides the title compound (22.4 mg, 14.6% yield) as a yellow solid.

Example 151: 1-(3,3-Difluorocyclobutyl)-N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)methanesulfonamide Compound 151

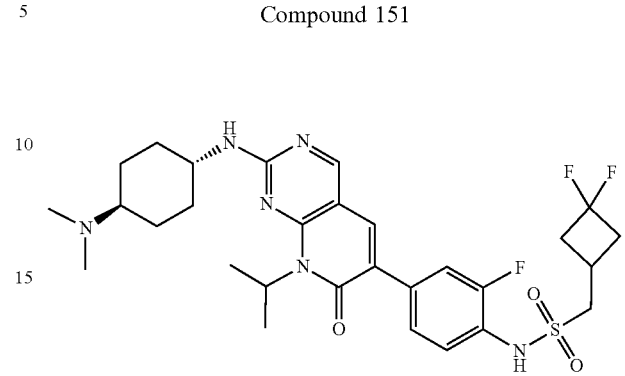

The title compound was prepared according to example 10. This provides the title compound (55.2 mg, 39.9% yield) as a yellow solid.

Example 152: 1-Cyclohexyl-N-(5-(2-(((1r,4r)-4-(dimethylamino)cyclohexyl)amino)-8-isopropyl-7-oxo-7,8-dihydropyrido[2,3-d]pyrimidin-6-yl)pyridin-2-yl)methanesulfonamide Compound 152

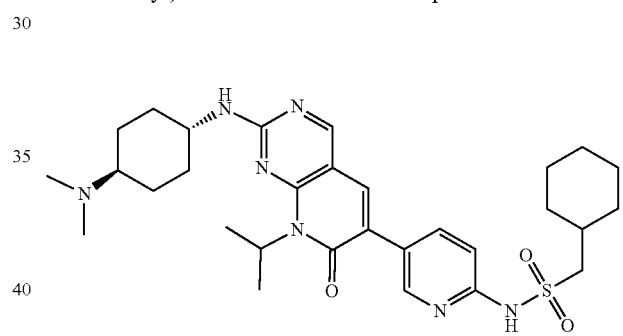

The title compound was prepared according to Example 105. This provides the title compound (51.3 mg, 37.2% yield) as an off-white solid.

Example 153; 1-(2,2-Difluorocyclobutyl)-N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)methanesulfonamide Compound 153 (Compound 153A Compound 153B)

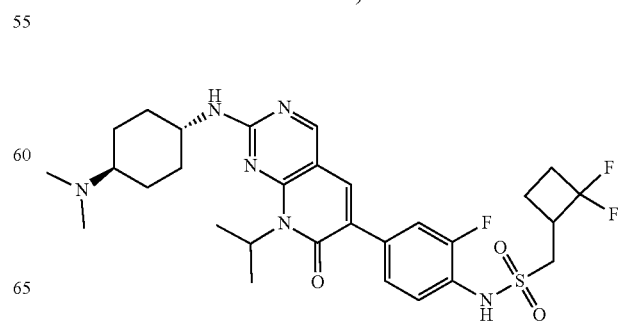

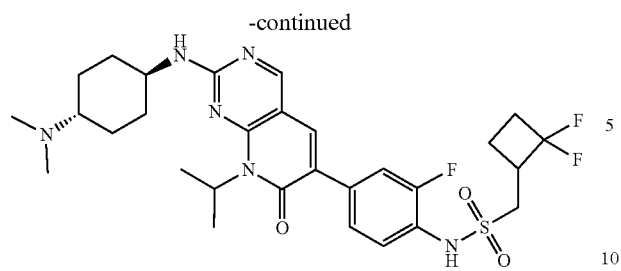

The title compound was prepared according to example 10. After Prep-HPLC and Chiral HPLC, two peaks were isolated out:

1-(2,2-Difluorocyclobutyl)-N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)methanesulfonamide (isomer 1) (28.3 mg, 14.3% yield) as a yellow solid. (rt=5.731 min, Reg AD 0.46*10 cm; 5 μm, Hex (0.1% DEA):EtOH=60:40, 1.0 mL/min).

1-(2,2-Difluorocyclobutyl)-N-(4-(2-(((1r,4r)-4-(dimethylamino)cyclohexyl)amino)-8-isopropyl-7-oxo-7,8-dihydropyrido[2,3-d]pyrimidin-6-yl)-2-fluorophenyl)methanesulfonamide (isomer 2) (30.1 mg, 15.5% yield) as a yellow solid. (rt=7.403 min, Reg AD 0.46*10 cm; 5 μm, Hex (0.1% DEA):EtOH=60:40, 1.0 mL/min).

Example 154: N-(4-(2-((4-(Dimethylamino)-3-fluorocyclohexyl)amino)-8-isopropyl-7-oxo-7,8-dihydropyrido[2,3-d]pyrimidin-6-yl)-2-fluorophenyl)-3,3,3-trifluoropropane-1-sulfonamide hydrochloride Compound 154 Compound 154A Compound 154B

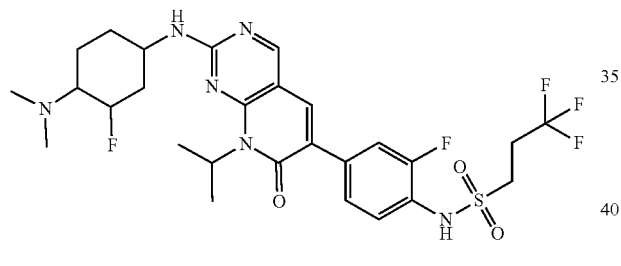

The title compound was prepared according to Example 110. The residue was purified by Prep-HPLC. This provides the title compound (82.4 mg, 39.4% yield) as a yellow solid and as a HCl salt. (cyclohexane is racemate of (1S,3R,4S) and (1R,3S,4R)).

Example 155: N-(2-Fluoro-4-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)phenyl)-1-(4-fluorophenyl)methanesulfonamide Compound 155

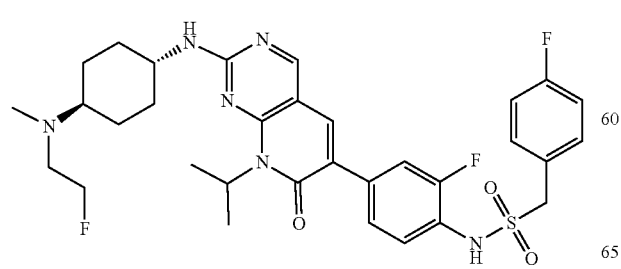

The title compound was prepared according to example 2. This provides the title compound (31.9 mg, 22.4% yield) as a white solid.

Example 156: 1-(3,3-Difluorocyclobutyl)-N-(2-fluoro-4-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)phenyl)methanesulfonamide Compound 156

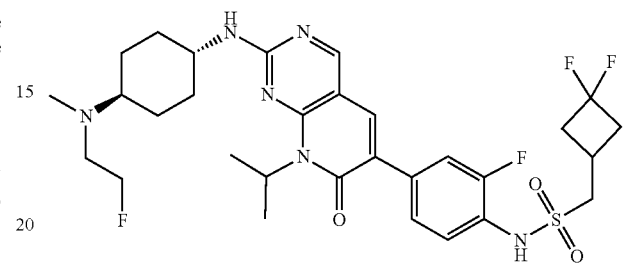

The title compound was prepared according to example 10. This provides the title compound (35.2 mg, 23.6% yield) as a white solid.

Example 157; 3,3,3-trifluoro-N-(2-Fluoro-4-(2-(((1r,4r)-4-((2-fluoroethyl)(methyl)amino)cyclohexyl)amino)-8-isopropyl-7-oxo-7,8-dihydropyrido[2,3-d]pyrimidin-6-yl)phenyl)propane-1-sulfonamide Compound 157

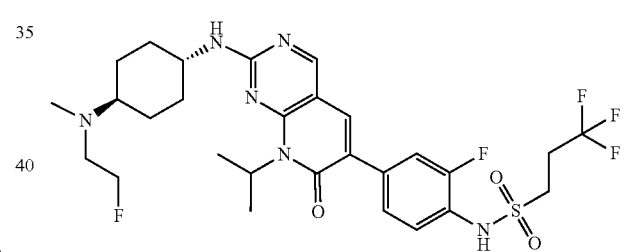

The title compound was prepared according to example 10. This provides the title compound (40.7 mg, 17% yield) as a yellow solid.

Example 158: N-(2,3,6-Trifluoro-4-(2-(((3S,5S)-5-fluoropiperidin-3-yl)amino)-8-isopropyl-7-oxo-7,8-dihydropyrido[2,3-d]pyrimidin-6-yl)phenyl)-1-(1-(2,2,2-trifluoroethyl)-1H-pyrazol-3-yl)methanesulfonamide Compound 158

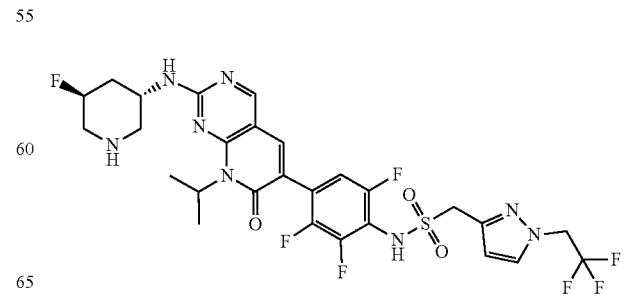

The title compound was prepared according to example 10. This provides the title compound (28.1 mg, 40.3% yield) as a white solid.

Example 159: 2-Chloro-N-(5-(2-((4-(dimethylamino)-3-fluorocyclohexyl)amino)-8-isopropyl-7-oxo-7,8-dihydropyrido[2,3-d]pyrimidin-6-yl)pyridin-2-yl)benzenesulfonamide hydrochloride (cyclohexane is racemate of (1S,3R,4S) and (1R,3S,4R)) Compound 159 Compound 159A Compound 159B

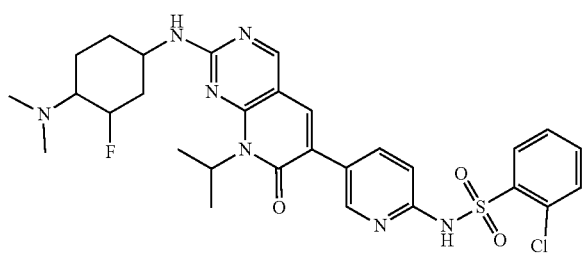 [SMILES: CC(C)n1c(=O)c(-c2ccc(NS(=O)(=O)c3ccccc3Cl)nc2)cc2cnc(NC3CCC(N(C)C)C(F)C3)nc21]

The title compound was prepared according to Example 110. The residue was purified by Prep-HPLC. This provides the title compound (4.4 mg, 3.8% yield) as a light green solid and as a HCl salt. (Cyclohexane is racemate of (1S,3R,4S) and (1R,3S,4R)).

Example 160; 2-Chloro-N-(5-(2-((4-(dimethylamino)-3-fluorocyclohexyl)amino)-8-isopropyl-7-oxo-7,8-dihydropteridin-6-yl)-6-methylpyridin-2-yl)benzenesulfonamide hydrochloride Compound 160 Compound 160A Compound 160B

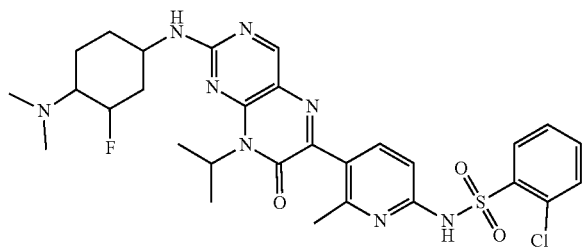 [SMILES: Cc1nc(NS(=O)(=O)c2ccccc2Cl)ccc1-c1nc2cnc(NC3CCC(N(C)C)C(F)C3)nc2n(C(C)C)c1=O]

The title compound was prepared according to Example 110. The residue was purified by Prep-HPLC. This provides the title compound (61.3 mg, 25.8% yield) as a yellow solid and as a HCl salt. (Cyclohexane is racemate of (1S,3R,4S) and (1R,3S,4R)).

Example 161; N-(4-(2-(((1r,4r)-4-(Dimethylamino)cyclohexyl)amino)-8-isopropyl-7-oxo-7,8-dihydropteridin-6-yl)-3-fluorophenyl)propane-1-sulfonamide Compound 161

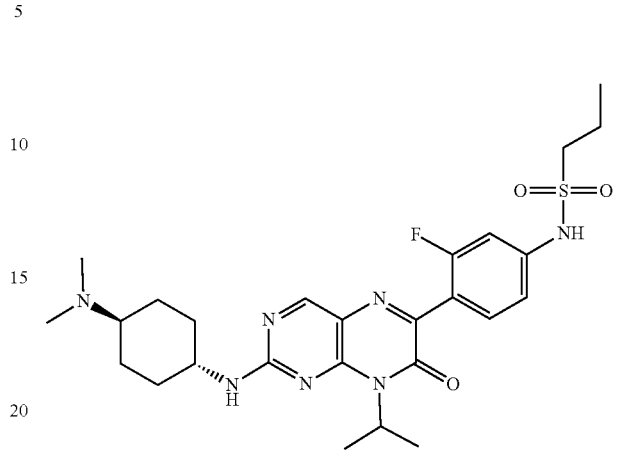

The title compound was prepared according to example 64. This provides the title compound (29.1 mg, 13.8% yield) as a yellow solid.

Example 162; N-(2-Fluoro-4-(2-(((3S,5S)-5-fluoropiperidin-3-yl)amino)-8-isopropyl-7-oxo-7,8-dihydropteridin-6-yl)phenyl)piperidine-1-sulfonamide Compound 162

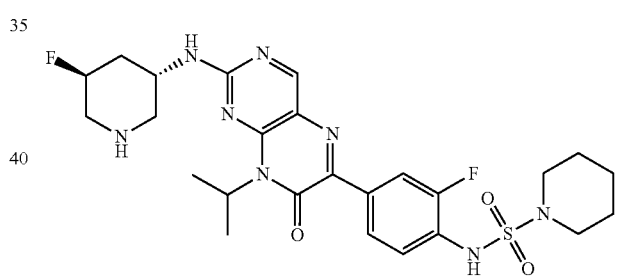

A mixture of tert-butyl (3S,5S)-3-((6-(4-amino-3-fluorophenyl)-8-isopropyl-7-oxo-pteridin-2-yl)amino)-5-fluoropiperidine-1-carboxylate (160 mg, 0.25 mmol) in pyridine (0.50 mL) was added piperidine-1-sulfonylchloride (150 mg, 0.82 mmol) and stirred at 80° C. for 1 h. The reaction mixture was diluted with water and extracted with ethyl acetate. The organic layers were combined. The organic layer was washed with brine. The organic layer was dried over anhydrous sodium sulfate and concentrated under vacuum to afford tert-butyl (3S,5S)-3-fluoro-5-((6-(3-fluoro-4-(1-piperidylsulfonylamino)phenyl)-8-isopropyl-7-oxo-pteridin-2-yl)amino)piperidine-1-carboxylate.

A solution of tert-butyl (3S,5S)-3-fluoro-5-((6-(3-fluoro-4-(1-piperidylsulfonylamino)phenyl)-8-isopropyl-7-oxo-pteridin-2-yl)amino)piperidine-1-carboxylate in dichloromethane (1 mL) was added 4M HCl in dioxane (3 mL) and stirred at 25° C. for 1 h. The solvent was concentrated under vacuum. The crude product was purified by Prep-HPLC to afford the title compound (45.4 mg, 43.9% yield) as a yellow solid.

Example 163; N-(2-Fluoro-4-(2-(((3S,5S)-5-fluoropiperidin-3-yl)amino)-8-isopropyl-7-oxo-7,8-dihydropteridin-6-yl)phenyl)pyrrolidine-1-sulfonamide Compound 163

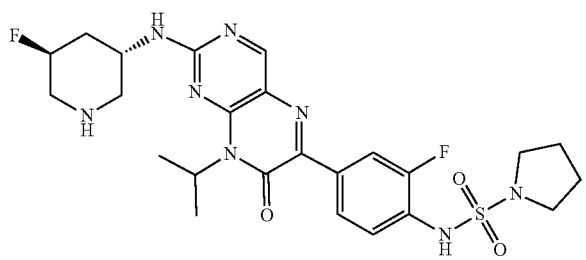 [SMILES: CC(C)n1c(=O)c(-c2ccc(NS(=O)(=O)N3CCCC3)c(F)c2)nc2cnc(N[C@@H]3CNC[C@@H](F)C3)nc21]

The title compound was prepared according to Example 162. This provides the title compound (26 mg, 30.7% yield) as a yellow solid.

Example 164; 6-(4-(Dimethylsulfamoylamino)-3-fluoro-phenyl)-2-(((3S,5S)-5-fluoro-3-piperidyl)amino)-8-isopropyl-7-oxo-pteridine Compound 164

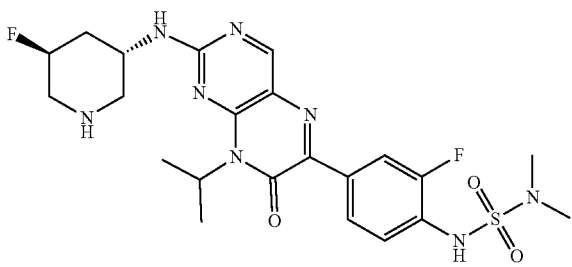 [SMILES: CC(C)n1c(=O)c(-c2ccc(NS(=O)(=O)N(C)C)c(F)c2)nc2cnc(N[C@@H]3CNC[C@@H](F)C3)nc21]

The title compound was prepared according to example 64. This provides the title compound (36.9 mg, 55% yield) as a yellow solid.

Example 165: N-(4-(2-(((1r,4r)-4-(Dimethylamino)cyclohexyl)amino)-8-isopropyl-7-oxo-7,8-dihydropteridin-6-yl)-2-fluorophenyl)-2,2-difluorobutane-1-sulfonamide hydrochloride Compound 165

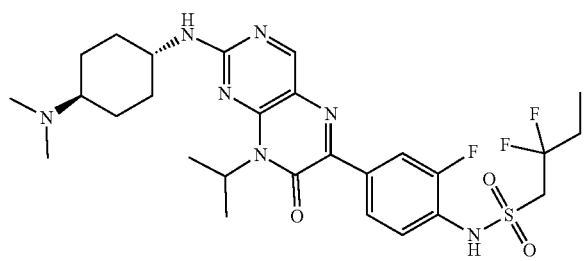 [SMILES: CCC(F)(F)CS(=O)(=O)Nc1ccc(-c2nc3cnc(N[C@H]4CC[C@H](N(C)C)CC4)nc3n(C(C)C)c2=O)cc1F]

The title compound was prepared according to example 66. This provides the title compound (32.7 mg, 22.4% yield) as a yellow solid and as HCl salt.

Example 166; 1-(2-Cyano-4-methylphenyl)-N-(2-fluoro-4-(2-(((3S,5S)-5-fluoropiperidin-3-yl)amino)-8-isopropyl-7-oxo-7,8-dihydropteridin-6-yl)phenyl)methanesulfonamide Compound 166

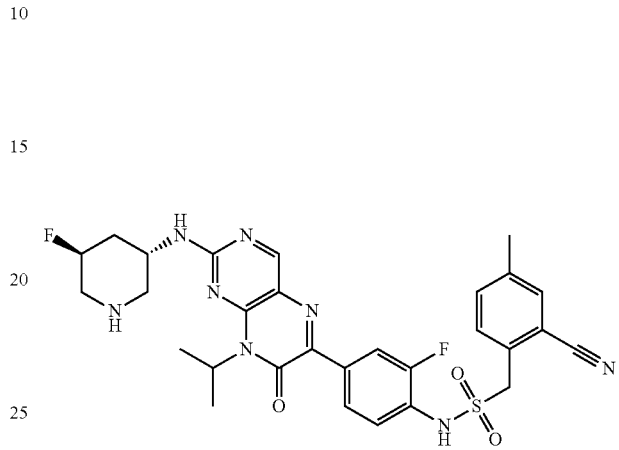

Step 1: 1-(2-Bromo-4-methylphenyl)-N-(2-fluoro-4-(8-isopropyl-2-(methylthio)-7-oxo-7,8-dihydropteridin-6-yl)phenyl)methanesulfonamide

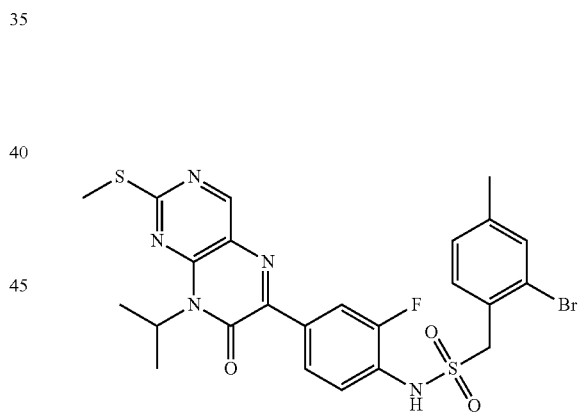

To a mixture of 6-(4-amino-3-fluoro-phenyl)-8-isopropyl-2-methylsulfanyl-pteridin-7-one (150 mg, 0.43 mmol) in pyridine (1 mL) was added (2-bromophenyl)methanesulfonyl chloride (360 mg, 1.34 mmol), the mixture was stirred for 1 h at rt. The reaction was quenched with water and extracted with dichloromethane. The organic layer was concentrated in vacuum. Then the resulting mixture was dissolved in tetrahydrofuran (3 mL), and then sat. lithium hydroxide solution (3 mL) was added and stirred for 0.5 h at rt. The resulting solution was diluted with water, extracted with dichloromethane and concentrated. The residue was purified by silica flash chromatography eluting with ethyl acetate/petroleum ether (1/4) to afford the title compound (205 mg, 81.6% yield) as a yellow solid. LCMS (ESI): $[M+H]^+$=592.0.

Step 2: 1-(2-Bromo-4-methylphenyl)-N-(2-fluoro-4-(8-isopropyl-2-(methylsulfonyl)-7-oxo-7,8-dihydropteridin-6-yl)phenyl)methanesulfonamide Step 4: tert-butyl (3S,5S)-3-((6-(4-(((2-cyano-4-methylphenyl)methyl)sulfonamido)-3-fluorophenyl)-8-isopropyl-7-oxo-7,8-dihydropteridin-2-yl)amino)-5-fluoropiperidine-1-carboxylate

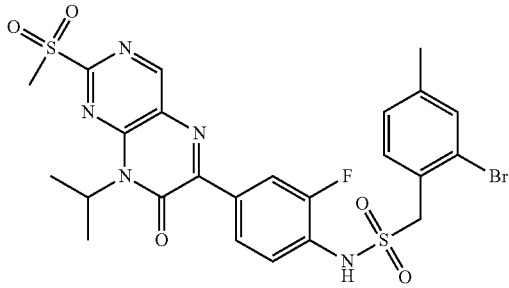 [SMILES: Cc1ccc(CS(=O)(=O)Nc2ccc(-c3nc4cnc(S(C)(=O)=O)nc4n(C(C)C)c3=O)cc2F)c(Br)c1]

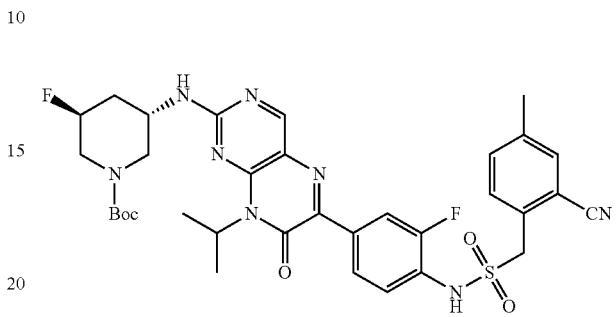

To a mixture of 1-(2-bromo-4-methyl-phenyl)-N-(2-fluoro-4-(8-isopropyl-2-methylsulfanyl-7-oxo-pteridin-6-yl)phenyl)methanesulfonamide (200 mg, 0.34 mmol) in dichloromethane (5 mL) was added 3-chloroperoxybenzoic acid (160 mg, 0.79 mmol), the mixture was stirred for 2 h at rt. The reaction was quenched with water and extracted with ethyl acetate. The organic layer was concentrated in vacuum to afford the title compound (210 mg, 99% yield). LCMS (ESI): [M+H]$^+$=624.0.

Step 3: tert-Butyl (3S,5S)-3-((6-(4-(((2-bromo-4-methylphenyl)methyl)sulfonamido)-3-fluorophenyl)-8-isopropyl-7-oxo-7,8-dihydropteridin-2-yl)amino)-5-fluoropiperidine-1-carboxylate A mixture of tert-butyl (3S,5S)-3-((6-(4-(((2-bromo-4-methylphenyl)methyl)sulfonamido)-3-fluorophenyl)-8-isopropyl-7-oxo-7,8-dihydropteridin-2-yl)amino)-5-fluoropiperidine-1-carboxylate (150 mg, 0.20 mmol), zinc cyanide (120 mg, 1.02 mmol) and tetrakis(triphenylphosphine)palladium(0) (105 mg, 0.09 mmol) in N,N-dimethylformamide (5 mL) was stirred at 120° C. for 2 h under nitrogen. The resulting solution was diluted with water, extracted with ethyl acetate, washed with brine, dried over sodium sulfate and concentrated. The residue was purified by silica flash chromatography eluting with ethyl acetate/petroleum ether (3/2) to afford the title compound (130 mg, 93.3% yield) as a yellow solid. LCMS (ESI): [M+H]$^+$=709.3.

Step 5: 1-(2-Cyano-4-methylphenyl)-N-(2-fluoro-4-(2-(((3S,5S)-5-fluoropiperidin-3-yl)amino)-8-isopropyl-7-oxo-7,8-dihydropteridin-6-yl)phenyl)methanesulfonamide Compound 166

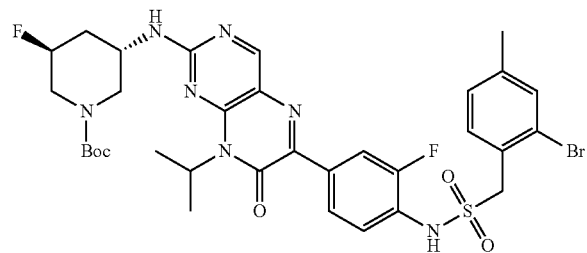 [SMILES: Cc1ccc(CS(=O)(=O)Nc2ccc(-c3nc4cnc(N[C@H]5C[C@H](F)CN(C(=O)OC(C)(C)C)C5)nc4n(C(C)C)c3=O)cc2F)c(Br)c1]

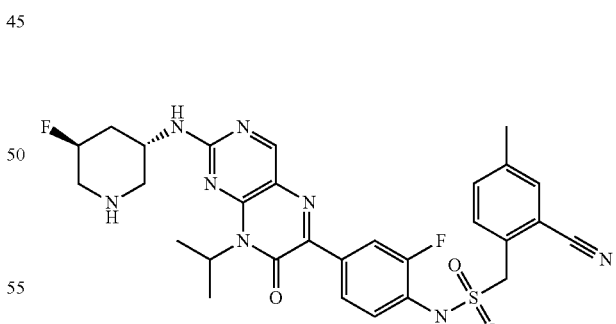

A mixture of 1-(2-bromo-4-methyl-phenyl)-N-(2-fluoro-4-(8-isopropyl-2-methylsulfonyl-7-oxo-pteridin-6-yl)phenyl)methanesulfonamide (210 mg, 0.34 mmol), tert-butyl (3S,5S)-3-amino-5-fluoro-piperidine-1-carboxylate (84 mg, 0.38 mmol), caesium fluoride (147 mg, 0.97 mmol) and N,N-diisopropylethylamine (273 mg, 2.12 mmol) in dimethyl sulfoxide (10 mL) was stirred at 100° C. for 2 h under nitrogen. The resulting solution was diluted with water, extracted with ethyl acetate, washed with brine, dried over Sodium sulfate and concentrated. The residue was purified by silica flash chromatography eluting with ethyl acetate/petroleum ether (50:50) to afford the title compound (170 mg, 66.3% yield) as a yellow solid. LCMS (ESI): [M+H]$^+$=762.2.

To a mixture of tert-butyl (3S,5S)-3-((6-(4-(((2-cyano-4-methylphenyl)methyl)sulfonamido)-3-fluorophenyl)-8-isopropyl-7-oxo-7,8-dihydropteridin-2-yl)amino)-5-fluoropiperidine-1-carboxylate (130 mg, 0.18 mmol) in dichloromethane (2 mL) was added 4 M HCl in dioxane (3 mL), the mixture was stirred for 1 h at rt. The organic layer was concentrated in vacuum. The crude product was purified by Prep-HPLC to afford the title compound (47.4 mg, 42% yield) as a yellow solid.

Example 167: 2-Chloro-N-(4-(2-(((1r,4r)-4-(dimethylamino)cyclohexyl)amino)-8-isopropyl-7-oxo-7,8-dihydropteridin-6-yl)-2-fluorophenyl)benzenesulfonamide Compound 167

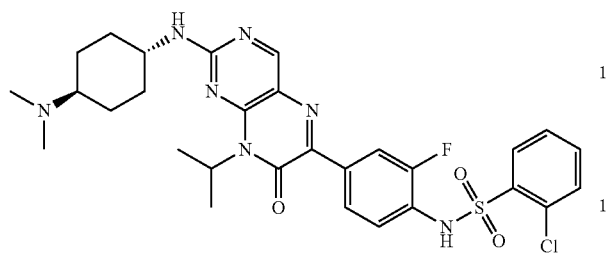

The title compound was prepared according to example 66. This provides the title compound (70 mg, 33.4% yield) as a yellow solid.

Example 168: N-(4-(2-((4-(Dimethylamino)-3-fluorocyclohexyl)amino)-8-isopropyl-7-oxo-7,8-dihydropteridin-6-yl)-2,6-difluorophenyl)-3,3,3-trifluoropropane-1-sulfonamide Compound 168 (Compound 168A Compound 168B)

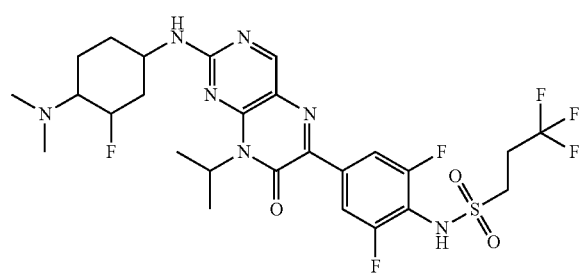 [SMILES: CC(C)n1c(=O)c(-c2cc(F)c(NS(=O)(=O)CCC(F)(F)F)c(F)c2)nc2cnc(NC3CCC(N(C)C)C(F)C3)nc21]

Step 1: tert-Butyl (4-((6-(3,5-difluoro-4-((3,3,3-trifluoropropyl)sulfonamido)phenyl)-8-isopropyl-7-oxo-7,8-dihydropteridin-2-yl)amino)-2-fluorocyclohexyl)carbamate (Cyclohexane is racemate of (1S,2S,4S) and (1R,2R,4R))

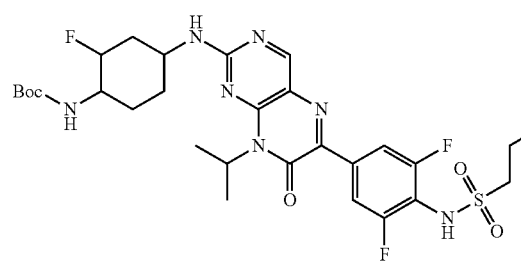

A mixture of N-(2,6-difluoro-4-(8-isopropyl-2-(methylsulfonyl)-7-oxo-7,8-dihydropteridin-6-yl)phenyl)-3,3,3-trifluoropropane-1-sulfonamide (310 mg, 0.56 mmol), tert-butyl (4-amino-2-fluorocyclohexyl)carbamate (Cyclohexane is racemate of (1S,2S,4S) and (1R,2R,4R)) (133 mg, 0.57 mmol), caesium fluoride (250 mg, 1.64 mmol) and N,N-diisopropylethylamine (0.3 mL, 1.69 mmol) in dimethyl sulfoxide (3 mL) was stirred at 80° C. for 2 h under nitrogen. The resulting solution was diluted with water and extracted with ethyl acetate. The organic layers was washed with brine, dried over anhydrous sodium sulfate and concentrated. The residue was purified by silica flash chromatography eluting with ethyl acetate/petroleum ether (1/1) to afford the title compound (300 mg, 76% yield) as a white solid. LCMS (ESI, m/z): [M+H]$^+$=708.2.

Step 2: N-(4-(2-((4-Amino-3-fluorocyclohexyl)amino)-8-isopropyl-7-oxo-7,8-dihydropteridin-6-yl)-2,6-difluorophenyl)-3,3,3-trifluoropropane-1-sulfonamide hydrochloride (Cyclohexane is a racemate of (1S,3S,4S) and (1R,3R,4R))

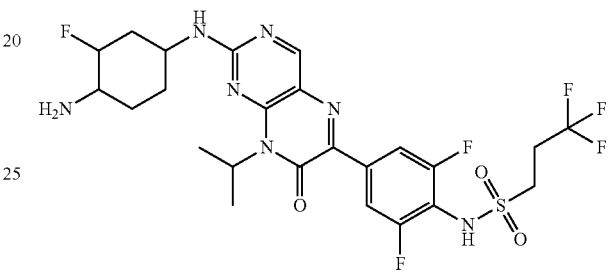 [SMILES: CC(C)n1c(=O)c(-c2cc(F)c(NS(=O)(=O)CCC(F)(F)F)c(F)c2)nc2cnc(NC3CCC(NC(=O)OC(C)(C)C)C(F)C3)nc21]

A solution of tert-butyl tert-butyl (4-((6-(3,5-difluoro-4-((3,3,3-trifluoropropyl)sulfonamido)phenyl)-8-isopropyl-7-oxo-7,8-dihydropteridin-2-yl)amino)-2-fluorocyclohexyl)carbamate (cyclohexane is a racemate of (1S,2S,4S) and (1R,2R,4R)) (300 mg, 0.42 mmol) in dichloromethane (2 mL) was added 4 M HCl in dioxane (4 mL, 16 mmol) and stirred for 2 h at rt. The solvent was removed to afford the title compound as HCl salt (272 mg, 99% yield). LCMS (ESI, m/z): [M+H]$^+$=608.1.

Step 3: N-(4-(2-((4-(Dimethylamino)-3-fluorocyclohexyl)amino)-8-isopropyl-7-oxo-7,8-dihydropteridin-6-yl)-2,6-difluorophenyl)-3,3,3-trifluoropropane-1-sulfonamide (Cyclohexane is (1S,3S,4S) or (1R, 3R,4R)) Compound 168 (Compound 168A Compound 168B)

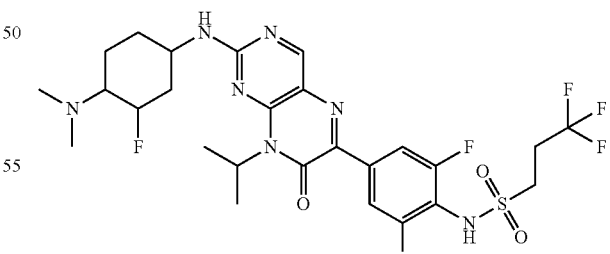

A solution of N-(4-(2-((4-amino-3-fluorocyclohexyl)amino)-8-isopropyl-7-oxo-7,8-dihydropteridin-6-yl)-2,6-difluorophenyl)-3,3,3-trifluoropropane-1-sulfonamide (Cyclohexane is (1S,3S,4S) or (1R,3R,4R)) (257 mg, 0.42 mmol) in methyl alcohol (4 mL) was added 37% formaldehyde solution (1 mL, 36 mmol) and acetic acid (1 mL). Then sodium cyanoborohydride (80 mg, 1.27 mmol) was added.

The mixture was stirred for 1 h at rt. The resulting solution was directly purified by reverse phase (10 mM ammonium bicarbonate/acetonitrile). Then further purified by Prep-HPLC and SFC to afford the title compounds.

N-(4-(2-((4-(Dimethylamino)-3-fluorocyclohexyl)amino)-8-isopropyl-7-oxo-7,8-dihydropteridin-6-yl)-2,6-difluorophenyl)-3,3,3-trifluoropropane-1-sulfonamide (isomer 1, cyclohexane is (1S,3S,4S) or (1R,3R,4R)) (22.9 mg, 8.5% yield) as a light yellow solid. (rt=2.554 min, SFC CHIRALPAK AD-3 3*100 mm, 3 μm, co-solvent: EtOH (0.1% DEA), 2.0 ml/min).

N-(4-(2-((4-(Dimethylamino)-3-fluorocyclohexyl)amino)-8-isopropyl-7-oxo-7,8-dihydropteridin-6-yl)-2,6-difluorophenyl)-3,3,3-trifluoropropane-1-sulfonamide (isomer 2, cyclohexane is (1S,3S,4S) or (1R,3R,4R)). (20.6 mg, 7.7% yield) as a light yellow solid. (rt=2.863 min, SFC CHIRALPAK AD-3 3*100 mm, 3 μm, co-solvent: EtOH (0.1% DEA), 2.0 mL/min).

Example 169; N-(4-(2-(((1r,4r)-4-(Dimethylamino)cyclohexyl)amino)-8-isopropyl-7-oxo-7,8-dihydropteridin-6-yl)-3,5-difluorophenyl)-3,3,3-trifluoropropane-1-sulfonamide Compound 169

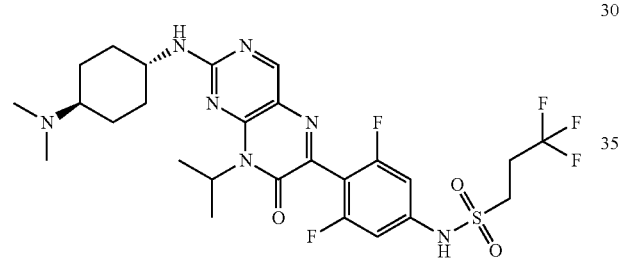

Step 1: tert-Butyl ((1r,4r)-4-((8-isopropyl-7-oxo-7,8-dihydropteridin-2-yl)amino)cyclohexyl)carbamate

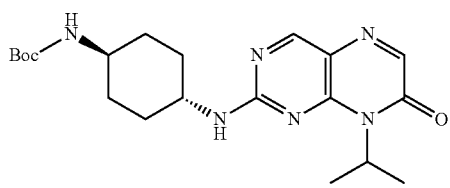 [SMILES: CC(C)n1c(=O)cnc2cnc(N[C@H]3CC[C@H](NC(=O)OC(C)(C)C)CC3)nc21]

A mixture of 2-chloro-8-isopropyl-pteridin-7-one (5.0 g, 22 mmol), tert-butyl ((1r,4r)-4-aminocyclohexyl)carbamate (5.8 g, 27 mmol), caesium fluoride (10.0 g, 66 mmol) and N,N-diisopropylethylamine (17.5 g, 136 mmol) in dimethyl sulfoxide (50 mL) was stirred at 100° C. for 2 h under nitrogen. The resulting solution was diluted with water. After filtration, the solids were collected. This resulted in the title compound (8.9 g, 99.4% yield) as a yellow solid. LCMS (ESI): [M+H]⁺=403.2.

Step 2: tert-Butyl ((1r,4r)-4-((6-bromo-8-isopropyl-7-oxo-7,8-dihydropteridin-2-yl)amino)cyclohexyl)carbamate

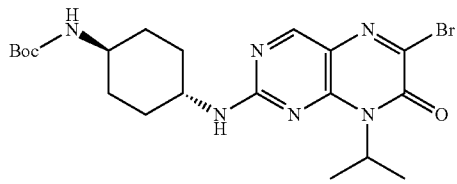 [SMILES: CC(C)n1c(=O)c(Br)nc2cnc(N[C@H]3CC[C@H](NC(=O)OC(C)(C)C)CC3)nc21]

To a mixture of tert-butyl ((1r,4r)-4-((8-isopropyl-7-oxo-7,8-dihydropteridin-2-yl)amino)cyclohexyl)carbamate (8.9 g, 22 mmol) in N,N-dimethylformamide (60 mL) was added 1-bromo-2,5-pyrrolidinedione (5.4 g, 30 mmol) at rt, the mixture was stirred for 2 h at rt. The resulting solution was diluted with water. After filtration, the solids were collected. This resulted in the title compound (10.6 g, 99.6% yield) as a yellow solid. LCMS (ESI): [M+H]⁺=481.1.

Step 2: tert-Butyl ((1r,4r)-4-((6-(4-amino-2,6-difluorophenyl)-8-isopropyl-7-oxo-7,8-dihydropteridin-2-yl)amino)cyclohexyl)carbamate

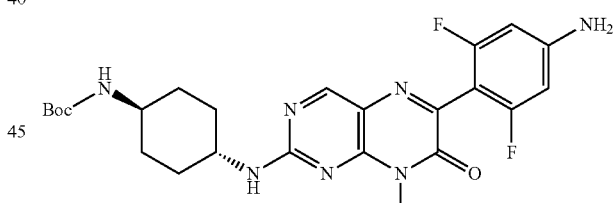

Under nitrogen, a mixture of tert-butyl ((1r,4r)-4-((6-bromo-8-isopropyl-7-oxo-7,8-dihydropteridin-2-yl)amino)cyclohexyl)carbamate (0.25 g, 0.52 mmol), 3,5-difluoro-4-(4,4,5,5-tetramethyl-1,3,2-dioxaborolan-2-yl)aniline (0.14 g, 0.55 mmol), [1,1'-bis(diphenylphosphino)ferrocene]dichloropalladium(II) (0.05 g, 0.07 mmol), sodium carbonate (0.17 g, 1.56 mmol) in 1,4-dioxane (2.5 mL) and water (0.5 mL) was stirred at 80° C. for 2 h. The reaction was quenched with water and extracted with ethyl acetate. The organic layers were combined and washed with brine, dried over anhydrous sodium sulfate and concentrated under vacuum. The residue was purified by silica flash chromatography eluting with ethyl acetate/petroleum ether (50%) to afford the title compound (0.20 g, 50.9% yield) as a yellow solid. LCMS (ESI) [M+H]⁺=530.3

Step 2: tert-Butyl ((1r,4r)-4-((6-(2,6-difluoro-4-((3,3,3-trifluoropropyl)sulfonamido)phenyl)-8-isopropyl-7-oxo-7,8-dihydropteridin-2-yl)amino)cyclohexyl)carbamate

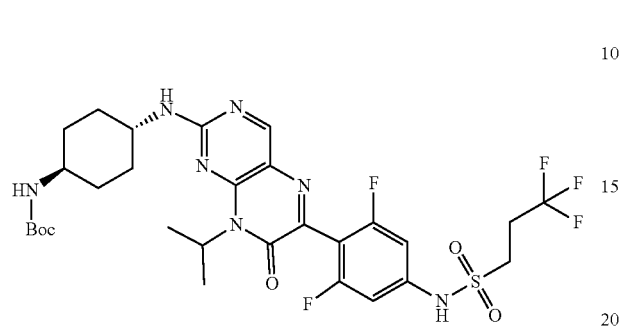

To a solution of tert-butyl ((1r,4r)-4-((6-(4-amino-2,6-difluorophenyl)-8-isopropyl-7-oxo-7,8-dihydropteridin-2-yl)amino)cyclohexyl)carbamate (280 mg, 0.48 mmol), N-methyl morphofine (300 mg, 3.0 mmol) in dichloromethane (5 mL) was added 3,3,3-trifluoropropane-1-sulfonylchloride (330 mg, 1.7 mmol) by dropwise and stirred at rt for 1 h. The organic layer was concentrated under vacuum. Then the residue was dissolved in tetrahydrofuran (3 ml). After sat. lithium hydroxide (2 mL) was added, the resulting solution was stirred at 25° C. for 1 h. The reaction was quenched with water and extracted with ethyl acetate. The organic layers were combined and washed with brine, dried over anhydrous sodium sulfate and concentrated under vacuum. The residue was purified by silica flash chromatography eluting with ethyl acetate/petroleum ether (60%) to afford the title compound (280 mg, 76.8% yield) as an yellow solid. LCMS (ESI): [M+H]$^+$=690.2

Step 3: N-(4-(2-(((1r,4r)-4-(Dimethylamino)cyclohexyl)amino)-8-isopropyl-7-oxo-7,8-dihydropteridin-6-yl)-3,5-difluorophenyl)-3,3,3-trifluoropropane-1-sulfonamide Compound 169

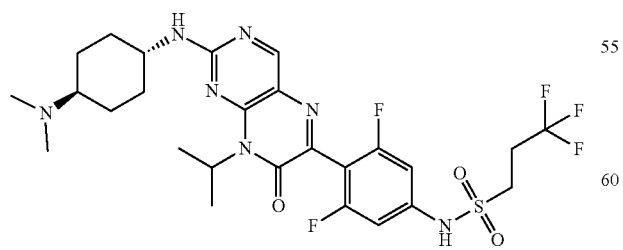

The title compound was prepared according to example 168. This provides the title compound (47.6 mg, 32.1% yield) as a yellow solid.

Example 170: 1-p-Tolyl-N-(2,3,6-trifluoro-4-(2-(((3S,5S)-5-fluoropiperidin-3-yl)amino)-8-isopropyl-7-oxo-7,8-dihydropteridin-6-yl)phenyl)methanesulfonamide hydrochloride Compound 170


The title compound was prepared according to example 64. This provides the title compound (32.8 mg, 35.4% yield) as a yellow solid and as HCl salt.

Example 171; 1-(4-Fluorophenyl)-N-(2,3,6-trifluoro-4-(2-(((3S,5S)-5-fluoropiperidin-3-yl)amino)-8-isopropyl-7-oxo-7,8-dihydropteridin-6-yl)phenyl)methanesulfonamide hydrochloride Compound 171

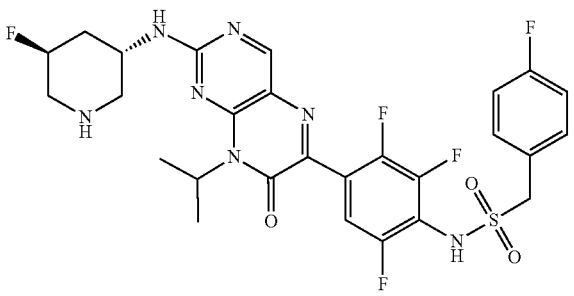 [SMILES: CC(C)n1c(=O)c(-c2cc(F)c(NS(=O)(=O)Cc3ccc(F)cc3)c(F)c2F)nc2cnc(N[C@@H]3CNC[C@@H](F)C3)nc21]

The title compound was prepared according to example 64. This provides the title compound (42.4 mg, 38.1% yield) as a yellow solid and as HCl salt.

Example 172; N-(4-(2-(((1r,4r)-4-(Dimethylamino)cyclohexyl)amino)-8-isopropyl-7-oxo-7,8-dihydropteridin-6-yl)-2,3,5-trifluorophenyl)-3,3,3-trifluoropropane-1-sulfonamide hydrochloride Compound 172

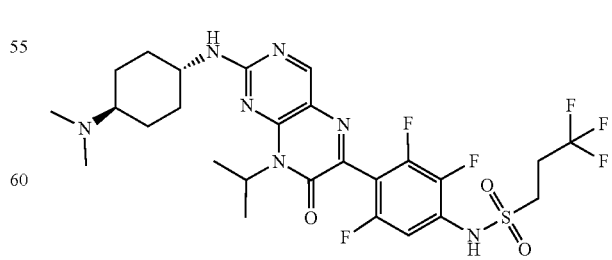

The title compound was prepared according to example 168. This provides the title compound (30.4 mg, 13.7% yield) as a yellow solid and as HCl salt.

Example 173: 2-Chloro-N-(5-(2-(((1r,4r)-4-(dimethylamino)cyclohexyl)amino)-8-isopropyl-7-oxo-7,8-dihydropteridin-6-yl)-6-methoxypyridin-2-yl)benzenesulfonamide Compound 173

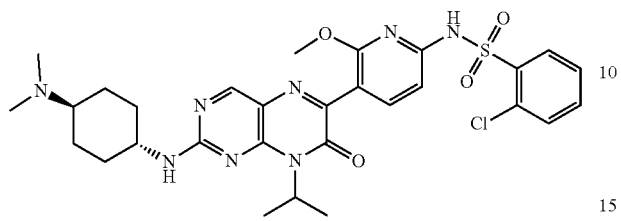

The title compound was prepared according to example 168. This provides the title compound (28.2 mg, 20.3% yield) as a yellow solid.

Example 174: N-(4-(2-(((1r,4r)-4-(Dimethylamino)cyclohexyl)amino)-8-isopropyl-7-oxo-7,8-dihydropteridin-6-yl)-2,5-difluorophenyl)-1-(4-fluorophenyl)methanesulfonamide hydrochloride Compound 174

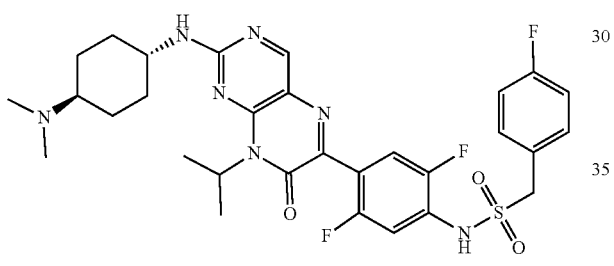

The title compound was prepared according to example 168. This provides the title compound (17 mg, 9.6% yield) as a yellow solid and as a HCl salt.

Example 175: N-(4-(2-(((1r,4r)-4-(Dimethylamino)cyclohexyl)amino)-8-isopropyl-7-oxo-7,8-dihydropteridin-6-yl)-2,3,6-trifluorophenyl)-1-(4-fluorophenyl)methanesulfonamide hydrochloride Compound 175

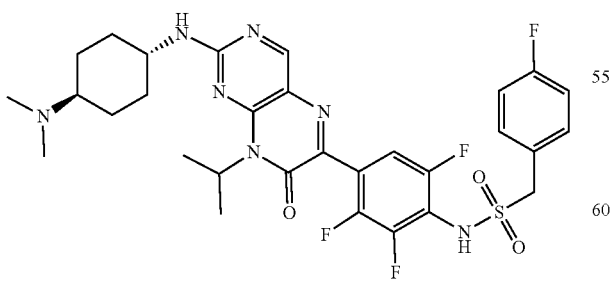

The title compound was prepared according to example 168. This provides the title compound (35 mg, 19.8% yield) as a light yellow solid and as a HCl salt.

Example 176: N-(2-Fluoro-4-(2-(((1r,4r)-4-((2-fluoroethyl)(methyl)amino)cyclohexyl)amino)-8-isopropyl-7-oxo-7,8-dihydropteridin-6-yl)phenyl)-1-(4-fluorophenyl)methanesulfonamide Compound 176

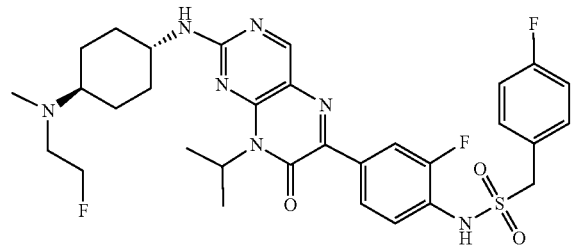 [SMILES: CC(C)n1c(=O)c(-c2ccc(NS(=O)(=O)Cc3ccc(F)cc3)c(F)c2)nc2cnc(N[C@H]3CC[C@H](N(C)CCF)CC3)nc21]

The title compound was prepared according to example 64. This provides the title compound (41.2 mg, 25% yield) as a yellow solid.

Example 177; 3,3,3-Trifluoro-N-(2-fluoro-4-(2-(((1r,4r)-4-((2-fluoroethyl)(methyl)amino)cyclohexyl)amino)-8-isopropyl-7-oxo-7,8-dihydropteridin-6-yl)phenyl)propane-1-sulfonamide Compound 177

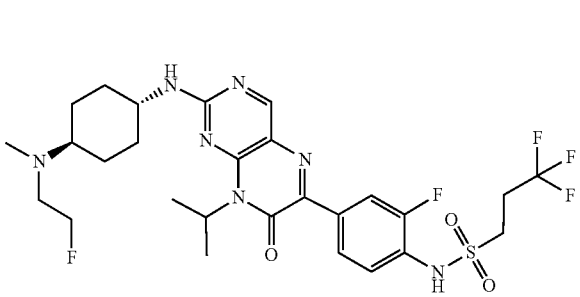 [SMILES: CC(C)n1c(=O)c(-c2ccc(NS(=O)(=O)CCC(F)(F)F)c(F)c2)nc2cnc(N[C@H]3CC[C@H](N(C)CCF)CC3)nc21]

The title compound was prepared according to example 64. This provides the title compound (32.2 mg, 22.8% yield) as a yellow solid.

Example 178; 2-Chloro-N-(5-(2-(((1r,4r)-4-(dimethylamino)cyclohexyl)amino)-8-isopropyl-7-oxo-7,8-dihydropteridin-6-yl)pyridin-2-yl)benzenesulfonamide Compound 178

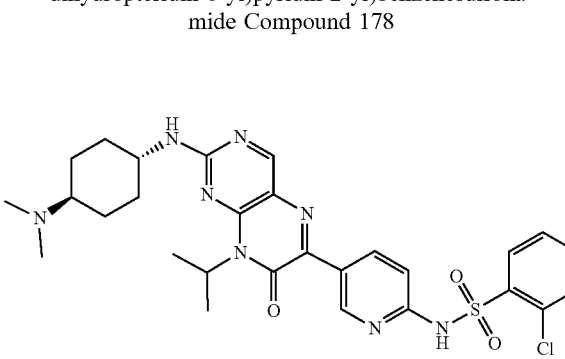

The title compound was prepared according to example 64. This provides the title compound (24.1 mg, 14.2% yield) as a yellow solid.

Example 179; N-(4-(2-((4-(Dimethylamino)-3-fluorocyclohexyl)amino)-8-isopropyl-7-oxo-7,8-dihydropteridin-6-yl)-2-fluorophenyl)-3,3,3-trifluoropropane-1-sulfonamide hydrochloride Compound 179 (Compound 179A Compound 179B)

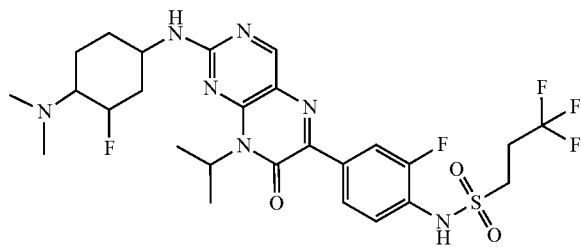 [SMILES: CC(C)n1c(=O)c(-c2ccc(NS(=O)(=O)CCC(F)(F)F)c(F)c2)nc2cnc(NC3CCC(N(C)C)C(F)C3)nc21]

The title compound was prepared according to example 168. The residue was purified by Prep-HPLC and Chiral HPLC to afford the title compound. After Chiral HPLC, two peaks were isolated out.

N-(4-(2-((4-(Dimethylamino)-3-fluorocyclohexyl)amino)-8-isopropyl-7-oxo-7,8-dihydropteridin-6-yl)-2-fluorophenyl)-3,3,3-trifluoropropane-1-sulfonamide (isomer 1, cyclohexane is (1S,3R,4S) or (1R,3S,4R)) (50.6 mg, 24.2% yield) as a yellow solid and as HCl salt. (rt=4.950 min, Reg AD 0.46*10 cm; 5 μm, Hex (0.1% DEA):EtOH=20%, 1.0 mL/min)

N-(4-(2-((4-(Dimethylamino)-3-fluorocyclohexyl)amino)-8-isopropyl-7-oxo-7,8-dihydropteridin-6-yl)-2-fluorophenyl)-3,3,3-trifluoropropane-1-sulfonamide (isomer 2, cyclohexane is (1S,3R,4S) or (1R,3S,4R)) (35.3 mg, 17.9% yield) as a yellow solid. (rt=6.224 min, Reg AD 0.46*10 cm; 5 μm, Hex (0.1% DEA):EtOH=20%, 1.0 mL/min)

Example 180; 1-(3,3-Difluorocyclobutyl)-N-(2-fluoro-4-(2-(((1r,4r)-4-((2-fluoroethyl)(methyl)amino)cyclohexyl)amino)-8-isopropyl-7-oxo-7,8-dihydropteridin-6-yl)phenyl)methanesulfonamide Compound 180

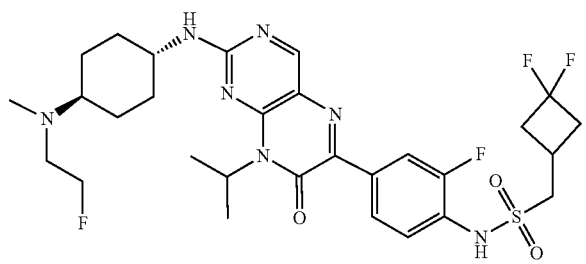 [SMILES: CC(C)n1c(=O)c(-c2ccc(NS(=O)(=O)CC3CC(F)(F)C3)c(F)c2)nc2cnc(N[C@H]3CC[C@H](N(C)CCF)CC3)nc21]

The title compound was prepared according to example 64. This provides the title compound (53.6 mg, 26.9% yield) as a yellow solid.

Example 181; N-(4-(2-((4-(Dimethylamino)-3-fluorocyclohexyl)amino)-8-isopropyl-7-oxo-7,8-dihydropteridin-6-yl)-2-fluorophenyl)-1-(4-fluorophenyl)methanesulfonamide Compound 181 (Compound 181A Compound 181B)

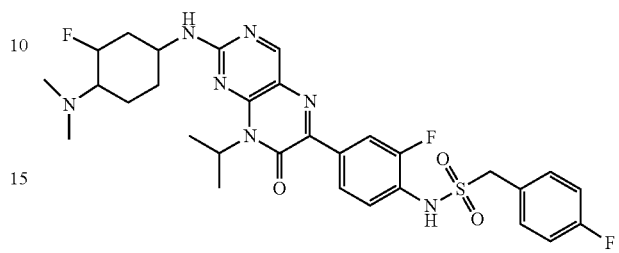

The title compound was prepared according to example 168. The residue was purified by Prep-HPLC and Chiral HPLC to afford the title compound. After Chiral HPLC, two peaks were isolated out.

N-(4-(2-((4-(Dimethylamino)-3-fluorocyclohexyl)amino)-8-isopropyl-7-oxo-7,8-dihydropteridin-6-yl)-2-fluorophenyl)-1-(4-fluorophenyl)methanesulfonamide (isomer 1, Cyclohexane is (1S,3R,4S) or (1R,3S,4R)) (19.8 mg, 9.4% yield) as a yellow solid. (rt=3.375 min, Reg AD, 4.6*50 mm 3 μm, Hex (0.1% DEA):EtOH=50:50, 1.0 mL/min).

N-(4-(2-((4-(Dimethylamino)-3-fluorocyclohexyl)amino)-8-isopropyl-7-oxo-7,8-dihydropteridin-6-yl)-2-fluorophenyl)-1-(4-fluorophenyl)methanesulfonamide (isomer 2, Cyclohexane is (1S,3R,4S) or (1R,3S,4R)) (17 mg, 8% yield) as a yellow solid. (rt=4.097 min, Reg AD, 4.6*50 mm 3 μm, Hex (0.1% DEA):EtOH=50:50, 1.0 mL/min).

Example 182: 2-(3,3-Difluoroazetidin-1-yl)-N-(4-(2-(((1r,4r)-4-(dimethylamino)cyclohexyl)amino)-8-isopropyl-7-oxo-7,8-dihydropteridin-6-yl)-2-fluorophenyl)ethane-1-sulfonamide Compound 182

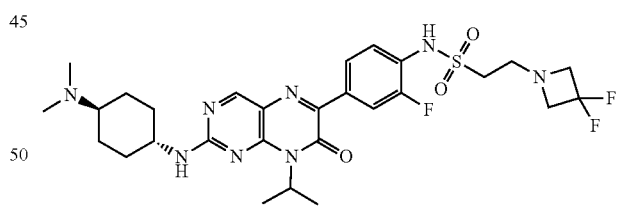

To a mixture of 6-(4-amino-3-fluoro-phenyl)-2-((4-(dimethylamino)cyclohexyl)amino)-8-isopropyl-pteridin-7-one (100 mg, 0.23 mmol) in dichloromethane (0.5 mL) was added N-methylmorpholine (0.25 mL, 2.3 mmol) and 2-chloroethanesulfonyl chloride (185 mg, 1.13 mmol), the mixture was stirred for 2 h at rt. Then 3,3-difluoroazetidine (110 mg, 1.18 mmol) was added into the mixture, stirred for 1 h at room temperature. The resulting solution was diluted with water, extracted with dichloromethane and concentrated under vacuum. The resulting mixture was dissolved in tetrahydrofuran (2 mL), and then sat. lithium hydroxide solution (2 mL) was added and stirred for 0.5 h at rt. The resulting solution was diluted with water, extracted with dichloromethane and concentrated under vacuum. The crude product was purified by Prep-HPLC to afford the title compound (41.3 mg, 28.6% yield) as a yellow solid.

Example 183; N-(2-fluoro-4-(2-(((1r,4r)-4-((2-fluoroethyl)(methyl)amino)cyclohexyl)amino)-8-isopropyl-7-oxo-7,8-dihydropteridin-6-yl)phenyl)-1-phenylmethanesulfonamide Compound 183

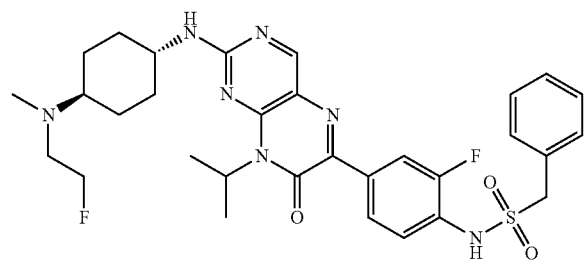 [SMILES: CC(C)n1c(=O)c(-c2ccc(NS(=O)(=O)Cc3ccccc3)c(F)c2)nc2cnc(N[C@H]3CC[C@H](N(C)CCF)CC3)nc21]

The title compound was prepared according to example 64. This provides the title compound (34.3 mg, 18.3% yield) as a yellow solid.

Example 184; N-(4-(2-(((1r,4r)-4-(dimethylamino)cyclohexyl)amino)-8-isopropyl-7-oxo-7,8-dihydropteridin-6-yl)-2-fluorophenyl)-1-(4-fluorophenyl)methanesulfonamide Compound 184

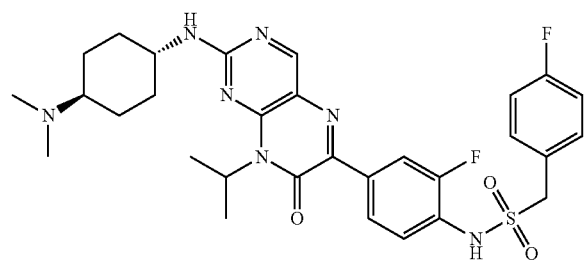 [SMILES: CC(C)n1c(=O)c(-c2ccc(NS(=O)(=O)Cc3ccc(F)cc3)c(F)c2)nc2cnc(N[C@H]3CC[C@H](N(C)C)CC3)nc21]

The title compound was prepared according to example 66. This provides the title compound (34.3 mg, 30.1% yield) as a yellow solid.

Example 185: 1-Phenyl-N-(2,3,6-trifluoro-4-(2-(((3S,5S)-5-fluoropiperidin-3-yl)amino)-8-isopropyl-7-oxo-7,8-dihydropteridin-6-yl)phenyl)methanesulfonamide Compound 185

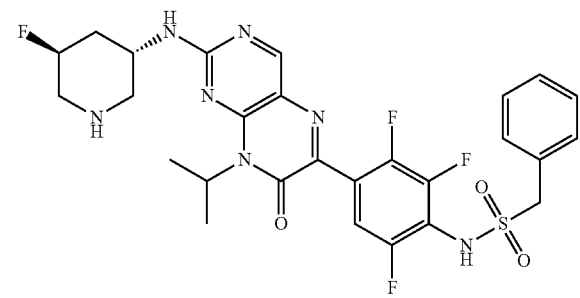 [SMILES: CC(C)n1c(=O)c(-c2cc(F)c(NS(=O)(=O)Cc3ccccc3)c(F)c2F)nc2cnc(N[C@@H]3CNC[C@@H](F)C3)nc21]

The title compound was prepared according to example 64. This provides the title compound (44 mg, 46.6% yield) as a yellow solid.

Example 186: N-(5-(2-(((1r,4r)-4-(Dimethylamino)cyclohexyl)amino)-8-isopropyl-7-oxo-7,8-dihydropteridin-6-yl)-4-methylpyridin-2-yl)-3,3,3-trifluoropropane-1-sulfonamide Compound 186

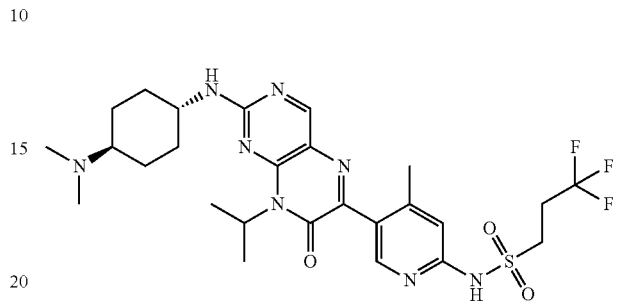

The title compound was prepared according to example 168. The residue was purified by Prep-HPLC. This provides the title compound (41 mg, 24.4% yield) as a yellow solid.

Example 187: 3,3,3-Trifluoro-N-(5-(2-(((1r,4r)-4-((2-fluoroethyl)(methyl)amino)cyclohexyl)amino)-8-isopropyl-7-oxo-7,8-dihydropteridin-6-yl)pyridin-2-yl)propane-1-sulfonamide Compound 187

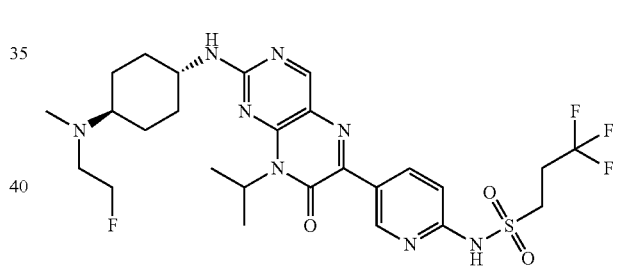

The title compound was prepared according to example 64. This provides the title compound (26.4 mg, 14.5% yield) as a yellow solid.

Example 188: 2-Chloro-N-(5-(2-(((1r,4r)-4-((2-fluoroethyl)(methyl)amino)cyclohexyl)amino)-8-isopropyl-7-oxo-7,8-dihydropteridin-6-yl)pyridin-2-yl)benzenesulfonamide hydrochloride Compound 188

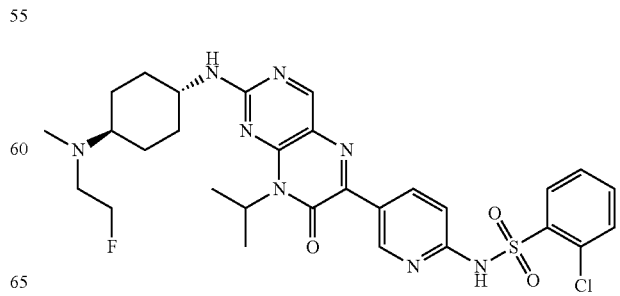

The title compound was prepared according to example 64. This provides the title compound (17.2 mg, 11.2% yield) as a yellow solid and as a HCl salt.

Example 189: N-(4-(2-(((1r,4r)-4-(dimethylamino)cyclohexyl)amino)-8-isopropyl-7-oxo-7,8-dihydropteridin-6-yl)-2,5-difluorophenyl)-3,3,3-trifluoropropane-1-sulfonamide Compound 189

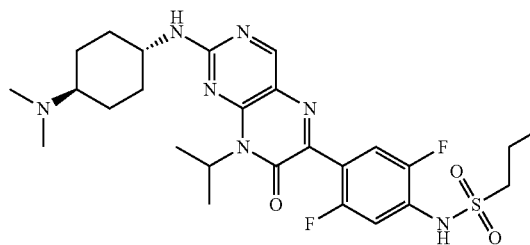

The title compound was prepared according to example 168. The residue was purified by Prep-HPLC. This provides the title compound (38.8 mg, 22.5% yield) as a yellow solid.

Example 190: 2-Cyano-N-(4-(2-(((1r,4r)-4-(dimethylamino)cyclohexyl)amino)-8-isopropyl-7-oxo-7,8-dihydropteridin-6-yl)-2-fluorophenyl)benzenesulfonamide Compound 190

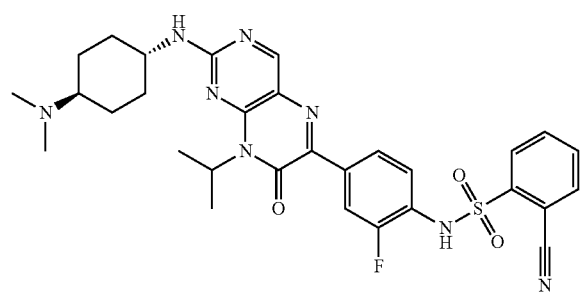 [SMILES: CC(C)n1c(=O)c(-c2ccc(NS(=O)(=O)c3ccccc3C#N)c(F)c2)nc2cnc(N[C@H]3CC[C@H](N(C)C)CC3)nc21]

The title compound was prepared according to example 64. This provides the title compound (56 mg, 33.5% yield) as a yellow solid.

Example 191: N-(4-(2-(((1r,4r)-4-(Dimethylamino)cyclohexyl)amino)-8-isopropyl-7-oxo-7,8-dihydropteridin-6-yl)-2-fluorophenyl)pyridine-3-sulfonamide hydrochloride Compound 191

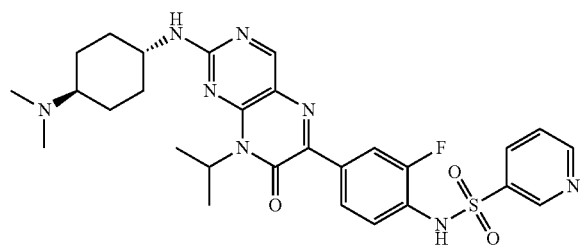 [SMILES: CC(C)n1c(=O)c(-c2ccc(NS(=O)(=O)c3cccnc3)c(F)c2)nc2cnc(N[C@H]3CC[C@H](N(C)C)CC3)nc21]

The title compound was prepared according to example 64. This provides the title compound (14.5 mg, 13.3% yield) as a yellow solid and as a HCl salt.

Example 192: N-(4-(2-((4-(Dimethylamino)-3-fluorocyclohexyl)amino)-8-isopropyl-7-oxo-7,8-dihydropteridin-6-yl)-2-fluorophenyl)-1-phenylmethanesulfonamide Compound 192 (Compound 192A Compound 192B)


The title compound was prepared according to example 168. The residue was purified by Prep-HPLC and Chiral HPLC to afford the title compound. After Chiral HPLC, two peaks were isolated out.

N-(4-(2-((4-(Dimethylamino)-3-fluorocyclohexyl)amino)-8-isopropyl-7-oxo-7,8-dihydropteridin-6-yl)-2-fluorophenyl)-1-phenylmethanesulfonamide (isomer 1, cyclohexane is (1S,3R,4S) or (1R,3S,4R)) (40.4 mg, 16.4% yield) as a yellow solid. (rt=3.676 min. Reg AD 0.46*10 cm; 5 μm, Hex (0.1% DEA):EtOH=50:50, 1 mL/min).

N-(4-(2-((4-(Dimethylamino)-3-fluorocyclohexyl)amino)-8-isopropyl-7-oxo-7,8-dihydropteridin-6-yl)-2-fluorophenyl)-1-phenylmethanesulfonamide (isomer 2, Cyclohexane is (1S,3R,4S) or (1R,3S,4R)) (38.9 mg, 15.8% yield) as a yellow solid. (rt=4.625 min. Reg AD 0.46*10 cm; 5 μm, Hex (0.1% DEA):EtOH=50:50, 1 mL/min).

Example 193: 1-(3,3-Difluorocyclobutyl)-N-(4-(2-((4-(dimethylamino)-3-fluorocyclohexyl)amino)-8-isopropyl-7-oxo-7,8-dihydropteridin-6-yl)-2-fluorophenyl)methanesulfonamide Compound 193 (Compound 193A Compound 193B)

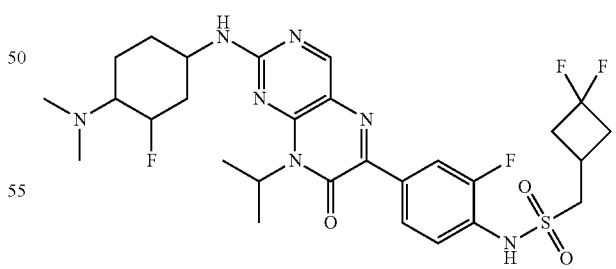

The title compound was prepared according to example 168. The residue was purified by Prep-HPLC and Chiral HPLC to afford the title compounds. After Chiral HPLC, two peaks were isolated out:

1-(3,3-Difluorocyclobutyl)-N-(4-(2-((4-(dimethylamino)-3-fluorocyclohexyl)amino)-8-isopropyl-7-oxo-7,8-dihydropteridin-6-yl)-2-fluorophenyl)methanesulfonamide (isomer 1, cyclohexane is (1S,3R,4S) or (1R,3S,4R)) (39.3 mg, 17.6% yield) as a yellow solid. (rt=6.253 min. Reg AD 0.46*10 cm; 5 µm, Hex (0.1% DEA):EtOH=70:30, 1 mL/min).

1-(3,3-Difluorocyclobutyl)-N-(4-(2-((4-(dimethyl-amino)-3-fluorocyclohexyl)amino)-8-isopropyl-7-oxo-7,8-dihydropteridin-6-yl)-2-fluorophenyl)methanesulfonamide (isomer 2, cyclohexane is (1S,3R,4S) or (1R,3S,4R)) (34.2 mg, 15.3% yield) as a yellow solid. (rt=7.833 min. Reg AD 0.46*10 cm; 5 µm, Hex (0.1% DEA):EtOH=70:30, 1 mL/min).

Example 194: 2-Cyano-N-(5-(2-(((1r,4r)-4-((2-fluoroethyl)(methyl)amino)cyclohexyl)amino)-8-isopropyl-7-oxo-7,8-dihydropteridin-6-yl)-6-methylpyridin-2-yl)benzenesulfonamide Compound 194

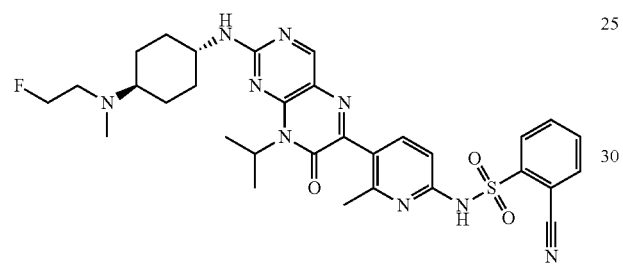

The title compound was prepared according to example 64. This provides the title compound (44.5 mg, 30.2% yield) as a yellow solid.

Example 195: 2-Chloro-N-(5-(2-(((1r,4r)-4-((2-fluoroethyl)(methyl)amino)cyclohexyl)amino)-8-isopropyl-7-oxo-7,8-dihydropteridin-6-yl)-6-methylpyridin-2-yl)benzenesulfonamide Compound 195

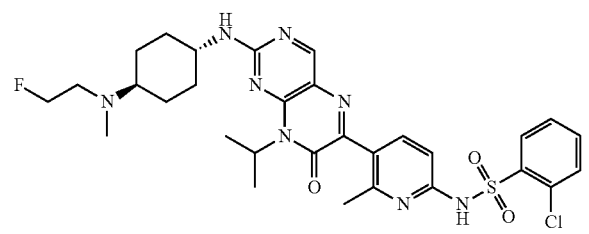 [SMILES: Cc1nc(NS(=O)(=O)c2ccccc2Cl)ccc1-c1nc2cnc(N[C@H]3CC[C@H](N(C)CCF)CC3)nc2n(C(C)C)c1=O]

The title compound was prepared according to example 64. This provides the title compound (49.1 mg, 27.9% yield) as a yellow solid.

Example 196: 2-Chloro-N-(5-(2-((4-(dimethyl-amino)-3-fluorocyclohexyl)amino)-8-isopropyl-7-oxo-7,8-dihydropteridin-6-yl)pyridin-2-yl)benzene-sulfonamide hydrochloride Compound 196 Compound 196A Compound 196B

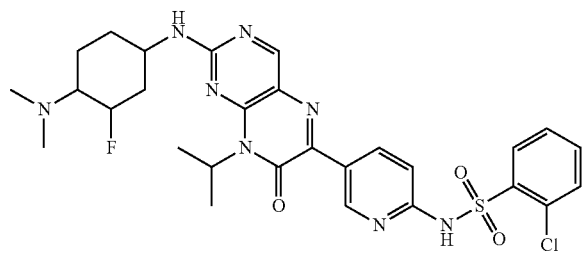 [SMILES: CC(C)n1c(=O)c(-c2ccc(NS(=O)(=O)c3ccccc3Cl)nc2)nc2cnc(NC3CCC(N(C)C)C(F)C3)nc21]

The title compound was prepared according to example 168. The residue was purified by Prep-HPLC. This provides the title compound (45.3 mg, 24.0% yield) as a yellow solid and as a HCl salt. (Cyclohexane is racemate of (1S,3R,4S) and (1R,3S,4R)).

Example 197: N-(4-(2-(((1,4-trans)-4-(Dimethyl-amino)cyclohexyl)amino)-8-isopropyl-7-oxo-7,8-dihydropyrido[2,3-d]pyrimidin-6-yl)-2,3-difluoro-phenyl)-3,3,3-trifluoropropane-1-sulfonamide Compound 197

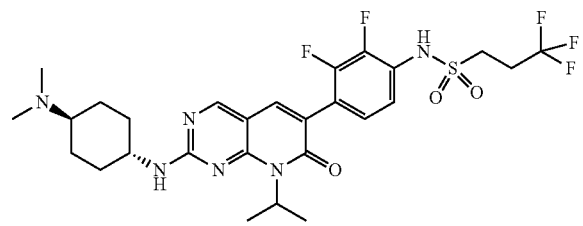 [SMILES: CC(C)n1c(=O)c(-c2ccc(NS(=O)(=O)CCC(F)(F)F)c(F)c2F)cc2cnc(N[C@H]3CC[C@H](N(C)C)CC3)nc21]

Step 1: tert-butyl ((1,4-trans)-4-((6-(4-amino-2,3-difluorophenyl)-8-isopropyl-7-oxo-7,8-dihydro-pyrido[2,3-d]pyrimidin-2-yl)amino)cyclohexyl)carbamate

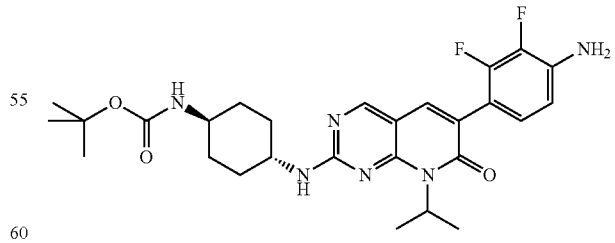

A mixture of tert-butyl ((1,4-trans)-4-((6-bromo-8-isopropyl-7-oxo-7,8-dihydropyrido[2,3-d]pyrimidin-2-yl)amino) cyclohexyl)carbamate (60 mg, 0.15 mmol), 2,3-difluoro-4-(4,4,5,5-tetramethyl-1,3,2-dioxaborolan-2-yl)aniline (75 mg, 0.29 mmol) and sodium carbonate (47 mg, 0.44 mmol), in a mixture of 1,4-dioxane (3.0 mL) and water (0.64 mL), was degased 10 minutes before the addition of 1,1-bis(diphenylphosphino)ferrocene-palladium dichloride (11 mg, 0.015 mmol). The reaction was stirred 2 h at 90° C. The reaction mixture was then filtered through celite and rinsed with EtOAc and MeOH. The filtrate was concentrated under reduced pressure and the crude material was purified by C18 reverse phase flash chromatography (20-80% MeCN/10 mM aqueous ammonium formate, pH=3.8 to provide 16 mg (24% yield) of the title compound. LCMS (ESI) [M+H]$^+$=457.3.

Step 2: N-(4-(2-(((1,4-trans)-4-(Dimethylamino)cyclohexyl)amino)-8-isopropyl-7-oxo-7,8-dihydro-pyrido[2,3-d]pyrimidin-6-yl)-2,3-difluorophenyl)-3,3,3-trifluoropropane-1-sulfonamide

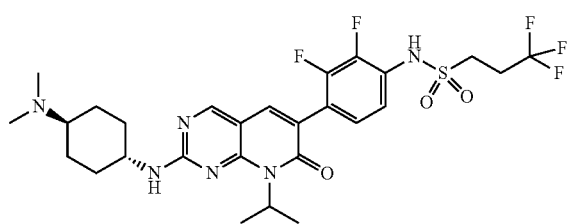 [SMILES: CC(C)n1c(=O)c(-c2ccc(NS(=O)(=O)CCC(F)(F)F)c(F)c2F)cc2cnc(N[C@H]3CC[C@H](N(C)C)CC3)nc21]

To a mixture of tert-butyl ((1,4-trans)-4-((6-(4-amino-2,3-difluorophenyl)-8-isopropyl-7-oxo-7,8-dihydropyrido[2,3-d]pyrimidin-2-yl)amino)cyclohexyl)carbamate (18 mg, 0.04 mmol) and 3,3,3-trifluoropropane-1-sulfonyl chloride (6.4 µL, 0.05 mmol), in CH$_2$Cl$_2$ (0.2 mL) was added pyridine (63 µL, 0.78 mmol). The reaction was stirred 6 h at rt to provide a mixture of mono and bis-sulfonamide species. Pyridine was evaporated in vacuo. The residue obtained was dissolved in THF (0.3 mL) and treated with 1M tetrabutylammonium fluoride in THF (25 µL, 0.03 mmol) and the mixture stirred at rt until complete conversion of the bis-sulfonamide to desired mono-sulfonamide was observed. THF was evaporated under reduced pressure and purified by C18 reverse phase flash chromatography (20-70% MeCN/10 mM aqueous ammonium bicarbonate, pH=10) to provide 8 mg (33% yield) of the title compound.

Example 198: N-(4-(2-(((1,4-trans)-4-(Azetidin-1-yl)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide formate Compound 198

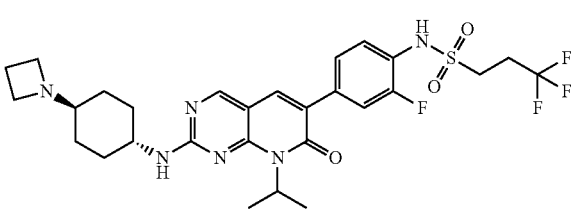 [SMILES: CC(C)n1c(=O)c(-c2ccc(NS(=O)(=O)CCC(F)(F)F)c(F)c2)cc2cnc(N[C@H]3CC[C@H](N4CCC4)CC3)nc21]

Step 1: 6-(4-Amino-3-fluorophenyl)-8-isopropyl-2-(methylthio)pyrido[2,3-d]pyrimidin-7(8H)-one

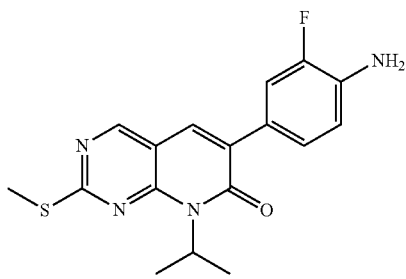 [SMILES: CSc1ncc2cc(-c3ccc(N)c(F)c3)c(=O)n(C(C)C)c2n1]

To 6-bromo-8-isopropyl-2-methylsulfanyl-pyrido[2,3-d]pyrimidin-7-one (777 mg, 2.47 mmol), 2-fluoro-4-(4,4,5,5-tetramethyl-1,3,2-dioxaborolan-2-yl)aniline (0.65 g, 2.74 mmol) and sodium carbonate (786.3 mg, 7.42 mmol) were added N$_2$ degassed 1,4-dioxane (40 mL) and N$_2$ degassed water (9 mL). To the solution was added 1,1-bis(diphenylphosphino)ferrocene-palladium dichloride (183 mg, 0.25 mmol). The flask was purged with nitrogen for 5 min and the reaction was stirred at 90° C. for 3 h. The reaction was cooled down to rt and filtered through celite and concentrated under reduced pressure. The residue was dissolved in a mixture of CH$_2$Cl$_2$ and EtOAc and concentrated under reduced pressure. The residue was dissolved again in CH$_2$Cl$_2$ and silica gel and concentrated under reduced pressure to adsorb onto silica gel. The dry-loaded crude material was purified by flash chromatography through silica gel (10-100% EtOAc/heptanes) to provide the title product (639 mg, 78.9% yield).

Step 2: 3,3,3-Trifluoro-N-(2-fluoro-4-(8-isopropyl-2-(methylthio)-7-oxo-7,8-dihydropyrido[2,3-d]pyrimidin-6-yl)phenyl)propane-1-sulfonamide

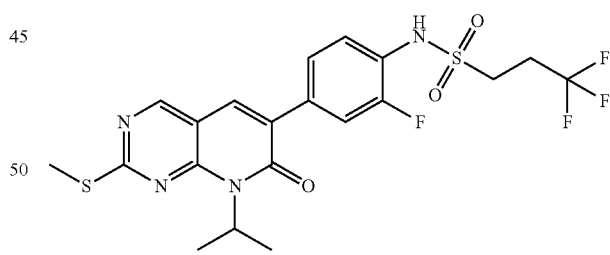

6-(4-Amino-3-fluoro-phenyl)-8-isopropyl-2-methylsulfanyl-pyrido[2,3-d]pyrimidin-7-one (639 mg, 1.86 mmol) was dissolved in CH$_2$Cl$_2$ (9.3 mL) and to the solution were added pyridine (2.3 mL) and 3,3,3-trifluoropropane-1-sulfonyl chloride (0.28 mL, 2.23 mmol). The reaction was stirred at for 4 h then MeOH was added and concentration to dryness. The residue was dissolved in CH$_2$Cl$_2$ and washed with 1M KHSO$_4$ aqueous solution, dried by passing through a phase cartridge separator and concentrated to provide the title compound (759 mg, 81% yield). LCMS (ESI) [M+H]$^+$=505.1.

421

Step 3: 3,3,3-Trifluoro-N-(2-fluoro-4-(8-isopropyl-2-(methylsulfonyl)-7-oxo-7,8-dihydropyrido[2,3-d]pyrimidin-6-yl)phenyl)propane-1-sulfonamide

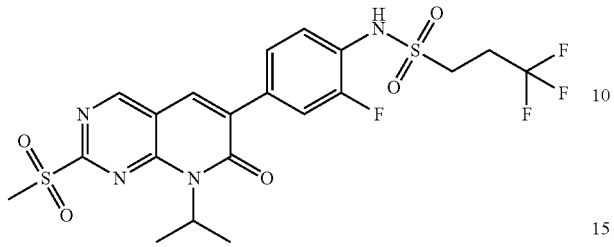

3,3,3-Trifluoro-N-[2-fluoro-4-(8-isopropyl-2-methylsulfanyl-7-oxo-pyrido[2,3-d]pyrimidin-6-yl)phenyl]propane-1-sulfonamide (759 mg, 1.5 mmol) was dissolved in CH₂Cl₂ (8.6 mL) and to the solution was added 3-chloroperbenzoic acid (779 mg, 4.51 mmol). The mixture was stirred at rt for 2 h and then diluted with CH₂Cl₂ and saturated aqueous NaHCO₃ (30 mL). The organic layer was separated and washed 3 times with saturated aqueous NaHCO₃ (3×50 mL), dried over anydrous Na₂SO₄, filtered and concentrated. The crude material was purified by silica flash chromatography (10-100% EtOAc/heptanes) to provide the title product (707 mg, 87% yield. LCMS (ESI) [M+H]+=537.0.

Step 4: tert-Butyl ((1,4-trans)-4-(azetidin-1-yl)cyclohexyl)carbamate

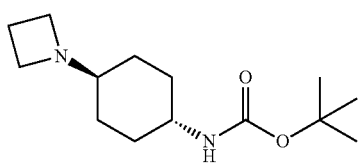 [SMILES: CC(C)(C)OC(=O)N[C@H]1CC[C@H](N2CCC2)CC1]

To a suspension of N-Boc-trans-1,4-cyclohexanediamine (250 mg, 1.17 mmol) in MeCN (2 mL) was added triethylamine (0.49 mL, 3.5 mmol) followed by 1,3-dibromopropane (0.14 mL, 1.4 mmol). The reaction vessel was sealed and the mixture was placed in a 80° C. oil bath for 18 h. MeCN was then removed under reduced pressure and the crude material was partitioned between EtOAc (40 mL) and saturated aqueous NaHCO₃ (10 mL) and the phases were separated. The organic phase was washed with H₂O (10 mL), then with saturated aqueous NaCl (5 mL), dried over anhydrous Na₂SO₄, filtered and concentrated under reduced pressure to provide the title compound (125 mg, 42% yield) which was used in the next step without further purification. LCMS (ESI) [M+H]⁺=255.3. ¹H NMR (400 MHz, CDCl₃) δ 4.54-4.26 (m, 1H), 3.45-3.19 (m, 1H), 3.12 (t, J=6.9 Hz, 2H), 2.52-2.28 (m, 1H), 2.06-1.90 (m, 4H), 1.90-1.80 (m, 1H), 1.80-1.65 (m, 2H), 1.40 (s, 9H), 1.27-1.18 (m, 1H), 1.17-0.96 (m, 4H).

422

Step 5: (1,4-trans)-4-(Azetidin-1-yl)cyclohexanamine dihydrochloride

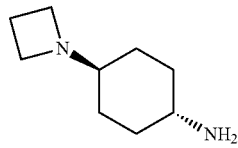 [SMILES: N[C@H]1CC[C@H](N2CCC2)CC1]

tert-Butyl N-[4-(azetidin-1-yl)cyclohexyl]carbamate (125 mg, 0.49 mmol) was dissolved in EtOAc (2 mL) and to this was then added 4 N HCl in dioxanes (2 mL) and the mixture stirred at rt for 18 h. Volatiles were removed under reduced pressure to provide the crude title compound (120 mg, 107% yield) which was used directly in the next step. LCMS (ESI) [M+H]⁺=155.4.

Step 6: N-(4-(2-(((1,4-trans)-4-(Azetidin-1-yl)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide formate

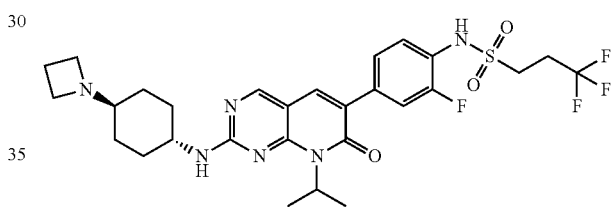

To 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (80 mg, 0.15 mmol) in isopropanol (1.5 mL) was added 4-(azetidin-1-yl)cyclohexanamine dihydrochloride (47 mg, 0.21 mmol) and N,N-diisopropylethylamine (130 µL, 0.75 mmol). The reaction was stirred at 50° C. for 72 h. The mixture was cooled down to rt and concentrated to dryness under reduced pressure. The crude material obtained was purified by C18 reverse phase chromatography (20-80% MeCN/10 mM aqueous ammonium formate, pH=3.8) to provide the title product (30 mg, 31% yield).

Example 199: 3,3,3-Trifluoro-N-(2-fluoro-4-(8-isopropyl-7-oxo-2-(((1,4-trans)-4-(pyrrolidin-1-yl)cyclohexyl)amino)-7,8-dihydropyrido[2,3-d]pyrimidin-6-yl)phenyl)propane-1-sulfonamide Compound 199

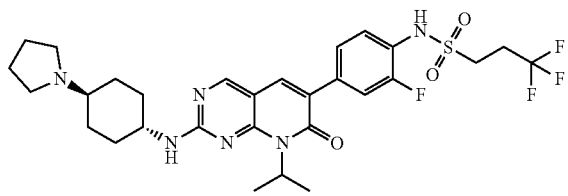 [SMILES: CC(C)n1c(=O)c(-c2ccc(NS(=O)(=O)CCC(F)(F)F)c(F)c2)cc2cnc(N[C@H]3CC[C@H](N4CCCC4)CC3)nc21]

Step 1: tert-Butyl ((1,4-trans)-4-(Pyrrolidin-1-yl)cyclohexyl)carbamate

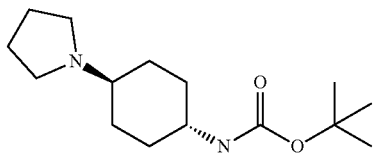

Prepared according to Example 198 step 4 using N-Boc-trans-1,4-cyclohexanediamine (250 mg, 1.17 mmol), triethylamine (0.49 mL, 3.5 mmol) and 1,4 dibromobutane (0.17 mL, 1.4 mmol) to provide the title product (122 mg, 39% yield). LCMS (ESI) [M+H]$^+$=269.3. $^1$H NMR (400 MHz, CDCl$_3$) δ 4.46-4.31 (m, 1H), 3.47-3.30 (m, 1H), 2.61-2.48 (m, 4H), 2.06-1.95 (m, 4H), 1.91 (t, J=11.1 Hz, 1H), 1.80-1.69 (m, 4H), 1.41 (s, 9H), 1.39-1.25 (m, 2H), 1.18-1.00 (m, 2H).

Step 2: (1,4-trans)-4-(Pyrrolidin-1-yl)cyclohexanamine dihydrochloride

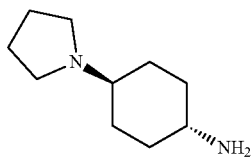 [SMILES: N[C@H]1CC[C@H](N2CCCC2)CC1]

Prepared according to Example 198 step 5 using tert-butyl N-(4-pyrrolidin-1-ylcyclohexyl)carbamate (122 mg, 0.45 mmol), 4 N HCl in dioxane (2 mL) and EtOAc (2 mL) to provide the title product (120 mg, 109% yield). LCMS (ESI) [M+H]$^+$=169.4.

Step 3: 3,3,3-Trifluoro-N-(2-fluoro-4-(8-isopropyl-7-oxo-2-(((1,4-trans)-4-(pyrrolidin-1-yl)cyclohexyl)amino)-7,8-dihydropyrido[2,3-d]pyrimidin-6-yl)phenyl)propane-1-sulfonamide

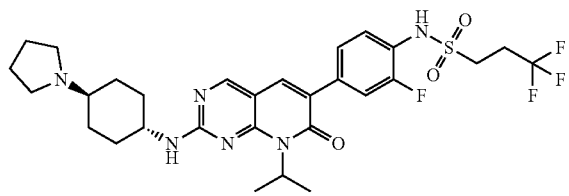 [SMILES: CC(C)n1c(=O)c(-c2ccc(NS(=O)(=O)CCC(F)(F)F)c(F)c2)cc2cnc(N[C@H]3CC[C@H](N4CCCC4)CC3)nc21]

Prepared according to Example 198 step 6 using 4-pyrrolidin-1-ylcyclohexanamine dihydrochloride (50 mg, 0.21 mmol), 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (80 mg, 0.15 mmol) and N,N-diisopropylethylamine (130 μL, 0.75 mmol) to provide the title product (30 mg, 32% yield).

Example 200: 3,3,3-Trifluoro-N-(2-fluoro-4-(8-isopropyl-2-((1-methylpiperidin-4-yl)amino)-7-oxo-7,8-dihydropyrido[2,3-d]pyrimidin-6-yl)phenyl)propane-1-sulfonamide formate Compound 200

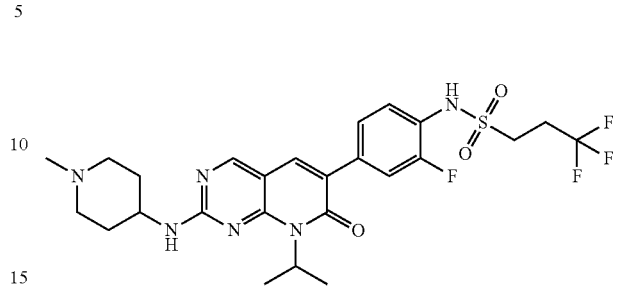

Prepared according to Example 198 step 6 using 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (60 mg, 0.11 mmol), 1-methylpiperidin-4-amine (20 mg, 0.18 mmol) and N,N-diisopropylethylamine (97 uL, 0.56 mmol) to provide the title product (36 mg, 53% yield).

Example 201: 3,3,3-Trifluoro-N-(2-fluoro-4-(8-isopropyl-7-oxo-2-(piperidin-4-ylamino)-7,8-dihydropyrido[2,3-d]pyrimidin-6-yl)phenyl)propane-1-sulfonamide Compound 201

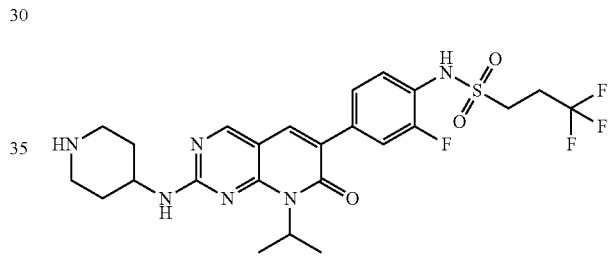

Step 1: tert-Butyl 4-((6-(3-fluoro-4-(3,3,3-trifluoropropylsulfonamido)phenyl)-8-isopropyl-7-oxo-7,8-dihydropyrido[2,3-d]pyrimidin-2-yl)amino)piperidine-1-carboxylate

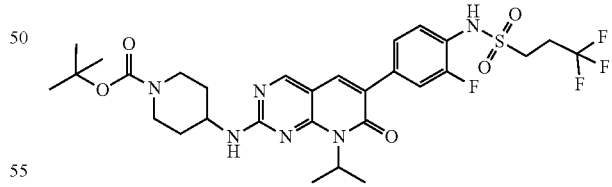

To 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (60 mg, 0.11 mmol) in IPA (1.1 mL) was added 1-boc-4-aminopiperidine (36 mg, 0.18 mmol) and N,N-diisopropylethylamine (97 μL, 0.56 mmol). The mixture was stirred at 50° C. for 72 h then cooled to rt and concentrated to dryness. The crude material was purified by flash chromatography through silica gel (0-100% EtOAc/CH$_2$Cl$_2$) to provide the title product (36 mg, 49% yield). LCMS (ESI) [M+H]$^+$=657.2

Step 2: 3,3,3-Trifluoro-N-(2-fluoro-4-(8-isopropyl-7-oxo-2-(piperidin-4-ylamino)-7,8-dihydropyrido[2,3-d]pyrimidin-6-yl)phenyl)propane-1-sulfonamide

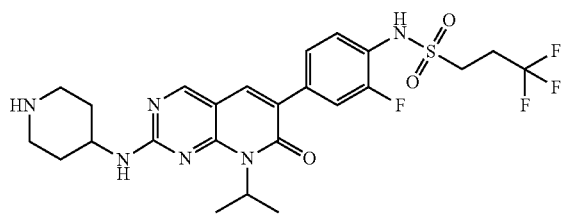 [SMILES: CC(C)n1c(=O)c(-c2ccc(NS(=O)(=O)CCC(F)(F)F)c(F)c2)cc2cnc(NC3CCNCC3)nc21]

To tert-butyl 4-[[6-[3-fluoro-4-(3,3,3-trifluoropropylsulfonylamino)phenyl]-8-isopropyl-7-oxo-pyrido[2,3-d]pyrimidin-2-yl]amino]piperidine-1-carboxylate (36 mg, 0.05 mmol) in CH$_2$Cl$_2$ (0.55 mL) was added 4N HCl in dioxane (0.6 mL, 2.4 mmol). The reaction was stirred at rt for 1 h then concentrated to dryness. The solid was partitioned between 20% iPrOH/CHCl$_3$ and saturated aqueous sodium bicarbonate. The phases were separated and the organic extract was dried over Na$_2$SO$_4$, filtered and concentrated under reduced pressure. The material thus obtained was dissolved in a mixture of water and MeCN and lyophilized to provide the title compound (23 mg, 75% yield).

Example 202: N-(4-(8-(sec-butyl)-2-(((3S,5S)-5-fluoropiperidin-3-yl)amino)-7-oxo-7,8-dihydropyrido[2,3-d]pyrimidin-6-yl)-2-fluorophenyl)-1-(2-fluorophenyl)methanesulfonamide hydrochloride
Compound 202 Compound 202A Compound 202B

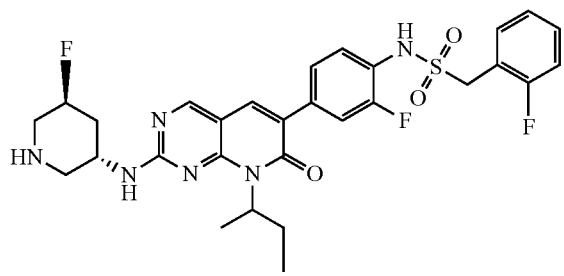 [SMILES: CCC(C)n1c(=O)c(-c2ccc(NS(=O)(=O)Cc3ccccc3F)c(F)c2)cc2cnc(N[C@@H]3CNC[C@@H](F)C3)nc21]

Step 1: rac-6-Bromo-8-(sec-butyl)-2-(methylthio)pyrido[2,3-d]pyrimidin-7(8H)-one

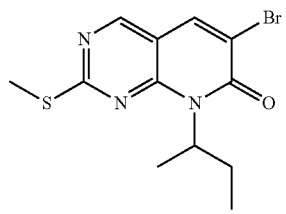 [SMILES: CCC(C)n1c(=O)c(Br)cc2cnc(SC)nc21]

To a suspension of 6-bromo-2-methylsulfanyl-8H-pyrido[2,3-d]pyrimidin-7-one (500 mg, 1.84 mmol) in DMF (5 mL) was added potassium carbonate (761.82 mg, 5.51 mmol) followed by 2-iodobutane (0.32 mL, 2.76 mmol) and the mixture stirred at rt overnight. The mixture was diluted with H$_2$O (50 mL) and EtOAc (75 mL) and the phases were separated. The organic extract was dried over anydrous Na$_2$SO$_4$, filtered through a silica plug topped with Celite and concentrated to provide the crude title compound (584 mg, 97% yield). LCMS (ESI) [M+H]$^+$=327.9, 329.5.

Step 2: rac-6-(4-Amino-3-fluorophenyl)-8-(sec-butyl)-2-(methylthio)pyrido[2,3-d]pyrimidin-7(8H)-one

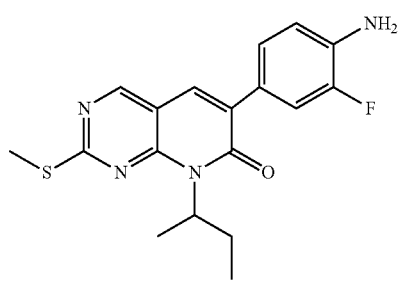 [SMILES: CCC(C)n1c(=O)c(-c2ccc(N)c(F)c2)cc2cnc(SC)nc21]

Prepared according to Example 198 step 1 using rac-6-bromo-2-methylsulfanyl-8-sec-butyl-pyrido[2,3-d]pyrimidin-7-one (584 mg, 1.78 mmol), 1,2-dimethoxyethane (10 mL), H$_2$O (2 mL), 2-fluoro-4-(4,4,5,5-tetramethyl-1,3,2-dioxaborolan-2-yl)aniline (633 mg, 2.67 mmol), palladium acetate (39.9 mg, 0.18 mmol), tri-o-tolylphosphine (108 mg, 0.36 mmol) and sodium carbonate (377 mg, 3.56 mmol) to provide the title compound (555 mg, 87% yield). LCMS (ESI) [M+H]$^+$=359.0.

Step 3: rac-N-(4-(8-(sec-Butyl)-2-(methylthio)-7-oxo-7,8-dihydropyrido[2,3-d]pyrimidin-6-yl)-2-fluorophenyl)-1-(2-fluorophenyl)methanesulfonamide

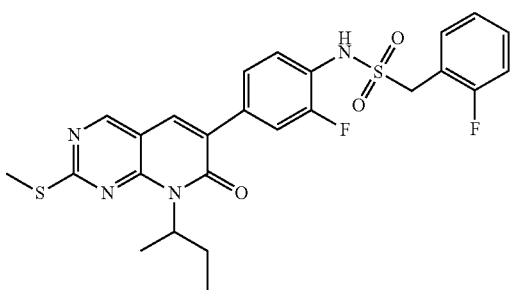 [SMILES: CCC(C)n1c(=O)c(-c2ccc(NS(=O)(=O)Cc3ccccc3F)c(F)c2)cc2cnc(SC)nc21]

Prepared according to Example 198 step 2 using rac-6-(4-amino-3-fluoro-phenyl)-2-methylsulfanyl-8-sec-butyl-pyrido[2,3-d]pyrimidin-7-one (270 mg, 0.75 mmol), CH$_2$Cl$_2$ (4 mL), pyridine (1 mL) and (2-fluorophenyl)methanesulfonyl chloride (189 mg, 0.90 mmol) to provide the title compound (239 mg, 60% yield). LCMS (ESI) [M+H]$^+$=530.9.

Step 4: rac-N-(4-(8-(sec-Butyl)-2-(methylsulfonyl)-7-oxo-7,8-dihydropyrido[2,3-d]pyrimidin-6-yl)-2-fluorophenyl)-1-(2-fluorophenyl)methanesulfonamide

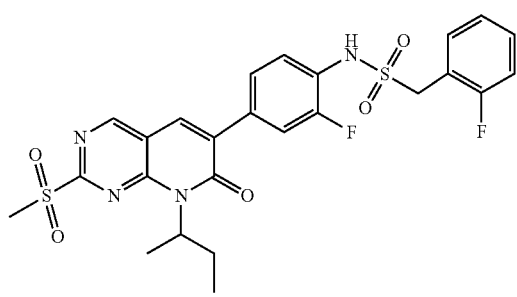 [SMILES: CCC(C)n1c(=O)c(-c2ccc(NS(=O)(=O)Cc3ccccc3F)c(F)c2)cc2cnc(S(C)(=O)=O)nc21]

Prepared according to Example 198 step 3 using rac-N-[2-fluoro-4-(2-methylsulfanyl-7-oxo-8-sec-butyl-pyrido[2,3-d]pyrimidin-6-yl)phenyl]-1-(2-fluorophenyl)methanesulfonamide (239 mg, 0.45 mmol), CH$_2$Cl$_2$ (3 mL) and 3-chloroperbenzoic acid (mCPBA) (233 mg, 1.35 mmol) to provide the crude title compound (253 mg, 100% yield). LCMS (ESI) [M+H]$^+$=562.9.

Step 5: (3S,5S)-tert-Butyl 3-((8-(sec-butyl)-6-(3-fluoro-4-((2-fluorophenyl)methylsulfonamido)phenyl)-7-oxo-7,8-dihydropyrido[2,3-d]pyrimidin-2-yl)amino)-5-fluoropiperidine-1-carboxylate

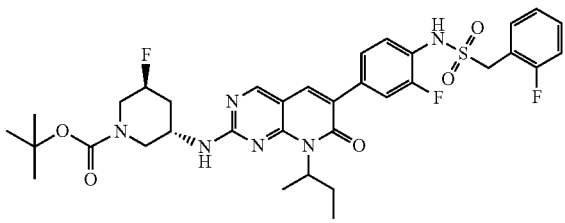 [SMILES: CCC(C)n1c(=O)c(-c2ccc(NS(=O)(=O)Cc3ccccc3F)c(F)c2)cc2cnc(N[C@H]3C[C@H](F)CN(C(=O)OC(C)(C)C)C3)nc21]

Prepared according to Example 198 step 6 using rac-N-[2-fluoro-4-(2-methylsulfonyl-7-oxo-8-sec-butyl-pyrido[2,3-d]pyrimidin-6-yl)phenyl]-1-(2-fluorophenyl)methanesulfonamide (269 mg, 0.48 mmol), tert-butyl (3S,5S)-3-amino-5-fluoro-piperidine-1-carboxylate (146 mg, 0.67 mmol), isopropanol (10 mL) and N,N-diisopropylethylamine (416 µL, 2.39 mmol) to provide the title product (110 mg, 33% yield) as a mixture of isomers stereogenic at the N-sec-butyl position. LCMS (ESI) [M+H]+=701.1.

Step 6: (3S,5S)-tert-Butyl 3-((8-((R)-sec-butyl)-6-(3-fluoro-4-((2-fluorophenyl)methylsulfonamido)phenyl)-7-oxo-7,8-dihydropyrido[2,3-d]pyrimidin-2-yl)amino)-5-fluoropiperidine-1-carboxylate and (3S,5S)-tert-butyl 3-((8-((S)-sec-butyl)-6-(3-fluoro-4-((2-fluorophenyl)methylsulfonamido)phenyl)-7-oxo-7,8-dihydropyrido[2,3-d]pyrimidin-2-yl)amino)-5-fluoropiperidine-1-carboxylate

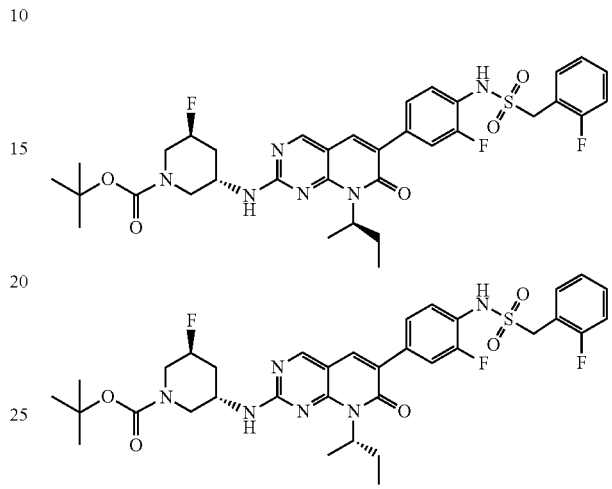

(3S,5S)-tert-butyl 3-((8-(sec-butyl)-6-(3-fluoro-4-((2-fluorophenyl)methylsulfonamido)phenyl)-7-oxo-7,8-dihydropyrido[2,3-d]pyrimidin-2-yl)amino)-5-fluoropiperidine-1-carboxylate stereogenic at the N-sec-butyl position was subjected to chiral normal phase semi-prep purification (conditions: Chiralpak IA, 5 µM, 4.6×250 mm, 18:12:78 MeOH:DCM:Hexane, 0.8 mL/min) to provide two stereoisomers enantiomeric at the N-sec-butyl position which was arbitrarily assigned: (3S,5S)-tert-butyl 3-((8-((R)-sec-butyl)-6-(3-fluoro-4-((2-fluorophenyl)methylsulfonamido)phenyl)-7-oxo-7,8-dihydropyrido[2,3-d]pyrimidin-2-yl)amino)-5-fluoropiperidine-1-carboxylate (isomer-1) (34 mg, 32% yield), 96% de, LCMS (ESI) [M+H]$^+$=701.1; and (3S,5S)-tert-butyl 3-((8-((S)-sec-butyl)-6-(3-fluoro-4-((2-fluorophenyl)methylsulfonamido)phenyl)-7-oxo-7,8-dihydropyrido[2,3-d]pyrimidin-2-yl)amino)-5-fluoropiperidine-1-carboxylate (isomer-2), (27 mg, 24% yield), 91.8% de, LCMS (ESI) [M+H]$^+$=701.1.

Step 7: N-(4-(8-(sec-Butyl)-2-(((3S,5S)-5-fluoropiperidin-3-yl)amino)-7-oxo-7,8-dihydropyrido[2,3-d]pyrimidin-6-yl)-2-fluorophenyl)-1-(2-fluorophenyl)methanesulfonamide hydrochloride

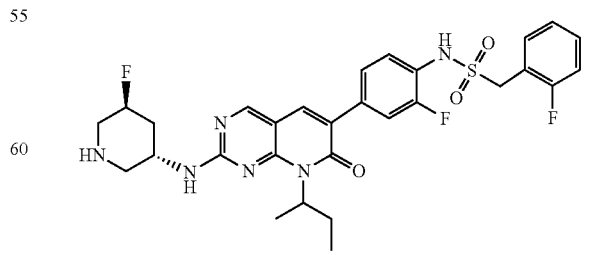

(3S,5S)-tert-Butyl 3-(8-sec-butyl)-6-(3-fluoro-4-((2-fluorophenyl)methylsulfonamido)phenyl)-7-oxo-7,8-dihydropyrido[2,3-d]pyrimidin-2-yl)amino)-5-fluoropiperidine-1-carboxylate (isomer 1) (34 mg, 0.05 mmol) was dissolved in EtOAc (2 mL) and treated with 4N HCl in dioxane (0.5 mL) and the mixture stirred at rt overnight. After 18 h, volatiles were removed and crude salt was washed using EtOAc (3×2 mL) then with MeCN (3×2 mL). The HCl salt residue was then dissolved in H₂O and MeCN and lyophilized to provide the title compound (23 mg, 74% yield).

Example 202A: N-(4-(8-(sec-Butyl)-2-(((3S,5S)-5-fluoropiperidin-3-yl)amino)-7-oxo-7,8-dihydro-pyrido[2,3-d]pyrimidin-6-yl)-2-fluorophenyl)-1-(2-fluorophenyl)methanesulfonamide hydrochloride Compound 202A

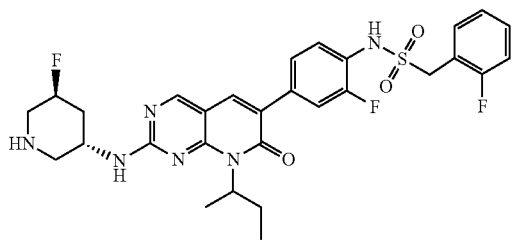 [SMILES: CCC(C)n1c(=O)c(-c2ccc(NS(=O)(=O)Cc3ccccc3F)c(F)c2)cc2cnc(N[C@@H]3CNC[C@@H](F)C3)nc21]

Prepared according to Example 202 step 7 using (3S,5S)-tert-butyl 3-((8-(-sec-butyl)-6-(3-fluoro-4-((2-fluorophenyl)methylsulfonamido)phenyl)-7-oxo-7,8-dihydropyrido[2,3-d]pyrimidin-2-yl)amino)-5-fluoropiperidine-1-carboxylate (isomer 2) (27 mg, 0.038 mmol), EtOAc (2 mL) and 4N HCl in dioxane (0.5 mL) to provide the title compound (23 mg, 99% yield).

Example 203: N-(4-(8-((R)-sec-Butyl)-2-(((1,4-trans)-4-(dimethylamino)cyclohexyl)amino)-7-oxo-7,8-dihydropyrido[2,3-d]pyrimidin-6-yl)-2-fluoro-phenyl)-3,3,3-trifluoropropane-1-sulfonamide Compound 203

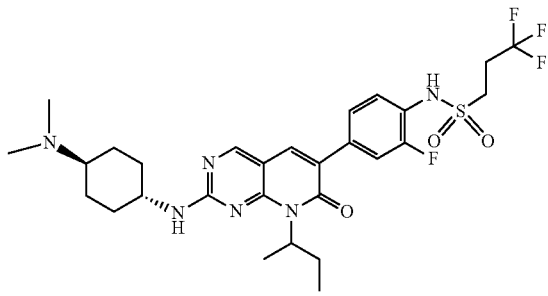 [SMILES: CCC(C)n1c(=O)c(-c2ccc(NS(=O)(=O)CCC(F)(F)F)c(F)c2)cc2cnc(N[C@H]3CC[C@H](N(C)C)CC3)nc21]

Step 1: rac-6-Bromo-2-methylsulfanyl-8-sec-butyl-pyrido[2,3-d]pyrimidin-7-one

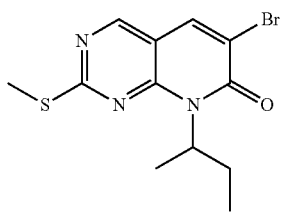 [SMILES: CCC(C)n1c(=O)c(Br)cc2cnc(SC)nc21]

To a suspension of 6-bromo-2-methylsulfanyl-8H-pyrido[2,3-d]pyrimidin-7-one (500 mg, 1.84 mmol) in DMF (5 mL) was added potassium carbonate (762 mg, 5.51 mmol) followed by 2-iodobutane (0.32 mL, 2.76 mmol) and the mixture stirred at rt overnight. After 16 h, a further portion of iodo-butane (0.21 mL, 1.81 mmol) was added and the reaction was stirred for 3 days. The mixture was then diluted with H₂O (50 mL) and EtOAc (75 mL) and the phases were separated. The organic extract was dried over anydrous Na₂SO₄, filtered through a silica plug topped with celite and concentrated in vacuo to provide the title compound (584 mg, 97% yield) which was used in the next step without further purification. LCMS (ESI) [M+H]⁺=329.9.

Step 2: rac-6-(4-Amino-3-fluoro-phenyl)-2-methyl-sulfanyl-8-sec-butyl-pyrido[2,3-d]pyrimidin-7-one

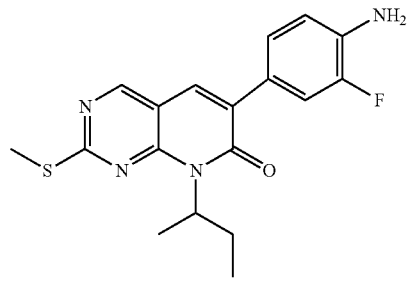 [SMILES: CCC(C)n1c(=O)c(-c2ccc(N)c(F)c2)cc2cnc(SC)nc21]

A flask was charged with rac-6-bromo-2-methylsulfanyl-8-sec-butyl-pyrido[2,3-d]pyrimidin-7-one (584 mg, 1.78 mmol) and 1,2-dimethoxyethane (10 mL) and H₂O (2 mL). To this mixture was then added 2-fluoro-4-(4,4,5,5-tetramethyl-1,3,2-dioxaborolan-2-yl)aniline (633 mg, 2.67 mmol), palladium acetate (40 mg, 0.1800 mmol), tri-o-tolylphosphine (108 mg, 0.36 mmol), and sodium carbonate (377 mg, 3.56 mmol) in that order. The flask was capped and N₂ purged 5 min then placed in a 85° C. oil bath overnight. After 16 h, the reaction was diluted with EtOAc (75 mL) and Na₂SO₄ was added to remove water. The mixture was filtered through a silica plug topped with celite using ethyl acetate (2×20 mL) to wash/elute and concentrated in vacuo. The crude material was purified by silica flash chromatography (0-100% EtOAc/heptanes) to provide the title compound (555 mg, 87% yield). LCMS (ESI) [M+H]⁺=359.0.

Step 3: rac-3,3,3-Trifluoro-N-[2-fluoro-4-(2-methyl-sulfanyl-7-oxo-8-sec-butyl-pyrido[2,3-d]pyrimidin-6-yl)phenyl]propane-1-sulfonamide

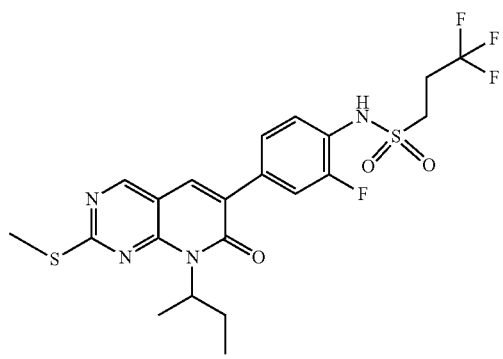 [SMILES: CCC(C)n1c(=O)c(-c2ccc(NS(=O)(=O)CCC(F)(F)F)c(F)c2)cc2cnc(SC)nc21]

To a solution of rac-6-(4-amino-3-fluoro-phenyl)-2-methylsulfanyl-8-sec-butyl-pyrido[2,3-d]pyrimidin-7-one (270 mg, 0.75 mmol) in a mixture of $CH_2Cl_2$ (4 mL) and pyridine (1 mL) was added 3,3,3-trifluoropropane-1-sulfonyl chloride (222 mg, 1.13 mmol) in $CH_2Cl_2$ (0.2 mL) and the mixture stirred at rt overnight. After 18 h, MeOH (10 mL) was added and volatiles removed under reduced pressure (repeated ×2). The crude material was then purified by silica flash chromatography (0-100% EA/heptane) to provide the title compound (177 mg, 45% yield). LCMS (ESI) $[M+H]^+$=518.8.

Step 4: rac-3,3,3-Trifluoro-N-[2-fluoro-4-(2-methyl-sulfonyl-7-oxo-8-sec-butyl-pyrido[2,3-d]pyrimidin-6-yl)phenyl]propane-1-sulfonamide

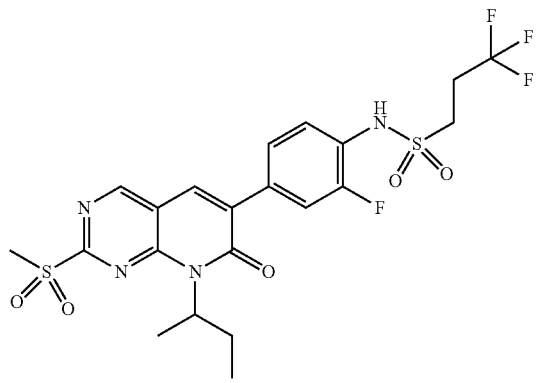 [SMILES: CCC(C)n1c(=O)c(-c2ccc(NS(=O)(=O)CCC(F)(F)F)c(F)c2)cc2cnc(S(C)(=O)=O)nc21]

rac-3,3,3-Trifluoro-N-[2-fluoro-4-(2-methylsulfanyl-7-oxo-8-sec-butyl-pyrido[2,3-d]pyrimidin-6-yl)phenyl]propane-1-sulfonamide (190 mg, 0.37 mmol) was dissolved in $CH_2Cl_2$ (11 mL) and to the mixture was added 2-chlorobenzenecarboperoxoic acid (271 mg, 1.1 mmol, ~70% purity). The reaction is stirred at rt for 20 min then diluted with $CH_2Cl_2$ (30 mL) and washed with saturated aqueous sodium bicarbonate (2×10 mL). The organic extract was dried over anydrous $Na_2SO_4$, filtered and concentrated in vacuo to provide the title compound (200 mg, 99% yield) which was used in the next step without further purification. LCMS (ESI) $[M+H]^+$=551.1.

Step 5: tert-Butyl (1,4-trans)-N-[4-[[6-[3-fluoro-4-(3,3,3-trifluoropropylsulfonylamino)phenyl]-8-[(1R)-1-methylpropyl]-7-oxo-pyrido[2,3-d]pyrimidin-2-yl]amino]cyclohexyl]carbamate and tert-butyl (1,4-trans)-N-[4-[[6-[3-fluoro-4-(3,3,3-trifluoropropylsulfonylamino)phenyl]-8-[(1S)-1-methylpropyl]-7-oxo-pyrido[2,3-d]pyrimidin-2-yl]amino]cyclohexyl]carbamate

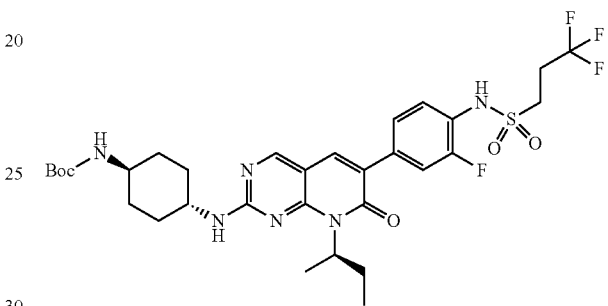

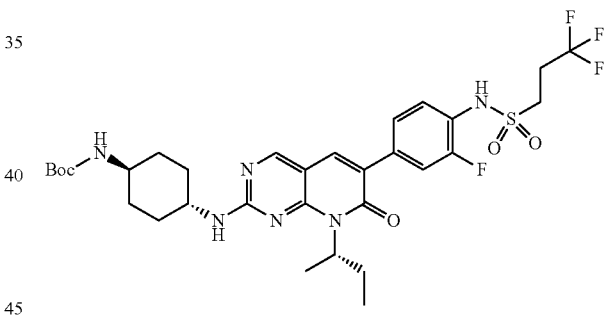

To rac-3,3,3-trifluoro-N-[2-fluoro-4-(2-methylsulfonyl-7-oxo-8-sec-butyl-pyrido[2,3-d]pyrimidin-6-yl)phenyl]propane-1-sulfonamide (200 mg, 0.36 mmol) in isopropanol (5 mL) was added N-Boc-trans-1,4-cyclohexanediamine (124 mg, 0.58 mmol) and N,N-diisopropylethylamine (317 µL, 1.82 mmol). The reaction was stirred at 50° C. for 2 days then concentrated to dryness with silica gel and purified by flash column chromatography through silica gel (0-8% MeOH/$CH_2Cl_2$) to give rac-tert-butyl 1,4-trans-N-[4-[[6-[3-fluoro-4-(3,3,3-trifluoropropylsulfonylamino)phenyl]-8-[1-methylpropyl]-7-oxo-pyrido[2,3-d]pyrimidin-2-yl]amino]cyclohexyl]carbamate.

Enantiomers of rac-tert-butyl 1,4-trans-N-[4-[[6-[3-fluoro-4-(3,3,3-trifluoropropylsulfonylamino)phenyl]-8-[1-methylpropyl]-7-oxo-pyrido[2,3-d]pyrimidin-2-yl]amino]cyclohexyl]carbamate were separated by Chiral HPLC purification to provide two stereoisomers enantiomeric at the N-sec-butyl position which was arbitrarily assigned (ChiralPak IA, 250 mm×4.6 mm ID, 5 µm. Mobile Phase: IA, 8:16:76 EtOH:DCM:Hexane (0.1% DEA). Isocratic Flow: 0.8 mL/min, (pressure was 47 bars). Column Temp.: ~ 26°

C. Run Time: 28 min) to provide: tert-butyl (1,4-trans)-N-[4-[[6-[3-fluoro-4-(3,3,3-trifluoropropylsulfonylamino)phenyl]-8-[(1R)-1-methylpropyl]-7-oxo-pyrido[2,3-d]pyrimidin-2-yl]amino]cyclohexyl]carbamate (62 mg, 25% yield) (isomer-1), LCMS (ESI) [M+H]⁺=685.3; and tert-butyl (1,4-trans)-N-[4-[[6-[3-fluoro-4-(3,3,3-trifluoropropylsulfonylamino)phenyl]-8-[(1S)-1-methylpropyl]-7-oxo-pyrido[2,3-d]pyrimidin-2-yl]amino]cyclohexyl]carbamate (51 mg, 20% in yield) (isomer-2), LCMS (ESI) [M+H]⁺=685.3.

Step 6: N-(4-(8-((R)-sec-Butyl)-2-(((1,4-trans)-4-(dimethylamino)cyclohexyl)amino)-7-oxo-7,8-dihydropyrido[2,3-d]pyrimidin-6-yl)-2-fluorophenyl)-3,3,3-trifluoropropane-1-sulfonamide

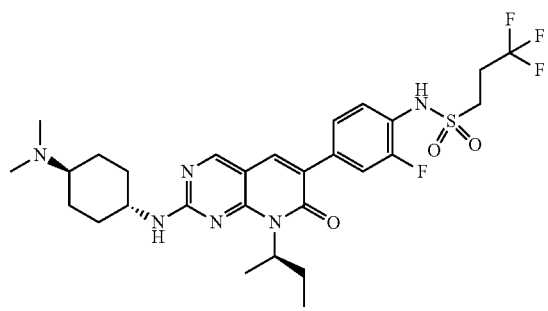 [SMILES: CC[C@@H](C)n1c(=O)c(-c2ccc(NS(=O)(=O)CCC(F)(F)F)c(F)c2)cc2cnc(N[C@H]3CC[C@H](N(C)C)CC3)nc21]

To tert-butyl (1,4-trans)-N-[4-[[6-[3-fluoro-4-(3,3,3-trifluoropropylsulfonylamino)phenyl]-8-[(1R)-1-methylpropyl]-7-oxo-pyrido[2,3-d]pyrimidin-2-yl]amino]cyclohexyl]carbamate (62 mg, 0.09 mmol) was added TFA (1 mL) and the reaction is stirred at rt for 20 min. To the reaction was added toluene (5 mL) and the solvent was removed in vacuo to give the crude amine salt which was dissolved in methanol (2 mL). To the solution was added sodium acetate (148 mg, 1.81 mmol) followed by 37% w/w aqueous formaldehyde (82 mg, 0.91 mmol). The reaction is stirred for 5 min before addition of sodium triacetoxyborohydride (76 mg, 0.36 mmol) and after 20 min at rt the mixture was directly purified by C18 reverse phase flash chromatography (10-100% MeCN/10 mM aqueous ammonium formate, pH=3.8). Appropriate fractions were combined and lyophilized to provide the title compound (41 mg, 74% yield). The stereochemistry at the N-sec-butyl position was arbitrarily assigned.

Example 203A: N-(4-(8-((S)-sec-Butyl)-2-(((1,4-trans)-4-(dimethylamino)cyclohexyl)amino)-7-oxo-7,8-dihydropyrido[2,3-d]pyrimidin-6-yl)-2-fluorophenyl)-3,3,3-trifluoropropane-1-sulfonamide Compound 203A

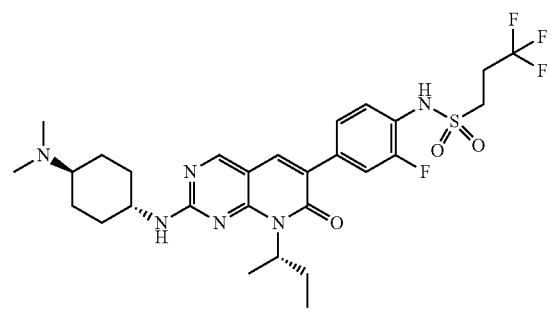 [SMILES: CC[C@H](C)n1c(=O)c(-c2ccc(NS(=O)(=O)CCC(F)(F)F)c(F)c2)cc2cnc(N[C@H]3CC[C@H](N(C)C)CC3)nc21]

Step 1: N-(4-(8-((S)-sec-Butyl)-2-(((1,4-trans)-4-(dimethylamino)cyclohexyl)amino)-7-oxo-7,8-dihydropyrido[2,3-d]pyrimidin-6-yl)-2-fluorophenyl)-3,3,3-trifluoropropane-1-sulfonamide

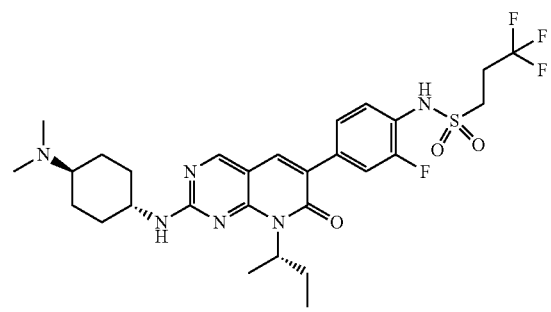 [SMILES: CC[C@H](C)n1c(=O)c(-c2ccc(NS(=O)(=O)CCC(F)(F)F)c(F)c2)cc2cnc(N[C@H]3CC[C@H](N(C)C)CC3)nc21]

Prepared according to the Example 203 step 6 using (1,4-trans)-N-[4-[[6-[3-fluoro-4-(3,3,3-trifluoropropylsulfonylamino)phenyl]-8-[(1S)-1-methylpropyl]-7-oxo-pyrido[2,3-d]pyrimidin-2-yl]amino]cyclohexyl]carbamate (51 mg, 0.07 mmol) to provide the title compound (27 mg, 59% yield). The stereochemistry at the N-sec-butyl position was arbitrarily assigned.

Example 204: 3,3,3-Trifluoro-N-(2-fluoro-4-(8-isopropyl-2-(((1,4-trans)-4-(methyl(oxetan-3-ylmethyl)amino)cyclohexyl)amino)-7-oxo-7,8-dihydropyrido[2,3-d]pyrimidin-6-yl)phenyl)propane-1-sulfonamide Compound 204

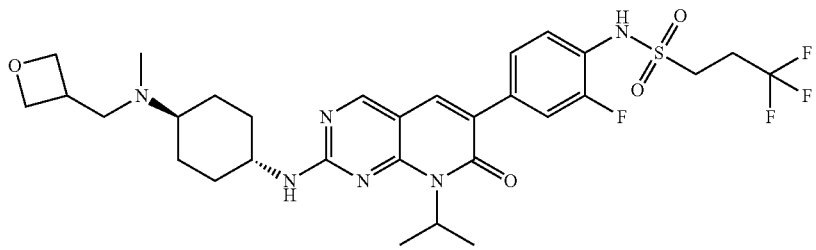 [SMILES: CC(C)n1c(=O)c(-c2ccc(NS(=O)(=O)CCC(F)(F)F)c(F)c2)cc2cnc(N[C@H]3CC[C@H](N(C)CC4COC4)CC3)nc21]

Step 1: tert-Butyl ((1,4-trans)-4-(methyl(oxetan-3-ylmethyl)amino)cyclohexyl)carbamate

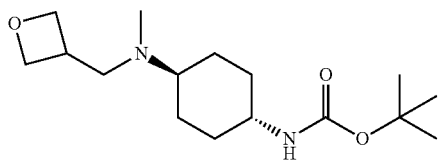 [SMILES: CN(CC1COC1)[C@H]1CC[C@H](NC(=O)OC(C)(C)C)CC1]

A sealed tube was charged with tert-butyl N-[4-(methylamino)cyclohexyl]carbamate (90 mg, 0.39 mmol), 3-(bromomethyl)oxetane (89 mg, 0.59 mmol) and triethylamine (0.16 mL, 1.18 mmol). To this mixture was then added MeCN (3.5 mL) and the reaction was stirred 65° C. After 23 h, the reaction mixture was diluted with H$_2$O and extracted twice with EtOAct, dried over Na$_2$SO$_4$, filtered and concentrated to provide the crude title compound (117 mg 99% yield) which was used in the next step without further purification. LCMS (ESI) [M+H]$^+$=299.1.

Step 2: (1,4-trans)-N$^1$-Methyl-N$^1$-(oxetan-3-ylmethyl)cyclohexane-1,4-diamine 2,2,2-trifluoroacetate

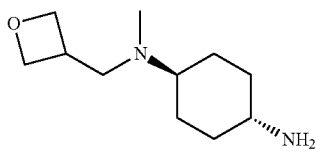

To a solution of tert-butyl N-[4-[methyl(oxetan-3-ylmethyl)amino]cyclohexyl]carbamate (117 mg, 0.39 mmol) in CH$_2$Cl$_2$ (1 mL) was added trifluoroacetic acid (461 µL, 6.03 mmol) and the solution was stirred at rt. After 90 min, the mixture was concentrated under reduced pressure. Toluene was added and the mixture was concentrated under reduced pressure (repeated×3) to provide the crude title compound which was used directly in the next step.

Step 3: 3,3,3-Trifluoro-N-(2-fluoro-4-(8-isopropyl-2-(((1,4-trans)-4-(methyl(oxetan-3-ylmethyl)amino)cyclohexyl)amino)-7-oxo-7,8-dihydropyrido[2,3-d]pyrimidin-6-yl)phenyl)propane-1-sulfonamide Prepared according to Example 198 step 6 using (1,4-trans)-N$^1$-methyl-N$^1$-(oxetan-3-ylmethyl)cyclohexane-1,4-diamine 2,2,2-trifluoroacetate (122 mg, 0.39 mmol), 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (100 mg, 0.19 mmol), N,N-diisopropylethylamine (162 µL, 0.93 mmol) to provide the title compound (13 mg, 11% yield).

Example 205: N-(4-(2-(((1,4-trans)-4-(Ethyl(methyl)amino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 205

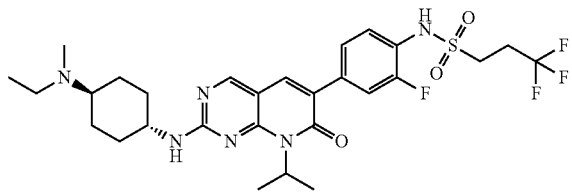 [SMILES: CCN(C)[C@H]1CC[C@H](Nc2ncc3cc(-c4ccc(NS(=O)(=O)CCC(F)(F)F)c(F)c4)c(=O)n(C(C)C)c3n2)CC1]

Step 1: tert-Butyl ((1,4-trans)-4-(ethyl(methyl)amino)cyclohexyl)carbamate

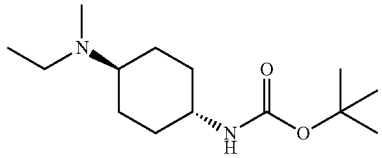 [SMILES: CCN(C)[C@H]1CC[C@H](NC(=O)OC(C)(C)C)CC1]

tert-Butyl N-[4-(methylamino)cyclohexyl]carbamate (80 mg, 0.35 mmol) was dissolved in methanol (3.0 mL) and to the solution was added acetaldehyde (0.2 mL, 3.5 mmol). The mixture was stirred at rt for 5 min then sodium triacetoxyborohydride (294 mg, 1.4 mmol) was added and the mixture stirred for 1 h at rt. The mixture was then partitioned between saturated aqueous sodium bicarbonate and CH$_2$Cl$_2$. The phases were separated and the organic extract dried over Na$_2$SO$_4$, filtered and concentrated to provide the crude title compound (78 mg, 87% yield) which was used directly in the next step without further purification.

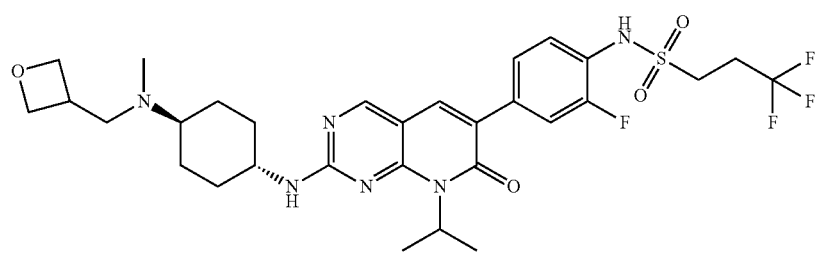

437

Step 2: (1,4-trans)-N¹-Ethyl-N¹-methylcyclohexane-1,4-diamine 2,2,2-trifluoroacetate

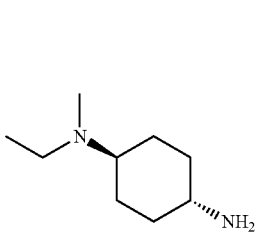

Prepared according to Example 204 step 2 using tert-butyl N-[4-[ethyl(methyl)amino]cyclohexyl]carbamate (78 mg, 0.30 mmol) trifluoroacetic acid (400 μL, 5.23 mmol) and CH$_2$Cl$_2$ (1.5 mL) to provide the crude title compound (82 mg, 100% yield). LCMS (ESI) [M+H]$^+$=157.1.

Step 3: N-(4-(2-(((1,4-trans)-4-(Ethyl(methyl)amino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide

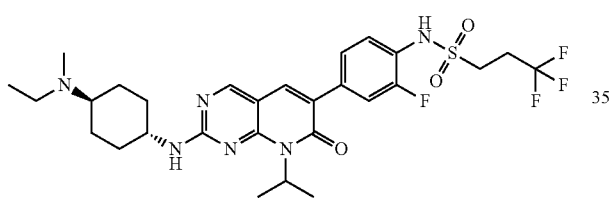

Prepared according to Example 198 step 6 using (1,4-trans)-N¹-ethyl-N¹-methylcyclohexane-1,4-diamine 2,2,2-trifluoroacetate (82 mg, 0.30 mmol) 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (80 mg, 0.15 mmol) and N,N-diisopropylethylamine (156 μL, 0.89 mmol) to provide the title compound (18 mg, 19% yield).

Example 206: 3,3,3-Trifluoro-N-(2-fluoro-4-(8-isopropyl-2-(((1,4-trans)-4-(methyl(oxetan-3-yl)amino)cyclohexyl)amino)-7-oxo-7,8-dihydropyrido[2,3-d]pyrimidin-6-yl)phenyl)propane-1-sulfonamide
Compound 206

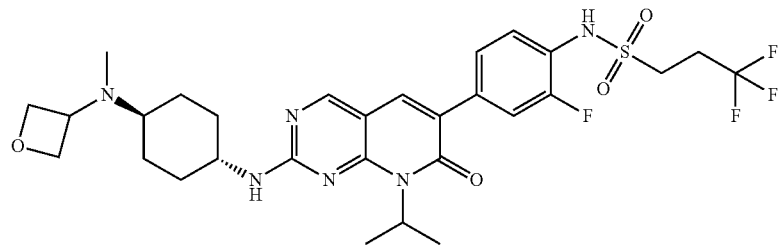 [SMILES: CC(C)n1c(=O)c(-c2ccc(NS(=O)(=O)CCC(F)(F)F)c(F)c2)cc2cnc(N[C@H]3CC[C@H](N(C)C4COC4)CC3)nc21]

438

Step 1: tert-Butyl ((1,4-trans)-4-(methyl(oxetan-3-yl)amino)cyclohexyl)carbamate

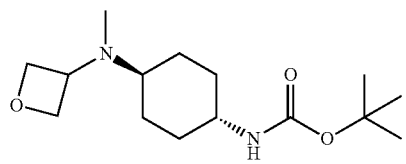 [SMILES: CN(C1COC1)[C@H]1CC[C@H](NC(=O)OC(C)(C)C)CC1]

To tert-butyl N-[4-(methylamino)cyclohexyl]carbamate (90 mg, 0.39 mmol) in methanol (7 mL) were added 3 Å MS (70 mg), oxetan-3-one (63 μL, 0.99 mmol) and zinc chloride (26 mg, 0.20 mmol). The mixture was stirred at rt for 30 min then acetic acid (68 μL, 1.18 mmol) was added followed by addition of sodium cyanoborohydride (40 mg, 0.63 mmol) and the mixture was stirred at 50° C. for 20 h. The mixture was filtered to remove molecular sieves, and partitioned between saturated aqueous sodium bicarbonate and EtOAc. The phases were separated and the organic extract was washed with saturated aqueous sodium chloride, dried over anhydrous Na$_2$SO$_4$ and concentrated to give the crude title crude compound (112 mg, 100% yield) which was used directly in the next step without further purification. LCMS (ESI) [M+H]$^+$=285.1.

Step 2: (1,4-trans)-N¹-Methyl-N¹-(oxetan-3-yl)cyclohexane-1,4-diamine 2,2,2-trifluoroacetate

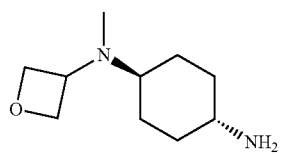

Prepared according to Example 204 step 2 using tert-butyl ((1,4-trans)-4-(methyl(oxetan-3-yl)amino)cyclohexyl)carbamate (101 mg, 0.35 mmol) trifluoroacetic acid (760 μL, 9.93 mmol) and CH$_2$Cl$_2$ (1.8 mL) to provide the crude title compound (104 mg, 100% yield) which was used directly in the next step without further purification.

Step 3: 3,3,3-Trifluoro-N-(2-fluoro-4-(8-isopropyl-2-(((1,4-trans)-4-(methyl(oxetan-3-yl)amino)cyclohexyl)amino)-7-oxo-7,8-dihydropyrido[2,3-d]pyrimidin-6-yl)phenyl)propane-1-sulfonamide

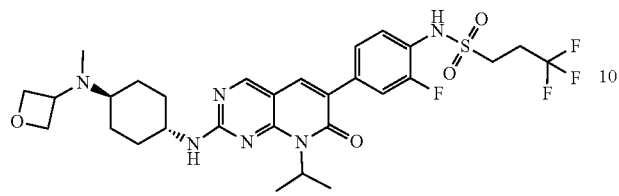

Prepared according to Example 198 step 6 using (1,4-trans)-N¹-methyl-N¹-(oxetan-3-yl)cyclohexane-1,4-diamine 2,2,2-trifluoroacetate (104 mg, 0.35 mmol), 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (95 mg, 0.18 mmol) and N,N-diisopropylethylamine (155 µL, 0.89 mmol) and isopropanol (1.8 mL) to provide the title compound (36 mg, 32% yield).

Example 207: N-(4-(2-(((1,4-trans)-4-(Cyclopropyl(methyl)amino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 207

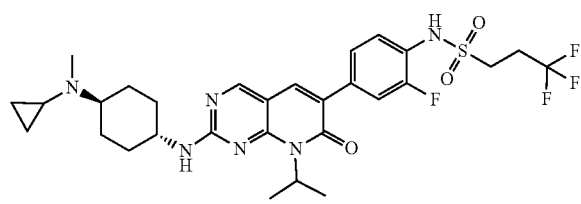 [SMILES: CC(C)n1c(=O)c(-c2ccc(NS(=O)(=O)CCC(F)(F)F)c(F)c2)cc2cnc(N[C@H]3CC[C@H](N(C)C4CC4)CC3)nc21]

Step 1: tert-Butyl ((1,4-trans)-4-(cyclopropyl(methyl)amino)cyclohexyl)carbamate

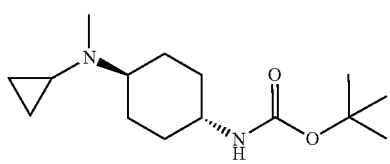 [SMILES: CN(C1CC1)[C@H]1CC[C@H](NC(=O)OC(C)(C)C)CC1]

To tert-butyl N-[4-(methylamino)cyclohexyl]carbamate (90 mg, 0.39 mmol) in methanol (2.2 mL) was added acetic acid (225 µL, 3.94 mmol), 3 Å MS (110 mg), (1-ethoxycyclopropoxy)trimethylsilane (0.4 mL, 2.0 mmol) and sodium cyanoborohydride (99 mg, 1.6 mmol) sequentially. The reaction was stirred at 70° C. under argon for 18 h then filtered using MeOH to wash and the filtrate was concentrated to dryness. The residue was partitioned between EtOAc and 1N NaOH and the phases were separated. The aqueous phase was extracted with EtOAc (×3) and the organic extracts were combined, washed with saturated aqueous sodium chloride, dried over Na₂SO₄, filtered and concentrated to provide the title compound (106 mg, 100% yield) which was used directly in the next step without further purification. LCMS (ESI) [M+H]⁺=269.2.

Step 2: (1,4-trans)-N¹-Cyclopropyl-N¹-methylcyclohexane-1,4-diamine 2,2,2-trifluoroacetate

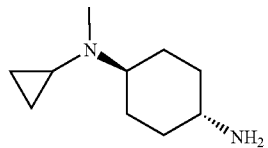

Prepared according to Example 204 step 2 using tert-butyl ((1,4-trans)-4-(cyclopropyl(methyl)amino)cyclohexyl)carbamate (106 mg, 0.39 mmol), trifluoroacetic acid (600 µL, 7.44 mmol) and CH₂Cl₂ (1 mL) to provide the crude title compound (110 mg, 100% yield) which was used directly in the next step.

Step 3: N-(4-(2-(((1,4-trans)-4-(Cyclopropyl(methyl)amino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide

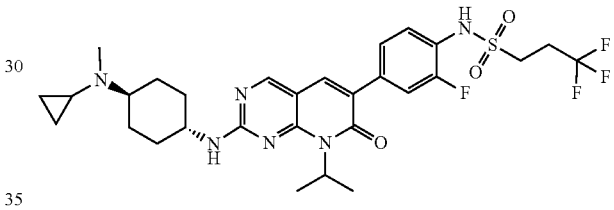

Prepared according to Example 198 step 6 using (1,4-trans)-N¹-cyclopropyl-N¹-methylcyclohexane-1,4-diamine 2,2,2-trifluoroacetate (110.1 mg, 0.39 mmol), 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (100 mg, 0.19 mmol), N,N-diisopropylethylamine (162 µL, 0.93 mmol) and iPrOH (1 mL) to provide the title compound (48 mg, 41% yield).

Example 208: N-[2-Fluoro-4-[2-[[(3S,5S)-5-fluoro-3-piperidyl]amino]-8-(2-hydroxyethyl)-7-oxo-pyrido[2,3-d]pyrimidin-6-yl]phenyl]-1-(2-fluorophenyl)methanesulfonamide Compound 208

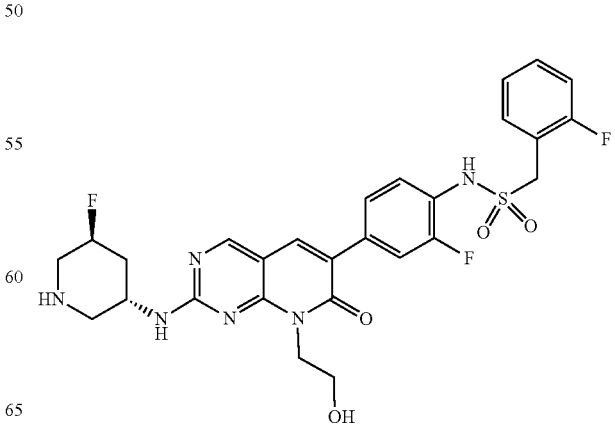

Step 1: 6-Bromo-8-[2-[tert-butyl(dimethyl)silyl]oxyethyl]-2-methylsulfanyl-pyrido[2,3-d]pyrimidin-7-one

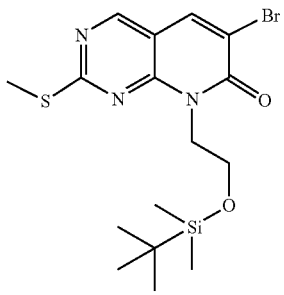 [SMILES: CSc1ncc2cc(Br)c(=O)n(CCO[Si](C)(C)C(C)(C)C)c2n1]

To a mixture of 6-bromo-2-methylsulfanyl-8H-pyrido[2,3-d]pyrimidin-7-one (0.2 g, 0.7 mmol) in DMF (5 mL) was added potassium carbonate (507 mg, 3.67 mmol) and (2-bromoethoxy)-tert-butyldimethylsilane (0.53 g, 2.2 mmol). The mixture was stirred at 50° C. for 2 h then diluted with EtOAc (50 mL) and washed with water then with saturated aqueous sodium chloride. The organic extract was concentrated and purified by flash chromatography through silica gel (0-50% EtOAc/heptanes) to provide the title compound (213 mg, 67% yield). LCMS (ESI) [M+H]$^+$=432.0.

Step 2: 6-(4-Amino-3-fluoro-phenyl)-8-[2-[tert-butyl(dimethyl)silyl]oxyethyl]-2-methylsulfanyl-pyrido[2,3-d]pyrimidin-7-one

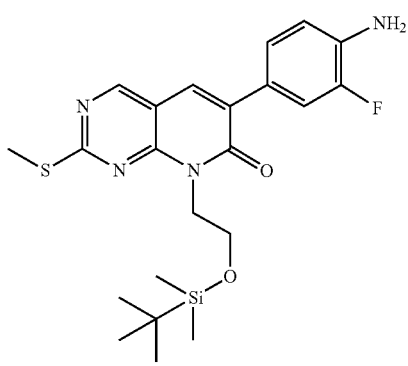 [SMILES: CSc1ncc2cc(-c3ccc(N)c(F)c3)c(=O)n(CCO[Si](C)(C)C(C)(C)C)c2n1]

6-Bromo-8-[2-[tert-butyl(dimethyl)silyl]oxyethyl]-2-methylsulfanyl-pyrido[2,3-d]pyrimidin-7-one (120 mg, 0.28 mmol) in 1,2-dimethoxyethane (4 mL) and water (1 mL) was degassed with N$_2$ for 10 min and to the solution was added 2-fluoro-4-(4,4,5,5-tetramethyl-1,3,2-dioxaborolan-2-yl)aniline (99 mg, 0.42 mmol), tri-o-tolylphosphine (34 mg, 0.11 mmol), Pd(OAc)$_2$ (12 mg, 0.06 mmol) and Na$_2$CO$_3$ (88 mg, 0.84 mmol). The reaction was stirred at 90° C. for 4 h then diluted with toluene (5 mL). Silica gel was added and the mixture was concentrated then purified by silica flash chromatography (0-100% EtOAc/heptanes) to provide the title compound (79 mg, 61% yield). LCMS (ESI) [M+H]+=461.2.

Step 3: N-[4-[8-[2-[tert-Butyl(dimethyl)silyl]oxyethyl]-2-methylsulfanyl-7-oxo-pyrido[2,3-d]pyrimidin-6-yl]-2-fluoro-phenyl]-1-(2-fluorophenyl)methanesulfonamide

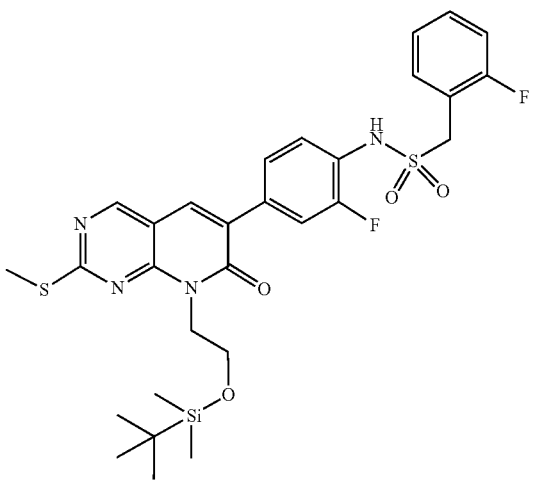 [SMILES: CSc1ncc2cc(-c3ccc(NS(=O)(=O)Cc4ccccc4F)c(F)c3)c(=O)n(CCO[Si](C)(C)C(C)(C)C)c2n1]

6-(4-Amino-3-fluoro-phenyl)-8-[2-[tert-butyl(dimethyl)silyl]oxyethyl]-2-methylsulfanyl-pyrido[2,3-d]pyrimidin-7-one (82 mg, 0.18 mmol) was dissolved in pyridine (1 mL) and to the solution was added (2-fluorophenyl)methanesulfonyl chloride (55 mg, 0.27 mmol). The reaction was stirred at rt for 1 h then a further portion of (2-fluorophenyl)methanesulfonyl chloride (73 mg, 0.36 mmol) was added. After stirring a further 30 min, the mixture was diluted with MeOH (1 mL) and toluene (5 mL) and silica gel was added and the mixture was concentrated and purified by silica flash chromatography (0-100% EtOAc/heptanes) to provide the title compound (76 mg, 67% yield). LCMS (ESI) [M+H]$^+$=633.2.

Step 4: N-[4-[8-[2-[tert-butyl(dimethyl)silyl]oxyethyl]-2-methylsulfonyl-7-oxo-pyrido[2,3-d]pyrimidin-6-yl]-2-fluoro-phenyl]-1-(2-fluorophenyl)methanesulfonamide

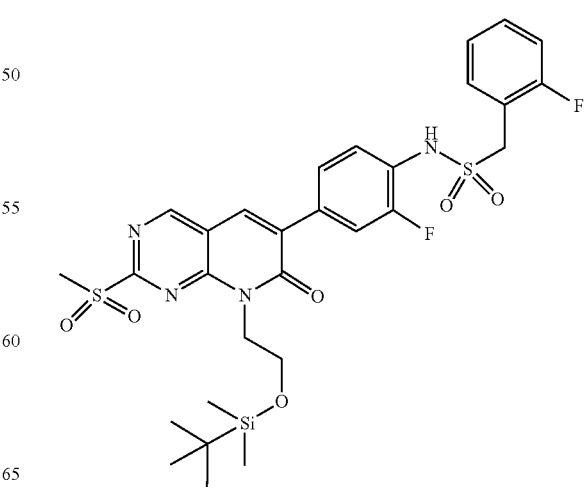

N-[4-[8-[2-[tert-Butyl(dimethyl)silyl]oxyethyl]-2-methylsulfanyl-7-oxo-pyrido[2,3-d]pyrimidin-6-yl]-2-fluorophenyl]-1-(2-fluorophenyl)methanesulfonamide (76 mg, 0.12 mmol) was dissolved in CH₂Cl₂ (2 mL) and to the solution was added 3-chlorobenzenecarboperoxoic acid (77 mg, 0.31 mmol). The reaction was stirred at rt for 30 min then diluted with CH₂Cl₂ (20 mL) and washed with 10% aqueous sodium carbonate (10 mL). The organic phase was dried over anydrous Na₂SO₄ and concentrated to dryness to provide the crude title compound (79 mg, 99% yield) which was used without further purification. LCMS (ESI) [M+H]⁺=665.2.

Step 5: tert-Butyl (3S,5S)-3-[[8-[2-[tert-butyl(dimethyl)silyl]oxyethyl]-6-[3-fluoro-4-[(2-fluorophenyl)methylsulfonylamino]phenyl]-7-oxo-pyrido[2,3-d]pyrimidin-2-yl]amino]-5-fluoro-piperidine-1-carboxylate

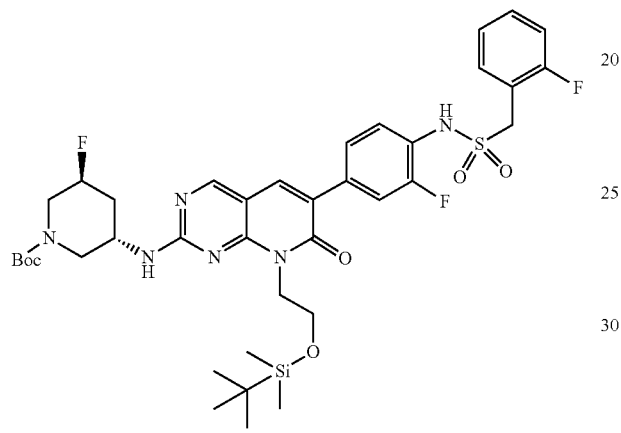

To N-[4-[8-[2-[tert-Butyl(dimethyl)silyl]oxyethyl]-2-methylsulfonyl-7-oxo-pyrido[2,3-d]pyrimidin-6-yl]-2-fluoro-phenyl]-1-(2-fluorophenyl)methanesulfonamide (79 mg, 0.12 mmol) in iPrOH (1.8 mL) was added tert-butyl (3S,5S)-3-amino-5-fluoro-piperidine-1-carboxylate (41 mg, 0.19 mmol) and N,N-diisopropylethylamine (103 μL, 0.59 mmol). The reaction was stirred at 50° C. for 2 days then concentrated to dryness. The crude was diluted with toluene and silica gel was added and concentrated and purified by silica flash chromatography (0-10% MeOH/CH₂Cl₂) to provide the title compound (47 mg, 49% yield). LCMS (ESI) [M+H]⁺=803.5.

Step 6: N-[2-Fluoro-4-[2-[[(3S,5S)-5-fluoro-3-piperidyl]amino]-8-(2-hydroxyethyl)-7-oxo-pyrido[2,3-d]pyrimidin-6-yl]phenyl]-1-(2-fluorophenyl)methanesulfonamide

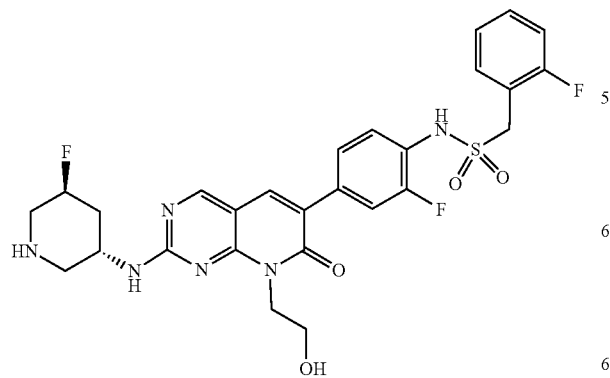

tert-Butyl (3S,5S)-3-[[8-[2-[tert-butyl(dimethyl)silyl]oxyethyl]-6-[3-fluoro-4-[(2-fluorophenyl)methylsulfonylamino]phenyl]-7-oxo-pyrido[2,3-d]pyrimidin-2-yl]amino]-5-fluoro-piperidine-1-carboxylate (47 mg, 0.06 mmol) was dissolved in TFA (1 mL) and stirred at rt for 20 min. Toluene (10 mL) was then added and the mixture was concentrated under reduced pressure and purified by C18 reverse phase chromatography (0-50% MeCN/10 mM aqueous ammonium formate, pH=3.8) to provide the title compound (19 mg, 55% yield).

Example 209: 3,3,3-Trifluoro-N-(2-fluoro-4-(8-isopropyl-2-(((1,4-trans)-4-(methyl(oxetan-2-ylmethyl)amino)cyclohexyl)amino)-7-oxo-7,8-dihydropyrido[2,3-d]pyrimidin-6-yl)phenyl)propane-1-sulfonamide (Compound 209)

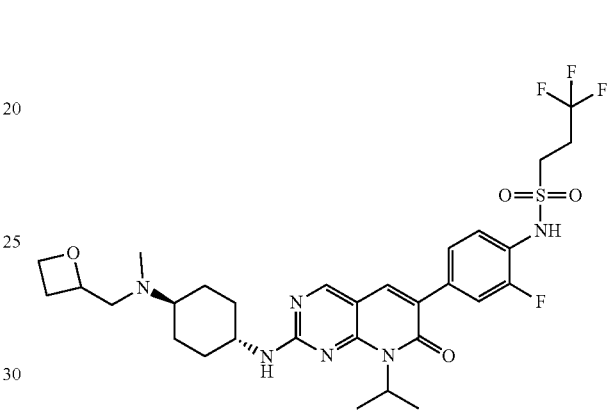

Step 1: tert-Butyl ((1,4-trans)-4-(methyl(oxetan-2-ylmethyl)amino)cyclohexyl)carbamate

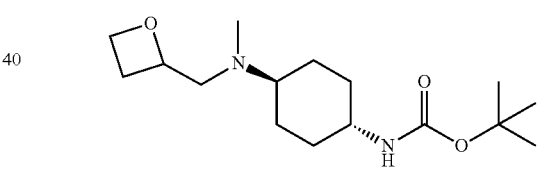

A mixture of tert-butyl N-[4-(methylamino)cyclohexyl]carbamate (80 mg, 0.35 mmol), 2-(bromomethyl)oxetane (212 mg, 1.4 mmol) and triethylamine (0.23 mL, 2.10 mmol), in MeCN (1.8 mL), was stirred 23 h at 65° C. The reaction mixture was diluted with H₂O and extracted twice with EtOAc, dried over anydrous Na₂SO₄, filtered and concentrated to provide the title compound (70 mg, 67% yield) which was used directly in the next step without further purification. LCMS (ESI) [M+H]⁺=299.1.

Step 2: (1,4-trans)-N¹-Methyl-N¹-(oxetan-2-ylmethyl)cyclohexane-1,4-diamine 2,2,2-trifluoroacetate

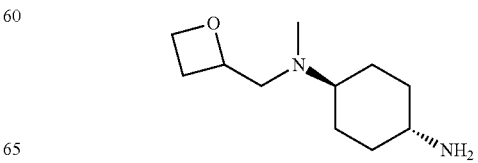

445

Prepared according to Example 204 step 2 using tert-butyl ((1,4-trans)-4-(methyl(oxetan-2-ylmethyl)amino)cyclohexyl)carbamate (70 mg, 0.23 mmol), trifluoroacetic acid (450 µL, 5.88 mmol) and CH₂Cl₂ (0.8 mL) to provide the crude title compound (73 mg, 100% yield).

Step 3: 3,3,3-Trifluoro-N-(2-fluoro-4-(8-isopropyl-2-(((1,4-trans)-4-(methyl(oxetan-2-ylmethyl)amino)cyclohexyl)amino)-7-oxo-7,8-dihydropyrido[2,3-d]pyrimidin-6-yl)phenyl)propane-1-sulfonamide

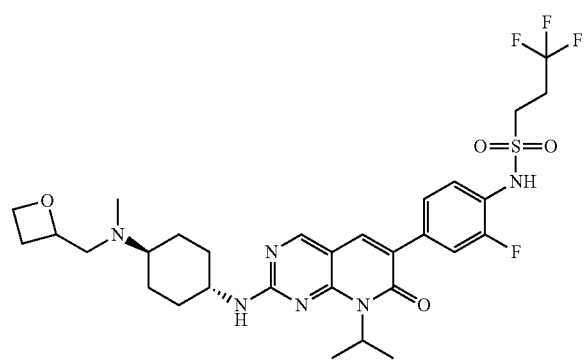 [SMILES: CC(C)n1c(=O)c(-c2ccc(NS(=O)(=O)CCC(F)(F)F)c(F)c2)cc2cnc(N[C@H]3CC[C@H](N(C)CC4CCO4)CC3)nc21]

Prepared according to Example 198 step 6 using (1,4-trans)-N¹-methyl-N¹-(oxetan-2-ylmethyl)cyclohexane-1,4-diamine 2,2,2-trifluoroacetate (73 mg, 0.23 mmol), 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (80 mg, 0.15 mmol) and N,N-diisopropylethylamine (130 µL, 0.75 mmol) and iPrOH (0.8 mL) to provide the title compound (28 mg, 29% yield) as mixture of enantiomers.

Example 210: N-(4-(2-(((1,4-trans)-4-(Bis(2-methoxyethyl)amino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 210

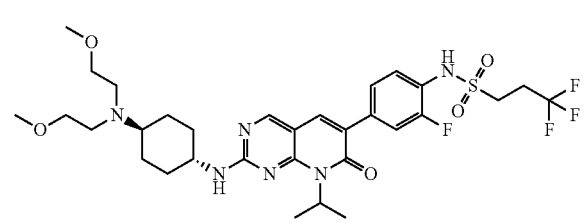 [SMILES: COCCN(CCOC)[C@H]1CC[C@H](Nc2ncc3cc(-c4ccc(NS(=O)(=O)CCC(F)(F)F)c(F)c4)c(=O)n(C(C)C)c3n2)CC1]

446

Step 1: tert-Butyl ((1,4-trans)-4-(bis(2-methoxyethyl)amino)cyclohexyl)carbamate

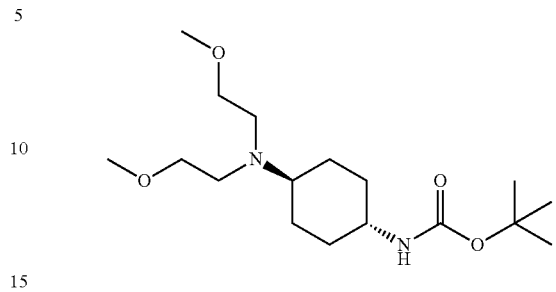

A mixture of N-Boc-trans-1,4-cyclohexanediamine (100 mg, 0.47 mmol), 2-bromoethyl methyl ether (0.13 mL, 1.4 mmol) and sodium carbonate (247 mg, 2.33 mmol), in MeCN (2.3 mL) was stirred at 75° C. for 2 days. The reaction was filtered, rinsed with acetonitrile and the filtrate was concentrated to provide the crude title compound (148 mg, 96% yield) which was used directly in the next step without further purification. LCMS (ESI) [M+H]⁺=331.2.

Step 2: (1,4-trans)-N¹,N¹-bis(2-Methoxyethyl)cyclohexane-1,4-diamine 2,2,2-trifluoroacetate

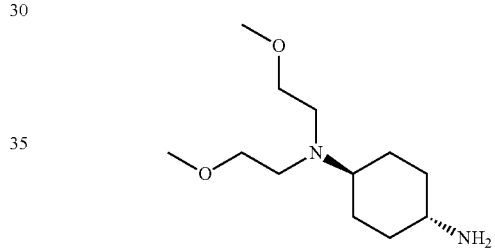

Prepared according to Example 204 step 2 using tert-butyl ((1,4-trans)-4-(bis(2-methoxyethyl)amino)cyclohexyl)carbamate (148 mg, 0.45 mmol), trifluoroacetic acid (600 µL, 7.84 mmol) and CH₂Cl₂ (1 mL) to provide the crude title compound (155 mg, 100% yield) which was used directly in the next step without further purification.

Step 3: N-(4-(2-(((1,4-trans)-4-(Bis(2-methoxyethyl)amino)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide

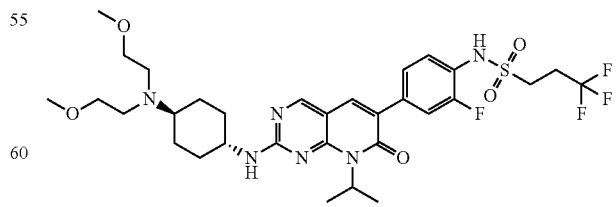

Prepared according to Example 198 step 6 using (1,4-trans)-N¹,N¹-bis(2-methoxyethyl)cyclohexane-1,4-diamine 2,2,2-trifluoroacetate (155 mg, 0.45 mmol), 3,3,3-trifluoro-N-[2-fluoro-4-(8-isopropyl-2-methylsulfonyl-7-oxo-pyrido

[2,3-d]pyrimidin-6-yl)phenyl]propane-1-sulfonamide (100 mg, 0.19 mmol) and N,N-diisopropylethylamine (195 µL, 1.12 mmol) and iPrOH (1.2 mL) to provide the title compound (64 mg, 50% yield).

Example 211: N-[2-Fluoro-4-[2-[[(3S,5S)-5-fluoro-3-piperidyl]amino]-8-(2-methoxyethyl)-7-oxo-pyrido[2,3-d]pyrimidin-6-yl]phenyl]-1-(2-fluorophenyl)methanesulfonamide hydrochloride Compound 211

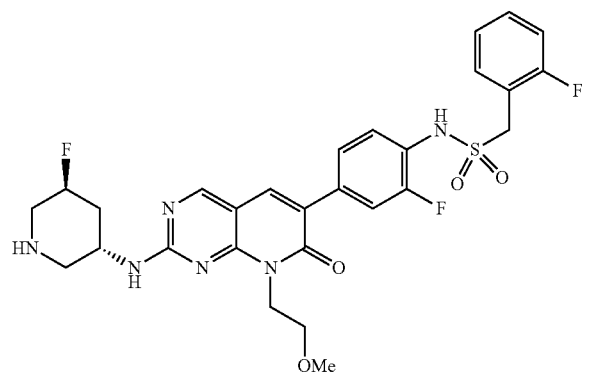 [SMILES: COCCn1c(=O)c(-c2ccc(NS(=O)(=O)Cc3ccccc3F)c(F)c2)cc2cnc(N[C@@H]3CNC[C@@H](F)C3)nc21]

Step 1: 6-Bromo-8-(2-methoxyethyl)-2-methylsulfanyl-pyrido[2,3-d]pyrimidin-7-one

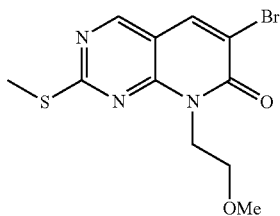 [SMILES: COCCn1c(=O)c(Br)cc2cnc(SC)nc21]

To a mixture of 6-bromo-2-methylsulfanyl-8H-pyrido[2,3-d]pyrimidin-7-one (0.10 g, 0.37 mmol) in DMF (2.5 mL) were added potassium carbonate (253 mg, 1.84 mmol) and 2-bromoethyl methyl ether (0.15 g, 1.1 mmol). The mixture was stirred at 50° C. for 2 hours then diluted with EtOAc (50 mL) and washed with water then with saturated aqueous sodium chloride. The organic layer was dried over Na$_2$SO$_4$, filtered and concentrated under reduced pressure to provide the title compound (115 mg, 95% yield) which was used in the next step without further purification. LCMS (ESI) [M+H]$^+$=331.9.

Step 2: 6-(4-Amino-3-fluoro-phenyl)-8-(2-methoxyethyl)-2-methylsulfanyl-pyrido[2,3-d]pyrimidin-7-one

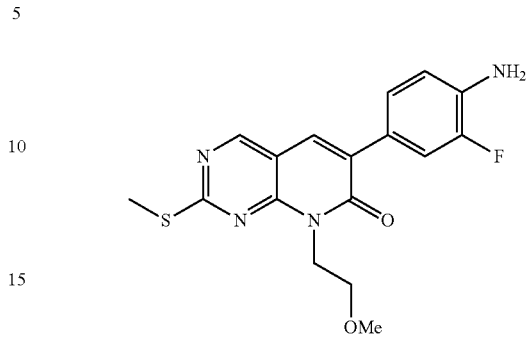

6-Bromo-8-(2-methoxyethyl)-2-methylsulfanyl-pyrido[2,3-d]pyrimidin-7-one (120 mg, 0.36 mmol) in a mixture of 1,2-dimethoxyethane (4 mL) and water (1 mL) was degassed with N$_2$ for 10 min. To the solution was then added 2-fluoro-4-(4,4,5,5-tetramethyl-1,3,2-dioxaborolan-2-yl)aniline (129 mg, 0.55 mmol), tri-o-tolylphosphine (44 mg, 0.15 mmol), Pd(OAc)$_2$ (16 mg, 0.07 mmol) and sodium carbonate (115 mg, 1.09 mmol). The reaction was stirred at 90° C. for 4 h. To the reaction was added toluene (5 mL) and silica gel and the mixture was concentrated under reduced pressure and purified by silica flash chromatography (0-100% EtOAc/heptanes) to provide the title compound (102 mg, 78% yield). LCMS (ESI) [M+H]$^+$=361.1.

Step 3: N-[2-Fluoro-4-[8-(2-methoxyethyl)-2-methylsulfanyl-7-oxo-pyrido[2,3-d]pyrimidin-6-yl]phenyl]-1-(2-fluorophenyl)methanesulfonamide

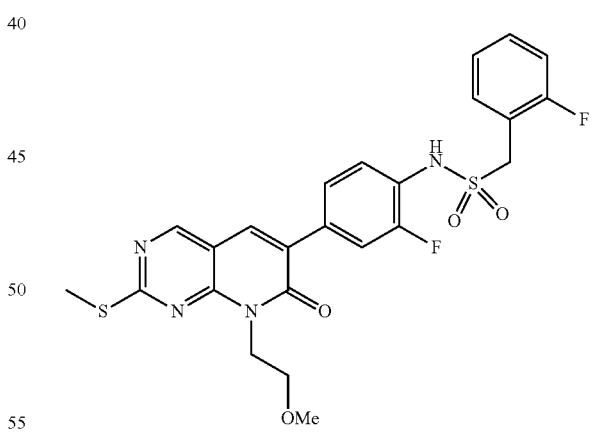

6-(4-Amino-3-fluoro-phenyl)-8-(2-methoxyethyl)-2-methylsulfanyl-pyrido[2,3-d]pyrimidin-7-one (115 mg, 0.32 mmol) was dissolved in pyridine (2 mL) and (2-fluorophenyl)methanesulfonyl chloride (133 mg, 0.64 mmol) was added. The reaction was stirred at rt for 1 h. Toluene and silica gel were added and the mixture was concentrated under reduced pressure and purified by silica flash chromatography (10-80% EtOAc/heptanes) to provide the title compound (92 mg, 54% yield). LCMS (ESI) [M+H]+=533.1.

Step 4: N-[2-Fluoro-4-[8-(2-methoxyethyl)-2-methylsulfonyl-7-oxo-pyrido[2,3-d]pyrimidin-6-yl]phenyl]-1-(2-fluorophenyl)methanesulfonamide

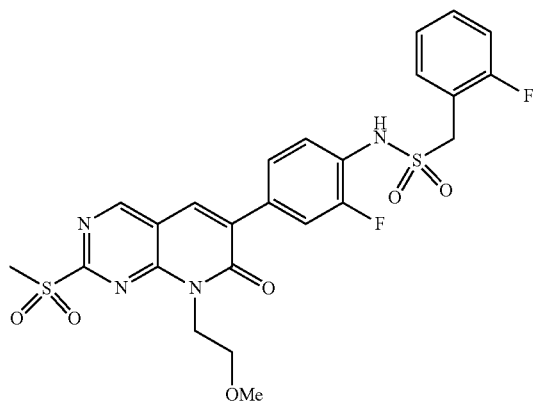 [SMILES: COCCn1c(=O)c(-c2ccc(NS(=O)(=O)Cc3ccccc3F)c(F)c2)cc2cnc(S(C)(=O)=O)nc21]

N-[2-Fluoro-4-[8-(2-methoxyethyl)-2-methylsulfanyl-7-oxo-pyrido[2,3-d]pyrimidin-6-yl]phenyl]-1-(2-fluorophenyl)methanesulfonamide (92 mg, 0.17 mmol) was dissolved in dichloromethane (5 mL). To the mixture was added 3-chlorobenzenecarboperoxoic acid (128 mg, 0.52 mmol, ~70% purity). The reaction was stirred at rt for 20 min then diluted with CH₂Cl₂ (30 mL) and washed with saturated aqueous sodium bicarbonate (2×10 mL). The organic layer was separated, dried over anhydrous Na₂SO₄, filtered and concentrated under reduced pressure to provide the title compound (97 mg, 99% yield) which was used directly in the next step without further purification. LCMS (ESI) [M+H]⁺=565.1.

Step 5: tert-Butyl (3S,5S)-3-fluoro-5-[[6-[3-fluoro-4-[(2-fluorophenyl)methylsulfonylamino]phenyl]-8-(2-methoxyethyl)-7-oxo-pyrido[2,3-d]pyrimidin-2-yl]amino]piperidine-1-carboxylate

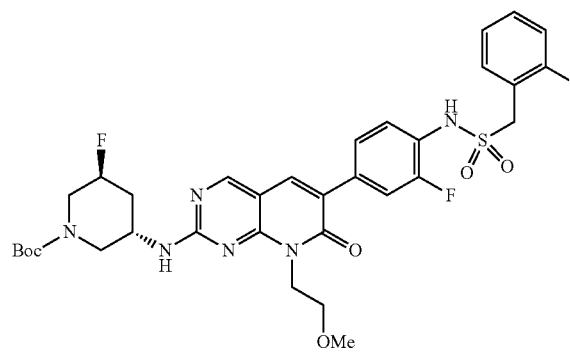

To N-[2-fluoro-4-[8-(2-methoxyethyl)-2-methylsulfonyl-7-oxo-pyrido[2,3-d]pyrimidin-6-yl]phenyl]-1-(2-fluorophenyl)methanesulfonamide (97 mg, 0.17 mmol) in iPrOH (3 mL) were added tert-butyl (3S,5S)-3-amino-5-fluoro-piperidine-1-carboxylate (60 mg, 0.27 mmol) and N,N-diisopropylethylamine (149 µL, 0.86 mmol). The reaction mixture was stirred at 50° C. for 1 day then concentrated to dryness with silica gel and purified by silica flash chromatography (20-100% EtOAc/heptanes) to provide the title compound (35 mg, 29% yield). LCMS (ESI) [M+H]⁺=565.1.

Step 6: N-[2-Fluoro-4-[2-[[(3S,5S)-5-fluoro-3-piperidyl]amino]-8-(2-methoxyethyl)-7-oxo-pyrido[2,3-d]pyrimidin-6-yl]phenyl]-1-(2-fluorophenyl)methanesulfonamide hydrochloride

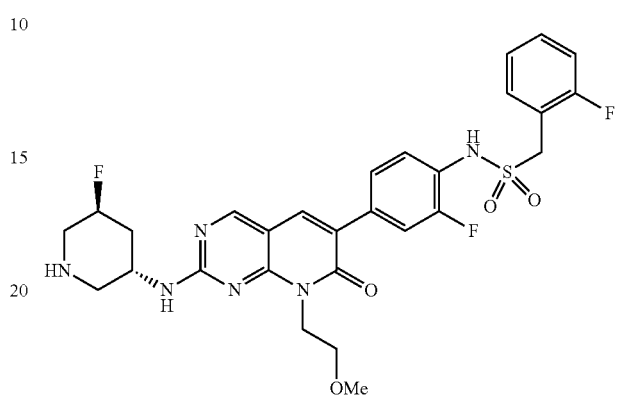

tert-Butyl (3S,5S)-3-fluoro-5-[[6-[3-fluoro-4-[(2-fluorophenyl)methylsulfonylamino]phenyl]-8-(2-methoxyethyl)-7-oxo-pyrido[2,3-d]pyrimidin-2-yl]amino]piperidine-1-carboxylate (35 mg, 0.05 mmol) was dissolved in 1,4-dioxane (1 mL). To the solution was added 2M HCl in dioxane (1 mL, 0.5 mmol). The reaction mixture was stirred at rt for 1 h then methyl-t-butyl-ether (15 mL) was added and the resulting solids were filtered off. The precipitate was dissolved in water and lyophilized to provide the title compound (24 mg, 75% yield).

Example 212: N-(4-(2-(((1,4-trans)-4-(2-Oxa-6-azaspiro[3.3]heptan-6-yl)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 212

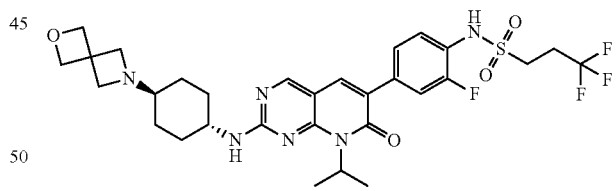

Step 1: tert-Butyl ((1,4-trans)-4-(2-oxa-6-azaspiro[3.3]heptan-6-yl)cyclohexyl)carbamate

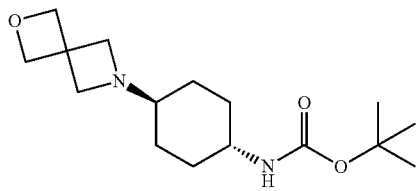 [SMILES: CC(C)(C)OC(=O)N[C@H]1CC[C@H](N2CC3(COC3)C2)CC1]

Prepared according to Example 198 step 4 using to N-Boc-trans-1,4-cyclohexanediamine (100 mg, 0.47 mmol), 3-bis(bromomethyl)oxetane (171 mg, 0.70 mmol) sodium carbonate (247 mg, 2.33 mmol) and MeCN (2.3 mL). The reaction was filtered, rinsed with MeCN and concentrated to provide the crude title compound (138 mg, 99% yield). LCMS (ESI) [M+H]$^+$=297.2.

Step 2: (1,4-trans)-4-(2-Oxa-6-azaspiro[3.3]heptan-6-yl)cyclohexanamine 2,2,2-trifluoroacetate

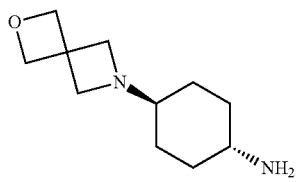

Prepared according to Example 204 step 2 using tert-butyl N-[4-(2-oxa-6-azaspiro[3.3]heptan-6-yl)cyclohexyl]carbamate (138 mg, 0.47 mmol), trifluoroacetic acid (800 μL, 10.4 mmol) and CH$_2$Cl$_2$ (4.7 mL) to provide the crude title compound (144 mg, 100% yield). LCMS (ESI) [M+H]$^+$=197.2.

Step 3: N-(4-(2-(((1,4-trans)-4-(2-Oxa-6-azaspiro[3.3]heptan-6-yl)cyclohexyl)amino)-8-isopropyl-7-oxo-7,8-dihydropyrido[2,3-d]pyrimidin-6-yl)-2-fluorophenyl)-3,3,3-trifluoropropane-1-sulfonamide

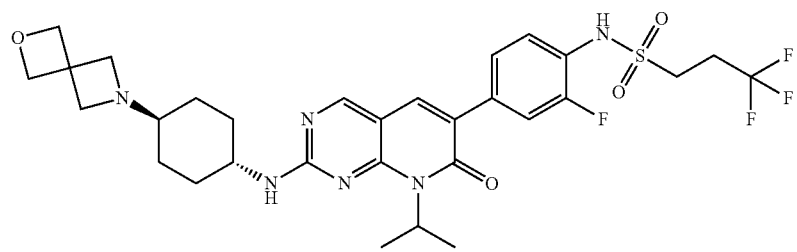 [SMILES: CC(C)n1c(=O)c(-c2ccc(NS(=O)(=O)CCC(F)(F)F)c(F)c2)cc2cnc(N[C@H]3CC[C@H](N4CC5(COC5)C4)CC3)nc21]

Prepared according to Example 198 step 6 using 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (85 mg, 0.16 mmol), 4-(2-oxa-6-azaspiro[3.3]heptan-6-yl)cyclohexanamine; 2,2,2-trifluoroacetic acid (143 mg, 0.46 mmol) and N,N-diisopropylethylamine (166 μL, 0.95 mmol). The crude was purified by Pre-HPLC (CSH column, 15-35% MeCN/10 mM aqueous ammonium bicarbonate, pH=10) to provide the title compound (31 mg, 30% yield).

Example 213: 3,3,3-Trifluoro-N-(2-fluoro-4-(8-isopropyl-2-(((1,4-trans)-4-morpholinocyclohexyl)amino)-7-oxo-7,8-dihydropyrido[2,3-d]pyrimidin-6-yl)phenyl)propane-1-sulfonamide Compound 213

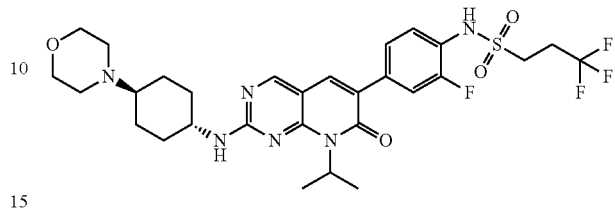

Step 1: tert-Butyl ((1,4-trans)-4-morpholinocyclohexyl)carbamate

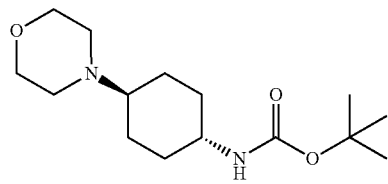 [SMILES: CC(C)(C)OC(=O)N[C@H]1CC[C@H](N2CCOCC2)CC1]

Prepared according to Example 210 step 1 using N-Boc-trans-1,4-cyclohexanediamine (100 mg, 0.47 mmol), bis(2-bromoethyl) ether (88 μL, 0.7 mmol), sodium carbonate (247 mg, 2.33 mmol) and MeCN (2.3 mL) to provide the crude title compound (132 mg, 100% yield). LCMS (ESI) [M+H]$^+$=285.2.

Step 2: (1,4-trans)-4-Morpholinocyclohexanamine 2,2,2-trifluoroacetate

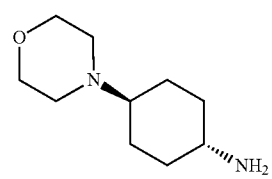 [SMILES: N[C@H]1CC[C@H](N2CCOCC2)CC1]

Prepared according to Example 204 step 2 using tert-butyl ((1,4-trans)-4-morpholinocyclohexyl)carbamate (132 mg, 0.47 mmol), trifluoroacetic acid (830 μL, 10.7 mmol) and CH₂Cl₂ (4.5 mL) to provide the crude title compound (138 mg, 100% yield).

Step 3: 3,3,3-Trifluoro-N-(2-fluoro-4-(8-isopropyl-2-(((1,4-trans)-4-morpholinocyclohexyl)amino)-7-oxo-7,8-dihydropyrido[2,3-d]pyrimidin-6-yl)phenyl)propane-1-sulfonamide

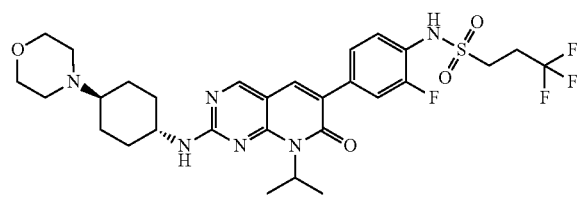 [SMILES: CC(C)n1c(=O)c(-c2ccc(NS(=O)(=O)CCC(F)(F)F)c(F)c2)cc2cnc(N[C@H]3CC[C@H](N4CCOCC4)CC3)nc21]

Prepared according to Example 204 step 3 using (1,4-trans)-4-morpholinocyclohexanamine 2,2,2-trifluoroacetate (138 mg, 0.47 mmol), 3,3,3-trifluoro-N-[2-fluoro-4-(8-isopropyl-2-methylsulfonyl-7-oxo-pyrido[2,3-d]pyrimidin-6-yl)phenyl]propane-1-sulfonamide (85 mg, 0.16 mmol) and N,N-diisopropylethylamine (165 μL, 0.95 mmol) and iPrOH (1.5 mL). The crude was purified by Prep-HPLC (CSH column, 20-40% MeCN/10 mM aqueous ammonium bicarbonate, pH=10) to provide the title compound (28 mg, 28% yield).

Example 214: N-(4-(2-((4-(dimethylamino)-4-methylcyclohexyl)amino)-8-isopropyl-7-oxo-7,8-dihydropyrido[2,3-d]pyrimidin-6-yl)-2,3,6-trifluorophenyl)-3,3,3-trifluoropropane-1-sulfonamide

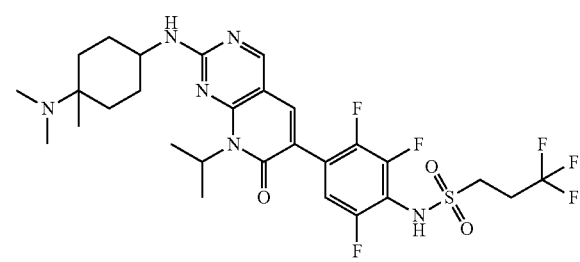 [SMILES: CC(C)n1c(=O)c(-c2cc(F)c(NS(=O)(=O)CCC(F)(F)F)c(F)c2F)cc2cnc(NC3CCC(C)(N(C)C)CC3)nc21]

The title compound was prepared analogous to Example 86 Steps 1-4 and Example 91 step 4.

Example 215

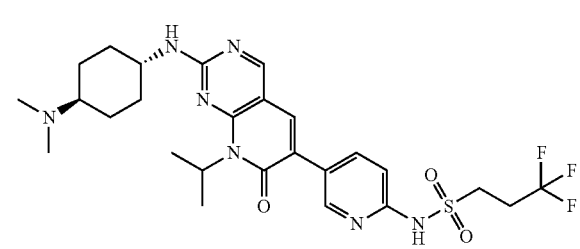

The title compound was prepared analogous to Example 91.

Example 216

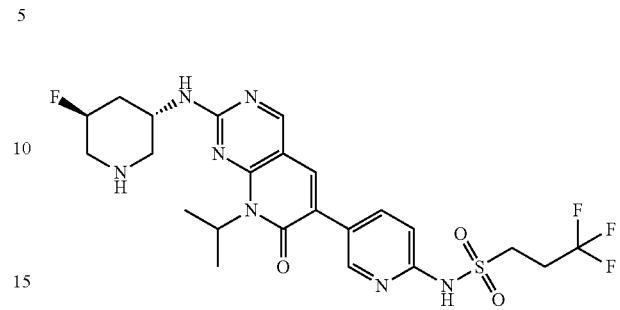

The title compound was prepared analogous to Example 91 Steps 1-3 and Example 86 steps 5-6.

Example 217

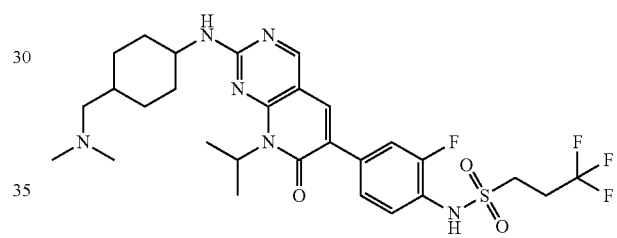

The title compound was prepared analogously to Example 91.

Example 218

The title compound was prepared analogously to Example 91.

Example 219

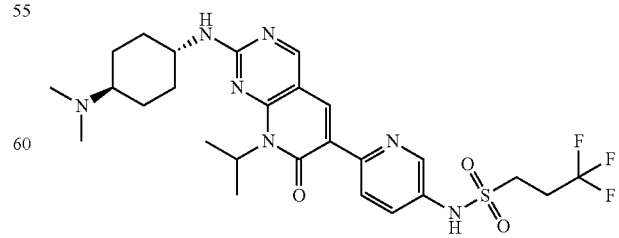

The title compound was prepared analogously to Example 91 and Example 86.

Example 220: N-(4-(2-((2-azaspiro[3.5]nonan-7-yl)amino)-8-isopropyl-7-oxo-7,8-dihydropyrido[2,3-d]pyrimidin-6-yl)-2-fluorophenyl)-3,3,3-trifluoropropane-1-sulfonamide

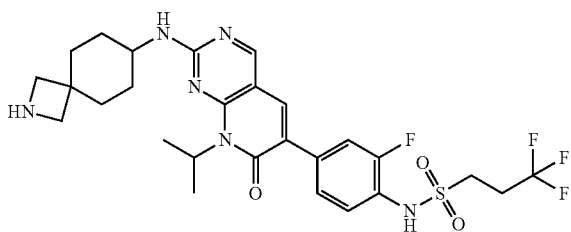 [SMILES: CC(C)n1c(=O)c(-c2ccc(NS(=O)(=O)CCC(F)(F)F)c(F)c2)cc2cnc(NC3CCC4(CC3)CNC4)nc21]

Starting with 3,3,3-trifluoro-N-(2-fluoro-4-(8-isopropyl-2-(methylsulfonyl)-7-oxo-7,8-dihydropyrido[2,3-d]pyrimidin-6-yl)phenyl)propane-1-sulfonamide and tert-butyl 7-amino-2-azaspiro[3.5]nonane-2-carboxylate and following step 5-6 of example 86, the title compound was obtained as an off-white solid. LCMS (ESI): [M+H]$^+$=597.3; $^1$H NMR (400 MHz, DMSO-d$_6$) δ 8.58 (br s, 1H), 8.29 (s, 1H), 7.80 (s, 1H), 7.72-7.62 (m, 1H), 7.36 (d, J=14.5 Hz, 1H), 7.29 (t, J=8.8 Hz, 1H), 7.21 (dd, J=8.7, 2.1 Hz, 1H), 5.80-5.70 (m, 1H), 3.64 (s, 2H), 3.58 (s, 2H), 3.41-3.39 (m, 2H), 2.97-2.90 (m, 2H), 2.65-2.58 (m, 1H), 2.05-1.97 (m, 2H), 1.89-1.80 (m, 2H), 1.61-1.46 (m, 10H).

Example 221: 3,3,3-Trifluoro-N-(2-fluoro-4-(8-isopropyl-2-((2-methyl-2-azaspiro[3.5]nonan-7-yl)amino)-7-oxo-7,8-dihydropyrido[2,3-d]pyrimidin-6-yl)phenyl)propane-1-sulfonamide

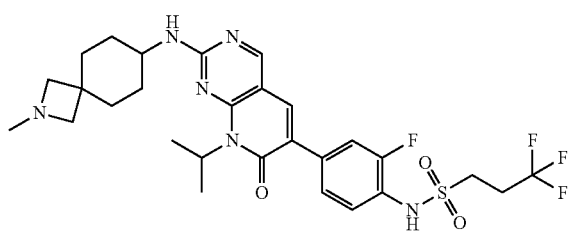 [SMILES: CC(C)n1c(=O)c(-c2ccc(NS(=O)(=O)CCC(F)(F)F)c(F)c2)cc2cnc(NC3CCC4(CC3)CN(C)C4)nc21]

To N-(4-(2-((2-azaspiro[3.5]nonan-7-yl)amino)-8-isopropyl-7-oxo-7,8-dihydropyrido[2,3-d]pyrimidin-6-yl)-2-fluorophenyl)-3,3,3-trifluoropropane-1-sulfonamide (65 mg, 0.11 mmol) in methanol (2.2 mL) was slowly added formaldehyde 13.3 M in water (0.041 mL, 0.55 mmol). The reaction mixture was stirred at 25° C. for 1 h and sodium cyanoborohydride (20.5 mg, 0.33 mmol) was added. The reaction mixture was stirred at 25° C. for 4 h. The residue was purified by prep-HPLC to afford the title compound (24.7 mg, 37% yield) as a beige solid. LCMS (ESI): [M+H]$^+$=611.3; $^1$H NMR (400 MHz, DMSO-d$_6$) δ 9.89 (br s, 1H), 8.64 (br s, 1H), 7.96 (s, 1H), 7.81 (d, J=7.6 Hz, 1H), 7.62 (dd, J=12.3, 2.0 Hz, 1H), 7.48 (dd, J=8.5, 2.0 Hz, 1H), 7.42 (t, J=8.4 Hz, 1H), 5.80-5.63 (m, 1H), 3.90-3.75 (m, 1H), 3.73 (s, 2H), 3.66 (s, 2H), 3.38-3.35 (m, 2H), 2.86-2.77 (m, 2H), 2.75 (s, 3H), 2.08-1.96 (m, 2H), 1.93-1.80 (m, 2H), 1.63-1.50 (m, 8H), 1.39-1.26 (m, 2H).

Example 222

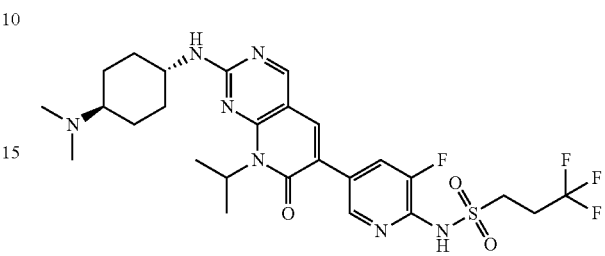

The title compound was prepared analogously to Example 91.

Example 223: N-(6-(2-(((1S,3R,4S)-4-(Dimethylamino)-3-fluorocyclohexyl)amino)-8-isopropyl-7-oxo-7,8-dihydropyrido[2,3-d]pyrimidin-6-yl)pyridin-3-yl)-3,3,3-trifluoropropane-1-sulfonamide

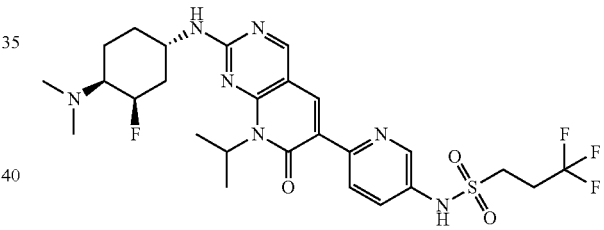

Step 1-3: N-(4-(2-((2-Azaspiro[3.5]nonan-7-yl)amino)-8-isopropyl-7-oxo-7,8-dihydropyrido[2,3-d]pyrimidin-6-yl)-2-fluorophenyl)-3,3,3-trifluoropropane-1-sulfonamide

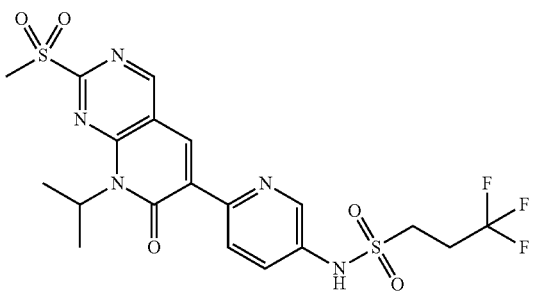 [SMILES: CC(C)n1c(=O)c(-c2ccc(NS(=O)(=O)CCC(F)(F)F)cn2)cc2cnc(S(C)(=O)=O)nc21]

Starting with 6-bromopyridin-3-amine and following steps 1-3 of example 91, the title compound was obtained a brown semi-solid. LCMS (ESI): [M+H]$^+$=520.2.

Step 4: tert-Butyl ((1S,2R,4S)-2-fluoro-4-((8-isopropyl-7-oxo-6-(5-((3,3,3-trifluoropropyl)sulfonamido)pyridin-2-yl)-7,8-dihydropyrido[2,3-d]pyrimidin-2-yl)amino)cyclohexyl)carbamate

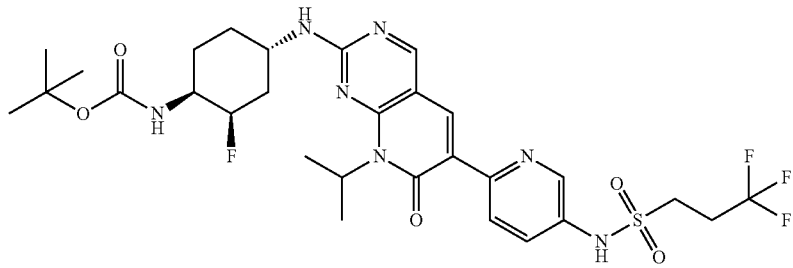 [SMILES: CC(C)n1c(=O)c(-c2ccc(NS(=O)(=O)CCC(F)(F)F)cn2)cc2cnc(N[C@H]3CC[C@H](NC(=O)OC(C)(C)C)[C@H](F)C3)nc21]

A solution of N-(4-(2-((2-azaspiro[3.5]nonan-7-yl)amino)-8-isopropyl-7-oxo-7,8-dihydropyrido[2,3-d]pyrimidin-6-yl)-2-fluorophenyl)-3,3,3-trifluoropropane-1-sulfonamide (104 mg, 0.20 mmol), cesium fluoride (91 mg, 0.60 mmol, DIEA (0.11 mL, 0.60 mmol) and tert-butyl N-[(1R,2S,4R)-4-amino-2-fluoro-cyclohexyl]carbamate hydrochloride (59 mg, 0.22 mmol) in DMSO (1.0 mL) was stirred at 50° C. for 18 h. The reaction mixture was diluted with dichloromethane (5 mL), 1N aq. NH₄Cl (3 mL) and water (3 mL). The aqueous layer was extracted with dichloromethane (5 mL). The combined organic layer was concentrated under reduced pressure to afford the title compound (233 mg, 173% yield) as a brown semi solid. LCMS (ESI): [M+H]⁺=672.4.

Step 5: N-(6-(2-(((1S,3R,4S)-4-Amino-3-fluorocyclohexyl)amino)-8-isopropyl-7-oxo-7,8-dihydropyrido[2,3-d]pyrimidin-6-yl)pyridin-3-yl)-3,3,3-trifluoropropane-1-sulfonamide

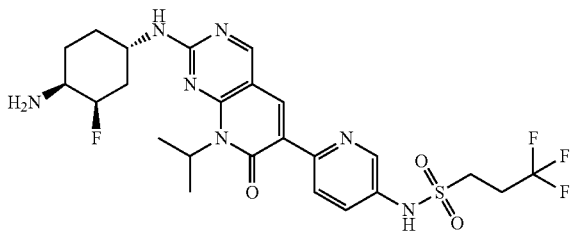 [SMILES: CC(C)n1c(=O)c(-c2ccc(NS(=O)(=O)CCC(F)(F)F)cn2)cc2cnc(N[C@H]3CC[C@H](N)[C@H](F)C3)nc21]

To crude tert-butyl ((1S,2R,4S)-2-fluoro-4-((8-isopropyl-7-oxo-6-(5-((3,3,3-trifluoropropyl)sulfonamido)pyridin-2-yl)-7,8-dihydropyrido[2,3-d]pyrimidin-2-yl)amino)cyclohexyl)carbamate (233 mg, 0.200 mmol) in dichloromethane (1.0 mL) was slowly added TFA (0.15 mL, 2.00 mmol). The reaction mixture was stirred at 25° C. for 18 h. The reaction mixture was diluted with 10% methanol in dichloromethane (5 mL) and 1N aq. NaHCO₃ (3.5 mL). The aqueous layer was extracted with 10% methanol in dichloromethane (3×5 mL). The combined organic layer was concentrated under reduced pressure to afford the title compound (115 mg, 101% yield) as a brown semi-solid. LCMS (ESI): [M+H]+=572.4.

Step 6: N-(6-(2-(((1S,3R,4S)-4-(Dimethylamino)-3-fluorocyclohexyl)amino)-8-isopropyl-7-oxo-7,8-dihydropyrido[2,3-d]pyrimidin-6-yl)pyridin-3-yl)-3,3,3-trifluoropropane-1-sulfonamide

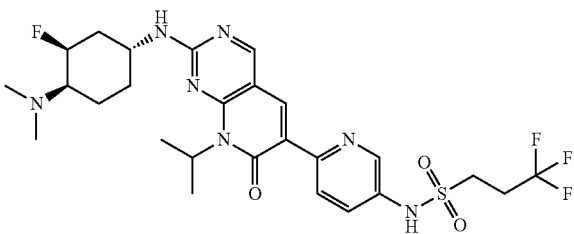 [SMILES: CC(C)n1c(=O)c(-c2ccc(NS(=O)(=O)CCC(F)(F)F)cn2)cc2cnc(N[C@@H]3CC[C@@H](N(C)C)[C@@H](F)C3)nc21]

To N-(6-(2-(((1S,3R,4S)-4-amino-3-fluorocyclohexyl)amino)-8-isopropyl-7-oxo-7,8-dihydropyrido[2,3-d]pyrimidin-6-yl)pyridin-3-yl)-3,3,3-trifluoropropane-1-sulfonamide (114 mg, 0.20 mmol) in methanol (4.0 mL) was slowly added formaldehyde (13.3 M in water) (0.075 mL, 1.00 mmol). The reaction mixture was stirred at 25° C. for 1 h and sodium cyanoborohydride (38 mg, 0.60 mmol) was added. The reaction mixture was stirred at 25° C. for 4 h. The mixture was neutralized with TFA (100 uL) and purified by prep-HPLC to afford the title compound contaminated with a reduced byproduct. The residue (20.0 mg, 0.033 mmol) and 2,3-dichloro-5,6-dicyano-1,4-benzoquinone (7.6 mg, 0.033 mmol) in 1,4-dioxane (0.17 mL) was stirred at 25° C. for 2 h. The crude mixture was purified by prep-HPLC to afford the title compound (16 mg, 13% yield) as a beige solid. LCMS (ESI): [M+H]⁺=600.3; ¹H NMR (400 MHz, DMSO-d₆) δ 10.42 (br s, 1H), 8.78 (br s, 1H), 8.54-8.49 (m, 2H), 8.35 (d, J=8.8 Hz, 1H), 8.06 (d, J=7.9 Hz, 1H), 7.71 (dd, J=8.8, 2.7 Hz, 1H), 5.85-5.68 (m, 1H), 5.64-5.38 (m, 1H), 4.25-4.10 (m, 1H), 3.46-3.43 (m, 2H), 2.85-2.75 (m, 8H), 2.22-2.05 (m, 2H), 1.93-1.65 (m, 2H), 1.65-1.45 (m, 8H), 1.40-1.24 (m, 1H).

Example 224

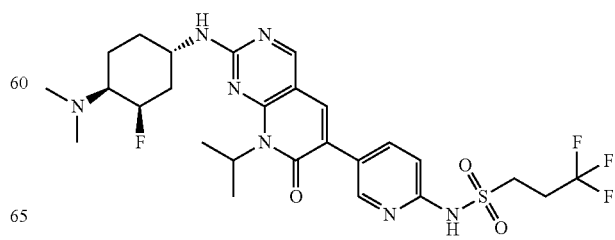

The title compound was prepared analogous to Example 223.

Example 225: N-(4-(2-((3-(Dimethylamino)-4-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide and N-(4-(2-((4-(dimethylamino)-3-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 225; Compound 226

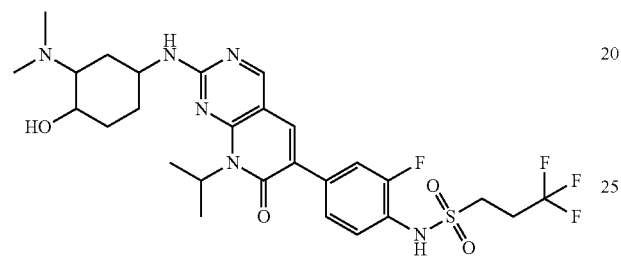

Step 1: tert-Butyl ((1S,3S,6R)-7-oxabicyclo[4.1.0]heptan-3-yl)carbamate

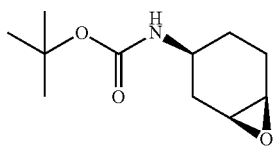

To a cooled to 0° C. solution of tert-butyl cyclohex-3-en-1-ylcarbamate (1000 mg, 5.07 mmol) in dichloromethane (16.9 mL) was added m-CPBA (1520 mg, 6.59 mmol). The reaction mixture was stirred at 0-25° C. for 3 h. The reaction mixture was diluted with dichloromethane (15 mL), sat. aq. NaHCO$_3$ (5 mL) and 1N aq. Na$_2$S$_2$O$_3$ (3.0 mL). The organic layer was washed with sat. aq. NaHCO$_3$ (5 mL), dried (Na$_2$SO$_4$) and concentrated under reduced pressure. The residue was purified by column chromatography (10% methanol in isopropyl acetate/heptane) to afford the title compound (865 mg, 80% yield) as a beige semi-solid. LCMS (ESI): [M+H]$^+$=214.2; $^1$H NMR (400 MHz, DMSO-d$_6$) δ 6.63 (d, J=8.1 Hz, 1H), 3.23-3.11 (m, 1H), 3.07-3.00 (m, 2H), 2.17-2.06 (m, 1H), 2.05-1.97 (m, 1H), 1.78 (ddd, J=15.5, 12.2, 5.3 Hz, 1H), 1.54 (dd, J=15.1, 11.0 Hz, 1H), 1.36 (s, 9H), 1.26-1.10 (m, 2H).

Step 2: tert-Butyl ((1S,3S,4S)-4-(dimethylamino)-3-hydroxycyclohexyl)carbamate and tert-butyl ((1S,3S,4S)-3-(dimethylamino)-4-hydroxycyclohexyl)carbamate

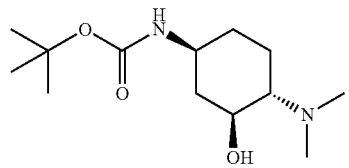

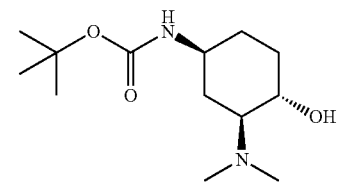

To a solution of tert-butyl ((1S,3S,6R)-7-oxabicyclo[4.1.0]heptan-3-yl)carbamate (200 mg, 0.94 mmol) and lithium perchlorate (998 mg, 9.34 mmol) in acetonitrile (4.69 mL) was added dimethylamine (2 M in THF) (2.34 mL, 4.69 mmol). The reaction mixture was stirred at 85° C. for 18 h. The reaction mixture was diluted with brine (5 mL). The aqueous layer was extracted with 10% methanol in dichloromethane (4×10 mL). The combined organic layer was concentrated under reduced pressure to afford the crude title compounds (681 mg, 281% yield) as a beige solid. LCMS (ESI): [M+H]$^+$=259.6.

Step 3: (1S,2S,5S)-5-Amino-2-(dimethylamino)cyclohexan-1-ol hydrogen chloride and (1S,2S,4S)-4-amino-2-(dimethylamino)cyclohexan-1-ol hydrogen chloride

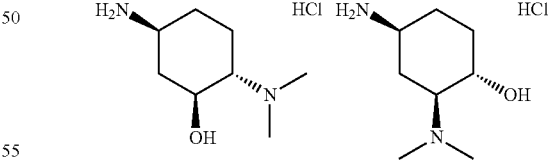

To crude tert-butyl ((1S,3S,4S)-4-(dimethylamino)-3-hydroxycyclohexyl)carbamate and tert-butyl ((1S,3S,4S)-3-(dimethylamino)-4-hydroxycyclohexyl)carbamate (300 mg, ~0.41 mmol) in dichloromethane (2.1 mL) was slowly added TFA (0.32 mL, 4.141 mmol). The reaction mixture was stirred at 25° C. for 4 h. Methanol (1 mL) and 1N aq. HCl (1 mL) were added and the reaction mixture was concentrated under reduced pressure to afford the crude title compounds (266 mg, 281% yield) as a beige semi-solid. LCMS (ESI): [M+H]+=159.2.

Step 4: N-(4-(2-((3-(Dimethylamino)-4-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide and N-(4-(2-((4-(dimethylamino)-3-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide

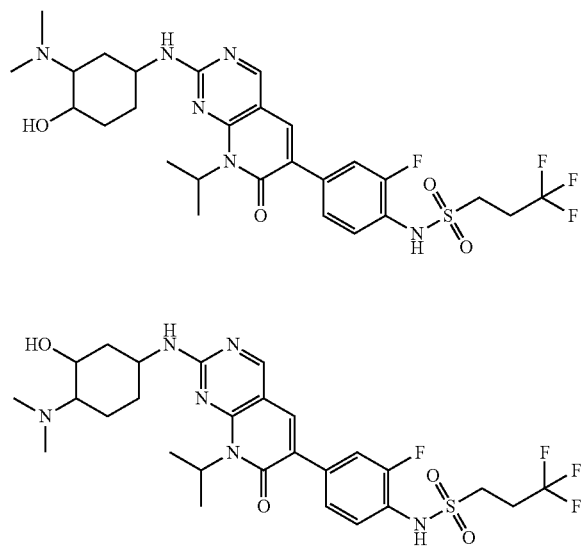

A solution of 3,3,3-trifluoro-N-(2-fluoro-4-(8-isopropyl-2-(methylsulfonyl)-7-oxo-7,8-dihydropyrido[2,3-d]pyrimidin-6-yl)phenyl)propane-1-sulfonamide (80.5 mg, 0.150 mmol), cesium fluoride (68.4 mg, 0.450 mmol), DIEA (0.079 mL, 0.450 mmol) and the crude mixture of (1S,2S,5S)-5-amino-2-(dimethylamino)cyclohexan-1-ol hydrogen chloride and (1S,2S,4S)-4-amino-2-(dimethylamino)cyclohexan-1-ol hydrogen chloride (1S,2S,5S)-5-amino-2-(dimethylamino)cyclohexanol (107 mg, ~ 0.17 mmol) in DMSO (0.75 mL) was stirred at 50° C. for 18 h. The reaction mixture was diluted with 10% methanol in dicholoromethane (7 mL) and 1N aq. NH₄Cl (2 mL). The aqueous layer was extracted with 10% methanol in dicholoromethane (2×7 mL). The combined organic layer was concentrated under reduced pressure. The residue was purified by prep-HPLC to afford N-(4-(2-((3-(dimethylamino)-4-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide (32 mg, 34% yield) as a beige solid. LCMS (ESI): [M+H]⁺=615.3; ¹H NMR (400 MHz, DMSO-d₆) δ 8.66 (br s, 1H), 8.03-7.94 (m, 2H), 7.64 (dd, J=12.2, 2.0 Hz, 1H), 7.50 (dd, J=8.4, 1.9 Hz, 1H), 7.44 (t, J=8.4 Hz, 1H), 5.85-5.70 (m, 2H), 4.10-3.82 (m, 1H), 3.81-3.70 (m, 1H), 3.44-3.35 (m, 2H), 3.10-3.01 (m, 1H), 2.85-2.67 (m, 8H), 2.31-2.20 (m, 1H), 2.15-1.92 (m, 2H), 1.56 (dd, J=19.7, 7.0 Hz, 6H), 1.51-1.33 (m, 3H). The minor regioisomer N-(4-(2-((3-(dimethylamino)-4-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide (11 mg, 12% yield) was isolated as a beige solid. LCMS (ESI): [M+H]⁺=615.3; ¹H NMR (400 MHz, DMSO-d₆) δ 8.69 (s, 1H), 8.13 (br s, 1H), 8.01 (s, 1H), 7.64 (dd, J=12.2, 1.9 Hz, 1H), 7.50 (dd, J=8.5, 2.0 Hz, 1H), 7.44 (t, J=8.4 Hz, 1H), 5.95-5.62 (m, 2H), 4.39-4.25 (m, 1H), 3.72-3.65 (m, 1H), 3.56-3.42 (m, 1H), 3.42-3.36 (m, 2H), 2.87-2.77 (m, 2H), 2.71 (s, 6H), 2.23-2.13 (m, 1H), 2.05-1.75 (m, 3H), 1.72-1.60 (m, 2H), 1.56 (d, J=6.9 Hz, 6H).

Example 227: N-(4-(2-(((1R,3R,4R)-4-(Dimethylamino)-3-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide and N-(4-(2-(((1S,3S,4S)-4-(dimethylamino)-3-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide Compound 227; Compound 228

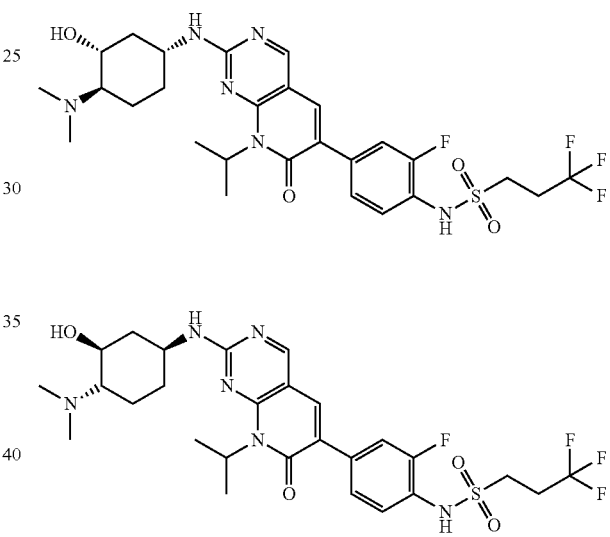

The title compounds were obtained after chiral SFC separation of N-(4-(2-((3-(dimethylamino)-4-hydroxycyclohexyl)amino)-8-isopropyl-7-oxo-7,8-dihydropyrido[2,3-d]pyrimidin-6-yl)-2-fluorophenyl)-3,3,3-trifluoropropane-1-sulfonamide.

Peak 1: LCMS (ESI): [M+H]⁺=615.3; ¹H NMR (400 MHz,) δ 8.67 (br s, 1H), 8.01-7.83 (m, 2H), 7.64 (dd, J=12.2, 2.0 Hz, 1H), 7.51 (dd, J=8.5, 2.0 Hz, 1H), 7.44 (t, J=8.3 Hz, 1H), 5.87-5.67 (m, 2H), 4.08-3.82 (m, 1H), 3.79-3.70 (m, 1H), 3.43-3.38 (m, 2H), 3.12-2.97 (m, 1H), 2.87-2.77 (m, 2H), 2.74 (s, 6H), 2.35-2.20 (m, 1H), 2.15-1.92 (m, 2H), 1.62-1.53 (m, 6H), 1.52-1.30 (m, 3H); tR=1.03 min, Cellulose-1, CO₂:MeOH (0.1% NH₄OH)=75:25.

Peak 2: LCMS (ESI): [M+H]⁺=615.3; ¹H NMR (400 MHz,) δ 8.63 (br s, 1H), 7.87 (s, 1H), 7.81 (d, J=7.8 Hz, 1H), 7.52-7.44 (m, 1H), 7.40-7.29 (m, 2H), 5.89-5.65 (m, 1H), 4.53-4.35 (m, 1H), 4.00-3.75 (m, 1H), 3.54-3.48 (m, 1H), 3.16-3.08 (m, 2H), 2.76-2.63 (m, 2H), 2.38-2.32 (m, 7H), 2.27-2.15 (m, 1H), 2.06-1.95 (m, 1H), 1.85-1.72 (m, 1H), 1.61-1.50 (m, 6H), 1.34-1.22 (m, 3H); tR=1.59 min, Cellulose-1, CO₂:MeOH (0.1% NH₄OH)=75:25.

Example 229: N-(4-(2-(((1r,4r)-4-(Dimethylamino)cyclohexyl)amino)-8-isopropyl-7-oxo-7,8-dihydropyrido[2,3-d]pyrimidin-6-yl)-2-fluorophenyl)-3,3-difluorobutane-1-sulfonamide Compound 229

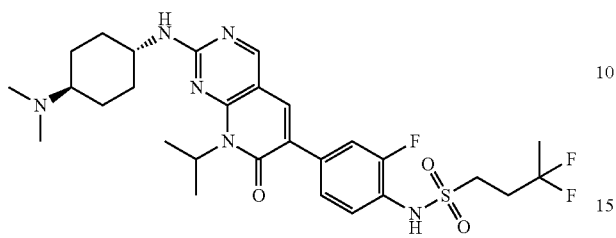

Step 1: 6-Bromo-8-isopropyl-2-(methylsulfonyl)pyrido[2,3-d]pyrimidin-7(8H)-one

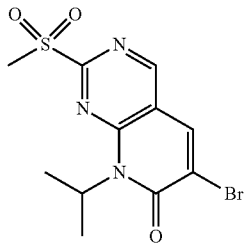 [SMILES: CC(C)n1c(=O)c(Br)cc2cnc(S(C)(=O)=O)nc21]

To a solution of 6-bromo-8-isopropyl-2-(methylthio)pyrido[2,3-d]pyrimidin-7(8H)-one (1000 mg, 3.18 mmol), in 1,4-dioxane (21.0 mL) was added oxone (4304 mg, 7.00 mmol) and water (5.30 mL). The reaction mixture was stirred at 25° C. for 18 h. The reaction mixture was diluted with dichloromethane (40 mL), brine (10 mL) and 1N aq. Na$_2$S$_2$O$_3$ (5 mL). The aqueous layer was extracted with dichloromethane (2×20 mL). The combined organic layer was dried (Na$_2$SO$_4$) and concentrated under reduced pressure to afford the title compound (1042 mg, 95% yield) as a beige semi-solid. LCMS (ESI): [M+H]$^+$=346.1.

Step 2: 6-Bromo-2-(((1r,4r)-4-(dimethylamino)cyclohexyl)amino)-8-isopropylpyrido[2,3-d]pyrimidin-7(8H)-one

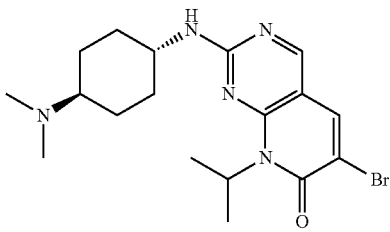 [SMILES: CC(C)n1c(=O)c(Br)cc2cnc(N[C@H]3CC[C@H](N(C)C)CC3)nc21]

A solution of 6-bromo-8-isopropyl-2-(methylsulfonyl)pyrido[2,3-d]pyrimidin-7(8H)-one (685 mg, 1.98 mmol), cesium fluoride (902 mg, 5.94 mmol), DIEA (1.04 mL, 5.94 mmol) and (1r,4r)-N$^1$,N$^1$-dimethylcyclohexane-1,4-diamine (310 mg, 2.18 mmol) in DMSO (9.9 mL) was stirred at 50° C. for 18 h. The reaction mixture was diluted with 10% methanol in dicholoromethane (25 mL) and 1N aq. NH$_4$Cl (15 mL). The aqueous layer was extracted with 10% methanol in dicholoromethane (2×10 mL). The combined organic layer was concentrated under reduced pressure. The residue was purified by prep-HPLC to afford the title compound (275 mg, 34% yield) as a beige solid. LCMS (ESI): [M+H]$^+$=408.2; $^1$H NMR (400 MHz, DMSO-d$_6$) δ 8.57 (br s, 1H), 8.21 (s, 1H), 7.91 (d, J=7.7 Hz, 1H), 5.83-5.65 (m, 1H), 3.83-3.60 (m, 1H), 2.17 (s, 6H), 2.14-2.07 (m, 1H), 2.03-1.92 (m, 2H), 1.87-1.75 (m, 2H), 1.57-1.47 (m, 6H), 1.33-1.19 (m, 4H).

Step 3: 6-(4-Amino-3-fluorophenyl)-2-(((1r,4r)-4-(dimethylamino)cyclohexyl)amino)-8-isopropylpyrido[2,3-d]pyrimidin-7(8H)-one

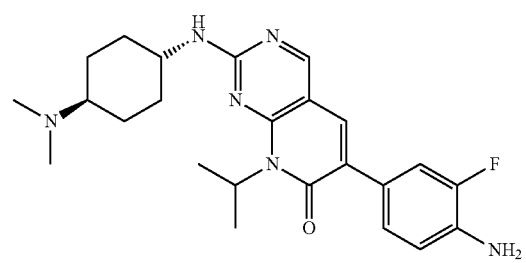

A solution of 6-bromo-2-(((1r,4r)-4-(dimethylamino)cyclohexyl)amino)-8-isopropylpyrido[2,3-d]pyrimidin-7(8H)-one (163 mg, 0.40 mmol), potassium phosphate (170 mg, 0.80 mmol), SPhos Pd G3 (15.6 mg, 0.020 mmol) and 2-fluoro-4-(4,4,5,5-tetramethyl-1,3,2-dioxaborolan-2-yl)aniline (104 mg, 0.44 mmol) in 1,4-dioxane (2.0 mL) and water (0.20 mL) was stirred at 60° C. for 18 h. The reaction mixture was diluted with aq. 1N NH$_4$Cl (0.8 mL), water (2 mL) and 10% methanol in dicholoromethane (7 mL). The aqueous layer was extracted with 10% methanol in dicholoromethane (2×5 mL). The combined organic layer was dried (Na$_2$SO$_4$) and concentrated under reduced pressure to afford the crude title compound (286 mg, 163% yield) as a brown oil. LCMS (ESI): [M+H]$^+$=439.3; $^1$H NMR (400 MHz, DMSO-d$_6$) δ 8.58 (br s, 1H), 7.77 (s, 1H), 7.68 (d, J=7.8 Hz, 1H), 7.44-7.35 (m, 1H), 7.22 (d, J=8.1 Hz, 1H), 6.76 (t, J=9.0 Hz, 1H), 5.82-5.62 (m, 1H), 5.26 (s, 2H), 3.83-3.63 (m, 1H), 2.18 (s, 6H), 2.15-2.08 (m, 1H), 2.05-1.92 (m, 2H), 1.91-1.80 (m, 2H), 1.60-1.51 (m, 6H), 1.40-1.26 (m, 4H).

Step 4: N-(4-(2-(((1r,4r)-4-(Dimethylamino)cyclohexyl)amino)-8-isopropyl-7-oxo-7,8-dihydropyrido[2,3-d]pyrimidin-6-yl)-2-fluorophenyl)-3,3-difluorobutane-1-sulfonamide

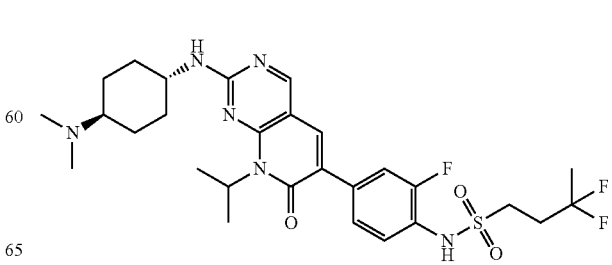

A cooled to 0° C. solution of 6-(4-amino-3-fluorophenyl)-2-(((1r,4r)-4-(dimethylamino)cyclohexyl)amino)-8-isopropylpyrido[2,3-d]pyrimidin-7(8H)-one (43.8 mg, 0.10 mmol), 3,3-difluorobutane-1-sulfonyl chloride (28.9 mg, 0.15 mmol) in pyridine (0.50 mL) was stirred at 0° C. to room temperature for 18 h. 3,3-difluorobutane-1-sulfonyl chloride (15 µL, ~ 0.075 mmol) was added and the mixture stirred at 25° C. for 48 h. The crude mixture was purified by prep-HPLC to afford the title compound (54 mg, 91% yield) as a beige solid. LCMS (ESI): [M+H]⁺=595.4; ¹H NMR (400 MHz, DMSO-d₆) δ 8.62 (br s, 1H), 7.89 (s, 1H), 7.78 (d, J=7.7 Hz, 1H), 7.55-7.47 (m, 1H), 7.41-7.31 (m, 2H), 5.85-5.65 (m, 1H), 3.85-3.67 (m, 1H), 3.15-3.06 (m, 2H), 2.40-2.26 (m, 2H), 2.23 (s, 6H), 2.10-1.77 (m, 5H), 1.69-1.51 (m, 9H), 1.37-1.23 (m, 4H).

Example 230

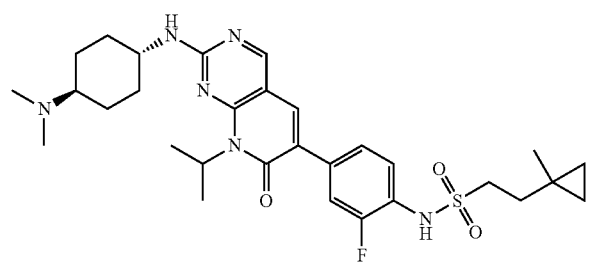 [SMILES: CC(C)n1c(=O)c(-c2ccc(NS(=O)(=O)CCC3(C)CC3)c(F)c2)cc2cnc(N[C@H]3CC[C@H](N(C)C)CC3)nc21]

The title compound was prepared analogous to Example 229.

Example 231

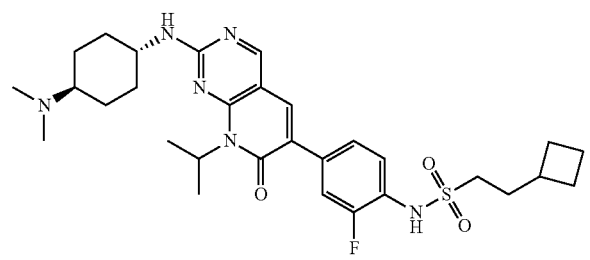 [SMILES: CC(C)n1c(=O)c(-c2ccc(NS(=O)(=O)CCC3CCC3)c(F)c2)cc2cnc(N[C@H]3CC[C@H](N(C)C)CC3)nc21]

The title compound was prepared analogous to Example 229.

Example 232

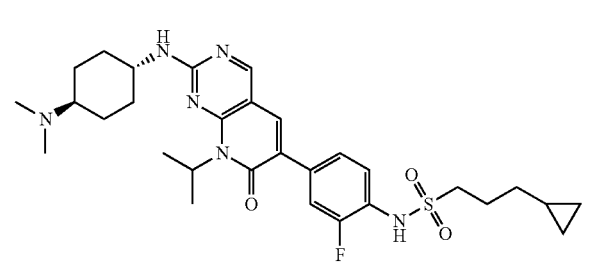 [SMILES: CC(C)n1c(=O)c(-c2ccc(NS(=O)(=O)CCCC3CC3)c(F)c2)cc2cnc(N[C@H]3CC[C@H](N(C)C)CC3)nc21]

The title compound was prepared analogous to Example 229.

Example 233: N-(5-(2-(((1r,4r)-4-(Dimethylamino)cyclohexyl)amino)-8-isopropyl-7-oxo-7,8-dihydropyrido[2,3-d]pyrimidin-6-yl)pyrimidin-2-yl)-3,3,3-trifluoropropane-1-sulfonamide Compound 233

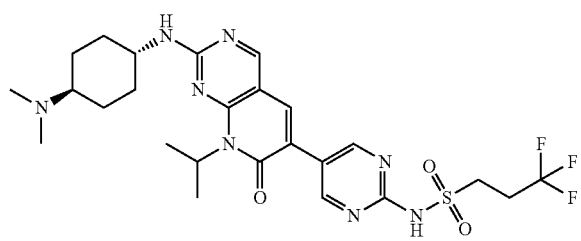 [SMILES: CC(C)n1c(=O)c(-c2cnc(NS(=O)(=O)CCC(F)(F)F)nc2)cc2cnc(N[C@H]3CC[C@H](N(C)C)CC3)nc21]

Step 1: N-(5-Chloropyrimidin-2-yl)-3,3,3-trifluoropropane-1-sulfonamide

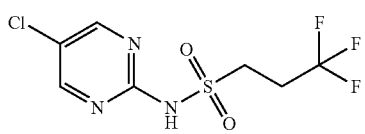 [SMILES: O=S(=O)(CCC(F)(F)F)Nc1ncc(Cl)cn1]

To a solution of 2,5-dichloropyrimidine (149 mg, 1.00 mmol) and 3,3,3-trifluoropropane-1-sulfonamide (213 mg, 1.20 mmol) in 1,4-dioxane (5.0 mL) was added DIEA (0.26 mL, 1.50 mmol). The reaction mixture was stirred at 100° C. for 24 h. NaH (48 mg, 1.20 mmol) was added and the reaction mixture was stirred at 100° C. for 3 days. The reaction mixture was neutralized with TFA (40 mL) and purified by prep-HPLC to afford the title compound (62 mg, 21% yield) as a beige solid. LCMS (ESI): [M+H]⁺=290.1; ¹H NMR (400 MHz, DMSO-d₆) δ 11.79 (s, 1H), 8.68 (s, 2H), 3.73 (dd, J=9.8, 6.1 Hz, 2H), 2.78-2.69 (m, 2H).

Step 2: N-(5-(2-(((1r,4r)-4-(Dimethylamino)cyclohexyl)amino)-8-isopropyl-7-oxo-7,8-dihydropyrido[2,3-d]pyrimidin-6-yl)pyrimidin-2-yl)-3,3,3-trifluoropropane-1-sulfonamide

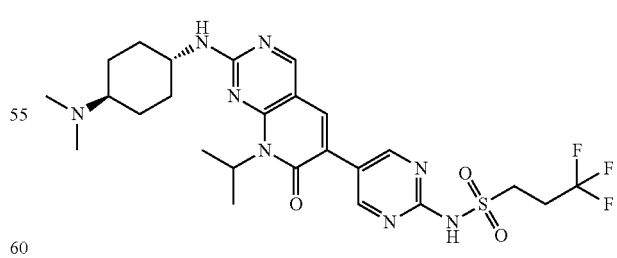

A solution of N-(5-chloropyrimidin-2-yl)-3,3,3-trifluoropropane-1-sulfonamide (24.0 mg, 0.083 mmol), cataCXium Pd G4 (3.1 mg, 0.0041 mmol), bis(pinacolato)diboron (27.4 mg, 0.11 mmol) and potassium acetate (24.4 mg, 0.25 mmol) in 1,4-dioxane (0.28 mL) was stirred at 60° C. for 3 days. CataCXium Pd G4 (3.1 mg, 0.0041 mmol), bis(pinacolato)diboron (27.4 mg, 0.11 mmol) and 6-bromo-2-(((1r,4r)-4-(dimethylamino)cyclohexyl)amino)-8-isopropylpyrido[2,3-d]pyrimidin-7(8H)-one (44 mg, 0.11 mmol) were added and the mixture was stirred at 60° C. for 18 h. Potassium phosphate (64 mg, 0.30 mmol), SPhos Pd G3 (4 mg, 0.005 mmol) and water (0.10 mL) were added and the mixture was stirred at 60° C. for 18 h. The crude mixture was purified by prep-HPLC to afford the title compound (5 mg, 10% yield) as a white solid. LCMS (ESI): $[M+H]^+=583.3$; $^1$H NMR (400 MHz, DMSO-$d_6$) δ 8.58 (br s, 1H), 8.50 (s, 2H), 7.82 (s, 1H), 7.70 (d, J=7.8 Hz, 1H), 5.80-5.64 (m, 1H), 4.12-4.06 (m, 2H), 3.49-3.40 (m, 2H), 2.18 (s, 6H), 2.03-1.98 (m, 2H), 1.88-1.80 (m, 2H), 1.60-1.54 (m, 6H), 1.30-1.26 (m, 6H).

Example 234: 3,3,3-Trifluoro-N-(2-fluoro-4-(8-isopropyl-2-((2-(2-methoxyethyl)-2-azaspiro[3.5]nonan-7-yl)amino)-7-oxo-7,8-dihydropyrido[2,3-d]pyrimidin-6-yl)phenyl)propane-1-sulfonamide Compound 234

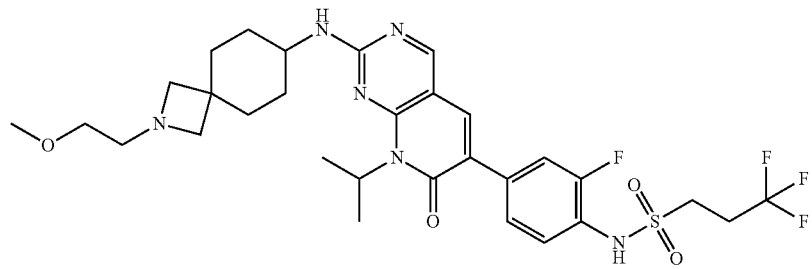 [SMILES: COCCN1CC2(CCC(Nc3ncc4cc(-c5ccc(NS(=O)(=O)CCC(F)(F)F)c(F)c5)c(=O)n(C(C)C)c4n3)CC2)C1]

A solution of N-(4-(2-((2-azaspiro[3.5]nonan-7-yl)amino)-8-isopropyl-7-oxo-7,8-dihydropyrido[2,3-d]pyrimidin-6-yl)-2-fluorophenyl)-3,3,3-trifluoropropane-1-sulfonamide (34.0 mg, 0.057 mmol), 2-bromoethyl methyl ether (9.51 mg, 0.068 mmol) and potassium carbonate (11.8 mg, 0.086 mmol) in DMF (0.29 mL) was stirred at 25° C. for 3 days. The crude mixture was purified by prep-HPLC to afford the title compound (6.7 mg, 18% yield) as a beige solid. LCMS (ESI): $[M+H]^+=655.3$; $^1$H NMR (400 MHz, DMSO-$d_6$) δ 8.62 (br s, 1H), 7.91 (s, 1H), 7.76 (d, J=7.8 Hz, 1H), 7.56 (dd, J=12.5, 1.8 Hz, 1H), 7.45-7.34 (m, 2H), 5.78-5.68 (m, 1H), 3.80-3.67 (m, 1H), 3.27-3.21 (m, 7H), 3.17 (d, J=3.8 Hz, 1H), 3.10 (br s, 2H), 3.04 (br s, 2H), 2.80-2.65 (m, 4H), 1.99-1.89 (m, 2H), 1.87-1.77 (m, 2H), 1.59-1.45 (m, 8H), 1.40-1.29 (m, 2H).

Example 235

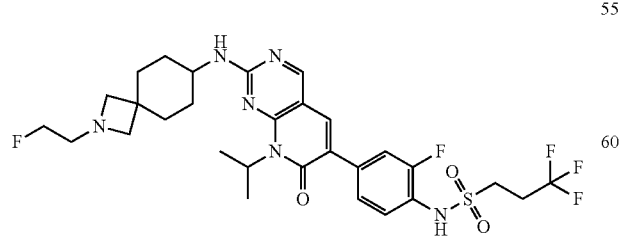

The title compound was prepared analogous to Example 234.

Example 236: N-[5-[2-[[(3S,5S)-5-fluoro-3-piperidyl]amino]-8-isopropyl-7-oxo-pteridin-6-yl]-2-pyridyl]-1-phenyl-methanesulfonamide Compound 236

Step 1: tert-Butyl (3S,5S)-3-[[6-(6-amino-3-pyridyl)-8-isopropyl-7-oxo-pteridin-2-yl]amino]-5-fluoro-piperidine-1-carboxylate

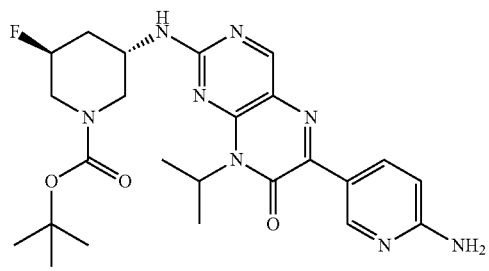 [SMILES: CC(C)n1c(=O)c(-c2ccc(N)nc2)nc2cnc(N[C@H]3C[C@H](F)CN(C(=O)OC(C)(C)C)C3)nc21]

tert-Butyl (3S,5S)-3-[(6-bromo-8-isopropyl-7-oxo-pteridin-2-yl)amino]-5-fluoro-piperidine-1-carboxylate (125 mg) was reacted with 2-aminopyridine-5-boronic acid pinacol ester as in example 73 (step 1) and purified via reverse phase HPLC to afford 129 mg (quantitative yield) of the title compound. LCMS (ESI): $[M+H]^+=499$ Step 2: tert-Butyl (3S,5S)-3-[[6-[6-(benzylsulfonylamino)-3-pyridyl]-8-isopropyl-7-oxo-pteridin-2-yl]amino]-5-fluoro-piperidine-1-carboxylate

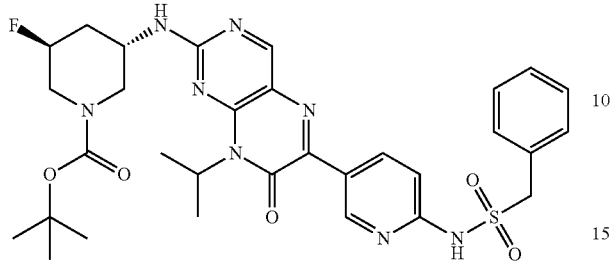

tert-Butyl (3S,5S)-3-[[6-(6-amino-3-pyridyl)-8-isopropyl-7-oxo-pteridin-2-yl]amino]-5-fluoro-piperidine-1-carboxylate (65 mg, 0.13 mmol) was reacted with alpha-toluenesulfonyl chloride (50 mg, 0.26 mmol) as in example 73 (step 2) and purified via normal phase chromatography (0-100% heptanes to IprOAc over 25 mins) to afford the title compound (50 mg, 23% yield). LCMS (ESI): $[M+H]^+=653.3$.

Step 3: N-[5-[2-[[(3S,5S)-5-Fluoro-3-piperidyl]amino]-8-isopropyl-7-oxo-pteridin-6-yl]-2-pyridyl]-1-phenyl-methanesulfonamide

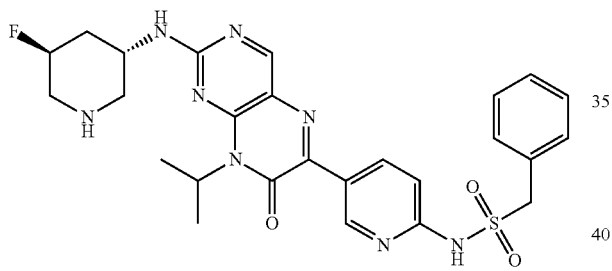

tert-Butyl (3S,5S)-3-[[6-[6-(benzylsulfonylamino)-3-pyridyl]-8-isopropyl-7-oxo-pteridin-2-yl]amino]-5-fluoro-piperidine-1-carboxylate (85 mg, 0.13 mmol) was reacted as in example 73 (step 3) and purified by reverse phase chromatography to afford the title compound (9.5 mg, 13% yield).

Example 237: 1-(2-Fluorophenyl)-N-[5-[2-[[(3S,5S)-5-fluoro-3-piperidyl]amino]-8-isopropyl-7-oxo-pteridin-6-yl]-2-pyridyl]methanesulfonamide Compound 237

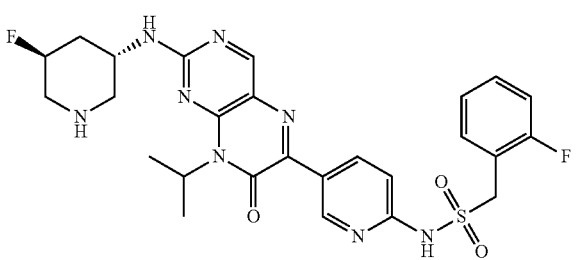 [SMILES: CC(C)n1c(=O)c(-c2ccc(NS(=O)(=O)Cc3ccccc3F)nc2)nc2cnc(N[C@@H]3CNC[C@@H](F)C3)nc21]

The title compound was prepared according to Example 236. This provides the title compound (16.8 mg, 23% yield) as a yellow solid.

Example 238: N-[5-[2-[[4-(Dimethylamino)cyclohexyl]amino]-8-isopropyl-7-oxo-pteridin-6-yl]-2-pyridyl]-3,3-difluoro-butane-1-sulfonamide Compound 238

Step 1: 6-(6-Amino-3-pyridyl)-2-[[4-(dimethylamino)cyclohexyl]amino]-8-isopropyl-pteridin-7-one

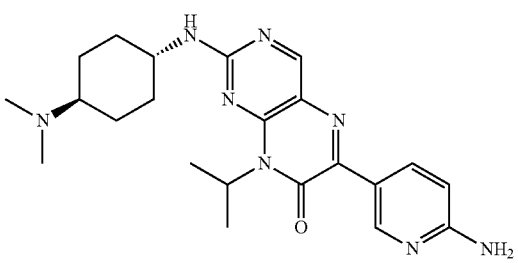

6-Bromo-2-[[4-(dimethylamino)cyclohexyl]amino]-8-isopropyl-pteridin-7-one (75 mg) was reacted with 2-aminopyridine-5-boronic acid pinacol ester as in example 73 (step 1) and purified via reverse phase HPLC to afford 40 mg (52%) of the title compound. LCMS (ESI): $[M+H]^+=423$.

Step 2: N-[5-[2-[[4-(Dimethylamino)cyclohexyl]amino]-8-isopropyl-7-oxo-pteridin-6-yl]-2-pyridyl]-3,3-difluoro-butane-1-sulfonamide

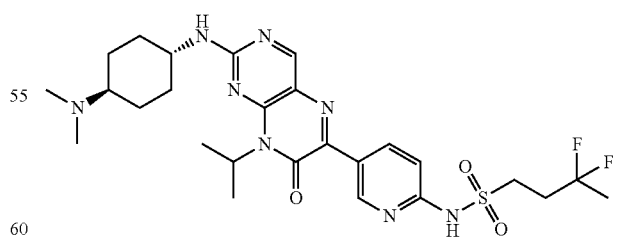

6-(6-Amino-3-pyridyl)-2-[[4-(dimethylamino)cyclohexyl]amino]-8-isopropyl-pteridin-7-one (40 mg) was reacted with 3,3-difluorobutane-1-sulfonyl chloride as in example 73 (step 2) and purified via reverse phase chromatography to afford the title compound (18.1 mg, 32% yield).

Example 239: N-[5-[2-[[4-(Dimethylamino)cyclohexyl]amino]-8-isopropyl-7-oxo-pteridin-6-yl]-2-pyridyl]-3,3-difluoro-butane-1-sulfonamide Compound 239

Step 1: 6-(4-Amino-3,5-difluoro-phenyl)-2-[[4-(dimethylamino)cyclohexyl]amino]-8-isopropyl-pteridin-7-one

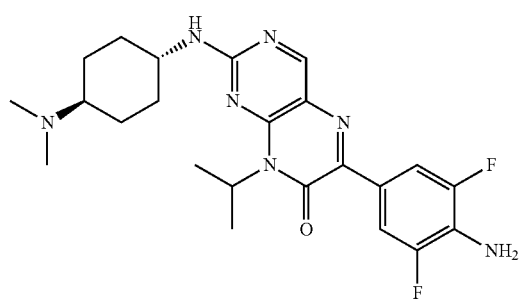 [SMILES: CC(C)n1c(=O)c(-c2cc(F)c(N)c(F)c2)nc2cnc(N[C@H]3CC[C@H](N(C)C)CC3)nc21]

6-Bromo-2-[[4-(dimethylamino)cyclohexyl]amino]-8-isopropyl-pteridin-7-one (1.1 g) was reacted with 2,6-difluoro-4-(4,4,5,5-tetramethyl-1,3,2-dioxaborolan-2-yl)aniline as in example 73 (step 1) and purified via normal phase chromatography (ISCO, 0-40% MeOH w/1% TEA in DCM to afford 1.1 g (91%) of the title compound. LCMS (ESI): [M+H]$^+$=458.

Step 2: N-[4-[2-[[4-(Dimethylamino)cyclohexyl]amino]-8-isopropyl-7-oxo-pteridin-6-yl]-2,6-difluoro-phenyl]-3,3,3-trifluoro-propane-1-sulfonamide

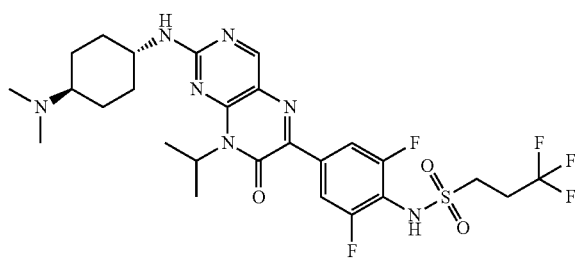 [SMILES: CC(C)n1c(=O)c(-c2cc(F)c(NS(=O)(=O)CCC(C)(F)F)c(F)c2)nc2cnc(N[C@H]3CC[C@H](N(C)C)CC3)nc21]

To a vial containing 6-(4-amino-3,5-difluoro-phenyl)-2-[[4-(dimethylamino)cyclohexyl]amino]-8-isopropyl-pteridin-7-one (50 mg, 0.11 mmol) in pyridine (0.7 mL) was added 3,3,3-trifluoropropane-1-sulfonyl chloride (108 mg, 0.52 mmol) in 3 portions over 18 hours at room temperature. The reaction was concentrated to dryness and then re-suspended in Acetone (1.0 mL), H$_2$O (0.6 mL) and NaHCO$_3$ (0.22 mmol, 20 mg) was added and the reaction was stirred at 50° C. for 1 hour. The reaction mixture was concentrated to dryness and purified by reverse phase HPLC to afford 39.1 mg (53%) of the title compound.

Example 240: N-[4-[2-[[4-(Dimethylamino)cyclohexyl]amino]-8-isopropyl-7-oxo-pteridin-6-yl]-2,6-difluoro-phenyl]-1-[1-(trifluoromethyl)cyclopropyl]methanesulfonamide Compound 240

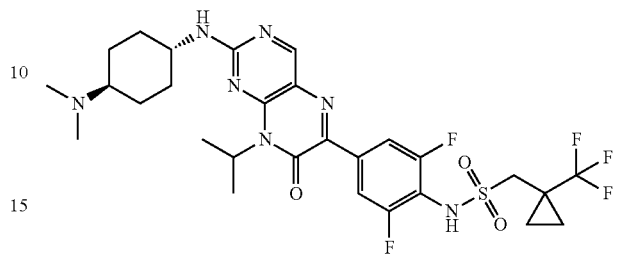

The title compound was prepared according to Example 239. This provides the title compound (51.8 mg, 71.4% yield) as a yellow solid.

Example 241: N-[4-[2-[[4-(Dimethylamino)cyclohexyl]amino]-8-isopropyl-7-oxo-pteridin-6-yl]-2,6-difluoro-phenyl]-3,3-difluoro-butane-1-sulfonamide Compound 241

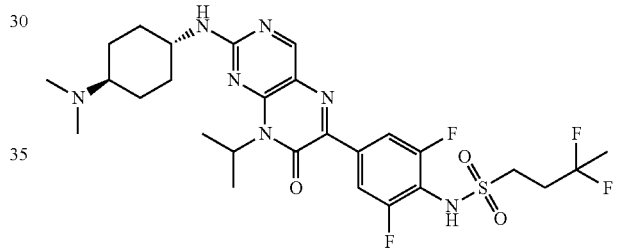

6-(4-amino-3,5-difluoro-phenyl)-2-[[4-(dimethylamino)cyclohexyl]amino]-8-isopropyl-pteridin-7-one (50 mg, 0.11 mmol) was reacted with 3,3-difluorobutane-1-sulfonyl chloride as in Example 239 and purified by reverse phase HPLC to afford 26.3 mg (36%) of the title compound.

Example 242: N-[4-[2-[[4-(Dimethylamino)cyclohexyl]amino]-8-isopropyl-7-oxo-pteridin-6-yl]-2,6-difluoro-phenyl]propane-1-sulfonamide Compound 242

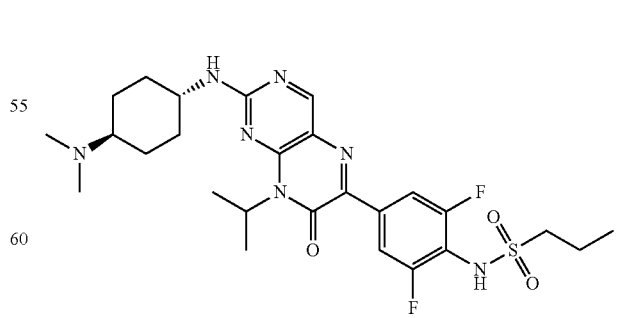

6-(4-Amino-3,5-difluoro-phenyl)-2-[[4-(dimethylamino)cyclohexyl]amino]-8-isopropyl-pteridin-7-one (50 mg, 0.11 mmol) was reacted with 1-propanesulfonyl chloride as in Example 239 and purified by reverse phase HPLC to afford 4.5 mg (7.3%) of the title compound.

Example 243: 1-(4-Chlorophenyl)-N-[4-[2-[[4-(dimethylamino)cyclohexyl]amino]-8-isopropyl-7-oxo-pteridin-6-yl]-2,6-difluoro-phenyl]methanesulfonamide Compound 243

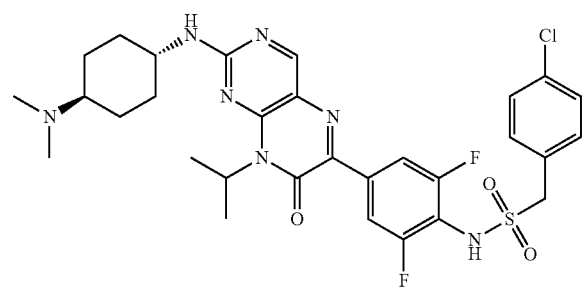 [SMILES: CC(C)n1c(=O)c(-c2cc(F)c(NS(=O)(=O)Cc3ccc(Cl)cc3)c(F)c2)nc2cnc(N[C@H]3CC[C@H](N(C)C)CC3)nc21]

The title compound was prepared according to Example 239. This provides the title compound (54 mg, 73.4% yield) as a yellow solid.

Example 244: 1-[4-(Difluoromethyl)phenyl]-N-[4-[2-[[4-(dimethylamino)cyclohexyl]amino]-8-isopropyl-7-oxo-pteridin-6-yl]-2,6-difluoro-phenyl]methanesulfonamide Compound 244

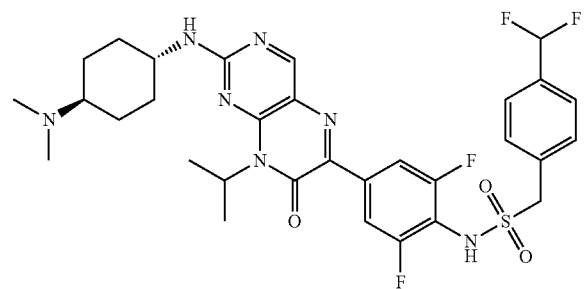 [SMILES: CC(C)n1c(=O)c(-c2cc(F)c(NS(=O)(=O)Cc3ccc(C(F)F)cc3)c(F)c2)nc2cnc(N[C@H]3CC[C@H](N(C)C)CC3)nc21]

The title compound was prepared according to Example 239. This provides the title compound (30.5 mg, 38.4% yield) as a yellow solid.

Example 245: N-[4-[2-[[4-(Dimethylamino)cyclohexyl]amino]-8-isopropyl-7-oxo-pteridin-6-yl]-2,6-difluoro-phenyl]-1-(4-fluorophenyl)methanesulfonamide Compound 245

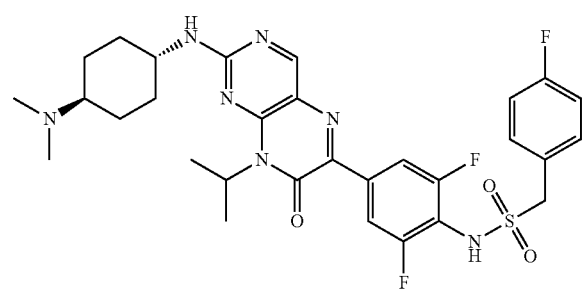 [SMILES: CC(C)n1c(=O)c(-c2cc(F)c(NS(=O)(=O)Cc3ccc(F)cc3)c(F)c2)nc2cnc(N[C@H]3CC[C@H](N(C)C)CC3)nc21]

The title compound was prepared according to Example 239. This provides the title compound (29.1 mg, 42.3% yield) as a yellow solid.

Example 246: N-[4-[2-[[4-(Dimethylamino)cyclohexyl]amino]-8-isopropyl-7-oxo-pteridin-6-yl]-2,6-difluoro-phenyl]-1-(p-tolyl)methanesulfonamide Compound 246


The title compound was prepared according to Example 239. This provides the title compound (12.5 mg, 17% yield) as a yellow solid.

Example 247: N-[4-[2-[[4-(Dimethylamino)cyclohexyl]amino]-8-isopropyl-7-oxo-pteridin-6-yl]-2,6-difluoro-phenyl]-1-phenyl-methanesulfonamide Compound 247

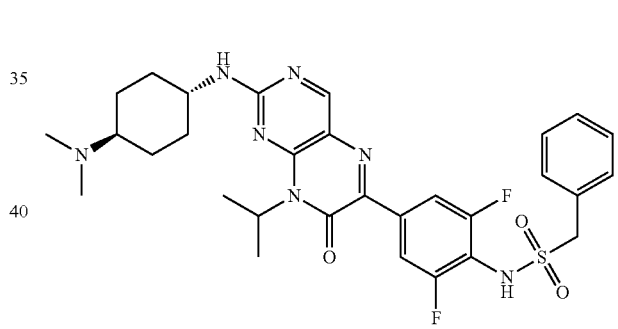

The title compound was prepared according to Example 239. This provides the title compound (21.3 mg, 28% yield) as a yellow solid.

Example 248: 3-Cyclopropyl-N-[4-[2-[[4-(dimethylamino)cyclohexyl]amino]-8-isopropyl-7-oxo-pteridin-6-yl]-2,6-difluoro-phenyl]-2,2-difluoro-propane-1-sulfonamide Compound 248

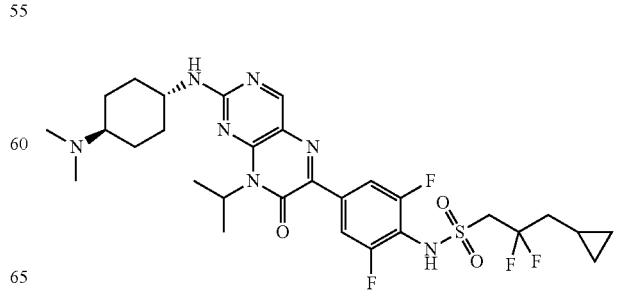

The title compound was prepared according to Example 239. This provides the title compound (6.3 mg, 11.3% yield) as a yellow solid.

Example 249: 1-(3,3-Difluorocyclobutyl)-N-[4-[2-[[4-(dimethylamino)cyclohexyl]amino]-8-isopropyl-7-oxo-pteridin-6-yl]-2,6-difluoro-phenyl]methane-sulfonamide Compound 249

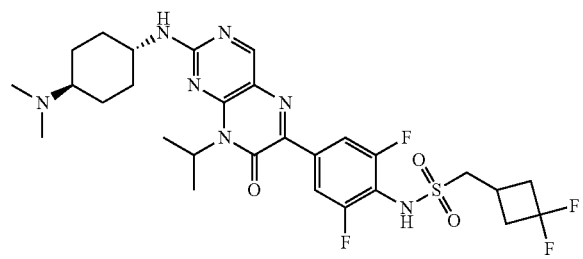 [SMILES: CC(C)n1c(=O)c(-c2cc(F)c(NS(=O)(=O)CC3CC(F)(F)C3)c(F)c2)nc2cnc(N[C@H]3CC[C@H](N(C)C)CC3)nc21]

The title compound was prepared according to Example 239. This provides the title compound (5.2 mg, 10% yield) as a yellow solid.

Example 250: 1-(2,2-Difluorocyclobutyl)-N-[4-[2-[[4-(dimethylamino)cyclohexyl]amino]-8-isopropyl-7-oxo-pteridin-6-yl]-2,6-difluoro-phenyl]methane-sulfonamide Compound 250

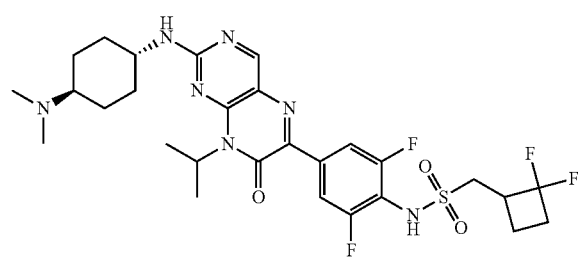 [SMILES: CC(C)n1c(=O)c(-c2cc(F)c(NS(=O)(=O)CC3CCC3(F)F)c(F)c2)nc2cnc(N[C@H]3CC[C@H](N(C)C)CC3)nc21]

The title compound was prepared according to Example 239. This provides the title compound as a mixture of enantiomers (18.2 mg, 33% yield, yellow solid).

Example 251: N-[5-[2-[[4-(Dimethylamino)cyclohexyl]amino]-8-isopropyl-7-oxo-pteridin-6-yl]-6-methyl-2-pyridyl]-3,3,3-trifluoro-propane-1-sulfonamide Compound 251

Step 1: 6-(4-Amino-3,5-difluoro-phenyl)-2-[[4-(dimethylamino)cyclohexyl]amino]-8-isopropyl-pteridin-7-one

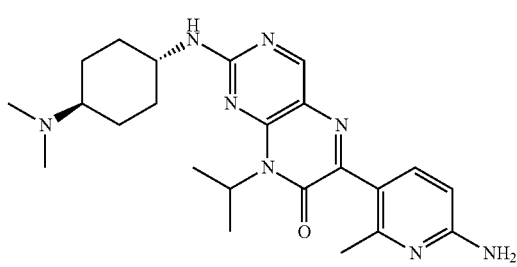 [SMILES: Cc1nc(N)ccc1-c1nc2cnc(N[C@H]3CC[C@H](N(C)C)CC3)nc2n(C(C)C)c1=O]

6-Bromo-2-[[4-(dimethylamino)cyclohexyl]amino]-8-isopropyl-pteridin-7-one (0.3 g) was reacted with 6-methyl-5-(4,4,5,5-tetramethyl-1,3,2-dioxaborolan-2-yl)pyridin-2-amine as in example 73 (step 1). The reaction mixture was treated with Fast-WoRX-S resin (1.5 g) to afford the title compound (210 mg, 66%) as a crude intermediate which was used in the following step without purification. LCMS (ESI): [M+H]$^+$=437.3.

Step 2: N-[5-[2-[[4-(Dimethylamino)cyclohexyl]amino]-8-isopropyl-7-oxo-pteridin-6-yl]-6-methyl-2-pyridyl]-3,3,3-trifluoro-propane-1-sulfonamide

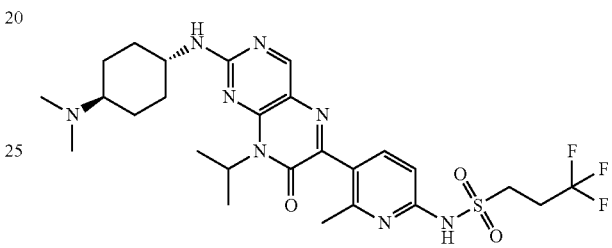

6-(4-Amino-3,5-difluoro-phenyl)-2-[[4-(dimethylamino)cyclohexyl]amino]-8-isopropyl-pteridin-7-one (40 mg) was reacted with 3,3,3-trifluoropropane-1-sulfonyl chloride as in example 73 (step 2) and purified via reverse phase chromatography to afford the title compound (8.7 mg, 16% yield).

Example 252: N-[5-[2-[[4-(Dimethylamino)cyclohexyl]amino]-8-isopropyl-7-oxo-pteridin-6-yl]-6-methyl-2-pyridyl]-1-(4-fluorophenyl)methanesulfonamide Compound 252

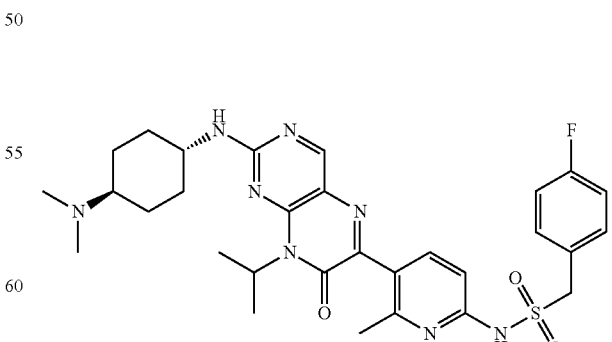

The title compound was prepared according to Example 251. This provides the title compound (11 mg, 18% yield) as a yellow solid.

Example 253: N-[5-[2-[[4-(Dimethylamino)cyclohexyl]amino]-8-isopropyl-7-oxo-pteridin-6-yl]-6-methyl-2-pyridyl]-2-fluoro-benzenesulfonamide Compound 253

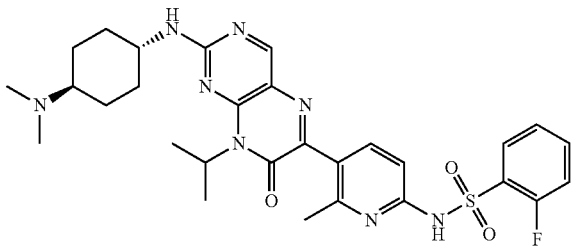 [SMILES: Cc1nc(NS(=O)(=O)c2ccccc2F)ccc1-c1nc2cnc(N[C@H]3CC[C@H](N(C)C)CC3)nc2n(C(C)C)c1=O]

The title compound was prepared according to Example 251. This provides the title compound (18 mg, 29% yield) as a yellow solid.

Example 254: N-[5-[2-[[4-(Dimethylamino)cyclohexyl]amino]-8-isopropyl-7-oxo-pteridin-6-yl]-6-methyl-2-pyridyl]-2-chloro-benzenesulfonamide Compound 254

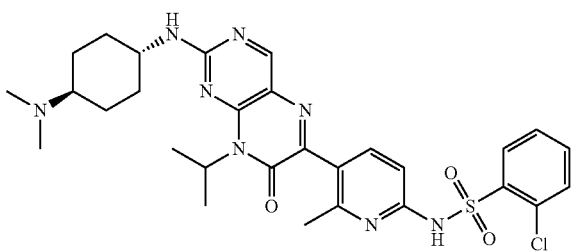 [SMILES: Cc1nc(NS(=O)(=O)c2ccccc2Cl)ccc1-c1nc2cnc(N[C@H]3CC[C@H](N(C)C)CC3)nc2n(C(C)C)c1=O]

The title compound was prepared according to Example 251. This provides the title compound (21.3 mg, 34% yield) as a yellow solid.

Example 255: N-[5-[2-[[4-(Dimethylamino)cyclohexyl]amino]-8-isopropyl-7-oxo-pteridin-6-yl]-6-methyl-2-pyridyl]-2-cyano-benzenesulfonamide Compound 255

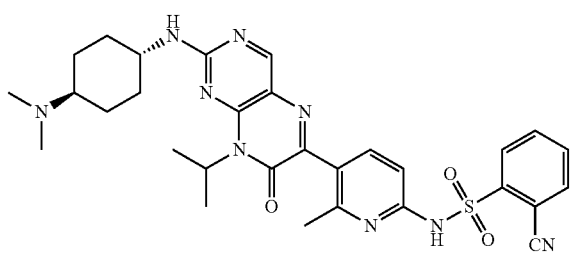 [SMILES: Cc1nc(NS(=O)(=O)c2ccccc2C#N)ccc1-c1nc2cnc(N[C@H]3CC[C@H](N(C)C)CC3)nc2n(C(C)C)c1=O]

The title compound was prepared according to Example 251. This provides the title compound (8 mg, 12.4% yield) as a yellow solid.

Example 256: N-[4-[2-[[4-(Dimethylamino)cyclohexyl]amino]-8-isopropyl-7-oxo-pteridin-6-yl]-2-fluoro-phenyl]-1-spiro[2.2]pentan-2-yl-methanesulfonamide Compound 256

Step 1: tert-Butyl N-[4-[(8-isopropyl-7-oxo-pteridin-2-yl)amino]cyclohexyl]carbamate

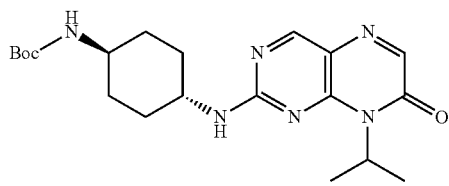 [SMILES: CC(C)n1c(=O)cnc2cnc(N[C@H]3CC[C@H](NC(=O)OC(C)(C)C)CC3)nc21]

A mixture of 2-chloro-8-isopropyl-pteridin-7-one (5.0 g, 22.26 mmol), tert-butyl N-(4-aminocyclohexyl)carbamate (5.75 g, 26.83 mmol), Caesium fluoride (10.0 g, 65.79 mmol) and N,N-Diisopropylethylamine (17.5 g, 135.66 mmol) in Dimethyl sulfoxide (50 mL) was stirred at 100° C. for 2 h under nitrogen. The resulting solution was diluted with water (300 mL). The solids were collected and washed with water. This resulted in the title compound (8.9 g, 99.4% yield) as a yellow solid. LCMS (ESI): [M+H]$^+$=403.2.

Step 2: tert-Butyl N-[4-[(6-bromo-8-isopropyl-7-oxo-pteridin-2-yl)amino]cyclohexyl]carbamate

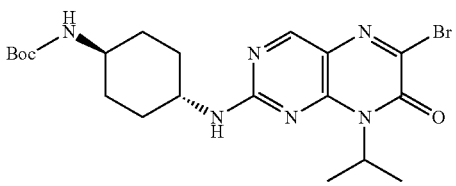 [SMILES: CC(C)n1c(=O)c(Br)nc2cnc(N[C@H]3CC[C@H](NC(=O)OC(C)(C)C)CC3)nc21]

To a mixture of tert-butyl N-[4-[(8-isopropyl-7-oxo-pteridin-2-yl)amino]cyclohexyl]carbamate (8.9 g, 22.11 mmol) in N,N-Dimethylformamide (60 mL) was added 1-bromo-2,5-pyrrolidinedione (5.4 g, 30.34 mmol) at 0° C. The mixture was stirred for 2 h at room temperature. The resulting solution was diluted with water (600 mL). The solids were collected and washed with water. This resulted in the title compound (10.6 g, 99.6% yield) as a yellow solid. LCMS (ESI): [M+H]$^+$=481.1.

Step 3: 2-[(4-Aminocyclohexyl)amino]-6-bromo-8-isopropyl-pteridin-7-one

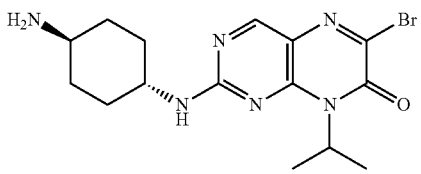 [SMILES: CC(C)n1c(=O)c(Br)nc2cnc(N[C@H]3CC[C@H](N)CC3)nc21]

A mixture of tert-butyl N-[4-[(6-bromo-8-isopropyl-7-oxo-pteridin-2-yl)amino]cyclohexyl]carbamate (12.5 g, 25.97 mmol) in 5% TFA in 1,1,1,3,3,3-Hexafluoro-2-propanol (100 mL) was stirred at room temperature for 2 h. 100 mL toluene was added into the mixture and concentrated. The resulting solid was dissolved in mixture of 10% methanol in dichloromethane, 5 eq MP-carbonate resin was added and stirred for 1 hour. The solids were filtered out and washed with solids with 10% methanol in dichloromethane. The filtrate was concentrated under reduced pressure to afford the title compound (9.8 g, 99% yield) as a yellow solid. LCMS (ESI): [M+H]$^+$=381.1.

Step 4: 6-Bromo-2-[[4-(dimethylamino)cyclohexyl]amino]-8-isopropyl-pteridin-7-one

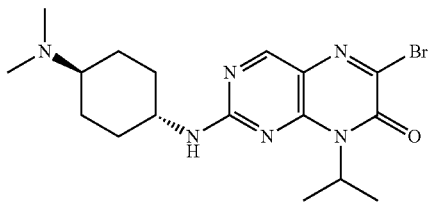 [SMILES: CC(C)n1c(=O)c(Br)nc2cnc(N[C@H]3CC[C@H](N(C)C)CC3)nc21]

To a mixture of 2-[(4-aminocyclohexyl)amino]-6-bromo-8-isopropyl-pteridin-7-one (10.0 g, 26.23 mmol) in methyl alcohol (200 mL) was added 37% formaldehyde solution (65.0 g, 800.87 mmol), acetic acid (1.5 mL, 26.2 mmol), and sodium cyanoborohydride (3.5 g, 55.7 mmol), the mixture was stirred for 1 h at room temperature. The mixture was concentrated under vacuum. The resulting residue was directly purified by reverse phase chromatography (acetonitrile/10 mmol NH$_4$HCO$_3$ in water) to the title compound (5 g, 46.6% yield) as a yellow solid. LCMS (ESI): [M+H]$^+$=409.1.

Step 5: 6-(4-Amino-3-fluoro-phenyl)-2-[[4-(dimethylamino)cyclohexyl]amino]-8-isopropyl-pteridin-7-one hydrochloride

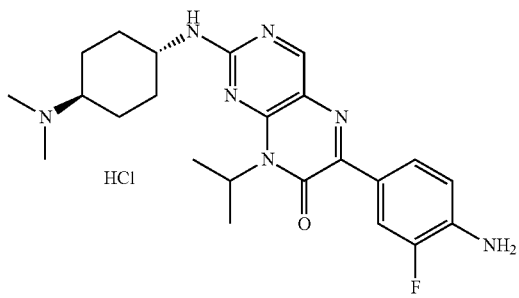 [SMILES: CC(C)n1c(=O)c(-c2ccc(N)c(F)c2)nc2cnc(N[C@H]3CC[C@H](N(C)C)CC3)nc21 ; Cl]

A mixture of 4-amino-3-fluorophenylboronic acid pinacol ester (2.1 g, 8.86 mmol), 6-bromo-2-[[4-(dimethylamino)cyclohexyl]amino]-8-isopropyl-pteridin-7-one (3.5 g, 8.55 mmol), [1,1'-bis(diphenylphosphino)ferrocene]dichloropalladium(II) (0.7 g, 0.94 mmol) and sodium carbonate (2.1 g, 19.44 mmol) in 1,4-dioxane (70 mL) and water (7 mL) was stirred at 85° C. for 2 h under nitrogen. The solids were filtered out. After filtration, the filtrate was concentrated under vacuum. The residue was purified by reverse phase chromatography (acetonitrile/0.10% HCl in water) to afford the title compound (2548.1 mg, 62.6% yield) as a brown solid. LCMS (ESI): [M+H]$^+$=440.2. $^1$H NMR (300 MHz, Methanol-d4) 8.80 (s, 1H), 8.24-8.19 (m, 2H), 7.44 (t, J=8.5 Hz, 1H), 5.67 (t, J=6.7 Hz, 1H), 4.06 (s, 1H), 3.42-3.32 (m, 1H), 2.93 (s, 6H), 2.36-2.24 (m, 4H), 1.88-1.67 (m, 10H).

Step 6: 6-(4-Amino-3-fluoro-phenyl)-2-[[4-(dimethylamino)cyclohexyl]amino]-8-isopropyl-pteridin-7-one

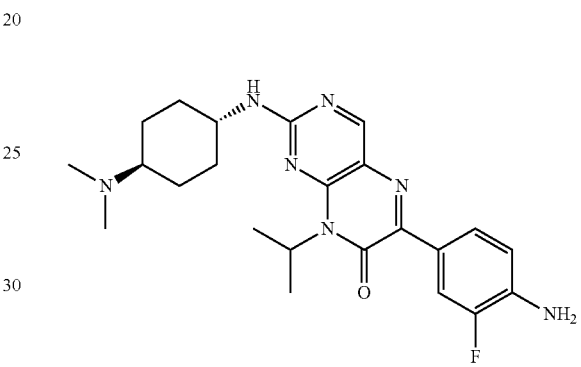

6-(4-Amino-3-fluoro-phenyl)-2-[[4-(dimethylamino)cyclohexyl]amino]-8-isopropyl-pteridin-7-one hydrochloride (2.5 g, 5.34 mmol) was suspended in DCM (1 L) and extracted with a solution of saturated sodium bicarbonate (1 L). The organic layer was dried over anydrous magnesium sulfate, filtered and concentrated to afford the title compound (2 g, 86% yield).

Step 7: N-[4-[2-[[4-(Dimethylamino)cyclohexyl]amino]-8-isopropyl-7-oxo-pteridin-6-yl]-2-fluoro-phenyl]-1-spiro[2.2]pentan-2-yl-methanesulfonamide

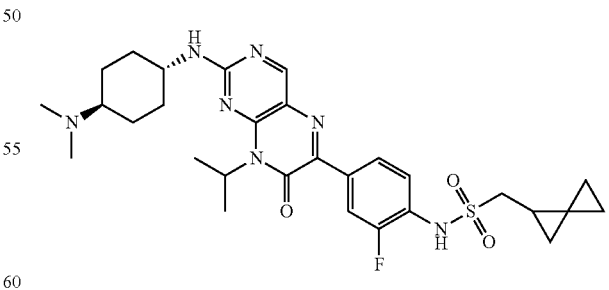

6-(4-Amino-3-fluoro-phenyl)-2-[[4-(dimethylamino)cyclohexyl]amino]-8-isopropyl-pteridin-7-one (30 mg) was reacted with (spiro[2.2]pentan-1-yl)methanesulfonyl chloride as in example 73 (step 2) and purified via reverse phase chromatography to afford the title compound (3 mg, 7% yield).

Example 257: 1-(2,2-Difluorospiro[2.3]hexan-1-yl)-
N-[4-[2-[[4-(dimethylamino)cyclohexyl]amino]-8-
isopropyl-7-oxo-pteridin-6-yl]-2-fluoro-phenyl]
methanesulfonamide Compound 257

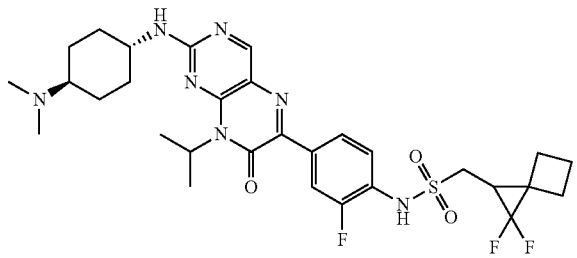 [SMILES: CC(C)n1c(=O)c(-c2ccc(NS(=O)(=O)CC3C(F)(F)C34CCC4)c(F)c2)nc2cnc(N[C@H]3CC[C@H](N(C)C)CC3)nc21]

The title compound was prepared according to Example 256. This provides the title compound (20 mg, 46% yield) as a yellow solid.

Example 258: 1-[1-(1,1-Difluoroethyl)cyclopropyl]-
N-[4-[2-[[4-(dimethylamino)cyclohexyl]amino]-8-
isopropyl-7-oxo-pteridin-6-yl]-2-fluoro-phenyl]
methanesulfonamide Compound 258

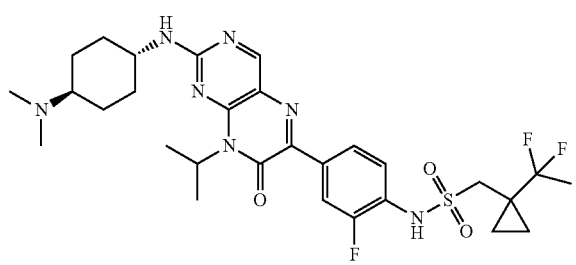 [SMILES: CC(C)n1c(=O)c(-c2ccc(NS(=O)(=O)CC3(C(C)(F)F)CC3)c(F)c2)nc2cnc(N[C@H]3CC[C@H](N(C)C)CC3)nc21]

The title compound was prepared according to Example 256. This provides the title compound (29 mg, 68% yield) as a yellow solid.

Example 259: 2-(2,2-Difluorocyclopropyl)-N-[4-[2-
[[4-(dimethylamino)cyclohexyl]amino]-8-isopropyl-
7-oxo-pteridin-6-yl]-2-fluoro-phenyl]ethanesulfona-
mide Compound 259

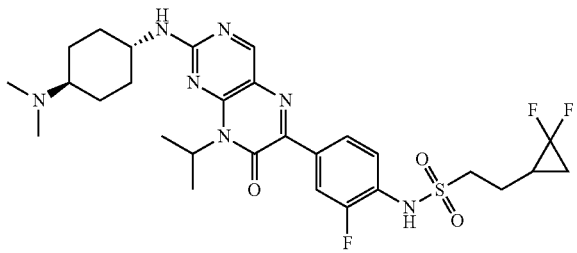 [SMILES: CC(C)n1c(=O)c(-c2ccc(NS(=O)(=O)CCC3CC3(F)F)c(F)c2)nc2cnc(N[C@H]3CC[C@H](N(C)C)CC3)nc21]

The title compound was prepared according to Example 256. This provides the title compound (13.5 mg, 33% yield) as a yellow solid.

Example 260: N-[4-[2-[[4-(Dimethylamino)cyclo-
hexyl]amino]-8-isopropyl-7-oxo-pteridin-6-yl]-2-
fluoro-phenyl]-1-spiro[3.3]heptan-2-yl-methane-
sulfonamide Compound 260

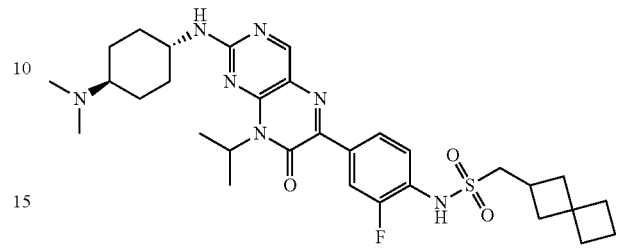

The title compound was prepared according to Example 256. This provides the title compound (9.8 mg, 23.5% yield) as a yellow solid.

Example 261: N-[4-[2-[[4-(Dimethylamino)cyclo-
hexyl]amino]-8-isopropyl-7-oxo-pteridin-6-yl]-2-
fluoro-phenyl]-1-[1-(trifluoromethyl)cyclobutyl]
methanesulfonamide Compound 261

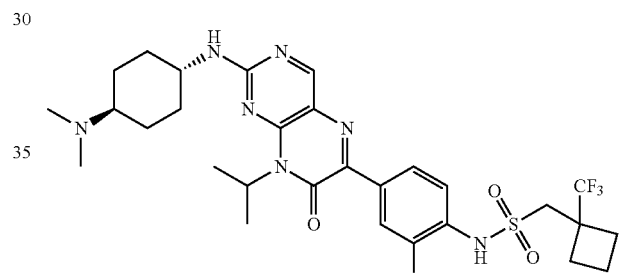

The title compound was prepared according to Example 256. This provides the title compound (28.6 mg, 65% yield) as a yellow solid.

Example 262: 1-(2,2-Difluorospiro[2.3]hexan-5-yl)-
N-[4-[2-[[4-(dimethylamino)cyclohexyl]amino]-8-
isopropyl-7-oxo-pteridin-6-yl]-2-fluoro-phenyl]
methanesulfonamide Compound 262

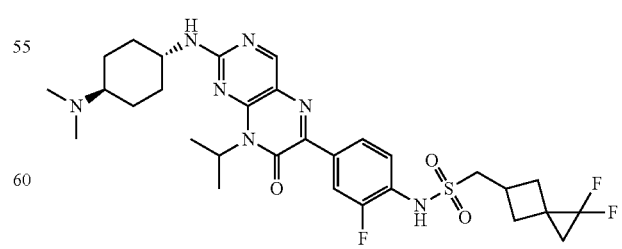

The title compound was prepared according to Example 256. This provides the title compound as a mixture of diastereomers (11.1 mg, 25% yield, and yellow solid).

Example 263: 1-(2,2-Difluorocyclobutyl)-N-[4-[2-[[4-(dimethylamino)cyclohexyl]amino]-8-isopropyl-7-oxo-pteridin-6-yl]-2-fluoro-phenyl]methanesulfonamide Compound 263

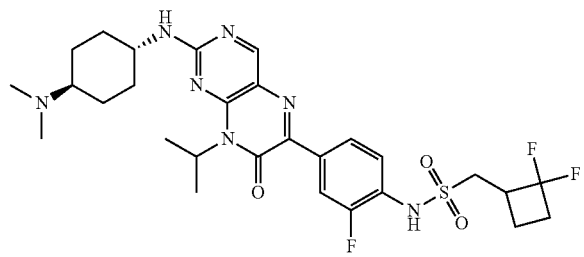 [SMILES: CC(C)n1c(=O)c(-c2ccc(NS(=O)(=O)CC3CCC3(F)F)c(F)c2)nc2cnc(N[C@H]3CC[C@H](N(C)C)CC3)nc21]

The title compound was prepared according to Example 256. This provides the title compound as a mixture of enantiomers (24.4 mg, 59% yield, and yellow solid).

Example 264: 1-(2,2-Difluorocyclopentyl)-N-[4-[2-[[4-(dimethylamino)cyclohexyl]amino]-8-isopropyl-7-oxo-pteridin-6-yl]-2-fluoro-phenyl]methanesulfonamide Compound 264

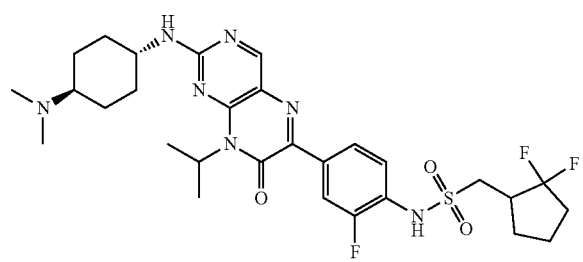 [SMILES: CC(C)n1c(=O)c(-c2ccc(NS(=O)(=O)CC3CCCC3(F)F)c(F)c2)nc2cnc(N[C@H]3CC[C@H](N(C)C)CC3)nc21]

The title compound was prepared according to Example 256. This provides the title compound as a mixture of enantiomers (25 mg, 510% yield, and yellow solid).

Example 265: 1-(6,6-Difluoro-3-bicyclo[3.1.0]hexanyl)-N-[4-[2-[[4-(dimethylamino)cyclohexyl]amino]-8-isopropyl-7-oxo-pteridin-6-yl]-2-fluoro phenyl]methanesulfonamide Compound 265

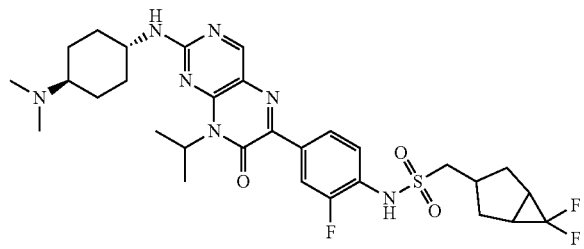 [SMILES: CC(C)n1c(=O)c(-c2ccc(NS(=O)(=O)CC3CC4C(C3)C4(F)F)c(F)c2)nc2cnc(N[C@H]3CC[C@H](N(C)C)CC3)nc21]

The title compound was prepared according to Example 256. This provides the title compound as a mixture of diasteromers (5 mg, 10% yield, and yellow solid).

Example 266: 1-[1-(Difluoromethyl)cyclopentyl]-N-[4-[2-[[4-(dimethylamino)cyclohexyl]amino]-8-isopropyl-7-oxo-pteridin-6-yl]-2-fluoro-phenyl]methanesulfonamide Compound 266

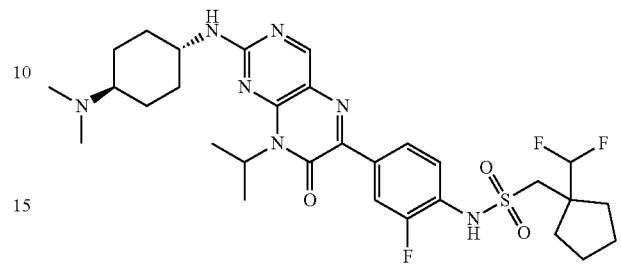

The title compound was prepared according to Example 256. This provides the title compound (13 mg, 26% yield) as a yellow solid.

Example 267: 1-Cyclopentyl-N-[4-[2-[[4-(dimethylamino)cyclohexyl]amino]-8-isopropyl-7-oxo-pteridin-6-yl]-2-fluoro-phenyl]methanesulfonamide Compound 267

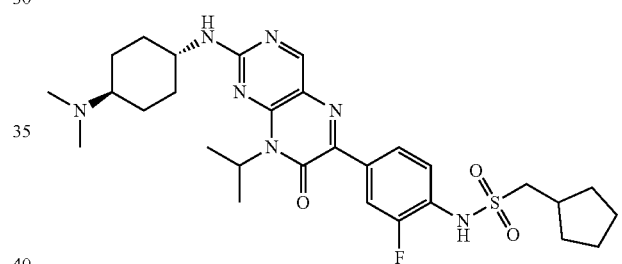

The title compound was prepared according to Example 256. This provides the title compound (17.6 mg, 38% yield) as a yellow solid.

Example 268: N-[4-[2-[[4-(Dimethylamino)cyclohexyl]amino]-8-isopropyl-7-oxo-pteridin-6-yl]-2-fluoro-phenyl]-1-indan-2-yl-methanesulfonamide Compound 268

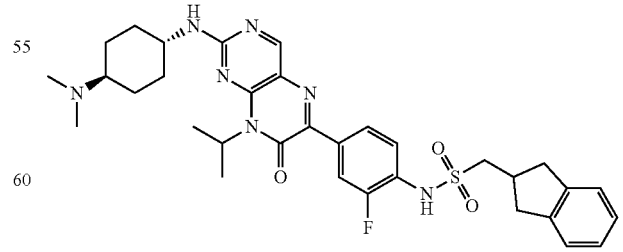

The title compound was prepared according to Example 256. This provides the title compound (26.7 mg, 51% yield) as a yellow solid.

Example 269: 1-Cyclohexyl-N-[4-[2-[[4-(dimethyl-amino)cyclohexyl]amino]-8-isopropyl-7-oxo-pteridin-6-yl]-2-fluoro-phenyl]methanesulfonamide Compound 269

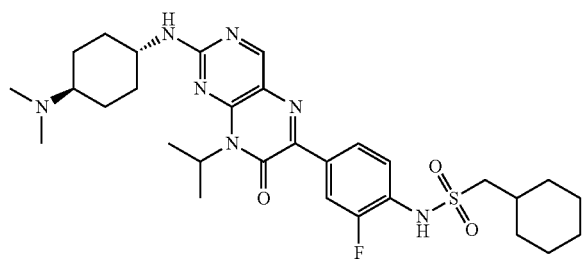 [SMILES: CC(C)n1c(=O)c(-c2ccc(NS(=O)(=O)CC3CCCCC3)c(F)c2)nc2cnc(N[C@H]3CC[C@H](N(C)C)CC3)nc21]

The title compound was prepared according to Example 256. This provides the title compound (13 mg, 27% yield) as a yellow solid.

Example 270: N-[4-[2-[[4-(Dimethylamino)cyclohexyl]amino]-8-isopropyl-7-oxo-pteridin-6-yl]-2-fluoro-phenyl]-1-norbornan-1-yl-methanesulfonamide Compound 270

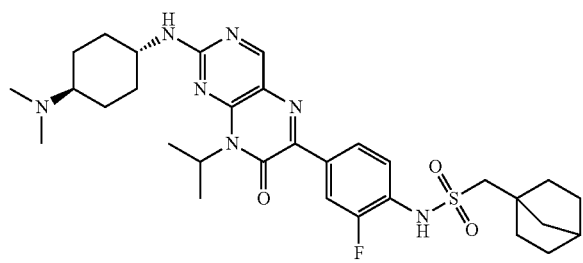 [SMILES: CC(C)n1c(=O)c(-c2ccc(NS(=O)(=O)CC34CCC(CC3)C4)c(F)c2)nc2cnc(N[C@H]3CC[C@H](N(C)C)CC3)nc21]

The title compound was prepared according to Example 256. This provides the title compound (3 mg, 6.3% yield) as a yellow solid.

Example 271: 1-(4,4-Difluorocyclohexyl)-N-[4-[2-[[4-(dimethylamino)cyclohexyl]amino]-8-isopropyl-7-oxo-pteridin-6-yl]-2-fluoro-phenyl]methanesulfonamide Compound 271

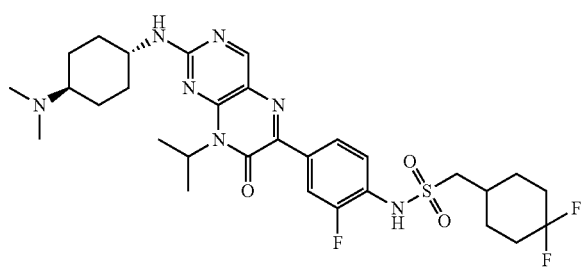 [SMILES: CC(C)n1c(=O)c(-c2ccc(NS(=O)(=O)CC3CCC(F)(F)CC3)c(F)c2)nc2cnc(N[C@H]3CC[C@H](N(C)C)CC3)nc21]

The title compound was prepared according to Example 256. This provides the title compound (13 mg, 25% yield) as a yellow solid.

Example 272: 1-(2,2-Difluorocyclohexyl)-N-[4-[2-[[4-(dimethylamino)cyclohexyl]amino]-8-isopropyl-7-oxo-pteridin-6-yl]-2-fluoro-phenyl]methanesulfonamide Compound 272

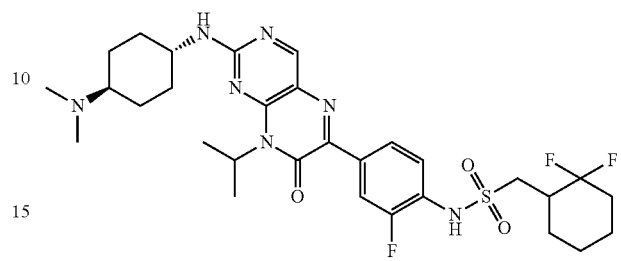

The title compound was prepared according to Example 256. This provides the title compound as a mixture of enantiomers (37 mg, 64% yield, and yellow solid).

Example 273: 1-(7,7-Difluoronorcaran-3-yl)-N-[4-[2-[[(1RS)-4-(dimethylamino)cyclohexyl]amino]-8-isopropyl-7-oxo-pteridin-6-yl]-2-fluoro-phenyl]methanesulfonamide Compound 273

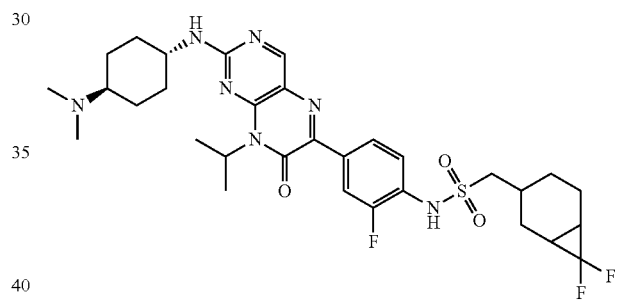

The title compound was prepared according to Example 256. This provides the title compound as a mixture of diastereomers (7 mg, 12% yield, and yellow solid).

Example 274: (1R,2S)—N-(4-(2-(((1r,4r)-4-(Dimethylamino)cyclohexyl)amino)-8-isopropyl-7-oxo-7,8-dihydropteridin-6-yl)-2-fluorophenyl)-2-phenylcyclopropane-1-sulfonamide Compound 274

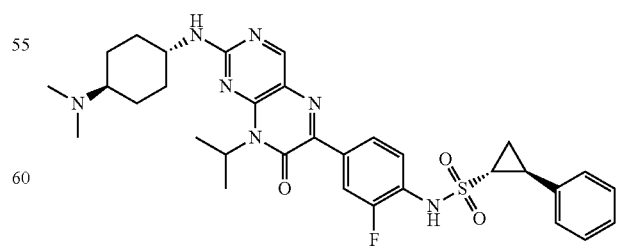

The title compound was prepared according to Example 256. This provides the title compound (23 mg, 53% yield) as a yellow solid.

Example 275: N-[4-[2-[[4-(Dimethylamino)cyclohexyl]amino]-8-isopropyl-7-oxo-pteridin-6-yl]-2-fluoro-phenyl]norcarane-7-sulfonamide Compound 275

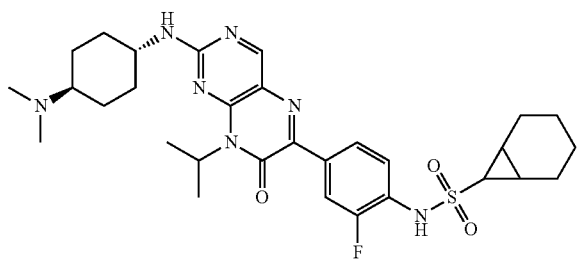 [SMILES: CC(C)n1c(=O)c(-c2ccc(NS(=O)(=O)C3C4CCCCC43)c(F)c2)nc2cnc(N[C@H]3CC[C@H](N(C)C)CC3)nc21]

The title compound was prepared according to Example 256. This provides the title compound as a mixture of diastereomers (27 mg, 65% yield, and yellow solid).

Example 276: N-[4-[2-[[4-(Dimethylamino)cyclohexyl]amino]-8-isopropyl-7-oxo-pteridin-6-yl]-2-fluoro-phenyl]cyclobutanesulfonamide Compound 276

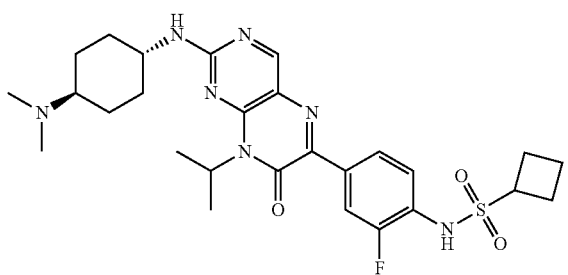 [SMILES: CC(C)n1c(=O)c(-c2ccc(NS(=O)(=O)C3CCC3)c(F)c2)nc2cnc(N[C@H]3CC[C@H](N(C)C)CC3)nc21]

The title compound was prepared according to Example 256. This provides the title compound (7 mg, 18.5% yield) as a yellow solid.

Example 277: N-[4-[2-[[4-(Dimethylamino)cyclohexyl]amino]-8-isopropyl-7-oxo-pteridin-6-yl]-2-fluoro-phenyl]spiro[3.3]heptane-2-sulfonamide Compound 277

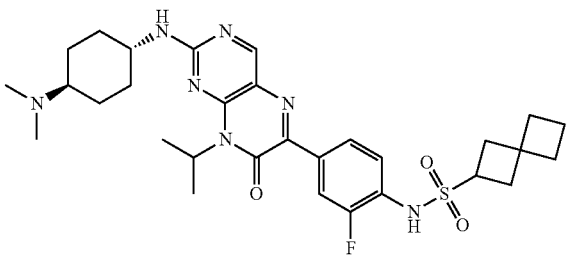 [SMILES: CC(C)n1c(=O)c(-c2ccc(NS(=O)(=O)C3CC4(CCC4)C3)c(F)c2)nc2cnc(N[C@H]3CC[C@H](N(C)C)CC3)nc21]

The title compound was prepared according to Example 256. This provides the title compound (7 mg, 17% yield) as a yellow solid.

Example 278: 1-Cyclobutyl-N-[4-[2-[[4-(dimethylamino)cyclohexyl]amino]-8-isopropyl-7-oxo-pteridin-6-yl]-2-fluoro-phenyl]methanesulfonamide Compound 278

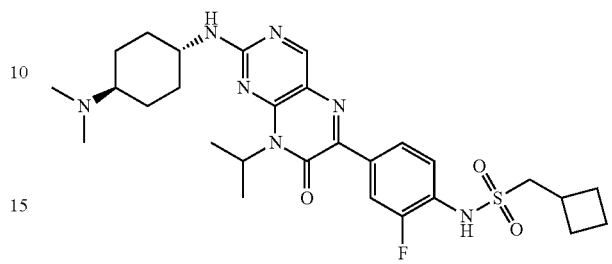

The title compound was prepared according to Example 256. This provides the title compound (8.3 mg, 18% yield) as a yellow solid.

Example 279: 1-(3,3-Difluorocyclobutyl)-N-[4-[2-[[4-(dimethylamino)cyclohexyl]amino]-8-isopropyl-7-oxo-pteridin-6-yl]-2-fluoro-phenyl]methanesulfonamide Compound 279

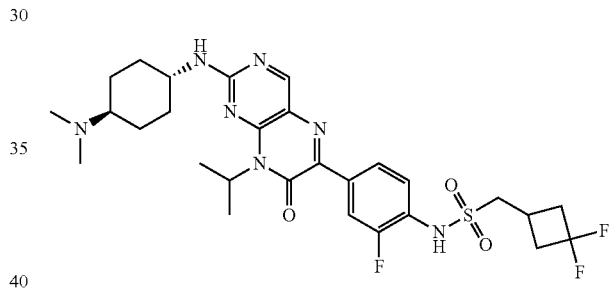

The title compound was prepared according to Example 256. This provides the title compound (13 mg, 26% yield) as a yellow solid.

Example 280: N-[4-[2-[[4-(Dimethylamino)cyclohexyl]amino]-8-isopropyl-7-oxo-pteridin-6-yl]-2-fluoro-phenyl]-4,4-difluoro-cyclohexanesulfonamide Compound 280

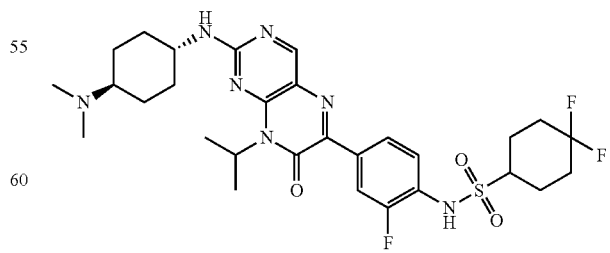

The title compound was prepared according to Example 256. This provides the title compound (26 mg, 61% yield) as a yellow solid.

Example 281: N-(4-(2-(((1r, 4r)-4-(dimethylamino)cyclohexyl)amino)-8-isopropyl-7-oxo-7,8-dihydropteridin-6-yl)-2-fluorophenyl)bicyclo[2.2.1]heptane-2-sulfonamide Compound 281

Example 282: N-[4-[2-[[4-(Dimethylamino)cyclohexyl]amino]-8-isopropyl-7-oxo-pteridin-6-yl]-2-fluoro-phenyl]tetralin-2-sulfonamide Compound 282

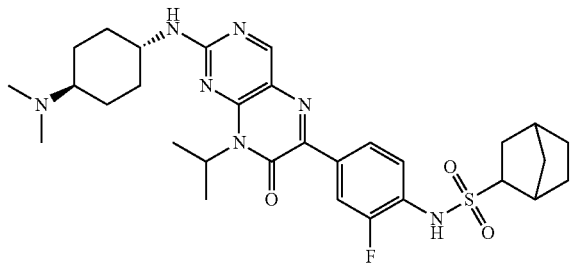 [SMILES: CC(C)n1c(=O)c(-c2ccc(NS(=O)(=O)C3CC4CCC3C4)c(F)c2)nc2cnc(N[C@H]3CC[C@H](N(C)C)CC3)nc21]

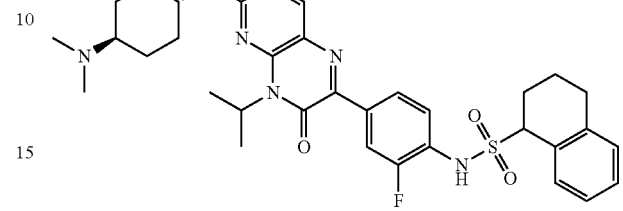

The title compound was prepared according to Example 256. This provides the title compound as a mixture of enantiomers (3.3 mg, 6.3% yield, and yellow solid).

The title compound was prepared according to Example 256. This provides the title compound as a mixture of enantiomers (14.6 mg, 27% yield, and yellow solid).

TABLE 3

| EX No | $^1$H NMR |
|---|---|
| 1 | (400 MHz, DMSO-d$_6$) 8.66 (s, 1H), 7.93 (s, 1H), 7.85-7.77 (m, 2H), 7.31-7.26 (m, 5H), 7.20-7.13 (m, 1H), 6.99 (t, J = 8.2 Hz, 1H), 4.24 (s, 2H), 4.08 (s, 1H), 3.61-3.57 (m, 3H), 3.32 (s, 3H), 3.03 (s, 1H), 2.80-2.59 (m, 1H), 2.06-1.71 (m, 2H), 1.60 (s, 2H). [Example 1] |
| 2 | (400 MHz, DMSO-d$_6$) δ 8.70 (d, J = 19.0 Hz, 1H), 7.99-7.77 (m, 2H), 7.42-7.28 (m, 5H), 7.21-7.11 (m, 2H), 4.93-4.81 (m, 1H), 4.49 (s, 2H), 4.35-4.06 (m, 1H), 3.61 (s, 2H), 3.56 (s, 1H), 3.21-2.97 (m, 2H), 2.86-2.66 (m, 1H), 2.57-2.50 (m, 1H), 2.29-2.10 (m, 1H), 1.96-1.74 (m, 1H). [Example 2] |
| 3 | (400 MHz, DMSO-d$_6$) δ 8.75-8.55 (m, 1H), 7.93 (d, J = 7.0 Hz, 1H), 7.86-7.64 (m, 2H), 7.36-7.24 (m, 5H), 7.17 (t, J = 8.3 Hz, 1H), 6.99 (t, J = 8.4 Hz, 1H), 4.46-4.27 (m, 2H), 4.23 (s, 2H), 4.17-3.97 (m, 1H), 3.41-3.28 (m, 2H), 3.10-2.98 (m, 1H), 2.79-2.63 (m, 2H), 2.03-1.91 (m, 1H), 1.88-1.76 (m, 1H), 1.69-1.52 (m, 2H), 1.32-1.15 (m, 3H). [Example 3] |
| 4 | (400 MHz, DMSO-d$_6$) δ 8.67 (s, 1H), 8.36 (d, J = 8.6 Hz, 1H), 7.88-7.72 (m, 2H), 7.59 (dd, J = 8.6, 7.0 Hz, 1H), 7.46 (dd, J = 9.3, 5.2 Hz, 1H), 7.40-7.30 (m, 2H), 4.04 (s, 1H), 3.69-3.58 (m, 3H), 3.27-3.17 (m, 4H), 3.02-2.88 (m, 1H), 2.85-2.76 (m, 2H), 2.67-2.59 (m, 2H), 1.98-1.90 (m, 1H), 1.76 (s, 1H), 1.57-1.56 (m, 2H). [Example 4] |
| 5 | (300 MHz, DMSO-d$_6$) δ 8.65 (d, J = 8.8 Hz, 1H), 8.23 (d, J = 8.6 Hz, 1H), 7.82-7.78 (m, 2H), 7.63-7.58 (m, 2H), 7.46-7.32 (m, 7H), 4.48 (s, 2H), 3.93 (s, 1H), 3.61-3.57 (m, 4H), 3.18-3.14 (m, 2H), 2.86-2.82 (m, 1H), 1.94-1.88 (m, 1H), 1.68 (s, 1H), 1.51-1.48 (m, 2H). [Example 4] |
| 6 | (400 MHz, DMSO-d$_6$) δ 8.68 (d, J = 14.2 Hz, 1H), 8.26 (d, J = 8.5 Hz, 1H), 7.88-7.84 (m, 2H), 7.75-7.65 (m, 1H), 7.58 (t, J = 7.6 Hz, 1H), 7.47-7.33 (m, 7H), 4.51 (s, 2H), 3.96 (s, 1H), 3.63-3.54(m, 3H), 3.20-3.08 (m, 3H), 2.89-2.86 (m, 1H), 1.97-1.91(m, 1H), 1.70 (s, 1H), 1.56-1.51 (m, 2H). [Example 4] |
| 7 | (300 MHz, CD$_3$OD) δ 8.64 (s, 1H), 8.42 (d, J = 8.4 Hz, 1H), 7.86 (s, 1H), 7.69 (d, J = 8.4 Hz, 1H), 7.63-7.58 (m, 1H), 7.47-7.39 (m, 2H), 4.20 (s, 1H), 3.76 (s, 3H), 3.48-3.39 (m, 3H), 3.12-3.08 (m, 1H), 2.93-2.67 (m, 4H), 2.18-2.14 (m, 1H), 1.95-1.91 (d, J = 12.2 Hz, 1H), 1.77-1.69 (m, 2H). [Example 4] |
| 8 | (400 MHz, DMSO-d$_6$) 8.68-8.64 (m, 1H), 8.29 (d, J = 8.6 Hz, 1H), 7.83-7.79 (m, 2H), 7.69-7.65 (m, 2H), 7.44-7.39 (m, 2H), 3.93 (s, 1H), 3.62-3.58 (m, 3H), 3.15 (t, J = 7.6 Hz, 3H), 2.87-2.79 (m, 1H), 2.50-2.45 (m, 2H), 1.98-1.81 (m, 3H), 1.66-1.65 (m, 1H), 1.49-1.48 (m, 2H), 1.03 (t, J = 7.4 Hz, 3H). [Example 4] |
| 9 | (400 MHz, CD$_3$OD) δ 8.60 (s, 1H), 7.77 (s, 1H), 7.40-7.10 (m, 7H), 5.98-5.79(m, 1H), 4.95-4.93(m, 1H), 4.50 (s, 2H), 4.41-4.35 (m, 1H), 3.28-3.10 (m, 2H), 2.85-2.74 (m, 1H), 2.65-2.30 (m, 2H), 1.89-1.72 (m, 1H), 1.69-1.58 (m, 6H). [Example 2] |
| 10 | (400 MHz, CD$_3$OD) δ 8.64-8.61 (m, 1H), 7.84 (s, 1H), 7.38-7.32 (m, 5H), 7.29-7.24 (m, 1H), 7.15 (t, J = 8.0 Hz, 1H), 6.01 (s, 1H), 5.24-5.15 (m, 2H), 5.06-5.00 (m, 2H), 4.99-4.89 (m, 1H) 4.51 (s, 2H), 4.39 (s, 1H), 3.31-3.30 (m, 1H), 3.17-3.11 (m, 1H), 2.85-2.71 (m, 1H), 2.55 (t, J = 11.3 Hz, 1H), 2.44-2.43 (m, 1H), 1.82 (dt, J = 40.9, 13.1 Hz, 1H). [Example 10] |

TABLE 3-continued

| EX No | $^1$H NMR |
|---|---|
| 11 | (400 MHz, CD$_3$OD) δ 8.70-8.65 (m, 1H), 7.87 (s, 1H), 7.38-7.32 (m, 5H), 7.28-7.24 (m, 1H), 7.16 (t, J = 7.9 Hz, 1H), 6.31 (t, J = 56.7 Hz, 1H), 4.90-4.81 (m, 3H), 4.49 (s, 2H), 4.38-4.35 (m, 1H), 3.32-3.30 (m, 1H), 3.17-3.11 (m, 1H), 2.82-2.71 (m, 1H), 2.61-2.37 (m, 2H), 1.89-1.79 (m, 1H). [Example 2] |
| 12 | (300 MHz, CD$_3$OD) δ 8.63 (s, 1H), 7.82 (s, 1H), 7.42-7.30 (m, 5H), 7.29-7.23 (m, 1H), 7.19-7.09 (m, 1H), 5.00-4.80 (m, 1H), 4.70-4.28 (m, 5H), 3.18-3.02 (m, 1H), 2.86-2.72 (m, 1H), 2.63-2.31 (m, 2H), 1.95-1.73 (m, 1H), 1.39-1.25 (m, 4H). [Example 2] |
| 13 | (300 MHz, CD$_3$OD) δ 8.63 (s, 1H), 7.85 (s, 1H), 7.42-7.37 (m, 1H), 7.26-7.20 (m, 1H), 4.80-4.75 (m, 1H), 4.58-4.30 (m, 3H), 3.19-3.11 (m, 3H), 2.80-2.71 (m, 1H), 2.62-2.32 (m, 2H), 1.98-1.72 (m, 3H), 1.33 (d, J = 15.6 Hz, 4H), 1.08 (t, J = 7.6 Hz, 3H). [Example 2] |
| 14 | (300 MHz, CD$_3$OD) δ 8.61 (s, 1H), 7.84 (s, 1H), 7.34-7.30 (m, 1H), 7.24-7.16 (m, 1H), 4.86-4.82 (m, 1H), 4.54-4.30 (m, 3H), 3.39-3.33 (m, 2H), 3.17-3.11 (m, 1H), 2.93-2.51 (m, 5H), 1.94-1.73 (m, 1H), 1.40-1.25 (m, 4H). [Example 2] |
| 15 | (300 MHz, CD$_3$OD) δ 8.62 (s, 1H), 7.89 (s, 1H), 7.49-7.46 (m, 2H), 7.40-7.30 (m, 3H), 7.21-7.11 (m, 1H), 5.11-4.95 (m, 1H), 4.49-4.46 (m, 5H), 3.32-3.31(m, 1H), 3.14 (t, J = 13.1 Hz, 1H), 2.91-2.37 (m, 3H), 1.95-1.70 (m, 1H), 1.33 (s, 3H). [Example 2] |
| 16 | (300 MHz, CD$_3$OD) δ 8.76 (s, 1H), 7.87 (s, 1H), 7.53-7.47 (m, 1H), 7.41-7.34 (m, 5H), 7.24-7.15 (m, 2H), 5.92-5.87 (m, 1H), 4.48 (s, 2H), 4.43 (s, 1H), 3.67-3.62 (m, 1H), 3.43-3.34 (m, 1H), 3.10-3.09 (m, 2H), 2.26-2.13 (m, 2H), 1.92-1.82 (m, 2H), 1.68 (d, J = 6.6 Hz, 6H). [Example 1] |
| 17 | (300 MHz, CD$_3$OD) δ 8.75 (s, 1H), 7.80-7.70 (m, 1H), 7.68 (m, 1H), 7.46-7.34 (m, 3H), 7.34-7.27 (m, 3H), 7.21 (m, 1H), 5.94-5.78 (m, 1H), 4.50 (s, 3H), 3.62 (d, J = 10.2 Hz, 1H), 3.38 (d, J = 13.5 Hz, 1H), 3.08 (s, 2H), 2.25-2.11 (m, 2H), 2.05-1.74 (m, 2H), 1.66 (d, J = 6.9 Hz, 6H). [Example 1] |
| 18 | (300 MHz, CD$_3$OD) δ 8.62 (s, 1H), 7.79 (s, 1H), 7.43-7.35 (m, 5H), 7.32-7.27 (m, 1H), 7.16-7.11 (m, 1H), 6.11 (m, 1H), 4.95-4.83 (m, 1H), 4.51 (s, 2H), 4.40 (s, 1H), 3.22-3.16 (m, 1H), 2.87-2.75 (m, 1H), 2.74-2.37 (m, 4H), 2.21-2.09 (m, 2H), 1.91-1.73 (m, 5H), 1.31 (s, 1H). [Example 2] |
| 19 | (300 MHz, CD$_3$OD) δ 8.59 (s, 1H), 7.78 (s, 1H), 7.49-7.43 (m, 2H), 7.41-7.28 (m, 4H), 7.16-7.05 (m, 1H), 6.00-5.82 (m, 1H), 4.49 (s, 2H), 4.15-4.08 (s, 1H), 3.33-3.32(m, 1H), 3.00-2.96 (m, 1H), 2.77-2.58 (m, 2H), 2.12-2.02 (m, 1H), 1.89-1.77 (m, 1H), 1.69-1.64 (m, 2H), 1.62 (d, J = 7.2 Hz, 6H). [Example 1] |
| 20 | (400 MHz, CD$_3$OD) δ 8.60 (s, 1H), 7.85 (s, 1H), 7.55-7.51 (m, 2H), 7.44-7.36 (m, 3H), 7.25-7.18 (m, 1H), 6.00-5.83 (m, 1H), 4.54 (s, 2H), 4.35-4.15 (m, 1H), 1.66 (d, J = 5.6 Hz, 6H), 1.32 (d, J = 5.6 Hz, 6H) [Example 20] |
| 21 | (400 MHz, CD$_3$OD) 8.70 (s, 1H), 7.92 (s, 1H), 7.28-7.24 (m, 1H), 5.80-5.76 (m, 1H), 4.37 (s, 1H), 3.52-3.48 (m, 2H), 2.87-2.80 (m, 2H), 1.65 (d, J = 6.9 Hz, 6H), 1.39 (d, J = 6.6 Hz, 6H). [Example 20] |
| 22 | (400 MHz, CD$_3$OD) δ 8.58 (s, 1H), 7.85 (s, 1H), 7.55-7.51 (m, 2H), 7.44-7.35 (m, 3H), 7.25-7.15 (m, 1H), 5.98-5.89 (m, 1H), 4.54 (s, 2H), 3.91-3.85 (m, 1H), 3.63-3.51 (m, 1H), 2.20-2.01 (m, 4H), 1.75-1.60 (m, 6H), 1.54-1.35 (m, 4H). [Example 20] |
| 23 | (300 MHz, CD$_3$OD) δ 8.66 (d, J = 12.7 Hz, 1H), 7.86 (s, 1H), 7.44-7.33 (m, 5H), 7.33-7.24 (m, 1H), 7.20-7.10 (m, 1H), 7.08-6.46 (m, 1H), 6.12-5.63 (m, 1H), 5.01-4.84 (m, 1H), 4.52 (s, 2H), 4.49-4.26 (m, 1H), 3.40-3.19 (m, 2H), 2.96-2.73 (m, 1H), 2.71-2.33 (m, 2H), 2.10-1.74 (m, 1H), 1.64 (s, 3H). [Example 23] |
| 24 | (400 MHz, CD$_3$OD) δ 8.59 (s, 1H), 7.83 (s, 1H), 7.55-7.50 (m, 2H), 7.48-7.37 (m, 3H), 7.19-7.12 (m, 1H), 5.89 (s, 1H), 4.47 (s, 2H), 3.90 (s, 1H), 2.70-2.62(m, 1H), 2.61 (s, 6H), 2.30-2.15(m, 2H), 2.11-2.02 (m, 2H), 1.69-1.58 (m, 6H), 1.56-1.37 (m, 4H). [Example 20] |
| 25 | (400 MHz, DMSO-d$_6$ with 10% CF$_3$COOD) δ 8.63 (d, J = 11.5 Hz, 1H), 7.93 (d, J = 7.5 Hz, 1H), 7.83-7.76 (m, 1H), 7.08-6.96 (m, 1H), 5.73-5.71 (m, 1H), 3.87-3.69 (m, 1H), 3.06-2.80 (m, 3H), 2.74-2.51 (m, 9H), 2.28-1.91 (m, 4H), 1.59-1.24 (m, 10H). |
| 26 | (400 MHz, CD$_3$OD) δ 8.61 (s, 1H), 7.84 (s, 1H), 7.50-7.48 (m, 2H), 7.42-7.31 (m, 3H), 7.21-7.15 (m, 1H), 5.92 (s, 1H), 4.95-4.80 (m, 1H), 4.47-4.30 (m, 3H), 3.30-3.08 (m, 2H), 2.90-2.66 (m, 1H), 2.59-2.41 (m, 2H), 1.85-1.75 (m, 1H), 1.66 (s, 6H). [Example 2] |
| 27 | (400 MHz, CD$_3$OD) δ 8.61 (s, 1H), 7.85 (s, 1H), 7.55-7.51 (m, 2H), 7.45-7.32 (m, 3H), 7.25-7.15 (m, 1H), 6.00-5.85 (m, 1H), 4.51 (s, 2H), 4.38-4.28 (m, 1H), 3.05-2.96 (m, 1H), 2.75-2.60 (m, 1H), 2.41-2.22 (m, 2H), 2.20-2.10(m, 1H), 1.85-1.60 (m, 7H), 1.37 (d, J = 20.4 Hz, 3H). [Example 2] |
| 28 | (400 MHz, CD$_3$OD) δ 8.60 (s, 1H), 7.85 (s, 1H), 7.54-7.47 (m, 2H), 7.44-7.36 (m, 3H), 7.21 (s, 1H), 5.94 (s, 1H), 4.98-4.84 (m, 1H), 4.52-4.47 (m, 3H), 3.34-3.17 (m, 3H), 2.88-2.75 (m, 2H), 2.65-2.43 (m, 4H), 2.18-1.71 (m, 3H). [Example 2] |

TABLE 3-continued

| EX No | ¹H NMR |
|---|---|
| 29 | (400 MHz, CD₃OD) δ 8.62 (s, 1H), 7.86 (s, 1H), 7.77 (d, J = 8.0 Hz, 2H), 7.70 (d, J = 8.0 Hz, 2H), 7.25-7.16 (m, 1H), 6.00-5.88 (m, 1H), 5.05-5.01 (m, 1H), 4.62 (s, 2H), 4.47-4.35 (m, 1H), 3.35-3.33 (m, 1H), 3.25-3.15 (m, 1H), 2.95-2.80 (m, 1H), 2.75-2.40 (m, 2H), 1.98-1.74 (m, 1H), 1.66 (d, J = 6.4 Hz, 6H). [Example 2] |
| 30 | (400 MHz, DMSO-d₆) δ 8.71-8.66 (m, 1H), 8.02-7.85 (m, 3H), 7.80-7.77 (m, 2H), 7.64-7.58 (m, 1H), 7.26-7.16 (m, 1H), 5.82-5.68 (m, 1H), 5.03-4.91 (m, 1H), 4.48 (s, 2H), 4.35-4.20 (m, 1H), 3.18-3.16 (m, 2H), 2.89-2.75 (m, 1H), 2.63-2.54 (m, 1H), 2.40-2.31(m, 1H), 2.30-2.12 (m, 1H), 1.95-1.70 (m, 1H), 1.71-1.55 (m, 6H). [Example 2] |
| 31 | (400 MHz, CD₃OD) δ 8.74 (s, 1H), 7.94 (s, 1H), 7.30-7.28 (m, 2H), 7.08-6.99 (m, 2H), 6.99-6.94 (m, 1H), 6.02-5.82 (m, 1H), 5.35-5.24 (m, 1H), 4.75 (t, J = 12.5 Hz, 1H), 4.55 (s, 2H), 3.83 (s, 3H), 3.70 (d, J = 10.6 Hz, 2H), 3.46-3.35 (m, 1H), 3.20-3.10 (m, 1H), 2.62 (brs, 1H), 2.10-1.95 (m, 1H), 2.05-2.01 (m, 6H). [Example 2] |
| 32 | (400 MHz, DMSO-d₆) δ 8.72-8.65 (m, 1H), 8.05-7.78 (m, 3H), 7.75-7.69 (m, 2H), 7.53-7.50 (m, 1H), 7.21-7.07 (m, 1H), 5.80 (s, 1H), 5.05-4.94 (m, 1H), 4.53 (s, 2H), 4.30-4.20 (m, 1H), 3.40-3.28 (m, 1H), 3.25-3.17 (m, 2H), 2.93-2.85 (m, 1H), 2.64-2.60 (m, 1H), 2.37-2.16 (m, 1H), 1.95-1.70 (m, 1H), 1.62-1.44 (m, 6H). [Example 2] |
| 33 | (400 MHz, CD₃OD) δ 8.56 (s, 1H), 7.79 (s, 1H), 7.19-7.03 (m, 1H), 5.85 (s, 1H), 3.95-3.72 (m, 1H), 2.92-2.85 (m, 1H), 2.66 (s, 6H), 2.58-2.01 (m, 7H), 1.73 (s, 1H), 1.66-1.58 (m, 10H), 1.55-1.41 (m, 3H). [Example 20] |
| 34 | (400 MHz, DMSO-d₆) δ 8.64 (d, J = 14.1 Hz, 1H), 8.00-7.69 (m, 2H), 7.28-7.12 (m, 1H), 5.71 (dd, J = 14.1, 7.8 Hz, 1H), 3.84-3.78 (m, 2H), 3.12-2.96 (m, 2H), 2.30 (s, 6H), 2.14-1.86 (m, 4H), 1.83-1.70 (m, 2H), 1.55-1.53 (m, 6H), 1.35-1.21 (m, 4H), 1.00 (t, J = 7.5 Hz, 3H). [Example 20] |
| 35 | (300 MHz, CD₃OD) δ 8.63 (s, 1H), 7.89 (s, 1H), 7.60-7.50 (m, 2H), 7.38-7.31 (m, 3H), 7.27-7.17 (m, 1H), 6.48-6.25 (m, 1H), 4.97-4.80 (m, 1H), 4.52 (s, 2H), 4.45-4.12 (m, 3H), 4.10-3.95 (m, 2H), 3.33-3.30 (m, 1H), 3.16 (t, J = 13.2 Hz, 1H), 2.90-2.70 (m, 1H), 2.60-2.50 (m, 2H), 2.45-2.15 (m, 2H), 2.02-1.69 (m, 1H). [Example 23] |
| 36 | (300 MHz, CD₃OD) δ 8.80 (s, 1H), 7.97 (s, 1H), 7.32-7.20 (m, 1H), 5.90-5.75 (m, 1H), 4.10-3.96 (m, 3H), 3.37-3.35 (m, 1H), 2.92 (s, 6H), 2.44-2.02 (m, 6H), 1.90-1.50 (m, 10H), 1.09 (t, J = 7.5 Hz, 3H) [Example 20] |
| 37 | (300 MHz, CD₃OD) δ 8.56 (s, 1H), 7.81 (s, 1H), 7.20-7.08 (m, 1H), 5.95-5.80 (m, 1H), 3.95-3.81 (m, 1H), 2.42-2.31(m, 7H), 2.27-1.99 (m, 4H), 1.90-1.85 (m, 1H), 1.64 (s, 6H), 1.50-1.35 (m, 4H), 1.04-0.82 (m, 4H). [Example 20] |
| 38 | (400 MHz, CD₃OD) δ 8.62 (s, 1H), 7.85 (s, 1H), 7.57 (d, J = 2.3 Hz, 1H), 7.20 (dd, J = 10.3, 6.0 Hz, 1H), 6.45 (d, J = 2.3 Hz, 1H), 5.92 (s, 1H), 4.96-4.85 (m, 1H), 4.55 (s, 2H), 4.42 (s, 1H), 3.90 (s, 3H), 3.29 (s, 1H), 3.18 (t, J = 12.7 Hz, 1H), 2.92-2.74 (m, 1H), 2.67-2.37 (m, 2H), 1.94-1.71 (m, 1H), 1.66 (s, 6H). [Example 10] |
| 39 | ¹H NMR (400 MHz, DMSO-d₆) δ 8.66 (s, 1H), 7.82 (s, 1H), 7.74 (s, 1H), 7.65 (d, J = 7.6 Hz, 1H), 7.58 (d, J = 7.9 Hz, 1H), 7.55-7.47 (m, 1H), 7.36-7.27 (m, 2H), 6.96-6.86 (m, 1H), 4.88-4.70 (m, 1H), 4.40-4.25 (m, 2H), 4.11 (s, 2H), 3.20-2.85 (m, 3H), 2.80-2.65 (m, 1H), 2.30-2.12 (m, 1H), 1.92-1.70 (m, 1H), 1.17 (t, J = 7.1 Hz, 3H). [Example 39] |
| 40 | ¹H NMR (400 MHz, DMSO-d₆) δ 8.66 (s, 1H), 9.23 (s, 1H), 8.81 (s, 1H), 8.40 (d, J = 7.2 Hz, 1H), 8.04 (s, 1H), 7.42-7.37 (m, 5H), 7.26-7.15 (m, 2H), 5.35-5.12 (m, 3H), 4.59 (s, 2H), 4.42-4.37 (m, 1H), 3.62-3.49 (m, 2H), 2.92-2.78 (m, 1H), 2.39-2.27 (m, 1H), 2.02-1.80 (m, 1H), 1.27-1.21 (m, 1H). [Example 40] |
| 41 | (400 MHz, DMSO-d₆) δ 9.29 (s, 1H), 8.75 (s, 1H), 8.21 (d, J = 7.3 Hz, 1H), 7.97 (s, 1H), 7.39-7.27 (m, 2H), 5.35-5.15 (m, 1H), 4.45-4.27 (m, 3H), 3.85-3.72 (m, 2H), 3.58-3.45 (m, 2H), 3.32-3.19 (m, 1H), 2.92-2.82 (m, 1H), 2.37-2.29 (m, 1H), 1.95-1.71 (m, 3H), 1.54-1.39 (m, 1H), 1.30-1.15 (m, 5H), 0.97 (t, J = 7.4 Hz, 3H). [Example 41] |
| 42 | ¹H NMR (400 MHz, DMSO-d₆) δ 10.10 (s, 1H), 9.23-9.10 (m, 2H), 8.30 (s, 1H), 8.13 (d, J = 8.2 Hz, 1H), 7.43-7.32 (m, 5H), 7.26-7.14 (m, 2H), 6.20-6.00 (m, 1H), 5.40-5.10 (m, 1H), 4.61 (s, 3H), 3.27-3.12 (m, 2H), 2.95-2.75 (m, 1H), 2.38-2.31 (m, 1H), 2.04-1.80 (m, 2H), 1.48 (dd, J = 6.5, 2.8 Hz, 3H). [Example 42] |
| 43 | (400 MHz, DMSO-d₆, 360K) δ 8.66 (s, 1H), 7.63 (d, J = 8.0 Hz, 1H), 7.41-7.29 (m, 5H), 7.29-7.16 (m, 2H), 5.57 (h, J = 6.9 Hz, 1H), 4.90-4.72 (m, 1H), 4.43 (s, 2H), 4.21-4.16 (m, 1H), 3.11-3.04 (m, 1H), 2.96-2.88 (m, 1H), 2.85-2.69 (m, 1H), 2.61-2.50 (m, 1H), 2.26-2.13 (m, 1H), 1.96-1.79 (m, 1H), 1.57 (d, J = 6.9 Hz, 6H). [Example 43] |
| 44 | (400 MHz, DMSO-d₆, 360K) δ 8.71 (s, 1H), 8.06 (dd, J = 12.7, 2.0 Hz, 1H), 7.98 (dd, J = 8.5, 2.1 Hz, 1H), 7.67 (d, J = 8.1 Hz, 1H), 7.42-7.30 (m, 6H), 5.63 (h, J = 6.8 Hz, 1H), 4.97-4.78 (m, 1H), 4.52 (s, 2H), 4.30-4.19 (m, 1H), 3.16-3.10 (m, 1H), 2.92-2.76 (m, 2H), 2.67-2.57 (m, 1H), 2.28-2.17 (m, 1H), 1.99-1.78 (m, 1H), 1.59 (d, J = 6.9 Hz, 6H). [Example 44] |

TABLE 3-continued

| EX No | ¹H NMR |
|---|---|
| 45 | (400 MHz, DMSO-d$_6$, 360K) δ 8.71 (s, 1H), 7.92-7.70 (m, 3H), 7.39-7.33 (m, 2H), 7.33-7.20 (m, 3H), 5.68-5.56 (m, 1H), 4.91-4.71 (m, 1H), 4.29-4.13 (m, 1H), 4.11 (s, 2H), 3.09-3.01 (m, 1H), 2.97-2.86 (m, 1H), 2.78-2.57 (m, 2H), 2.26-2.14 (m, 1H), 1.91-1.70 (m, 1H), 1.62-1.52 (m, 6H).<br>[Example 45] |
| 46 | (400 MHz, DMSO-d$_6$, 360K) δ 8.65 (s, 1H), 7.85-7.72 (m, 2H), 5.61 (hept, J = 6.8 Hz, 1H), 4.91-4.68 (m, 1H), 4.21-4.11 (m, 1H), 3.08-3.04 (m, 1H), 2.95-2.82 (m, 4H), 2.83-2.49 (m, 4H), 2.24-2.12 (m, 1H), 1.96-1.77 (m, 1H), 1.58 (d, J = 6.9 Hz, 6H).<br>[Example 46] |
| 47 | ¹H NMR (400 MHz, DMSO-d$_6$) δ 8.69 (s, 1H), 8.05-7.97 (m, 1H), 7.93 (s, 1H), 7.82 (d, J = 8.2 Hz, 2H), 7.62 (d, J = 8.3 Hz, 2H), 7.17 (dd, J = 10.8, 5.1 Hz, 1H), 5.05-4.86 (m, 1H), 4.44 (s, 2H), 4.36 (d, J = 7.5 Hz, 2H), 4.28-4.17 (m, 1H), 3.16-3.05 (m, 2H), 2.95-2.79 (m, 1H), 2.66-2.59 (m, 1H), 2.33-2.20 (m, 1H), 1.96-1.75 (m, 1H), 1.26-1.21 (m, 3H).<br>[Example 39] |
| 48 | ¹H NMR (400 MHz, CD$_3$OD) δ 8.72 (s, 1H), 7.97 (s, 1H), 7.30-7.22 (m, 1H), 5.35-5.20 (m, 1H), 4.73-4.63 (m, 1H), 4.55-4.42 (m, 2H), 3.74-3.60 (m, 4H), 2.68 (s, 2H), 2.10-1.95 (m, 1H), 1.60-1.53 (m, 1H), 1.42-1.37 (m, 3H), 1.05-0.94 (m, 4H).<br>[Example 39] |
| 49 | ¹H NMR (400 MHz, DMSO-d$_6$) δ 8.73 (s, 1H), 8.57 (d, J = 5.2 Hz, 1H), 8.13 (d, J = 7.6 Hz, 1H), 8.00 (s, 1H), 7.83 (td, J = 7.7, 1.9 Hz, 1H), 7.56 (d, J = 7.8 Hz, 1H), 7.42-7.28 (m, 2H), 5.15-4.95 (m, 1H), 4.65 (d, J = 6.2 Hz, 1H), 4.45-4.25 (m, 4H), 4.05-3.94 (m, 1H), 2.78-2.63 (m, 2H), 2.05-1.77 (m, 1H), 1.59-1.50 (m, 2H), 1.18-1.15 (m, 3H).<br>[Example 39] |
| 50 | ¹H NMR (400 MHz, DMSO-d$_6$) δ 9.99 (s, 1H), 9.52-9.45 (m, 1H), 8.83-8.70 (m, 1H), 8.28 (d, J = 7.4 Hz, 1H), 8.04 (s, 1H), 7.79 (d, J = 8.2 Hz, 2H), 7.70 (d, J = 8.2 Hz, 2H), 7.40 (ddd, J = 10.3, 6.0, 2.2 Hz, 1H), 5.25 (d, J = 45.2 Hz, 1H), 4.71 (s, 2H), 4.65-4.30 (m, 3H), 3.35-3.12 (m, 2H), 2.93-2.80 (m, 1H), 2.40 (s, 1H), 1.92 (dt, J = 44.7, 13.3 Hz, 1H), 1.30-1.10 (m, 4H).<br>[Example 39] |
| 51 | ¹H NMR (400 MHz, DMSO-d$_6$) δ 8.70 (s, 1H), 8.01 (s, 1H), 7.95 (s, 1H), 7.50-7.35 (m, 1H), 7.25-7.05 (m, 3H), 4.95 (d, J = 47.2 Hz, 1H), 4.44 (s, 2H), 4.39-4.15 (m, 3H), 3.15-3.10 (m, 1H), 3.00-2.80 (m, 1H), 2.70-2.55 (m, 1H), 2.40-2.15 (m, 1H), 2.03 (dt, J = 33.7, 3.1 Hz, 1H), 1.85 (dt, J = 41.6, 12.9 Hz, 1H), 1.27-1.15 (m, 3H).<br>[Example 39] |
| 52 | ¹H NMR (400 MHz, DMSO-d$_6$) δ 10.04 (s, 1H), 9.18 (brs, 2H), 8.80-8.72 (m, 1H), 8.19 (d, J = 7.7 Hz, 1H), 7.94 (s, 1H), 7.45-7.37 (m, 6H), 7.33-7.29 (m, 1H), 7.23-7.16 (m, 2H), 5.32-5.16 (m, 1H), 4.58 (s, 2H), 4.31-4.24 (m, 1H), 3.32-3.12 (m, 2H), 3.00-2.80 (m, 1H), 2.41-2.28 (m, 1H), 1.29 (d, J = 40.0 Hz, 2H), 0.89-0.80 (m, 1H), 0.48-0.41 (m, 4H).<br>[Example 39] |
| 53 | (300 MHz, CD$_3$OD) δ 8.64 (s, 1H), 7.86 (s, 1H), 7.42-7.34 (m, 5H), 7.31-7.25 (m, 1H), 7.18-7.13 (m, 1H), 4.97-4.90 (m, 1H), 4.86-4.81 (m, 3H), 4.72 (s, 1H), 4.51 (s, 2H), 4.40-4.37 (m, 1H), 3.37-3.34 (m, 1H), 3.16 (t, J = 13.3 Hz, 1H), 2.81 (dd, J = 37.1, 14.2 Hz, 1H), 2.56 (t, J = 11.5 Hz, 1H), 2.44-2.43 (m, 1H), 1.84 (dt, J = 38.8, 12.6 Hz, 1H).<br>[Example 23] |
| 54 | (400 MHz, CD$_3$OD) δ 8.60 (s, 1H), 7.88-7.81 (m, 3H), 7.67-7.60 (m, 1H), 7.58-7.51 (m, 2H), 7.07 (d, J = 14.5 Hz, 1H), 5.91 (s, 1H), 4.95-4.84 (m, 1H), 4.41 (s, 1H), 3.28-3.25 (m, 1H), 3.15-3.10 (m, 1H), 2.90-2.82 (m, 1H), 2.59-2.50 (m, 1H), 2.48-2.40 (m, 1H), 1.90-1.74 (m, 1H), 1.64 (s, 6H).<br>[Example 2] |
| 55 | (400 MHz, DMSO-d$_6$) δ 9.98 (s, 2H), 9.29-9.11 (m, 2H), 8.35 (s, 1H), 8.14 (d, J = 8.4 Hz, 1H), 7.60-7.33 (m, 6H), 5.48-5.12 (m, 2H), 4.59 (s, 3H), 3.59-3.35 (m, 3H), 3.33-3.08 (m, 3H), 2.95-2.62 (m, 3H), 2.35 (s, 1H), 2.07-1.80 (m, 1H).<br>[Example 2] |
| 56 | (400 MHz, DMSO-d$_6$) δ 8.63 (d, J = 14.8 Hz, 1H), 7.95-7.64 (m, 2H), 7.51-7.42 (m, 3H), 7.39-7.33 (m, 2H), 7.32-7.20 (m, 3H), 6.95-6.92 (m, 1H), 5.85-5.71 (m, 1H), 4.07 (s, 2H), 3.85-3.77 (m, 1H), 3.05-2.99 (m, 1H), 2.10-1.90 (m, 4H), 1.60-1.55 (m, 6H), 1.46-1.35 (m, 4H).<br>[Example 20] |
| 57 | (300 MHz, CD$_3$OD) δ 8.61 (s, 1H), 7.85 (s, 1H), 7.41 (d, J = 8.6 Hz, 2H), 7.25-7.15 (m, 1H), 6.94 (d, J = 8.7 Hz, 2H), 5.95-5.92 (m, 1H), 4.95-4.81 (m, 1H), 4.46 (s, 3H), 4.41-4.30 (m, 1H), 3.81 (s, 3H), 3.20-3.16 (m, 1H), 2.90-2.81 (m, 1H), 2.80-2.40 (m, 2H), 1.95-1.72 (m, 1H), 1.64 (s, 6H).<br>[Example 2] |
| 58 | (300 MHz, CD$_3$OD) δ 8.58 (s, 1H), 7.83 (s, 1H), 7.24-7.15 (m, 1H), 5.96-5.87 (m, 1H), 3.97-3.89 (m, 1H), 2.50-2.39 (m, 7H), 2.28-1.87 (m, 5H), 1.65 (s, 6H), 1.49-1.31(m, 5H), 1.20 (d, J = 6.2 Hz, 3H), 1.11-0.91 (m, 2H).<br>[Example 58] |
| 59 | (300 MHz, CD$_3$OD) δ 8.56 (s, 1H), 7.82 (s, 1H), 7.21-7.11 (m, 1H), 5.90-5.86 (m, 1H), 3.86 (s, 1H), 2.35-2.32 (m, 9H), 2.26-2.11 (m, 3H), 2.04-1.96 (m, 2H), 1.75-1.63 (m, 6H), 1.50-1.42 (m, 4H), 1.11-1.05 (m, 6H).<br>[Example 59] |
| 60 | (300 MHz, CD$_3$OD) δ 8.57 (s, 1H), 7.81 (d, J = 4.7 Hz, 1H), 7.29-7.06 (m, 1H), 5.85 (s, 1H), 5.47-5.15 (m, 1H), 4.45-4.21 (m, 1H), 3.39-3.33 (m, 2H), 2.90-2.70 (m, 2H), 2.67-2.41 (m, 7H), 2.29-2.15 (m, 1H), 2.12-1.70 (m, 2H), 1.69-1.46 (m, 9H).<br>[Example 60] |

TABLE 3-continued

| EX No | $^1$H NMR |
|---|---|
| 61 | (400 MHz, CD$_3$OD) δ 8.70 (s, 1H), 7.97 (dd, J = 8.0, 1.5 Hz, 1H), 7.89 (s, 1H), 7.70-7.55 (m, 2H), 7.48-7.44 (m, 1H), 7.12 (t, J = 7.9 Hz, 1H), 5.87 (s, 1H), 5.34-5.23 (m, 1H), 4.80-4.63 (m, 1H), 3.68 (d, J = 11.5 Hz, 2H), 3.41-3.36 (m, 1H), 3.06 (s, 1H), 2.60 (s, 1H), 2.00 (dt, J = 42.8, 13.6 Hz, 1H), 1.63 (s, 6H). [Example 2] |
| 62 | (300 MHz, CD$_3$OD) δ 8.57 (s, 1H), 7.84 (s, 1H), 7.20-7.17 (m, 1H), 5.88 (s, 1H), 3.90 (s, 1H), 3.00-2.79 (m, 1H), 2.58-2.44 (m, 9H), 2.29-2.02 (m, 6H), 2.00-1.81 (m, 4H), 1.72-1.56 (m, 6H), 1.56-1.40 (m, 4H). [Example 58] |
| 63 | (300 MHz, DMSO-d$_6$) δ 10.26 (s, 2H), 8.66 (d, J = 12.0 Hz, 1H), 8.10-8.89 (m, 2H), 7.40-7.31 (m, 1H), 5.89-5.60 (m, 1H), 5.13-4.78 (m, 1H), 3.85-3.70 (m, 1H), 3.10-3.30 (m, 1H), 2.73 (s, 6H), 2.16-2.05 (m, 5H), 1.70-1.55 (m, 9H), 1.45-1.30 (m, 2H), 1.20-1.10 (m, 1H). [Example 58] |
| 64 | (300 MHz, DMSO-d$_6$) δ 8.75 (d, J = 14.8 Hz, 1H), 8.14-7.84 (m, 3H), 7.38 (d, J = 9.9 Hz, 6H), 5.73-5.57 (m, 1H), 4.51 (s, 2H), 4.30-4.02 (m, 1H), 3.15 (t, J = 13.2 Hz, 1H), 2.92 (t, J = 12.3 Hz, 1H), 2.81-2.59 (m, 1H), 2.45-2.01 (m, 3H), 1.58-1.78 (m, 7H), 1.28 (d, J = 21.0 Hz, 3H). [Example 64] |
| 65 | (300 MHz, DMSO-d$_6$) δ 8.74 (d, J = 13.1 Hz, 1H), 8.09-7.85 (m, 3H), 7.45-7.28 (m, 6H), 5.73-5.53 (m, 1H), 4.40 (s, 3H), 4.32-4.17 (m, 1H), 4.08-3.92 (m, 1H), 3.20 (d, J = 11.8 Hz, 1H), 3.05 (d, J = 11.8 Hz, 1H), 2.43-2.23 (m, 2H), 2.12-1.88 (s, 2H), 1.67-1.47 (m, 6H), 1.26 (q, J = 12.4 Hz, 1H). [Example 64] |
| 66 | (300 MHz, DMSO-d$_6$) δ 8.72-8.68 (m, 1H), 8.03-7.82 (m, 3H), 7.43 (t, J = 8.9 Hz, 1H), 5.66-5.57 (m, 1H), 3.84-3.70 (m, 1H), 3.31-3.12 (m, 2H), 2.52-2.51 (m, 1H), 2.50-2.26 (m, 8H), 2.08-1.94 (m, 4H), 1.71-1.54 (m, 9H), 1.40-1.24 (m, 4H). [Example 66] |
| 67 | (300 MHz, DMSO-d$_6$) δ 8.72-8.68 (m, 1H), 8.00-7.80 (m, 3H), 7.40 (t, J = 8.9 Hz, 1H), 5.64-5.62 (m, 1H), 3.84-3.69 (m, 1H), 3.19-3.14 (m, 2H), 2.77-2.61 (m, 3H), 2.50-2.48 (m, 6H), 2.08-1.97 (m, 4H), 1.61-1.54 (m, 6H), 1.42-1.24 (m, 4H). [Example 66] |
| 68 | (300 MHz, DMSO-d$_6$) δ 8.71 (d, J = 13.9 Hz, 1H), 8.10-7.90 (m, 3H), 7.43-7.30 (m, 6H), 5.70-5.53 (m, 1H), 4.41 (s, 2H), 2.33 (s, 7H), 2.11-1.82 (m, 5H), 1.66-1.51 (m, 6H), 1.43-1.30 (m, 4H). [Example 64] |
| 69 | $^1$H NMR (400 MHz, CD$_3$OD) δ 8.66 (s, 1H), 8.57 (s, 1H), 7.88 (d, J = 1.8 Hz, 1H), 7.50-7.42 (m, 2H), 7.40-7.32 (m, 3H), 6.13 (s, 1H), 4.53 (s, 6H), 3.74 (s, 3H), 3.20-3.00 (m, 2H), 2.90-2.71 (m, 1H), 2.60-2.05 (m, 2H), 1.95-1.74 (m, 1H), 1.38-1.31 (m, 3H). [Example 69] |
| 70 | (400 MHz, d$_6$-DMSO) δ 8.66-8.42 (m, 1H), 7.89 (s, 1H), 7.81-7.73 (m, 1H), 7.25-7.17 (m, 2H), 3.97 (bs, 4H), 2.86-2.76 (m, 2H), 2.73-2.64 (m, 2H), 2.18 (s, 6H), 2.06-1.93 (m, 2H), 1.93-1.75 (m, 2H), 1.58 (d, J = 6.6 Hz, 3H), 1.52 (d, J = 7.5 Hz, 2H), 1.40-1.19 (m, 4H). [Example 70] |
| 71 | (400 MHz, d$_6$-DMSO) δ 8.67-8.52 (m, 1H), 8.16 (s, 1H), 7.81 (d, J = 6.8 Hz, 1H), 7.72 (s, 1H), 7.17-7.03 (m, 2H), 5.83-5.63 (m, 1H), 3.92-3.77 (m, 1H), 3.75-3.63 (m, 2H), 3.02-2.92 (m, 2H), 2.66-2.57 (m, 2H), 2.11-1.88 (m, 4H), 1.57 (d, J = 6.6 Hz, 4H), 1.53-1.47 (m, 2H), 1.45-1.31 (m, 4H). [Example 71] |
| 72 | $^1$H NMR (400 MHz, DMSO-d$_6$) δ 8.76 (s, 1H), 8.04-7.86 (m, 3H), 7.46-7.35 (m, 5H), 5.67-5.57 (m, 1H), 4.92-4.71 (m, 1H), 4.48 (s, 2H), 4.28-4.05 (m, 1H), 3.10-2.99 (m, 1H), 2.99-2.87 (m, 1H), 2.79-2.62 (m, 1H), 2.48-2.42 (m, 1H), 2.38 (s, 3H), 2.26-2.12 (m, 1H), 1.93-1.71 (m, 1H), 1.63-1.52 (m, 6H). [Example 72] |
| 73 | $^1$H NMR (400 MHz, DMSO-d$_6$) δ 8.74 (s, 1H), 8.08-7.85 (m, 3H), 7.50-7.44 (m, 1H), 5.69-5.58 (m, 1H), 4.99-4.82 (m, 1H), 4.37-4.11 (m, 1H), 3.22-3.00 (m, 4H), 2.90-2.70 (m, 3H), 2.62-2.52 (m, 1H), 2.30-2.15 (m, 1H), 1.93-1.73 (m, 1H), 1.62-1.52 (m, 6H). [Example 73] |
| 74 | $^1$H NMR (400 MHz, DMSO-d$_6$) δ 8.75-8.65 (m, 1H), 8.02-7.85 (m, 3H), 7.81-7.74 (m, 2H), 7.64-7.49 (m, 3H), 7.40-7.30 (m, 1H), 5.67-5.53 (m, 1H), 4.96-4.78 (m, 1H), 4.31-4.04 (m, 1H), 3.20-3.14 (m, 1H), 3.14-2.96 (m, 2H), 2.87-2.68 (m, 1H), 2.28-2.12 (m, 1H), 1.91-1.70 (m, 1H), 1.59-1.44 (m, 6H). [Example 73] |
| 75 | $^1$H NMR (400 MHz, DMSO-d$_6$) δ 10.68 (s, 1H), 8.85-8.73 (m, 1H), 8.31-8.10 (m, 1H), 8.00-7.89 (m, 3H), 7.73-7.61 (m, 2H), 7.55-7.47 (m, 1H), 7.42-7.33 (m, 1H), 5.73-5.53 (m, 1H), 5.35-5.13 (m, 1H), 4.64-4.32 (m, 1H), 3.75-3.59 (m, 2H), 3.26-3.14 (m, 1H), 2.97-2.79 (m, 1H), 2.42-2.24 (m, 1H), 1.63-1.48 (m, 6H). [Example 73] |
| 76 | $^1$H NMR (400 MHz, DMSO-d$_6$, 360 K) δ 8.67 (s, 1H), 8.04-7.97 (m, 2H), 7.59 (d, J = 7.9 Hz, 1H), 7.47-7.41 (m, 1H), 6.16-5.99 (m, 1H), 5.62 (hept, J = 6.9 Hz, 1H), 4.41-4.19 (m, 2H), 4.01-3.92 (m, 1H), 3.29-3.26 (m, 2H), 2.77-2.68 (m, 3H), 2.42-2.27 (m, 2H), 2.11-1.96 (m, 2H), 1.58 (d, J = 6.9 Hz, 6H), 1.35-1.21 (m, 1H). [Example 76] |
| 77 | $^1$H NMR (400 MHz, DMSO-d$_6$) δ 8.77-8.68 (m, 1H), 8.07-7.85 (m, 3H), 7.49-7.39 (m, 1H), 5.69-5.55 (m, 1H), 4.45-4.22 (m, 2H), 4.15-3.88 (m, 1H), 3.22-3.05 (m, 5H), 2.44-2.29 (m, 4H), 2.09-1.95 (m, 2H), 1.70-1.63 (m, 2H), 1.61-1.53 (m, 6H), 1.32-1.21 (m, 1H). [Example 76] |
| 78 | $^1$H NMR (400 MHz, DMSO-d$_6$, 360K) δ 8.67 (s, 1H), 8.06-7.97 (m, 2H), 7.59 (d, J = 8.0 Hz, 1H), 7.50-7.40 (m, 1H), 6.35-6.04 (m, 1H), 5.62 (hept, J = 6.9 Hz, 1H), 4.40-4.20 (m, 2H), 3.99- |

TABLE 3-continued

| EX No | ¹H NMR |
|---|---|
| | 3.87 (m, 1H), 3.24-3.16 (m, 4H), 2.41-2.25 (m, 4H), 2.10-2.02 (m, 1H), 2.01-1.91 (m, 1H), 1.58 (d, J = 6.9 Hz, 6H), 1.33-1.19 (m, 1H). [Example 76] |
| 79 | ¹H NMR (400 MHz, DMSO-$d_6$, 360K) δ 8.69 (s, 1H), 8.10-7.98 (m, 2H), 7.61 (d, J = 7.8 Hz, 1H), 7.54-7.43 (m, 1H), 5.68-5.56 (m, 1H), 4.38-4.21 (m, 2H), 3.98-3.85 (m, 1H), 3.20-3.10 (m, 4H), 2.39-2.32 (m, 1H), 2.27-2.20 (m, 1H), 2.05 (d, J = 12.3 Hz, 1H), 1.99-1.89 (m, 1H), 1.82-1.73 (m, 2H), 1.59 (d, J = 6.8 Hz, 6H), 1.29-1.20 (m, 1H), 1.03-0.96 (m, 3H). [Example 76] |
| 80 | ¹H NMR (400 MHz, DMSO-$d_6$, 360K) δ 8.69 (s, 1H), 8.05 (dd, J = 12.9, 2.0 Hz, 1H), 7.98 (dd, J = 8.6, 2.0 Hz, 1H), 7.81 (dd, J = 7.7, 1.3 Hz, 1H), 7.73-7.61 (m, 2H), 7.61-7.49 (m, 2H), 7.49-7.40 (m, 1H), 5.62 (hept, J = 6.9 Hz, 1H), 4.93-4.73 (m, 1H), 4.63 (s, 2H), 4.26-4.14 (m, 1H), 3.12-3.09 (m, 1H), 2.86-2.77 (m, 1H), 2.77-2.69 (m, 1H), 2.61-2.53 (m, 1H), 2.25-2.13 (m, 1H), 1.97-1.77 (m, 1H), 1.59 (d, J = 7.0 Hz, 6H). [Example 80] |
| 81 | ¹H NMR (400 MHz, DMSO-$d_6$, 360K) δ 8.69 (s, 1H), 8.03 (dd, J = 12.8, 2.0 Hz, 1H), 7.97 (dd, J = 8.6, 2.0 Hz, 1H), 7.79-7.74 (m, 2H), 7.63-7.54 (m, 3H), 7.43-7.37 (m, 1H), 5.62 (hept, J = 6.8 Hz, 1H), 4.91-4.72 (m, 1H), 4.60 (s, 2H), 4.27-4.13 (m, 1H), 3.12-3.09 (m, 1H), 2.85-2.78 (m, 1H), 2.77-2.70 (m, 1H), 2.61-2.53 (m, 1H), 2.25-2.14 (m, 1H), 1.97-1.79 (m, 1H), 1.59 (d, J = 6.9 Hz, 6H). [Example 80] |
| 82 | ¹H NMR (400 MHz, DMSO-$d_6$, 360K) δ 8.69 (s, 1H), 8.07-7.99 (m, 2H), 7.59 (d, J = 8.0 Hz, 1H), 7.52-7.42 (m, 1H), 5.62 (hept, J = 6.9 Hz, 1H), 4.91-4.69 (m, 1H), 4.24-4.11 (m, 1H), 3.14-3.11 (m, 1H), 2.94-2.88 (m, 2H), 2.82-2.75 (m, 1H), 2.75-2.67 (m, 1H), 2.58-2.51 (m, 1H), 2.23-2.13 (m, 1H), 1.96-1.81 (m, 1H), 1.80-1.73 (m, 2H), 1.58 (d, J = 6.9 Hz, 6H), 0.99 (t, J = 7.4 Hz, 3H). [Example 80] |
| 83 | ¹H NMR (400 MHz, DMSO-$d_6$, 360K) δ 8.70 (s, 1H), 8.10-7.98 (m, 2H), 7.61 (d, J = 7.7 Hz, 1H), 7.53-7.46 (m, 1H), 5.67-5.57 (m, 1H), 4.94-4.73 (m, 1H), 4.21 (s, 1H), 3.91-3.80 (m, 2H), 3.13-3.06 (m, 2H), 2.87-2.74 (m, 1H), 2.64-2.54 (m, 1H), 2.25-2.01 (m, 3H), 1.95-1.79 (m, 1H), 1.62-1.55 (m, 6H), 1.00-0.93 (m, 3H). [Example 80] |
| 84 | ¹H NMR (400 MHz, DMSO-$d_6$, 360K) δ 8.69 (s, 1H), 8.08-8.00 (m, 2H), 7.60 (d, J = 8.0 Hz, 1H), 7.51-7.44 (m, 1H), 5.62 (hept, J = 6.9 Hz, 1H), 4.89-4.72 (m, 1H), 4.25-4.13 (m, 1H), 3.29-3.23 (m, 2H), 2.95-2.87 (m, 2H), 2.85-2.76 (m, 1H), 2.76-2.68 (m, 1H), 2.61-2.52 (m, 1H), 2.45-2.32 (m, 2H), 2.24-2.13 (m, 1H), 1.96-1.78 (m, 1H), 1.71-1.63 (m, 2H), 1.58 (d, J = 6.9 Hz, 6H). [Example 80] |
| 85 | ¹H NMR (400 MHz, DMSO-$d_6$) δ 8.69 (s, 1H), 8.00 (d, J = 7.7 Hz, 1H), 7.89 (s, 1H), 6.13 (s, 1H), 5.82-5.65 (m, 1H), 5.05-4.85 (m, 1H), 4.38-4.15 (m, 1H), 3.62 (s, 3H), 3.50-3.42 (m, 2H), 3.18-3.11 (m, 2H), 2.95-2.71 (m, 3H), 2.67-2.57 (m, 1H), 2.30-2.15 (m, 1H), 1.90-1.72 (m, 1H), 1.60-1.50 (m, 6H). [Example 86] |
| 86 | ¹H NMR (400 MHz, DMSO-$d_6$) δ 8.68 (s, 1H), 8.01 (d, J = 7.9 Hz, 1H), 7.93 (s, 1H), 7.53 (t, J = 7.6 Hz, 1H), 7.47-7.37 (m, 1H), 7.34-7.19 (m, 3H), 5.85-5.68 (m, 1H), 5.07-4.85 (m, 1H), 4.52 (s, 2H), 4.39-4.18 (m, 1H), 3.18-3.12 (m, 2H), 2.98-2.81 (m, 1H), 2.66-2.55 (m, 1H), 2.31-2.20 (m, 1H), 1.93-1.72 (m, 1H), 1.55 (dd, J = 14.5, 6.8 Hz, 6H). [Example 86] |
| 87 | ¹H NMR (400 MHz, DMSO-$d_6$) δ 8.66 (s, 1H), 7.90-7.70 (m, 2H), 7.53 (t, J = 7.6 Hz, 1H), 7.34-7.23 (m, 1H), 7.20-7.10 (m, 2H), 7.04-6.95 (m, 1H), 5.83-5.69 (m, 1H), 5.12-5.00 (m, 1H), 4.20 (s, 2H), 4.13-4.04 (m, 1H), 4.00-3.90 (m, 1H), 3.17-3.10 (m, 2H), 2.93-2.70 (m, 2H), 1.95-1.75 (m, 2H), 1.62-1.47 (m, 6H). [Example 86] |
| 88 | ¹H NMR (400 MHz, DMSO-$d_6$) δ 8.66 (s, 1H), 7.88 (s, 1H), 7.81-7.73 (m, 1H), 7.53 (td, J = 7.6, 1.8 Hz, 1H), 7.41-7.31 (m, 1H), 7.23-7.08 (m, 3H), 5.82-5.65 (m, 1H), 5.22-5.12 (m, 1H), 4.35 (s, 2H), 4.20-3.97 (m, 1H), 3.74-3.62 (m, 1H), 3.12-2.90 (m, 2H), 2.47-2.35 (m, 2H), 2.25-2.10 (m, 1H), 1.62-1.42 (m, 7H). [Example 86] |
| 89 | ¹H NMR (400 MHz, DMSO-$d_6$) δ 8.70 (s, 1H), 7.94 (s, 1H), 7.91-7.83 (m, 1H), 7.53 (td, J = 7.6, 1.8 Hz, 1H), 7.47-7.37 (m, 1H), 7.32-7.18 (m, 3H), 5.82-5.68 (m, 1H), 5.50-5.35 (m, 1H), 4.51 (s, 2H), 4.30-4.10 (m, 1H), 3.90-3.70 (m, 1H), 3.25-3.15 (m, 2H), 2.77-2.55 (m, 2H), 2.27-2.12 (m, 1H), 1.65-1.45 (m, 7H). [Example 86] |
| 90 | ¹H NMR (400 MHz, DMSO-$d_6$) δ 8.72-8.59 (m, 1H), 7.96 (s, 1H), 7.81 (d, J = 8.0 Hz, 1H), 7.60 (dd, J = 12.5, 2.0 Hz, 1H), 7.51-7.32 (m, 4H), 7.28-7.18 (m, 2H), 5.85-5.69 (m, 1H), 4.92-4.75 (m, 1H), 4.53 (s, 2H), 4.27-4.10 (m, 1H), 3.10-2.90 (m, 2H), 2.81-2.65 (m, 2H), 2.57-2.52 (m, 1H), 2.28-2.10 (m, 1H), 1.93-1.70 (m, 1H), 1.61-1.51 (m, 6H). [Example 90] |
| 91 | ¹H NMR (400 MHz, DMSO-$d_6$) δ 8.64 (s, 1H), 7.96 (s, 1H), 7.89 (d, J = 7.7 Hz, 1H), 7.62 (dd, J = 12.3, 1.9 Hz, 1H), 7.48 (dd, J = 8.5, 2.0 Hz, 1H), 7.42 (t, J = 8.4 Hz, 1H), 5.84-5.66 (m, 1H), 3.90-3.68 (m, 1H), 3.22-3.01 (m, 2H), 2.88-2.71 (m, 3H), 2.58 (s, 6H), 2.13-1.93 (m, 4H), 1.62-1.51 (m, 6H), 1.50-1.31 (m, 4H). [Example 91] |
| 92 | ¹H NMR (400 MHz, DMSO-$d_6$) δ 8.71 (br s, 1H), 8.08 (d, J = 7.6 Hz, 1H), 8.02 (s, 1H), 7.64 (dd, J = 12.1, 1.9 Hz, 1H), 7.51 (dd, J = 8.4, 1.9 Hz, 1H), 7.45 (t, J = 8.3 Hz, 1H), 5.86-5.76 (m, 1H), 5.30-5.10 (m, 1H), 4.58-4.34 (m, 1H), 3.56-3.37 (m, 4H), 3.21-3.11 (m, 1H), 2.90-2.73 (m, 3H), 2.40-2.25 (m, 1H), 2.00-1.77 (m, 1H), 1.61-1.51 (m, 6H). [Example 92] |

TABLE 3-continued

| EX No | $^1$H NMR |
|---|---|
| 93 | $^1$H NMR (400 MHz, DMSO-$d_6$) δ 8.71-8.65 (m, 1H), 8.51 (d, J = 2.5 Hz, 1H), 8.02 (dd, J = 8.8, 2.4 Hz, 1H), 8.00 (s, 1H), 7.92 (d, J = 7.8 Hz, 1H), 7.43-7.37 (m, 2H), 7.24-7.18 (m, 2H), 7.03 (d, J = 8.8 Hz, 1H), 5.86-5.70 (m, 1H), 5.07-4.91 (m, 1H), 4.78 (s, 2H), 4.38-4.23 (m, 1H), 3.23-3.15 (m, 2H), 2.93 (dd, J = 37.4, 13.2 Hz, 1H), 2.72-2.60 (m, 1H), 2.32-2.20 (m, 1H), 1.90-1.72 (m, 1H), 1.60-1.54 (m, 6H). [Example 90] |
| 94 | $^1$H NMR (400 MHz, CD$_3$OD) δ 8.60 (s, 1H), 8.34 (d, J = 2.6 Hz, 1H), 8.16 (s, 1H), 7.99 (d, J = 8.8 Hz, 1H), 7.60 (dd, J = 8.7, 2.7 Hz, 1H), 7.45 (t, J = 7.6 Hz, 1H), 7.34 (q, J = 7.1, 6.5 Hz, 1H), 7.16 (t, J = 7.6 Hz, 1H), 7.06 (t, J = 9.1 Hz, 1H), 5.98-5.82 (m, 1H), 4.53 (s, 2H), 3.93-3.80 (m, 1H), 2.54-2.45 (m, 1H), 2.42 (s, 6H), 2.27-2.13 (m, 2H), 2.10-2.00 (m, 2H), 1.68-1.64 (m, 4H), 1.29 (s, 6H). [Example 94] |
| 95 | $^1$H NMR (400 MHz, DMSO-$d_6$) δ 8.81 (s, 1H), 8.49 (s, 1H), 8.42 (d, J = 2.7 Hz, 1H), 8.29 (d, J = 8.8 Hz, 1H), 7.91 (d, J = 7.9 Hz, 1H), 7.58 (dd, J = 8.8, 2.7 Hz, 1H), 7.46-7.38 (m, 2H), 7.25-7.18 (m, 2H), 5.89-5.72 (m, 1H), 4.98-4.81 (m, 1H), 4.60 (s, 2H), 4.28-4.13 (m, 1H), 3.14-2.98 (m, 2H), 2.88-2.70 (m, 1H), 2.61-2.53 (m, 1H), 2.30-2.12 (m, 1H), 1.92-1.72 (m, 1H), 1.63-1.52 (m, 6H). [Example 90] |
| 96 | (300 MHz, CD$_3$OD) δ 8.59 (s, 1H), 7.84 (s, 1H), 7.27-7.15 (m, 1H), 5.88 (s, 1H), 5.06-4.71 (m, 1H), 3.88 (s, 1H), 3.33-3.32 (m, 1H), 2.36 (s, 7H), 2.26-1.95 (m, 5H), 1.88-1.56 (m, 6H), 1.54-1.38 (m, 4H), 1.32-1.16 (m, 1H). [Example 58] |
| 97 | (300 MHz, CD3OD) δ 8.24 (s, 1H), 7.96 (s, 1H), 7.47 (s, 1H), 7.35 (d, J = 9.0 Hz, 1H), 7.28-7.23(m, 1H), 7.06 (d, J = 9.0 Hz, 1H), 5.90-5.85(m, 1H), 5.30 (d, J = 54.4 Hz, 1H), 4.85-4.75 (m, 1H), 4.66 (s, 2H), 3.86 (s, 3H), 3.73-3.69 (m, 2H), 3.46-3.42 (m, 1H), 3.29-3.15 (m, 1H), 2.72-2.50 (m, 1H), 2.20-1.95 (m, 1H), 1.65 (d, J = 6.6 Hz, 6H) [Example 97] |
| 98 98A 98B | (300 MHz, CD$_3$OD) δ 8.60 (s, 1H), 7.84 (s, 1H), 7.21-7.16 (m, 1H), 5.93-5.83 (m, 1H), 4.97-4.73 (m, 1H), 3.96 (s, 1H), 3.25 (d, J = 10.8 Hz, 1H), 2.89 (s, 6H), 2.33 (t, J = 8.7 Hz, 5H), 1.78-1.64 (m, 11H), 1.62-1.49 (m, 1H). (300 MHz, CD$_3$OD) δ 8.59 (s, 1H), 7.83 (s, 1H), 7.21-7.16 (m, 1H), 5.93-5.83 (m, 1H), 4.97-4.75 (m, 1H), 3.91 (s, 1H), 2.75 (s, 1H), 2.58 (s, 6H), 2.23-2.10 (m, 5H), 1.63-1.49 (m, 12H). [Example 58] |
| 99 | (300 MHz, CD$_3$OD) δ 8.56 (s, 1H), 7.71 (s, 1H), 6.96-6.89 (m, 1H), 5.87 (s, 1H), 4.84-4.75(m, 1H), 3.95 (s, 1H), 3.66 (d, J = 5.1 Hz, 3H), 3.23 (d, J = 10.2 Hz, 6H), 2.36-2.28 (m, 4H), 1.85 (t, J = 11.7 Hz, 2H), 1.28-0.91 (m, 8H). (300 MHz, CD$_3$OD) δ 8.56 (s, 1H), 7.71 (s, 1H), 6.96-6.89 (m, 1H), 5.87 (s, 1H), 4.84-4.75(m, 1H), 3.95 (s, 1H), 3.66 (d, J = 5.1 Hz, 3H), 3.23 (d, J = 10.2 Hz, 6H), 2.36-2.28 (m, 4H), 1.85 (t, J = 11.7 Hz, 2H), 1.28-0.91 (m, 8H) [Example 99] |
| 100 | (300 MHz, CD$_3$OD) δ 8.59 (s, 1H), 7.81 (s, 1H), 7.28 (d, J = 4.7 Hz, 2H), 5.88 (s, 1H), 4.02-3.69 (m, 3H), 3.34-3.25 (m, 1H), 2.74-1.84 (m, 14H), 1.79-1.49 (m, 7H), 1.52-1.36 (m, 4H), 1.07 (t, J = 7.4 Hz, 3H) [Example100] |
| 101 101A 101B | (300 MHz, DMSO-$d_6$) δ 9.71 (s, 1H), 8.64 (d, J = 15.1 Hz, 1H), 7.98-7.74 (m, 2H), 7.37-7.20 (m, 1H), 5.87-5.59 (m, 1H), 3.90-3.70 (m, 1H), 3.40 (t, J = 6.1 Hz, 2H), 3.25 (s, 3H), 3.17-3.06 (m, 2H), 2.63 (t, J = 6.1 Hz, 2H), 2.44 (s, 1H), 2.26 (s, 3H), 2.03-1.98 (m, 2H), 1.89-1.72 (m, 4H), 1.67-1.45 (m, 6H), 1.44-1.26 (m, 4H), 1.02 (t, J = 7.4 Hz, 3H). (300 MHz, CD$_3$OD) δ 8.65 (s, 1H), 7.88 (s, 1H), 7.28-7.16 (m, 1H), 5.92 (s, 1H), 4.33 (s, 1H), 3.76 (t, J = 4.9 Hz, 2H), 3.53-3.38 (m, 6H), 3.28-3.20 (m, 2H), 2.92 (s, 3H), 2.24 (d, J = 12.4 Hz, 2H), 2.03-1.87 (m, 8H), 1.64 (d, J = 6.9 Hz, 6H), 1.12 (t, J = 7.5 Hz, 3H). [Example 101] |
| 102 102A 102B | (300 MHz, DMSO-$d_6$) δ 8.65 (d, J = 14.2 Hz, 1H), 7.98-7.74 (m, 2H), 7.50-7.31 (m, 5H), 7.26 (dd, J = 10.7, 4.3 Hz, 1H), 5.87-5.62 (m, 1H), 4.43 (s, 2H), 3.92-3.61 (m, 1H), 3.44 (t, J = 5.9 Hz, 2H), 3.27 (s, 3H), 2.80-2.68 (m, 2H), 2.57-2.51 (m, 1H), 2.34 (s, 3H), 2.06-2.00 (m, 2H), 1.86-1.79 (m, 2H), 1.65-1.48 (m, 6H), 1.41-1.36 (m, 4H) (300 MHz, DMSO-$d_6$) δ 9.70 (s, 1H), 8.66 (s, 1H), 8.05 (d, J = 7.4 Hz, 1H), 7.90 (s, 1H), 7.51-7.30 (m, 5H), 7.25 (dd, J = 10.6, 4.0 Hz, 1H), 5.94-5.63 (m, 1H), 4.42 (s, 2H), 4.09 (s, 1H), 3.46 (t, J = 5.9 Hz, 2H), 3.27 (s, 3H), 2.77 (t, J = 6.1 Hz, 2H), 2.57-2.51 (m, 1H), 2.36 (s, 3H), 1.97-1.72 (m, 4H), 1.65-1.54 (m, 10H). [Example 101] |
| 103 | (300 MHz, CD$_3$OD) δ 8.56 (s, 1H), 7.75 (s, 1H), 7.51-7.24 (m, 3H), 5.95-5.90 (m, 1H), 4.39 (s, 1H), 3.26-3.15 (m, 2H), 2.85-2.71 (m, 2H), 2.30-2.22 (m, 1H), 1.98-1.95 (m, 1H), 1.85-1.79 (m, 5H), 1.75-1.62 (m, 7H), 1.47-1.41 (m, 1H) [Example 2] |
| 104 | (300 MHz, CD$_3$OD) δ 8.74 (s, 1H), 7.94 (s, 1H), 7.65-7.53 (m, 2H), 7.47 (d, J = 8.2 Hz, 1H), 5.90-5.82 (m, 1H), 4.69-4.63 (m, 1H), 3.70-3.64 (m, 1H), 3.41-3.33 (m, 2H), 2.88 (d, J = 8.0 Hz, 6H), 2.82-2.67 (m, 2H), 2.45-2.41 (m, 1H), 2.21-2.16 (m, 1H), 1.96-1.91 (m, 3H), 1.80-1.73 (m, 2H), 1.64 (d, J = 6.9 Hz, 7H) [Example 2] |
| 105 | (300 MHz, DMSO-$d_6$) δ 8.59 (d, J = 15.0 Hz, 1H), 8.28 (d, J = 2.4 Hz, 1H), 8.15-8.07 (m, 1H), 8.00-7.61 (m, 3H), 7.58-7.40 (m, 3H), 7.11 (d, J = 9.0 Hz, 1H), 5.73 (s, 1H), 3.80-3.69 (m, 2H), 2.28 (s, 7H), 2.12-1.79 (m, 4H), 1.52-1.57 (m, 6H), 1.42-1.22 (m, 4H) [Example 105] |
| 106 | (300 MHz, DMSO-$d_6$) δ 8.61-8.56 (m, 1H), 8.33 (d, J = 2.4 Hz, 1H), 7.95 (dd, J = 8.8, 2.4 Hz, 1H), 7.91-7.85 (m, 3H), 7.80 (d, J = 7.6 Hz, 1H), 7.59-7.48 (m, 3H), 7.15 (d, J = 8.8 Hz, 1H), |

TABLE 3-continued

| EX No | $^1$H NMR |
|---|---|
| | 5.70 (s, 1H), 3.68-3.35 (m, 2H), 2.23 (s, 7H), 2.01 (m, 2H), 1.88 (d, J = 12.4 Hz, 2H), 1.56-1.50 (m, 6H), 1.49-1.38 (m, 4H)<br>[Example 105] |
| 107 | (300 MHz, DMSO-d$_6$) δ 8.66 (d, J = 13.3 Hz, 1H), 7.99-7.84 (m, 2H), 7.65 (d, J = 1.5 Hz, 1H), 7.59-7.47 (m, 2H), 7.18 (dd, J = 10.0, 6.3 Hz, 1H), 5.73 (s, 1H), 4.96 (d, J = 47.2 Hz, 1H), 4.50 (s, 2H), 4.36-4.26 (m, 1H), 3.15 (t, J = 13.3 Hz, 2H), 2.89 (dd, J = 36.8, 14.0 Hz, 1H), 2.67-2.51 (m, 1H), 2.36-2.27 (m, 4H), 1.93-1.71 (m, 1H), 1.55 (d, J = 7.8 Hz, 6H).<br>[Example 107] |
| 108 | (300 MHz, CD$_3$OD) δ 8.74 (s, 1H), 7.96 (s, 1H), 7.65-7.56 (m, 2H), 7.50 (d, J = 8.7 Hz, 1H), 5.91-5.80 (m, 1H), 4.16 (s, 1H), 3.44-3.35 (m, 3H), 2.86-2.67 (m, 2H), 2.46 (d, J = 12.0 Hz, 1H), 2.26-1.98 (m, 3H), 1.75-1.38 (m, 10H)<br>[Example 2] |
| 109 | (300 MHz, DMSO-d$_6$) δ 9.65 (s, 1H), 8.63 (d, J = 19.6 Hz, 1H), 7.93 (s, 1H), 7.79-7.69 (m, 1H), 7.64-7.54 (m, 1H), 7.49-7.37 (m, 2H), 5.74 (s, 1H), 3.85-3.66 (m, 1H), 3.15 (d, J = 6.8 Hz, 2H), 2.35-2.15 (m, 8H), 2.09-1.93 (m, 2H), 1.88-1.80 (m, 4H), 1.66-1.42 (m, 10H), 1.41-1.19 (m, 6H).<br>[Example 10] |
| 110<br>110A<br>110B | (300 MHz, CD$_3$OD) δ 8.66 (s, 1H), 7.89 (s, 1H), 7.66-7.40 (m, 3H), 5.94-5.78 (m, 1H), 5.19-4.94 (m, 1H), 4.14 (s, 1H), 3.64 (s, 1H), 3.40-3.33 (m, 2H), 3.04-2.91 (m, 6H), 2.83-2.64 (m, 3H), 2.26 (s, 2H), 1.88-1.41 (m, 9H)<br>(300 MHz, CD$_3$OD) δ 8.66 (s, 1H), 7.89 (s, 1H), 7.70-7.57 (m, 2H), 7.45 (d, J = 8.9 Hz, 1H), 5.90-5.81 (m, 1H), 5.20-5.11 (m, 1H), 4.14 (s, 1H), 3.71-3.63 (m, 1H), 3.40-3.33 (m, 2H), 3.01-2.91 (m, 6H), 2.80-2.75 (m, 3H), 2.45-2.27 (m, 2H), 1.89-1.51 (m, 9H)<br>[Example 110] |
| 111 | (300 MHz, CD$_3$OD) δ 8.58 (s, 1H), 7.82 (s, 1H), 7.59-7.45 (m, 2H), 7.45-7.32 (m, 3H), 7.15-7.02 (m, 2H), 5.96-5.85 (m, 1H), 4.45 (s, 2H), 3.87 (s, 1H), 2.38 (s, 7H), 2.21 (brs, 2H), 2.06 (brs, 2H), 1.79-1.61 (m, 6H), 1.49-1.31 (m, 4H)<br>[Example 2] |
| 112 | (300 MHz, CD$_3$OD) δ 8.61 (s, 1H), 7.84 (s, 1H), 7.61-7.46 (m, 2H), 7.46-7.32 (m, 3H), 7.08 (t, J = 8.7 Hz, 2H), 5.94 (s, 1H), 4.95-4.80 (m, 1H), 4.49-4.34 (m, 3H), 3.34-3.32(m, 1H), 3.15 (t, J = 13.2 Hz, 1H), 2.80 (dd, J = 36.9, 14.1 Hz, 1H), 2.76-2.43 (m, 2H), 1.96-1.76 (m, 1H), 1.66 (d, J = 6.9 Hz, 6H)<br>[Example 2] |
| 113 | (300 MHz, DMSO-d$_6$) δ 9.59 (s, 1H), 8.63 (d, J = 11.5 Hz, 1H), 7.95-7.68 (m, 2H), 7.62 (d, J = 1.7 Hz, 1H), 7.56 (d, J = 8.0 Hz, 1H), 7.47 (dd, J = 8.3, 1.9 Hz, 1H), 7.04 (s, 1H), 5.71 (s, 1H), 4.36 (s, 2H), 3.86-3.69 (m, 1H), 2.85 (s, 1H), 2.58 (s, 6H), 2.34 (s, 3H), 2.12-1.93 (m, 4H), 1.55 (dd, J = 17.3, 6.9 Hz, 6H), 1.43-1.32 (m, 4H)<br>[Example 107] |
| 114 | (300 MHz, CD$_3$OD) δ 8.63 (s, 1H), 7.82 (s, 1H), 7.59-7.46 (m, 2H), 7.45-7.37 (m, 1H), 5.88-5.79 (m, 1H), 3.94 (s, 1H), 3.33-3.30 (m, 2H), 2.82-2.66 (m, 2H), 2.60-2.56 (m, 1H), 2.45-2.39 (m, 7H), 2.15-1.96 (m, 3H), 1.64 (s, 6H), 1.50-1.21 (m, 4H)<br>[Example 2] |
| 115 | (300 MHz, CD$_3$OD) δ 8.58 (s, 1H), 7.84 (s, 1H), 7.62-7.50 (m, 2H), 7.45-7.36 (m, 1H), 5.90 (s, 1H), 3.87 (s, 1H), 3.03 (d, J = 6.0 Hz, 2H), 2.38 (s, 7H), 2.21 (s, 2H), 2.12-1.91 (m, 5H), 1.79-1.59 (m, 9H), 1.55-0.96 (m, 9H)<br>[Example 10] |
| 116 | (300 MHz, DMSO-d$_6$) δ 8.65 (d, J = 15.1 Hz, 1H), 8.04 (s, 1H), 7.94-7.73 (m, 1H), 7.55-7.40 (m, 6H), 5.74 (s, 1H), 4.43 (s, 2H), 3.87-3.66 (m, 1H), 2.31 (s, 7H), 2.21-1.80 (m, 4H), 1.65-1.49 (m, 6H), 1.44-1.25 (m, 4H)<br>[Example 10] |
| 117 | (300 MHz, DMSO-d$_6$) δ 8.64 (d, J = 20.8 Hz, 1H), 8.04 (s, 1H), 7.87-7.77 (m, 1H), 7.50 (d, J = 9.4 Hz, 2H), 7.46-7.41 (m, 2H), 7.41-7.32 (m, 3H), 5.79-5.72 (m, 1H), 4.42 (s, 2H), 3.79-3.65 (m, 1H), 2.50 (s, 1H), 2.25 (s, 7H), 2.10-1.80 (m, 2H), 1.61-1.51 (m, 6H), 1.38-1.28 (m, 4H)<br>[Example 10] |
| 118<br>118A<br>118B | (300 MHz, CD$_3$OD) δ 8.70 (s, 1H), 7.98 (s, 1H), 7.47 (d, J = 9.2 Hz, 2H), 5.93-5.81 (m, 1H), 5.15 (s, 1H), 4.18 (s, 1H), 3.74-3.57 (m, 1H), 3.54-3.43 (m, 2H), 2.99 (d, J = 9.9 Hz, 6H), 2.89-2.71 (m, 3H), 2.29 (s, 2H), 1.95-1.70 (m, 2H), 1.67-1.65 (m, 7H)<br>(300 MHz, CD$_3$OD) δ 8.70 (s, 1H), 7.97 (s, 1H), 7.47 (d, J = 9.2 Hz, 2H), 5.93-5.81 (m, 1H), 5.15 (s, 1H), 4.18 (s, 1H), 3.73-3.55 (m, 1H), 3.53-3.42 (m, 2H), 2.99 (d, J = 9.9 Hz, 6H), 2.88-2.67 (m, 3H), 2.29 (s, 2H), 1.95-1.70 (m, 2H), 1.67-1.65 (m, 7H)<br>[Example 118] |
| 119 | (300 MHz, CD$_3$OD) δ 8.56 (s, 1H), 7.82 (s, 1H), 7.63-7.48 (m, 2H), 7.39 (d, J = 8.5 Hz, 1H), 5.95-5.81 (m, 1H), 3.85 (s, 1H), 3.08-2.94 (m, 1H), 2.34 (s, 7H), 2.19 (d, J = 11.3 Hz, 4H), 2.03 (s, 2H), 1.87 (d, J = 11.9 Hz, 2H), 1.71-1.63 (m, 6H), 1.57-1.36 (m, 6H), 1.31-1.18 (m, 4H)<br>[Example 119] |
| 120 | (300 MHz, CD$_3$OD) δ 8.69 (s, 1H), 7.96 (s, 1H), 7.46 (d, J = 9.1 Hz, 2H), 7.38 (d, J = 8.0 Hz, 2H), 7.22 (d, J = 7.9 Hz, 2H), 5.91-5.79 (m, 1H), 4.50 (s, 2H), 4.01 (s, 1H), 3.32-3.29 (m, 1H), 2.92 (s, 6H), 2.40-2.28 (m, 5H), 2.24 (d, J = 12.3 Hz, 2H), 1.81-1.54 (m, 10H)<br>[Example 10] |
| 121 | (300 MHz, DMSO-d$_6$) δ 10.45 (s, 1H), 8.65 (s, 1H), 8.53 (d, J = 2.4 Hz, 1H), 8.09-7.83 (m, 3H), 7.47-7.29 (m, 2H), 7.26-7.13 (m, 2H), 6.98 (d, J = 8.7 Hz, 1H), 5.76 (s, 1H), 4.78 (s, 2H), 3.90-3.75 (m, 1H), 3.17 (s, 1H), 2.90-2.58 (m, 6H), 2.12-2.00 (m, 4H), 1.86-1.42 (m, 8H), 1.40-0.74 (m, 2H)<br>[Example 105] |

TABLE 3-continued

| EX No | ¹H NMR |
|---|---|
| 122 | (300 MHz, DMSO-$d_6$) δ 9.54 (s, 1H), 8.62 (d, J = 16.3 Hz, 1H), 8.04 (s, 1H), 7.92-7.75 (m, 1H), 7.57-7.41 (m, 4H), 7.21 (t, J = 8.9 Hz, 2H), 5.73 (s, 1H), 4.46 (s, 2H), 3.88-3.60 (m, 1H), 3.38 (t, J = 6.1 Hz, 2H), 3.29 (s, 3H), 2.61 (t, J = 6.1 Hz, 2H), 2.51-2.44 (m, 1H), 2.24 (s, 3H), 2.01 (s, 2H), 1.80 (s, 2H), 1.60-1.53 (m, 6H), 1.35 (q, J = 11.0, 9.5 Hz, 4H)<br>[Example 10] |
| 123 | (300 MHz, CD$_3$OD) δ 8.55 (s, 1H), 7.80 (s, 1H), 7.55-7.42 (m, 2H), 7.39-7.35 (m, 3H), 7.10-7.06 (m, 2H), 5.97-5.79 (m, 1H), 4.43 (s, 2H), 3.90-3.84 (m, 1H), 3.52 (t, J = 5.7 Hz, 2H), 3.35 (s, 3H), 2.75 (t, J = 5.7 Hz, 2H), 2.63-2.58 (s, 1H), 2.37 (s, 3H), 2.20-2.16 (m, 2H), 2.10-1.97 (m, 2H), 1.64 (s, 6H), 1.60-1.44 (m, 4H)<br>[Example 122] |
| 124 | (300 MHz, CD$_3$OD) δ 8.70 (s, 1H), 7.90 (s, 1H), 7.57-7.43 (m, 2H), 7.37 (d, J = 10.1 Hz, 6H), 5.88-5.72 (m, 1H), 4.50 (s, 2H), 4.11-4.02 (m, 1H), 3.76-3.73 (m, 2H), 3.58-3.56 (m, 1H), 3.49-3.45 (m, 4H), 3.33-3.35 (m, 1H), 2.93 (s, 3H), 2.41-2.13 (m, 4H), 1.95-1.82 (m, 2H), 1.71-1.67 (m, 8H)<br>[Example 122] |
| 125 | (300 MHz, CD$_3$OD) δ 8.68 (s, 1H), 7.96 (s, 1H), 7.66-7.57 (m, 4H), 7.49-7.43 (m, 2H), 6.80 (t, J = 56.2 Hz, 1H), 5.90-5.84 (m, 1H), 4.62 (s, 2H), 4.02-3.96 (m, 1H), 3.38-3.35 (m, 1H), 2.92 (s, 6H), 2.38-2.15 (m, 4H), 1.85-1.50 (m, 10H)<br>[Example 10] |
| 126 | (300 MHz, DMSO-$d_6$) δ 8.63 (d, J = 14.9 Hz, 1H), 8.44 (d, J = 2.4 Hz, 1H), 8.03 (dd, J = 8.8, 2.4 Hz, 1H), 7.94 (s, 1H), 7.90-7.65 (m, 1H), 7.08 (d, J = 8.8 Hz, 1H), 5.74 (s, 1H), 3.59 (d, J = 8.4 Hz, 4H), 3.31-3.22 (m, 4H), 2.81-2.68 (m, 2H), 2.62 (t, J = 6.2 Hz, 2H), 2.26 (s, 3H), 2.10-1.90 (m, 2H), 1.83 (s, 2H), 1.60-1.52 (m, 7H), 1.38-1.31 (m, 5H)<br>[Example 105] |
| 127 | (300 MHz, DMSO-$d_6$) δ 8.60 (d, J = 12.2 Hz, 1H), 7.85-7.64 (m, 2H), 7.36 (dd, J = 8.5, 5.6 Hz, 2H), 7.27-7.03 (m, 4H), 5.68 (s, 1H), 4.33 (s, 2H), 3.85-3.67 (m, 1H), 2.59-2.51 (m, 1H), 2.40 (s, 6H), 2.04-1.93 (m, 4H), 1.63-1.44 (m, 6H), 1.39-1.32 (m, 4H)<br>[Example 10] |
| 128 | (300 MHz, CD$_3$OD) δ 8.69 (s, 1H), 7.86 (s, 1H), 7.43-7.40 (m, 2H), 7.12-7.06 (m, 3H), 5.88-5.79 (m, 1H), 4.57 (s, 2H), 4.10-3.96 (m, 1H), 3.33-3.31 (m, 1H), 2.92 (s, 6H), 2.38-2.15 (m, 4H), 1.66-1.65 (m, 10H)<br>[Example 10] |
| 129 | (300 MHz, CD$_3$OD) δ 8.68 (s, 1H), 7.82 (s, 1H), 7.42-7.28 (m, 2H), 7.08 (t, J = 8.7 Hz, 2H), 6.82 (d, J = 9.3 Hz, 2H), 5.90-5.67 (m, 1H), 4.52 (s, 2H), 4.01 (s, 1H), 3.39-3.32 (m, 1H), 2.90 (s, 6H), 2.42-2.15 (m, 4H), 1.88-1.47 (m, 10H)<br>[Example 10] |
| 130 | (300 MHz, CD$_3$OD) δ 8.67 (s, 1H), 7.80 (s, 1H), 7.36 (dd, J = 8.7, 5.4 Hz, 2H), 7.09 (t, J = 8.7 Hz, 2H), 6.83 (d, J = 9.6 Hz, 2H), 5.92-5.87 (m, 1H), 5.34-5.20 (m, 1H), 4.71 (s, 1H), 4.52 (s, 2H), 3.69 (d, J = 13.2 Hz, 2H), 3.32-3.30 (m, 2H), 3.00 (s, 1H), 2.65-2.50 (m, 1H), 1.63 (d, J = 6.8 Hz, 6H)<br>[Example 2] |
| 131 | (300 MHz, DMSO-$d_6$) δ 8.54-8.51 (m, 1H), 8.23-8.20 (m, 1H), 7.74-7.72 (m, 1H), 7.59-7.47 (m, 6H), 6.47-6.43 (m, 1H), 5.66-5.62 (m, 1H), 3.82-3.66 (m, 1H), 3.39 (s, 3H), 2.35 (s, 6H), 2.03-1.91 (m, 5H), 1.76-1.24 (m, 10H)<br>[Example 105] |
| 132 | (300 MHz, DMSO-$d_6$) δ 8.57 (d, J = 13.5 Hz, 1H), 7.99-7.89 (m, 2H), 7.86-7.62 (m, 2H), 7.53 (d, J = 8.8 Hz, 2H), 7.41-7.31 (m, 2H), 7.01 (d, J = 8.8 Hz, 1H), 5.67 (s, 1H), 3.91-3.60 (m, 1H), 2.26-2.14 (m, 10H), 2.08-1.78 (m, 4H), 1.62-1.44 (m, 6H), 1.43-1.20 (m, 4H)<br>[Example 105] |
| 133 | (300 MHz, DMSO-$d_6$) δ 8.58 (d, J = 13.2 Hz, 1H), 8.18-8.08 (m, 1H), 7.81 (d, J = 8.1 Hz, 1H), 7.70 (s, 1H), 7.62-7.45 (m, 4H), 7.02 (d, J = 9.0 Hz, 1H), 5.70 (s, 1H), 4.88-4.72 (m, 1H), 4.12 (s, 1H), 3.05-2.88 (m, 2H), 2.73-2.61 (m, 1H), 2.50-2.49 (m, 1H), 2.43 (s, 4H), 1.85-1.72 (m, 1H), 1.57-1.46 (m, 5H)<br>[Example 105] |
| 134 | (300 MHz, CD$_3$OD) 8.74 (s, 1H), 7.93 (s, 1H), 7.67-7.52 (m, 2H), 7.49-7.40 (m, 1H), 5.92-5.71 (m, 1H), 4.07 (s, 1H), 3.74-3.55 (m, 1H), 3.40 (d, J = 12.0 Hz, 1H), 2.92 (s, 6H), 2.31 (t, J = 15.6 Hz, 4H), 2.13-1.94 (m, 4H), 1.79-1.69 (m, 14H)<br>[Example 134] |
| 135 | (300 MHz, CD$_3$OD) δ 8.61 (s, 1H), 8.23 (d, J = 7.5 Hz, 1H), 7.70 (s, 1H), 7.63-7.42 (m, 4H), 7.16 (d, J = 9.0 Hz, 1H), 5.81 (s, 1H), 3.97 (s, 1H), 3.32-3.31 (m, 1H), 2.91 (s, 6H), 2.40-2.15 (m, 7H), 1.74-1.61 (m, 10H)<br>[Example 105] |
| 136 | (300 MHz, DMSO-$d_6$) δ 8.57 (d, J = 13.2 Hz, 1H), 8.12 (d, J = 8.0 Hz, 1H), 7.97 (d, J = 7.6 Hz, 1H), 7.88-7.64 (m, 4H), 7.55 (d, J = 8.9 Hz, 1H), 6.98 (d, J = 9.0 Hz, 1H), 5.67 (s, 1H), 3.91-3.62 (m, 1H), 2.30 (s, 7H), 2.18 (s, 3H), 2.12-1.80 (m, 4H), 1.62-1.44 (m, 6H), 1.43-1.20 (m, 4H)<br>[Example 105] |
| 137 | (300 MHz, DMSO-$d_6$) δ 8.57 (d, J = 13.6 Hz, 1H), 7.88-7.64 (m, 3H), 7.56 (d, J = 8.9 Hz, 1H), 7.52-7.44 (m, 1H), 7.28-7.18 (m, 1H), 7.06 (d, J = 9.0 Hz, 1H), 5.67 (s, 1H), 3.90-3.60 (m, 1H), 2.30-2.13 (m, 13H), 2.09-1.80 (m, 4H), 1.62-1.44 (m, 6H), 1.43-1.20 (m, 4H)<br>[Example 105] |
| 138 | (300 MHz, CD$_3$OD) δ 8.57 (s, 1H), 7.84 (s, 1H), 7.59-7.48 (m, 2H), 7.42 (d, J = 8.9 Hz, 1H), 5.92-5.89 (m, 1H), 3.87 (s, 1H), 3.61-3.56 (m, 2H), 3.38 (s, 3H), 3.37-3.36 (m, 1H), 3.35-3.34 (m, 1H), 2.85-2.62 (m, 5H), 2.43 (s, 3H), 2.25-2.20 (m, 2H), 2.02-1.96 (m, 2H), 1.66 (s, 6H), 1.56-1.36 (m, 4H)<br>[Example 122] |

TABLE 3-continued

| EX No | $^1$H NMR |
|---|---|
| 139 | (300 MHz, CD$_3$OD) δ 8.68 (d, J = 4.4 Hz, 1H), 8.64-8.62 (m, 1H), 8.29 (d, J = 8.1 Hz, 1H), 7.86 (s, 1H), 7.73-7.69 (m, 1H), 7.22-7.18 (m, 1H), 5.91 (s, 1H), 5.05-5.03 (m, 1H), 4.82-4.79 (m, 2H), 4.54-4.46 (m, 1H), 3.40-3.38 (m, 1H), 3.25-3.22 (d, J = 12.7 Hz, 1H), 2.95-2.89 (m, 1H), 2.70-2.65 (m, 1H), 2.47-2.44 (m, 1H), 1.98-1.97 (m, 1H), 1.70-1.64 (s, 6H) [Example 2] |
| 140 | (300 MHz, DMSO-d$_6$) δ 12.85 (s, 1H), 8.57 (s, 1H), 7.93 (td, J = 7.7, 1.9 Hz, 1H), 7.85 (d, J = 7.8 Hz, 1H), 7.68 (s, 1H), 7.65-7.53 (m, 2H), 7.38-7.26 (m, 2H), 7.05 (d, J = 8.9 Hz, 1H), 5.67 (s, 1H), 3.90-3.60 (m, 1H), 2.23-2.19 (m, 10H), 2.10-1.77 (m, 4H), 1.62-1.44 (m, 6H), 1.43-1.20 (m, 4H) [Example 105] |
| 141 | (300 MHz, DMSO-d$_6$) δ 9.84 (s, 1H), 8.63 (d, J = 14.9 Hz, 1H), 8.00-7.78 (m, 2H), 7.47 (dd, J = 8.6, 5.5 Hz, 2H), 7.35-7.16 (m, 3H), 5.69 (s, 1H), 4.59-4.35 (m, 4H), 3.82-3.68(m, 1H), 2.76 (dt, J = 26.7, 5.1 Hz, 2H), 2.44 (s, 1H), 2.27 (s, 3H), 2.04-1.96 (m, 2H), 1.83-1.76 (m, 2H), 1.59-1.53 (m, 6H), 1.35-1.25 (m, 4H) [Example 122] |
| 142 | (300 MHz, DMSO-d$_6$) δ 8.57 (d, J = 12.9 Hz, 1H), 8.28 (s, 1H), 8.16 (d, J = 7.9 Hz, 1H), 8.00 (d, J = 7.7 Hz, 1H), 7.84 (d, J = 7.8 Hz, 1H), 7.77-7.63 (m, 2H), 7.52 (d, J = 8.9 Hz, 1H), 6.98 (d, J = 8.9 Hz, 1H), 5.67 (s, 1H), 3.91-3.62 (m, 1H), 2.28 (s, 7H), 2.18 (s, 3H), 2.10-1.81 (m, 4H), 1.62-1.44 (m, 6H), 1.43-1.20 (m, 4H) [Example 105] |
| 143 | (300 MHz, DMSO-d$_6$) δ 11.55 (s, 1H), 8.62 (d, J = 15.5 Hz, 1H), 8.45 (d, J = 2.4 Hz, 1H), 8.06 (dd, J = 8.9, 2.4 Hz, 1H), 7.95 (s, 1H), 7.91-7.67 (m, 1H), 7.12 (d, J = 8.8 Hz, 1H), 5.73 (s, 1H), 4.47 (dt, J = 47.7, 5.1 Hz, 2H), 3.62 (t, J = 8.0 Hz, 3H), 2.89-2.63 (m, 4H), 2.47-2.38 (m, 1H), 2.26 (s, 3H), 2.08-1.91 (m, 2H), 1.87-1.70 (m, 2H), 1.64-1.46 (m, 6H), 1.44-1.16 (m, 4H). [Example 105] |
| 144 | (300 MHz, DMSO-d$_6$) δ 12.02 (s, 1H), 8.59 (d, J = 16.1 Hz, 1H), 8.34 (d, J = 2.4 Hz, 1H), 8.04-7.95 (m, 1H), 7.94-7.81 (m, 4H), 7.73-7.46 (m, 3H), 7.19 (d, J = 9.0 Hz, 1H), 5.71 (s, 1H), 4.45 (dt, J = 47.8, 5.2 Hz, 2H), 3.92-3.56 (m, 1H), 2.70 (dt, J = 26.3, 5.2 Hz, 2H), 2.39 (s, 3H), 2.08-1.90 (m, 2H), 1.86-1.68 (m, 2H), 1.63-1.43 (m, 6H), 1.42-1.16 (m, 4H). [Example 105] |
| 145 | (300 MHz, CD$_3$OD) δ 8.53 (s, 1H), 8.23 (d, J = 7.5 Hz, 1H), 7.67 (s, 1H), 7.62-7.44 (m, 4H), 7.17 (d, J = 8.9 Hz, 1H), 5.87 (s, 1H), 4.56 (dt, J = 47.8, 4.9 Hz, 2H), 3.86 (s, 1H), 2.86 (dt, J = 27.5, 5.0 Hz, 2H), 2.58 (s, 1H), 2.39 (s, 3H), 2.28 (s, 3H), 2.19 (s, 2H), 1.96 (s, 2H), 1.68-1.55 (m, 6H), 1.43-1.38 (m, 4H) [Example 105] |
| 146 | (300 MHz, DMSO-d$_6$) δ 10.92 (s, 1H), 8.63 (d, J = 7.8 Hz, 1H), 8.29 (d, J = 2.4 Hz, 1H), 8.20-7.87 (m, 4H), 7.67-7.46 (m, 3H), 7.22 (d, J = 9.2 Hz, 1H), 5.72 (s, 1H), 4.98-4.88 (m, 3H), 4.03-3.13 (m, 4H), 2.76 (d, J = 4.8 Hz, 3H), 2.12 (d, J = 11.7 Hz, 4H), 1.76-1.30 (m, 10H). [Example 105] |
| 147 | (300 MHz, DMSO-d$_6$) δ 8.62 (d, J = 15.0 Hz, 1H), 8.29 (d, J = 2.4 Hz, 1H), 8.18-8.07 (m, 1H), 8.07-7.98 (m, 1H), 7.95 (s, 1H), 7.88-7.67 (m, 1H), 7.62-7.46 (m, 3H), 7.17 (d, J = 9.1 Hz, 1H), 5.74 (s, 1H), 4.90-4.74 (m, 1H), 4.30-4.02 (m, 1H), 3.12-2.87 (m, 2H), 2.84-2.57 (m, 1H), 2.45 (s, 1H), 2.26-2.05 (m, 1H), 1.92-1.68 (m, 1H), 1.60-1.45 (m, 6H). [Example 105] |
| 148 | (300 MHz, DMSO-d$_6$) δ 8.60 (d, J = 16.5 Hz, 1H), 8.32 (d, J = 2.4 Hz, 1H), 8.20-8.08 (m, 2H), 8.06-7.96 (m, 2H), 7.94-7.68 (m, 3H), 7.29 (d, J = 9.3 Hz, 1H), 5.72 (s, 1H), 4.56 (dt, J = 47.8, 4.9 Hz, 2H), 3.67 (s, 1H), 2.77 (dt, J = 27.5, 5.0 Hz, 2H), 2.28 (s, 3H), 2.01-1.75 (m, 4H), 1.58-1.48 (m, 7H), 1.41-1.31 (m, 5H) [Example 105] |
| 149 | (400 MHz, DMSO-d$_6$) δ 8.58 (d, J = 20.4 Hz, 1H), 8.36-8.17 (m, 2H), 7.94 (dd, J = 9.1, 2.5 Hz, 1H), 7.90 (s, 1H), 7.89-7.65 (m, 4H), 7.05 (d, J = 9.1 Hz, 1H), 5.70 (s, 1H), 3.81-3.51 (m, 1H), 2.38-2.31 (m, 7H), 2.11-1.82 (m, 4H), 1.56-1.49 (m, 6H), 1.39-1.32 (m, 4H) [Example 105] |
| 150 | (300 MHz, DMSO-d$_6$) δ 8.60 (d, J = 15.3 Hz, 1H), 8.28 (d, J = 2.4 Hz, 1H), 8.06 (dd, J = 7.8, 1.8 Hz, 1H), 7.97 (dd, J = 9.2, 2.5 Hz, 1H), 7.92 (s, 1H), 7.89-7.69 (m, 1H), 7.68-7.52 (m, 1H), 7.55-7.41 (m, 2H), 7.13 (d, J = 9.1 Hz, 1H), 5.88-5.59 (m, 1H), 3.68-3.51 (m, 1H), 2.29-2.28 (m, 7H), 2.13-1.78 (m, 4H), 1.74-1.58 (m, 6H), 1.52-1.24 (m, 4H) [Example 105] |
| 151 | (300 MHz, CD$_3$OD) δ 8.57 (s, 1H), 7.82 (s, 1H), 7.60-7.51 (m, 2H), 7.46-7.38 (m, 1H), 5.89 (s, 1H), 3.86 (s, 1H), 3.36 (d, J = 7.0 Hz, 2H), 2.89-2.61 (m, 3H), 2.56-2.41 (m, 3H), 2.39 (s, 6H), 2.27-2.14 (m, 2H), 2.12-1.98 (m, 2H), 1.77-1.57 (m, 6H), 1.54-1.30 (m, 4H) [Example 10] |
| 152 | (300 MHz, CD$_3$OD) δ 8.70 (s, 1H), 8.58 (dd, J = 2.4, 0.8 Hz, 1H), 8.21 (dd, J = 8.9, 2.4 Hz, 1H), 7.97 (s, 1H), 7.32 (dd, J = 8.9, 0.7 Hz, 1H), 5.84-5.77 (m, 1H), 4.15-3.90 (m, 1H), 3.35 (d, J = 6.1 Hz, 2H), 2.90 (s, 6H), 2.44-2.19 (m, 4H), 2.13 1.89 (m, 3H), 1.66-1.63 (m, 13H), 1.35-1.24 (m, 3H), 1.24-1.04 (m, 3H). [Example 105] |
| 153 153A 153B | (300 MHz, CD$_3$OD) δ 8.58 (s, 1H), 7.85 (s, 1H), 7.62-7.51 (m, 2H), 7.43 (dd, J = 9.4, 1.5 Hz, 1H), 5.91 (s, 1H), 3.87 (s, 1H), 3.51-3.40 (m, 1H), 3.30-3.23 (m, 1H), 2.55-2.36 (m, 9H), 2.28-1.98 (m, 5H), 1.78-1.56 (m, 7H), 1.45-1.28 (m, 5H) (300 MHz, CD$_3$OD) δ 8.58 (s, 1H), 7.85 (s, 1H), 7.62-7.51 (m, 2H), 7.43 (dd, J = 9.4, 1.5 Hz, 1H), 5.91 (s, 1H), 3.87 (s, 1H), 3.51-3.40 (m, 1H), 3.30-3.23 (m, 1H), 2.59-2.39 (m, 9H), 2.28-1.98 (m, 5H), 1.78-1.56 (m, 7H), 1.49-1.42 (m, 4H), 1.38-1.28 (m, 1H) [Example 10] |

TABLE 3-continued

| EX No | $^1$H NMR |
|---|---|
| 154 | (300 MHz, CD$_3$OD) δ 8.66 (s, 1H), 7.90 (s, 1H), 7.64-7.51 (m, 2H), 7.49-7.42 (m, 1H), 5.91-5.73 (m, 1H), 5.51 (d, J = 50.0 Hz, 1H), 4.36 (s, 1H), 3.66-3.41 (m, 1H), 3.40-3.32 (m, 2H), 3.01 (d, J = 8.0 Hz, 6H), 2.84-2.56 (m, 3H), 2.40-2.22 (m, 2H), 2.12-1.48 (m, 9H) [Example 110] |
| 155 | (300 MHz, DMSO-d$_6$) 9.73 (s, 1H), 8.62 (d, J = 15.2 Hz, 1H), 7.92 (s, 1H), 7.84 (d, J = 7.7 Hz, 1H), 7.64-7.54 (m, 1H), 7.45-7.35 (m, 3H), 7.32 (t, J = 8.4 Hz, 1H), 7.20 (t, J = 8.9 Hz, 2H), 5.73 (s, 1H), 4.51 (d, J = 7.8 Hz, 3H), 4.36 (t, J = 5.2 Hz, 1H), 3.90-3.63 (m, 1H), 2.75-2.65 (m, 2H), 2.39 (s, 1H), 2.23 (s, 3H), 2.02-1.97 (m, 2H), 1.90-1.64 (m, 2H), 1.59-1.49 (m, 6H), 1.37-1.31 (m, 4H) [Example 2] |
| 156 | (300 MHz, DMSO-d$_6$) δ 9.83 (s, 1H), 8.64 (d, J = 15.2 Hz, 1H), 7.95 (s, 1H), 7.92-7.69 (m, 1H), 7.67-7.56 (m, 1H), 7.52-7.37 (m, 2H), 5.90-5.60 (m, 1H), 4.47 (dt, J = 47.8, 5.2 Hz, 2H).), 3.86-3.62 (m, 1H), 3.43 (d, J = 6.4 Hz, 2H), 2.82-2.64 (m, 4H), 2.65-2.55 (m, 2H), 2.49-2.34 (m, 2H), 2.25 (s, 3H), 2.10-1.90 (m, 2H), 1.86-1.70 (m, 2H), 1.64-1.48 (m, 6H), 1.45-1.24 (m, 4H) [Example 10] |
| 157 | (300 MHz, CD$_3$OD) δ 8.57 (s, 1H), 7.85 (s, 1H), 7.64-7.36 (m, 3H), 6.04-5.73 (m, 1H), 4.57 (dt, J = 47.8, 4.9 Hz, 2H), 3.86 (s, 1H), 3.40-3.33 (m, 2H), 2.95-2.80 (m, 1H), 2.79-2.50 (m, 4H), 2.40 (s, 3H), 2.26-1.90 (m, 4H), 1.78-1.23 (m, 10H) [Example 10] |
| 158 | (300 MHz, CD$_3$OD) δ 8.61 (s, 1H), 7.85 (s, 1H), 7.74 (d, J = 2.4 Hz, 1H), 7.33-7.04 (m, 1H), 6.58 (d, J = 2.5 Hz, 1H), 5.91 (s, 1H), 5.01-4.80 (m, 3H), 4.58 (s, 2H), 4.50-4.24 (m, 1H), 3.25-3.08 (m, 1H), 2.98-2.70 (m, 1H), 2.66-2.32 (m, 2H), 1.98-1.71 (m, 2H), 1.71-1.57 (m, 6H) [Example 10] |
| 159 | (300 MHz, CD$_3$OD) δ 8.67 (s, 1H), 8.39 (s, 1H), 8.25 (d, J = 7.5 Hz, 1H), 8.09-8.02 (m, 1H), 7.91 (s, 1H), 7.60-7.46 (m, 3H), 7.28 (d, J = 9.0 Hz, 1H), 5.92-5.71 (m, 1H), 5.52 (d, J = 49.9 Hz, 1H), 4.39 (s, 1H), 3.69-3.44 (m, 1H), 3.03 (d, J = 8.1 Hz, 6H), 2.68 (s, 1H), 2.41-2.25 (m, 2H), 2.13-1.92 (m, 2H), 1.84-1.72 (m, 1H), 1.64 (d, J = 6.9 Hz, 6H) [Example 110] |
| 160 | (300 MHz, CD$_3$OD) δ 8.71 (s, 1H), 8.28-8.19 (m, 1H), 7.89 (d, J = 9.1 Hz, 1H), 7.60-7.46 (m, 3H), 7.17 (d, J = 9.0 Hz, 1H), 5.74-5.41 (m, 2H), 4.45-4.28 (m, 1H), 3.66-3.42 (m, 1H), 3.03 (d, J = 7.8 Hz, 6H), 2.78-2.57 (m, 1H), 2.42 (s, 3H), 2.33 (d, J = 12.0 Hz, 2H), 2.12-1.95 (m, 1H), 1.94-1.72 (m, 1H), 1.83-1.72 (m, 1H), 1.64 (d, J = 6.9 Hz, 6H) [Example 110] |
| 161 | (400 MHz, CD$_3$OD) 8.66 (s, 1H), 8.13-8.07 (m, 2H), 7.60 (t, J = 8.5 Hz, 1H), 5.77-5.74 (m, 1H), 3.86 (s, 1H), 3.20-3.09 (m, 2H), 2.38 (s, 7H), 2.20 (s, 2H), 2.06 (s, 2H), 1.93-1.81 (m, 2H), 1.67 (s, 6H), 1.52-1.38 (m, 4H), 1.05 (t, J = 7.5 Hz, 3H) [Example 64] |
| 162 | (300 MHz, CD$_3$OD) δ 8.68 (s, 1H), 8.26-8.00 (m, 2H), 7.62 (t, J = 8.7 Hz, 1H), 5.79 (s, 1H), 5.06-4.72 (m, 1H), 4.37 (s, 1H), 3.28-3.04 (m, 6H), 2.92-2.66 (m, 1H), 2.64-2.34 (m, 2H), 1.97-1.41 (m, 13H) [Example 162] |
| 163 | (300 MHz, DMSO-d$_6$) δ 8.72 (d, J = 14.3 Hz, 1H), 8.21-7.77 (m, 3H), 7.53 (t, J = 8.7 Hz, 1H), 5.60 (s, 1H), 4.99-4.58 (m, 1H), 4.32-3.96 (m, 1H), 3.46-3.12 (m, 4H), 3.09-2.58 (m, 3H), 2.31-2.03 (m, 1H), 1.90-1.69 (m, 5H), 1.55 (t, J = 9.3 Hz, 6H) [Example 162] |
| 164 | (300 MHz, CD$_3$OD) δ 8.70 (s, 1H), 8.21-8.02 (m, 2H), 7.64 (t, J = 8.6 Hz, 1H), 5.79 (s, 1H), 5.01-4.73 (m, 1H), 4.38 (s, 1H), 3.32-3.22 (m, 1H), 3.20-3.08 (m, 7H), 2.93-2.65 (m, 7H), 2.63-2.32 (m, 2H), 1.99-1.58 (m, 7H) [Example 64] |
| 165 | (300 MHz, CD$_3$OD) δ 8.75 (s, 1H), 8.19-8.12 (m, 2H), 7.66 (t, J = 8.6 Hz, 1H), 5.77-5.68 (m, 1H), 3.99-3.92 (m, 1H), 3.88 (t, J = 13.3 Hz, 2H), 3.34-3.32 (m, 1H), 2.92 (s, 6H), 2.42-2.01 (m, 6H), 1.92-1.48 (m, 10H), 1.05 (t, J = 7.5 Hz, 3H) [Example 66] |
| 166 | (300 MHz, DMSO-d$_6$) δ 8.75 (d, J = 11.4 Hz, 1H), 8.07-7.90 (m, 3H), 7.69 (s, 1H), 7.64-7.47 (m, 3H), 5.66-5.62 (m, 1H), 4.92 (d, J = 47.4 Hz, 2H), 4.57 (s, 2H), 4.19-4.17 (m, 1H), 3.17-3.03 (m, 2H), 2.91-2.73 (m, 1H), 2.62-2.52 (m, 1H), 2.35 (s, 3H), 2.28-2.20 (m, 1H), 1.94-1.77 (m, 1H), 1.60 (d, J = 7.5 Hz, 6H) [Example 166] |
| 167 | (300 MHz, DMSO-d$_6$) δ 8.63 (d, J = 10.4 Hz, 1H), 8.02-7.68 (m, 4H), 7.54-7.27 (m, 3H), 7.16 (t, J = 8.8 Hz, 1H), 5.56 (s, 1H), 3.85-3.67 (m, 1H), 2.81 (s, 1H), 2.55 (s, 6H), 2.10-1.98 (m, 4H), 1.65-1.18 (m, 10H) [Example 66] |
| 168 168A 168B | (300 MHz, CD$_3$OD) δ 8.73 (s, 1H), 8.07 (d, J = 9.7 Hz, 2H), 5.94-5.62 (m, 1H), 4.85-4.67 (m, 1H), 4.03 (s, 1H), 3.52-3.39 (m, 2H), 3.02-2.72 (m, 3H), 2.56 (s, 7H), 2.30-1.88 (m, 2H), 1.78-1.36 (m, 9H)<br>(300 MHz, CD$_3$OD) δ 8.73 (s, 1H), 8.08 (d, J = 9.8 Hz, 2H), 5.90-5.69 (m, 1H), 4.86-4.69 (m, 1H), 4.04 (s, 1H), 3.52-3.38 (m, 2H), 3.02-2.72 (m, 3H), 2.57 (s, 7H), 2.25-1.93 (m, 2H), 1.78-1.29 (m, 9H) [Example 168] |
| 169 | (300 MHz, CD$_3$OD) δ 8.63 (s, 1H), 6.93-6.79 (m, 2H), 5.81-5.61 (m, 1H), 3.89 (s, 1H), 3.37-3.27 (m, 2H), 2.82-2.63 (m, 3H), 2.58 (s, 6H), 2.35-2.05 (m, 4H), 1.76-1.36 (m, 10H) [Example 168] |
| 170 | (300 MHz, CD$_3$OD) δ 8.79 (s, 1H), 7.39 (d, J = 8.0 Hz, 3H), 7.23 (d, J = 7.8 Hz, 2H), 5.77 (s, 1H), 5.29 (d, J = 44.9 Hz, 1H), 4.72 (s, 1H), 4.55 (s, 2H), 3.73-3.69 (m, 2H), 3.43-3.34 (m, 1H), 3.10-3.01 (m, 1H), 2.61-2.58 (m, 1H), 2.37 (s, 3H), 2.02-1.85 (m, 1H), 1.66 (d, J = 5.5 Hz, 6H) [Example 64] |

TABLE 3-continued

| EX No | $^1$H NMR |
|---|---|
| 171 | (400 MHz, CD$_3$OD) δ 8.79 (s, 1H), 7.54 (dd, J = 8.6, 5.3 Hz, 2H), 7.40-7.39 (m, 1H), 7.14 (t, J = 8.7 Hz, 2H), 5.76 (s, 1H), 5.29 (d, J = 45.3 Hz, 1H), 4.72 (s, 1H), 4.58 (s, 2H), 3.71-3.65 (m, 2H), 3.33-3.31 (m, 1H), 3.06-2.95 (m, 1H), 2.62-2.59 (m, 1H), 2.12-1.96 (m, 1H), 1.66 (d, J = 5.5 Hz, 6H)<br>[Example 64] |
| 172 | (300 MHz, CD$_3$OD) δ 8.77 (s, 1H), 7.40-7.23 (m, 1H), 5.77-5.60 (m, 1H), 4.00 (s, 1H), 3.59-3.43 (m, 2H), 3.40-3.35 (m, 1H), 2.91 (s, 6H), 2.84-2.66 (m, 2H), 2.42-2.13 (m, 4H), 1.86-1.49 (m, 10H)<br>[Example 168] |
| 173 | (300 MHz, CD$_3$OD) δ 8.54 (s, 1H), 8.30 (dt, J = 7.7, 1.2 Hz, 1H), 7.68-7.37 (m, 4H), 6.55 (d, J = 8.0 Hz, 1H), 5.74-5.41 (m, 1H), 3.83 (s, 1H), 3.58 (s, 3H), 2.67-2.53 (m, 1H), 2.47 (s, 6H), 2.31-1.97 (m, 4H), 1.74-1.24 (m, 10H)<br>[Example 168] |
| 174 | (300 MHz, DMSO-d$_6$) δ 10.30 (s, 1H), 10.14 (s, 1H), 8.70 (d, J = 14.1 Hz, 1H), 8.19-8.03 (m, 1H), 7.51-7.41 (m, 3H), 7.25-7.12 (m, 3H), 5.63-5.53 (m, 1H), 4.66 (s, 2H), 3.92-3.67 (m, 1H), 3.19-3.18 (m, 1H), 2.79-2.70 (m, 6H), 2.15-2.06 (m, 4H), 1.64-1.35 (m, 10H)<br>[Example 168] |
| 175 | (300 MHz, CD$_3$OD) δ 8.68 (s, 1H), 7.52 (dd, J = 8.7, 5.3 Hz, 2H), 7.40-7.32 (m, 1H), 7.13 (t, J = 8.8 Hz, 2H), 5.78-5.69 (m, 1H), 4.56 (s, 2H), 3.96 (s, 1H), 3.38-3.30 (m, 1H), 2.90 (s, 6H), 2.34-2.19 (m, 4H), 1.79-1.46 (m, 10H)<br>[Example 168] |
| 176 | (300 MHz, DMSO-d$_6$) δ 9.90 (s, 1H), 8.73 (d, J = 16.3 Hz, 1H), 8.08-7.90 (m, 3H), 7.44-7.38 (m, 3H), 7.24-7.18 (m, 2H), 5.65-5.58 (m, 1H), 4.57-4.38 (m, 3H), 4.40 (t, J = 5.2 Hz, 1H), 3.90-3.60 (m, 1H), 2.80-2.70 (m, 2H), 2.49-2.44 (m, 1H), 2.27 (s, 3H), 2.04-1.99 (m, 2H), 1.81 (s, 2H), 1.72-1.51 (m, 6H), 1.40-1.31 (m, 4H)<br>[Example 64] |
| 177 | (300 MHz, DMSO-d$_6$) δ 10.10 (s, 1H), 8.70 (d, J = 16.1 Hz, 1H), 8.12-7.77 (m, 3H), 7.47 (t, J = 8.5 Hz, 1H), 5.76-5.41 (m, 1H), 4.47 (dt, J = 47.8, 5.1 Hz, 2H), 3.81-3.66 (m, 1H), 3.44-3.18 (m, 3H), 2.91-2.62 (m, 4H), 2.27 (s, 3H), 2.11-1.90 (m, 2H), 1.89-1.70 (m, 2H), 1.63-1.49 (m, 6H), 1.44-1.21 (m, 4H)<br>[Example 64] |
| 178 | (300 MHz, DMSO-d$_6$) δ 8.89 (d, J = 2.4 Hz, 1H), 8.73 (s, 1H), 8.47 (dd, J = 9.6, 2.4 Hz, 1H), 8.23-8.08 (m, 1H), 7.64-7.47 (m, 3H), 7.35 (d, J = 9.5 Hz, 1H), 5.59 (s, 1H), 3.86-3.73 (m, 1H), 3.20-3.15 (m, 1H), 2.76 (s, 6H), 2.08-2.05 (m, 4H), 1.70-1.18 (m, 10H)<br>[Example 64] |
| 179<br>179A<br>179B | (300 MHz, CD$_3$OD) δ 8.72 (s, 1H), 8.24-8.04 (m, 2H), 7.60 (t, J = 8.4 Hz, 1H), 5.78-5.73 (m, 1H), 5.50 (d, J = 50.1 Hz, 1H), 4.32 (s, 1H), 3.70-3.34 (m, 3H), 3.02 (s, 6H), 2.88-2.51 (m, 3H), 2.31 (d, J = 12.5 Hz, 2H), 2.13-1.48 (m, 9H)<br>(300 MHz, CD$_3$OD) δ 8.68 (s, 1H), 8.13 (t, J = 11.5 Hz, 2H), 7.59 (t, J = 8.4 Hz, 1H), 5.78-5.73 (m, 1H), 5.27 (d, J = 50.1 Hz, 1H), 4.43-4.18 (m, 1H), 3.45-3.35 (m, 2H), 2.87-2.57 (m, 3H), 2.52 (s, 7H), 2.23 (d, J = 12.8 Hz, 1H), 2.08-1.80 (m, 2H), 1.78-1.44 (m, 8H)<br>[Example 168] |
| 180 | (300 MHz, DMSO-d$_6$) δ 9.98 (s, 1H), 8.73 (d, J = 16.5 Hz, 1H), 8.13-7.86 (m, 3H), 7.51 (t, J = 8.5 Hz, 1H), 5.71-5.53 (m, 1H), 4.47 (dt, J = 47.8, 5.1 Hz, 2H), 3.90-3.62 (m, 1H), 3.46 (d, J = 6.4 Hz, 2H), 2.86-2.65 (m, 4H), 2.64-2.52 (m, 2H), 2.48-2.37 (m, 2H), 2.27 (s, 3H), 2.12-1.90 (m, 2H), 1.88-1.72 (m, 2H), 1.69-1.50 (m, 6H), 1.47-1.25 (m, 4H)<br>[Example 64] |
| 181<br>181A<br>181B | (300 MHz, DMSO-d$_6$) δ 9.92 (s, 1H), 8.75 (d, J = 17.6 Hz, 1H), 8.10-7.93 (m, 3H), 7.44-7.38 (m, 3H), 7.24-7.18 (m, 2H), 5.65-5.58 (m, 1H), 5.18 (d, J = 50.2 Hz, 1H), 4.54 (s, 2H), 4.11-4.09 (m, 1H), 2.34-2.27 (m, 8H), 2.10-2.06 (m, 1H), 1.80-1.35 (m, 10H)<br>(300 MHz, DMSO-d$_6$) δ 9.87 (s, 1H), 8.74 (d, J = 23.6 Hz, 1H), 8.06-7.93 (m, 3H), 7.42-7.38 (m, 3H), 7.22-7.18 (m, 2H), 5.59-5.56 (m, 1H), 5.16 (d, J = 50.2 Hz, 1H), 4.52 (s, 2H), 4.19-4.08 (m, 1H), 2.41-2.21 (m, 8H), 2.08-2.05 (m, 1H), 1.78-1.41 (m, 10H)<br>[Example 168] |
| 182 | (300 MHz, CD$_3$OD) δ 8.67 (s, 1H), 8.11 (t, J = 10.7 Hz, 2H), 7.61 (t, J = 8.5 Hz, 1H), 5.81-5.72 (m, 1H), 3.87 (s, 1H), 3.63 (t, J = 12.1 Hz, 4H), 3.27 (t, J = 7.1 Hz, 2H), 3.07 (t, J = 7.1 Hz, 2H), 2.50-2.44 (m, 7H), 2.24-2.06 (m, 4H), 1.67 (s, 6H), 1.67-1.48 (m, 4H)<br>[G03427877] |
| 183 | (300 MHz, DMSO-d$_6$) δ 9.92 (s, 1H), 8.73 (d, J = 16.4 Hz, 1H), 8.11-7.87 (m, 3H), 7.46-7.23 (m, 6H), 5.72-5.52 (m, 1H), 4.60-4.29 (m, 4H), 3.91-3.60 (m, 1H), 2.82-2.64 (m, 2H), 2.48-2.35 (m, 1H), 2.27 (s, 3H), 2.11-1.93 (m, 2H), 1.89-1.71 (m, 2H), 1.66-1.50 (m, 6H), 1.44-1.28 (m, 4H)<br>[Example 64] |
| 184 | (300 MHz, DMSO-d$_6$) δ 8.72 (d, J = 14.0 Hz, 1H), 8.04-7.85 (m, 3H), 7.42-7.35 (m, 3H), 7.21-7.15 (m, 2H), 5.65-5.58 (m, 1H), 4.41 (s, 2H), 3.84-3.70 (m, 1H), 2.49-2.36 (m, 7H), 2.08-1.92 (m, 4H), 1.62-1.51 (m, 6H), 1.44-1.24 (m, 4H)<br>[Example 66] |
| 185 | (400 MHz, DMSO-d$_6$) δ 8.76 (d, J = 21.5 Hz, 1H), 8.12 (dd, J = 50.6, 7.9 Hz, 1H), 7.48-7.25 (m, 6H), 5.60 (s, 1H), 4.94 (d, J = 47.1 Hz, 1H), 4.42 (s, 2H), 4.33-4.18 (m, 1H), 3.23-3.04 (m, 3H), 2.93-2.79 (m, 1H), 2.68-2.54 (m, 1H), 2.27 (s, 1H), 1.93-1.75 (m, 1H), 1.66-1.46 (m, 6H)<br>[Example 64] |
| 186 | (400 MHz, DMSO-d$_6$) δ 8.68 (d, J = 20.2 Hz, 1H), 8.14 (d, J = 2.7 Hz, 1H), 8.09-7.78 (m, 1H), 6.88 (s, 1H), 5.69-5.41 (m, 1H), 3.94-3.65 (m, 1H), 3.63-3.51 (m, 2H), 2.85-2.66 (m, 2H), 2.47-2.37 (m, 1H), 2.33 (s, 6H), 2.24 (s, 3H), 2.12-1.83 (m, 4H), 1.63-1.49 (m, 6H), 1.43-1.21 (m, 4H)<br>[Example 168] |

TABLE 3-continued

| EX No | ¹H NMR |
|---|---|
| 187 | (300 MHz, DMSO-d$_6$) δ 8.98 (s, 1H), 8.72 (d, J = 15.8 Hz, 1H), 8.45 (d, J = 9.3 Hz, 1H), 8.10-7.84 (m, 1H), 7.19 (d, J = 9.1 Hz, 1H), 5.58 (s, 1H), 4.47 (dt, J = 47.8, 5.1 Hz, 2H), 3.95-3.61 (m, 1H), 3.61-3.45 (m, 2H), 2.86-2.61 (m, 4H), 2.47-2.38 (m, 1H), 2.26 (s, 3H), 2.09-1.90 (m, 2H), 1.88-1.71 (m, 2H), 1.66-1.48 (m, 6H), 1.42-1.22 (m, 4H) [Example 64] |
| 188 | (300 MHz, DMSO-d$_6$) δ 11.19 (s, 1H), 8.88 (s, 1H), 8.71 (d, J = 8.4 Hz, 1H), 8.51-8.41 (m, 1H), 8.15 (t, J = 9.2 Hz, 2H), 7.67-7.27 (m, 4H), 5.59 (s, 1H), 5.24-4.77 (m, 3H), 3.96-3.11 (m, 4H), 2.74 (s, 3H), 2.27-2.00 (m, 4H), 1.76-1.24 (m, 10H) [Example 64] |
| 189 | (300 MHz, DMSO-d$_6$) δ 8.67 (d, J = 13.5 Hz, 1H), 8.10-7.80 (m, 1H), 7.28-7.15 (m, 2H), 5.55 (s, 1H), 3.96-3.62 (m, 1H), 3.09-2.89 (m, 3H), 2.65 (s, 8H), 2.18-1.90 (m, 4H), 1.63-1.33 (m, 10H) [Example 168] |
| 190 | (300 MHz, DMSO-d$_6$) δ 9.76-9.13 (m, 1H), 8.63 (d, J = 10.3 Hz, 1H), 7.98-7.63 (m, 6H), 7.59-7.48 (m, 1H), 7.15 (t, J = 9.0 Hz, 1H), 5.66-5.47 (m, 1H), 3.86-3.67 (m, 1H), 3.05 (s, 1H), 2.67 (s, 6H), 2.17-1.92 (m, 4H), 1.61-1.19 (m, 10H) [Example 64] |
| 191 | (300 MHz, CD$_3$OD) δ 9.24-9.09 (m, 1H), 9.04-8.91 (m, 1H), 8.79 (s, 1H), 8.75-8.57 (m, 1H), 8.17-8.09 (m, 1H), 8.07-8.00 (m, 1H), 7.98-7.92 (m, 1H), 7.67 (t, J = 8.4 Hz, 1H), 5.76-5.53 (m, 1H), 4.05 (s, 1H), 3.41-3.35 (m, 1H), 2.91 (s, 6H), 2.42-2.21 (m, 4H), 1.88-1.73 (m, 2H), 1.65 (d, J = 7.3 Hz, 8H) [Example 64] |
| 192 192A 192B | (300 MHz, DMSO-d$_6$) δ 9.90 (s, 1H), 8.75 (d, J = 17.8 Hz, 1H), 8.13-7.90 (m, 3H), 7.45-7.32 (m, 6H), 5.70-5.52 (m, 1H), 5.16 (d, J = 50.0 Hz, 1H), 4.52 (s, 2H), 4.25-4.09 (m, 1H), 2.31 (s, 8H), 2.12-1.95 (m, 1H), 1.87-1.38 (m, 10H) (300 MHz, DMSO-d$_6$) δ 9.90 (s, 1H), 8.75 (d, J = 17.8 Hz, 1H), 8.13-7.90 (m, 3H), 7.45-7.32 (m, 6H), 5.70-5.52 (m, 1H), 5.16 (d, J = 50.0 Hz, 1H), 4.52 (s, 2H), 4.24-4.08 (m, 1H), 2.31 (s, 8H), 2.12-1.95 (m, 1H), 1.87-1.38 (m, 10H) [Example 168] |
| 193 193A 193B | (300 MHz, DMSO-d$_6$) δ 8.74 (d, J = 17.9 Hz, 1H), 8.12-7.90 (m, 3H), 7.50 (t, J = 8.5 Hz, 1H), 5.75-5.48 (m, 1H), 5.16 (d, J = 50.3 Hz, 1H), 4.29-4.01 (m, 1H), 3.44 (d, J = 6.4 Hz, 2H), 2.81-2.66 (m, 2H), 2.61-2.55 (m, 1H), 2.46-2.39 (m, 1H), 2.31 (s, 8H), 2.12-1.98 (m, 1H), 1.88-1.50 (m, 9H), 1.50-1.39 (m, 1H), 1.28-1.21 (m, 1H) (300 MHz, DMSO-d$_6$) δ 8.74 (d, J = 17.9 Hz, 1H), 8.12-7.90 (m, 3H), 7.50 (t, J = 8.5 Hz, 1H), 5.75-5.48 (m, 1H), 5.16 (d, J = 50.3 Hz, 1H), 4.29-4.01 (m, 1H), 3.44 (d, J = 6.4 Hz, 2H), 2.81-2.66 (m, 2H), 2.61-2.55 (m, 1H), 2.46-2.39 (m, 1H), 2.31 (s, 8H), 2.12-1.98 (m, 1H), 1.88-1.50 (m, 9H), 1.50-1.39 (m, 1H), 1.28-1.21 (m, 1H) [Example 168] |
| 194 | (300 MHz, DMSO-d$_6$) δ 13.21 (s, 1H), 8.63 (d, J = 16.3 Hz, 1H), 8.16-8.09 (m, 1H), 8.06-7.94 (m, 2H), 7.89-7.78 (m, 2H), 7.75-7.66 (m, 1H), 7.12 (d, J = 9.1 Hz, 1H), 5.63-5.36 (m, 1H), 4.45 (dt, J = 47.8, 5.1 Hz, 2H), 3.96-3.52 (m, 1H), 2.71 (dt, J = 26.5, 5.1 Hz, 2H), 2.41 (s, 1H), 2.32 (s, 3H), 2.24 (s, 3H), 2.06-1.88 (m, 2H), 1.85-1.70 (m, 2H), 1.60-1.41 (m, 6H), 1.40-1.25 (m, 4H) [Example 64] |
| 195 | (300 MHz, DMSO-d$_6$) δ 8.64 (d, J = 16.7 Hz, 1H), 8.14 (d, J = 7.4 Hz, 1H), 8.06-7.72 (m, 2H), 7.65-7.44 (m, 3H), 7.07 (d, J = 9.0 Hz, 1H), 5.71-5.14 (m, 1H), 4.45 (dt, J = 47.9, 5.2 Hz, 2H), 3.93-3.51 (m, 1H), 2.71 (dt, J = 26.1, 5.2 Hz, 2H), 2.45-2.15 (m, 7H), 2.07-1.90 (m, 2H), 1.84-1.69 (m, 2H), 1.61-1.46 (m, 6H), 1.42-1.25 (m, 4H) [Example 64] |
| 196 | (300 MHz, DMSO-d$_6$) δ 11.12 (s, 1H), 8.89 (d, J = 2.4 Hz, 1H), 8.73 (d, J = 10.1 Hz, 1H), 8.51-8.41 (m, 1H), 8.28-7.99 (m, 2H), 7.64-7.47 (m, 3H), 7.35 (d, J = 9.4 Hz, 1H), 5.68-5.40 (m, 3H), 4.30-4.09 (m, 1H), 3.65-3.34 (m, 1H), 2.79 (d, J = 4.7 Hz, 6H), 2.45-2.00 (m, 3H), 1.99-1.41 (m, 9H) [Example 168] |
| 197 | ¹H NMR (400 MHz, DMSO-d$_6$) δ 8.61 (d, J = 16.6 Hz, 1H), 7.84 (d, J = 6.1 Hz, 1H), 7.73 (s, 1H), 7.12 (t, J = 9.6 Hz, 1H), 6.94 (t, J = 9.3 Hz, 1H), 5.85-5.59 (m, 1H), 3.95-3.57 (m, 1H), 3.02 (bs, 2H), 2.65-2.57 (m, 1H), 2.17-1.84 (m, 5H), 1.63-1.51 (m, 6H), 1.45-1.28 (m, 4H). [Example 197] |
| 198 | ¹H NMR (400 MHz, DMSO-d$_6$) δ 8.69-8.54 (m, 1H), 8.19 (s, 1H), 7.91 (s, 1H), 7.90-7.79 (m, 1H), 7.54 (d, J = 11.8 Hz, 1H), 7.46-7.32 (m, 2H), 5.85-5.65 (m, 1H), 3.88-3.60 (m, 2H), 3.29-3.14 (m, 4H), 2.82-2.61 (m, 3H), 2.29-2.16 (m, 3H), 2.10-1.89 (m, 4H), 1.89-1.74 (m, 2H), 1.65-1.44 (m, 7H), 1.44-1.18 (m, 2H), 1.15-0.94 (m, 2H). [Example 198] |
| 199 | ¹H NMR (400 MHz, DMSO-d$_6$) δ 8.71-8.55 (m, 1H), 8.18 (s, 1H), 7.91 (s, 1H), 7.85 (d, J = 8.0 Hz, 1H), 7.53 (d, J = 13.3 Hz, 1H), 7.45-7.32 (m, 2H), 5.87-5.62 (m, 1H), 3.94-3.64 (m, 1H), 3.25-3.16 (m, 3H), 2.83-2.68 (m, 6H), 2.11-1.93 (m, 4H), 1.81-1.70 (m, 4H), 1.58 (d, J = 6.8 Hz, 4H), 1.52 (d, J = 6.9 Hz, 2H), 1.43-1.28 (m, 4H). [Example 199] |
| 200 | ¹H NMR (400 MHz, DMSO-d$_6$) δ 8.70-8.55 (m, 1H), 8.15 (s, 1H), 7.93 (s, 1H), 7.89 (d, J = 5.9 Hz, 1H), 7.57 (d, J = 12.8 Hz, 1H), 7.48-7.35 (m, 2H), 5.91-5.49 (m, 1H), 2.94-2.69 (m, 4H), 2.23 (s, 3H), 2.15-2.00 (m, 2H), 1.98-1.78 (m, 3H), 1.68-1.46 (m, 9H). [Example 200] |
| 201 | ¹H NMR (400 MHz, DMSO-d$_6$) δ 8.62 (s, 1H), 7.95 (s, 1H), 7.85 (s, 1H), 7.41 (d, J = 13.4 Hz, 1H), 7.37-7.21 (m, 2H), 5.76 (bs, 1H), 4.16-3.85 (m, 1H), 3.24 (d, J = 12.4 Hz, 3H), 3.09-2.97 (m, 2H), 2.90 (t, J = 11.2 Hz, 2H), 2.75-2.57 (m, 2H), 2.07-1.95 (m, 2H), 1.73-1.45 (m, 8H). [Example 201] |

TABLE 3-continued

| EX No | $^1$H NMR |
|---|---|
| 202 202A 202B | $^1$H NMR (400 MHz, DMSO-d$_6$) δ 9.96 (s, 1H), 9.49-9.16 (m, 2H), 8.79-8.65 (m, 1H), 8.20-8.07 (m, 1H), 8.03 (s, 1H), 7.62 (d, J = 12.1 Hz, 1H), 7.52-7.33 (m, 4H), 7.29-7.19 (m, 2H), 5.23 (d, J = 46.0 Hz, 1H), 4.57 (s, 2H), 4.52-4.35 (m, 1H), 3.61-3.49 (m, 2H), 3.26-3.12 (m, 2H), 3.05-2.79 (m, 2H), 2.09-1.77 (m, 2H), 1.67-1.43 (m, 3H), 1.16 (t, J = 7.2 Hz, 1H), 0.86-0.69 (m, 3H). $^1$H NMR (400 MHz, DMSO-d$_6$) δ 9.95 (s, 1H), 9.53-8.98 (m, 2H), 8.78-8.63 (m, 1H), 8.20-8.06 (m, 1H), 8.02 (s, 1H), 7.61 (d, J = 12.4 Hz, 1H), 7.51-7.31 (m, 4H), 7.29-7.15 (m, 2H), 5.22 (d, J = 44.5 Hz, 1H), 4.55 (s, 2H), 4.49-4.25 (m, 1H), 3.60-3.45 (m, 2H), 3.28-3.14 (m, 2H), 2.96-2.80 (m, 2H), 2.05-1.71 (m, 2H), 1.62-1.43 (m, 3H), 1.14 (t, J = 7.2 Hz, 1H), 0.75 (t, J = 7.4 Hz, 3H). [Example 202] |
| 203 | $^1$H NMR (400 MHz, DMSO-d$_6$) δ 8.59 (d, J = 17.5 Hz, 1H), 7.84 (s, 1H), 7.74 (d, J = 7.8 Hz, 1H, NH), 7.57 (s, 1H, NH), 7.41 (d, J = 13.0 Hz, 1H), 7.35-7.24 (m, 2H), 3.78-3.67 (m, 1H), 3.07-2.97 (m, 3H), 2.72-2.60 (m, 2H), 2.21 (s, 6H), 2.07-1.91 (m, 5H), 1.68-1.27 (m, 7H), 0.78-0.71 (m, 3H). [Example 2203] |
| 203A | $^1$H NMR (400 MHz, DMSO-d$_6$) δ 8.61 (d, J = 17.6 Hz, 1H), 7.92 (s, 1H), 7.82 (d, J = 7.5 Hz, 1H), 7.65 (s, 1H) 7.53 (d, J = 12.9 Hz, 1H), 7.46-7.32 (m, 2H), 3.88-3.71 (m, 1H), 3.25-3.18 (m, 3H), 2.79-2.65 (m, 2H), 2.31 (s, 6H), 1.85-1.99 (m, 5H), 1.21-1.62 (m, 8H), 0.72-0.79 (m, 3H). [Eexample 203A] |
| 204 | $^1$H NMR (400 MHz, DMSO-d$_6$) δ 8.66-8.57 (m, 1H), 7.85-7.63 (m, 2H), 7.30 (dd, J = 13.5, 2.1 Hz, 1H), 7.28-7.22 (m, 1H), 7.15 (dd, J = 8.6, 1.9 Hz, 1H), 5.75 (m, 1H), 4.55 (t, J = 10.5 Hz, 1H), 4.27 (t, J = 10.0 Hz, 1H), 4.18-3.89 (m, 2H), 3.83-3.61 (m, 1H), 3.53 (dd, J = 11.3, 4.4 Hz, 2H), 3.14-2.92 (m, 3H), 2.92-2.74 (m, 3H), 2.25-1.75 (m, 5H), 1.72-1.30 (m, 12H). [Example 204] |
| 205 | $^1$H NMR (400 MHz, DMSO-d$_6$) δ 8.61 (d, J = 19.3 Hz, 1H), 7.86 (s, 1H), 7.84-7.57 (m, 1H), 7.47 (d, J = 13.4 Hz, 1H), 7.39-7.28 (m, 2H), 5.77 (bs, 1H), 3.17-3.03 (m, 2H), 2.67 (s, 2H), 2.24 (s, 3H), 2.11-1.93 (m, 2H), 1.90-1.73 (m, 2H), 1.55 (dd, J = 21.8, 7.7 Hz, 6H), 1.44-1.28 (m, 4H), 1.01 (t, J = 7.2 Hz, 3H). [Example 205] |
| 206 | $^1$H NMR (400 MHz, DMSO-d$_6$) δ 8.62 (d, J = 20.4 Hz, 1H), 7.94 (s, 1H), 7.77 (dd, J = 57.0, 7.7 Hz, 1H), 7.60 (d, J = 12.6 Hz, 1H), 7.52-7.35 (m, 2H), 5.84-5.63 (m, 1H), 4.48 (d, J = 6.8 Hz, 4H), 3.96-3.84 (m, 1H), 3.82-3.55 (m, 1H), 2.86-2.71 (m, 2H), 2.37-2.18 (m, 1H), 2.12 (s, 3H), 2.09-1.87 (m, 2H), 1.73-1.61 (m, 2H), 1.58 (d, J = 6.7 Hz, 4H), 1.52 (d, J = 6.6 Hz, 2H), 1.41-1.22 (m, 4H). [Example 206] |
| 207 | $^1$H NMR (400 MHz, DMSO-d$_6$) δ 8.63 (d, J = 20.5 Hz, 1H), 7.93 (s, 1H), 7.76 (dd, J = 56.9, 8.1 Hz, 1H), 7.57 (dd, J = 12.5, 1.6 Hz, 1H), 7.49-7.36 (m, 2H), 5.91-5.62 (m, 1H), 3.74 (d, J = 44.7 Hz, 1H), 2.84-2.64 (m, 2H), 2.47-2.39 (m, 1H), 2.26 (s, 3H), 2.06-1.72 (m, 6H), 1.58 (d, J = 6.9 Hz, 4H), 1.52 (d, J = 6.5 Hz, 2H), 1.44-1.17 (m, 5H), 0.50-0.37 (m, 2H), 0.33-0.21 (m, 2H). [Example 207] |
| 208 | $^1$H NMR (400 MHz, DMSO-d$_6$) δ 8.66 (d, J = 20.2 Hz, 1H), 8.19 (s, 1H), 7.98 (s, 1H), 7.86-7.67 (m, 1H), 7.59 (d, J = 12.5 Hz, 1H), 7.48-7.38 (m, 4H), 7.20 (dd, J = 13.1, 6.2 Hz, 2H), 4.79-4.39 (m, 1H), 4.46 (s, 2H), 4.44-4.39 (m, 2H), 4.13-4.04 (m, 1H), 3.67-3.61 (m, 2H), 2.94-2.89 (m, 2H), 2.79-2.57 (m, 2H), 2.17-2.11 (m, 1H), 1.96-1.74 (m, 1H) [Example 208] |
| 209 | $^1$H NMR (400 MHz, DMSO-d$_6$) δ 8.62 (d, J = 20.9 Hz, 1H), 7.90 (s, 1H), 7.86-7.64 (m, 1H), 7.54 (d, J = 12.2 Hz, 1H), 7.47-7.29 (m, 2H), 5.74 (bs, 1H), 4.86-4.72 (m, 1H), 4.48 (dd, J = 13.7, 8.0 Hz, 1H), 4.36 (dt, J = 9.1, 5.7 Hz, 1H), 3.88-3.58 (m, 1H), 3.26-3.17 (m, 3H), 2.83-2.65 (m, 3H), 2.42-2.25 (m, 3H), 2.21 (s, 3H), 2.11-1.91 (m, 2H), 1.90-1.67 (m, 2H), 1.55 (dd, J = 24.0, 6.5 Hz, 6H), 1.44-1.15 (m, 4H). [Example 209] |
| 210 | $^1$H NMR (400 MHz, DMSO-d$_6$) δ 10.00 (br.s, 1H), 8.63 (d, J = 21.9 Hz, 1H), 7.95 (s, 1H), 7.85 (d, J = 7.8 Hz, 1H), 7.70 (d, J = 8.3 Hz, 1H), 7.61 (dd, J = 12.3, 1.7 Hz, 1H), 7.44 (dt, J = 16.7, 8.5 Hz, 2H), 5.93-5.61 (m, 1H), 3.93-3.57 (m, 1H), 3.32-3.25 (m, 6H), 3.23 (s, 6H), 2.90-2.72 (m, 2H), 2.64 (t, J = 6.3 Hz, 4H), 2.13-1.86 (m, 2H), 1.84-1.67 (m, 2H), 1.55 (dd, J = 23.8, 6.7 Hz, 6H), 1.43-1.23 (m, 4H). [Example 210] |
| 211 | $^1$H NMR (400 MHz, DMSO-d$_6$) δ 9.96 (s, 1H), 9.73 (s, 1H), 9.42-9.13 (m, 1H), 8.79-8.53 (m, 1H), 8.27-7.98 (m, 2H), 7.64 (d, J = 12.2 Hz, 1H), 7.54-7.33 (m, 4H), 7.28-7.14 (m, 2H), 5.21 (d, J = 44.2 Hz, 1H), 4.56 (s, 2H), 4.53-4.41 (m, 1H), 3.25 (s, 3H), 3.13-2.53 (m, 1H), 2.49-2.34 (m, 2H), 1.94-1.83 (m, 1H). [Example 211] |
| 212 | $^1$H NMR (400 MHz, DMSO-d$_6$) δ 8.62 (d, J = 19.3 Hz, 1H), 7.93 (s, 1H), 7.77 (dd, J = 68.4, 8.2 Hz, 1H), 7.59 (d, J = 12.3 Hz, 1H), 7.42 (dt, J = 16.7, 8.3 Hz, 2H), 5.86-5.59 (m, 1H), 4.58 (s, 4H), 3.87-3.62 (m, 2H), 3.30 (s, 4H), 2.86-2.69 (m, 2H), 2.04-1.84 (m, 3H), 1.84-1.67 (m, 2H), 1.54 (dd, J = 15.7, 6.9 Hz, 6H), 1.38-1.19 (m, 2H), 1.10-0.88 (m, 2H). [Example 212] |
| 213 | $^1$H NMR (400 MHz, DMSO-d$_6$) δ 8.63 (d, J = 20.4 Hz, 1H), 7.93 (s, 1H), 7.91-7.67 (m, 1H), 7.58 (d, J = 12.5 Hz, 1H), 7.41 (dt, J = 16.7, 8.4 Hz, 2H), 5.86-5.64 (m, 1H), 3.90-3.63 (m, 2H), 3.63-3.53 (m, 6H), 2.88-2.69 (m, 2H), 2.28-2.11 (m, 1H), 2.11-1.76 (m, 4H), 1.58 (d, J = 6.8 Hz, 4H), 1.52 (d, J = 6.7 Hz, 2H), 1.42-1.19 (m, 4H). [Example 213] |
| 214 | $^1$H NMR (400 MHz, DMSO-d$_6$) δ 8.63-8.53 (m, 1H), 7.80-7.76 (m, 1H), 6.98-6.88 (m, 1H), 5.78-5.62 (m, 1H), 3.80-3.75 (m, 1H), 2.94-2.88 (m, 2H), 2.71-2.62 (m, 2H), 2.48-2.35 (m, 6H), 1.96-1.80 (m, 3H), 1.76-1.62 (m, 3H), 1.60-1.44 (m, 8H), 1.30-1.10 (m, 3H). [Example 86 and Example 91] |

| EX No | ¹H NMR |
|---|---|
| | ¹H NMR (400 MHz, DMSO-d₆) δ 8.66 (s, 1H), 8.00-7.82 (m, 2H), 7.37-7.29 (m, 1H), 5.81-5.65 (m, 1H), 4.06-3.92 (m, 1H), 3.46-3.37 (m, 2H), 2.89-2.78 (m, 2H), 2.70 (br s, 6H), 2.05-1.94 (m, 2H), 1.92-1.76 (m, 4H), 1.76-1.60 (m, 2H), 1.55 (d, J = 7.0 Hz, 6H), 1.31-1.18 (m, 3H).<br>[Example 86 and Example 91]<br>¹H NMR (400 MHz, DMSO-d₆) δ 8.65 (s, 1H), 7.95-7.88 (m, 2H), 7.35-7.20 (m, 1H), 5.84-5.61 (m, 1H), 3.87-3.72 (m, 1H), 2.85-2.69 (m, 8H), 2.55-2.52 (m, 2H), 2.04-1.88 (m, 4H), 1.73-1.62 (m, 2H), 1.61-1.50 (m, 8H), 1.29 (s, 3H).<br>[Example 86 and Example 91] |
| 215 | ¹H NMR (400 MHz, DMSO-d₆) δ 8.63 (s, 1H), 8.45 (d, J = 2.4 Hz, 1H), 8.05 (dd, J = 8.8, 2.4 Hz, 1H), 7.96 (s, 1H), 7.87 (d, J = 7.8 Hz, 1H), 7.11 (d, J = 8.8 Hz, 1H), 5.88-5.62 (m, 1H), 3.90-3.71 (m, 1H), 3.70-3.60 (m, 2H), 2.82-2.72 (m, 2H), 2.71-2.65 (m, 1H), 2.49 (s, 6H), 2.10-1.90 (m, 4H), 1.56 (d, J = 6.9 Hz, 6H), 1.45-1.32 (m, 4H).<br>[Example 91] |
| 216 | ¹H NMR (400 MHz, DMSO-d₆) δ 8.70 (br s, 1H), 8.47 (s, 1H), 8.10-8.03 (m, 2H), 8.01 (s, 1H), 7.14 (d, J = 8.6 Hz, 1H), 5.88-5.69 (m, 1H), 5.30-5.12 (m, 1H), 4.55-4.34 (m, 1H), 3.78-3.57 (m, 2H), 3.50-3.37 (m, 3H), 2.85-2.70 (m, 3H), 2.44-2.27 (m, 1H), 1.95-1.77 (m, 1H), 1.56 (d, J = 6.9 Hz, 6H).<br>[Example 91 and Example 86] |
| 217 | ¹H NMR (400 MHz, DMSO-d₆) δ 9.63 (br s, 1H), 8.64 (br s, 1H), 7.98 (s, 1H), 7.82 (d, J = 7.0 Hz, 1H), 7.64 (dd, J = 12.3, 2.0 Hz, 1H), 7.50 (dd, J = 8.3, 2.0 Hz, 1H), 7.43 (t, J = 8.4 Hz, 1H), 5.84-5.67 (m, 1H), 4.15-3.95 (m, 1H), 3.42-3.37 (m, 2H), 2.88-2.75 (m, 4H), 2.66 (br s, 6H), 1.92-1.82 (m, 1H), 1.80-1.63 (m, 4H), 1.63-1.45 (m, 10H).<br>[Example 91]<br>¹H NMR (400 MHz, DMSO-d₆) δ 8.63 (br s, 1H), 7.95 (s, 1H), 7.87 (d, J = 7.7 Hz, 1H), 7.62 (dd, J = 12.3, 2.0 Hz, 1H), 7.48 (dd, J = 8.5, 2.0 Hz, 1H), 7.42 (t, J = 8.4 Hz, 1H), 5.89-5.62 (m, 1H), 3.93-3.59 (m, 1H), 3.40-3.35 (m, 2H), 2.86-2.73 (m, 2H), 2.40-2.20 (m, 8H), 2.04-1.90 (m, 2H), 1.88-1.76 (m, 2H), 1.60-1.52 (m, 6H), 1.40-1.20 (m, 3H), 1.07-0.92 (m, 2H).<br>[Example 91] |
| 218 | ¹H NMR (400 MHz, DMSO-d₆) δ 8.79 (br s, 1H), 8.52-8.45 (m, 2H), 8.34 (d, J = 8.8 Hz, 1H), 8.01-7.75 (m, 1H), 7.67 (dd, J = 8.8, 2.7 Hz, 1H), 5.84-5.73 (m, 1H), 3.90-3.71 (m, 1H), 3.47-3.41 (m, 2H), 3.13-2.92 (m, 1H), 2.84-2.72 (m, 2H), 2.67 (s, 6H), 2.17-1.95 (m, 4H), 1.63-1.38 (m, 10H).<br>[Example 91] |
| 219 | ¹H NMR (400 MHz, DMSO-d₆) δ 8.77 (br s, 1H), 8.45 (s, 1H), 8.34 (d, J = 2.7 Hz, 1H), 8.24 (d, J = 8.8 Hz, 1H), 7.81 (d, J = 7.8 Hz, 1H), 7.53 (dd, J = 8.8, 2.8 Hz, 1H), 5.86-5.73 (m, 1H), 4.92-4.74 (m, 1H), 4.26-4.12 (m, 1H), 3.49-3.44 (m, 2H), 3.03-2.90 (m, 2H), 2.80-2.61 (m, 4H), 2.25-2.11 (m, 1H), 1.88-1.72 (m, 1H), 1.61-1.53 (m, 6H).<br>[Example 91 and Example 86] |
| 220 | ¹H NMR (400 MHz, DMSO-d₆) δ 8.58 (br s, 1H), 8.29 (s, 1H), 7.80 (s, 1H), 7.72-7.62 (m, 1H), 7.36 (d, J = 14.5 Hz, 1H), 7.29 (t, J = 8.8 Hz, 1H), 7.21 (dd, J = 8.7, 2.1 Hz, 1H), 5.80-5.70 (m, 1H), 3.64 (s, 2H), 3.58 (s, 2H), 3.41-3.39 (m, 2H), 2.97-2.90 (m, 2H), 2.65-2.58 (m, 1H), 2.05-1.97 (m, 2H), 1.89-1.80 (m, 2H), 1.61-1.46 (m, 10H).<br>[Example 220] |
| 221 | ¹H NMR (400 MHz, DMSO-d₆) δ 9.89 (br s, 1H), 8.64 (br s, 1H), 7.96 (s, 1H), 7.81 (d, J = 7.6 Hz, 1H), 7.62 (dd, J = 12.3, 2.0 Hz, 1H), 7.48 (dd, J = 8.5, 2.0 Hz, 1H), 7.42 (t, J = 8.4 Hz, 1H), 5.80-5.63 (m, 1H), 3.90-3.75 (m, 1H), 3.73 (s, 2H), 3.66 (s, 2H), 3.38-3.35 (m, 2H), 2.86-2.77 (m, 2H), 2.75 (s, 3H), 2.08-1.96 (m, 2H), 1.93-1.80 (m, 2H), 1.63-1.50 (m, 8H), 1.39-1.26 (m, 2H).<br>[Example 221] |
| 222 | ¹H NMR (400 MHz, DMSO-d₆) δ 8.61 (br s, 1H), 8.16 (s, 1H), 7.91 (s, 1H), 7.82 (d, J = 7.7 Hz, 1H), 7.67 (d, J = 11.4 Hz, 1H), 5.81-5.70 (m, 1H), 3.89-3.67 (m, 1H), 3.54-3.46 (m, 2H), 3.08-2.93 (m, 1H), 2.66 (s, 6H), 2.63-2.57 (m, 2H), 2.13-1.98 (m, 4H), 1.60-1.50 (m, 8H), 1.42-1.32 (m, 2H).<br>[Example 91] |
| 223 | ¹H NMR (400 MHz, DMSO-d₆) δ 10.42 (br s, 1H), 8.78 (br s, 1H), 8.54-8.49 (m, 2H), 8.35 (d, J = 8.8 Hz, 1H), 8.06 (d, J = 7.9 Hz, 1H), 7.71 (dd, J = 8.8, 2.7 Hz, 1H), 5.85-5.68 (m, 1H), 5.64-5.38 (m, 1H), 4.25-4.10 (m, 1H), 3.46-3.43 (m, 2H), 2.85-2.75 (m, 8H), 2.22-2.05 (m, 2H), 1.93-1.65 (m, 2H), 1.65-1.45 (m, 8H), 1.40-1.24 (m, 1H).<br>[Example 223] |
| 224 | ¹H NMR (400 MHz, DMSO-d₆) δ 8.65 (br s, 1H), 8.46 (d, J = 2.5 Hz, 1H), 8.07 (dd, J = 8.8, 2.5 Hz, 1H), 7.98 (s, 1H), 7.93 (d, J = 8.1 Hz, 1H), 7.14 (d, J = 9.0 Hz, 1H), 5.82-5.65 (m, 1H), 5.42-5.20 (m, 1H), 4.25-4.05 (m, 1H), 3.73-3.55 (m, 2H), 2.80-2.72 (m, 2H), 2.70-2.52 (m, 6H), 2.42-2.33 (m, 1H), 2.14-1.95 (m, 2H), 1.83-1.65 (m, 2H), 1.61-1.53 (m, 6H), 1.52-1.41 (m, 2H).<br>[Example 223] |
| 225 | ¹H NMR (400 MHz, DMSO-d₆) δ 8.69 (s, 1H), 8.13 (br s, 1H), 8.01 (s, 1H), 7.64 (dd, J = 12.2, 1.9 Hz, 1H), 7.50 (dd, J = 8.5, 2.0 Hz, 1H), 7.44 (t, J = 8.4 Hz, 1H), 5.95-5.62 (m, 2H), 4.39-4.25 (m, 1H), 3.72-3.65 (m, 1H), 3.56-3.42 (m, 1H), 3.42-3.36 (m, 2H), 2.87-2.77 (m, 2H), 2.71 (s, 6H), 2.23-2.13 (m, 1H), 2.05-1.75 (m, 3H), 1.72-1.60 (m, 2H), 1.56 (d, J = 6.9 Hz, 6H).<br>[Example 225] |
| 226 | ¹H NMR (400 MHz, DMSO-d₆) δ 8.66 (br s, 1H), 8.03-7.94 (m, 2H), 7.64 (dd, J = 12.2, 2.0 Hz, 1H), 7.50 (dd, J = 8.4, 1.9 Hz, 1H), 7.44 (t, J = 8.4 Hz, 1H), 5.85-5.70 (m, 2H), 4.10-3.82 (m, 1H), 3.81-3.70 (m, 1H), 3.44-3.35 (m, 2H), 3.10-3.01 (m, 1H), 2.85-2.67 (m, 8H), 2.31-2.20 (m, 1H), 2.15-1.92 (m, 2H), 1.56 (dd, J = 19.7, 7.0 Hz, 6H), 1.51-1.33 (m, 3H).<br>[Example 226] |

TABLE 3-continued

| EX No | ¹H NMR |
|---|---|
| 227 | ¹H NMR (400 MHz,) δ 8.67 (br s, 1H), 8.01-7.83 (m, 2H), 7.64 (dd, J = 12.2, 2.0 Hz, 1H), 7.51 (dd, J = 8.5, 2.0 Hz, 1H), 7.44 (t, J = 8.3 Hz, 1H), 5.87-5.67 (m, 2H), 4.08-3.82 (m, 1H), 3.79-3.70 (m, 1H), 3.43-3.38 (m, 2H), 3.12-2.97 (m, 1H), 2.87-2.77 (m, 2H), 2.74 (s, 6H), 2.35-2.20 (m, 1H), 2.15-1.92 (m, 2H), 1.62-1.53 (m, 6H), 1.52-1.30 (m, 3H). [Example 227] |
| 228 | ¹H NMR (400 MHz,) δ 8.63 (br s, 1H), 7.87 (s, 1H), 7.81 (d, J = 7.8 Hz, 1H), 7.52-7.44 (m, 1H), 7.40-7.29 (m, 2H), 5.89-5.65 (m, 1H), 4.53-4.35 (m, 1H), 4.00-3.75 (m, 1H), 3.54-3.48 (m, 1H), 3.16-3.08 (m, 2H), 2.76-2.63 (m, 2H), 2.38-2.32 (m, 7H), 2.27-2.15 (m, 1H), 2.06-1.95 (m, 1H), 1.85-1.72 (m, 1H), 1.61-1.50 (m, 6H), 1.34-1.22 (m, 3H). [Example 228] |
| 229 | ¹H NMR (400 MHz, DMSO-d₆) δ 8.62 (br s, 1H), 7.89 (s, 1H), 7.78 (d, J = 7.7 Hz, 1H), 7.55-7.47 (m, 1H), 7.41-7.31 (m, 2H), 5.85-5.65 (m, 1H), 3.85-3.67 (m, 1H), 3.15-3.06 (m, 2H), 2.40-2.26 (m, 2H), 2.23 (s, 6H), 2.10-1.77 (m, 5H), 1.69-1.51 (m, 9H), 1.37-1.23 (m, 4H). [Example 229] |
| 230 | ¹H NMR (400 MHz, DMSO-d₆) δ 8.64 (br s, 1H), 7.96 (s, 1H), 7.87 (d, J = 7.7 Hz, 1H), 7.62 (dd, J = 12.2, 1.8 Hz, 1H), 7.52-7.45 (m, 1H), 7.42 (t, J = 8.4 Hz, 1H), 5.85-5.67 (m, 1H), 3.90-3.65 (m, 1H), 3.19-3.13 (m, 2H), 2.61-2.52 (m, 1H), 2.40 (s, 6H), 2.10-1.87 (m, 4H), 1.72-1.63 (m, 2H), 1.62-1.50 (m, 6H), 1.44-1.29 (m, 4H), 0.99 (s, 3H), 0.35-0.22 (m, 4H). [Example 229] |
| 231 | ¹H NMR (400 MHz, DMSO-d₆) δ 8.64 (br s, 1H), 7.95 (s, 1H), 7.86 (d, J = 7.7 Hz, 1H), 7.61 (d, J = 12.3 Hz, 1H), 7.47 (d, J = 8.6 Hz, 1H), 7.41 (t, J = 8.3 Hz, 1H), 5.86-5.67 (m, 1H), 3.90-3.67 (m, 1H), 3.03-2.95 (m, 2H), 2.40-2.28 (m, 7H), 2.12-1.85 (m, 7H), 1.85-1.74 (m, 4H), 1.62-1.50 (m, 8H), 1.42-1.29 (m, 4H). [Example 229] |
| 232 | ¹H NMR (400 MHz, DMSO-d₆) δ 8.63 (br s, 1H), 7.94 (s, 1H), 7.84 (d, J = 7.7 Hz, 1H), 7.64-7.56 (m, 1H), 7.47 (d, J = 8.6 Hz, 1H), 7.41 (t, J = 8.3 Hz, 1H), 5.83-5.66 (m, 1H), 3.86-3.63 (m, 1H), 3.16-3.10 (m, 2H), 2.29-2.22 (m, 7H), 2.10-1.94 (m, 2H), 1.93-1.77 (m, 4H), 1.61-1.50 (m, 6H), 1.40-1.25 (m, 6H), 0.72-0.59 (m, 1H), 0.43-0.32 (m, 2H), 0.03--0.01 (m, 2H). [Example 229] |
| 233 | ¹H NMR (400 MHz, DMSO-d₆) δ 8.58 (br s, 1H), 8.50 (s, 2H), 7.82 (s, 1H), 7.70 (d, J = 7.8 Hz, 1H), 5.80-5.64 (m, 1H), 4.12-4.06 (m, 2H), 3.49-3.40 (m, 2H), 2.18 (s, 6H), 2.03-1.98 (m, 2H), 1.88-1.80 (m, 2H), 1.60-1.54 (m, 6H), 1.30-1.26 (m, 6H). [Example 233] |
| 234 | ¹H NMR (400 MHz, DMSO-d₆) δ 8.62 (br s, 1H), 7.91 (s, 1H), 7.76 (d, J = 7.8 Hz, 1H), 7.56 (dd, J = 12.5, 1.8 Hz, 1H), 7.45-7.34 (m, 2H), 5.78-5.68 (m, 1H), 3.80-3.67 (m, 1H), 3.27-3.21 (m, 7H), 3.17 (d, J = 3.8 Hz, 1H), 3.10 (br s, 2H), 3.04 (br s, 2H), 2.80-2.65 (m, 4H), 1.99-1.89 (m, 2H), 1.87-1.77 (m, 2H), 1.59-1.45 (m, 8H), 1.40-1.29 (m, 2H). [Example 234] |
| 235 | ¹H NMR (400 MHz, DMSO-d₆) δ 8.55 (s, 1H), 7.80 (s, 1H), 7.54-7.44 (m, 2H), 7.37 (d, J = 8.5 Hz, 1H), 5.94-5.80 (m, 1H), 4.46 (dt, J = 47.5, 4.8 Hz, 2H), 3.90-3.80 (m, 1H), 3.28-3.21 (m, 4H), 3.14 (s, 2H), 2.83 (dt, J = 28.4, 4.9 Hz, 2H), 2.77-2.67 (m, 2H), 2.08-1.93 (m, 4H), 1.68-1.56 (m, 8H), 1.48-1.35 (m, 2H). [Example 235] |
| 236 | ¹H NMR (400 MHz, 360K, DMSO-d₆), δ 9.05 (d, J = 2.3 Hz, 1H), 8.69 (s, 1H), 8.39 (dd, J = 8.9, 2.4 Hz, 1H), 7.58 (d, J = 8.1 Hz, 1H), 7.37-7.26 (m, 5H), 7.04 (d, J = 8.9 Hz, 1H), 5.63 (hept, J = 6.9 Hz, 1H), 4.90-4.70 (m, 1H), 4.66 (s, 2H), 4.24-4.12 (m, 1H), 3.09-3.06 (m, 1H), 2.95-2.86 (m, 2H), 2.82-2.68 (m, 1H), 2.59-2.51 (m, 1H), 2.25-2.12 (m, 1H), 1.97-1.75 (m, 1H), 1.59 (d, J = 6.8 Hz, 6H). [Example 73] |
| 237 | ¹H NMR (400 MHz, 360K, DMSO-d₆) δ 9.02 (d, J = 2.4 Hz, 1H), 8.69 (s, 1H), 8.40 (dd, J = 9.0, 2.3 Hz, 1H), 7.59 (d, J = 7.9 Hz, 1H), 7.47-7.40 (m, 1H), 7.40-7.30 (m, 3H), 7.20-7.05 (m, 3H), 5.63 (hept, J = 6.9 Hz, 1H), 4.89-4.70 (m, 1H), 4.67 (s, 2H), 4.25-4.12 (m, 1H), 3.08 (d, J = 4.1 Hz, 1H), 2.96-2.88 (m, 2H), 2.82-2.69 (m, 1H), 2.59-2.51 (m, 1H), 2.23-2.13 (m, 1H), 1.96-1.78 (m, 1H), 1.59 (d, J = 6.9 Hz, 6H). [Example 236] |
| 238 | ¹H NMR (400 MHz, 360K, DMSO-d₆) δ 8.97 (d, J = 2.4 Hz, 1H), 8.64 (s, 1H), 8.30 (dd, J = 8.9, 2.5 Hz, 1H), 7.47 (d, J = 7.9 Hz, 1H), 6.92 (d, J = 8.9 Hz, 1H), 5.61 (hept, J = 7.0 Hz, 1H), 3.81-3.67 (m, 1H), 3.57-3.52 (m, 1H), 3.52-3.45 (m, 1H), 3.37-3.24 (m, 4H), 2.67-2.63 (m, 1H), 2.21 (s, 6H), 2.07-1.99 (m, 2H), 1.91-1.84 (m, 2H), 1.60-1.57 (m, 7H), 1.42-1.25 (m, 4H). [Example 73] |
| 239 | ¹H NMR (400 MHz, 360K, DMSO-d₆) δ 8.68 (s, 1H), 7.93-7.84 (m, 2H), 7.69-7.58 (m, 1H), 5.61 (hept, J = 6.9 Hz, 1H), 3.83-3.71 (m, 1H), 3.22-3.17 (m, 4H), 2.44-2.40 (m, 1H), 2.35 (s, 6H), 2.09-2.02 (m, 2H), 1.97-1.88 (m, 2H), 1.59 (d, J = 6.9 Hz, 6H), 1.44-1.31 (m, 4H). [Example 73] |
| 240 | ¹H NMR (400 MHz, 360K, DMSO-d₆) δ 8.68 (s, 1H), 7.94-7.85 (m, 2H), 7.70-7.60 (m, 1H), 5.61 (hept, J = 7.4 Hz, 1H), 3.84-3.69 (m, 1H), 3.47 (s, 2H), 2.39-2.29 (m, 8H), 2.09-2.02 (m, 2H), 1.95-1.87 (m, 2H), 1.59 (d, J = 6.9 Hz, 6H), 1.46-1.26 (m, 7H). [Example 239] |
| 241 | ¹H NMR (400 MHz, 360K, DMSO-d6) δ 8.68 (s, 1H), 7.94-7.88 (m, 2H), 7.65 (d, J = 7.9 Hz, 1H), 5.67-5.55 (m, 1H), 3.84-3.70 (m, 1H), 3.21-3.15 (m, 4H), 2.27 (s, 6H), 2.08-2.01 (m, 2H), 1.93-1.86 (m, 2H), 1.72-1.61 (m, 4H), 1.59 (d, J = 6.9 Hz, 6H), 1.41-1.29 (m, 4H). [Example 239] |
| 242 | ¹H NMR (400 MHz, 360K, DMSO-d₆) δ 8.73 (s, 1H), 8.00-7.93 (m, 2H), 7.89-7.74 (m, 1H), 5.61 (hept, J = 6.9 Hz, 1H), 3.95-3.71 (m, 1H), 3.21-3.14 (m, 2H), 2.70 (s, 6H), 2.16-2.07 (m, 4H), 1.90-1.79 (m, 2H), 1.62-1.41 (m, 11H), 1.03 (t, J = 7.4 Hz, 3H). [Example 239] |

TABLE 3-continued

| EX No | ¹H NMR |
|---|---|
| 243 | ¹H NMR (400 MHz, 360K, DMSO-$d_6$) δ 8.70 (s, 1H), 7.98-7.88 (m, 2H), 7.71-7.65 (m, 1H), 7.48-7.41 (m, 2H), 7.41-7.35 (m, 2H), 5.60 (h, J = 6.9 Hz, 1H), 4.40 (s, 2H), 3.84-3.70 (m, 1H), 2.34-2.27 (m, 7H), 2.09-2.01 (m, 2H), 1.95-1.87 (m, 2H), 1.59 (d, J = 6.8 Hz, 6H), 1.44-1.29 (m, 4H). [Example 239] |
| 244 | ¹H NMR (400 MHz, 360K, DMSO-$d_6$) δ 8.69 (s, 1H), 7.97-7.88 (m, 2H), 7.71-7.62 (m, 1H), 7.60-7.50 (m, 4H), 7.11-6.80 (m, 1H), 5.61 (hept, J = 6.8 Hz, 1H), 4.45 (s, 2H), 3.83-3.71 (m, 1H), 2.34-2.26 (m, 7H), 2.08-2.01 (m, 2H), 1.94-1.87 (m, 2H), 1.59 (d, J = 7.0 Hz, 6H), 1.45-1.27 (m, 4H). [Example 239] |
| 245 | ¹H NMR (400 MHz, 360K, DMSO-$d_6$) δ 8.70 (s, 1H), 8.00-7.89 (m, 2H), 7.77-7.63 (m, 1H), 7.51-7.42 (m, 2H), 7.20-7.10 (m, 2H), 5.61 (hept, J = 7.0 Hz, 1H), 4.43 (s, 2H), 3.86-3.69 (m, 1H), 2.39-2.32 (m, 1H), 2.30 (s, 6H), 2.09-2.01 (m, 2H), 1.96-1.87 (m, 2H), 1.59 (d, J = 6.9 Hz, 6H), 1.46-1.29 (m, 4H). [Example 239] |
| 246 | ¹H NMR (400 MHz, 360K, DMSO-$d_6$) δ 8.63 (s, 1H), 7.87-7.75 (m, 2H), 7.45 (d, J = 7.7 Hz, 1H), 7.29-7.23 (m, 2H), 7.06 (d, J = 7.8 Hz, 2H), 5.60 (h, J = 7.0 Hz, 1H), 4.07 (s, 2H), 3.78-3.71 (m, 1H), 2.66-2.64 (m, 1H), 2.27 (s, 3H), 2.20 (s, 6H), 2.07-1.99 (m, 2H), 1.90-1.82 (m, 2H), 1.58 (d, J = 7.0 Hz, 6H), 1.42-1.24 (m, 4H). [Example 239] |
| 247 | ¹H NMR (400 MHz, 360K, DMSO-$d_6$) δ 8.73-8.68 (m, 1H), 7.99-7.91 (m, 2H), 7.75-7.65 (m, 1H), 7.47-7.40 (m, 2H), 7.40-7.28 (m, 3H), 5.61 (hept, J = 6.8 Hz, 1H), 4.44 (s, 2H), 3.84-3.70 (m, 1H), 2.34-2.18 (m, 7H), 2.08-2.01 (m, 2H), 1.94-1.87 (m, 2H), 1.59 (d, J = 7.0 Hz, 6H), 1.45-1.24 (m, 4H). [Example 239] |
| 248 | ¹H NMR (400 MHz, DMSO-$d_6$) δ 8.77-8.68 (m, 1H), 8.07-7.80 (m, 3H), 5.70-5.54 (m, 1H), 3.96-3.60 (m, 3H), 2.90-2.72 (m, 1H), 2.59-2.52 (m, 6H), 2.12-1.92 (m, 6H), 1.63-1.52 (m, 6H), 1.52-1.31 (m, 4H), 0.89-0.77 (m, 1H), 0.48-0.42 (m, 2H), 0.21-0.13 (m, 2H). [Example 239] |
| 249 | ¹H NMR (400 MHz, 360K, DMSO-$d_6$) δ 8.68 (s, 1H), 7.97-7.86 (m, 2H), 7.68-7.61 (m, 1H), 5.60 (hept, J = 6.9 Hz, 1H), 3.83-3.70 (m, 1H), 3.30 (d, J = 6.9 Hz, 2H), 2.79-2.62 (m, 4H), 2.57-2.51 (m, 1H), 2.28-2.18 (m, 7H), 2.08-2.01 (m, 2H), 1.93-1.85 (m, 2H), 1.59 (d, J = 6.9 Hz, 6H), 1.43-1.25 (m, 4H). [Example 239] |
| 250 | ¹H NMR (400 MHz, 360K, DMSO-$d_6$) δ 8.68 (s, 1H), 7.96-7.87 (m, 2H), 7.70-7.61 (m, 1H), 5.61 (hept, J = 6.8 Hz, 1H), 3.82-3.71 (m, 1H), 3.41-3.26 (m, 3H), 3.26-3.18 (m, 2H), 2.26 (s, 7H), 2.12-2.01 (m, 3H), 1.94-1.86 (m, 2H), 1.76-1.65 (m, 1H), 1.59 (d, J = 6.8 Hz, 6H), 1.46-1.28 (m, 4H). [Example 239] |
| 251 | ¹H NMR (400 MHz, 360K, DMSO-$d_6$) δ 8.59 (s, 1H), 7.69 (d, J = 8.6 Hz, 1H), 7.53 (d, J = 7.7 Hz, 1H), 6.88 (d, J = 8.7 Hz, 1H), 6.09 (s, 1H), 5.57 (hept, J = 6.3 Hz, 1H), 3.78-3.71 (m, 1H), 3.53-3.47 (m, 2H), 2.74-2.64 (m, 2H), 2.32 (s, 3H), 2.21 (s, 6H), 2.06-2.00 (m, 2H), 1.91-1.84 (m, 2H), 1.59-1.54 (m, 6H), 1.40-1.26 (m, 4H). [Example 73] |
| 252 | ¹H NMR (400 MHz, 360K, DMSO-$d_6$) δ 8.60 (s, 1H), 7.70 (d, J = 8.6 Hz, 1H), 7.59-7.52 (m, 1H), 7.41-7.34 (m, 2H), 7.17-7.08 (m, 2H), 6.86 (d, J = 8.6 Hz, 1H), 5.59 (h, J = 6.9 Hz, 1H), 4.67 (s, 2H), 3.80-3.70 (m, 1H), 2.39 (s, 3H), 2.22-2.14 (m, 7H), 2.07-1.99 (m, 2H), 1.93-1.84 (m, 2H), 1.61-1.55 (m, 6H), 1.43-1.25 (m, 4H). [Example 251] |
| 253 | ¹H NMR (400 MHz, 360K, DMSO-$d_6$) δ 8.61 (s, 1H), 8.00-7.92 (m, 1H), 7.75 (d, J = 8.9 Hz, 1H), 7.64-7.54 (m, 2H), 7.37-7.24 (m, 2H), 7.09 (d, J = 8.9 Hz, 1H), 5.56 (hept, J = 6.9 Hz, 1H), 3.80-3.72 (m, 1H), 2.29 (s, 3H), 2.27-2.19 (m, 7H), 2.09-2.00 (m, 2H), 1.94-1.87 (m, 2H), 1.57 (d, J = 6.8 Hz, 6H), 1.45-1.26 (m, 4H). [Example 251] |
| 254 | ¹H NMR (400 MHz, 360K, DMSO-$d_6$) δ 8.61 (s, 1H), 8.19-8.13 (m, 1H), 7.73 (d, J = 8.8 Hz, 1H), 7.63-7.56 (m, 1H), 7.56-7.45 (m, 3H), 7.03 (d, J = 8.9 Hz, 1H), 5.56 (hept, J = 7.0 Hz, 1H), 3.81-3.72 (m, 1H), 2.27 (s, 3H), 2.26-2.17 (m, 7H), 2.10-2.00 (m, 2H), 1.94-1.86 (m, 2H), 1.57 (d, J = 6.9 Hz, 6H), 1.47-1.24 (m, 4H). [Example 251] |
| 255 | ¹H NMR (400 MHz, 360K, DMSO-$d_6$) δ 8.61 (s, 1H), 7.95-7.89 (m, 1H), 7.85-7.74 (m, 2H), 7.74-7.66 (m, 1H), 7.64-7.56 (m, 1H), 7.07 (d, J = 9.0 Hz, 1H), 5.57 (hept, J = 6.7 Hz, 1H), 3.81-3.75 (m, 1H), 2.35-2.30 (m, 10H), 2.10-2.03 (m, 2H), 1.96-1.89 (m, 2H), 1.64-1.60 (m, 1H), 1.57 (d, J = 6.9 Hz, 6H), 1.44-1.32 (m, 4H). [Example 251] |
| 256 | ¹H NMR (400 MHz, 360K, DMSO-$d_6$) δ 8.68 (s, 1H), 8.13-7.99 (m, 2H), 7.68-7.58 (m, 1H), 7.55-7.46 (m, 1H), 5.61 (hept, J = 7.0 Hz, 1H), 3.79-3.72 (m, 1H), 3.20 (d, J = 6.8 Hz, 2H), 2.34-2.28 (m, 7H), 2.08-2.02 (m, 2H), 1.95-1.87 (m, 2H), 1.59 (d, J = 6.8 Hz, 6H), 1.51-1.26 (m, 6H), 1.08 (dd, J = 7.9, 4.4 Hz, 1H), 0.90-0.85 (m, 1H), 0.79-0.74 (m, 2H), 0.67-0.61 (m, 1H). [Example 73] |
| 257 | ¹H NMR (400 MHz, 360K, DMSO-$d_6$) δ 8.69 (s, 1H), 8.13-7.99 (m, 2H), 7.70-7.63 (m, 1H), 7.56-7.47 (m, 1H), 5.61 (hept, J = 6.6 Hz, 1H), 3.84-3.73 (m, 1H), 2.76-2.63 (m, 3H), 2.47-2.38 (m, 2H), 2.36-1.91 (m, 14H), 1.83-1.72 (m, 1H), 1.59 (d, J = 6.8 Hz, 6H), 1.50-1.35 (m, 4H). [Example 256] |
| 258 | ¹H NMR (400 MHz, 360K, DMSO-$d_6$) δ 8.67 (s, 1H), 8.08-7.97 (m, 2H), 7.63-7.57 (m, 1H), 7.51-7.41 (m, 1H), 5.61 (hept, J = 6.8 Hz, 1H), 3.81-3.71 (m, 1H), 3.47 (s, 2H), 2.40-2.30 (m, 7H), |

TABLE 3-continued

| EX No | ¹H NMR |
|---|---|
| | 2.09-2.01 (m, 2H), 1.96-1.88 (m, 2H), 1.71-1.57 (m, 9H), 1.44-1.30 (m, 4H), 1.09-1.03 (m, 2H), 0.96-0.90 (m, 2H). [Example 256] |
| 259 | ¹H NMR (400 MHz, 360K, DMSO-$d_6$) δ 8.68 (s, 1H), 8.09-7.99 (m, 2H), 7.66-7.60 (m, 1H), 7.52-7.44 (m, 1H), 5.61 (hept, J = 6.9 Hz, 1H), 3.83-3.74 (m, 1H), 2.33 (s, 8H), 2.09-1.76 (m, 8H), 1.59 (d, J = 7.0 Hz, 6H), 1.55-1.46 (m, 1H), 1.43-1.33 (m, 4H), 1.21-1.09 (m, 1H). [Example 256] |
| 260 | ¹H NMR (400 MHz, 360K, DMSO-$d_6$) δ 8.69 (s, 1H), 8.09-7.98 (m, 2H), 7.74-7.65 (m, 1H), 7.54-7.44 (m, 1H), 5.61 (hept, J = 6.9 Hz, 1H), 3.87-3.73 (m, 1H), 2.88-2.80 (m, 1H), 2.58 (s, 6H), 2.13-1.91 (m, 8H), 1.91-1.65 (m, 9H), 1.59 (d, J = 6.8 Hz, 6H), 1.54-1.36 (m, 4H). [Example 256] |
| 261 | ¹H NMR (400 MHz, 360K, DMSO-$d_6$) δ 8.68 (s, 1H), 8.13-7.99 (m, 2H), 7.64 (d, J = 7.6 Hz, 1H), 7.55-7.46 (m, 1H), 5.61 (hept, J = 6.9 Hz, 1H), 3.84-3.72 (m, 1H), 3.49 (s, 2H), 2.66-2.59 (m, 3H), 2.44 (s, 6H), 2.31-2.23 (m, 2H), 2.11-2.02 (m, 2H), 2.02-1.93 (m, 4H), 1.59 (d, J = 6.8 Hz, 6H), 1.49-1.33 (m, 4H). [Example 256] |
| 262 | ¹H NMR (400 MHz, 360K, DMSO-$d_6$) δ 8.67 (s, 1H), 8.08-8.00 (m, 2H), 7.63 (d, J = 7.7 Hz, 1H), 7.52-7.46 (m, 1H), 5.61 (p, J = 7.0 Hz, 1H), 3.81-3.71 (m, 1H), 3.44-3.36 (m, 3H), 2.41-2.32 (m, 2H), 2.29 (s, 6H), 2.23-2.02 (m, 5H), 1.94-1.89 (m, 2H), 1.59 (d, J = 6.9 Hz, 6H), 1.44-1.28 (m, 6H). [Example 256] |
| 263 | ¹H NMR (400 MHz, 360K, DMSO-$d_6$) δ 8.67 (s, 1H), 8.08-7.98 (m, 2H), 7.61 (d, J = 7.8 Hz, 1H), 7.51-7.43 (m, 1H), 5.61 (hept, J = 6.9 Hz, 1H), 3.81-3.71 (m, 1H), 3.48-3.38 (m, 2H), 3.34-3.24 (m, 4H), 2.30 (s, 6H), 2.10-1.97 (m, 3H), 1.95-1.87 (m, 2H), 1.70-1.62 (m, 1H), 1.59 (d, J = 7.0 Hz, 6H), 1.45-1.29 (m, 4H). [Example 256] |
| 264 | ¹H NMR (400 MHz, 360K, DMSO-$d_6$) δ 8.68 (s, 1H), 8.12-8.00 (m, 2H), 7.71-7.62 (m, 1H), 7.53-7.44 (m, 1H), 5.61 (hept, J = 6.9 Hz, 1H), 3.83-3.73 (m, 1H), 3.39 (dd, J = 14.4, 3.1 Hz, 1H), 2.61-2.54 (m, 1H), 2.42 (s, 6H), 2.23-2.00 (m, 6H), 1.98-1.92 (m, 2H), 1.81-1.60 (m, 4H), 1.59 (d, J = 6.8 Hz, 6H), 1.47-1.35 (m, 4H). [Example 256] |
| 265 | ¹H NMR (400 MHz, 360K, DMSO-$d_6$) δ 8.67 (s, 1H), 8.08-7.97 (m, 2H), 7.62 (d, J = 7.5 Hz, 1H), 7.50-7.42 (m, 1H), 5.61 (hept, J = 6.9 Hz, 1H), 3.82-3.71 (m, 1H), 3.24-3.23 (m, 1H), 2.44-2.34 (m, 2H), 2.27 (s, 6H), 2.23-2.14 (m, 2H), 2.12-2.00 (m, 4H), 1.94-1.87 (m, 2H), 1.86-1.74 (m, 2H), 1.59 (d, J = 6.8 Hz, 6H), 1.48-1.26 (m, 5H). [Example 256] |
| 266 | ¹H NMR (400 MHz, 360K, DMSO-$d_6$) δ 8.68 (s, 1H), 8.13-7.99 (m, 2H), 7.66 (d, J = 7.5 Hz, 1H), 7.52-7.43 (m, 1H), 6.59-6.17 (m, 1H), 5.61 (hept, J = 6.9 Hz, 1H), 3.84-3.73 (m, 1H), 3.37 (s, 2H), 2.62-2.56 (m, 1H), 2.44 (s, 6H), 2.11-2.03 (m, 2H), 1.99-1.76 (m, 6H), 1.70-1.57 (m, 10H), 1.47-1.35 (m, 4H). [Example 256] |
| 267 | ¹H NMR (400 MHz, 360K, DMSO-$d_6$) δ 8.68 (s, 1H), 8.13-7.99 (m, 2H), 7.65 (d, J = 7.3 Hz, 1H), 7.54-7.44 (m, 1H), 5.61 (hept, J = 6.9 Hz, 1H), 3.83-3.72 (m, 1H), 3.21 (d, J = 6.8 Hz, 3H), 2.36 (s, 7H), 2.06 (d, J = 8.4 Hz, 2H), 1.97-1.83 (m, 4H), 1.59 (d, J = 6.8 Hz, 7H), 1.55-1.24 (m, 9H). [Example 256] |
| 268 | ¹H NMR (400 MHz, 360K, DMSO-$d_6$) δ 8.66 (s, 1H), 8.07-7.97 (m, 2H), 7.57 (d, J = 7.8 Hz, 1H), 7.53-7.46 (m, 1H), 7.19-7.06 (m, 4H), 5.61 (hept, J = 6.8 Hz, 1H), 3.80-3.70 (m, 1H), 3.34 (d, J = 6.8 Hz, 2H), 3.17-3.10 (m, 2H), 2.93-2.87 (m, 1H), 2.82-2.75 (m, 2H), 2.24-2.15 (m, 7H), 2.07-1.99 (m, 2H), 1.92-1.84 (m, 2H), 1.58 (d, J = 6.8 Hz, 6H), 1.42-1.26 (m, 4H). [Example 256] |
| 269 | ¹H NMR (400 MHz, 360K, DMSO-$d_6$) δ 8.67 (s, 1H), 8.09-7.98 (m, 2H), 7.63 (d, J = 7.6 Hz, 1H), 7.52-7.43 (m, 1H), 5.61 (hept, J = 6.9 Hz, 1H), 3.81-3.71 (m, 1H), 2.26 (s, 6H), 2.08-2.00 (m, 2H), 1.95-1.81 (m, 5H), 1.68-1.61 (m, 2H), 1.59 (d, J = 6.9 Hz, 7H), 1.44-1.02 (m, 10H). [Example 256] |
| 270 | ¹H NMR (400 MHz, 360K, DMSO-d6) δ 8.68 (s, 1H), 8.09-7.99 (m, 2H), 7.70-7.60 (m, 1H), 7.55-7.46 (m, 1H), 5.61 (hept, J = 6.8 Hz, 1H), 3.83-3.71 (m, 1H), 3.48 (s, 2H), 2.34 (s, 6H), 2.20-2.13 (m, 1H), 2.09-2.03 (m, 2H), 1.96-1.89 (m, 2H), 1.59 (d, J = 7.1 Hz, 9H), 1.55-1.43 (m, 3H), 1.43-1.24 (m, 9H). [Example 256] |
| 271 | ¹H NMR (400 MHz, 360K, DMSO-$d_6$) δ 8.67 (s, 1H), 8.07-7.99 (m, 2H), 7.61 (d, J = 7.6 Hz, 1H), 7.52-7.43 (m, 1H), 5.61 (hept, J = 7.0 Hz, 1H), 3.81-3.71 (m, 1H), 3.16-3.14 (m, 2H), 2.25 (s, 6H), 2.13-1.72 (m, 12H), 1.59 (d, J = 6.8 Hz, 6H), 1.44-1.28 (m, 6H). [Example 256] |
| 272 | ¹H NMR (400 MHz, DMSO-$d_6$) δ 8.73 (d, J = 18.3 Hz, 1H), 8.09-7.89 (m, 3H), 7.52-7.43 (m, 1H), 5.69-5.55 (m, 1H), 3.89-3.69 (m, 1H), 3.08-3.02 (m, 1H), 2.77-2.71 (m, 1H), 2.54-2.53 (m, 4H), 2.33-2.16 (m, 2H), 2.11-1.91 (m, 6H), 1.79-1.64 (m, 3H), 1.63-1.53 (m, 7H), 1.46-1.22 (m, 8H). [Example 256] |
| 273 | ¹H NMR (400 MHz, 360K, DMSO-$d_6$) δ 8.66 (s, 1H), 8.07-7.97 (m, 2H), 7.59 (d, J = 7.8 Hz, 1H), 7.50-7.41 (m, 1H), 5.61 (hept, J = 6.8 Hz, 1H), 3.79-3.70 (m, 1H), 2.29-2.15 (m, 8H), 2.07-1.99 (m, 2H), 1.96-1.83 (m, 4H), 1.83-1.54 (m, 11H), 1.47-1.24 (m, 5H), 1.22-0.83 (m, 2H). [Example 256] |

TABLE 3-continued

| EX No | $^1$H NMR |
|---|---|
| 274 | $^1$H NMR (400 MHz, 360K, DMSO-$d_6$) δ 8.70 (s, 1H), 8.05-7.97 (m, 2H), 7.70 (d, J = 6.9 Hz, 1H), 7.56-7.47 (m, 1H), 7.27-7.17 (m, 3H), 7.15-7.08 (m, 2H), 5.62 (hept, J = 6.9 Hz, 1H), 3.87-3.73 (m, 1H), 2.89-2.84 (m, 1H), 2.62-2.55 (m, 7H), 2.13-2.06 (m, 2H), 2.06-1.99 (m, 2H), 1.59 (d, J = 6.8 Hz, 6H), 1.56-1.38 (m, 6H), 1.28-0.88 (m, 1H). [Example 256] |
| 275 | $^1$H NMR (400 MHz, 360K, DMSO-$d_6$) δ 8.69 (s, 1H), 8.12-8.01 (m, 2H), 7.68 (d, J = 7.7 Hz, 1H), 7.53-7.45 (m, 1H), 5.62 (hept, J = 6.9 Hz, 1H), 3.84-3.73 (m, 1H), 2.63 (s, 1H), 2.46 (s, 6H), 2.11-2.04 (m, 2H), 2.02-1.95 (m, 2H), 1.87-1.77 (m, 2H), 1.62-1.54 (m, 10H), 1.47-1.37 (m, 4H), 1.28-1.07 (m, 5H). [Example 256] |
| 276 | [Example 256] |
| 277 | $^1$H NMR (400 MHz, 360K, DMSO-$d_6$) δ 8.68 (s, 1H), 8.07-7.98 (m, 2H), 7.66 (d, J = 7.4 Hz, 1H), 7.51-7.42 (m, 1H), 5.61 (hept, J = 6.8 Hz, 1H), 3.87-3.71 (m, 2H), 2.45-2.39 (m, 1H), 2.37-2.24 (m, 10H), 2.09-1.98 (m, 4H), 1.96-1.89 (m, 4H), 1.78-1.72 (m, 2H), 1.59 (d, J = 6.9 Hz, 6H), 1.46-1.31 (m, 4H). [Example 256] |
| 278 | $^1$H NMR (400 MHz, 360K, DMSO-$d_6$) δ 8.69 (s, 1H), 8.13-7.99 (m, 2H), 7.70 (d, J = 7.7 Hz, 1H), 7.54-7.45 (m, 1H), 5.61 (h, J = 6.8 Hz, 1H), 3.88-3.73 (m, 1H), 3.31 (d, J = 7.2 Hz, 2H), 2.92-2.88 (m, 1H), 2.83-2.72 (m, 1H), 2.61 (s, 6H), 2.15-2.00 (m, 6H), 1.89-1.75 (m, 4H), 1.59 (d, J = 6.9 Hz, 6H), 1.56-1.37 (m, 4H). [Example 256] |
| 279 | $^1$H NMR (400 MHz, 360K, DMSO-$d_6$) δ 8.68 (s, 1H), 8.09-7.99 (m, 2H), 7.66 (d, J = 7.5 Hz, 1H), 7.52-7.45 (m, 1H), 5.61 (hept, J = 6.9 Hz, 1H), 3.83-3.72 (m, 1H), 3.44 (d, J = 7.0 Hz, 2H), 2.81-2.69 (m, 3H), 2.65-2.54 (m, 3H), 2.43 (s, 6H), 2.10-2.03 (m, 2H), 2.01-1.91 (m, 2H), 1.59 (d, J = 7.0 Hz, 6H), 1.49-1.33 (m, 4H). [Example 256] |
| 280 | $^1$H NMR (400 MHz, 360K, DMSO-$d_6$) δ 8.68 (s, 1H), 8.09-7.97 (m, 2H), 7.65 (d, J = 7.6 Hz, 1H), 7.56-7.47 (m, 1H), 5.61 (hept, J = 6.9 Hz, 1H), 3.85-3.68 (m, 1H), 3.36-3.27 (m, 1H), 2.45-2.39 (m, 1H), 2.34 (s, 6H), 2.21-2.02 (m, 6H), 1.98-1.72 (m, 6H), 1.59 (d, J = 6.9 Hz, 6H), 1.47-1.29 (m, 4H). [Example 256] |
| 281 | $^1$H NMR (400 MHz, 360K, DMSO-$d_6$) δ 8.65 (s, 1H), 8.04-7.95 (m, 2H), 7.59-7.53 (m, 1H), 7.51-7.44 (m, 1H), 5.61 (hept, J = 6.9 Hz, 1H), 3.81-3.70 (m, 1H), 2.59-2.53 (m, 1H), 2.30-2.28 (m, 1H), 2.20 (s, 6H), 2.04-2.01 (m, 1H), 1.88-1.85 (m, 1H), 1.80-1.75 (m, 1H), 1.67-1.63 (m, 2H), 1.60-1.56 (m, 8H), 1.54-1.49 (m, 3H), 1.39-1.25 (m, 6H), 1.18-1.11 (m, 2H). [Example 256] |
| 282 | $^1$H NMR (400 MHz, 360K, DMSO-$d_6$) δ 8.70-8.64 (m, 1H), 8.06-7.96 (m, 2H), 7.75-7.58 (m, 1H), 7.57-7.51 (m, 1H), 7.12-7.02 (m, 4H), 5.61 (h, J = 6.9 Hz, 1H), 3.88-3.70 (m, 1H), 3.50-3.36 (m, 2H), 3.19-3.17 (m, 1H), 2.88-2.71 (m, 5H), 2.37-2.30 (m, 1H), 2.28-2.12 (m, 6H), 2.07-1.99 (m, 1H), 1.94-1.80 (m, 2H), 1.68-1.27 (m, 10H). [Example 256] |

BIOLOGICAL EXAMPLES

Example 283

IRE1α TR-FRET Competition Binding Assay. The affinity of compound binding to the kinase domain of IRE1α was determined using a time-resolved fluorescence resonance energy transfer (TR-FRET) competition assay.

A His-tagged IRE1α kinase dead construct containing the kinase and RNase domains (KR, AA G547-L977, D688N) was expressed in Sf9 insect cells. The purified protein (final concentration 0.25 nM) was pre-incubated with anti-His Europium labeled antibody (Life Technologies PV5596, final concentration 2 nM) for one hour at 4° C. in TR-FRET Assay Buffer (50 mM HEPES, pH 7.5, 10 mM MgCl2, 0.083 mM Brij 35, 1 mM DTT, and 0.1% bovine gamma globulin) prior to addition to test compounds. An Alexa fluor 647-labeled probe based on an ATP competitive inhibitor was added to a final concentration of 2 nM. Reactions were carried out for one hour at room temperature in a final volume of 20 µL in 384 well white ProxiPlates (Perkin Elmer 6008289). Binding of the probe to the IRE1α protein was detected in an Envision instrument (PerkinElmer) equipped with a TRF laser option and a LANCE/Delfia Dual/Bias D400/D630 mirror (Ex 347 nm, 1st Em 665 nm, 2nd Em 615 nm).

Example 284. IRE1α RNase Activity Assay. Inhibitors of the RNase activity of IRE1α were assessed by using a mini-XBP-1 stem-loop RNA as a substrate for the IRE1α RNase activity. A 5'-Carboxyfluorescein (FAM)- and 3'-Black Hole Quencher (BHQ)-labeled XBP1 single stem-loop mini-substrate (5'FAM-CAUGUCCGCAGCGCAUG-3'BHQ) (SEQ ID NO: 1) is cleaved by IRE1α. When the oligo is intact, the fluorescence signal is quenched by BHQ. Upon cleavage, the fluorescence is no longer quenched and can be quantified.

An IRE1α construct corresponding to the linker, kinase and RNase domains (LKR, AA Q470-L977) was expressed in Sf9 insect cells. All reagent preparation and procedures were done under RNase free conditions. Test compounds and purified enzyme were combined in RNase Assay Buffer (20 mM HEPES, pH 7.5, 50 mM KAc, 1 mM MgAc, 1 mM DTT, and 0.05% Triton X-100) in a 384 well white Proxi-Plate (Perkin Elmer 6008289). Upon addition of the RNA substrate (final assay volume 20 µL), the plates were placed into a Flexstation 3 instrument (Molecular Devices) for kinetic fluorescence reading at 2 minute intervals (Ex 485, Em 535). The velocity of the reaction, using the first 50 minutes, was used to calculate the RNase activity and inhibition of test compounds.

Example 285: IRE1α Ribonuclease Luciferase Reporter Assay. HEK293 cells expressing a pBABE.puro_HA-2× XBP1delta DBD firefly luciferase reporter, obtained from the University of California at San Francisco (UCSF, Walter lab), were cultured in DMEM high glucose media containing L-glutamine, 10% fetal bovine serum, 100 units/mL of penicillin and 100 μg/mL of streptomycin, plus 2 μg/ml puromycin to maintain selective pressure. Upon stimulation of IRE1 and activation of the endogenous RNase activity, a 26 nt intron is removed from XBP1 resulting in a frame shift allowing the transcription of the luciferase.

Cells were seeded without puromycin at 10,000/well in 384 well clear bottom white tissue culture plates (Corning 3707), 25 μL volume. The following morning, test compounds were added and incubated for one hour at 37° C. prior to stimulation of the cells with thapsigargin at 50 μM final concentration for an additional 5 hours. After equilibration to room temperature, 25 μL of One-Glo luciferase detection reagent (Promega cat #E6120) was added, plates sealed and shaken for 5 minutes to lyse cells, then luciferase quantified by luminescence detection using an Envision instrument (PerkinElmer).

XBP1s reporter cell line is referenced in: Mendez A S, Alfaro J, Morales-Soto M A, Dar A C, McCullagh E, Gotthardt K, Li H, Acosta-Alvear D, Sidrauski C, Korennykh A V, Bernales S, Shokat K M, Walter P. 2015. Endoplasmic reticulum stress-independent activation of unfolded protein response kinases by a small molecule ATP-mimic. eLife 2015; 4:e05434

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments 10%, in some embodiments ±5%, in some embodiments ±1%, in some embodiments ±0.5%, and in some embodiments ±0.10% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. A compound having formula (Ic), (Id), (Ie), (Ie1), or (Ig):

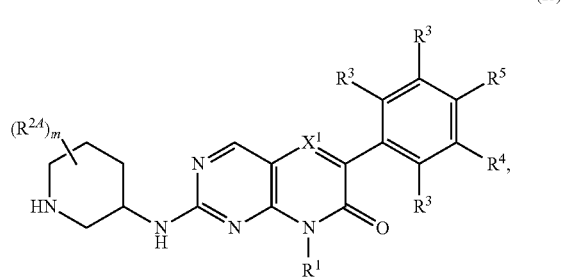

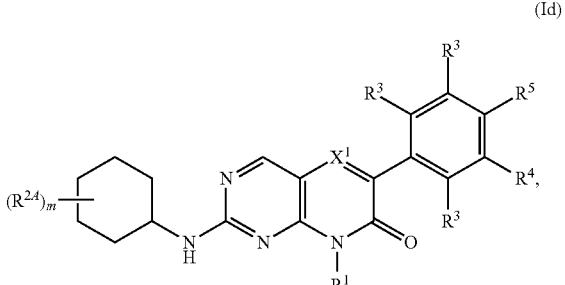

-continued

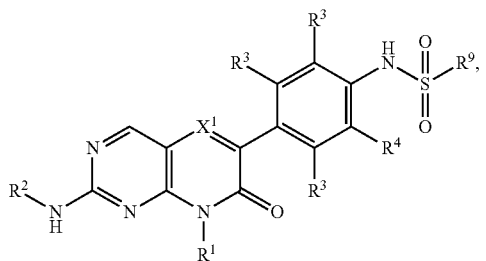
(Ie)

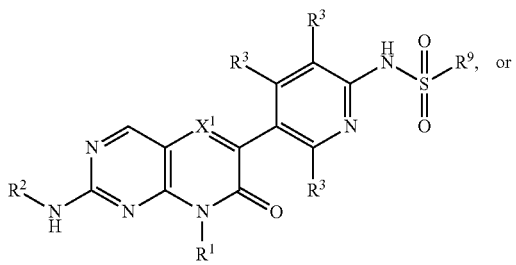
(Ie1)

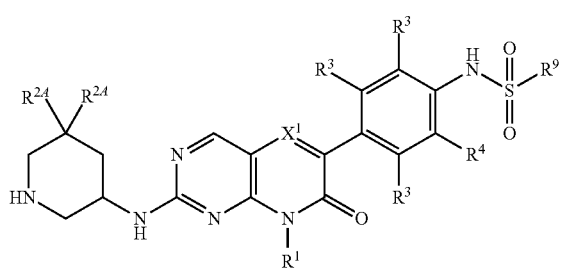
(Ig)

or a stereoisomer, tautomer, or pharmaceutically acceptable salt thereof,
wherein
$X^1$ is —$CR^x$ or —N, wherein $R^x$ is hydrogen, $C_1$-$C_4$ alkyl, cyclopropyl, or halogen;
$R^1$ is $C_1$-$C_4$ alkyl, $C_3$-$C_6$ cycloalkyl, or 3- to 14-membered heterocyclyl, each of which is unsubstituted or substituted with one or more substituents selected from the group consisting of —$CH_2F$, —$CHF_2$, —$CF_3$, halogen, $C_3$-$C_6$ cycloalkyl, hydroxyl, and —O—($C_1$-$C_4$) alkyl;
$R^2$ is $C_1$-$C_4$ alkyl, $C_3$-$C_6$ cycloalkyl, or 4- to 10-membered-heterocyclyl, each of which is unsubstituted or substituted with one or more $R^{2A}$,
$R^{2A}$ is selected from the group consisting of hydrogen, $R^{2C}$-substituted or -unsubstituted $C_1$-$C_4$ alkyl, $C_1$-$C_4$ fluoroalkyl, halogen, —OH, —$(CH_2)_q$—$N(R^{2B})_2$, wherein q is 1 or zero, —$CH_2F$, —$CHF_2$, and —$CF_3$;
or wherein two $R^{2A}$ together with the carbon to which each is attached form a substituted or unsubstituted aziridinyl, azetidinyl, pyrrolidinyl, imidazolyl, piperidinyl, piperazinyl, morpholino;
$R^{2B}$, in each instance, is hydrogen, $R^{2C}$-substituted or -unsubstituted $C_1$-$C_3$ alkyl, unsubstituted $C_3$-$C_6$ cycloalkyl; or unsubstituted $C_3$-$C_6$ heterocyclyl;
or wherein two $R^{2B}$ together form a substituted or unsubstituted heterocyclyl, wherein the heterocyclyl can be spiro, an unsubstituted aziridinyl, azetidinyl, pyrrolidinyl, imidazolyl, piperidinyl, piperazinyl, morpholino;

$R^{2C}$ is halogen, —OH, —$OCH_3$, or $C_3$-$C_5$ heterocyclyl;
each $R^3$ is independently hydrogen, halogen, —CN, $C_1$-$C_6$ alkyl, $C_1$-$C_6$ haloalkyl, $C_3$-$C_6$ cycloalkyl, $O(C_{1-6}$ alkyl), or —$O(C_1$-$C_6$ haloalkyl);
$R^4$ is hydrogen, halogen, —CN, —$NO_2$, $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, —$OR^6$, —$NR^{8A}R^9$, —$NRC(O)R^9$, —$NR^8C(O)OR^6$, —$NR^8C(O)NR^{8A}R^{8B}$, —$NR^8SO_2R^9$, —$NR^8SO_2NR^{8A}R^{8B}$, —$NR^8S(O)(=NR^{8C})$ $R^9$, —$C(O)N(R^8)$ $SO_2R^9$, —$C(O)NR^8R^9$, —$C(O)R^7$, —$C(O)OR^6$, —$SO_2R^9$, —$NR^8S(O)(=NR^{8C})$ $R^9$, or —$SO_2NR^8R^9$; wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$;
wherein $R^5$ is —$NR^{8A}R^9$, —$C(O)NR^8R^9$, —$SO_2NR^8R^9$, —$NR^8SO_2R^9$, —$NR^8C(O)$—$C_1$-$C_6$ alkyl, —$NR^8C(O)$—$C_2$-$C_6$ alkenyl, —$NR^8C(O)$—$C_3$-$C_8$ cycloalkyl, —$NR^8C(O)$-5- to 14-membered heteroaryl, or —$NR^8C(O)$-3- to 12-membered heterocyclyl, wherein said alkyl, alkenyl, cycloalkyl, heteroaryl, or heterocyclyl in —$NR^8C(O)$—$C_1$-$C_6$ alkyl, —$NR^8C(O)$—$C_2$-$C_6$ alkenyl, —$NR^8C(O)$—$C_3$-$C_8$ cycloalkyl, —$NR^8C(O)$-5- to 14-membered heteroaryl, or —$NR^8C(O)$-3- to 12-membered heterocyclyl is unsubstituted or substituted with one or more $R^{10}$;
each $R^6$ and $R^7$ is independently hydrogen, $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$;
each $R^8$, $R^{8A}$, and $R^{8C}$ are independently hydrogen or $C_1$-$C_6$ alkyl;
each $R^{8B}$ is independently hydrogen, $C_1$-$C_6$ alkyl, $C_2$-$C_6$ alkenyl, $C_3$-$C_8$ cycloalkyl, $C_6$-$C_{10}$ aryl, or 3- to 12-membered heterocyclyl, each of which is unsubstituted or substituted with one or more $R^{10}$;
each $R^9$ is independently $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$,
or $R^8$ and $R^9$ together with the atom to which each is attached form a substituted or unsubstituted 5- or 6-member lactam ring;
each $R^{10}$ is independently oxo, $C_1$-$C_6$ alkyl, $C_2$-$C_6$ alkenyl, $C_3$-$C_8$ cycloalkyl, $C_0$-$C_{10}$ aryl, 4- to 10-membered heteroaryl, 3- to 12-membered heterocyclyl, halogen, cyano, —C(O)H, —$C(O)CH_3$, —C(O)OH, —$C(O)OCH_3$, —$C(O)NH_2$, —OH, —O—$CF_3$, —$CF_3$, —$CH_2F$, $CHF_2$, —$OCH_3$, —OC(O)H, —$OC(O)CH_3$, —$OC(O)NH_2$, —SH, —S(O) H, —$S(O)_2H$, —S(O)(=NH) H, —$S(O)_2NH_2$, —$NH_2$, —NHC(O)H, —NHC(O)OH, —N(H)C(O) $NH_2$, —$NHS(O)_2H$, —$NHS(O)_2NH_2$, or -P(O) $(CH_3)_2$, wherein each $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 10-membered heteroaryl, 3- to 12-membered heterocyclyl is unsubstituted or substituted with one or more $R^{11}$;
or two $R^{10}$ together with the carbon to which each is attached forms a $C_3$-$C_8$ cycloalkyl;

each $R^{11}$ is independently $C_{1-6}$ alkyl, $C_3$-$C_6$ cycloalkyl, 4- to 6-membered-heteroaryl, phenyl, halogen, cyano, —$SO_2CH_3$, —$O(C_{1-3}$ alkyl), —$CH_2F$, —$CHF_2$, or -$(CH_2)_f$-$CF_3$, wherein f is zero or 1; and wherein m is 1, 2, 3, or 4.

2. A compound having a formula:

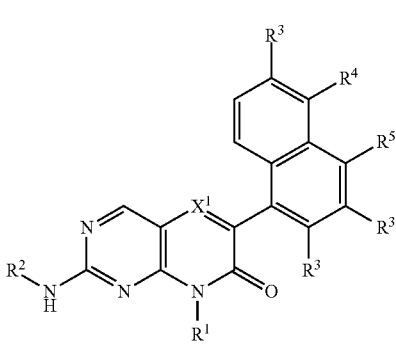

(Ib)

or a stereoisomer, tautomer, or pharmaceutically acceptable salt thereof, wherein:
$X^1$ is —$CR^x$ or —N, wherein $R^x$ is hydrogen, $C_1$-$C_4$ alkyl, cyclopropyl, or halogen;
$R^1$ is $C_1$-$C_4$ alkyl, $C_3$-$C_6$ cycloalkyl, or 3- to 14-membered heterocyclyl, each of which is unsubstituted or substituted with one or more substituents selected from the group consisting of —$CH_2F$, —$CHF_2$, —$CF_3$, halogen, $C_3$-$C_6$ cycloalkyl, and hydroxyl;
$R^2$ is $C_1$-$C_4$ alkyl, $C_3$-$C_6$ cycloalkyl, or 4- to 6-membered-heterocyclyl, each of which is unsubstituted or substituted with one or more $R^{2A}$,
$R^{2A}$ is selected from the group consisting of hydrogen, $C_1$-$C_4$ alkyl, $C_1$-$C_4$ fluoroalkyl, halogen, —OH, —$N(R^{2B})_2$—$CH_2F$, —$CHF_2$, and —$CF_3$;
$R^{2B}$ is hydrogen or $C_{1-3}$ alkyl;
each $R^3$ is independently hydrogen, halogen, —CN, $C_1$-$C_6$ alkyl, $C_1$-$C_6$ haloalkyl, $C_3$-$C_6$ cycloalkyl, $O(C_{1-6}$ alkyl), or —$O(C_1$-$C_6$ haloalkyl);
each $R^4$ and $R^5$ are independently hydrogen, halogen, —CN, —$NO_2$, $C_1$-$C_6$ alkyl, $C_2$-$C_6$ alkenyl, $C_2$-$C_6$ alkynyl, $C_3$-$C_{12}$ cycloalkyl, $C_6$-$C_{20}$ aryl, 3- to 14-membered heterocyclyl, 5- to 14-membered heteroaryl, —$OR^6$, —$NR^{8A}R^9$, —$NR^8C(O)R^9$, —$NR^8C(O)OR^6$, —$NR^8C(O)NR^{8A}R^{8B}$, —$NR^8SO_2R^9$, —$NR^8SO_2NR^{8A}R 8B$, —$NR^8S(O)(=NR^8C)R^9$, —$C(O)N(R^8) SO_2R^9$, —$C(O)NR^8R^9$, —$C(O)R^7$, —$C(O)OR^6$, —$SO_2R^9$, —$NR^8S(O)(—NR^8C)R^9$, or —$SO_2NR^8R^9$; wherein the $C_1$-$C_6$ alkyl, $C_3$-$C_{12}$ cycloalkyl, $C_6$-$C_{20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$;
wherein at least one of $R^4$ and $R^5$ is —$NR^{8A}R^9$, —$NR^8C(O)R^9$, —$NR^8SO_2R^9$—, —$C(O)NR^8R^9$, or —$SO_2NR^8R^9$;
each $R^6$ and $R^7$ is independently hydrogen, $C_1$-$C_6$ alkyl, $C_2$-$C_6$ alkenyl, $C_3$-$C_8$ cycloalkyl, $C_6$-$C_{10}$ aryl, 5- to 14-membered heteroaryl, or 3- to 12-membered heterocyclyl, each of which is unsubstituted or substituted with one or more $R^{10}$;
each $R^8$, $R^{8A}$, and $R^{8C}$ are independently hydrogen or $C_1$-$C_6$ alkyl;

each $R^{8B}$ is independently hydrogen, $C_1$-$C_6$ alkyl, $C_2$-$C_6$ alkenyl, $C_3$-$C_8$ cycloalkyl, $C_6$-$C_{10}$ aryl, or 3- to 12-membered heterocyclyl, each of which is unsubstituted or substituted with one or more $R^{10}$;
each $R^9$ is independently $C_1$-$C_6$ alkyl, $C_2$-$C_6$ alkenyl, $C_3$-$C_8$ cycloalkyl, $C_6$-$C_{10}$ aryl, 5- to 14-membered heteroaryl and 3- to 12-membered heterocyclyl, each of which is unsubstituted or substituted with one or more $R^{10}$;
each $R^{10}$ is independently oxo, $C_1$-$C_6$ alkyl, $C_2$-$C_6$ alkenyl, $C_3$-$C_8$ cycloalkyl, $C_6$-$C_{10}$ aryl, 4- to 10-membered heteroaryl, 3- to 12-membered heterocyclyl, halogen, cyano, —$C(O)H$, —$C(O)CH_3$, —$C(O)OH$, —$C(O)OCH_3$, —$C(O)NH_2$, —OH, —$OCH_3$, —$OC(O)H$, —$OC(O)CH_3$, —$OC(O)NH_2$, —SH, —$S(O)H$, —$S(O)_2H$, —$S(O)(=NH)H$, —$S(O)_2NH_2$, —$NH_2$, —$NHC(O)H$, —$NHC(O)OH$, —$N(H)C(O)NH_2$, —$NHS(O)_2H$, —$NHS(O)_2NH_2$, or -$P(O)(CH_3)_2$, wherein each $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 10-membered heteroaryl, 3- to 12-membered heterocyclyl is unsubstituted or substituted with one or more $R^{11}$; and
each $R^{11}$ is independently $C_{1-6}$ alkyl, $C_3$-$C_6$ cycloalkyl, 4- to 6-membered-heteroaryl, phenyl, halogen, cyano, —$O(C_{1-3}$ alkyl), —$CH_2F$, —$CHF_2$, or -$CF_3$.

3. The compound of claim 1 or a stereoisomer, tautomer, or pharmaceutically acceptable salt thereof, wherein $R^1$ is $C_1$-$C_4$ alkyl, $C_3$-$C_6$ cycloalkyl, or $C_3$-$C_6$ heterocyclyl, each of which is unsubstituted or substituted with one or more substituents selected from the group consisting of halogen, $C_3$-$C_6$ cycloalkyl, and hydroxyl.

4. The compound of claim 1 or a stereoisomer, tautomer, or pharmaceutically acceptable salt thereof, wherein $R^1$ is selected from the group consisting of methyl, ethyl, isopropyl, cyclopropyl, cyclobutyl, cyclopentyl, —$CH_2CHF_2$, —$CHCH_3CHF_2$, —$CH_2CF_3$, —$CHCH_3CF_3$, —$CH_2CHOHCH_2CH_3$, —$CH_2$-cyclopropyl, oxetanyl, and tetrahydrofuranyl.

5. The compound of claim 1 or a stereoisomer, tautomer, or pharmaceutically acceptable salt thereof, wherein $R^2$ is selected from the group consisting of isopropyl, cyclohexyl, or piperidinyl, each of which is unsubstituted or substituted with one or more methyl, fluoro, hydroxyl, —$NH_2$, —$NHCH_3$, and —$N(CH_3)_2$.

6. The compound of claim 1 or a stereoisomer, tautomer, or pharmaceutically acceptable salt thereof, wherein the compound has formula (Ic):

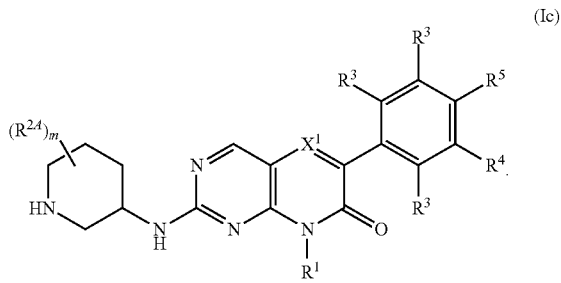

(Ic)

7. The compound of claim 6 or a stereoisomer, tautomer, or pharmaceutically acceptable salt thereof, wherein $R^{2A}$ is —F and m is 1; wherein $R^{2A}$ is —$CH_2F$ and m is 1; wherein $R^{2A}$ is —F and —$CH_3$ and m is 2; or, wherein $R^{2A}$ is —$CH_2F$ and —$CH_3$ and m is 2.

8. The compound of claim 1 or a stereoisomer, tautomer, or pharmaceutically acceptable salt thereof, wherein the compound has formula (Id):

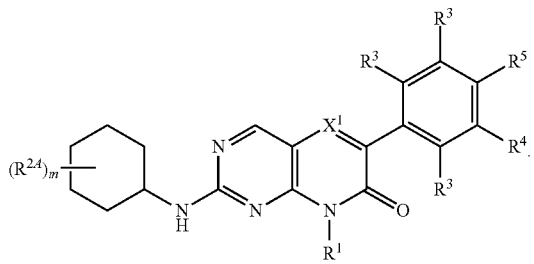

(Id)

9. The compound of claim 8, or a stereoisomer, tautomer, or pharmaceutically acceptable salt thereof, wherein $R^{24}$ is —N(CH$_3$)$_2$ and m is 1; or, wherein $R^{24}$ is —N(CH$_3$)$_2$ and —F and m is 2.

10. The compound of claim 1, or a stereoisomer, tautomer, or pharmaceutically acceptable salt thereof, wherein at least one $R^3$ is halogen.

11. The compound of claim 1 or a stereoisomer, tautomer, or pharmaceutically acceptable salt thereof, wherein each $R^3$ and $R^4$ are independently hydrogen or fluoro, and $R^5$ is —NR$^{8A}$R$^9$, —NR$^8$SO$_2$R$^9$, —NR$^8$C(O)—C$_1$-C$_6$ alkyl, —NR$^8$C(O)—C$_2$-C$_6$ alkenyl, —NR$^8$C(O)—C$_3$-C$_8$ cycloalkyl, —NR$^8$C(O)-5- to 14-membered heteroaryl, or —NR$^8$C(O)-3- to 12-membered heterocyclyl, wherein said alkyl, alkenyl, cycloalkyl, heteroaryl, or heterocyclyl in —NR$^8$C(O)—C$_1$-C$_6$ alkyl, —NR$^8$C(O)—C$_2$-C$_6$ alkenyl, —NR$^8$C(O)—C$_3$-C$_8$ cycloalkyl, —NR$^8$C(O)-5- to 14-membered heteroaryl, or —NR$^8$C(O)-3- to 12-membered heterocyclyl is unsubstituted or substituted with one or more $R^{10}$.

12. The compound of claim 2 or a stereoisomer, tautomer, or pharmaceutically acceptable salt thereof, wherein each $R^3$ is independently hydrogen or fluoro, and $R^4$ is —NR$^{8A}$R$^9$, —NR$^8$C(O)R$^9$, or —NR$^8$SO$_2$R$^9$.

13. The compound of claim 2 or a stereoisomer, tautomer, or pharmaceutically acceptable salt thereof, wherein $R^5$ is hydrogen or fluoro.

14. The compound of claim 1 or a stereoisomer, tautomer, or pharmaceutically acceptable salt thereof, wherein the compound has formula (Ie), (Ie1), or (Ig):

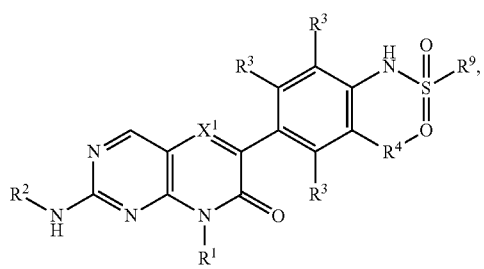

(Ie)

-continued

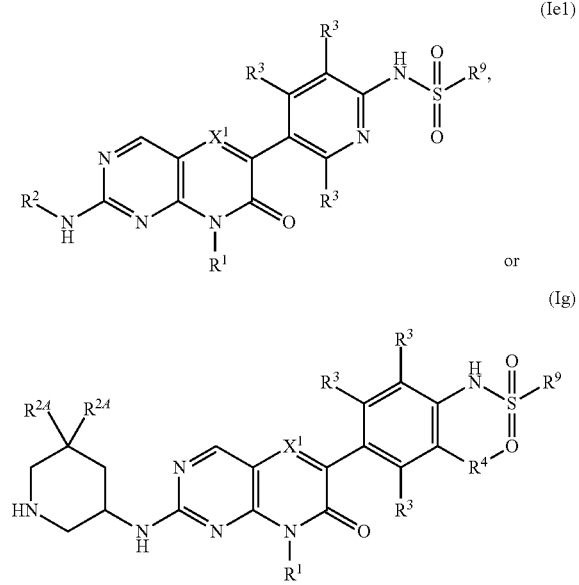

(Ie1)

or (Ig)

wherein:

each $R^{24}$ is independently hydrogen, methyl, fluoro, or —CH$_2$F.

15. The compound of claim 1 or a stereoisomer, tautomer, or pharmaceutically acceptable salt thereof, wherein the compound has the formula (Ii), (Ij), (In), or (Io):

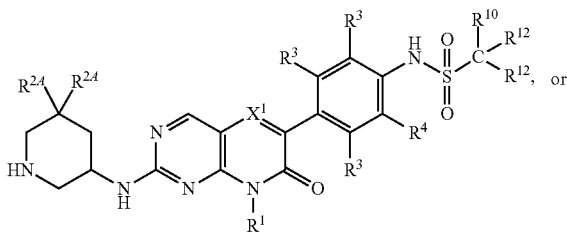

(Ii)

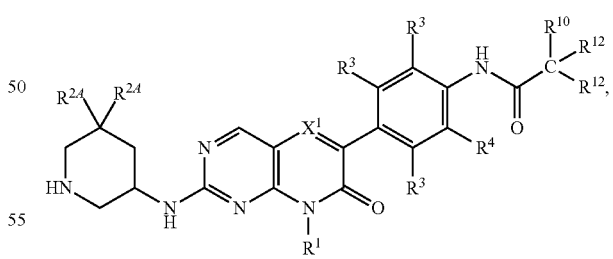

(Ij)

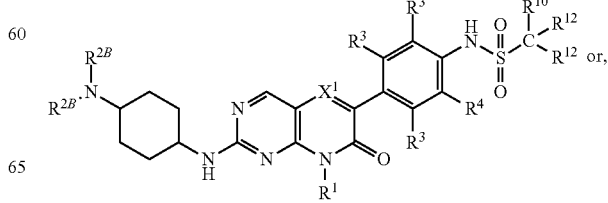

(In)

-continued

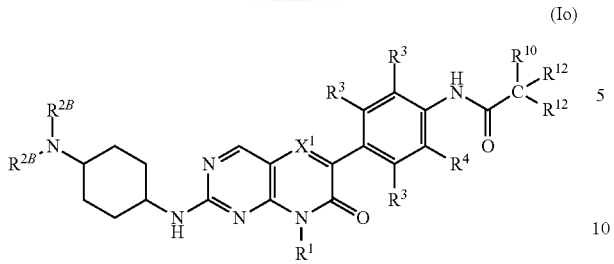

(Io)

wherein:
each $R^{2A}$ is independently hydrogen, methyl, fluoro, or —CH$_2$F;
$R^{10}$ is substituted phenyl or substituted C$_{1-3}$ alkyl; and
$R^{12}$ is hydrogen, halogen, or C$_{1-3}$ alkyl or wherein both $R^{12}$ together form a cyclopropanyl, which may be unsubstituted or substituted with methyl or fluoro.

16. The compound of claim 1 or a stereoisomer, tautomer, or pharmaceutically acceptable salt thereof, wherein the compound has formula (Ik):

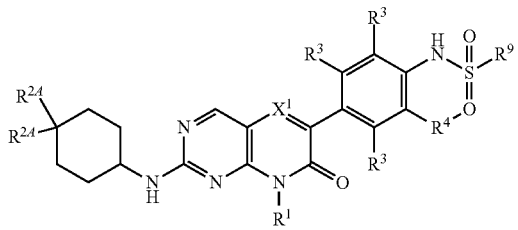

(Ik)

wherein:
each $R^{2A}$ is independently hydrogen, hydroxyl, or —N(CH$_3$)$_2$.

17. The compound of claim 15 or a stereoisomer, tautomer, or pharmaceutically acceptable salt thereof, wherein each $R^{2B}$ is CH$_3$.

18. A compound or stereoisomer, tautomer, or pharmaceutically acceptable salt thereof, selected from the group consisting of:

| Compound No. | Structure |
|---|---|
| 1 | 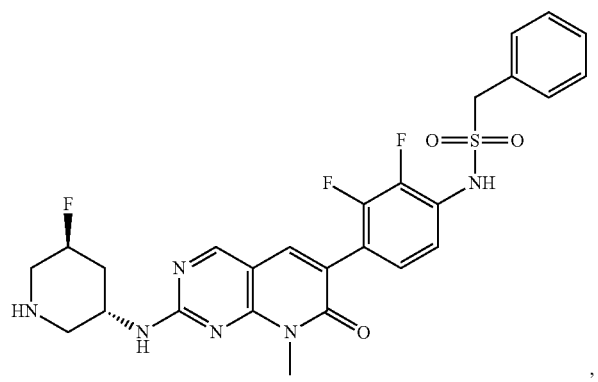 |
| 2 | 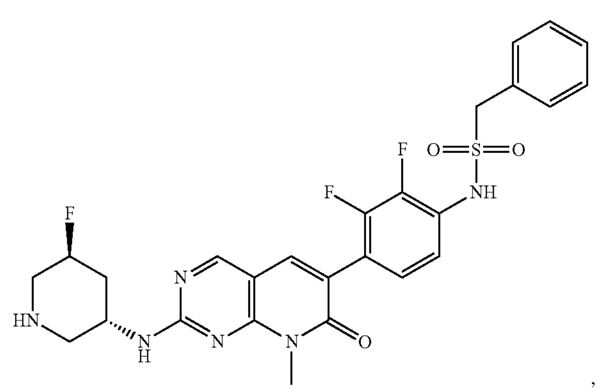 [SMILES: Cn1c(=O)c(-c2ccc(NS(=O)(=O)Cc3ccccc3)c(F)c2F)cc2cnc(N[C@@H]3CNC[C@@H](F)C3)nc21] |

,

,

| Compound No. | Structure |
|---|---|
| 3 | 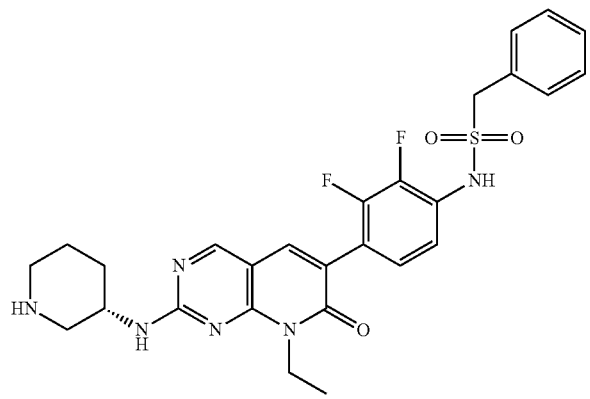 |
| 4 | 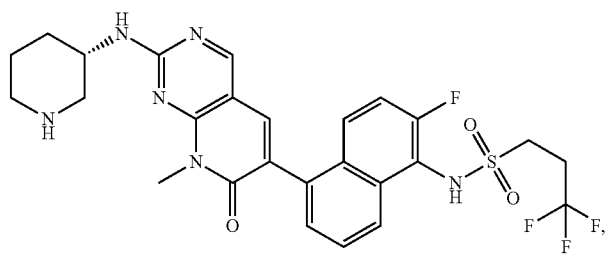 [SMILES: Cn1c(=O)c(-c2cccc3c(NS(=O)(=O)CCC(F)(F)F)c(F)ccc23)cc2cnc(N[C@H]3CCCNC3)nc21] |
| 5 | 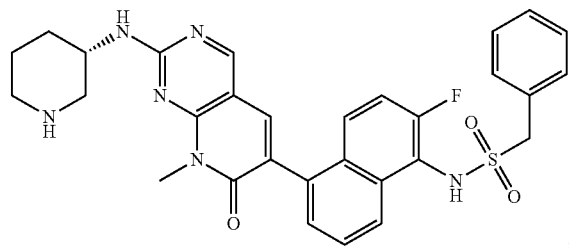 [SMILES: Cn1c(=O)c(-c2cccc3c(NS(=O)(=O)Cc4ccccc4)c(F)ccc23)cc2cnc(N[C@H]3CCCNC3)nc21] |
| 6 | 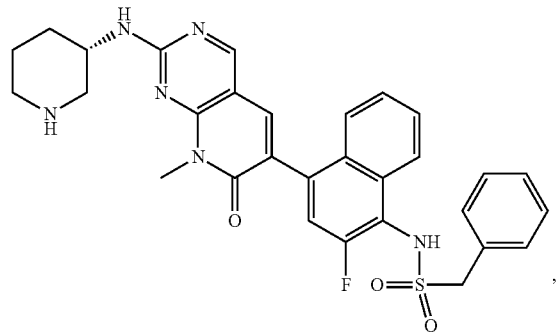 [SMILES: Cn1c(=O)c(-c2cc(F)c(NS(=O)(=O)Cc3ccccc3)c3ccccc23)cc2cnc(N[C@H]3CCCNC3)nc21] |

| Compound No. | Structure |
|---|---|
| 7 | 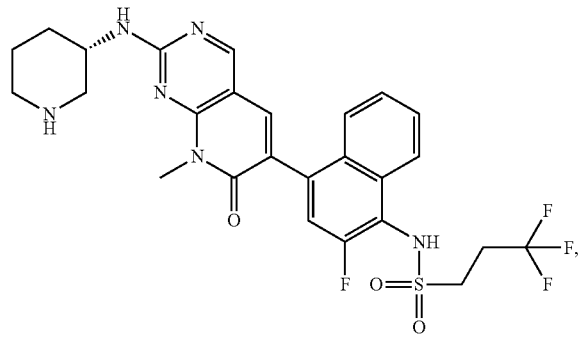 [SMILES: Cn1c(=O)c(-c2cc(F)c(NS(=O)(=O)CCC(F)(F)F)c3ccccc23)cc2cnc(N[C@H]3CCCNC3)nc21] |
| 8 | 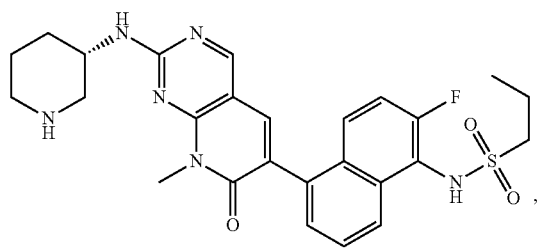 [SMILES: CCCS(=O)(=O)Nc1c(F)ccc2c(-c3cc4cnc(N[C@H]5CCCNC5)nc4n(C)c3=O)cccc12] |
| 9 | 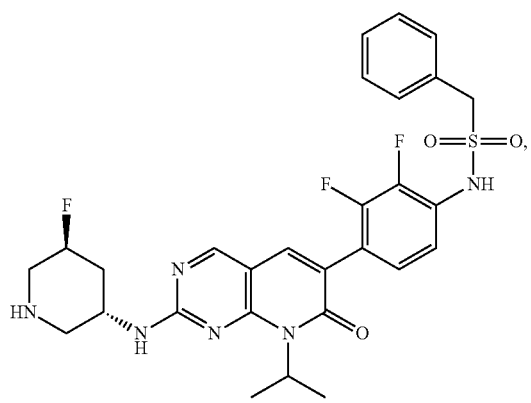 [SMILES: CC(C)n1c(=O)c(-c2ccc(NS(=O)(=O)Cc3ccccc3)c(F)c2F)cc2cnc(N[C@@H]3CNC[C@@H](F)C3)nc21] |
| 10 | 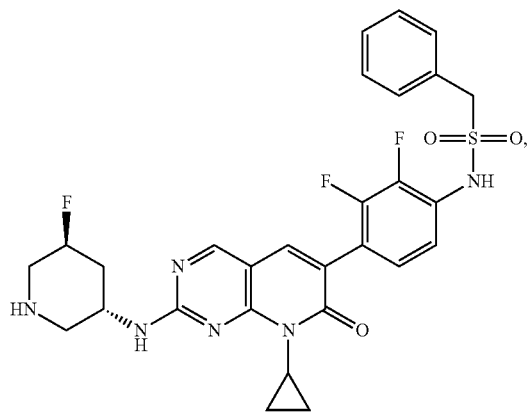 [SMILES: O=c1c(-c2ccc(NS(=O)(=O)Cc3ccccc3)c(F)c2F)cc2cnc(N[C@@H]3CNC[C@@H](F)C3)nc2n1C1CC1] |

| Compound No. | Structure |
|---|---|
| 11 | 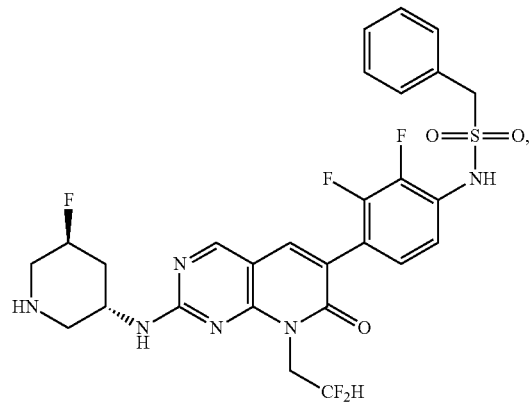 [SMILES: O=c1c(-c2ccc(NS(=O)(=O)Cc3ccccc3)c(F)c2F)cc2cnc(N[C@@H]3CNC[C@@H](F)C3)nc2n1CC(F)F] |
| 12 | 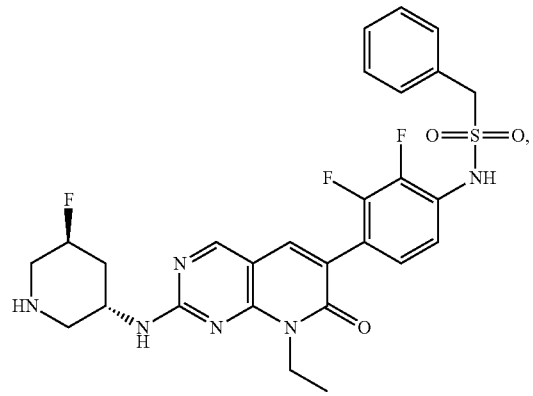 [SMILES: CCn1c(=O)c(-c2ccc(NS(=O)(=O)Cc3ccccc3)c(F)c2F)cc2cnc(N[C@@H]3CNC[C@@H](F)C3)nc21] |
| 13 | 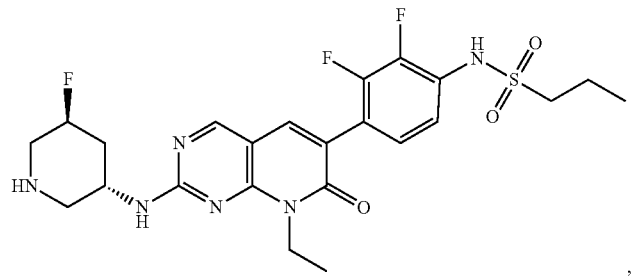 [SMILES: CCCS(=O)(=O)Nc1ccc(-c2cc3cnc(N[C@@H]4CNC[C@@H](F)C4)nc3n(CC)c2=O)c(F)c1F] |
| 14 | 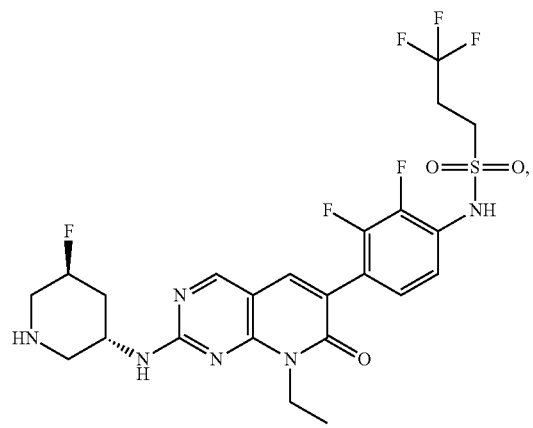 [SMILES: CCn1c(=O)c(-c2ccc(NS(=O)(=O)CCC(F)(F)F)c(F)c2F)cc2cnc(N[C@@H]3CNC[C@@H](F)C3)nc21] |

-continued
| Compound No. | Structure |
|---|---|
| 15 | 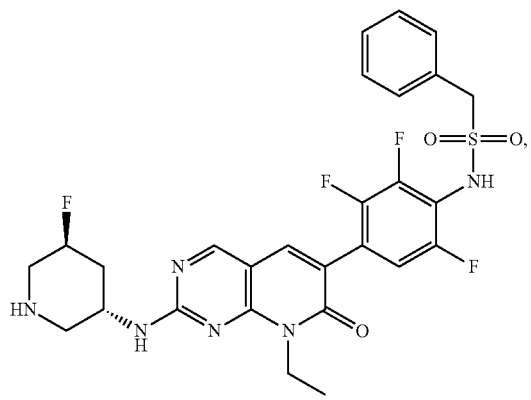 [SMILES: CCn1c(=O)c(-c2cc(F)c(NS(=O)(=O)Cc3ccccc3)c(F)c2F)cc2cnc(N[C@@H]3CNC[C@@H](F)C3)nc21] |
| 16 | 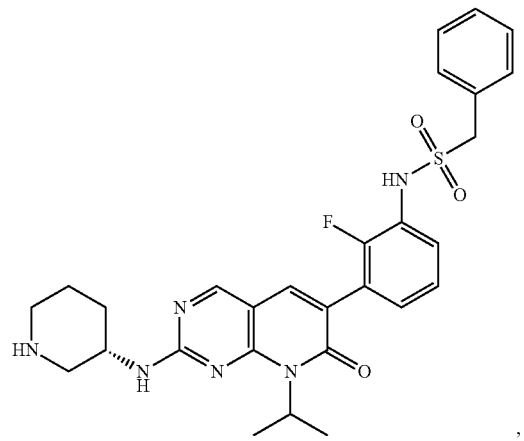 [SMILES: CC(C)n1c(=O)c(-c2cccc(NS(=O)(=O)Cc3ccccc3)c2F)cc2cnc(N[C@H]3CCCNC3)nc21] |
| 17 | 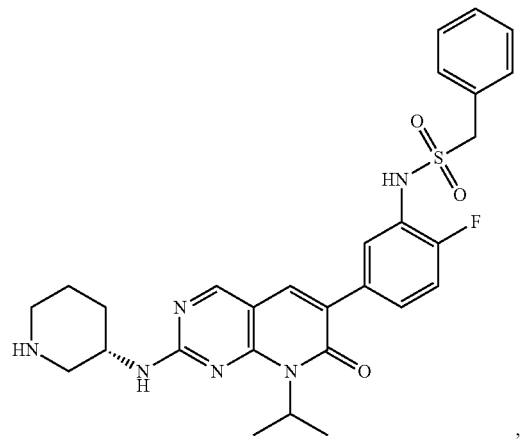 [SMILES: CC(C)n1c(=O)c(-c2ccc(F)c(NS(=O)(=O)Cc3ccccc3)c2)cc2cnc(N[C@H]3CCCNC3)nc21] |

| Compound No. | Structure |
|---|---|
| 18 | 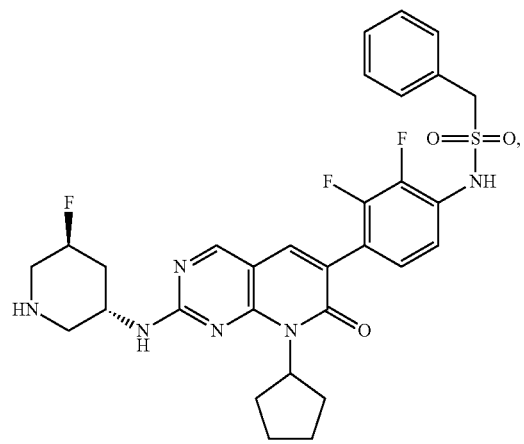 [SMILES: O=c1c(-c2ccc(NS(=O)(=O)Cc3ccccc3)c(F)c2F)cc2cnc(N[C@@H]3CNC[C@@H](F)C3)nc2n1C1CCCC1] |
| 19 | 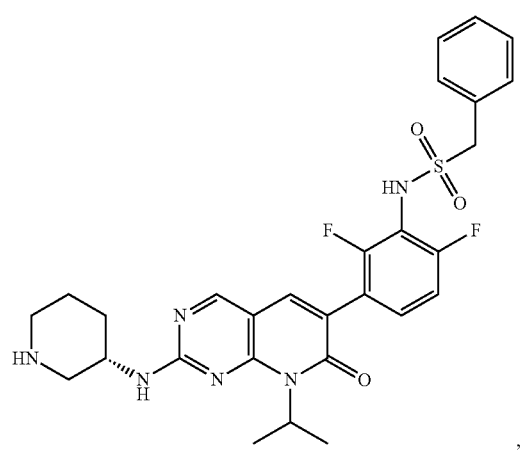 [SMILES: CC(C)n1c(=O)c(-c2ccc(F)c(NS(=O)(=O)Cc3ccccc3)c2F)cc2cnc(N[C@H]3CCCNC3)nc21] |
| 20 | 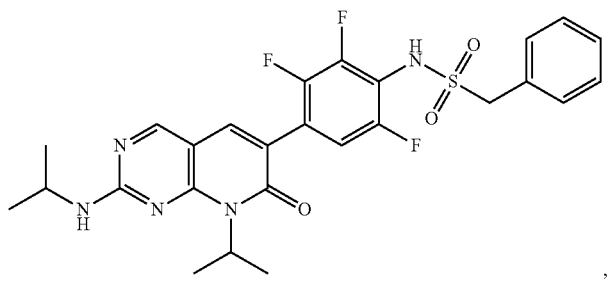 [SMILES: CC(C)Nc1ncc2cc(-c3cc(F)c(NS(=O)(=O)Cc4ccccc4)c(F)c3F)c(=O)n(C(C)C)c2n1] |
| 21 | 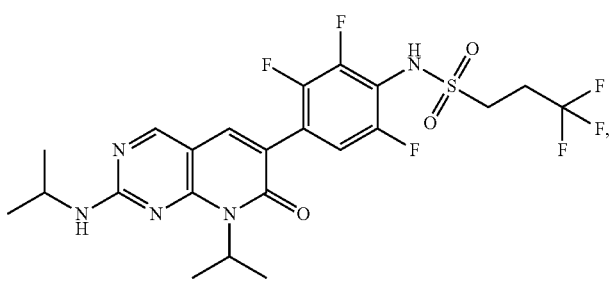 [SMILES: CC(C)Nc1ncc2cc(-c3cc(F)c(NS(=O)(=O)CCC(F)(F)F)c(F)c3F)c(=O)n(C(C)C)c2n1] |

| Compound No. | Structure |
|---|---|
| 22 | 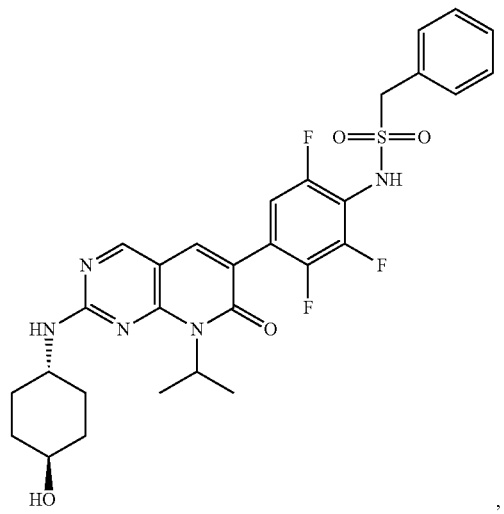 [SMILES: CC(C)n1c(=O)c(-c2cc(F)c(NS(=O)(=O)Cc3ccccc3)c(F)c2F)cc2cnc(N[C@H]3CC[C@H](O)CC3)nc21] |
| 23 | 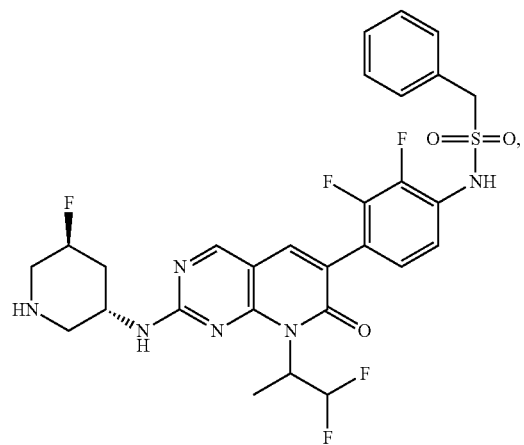 [SMILES: CC(C(F)F)n1c(=O)c(-c2ccc(NS(=O)(=O)Cc3ccccc3)c(F)c2F)cc2cnc(N[C@@H]3CNC[C@@H](F)C3)nc21] |
| 24 | 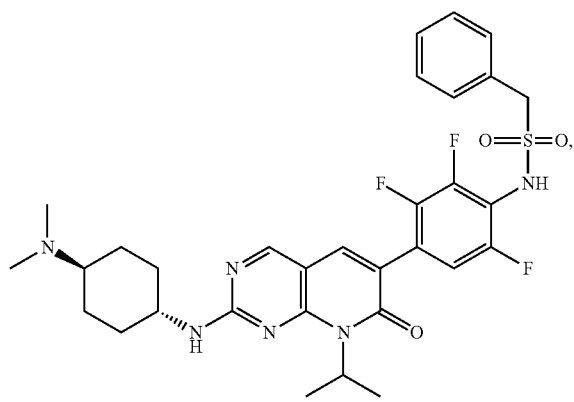 [SMILES: CC(C)n1c(=O)c(-c2cc(F)c(NS(=O)(=O)Cc3ccccc3)c(F)c2F)cc2cnc(N[C@H]3CC[C@H](N(C)C)CC3)nc21] |

| Compound No. | Structure |
|---|---|
| 25 | 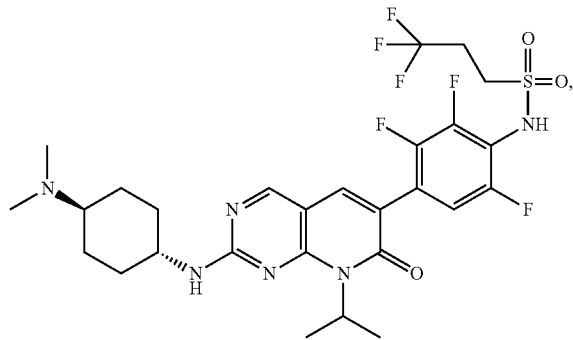 [SMILES: CC(C)n1c(=O)c(-c2cc(F)c(NS(=O)(=O)CCC(F)(F)F)c(F)c2F)cc2cnc(N[C@H]3CC[C@H](N(C)C)CC3)nc21] |
| 26 | 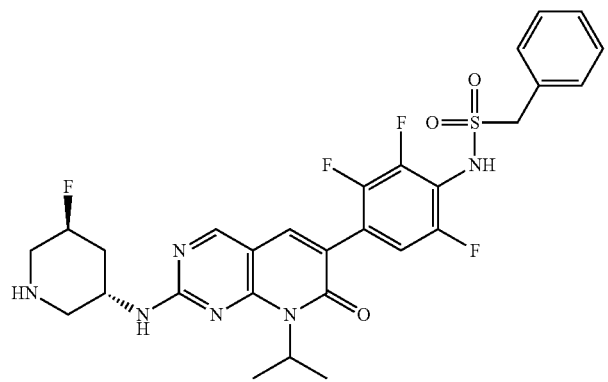 |
| 27 | 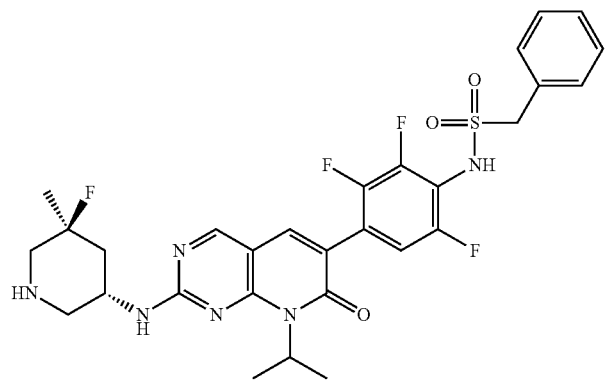 [SMILES: CC(C)n1c(=O)c(-c2cc(F)c(NS(=O)(=O)Cc3ccccc3)c(F)c2F)cc2cnc(N[C@@H]3CNC[C@@](C)(F)C3)nc21] |
| 28 | 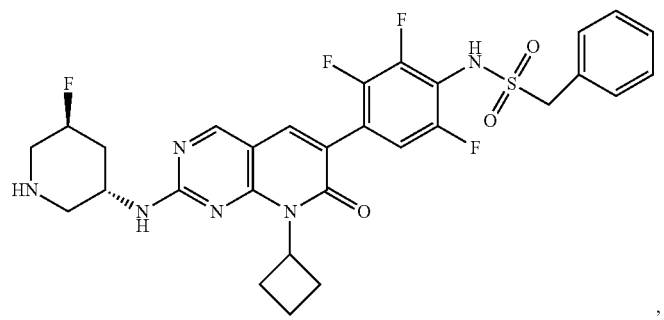 [SMILES: O=c1c(-c2cc(F)c(NS(=O)(=O)Cc3ccccc3)c(F)c2F)cc2cnc(N[C@@H]3CNC[C@@H](F)C3)nc2n1C1CCC1] |

-continued
| Compound No. | Structure |
|---|---|
| 29 | 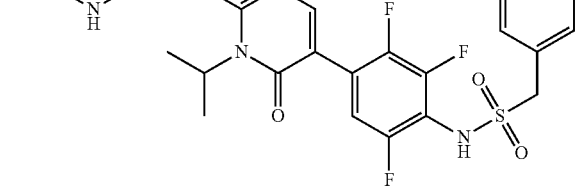 , |
| 30 | 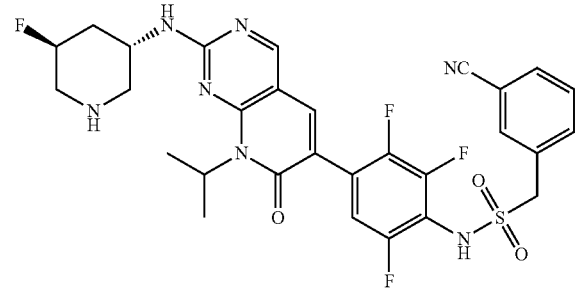 , |
| 31 | 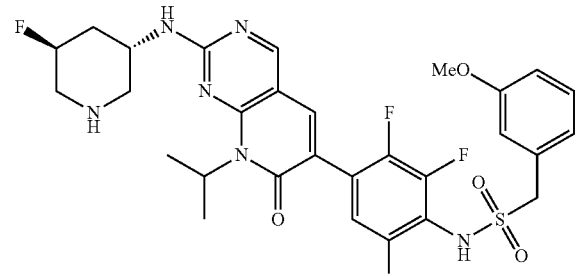 , |
| 32 | 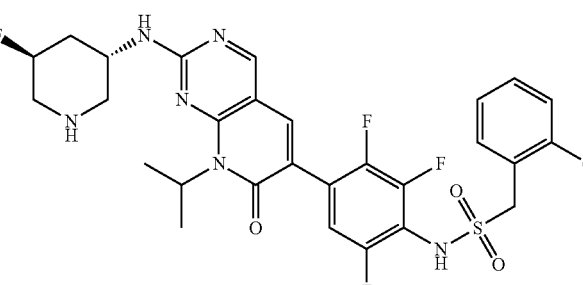 , |
| 33 | 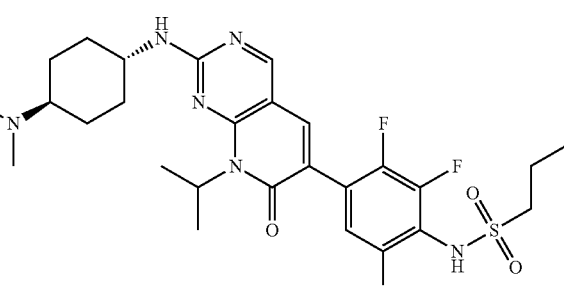 , |

| Compound No. | Structure |
|---|---|
| 34 | 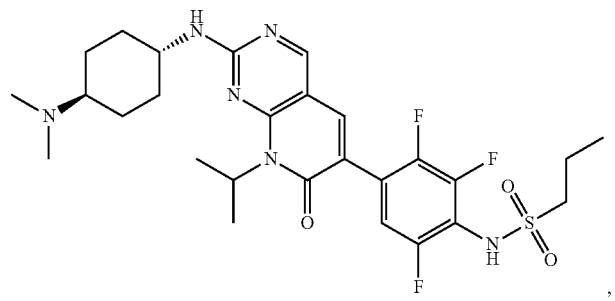 [SMILES: CCCS(=O)(=O)Nc1c(F)cc(-c2cc3cnc(N[C@H]4CC[C@H](N(C)C)CC4)nc3n(C(C)C)c2=O)c(F)c1F] |
| 35 | 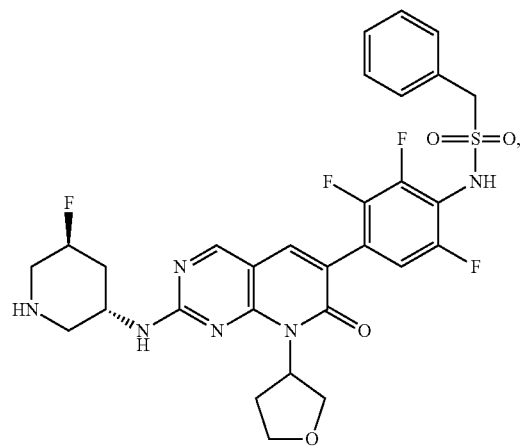 [SMILES: O=c1c(-c2cc(F)c(NS(=O)(=O)Cc3ccccc3)c(F)c2F)cc2cnc(N[C@@H]3CNC[C@@H](F)C3)nc2n1C1CCOC1] |
| 36 | 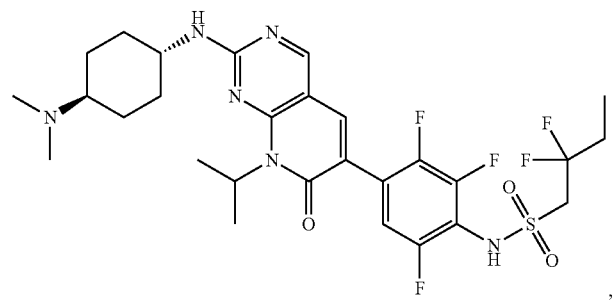 [SMILES: CCC(F)(F)CS(=O)(=O)Nc1c(F)cc(-c2cc3cnc(N[C@H]4CC[C@H](N(C)C)CC4)nc3n(C(C)C)c2=O)c(F)c1F] |
| 37 | 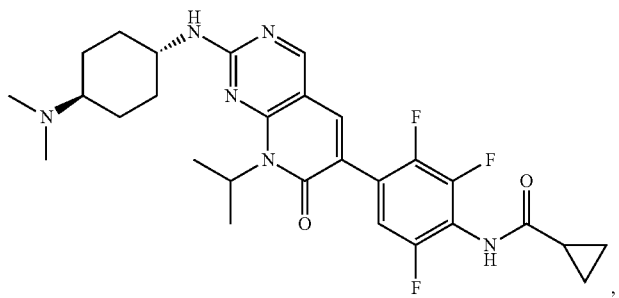 [SMILES: CC(C)n1c(=O)c(-c2cc(F)c(NC(=O)C3CC3)c(F)c2F)cc2cnc(N[C@H]3CC[C@H](N(C)C)CC3)nc21] |

-continued
| Compound No. | Structure |
|---|---|
| 38 | 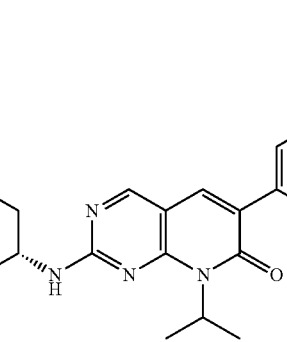 |
| 39 | 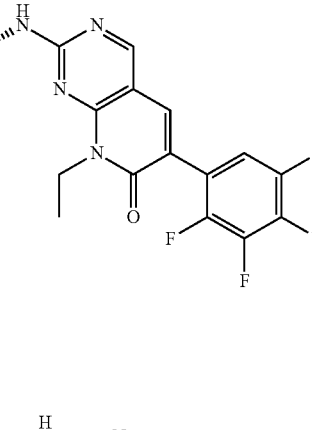 |
| 40 | 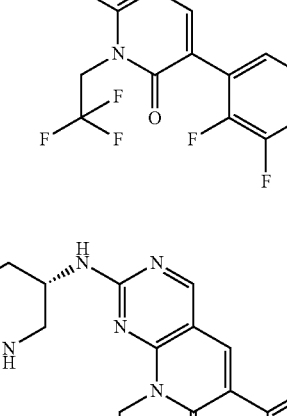 |
| 41 | 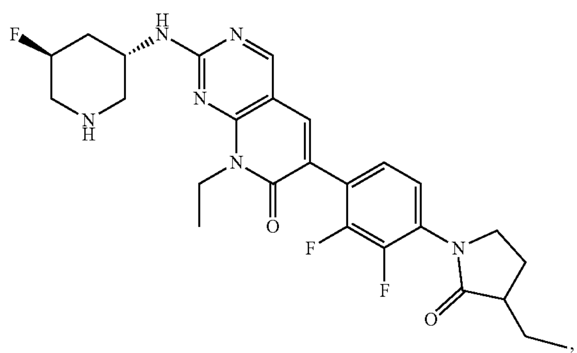 [SMILES: CCC1CCN(c2ccc(-c3cc4cnc(N[C@@H]5CNC[C@@H](F)C5)nc4n(CC)c3=O)c(F)c2F)C1=O] |

| Compound No. | Structure |
|---|---|
| 42 | 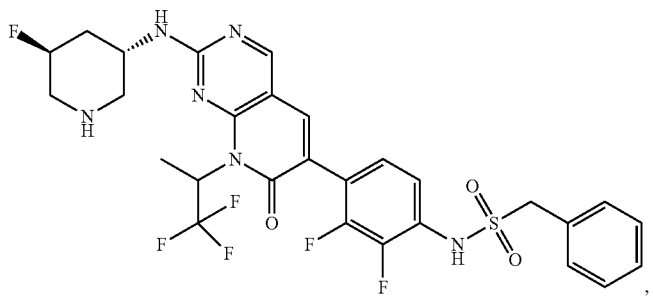 [SMILES: CC(n1c(=O)c(-c2ccc(NS(=O)(=O)Cc3ccccc3)c(F)c2F)cc2cnc(N[C@@H]3CNC[C@@H](F)C3)nc21)C(F)(F)F] |
| 43 | 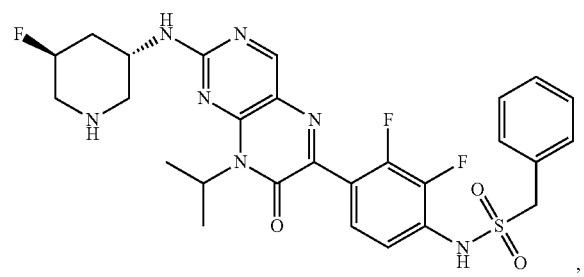 [SMILES: CC(C)n1c(=O)c(-c2ccc(NS(=O)(=O)Cc3ccccc3)c(F)c2F)nc2cnc(N[C@@H]3CNC[C@@H](F)C3)nc21] |
| 44 | 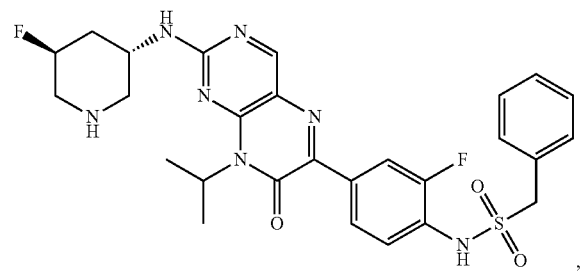 [SMILES: CC(C)n1c(=O)c(-c2ccc(NS(=O)(=O)Cc3ccccc3)c(F)c2)nc2cnc(N[C@@H]3CNC[C@@H](F)C3)nc21] |
| 45 | 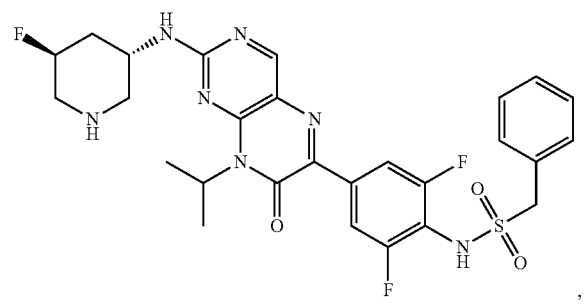 |
| 46 | 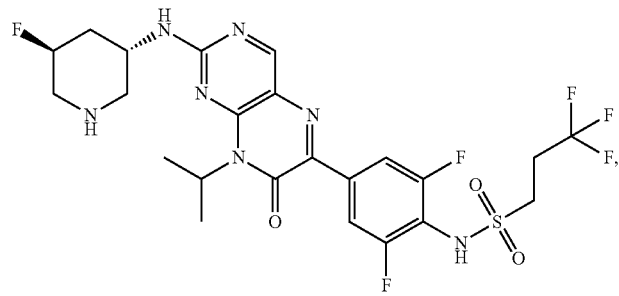 [SMILES: CC(C)n1c(=O)c(-c2cc(F)c(NS(=O)(=O)CCC(F)(F)F)c(F)c2)nc2cnc(N[C@@H]3CNC[C@@H](F)C3)nc21] |

-continued
| Compound No. | Structure |
|---|---|
| 47 | 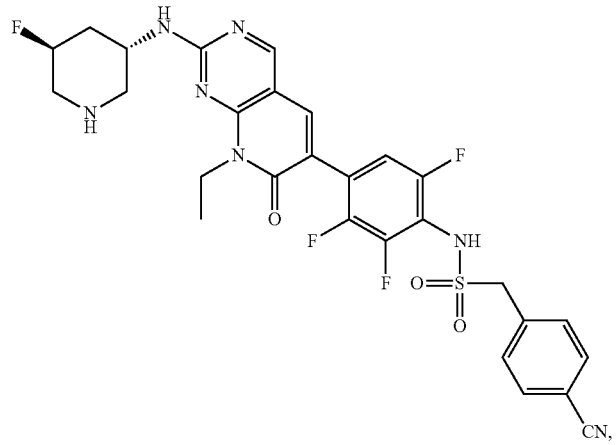 [SMILES: CCn1c(=O)c(-c2cc(F)c(NS(=O)(=O)Cc3ccc(C#N)cc3)c(F)c2F)cc2cnc(N[C@@H]3CNC[C@@H](F)C3)nc21] |
| 48 | 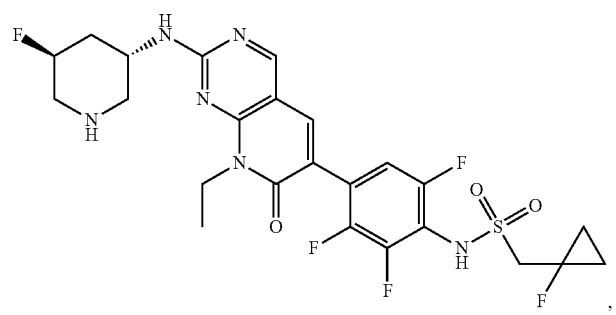 [SMILES: CCn1c(=O)c(-c2cc(F)c(NS(=O)(=O)CC3(F)CC3)c(F)c2F)cc2cnc(N[C@@H]3CNC[C@@H](F)C3)nc21] |
| 49 | 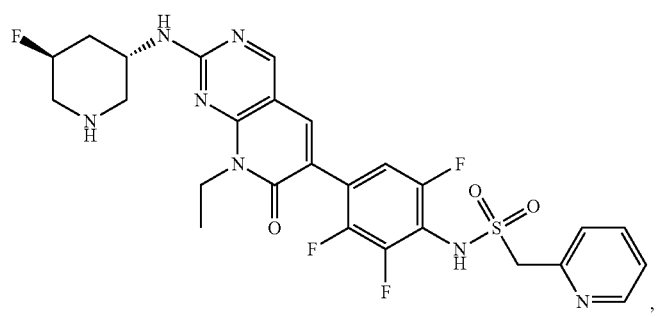 [SMILES: CCn1c(=O)c(-c2cc(F)c(NS(=O)(=O)Cc3ccccn3)c(F)c2F)cc2cnc(N[C@@H]3CNC[C@@H](F)C3)nc21] |
| 50 | 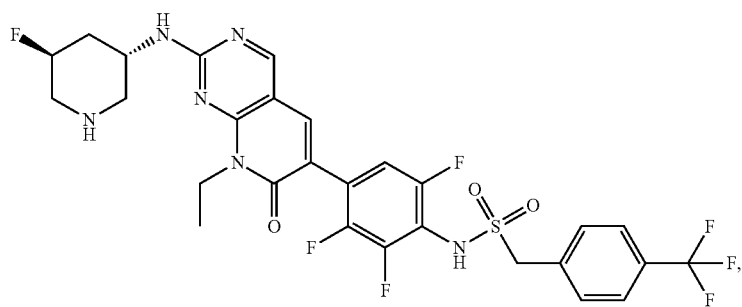 [SMILES: CCn1c(=O)c(-c2cc(F)c(NS(=O)(=O)Cc3ccc(C(F)(F)F)cc3)c(F)c2F)cc2cnc(N[C@@H]3CNC[C@@H](F)C3)nc21] |

| Compound No. | Structure |
|---|---|
| 51 | (structure) |
| 52 | (structure) |
| 53 | (structure) |
| 54 | (structure) |

-continued
| Compound No. | Structure |
|---|---|
| 55 | 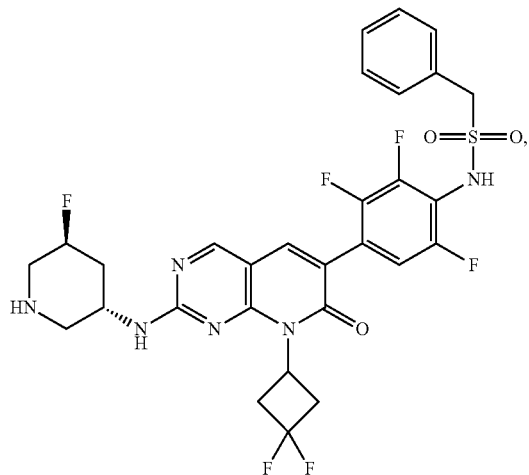 [SMILES: O=c1c(-c2cc(F)c(NS(=O)(=O)Cc3ccccc3)c(F)c2F)cc2cnc(N[C@@H]3CNC[C@@H](F)C3)nc2n1C1CC(F)(F)C1] |
| 56 | 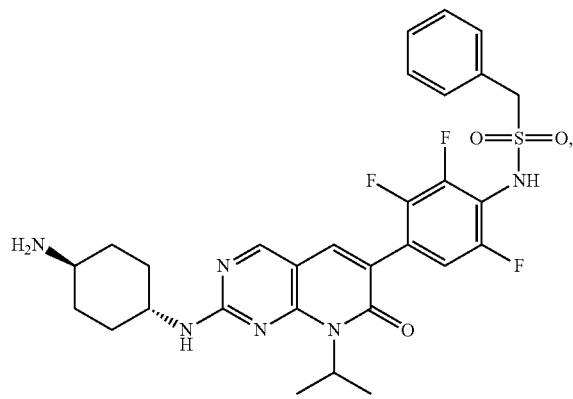 [SMILES: CC(C)n1c(=O)c(-c2cc(F)c(NS(=O)(=O)Cc3ccccc3)c(F)c2F)cc2cnc(N[C@H]3CC[C@H](N)CC3)nc21] |
| 57 | 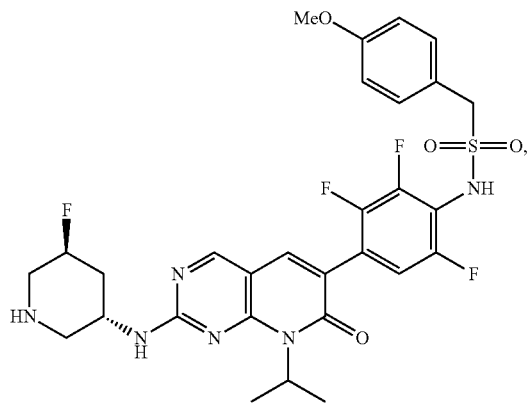 [SMILES: COc1ccc(CS(=O)(=O)Nc2c(F)cc(-c3cc4cnc(N[C@@H]5CNC[C@@H](F)C5)nc4n(C(C)C)c3=O)c(F)c2F)cc1] |
| 58<br>58A<br>58B<br>58C<br>58D | 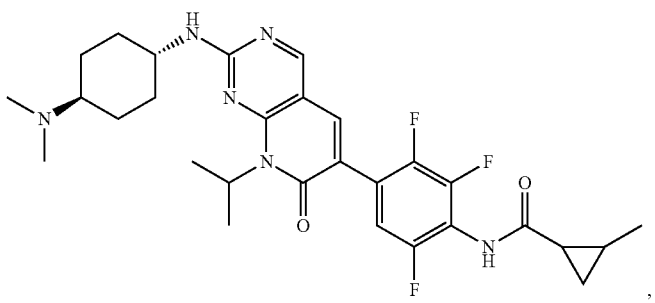 |

| Compound No. | Structure |
|---|---|
| | 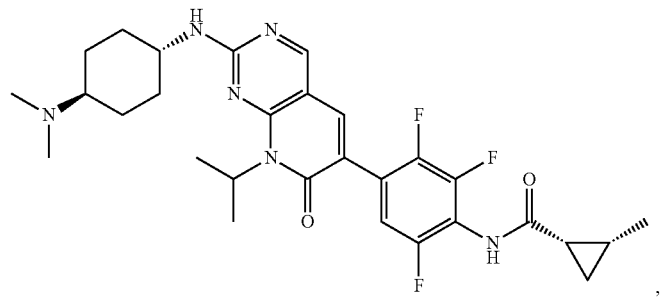 |
| | 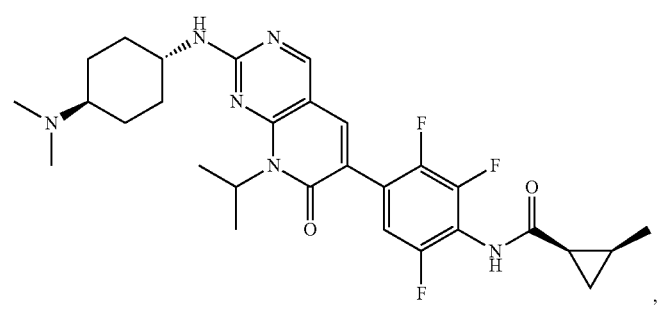 |
| | 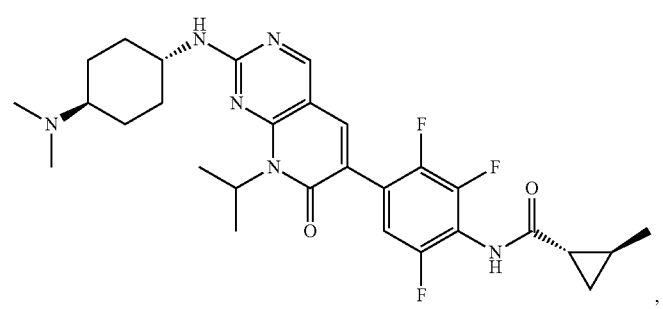 |
| | 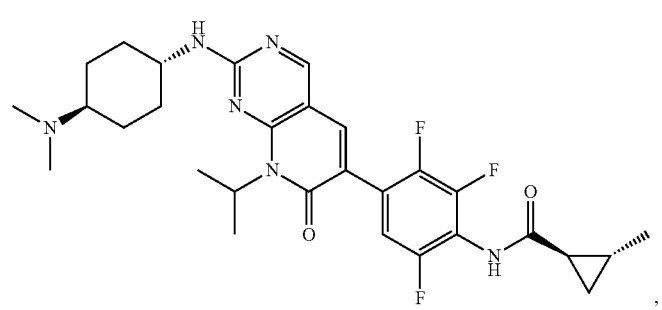 |
| 59 | 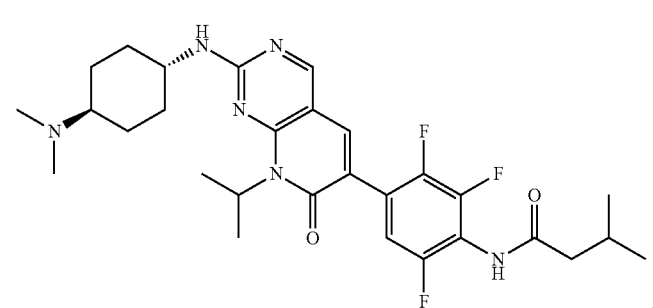 |

| Compound No. | Structure |
|---|---|
| 60 | 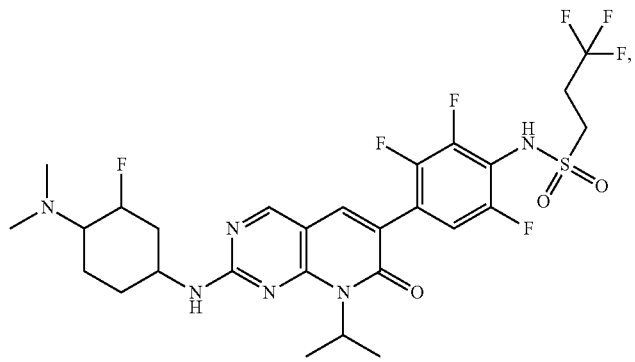 [SMILES: CC(C)n1c(=O)c(-c2cc(F)c(NS(=O)(=O)CCC(F)(F)F)c(F)c2F)cc2cnc(NC3CCC(N(C)C)C(F)C3)nc21] |
| 61 | 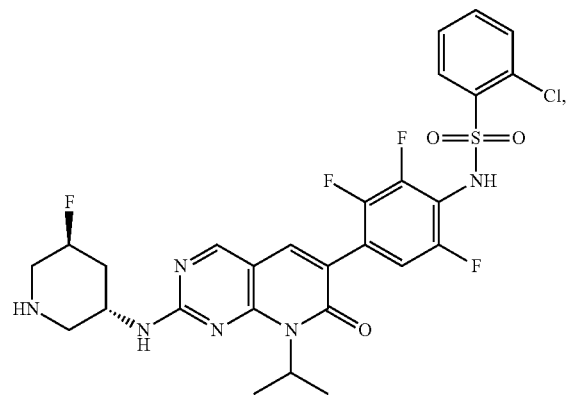 [SMILES: CC(C)n1c(=O)c(-c2cc(F)c(NS(=O)(=O)c3ccccc3Cl)c(F)c2F)cc2cnc(N[C@@H]3CNC[C@@H](F)C3)nc21] |
| 62 | 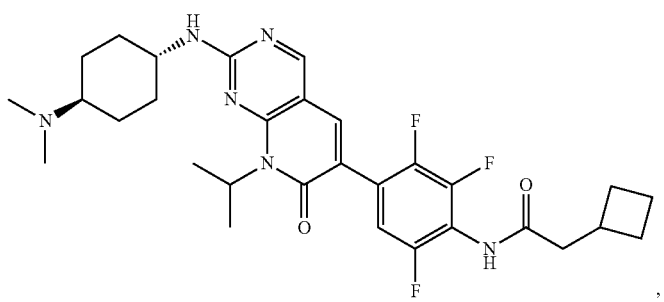 [SMILES: CC(C)n1c(=O)c(-c2cc(F)c(NC(=O)CC3CCC3)c(F)c2F)cc2cnc(N[C@H]3CC[C@H](N(C)C)CC3)nc21] |
| 63 | 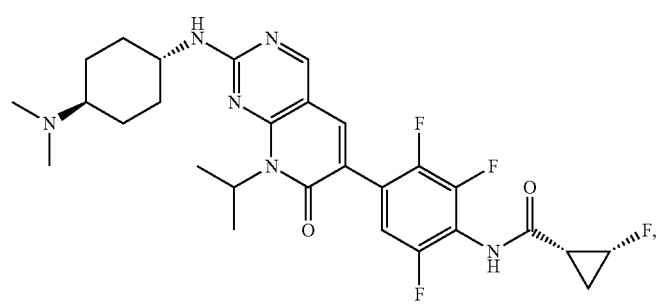 [SMILES: CC(C)n1c(=O)c(-c2cc(F)c(NC(=O)[C@H]3C[C@H]3F)c(F)c2F)cc2cnc(N[C@H]3CC[C@H](N(C)C)CC3)nc21] |

| Compound No. | Structure |
|---|---|
| 64 | 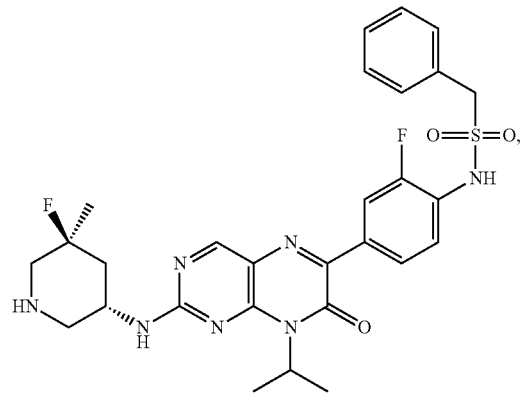 [SMILES: CC(C)n1c(=O)c(-c2ccc(NS(=O)(=O)Cc3ccccc3)c(F)c2)nc2cnc(N[C@@H]3CNC[C@@](C)(F)C3)nc21] |
| 65 | 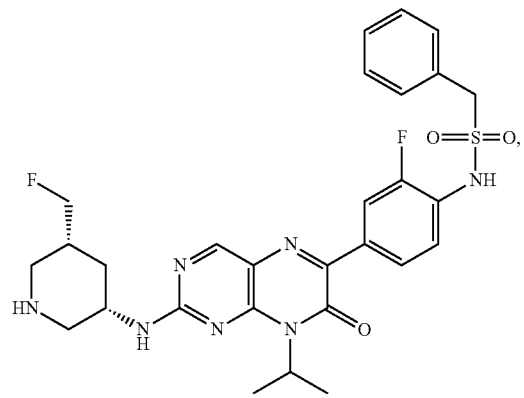 [SMILES: CC(C)n1c(=O)c(-c2ccc(NS(=O)(=O)Cc3ccccc3)c(F)c2)nc2cnc(N[C@@H]3CNC[C@H](CF)C3)nc21] |
| 66 | 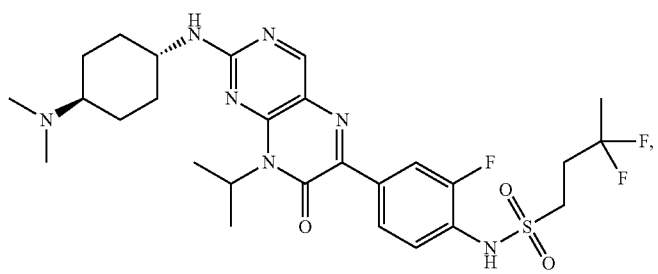 [SMILES: CC(C)n1c(=O)c(-c2ccc(NS(=O)(=O)CCC(C)(F)F)c(F)c2)nc2cnc(N[C@H]3CC[C@H](N(C)C)CC3)nc21] |
| 67 | 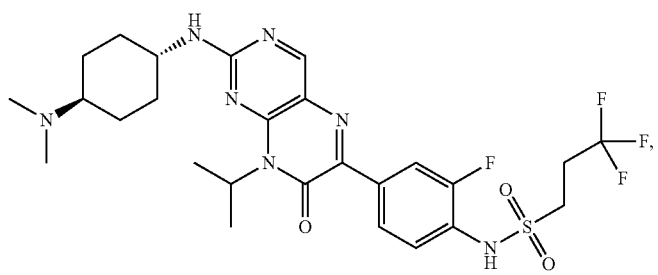 [SMILES: CC(C)n1c(=O)c(-c2ccc(NS(=O)(=O)CCC(F)(F)F)c(F)c2)nc2cnc(N[C@H]3CC[C@H](N(C)C)CC3)nc21] |

-continued
| Compound No. | Structure |
|---|---|
| 68 | 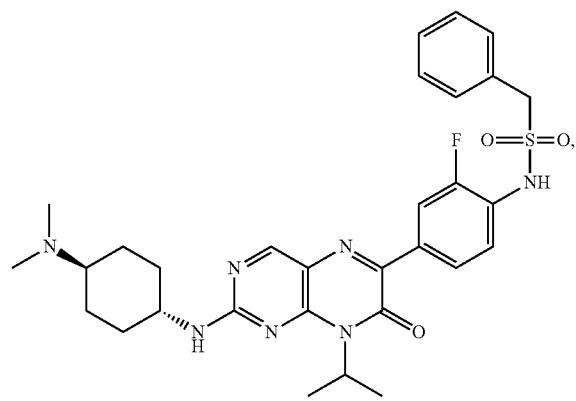 [SMILES: CC(C)n1c(=O)c(-c2ccc(NS(=O)(=O)Cc3ccccc3)c(F)c2)nc2cnc(N[C@H]3CC[C@H](N(C)C)CC3)nc21] |
| 69 | 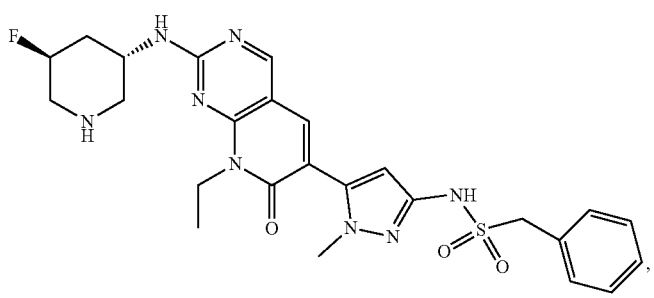 [SMILES: CCn1c(=O)c(-c2cc(NS(=O)(=O)Cc3ccccc3)nn2C)cc2cnc(N[C@@H]3CNC[C@@H](F)C3)nc21] |
| 70 | 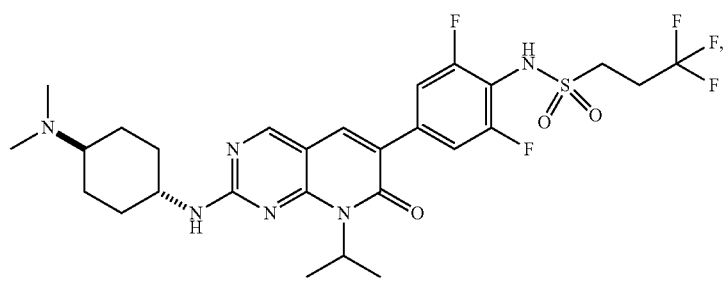 [SMILES: CC(C)n1c(=O)c(-c2cc(F)c(NS(=O)(=O)CCC(F)(F)F)c(F)c2)cc2cnc(N[C@H]3CC[C@H](N(C)C)CC3)nc21] |
| 71 | 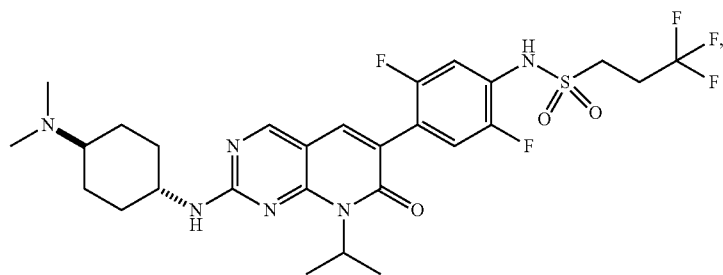 [SMILES: CC(C)n1c(=O)c(-c2cc(F)c(NS(=O)(=O)CCC(F)(F)F)cc2F)cc2cnc(N[C@H]3CC[C@H](N(C)C)CC3)nc21] |
| 72 | 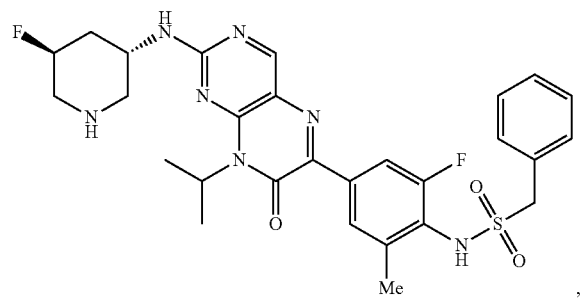 [SMILES: Cc1cc(-c2nc3cnc(N[C@@H]4CNC[C@@H](F)C4)nc3n(C(C)C)c2=O)cc(F)c1NS(=O)(=O)Cc1ccccc1] |

-continued
| Compound No. | Structure |
|---|---|
| 73 | 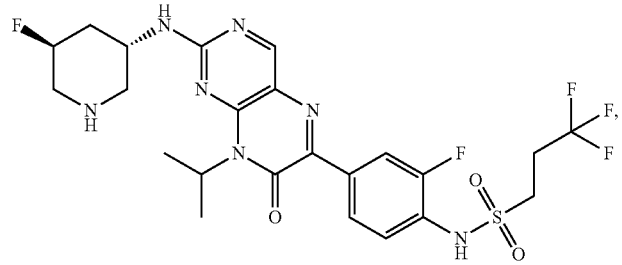 |
| 74 | 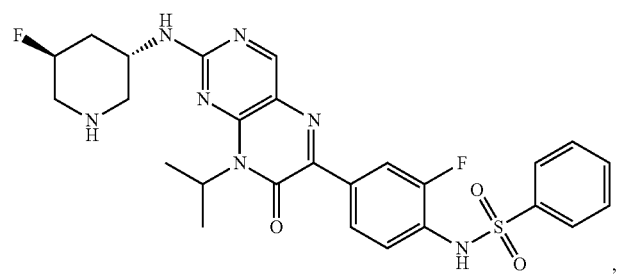 [SMILES: CC(C)n1c(=O)c(-c2ccc(NS(=O)(=O)c3ccccc3)c(F)c2)nc2cnc(N[C@@H]3CNC[C@@H](F)C3)nc21] |
| 75 | 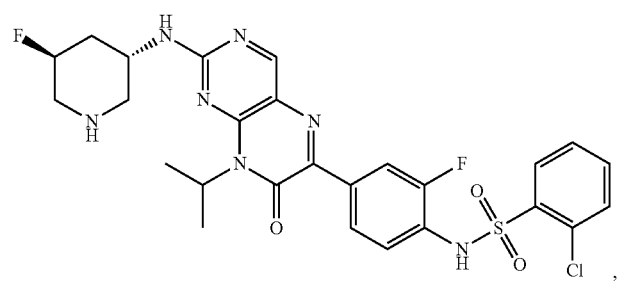 [SMILES: CC(C)n1c(=O)c(-c2ccc(NS(=O)(=O)c3ccccc3Cl)c(F)c2)nc2cnc(N[C@@H]3CNC[C@@H](F)C3)nc21] |
| 76 | 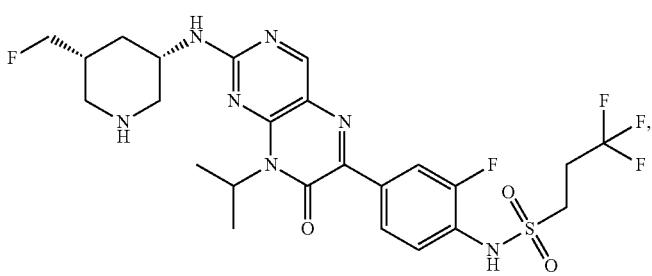 [SMILES: CC(C)n1c(=O)c(-c2ccc(NS(=O)(=O)CCC(F)(F)F)c(F)c2)nc2cnc(N[C@@H]3CNC[C@H](CF)C3)nc21] |
| 77 | 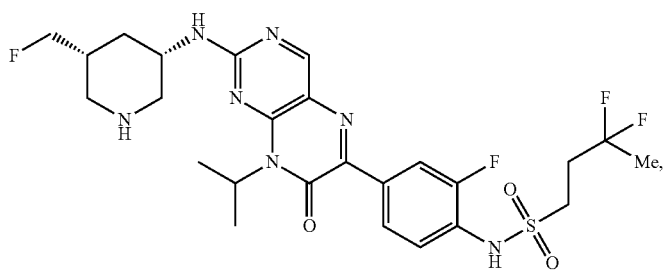 [SMILES: CC(C)n1c(=O)c(-c2ccc(NS(=O)(=O)CCC(C)(F)F)c(F)c2)nc2cnc(N[C@@H]3CNC[C@H](CF)C3)nc21] |

| Compound No. | Structure |
|---|---|
| 78 | 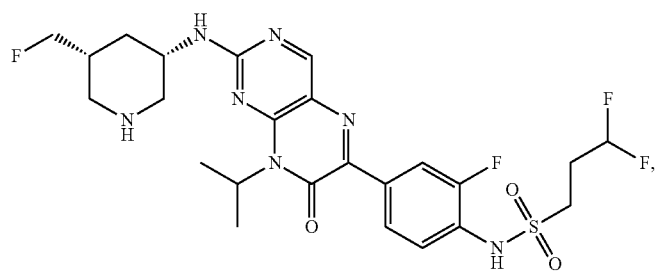 [SMILES: CC(C)n1c(=O)c(-c2ccc(NS(=O)(=O)CCC(F)F)c(F)c2)nc2cnc(N[C@@H]3CNC[C@H](CF)C3)nc21] |
| 79 | 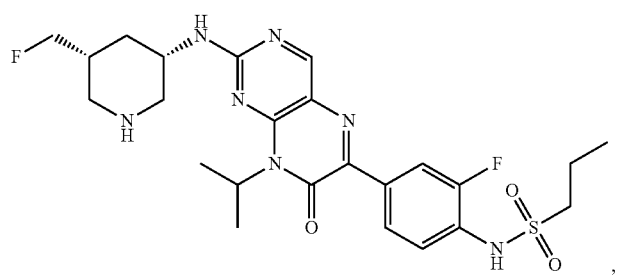 [SMILES: CCCS(=O)(=O)Nc1ccc(-c2nc3cnc(N[C@@H]4CNC[C@H](CF)C4)nc3n(C(C)C)c2=O)cc1F] |
| 80 | 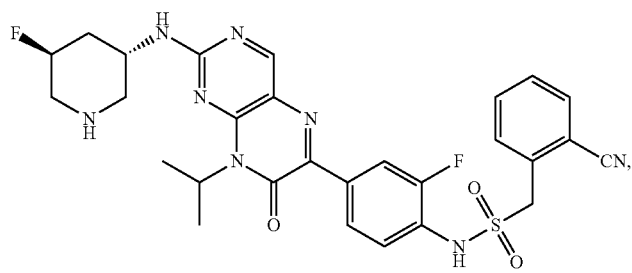 [SMILES: CC(C)n1c(=O)c(-c2ccc(NS(=O)(=O)Cc3ccccc3C#N)c(F)c2)nc2cnc(N[C@@H]3CNC[C@@H](F)C3)nc21] |
| 81 | 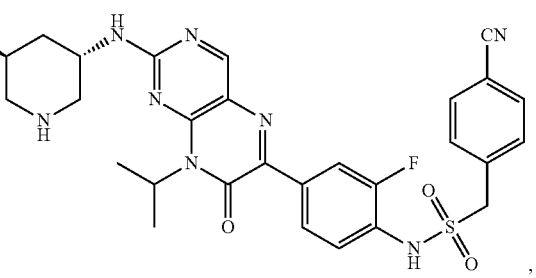 |
| 82 | 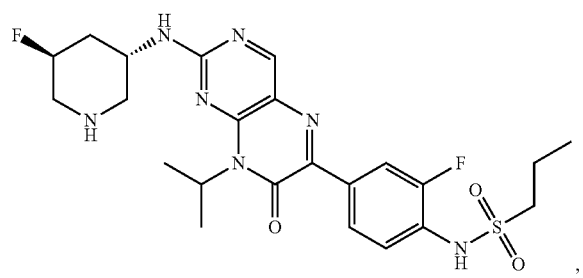 [SMILES: CCCS(=O)(=O)Nc1ccc(-c2nc3cnc(N[C@@H]4CNC[C@@H](F)C4)nc3n(C(C)C)c2=O)cc1F] |

-continued
| Compound No. | Structure |
|---|---|
| 83 | 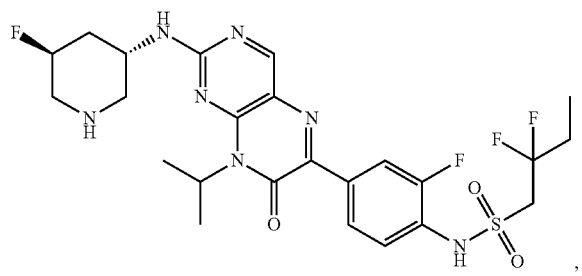 [SMILES: CCC(F)(F)CS(=O)(=O)Nc1ccc(-c2nc3cnc(N[C@@H]4CNC[C@@H](F)C4)nc3n(C(C)C)c2=O)cc1F] |
| 84 | 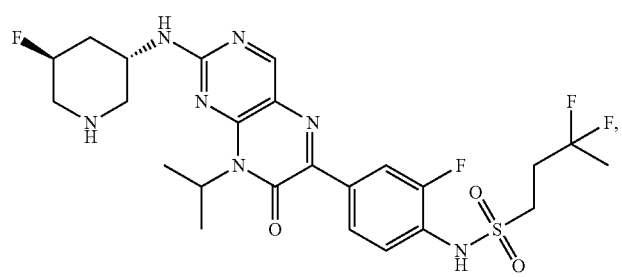 |
| 85 | 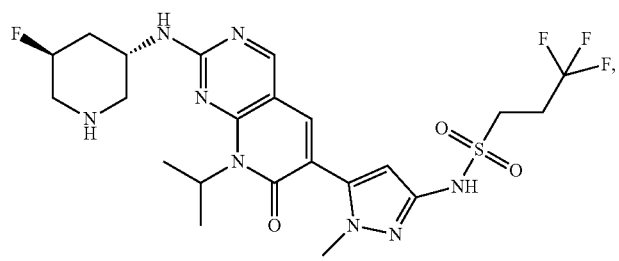 [SMILES: CC(C)n1c(=O)c(-c2cc(NS(=O)(=O)CCC(F)(F)F)nn2C)cc2cnc(N[C@@H]3CNC[C@@H](F)C3)nc21] |
| 86 | 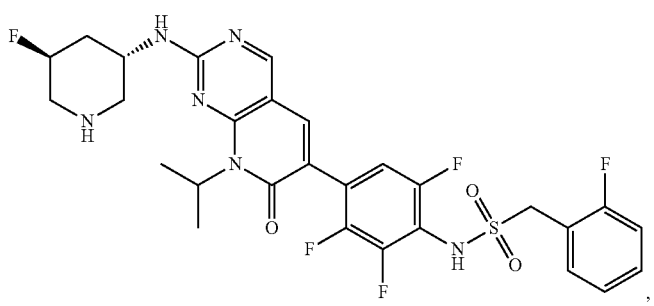 [SMILES: CC(C)n1c(=O)c(-c2cc(F)c(NS(=O)(=O)Cc3ccccc3F)c(F)c2F)cc2cnc(N[C@@H]3CNC[C@@H](F)C3)nc21] |
| 87 87A | 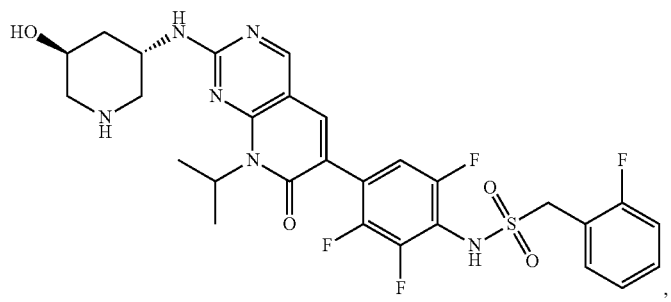 [SMILES: CC(C)n1c(=O)c(-c2cc(F)c(NS(=O)(=O)Cc3ccccc3F)c(F)c2F)cc2cnc(N[C@@H]3CNC[C@@H](O)C3)nc21] |

-continued
| Compound No. | Structure |
|---|---|
| | 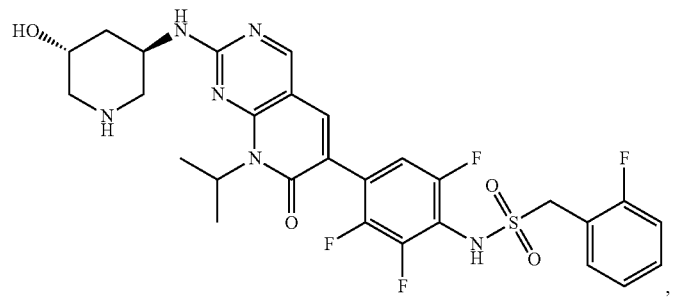 [SMILES: CC(C)n1c(=O)c(-c2cc(F)c(NS(=O)(=O)Cc3ccccc3F)c(F)c2F)cc2cnc(N[C@H]3CNC[C@H](O)C3)nc21] |
| 88 | 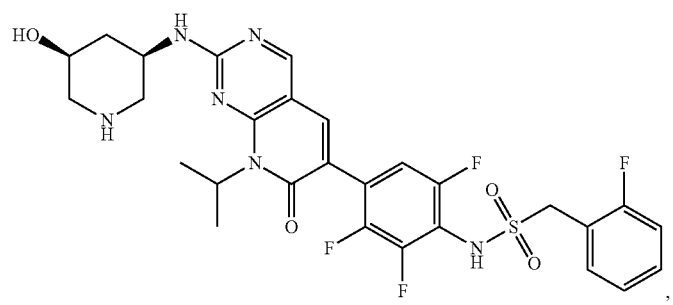 [SMILES: CC(C)n1c(=O)c(-c2cc(F)c(NS(=O)(=O)Cc3ccccc3F)c(F)c2F)cc2cnc(N[C@H]3CNC[C@@H](O)C3)nc21] |
| 89 | 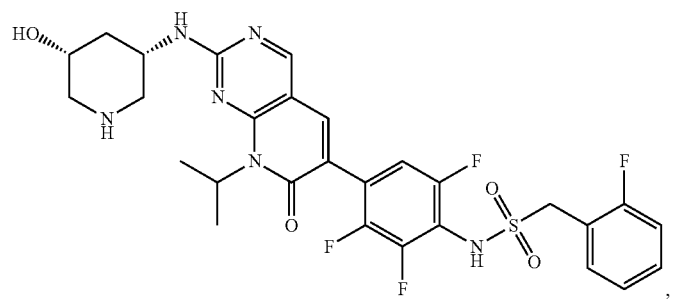 [SMILES: CC(C)n1c(=O)c(-c2cc(F)c(NS(=O)(=O)Cc3ccccc3F)c(F)c2F)cc2cnc(N[C@@H]3CNC[C@H](O)C3)nc21] |
| 90 | 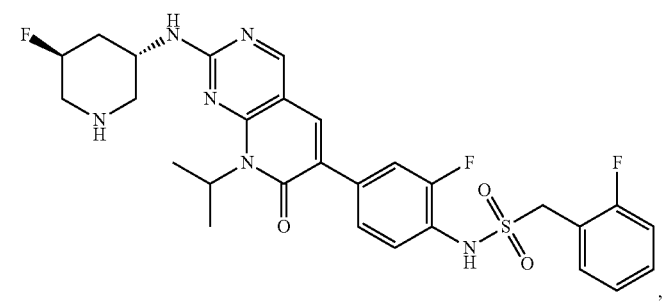 [SMILES: CC(C)n1c(=O)c(-c2ccc(NS(=O)(=O)Cc3ccccc3F)c(F)c2)cc2cnc(N[C@@H]3CNC[C@@H](F)C3)nc21] |
| 91 | 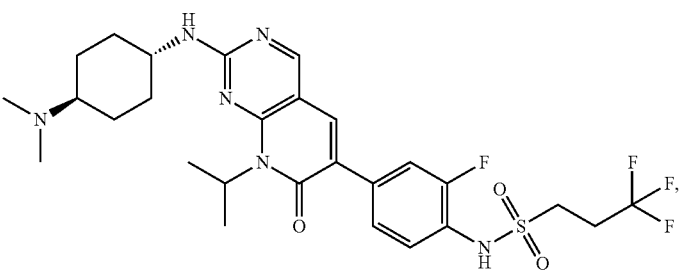 [SMILES: CC(C)n1c(=O)c(-c2ccc(NS(=O)(=O)CCC(F)(F)F)c(F)c2)cc2cnc(N[C@H]3CC[C@H](N(C)C)CC3)nc21] |

| Compound No. | Structure |
|---|---|
| 92 | 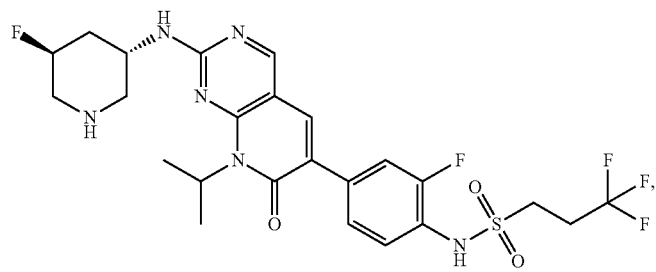 [SMILES: CC(C)n1c(=O)c(-c2ccc(NS(=O)(=O)CCC(F)(F)F)c(F)c2)cc2cnc(N[C@@H]3CNC[C@@H](F)C3)nc21] |
| 93 | 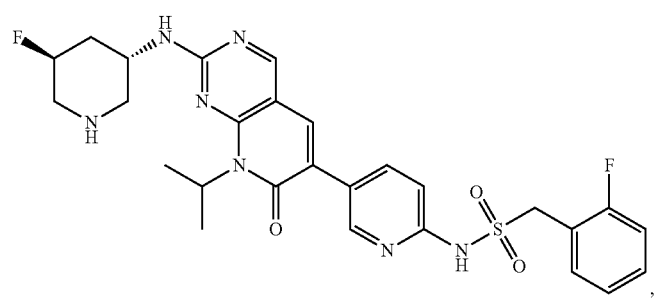 |
| 94 | 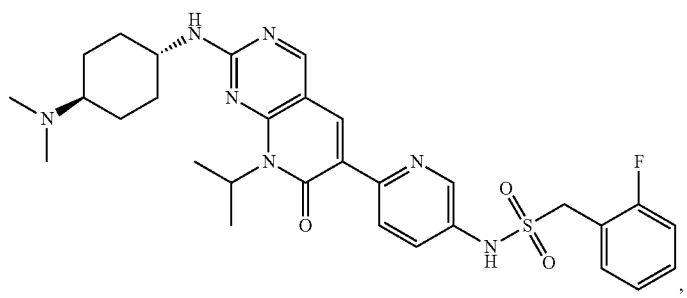 [SMILES: CC(C)n1c(=O)c(-c2ccc(NS(=O)(=O)Cc3ccccc3F)cn2)cc2cnc(N[C@H]3CC[C@H](N(C)C)CC3)nc21] |
| 95 | 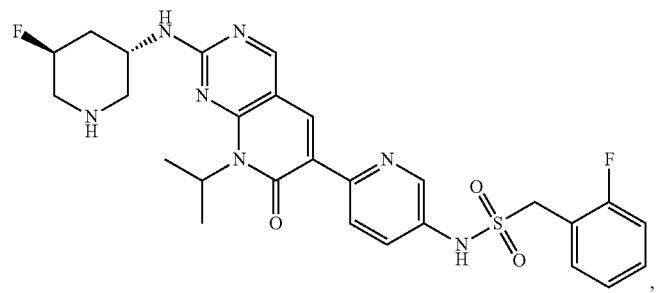 [SMILES: CC(C)n1c(=O)c(-c2ccc(NS(=O)(=O)Cc3ccccc3F)cn2)cc2cnc(N[C@@H]3CNC[C@@H](F)C3)nc21] |
| 96 | 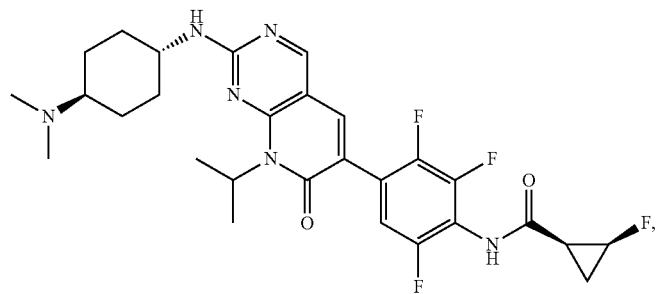 [SMILES: CC(C)n1c(=O)c(-c2cc(F)c(NC(=O)[C@@H]3C[C@@H]3F)c(F)c2F)cc2cnc(N[C@H]3CC[C@H](N(C)C)CC3)nc21] |

| Compound No. | Structure |
|---|---|
| 97 | 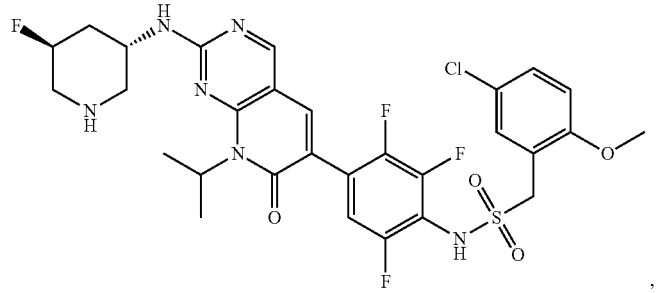 [SMILES: COc1ccc(Cl)cc1CS(=O)(=O)Nc1c(F)cc(-c2cc3cnc(N[C@@H]4CNC[C@@H](F)C4)nc3n(C(C)C)c2=O)c(F)c1F] |
| 98 98A 98B | 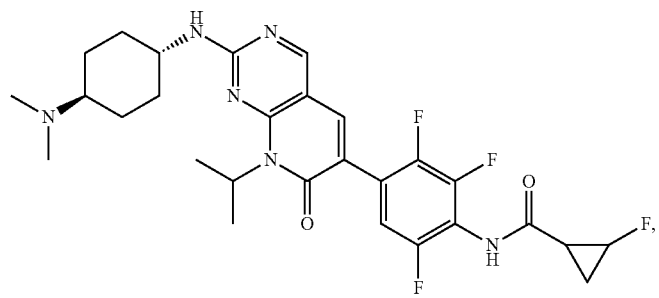 [SMILES: CC(C)n1c(=O)c(-c2cc(F)c(NC(=O)C3CC3F)c(F)c2F)cc2cnc(N[C@H]3CC[C@H](N(C)C)CC3)nc21] |
| | 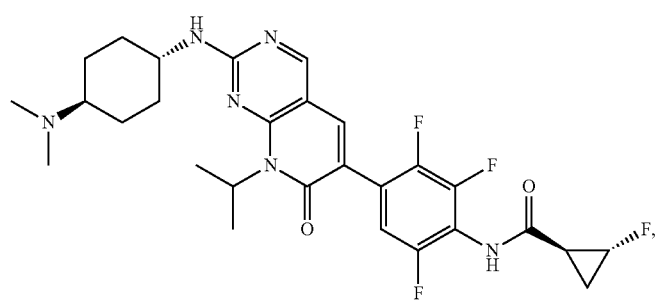 [SMILES: CC(C)n1c(=O)c(-c2cc(F)c(NC(=O)[C@@H]3C[C@H]3F)c(F)c2F)cc2cnc(N[C@H]3CC[C@H](N(C)C)CC3)nc21] |
| | 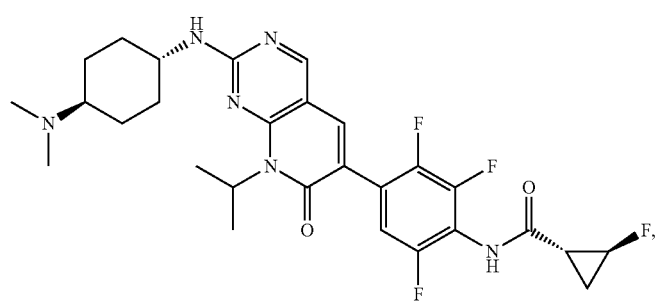 [SMILES: CC(C)n1c(=O)c(-c2cc(F)c(NC(=O)[C@H]3C[C@@H]3F)c(F)c2F)cc2cnc(N[C@H]3CC[C@H](N(C)C)CC3)nc21] |
| 99 99A | 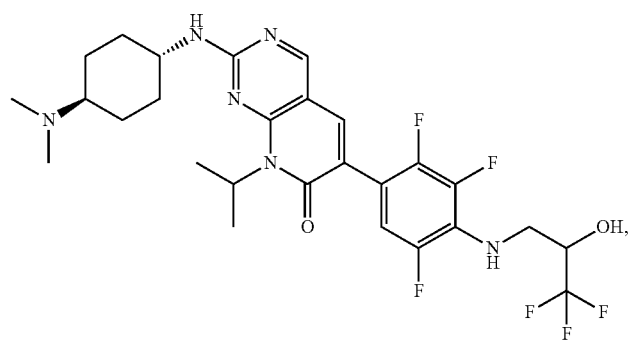 [SMILES: CC(C)n1c(=O)c(-c2cc(F)c(NCC(O)C(F)(F)F)c(F)c2F)cc2cnc(N[C@H]3CC[C@H](N(C)C)CC3)nc21] |

| Compound No. | Structure |
|---|---|
| 100 | 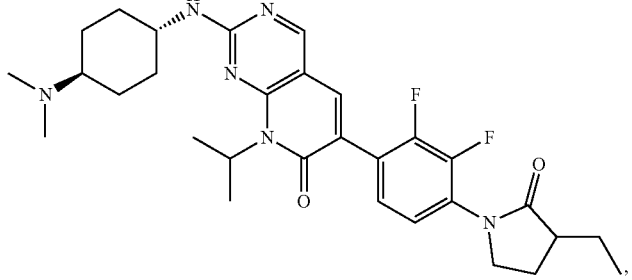 |
| 101<br>101A<br>101B | 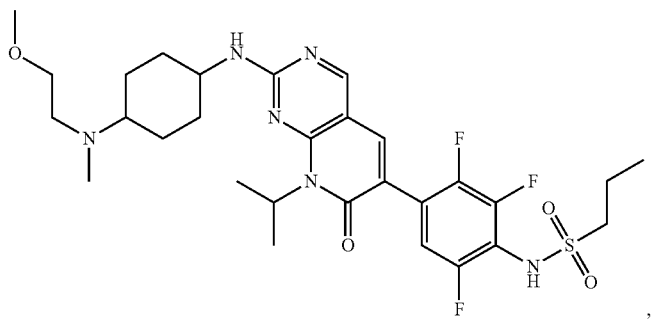 [SMILES: CCCS(=O)(=O)Nc1c(F)cc(-c2cc3cnc(NC4CCC(N(C)CCOC)CC4)nc3n(C(C)C)c2=O)c(F)c1F]<br><br>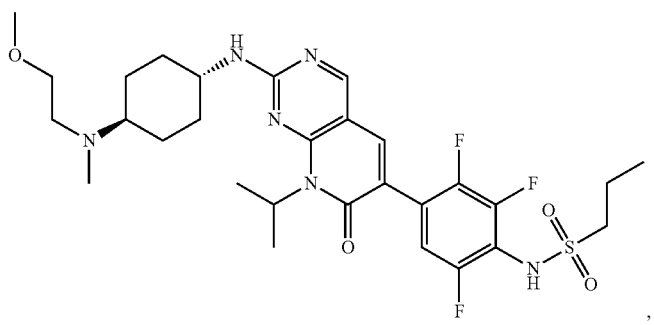 [SMILES: CCCS(=O)(=O)Nc1c(F)cc(-c2cc3cnc(N[C@H]4CC[C@H](N(C)CCOC)CC4)nc3n(C(C)C)c2=O)c(F)c1F]<br><br>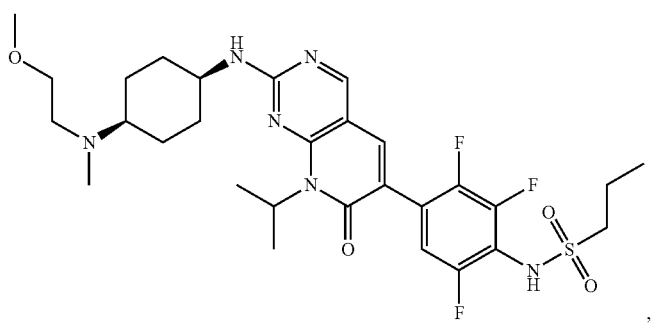 [SMILES: CCCS(=O)(=O)Nc1c(F)cc(-c2cc3cnc(N[C@H]4CC[C@@H](N(C)CCOC)CC4)nc3n(C(C)C)c2=O)c(F)c1F] |

-continued
| Compound No. | Structure |
|---|---|
| 102<br>102A<br>102B | 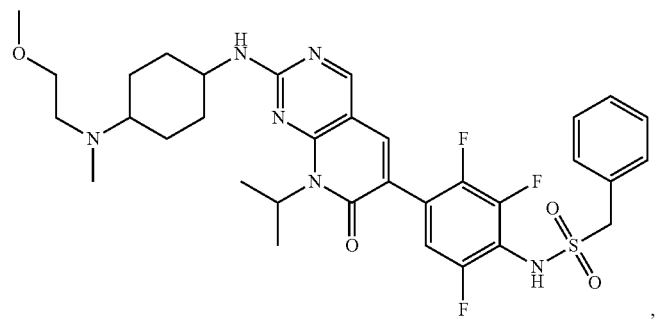 [SMILES: COCCN(C)C1CCC(Nc2ncc3cc(-c4cc(F)c(NS(=O)(=O)Cc5ccccc5)c(F)c4F)c(=O)n(C(C)C)c3n2)CC1]<br><br>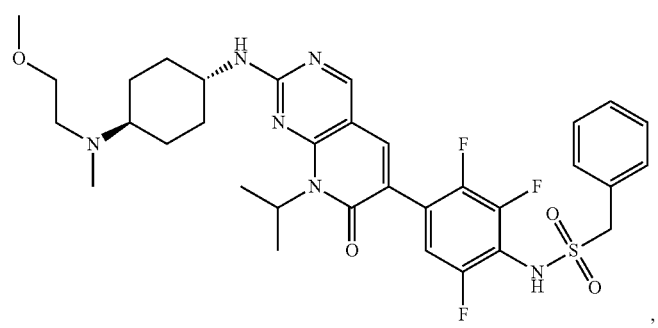 [SMILES: COCCN(C)[C@H]1CC[C@H](Nc2ncc3cc(-c4cc(F)c(NS(=O)(=O)Cc5ccccc5)c(F)c4F)c(=O)n(C(C)C)c3n2)CC1]<br><br>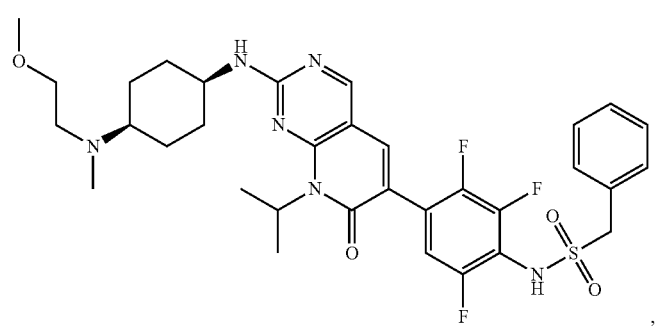 [SMILES: COCCN(C)[C@H]1CC[C@@H](Nc2ncc3cc(-c4cc(F)c(NS(=O)(=O)Cc5ccccc5)c(F)c4F)c(=O)n(C(C)C)c3n2)CC1] |
| 103 | 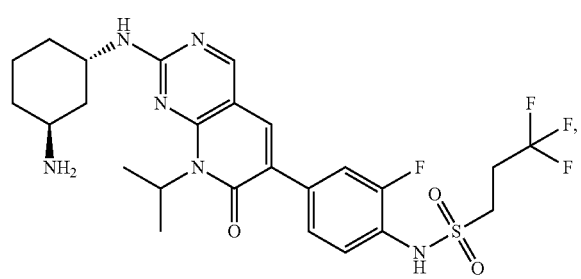 [SMILES: CC(C)n1c(=O)c(-c2ccc(NS(=O)(=O)CCC(F)(F)F)c(F)c2)cc2cnc(N[C@H]3CCC[C@H](N)C3)nc21] |
| 104 | 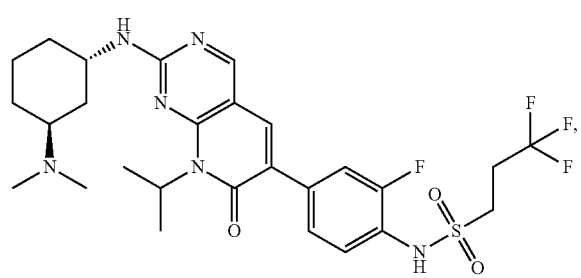 [SMILES: CC(C)n1c(=O)c(-c2ccc(NS(=O)(=O)CCC(F)(F)F)c(F)c2)cc2cnc(N[C@H]3CCC[C@H](N(C)C)C3)nc21] |

| Compound No. | Structure |
|---|---|
| 105 | 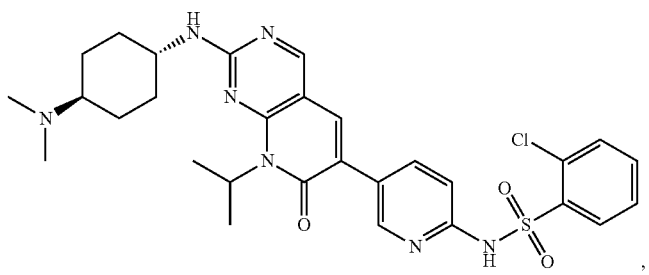 |
| 106 | 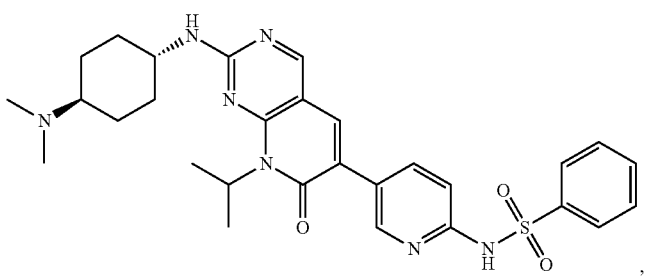 [SMILES: CC(C)n1c(=O)c(-c2ccc(NS(=O)(=O)c3ccccc3)nc2)cc2cnc(N[C@H]3CC[C@H](N(C)C)CC3)nc21] |
| 107 | 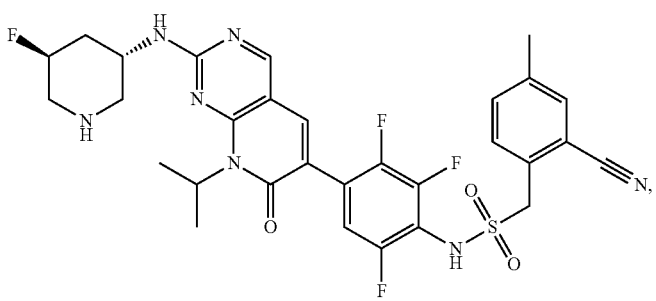 [SMILES: Cc1ccc(CS(=O)(=O)Nc2c(F)cc(-c3cc4cnc(N[C@@H]5CNC[C@@H](F)C5)nc4n(C(C)C)c3=O)c(F)c2F)c(C#N)c1] |
| 108 | 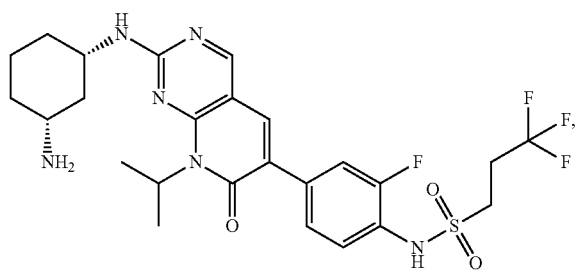 [SMILES: CC(C)n1c(=O)c(-c2ccc(NS(=O)(=O)CCC(F)(F)F)c(F)c2)cc2cnc(N[C@H]3CCC[C@@H](N)C3)nc21] |
| 109 | 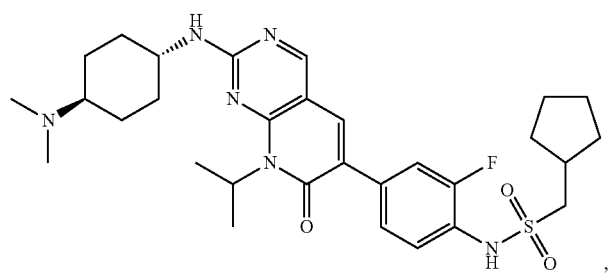 [SMILES: CC(C)n1c(=O)c(-c2ccc(NS(=O)(=O)CC3CCCC3)c(F)c2)cc2cnc(N[C@H]3CC[C@H](N(C)C)CC3)nc21] |

| Compound No. | Structure |
|---|---|
| 110<br>110A<br>110B | 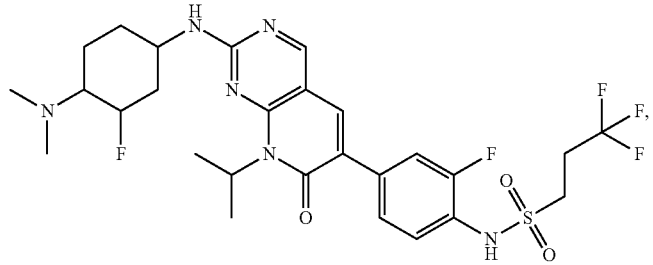 [SMILES: CC(C)n1c(=O)c(-c2ccc(NS(=O)(=O)CCC(F)(F)F)c(F)c2)cc2cnc(NC3CCC(N(C)C)C(F)C3)nc21]<br><br>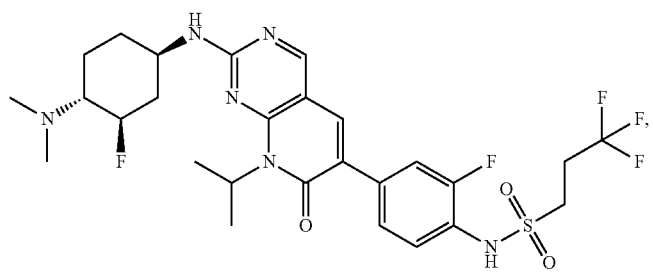 [SMILES: CC(C)n1c(=O)c(-c2ccc(NS(=O)(=O)CCC(F)(F)F)c(F)c2)cc2cnc(N[C@@H]3CC[C@@H](N(C)C)[C@H](F)C3)nc21]<br><br>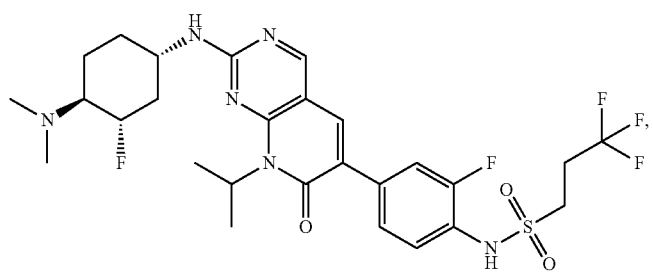 [SMILES: CC(C)n1c(=O)c(-c2ccc(NS(=O)(=O)CCC(F)(F)F)c(F)c2)cc2cnc(N[C@H]3CC[C@H](N(C)C)[C@@H](F)C3)nc21] |
| 111 | 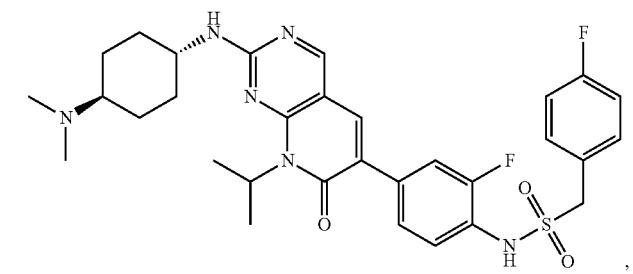 |
| 112 | 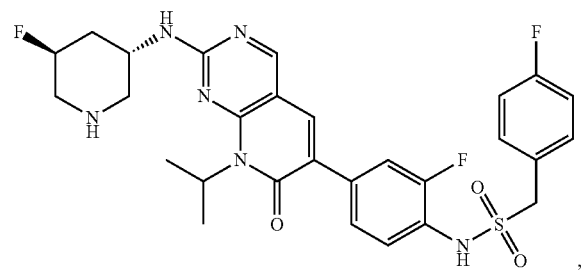 [SMILES: CC(C)n1c(=O)c(-c2ccc(NS(=O)(=O)Cc3ccc(F)cc3)c(F)c2)cc2cnc(N[C@@H]3CNC[C@@H](F)C3)nc21] |

| Compound No. | Structure |
|---|---|
| 113 | 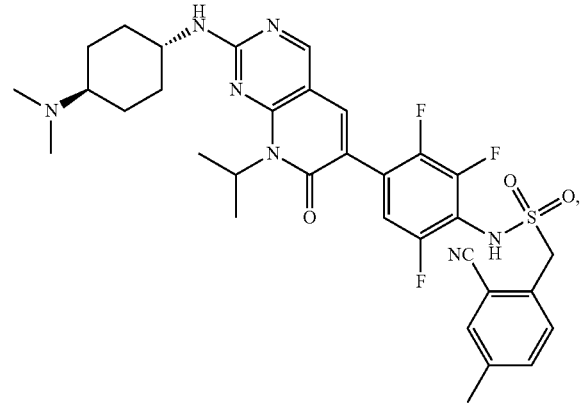 [SMILES: Cc1ccc(CS(=O)(=O)Nc2c(F)cc(-c3cc4cnc(N[C@H]5CC[C@H](N(C)C)CC5)nc4n(C(C)C)c3=O)c(F)c2F)c(C#N)c1] |
| 114 | 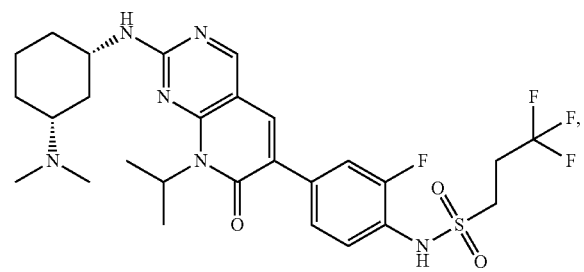 [SMILES: CC(C)n1c(=O)c(-c2ccc(NS(=O)(=O)CCC(F)(F)F)c(F)c2)cc2cnc(N[C@H]3CCC[C@@H](N(C)C)C3)nc21] |
| 115 | 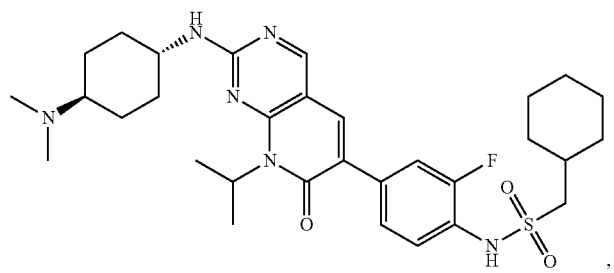 [SMILES: CC(C)n1c(=O)c(-c2ccc(NS(=O)(=O)CC3CCCCC3)c(F)c2)cc2cnc(N[C@H]3CC[C@H](N(C)C)CC3)nc21] |
| 116 | 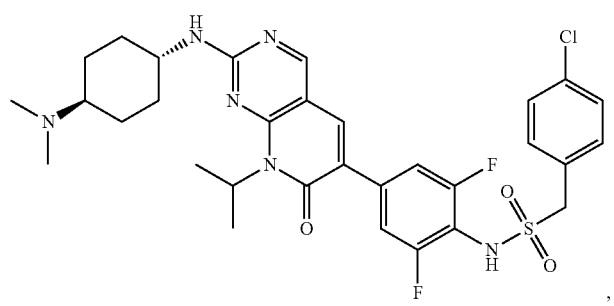 |
| 117 | 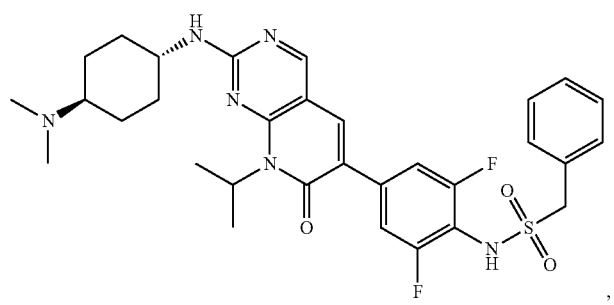 [SMILES: CC(C)n1c(=O)c(-c2cc(F)c(NS(=O)(=O)Cc3ccccc3)c(F)c2)cc2cnc(N[C@H]3CC[C@H](N(C)C)CC3)nc21] |

| Compound No. | Structure |
|---|---|
| 118<br>118A<br>118B | 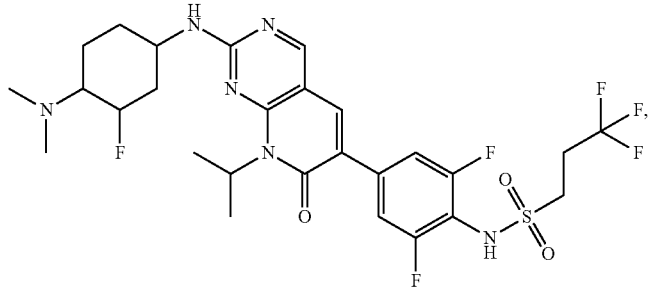 [SMILES: CC(C)n1c(=O)c(-c2cc(F)c(NS(=O)(=O)CCC(F)(F)F)c(F)c2)cc2cnc(NC3CCC(N(C)C)C(F)C3)nc21]<br>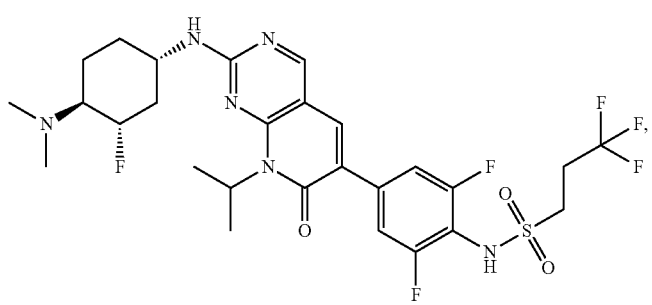 [SMILES: CC(C)n1c(=O)c(-c2cc(F)c(NS(=O)(=O)CCC(F)(F)F)c(F)c2)cc2cnc(N[C@H]3CC[C@H](N(C)C)[C@@H](F)C3)nc21]<br>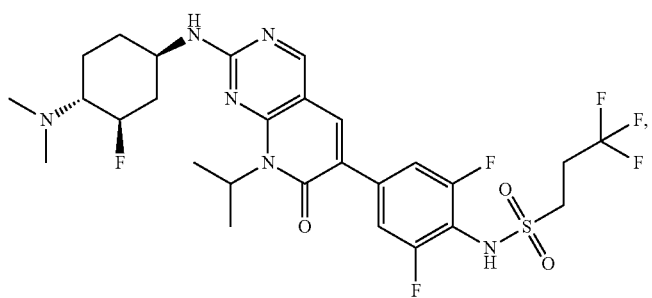 |
| 119 | 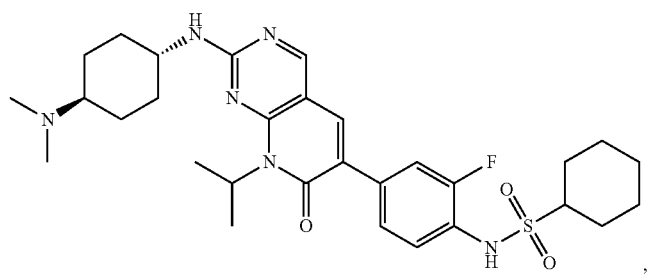 [SMILES: CC(C)n1c(=O)c(-c2ccc(NS(=O)(=O)C3CCCCC3)c(F)c2)cc2cnc(N[C@H]3CC[C@H](N(C)C)CC3)nc21] |
| 120 | 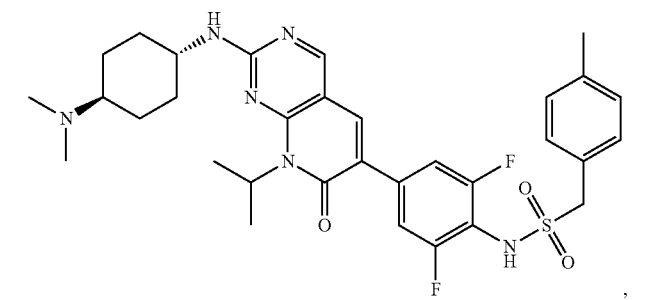 [SMILES: Cc1ccc(CS(=O)(=O)Nc2c(F)cc(-c3cc4cnc(N[C@H]5CC[C@H](N(C)C)CC5)nc4n(C(C)C)c3=O)cc2F)cc1] |

| Compound No. | Structure |
|---|---|
| 121 | 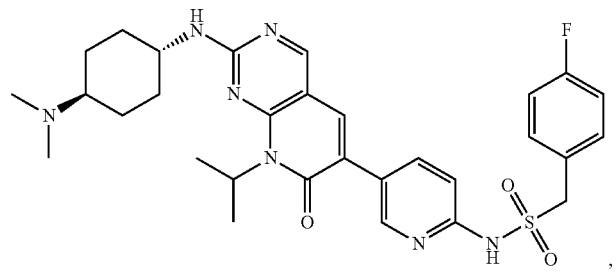 [SMILES: CC(C)n1c(=O)c(-c2ccc(NS(=O)(=O)Cc3ccc(F)cc3)nc2)cc2cnc(N[C@H]3CC[C@H](N(C)C)CC3)nc21] |
| 122 | 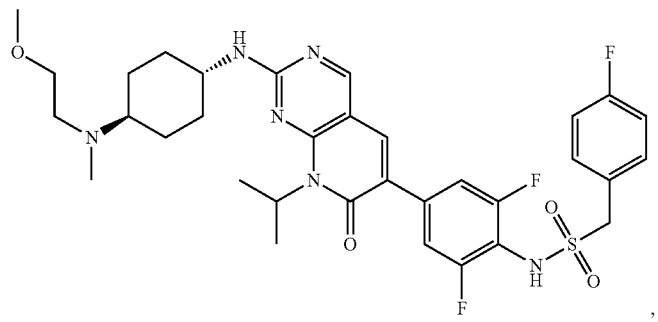 [SMILES: COCCN(C)[C@H]1CC[C@H](Nc2ncc3cc(-c4cc(F)c(NS(=O)(=O)Cc5ccc(F)cc5)c(F)c4)c(=O)n(C(C)C)c3n2)CC1] |
| 123 | 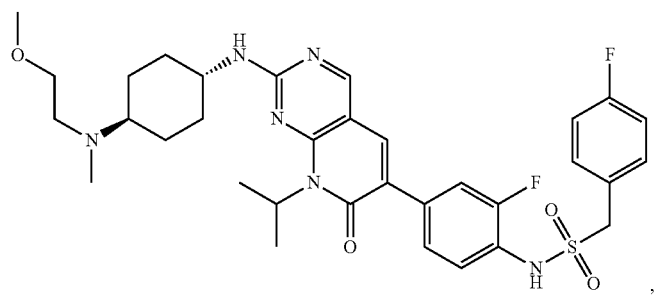 |
| 124 | 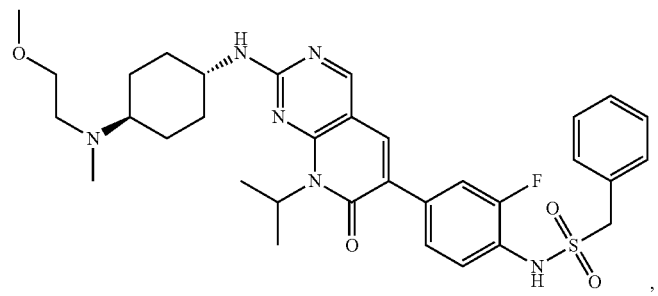 [SMILES: COCCN(C)[C@H]1CC[C@H](Nc2ncc3cc(-c4ccc(NS(=O)(=O)Cc5ccc(F)cc5)c(F)c4)c(=O)n(C(C)C)c3n2)CC1] |
| 125 | 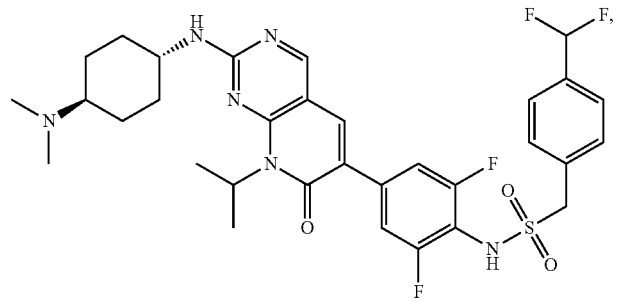 [SMILES: CC(C)n1c(=O)c(-c2cc(F)c(NS(=O)(=O)Cc3ccc(C(F)F)cc3)c(F)c2)cc2cnc(N[C@H]3CC[C@H](N(C)C)CC3)nc21] |

-continued
| Compound No. | Structure |
|---|---|
| 126 | 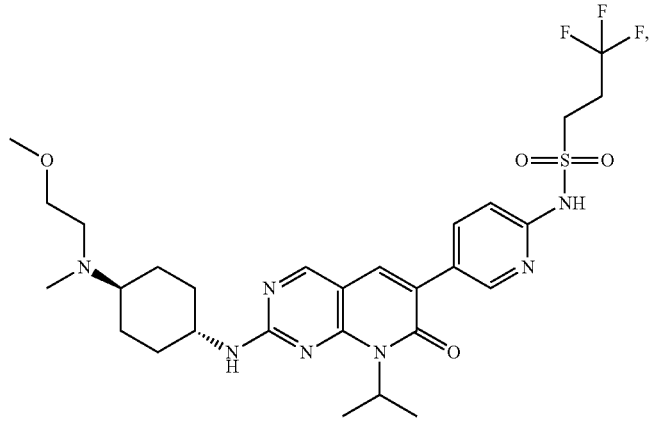 [SMILES: COCCN(C)[C@H]1CC[C@H](Nc2ncc3cc(-c4ccc(NS(=O)(=O)CCC(F)(F)F)nc4)c(=O)n(C(C)C)c3n2)CC1] |
| 127 | 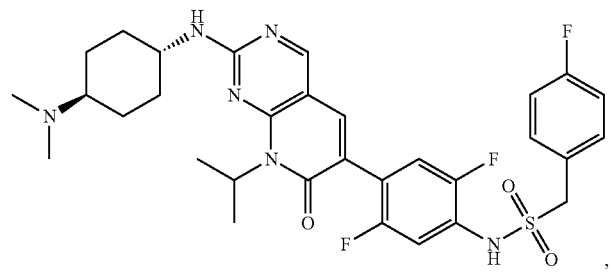 [SMILES: CC(C)n1c(=O)c(-c2cc(F)c(NS(=O)(=O)Cc3ccc(F)cc3)cc2F)cc2cnc(N[C@H]3CC[C@H](N(C)C)CC3)nc21] |
| 128 | 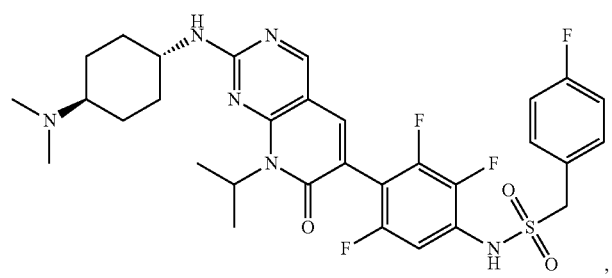 [SMILES: CC(C)n1c(=O)c(-c2c(F)cc(NS(=O)(=O)Cc3ccc(F)cc3)c(F)c2F)cc2cnc(N[C@H]3CC[C@H](N(C)C)CC3)nc21] |
| 129 | 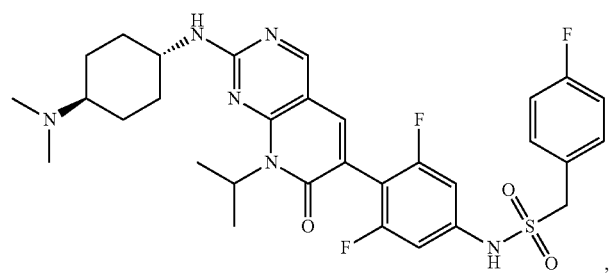 [SMILES: CC(C)n1c(=O)c(-c2c(F)cc(NS(=O)(=O)Cc3ccc(F)cc3)cc2F)cc2cnc(N[C@H]3CC[C@H](N(C)C)CC3)nc21] |
| 130 | 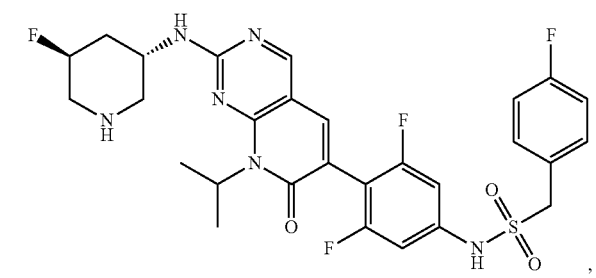 |

| Compound No. | Structure |
|---|---|
| 131 | 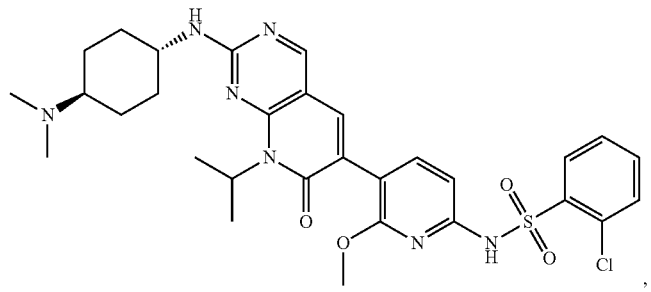 [SMILES: COc1nc(NS(=O)(=O)c2ccccc2Cl)ccc1-c1cc2cnc(N[C@H]3CC[C@H](N(C)C)CC3)nc2n(C(C)C)c1=O] |
| 132 | 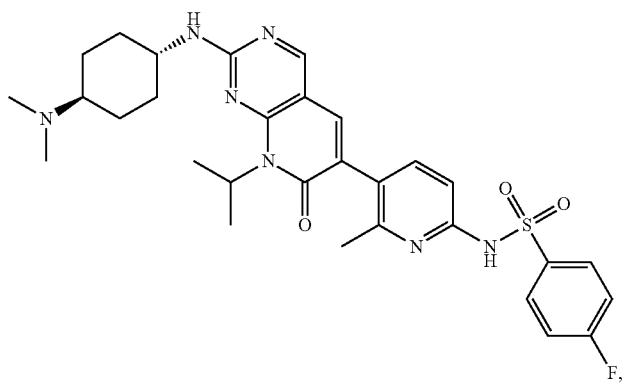 [SMILES: Cc1nc(NS(=O)(=O)c2ccc(F)cc2)ccc1-c1cc2cnc(N[C@H]3CC[C@H](N(C)C)CC3)nc2n(C(C)C)c1=O] |
| 133 | 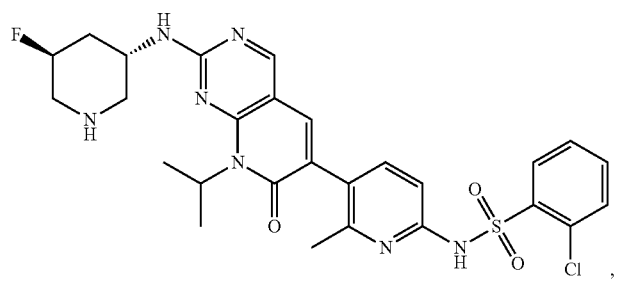 [SMILES: Cc1nc(NS(=O)(=O)c2ccccc2Cl)ccc1-c1cc2cnc(N[C@@H]3CNC[C@@H](F)C3)nc2n(C(C)C)c1=O] |
| 134 | 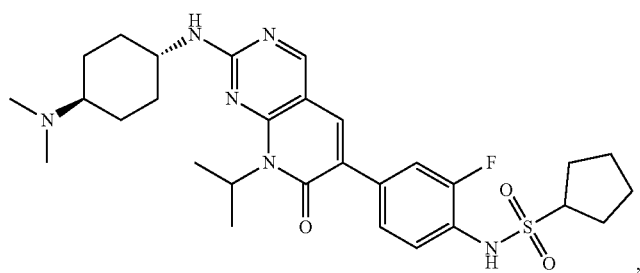 [SMILES: CC(C)n1c(=O)c(-c2ccc(NS(=O)(=O)C3CCCC3)c(F)c2)cc2cnc(N[C@H]3CC[C@H](N(C)C)CC3)nc21] |
| 135 | 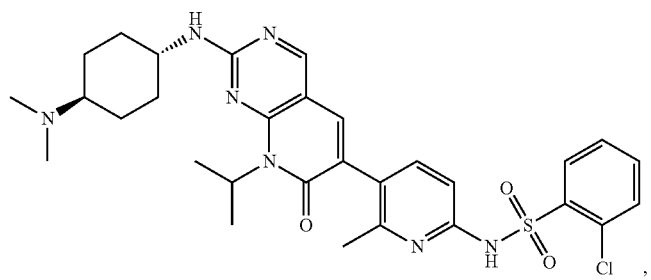 |

-continued
| Compound No. | Structure |
|---|---|
| 136 | 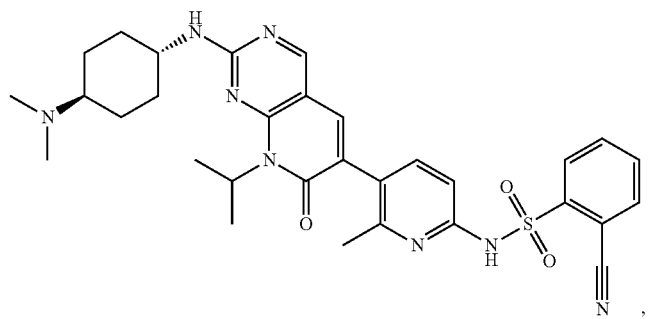 [SMILES: Cc1nc(NS(=O)(=O)c2ccccc2C#N)ccc1-c1cc2cnc(N[C@H]3CC[C@H](N(C)C)CC3)nc2n(C(C)C)c1=O] |
| 137 | 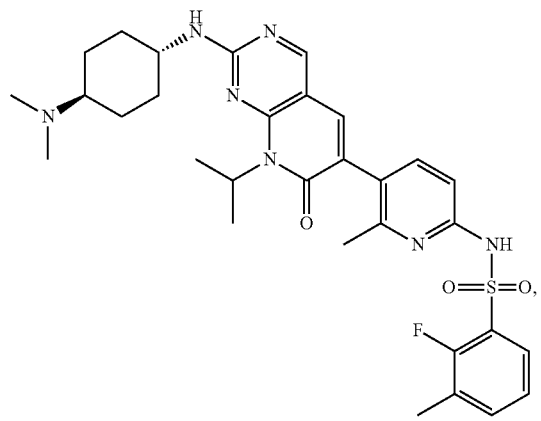 [SMILES: Cc1cccc(S(=O)(=O)Nc2ccc(-c3cc4cnc(N[C@H]5CC[C@H](N(C)C)CC5)nc4n(C(C)C)c3=O)c(C)n2)c1F] |
| 138 | 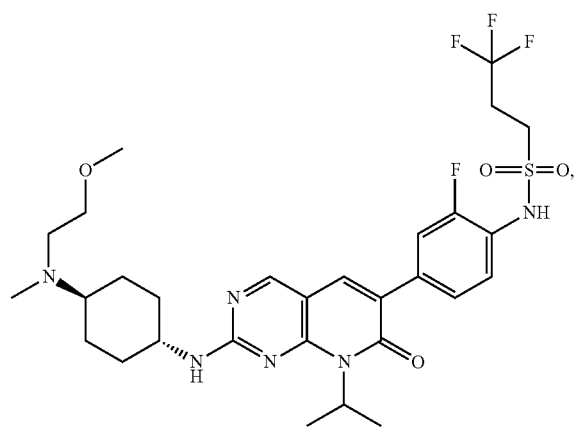 [SMILES: COCCN(C)[C@H]1CC[C@H](Nc2ncc3cc(-c4ccc(NS(=O)(=O)CCC(F)(F)F)c(F)c4)c(=O)n(C(C)C)c3n2)CC1] |

| Compound No. | Structure |
|---|---|
| 139 | 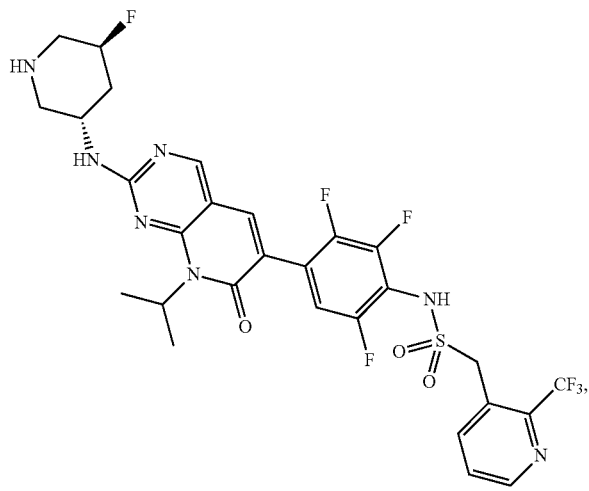 [SMILES: CC(C)n1c(=O)c(-c2cc(F)c(NS(=O)(=O)Cc3cccnc3C(F)(F)F)c(F)c2F)cc2cnc(N[C@@H]3CNC[C@@H](F)C3)nc21] |
| 140 | 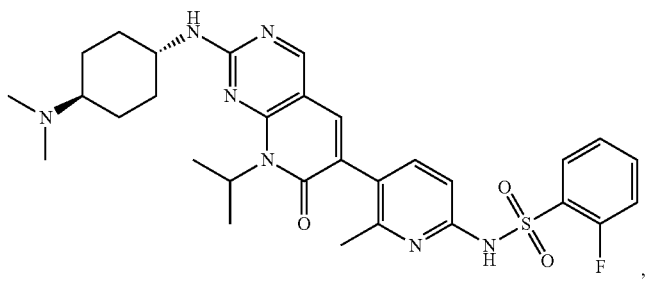 [SMILES: Cc1nc(NS(=O)(=O)c2ccccc2F)ccc1-c1cc2cnc(N[C@H]3CC[C@H](N(C)C)CC3)nc2n(C(C)C)c1=O] |
| 141 | 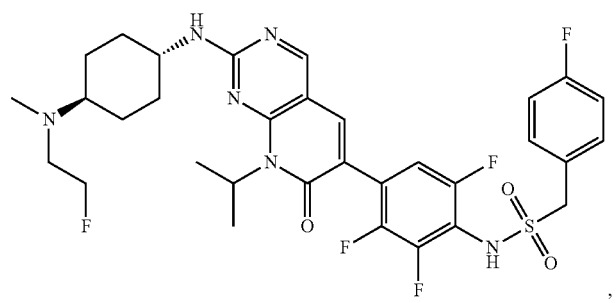 [SMILES: CC(C)n1c(=O)c(-c2cc(F)c(NS(=O)(=O)Cc3ccc(F)cc3)c(F)c2F)cc2cnc(N[C@H]3CC[C@H](N(C)CCF)CC3)nc21] |
| 142 | 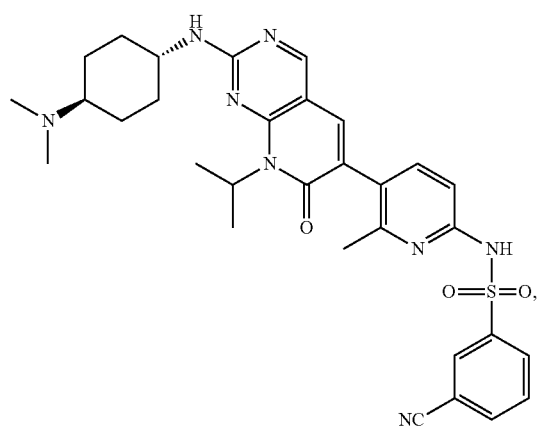 [SMILES: Cc1nc(NS(=O)(=O)c2cccc(C#N)c2)ccc1-c1cc2cnc(N[C@H]3CC[C@H](N(C)C)CC3)nc2n(C(C)C)c1=O] |

| Compound No. | Structure |
|---|---|
| 143 | 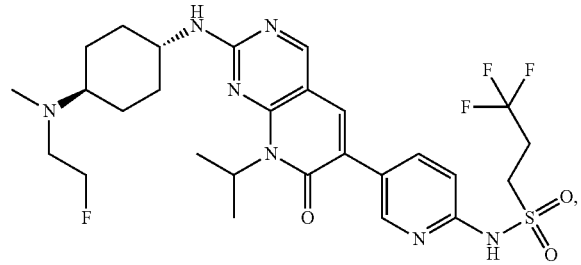 [SMILES: CC(C)n1c(=O)c(-c2ccc(NS(=O)(=O)CCC(F)(F)F)nc2)cc2cnc(N[C@H]3CC[C@H](N(C)CCF)CC3)nc21] |
| 144 | 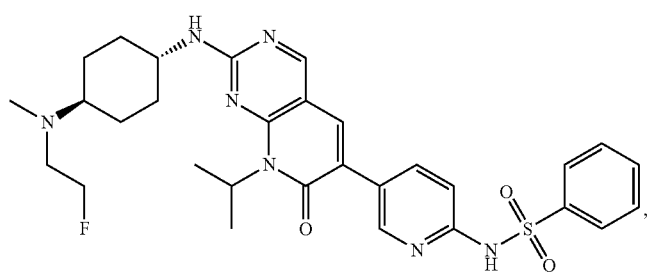 [SMILES: CC(C)n1c(=O)c(-c2ccc(NS(=O)(=O)c3ccccc3)nc2)cc2cnc(N[C@H]3CC[C@H](N(C)CCF)CC3)nc21] |
| 145 | 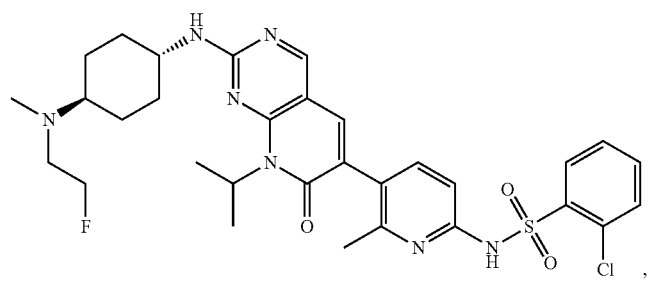 [SMILES: Cc1nc(NS(=O)(=O)c2ccccc2Cl)ccc1-c1cc2cnc(N[C@H]3CC[C@H](N(C)CCF)CC3)nc2n(C(C)C)c1=O] |
| 146 | 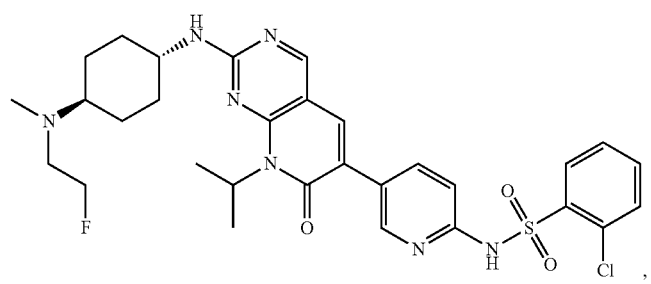 [SMILES: CC(C)n1c(=O)c(-c2ccc(NS(=O)(=O)c3ccccc3Cl)nc2)cc2cnc(N[C@H]3CC[C@H](N(C)CCF)CC3)nc21] |
| 147 | 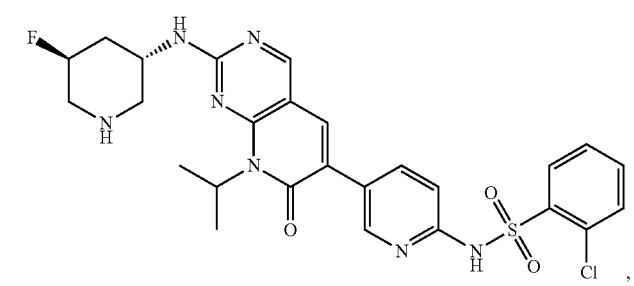 [SMILES: CC(C)n1c(=O)c(-c2ccc(NS(=O)(=O)c3ccccc3Cl)nc2)cc2cnc(N[C@@H]3CNC[C@@H](F)C3)nc21] |

| Compound No. | Structure |
|---|---|
| 148 | 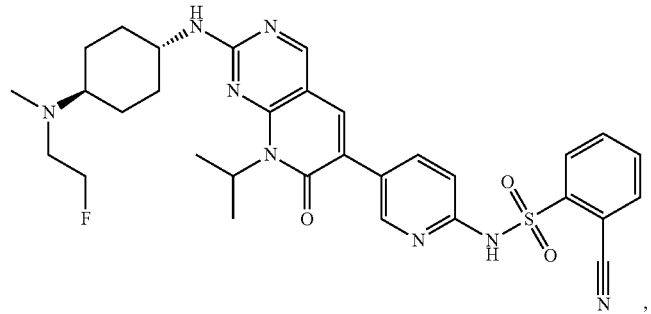 [SMILES: CC(C)n1c(=O)c(-c2ccc(NS(=O)(=O)c3ccccc3C#N)nc2)cc2cnc(N[C@H]3CC[C@H](N(C)CCF)CC3)nc21] |
| 149 | 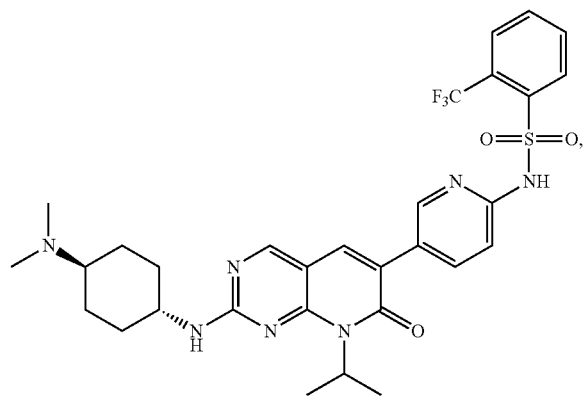 [SMILES: CC(C)n1c(=O)c(-c2ccc(NS(=O)(=O)c3ccccc3C(F)(F)F)nc2)cc2cnc(N[C@H]3CC[C@H](N(C)C)CC3)nc21] |
| 150 | 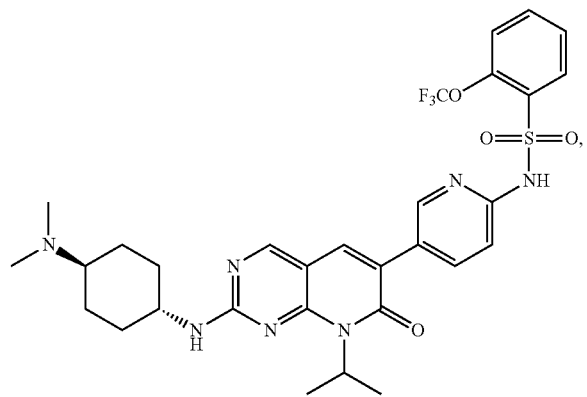 [SMILES: CC(C)n1c(=O)c(-c2ccc(NS(=O)(=O)c3ccccc3OC(F)(F)F)nc2)cc2cnc(N[C@H]3CC[C@H](N(C)C)CC3)nc21] |
| 151 | 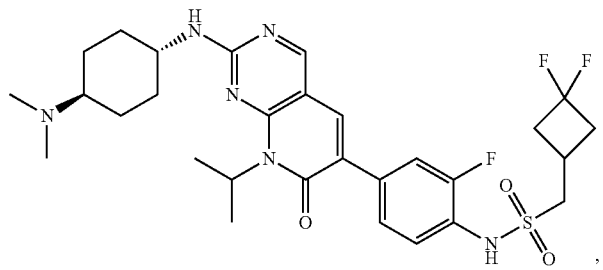 [SMILES: CC(C)n1c(=O)c(-c2ccc(NS(=O)(=O)CC3CC(F)(F)C3)c(F)c2)cc2cnc(N[C@H]3CC[C@H](N(C)C)CC3)nc21] |

| Compound No. | Structure |
|---|---|
| 152 | 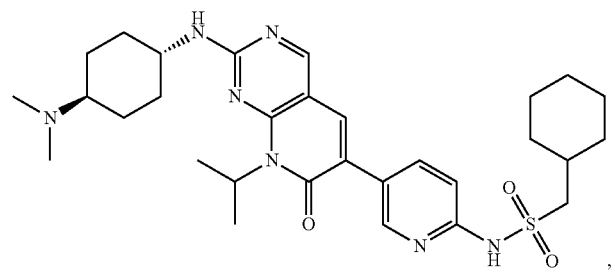 [SMILES: CC(C)n1c(=O)c(-c2ccc(NS(=O)(=O)CC3CCCCC3)nc2)cc2cnc(N[C@H]3CC[C@H](N(C)C)CC3)nc21] |
| 153 153A 153B | 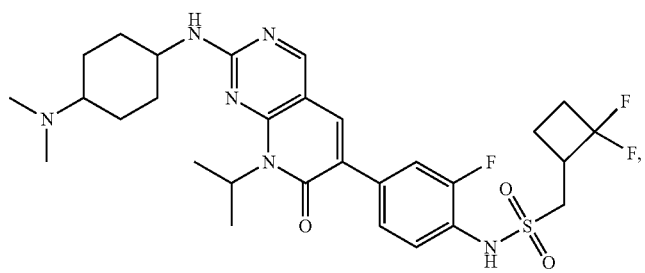 [SMILES: CC(C)n1c(=O)c(-c2ccc(NS(=O)(=O)CC3CCC3(F)F)c(F)c2)cc2cnc(NC3CCC(N(C)C)CC3)nc21]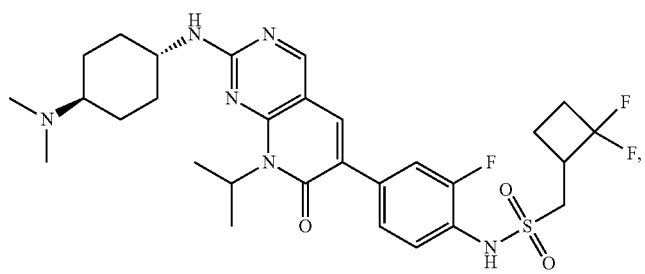 [SMILES: CC(C)n1c(=O)c(-c2ccc(NS(=O)(=O)CC3CCC3(F)F)c(F)c2)cc2cnc(N[C@H]3CC[C@H](N(C)C)CC3)nc21]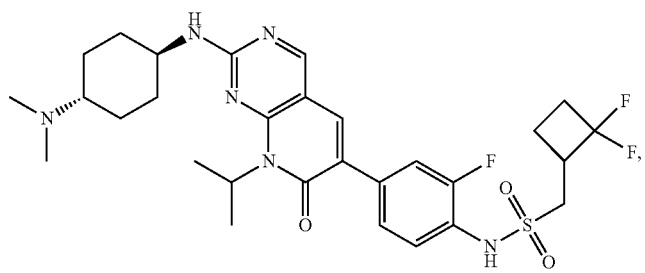 [SMILES: CC(C)n1c(=O)c(-c2ccc(NS(=O)(=O)CC3CCC3(F)F)c(F)c2)cc2cnc(N[C@H]3CC[C@H](N(C)C)CC3)nc21] |
| 154 | 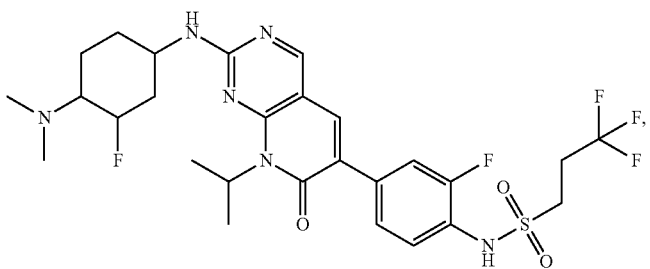 [SMILES: CC(C)n1c(=O)c(-c2ccc(NS(=O)(=O)CCC(F)(F)F)c(F)c2)cc2cnc(NC3CCC(N(C)C)C(F)C3)nc21] |

| Compound No. | Structure |
|---|---|
| 155 | 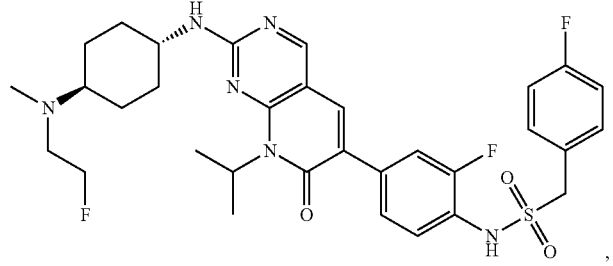 |
| 156 | 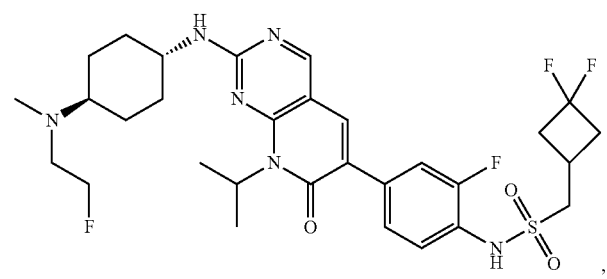 [SMILES: CC(C)n1c(=O)c(-c2ccc(NS(=O)(=O)CC3CC(F)(F)C3)c(F)c2)cc2cnc(N[C@H]3CC[C@H](N(C)CCF)CC3)nc21] |
| 157 | 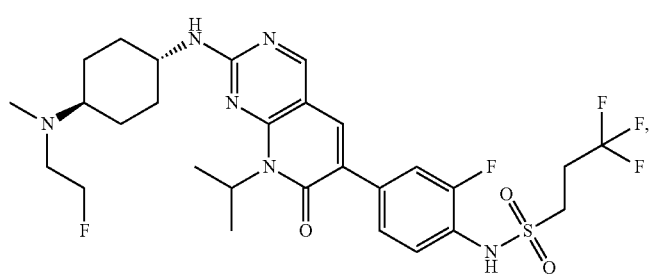 [SMILES: CC(C)n1c(=O)c(-c2ccc(NS(=O)(=O)CCC(F)(F)F)c(F)c2)cc2cnc(N[C@H]3CC[C@H](N(C)CCF)CC3)nc21] |
| 158 | 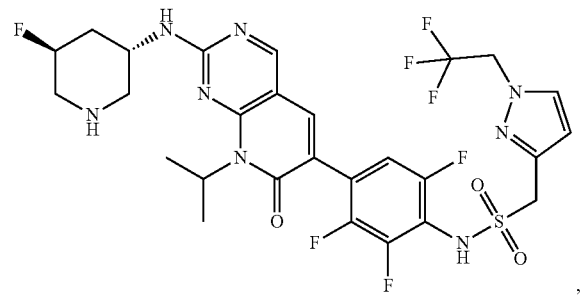 [SMILES: CC(C)n1c(=O)c(-c2cc(F)c(NS(=O)(=O)Cc3ccn(CC(F)(F)F)n3)c(F)c2F)cc2cnc(N[C@@H]3CNC[C@@H](F)C3)nc21] |
| 159 | 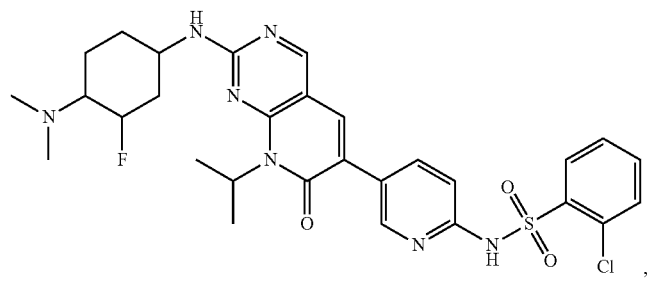 |

| Compound No. | Structure |
|---|---|
| 160 | 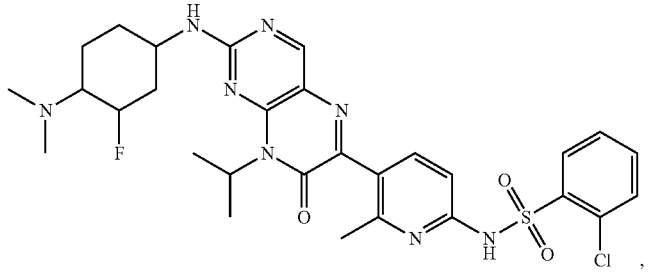 [SMILES: Cc1nc(NS(=O)(=O)c2ccccc2Cl)ccc1-c1nc2cnc(NC3CCC(N(C)C)C(F)C3)nc2n(C(C)C)c1=O] |
| 161 | 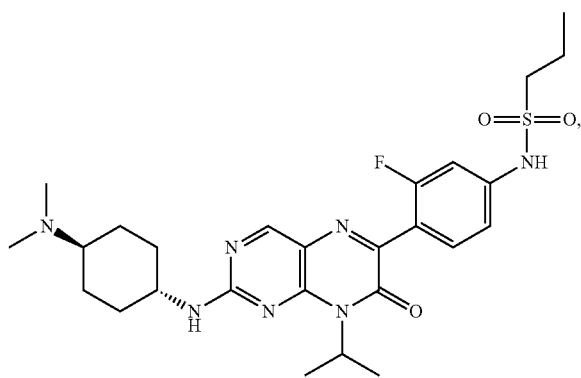 [SMILES: CCCS(=O)(=O)Nc1ccc(-c2nc3cnc(N[C@H]4CC[C@H](N(C)C)CC4)nc3n(C(C)C)c2=O)c(F)c1] |
| 162 | 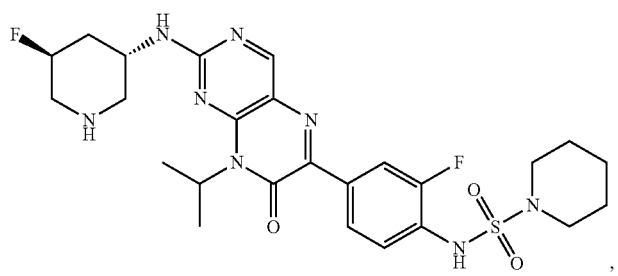 [SMILES: CC(C)n1c(=O)c(-c2ccc(NS(=O)(=O)N3CCCCC3)c(F)c2)nc2cnc(N[C@@H]3CNC[C@@H](F)C3)nc21] |
| 163 | 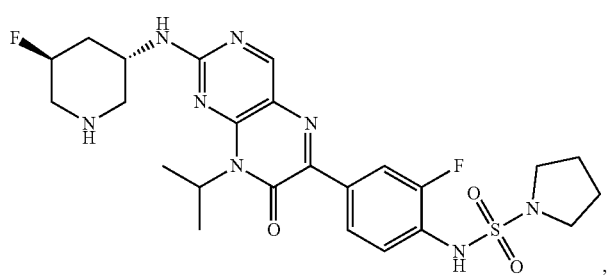 [SMILES: CC(C)n1c(=O)c(-c2ccc(NS(=O)(=O)N3CCCC3)c(F)c2)nc2cnc(N[C@@H]3CNC[C@@H](F)C3)nc21] |
| 164 | 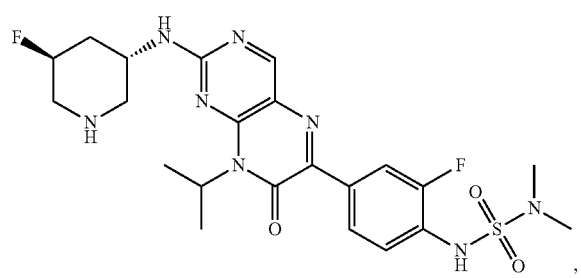 [SMILES: CC(C)n1c(=O)c(-c2ccc(NS(=O)(=O)N(C)C)c(F)c2)nc2cnc(N[C@@H]3CNC[C@@H](F)C3)nc21] |

-continued
| Compound No. | Structure |
|---|---|
| 165 | 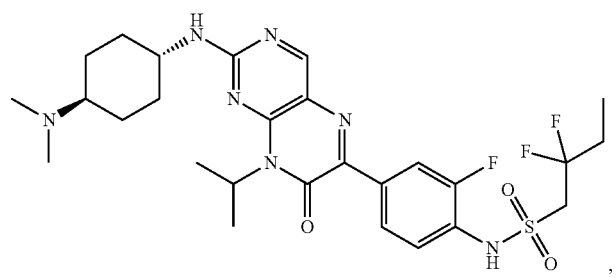 [SMILES: CCC(F)(F)CS(=O)(=O)Nc1ccc(-c2nc3cnc(N[C@H]4CC[C@H](N(C)C)CC4)nc3n(C(C)C)c2=O)cc1F] |
| 166 | 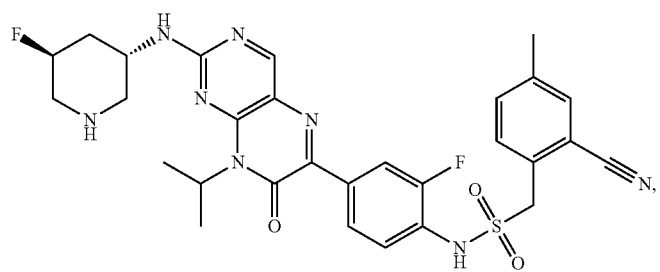 |
| 167 | 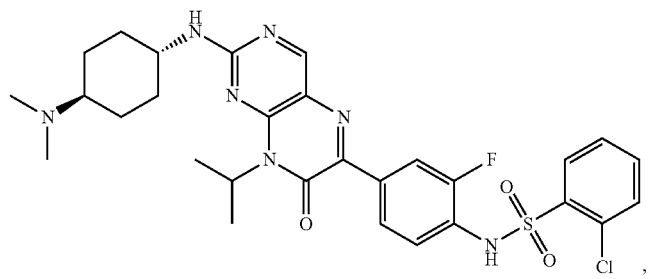 [SMILES: CC(C)n1c(=O)c(-c2ccc(NS(=O)(=O)c3ccccc3Cl)c(F)c2)nc2cnc(N[C@H]3CC[C@H](N(C)C)CC3)nc21] |
| 168 168A 168B | 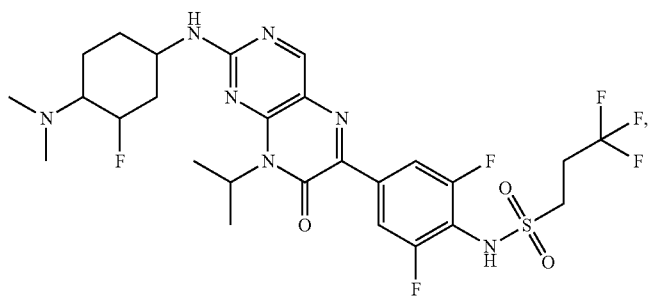 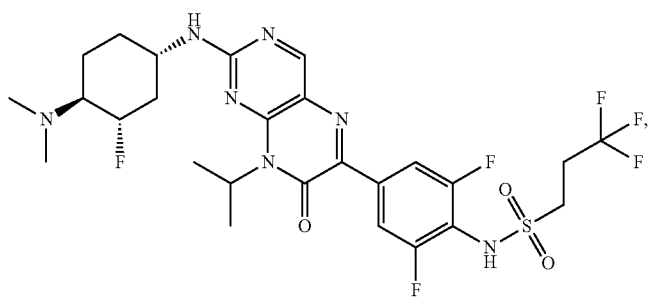 [SMILES: CC(C)n1c(=O)c(-c2cc(F)c(NS(=O)(=O)CCC(F)(F)F)c(F)c2)nc2cnc(N[C@H]3CC[C@H](N(C)C)[C@@H](F)C3)nc21] |

| Compound No. | Structure |
|---|---|
| | 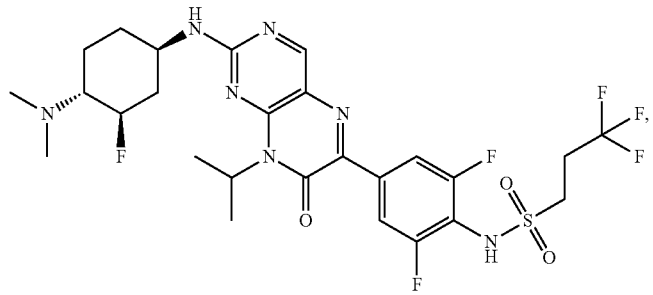 [SMILES: CC(C)n1c(=O)c(-c2cc(F)c(NS(=O)(=O)CCC(F)(F)F)c(F)c2)nc2cnc(N[C@@H]3CC[C@@H](N(C)C)[C@H](F)C3)nc21] |
| 169 | 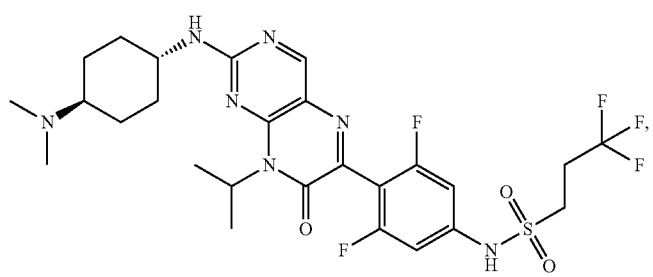 [SMILES: CC(C)n1c(=O)c(-c2c(F)cc(NS(=O)(=O)CCC(F)(F)F)cc2F)nc2cnc(N[C@H]3CC[C@H](N(C)C)CC3)nc21] |
| 170 | 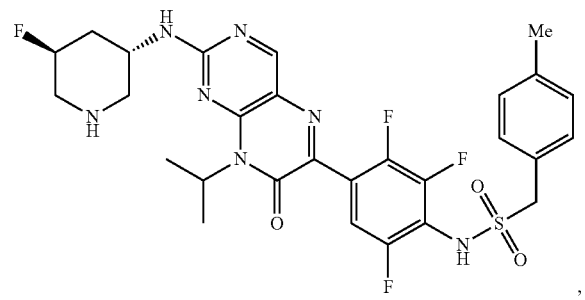 [SMILES: Cc1ccc(CS(=O)(=O)Nc2c(F)cc(-c3nc4cnc(N[C@@H]5CNC[C@@H](F)C5)nc4n(C(C)C)c3=O)c(F)c2F)cc1] |
| 171 | 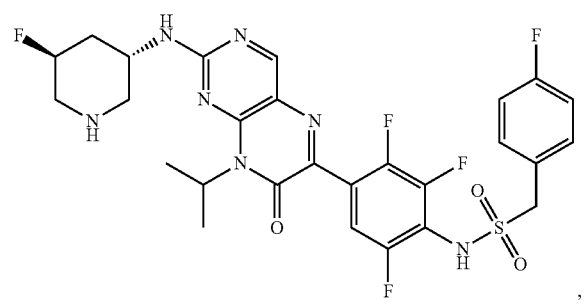 [SMILES: CC(C)n1c(=O)c(-c2cc(F)c(NS(=O)(=O)Cc3ccc(F)cc3)c(F)c2F)nc2cnc(N[C@@H]3CNC[C@@H](F)C3)nc21] |
| 172 | 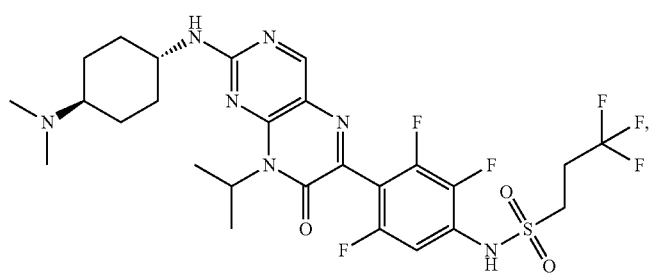 [SMILES: CC(C)n1c(=O)c(-c2c(F)cc(NS(=O)(=O)CCC(F)(F)F)c(F)c2F)nc2cnc(N[C@H]3CC[C@H](N(C)C)CC3)nc21] |

| Compound No. | Structure |
|---|---|
| 173 | 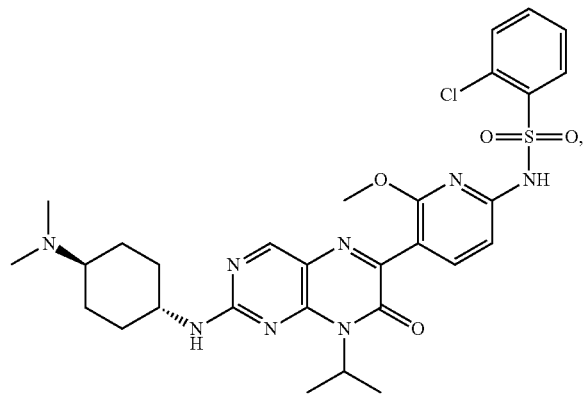 [SMILES: COc1nc(NS(=O)(=O)c2ccccc2Cl)ccc1-c1nc2cnc(N[C@H]3CC[C@H](N(C)C)CC3)nc2n(C(C)C)c1=O] |
| 174 | 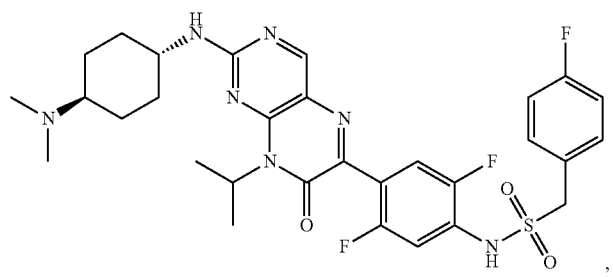 |
| 175 | 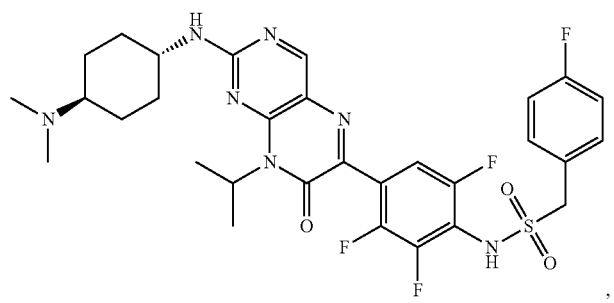 [SMILES: CC(C)n1c(=O)c(-c2cc(F)c(NS(=O)(=O)Cc3ccc(F)cc3)c(F)c2F)nc2cnc(N[C@H]3CC[C@H](N(C)C)CC3)nc21] |
| 176 | 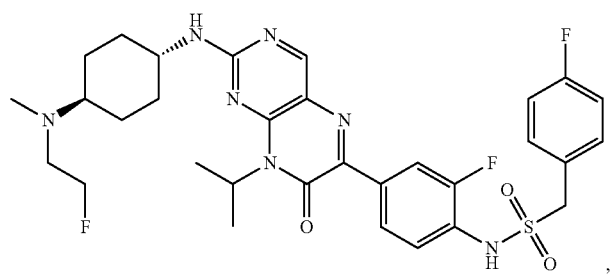 [SMILES: CC(C)n1c(=O)c(-c2ccc(NS(=O)(=O)Cc3ccc(F)cc3)c(F)c2)nc2cnc(N[C@H]3CC[C@H](N(C)CCF)CC3)nc21] |
| 177 | 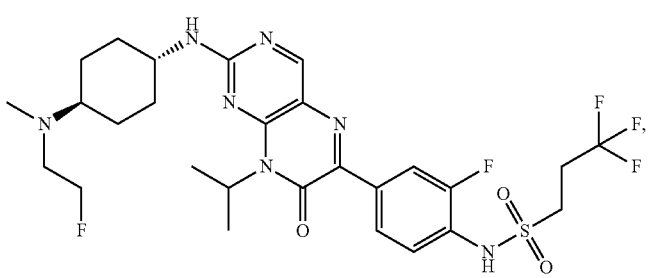 [SMILES: CC(C)n1c(=O)c(-c2ccc(NS(=O)(=O)CCC(F)(F)F)c(F)c2)nc2cnc(N[C@H]3CC[C@H](N(C)CCF)CC3)nc21] |

| Compound No. | Structure |
|---|---|
| 178 | 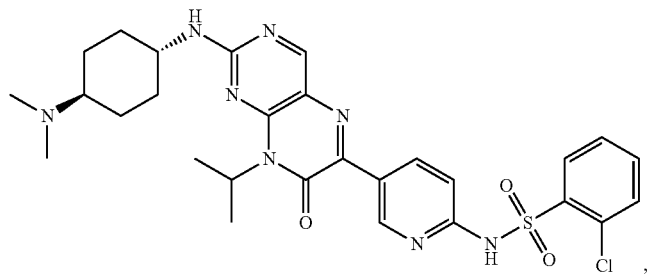 [SMILES: CC(C)n1c(=O)c(-c2ccc(NS(=O)(=O)c3ccccc3Cl)nc2)nc2cnc(N[C@H]3CC[C@H](N(C)C)CC3)nc21] |
| 179 179A 179B | 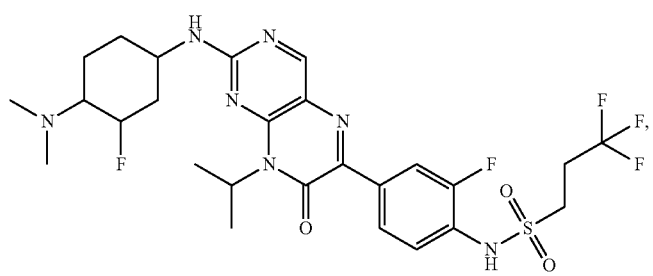 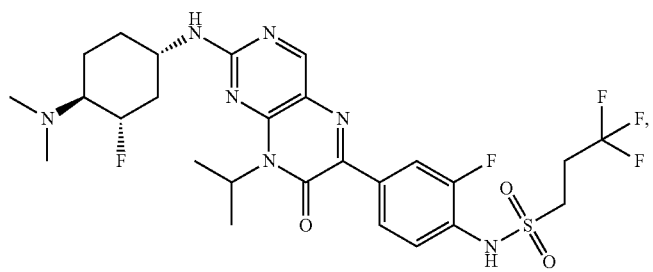 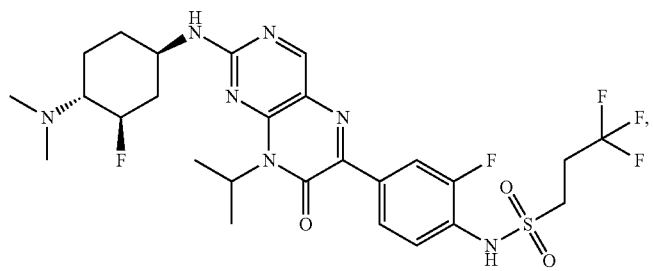 [SMILES: CC(C)n1c(=O)c(-c2ccc(NS(=O)(=O)CCC(F)(F)F)c(F)c2)nc2cnc(N[C@@H]3CC[C@@H](N(C)C)[C@H](F)C3)nc21] |
| 180 | 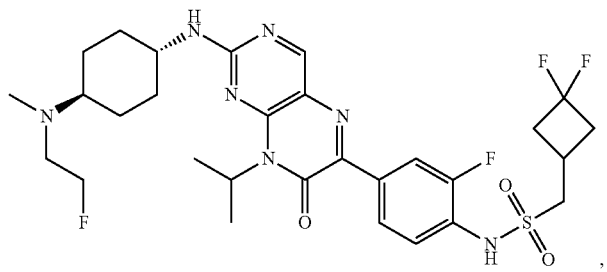 [SMILES: CC(C)n1c(=O)c(-c2ccc(NS(=O)(=O)CC3CC(F)(F)C3)c(F)c2)nc2cnc(N[C@H]3CC[C@H](N(C)CCF)CC3)nc21] |

-continued
| Compound No. | Structure |
|---|---|
| 181<br>181A<br>181B | 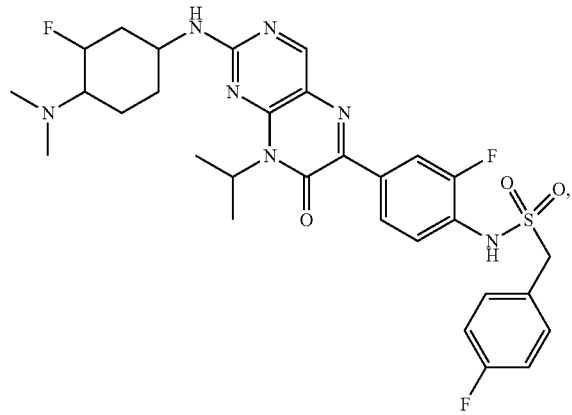 [SMILES: CC(C)n1c(=O)c(-c2ccc(NS(=O)(=O)Cc3ccc(F)cc3)c(F)c2)nc2cnc(NC3CCC(N(C)C)C(F)C3)nc21]<br>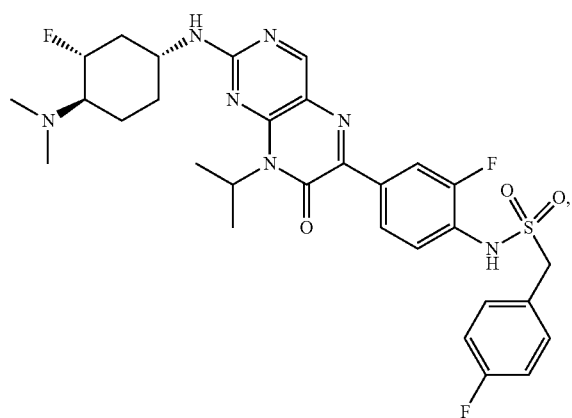 [SMILES: CC(C)n1c(=O)c(-c2ccc(NS(=O)(=O)Cc3ccc(F)cc3)c(F)c2)nc2cnc(N[C@@H]3CC[C@@H](N(C)C)[C@H](F)C3)nc21]<br>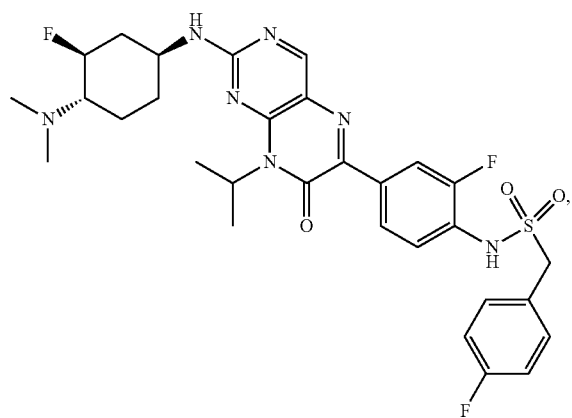 [SMILES: CC(C)n1c(=O)c(-c2ccc(NS(=O)(=O)Cc3ccc(F)cc3)c(F)c2)nc2cnc(N[C@H]3CC[C@H](N(C)C)[C@@H](F)C3)nc21] |
| 182 | 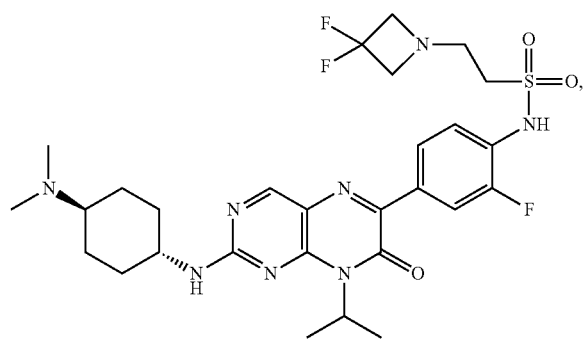 [SMILES: CC(C)n1c(=O)c(-c2ccc(NS(=O)(=O)CCN3CC(F)(F)C3)c(F)c2)nc2cnc(N[C@H]3CC[C@H](N(C)C)CC3)nc21] |

| Compound No. | Structure |
|---|---|
| 183 | 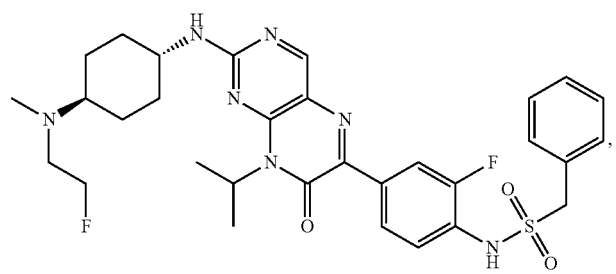 [SMILES: CC(C)n1c(=O)c(-c2ccc(NS(=O)(=O)Cc3ccccc3)c(F)c2)nc2cnc(N[C@H]3CC[C@H](N(C)CCF)CC3)nc21] |
| 184 | 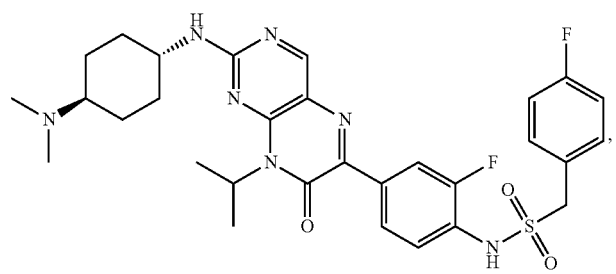 [SMILES: CC(C)n1c(=O)c(-c2ccc(NS(=O)(=O)Cc3ccc(F)cc3)c(F)c2)nc2cnc(N[C@H]3CC[C@H](N(C)C)CC3)nc21] |
| 185 | 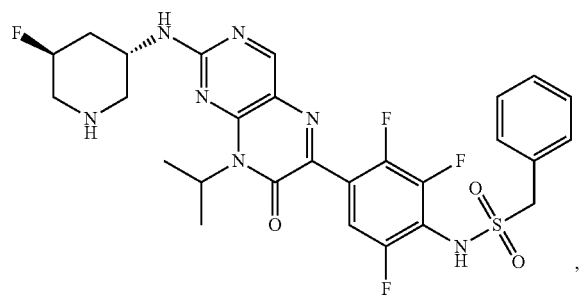 [SMILES: CC(C)n1c(=O)c(-c2cc(F)c(NS(=O)(=O)Cc3ccccc3)c(F)c2F)nc2cnc(N[C@@H]3CNC[C@@H](F)C3)nc21] |
| 186 | 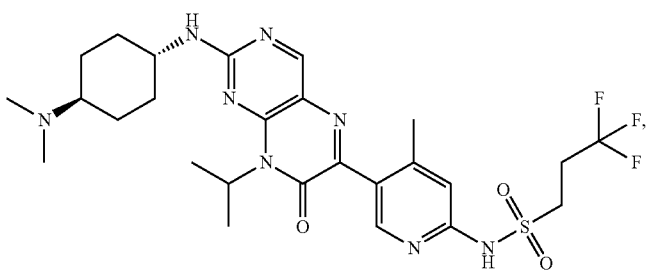 [SMILES: Cc1cc(NS(=O)(=O)CCC(F)(F)F)ncc1-c1nc2cnc(N[C@H]3CC[C@H](N(C)C)CC3)nc2n(C(C)C)c1=O] |
| 187 | 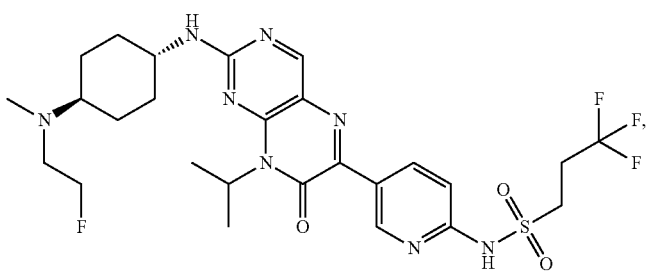 [SMILES: CC(C)n1c(=O)c(-c2ccc(NS(=O)(=O)CCC(F)(F)F)nc2)nc2cnc(N[C@H]3CC[C@H](N(C)CCF)CC3)nc21] |

-continued
| Compound No. | Structure |
|---|---|
| 188 | 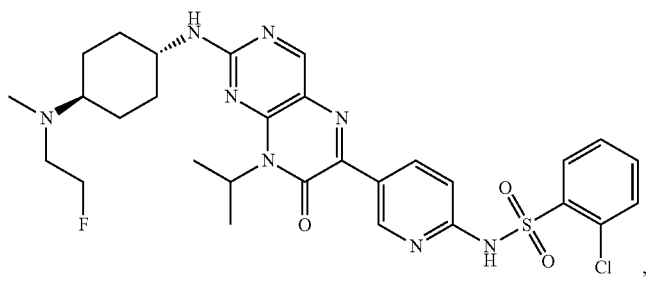 [SMILES: CC(C)n1c(=O)c(-c2ccc(NS(=O)(=O)c3ccccc3Cl)nc2)nc2cnc(N[C@H]3CC[C@H](N(C)CCF)CC3)nc21] |
| 189 | 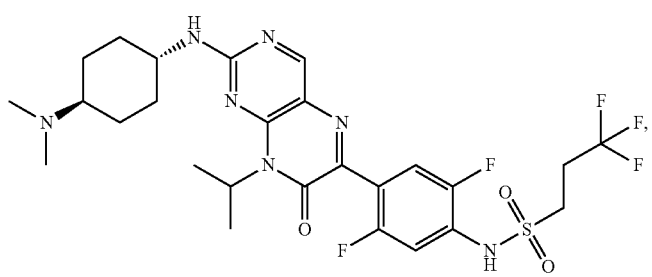 [SMILES: CC(C)n1c(=O)c(-c2cc(F)c(NS(=O)(=O)CCC(F)(F)F)cc2F)nc2cnc(N[C@H]3CC[C@H](N(C)C)CC3)nc21] |
| 190 | 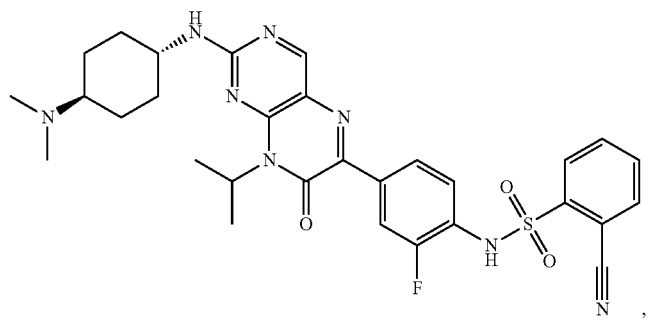 [SMILES: CC(C)n1c(=O)c(-c2ccc(NS(=O)(=O)c3ccccc3C#N)c(F)c2)nc2cnc(N[C@H]3CC[C@H](N(C)C)CC3)nc21] |
| 191 | 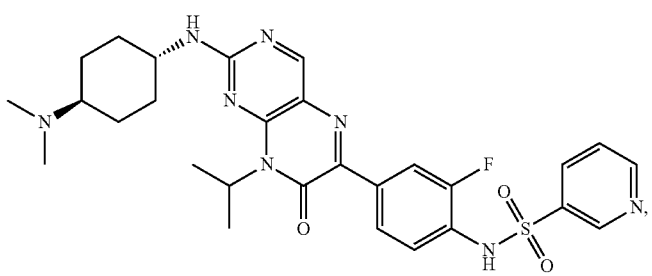 [SMILES: CC(C)n1c(=O)c(-c2ccc(NS(=O)(=O)c3cccnc3)c(F)c2)nc2cnc(N[C@H]3CC[C@H](N(C)C)CC3)nc21] |
| 192<br>192A<br>192B | 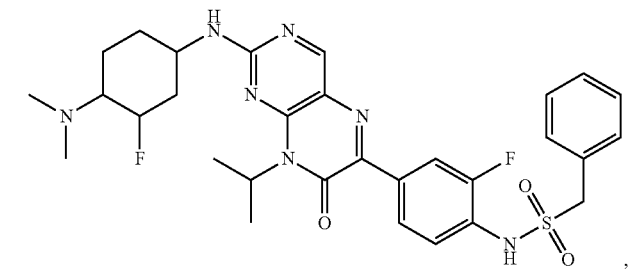 [SMILES: CC(C)n1c(=O)c(-c2ccc(NS(=O)(=O)Cc3ccccc3)c(F)c2)nc2cnc(NC3CCC(N(C)C)C(F)C3)nc21] |

| Compound No. | Structure |
|---|---|
|  | 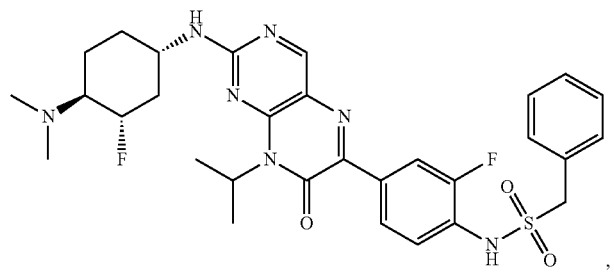 |
|  | 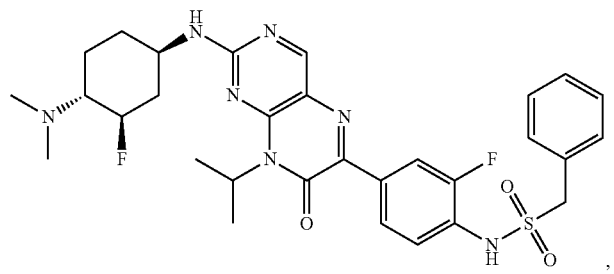 [SMILES: CC(C)n1c(=O)c(-c2ccc(NS(=O)(=O)Cc3ccccc3)c(F)c2)nc2cnc(N[C@@H]3CC[C@@H](N(C)C)[C@H](F)C3)nc21] |
| 193<br>193A<br>193B | 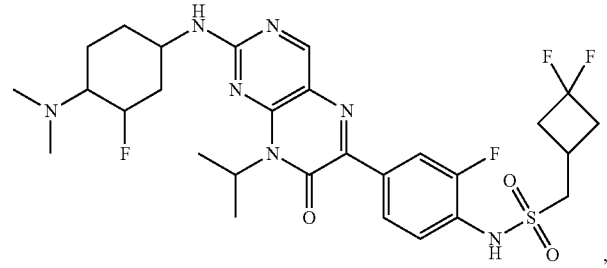 [SMILES: CC(C)n1c(=O)c(-c2ccc(NS(=O)(=O)CC3CC(F)(F)C3)c(F)c2)nc2cnc(NC3CCC(N(C)C)C(F)C3)nc21] |
|  | 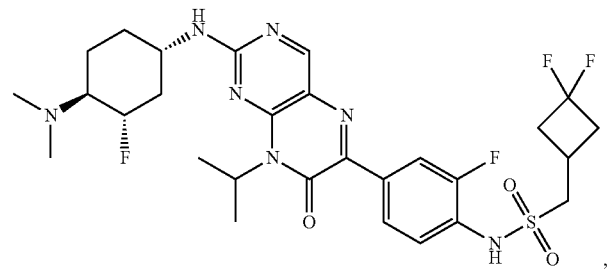 [SMILES: CC(C)n1c(=O)c(-c2ccc(NS(=O)(=O)CC3CC(F)(F)C3)c(F)c2)nc2cnc(N[C@H]3CC[C@H](N(C)C)[C@@H](F)C3)nc21] |
|  | 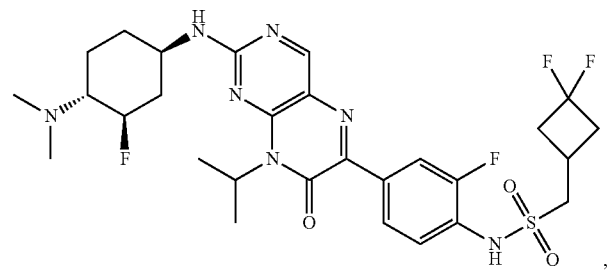 [SMILES: CC(C)n1c(=O)c(-c2ccc(NS(=O)(=O)CC3CC(F)(F)C3)c(F)c2)nc2cnc(N[C@@H]3CC[C@@H](N(C)C)[C@H](F)C3)nc21] |

| Compound No. | Structure |
|---|---|
| 194 | 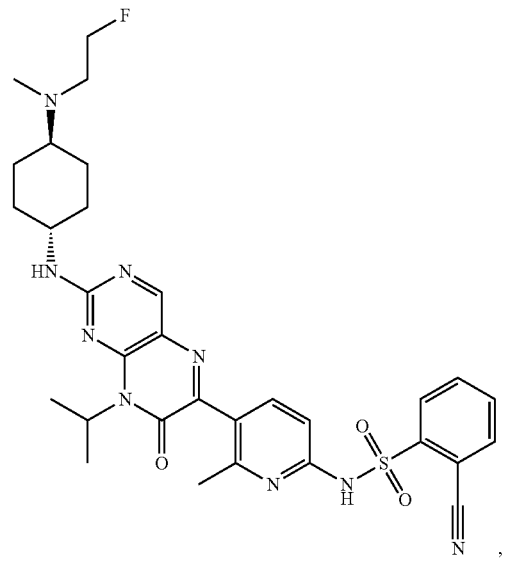 [SMILES: Cc1nc(NS(=O)(=O)c2ccccc2C#N)ccc1-c1nc2cnc(N[C@H]3CC[C@H](N(C)CCF)CC3)nc2n(C(C)C)c1=O] |
| 195 | 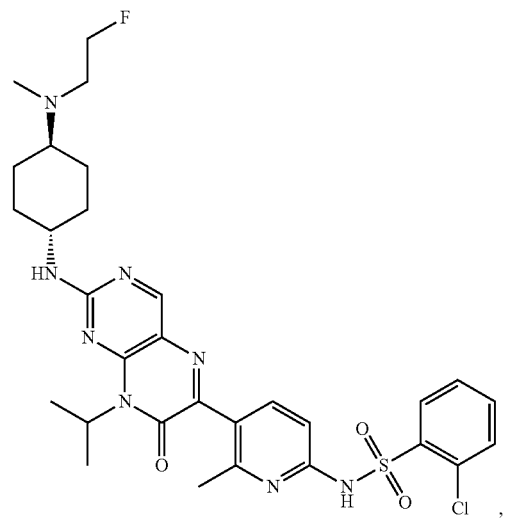 [SMILES: Cc1nc(NS(=O)(=O)c2ccccc2Cl)ccc1-c1nc2cnc(N[C@H]3CC[C@H](N(C)CCF)CC3)nc2n(C(C)C)c1=O] |
| 196 | 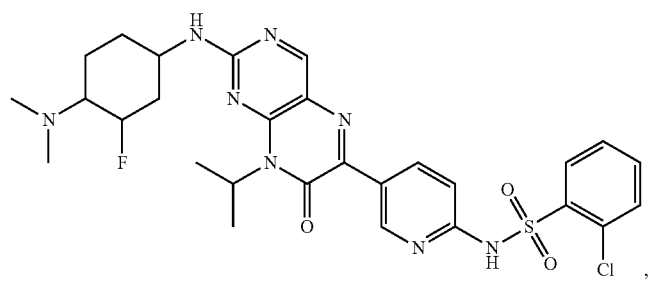 [SMILES: CC(C)n1c(=O)c(-c2ccc(NS(=O)(=O)c3ccccc3Cl)nc2)nc2cnc(NC3CCC(N(C)C)C(F)C3)nc21] |

-continued
| Compound No. | Structure |
|---|---|
| 197 | 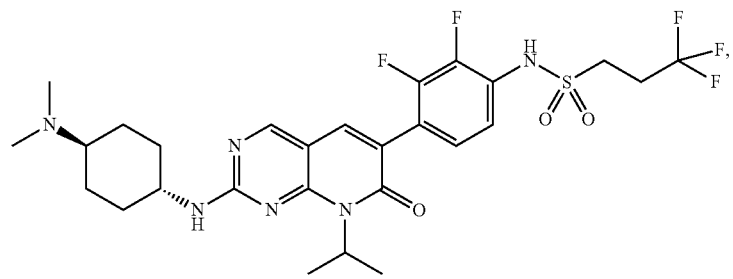 [SMILES: CC(C)n1c(=O)c(-c2ccc(NS(=O)(=O)CCC(F)(F)F)c(F)c2F)cc2cnc(N[C@H]3CC[C@H](N(C)C)CC3)nc21] |
| 198 | 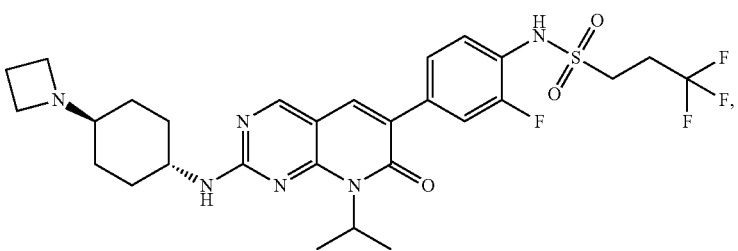 [SMILES: CC(C)n1c(=O)c(-c2ccc(NS(=O)(=O)CCC(F)(F)F)c(F)c2)cc2cnc(N[C@H]3CC[C@H](N4CCC4)CC3)nc21] |
| 199 | 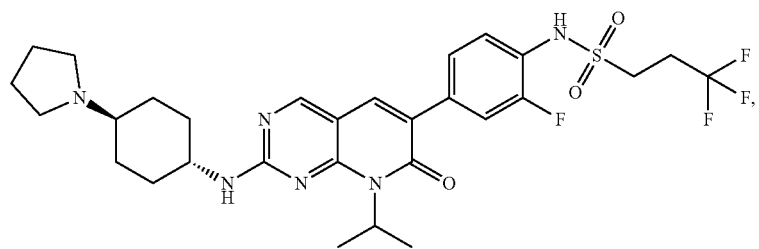 [SMILES: CC(C)n1c(=O)c(-c2ccc(NS(=O)(=O)CCC(F)(F)F)c(F)c2)cc2cnc(N[C@H]3CC[C@H](N4CCCC4)CC3)nc21] |
| 200 | 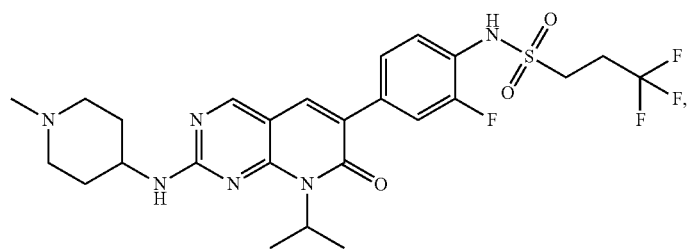 [SMILES: CC(C)n1c(=O)c(-c2ccc(NS(=O)(=O)CCC(F)(F)F)c(F)c2)cc2cnc(NC3CCN(C)CC3)nc21] |
| 201 | 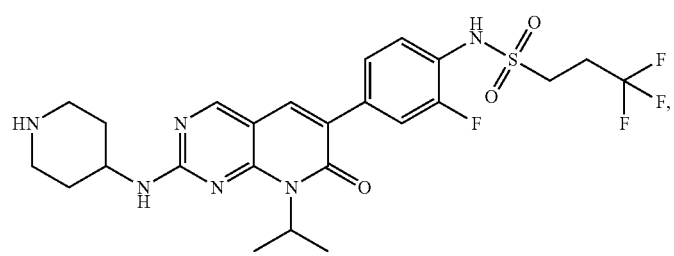 [SMILES: CC(C)n1c(=O)c(-c2ccc(NS(=O)(=O)CCC(F)(F)F)c(F)c2)cc2cnc(NC3CCNCC3)nc21] |

| Compound No. | Structure |
|---|---|
| 202<br>202A<br>202B | 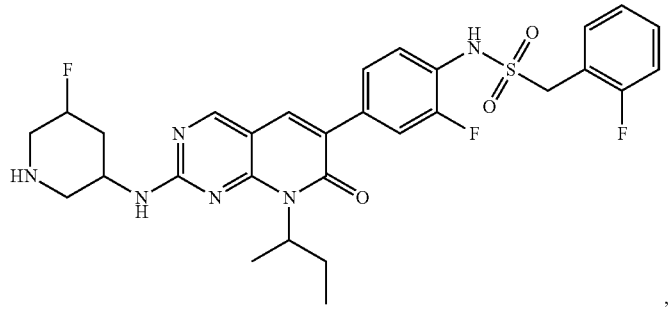 [SMILES: CCC(C)n1c(=O)c(-c2ccc(NS(=O)(=O)Cc3ccccc3F)c(F)c2)cc2cnc(NC3CNCC(F)C3)nc21], 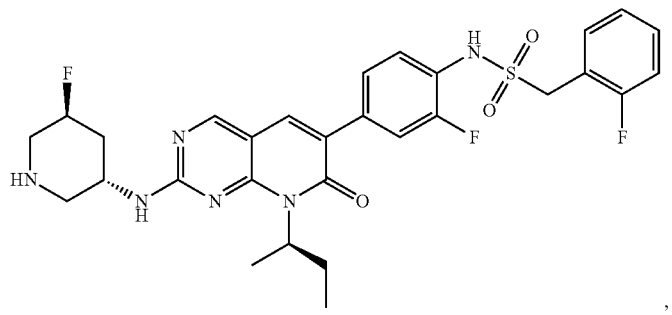 [SMILES: CC[C@@H](C)n1c(=O)c(-c2ccc(NS(=O)(=O)Cc3ccccc3F)c(F)c2)cc2cnc(N[C@@H]3CNC[C@@H](F)C3)nc21], 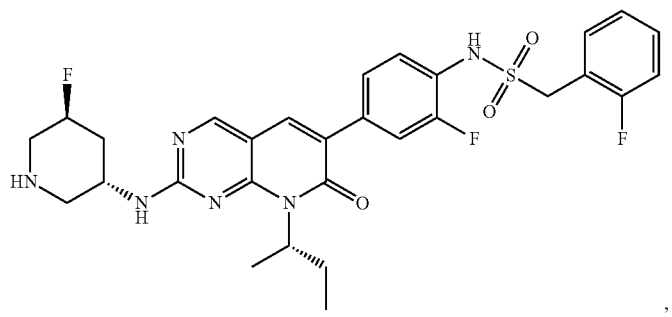 [SMILES: CC[C@H](C)n1c(=O)c(-c2ccc(NS(=O)(=O)Cc3ccccc3F)c(F)c2)cc2cnc(N[C@@H]3CNC[C@@H](F)C3)nc21], |
| 203 | 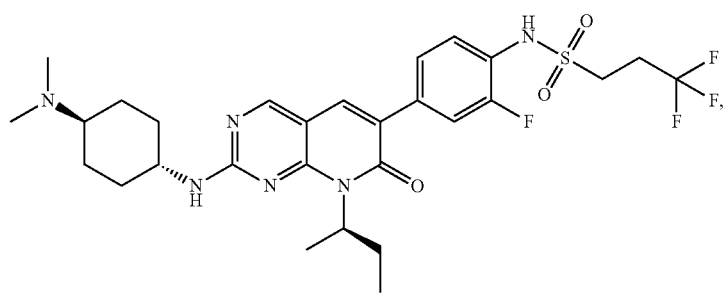 [SMILES: CC[C@@H](C)n1c(=O)c(-c2ccc(NS(=O)(=O)CCC(F)(F)F)c(F)c2)cc2cnc(N[C@H]3CC[C@H](N(C)C)CC3)nc21] |
| 203A | 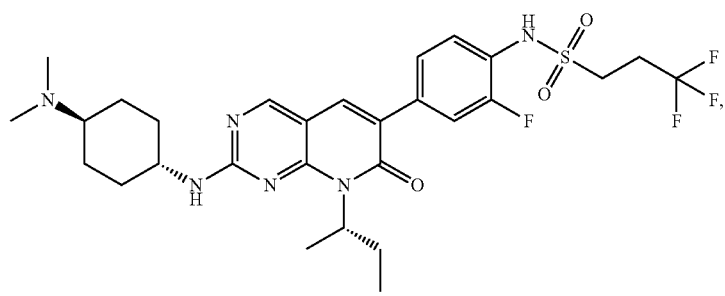 [SMILES: CC[C@H](C)n1c(=O)c(-c2ccc(NS(=O)(=O)CCC(F)(F)F)c(F)c2)cc2cnc(N[C@H]3CC[C@H](N(C)C)CC3)nc21] |

| Compound No. | Structure |
|---|---|
| 204 | 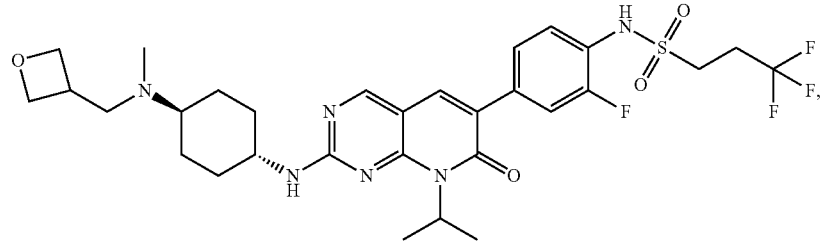 [SMILES: CC(C)n1c(=O)c(-c2ccc(NS(=O)(=O)CCC(F)(F)F)c(F)c2)cc2cnc(N[C@H]3CC[C@H](N(C)CC4COC4)CC3)nc21] |
| 205 | 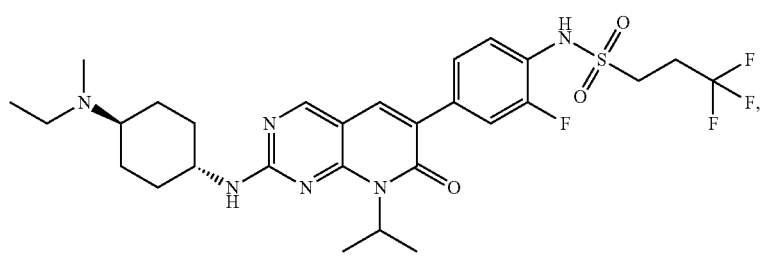 [SMILES: CCN(C)[C@H]1CC[C@H](Nc2ncc3cc(-c4ccc(NS(=O)(=O)CCC(F)(F)F)c(F)c4)c(=O)n(C(C)C)c3n2)CC1] |
| 206 | 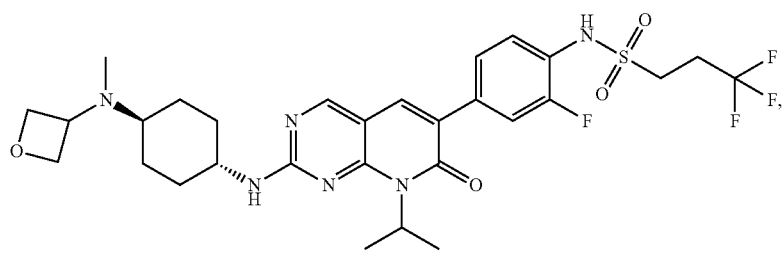 [SMILES: CC(C)n1c(=O)c(-c2ccc(NS(=O)(=O)CCC(F)(F)F)c(F)c2)cc2cnc(N[C@H]3CC[C@H](N(C)C4COC4)CC3)nc21] |
| 207 | 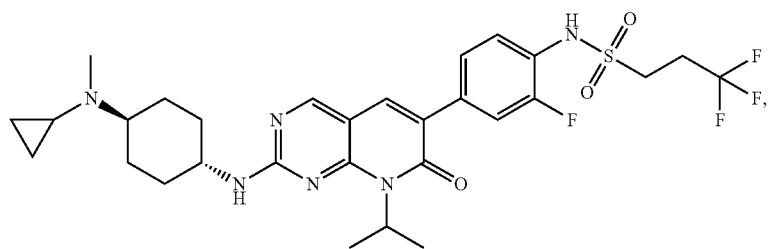 [SMILES: CC(C)n1c(=O)c(-c2ccc(NS(=O)(=O)CCC(F)(F)F)c(F)c2)cc2cnc(N[C@H]3CC[C@H](N(C)C4CC4)CC3)nc21] |
| 208 | 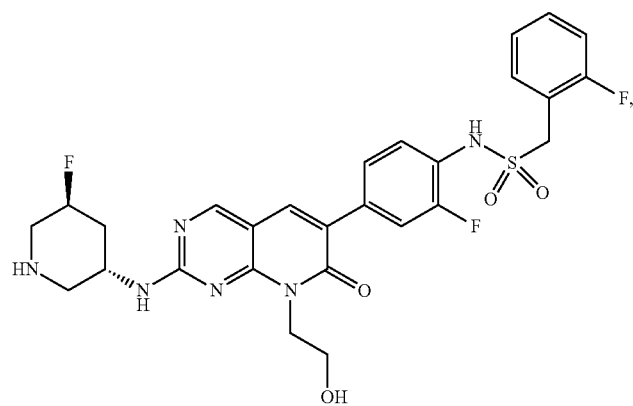 [SMILES: O=c1c(-c2ccc(NS(=O)(=O)Cc3ccccc3F)c(F)c2)cc2cnc(N[C@@H]3CNC[C@@H](F)C3)nc2n1CCO] |

| Compound No. | Structure |
|---|---|
| 209 | 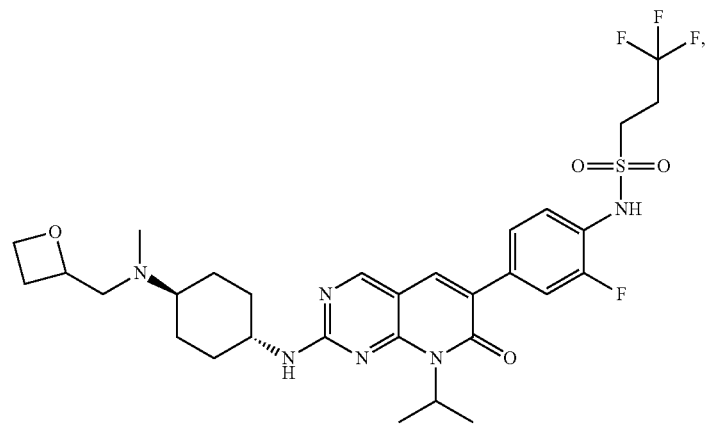 [SMILES: CC(C)n1c(=O)c(-c2ccc(NS(=O)(=O)CCC(F)(F)F)c(F)c2)cc2cnc(N[C@H]3CC[C@H](N(C)CC4CCO4)CC3)nc21] |
| 210 | 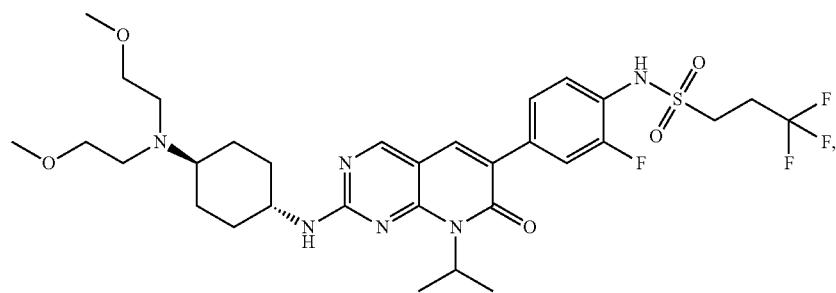 [SMILES: COCCN(CCOC)[C@H]1CC[C@H](Nc2ncc3cc(-c4ccc(NS(=O)(=O)CCC(F)(F)F)c(F)c4)c(=O)n(C(C)C)c3n2)CC1] |
| 211 | 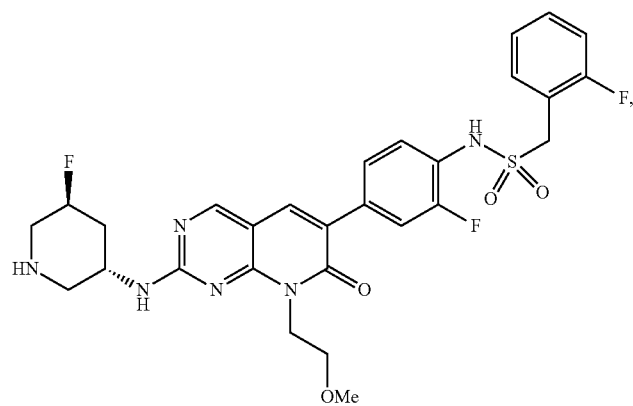 [SMILES: COCCn1c(=O)c(-c2ccc(NS(=O)(=O)Cc3ccccc3F)c(F)c2)cc2cnc(N[C@@H]3CNC[C@@H](F)C3)nc21] |
| 212 | 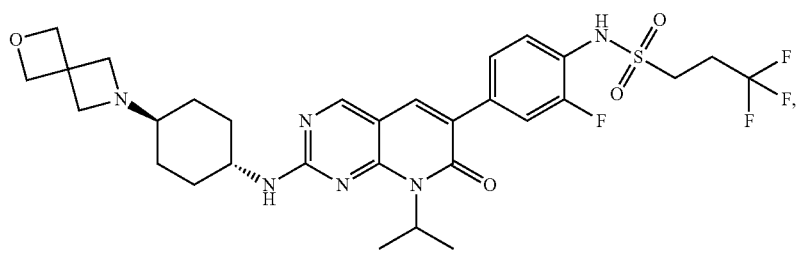 [SMILES: CC(C)n1c(=O)c(-c2ccc(NS(=O)(=O)CCC(F)(F)F)c(F)c2)cc2cnc(N[C@H]3CC[C@H](N4CC5(COC5)C4)CC3)nc21] |

| Compound No. | Structure |
|---|---|
| 213 | 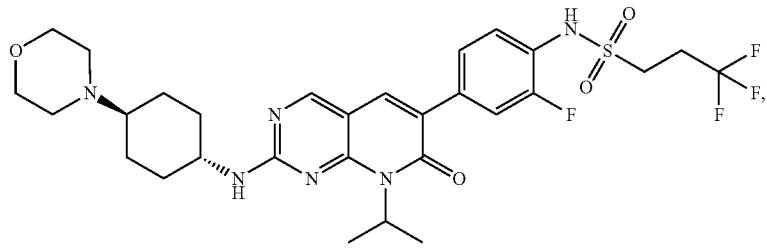 [SMILES: CC(C)n1c(=O)c(-c2ccc(NS(=O)(=O)CCC(F)(F)F)c(F)c2)cc2cnc(N[C@H]3CC[C@H](N4CCOCC4)CC3)nc21] |
| 214 214A 214B 214C 214D | 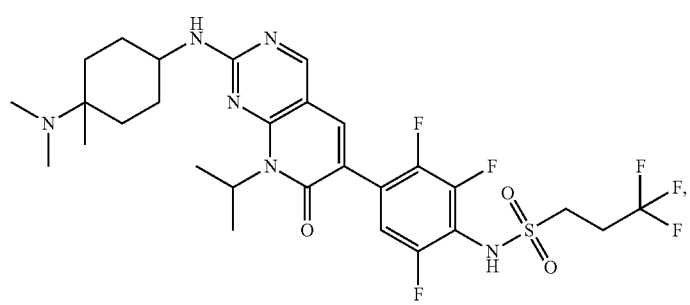 [SMILES: CC(C)n1c(=O)c(-c2cc(F)c(NS(=O)(=O)CCC(F)(F)F)c(F)c2F)cc2cnc(NC3CCC(C)(N(C)C)CC3)nc21]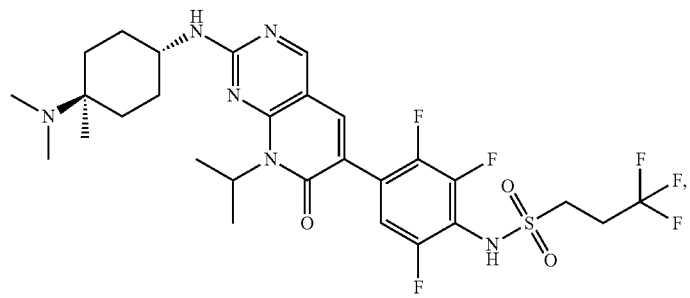 [SMILES: CC(C)n1c(=O)c(-c2cc(F)c(NS(=O)(=O)CCC(F)(F)F)c(F)c2F)cc2cnc(N[C@H]3CC[C@](C)(N(C)C)CC3)nc21]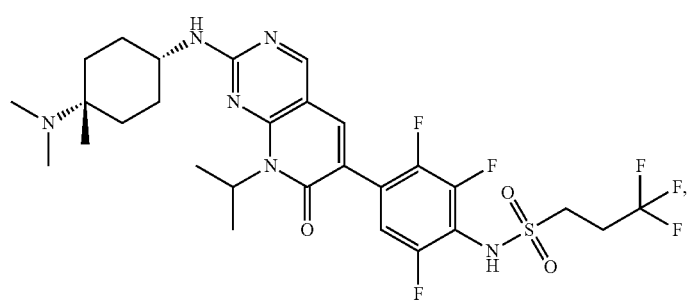 [SMILES: CC(C)n1c(=O)c(-c2cc(F)c(NS(=O)(=O)CCC(F)(F)F)c(F)c2F)cc2cnc(N[C@H]3CC[C@@](C)(N(C)C)CC3)nc21]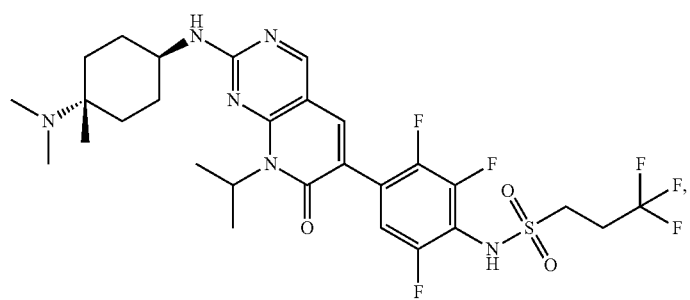 [SMILES: CC(C)n1c(=O)c(-c2cc(F)c(NS(=O)(=O)CCC(F)(F)F)c(F)c2F)cc2cnc(N[C@H]3CC[C@](C)(N(C)C)CC3)nc21] |

| Compound No. | Structure |
|---|---|
| | 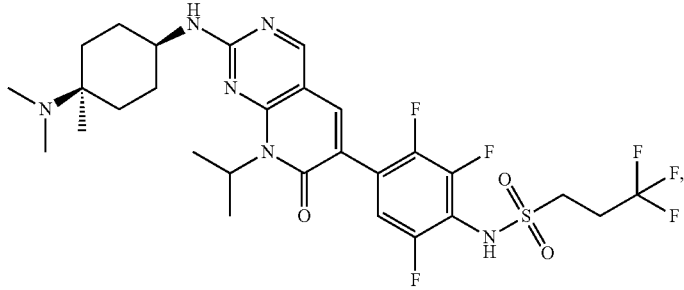 [SMILES: CC(C)n1c(=O)c(-c2cc(F)c(NS(=O)(=O)CCC(F)(F)F)c(F)c2F)cc2cnc(N[C@H]3CC[C@@](C)(N(C)C)CC3)nc21] |
| 215 | 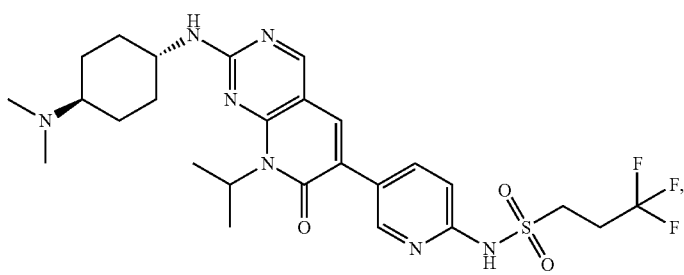 [SMILES: CC(C)n1c(=O)c(-c2ccc(NS(=O)(=O)CCC(F)(F)F)nc2)cc2cnc(N[C@H]3CC[C@H](N(C)C)CC3)nc21] |
| 216 | 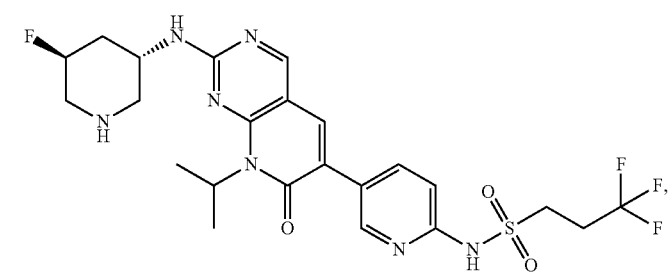 [SMILES: CC(C)n1c(=O)c(-c2ccc(NS(=O)(=O)CCC(F)(F)F)nc2)cc2cnc(N[C@@H]3CNC[C@@H](F)C3)nc21] |
| 217<br>217A<br>217B<br>217C<br>217D | 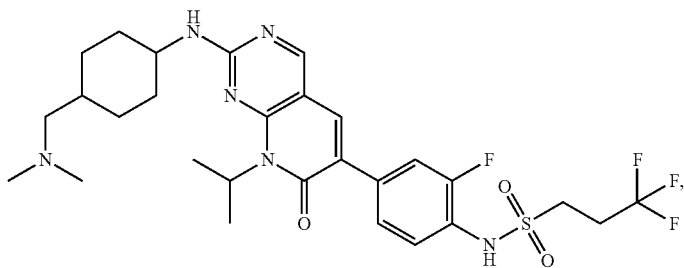 [SMILES: CC(C)n1c(=O)c(-c2ccc(NS(=O)(=O)CCC(F)(F)F)c(F)c2)cc2cnc(NC3CCC(CN(C)C)CC3)nc21]<br>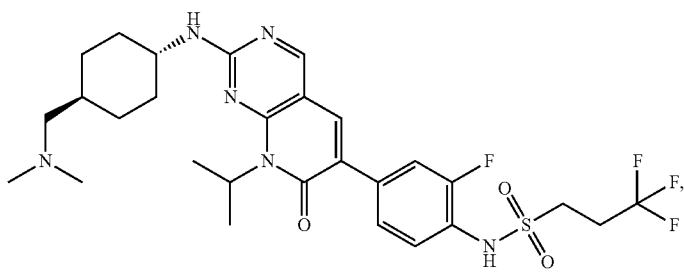 [SMILES: CC(C)n1c(=O)c(-c2ccc(NS(=O)(=O)CCC(F)(F)F)c(F)c2)cc2cnc(N[C@H]3CC[C@H](CN(C)C)CC3)nc21] |

| Compound No. | Structure |
|---|---|
| | 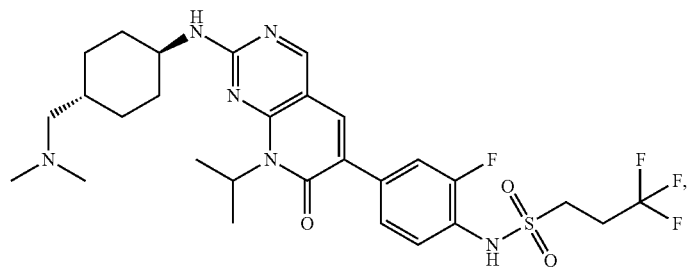 [SMILES: CC(C)n1c(=O)c(-c2ccc(NS(=O)(=O)CCC(F)(F)F)c(F)c2)cc2cnc(N[C@H]3CC[C@H](CN(C)C)CC3)nc21] |
| | 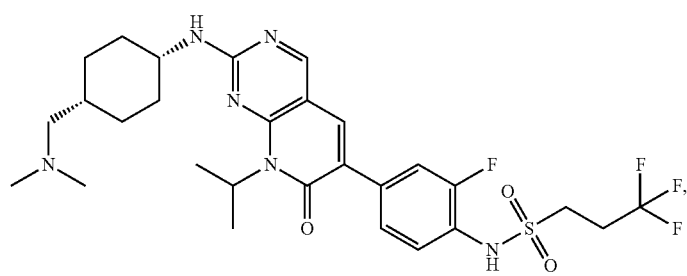 [SMILES: CC(C)n1c(=O)c(-c2ccc(NS(=O)(=O)CCC(F)(F)F)c(F)c2)cc2cnc(N[C@H]3CC[C@@H](CN(C)C)CC3)nc21] |
| | 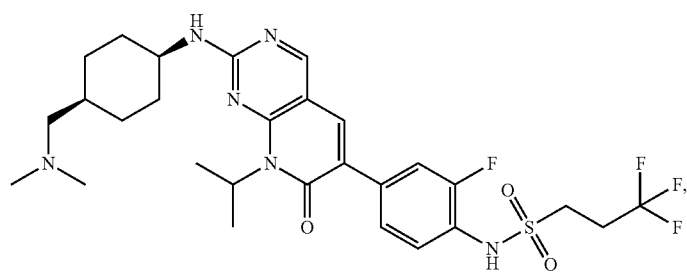 [SMILES: CC(C)n1c(=O)c(-c2ccc(NS(=O)(=O)CCC(F)(F)F)c(F)c2)cc2cnc(N[C@H]3CC[C@@H](CN(C)C)CC3)nc21] |
| 218 | 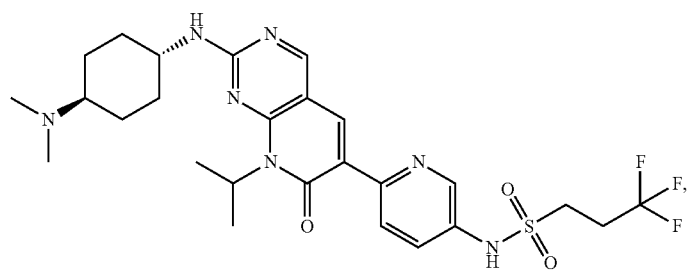 [SMILES: CC(C)n1c(=O)c(-c2ccc(NS(=O)(=O)CCC(F)(F)F)cn2)cc2cnc(N[C@H]3CC[C@H](N(C)C)CC3)nc21] |
| 219 | 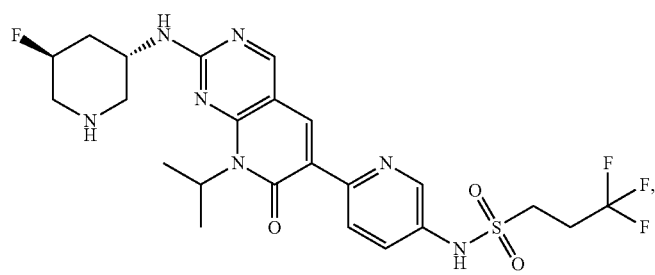 [SMILES: CC(C)n1c(=O)c(-c2ccc(NS(=O)(=O)CCC(F)(F)F)cn2)cc2cnc(N[C@@H]3CNC[C@@H](F)C3)nc21] |

| Compound No. | Structure |
|---|---|
| 220 | 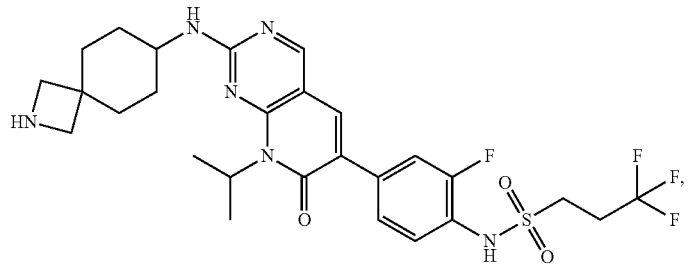 [SMILES: CC(C)n1c(=O)c(-c2ccc(NS(=O)(=O)CCC(F)(F)F)c(F)c2)cc2cnc(NC3CCC4(CC3)CNC4)nc21] |
| 221 | 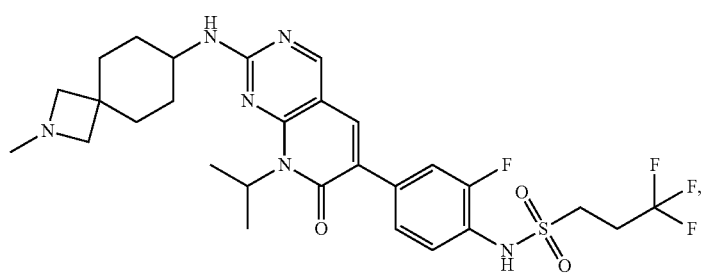 [SMILES: CC(C)n1c(=O)c(-c2ccc(NS(=O)(=O)CCC(F)(F)F)c(F)c2)cc2cnc(NC3CCC4(CC3)CN(C)C4)nc21] |
| 222 | 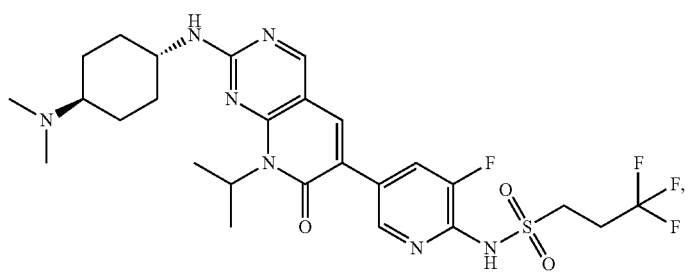 [SMILES: CC(C)n1c(=O)c(-c2cnc(NS(=O)(=O)CCC(F)(F)F)c(F)c2)cc2cnc(N[C@H]3CC[C@H](N(C)C)CC3)nc21] |
| 223 | 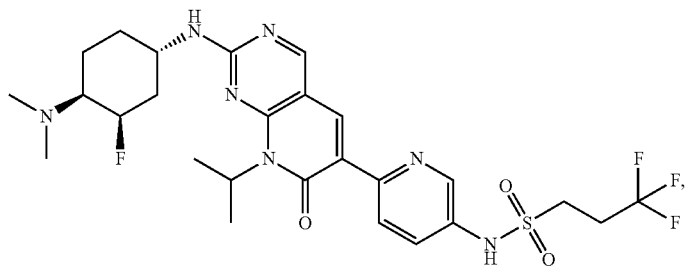 [SMILES: CC(C)n1c(=O)c(-c2ccc(NS(=O)(=O)CCC(F)(F)F)cn2)cc2cnc(N[C@H]3CC[C@H](N(C)C)[C@H](F)C3)nc21] |
| 224 | 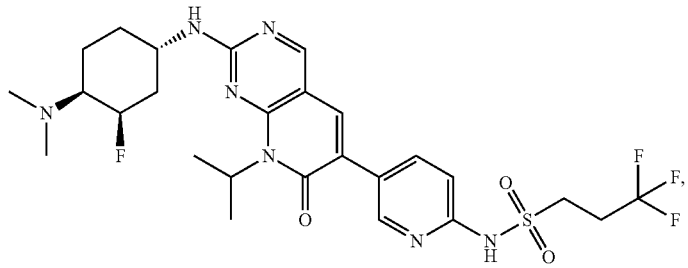 [SMILES: CC(C)n1c(=O)c(-c2ccc(NS(=O)(=O)CCC(F)(F)F)nc2)cc2cnc(N[C@H]3CC[C@H](N(C)C)[C@H](F)C3)nc21] |

| Compound No. | Structure |
|---|---|
| 225 | 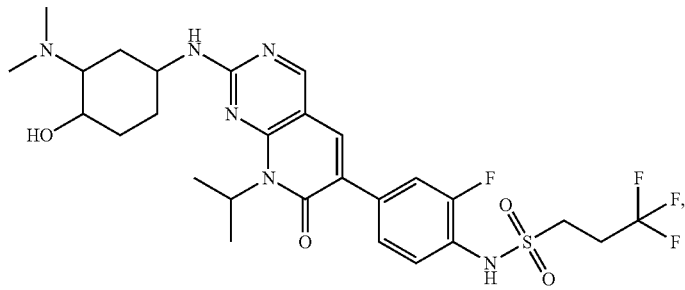 [SMILES: CC(C)n1c(=O)c(-c2ccc(NS(=O)(=O)CCC(F)(F)F)c(F)c2)cc2cnc(NC3CCC(O)C(N(C)C)C3)nc21] |
| 226 | 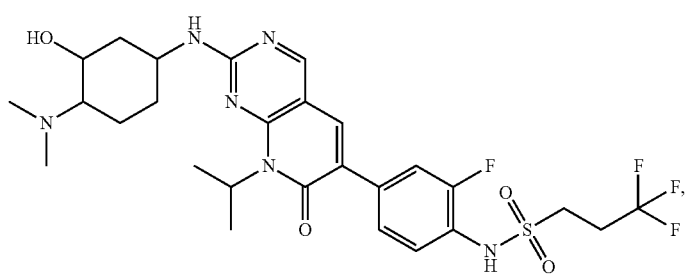 [SMILES: CC(C)n1c(=O)c(-c2ccc(NS(=O)(=O)CCC(F)(F)F)c(F)c2)cc2cnc(NC3CCC(N(C)C)C(O)C3)nc21] |
| 227 | 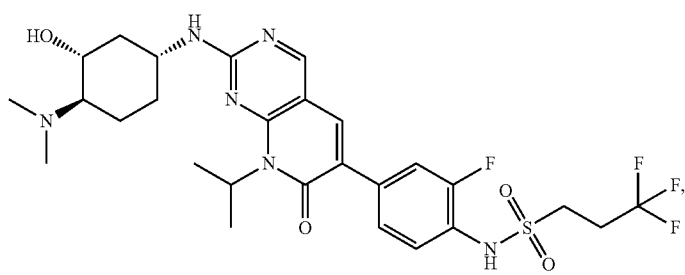 [SMILES: CC(C)n1c(=O)c(-c2ccc(NS(=O)(=O)CCC(F)(F)F)c(F)c2)cc2cnc(N[C@@H]3CC[C@@H](N(C)C)[C@H](O)C3)nc21] |
| 228 | 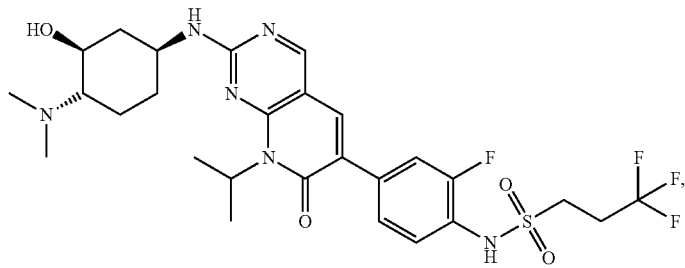 |
| 229 | 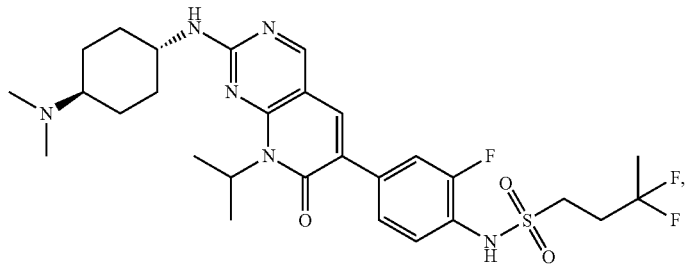 [SMILES: CC(C)n1c(=O)c(-c2ccc(NS(=O)(=O)CCC(C)(F)F)c(F)c2)cc2cnc(N[C@H]3CC[C@H](N(C)C)CC3)nc21] |

| Compound No. | Structure |
|---|---|
| 230 | 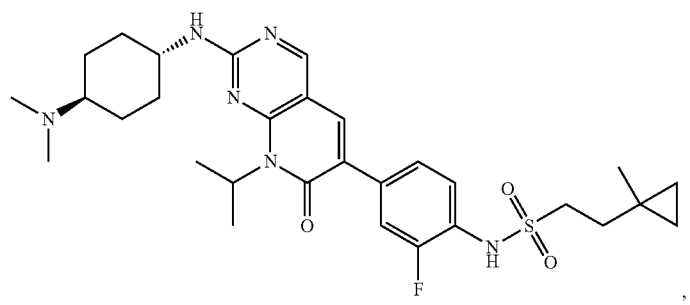 [SMILES: CC(C)n1c(=O)c(-c2ccc(NS(=O)(=O)CCC3(C)CC3)c(F)c2)cc2cnc(N[C@H]3CC[C@H](N(C)C)CC3)nc21] , |
| 231 | 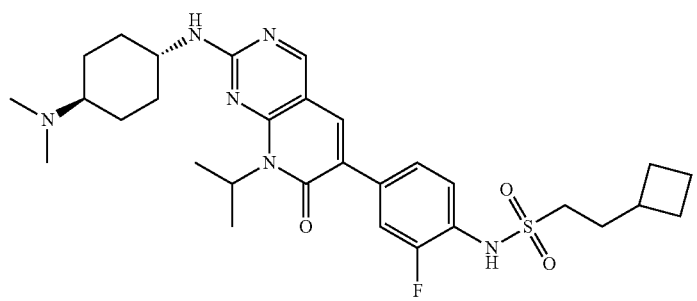 , |
| 232 | 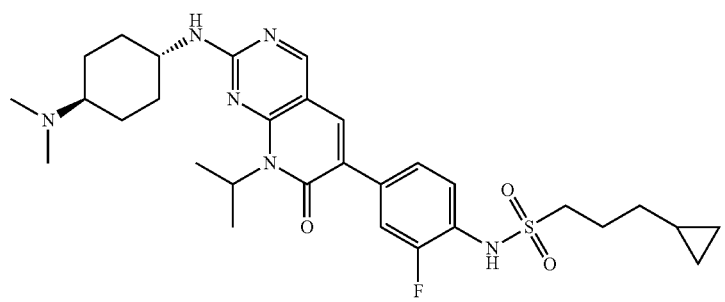 , |
| 233 | 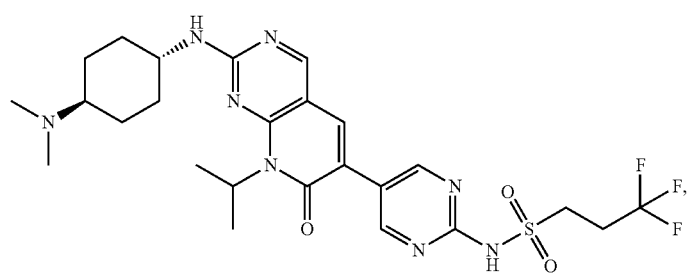 [SMILES: CC(C)n1c(=O)c(-c2cnc(NS(=O)(=O)CCC(F)(F)F)nc2)cc2cnc(N[C@H]3CC[C@H](N(C)C)CC3)nc21] , |
| 234 | 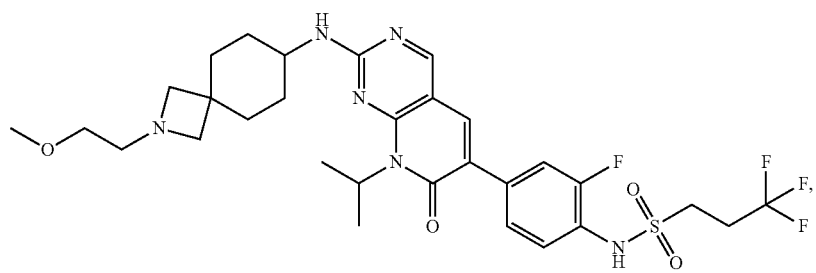 [SMILES: COCCN1CC2(CCC(Nc3ncc4cc(-c5ccc(NS(=O)(=O)CCC(F)(F)F)c(F)c5)c(=O)n(C(C)C)c4n3)CC2)C1] , |

| Compound No. | Structure |
|---|---|
| 235 | 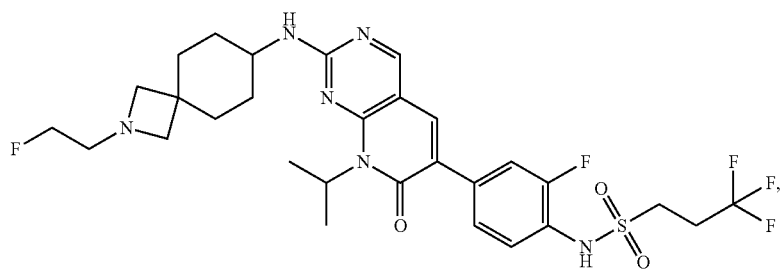 [SMILES: CC(C)n1c(=O)c(-c2ccc(NS(=O)(=O)CCC(F)(F)F)c(F)c2)cc2cnc(NC3CCC4(CC3)CN(CCF)C4)nc21] |
| 236 | 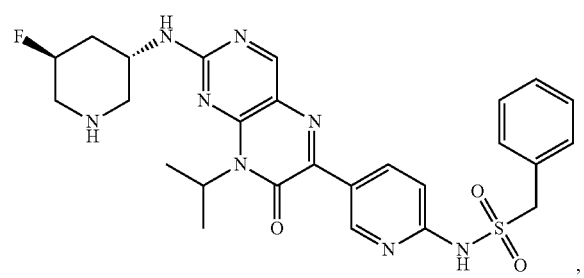 [SMILES: CC(C)n1c(=O)c(-c2ccc(NS(=O)(=O)Cc3ccccc3)nc2)nc2cnc(N[C@@H]3CNC[C@@H](F)C3)nc21] |
| 237 | 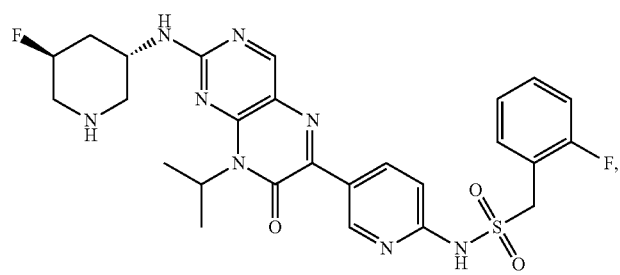 [SMILES: CC(C)n1c(=O)c(-c2ccc(NS(=O)(=O)Cc3ccccc3F)nc2)nc2cnc(N[C@@H]3CNC[C@@H](F)C3)nc21] |
| 238 | 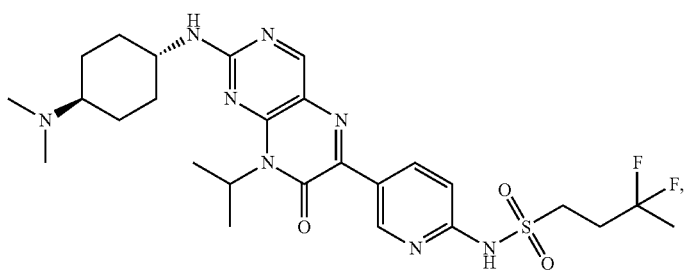 [SMILES: CC(C)n1c(=O)c(-c2ccc(NS(=O)(=O)CCC(C)(F)F)nc2)nc2cnc(N[C@H]3CC[C@H](N(C)C)CC3)nc21] |
| 239 | 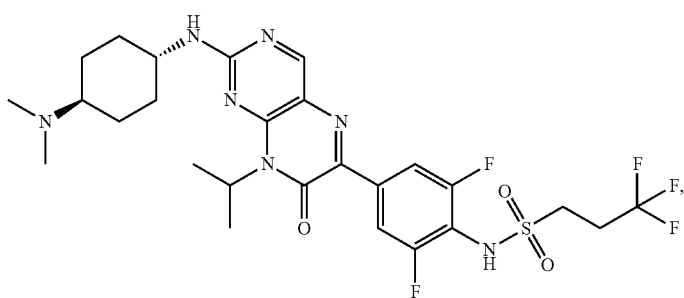 [SMILES: CC(C)n1c(=O)c(-c2cc(F)c(NS(=O)(=O)CCC(F)(F)F)c(F)c2)nc2cnc(N[C@H]3CC[C@H](N(C)C)CC3)nc21] |

| Compound No. | Structure |
|---|---|
| 240 | 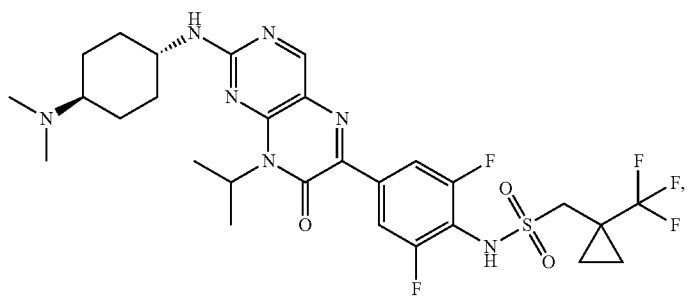 [SMILES: CC(C)n1c(=O)c(-c2cc(F)c(NS(=O)(=O)CC3(C(F)(F)F)CC3)c(F)c2)nc2cnc(N[C@H]3CC[C@H](N(C)C)CC3)nc21] |
| 241 | 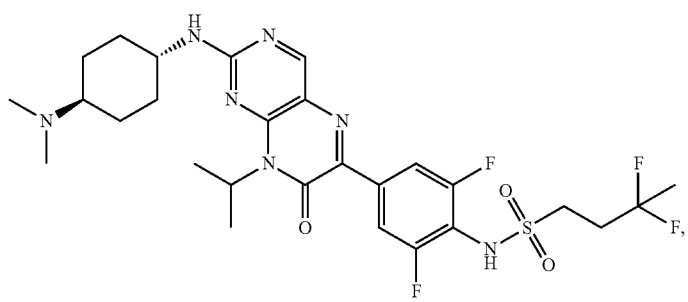 |
| 242 | 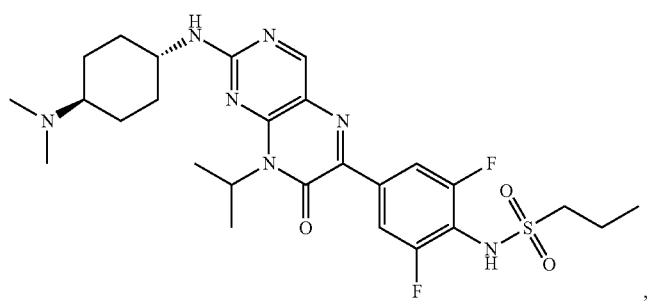 [SMILES: CCCS(=O)(=O)Nc1c(F)cc(-c2nc3cnc(N[C@H]4CC[C@H](N(C)C)CC4)nc3n(C(C)C)c2=O)cc1F] |
| 243 | 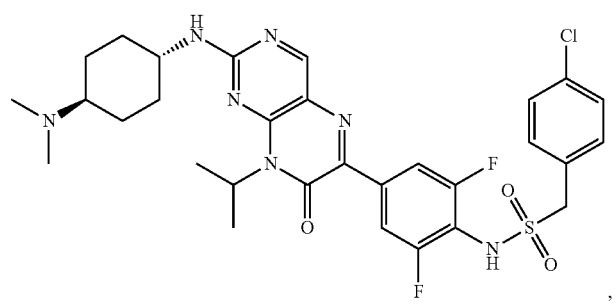 |
| 244 | 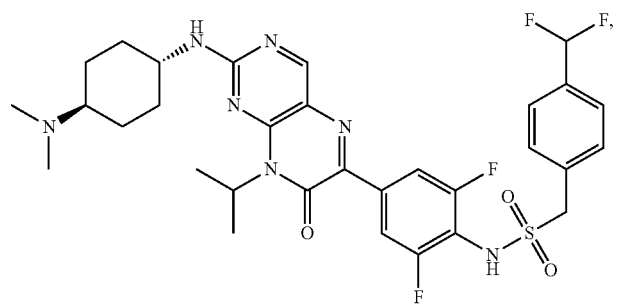 [SMILES: CC(C)n1c(=O)c(-c2cc(F)c(NS(=O)(=O)Cc3ccc(C(F)F)cc3)c(F)c2)nc2cnc(N[C@H]3CC[C@H](N(C)C)CC3)nc21] |

| Compound No. | Structure |
|---|---|
| 245 | 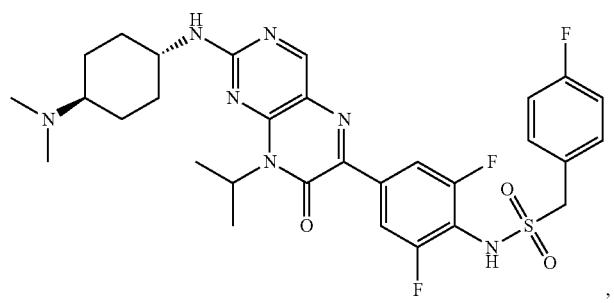 [SMILES: CC(C)n1c(=O)c(-c2cc(F)c(NS(=O)(=O)Cc3ccc(F)cc3)c(F)c2)nc2cnc(N[C@H]3CC[C@H](N(C)C)CC3)nc21] |
| 246 | 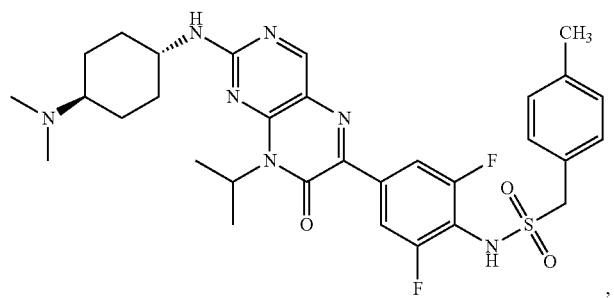 |
| 247 | 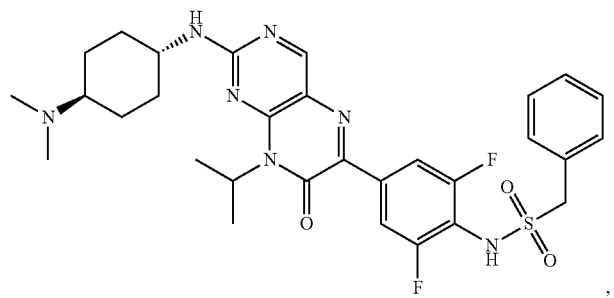 [SMILES: CC(C)n1c(=O)c(-c2cc(F)c(NS(=O)(=O)Cc3ccccc3)c(F)c2)nc2cnc(N[C@H]3CC[C@H](N(C)C)CC3)nc21] |
| 248 | 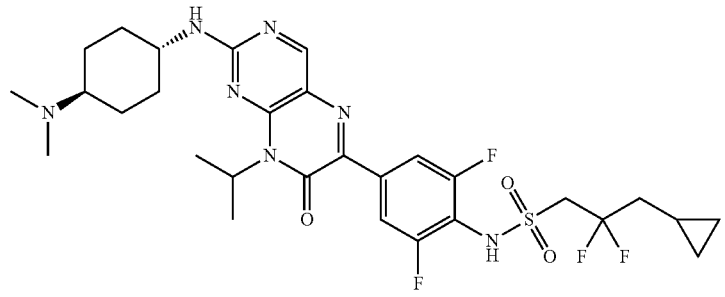 |
| 249 | 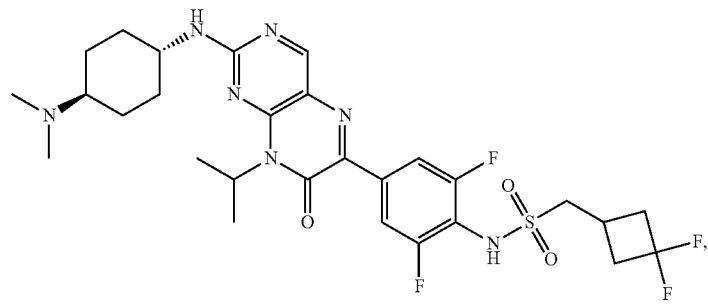 [SMILES: CC(C)n1c(=O)c(-c2cc(F)c(NS(=O)(=O)CC3CC(F)(F)C3)c(F)c2)nc2cnc(N[C@H]3CC[C@H](N(C)C)CC3)nc21] |

| Compound No. | Structure |
|---|---|
| 250 | 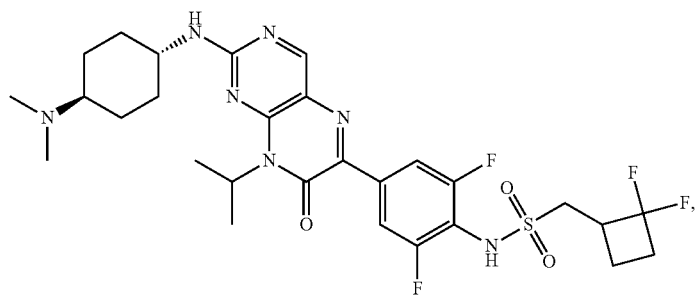 [SMILES: CC(C)n1c(=O)c(-c2cc(F)c(NS(=O)(=O)CC3CCC3(F)F)c(F)c2)nc2cnc(N[C@H]3CC[C@H](N(C)C)CC3)nc21] |
| 251 | 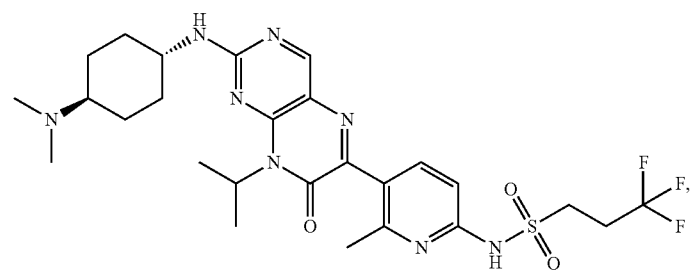 [SMILES: Cc1nc(NS(=O)(=O)CCC(F)(F)F)ccc1-c1nc2cnc(N[C@H]3CC[C@H](N(C)C)CC3)nc2n(C(C)C)c1=O] |
| 252 | 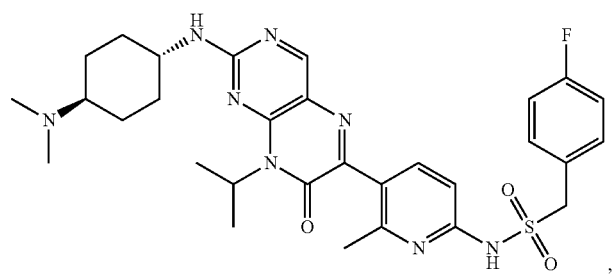 [SMILES: Cc1nc(NS(=O)(=O)Cc2ccc(F)cc2)ccc1-c1nc2cnc(N[C@H]3CC[C@H](N(C)C)CC3)nc2n(C(C)C)c1=O] |
| 253 | 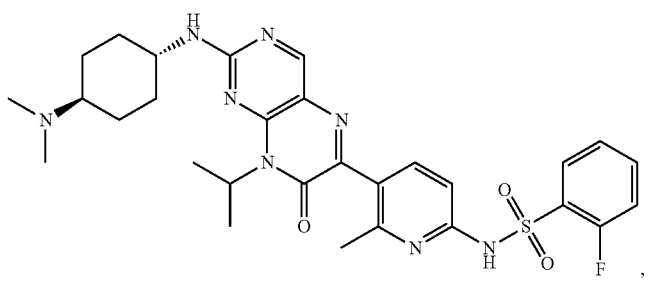 |
| 254 | 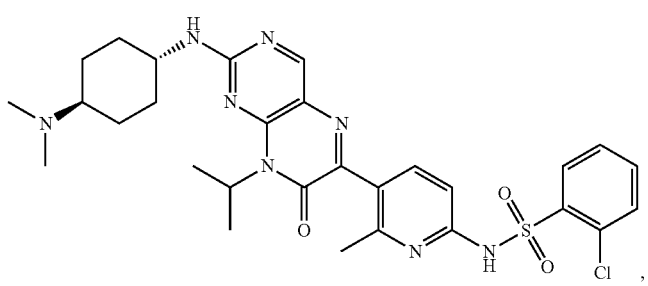 |

-continued
| Compound No. | Structure |
|---|---|
| 255 | 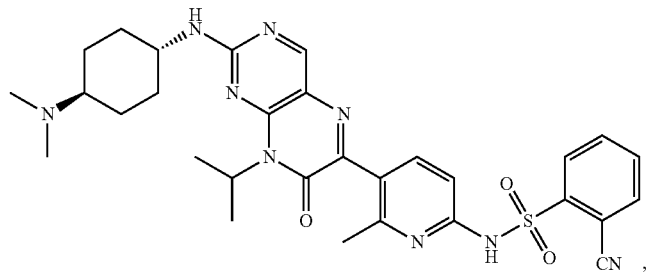 |
| 256 | 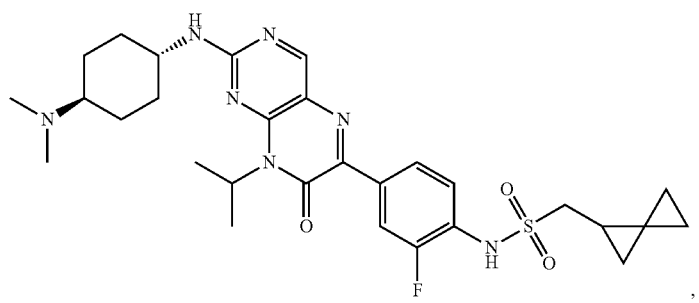 [SMILES: CC(C)n1c(=O)c(-c2ccc(NS(=O)(=O)CC3CC34CC4)c(F)c2)nc2cnc(N[C@H]3CC[C@H](N(C)C)CC3)nc21] |
| 257 | 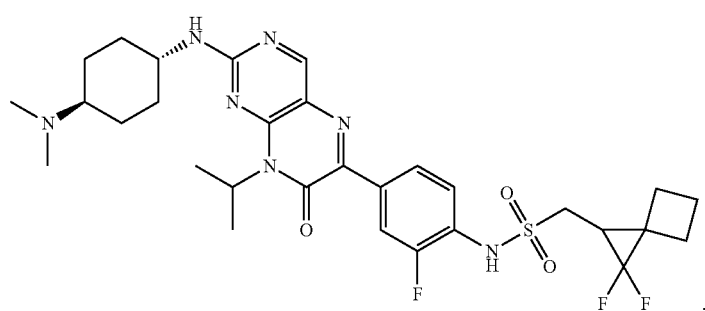 [SMILES: CC(C)n1c(=O)c(-c2ccc(NS(=O)(=O)CC3C(F)(F)C34CCC4)c(F)c2)nc2cnc(N[C@H]3CC[C@H](N(C)C)CC3)nc21] |
| 258 | 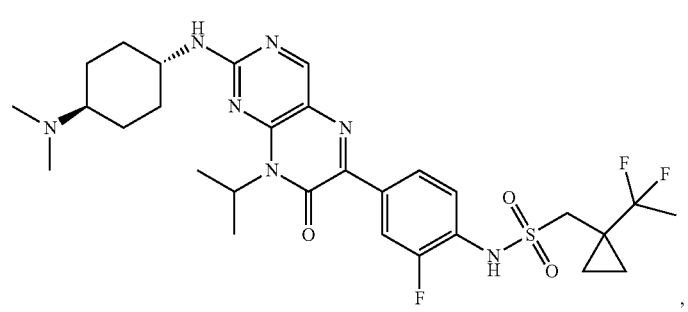 [SMILES: CC(C)n1c(=O)c(-c2ccc(NS(=O)(=O)CC3(C(C)(F)F)CC3)c(F)c2)nc2cnc(N[C@H]3CC[C@H](N(C)C)CC3)nc21] |
| 259 | 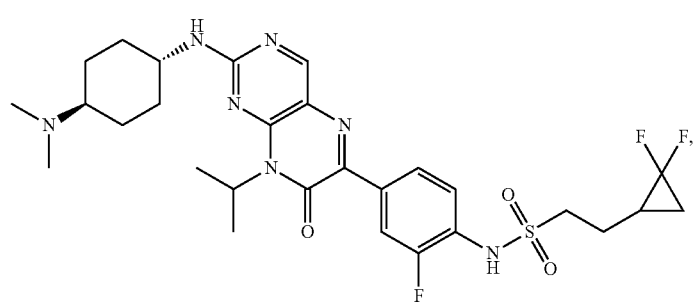 [SMILES: CC(C)n1c(=O)c(-c2ccc(NS(=O)(=O)CCC3CC3(F)F)c(F)c2)nc2cnc(N[C@H]3CC[C@H](N(C)C)CC3)nc21] |

-continued
| Compound No. | Structure |
|---|---|
| 260 | 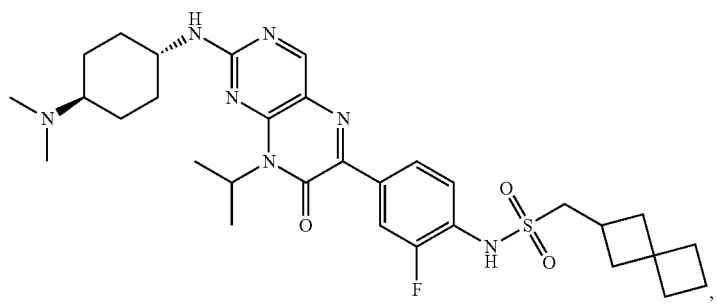 [SMILES: CC(C)n1c(=O)c(-c2ccc(NS(=O)(=O)CC3CC4(CCC4)C3)c(F)c2)nc2cnc(N[C@H]3CC[C@H](N(C)C)CC3)nc21] |
| 261 | 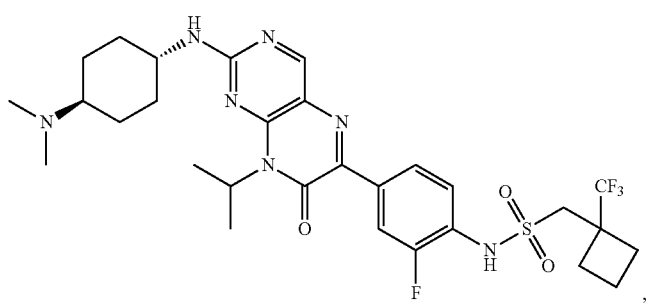 [SMILES: CC(C)n1c(=O)c(-c2ccc(NS(=O)(=O)CC3(C(F)(F)F)CCC3)c(F)c2)nc2cnc(N[C@H]3CC[C@H](N(C)C)CC3)nc21] |
| 262 | 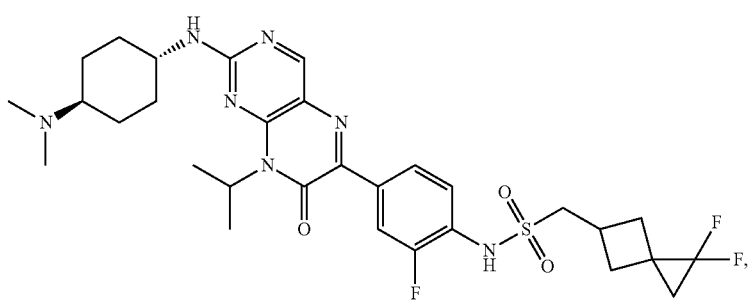 [SMILES: CC(C)n1c(=O)c(-c2ccc(NS(=O)(=O)CC3CC4(C3)CC4(F)F)c(F)c2)nc2cnc(N[C@H]3CC[C@H](N(C)C)CC3)nc21] |
| 263 | 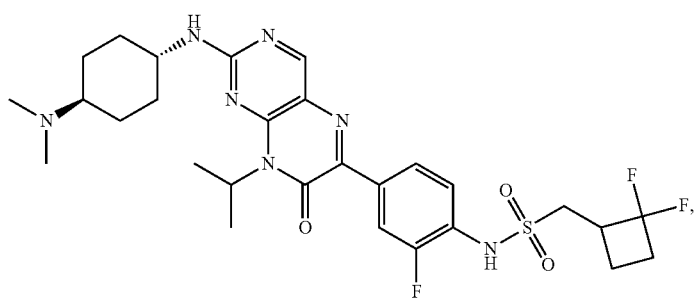 [SMILES: CC(C)n1c(=O)c(-c2ccc(NS(=O)(=O)CC3CCC3(F)F)c(F)c2)nc2cnc(N[C@H]3CC[C@H](N(C)C)CC3)nc21] |
| 264 | 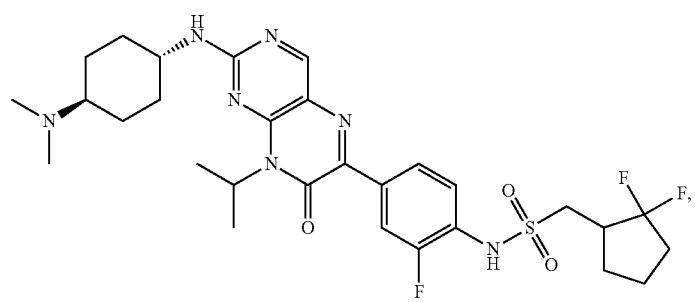 [SMILES: CC(C)n1c(=O)c(-c2ccc(NS(=O)(=O)CC3CCCC3(F)F)c(F)c2)nc2cnc(N[C@H]3CC[C@H](N(C)C)CC3)nc21] |

| Compound No. | Structure |
|---|---|
| 265 | 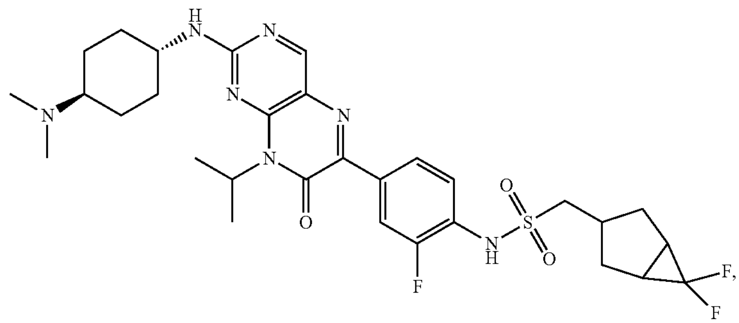 [SMILES: CC(C)n1c(=O)c(-c2ccc(NS(=O)(=O)CC3CC4C(C3)C4(F)F)c(F)c2)nc2cnc(N[C@H]3CC[C@H](N(C)C)CC3)nc21] |
| 266 | 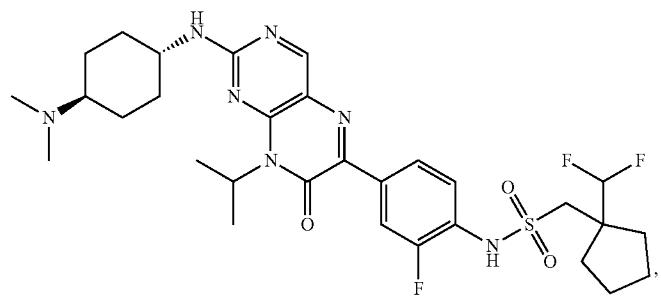 [SMILES: CC(C)n1c(=O)c(-c2ccc(NS(=O)(=O)CC3(C(F)F)CCCC3)c(F)c2)nc2cnc(N[C@H]3CC[C@H](N(C)C)CC3)nc21] |
| 267 | 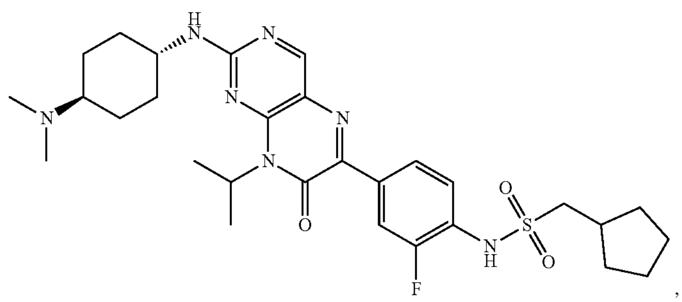 [SMILES: CC(C)n1c(=O)c(-c2ccc(NS(=O)(=O)CC3CCCC3)c(F)c2)nc2cnc(N[C@H]3CC[C@H](N(C)C)CC3)nc21] |
| 268 | 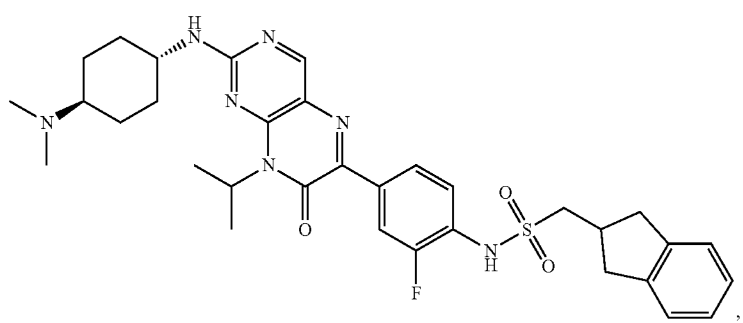 [SMILES: CC(C)n1c(=O)c(-c2ccc(NS(=O)(=O)CC3Cc4ccccc4C3)c(F)c2)nc2cnc(N[C@H]3CC[C@H](N(C)C)CC3)nc21] |
| 269 | 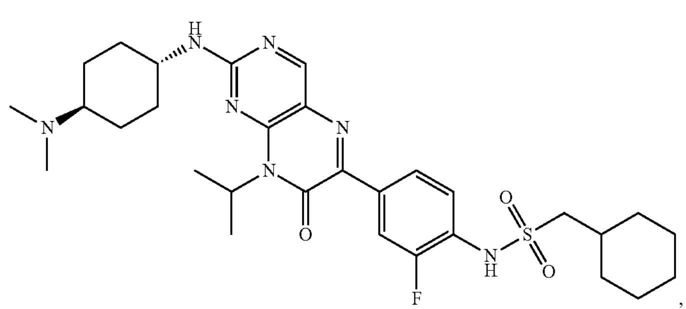 [SMILES: CC(C)n1c(=O)c(-c2ccc(NS(=O)(=O)CC3CCCCC3)c(F)c2)nc2cnc(N[C@H]3CC[C@H](N(C)C)CC3)nc21] |

-continued
| Compound No. | Structure |
|---|---|
| 270 | 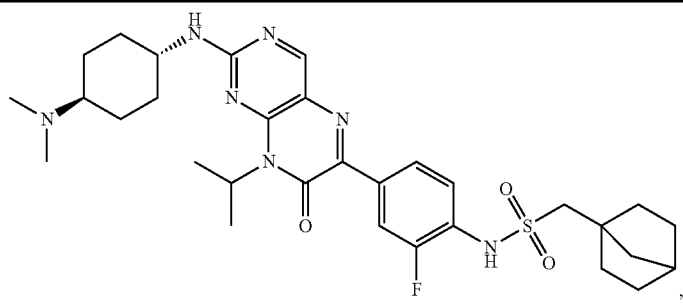 |
| 271 | 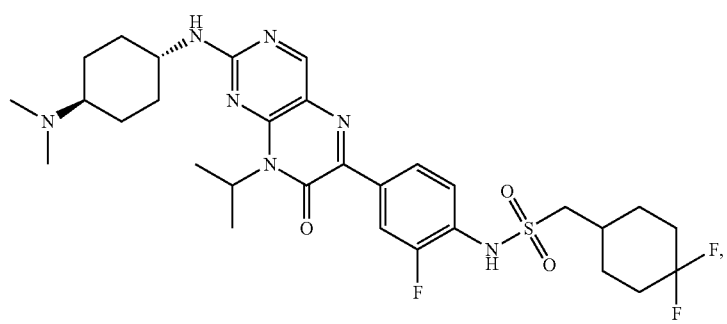 [SMILES: CC(C)n1c(=O)c(-c2ccc(NS(=O)(=O)CC3CCC(F)(F)CC3)c(F)c2)nc2cnc(N[C@H]3CC[C@H](N(C)C)CC3)nc21] |
| 272 | 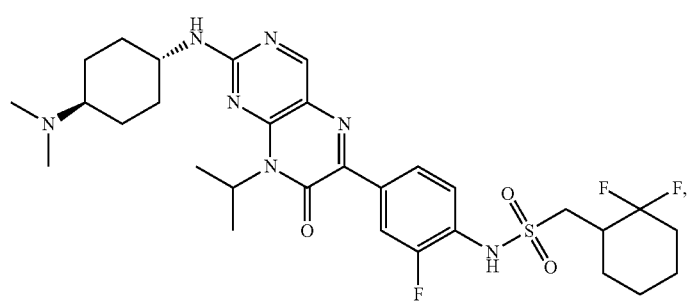 [SMILES: CC(C)n1c(=O)c(-c2ccc(NS(=O)(=O)CC3CCCCC3(F)F)c(F)c2)nc2cnc(N[C@H]3CC[C@H](N(C)C)CC3)nc21] |
| 273 | 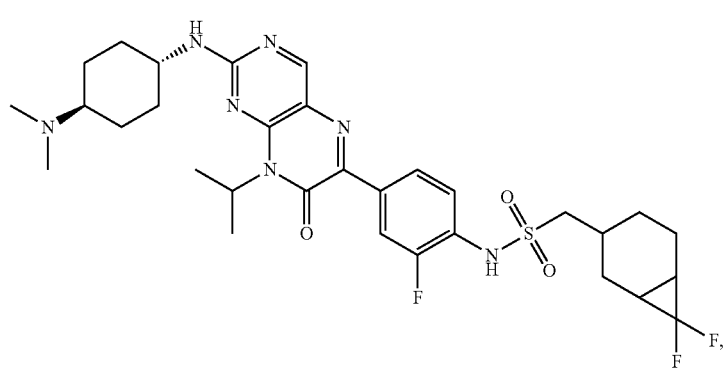 [SMILES: CC(C)n1c(=O)c(-c2ccc(NS(=O)(=O)CC3CCC4C(C3)C4(F)F)c(F)c2)nc2cnc(N[C@H]3CC[C@H](N(C)C)CC3)nc21] |
| 274 | 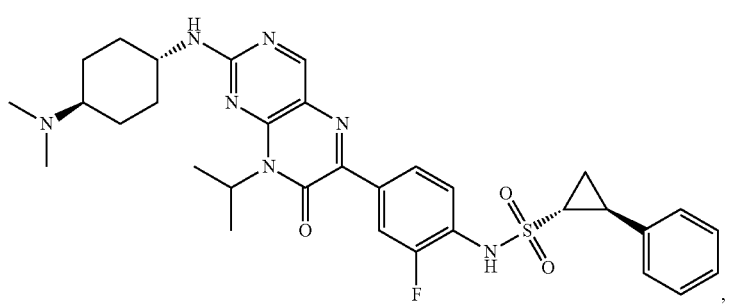 [SMILES: CC(C)n1c(=O)c(-c2ccc(NS(=O)(=O)[C@@H]3C[C@H]3c3ccccc3)c(F)c2)nc2cnc(N[C@H]3CC[C@H](N(C)C)CC3)nc21] |

-continued
| Compound No. | Structure |
|---|---|
| 275 | 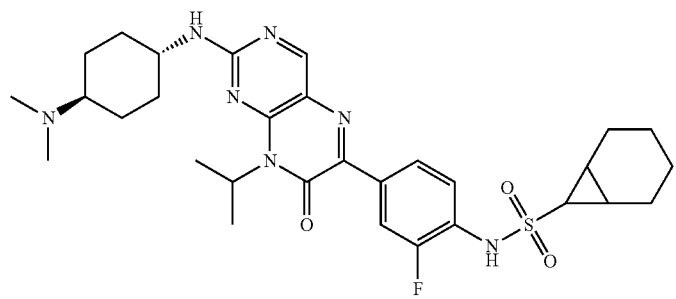 |
| 276 | 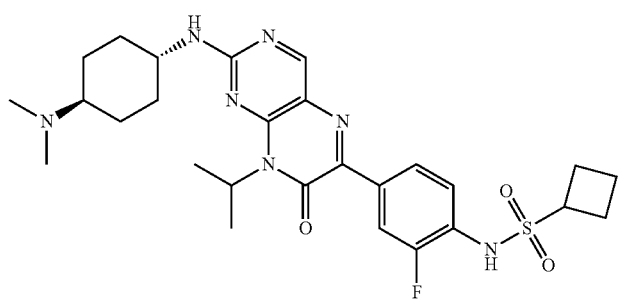 |
| 277 | 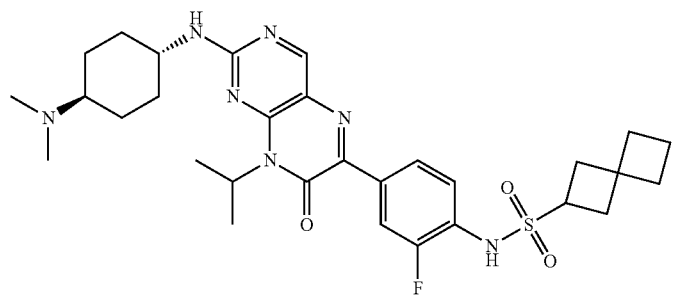 |
| 278 | 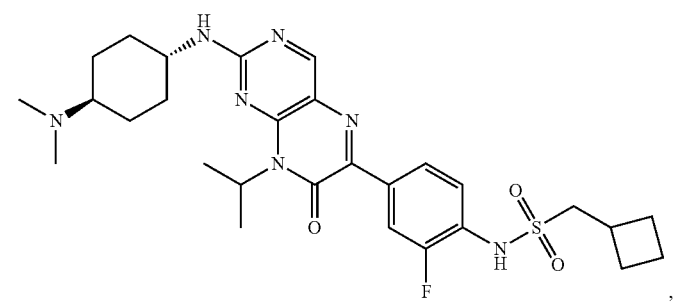 [SMILES: CC(C)n1c(=O)c(-c2ccc(NS(=O)(=O)CC3CCC3)c(F)c2)nc2cnc(N[C@H]3CC[C@H](N(C)C)CC3)nc21] |
| 279 | 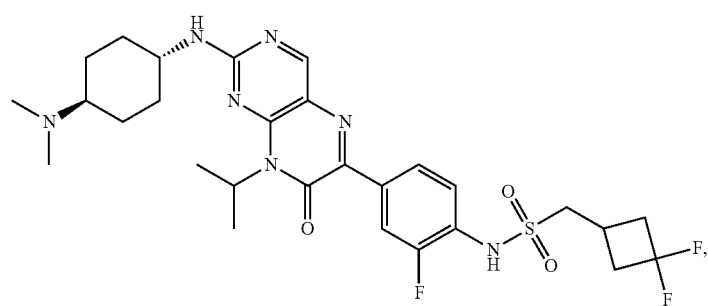 [SMILES: CC(C)n1c(=O)c(-c2ccc(NS(=O)(=O)CC3CC(F)(F)C3)c(F)c2)nc2cnc(N[C@H]3CC[C@H](N(C)C)CC3)nc21] |

| Compound No. | Structure |
|---|---|
| 280 | 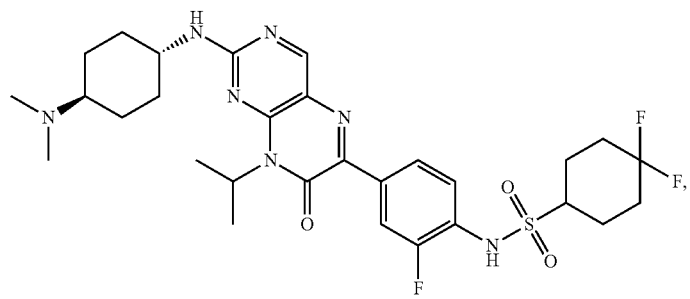 [SMILES: CC(C)n1c(=O)c(-c2ccc(NS(=O)(=O)C3CCC(F)(F)CC3)c(F)c2)nc2cnc(N[C@H]3CC[C@H](N(C)C)CC3)nc21] |
| 281 | 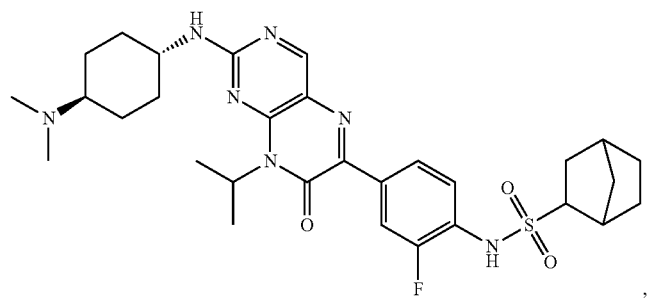 [SMILES: CC(C)n1c(=O)c(-c2ccc(NS(=O)(=O)C3CC4CCC3C4)c(F)c2)nc2cnc(N[C@H]3CC[C@H](N(C)C)CC3)nc21] |
| 282 | 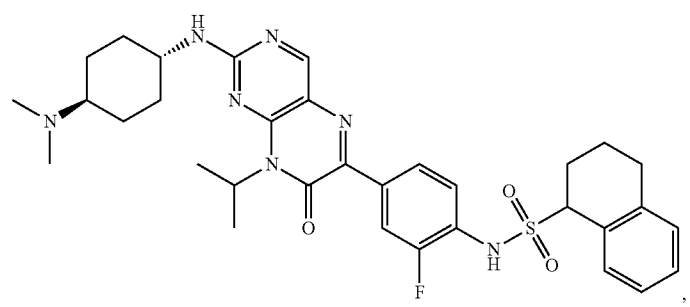 [SMILES: CC(C)n1c(=O)c(-c2ccc(NS(=O)(=O)C3CCCc4ccccc43)c(F)c2)nc2cnc(N[C@H]3CC[C@H](N(C)C)CC3)nc21] |
| 501 | 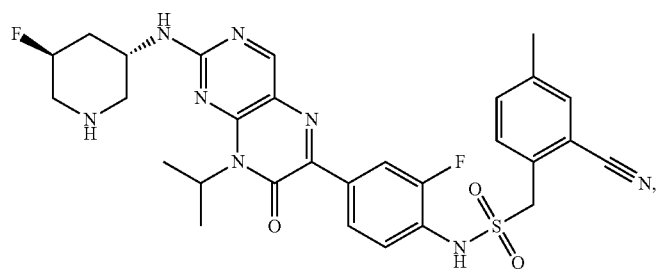 [SMILES: Cc1ccc(CS(=O)(=O)Nc2ccc(-c3nc4cnc(N[C@@H]5CNC[C@@H](F)C5)nc4n(C(C)C)c3=O)cc2F)c(C#N)c1] |
| 502 | 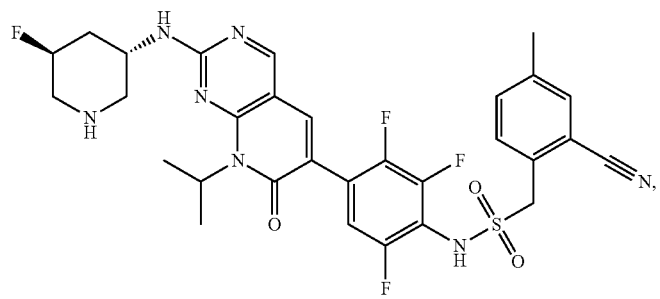 [SMILES: Cc1ccc(CS(=O)(=O)Nc2c(F)cc(-c3cc4cnc(N[C@@H]5CNC[C@@H](F)C5)nc4n(C(C)C)c3=O)c(F)c2F)c(C#N)c1] |

-continued
| Compound No. | Structure |
|---|---|
| 503 | 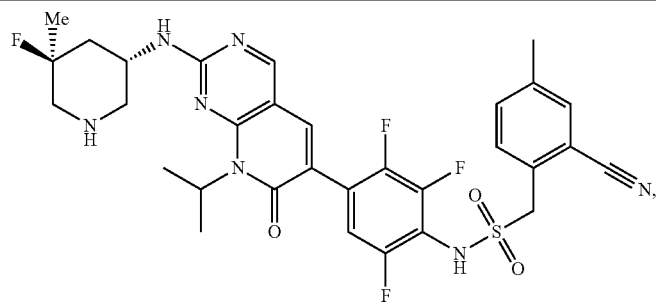 |
| 504 | 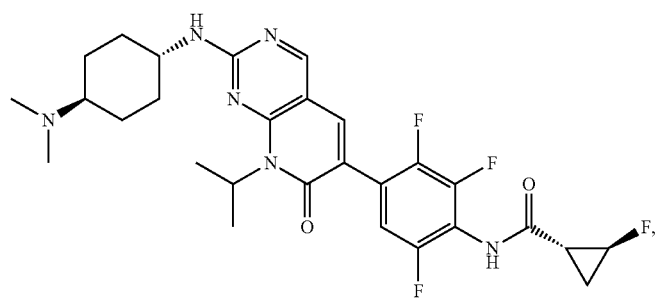 [SMILES: CC(C)n1c(=O)c(-c2cc(F)c(NC(=O)[C@H]3C[C@@H]3F)c(F)c2F)cc2cnc(N[C@H]3CC[C@H](N(C)C)CC3)nc21] |
| 505 | 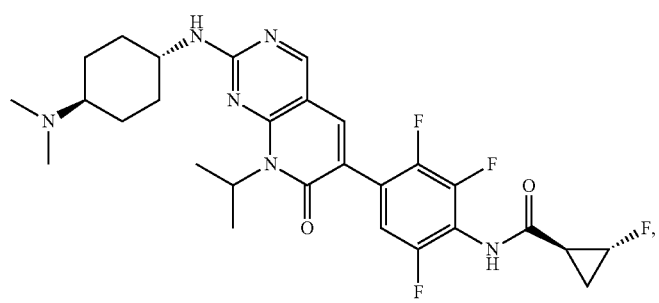 [SMILES: CC(C)n1c(=O)c(-c2cc(F)c(NC(=O)[C@@H]3C[C@H]3F)c(F)c2F)cc2cnc(N[C@H]3CC[C@H](N(C)C)CC3)nc21] |
| 506 | 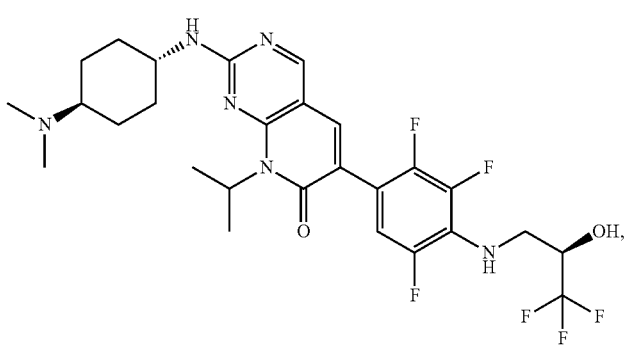 [SMILES: CC(C)n1c(=O)c(-c2cc(F)c(NC[C@@H](O)C(F)(F)F)c(F)c2F)cc2cnc(N[C@H]3CC[C@H](N(C)C)CC3)nc21] |
| 507 | 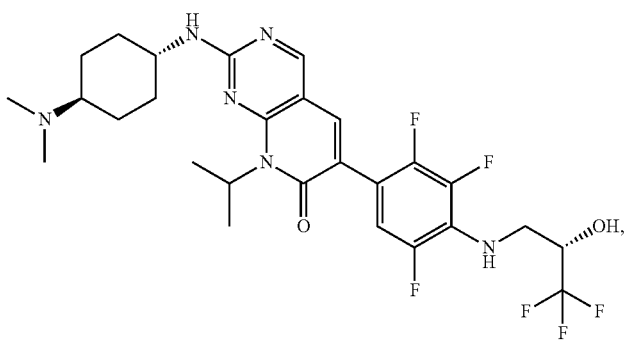 [SMILES: CC(C)n1c(=O)c(-c2cc(F)c(NC[C@H](O)C(F)(F)F)c(F)c2F)cc2cnc(N[C@H]3CC[C@H](N(C)C)CC3)nc21] |

| Compound No. | Structure |
|---|---|
| 508 | 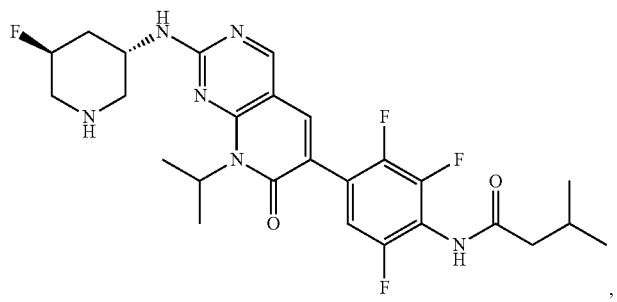 [SMILES: CC(C)CC(=O)Nc1c(F)cc(-c2cc3cnc(N[C@@H]4CNC[C@@H](F)C4)nc3n(C(C)C)c2=O)c(F)c1F] |
| 509 | 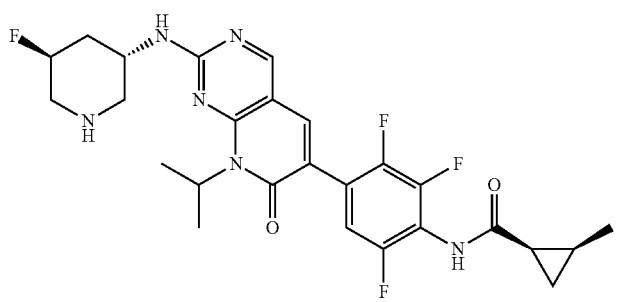 |
| 510 | 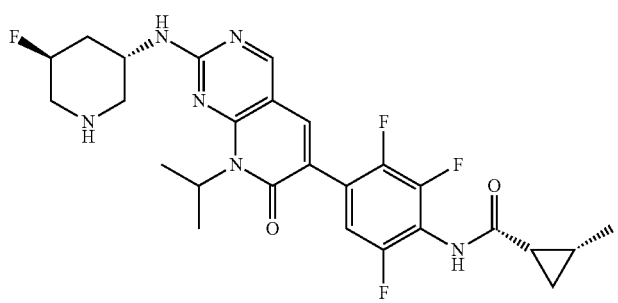 |
| 511 | 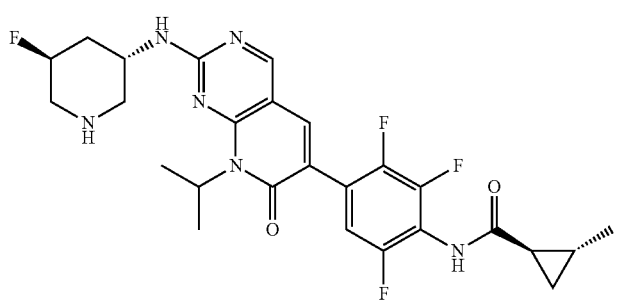 |
| 512 | 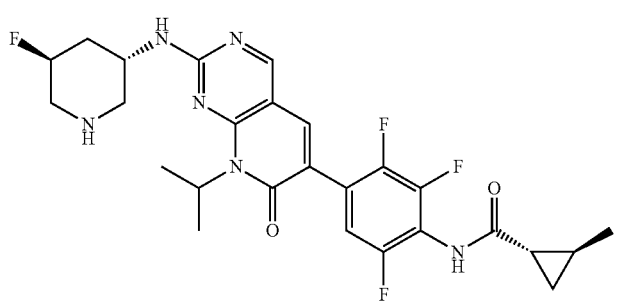 |

| Compound No. | Structure |
|---|---|
| 513 | 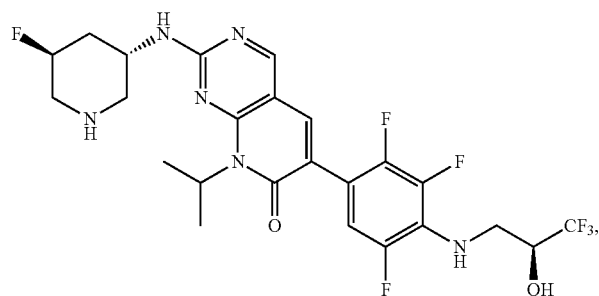 [SMILES: CC(C)n1c(=O)c(-c2cc(F)c(NC[C@H](O)C(F)(F)F)c(F)c2F)cc2cnc(N[C@@H]3CNC[C@@H](F)C3)nc21] |
| 514 | 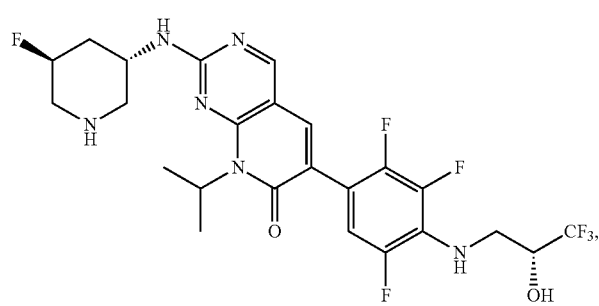 [SMILES: CC(C)n1c(=O)c(-c2cc(F)c(NC[C@@H](O)C(F)(F)F)c(F)c2F)cc2cnc(N[C@@H]3CNC[C@@H](F)C3)nc21] |
| 515 | 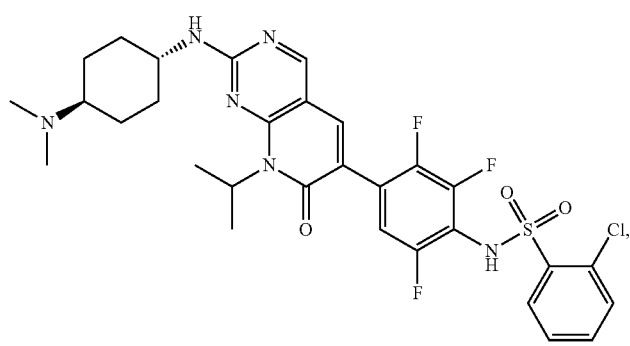 [SMILES: CC(C)n1c(=O)c(-c2cc(F)c(NS(=O)(=O)c3ccccc3Cl)c(F)c2F)cc2cnc(N[C@H]3CC[C@H](N(C)C)CC3)nc21] |
| 516 | 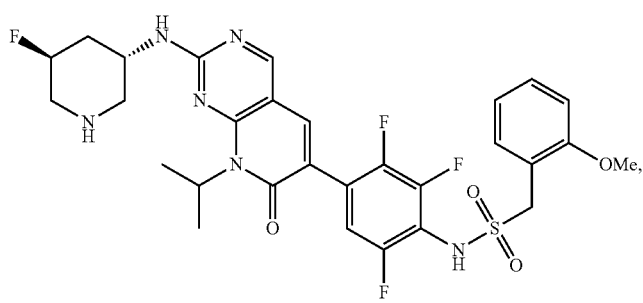 [SMILES: COc1ccccc1CS(=O)(=O)Nc1c(F)cc(-c2cc3cnc(N[C@@H]4CNC[C@@H](F)C4)nc3n(C(C)C)c2=O)c(F)c1F] |
| 517 | 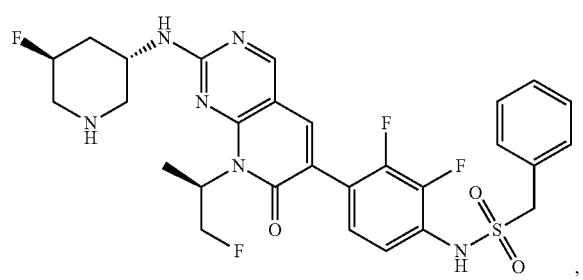 [SMILES: C[C@H](CF)n1c(=O)c(-c2ccc(NS(=O)(=O)Cc3ccccc3)c(F)c2F)cc2cnc(N[C@@H]3CNC[C@@H](F)C3)nc21] |

| Compound No. | Structure |
|---|---|
| 518 | 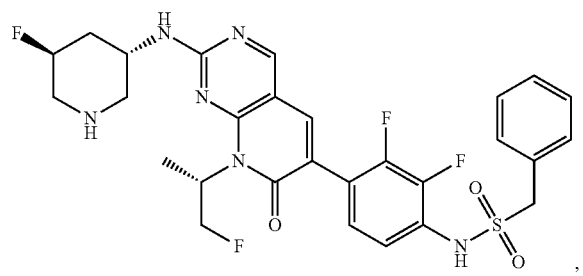 [SMILES: C[C@@H](CF)n1c(=O)c(-c2ccc(NS(=O)(=O)Cc3ccccc3)c(F)c2F)cc2cnc(N[C@@H]3CNC[C@@H](F)C3)nc21] |
| 519 | 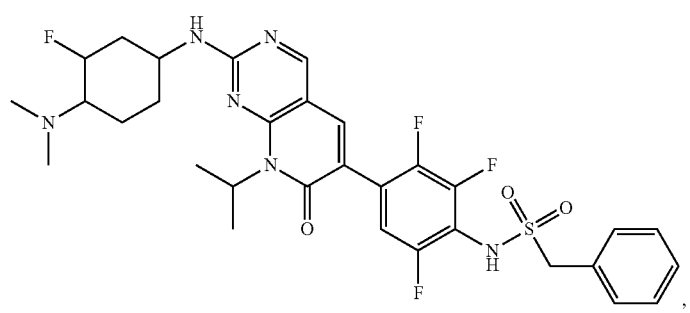 [SMILES: CC(C)n1c(=O)c(-c2cc(F)c(NS(=O)(=O)Cc3ccccc3)c(F)c2F)cc2cnc(NC3CCC(N(C)C)C(F)C3)nc21] |
| 520 | 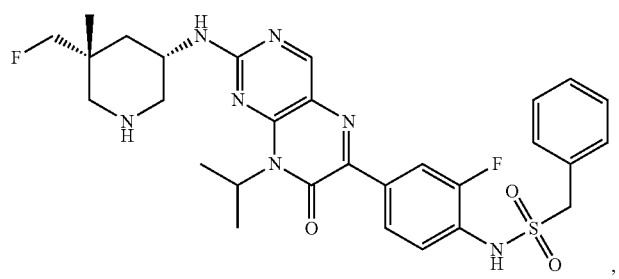 [SMILES: CC(C)n1c(=O)c(-c2ccc(NS(=O)(=O)Cc3ccccc3)c(F)c2)nc2cnc(N[C@@H]3CNC[C@](C)(CF)C3)nc21] |
| 521 | 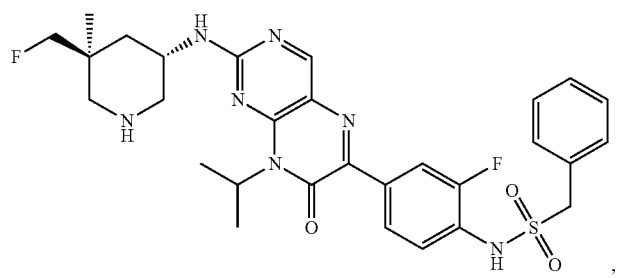 [SMILES: CC(C)n1c(=O)c(-c2ccc(NS(=O)(=O)Cc3ccccc3)c(F)c2)nc2cnc(N[C@@H]3CNC[C@@](C)(CF)C3)nc21] |
| 522 | 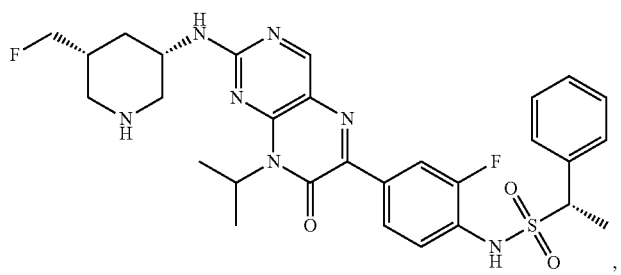 [SMILES: CC(C)n1c(=O)c(-c2ccc(NS(=O)(=O)[C@@H](C)c3ccccc3)c(F)c2)nc2cnc(N[C@@H]3CNC[C@H](CF)C3)nc21] |

| Compound No. | Structure |
|---|---|
| 523 | 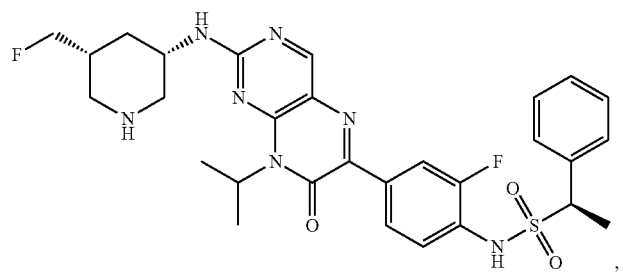 [SMILES: CC(C)n1c(=O)c(-c2ccc(NS(=O)(=O)[C@H](C)c3ccccc3)c(F)c2)nc2cnc(N[C@@H]3CNC[C@H](CF)C3)nc21] |
| 524 | 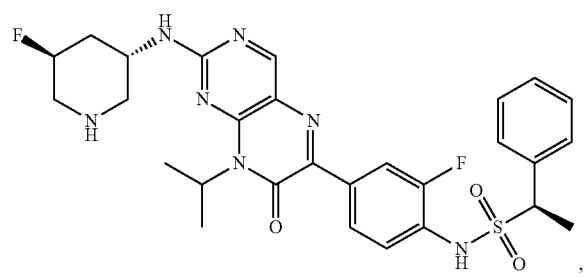 |
| 525 | 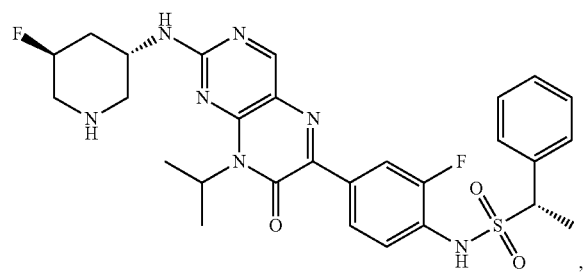 [SMILES: CC(C)n1c(=O)c(-c2ccc(NS(=O)(=O)[C@@H](C)c3ccccc3)c(F)c2)nc2cnc(N[C@@H]3CNC[C@@H](F)C3)nc21] |
| 526 | 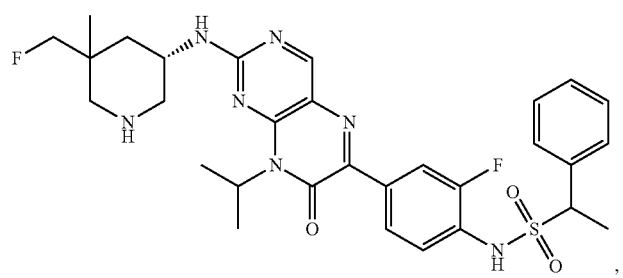 [SMILES: CC(C)n1c(=O)c(-c2ccc(NS(=O)(=O)C(C)c3ccccc3)c(F)c2)nc2cnc(N[C@@H]3CNCC(C)(CF)C3)nc21] |
| 527 | 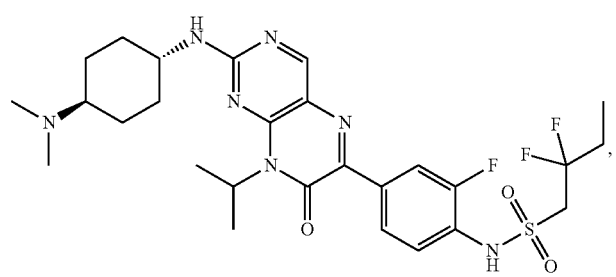 [SMILES: CCC(F)(F)CS(=O)(=O)Nc1ccc(-c2nc3cnc(N[C@H]4CC[C@H](N(C)C)CC4)nc3n(C(C)C)c2=O)cc1F] |

| Compound No. | Structure |
|---|---|
| 528 | 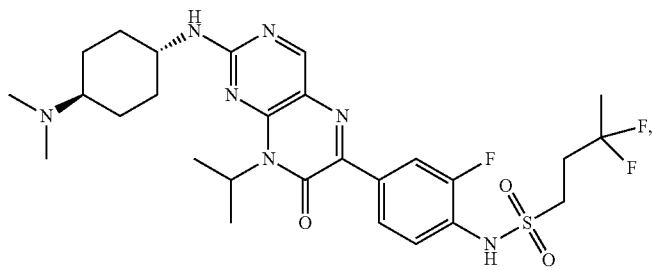 [SMILES: CC(C)n1c(=O)c(-c2ccc(NS(=O)(=O)CCC(C)(F)F)c(F)c2)nc2cnc(N[C@H]3CC[C@H](N(C)C)CC3)nc21] |
| 529 | 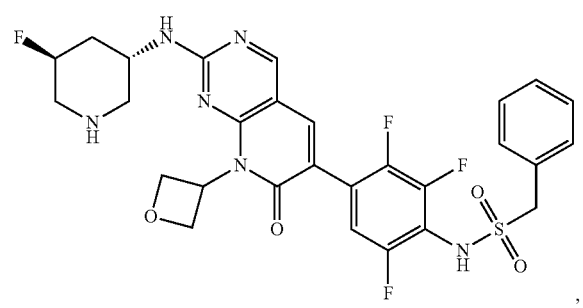 [SMILES: O=c1c(-c2cc(F)c(NS(=O)(=O)Cc3ccccc3)c(F)c2F)cc2cnc(N[C@@H]3CNC[C@@H](F)C3)nc2n1C1COC1] |
| 530 | 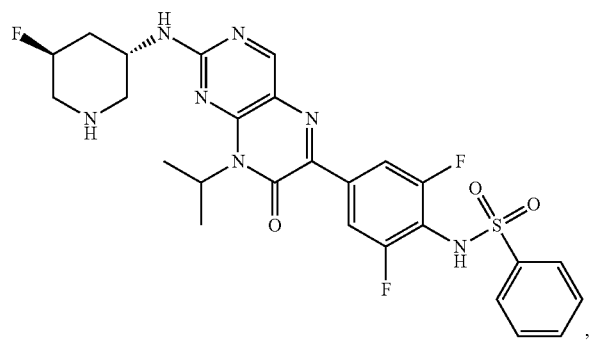 [SMILES: CC(C)n1c(=O)c(-c2cc(F)c(NS(=O)(=O)c3ccccc3)c(F)c2)nc2cnc(N[C@@H]3CNC[C@@H](F)C3)nc21] |
| 531 | 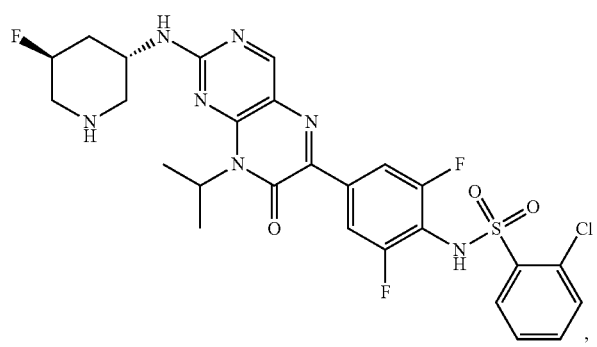 [SMILES: CC(C)n1c(=O)c(-c2cc(F)c(NS(=O)(=O)c3ccccc3Cl)c(F)c2)nc2cnc(N[C@@H]3CNC[C@@H](F)C3)nc21] |

| Compound No. | Structure |
|---|---|
| 532 | 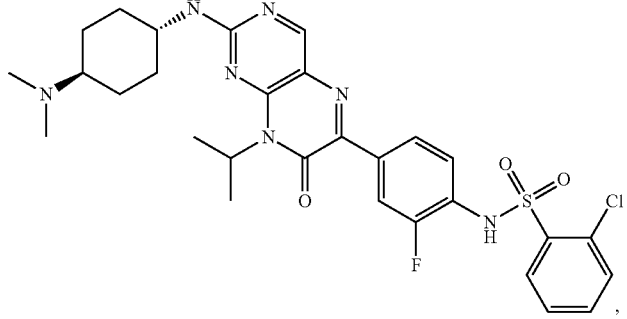 |
| 533 | 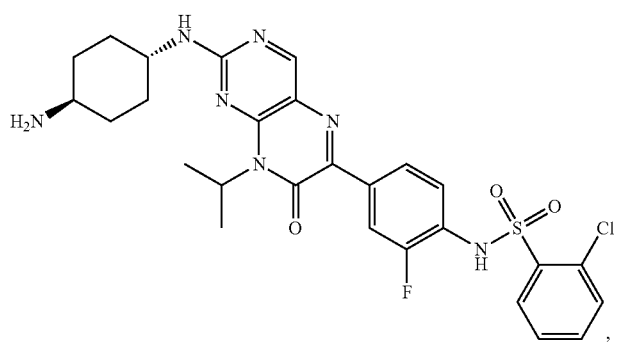 [SMILES: CC(C)n1c(=O)c(-c2ccc(NS(=O)(=O)c3ccccc3Cl)c(F)c2)nc2cnc(N[C@H]3CC[C@H](N)CC3)nc21] |
| 534 | 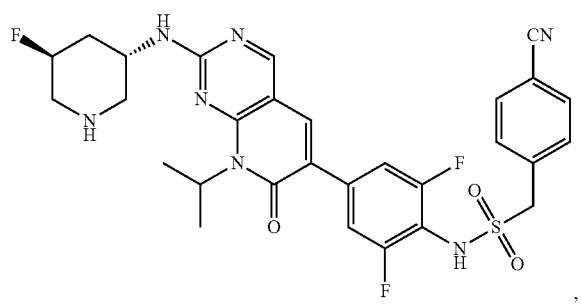 [SMILES: CC(C)n1c(=O)c(-c2cc(F)c(NS(=O)(=O)Cc3ccc(C#N)cc3)c(F)c2)cc2cnc(N[C@@H]3CNC[C@@H](F)C3)nc21] |
| 535 | 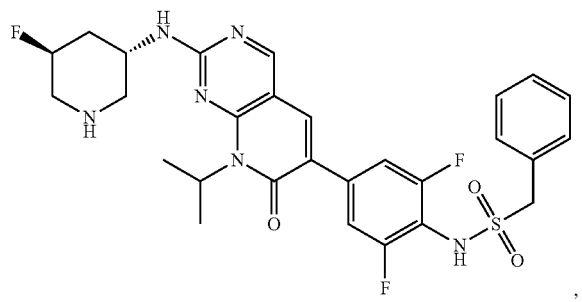 |

| Compound No. | Structure |
|---|---|
| 536 | 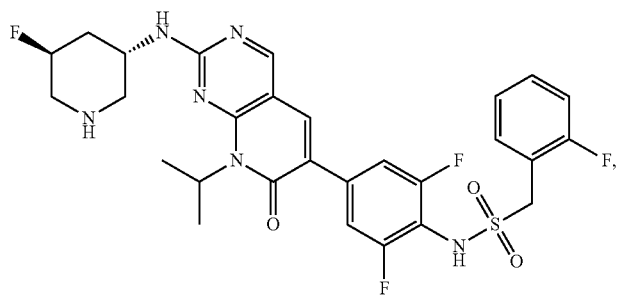 [SMILES: CC(C)n1c(=O)c(-c2cc(F)c(NS(=O)(=O)Cc3ccccc3F)c(F)c2)cc2cnc(N[C@@H]3CNC[C@@H](F)C3)nc21] |
| 537 | 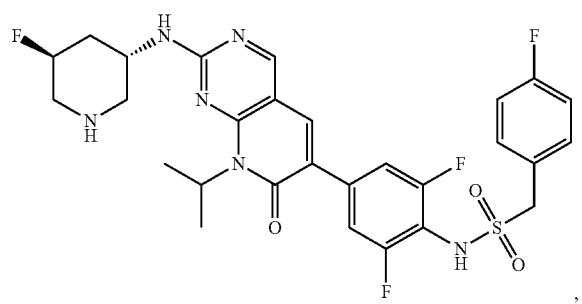 |
| 538 | 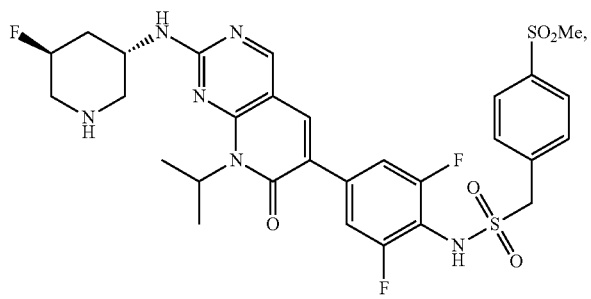 [SMILES: CC(C)n1c(=O)c(-c2cc(F)c(NS(=O)(=O)Cc3ccc(S(C)(=O)=O)cc3)c(F)c2)cc2cnc(N[C@@H]3CNC[C@@H](F)C3)nc21] |
| 539 | 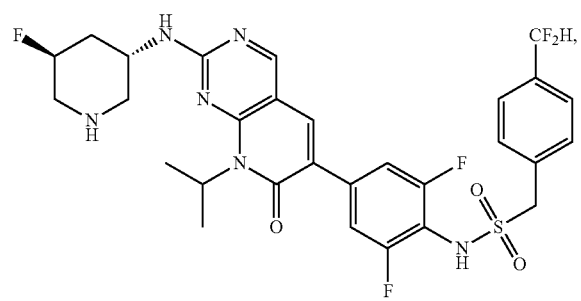 [SMILES: CC(C)n1c(=O)c(-c2cc(F)c(NS(=O)(=O)Cc3ccc(C(F)F)cc3)c(F)c2)cc2cnc(N[C@@H]3CNC[C@@H](F)C3)nc21] |
| 540 | 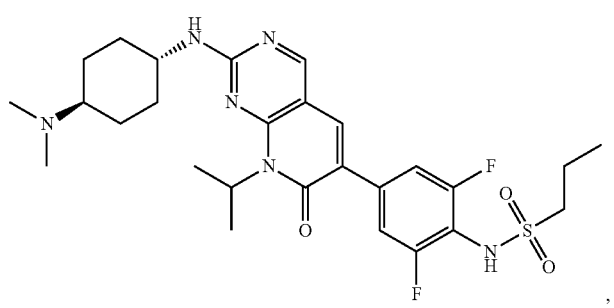 [SMILES: CCCS(=O)(=O)Nc1c(F)cc(-c2cc3cnc(N[C@H]4CC[C@H](N(C)C)CC4)nc3n(C(C)C)c2=O)cc1F] |

| Compound No. | Structure |
|---|---|
| 541 | 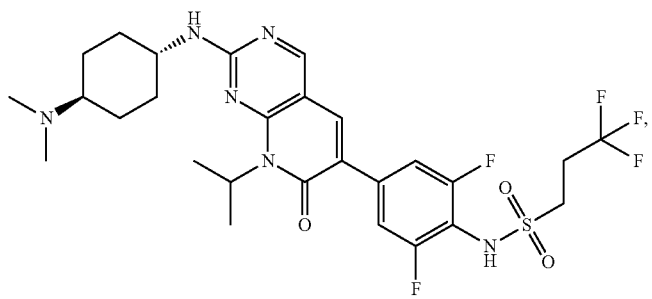 [SMILES: CC(C)n1c(=O)c(-c2cc(F)c(NS(=O)(=O)CCC(F)(F)F)c(F)c2)cc2cnc(N[C@H]3CC[C@H](N(C)C)CC3)nc21] |
| 542 | 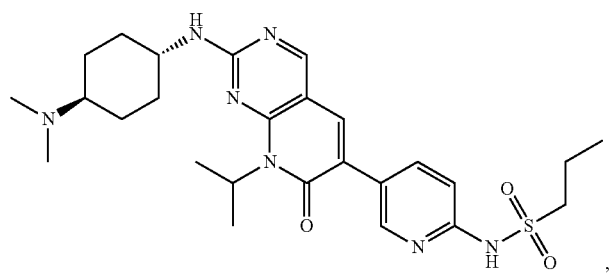 [SMILES: CCCS(=O)(=O)Nc1ccc(-c2cc3cnc(N[C@H]4CC[C@H](N(C)C)CC4)nc3n(C(C)C)c2=O)cn1] |
| 543 | 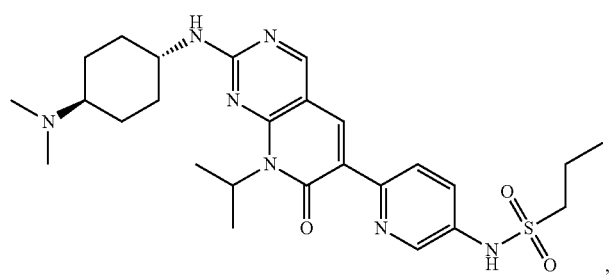 |
| 544 | 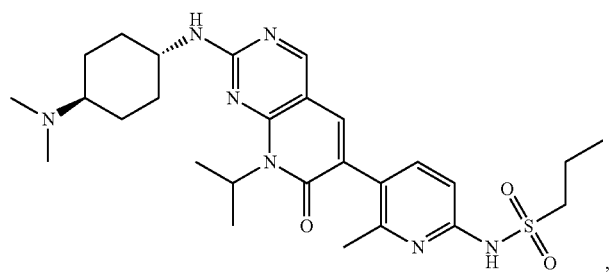 [SMILES: CCCS(=O)(=O)Nc1ccc(-c2cc3cnc(N[C@H]4CC[C@H](N(C)C)CC4)nc3n(C(C)C)c2=O)c(C)n1] |
| 545 | 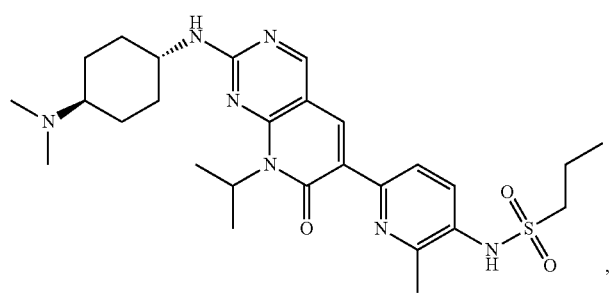 [SMILES: CCCS(=O)(=O)Nc1ccc(-c2cc3cnc(N[C@H]4CC[C@H](N(C)C)CC4)nc3n(C(C)C)c2=O)nc1C] |

| Compound No. | Structure |
|---|---|
| 546 | 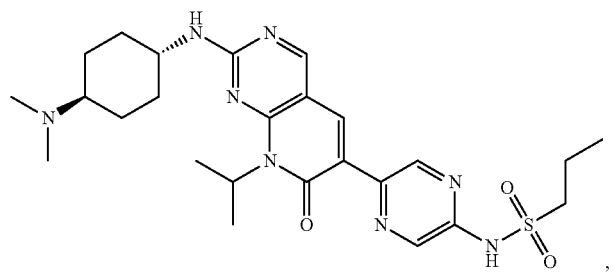 |
| 547 | 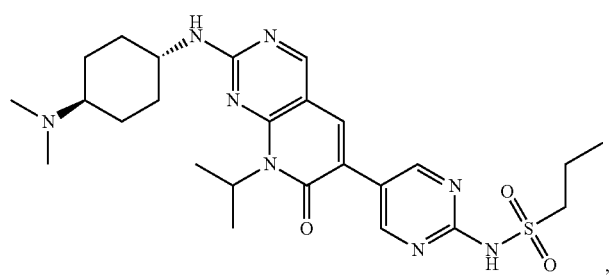 [SMILES: CCCS(=O)(=O)Nc1ncc(-c2cc3cnc(N[C@H]4CC[C@H](N(C)C)CC4)nc3n(C(C)C)c2=O)cn1] |
| 548 | 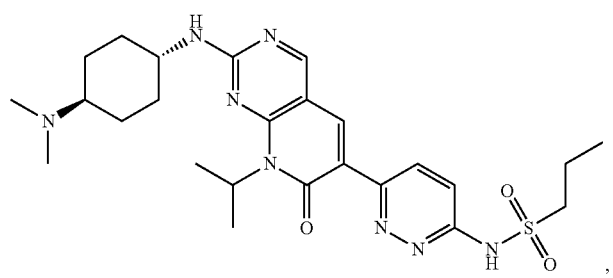 [SMILES: CCCS(=O)(=O)Nc1ccc(-c2cc3cnc(N[C@H]4CC[C@H](N(C)C)CC4)nc3n(C(C)C)c2=O)nn1] |
| 549 | 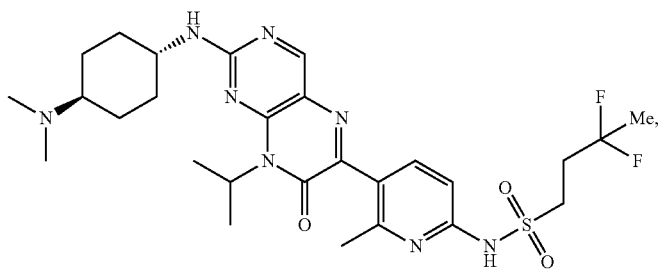 [SMILES: Cc1nc(NS(=O)(=O)CCC(C)(F)F)ccc1-c1nc2cnc(N[C@H]3CC[C@H](N(C)C)CC3)nc2n(C(C)C)c1=O] |
| 550 | 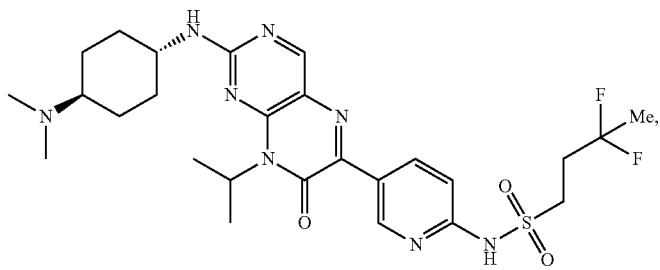 [SMILES: CC(C)n1c(=O)c(-c2ccc(NS(=O)(=O)CCC(C)(F)F)nc2)nc2cnc(N[C@H]3CC[C@H](N(C)C)CC3)nc21] |

| Compound No. | Structure |
|---|---|
| 551 | 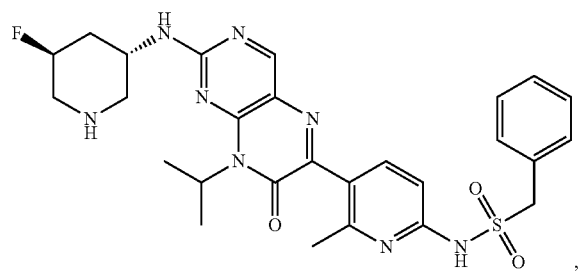 [SMILES: Cc1nc(NS(=O)(=O)Cc2ccccc2)ccc1-c1nc2cnc(N[C@@H]3CNC[C@@H](F)C3)nc2n(C(C)C)c1=O] |
| 552 | 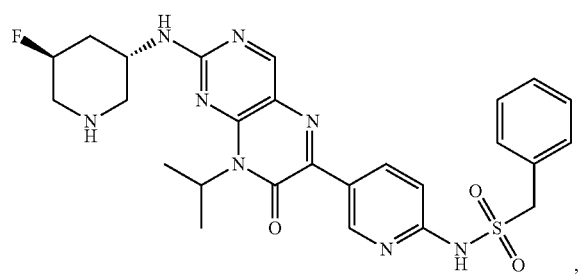 [SMILES: CC(C)n1c(=O)c(-c2ccc(NS(=O)(=O)Cc3ccccc3)nc2)nc2cnc(N[C@@H]3CNC[C@@H](F)C3)nc21] |
| 553 | 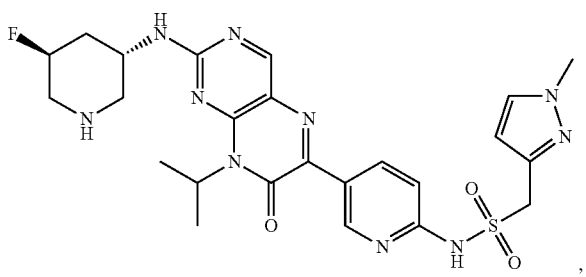 [SMILES: CC(C)n1c(=O)c(-c2ccc(NS(=O)(=O)Cc3ccn(C)n3)nc2)nc2cnc(N[C@@H]3CNC[C@@H](F)C3)nc21] |
| 554 | 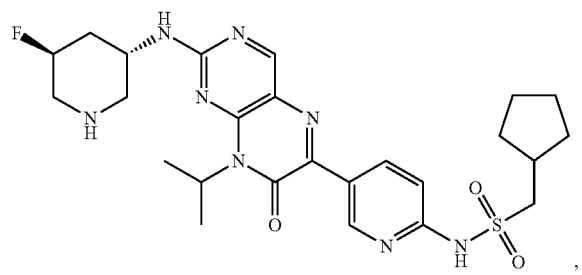 [SMILES: CC(C)n1c(=O)c(-c2ccc(NS(=O)(=O)CC3CCCC3)nc2)nc2cnc(N[C@@H]3CNC[C@@H](F)C3)nc21] |
| 555 | 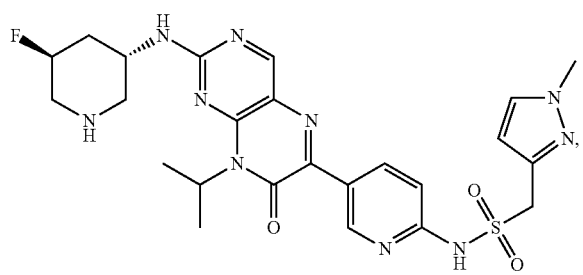 |

-continued

| Compound No. | Structure |
|---|---|
| 556 | 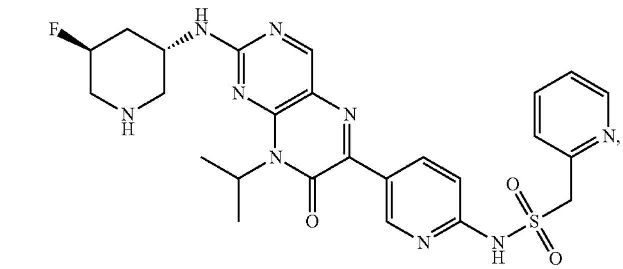 [SMILES: CC(C)n1c(=O)c(-c2ccc(NS(=O)(=O)Cc3ccccn3)nc2)nc2cnc(N[C@@H]3CNC[C@@H](F)C3)nc21] |
| 557 | 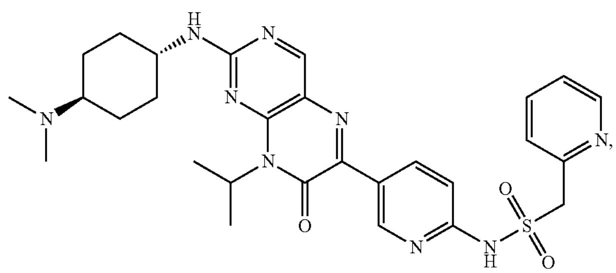 [SMILES: CC(C)n1c(=O)c(-c2ccc(NS(=O)(=O)Cc3ccccn3)nc2)nc2cnc(N[C@H]3CC[C@H](N(C)C)CC3)nc21] |
| 558 | 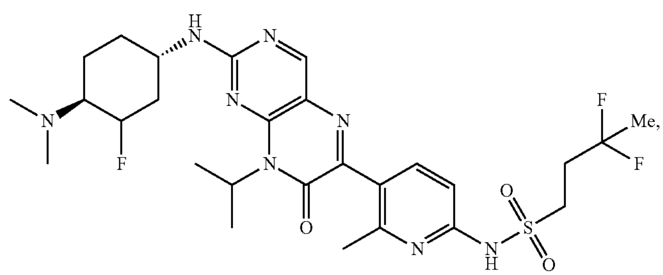 [SMILES: Cc1nc(NS(=O)(=O)CCC(C)(F)F)ccc1-c1nc2cnc(N[C@H]3CC[C@H](N(C)C)C(F)C3)nc2n(C(C)C)c1=O] |
| 559 | 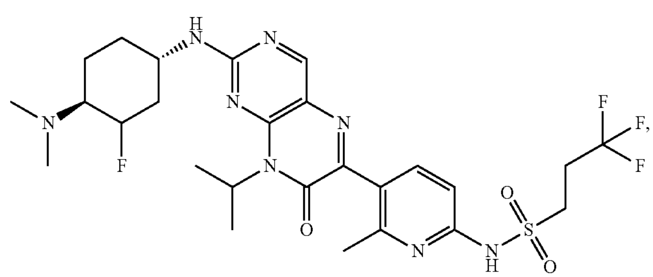 [SMILES: Cc1nc(NS(=O)(=O)CCC(F)(F)F)ccc1-c1nc2cnc(N[C@H]3CC[C@H](N(C)C)C(F)C3)nc2n(C(C)C)c1=O] |
| 560 | 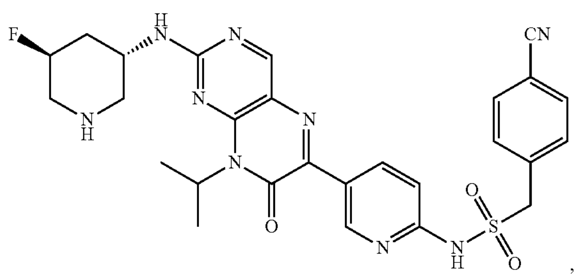 |

| Compound No. | Structure |
|---|---|
| 561 | 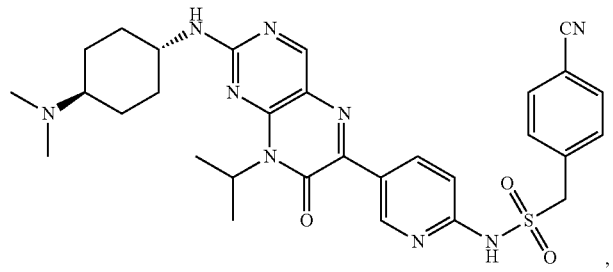 [SMILES: CC(C)n1c(=O)c(-c2ccc(NS(=O)(=O)Cc3ccc(C#N)cc3)nc2)nc2cnc(N[C@H]3CC[C@H](N(C)C)CC3)nc21] , |
| 562 | 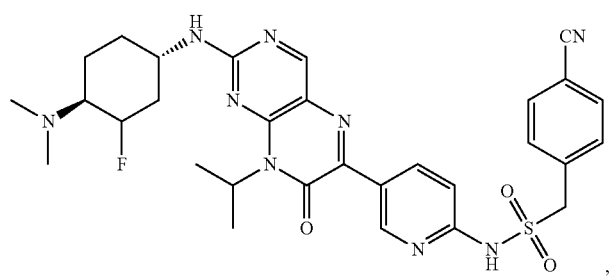 [SMILES: CC(C)n1c(=O)c(-c2ccc(NS(=O)(=O)Cc3ccc(C#N)cc3)nc2)nc2cnc(N[C@H]3CC[C@H](N(C)C)C(F)C3)nc21] , |
| 563 | 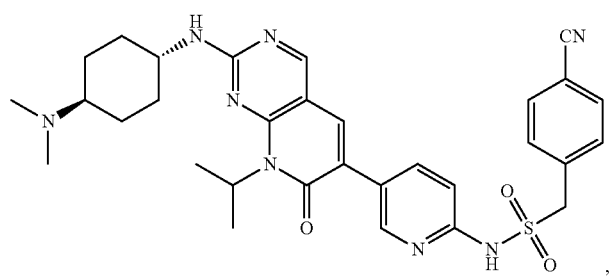 , |
| 564 | 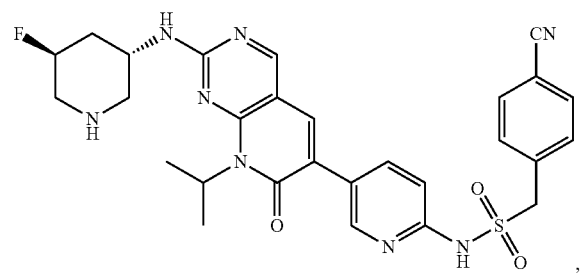 , |
| 565 | 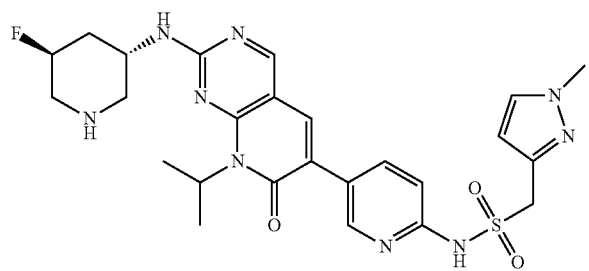 , |

| Compound No. | Structure |
|---|---|
| 566 | 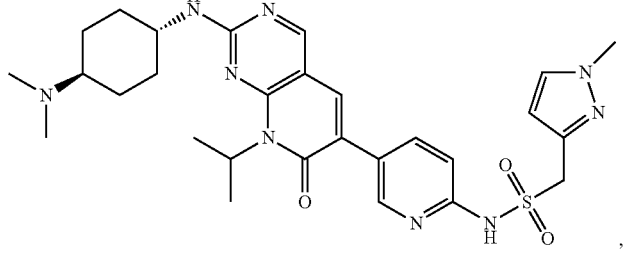 |
| 567 | 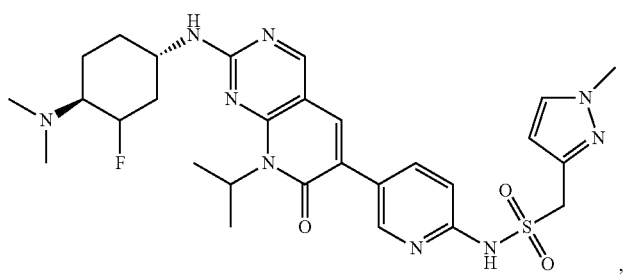 |
| 568 | 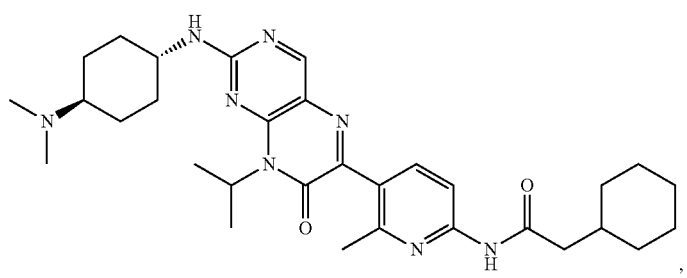 [SMILES: Cc1nc(NC(=O)CC2CCCCC2)ccc1-c1nc2cnc(N[C@H]3CC[C@H](N(C)C)CC3)nc2n(C(C)C)c1=O] |
| 569 | 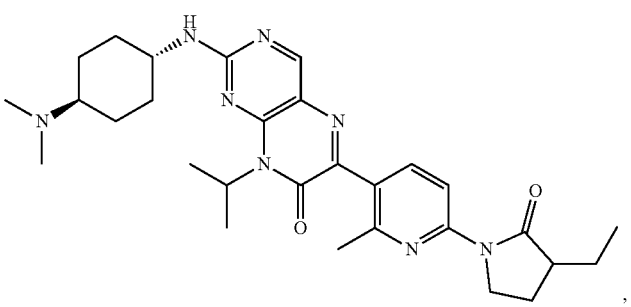 [SMILES: CCC1CCN(c2ccc(-c3nc4cnc(N[C@H]5CC[C@H](N(C)C)CC5)nc4n(C(C)C)c3=O)c(C)n2)C1=O] |
| 570 | 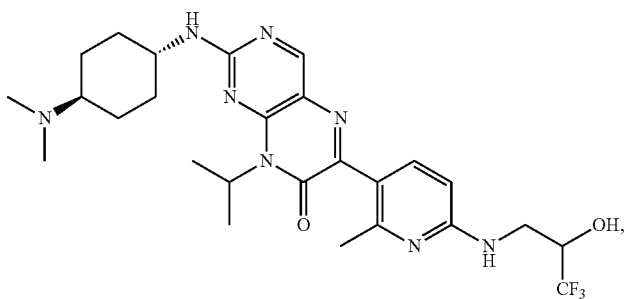 [SMILES: Cc1nc(NCC(O)C(F)(F)F)ccc1-c1nc2cnc(N[C@H]3CC[C@H](N(C)C)CC3)nc2n(C(C)C)c1=O] |

| Compound No. | Structure |
|---|---|
| 571 | 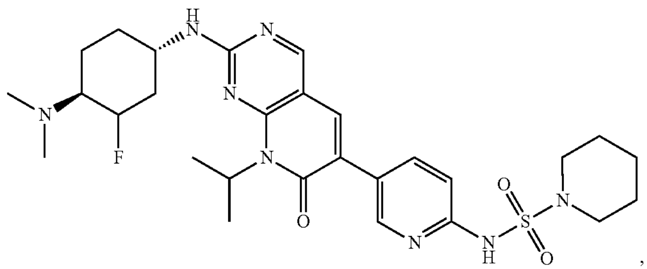 [SMILES: CC(C)n1c(=O)c(-c2ccc(NS(=O)(=O)N3CCCCC3)nc2)cc2cnc(N[C@H]3CC[C@H](N(C)C)C(F)C3)nc21] |
| 572 | 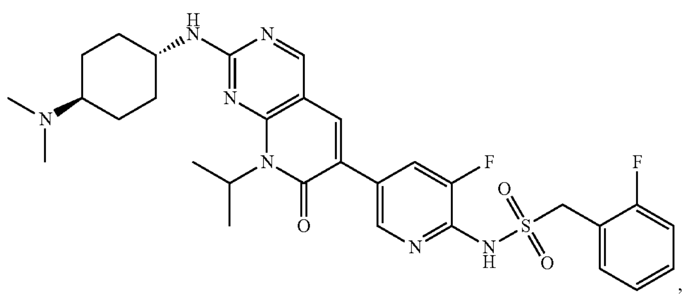 [SMILES: CC(C)n1c(=O)c(-c2cnc(NS(=O)(=O)Cc3ccccc3F)c(F)c2)cc2cnc(N[C@H]3CC[C@H](N(C)C)CC3)nc21] |
| 573 | 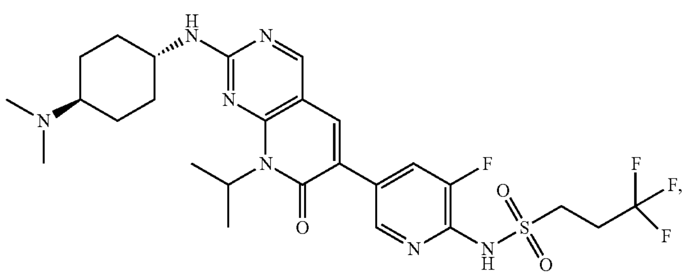 [SMILES: CC(C)n1c(=O)c(-c2cnc(NS(=O)(=O)CCC(F)(F)F)c(F)c2)cc2cnc(N[C@H]3CC[C@H](N(C)C)CC3)nc21] |
| 574 | 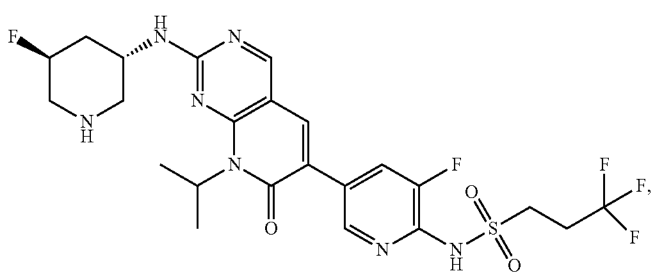 [SMILES: CC(C)n1c(=O)c(-c2cnc(NS(=O)(=O)CCC(F)(F)F)c(F)c2)cc2cnc(N[C@@H]3CNC[C@@H](F)C3)nc21] |
| 575 | 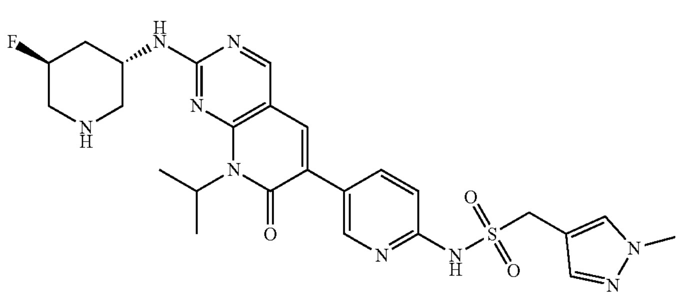 |

| Compound No. | Structure |
|---|---|
| 576 | 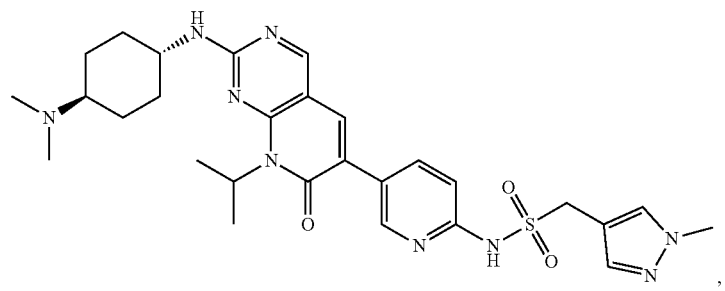 , |
| 577 | 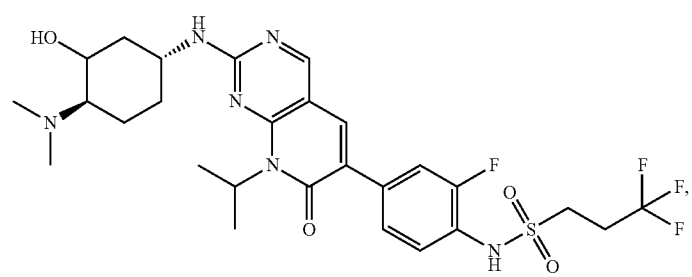 [SMILES: CC(C)n1c(=O)c(-c2ccc(NS(=O)(=O)CCC(F)(F)F)c(F)c2)cc2cnc(N[C@@H]3CC[C@@H](N(C)C)C(O)C3)nc21] |
| 578 | 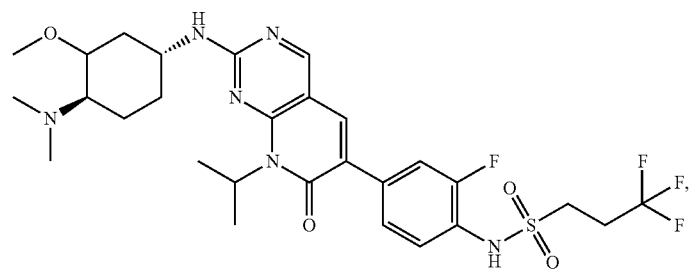 [SMILES: COC1C[C@H](Nc2ncc3cc(-c4ccc(NS(=O)(=O)CCC(F)(F)F)c(F)c4)c(=O)n(C(C)C)c3n2)CC[C@H]1N(C)C] |
| 579 | 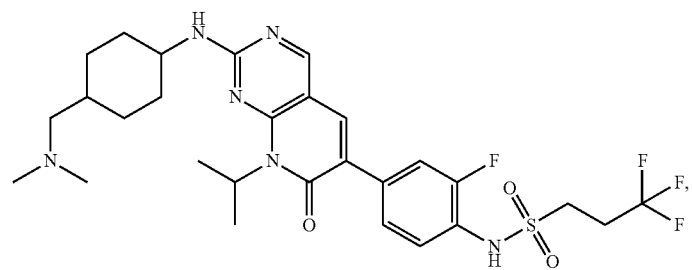 [SMILES: CC(C)n1c(=O)c(-c2ccc(NS(=O)(=O)CCC(F)(F)F)c(F)c2)cc2cnc(NC3CCC(CN(C)C)CC3)nc21] |
| 580 | 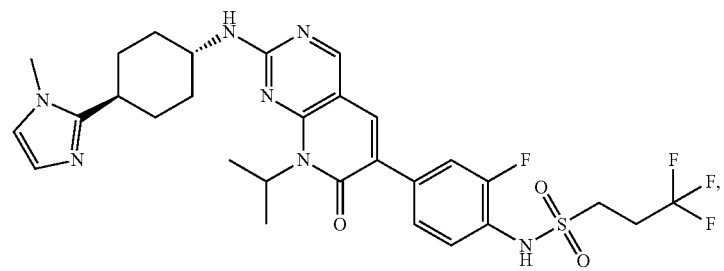 [SMILES: CC(C)n1c(=O)c(-c2ccc(NS(=O)(=O)CCC(F)(F)F)c(F)c2)cc2cnc(N[C@H]3CC[C@H](c4nccn4C)CC3)nc21] , |

| Compound No. | Structure |
|---|---|
| 581 | 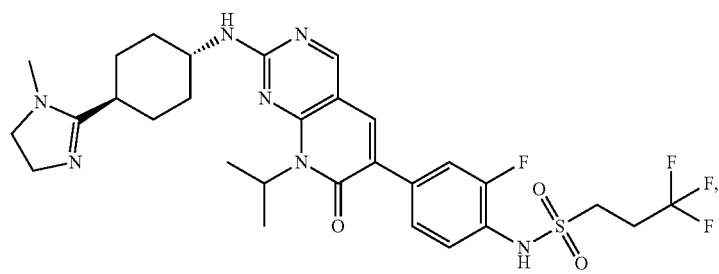 [SMILES: CC(C)n1c(=O)c(-c2ccc(NS(=O)(=O)CCC(F)(F)F)c(F)c2)cc2cnc(N[C@H]3CC[C@H](C4=NCCN4C)CC3)nc21] |
| 582 | 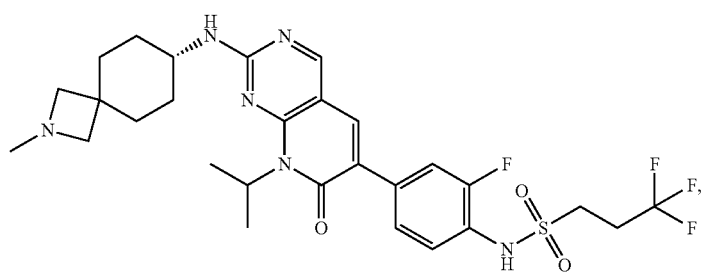 |
| 583 | 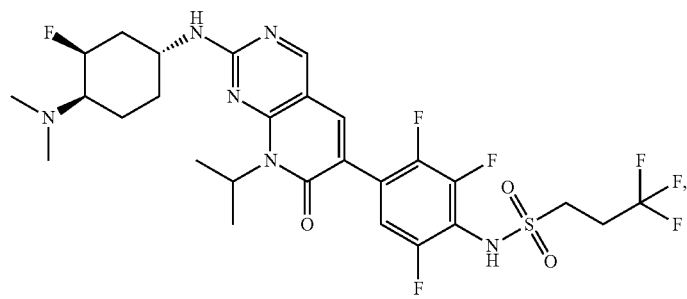 [SMILES: CC(C)n1c(=O)c(-c2cc(F)c(NS(=O)(=O)CCC(F)(F)F)c(F)c2F)cc2cnc(N[C@@H]3CC[C@@H](N(C)C)[C@@H](F)C3)nc21] |
| 584 | 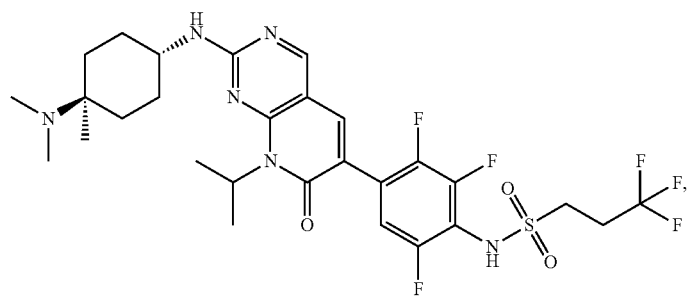 [SMILES: CC(C)n1c(=O)c(-c2cc(F)c(NS(=O)(=O)CCC(F)(F)F)c(F)c2F)cc2cnc(N[C@H]3CC[C@](C)(N(C)C)CC3)nc21] |
| 585 | 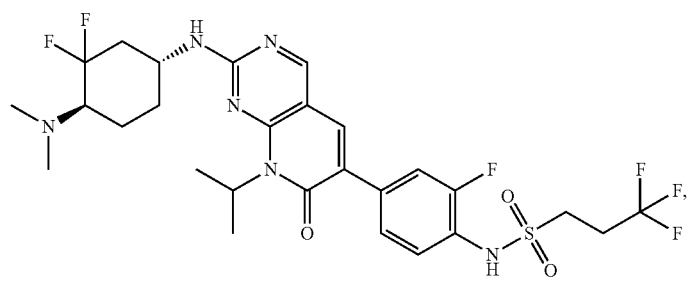 [SMILES: CC(C)n1c(=O)c(-c2ccc(NS(=O)(=O)CCC(F)(F)F)c(F)c2)cc2cnc(N[C@@H]3CC[C@@H](N(C)C)C(F)(F)C3)nc21] |

| Compound No. | Structure |
|---|---|
| 586 | 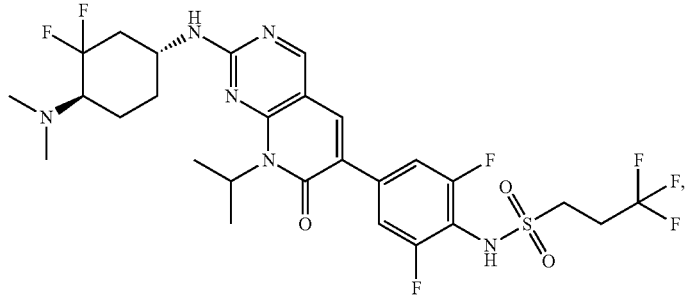 [SMILES: CC(C)n1c(=O)c(-c2cc(F)c(NS(=O)(=O)CCC(F)(F)F)c(F)c2)cc2cnc(N[C@@H]3CC[C@@H](N(C)C)C(F)(F)C3)nc21] |
| 587 | 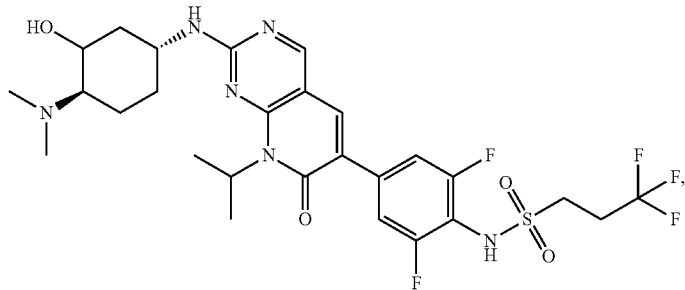 [SMILES: CC(C)n1c(=O)c(-c2cc(F)c(NS(=O)(=O)CCC(F)(F)F)c(F)c2)cc2cnc(N[C@@H]3CC[C@@H](N(C)C)C(O)C3)nc21] |
| 588 | 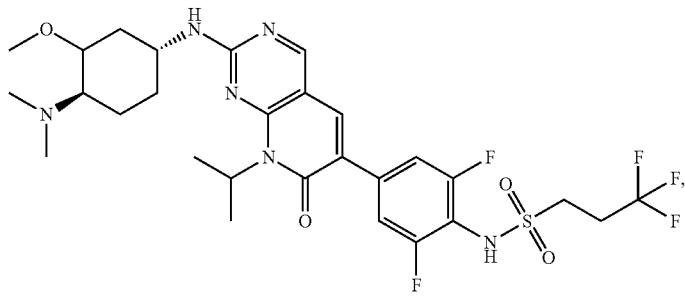 [SMILES: COC1C[C@H](Nc2ncc3cc(-c4cc(F)c(NS(=O)(=O)CCC(F)(F)F)c(F)c4)c(=O)n(C(C)C)c3n2)CC[C@H]1N(C)C] |
| 589 | 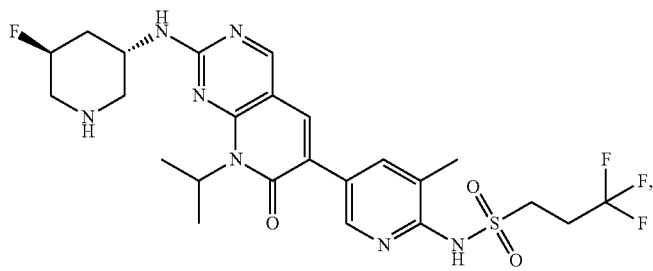 [SMILES: Cc1cc(-c2cc3cnc(N[C@@H]4CNC[C@@H](F)C4)nc3n(C(C)C)c2=O)cnc1NS(=O)(=O)CCC(F)(F)F] |
| 590 | 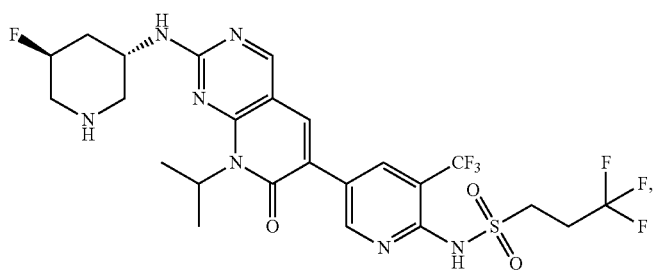 [SMILES: CC(C)n1c(=O)c(-c2cnc(NS(=O)(=O)CCC(F)(F)F)c(C(F)(F)F)c2)cc2cnc(N[C@@H]3CNC[C@@H](F)C3)nc21] |

| Compound No. | Structure |
|---|---|
| 591 | 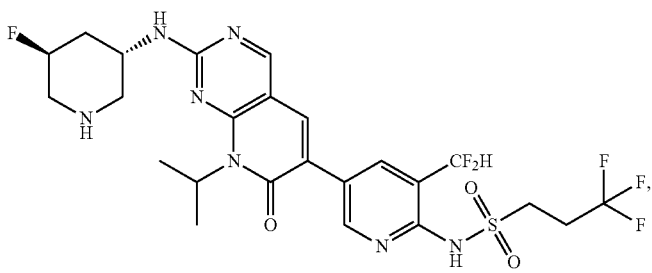 [SMILES: CC(C)n1c(=O)c(-c2cnc(NS(=O)(=O)CCC(F)(F)F)c(C(F)F)c2)cc2cnc(N[C@@H]3CNC[C@@H](F)C3)nc21] |
| 592 | 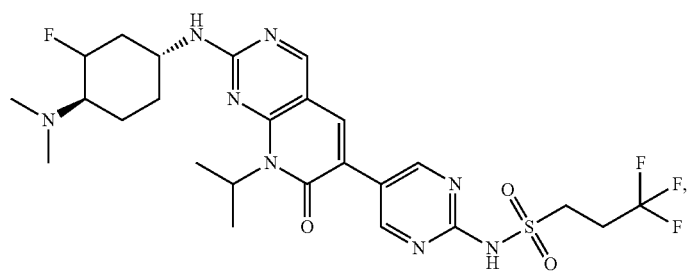 [SMILES: CC(C)n1c(=O)c(-c2cnc(NS(=O)(=O)CCC(F)(F)F)nc2)cc2cnc(N[C@@H]3CC[C@@H](N(C)C)C(F)C3)nc21] |
| 593 | 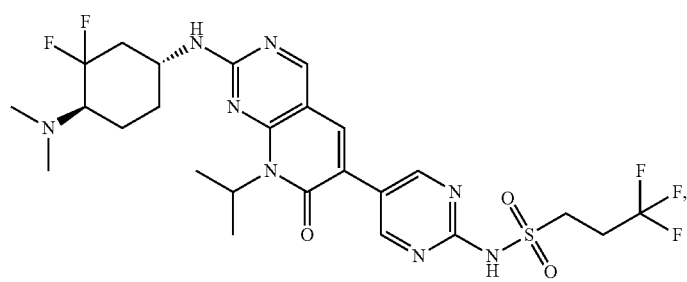 [SMILES: CC(C)n1c(=O)c(-c2cnc(NS(=O)(=O)CCC(F)(F)F)nc2)cc2cnc(N[C@@H]3CC[C@@H](N(C)C)C(F)(F)C3)nc21] |
| 594 | 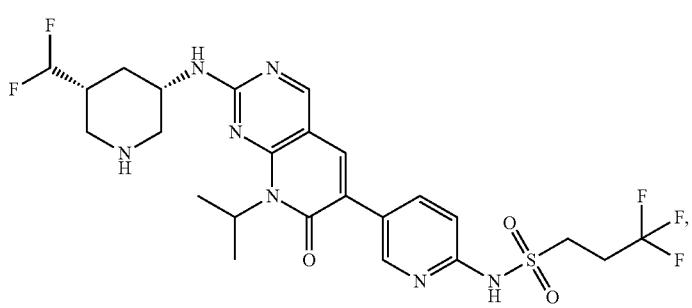 [SMILES: CC(C)n1c(=O)c(-c2ccc(NS(=O)(=O)CCC(F)(F)F)nc2)cc2cnc(N[C@@H]3CNC[C@H](C(F)F)C3)nc21] |
| 595 | 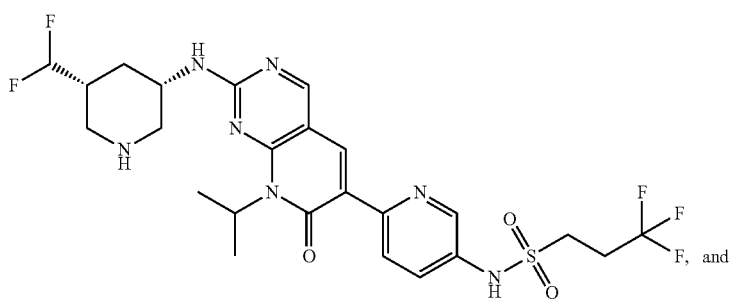 [SMILES: CC(C)n1c(=O)c(-c2ccc(NS(=O)(=O)CCC(F)(F)F)cn2)cc2cnc(N[C@@H]3CNC[C@H](C(F)F)C3)nc21 ; "and"] |

| Compound No. | Structure |
|---|---|
| 596 | 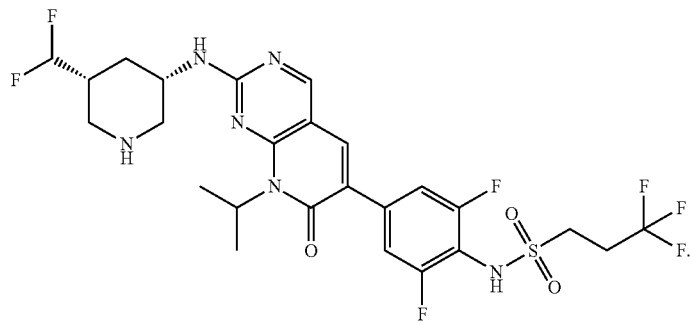 [SMILES: CC(C)n1c(=O)c(-c2cc(F)c(NS(=O)(=O)CCC(F)(F)F)c(F)c2)cc2cnc(N[C@@H]3CNC[C@H](C(F)F)C3)nc21] |

19. The compound of claim 1 or a stereoisomer, tautomer, or pharmaceutically acceptable salt thereof, wherein the compound has formula (Id1):

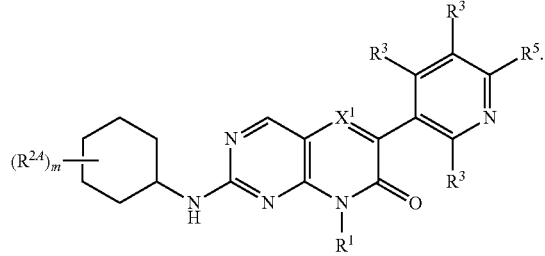

(Id1)

20. The compound of claim 1 or a stereoisomer, tautomer, or pharmaceutically acceptable salt thereof, wherein the compound has formula (Ik2):

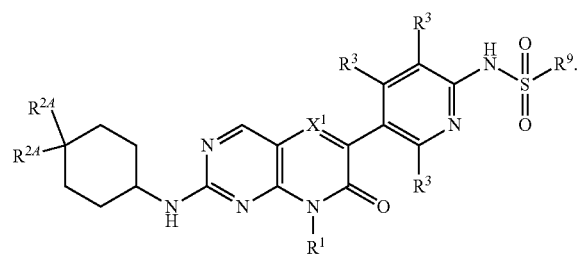

(Ik2)

21. A pharmaceutical composition comprising a compound of claim 1, or a pharmaceutically acceptable salt thereof, and one or more pharmaceutically acceptable excipients.

22. A method of treating an IRE1-related disease or disorder, wherein the IRE1-related disease or disorder is cancer, the method comprising administering to a subject having an IRE1-related disease or disorder an effective amount of the compound of claim 1 or a pharmaceutically acceptable salt thereof.

23. The method of claim 22, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

24. The method of claim 22, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

25. A pharmaceutical composition comprising a compound of claim 2, or a pharmaceutically acceptable salt thereof, and one or more pharmaceutically acceptable excipients.

26. A method of treating an IRE1-related disease or disorder, wherein the IRE1-related disease or disorder is cancer, the method comprising administering to a subject having an IRE1-related disease or disorder an effective amount of the compound of claim 2 or a pharmaceutically acceptable salt thereof.

* * * * *

UNITED STATES PATENT AND TRADEMARK OFFICE
CERTIFICATE OF CORRECTION

PATENT NO. : 12,344,603 B2
APPLICATION NO. : 17/366923
DATED : July 1, 2025
INVENTOR(S) : Marie-Gabrielle Braun et al.

It is certified that error appears in the above-identified patent and that said Letters Patent is hereby corrected as shown below:

On the Title Page

In Column 1, below item (63), insert -- (30) Foreign Application Priority Data
Apr. 8, 2019 (CN) ............................ PCT/CN2019/081673
Jan. 3, 2019 (CN) ............................ PCT/CN2019/070275 --, therefor.

In the Claims

In Column 529, Line 51, Claim 1, delete "$R^{2A}$," and insert -- $R^{2A}$; --, therefor.

In Column 530, Line 10, Claim 1, delete "—NRC(O)$R^9$," and insert -- —$NR^8C(O)R^9$, --, therefor.

In Column 530, Line 14, Claim 1, delete "—$NR^8S(O)(=NR^8C)R^9$" and insert
-- —$NR^8S(O)(=NR^{8C})R^9$ --, therefor.

In Column 530, Line 19, Claim 1, delete "$R^{10}$;" and insert -- $R^{10}$, --, therefor.

In Column 530, Line 47, Claim 1, delete "$R^{10}$," and insert -- $R^{10}$; --, therefor.

In Column 530, Line 58, Claim 1, delete "—S(O)(=NH) H," and insert -- —S(O)(=NH)H, --, therefor.

In Column 531, Line 4, Claim 1, delete "-(CH$_2$)$_f$-CF$_3$," and insert -- —(CH$_2$)$_f$-CF$_3$, --, therefor.

In Column 531, Line 35, Claim 2, delete "$R^{2A}$," and insert -- $R^{2A}$; --, therefor.

In Column 531, Lines 50-51, Claim 2, delete "—$NR^8SO_2NR^8AR$ 8B, —$NR^8S(O)(=NR^8C)R^9$,
—C(O)N($R^8$) SO$_2R^9$," and insert -- —$NR^8SO_2NR^{8A}R^{8B}$, —$NR^8S(O)(=NR^{8C})R^9$,
—C(O)N($R^8$)SO$_2R^9$, --, therefor.

Signed and Sealed this
Sixth Day of January, 2026

John A. Squires
*Director of the United States Patent and Trademark Office*

CERTIFICATE OF CORRECTION (continued) Page 2 of 3
U.S. Pat. No. 12,344,603 B2

In Column 531, Lines 52-53, Claim 2, delete "—NR⁸S(O)(—NR⁸C)R⁹," and insert -- —NR$^8$S(O)(=NR$^{8C}$)R$^9$, --, therefor.

In Column 532, Line 26, Claim 2, delete "-CF₃." and insert -- —CF$_3$. --, therefor.

In Column 532, Line 39, Claim 4, delete "tetrahydrafuranyl." and insert -- tetrahydrofuranyl. --, therefor.

In Column 533, Lines 56-66, Claim 14, delete

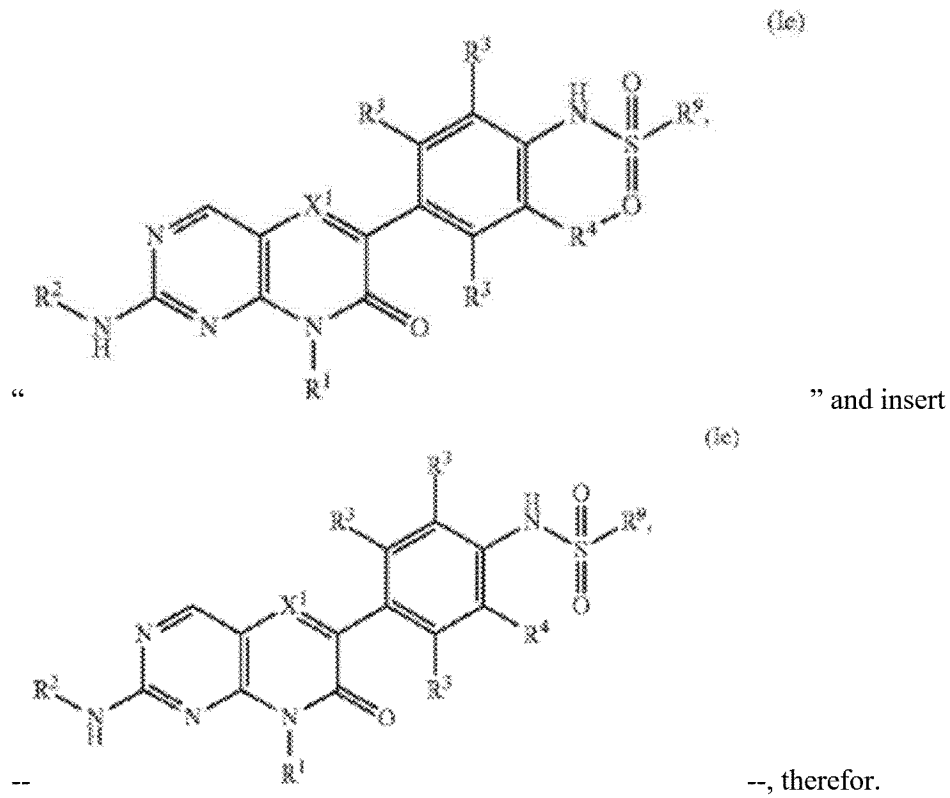

" and insert

-- --, therefor.

In Column 534, Lines 13-23, Claim 14, delete

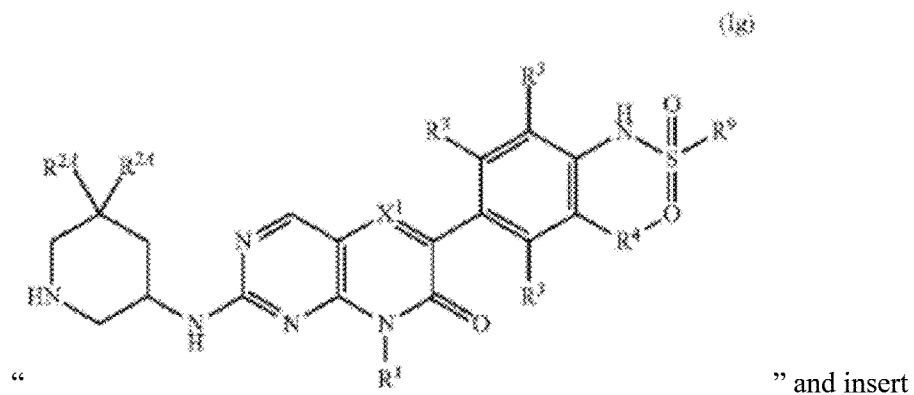

" and insert

CERTIFICATE OF CORRECTION (continued)
U.S. Pat. No. 12,344,603 B2

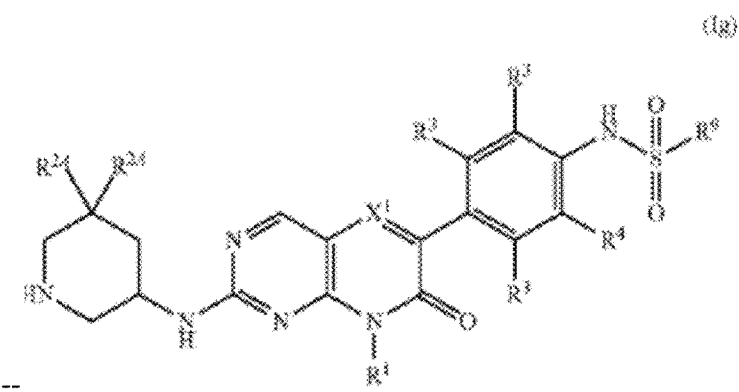

--, therefor.

In Column 536, Lines 1-13, Claim 16, delete

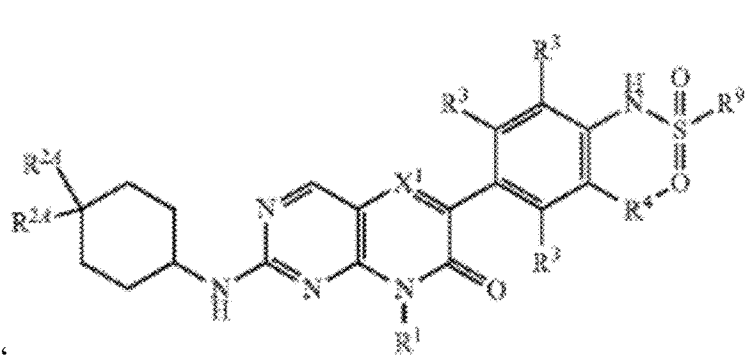

" and insert

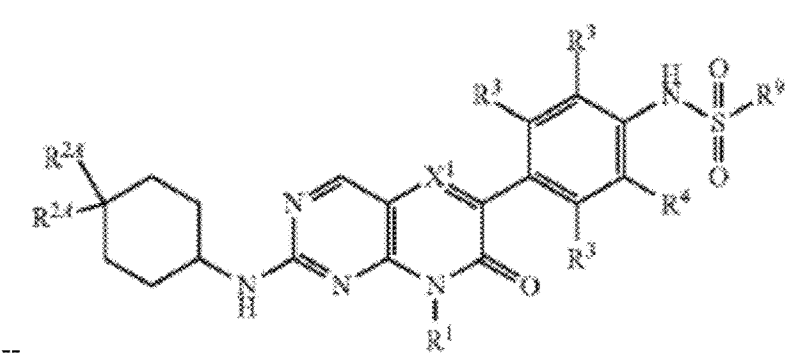

--, therefor.

SEQUENCE LISTING

```
<160> NUMBER OF SEQ ID NOS: 1

<210> SEQ ID NO 1
<211> LENGTH: 17
<212> TYPE: RNA
<213> ORGANISM: Artificial Sequence
<220> FEATURE:
<223> OTHER INFORMATION: Synthetic

<400> SEQUENCE: 1
cauguccgca gcgcaug                                                  17
```